US009737579B2

(12) United States Patent
Da Costa Garcia et al.

(10) Patent No.: US 9,737,579 B2
(45) Date of Patent: Aug. 22, 2017

(54) ANTIBACTERIAL PHAGE, PHAGE PEPTIDES AND METHODS OF USE THEREOF

(71) Applicants: TECNIFAR-INDÚSTRIA TÉCNICA FARMACÊUTICA, S.A, Lisbon (PT); TECHNOPHAGE, INVESTIGAÇÃO E DESENVOLVIMENTO EM BIOTECNOLOGIA, SA, Lisbon (PT)

(72) Inventors: Miguel Ângelo Da Costa Garcia, Lisbon (PT); Carlos Jorge Sousa De São José, Lisbon (PT); Clara Isabel Rodrigues Leandro, Parede (PT); Filipa Maria Rodrigues Pardal Dias Antunes Marçal Da Silva, Belas (PT); Ana Raquel Martins Barbosa, Sobreda (PT)

(73) Assignees: Technophage, Investigacao E Desenvolvimento Em Biotecnologia, SA, Lisbon (PT); Tecnifar—Industria Tecnica Farmaceutica, S.A., Lisbon (PT)

( * ) Notice: Subject to any disclaimer, the term of this patent is extended or adjusted under 35 U.S.C. 154(b) by 0 days.

(21) Appl. No.: 15/216,875

(22) Filed: Jul. 22, 2016

(65) Prior Publication Data

US 2016/0317590 A1    Nov. 3, 2016

Related U.S. Application Data

(62) Division of application No. 14/943,082, filed on Nov. 17, 2015, now Pat. No. 9,399,049, and a division of application No. 13/823,519, filed as application No. PCT/PT2011/000031 on Sep. 19, 2011, now Pat. No. 9,222,077.

(60) Provisional application No. 61/384,015, filed on Sep. 17, 2010.

(51) Int. Cl.
| *A61K 35/76* | (2015.01) |
| *A61K 31/505* | (2006.01) |
| *A61K 38/14* | (2006.01) |
| *A61K 31/7056* | (2006.01) |
| *A61K 38/47* | (2006.01) |
| *A61K 38/48* | (2006.01) |
| *C12N 7/00* | (2006.01) |
| *C12N 9/36* | (2006.01) |
| *C12N 9/50* | (2006.01) |
| *A61K 45/06* | (2006.01) |
| *A61K 9/00* | (2006.01) |

(52) U.S. Cl.
CPC .............. *A61K 35/76* (2013.01); *A61K 9/007* (2013.01); *A61K 9/0014* (2013.01); *A61K 9/0019* (2013.01); *A61K 9/0053* (2013.01); *A61K 31/505* (2013.01); *A61K 31/7056* (2013.01); *A61K 38/14* (2013.01); *A61K 38/47* (2013.01); *A61K 38/48* (2013.01); *A61K 45/06* (2013.01); *C12N 7/00* (2013.01); *C12N 9/2462* (2013.01); *C12N 9/503* (2013.01); *C12N 2795/00022* (2013.01); *C12N 2795/00031* (2013.01); *C12N 2795/00032* (2013.01)

(58) Field of Classification Search
None
See application file for complete search history.

(56) References Cited

U.S. PATENT DOCUMENTS

2010/0172918 A1    7/2010 Yoon

FOREIGN PATENT DOCUMENTS

| WO | WO 9739111 | 10/1997 |
| WO | WO 02/076483 | 10/2002 |
| WO | WO 03/080823 | 10/2003 |
| WO | WO 2007/130655 | 11/2007 |
| WO | WO 2008121830 | 10/2008 |
| WO | WO 2010/011960 | 1/2010 |
| WO | WO 2010023207 A2 | 3/2010 |
| WO | WO 2010/041970 | 4/2010 |
| WO | WO 2010/090542 | 8/2010 |
| WO | WO 2010/149795 | 12/2010 |

OTHER PUBLICATIONS

Ceyssens et al., GenBank Accession No. CAK25969, Oct. 12, 2006, 1 page.
Ceyssens, GenBank Accession No. CAP45518, Nov. 19, 2007, 1 page.
Ceyssens, GenBank Accession No. CAP45519, Nov. 19, 2007.
Chhibber et al., "Therapeutic Potential of Bacteriophage in Treating Klebsiella Pneumoniae B5055-Mediated Lobar Pneumonia in Mice," J. Med. Microbiol., 57, pp. 1508-1513, 2008.
Chica et al., Curr. Opin. Biotechnol., 16(4), pp. 378-384, 2005.
El Sohl et al., "Update on the Treatment of Pseudomonas Aeruginosa Pneumonia," Journal of Antimicrobial Chemotherapy, vol. 64, pp. 229-238, 2009.

(Continued)

*Primary Examiner* — Christian Fronda
(74) *Attorney, Agent, or Firm* — Margaret B. Brivanlou; Nicole Fortune; King & Spalding LLP

(57) ABSTRACT

The present invention is directed to the field of phage therapy for the treatment and control of bacterial infections. In particular, the present invention is directed to the novel bacteriophage F387/08, F391/08, F394/08, F488/08, F510/08, F44/10, and F125/10, isolated polypeptides thereof, compositions comprising one or more of the novel bacteriophage and/or isolated polypeptides, as well as to methods for the treatment and prevention of bacterial infections using same, either alone or in combination with other antibacterial therapies, e.g., antibiotics and/or other phage therapies.

23 Claims, 758 Drawing Sheets

(56) References Cited

OTHER PUBLICATIONS

Figure 1A:
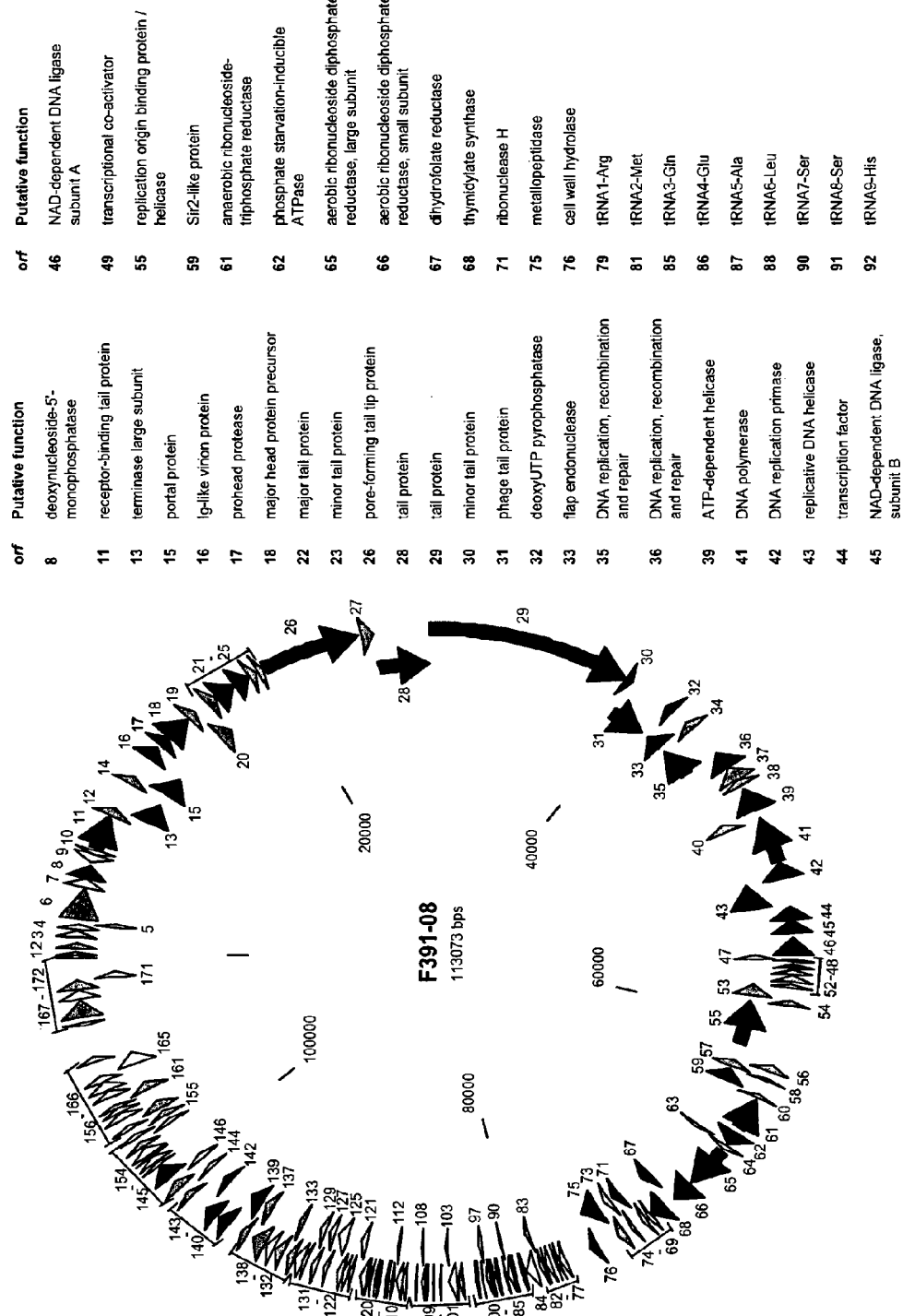

Glonti et al., GenBank Accession No. ABW23129, Jul. 25, 2007, 1 page.
Glonti et al., GenBank Accession No. ABW23119 Jul. 25, 2007, 1 page.
Glonti et al, GenBank Accession No. ABW23128, Jul. 25, 2007, 1 page.
Glonti et al., GenBank Accession No. ABY71007, Oct. 19, 2007, 1 page.
Glonti et al., GenBank Accession No. ABY71009, Oct. 19, 2007, 1 page.
Glonti et al., GenBank Accession No. ABY71011, Oct. 19, 2007, 1 page.
Kulakov et al., GenBank Accession No. CAX63154, Mar. 23, 2009, 1 page.
Lavigne, GenBank Accession No. CAD44231, Aug. 9, 2002, 1 page.
Lavigne, GenBank Accession No. CAD44229, Aug. 9, 2002, 1 page.
Lammens et al., GenBank Accession No. CAP45507, Nov. 19, 2007, 1 page.
Lavigne, GenBank Accession No. CAD44225, Aug. 9, 2002, 1 page.
"Pseudomonas phage LUZ19, Complete Genome," Nov. 27, 2007, retrieved from GenBank Accession No. AM910651.1, http://www.ncbi.nlm.nih.gov/nuccore/161168305?sat=43&satkey=10346167, 18 pages.
Rossolini et al, "Treatment and Control of Severe Infections Caused by Multiresistant Pseudomonas Aeruginosa," European Society of Clinical Microbiology and Infectious Disease, 11 (suppl. 4), pp. 17-32, 2005.
Sen et al., Appl. Biochem. Biotechnol., 143(3), pp. 212-223, 2007.
Tecnifar-Industria Tecnica Farmaceutica, S.A. and Technophage, Investigacao e desenvolvimento em biotecnologia SA, Patent Examination Report No. 2 issued in counterpart Australian Patent Application No. 2011302722 on Jan. 6, 2016.
Tecnifar-Industria Tecnica Farmaceutica, S.A. and Technophage, Investigacao e desenvolvimento em biotecnologia SA, Notification of the First Office Action issued in counterpart Chinese Patent Application No. 201180054190.X on Feb. 3, 2016, 13 pages.
Tecnifar-Indústria Técnica Farmacêutica, S.A and Technopage, Investigação E Desenvolvimento Em Biotecnologia, SA, Search Report for Singapore Patent Application No. 201301938-5, 6 pages, Nov. 11, 2014.
"Pseudomonas phage LUZ19, Complete Genome," Nov. 27, 2007, retrieved from GenBank Accession No. AM910651.1, http://www.ncbi.nlm.nih.gov/nuccore/161168305?sat=43&satkey=0346167, 18 pages.
Technophage et al., English translation of the Notification of Reasons for Refusal issued for Japanese Patent Application No. 2013-529096, dated Sep. 14, 2015, 7 pages.
Staphylococcus phage K Virion, Complete Genome, Jun. 14, 2004, retrieved from GenBank [online] Accession No. NC_005880.1, retrieved on Dec. 12, 2016, https://www.ncbi.nlm.nih.gov/nuccore/48696391?sat=23&satkey=6871964, 46 pages.
Notification of Reasons for Refusal for Japanese Patent Application No. 2015-243657, Dec. 19, 2016, 9 pages, with English translation.
O'Flaherty et al., "Genome of Staphylococcal Phage K: a New Lineage of Myoviridae Infecting Gram-Positive Bacteria with a Low GC Content," Journal of Bacteriology, vol. 186, No. 9, p. 2862-2871, May 2004.
Kwan, T et al., "The complete genomes and proteomes of 27 *Staphylococcus aureus* bacteriophages," PNAS, vol. 102, No. 14, p. 5174-5179, Apr. 5,2005.
O'Flaherty et al., GenBank Accession No. AAO47545, 1 page, 2004.
Kwan et al., GenBank Accession No. YP_240966, 2 pages, 2009.
Kwan et al., GenBank Accession No. AAX92161 1 page, 2005.
O'Flaherty et al., GenBank Accession No. AAO47480, 1 page, 2004.
Kwan et al., GenBank Accession No. AAX92164, 1 page, 2005.
Pantucek et al., GenBank Accession No. ABL87138, 1 page, 1998.
Pantucek et al., GenBank Accession No. ABL87141, 1 page, 1998.
O'Flaherty et al., GenBank Accession No. AAO47496, 1 page, 2004.
Kwan et al., GenBank Accession No. AAX92093, 1 page, 2005.
Pantucek et al., GenBank Accession No. ABL87117, 2 pages, 1998.
Kwan et al., GenBank Accession No. AAX92087, 2 pages, 2005.
O'Flaherty et al., GenBank Accession No. AAO47505, 2 pages, 2004.
Kwan et al., GenBank Accession No. AAX92134, 1 page, 2005.
O'Flaherty et al., GenBank Accession No. AAO47510, 1 page, 2004.
Kwan et al., GenBank Accession No. $YP_{13}$ 240926, 2 pages, 2009.
O'Flaherty et al., GenBank Accession No. AAO47477, 2 pages, 2004.
Pantucek et al., GenBank Accession No. ABL87139, 2 pages, 1998.
Technophage, Investigação E Desenvolvimento Em Biotecnologia, SA, et al., Examinaton Report No. 1 for Australian Patent Application No. 2016219667, 16 pages, Apr. 1, 2017.

Fig. 1B

| orf | Putative function |
|---|---|
| 93 | tRNA10-Arg |
| 94 | tRNA11-Gln |
| 95 | tRNA12-Met |
| 98 | tRNA13-Ile |
| 99 | tRNA14-Met |
| 100 | tRNA15-Val |
| 104 | tRNA16-Asp |
| 105 | tRNA17-Asn |
| 106 | tRNA18-Cys |
| 108 | tRNA19-Lys |
| 109 | tRNA20-Phe |
| 113 | tRNA21-Leu |
| 114 | tRNA22-Pro |
| 115 | tRNA23-Thr |
| 116 | tRNA24-Gly |
| 119 | tRNA25-Trp |
| 139 | deoxynucleoside-5'-monophosphate kinase |
| 140 | ATP-dependent Clp protease |
| 141 | holin |
| 142 | lysozyme |
| 144 | thioredoxin |
| 147 | serine/threonine protein phosphatase |

Table 1 - Features of phage F391/08 gene products and assignment of putative functions.

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 1 | 52 | 240 | 5 | MKRFVISSKPAAKLNKMASSELVK MQRDMARRYRSYQRGGQQGLPMI WDNMMRYLKSLQNNV | 62 | Hypothetical protein T5.008 [Enterobacteria phage T5] | YP_006836.1 | 4e-04 (23/54) | | No putative conserved domains have been detected | | |
| 2 | 408 | 668 | 6 | MQNVKTPMIGDSVFIPFVTGDVSKP GENEKIGYIKGAAMIPFDKINAVYAE TEKAKNSDAKIYSVRVDSGDVVKVI RKDDKWLAVA | 86 | Hypothetical protein AGC_0006 [Enterobacteria phage EPS7] | YP_001836929.1 | 8e-18 (53/87) | | No putative conserved domains have been detected | | |
| 3 | 1007 | 1411 | 7 | MTATKTEKFAWNETNAATAVEMYE KIIASDGLEVANSQGLIDIAKAVGAE SHVKVRSKLVSAKVYQKSDKPRKV GGGSSLRKA-HYVRVLTQHAIADGLI DDADGLASLEQMKLDQLDVIARMV GVQDEVKESAE | 134 | A2 [Enterobacteria phage T5] | YP_006834.1 | 8e-44 (88/133) | | No putative conserved domains have been detected | | |
| 4 | 1479 | 1748 | 8 | MALIKGSVIKLTGTVVDELIQTGYQD NKVMTPPSVKVPEYIVLWVNPDAD TFGMAINREVFKPEMLELSSREIYLL NYAFSVEEKEVVK | 89 | No significant similarity found. | | | | No putative conserved domains have been detected | | |
| 5 | 1745 | 1972 | 9 | MIFFPTESLILIAGFFAAACLYGYYN FMEIGSEQTDLLRRDFWFKKASICR RWSIIFIILAVTFGISASIIPAIV | 75 | No significant similarity found. | | | | No putative conserved domains have been detected | | |
| 6 | 2056 | 3732 | 10 | MIIAIEKQKAILTAANNLNFWGKRLR AKKLEICDELSKEHYGTAKHSSEIC DWLDSNKPVKPAAEKRAQRVAVE DSRPVAAGQLNSSVESWKVIPGRR FLLTSIQNNTFPHANFWKTLQEAAK YLGATLLVSKYAYNKKGFQNGQGN DELKYDDAFSDFICDENVFLGNRET GFAFMAEINILPTADFPLSGFGETAT AYGLKGLAIGHAKITAESVPAMKGD TVRRMYSTGTATLKNYIQQKAGQK AEALHNYGALLVEIDDNGNFFARQI ETMDESGMFYDLNHKFTVNGGEE VTGHVAALQYGDIHAEKLDHAVAFA SWGPCDDSLVNVLRPRYQIVHDVH DFTSRNHHNRASGVFLAKQYAAGR DKVIDDLIDTGRVLEAMEREFSQTVI VESNHDLALSRWLDDSKANIQQDP ANAHLYYRLNAAIYEAIENKDDTFN VLDYALRNVAGCDFAAIFLTTDESM KIAGIECGSHGHNGINGARGNPKG FRKLGKMNTGHTHTPSIYGGVYTA GVAGSLDMGYNIGASSWSQTHLIT | 558 | A1 [Enterobacteria phage T5] | YP_006832.1 | 0.0 (402/559) | | No putative conserved domains have been detected | | |

Fig 2A

| | | | | | | | |
|---|---|---|---|---|---|---|---|
| 7 | 3801 | | | YENGQRTLIDFKDGVFFA | 150 | No significant similarity found. | | | No putative conserved domains have been detected |
| | 4253 | 11 | MKLTFIYNNRKSFTASNVVENSLVIS RDSEGRPHVSYQKVNTVDGDTVLK ALAAILPRPAEFKESGIVSQLVAADS ILYEADICEIVEIDAAAAGLMFIVVSE NDYDDTYLLGDVMDYSSSEYTPPL AIVPVMATRIKPAELADALTLFF | | | | | |
| 8 | 4327 | 12 | MAFNKLAIKAIKLWDLDGTVINSFAR VFPCMDDKGNLDLNMYREKACVH DAIMTDTLLPLVEYMRASLNDPTVL NIIVTARYMGKSDYYFLRKQRIRAG RGGNIQILSRDVLHRYIGDADYKEV YYSKDGIYKTHYFEMLKAEYPNATI TMIDDNRGYLAAAAAGLQTMDAT AINDILSIGVRLAGESFIDEALDDDN DYQYLCERLAHCWEGMTEEERSD YGIKPQQFIQSLAIAS | 238 | Deoxynucleoside-5-monophosphatase [Enterobacteria phage T5] | YP_006829.1 | 2e-81 (142/231) | deoxy-nucleoside-5-mono-phosphatase | No putative conserved domains have been detected |
| 9 | 5660 | 13 | MTIVLIFTFFFLAAVWFGVRAHDLR NAVVAADLRNKSLHQEILQTRAER QVAISKHQRVMNDLRNDPSNPYYI PPVTPQVAKRKQKRAGSDNSRKVS GSPSSNSGSSRSDDGSTAAIIATTA AVATYSGYDSGSSYCDSGSSSSSF DSGCSF | 153 | No significant similarity found. | | | | No putative conserved domains have been detected |
| 10 | 5888 | 14 | MEVVIGALVLLSIVLFVITVKQGKAIK QLERTNGVLQKSYDNQTRLLHHKAQ LNLSECKAELESANKIYITKGMV | 74 | No significant similarity found. | | | | No putative conserved domains have been detected |
| 11 | 6002 | 15 | MGFYAGRIGDKKVLSLTSGNNKDV NNHTNPGWDTIFHSDMPHVVVLET HERDLWDGGDWYRCTRMPDRIIQ VLSADYDRVVLTEVEFEDGTRRFIY GTSLGVGAKAYNAYFSNTVGSQAS AGTMASMKTNVCASADLHMDISFY FEETPGTINEKLRDGTGCMYTWGV NSEWGDRGPGPPVGAPIRPNFETII KAGWVLYRGAFSGNIAGSVSPPNR PLTIGVDAMRHPWMRTTGVNSICL RGETLNRNMYGHMGPRYGQSSNP VGGPYAHNIQTESYQEVQYKAGFF RGPPNNFMGWENTDNNNAGSGW GNNAYRDNNFRVPKRVRVWYITNM KYNGQGFYAENVFGSRNQEKISP REFIVNGINLMNTGWKFINONDINY SPGNRPDIRVIATNVARFSGNPTVG NNGYVHFNQPLTRPDNGAEFGQG NVSEMHVTTVGVYNFRSDAQWYV KSNPPEIGNQWGPVWSESTRPLRL VGGTGSADIGGNLRTSGNASHHLA | 658 | Receptor-binding tail protein Pb5 [Enterobacteria phage T5] | YP_006985.1 | 1e-127 (269/674) | receptor-binding tail protein | No putative conserved domains have been detected |

Fig 2B

| | | | | | | | | |
|---|---|---|---|---|---|---|---|---|
| 12 | 7989 | 8462 | TLWLGVNNSRNGACVVTLDWKND EWIAAAGIGCYNPLEDLTQWSEVD SRLRIFGNHFQKRVHQIMCLPVNM CVPFHFIRGTVTQCGVIPGNNAMQ MKAMWAPTTTNSATQGDYAIIYWLI ARADGSVEWWNVEMSNIMNMRV LPEVRIAVQRLA | | | | | |
| 13 | 8462 | 9778 | MSNDLIVPDTMSPEGMLVIEAYLES GSDVAKAALAVGMEEPKFREIMRK PEVKAYLTDIFMESGFRNRDKFFGI LDTVLTMKMEELDETGMGSEMDIM DILKLMHKMKDEMKMQIEYEKVK QAKAPIHQMNTQINLAGGHDSNYT DLLSRIVGAGK | 157 | Hypothetical protein T5.156 [Enterobacteria phage T5] | YP_006984.1 | 2e-42 (98/159) | No putative conserved domains have been detected | |
| | | | MEISRSYINTTDVVDFGVDKRFFKF PVSGLLATEGIVPNGPQCAIINALED PRHRFVTACVSRRVGKSFIAYTLGF LKLLEPNVKVLVVAPNYSLANIGWA QIKGLIKKYGLQTERENAKDKEIELA NGSLFKLASAAQADSAVGRSYDFII FDEAAISDVGGDAFDIQLRPTLDKP NSKALFISTPRGGNWFKRFYEQGF REDLPQWVSIHGTYRDNPRVSLADI EEARKTVSKNYFKQEYEADFSVFE GQIYDTFSVSEHVQDLAGMGHFFA ADHEFETILGIDVGYRDPTAVLTIKY HYDQDVYYILEEYQQAEKTTAQHA MYIQHCIDRYNVDRIFVDSAAAQFR QDLAYEHEISSAPAKKSVLDGLACL AALFQQGKIVDASCTALIHALQNYK WDFQEGEEKLSREKPRHDANSHL CDALRYGIYSISRGK | 438 | Terminase, large subunit [Enterobacteria phage EPS7] | YP_001837088.1 | 0,0 (393/438) | terminase large subunit | Terminase_6, terminase-like family | pfam03237 | 2e-24 |
| 14 | 9970 | 10452 | LASNVKYKRDAISIMRDGIKAQYKR GNCCAICDSQENLELHHYSTVALLV KNFAKEFQLDFTDSEVVLSNRDKF YKHYWHELVEDTVTLCVFHHQTLH KVYTKEPPLFSANKQKIWVEKQRE RCMNPEAPRTSNTGERSGFAKWL PTDVKTEKSGFARFL | 160 | Hypothetical protein T5.153 [Enterobacteria phage T5] | YP_001837081.1 | 6e-53 (95/145) | No putative conserved domains have been detected | |
| 15 | 10452 | 11663 | MAIRDWLVTKLNRGQRIIRDLEDVS HRTNVKPFTTGKAYSSIEILNRSAN MVIDSAAECSYTVGEQYKTITTYGTI RSKTLETLLNVRPNPYMDSSTFRRL IVSDLLFEGCAYIHWDGSSLYHLPA ALMEYKADDKKFVNKFVFNNMIDY RVDEIIFIKDNGQNGGINSQITGQSR VATVINSLTKREKMLEFKEKFLDNG TVIGLILETDEILNKKLRERKQEELQ | 403 | Portal protein [Enterobacteria phage EPS7] | YP_001837086.1 | 0,0 (314/396) | portal protein | Phage portal protein | pfam04860 | 3e-23 |

Fig 2C

| | | | | | | | | | |
|---|---|---|---|---|---|---|---|---|---|
| 16 | 11660 | 12379 | 20 | LDYNPSTGQSTVLILDGGMKAKPY SQISSFKDLDFENDIARFNKDVCIAL GVPQLLIDGGNNANIRPNIELFYYM TIVPMLNKVCSSLTFFGFKVTPNT KDVVALTPDKEKEAKFVTALVNNGI LTGNEGRIELGYEELADEGMKKIRI PANVAGSATGVSGQEGGAPNKDE EKQ MIDYKALKALFPNGLPEAHNVFATV KAHLTYQILRKEYGYAATNSKTWD QFKEAYAEATKPVPVASVSITGAPA SLDYTKTVQLAATVLPTNADNKTVT WKTSDATLATVSSTGLVTALSKAGT VKITATAGGKSSEVSIQVKAPVVAV TGVTMSPKTITIEAGKTGKLTGTVA PANATNKSVTYTSADTTKATVAAD GTVTVPANLAADSTVTVTVKTADGN KTDTAIVTVKVPTAGV | 239 | Ig-like virion protein [Serratia phage KSP90] | BAH15178.1 | 8e-21 (84/186) | Ig-like virion protein | Bacterial surface proteins containing Ig-like domains | COG549 2 | 7e-07 |
| 17 | 12576 | 13172 | 21 | MQNINLNAEIKSVKAVGEGDNPPLK IKGYANTITKDRAGDVILSEAWTTS NALKNFMKNPIMLFGHNHSRPIGKI LDLVPTESGLMVEGEVSAADLQIYS LIRDEVLKTFSVGFYIKDAEWDDMT ETFIIKDLELLEISVVSVPCNQDSTF SLSKSVNHNDYMELRKSFYKSSQV QPVEQPELSNLEKFLVAAGYAKG | 198 | Putative prohead protease [Enterobacteria phage T5] | YP_006978.1 | 4e-60 (117/196) | prohead protease | Peptidase_U 35, caudovirus prohead protease | pfam045 86 | 2e-25 |
| 18 | 13186 | 14568 | 22 | MSYDIAQLSKDLGLGDIAEQLKGLT ASQKAEEAARKFAAEQEAKELKRME DLVAKATGEDRKNLAEALELVKNLD EKSKQSAEAFVKAMNSQQEEITGL KEEIKSLLAARENGRSFVADGVAKA MFGKQEDFEDEVEKLVLLSYMQK DVFGTKRGEAHLKAVNGSSSIEVST EAYETIFSLRILRDIQAKLIIGTMFEE LPMSSKLLTMMVEPEAGEASWVDA STYGTPATVGAEDKTKLSEITFKTY KLAAKAYMTDETEEDAIFTLPIMRR RLIEAHAIAIEKAFLTGTGAAGTPKG LIQFAKDDGKVVATTAKADGSVKVT AKEIHKLRRSLGRHGLDLNKLALVV SMDAYYDLIEDEEFQDVAQVTATTA IKLQGGVGRIYGLPVLVSEFFPAKA ASAEFCVVVYRDNFIVPRQRAITVE KERQAERQRDAYYYTQRLNLMRFF ENGVVAGAYAA | 460 | Major head protein precursor [Enterobacteria phage EPS7] | YP_001837083. 1 | 0,0 (325/460) | major head protein precursor | No putative conserved domains have been detected | | |
| 19 | 14627 | 15139 | 23 | MQFMTDSDWRTYGGLKRPDLESNI PMLIKAANALLTQLLGIDDTANVUDV LPTKPARKKYFLSSPVPSTITKITIND | 170 | Hypothetical protein T5.148 [Enterobacteria | YP_006976.1 | 3e-55 (115/170) | | No putative conserved domains have been detected | | |

Fig 2D

| | | | | | | |
|---|---|---|---|---|---|---|
| 20 | 15139 | 15900 | QEIDKSQYKNYPDGTLLLKFSPPEG YMEVEFTQTGFTSIPDDLVLAACFL VDHWVKKDYRESRTFGGETVTFNT TKSGVPEHIRTIIEVYRRL | | | |
| | | 24 | VALGDLARGIVKEQLDIMSGGSHST KNTVIYSAETMDNHKDGTIGKVSFR FTKPVSEDLLNVRTSSILKAVSSSLN LEGDVGVIDNLLNSITGKKSKIGRKR STGRVEVNFGDPSDADNGYAGAIS GASGRFVSNTNLRALLELVAKEYLV KDMKKAGAPLKFRTGRFANSLKIKD VLLREDAGAKTPDLNITYNYMLKPY SVFNPAVSTYRGLSLRPFPGARNP QKLIGEAIAKAARDLIHSRYRIRVNQ GT | 253 | Hypothetical protein T5.147 [Enterobacteria phage T5] | YP_006975.1 | 1e-106 (185/256) | No putative conserved domains have been detected |
| 21 | 15900 | 16385 | MNYRTSIADALVERLKKDMDGSNP TEFFTNMYGNVSRQTYSFEQINEF PYIAVHVGTETGNYLPSAQQWVYL EIPILLYDKEKDDINMQLEKLIADVKT SIDTGGNLQYTIMKPDGSTIDSEAT DMQITSVSTDEGILSPFGFAGVNVT VRYMPLRRALDR | 161 | Hypothetical protein T5.146 [Enterobacteria phage T5] | YP_006974.1 | 8e-66 (113/161) | No putative conserved domains have been detected |
| 22 | 16409 | 17536 | MSVQLLRNTRIFVSTVTTGFTKANT QEILVQDDVSWSQDSNSTDITLNEA GPKPTRGSQRFNDSLNAAEWSFST YILPYDDAGKQILPDYILWHGLATG AAVNLAGTTGVFQNATNLVVNFKD NGYHELAMLNIYILTDSSWSVIRNC QVGQAEVNVDIDDIGRVTWSGNGT RLETLASQPFDPKTIGDDALYAKIQ SSYIKNKLTILKLKNNATGGKTYNIPI TGGSFTMNNNVTYLTPNIMSRVDV PIGSFTGSFELTGSLTAYMNDAANG SIQLYKDLVSDLKAVNDFEVAIILGG EYDTARPAAVLVAKHANLNIPSIETD DVLGVSIEFKAIPTQMDAGDEGYLG FSSKYTKTSIAKLISSGDGNPVTP | 375 | Major tail protein [Enterobacteria phage EPS7] | YP_001837079.1 | 9e-164 (276/377) | major tail protein |
| 23 | 17546 | 18433 | MLYSLMRESRVVIEYDGRAYGFDA LSDYTAGTSYEEFKANRRTIHRRSN YAYSKITAQSPSSISLTLNFSSNALE GLFFELMGFIEIDGMYQMPLFSNNI EPKMFSVYIINKNTSLRFDNCFATT CDFSLDKSVPVLNVGIESGYFEEVG HPLNSYTLDQGEVLPFSLPQVSSN GRVLPGLMSAGMSFQQQCEWRG DRSLFDINKIYNNRRAIVNELNSSAL ISMYYAKSLQIDSTHNIKPDIGLPVQI RNKYNVDFPSTRITKRLDLTDVYKI | 295 | Minor tail protein gp24 [Enterobacteria phage BF23] | BAA02256.1 | 6e-95 (171/296) | No putative conserved domains have been detected minor tail protein |

Fig 2E

| | | | | DYDVIPTEQSDPVRIKLIGE | | | | | |
|---|---|---|---|---|---|---|---|---|---|
| 24 | 18437 | 18859 | 28 | MSINLKDIALDTKQITAYPGLPHFKL KYNYVSRKLSKKILEAAQENQFVNG IAVKVQNDDKFAEEFVKVAIAGWEG LTVADVEKLMLIEVPEDRLEDKVEF SIDNAMMLVRNSSAFETWMNSTVF HLDTFRGSKSEPTA | 140 | Hypothetical protein AGC_0154 [Enterobacteria phage EPS7] | YP_001837077.1 | 5e-42 (79/134) | No putative conserved domains have been detected |
| 25 | 18933 | 19259 | 29 | MCESLGEEPNPEVLKRFVEIHDFPE IAQTALTIYNNLSDNYIPGDYPTYLG KDKSALLVFFDIYGVEDADEKSLILQ IINIFDSHAVAASRKRVEAAIKKSKM KSSSR | 108 | Hypothetical protein AGC_0153 [Enterobacteria phage EPS7] | YP_001837076.1 | 2e-25 (56/95) | No putative conserved domains have been detected |
| 26 | 19343 | 24421 | 30 | MTDRLIRELLVDIKQRGGSKAAKQI RDVEAALDGAAQSSEGLNTSLGKL PGSFTALERSVSRTAKSLEKLSSTT SITALAASIGMLSGKFTSFEVDLAKS VLKINANLNGVTSAANKMASGFDTA ATSSVADLNRYNKALQELDAHASS VAKVLQTLKAGAGLESISSSAAKAS TDLSHLVSGVEKIGNQLARMAEQA VLAGRSLQGLKADSLGAAGEHLSK AASGISVAVSSMGEEVNKLNKILLE LAVKADLASKSIANIAPGTKLNSLGT EIQKINTSLATAANTSVAEISKIKAAL TSLVSSTATAAASMKTVGTGSGLS KLISEISAATSASTSDISKVTAALKQL NVDATAAGKALQSIKAGANLSSVPT VVGKIGTSMTQLRAQLEGSYTGIEK SLNDLSRAFATMGGTGNLNPLGNS IRGMIPSLTQLAKAAVQVNSALSKIQ AGRGVLQLPTQFKAVTASLNALETK LASTSQILERGFSKGFQDMASKSTS SSTRMINNFQKVVPELNAIEAAAIRS AAAIDKLIAKRIRLGQAGGGNPAA FNMGALVAEMNRIVTSIEAMGNKM NTTMADMARSTDKVSDKLTDLNSG VRDVNTGLGGLNSTLTGTGSAANR ASRALGNTSGSARGATRNFAALAM VTGPMPLIYGAIASNVVYLKAAFDQ LKLGDQLNRLEQFGSIVGAKTGTPI QSLAVALQEATGHAVSFEEAMRQA STAAAYGFDAKQISEFALVARRAAA TLGVDMTDALNRVIKGVSKQEIELL DELGVTIRLNDAYAEYYIKLNAANT GITYNIQGLTSFQKQQAYANAVVAE STKRFGYLDEVLRATPWEQFAANA DSALRKVQQAAAKYLGPVIASINAA FYTSKASVSAEAATAQQESKQMD | 1692 | Pore-forming tail tip protein Pb2 [Enterobacteria phage T5] | YP_006968.1 | 0,0 (626/1196) | pore-forming tail tip protein | SMC_N, RecF/RecN/S MC N terminal domain | pfam024 63 | 4e-05 |

Fig 2F

| | | | | | | | |
|---|---|---|---|---|---|---|---|
| 27 | 24536 | | GKDSNAVVMNLEASQKGLDDAVKA KEEVKNKLAALNKEIMDREAKMDM STALATAANYSGFGNLLTLGASKAN KEFTQQTADMRRQAYMLQQELAD SAGAIQKWKDARDSALSKAQKENP ELAGKLNIGQNVEASNGLYTFDNAA LDGAVALRKEFNNIKKTSGDLSNDI QNFAQDSNTASRATAALGDALKAV ESLAGGSTEKANQMTKDLNLGYST VTEMNTAYKAMSNYQKIVNDEAKS KLDVEKRIAEVYAATRNKDKAEEAG RALEMQQLSAKKEALKAVLATNKD NKAIQKELTLLETEELKVKNQGMEA TKKEKFYKDKIVGIDREIALLNNRTM TDSQYNVANLKLNLQVEKDRLALLK TQADKEKEAEQSRRNIASIEREIWK EQLDRNAKTAEMRKEEFERNQSM KPLMGESQKMQEQLAFYQEMKEF TKGNADEQARWSKEIANTTAQMAA LKAQRTAQMMDRVGQSLGADYTP TTGLEGEDKKFADMENQMASYDTA IGKLSQLNSEATATAQSMGNLANA MIQFSQGSLDTTSMIAAGMQTVSQ MISYGTNQQISAIDAAIAAEQKRDG KSEQSKNIKIKKMEAEKIKLQQESAK KQIIIQTAVAVMQAATAVPYPFSIPL MIAAGLAGALSLAQASSATGMTDIA GSGGETASYLTLGERQKNVDVSM GANAGELSYVRGDKGIGSANGFIP RAEGGNTYPGVSYKMGEHGTEVA TPMVPTKVTPADKVASETSSGGAR RPVNLNIQAMDAKSFMEYALENPA AFQAAVELALNEQGLSLKNLN | | | | |
| 27 | 25150 | 31 | MRLPDPFTHPQYNGLGFDKATLID NDPVIRDELPNGKVNEVKTATQYW GLNISYPVMFPDEYAVLSSAILEYK RTRGYLDDVILPHYESYRVRGDANN CRIAAGQKGSTLVITNTNSLSGEPK PGDLFQLTTHPKVYKITSFKNVAGV WTLNLYPDLLLTTNGSERPRFNGIL FQTKLMNGDSFSEEITVDGVYDGV NLVLRESL | 204 | Hypothetical protein T5.139 [Enterobacteria phage T5] | YP_006967.1 | 6e-76 (130/204) | No putative conserved domains have been detected |
| 28 | 25147 27993 | 32 | MRQILPSAKAYLANNDKIRLAYLVSI ELPGSTGNNAVYAYMTDYMRDINY GGILFQSGKIKTISSHKQNRTLTVGS LSFSVTGTDANEVIKLVQSGVSFLD RSISIYQAIIDDNGEILPVDPDTNGPL LFFRGKIVGGGIKESNTVSGVGTSV | 948 | Tail protein Pb3 [Enterobacteria phage EPS7] | YP_001837072.1 | 0.0 (681/949) | tail protein |

Fig 2G

| | | | | | | | |
|---|---|---|---|---|---|---|---|
| 29 | 27994 | 38385 | 33 | ITWNCSNEFYDFERVAGRFTDDAS HRGLEIVNGELLPSHGAKRPEYQE DYGFFHANKSVNFLAKYQVKEERY KLESKKKLFGLSKSYSLKKYYETVT KEVDLDFNLAAKFIPVVYGTQKVPG IPVFADTERNNPNVVYVVAFCEGE IEGFLDFQFGDAPMICTDQTDSTSR TCFGQKRVSGDTMARISTGLPSTS LSTHGQEYKYNDGNGDIRIWTFHG KPDQTVATVLRDIAAANNFFLQGEN GNGPEYWDSRYKLLDTAYAVIRFTI TENRTDIPEVSAELSGRKVKVYQAD GSVKMDKTSQNGVWQTFDYLTST TFGASIPIDRMVIGDWRKEADLLNII DTSYQTSWQPFWRVVGWESWTA ENRQIMQMNTILDNSNSVFKNVQE LLESFQGALNNLSGIFRITVEKDSKT PLELNFLDTYGDLDLSDTTGRNKYN SVQASLIDPTLNWKTNSITFYNSKF KNEDRGVDKKLQLSFANITNYYTAR SLADRELKKSRYSRSLSFSLPYKFL GIEPNDPVVFTYDRYGWNKKFFLV DEVENTRDGKINVTLQEYGEDVFIN STQVDNSSEAVPEISNNVLPPRDFK YTPTPGGMVGDVGKNGELSWLPS LTPNVVYYSIRKSDRVDPYIVCQTA FTPNVRMFQDIVGEPAGLTIFEIRAV DINGRRSSPVTISVDLNSAKNLSMV ENFRVLNLAPDPAEWVGPDLELGW DKLQEEGLISGIFYTLEIRDNTNKLL RSAKITSLYNYSLLGYNKLDYKAN NSNTLGIYRALQPRIQAEGPKGEKS VAWAYI MISNIAPAKMVLQNIVTGYTIASIQH SIFSDYDVIGRTFWLLTGGVTTRRD FTGVDTFIATINNLIAGATYSAQGAF YDSMVDAELMAAKVGMNLSSTINF KMKTAPKITKVSSFAESVDVGVGAP MVVVELSGEAEYVTIEMKPEGSST WTKYYRGPITEQIIFGGVPVGRYNI RVSGVVTMPDGVTVDVSGYDTWP SLFNLTYNFTPPSAPTNLRFKTAHI QDGMERFDVRLEWDWTRGTGAN VREFIIQYISNDEFAKTGWTKANKL NVGAAKAGTITSFPYKIRHRFRVLS VAWGPDTQSITNSNEVTYIIDESTTF DNAFINETGVEMTYAGIKGKLWNS NTKQWEQTFLVDAATGAVVLGTLD | 346 3 | Tail protein Pb4 [Bacteriophage T5] | AAP75894.1 | 0,0 (338/580 )675 | tail protein | Collagen triple helix repeat (20 copies) | pfam013 91 | 2e-05 |

Fig 2H

| |
|---|
| ENGKAPISFDPVNKIVNVDGKVITK |
| DINAANVILTNLTGKDNPAIFTQGKK |
| YGNNAGGVWMGVDNVDGKAKFDL |
| GNNTQYVRWDGDTLRISGNVVIGT |
| PGGDVDLETGMQGKQTVFAYKLG |
| TSLPSRPLDQVYPPAGWSAFPPNR |
| TAQNQNVVVVQGTLDPKKSPPALV |
| DGTNYSAASQWSGVPGTGGTDGS |
| NGDYTVCIYQISASKPTKPGNIINDP |
| SGWSRTPPTGTPLWMCSGRFNGD |
| TNALTVEGWSDPIRVDGEKGATGA |
| TGATGPQGPQGPAGGSVEVQWSK |
| DGTTNWIHANFTTGDIYMRQRVGT |
| GGWSSAIRAVGEDGTNGTPGSKG |
| NYIGMRFRVAAEKPATPTGQTPSG |
| WSDAPPQGNPLWMVKAEFNGQTN |
| ALVGTWSEPVRIDGEGIGVNLYPVK |
| KTLDQWTGMSNGTMVKNPDTLSF |
| TITNTESTTSSTGPGAHPVPFQGSQ |
| GPIVEIPVKPNTAYIFTYEVSTDSTS |
| FVLRDLLEFSSITGSFTNFQELLTG |
| AKGKQEAKIVTRADTKFLSFRPGVR |
| TAGATVTYSNLKLEEGIKATAYSVE |
| ASDSIGEKGDQGTQGPQGPQGNQ |
| GPQGNQGPQGAKGDNAKGFSLSS |
| LGQTFTYDAEGKLKSDATILFQAFR |
| QNTTANVTWSAKDEKGGNITLTST |
| SNTGATLTAANFKTSKSVVVTAVCD |
| GITDQITIVRLDDGSNALVGLLTNEG |
| STVLANYAGYVQNYSTGSGDFKVF |
| YGAKDITSECTFSTMEKNNLDADIT |
| SAGKYTLKGMPAGTDVINGWWDLR |
| AVHPTYGAVRRVATTKSILAKGYD |
| RVITTSFENGNKGTWSTGSVQGVS |
| GATIVAAGFSKALVISARDCIEDANA |
| FPVVAGGQKYRLGMWIMASESKVNI |
| NMGVRIVRAADGVVDWQGTLMIA |
| QGTVVPGGWSYIEKEFTVGSSNTG |
| IAMPWIQMAGSSSGSDLGKAYYTDIH |
| IFALEMDGEKGDTGATGATGSQGP |
| QGPQGNKGDKGDTGATGAQGPA |
| GSSVNVQWSKDGSTNWHAGFQP |
| GDIFMRQQVNGVWGSAIRAVGED |
| GKNGADGTDGDYISMKFIVQDTKP |
| GTPTGNNPGSWSDAPPVGSPLWM |
| TKGTMNASGQLQGTWSNPVRLDG |
| TINPNLFAVRKVWMAGMTGTEAGTS |
| KNDIEKLAHTLTRTSGTDNTAPGCY |

Fig 2I

Fig 2J

```
ATPYLGSGAFSHPVTPGKRYTLTY
NIDAASEVQTRDTIFWQANPDSGQ
STYIEELNTGTSIKVKRTFVVPTGM
NYLTLRPSALTLNVATTWSKIKLEE
GGEKTEYQVEYSDSIGIVGKSVLVQ
WSKDSSSSNWHDTFQTGDLFMRQ
NVDGVWGPAIRAIGEKGEIGPDGK
KGNYTNIIFRISDTKPAKPTGNKPTD
WFDAPPDGSPLWMATATFNGDTN
AIIGAWSDPVRIDASGVGENFLAFK
EWMMSIQRAEGTGSSVSKNPDQM
RFRVTAGPSRNDAYTTPYQGTGTH
FIEVSPNTVYTLSFEMETAVSTRMM
LLQFDNGNGGTHARNNQVISTSTGI
NSLTITTGANTTHLSMRMSISNMGE
TNVLMKPKLELGAFPTAYVAHPSDL
LGKDGATGATGPQGPQGNTGATG
ATGPQGSKGDTGATGPQGPQGPK
GNAGENAKGFALTSDYQSFVYDTV
GDIKSATTILFKGLKQNTTAGITWSA
VNNTGAAVTLMNSGDNRQLTAANF
GASKWVTITATCDGLSDQITVVRLQ
DGENVLTAVMTNEAATVLANYSGY
CQSYENAKGQMRVWYGSTDVTGQ
CTFSEGGRSNVTPSINSANGNYSV
TGMLDGTDITEGWVDVKATHPKYG
AITKRFAVTKVFLAKSYEMVTNTFE
NGNKGSWAGALQSVSGPTNQSISK
ALRITARDNLEGRNTIPVAGGQKVR
IRFWYNPLGLEEAIFRVGFIVHRKD
GGKGYPSRTVVTGPAPNSSWAYF
DQELTLSANDEGIAWPWFQLDNKT
SGSSLGYMLVADIHFEDLSMDGAD
GATGPQGPQGNTGATGPQGNKGD
TGPQGPQGPAGASVGVQWSKTGN
ASDWHTNYATGDIYMRQQVNGVW
SSAIRAVGEDGRVGADGKYTSLRF
QVAATKPARPTGNSPANWSDSPP
EGSPLWMVKGEFDSSNQLQGTWS
DPVRLDGETVNLNLFANKAWIASIT
GASGSGSVVAKNPDELRLRITAGS
GATDAYTMPSGGDGTFFTKVTAGK
RYTMSFDTDSALEMRMHVFFIQAG
ANTTTSSFSWIASTTAGRTSWSFTV
PAGCDRVSVRVSLNNNPGGTNVV
SNIKLEEGDFATAFIRNELDTIGADG
SQGPQGPQGSKGDKGDTGATGPQ
GPQGPNGTSAKAFALTSDSLSFSF
```

| | | | | | | | |
|---|---|---|---|---|---|---|---|
| 30 | 38389 | | DTSGNLKSNGTIKIDSWRQNTTAAI TWTAKNQAGSNITLGGTATNKTITS AQFGSSEVVTVTATCDGITDSITIVR LQDGVNSLVGYLTNEAANLSCNSY GFVQNWDGTTGNFKVFYGTVDVT SQCTFGVEDKSNLNGNIGSSGYYA PSAMPNGLEITSGWVDYKATHPKY GTLIKRFTLKKSLPGIGYDRVFTGSF DSGNNGSWGRTVVDIATGSPGGH TKAIQCTSRDTMESSNWFPTRKGM RYRVTAWVNNSEGEYQLRLGLHT QNSSGSVNTGYPTMLAASAKDSEG WKLVTGIVTVGDGSTAETGRARPFI QMNGSASPFGNAYVAAIAIEDLSM DGADGATGPQGPQGNTGATGPQG DKGDTGPQGPQGPAGNSVNVQW SKDGSTNWHSTFTSGDLYMRQQV NGSWGPAIRAVGENGANGTPGSK GNYVSMKFAVMASTPSRPSGSNP AGWSDSPPPGNPLWMIKAEFNGE TNAIIGNWSDPIRLDGDSINENLFYF KAWILDSITGVAGNGSSIGKNYELLR ARIIAGTGVTDAYTLPSDGSASMFT YLPPSTTYTMSFETDNAVEVRCHV FWYAKGSNTTGGVLKTIASTTAGLS SFTFTTPANSDRISVRFSVNESGGN NVVGRCKIEKGAFVTSYVRNGYDA VGDRGPGFEYTQAITNLTGWNDTQA ASFFQSTFGGPPVKYDVLTQYKSG SPQNSWTRQWNGSAWTAPALTVH GDMIVSGSITADKIIANNAFLAQIGV DILYNRAAALSSNPEGTYTMKIDLA NGYIHIR | | | | |
| 30 | 38808 | 34 | MSTENRVVDIILDQNVSYGLMLQFM DIDDSAYPATETPVNLTGVTLKSSIK DSLESTGVKLADFVVTVVNATQGQ ASLGLTAATVATIVSKASKERDKYN PRLRFAGYYDVIMTKGTGATATSY RVMEGSYVVSDGVTA | 139 | 15kDa minor tail protein [Enterobacteria phage T5] | AAU05271.1 | 3e-43 (82/139) | minor tail protein |
| 31 | 40847 | 35 | MAITTRIIAQQVTALDGANSRVSKY PKFTVQLGYSVSSLAATELLDAATR SAASAAAKTSETNAKASETASKN SQTAAKTSETNAASAQVAQNLAG KASLVTPLGVMTGSAEAKIASITIAA NQSSSVHVLFALYATGNGANRDDI YNMEIVSLALPGPVTSVTADNIGSF LSHRVIGPANTNGFMVGLKSTIEGS NVTYDVYLKSRSSFRDPKMAFLSG | 679 | Hypothetical protein ACICU_01051 [Acinetobacter baumannii ACICU] | YP_001845710.1 | 1e-19 (54/139) | No putative conserved domains have been detected |
| | | | | | | | No putative conserved domains have been detected |

Fig 2K

| | | | Sequence | | | | | | | |
|---|---|---|---|---|---|---|---|---|---|---|
| | | | SISVTPPTGPLVDGTSPAWKTTGFD TDVIYVNRAQVIDDGISLARIKQLAIT NGKTDSSILLLSYLNETGILSTNKKSI SLRPGGTSDSSIAATEFLPNGNIILP NGDTGNQTISWLGGPRIRVNSNGS FVLSTNNPSNQTSGFITFRPQGDQ VTSTELQIRDDGNIKQTAPQSSAGN ALIRQDAAIQHIMDKAPAAGITANPL SDLNVIPTPEGTDPWGADGVRVFQ SGVSTKNTPDGTTGRLGTILNVRHT QYRIMQFFMQSNATAPILHIRSLRA DQGNTPPAWFKVTEYSKPNIQSDI AGITIDGNGFVKKASPIAKLIAEIPSK EDSFFWTGVETVGGYVGCNAEAQ GVFAVKTGLGKYTIKGSLGWNTEG WKFELPRDDNGNMLCFVESDWNE EEKELNIQVFTRKFDINTGNIIAGEP MEIPQGRWIDLRLEMPKVEIPEVEF PEDPEV | | Putative phage tail protein [Enterobacteria phage EPS7] | YP_001837069.1 | 3e-09 (53/105) | phage tail protein | | | |
| 32 | 40892 | 36 | MRIKLSHPDCKPHVGSSEAAGMDL RAYFGDRASDLLRAIPPGESLMIDT GVAVEIPEGWVGIVVPRSSLGKRRL MIANTTGVIDSDYRGTIKMNLLNMS NETQPIDNFERLCQLVIVPHYNPNDI EIVDSLTDTDRGEGGFGSSGKM | | Putative deoxyUTP pyrophosphatase [Enterobacteria phage EPS7] | YP_001837067.1 | 6e-52 (100/140) | deoxyUTP pyro-phosphatase | Deoxyuridine 5'-triphosphate nucleotido-hydrolase (dut) | TIGR00576 | 9e-43 |
| 33 | 42213 | 37 | MSKSWGTMKREAEQRLASRRNLM IVDGTNLGFRFKKDSGKPIAASFAN TINSLANSYDAKHTIVLGDKGKSIFR TNIFPEYKGNRDAKYADRSEAEVE ADRQFFEYLDDAFIIQLIGHHYDHIWLI RGVEADDMAAFIIOLIGHHYDHIWLI STDGDWDTLLAPNISRFSFTTRKEY HEKDMFDNHNVDTVDQFISLKAIM GDMGDNIRGVEGIGEKRGYNLIRE HGSVLDIIDALPLPGTOKFVQALNK SGELMERNLTLVDLPSFCGEAVAA AGODIYDQFVKDTAIATGEV | 292 | Flap endonuclease [Enterobacteria phage T5] | YP_006958.1 | 1e-118 (203/289) | flap endonuclease | 5'-3' exonuclease | TIGR00593 | 5e-48 |
| 34 | 42692 | 38 | MAVDSREKGKRAEYQIRDMLRKYT SLDWERVPCSGAFGCOSHSLKGDV YLPPSVGKMSQYCFEIKHYADEKF NSNILNVGESQLEKWWAQAAREG EQMNMKPALIFKKDRGQWLIALDS SDPMIDNLMSRAHFIVNKRGMEIVI GLFEPWLNACEIGDLVK | 160 | D14 protein [Enterobacteria phage T5] | YP_006957.1 | 2e-68 (118/160) | | No putative conserved domains have been detected | | |

Fig 2L

| 35 | 44527 | 42692 | 39 | MSIVINKLTISHFMSYAENVVIEFDN HRVTQLIGRNGLGKSTIGTALEELL YNKNSRGIKKDDLFNWHTGSKAYT LEGQFTKDGDVVNVKKVVKSTAKV TLTKNGEDISGHTATQTYKLIEEVLA CDFTFTKLVYQSVGSSLDFLKTTD AQRKTFLVNLFDQEQYKEVSERVK AGRKAVSAKLSGLEGSLRTAQSILS SKASLGAPQSEIPIPVFDEEPLVEEL TEAKVKVALAQKQKASIAKRSSLDM AVQAAEKTFAFFENLPAPTSKSEEL LSVTRNLTVVATRADDLKKRYYDFK NAAGKTQCSACGTHLDTSAAQEA MRRTKEEYDPLYKERQKLEAEVEE LRKEDRAFKDYISKFNALEQARKNL KEFDEVNGTQDEIVDASGLAERIKAI ESSIRQGRSSVELARTHNESVVRE NAKYEAKREQIQKAEQEFDKIQAEL SLVAEEVADLDILITGLKDLVGYKLE HSVKVFEEMINHYLSIMTSGKFALG FELDETKLQVVIYNDGNRTSMVNC STGQQSRINISTLLAIRMLLSTISKVN INLLFLDEVVSYIDPDGINTLVELLQE EDQLNSIIVSHGHTHPYAHKIEVKQ DEAGLSILEA | 611 | Probable exonuclease subunit 2 [Enterobacteria phage EPS7] | YP_001837064.1 | 0.0 (377/598) | DNA replication, recombination and repair | SbcC, ATPase involved in DNA repair | COG0419 | 2e-12 |
| 36 | 45503 | 44511 | 40 | MKILFSADHHIKLGAKNVPQEWQK NRFILLGEKLDEVFGATGCDLHIIGG DIMDVSDPSSEEVELLFAFLATLQH PGIIYTGNHEMKSKTISCLDHYAAAI SDATDGLWKVVKDYRSPEFDIIPYS SLHKASWKPRVSDICFTHVRGAIPP HVVPEIYLERFVEHGYSKVFAGDLH SYKNSQKIGDVDLLYPGSPLTTSFH RERTKGTNGAFIIDTVLPRDHEHYL SWIELGDLPQLIRKTIEVGEPMEAD AYDRVIYEVTGDVSQLKTLKNSELL DKKINNRVTKDAKLDLDDMSLLQEL DTYFTNVQKLDEASRTRILKRAAEY VDSN | 330 | Putative recombination endonuclease, subunit D12 [Enterobacteria phage T5] | YP_006955.1 | 1e-121 (216/328) | DNA replication, recombination and repair | Exonuclease SbcD | TIGR00619 | 4e-05 |
| 37 | 46316 | 45543 | 41 | MATKSWGSTTGGSNGDKLDYMKF NNGKNVVRIVSGVLPRYVYWIQNK EGKPAPFECLRFDREKERFIRGAS DPVHDMGFKDPEKKDGKAQPLRP KKNYLAYVIDRTDNKLKLMEVKATIL TGIHSIMAQLNLEDPGEIDITSKSGT GFDTKYDVQQIAAMQFQMAKNQP GSKEAALHEADVALIGEALYNEADE FEGFEKVPKLDVTYPVPSYDEQKK | 257 | D11 protein [Enterobacteria phage T5] | YP_006954.1 | 1e-88 (161/256) | | | No putative conserved domains have been detected | |

Fig 2M

| | | | | | | | | |
|---|---|---|---|---|---|---|---|---|
| 38 | 46672 | 46319 | 42 | AIQAWLEGKKDEEGDESKGNEGSA NSGNIDHEAASDLD | | | | |
| | | | | MLFVDYEKIYILARGNSSLIVQIIRRM VEDPEAHVMLTGRSFILNEDTIVVN KRKLSDRQLAEYLGLLSFRNYAEYS FSKDTSLDMQYIPPWVPRAVIEHHP LIAINKSKLTFIEEN | 117 | Hypothetical protein AGC_0138 [Enterobacteria phage EPS7] | YP_001837061.1 | 5e-40 (78/116) | | No putative conserved domains have been detected | |
| 39 | 48232 | 46874 | 43 | MKIVISNKIYCKPSNELWEYLLKHTS YQIFKPGAKYPLMFQNSGSVGKEIK WFPVTRLDLLESFGQKVTEIVDKRT LVPMDIPKPSFTLRPGDQLPIYEDC NDTCIINGKPGFGKTILALAIAHKLG QKTLVICTNTTIRAMWEKEVRKFFG IEPGVIGSGKFNIDSPIVISNIQTVNK HGAALAKEFGTVIVDEVHHCVATTF TKFLEQSSARYKIGLSGTLKRKDGL QVMFKDYFGTKVYSPPVNNTMPPT IHRFALKTQVSGNMNVPWAIRAND VYSQPEYFQQVVDLCELYSMAGHK VLFVSDRIDLIERVTNALELRGVKTY TITGVTSLDDREQVQIDVTNDGPCV LAASQSIFSEGVSLNALSCLVLGSLI NNESLIEQLAGRVQRMADDKLDPIL VDLKLGGVGFKQAAGREAVYRLNG WEVLDFNEKNMANLDKILFAKNPK V | 452 | Putative ATP-dependent helicase [Enterobacteria phage EPS7] | YP_001837060.1 | 0,0 (304/448) | ATP-dependent helicase | SSL2, DNA or RNA helicases of superfamily II | COG1061 | 4e-30 |
| 40 | 48726 | 46874 | 44 | VLNFSLPVYALRAYDVLFQEGEYIVI QTRFTRYVLDNPSLPGTFSQRRLFL YGERENLPYKLYPLKKQFKYLSQIIN SGLKHFIDSTGKIVTWKPTTYYNIT ERVRGSTRIFNGKYQCYVKNVPYP FLLSEPANYISYALVRGSPVIFDTHE EEPETPRLRVKI | 165 | Hypothetical protein T5.123 [Enterobacteria phage T5] | YP_006951.1 | 9e-52 (96/165) | | No putative conserved domains have been detected | | |
| 41 | 51289 | 48719 | 45 | MKIAVVDKSPNNVRYQKHFELFDH EVETFFMASEKVTGRLLKKHTIGTP ENPFNPEDFDYVILVGADPFLKFAA KKGISDYSGKRVEHDGYANWIASIS PAQLHFKPEMKPVFEATVESIHAIL NGREKRSKAGDYRPIQCPDEAEAY VKMVYTMCPGMIAYDSETSALYCR DGYMLGISISHQEYQGVVIDADVITE NTVYYLQKLFDSPEHGVVFHNLKF DMHFYCYHLGLSFDKAAEEKRLHD TMLMHYALDERRGTHGLKSLAMKY TDMGDYDFELDQFKETYCKTHKIK KEDFSYDLIPFDIMWPYAAKDTDAT LRLSNFFLPKVEANPRLKSLYYDVL MPGCVFLQRMEDRGVPISKDRLKE | 856 | DNA polymerase [Enterobacteria phage T5] | YP_006950.1 | 0,0 (663/856) | DNA polymerase | PolA, DNA polymerase I -3'-5' exonuclease and polymerase domains | COG0749 | 6e-84 |

Fig 2N

| | | | | | | | |
|---|---|---|---|---|---|---|---|
| 42 | 52241 | | AGVQLMTALQLAKAKLYEYPEVRK LEEDQGSVFNAASVVQLRKLLFDY VGLTPTGIMTDTGADSTGADALKEL SDQHPIAKTLLEIRKISKLLSTYIEKM LISIDADGCIRTGFHIHMTTSGRLSS SGKLNLQQLPRDESVIKGCIVAPVG YRIIAWDLTTAEIYYAAVLSGDINMQ QVFINMQNDPENYSDFHGSIAHMV FALPCKPTEVKKLYPALRQAAKAIS FGILYGSGPAKVAASVNEALLEEHM KTGKPYTECTTGDAKEYIETYFGRF PQLKKWIDKSHAQIQTNGFIYSHFG RKRRLHNINSEDRGVQGEELRSGF NAIIQSASSDSLLLGAIDTTDNEIRSL GLQDEMKIIMLVHDSVVAIVREDLV DQYNEVILRNIQVDRGISIPGCPIGI DSDSEAGGSRDYSCGKIKKQRPSV ACIEDKEFEEKVRSIIGMEDFDYAAI AANDENHPDHDKYANIKFLPEISKDI VNVRRVLGA | | | | |
| 43 | 51357 | 46 | MSRITELLDLKGIEYRDTGGDILRC LNPDHEDAHPSLRVDPSGVFHCL SCGFGRGIPSIFHYFNEEQYRTSPR LLRVRRMISDLRTEGRSLEIPESAMI FDQDFRGIKAETFKKYFAFQQTED WEGRVVFPITDAVGRNLFFLGRNM DSSAPPKYMIRPKKYSPPIFPVRYN TPALILVEGIFDMLNLEDKGCHNVS CCFGTHQFSLDNIADKFMPFQIAGT THVVIILDNDKSGNEAAKKLAKIJRD KTRIIPIIGNFLLPEGKDPGDLDAEE VDQLIRNVEILIAEHVKI | 294 | Putative DNA replication primase [Enterobacteria phage EPS7] | YP_001837057. 1 | 8e-130 (215/293 ) | DNA replication primase | DnaG, DNA primase (bacterial type) | COG035 8 | 5e-15 |
| 43 | 52238 | 47 | MYNVQAVVLKMLLASDQKQVALET FSRLRKDHFNDAFTAIYQAVQNYYK KHNGMPSLDALMLESNRNARLSQA LTVLANTQIPDVDISHAIHVLESEYT QDLFLNLLETDVLQDITILDQGELLD RVAALHMKLEERVTTTGKVFNADT MRVFKRKEDSMLNLISLGISNEFDA QLGGIARKETLLLGGWRGTGKSIIC SNIQVAQYYNGDIAPYFSIEMPENE VFRRNLAIMAGVSAKAMRNDSLQG IELNKLAKTRAKMFEGGLEVYNDFV SRYTLNEMSDFHDMETMLMQERP LHTPMIIVYDPELSTATIDVELTKLTS KYGDKVTIALLDYINQVRLPDTKTLD MYDWKQQMVVSSTFKSTCQKHNV AGVAPYQIDCQGNARMARGILDSC | 492 | Putative replicative DNA helicase [Enterobacteria phage EPS7] | YP_001837056. 1 | 0.0 (36/492 ) | replicative DNA helicase | DnaB, Replicative DNA helicase | COG030 5 | 3e-08 |

Fig 20

| | | | Sequence | | | | | | |
|---|---|---|---|---|---|---|---|---|---|
| 44 | 53716 | | DMAANLNAAKQNEGHDGAIKFDFV KTRNSEGMTFMPKINWNSLRMDQ TSDLKLEDIRQMEAEFVIPLESDKP KDKPKRKKASDEDTNPTGESSRDL | | | | | | |
| | | 48 | MAKLTWNEEITASLTAKANALNATV ISQEAVANIAAELAAETGKEVTARS VGSKLRKEGFEVQKASDVTKSPWT PGQEDELVAFLNDHPGQYTYAEIA AAVVGGAYTAKQVQGKILSLELTAA VKPTEKAAAVRSFSPDQEAAFINAV ASGASVEAIAAQFERTYKQIRGKAL SLLREGREAMPVQEVSNAKARED VLEGLNIADMTVAEIAEATGKSERG VKSMLSRRGISAKDHDGVAKRAKL DAKSAK | 252 | Putative transcription factor [Enterobacteria phage T5] | AAU05255.1 | 5e-95 (185/240) | transcription factor | No putative conserved domains have been detected | |
| 45 | 55311 | 49 | MKIEIPLNCHSCGSKLDLVNDQLFC RNKSM/CPAQSSKLIENFCSKMKLK GFGPQTIAKLETTKVSELFFLTKEDL VRAVGDKVATKLELELETKLRQDV DFGSVLGSLSIPLIGEVAAKKLSQLY NDFQSVKAEGKAGENLASWKNTP AGQNVINLPWKFSGAREAQVTPAT ESNGWVLCITGKLNDFKNRADATKY LESLGYTVKTSVTKAVNYLICEDET KIGSSSYKKAQSLGIEVLTIKILLENK | 249 | NAD-dependent DNA ligase, subunit B [Enterobacteria phage T5] | YP_006945.1 | 5e-91 (181/254) | NAD-dependent DNA ligase, subunit B | Lig, NAD-dependent DNA ligase (contains BRCT domain type II) | COG027 2 | 3e-30 |
| 46 | 56473 | 50 | MQHVKEFIKLCQDAYYKGMSIISDE EYDALIRRFPLEEEIGPKGDVPHLF RMFSLQKVYPGRGEEVPFQGIETP KLDGCAISLLYIDGKFVSALTRGNG VLGNDVTHNVKLLNIPKRISQKTPV QITGEVHTKEVENMRNFASGAINL KDSGEFLSRIAEGGLMFTAYSIQCE TGKVGLTATFCGDMHILQGDGFVT CLDISSRVDWFPTDGVVRMDGNN QFNAAGWTNKFPRGAYAIKEDDEG EVTTLERVEWQVGASGKVTPVGYF TPVVIDDAVISKATLNNVGYITALDL EIGCQIRVIRSGVIPIRVERVYE | 320 | NAD-dependent DNA ligase subunit A [Enterobacteria phage EPS7] | YP_001837053.1 | 6e-136 (234/323) | NAD-dependent DNA ligase subunit A | LIGANc, Ligase N family | smart00 532 | 3e-56 |
| 47 | 56748 | 51 | MQKITLNAYSSPPLQGQELVLTWLE KEKGKPVVRTMSGFQMLGMMYEK NVLVCELYSPKSKRRVMSTFQAVC ENFYWEGKTQMLFDYYEAK | 91 | No significant similarity found. | | | | No putative conserved domains have been detected | |
| 48 | 56866 | 52 | MKDHEIAQLVNKLTEAAKTYAHTQ QLRAHMSRIVNEALKNAKDNA | 45 | No significant similarity found. | | | | No putative conserved domains have been detected | |
| 49 | 57258 | 53 | MNGNICQDYEGHIDDQSHVIFEDE GRQIRMTVSEFRGNLYFGFRLWLL | 102 | Putative transcriptional | AAU05252.1 | 2e-34 (66/101) | transcriptional co-activator | No putative conserved domains have been detected | |

Fig 2P

| | | | | | | | | |
|---|---|---|---|---|---|---|---|---|
| 50 | 57605 | | | DIEDNWFPTKSGFSFPYTLEMTSTL FRAFTKILSNSEVLHEYYRESQKTQ ASDD | | coactivator p15 [Enterobacteria phage T5] | | |
| 51 | 57309 | 54 | MNKAQVVAICEKHGEFCMQYTKLR TKGVTYLYGTTEFDPKQDKYLAERI VREGLEPADKDHILVFSRSSDKFRY IPIANIKRITSLNQELDRATPVGR | 98 | Hypothetical protein AGC_0128 [Enterobacteria phage EPS7] | YP_001837051.1 | 5e-31 (62/68) | | No putative conserved domains have been detected |
| 52 | 58022 | 55 | MSTPTQWSPELEAELTSAYVAKIEL FPEDERPGVSMEIVAEIAKEHGVSP NGLRMKLSKAGVYVKKEAGKSTAK TGGDAPKAGGRTSKSDAQAELRAA FNDAGLEDGFLDESIVDKLTGKAAS HLAEAIRKITK | 134 | D3 protein [Enterobacteria phage T5] | YP_006941.1 | 5e-45 (92/137) | Arginine decarboxylase | PRK05354 0,008 |
| 53 | 58315 | 56 | VSKYQLLNLFQIYSEGATAIRDLHYA LPMDEAEDNGWLTKYDRGLLKMY RLSPNGLVAVNQILENSVCFAAQ | 72 | No significant similarity found. | | | | |
| 54 | 59003 | 57 | MAIRKKLHANSIPDEKFKEAIQWLE EGKTKKGACEILGVASNSTMERLIE EWKDNQRVSAEMRKKKRGTKIEG AELANVIDSYLSGDSFEAIAERFYR SANMIRMVLSAHGALLRVNGEVDP LFPPAIPEESMKEVFEVGEHVWVP GYQCIGEVKKALDNPVGAYRVYLL SEARQQYVNYMYMWDLASVEHLVAL GVDIKSLGFKWGKEDVAELVNNAV KAALKLEKRGKGE | 231 | D2 protein [Enterobacteria phage T5] | YP_001837048.1 | 6e-82 (152/223) | | No putative conserved domains have been detected |
| 55 | 59320 | 58 | MSKRDARWETRKFPKRDTKARFA KEIELCRVIPIRLAQMPNIYDWLEAQ RKTRLSIRINMELNMGYKSLSEFMH VTFDPTFYENRDCLEAKSVL | 94 | Hypothetical protein AGC_0124 [Enterobacteria phage EPS7] | YP_001837047.1 | 1e-10 (34/74) | | No putative conserved domains have been detected |
| 56 | 62096 | 59 | MFSILEGHAGFSRDPASGNWKEVK TTDYLFAKEFSNEHEPEGKPASMPY KFNVVDTVDPKNLNEAYELMVQLT QDPHLVAVRGTCLVAEKAVRRKRT NFKIDHKSNIIAMDVDGISDTGGCD RFDIVGMGRHVIKLLNSISEDMFPL NAGFIAHASSSAGIKPGIRMHMLLE SNIPVTQGQLKFLFTSLNDSSRQKY GFDIADLAYYSSVQLHYFADPIFRD QFTDPFKAEGKPRLVKVNGARIELP NTMPDYEATRGEFKEEFLSLLNQIK GKRVASEKVEQTIAELEEAEDGVYL RIIPKLYHRALEDGVDFAWLEKEITS ALSDYINTKDNSRSLQDYFNNGRK OALKAFVNNSMRDIPESNVKGVPV HKLTSDSPDGMNYLKINRPPPEGH LTFIKASLGTGKTTAVTKWLERDQL KGNFLAVTNTRALVSSNAKKFEAG | 929 | Putative replication origin binding protein [Enterobacteria phage EPS7] | YP_006936.1 | 0,0 (731/929) | replication origin binding protein / helicase | DEXDc, DEAD-like helicases superfamily | smart00487 3e-05 |

Fig 2Q

| | | | | | | | |
|---|---|---|---|---|---|---|---|
| | | | QYDKSVDMLNFKRGAIDRMSTTIHS IHKFKNFVGQIDVIFIDECDAVMNDL LFAPVVKQRRECISVLREILLSAKVV ILSDGDISAETIEAYGSLIDFDKPVSY YKHHRKMLSDAQAYEFPDESSIWV ALQTSLEMGEKSILVSDCGPDELNE KGLTLRNNTGANVKEIHSNSTSDIDI RRILDYTTNELIEQCIDCLLCSPSVT SGVDFNYFDNVFVITRTANQAPNM RFQAIRRDRGAKNIFYFIDKSTSGF SAGSEQYNIDEGWLELAQQLYVKR RELESRNFISTLRYYLLDDQGATIDIF SESWGKIDSSAAEYTAERVSAILSS TPDWCAPRHADAYEAKLMLVKYFH LDSIKSITQEHAEMWISKKPHKRAE FFHKLQDIFWKDIKKCSNVTISPFIE ALKKHKKDFFIRTGQSANPKYARM YLTQMGINKEMETEQIVDWYRTYC SIEGISVPYEFMTDEEKALADEAQN ELGVRNEQA | | | | |
| 56 | 63090 | 62695 | 60 | VSIPKMERISWADIPKELIDVAENLL RAALRDEELCFIIQHDVCVGLSKGS LAQDYEILFDWDDLSDLGLMLVLVN NVVFHPSNFAAFREPGAGISPGFLV ADEPWTYAPEVLREGKQNASSNSI NIMGWNA | Hypothetical protein T5.107 [Enterobacteria phage T5] | YP_006935.1 | 8e-13 (48/130) | No putative conserved domains have been detected |
| 57 | 63488 | 63087 | 61 | MLVNEKVVNQGVGLVPWAEIPLDV KESLLDHLRVWCDNMEVYFDYDN MHLGLWVPMDEDQDEVLDWGDLT EMGLVFALGYVCLLRESYIPVGVTG VSAGIWVGRNEDYYAPENINGWIQ VLRRFGFQVEGLTK | Hypothetical protein T5.106 [Enterobacteria phage T5] | YP_006934.1 | 2e-13 (43/124) | No putative conserved domains have been detected |
| 58 | 63639 | 63475 | 62 | MYHPDDILLWPNGSWCYRSDVQD MSHLSDDYQVLRADSEQWHEFIQ MGEEYAGQ | Hypothetical protein T5.104 [Enterobacteria phage T5] | YP_006932.1 | 2e-05 (20/44) | No putative conserved domains have been detected |
| 59 | 64405 | 63623 | 63 | VPTFRKGAITPLWDKYKLTEVCNIQ AFDKGFHYLNDPMPPLEALSEGSD DEPSRNLYELTHEFYNMRRQELGT VEPNIAHLRIAEWYERFPGQVVNFT TNVDDLLERAGIPHDDVIHAHGYLT EIMYRRGKDVIVEDIGYTAVDYRKY EWVKPAITFFGETAPWYMGQINLF DTLTTQDLVIVVGASNQVIDFNWEL FPAHSRGTKVWVVNNGINYLEQSL YEERGIPVWYDTAANVFSNKHFIG QVEAWLEEKIYVPSR | Putative Sir2-like protein [Escherichia phage rv5] | YP_002003582.1 | 2e-64 (127/263) | Sir2-like protein | NAD-dependent deacetylase | PRK004 81 | 2e-21 |
| 60 | 64654 | 64442 | 64 | MKIHKTDEKRIYFMMDSGAYGSISR | No significant similarity found. | | | |

Fig 2R

| | | | | | | | | | |
|---|---|---|---|---|---|---|---|---|---|
| | | | EDVVKLLRCRNHLWKDKVDPRTSE CLSEKAEQLRKEEMRNYMEFL | | | | | | |
| 61 | 66544 | 64715 | 65 | MNELDLIDNIYSILDNEGEEDLMFN NANKASEQFPTQRDMIAGEVSKYV VAQELPAYLLAAHNRGEIHHDMDY RAQGYTNCCLVDLAGMFKNGTKIG GAEIETPKSISTAAAVTAQVIAQVSS CQYGGTSIDRIDEVFAPYVRKSYDK HLAIGQRWLHDSKKAAVYATEM/TE KEVYDACQGLEYEVNTLFNSNGQQ PFVTFGFGLGESWEARMLQKAMLE VRIRGLGASGHTAVFPKLIFAVKEG LNKSPSDPNYDIKQLALTCTSKRMY PDYVSYERVTAVTGDFKFPMGCRS FLSAIESGETAGRNNLGVVSINLPLV AVESEGYFDRFWKLLDEYIDKAMA AHDWAIERLKRVRAKQAPILYMHG GYIGINELVEVMFEDTDPMSPPAIE FAYQVLNHMKDRCNKKAEETNLGF SLYATPSESLCNRFNTKIAEQYPEY DWLTDKGYLTNSHHLDVRTKVAPN VKFDYEANFTTIANGGNISFVELPE MRKFIPALEWVDYGLSKSHYIGVN IPVDECEECGYLGESVSGEHGFVC PQCCSGNISVTRRVCGYLGSPGSR PFNPGKQQEVMQRVKHMNLK | 609 | Anaerobic ribonucleoside-triphosphate reductase [Enterobacteria phage T5] | AAX12030.1 | 0.0 (379/608) | anaerobic ribonucleoside-triphosphate reductase | Anaerobic ribonucleoside triphosphate reductase | PRK0923 | <1,0 e-180 |
| 62 | 66854 | 67603 | 66 | MRKAARRKESRRNGSAKRERHEN VIPVDFEARERFQPTAKELKPKNAE QKHYISTIRNFTVTVGIGEAGTGKTF IPSVLAAQELATPGSVYEKFILVRPN EPLGKSLGMLPGDLNEKMAPWLEP IADGFKWALGERSYQGLVERKAIQ YLAIEHARGRTFNNSYVIVDEACNIS VEAMKCILTRVGQDCKLVICGDVAQ KDIKSDSGLQLIMDIYDQYEHVPFSL VELHDNVRSAESKAFQAIFNDMGI | 249 | Phosphate starvation-inducible protein [Enterobacteria phage T5] | AAU05235.1 | 7e-96 (173/246) | phosphate starvation-inducible ATPase | PhoH-like protein | pfam02562 | 5e-40 |
| 63 | 67539 | 67718 | 67 | MITCVPLNPKHSRQSLTIWESNMVT ELIIGYGEGITSEENWGFVGFGEGIT SHDERPDL | 59 | No significant similarity found. | | | | No putative conserved domains have been detected | |
| 64 | 67733 | 67942 | 68 | MNNVFTLNNFRTRKTKVHPVSLAT VNKYNANYPEDERRHHAAFKIANE FPNQPLGTKELVSRMKLHFY | 69 | No significant similarity found. | | | | | |
| 65 | 68071 | 70395 | 69 | MTQRIEYVIKRDGTKEPFMAQKLND WAKYIGIRSDVPWPSVAVAAVKNL PKGDVHSDDLQTMLIKSAESMIERD HRYDRFALELRLAQLRKNLFDSYTP PSLRFFHDHMVELGAWEDMSGWI | 774 | Putative aerobic ribonucleoside diphosphate reductase, large subunit | YP_006924.1 | 0.0 (534/776) | aerobic ribonucleoside diphosphate reductase, large subunit | Ribonucleotide diphosphate reductase subunit alpha | PRK09103 | 9e-145 |

Fig 2S

| | | | | | | | | |
|---|---|---|---|---|---|---|---|---|
| 66 | 70492 | 71652 | SDDQFEALNEVIDHSRDELFTNAGL KQFMDKYSRRNIYTEEIYETPQFAY MGMAMAMLSQPHWSMLDAIDLYN ALSLQKINVPTPPLVGLRSADRGFA SCCLVDGTDTLDSIDAAEHVVFKMV AARAGIGYHLESRSIADPVRKGAFP HSGKLPYYRHIDRSVKANTQQSRG GSATVVTAFFDPEIIQVMEAKSNRS PDEKKIDKMDYNLKFNSILLKRFLRK ENITLMSFLYAPEVYAAFDSGDVAE FERLYIAAEKRLAGVTKRGFKGEVL PVAPVIPAAELIEFWKTVRMETGRL YTMDAGEVNRNSRYKDPVRMSNL CVEIVQPTFPIPHVVDLYRTDEELD KMDVSEYGEVSLCNLGGFALGRIK TLEEWEKISYILLKFVDTIIEIQHYPF PAMKYTALRRRNVGIGLMNAAGAM AAEGLAFEGEEARNWIHREAEKAS FFLHKASVRLAKEIGPCEWFHRTHT SDGTLLIDTYKKTVDDLVSVGLEMD WESLREEIKTHGMRNSVLTASMPG ESSSVLIGVTNAVEPPRSAVTIKTS GVNKVITVAPGLDDWDTMQSYKYA FDIDRTEHIKWLAVLQKFTDQAISAN LYYDFNKYPGGIIPGTEIIKDLLNSTK YGIKNLYYANFDVDTGGSAAEQGC SSGGCTL | [Enterobacteria phage T5] | | | | | |
| | | 70 | MATVFNREWDHTESKLFLGQDLGI ADYVNVRYPRLEELALLQRSQFWV ETEISLEADKKQWPNLPQHIKNKTL LNLAWQTQADSIITRAPEDAILKLVS RPELEGMLIQWSYFENIHSRAYSNII RNVLPNPGEFIATVQANDEAFARLA LPVSVIDELAEIADIWLDARANLEIAE KEGTLEYTEEADFLALTEQVQQKIL EFYYAVYALEAIMFYASFACTFALA ENDILTGIAKNLQLIAKDEALHTVMA MEVLRILQNGEIPPHVVAAAQANAP KILRSILETEINWAHYIFPEGEDIPGL NADLLVEYLYYNARLAFMAINIPWP EDLPVIMEDPIGWMKGWLNTKNQQ VAPQEAQITNYRVGATSQANPDDL SDEFGEFL | 386 | Putative aerobic ribonucleoside diphosphate reductase, small subunit [Enterobacteria phage T5] | YP_006922.1 | 5e-118 (225/390) | aerobic ribonucleosid e diphosphate reductase, small subunit | NrdB, ribonucleotide -diphosphate reductase subunit beta | PRK091 01 | 2e-63 |
| 67 | 71652 | 72215 | 71 | MITALYAMRVDAAFGIFNPATMDAY GELPWGSIPEELEQFYRILDTYQVVI VGHNTYETAPPRLKKALEKKSMVY VVGSKAPVLIKNPPRNVRFITHLGS KIRDFCNEVEVVCIGGKALLETLAT | 187 | Putative dihydrofolate reductase [Enterobacteria phage EPS7] | YP_001837029.1 | 1e-08 (40/122) | dihydrofolate reductase | Dihydrofolate reductase (DHFR) | cd00209 | 9e-07 |

Fig 2T

| | | | | | | | | | |
|---|---|---|---|---|---|---|---|---|---|
| | | | MGCLDAIYRSTIYPKAGTVPSLDHI MYLEHPILTSTPPDAVVTHIASGEN ERYRFVMEGVYL | | | | | | |
| 68 | 72212 | 73066 | 72 | VIHYINEGKRILEEGVWLENPRTGV RCLTVIGSNFEYDVLGKKFPLTTRK AYALQAIMELIGYLRGYDSAEQFRAI GCNTVNANANENEAWLVNPNRKG TDDMGRVYGVQGRTWLRPDGSHF DQLYKIYENLRRGIDDRGEILTFWN PGEFDQGCLRPCMHTHQFSLLNG NLYLDSFQRSNDFLLGQAFNMVQC YTFLALMAQITGNRAIRANQRIVNM HIYENQYKVLMEHGQFDRKPFPAP RLEINPEIKTLEDVLTWVSKDDFKIV GYKSHDPIAYPFTA | 284 | Thymidylate synthase [Enterobacteria phage EPS7] | YP_001837028. 1 | 9e-120 (204/282) | thymidylate synthase | ThyA, thymidylate synthase | PRK018 27 | 2e-82 |
| 69 | 73073 | 73306 | 73 | MGLFNRRPKITFSEREESQLKFLVQ SSGLHIDVILGMVKYKGMDALMRQ FAPKPPKENPPAKRDYNSNLLVPP AKLL | 77 | No significant similarity found. | | | | No putative conserved domains have been detected | |
| 70 | 73404 | 73679 | 74 | MSFTDAKAMAAKAKRSNDMAVIAA RRSIISNIDGSASSGKTEVDSYALN GLPIAARSQIMEDLKDAGYEVKVNH PFDQRDTESITISWGHA | 91 | No significant similarity found. | | | | No putative conserved domains have been detected | |
| 71 | 73679 | 74161 | 75 | MFHVYTDGGCRGNTRGVDNVGA WAMVVYNSSEEQIGTKSAPKRNTT NNEMELQAVLEALLWSNKNPGRP MTIYLDSTYVKNGCESWVWGWER KGWKKADGDTPLNLDQWRWIIDEL KKYRLNHNEIPTFVKVKGHSGVEG NEAADNLLNVRMTELEMEDM | 160 | Ribonuclease H [Enterobacteria phage EPS7] | YP_001837024. 1 | 7e-44 (85/160) | ribonuclease H | RnaseH | cd06222 | 6e-26 |
| 72 | 74161 | 74322 | 76 | MLENLRRLVSEMKYEVLLMEPGVD RVVMKLRIARMEAQIFEAEWKALR GGDEL | 53 | No significant similarity found. | | | | | |
| 73 | 74322 | 74672 | 77 | MAPDLRDLFPNVPQVQLDLYAAFL EASKSGNPLRVYRQDRRHGKSWIL RWLKENEPLLKKLSERNSVQHRHT TKVGTSTSAQKSRQNISGGNRYEFI IFDDLVDENEKTQLLNAKN | 116 | No significant similarity found. | | | | No putative conserved domains have been detected | |

Fig 2U

| | | | | | | | | |
|---|---|---|---|---|---|---|---|---|
| 74 | 74726 | 75136 | 78 | MAKQTSKKAVETKVATFPKTEANR KARLERHLRKHPADTQAASAVGKP APRRKKPVTKGSTSGYYSKIVGWS TPDKADTKEVLRKTQGRFGSVKPNI FGCEYSRENVRALCYGVGIKFTGK ANKPRNQKRKPAKKA | 136 | Hypothetical protein T5.089 [Enterobacteria phage T5] | YP_006917.1 | 8e-31 (83/170) | | No putative conserved domains have been detected |
| 75 | 75136 | 76140 | 79 | MRNFVAKNDFNRAATHKSALDYSR VNSRELMDSCYEELEDWAADWPS MEENWDVSEDMTKPPPEVASKCD NTSRSNFNNKGNNMQNLQDRWIS VCDIESLGTPGDCKSTFIAMPFFAF VLMKDLSLDPYIVLGTPNVAQQLAL GAKVSAGTIAFWMNEARAGSAPSL SIIEALNAKDGESTVLVCNPTHESP VSKHTFMDLICPFVEAKQVIEGIIDE QGIDTRSLRHYGNGPQFDMSIYET VAAQANVFSPSDPAIVPWKFWDIS SARNPRDYFEALGGDWKALVRCA EIYAHDVIERYNLIPEGVYPSKHDPV FDALVEAYCIKTIESKLKI | 334 | Putative metallopeptidase [Enterobacteria phage T5] | YP_006915.1 | 2e-39 (96/244) | metallo-peptidase | No putative conserved domains have been detected |
| 76 | 76205 | 76666 | 80 | MKAAILMISILTSFHAQAKIDAHEIEC IAKNAYFEARGEGVKGMTAVAQVT KNRVNYGKFPSTYCKVVYQPGQFS WVGKKKHKLDRKDEEWKQAKEIAR LVYYMDLPVDPTKGALYFHSKDTK PYWTKDKDFKRTSKIGNHVFYKLK SQLPNA | 153 | Spore cortex-lytic enzyme precursor [Enterobacteria phage T5] | AAX12015.1 | 2e-44 (96/146) | cell wall hydrolase | Hydrolase_2, cell wall hydrolase / pfam074 86 / 7e-23 |
| 77 | 77991 | 78317 | 81 | MNDLSMLTKIRSDIESMVSRRSELT KAKQIISGGTQKRFTLQAGDIKFDL CGSQTRDYTFEMKPCYDMVKLGLI KALDKQIDQCTDAIKTLNVQFAAEC DRLKNSIKV | 108 | No significant similarity found. | | | | No putative conserved domains have been detected |
| 78 | 78320 | 78496 | 82 | MVASVHTPPYERPAPNLTPEQKQLI ARRTLEFKESLHKSVGRYSEQVHD LVVKTLKLY | 58 | No significant similarity found. | | | | No putative conserved domains have been detected |
| 79 | 78498 | 78570 | 83 | GCUCCUUAGCUCAGAGGAUAGA GCAACGGUCGUCUAAACCGUGG GuCACAGGJUCGAAUCCUGUAGG GAGUA | | | | | tRNA1-Arg | |

Fig 2V

| | | | | | |
|---|---|---|---|---|---|
| 80 | 78725 | 84 | MAYKIEVLKKGVLTELVIDANMARN EGTKSVFYKDGSVARMINTEDIQDL YVISDEEAGFVKDPEPAEDTPTEDT PVADTTTEEPPVEGTPEDEAAV | 97 | No significant similarity found. | | No putative conserved domains have been detected |
| 81 | 79051 | 85 | GGGCCGGUAGCUUAAAGUuAAAG CAGUGGCCUCAUAAGCCAACGAg UGGGAGUUAGAGUCUCCCCUGG CCCA | | | tRNA2-Met | |
| 82 | 79122 | 86 | MSTKNAIVSFVDDSGIVLESTVTDIS PKRLLHRDGDILEILNKRSETMLVIP VNRLLSIKIVWED | 65 | No significant similarity found. | | |
| 80 | 79147 | 87 | MDAQLQTQYYMLLGMLEDAGPTV RGHYERHKAAFEALLKEVNENEGG KGSDSYAAFIIALQVFLINQLK | 69 | No significant similarity found. | | No putative conserved domains have been detected |
| 84 | 79344 | 88 | MLNIKRKGFFYKWLNFSSASFTYRL NDNRVTLCSLFWHSVWYFLLQIGV TAIAVLFSLGMGSILSTFLGLTFELGI TPWYMLVGLSLAGLSTIIAILLAIAGI GWACAKIGDRIQEWNASKSFERAQ KEYNARDEELRFGNIYQKMRIYKKD KLCPLIRVDHGE | 164 | No significant similarity found. | | No putative conserved domains have been detected |
| 85 | 79553 | 89 | AAGGGAAUAGCCAAGUGGUuACG GCAUCGGCCUUUGACUCCCAGA UcGUAGGUUCAAACUCCCUUC CCUUG | | | tRNA3-Gln | |
| 86 | 79564 | 90 | GCUCCUGUCGUCUAAGCuGGUuA GGACACCACUCUUUCACAGUGG GAACACGGUUCGAACCCCGUU GGGAGUACCA | | | tRNA4-Glu | |
| 87 | 80058 | 91 | GGGGGAUGGGUCUGGCUGGGAgu GGACACCGCACUUGCAAUCGG GAAuCagAACGGUUCAAAUCCGU UAUCCUCCACCA | | | tRNA5-Ala | |
| 88 | 80225 | 92 | GGGGAUGUGGCGAAAUUGGCaG CCGCCUAGAAUAUCCGUGGGUU UGGuGAAAUAUCCGUGUGGGUU CGACCCCCUCCAUCCCUACCA | | | tRNA6-Leu | |

Fig 2W

| | | | | | |
|---|---|---|---|---|---|
| 89 | 80779 | | | No significant similarity found. | |
| 90 | 81007 | 81015 | 93 | MNIEIMQLDRKNEFRKVHTFPSKE ALEFHIKCMGLVLPESEIFDLACAN GVLYVWEITYHADPDELRKEVEQIL TGE | 78 | | |
| 91 | 81099 | 81091 | 94 | GGAGAGUAGUGCUCAUGGAGC AAGCUGACUUGAAAUCAGUCGCC AUCGGAAACGGUGAGGGUUCGA UUCCUUAUCUCCGCCA | | tRNA7-Ser | |
| 92 | 81444 | 81184 | 95 | GGAAAGCUGGUGAAAUGGUaGC CACGCAUCACUGCUAAUGAUGAG UCCGCAAGGGCAUGAAGGUUCA AGUCCUUCGCUUUCCGCCA | | tRNA8-Ser | |
| 93 | 81528 | 81520 | 96 | GGGAUAUUAUCAUAACUGGAuAA UGACCUCGAUUGGUGGAUCGAGU CUauCUUGGUUCGAAUCCAAGAU AUCCUCCA | | tRNA9-His | |
| 94 | 81732 | 81602 | 97 | GCACCAUUAGUUUAAUGGAuAGA AUAUAGAGCUACGAACUCUAUGG UUGAGGUUCGAUUCCUCGAUGG UGUACCA | | tRNA10-Arg | |
| 95 | 81810 | 81807 | 98 | UGGGGUAUAGCUCAGUAGGUAG AGCGGAGGUCUCUGAAGCCUAG GuCACAAGUUCGAUUCUUGUUGC CCCUGCCA | | tRNA11-Gln | |
| 96 | 81900 | 81886 | 99 | UGCACCGUAGAGGAGAGGCgUC CUCGCCAGUCUCAUAAGCUGGA GAuCGCAAGUUCGAAUCUUGCCG GAGCAUCCA | | tRNA12-Met | |
| 97 | 82081 | 82094 | 100 | MMRISFTERVLGTGVMLITSWDGD SWCNVTGLRKSEQTPENIAKIKKR MAEAASRPGAPRNGKR | 64 | Hypothetical protein [Bacteriophage 5] | CAE53211.1 | 2e-18 (41/63) | | No putative conserved domains have been detected |
| 98 | 82262 | 82260 | 101 | MVNVEVTMTRYQGMLINTHTKEIVF LAPAFHDTYNEAEEDARIAKIHPDE EICVRQQFQ | 59 | No significant similarity found. | | | | No putative conserved domains have been detected |
| | | 82337 | 102 | GCUUCAAUAGCUCAGUUGGUAG AGCAAACGACCGAUAAUCGUUAG GUCACUGGUUCGAGUCCAGUUC GGAGUACCA | | tRNA13-Ile | |

Fig 2X

| | | | | | | |
|---|---|---|---|---|---|---|
| 99 | 82495 | 82571 | 103 | GGUCAGUUGGCAGAGAUGGUuU AUGCACUCGCUUCAUACGUGAGA CUaCAGUGGUUCGAGUCCACUAU UGACCACCA | | | tRNA14-Met |
| 100 | 82575 | 82650 | 104 | ACUUGCUUAGCUCAAUCGGGAG AGCAUCGUCUUUACACGGCGAG GGuAGCUGGUUCGAAACCAGCAG CAAGUACCA | | | tRNA15-Val |
| 101 | 83285 | 83566 | 105 | MEKITATGIESALVVDWAGWDGDH EWMVFYSCTLQPELWTRLTDEHA MPYGIIDVEEINKLVGTIMVHRAEG DHKEIFRKSIKLVVSTGDFI | 93 | Hypothetical protein AGC_0078 [Enterobacteria phage EPS7] | YP_001837001.1 | 3e-09 (31/87) | No putative conserved domains have been detected |
| 102 | 83587 | 83964 | 106 | MYTRPTNGNSAVVRLMIVQDNLSN NIESLDRRIEEYRTEMLSLMREREA KIEEQLEVCEAIDRLVDGTAVFMAE APAEPTFTPVAPADMQYAILPFHLE EEDGEGPSLEDVVRFLLASGFPNG GR | 125 | No significant similarity found. | | | |
| 103 | 83964 | 84179 | 107 | MDFIVVCGANTDCFELLNDALDKVD EHMQEGRTPTFIDLSQGKTYFYPSL DVEPTVLPIFMHSLSWDEEDD | 71 | No significant similarity found. | | | No putative conserved domains have been detected |
| 104 | 84374 | 84450 | 108 | GCGGCUUAUGGCGUcAGCGGUcA ACAUACCGGCCUGUCACGUCGG AGcCACGGGUUCGAAUCCCGUUA GCCGCGCCA | | | | tRNA16-Asp |
| 105 | 84784 | 84861 | 109 | GGGAGAGAAGCagUAAGUGGUAU AgGCGUCGCCUGUUAAGCGAAU GAcAGUGAGUUCGAAUCUCACCU CUCCCGCCA | | | | tRNA17-Asn |
| 106 | 85090 | 85163 | 110 | GCAUCAUUGGCCGAGUGACUAG GCAGAGGCUUGCAAACCCUCGAA GCAUGGUUAAAAUCCAUGAUGGU GCUCCA | | | | tRNA18-Cys |
| 107 | 85180 | 85359 | 111 | MIKYKAFVTRESQTGDSSIKFEGTT LHDTFEAALTEAETHIVSKSCYAHV WEVNTILDR | 59 | No significant similarity found. | | | |

Fig 2Y

| 108 | 85350 | 85425 | 112 | AGAUCGCUAGCUCAAUGGUuAGA GCACUCGCCUUUUAAGCGAUAG GuUCCGGGUUCGAGUCCCGGGC GGUCUACCA | | | tRNA19-Lys | |
|---|---|---|---|---|---|---|---|---|
| 109 | 85601 | 85678 | 113 | GCAACUGUAGCUCAGgaGGUgA GAGCACUGGUUUGAAAGUCCAG GGGuCGUUCGUUCAAAUCGAACC GGUUGCACCA | | | tRNA20-Phe | |
| 110 | 86126 | 86320 | 114 | MNQKILMRYNPRALWFRWEVIVSY QIRVRNGDPENNIIVLETFSNRDAA VKFLNTIDNTLIKVY | 64 | No significant similarity found. | | |
| 111 | 86323 | 86661 | 115 | MDIFTTPAINLVGVGLFQATYYRIDD STDVVTFIVPEFFLEKFFEEFEQFRE EHDAYSNMEDLAAMFPTVYGYIFE GNDLLDKSELVELNWGISFEVGSP FPRYFQGLEIR | 112 | Hypothetical protein AGC_0081 [Enterobacteria phage EPS7] | YP_001837004. 1 | 3e-20 (48/53) | | |
| 112 | 86661 | 86810 | 116 | MGGYSNFIENYINSVDSWNQETLV VVLKERFNISTLEALEAIEAYLDND | 49 | No significant similarity found. | | | No putative conserved domains have been detected |
| 113 | 86812 | 86889 | 117 | ACCCACUUGGCUCCAAUCuGGUaG AGCAUGAGGCUUAAGACUUCA GGGuUCCCGGUUCGAGUCCGGG AGUGGGUACCA | | | tRNA21-Leu | |
| 114 | 87022 | 87098 | 118 | UUCCCCUUAGCAGUCuGGCAG ACCGGGCCUUUGGGAGCGUCA GGuCAAGUGUUCAAAUCACUUAG GGGAGACCA | | | tRNA22-Pro | |
| 115 | 87104 | 87179 | 119 | GCCUCAAUAGCUCAGCCGGAG AGCAACCGCCUUGUAAGCGGUA GGuCGUGGGUUCGAUCCCUACU UGGGGCACCA | | | tRNA23-Thr | |
| 116 | 87472 | 87547 | 120 | GCGACUAACUGUACGGGuuACAG CGUCCGCCUUCCAAGCGGUACU GAGuGGGGUUCGAUCCCCCUA GUCCGUCCA | | | tRNA24-Gly | |
| 117 | 87647 | 87748 | 121 | MKAFDAELVFSLLAEMEACVDRVR ALRLSMFSS | 33 | No significant similarity found. | | | No putative conserved domains have been detected |

Fig 22

| | | | | | | | |
|---|---|---|---|---|---|---|---|
| 118 | 87867 | 88058 | 122 | MLTVKVMSPNGGEEIHDGSSVGFN PKQKSISIAGLDQHIFLKEDEVAYVM NQNGKTVSVYHGS | 63 | Hypothetical protein ykris0001_9300 [Yersinia kristensenii ATCC 33638] | ZP_04623722.1 | 5e-18 (45/60) | | No putative conserved domains have been detected |
| 119 | 88063 | 88139 | 123 | AUUCCCGAGUGUUACUGGACAG CACGCCGGUCUCCAAAACCGuGC AGUAGGAGUUCGAGUCUCCUGG GGUUUGCCA | | | | | tRNA25-Trp | |
| 120 | 88156 | 88512 | 124 | MITYSTNFMGPVSNNWYIRMGIPYT EVTEPNRFADGGQLTRKVFAKRYA GGRIDVRGTDDYFGQEIGVPIMEAE SWNELQQFLWTFSSDKVLTLEQIV QALEDETGFRIWWFKEPACT | 118 | No significant similarity found. | | | | No putative conserved domains have been detected |
| 121 | 88503 | 88883 | 125 | MYIDRNQLFKFLELDLRWPLSVNP GRATGKTFEAINTAYEFAVFKGIQA VYVASGVREMARLEKKYNELQPHV KITTYSMLEPYRIGRRFSCIMFDEPS LAIKYGVNAYVVRIARENQCPVIIFG E | 126 | No significant similarity found. | | | | No putative conserved domains have been detected |
| 122 | 88885 | 89061 | 126 | VEQEFQVFVDASKRVLFIQATDEG HGLQLSFDSLEQINQIVLRAQKSLE KNTEAPPDL | 58 | No significant similarity found. | | | | |
| 123 | 89156 | 89371 | 127 | MREISKMKVTMENTEEFIAICTAYA DTLPPEGMDDHTMQLVADIYRLAE LAKEQHNRLVYVKERLEMMDKE | 71 | No significant similarity found. | | | | |
| 124 | 89375 | 89647 | 128 | MNELNELNELHYAERAIDELDFAGG YYTRHVNAMTAEGLNSKSAIAAELA VRDFVIDSLQKTISNLSENNKAALEA LDKLSNHLLALGIK | 90 | No significant similarity found. | | | | No putative conserved domains have been detected |
| 125 | 89647 | 90189 | 129 | MNKQSLRGIRVFRSSLVDSFYIWG KATRRTVEQALDGTFYDWREKERN PVFSRPGLYHDRVSKTAWYEIEVT PGVIRAFYTDWEHEKWVWDNQIAP GDRMNYAEYKEMKRMFELYDVPR LSRPAIFIASQEYWHTVRMKRDFNK HHLRYEKEHGTLRERVAKRKAELR EKRLEKKYGES | 180 | No significant similarity found. | | | | No putative conserved domains have been detected |

Fig 2AA

| | | | | | | |
|---|---|---|---|---|---|---|
| 126 | 90176 | 90403 | 130 | MVKASLLRFTPGVGLQYKIVGGHK FQYFTPGKLYFVELHDSRAGYKLR SDANEGIWVSFTQVKRWFTVEGYN DYE | 75 | No significant similarity found. | | |
| 127 | 90390 | 90758 | 131 | MIMSKVVYFVKCCRDTLELVDHKM QTCKCGASSIDGVAGAYVRFLGDK SNFMRLNEFQLEVEKNRPALEAEA ERLKDFDGNIVAYNMVSGKDFWSE LAEKLNMPRQAAKALYHGFNYSPR WN | 122 | No significant similarity found. | | No putative conserved domains have been detected |
| 128 | 90727 | 90993 | 132 | MASTTRHVGIKFSNSNRTVYYRVP SYWKYSPEIGDVVVIPGNVMFNNP RRAKVVEHGMYGKPEYKERKNIS YVELHDYLPKEERNGR | 88 | No significant similarity found. | | No putative conserved domains have been detected |
| 129 | 90983 | 91288 | 133 | MDDKIAREAIELVRKRLEFRNVEVP KIMLIGYGGIGGFPSFTDLERMERE SQASFLELESYAREMEHPIGNN FMPRSSRQEVTHGKTNSWPTPKR RGRK | 101 | No significant similarity found. | | No putative conserved domains have been detected |
| 130 | 91285 | 91494 | 134 | MITTGFGYSHEELCKMVESAPFIKK LVEEQRPVCLHAACTKCHGTGVDK NGKMCVHALSCPCPKCSWSC | 69 | No significant similarity found. | | No putative conserved domains have been detected |
| 131 | 91496 | 91933 | 135 | MDLGYCVVHEFMEQGLPDRICVVT SRNLEAAQSLVERLSGYYRDHERY QQKVFDLTKLYHQKALDMPTPQLD DLKQFSPEAWYSVKDASPVDYTVQ VFSHYGTRHWINRKWDSMVDYLN SELEKGAAEYKRKRAEAKVLKNSV AL | 145 | No significant similarity found. | | No putative conserved domains have been detected |
| 132 | 91980 | 92303 | 136 | MSKLSIESIIRPLMHGYVQGSCVSE TEALNVIEEELVANGYNLHEGVIEDL FWQTAEDMEIFRCVNCGWWCPAF ERAENQIEEICRDCEPDLEGEVDEQ DNEGEDYE | 107 | Hypothetical protein T5.053 [Enterobacteria phage T5] | YP_006881.1 | 2e-05 (31/87) | No putative conserved domains have been detected |
| 133 | 92296 | 92568 | 137 | MNKITKVKTMSKRSIAAIIAFSMMYS GVSLAERNKVEISDNGRVRVTTN GITKGAGKFRKSETRFGETKIYTNK TYGKPAVTLDRYGRQVEDEDDSDE | 99 | Hypothetical protein AGC_0054 [Enterobacteria phage EPS7] | YP_001836977.1 | 6e-04 (25/70) | No putative conserved domains have been detected |

Fig 2BB

| | | | | | | | |
|---|---|---|---|---|---|---|---|
| 134 | 92561 | 92995 | 138 | MSNLHPKLQETLDWINEECAFEEA PYCVWARAGAVAPSEWCTVFDNRY RITVELSLKEDKVYAKASMTALGLS GFVEMQELCMPNTHLRVQIEQLATI RLMLPEDNINDHFHKVIENEYKLRR QRRKARREVEKTRMMCNMNPHV | 144 | Hypothetical protein AGC_0053 [Enterobacteria phage EPS7] | YP_001836976.1 | 1e-14 (43/115) | No putative conserved domains have been detected |
| 135 | 93115 | 93507 | 139 | MFTLFILAVSAWMAVGINHGLDSAK LLSAKAFEFLAKFATRKDIEAIIAKG GAKDASSVLKSFDKILELRNGKHAA ELRCMSRKTIGRLCKAIFIVQGALK GPFAKYKPDSIKRAKIFNDYCVEHH PLNR | 130 | No significant similarity found. | | | No putative conserved domains have been detected |
| 136 | 93616 | 94314 | 140 | MRIISKLKDVYDLQGTMVDAERAW YREEVKEVVNVSADFEQIIFYAEILR NRTSSGYGGVNMGTLEVRPVLICG TLRWLYGYHTGLGADAVHIQTFDP VKVKEVLEEQGYYLRMGWDMNTIE KIDAHVRNATATASAFLETFNKPIA MAWDAAKSKTDPTVNTVKTDFNF HAEDFPWQEIDPNLYRWHQTLESY IFGVLGQGEPKTESTSDRDRLIAKG FDAKVSFRNMER | 232 | Hypothetical protein AGC_0049 [Enterobacteria phage EPS7] | YP_001836972.1 | 1e-34 (92/237) | No putative conserved domains have been detected |
| 137 | 94280 | 94741 | 141 | MLKFLSGIWSGKTGAILFLAIAAGTF GGAYYITNKLTDMSSSSLQSLSNRN EQLEKTVGNLQTEIRNRDRNTTTYI TNLAKNQEDLDGRINKLDAARAKE GVVAAKPKLATKVAKDKVNEFQER LSCVTGNMDSCSRLQLSHPGVQN. GQTQVAQ | 153 | Hypothetical protein AGC_0048 [Enterobacteria phage EPS7] | YP_001836971.1 | 2e-20 (56/143) | No putative conserved domains have been detected |
| 138 | 94654 | 94983 | 142 | MRNWKYGLLLSAAIIASGCAERPDP SSTVTGVEPQHLPWPASLQTCPFN FEFINEEGKVYVRIPYQDWITMGKC NEQVYTYIANLTALTCTYRVSLNEY RCKPFNKETK | 109 | Hypothetical protein AGC_0047 [Enterobacteria phage EPS7] | YP_001836970.1 | 1e-19 (50/108) | No putative conserved domains have been detected |

Fig 2CC

| | | | | | | | | |
|---|---|---|---|---|---|---|---|---|
| 139 | 94980 | 95741 | 143 | MKYVLGLIGDAGAGKDTFADMAKV WAWEVLGPEYSISKFSFAAPVYEL AAVILGVTPEKLAERRTKEKQWFW VTQEALERTANVWKRFGIDKYADF SYVWPQFEASALYPLIAKTAPDFYQ GRETPLYLYTSPRKMLEFVGTEL GRALVDENLWLNIVVDRITATKADIS IISDVRFDNEAALVRNFPGAQNSSIL KVHAPNNIHAIQSTHASARGVAPEF IDDVVTNNFDGLENFRKNVNAFCD ERILFI | 253 | Deoxynucleoside-5-monophosphate kinase [Enterobacteria phage T5] | YP_006871.1 | 9e-54 (117/250) | deoxy-nucleoside-5-mono-phosphate kinase | No putative conserved domains have been detected |
| 140 | 95751 | 96362 | 144 | MGGINNVEQKGGNKTPNYFASLVA TKAEYNIYHYHLDGPIVDVDYYRDL SVTLATMQEGDTLNLYINSPGGYV DTAVQLCNLIMNCQGTVIGHLVGPS ASAACSIFLACHGWLVHPYVMLMG HTYRGAHYGKGKNEIQHYADQFNS FFEDMMLDLYYPFFSLEEITEMIEG GKDIWLTSKEINERVDRMAAHREQ EARKAAGQ | 203 | Putative ATP-dependent Clp protease [Enterobacteria phage T5] | YP_006870.1 | 7e-51 (96/181) | ATP-dependent Clp protease | S14_ClpP_1, caseinolytic protease (ClpP) | cd07016 | 5e-19 |
| 141 | 96520 | 97182 | 145 | MDKFIQLISLLLQEAKDPASLLKRLL TLLVGLVYLFIANTSEVMSYLKTFS TSAVLQDVKVQRTLEFPNVAREKA MILFSQTRADAVFVVKYKPEAINDY QTIIAWESNVQLDKSDVSDKAVDKT SMLYRAHLDGLNFAIDAREKRGLSK WSGTGLPPFKSANFEYVYTCPYFN LNNIYSGYVAVAWEKYPLQDEDMG MFNDYMAKICASPQRSLGRSI | 220 | Putative holin [Enterobacteria phage T5] | YP_006869.1 | 1e-82 (144/220) | holin | Bacteriophage T holin | pfam110 31 | 8e-47 |
| 142 | 97179 | 97592 | 146 | MSFRFGNRSLQQLDTVDPKLKALAI RALELSPHDFTIIQGKRTVQQSAQN IANGTSFLKDPSKSKHVTGKAIDFA PYINGKIDWNDLEAFWAIVGAFKKA ANEMNJAVRFGADWNNSGDYRDEI QRGTYDGGHVELL | 137 | Lysozyme [Enterobacteria phage T5] | YP_006868.1 | 8e-57 (104/137) | lysozyme | No putative conserved domains have been detected |

Fig 2DD

| | | | | | | | | |
|---|---|---|---|---|---|---|---|---|
| 143 | 98142 | 98546 | 147 | MSDRFYTQMCEHFKVSPYELNIAL WDRESPEFKKIAKKSEGVMSNGKK MTRIDLNNALTKLLGVNIEGQKLSM PTLTTILEKVKAGDVKKVAVPEGRL KKPYQEAIIEAFGEKLDTATVKT MKALLESINNV | | YP_006866.1 | 1e-37 (86/141) | | No putative conserved domains have been detected |
| 144 | 98539 | 98823 | 148 | MSKKIVFLKGSSCVPCKQFEPVFDK LTAEFNLPVEKRTDDVDSLRKFGLR TVPAVVLVDVENGREEAHHILSGAT LRSAVVSKAIQDFIDYVEE | Putative thioredoxin [Enterobacteria phage T5] | YP_006865.1 | 6e-21 (48/91) | thioredoxin | TRX_family | cd02947 | 8e-04 |
| 145 | 98925 | 99329 | 149 | MTKQAYLILNNGFAVGTTFVDLGYT KEEWQALDAAQKNQLVNEAAWEY AEAYVEAVDDELVIVVSLGAVGCDA HVHTDFQSEEEWDELDLTHQNALI NEAFWEVVDCYVAFCKDDDEANT CTNYGYEHDDVECA | Hypothetical protein AGC_0039 [Enterobacteria phage EPS7] | YP_001836962.1 | 3e-21 (49/103) | | No putative conserved domains have been detected |
| 146 | 99329 | 99691 | 150 | MQKFSRDWSSDMARKNRAAAYYN KKIQLDKLIKGITYNVERGFSGIKVD ARSLDYSCILWAKQNGYAFKRIGNE ILIAWEPEGLVQVYIVDPYRGEYVR DHRQQPTDFSLPKRYLETRY | No significant similarity found. | | | | No putative conserved domains have been detected |
| 147 | 99691 | 100521 | 151 | MNVHETVTVPDNANIFFIGDIHGEY DMMMGALKLAGYEEGRDYVFCVG DLIDRGPKNLQVLAKFLYNPKFRSV RGNHDEFMIQDDYANWMYNGGS WTITEGFDTDTMKGIAEDMDSKMP YIMTVEHRGKRYGVVHAGIPLRYQ AQGMGVTVPVWDDIVHEHESTPDL RRLGVLLWDRDVIQEVGFNLYRSG EKHPYFDRYASFSEECAVDVPEIVG VDYTFHGHTGVPFPIRWKNRVYLD TGGTFNGRMTVASPVLGQLYTFTT DRDDPCGSADII | Putative serine/threonine protein phosphatase [Enterobacteria phage EPS7] | YP_001836961.1 | 3e-98 (176/283) | serine/threonine protein phosphatase | PP2Ac, protein phosphatase 2A homologues, catalytic domain | cd00144 | 2e-08 |
| 148 | 100532 | 100765 | 152 | MKLFKDLEEGEVFVVAGGFELQKC VAMLDNGNSVFTDDANISVTIAPDT ETWKPKEFWEHKDRPLDDLLDDIL FTA | No significant similarity found. | | | | No putative conserved domains have been detected |

Fig 2EE

| | | | | | | |
|---|---|---|---|---|---|---|
| 149 | 100774 | 101142 | 153 | MKLESRYIVFKQSDAAKYLTSTAIR EINDSLSLIYKGREADGKVGFPNYIV LEEDWPEYPIAKEALEGRIVLEEFN KRAEKKRGAKAAEDHYKQHQSTEL LRGISPFCAGWNDYMRRLVIEE | 122 | No significant similarity found. | | | No putative conserved domains have been detected |
| 150 | 101145 | 101264 | 154 | MYTGMGNDMAKMFIGLLILAALVGA AIVGGIWALVAFVF | 39 | No significant similarity found. | | | |
| 151 | 101328 | 101756 | 155 | MKNAMIELNANMESLRHAVNTARA SFNLLMRDESIPLSARVKAFEEFAD ELLHMGDYLSDSPFNEDRRDYQHA YCNRGEIVYLTDVLESVLEYANSFM RTPDEWEDASNDYVLDEIQKNWPE IKKLVEEHIHSEVYAYRIDW | 142 | No significant similarity found. | | | No putative conserved domains have been detected |
| 152 | 101838 | 102143 | 156 | MAKNTISYTTGKTADEQANTLTKDE MVAVLVILLDMSGFEGQLAKLSLPA LRALYEGTNKNAAAYNLAKNEARW AKEHQQVAERRAESFERDLKREKA KKK | 101 | Hypothetical protein T5.032 [Enterobacteria phage T5] | YP_006860.1 | 2e-23 (52/81) | No putative conserved domains have been detected |
| 153 | 102143 | 102424 | 157 | MVLEILSGLLIAALVTGTGLAVWVSI LRENNRMRLTNNGLHEKLMDQV QDADEFSAAAERLLVRLAKIEEIIGQ DSTMSKTTIKMRLITEIKK | 93 | No significant similarity found. | | | No putative conserved domains have been detected |
| 154 | 102421 | 102669 | 158 | MISPIVAALYLVVVGYLSGKYHGFG LKGTIKAAMLVPLYPLAILLTGYYAC VLRIFGRGKVNYDNCTALLDDIENTI KKEEK | 82 | No significant similarity found. | | | No putative conserved domains have been detected |
| 155 | 102666 | 103007 | 159 | MNLNSKERQVLVDALRQVVDHDLL CDEDIVESIAIJAKIELAEKDSWRPL SELPPLGLAIVVQRADGAPFNTVMV RRDLAKSYSPDIITLHTKITNEPEF NTRHYYWRLTNA | 113 | Hypothetical protein T5.028 [Enterobacteria phage T5] | YP_006856.1 | 7e-08 (40/111) | No putative conserved domains have been detected |
| 156 | 103000 | 103227 | 160 | MLNQLRIYNFLDCNFQWWRELPSR FLGWALFLSMVVSVFHNVPATFYM EAIQPVTVFIYEMYLVAINGWKDGRI N | 75 | No significant similarity found. | | | No putative conserved domains have been detected |

Fig 2FF

| | | | | | | |
|---|---|---|---|---|---|---|
| 157 | 103211 | 103678 | 161 | MAASTEVLNQYFNREHQEFSDLFI QMFVNANNALDYRFFNEFHETTFS HODINSALKELIGSKVIPFRQTANAE TLELSVWWGLFKKAYEFGKYQNAR HWIYEVYLNTEVILPRQMMLGWIAK QRPERNAKSFAPINDGNLYHASEK FDAPKSVA | 155 | Hypothetical protein AGC_0027 [Enterobacteria phage EPS7] | YP_001836950.1 | 7e-32 (65/147) | No putative conserved domains have been detected |
| 158 | 103701 | 104027 | 162 | MLLVEGLTEEDICLNSFYNCKTHVM QALDEERVELSKFMVNIATAQVHW QTQGLSADDILKHTLNAIAEYGKAR GEALLASKKEFDKSESMLKMAIDIH MEGIDGTIH | 108 | No significant similarity found. | | | No putative conserved domains have been detected |
| 159 | 104039 | 104326 | 163 | MAKKRVVVNFLEEDSGDCEYGCW NTGYGVEVMVDGKCVHRQEAWAS CTNNSSVDFDVLAHVLQGIKTKEGY PVKADHIDFGDPSDYPEEFLDLFT | 95 | No significant similarity found. | | | No putative conserved domains have been detected |
| 160 | 104378 | 104566 | 164 | MKSIDNYLRGENPVDQAAVTVEKV RKECFILTQRGGGNRPNRVVLNWT QSKDLYERLKREFE | 62 | No significant similarity found. | | | |
| 161 | 104566 | 105042 | 165 | VEELRQKINQELVWEAKSFPINQFL KRDGSINHNIKIQLRPDFRQDAKNL IFINRALDAHGVFFGYEKLVFHSLN QLVEIWCPDHQDYFMQTARSHLEG NGCQKCRHRMVTRVTDYGSYTVP AYYHKFSIDGDSIIWYNNSSKLIKPL EVKDEIRFPE | 158 | ORF022 [Enterobacteria phage T5] | AAX11959.1 | 2e-50 (91/153) | No putative conserved domains have been detected |
| 162 | 105020 | 105421 | 166 | MKYDSLNNPSTNYLTDQSVSEIKFH PNYSPDSSKPSVAAISFRFRNLRFT FVGEEDKMISIIDKVKAVSELSGSDT VKFEALTSLLLTSGATVGKFELIQPH VSALTNTRNFWDQANVESLIKWDS ATEFYNK | 133 | No significant similarity found. | | | No putative conserved domains have been detected |
| 163 | 105434 | 105943 | 167 | MLFCTVDFEEANETYIYYGMSESKV RILWNQFQLEVPDDISKTPKDFFHLI DIKAVKARKKLTPYVFPGAVFVHEL TAYTNVVLKKSRQHPGYLTMLTYK VGAIHDGELVVRVDARLCQEVEEMI RQCCONKAELKQRARLFDMAAPSEA VAAYHGFYKEMAESDEDFFM | 169 | No significant similarity found. | | | No putative conserved domains have been detected |

Fig 2GG

| | | | | | | |
|---|---|---|---|---|---|---|
| 164 | 105956 | 106276 | 168 | MNEKYEVWTPVGENCSYLLRTLCT REDGTSFSEYLSECHAKAQQDNPL FKIRGEDILKVNGVPYTPVDSFAAL QVFKEHREREHRRMIERLTGREPF SHPRWNEET | 106 | No significant similarity found. | No putative conserved domains have been detected |
| 165 | 106276 | 107040 | 169 | MSRVEKLQHIYNLVKKADQKKLSEL SEEEYQAVLFCCSAMPAKLDGVLA KSDIHNGKETTFQPPYKWLASNIQQ MVGKVTGFSNRKTPNIFIDITPRTPE FTKDWRDALDSFPSWKVFYKPDDE TYAHLPFLKHPGYTVEDPSSGVNF KDFKCTDENIAYGLMRTSVRIAMDH ELDKQDLAVIALCKDRYIKVKRIAEK LSVLSCFETIRDCEPEGEYPKGSLY WKDVKHLGLSEEAVFLGLVVTGRF LRLQEK | 254 | No significant similarity found. | No putative conserved domains have been detected |
| 166 | 107102 | 107431 | 170 | VGYSRDPFYRLNSLQLHRLPHRGL QDIVIHSVYIIDDASEFSAKLLEKAAH KKFKPMRVNFGDKFDGHTEWFDV EPHVIEKFFLSVGAKQVPIDKLIAQE QKIRKSTKK | 109 | No significant similarity found. | T5orf172 domain / pfam105 44 / 1e-05 |
| 167 | 109330 | 109160 | 171 | MRTLRGGSPKSRSHNTYQLNVIRD GQKKGGDGGGEWGFRVIMVIIMT LVFLQSCQ | 56 | No significant similarity found. | |
| 168 | 109640 | 110605 | 172 | MLQKFTPVANLPMVRGGARNLLDG SKCASIGHILGVYRSNMESRTSRAF EHSRDYVLANPGAAIVIFHDDQYLV DSQPIDLIVSTTTDAYLYKASEGKQ ASRRFCYHESELLAFTDARAWIKNL CDHLELPPARISSEMMIFVLDKDGSI LLPCDPYDIDIEEGARTGNYRYDGE LEEVAPAVTENVVNPNNFETGALQ MNTIKSTATAIVAANKNAAVNAAKL EAGSIVLKKVSGIAASKAPFMVRGY VDTAVGRVVIANLLNFAVSQYAPNN RKAVIAADAAMQAAMLELVQSFNV GEMIDEVLKGVNLSSLLESDVAE | 321 | Hypothetical protein T5.011 [Enterobacteria phage T5] / YP_006839.1 | 3e-39 (116/324) | No putative conserved domains have been detected |

Fig 2HH

| | | | | | |
|---|---|---|---|---|---|
| 169 | 110672 | 173 | MERLTATFEGEKMTIANVWQRLRQ NGDRGNFAIFIEPKNLDNLARQIDR RDCYPDTDDMLGIPLRIIGVYGYGF DICIGDSSFEIDCESGATEIEVFLINL GSLTFLDTPPAEPEPEKLEVKTSVIV SSLTMDELADIVSTYDEIHADAIKEL NNRLDTFRDKL | 164 | No significant similarity found. | | No putative conserved domains have been detected |
| 170 | 111218 | 174 | MFHVKSCVPGINYTVEAEEGLYLE GGRIESQEVAAVLKCDTNVCGTSW TDLHFLGRGIDVDSLSWEKACEHA ESMLNEDDWDDDDSDEKYANAGV EGSFYMYWPGHSCNLVNGGSPLH SVLERAIYLGYIQMDGKAVINLRELK TFIYIPDAETILHIEEGLKSGWKVSG VVYL | 175 | Hypothetical protein AGC_0009 [Enterobacteria phage EPS7] | YP_001836932. 1 | 2e-09 (43/137) |
| 171 | 111742 | 175 | MIYIYVNKYFLAHYKTMESVIQYVSR QNARHIDEVATLKIGLRGDAINISWP LLILICRDLVAGKPVSVSALGESYPL SDDLDLYDLLTKYKTERLFYRGGSV CSSGETIETVFR | 115 | No significant similarity found. | | No putative conserved domains have been detected |
| 172 | 112942 | 176 | MLKENVMSSEIVNEFTVADAEHFIE TYLNVYDVDLAFIHKDGQI | 44 | No significant similarity found. | | |
| | >113073 | | | | | |

Fig 2ll

Table 3 - Features of phage F394/08 gene products and assignment of putative functions.

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| 1 | <2 | 268 | 177 | NPECGQAAAESTPADPAANVS RETKPEDLIKNDVAPAELTPAFYV VAEGRAITSKRGILAAGEAVEARD FVGGEETLNSLLERGLVE | 88 | No significant similarity found. | | | | No putative conserved domains have been detected | | |
| 2 | 265 | 720 | 178 | MNIRDLAAQDFLNIVNDKNSGFG VPVVLIAPDGNAQPLSGLTTDISS YIDPETGVLVAGRVASVTFANKAI RAAGFAEMPVAVADSNKRPWVV CFRDPEGIPYLFKVVKAMPDRAIS GIVLELEVYKRSIYFNGAYKFDGT TLYDGVLDLL | 151 | Hypothetical protein orf10T [Vibrio parahaemolyticus phage VP16T] | AAQ964 77.1 | 4e-17 (51/129) | | No putative conserved domains have been detected | | |
| 3 | 717 | 1394 | 179 | MNIEGFKKLQSPINKLDSFEIVRD QIAAILFLELENQKAIAGRAQIDPA RFDMKVYKERSNPWDLFDDGEN KPIINVWFSNSDFDYTNSSTVDK QKTTAIFNIDCIATAISQETATGQT LGDEMASLEVQRVAKVIRNILMS DTNTYLQLRGLVWSRRVLSLNIF QPSAENGMMQNLCAARLVLQAT FSEFSPQYEPQELEILSVTVHNCD GQILFNKEIAKNGN | 225 | Hypothetical protein orf11C [Vibrio parahaemolyticus phage VP16C] | AAQ965 42.1 | 3e-35 (87/218) | | No putative conserved domains have been detected | | |
| 4 | 1384 | 2886 | 180 | MAISTAVDISAVARVLGIKTNFKNL RDGRVVILPQRIALIGQGSTGMVF ATSKRQVTSANEVGSLYGYGSPL HLAAKQLFPNNGDGVGTIPVTVY PLSDADGSQAATGSIELLGTQLE SGAYRVVVNGIRSEQFSILINEAG QTVLNRVAAINSVLDMPVRATA DSELQKVTLVSKWVKGLSANAISV QVDGDLGQGIEFAVTQPAGGLIN PSVSGALSQFGNVWETMVLNCL NIQDTEALSAYSDFGEGRWGALV RKPLIVFTGNTEADVNSAVSVPD ARKRDRTNVQLVAPDSIDLPFVV ASRQLARIVKIANENPACDYGSQ VADGINPGEDGKQWLYNVRDMA VKKGSSTIEIRDNQVFIGDVVTFY HPEGEENPPYRYVCDIVKLQNIIF NLNLIFAVPEWDGAPLIPNDQPTT NPRAKKPSMAVAAIASLVDSLGL | 500 | Putative tail protein orf12C [Vibrio parahaemolyticus phage VP16C] | AAQ965 43.1 | 4e-120 (228/50 1) | tail sheath protein | Mu-like_GpL, bacteriophage Mu tail sheath protein (GpL) | pfam 0627 4 | 3e-26 |

Fig. 4A

| | | | | | | | | |
|---|---|---|---|---|---|---|---|---|
| 5 | 2894 | 3271 | 181 | NAIISDAAFTKKNTFAQINEQNPK RLDVSTTVKLSGNTNILSVDLNFG FYFGNSVIVG MSVGGSIESLTLDGRTFSVAADA DSTRNLGGTDNEVEMNGDGTYR IVKTRVPSKLDGITVAIDDVRGDA EYLQELKDRKEGFPYSITYASGVI YQGTGTIVGETGISSQNATASITIS GSALTKQ | 125 | Hypothetical protein orf13T [Vibrio parahaemolyticus phage VP16T] | AAQ964 80.1 | 7e-28 (65/123) | 2-C-methyl-D-erythritol 4-phosphate cytidylyl-transferase | PRK1 3385 | 0.010 |
| 6 | 3328 | 3774 | 182 | VEHIENTENQTLWGLPVKVAREV AEAEFIRFCDAMDVDYNTDRMTD EDAKDFNESKGLLLDALQIGVLEI DSDGMAVVYPKKGDIKQIKFNEL CGADYVAMDNKKDTQSFAKMFA MMGSITKLPPATFSKLKKFDAKV CLSIAKLFLV | 148 | Hypothetical protein orf14T [Vibrio parahaemolyticus phage VP16T] | AAQ964 81.1 | 2e-07 (41/133) | No putative conserved domains have been detected | | |
| 7 | 4072 | 5565 | 183 | MQSGISRFTRRAESGLRRVSDMT WNISKVSGAAAAAIGGAFMAAAG GIALFVAETNRANSEINEMSKAM GVSALSARAADSLLTPLGMNWE NYTDLIEELGNKMGELKNTGEMK TFQEAIGLTNIKMKELKALKPEQQ FTRIMDSLAKMEDQQKAQFIADEI FGGEGNKFVSALKARGLTMTSLI ENYKKYNFYNEQGEKATAAFNAA LTPLTTANSAKSQIAALTGGAMV PYIQKATEWAAANKELINSKIEVF AKGLADSLVWVVVNFSEIVTWVK RVAIGIGIFLALTAVLKTFVLIMTAV NLVMMNPIGLIIAVVALIAVIAYLI NKFFGLGQVIAAANGVLMGIGAAI LVAMGPIGWLIGAAVLIWKNWGV LSGFFSGLWAGIVSVFQGAQNIIM GIINGIMGAIDNVINKAVSMGSAV KGFFSFGGGGDQKQAAAAGG RVASPQERTAKSVTENNSHSTVT IQDKTGRAKMSGKPGNGVRLVKT GTM | 497 | Hypothetical protein orf16C [Vibrio parahaemolyticus phage VP16C] tail tape measure protein [Phage PY100] | CAJ2846 8.1 | 2e-05 (72/316) | tail tape measure protein | No putative conserved domains have been detected | |
| 8 | 5569 | 6801 | 184 | MSWEDRLKEAAYTAPGGTRATF LVEDVSRSFDKKTNGFTFPDASG TYVQDSGVSGFKYPLTIYFSGPD CDVEAEAFEALLRETGIGRLEHPL YGVINVVPFGTITRTDAIKTEANQ TKIELEFWETNLLYPLPQADQLS AVFFEAISDVKAALSGDVLDSIDVT DASALARFKNKITGALSKVKTALG KIKNLADLPGQLMDKVNGLISPGL | 410 | Hypothetical protein orf17T [Vibrio parahaemolyticus phage VP16T] | AAQ964 84.1 | 4e-59 (153/419) | Mu-like prophage DNA circulation protein | COG 4228 | 8e-08 |

Fig. 4B

| | | | | | | | | | |
|---|---|---|---|---|---|---|---|---|---|
| 9 | 6794 | 7990 | 185 | EFISDVKAQLGDVVNSFFELATLP EQIVDSFKEKIAYYKDLFSELTSFE GIFPSNEEYEAACTGVTVTLSGLV VDLVESEFNTQSEALEAAEDLLAI FDDVTGWIEEKAQGLGRTDSNAV YQRLHSAVMTAASYLVQQSFTLK KERKLVLNRSRTIDLCAELYGEV DSALDFFITSNDLSGAEILEIPKGR EVFYYV MSDVSMIHGTRFHFWSGVRISL NIDAVATISFNAPFDHEAPGFKRN FAPFGFSPVAIDVDDQRLFTGTM LDVSPVISEDGKKEISVNAYAKCG VLQDCTAPPESMPLEFNKLNLLDI ARKMASYFGVGVVFNADPGPAF DRVACDPDKKVLEFLADLAKQRG FVIGSDENGNLLFSKSSIGGIVAKL EQGVSPLLSVSPTFNPQEYYSHIT GLSPVEVAKPAAKSTAKVKDAA TPEKAGQGSEKATDKAGQAEIKK EPKKEEKTKKEKQKPKPTTYKKF TAIDEAPVYRPLVFKIDDAEGATD VETATKAKMARMLGNIMCTYAITV STWFDASGDLWRPNTKIKLKAPD SMIYDFFEFDIKSVELSADENSQQ ANLTLCLPGSFTGEPPEIFPWEL | Putative tail protein orf18C [Vibrio parahaemolyticus phage VP16C] | AAQ965 49.1 | 2e-57 (130/39 6) | tail protein | Mu-like tail protein gpP | COG 4379 | 2e-17 |
| 10 | 7978 | 8463 | 186 | VGIVATVLSNDGKDLKVDRGNGD NVTAQQFGPSGDDAPPLKNDYS VLGSAKGSGNASAVAYRDQKAE NYIAKAGEKRIYSRDESGAVKAEV YLKADGTAEIKNASGLFVMEPGG DVVINGVRITKAGVMQTPGGASMS SDFTNAGGITLGDHAADTSLHKP | Hypothetical protein orf19C [Vibrio parahaemolyticus phage VP16C] | AAQ965 50.1 | 4e-08 (38/105) | | No putative conserved domains have been detected | | |
| 11 | 8480 | 9217 | 187 | MSFFDVHLFDSVDGGNVTDDLET RDGLETAVYLSLFGGNALDDGRP QNLSTWWGNIGENEAAKQYKSE AAFLLRTVPPNTANLKRIEAAASR DLAWLIPEYNKIQVKAFMPKLNA VNLTVSLDGLDPLQFRTNWGEKV KEPVYRLLPPKVSRNNGVNLEGT AETKTKLILIRADGSRLSTLVDGS GNWKFDFYPLYGGERARMYVEG VGGKISAIVTVIGVLPLRYDGMAIY DGTHKYNGVRLN | Hypothetical protein orf21T [Vibrio parahaemolyticus phage VP16T] | AAQ964 88.1 | 7e-17 (51/124) | | Mu-like protein gp46 | COG 4381 | 5e-05 |
| 12 | 9217 | 10380 | 188 | MSTPTTKEISNRILSKLETTFGQS LPKSFTRVLSTVLGGVFVILYKYG GFIALQMFVSTASAKDTDFNGKTI | Hypothetical protein orf22T [Vibrio parahaemolyticus phage VP16T] | AAQ964 89.1 | 4e-68 (159/39 | baseplate protein | P2 baseplate J-like protein | pfam 0486 | 3e-12 |

Fig. 4C

| | | | | | | | | | | |
|---|---|---|---|---|---|---|---|---|---|---|
| | | | | NPLREWGRLIGAGDPNPAVNAIL TRIVVEKPGEILPAGTQLVNSGNG VTYTQEDIELVEGAQDIEVLAASD TSGNSGAGKAGNLNAGDVLTFA NPLGSVGRYSTVTTIREGLDAE AIETYRARVVSRFQLRAQGGAMV DYKIWGESVSGVSRIYPYTSDLP GQVDIYVDVLEGVASQAILNQVK NAVEFDANNGLAQNRPLNALVNY LPMEFVEFNVTISGLSVEGALSVR AEIRAALEHYFNIRAPYIVGLSTDS RADRITLAAASGVVDDVVNKAGG IFNDMQLFKGQTPISFYMLGIGEK ATLVNVEYL | | phage VP16T] | | 2) | | 5 | |
| 13 | 10382 | 11101 | 189 | MNMFKHLLPSGRAWNLTAEKPL KAFFRCLDVLRTDAVNYFNLLFLD INPKTTRLLDQWEQGFGINRGFL TEAQRRERVAAAWRDVGGQSPA YIQEVLRNNGFDVYIHEWFDPAD RGEVGEKQPITPRNPLSIMSAQY AEVLPVVDCGEPLALCGEEFAHA GNYLGLVGYPLVNKFVYDADKYG YTYPVDPAYWYHFFVYCGPNFG DVAQVEATRRAEFEAULRIKPAH LWAGVIVRYV | 239 | Hypothetical protein orf23T [Vibrio parahaemolyticus phage VP16T] | AAQ964 90.1 | 2e-45 (101/242) | Uncharacterized protein conserved in bacteria (DUF2313) | pfam 1007 6 | 1e-09 |
| 14 | 11103 | 11705 | 190 | MSLVFNEKFPGKTAGATQNYPY GEARNVSGPGNGDGTPWDAALV NDIFGLLQGLLVRANIQPNGQSDT ALNSQYLQALLALFMPKQTPISGK LEGNGYLTIPFPVVINGQTVEREF TIQWGSKDWSSYPGEIQDSIVFE KPFKTACFGVFPIRKMSQHSAYG DGGVKPISVSKTGFTVSLQAYGG SVGHLLGYYWFAVGV | 200 | Putative tail-fiber protein orf24C [Vibrio parahaemolyticus phage VP16C] | AAQ965 55.1 | 1e-13 (46/108) | tail-fiber protein | No putative conserved domains have been detected | |
| 15 | 11765 | 12151 | 191 | MEPISTGGTAAFLKVYGWLAVV TALVFVATVVLMMRLPRSPQEFL VGIITTVVSSLMGGSFLILYFDLQI WANSAYGLMVIGGLYFVAGIPGW ALVRWVFNFIDAREGSTLLDIFRE FNEEFRGGKK | 128 | Hypothetical protein ACICU_01067 [Acinetobacter baumannii ACICU] | YP_0018 45726.1 | 2e-33 (66/121) | | No putative conserved domains have been detected | |
| | | | | | | Hypothetical protein PAJU2_gp73 [Pseudomonas phage PAJU2] | YP_0022 84407.1 | 2e-07 (27/75) | | | |
| 16 | 12148 | 12696 | 192 | MSKIIIAICAGHSDKDPGAVNGKRT EAAIVLDMRKMVASYLEKAGVKY LTDGKGGVNQPLAEAIKVAKQASI AVEFHCNAATSKKATGVEVLSAE | 182 | N-acetylmuramoyl-L-alanine amidase [Psychrobacter arcticus 273-4] | YP_2637 37.1 | 1e-44 (88/173) | N-acetylmur amoyl-L-alanine | N-acetylmuramoyl-L-alanine amidase or MurNAc-LAA | cd026 96 | 7e-20 |

Fig. 4D

| | | | | | | | amidase | | |
|---|---|---|---|---|---|---|---|---|---|
| | | | | | | | | endolysin | |
| | | | | KNKALAKQIAAKINGVLNPLRGE SGWKSEGSGQHSRLGFISSGGG LIVELFFISNDDDLAKWDAKKWLV AKEVAAVLIEQVKKAEAA | | PlyB054 [Listeria phage B054] | YP_0014 6873Z.1 | 5e-07 (46/171) | |
| 17 | 12697 | 12954 | 193 | MAALTIFNAISEVTSFAGVAREIFD TAANAMDAAQNEKKGGGNKKV WVMAYMESFINDLGENWERWAK AIFSFIDFAKSIFNSKR | 85 | No significant similarity found. | | | No putative conserved domains have been detected |
| 18 | 13318 | 13079 | 194 | MRNTADKSTIDFIEETTGDAYKPV KGCGTVRGYKAGCACNNCHKAQ IGRMADKIVKAALRTRIKSSEPTH QPKEQAWNF | 79 | No significant similarity found. | | | |
| 19 | 13809 | 13393 | 195 | MTKTELKTAIIEFSALTTLQVAGQF SIEELTGLKTHLNGQREALLMDKA PAHIKGEKEAKINAQLSDVNNLIK KANKAIGLIQVNQAELKQSKVKQ DTHFLSTFHDVAQSYLTNELYAD LKQKALNVMRIAKANGKNID | 138 | No significant similarity found. | | | No putative conserved domains have been detected |
| 20 | 14092 | 13865 | 196 | MSETTNLFNPDALDANFFYENSG QALAAALDPIEKCVLEKALKYSKY NIAEVSRILGINRLTVIKMKKHGL TEI | 75 | No significant similarity found. | | | No putative conserved domains have been detected |
| 21 | 14306 | 14076 | 197 | MKQPVIQRQQLSNFSQETANHG AKIKEILSTLFFCFMLAALSYMFIIK QADEIDKQAEFVAEYNAQFKEYP NERNH | 76 | No significant similarity found. | | | |
| 22 | 14582 | 15553 | 198 | VKKFNTKFKQNLDDANNNAFIPN SFQITNAFVDNIMDKISDAAVKIYLI TVRKTTGWGKQIDSISLSQYEAY SGKSRPTVVKCLKELVKVGLLVE HTGTRYGNSYSVALVNSIGFELLS ASKKILLVKSFNYTSKKSLLPLVKI FNTQKQLSKNTNQKQINKRDWFS LKTLKDELFKTGLQIEAEDLTAAK WFDREKTAFENYAPNQNLSDPQ KMYYFVDWLLKAKRKYDAAERQ QAAKAKAEGKNQNQNPEDTKTE NDPFKLSTKQISFFASQLAHLPSF AKYCTGNKGFKEFEMWIASMLN NPENVKKWNKYLNELGYLIG | 323 | Hypothetical protein ACICU_02758 [Acinetobacter baumannii ACICU] | YP_0018 47417.1 | 9e-48 (136/365) | No putative conserved domains have been detected |
| 23 | 15572 | 15802 | 199 | MKISNFHFQMQILLLISKNTVLDFE GLKEKLAPSITDNALTECLEELLM WGWVQVQKGLYMVSGVAYQIM | 76 | No significant similarity found. | | | |

Fig. 4E

| | | | | | | |
|---|---|---|---|---|---|---|
| 24 | 15843 | 16067 | 200 | MEKYKYSESNAVLSPHLNCGLTS VSRVGSSGQAKHKPHKRSEIADQ AEKEICKNWALRQQAFLNNSVSN AVLGG | No significant similarity found. | |
| 25 | 16069 | 16590 | 201 | MNKFIHIEGKPTAQQVREALAMY AKDIKRPEFSLIVQRELIESFRNDT AHALKSAVAFYFKNRVIQRPGLVL ASGKDQALIVESCENKALKRHLV AVSGYSSQFLQMVIDHKTPLSAV AARDLKQALPKAEKLYKAECKEK DAKLKKNICGFVACYRNGCHCTK CTTAYKKYR | No significant similarity found. | | No putative conserved domains have been detected |
| 26 | 16721 | 16912 | 202 | MGVSIINLVLLVGVCLLLTNIALNC LFHTENKTYLVYACGFSAASVAG AIAGVIGCLAYGVTV | No significant similarity found. | |
| 27 | 16912 | 17187 | 203 | MKNKSILMGLFVAAAGVVFYMGA DSACNQKAVIDPGALMSLGGITV ENKKASLVRVCDTPVKENLVSFV LIKDGLRVGGVVDKSHVALIGE | No significant similarity found. | | No putative conserved domains have been detected |
| 28 | 17188 | 17355 | 204 | MSLGKRPAGATHESDGTYWKN EDADWYFWRDLWGWCQYVGPK NRNFLNKFSVLG | Hypothetical protein ACICU_02216 [Acinetobacter baumannii ACICU] | YP_0018 46875.1 | 4e-04 (23/49) |
| 29 | 17355 | 17540 | 205 | MDLYIGQIVGHSSPTWVVQGKLKI TKINEGKRSGLKITATDESGKEFT AVYGVFFSVDRY | No significant similarity found. | | No putative conserved domains have been detected |
| 30 | 17561 | 17968 | 206 | VRNENFEDYLKQTDDYAVLLNNY GSSLFHENGVYRALPVRVAYAA WVSGGDRWGEVQIHLKGKIKKMA ERAAETADFYHTKIEKLESSTVKK AGLLDMAEQWDGLELRGRDLEL NRVQESIYKRCAYLLRVAVNG | No significant similarity found. | | No putative conserved domains have been detected |
| 31 | 17961 | 18461 | 207 | MGNRWTLSGKVKGLKDLPESITA AQFREMIERGQVKNTPQAPKKR RSGKVSSPGEATLAQALKALKIEF VQEYRFCEYRKWRADFHIPGTNL LIEVEGGVRSGGRHVRPQGYIND TEKYNEAAKLGFVVLRFDTETVS RGTAINEIESYLERRGYFQNKGLT CEES | Conserved hypothetical protein [Acinetobacter calcoaceticus RUH2202] | ZP_0605 7626.1 | 6e-29 (68/112) | No putative conserved domains have been detected |

Fig. 4F

| 32 | 18448 | 18720 | 208 | VKKVKFKYDWRAVPDHINWLAT YEGGEMAWGYNKPYRKENAGI WYETGEWRHRVPVAPYRGHW TQSLEKRPSKAQLVEWVLNGAVV V | 90 | No significant similarity found. | | No putative conserved domains have been detected |
|---|---|---|---|---|---|---|---|---|
| 33 | 18896 | 20953 | 209 | MAENSFIQPIARKDAIALIGRDELV EGGPEGAANKQAIALANNIKYLM GLIPENWGVEKTEYGLDEVVRLS NGDVVKSVIDENINNPNENLSGW SFVTSNSVNTISDLLSIKNPKNGM KVYVLGYHKPDNFALLSPYEGGG LFIYSGNKAAENDGGVVLNGWIR QYVGDVDISWFGAKQGQDASPFI EAALKVKMSIVIRGEYKLETICGIP RQNNYAAKVIRIKGENQASLTVN CPDGAVFTSLDAKANPTSLSNIFT AKIDVFGINFVGTTVANSVLFNGD RLYNINIHHNNFKTNITIVKAYLKR EASRQYTQSVSININHNHLAEIHRVI ESDKSYNFDFAYNMCEACKGGM YIGVDAPYDPSGISITIHRNLWEA SGVLLKTNGGIIAGSVSKNYFEAN VYQDAAIDKCLIYINRSGTGAGYS GGLTFENNLFSGTSSIPDYVDVR VLGQSTETSGNSKSATTRPPVFI GNWSNSYMLTNMAQAILIGNKCS NREKMLNAYSPQEARVTYYSGY FTKQLANILTDKKLNLLKVNTSAV HAIGSSQANFKTTLDVIVFFKTSG AVGTAMIATFKLDLFYYESVGLGA GNVPKANLKAVMYNFMQSTADD KITPTVNMFSAISDPLINVVDNSD GTYSIELSSFTNKSSPNWGFVSE LHIEYTAQATLIASHTSSYSAANLL TIS | 685 | No significant similarity found. | | No putative conserved domains have been detected |

Fig. 4G

| | | | | | | | | |
|---|---|---|---|---|---|---|---|---|
| 34 | 21027 | 21707 | 210 | MFDIDTKQLHGLERRLERLNRRG LPYATRQTMNDLAFESRAVARAE LPTRMVLRNKHAINSKVTKATSL NISQQAAHVGSTADYMATQETG GIKTKQGGAAVSIPTTTAAGQGR NAKPRTRLPRAALKMGAIHLKRIA ASRNAKNRKQRNAIAMATSDKYV FLDLGRRKGIFRKDKGGGVTMLH DLTRASVQIPKNEWLKPATEAAE RKLPGFYGRALEFQLRRF | 226 | Hypothetical protein orf62C [Vibrio parahaemolyticus phage VP16C] | AAQ965 93.1 | 7e-29 (86/232) | No putative conserved domains have been detected |
| 35 | 21993 | 22844 | 211 | MVKKLISRSDFAAKAGVSGAAISK ACKGPLLDAVEGKFIDLNHKSAIA YLESKKNGKTTPALEGIDSLYEEA LEVCREAGRCSQTLLRDKLMIGS DRARKLVALIQNANICDFEKPAAE KVKREEKARPHTRGTAAKKQQAI QEDDEELFELLDRNVAQYADMTL RDIVRKFGTATRFAEYLRAMKEIS MIEDREIKIAQTKGELVHRDLVSQ LIIEPIDSAHVKLMRDGSKTIAVRM AAMHGSGADINEMQLVTSELIAS FIKPVKAKVNKIATELKRGAEA | 283 | Hypothetical protein orf2T [Vibrio parahaemolyticus phage VP16T] Likely small subunit of terminase | AAQ964 69.1 | 2e-07 (35/121) | small terminase subunit | Ftsk_gamma, directs oriented DNA translocation and forms a winged helix structure | smart 0084 3 | 0.005 |

Fig. 4H

| | | | | | | | | | |
|---|---|---|---|---|---|---|---|---|---|
| 36 | 22847 | 24826 | 212 | MNFIGMDWLCDKVENLTEYIKHV TPSQFNEENRYLPESVTSIPGFIR YDVNPFMREIVDCFDINSPVREV NLKKGVQITYSTVLESGALYMG HVKTLPIMYMTADKELAKARIENN FIPMLAQSDMAHIVRSSDEGNSR KTGKTDNHQFEGGGYLVPFGAI NANKMRSFSIAVMLKDEIDAWPD RVGKDGDPDKLSDDRCSAYWER RKIFRGSTPLIKGSSKIEKAYLRG DQRKYHVLCKKCSFPQELRWST PDGVGGFKWDTDEDGILKLDSVR YCCQQCGEPHFEHDKERLFSEK FGAKWIPTARPVEPGIRSYHLPAL YSPFGMQPWYKCVIAVLDAFDPV ERKVKDIELYQVFYNNVLAEPFEI QGAKVRFETVSHHRRTVYRLGHI PNRYAVQYAGSPILFLTCQVDVH KSFLAVSVMGWAKDAKCFVIDYL RIEGEDFSDSAEPGWGKLRELIE EKQYIADDGKKYRVALTFIDSGYA NDTVVKFCSEYSSSVYPILGRDR PSKNQAIKEFADFKTQEGTTGFRI IVDHYKDRLAPVLRREWDEMGG GLQPVYHFNAPVDLSDKSLKELT VETRKEKTDASGNTSYFWHRPG NARNELWDILCYGHAAVEIFAWS LCVKNMEQKEVDWAWFWEFLET EAPYFEQGEPVASE | 659 | Putative large terminase subunit orf3T Vibrio parahaemolyticus phage VP16T | AAQ964 70.1 | 4e-127 (252/65 6) | large terminase subunit | Phage terminase large subunit (GpA) | pfam 0587 6 | 1e-69 |
| 37 | 25079 | 24870 | 213 | MQYENNLEKLKGNKPEGATIVAV KGDRIAYFKEAEQKGRLLTFNRIM WVKTWFTPDHLNLKHFDFIAVL | 69 | No significant similarity found. | | | | | |
| 38 | 25316 | 25092 | 214 | MNNQSFNNWRGHKIEIVQAGATI QQHGYPVQITDQNTIAFDGKIYMT QNTYNSIAKNMPQCQTPNFNNQ GLNIF | 74 | No significant similarity found. | | | | | |
| 39 | 25582 | 25334 | 215 | MIDKYLVFGGWVRSKHDKQSH YVAPRMVAYLYNVNPHECIFITDK TELNPRTHLPYGLNEHNHLIKLGP QTNGKYNLPATN | 82 | No significant similarity found. | | | No putative conserved domains have been detected | | |

Fig. 41

| | | | | | | | | |
|---|---|---|---|---|---|---|---|---|
| 40 | 25770 | 25579 | 216 | MGQSEARQKQKSDYEKKRVIKN FSLLKERDKHLIEYIETVPNVGDL VRDLLNQHLKNEAVSKK | 63 | No significant similarity found. | | | No putative conserved domains have been detected |
| 41 | 26098 | 25883 | 217 | MLMGNTQVKTPRELTKPLKKILG PEYKVKRDVWLMVEGKNLNEAK RIIESIGLFANDMGGFLTVFMAEE M | 71 | No significant similarity found. | | | No putative conserved domains have been detected |
| 42 | 26286 | 26540 | 218 | LDQAFLKERIEATKRQIVAYEDAV NQLSSGAVQSYSLNTGQTTQNV TRFDVARLNGDIDGLYNRLATLEA RLNGSGSTLVRPGW | 84 | No significant similarity found. | | | No putative conserved domains have been detected |
| 43 | 26544 | 28217 | 219 | MNYDFSRGLVKVPTVGLKTEFKY SGATIAPPPMQGAKSDAIEINALG GGFNHSAFTGEKFIGGFGPTSLF TMDYWTLRKRSEQLFSENLYAA GLIERLVTNEINTGLTPEACPDERI LGLKPGDLEDWTELVENRFSIWA NSSEYCDFYGQNSLGEIQRIARR EALICGDVLVLRQNQSTKMPQV QLVSGSLIRTPPDIPRKGHKIKHG VELDTQGRQCAYWVLQDDGTYK RLPAFGEKSKRRIAWMVYGAQR RLGELRGQPLLSIVLQSLKEIDRY RDAAGRKAVVNSILAMFIEKTQDK MSTLPTGGAIRRDKVTDNSNTAA PRSFEIASQVPGVVLQELQAGEK PVGFHSQGTDINFPAFEEAVISAV AWCKQIPPEILKLSFSSNYSASQA AINEFKIYLNMVWNEWGANFCQP IYTEFLISEALLGKIDAPGFLDAWR DPVKMDIFGAWLWCDWFGSIKP STDMRKMGQGLALAVEQGWTTN AQASRQMFGTKFTKNIARQRRER ELQASLLRPMLELQKEYGISAEHL VNVAHAIGGTISAQTEETEEI | 557 | Putative capsid protein orf5T [Vibrio parahaemolyticus phage VP16T] | AAQ964 72.1 | 4e-96 (186/48 7) | portal protein | Portal_lambda, phage portal protein, lambda family | TIGR 0153 9 | 1e-25 |
| 44 | 28217 | 29368 | 220 | MDWFLTPEALKEIQELHARGLVL TAEQMTEFNALYSDDFPGSRIFQ KVGTVAQVNIAGVLTKEPNWMYR YYGGGNTAYSEIISAINEAERDPAI KEIILAIDSPGGQTNGLCSAMDAIK NTKKTVLAVVEGQAASAAYGLAS QANKIIAADRGCMVGSVGAAASIV | 383 | Putative protease orf6C [Vibrio parahaemolyticus phage VP16C] | AAQ965 37.1 | 1e-46 (137/36 8) | Clp_prote ase | Clp_protease_like superfamily | cd003 94 | 1e-07 |

Fig. 4J

| | | | | | | | |
|---|---|---|---|---|---|---|---|
| | | | VSENVVDIASTNAPKKRPDVTTD AGKAVIRETLDQIESIFIADIAAGR KVTADKVKLEFGQGGMYVAAHA LERGMIDEIKTADSSATTNAKSSA TYTASEENSTMDAATLKAQFPAV YTAIYNEGKTAENERVSAHLTLGE ASGDMQTAISAINDGSELTASIQA KYMAANMKRGQVAGRETDDTAA ANALDGVKPGATATDANAVTNM VAKNLGVA | | | | | |
| 45 | 29414 | 29803 | 221 | MMQVTQHTNSSINWGEVACQDD TLTLGANATLKEGTILARAATGKLI PVKGGADGAGVPVAIAMHEIKT VAAGDVSVRAGISGQVRKNNLVI HADGNATNIDGAVTDALRSYGIV AFTVNSTNKFPDNQ | 129 | Hypothetical protein orf7T [Vibrio parahaemolyticus phage VP16T] | AAQ964 74.1 | 1e-06 (38/106) | No putative conserved domains have been detected |
| 46 | 29818 | 30903 | 222 | MTTSTIAGYYTQVAPKPLFLSGFF KAPPQNHFNTESVELDIERDSOQ VAAVVQSLGSDYNKNETGEFTNK KFTPPVYKEGFSLNAFDLLKREA GQSGFNTPSEQIRGNLITRFIKGA RKVEAKILRGIELQASQILQTGNLL LKDQEGKDAFKIDYKPKATHFVN VANVWTGANADPMKDLESLSEVI QTDGLVIPDIIIMGASALAAAKGNE KFIKNFDSRNISGNVLADMQITAR GGIYQGTLRVGNAVCELYTYGVG YQASSAVATPFLNTNKYVLMLSS ESOLDALFGAVPNIADILGVSLRE QLLPELPTRFDSNSTDLFTNVYLS ASGEQLMGGVASRPILVPTAIDSF GCLTVA | 361 | Hypothetical protein orf8C [Vibrio parahaemolyticus phage VP16C] | AAQ965 39.1 | 4e-57 (133/347) | No putative conserved domains have been detected |
| 47 | 30912 | >31076 | 223 | MNPLQWGFFLNLEIFDVTKTDLI NAIKAIDSNAKTSGLDKDELQALL TELQAKA | 55 | No significant similarity found. | | | |

Fig. 4K

Fig. 5B

| orf | Putative function | orf | Putative function |
|---|---|---|---|
| 105 | Protease inhibitor | 169 | postulated decoy of host sigma70 or sigmaS |
| 107 | EndoVII packaging and recombination endonuclease VII | 171 | DNA helicase |
| 108 | anaerobic ribonucleotide reductase subunit | 175 | DexA exonuclease A |
| 109 | anaerobic nucleotide reductase subunit | 178 | MotB modifier of transcription |
| 113 | glutaredoxin | 179 | modifier of suppressor T4 tRNAs |
| 126 | alpha-glucosyl-transferase | 180 | RNA metabolism moderator |
| 127 | recombination endonuclease subunit | 184 | DNA topoisomerase subunit |
| 130 | recombination endonuclease subunit | 186 | membrane-associated affects host membrane ATPase |
| 132 | RNA polymerase binding protein | 187 | rIIB protector from prophage-induced early lysis |
| 133 | sliding clamp DNA polymerase | 189 | endonuclease IV |
| 134 | clamp loader subunit, DNA polymerase accessory protein | 196 | Nucleoid disruption protein |
| 135 | clamp-loader subunit | 197 | acridine resistance protein |
| 136 | RegA translational repressor protein | 198 | DNA topoisomerase subunit |
| 138 | DNA polymerase | 201 | activator middle promoter |
| 140 | immunity to superinfection membrane protein | 206 | inhibitor of McrBC restriction nuclease |
| 141 | dCMP hydroxymethylase | 208 | AsiA anti-sigma 70 protein |
| 142 | Endodeoxyribonuclease | 209 | holin |
| 144 | RecA-like recombinase protein | 210 | tail fiber protein |
| 145 | head vertex assembly chaperone | 211 | tail fiber protein |
| 146 | DNA primase-helicase subunit | 212 | hinge connector long tail fiber |
| 147 | discriminator of mRNA degradation | 213 | tail fiber hinge |
| 151 | spackle periplasmic protein, lysis regulation | 214 | proximal tail fiber subunit |
| 154 | primase | 215 | Ribonuclease H |
| 156 | dCTP pyrophosphatase | 216 | dsDNA binding protein |
| 159 | small outer capsid protein | 217 | late promoter transcription accessory protein |
| 162 | affects phosphorylation of host sigma32 | 218 | loader of Ori146 DNA helicase |
| 163 | postulated decoy of host sigma32 | 219 | ssDNA binding, DNA repair, recombination and pre-synthesis |
| 167 | adenylribosylating enzyme | 225 | dihydrofolate reductase |
| 168 | adenylribosylating enzyme | 227 | thymidylate synthase |
| 228 | I-TevI homing endonuclease | | |
| 229 | thymidylate synthase | | |
| 232 | ribonucleotide reductase A subunit | | |
| 233 | ribonucleotide reductase B subunit | | |
| 234 | endonuclease II | | |
| 235 | RNA ligase | | |
| 236 | inhibitor of host transcription | | |
| 241 | dN 3'phosphatase | | |
| 248 | dCMP deaminase | | |
| 251 | head assembly cochaperone | | |
| 252 | rIII lysis inhibition accessory protein | | |
| 261 | DNA ligase | | |
| 263 | adenosyltribosyl-transferase packaged protein | | |
| 264 | Alt RNA polymerase ADP-ribosylase | | |
| 266 | base plate-tail tube initiator | | |
| 267 | base plate | | |
| 268 | baseplate hub subunit, tail length determinator | | |
| 269 | base plate distal hub subunit | | |
| 270 | base plate hub subunit | | |
| 271 | base plate hub assembly catalyst | | |
| 272 | baseplate hub subunit | | |
| 273 | baseplate wedge subunit | | |
| 274 | recombination, repair and ssDNA binding protein | | |
| 277 | RNA-DNA and DNA-DNA helicase, ATPase | | |
| 278 | RNA-DNA and DNA-DNA helicase | | |
| 279 | minor capsid protein | | |
| 280 | outer capsid protein Hoc | | |
| 283 | RnIB RNA ligase 2 | | |

Table 5 - Features of phage F488/08 gene products and assignment of putative functions.

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 1 | 1232 | <3 | 224 | MAKINELLRESTTTNSNSIGRPNL VALTRATTKLIYSDIVATQRTNQP VAAFYGIKYLNPDNEFTFKTGAT YAGEAGYVDREQITELTEESKLT LNKGDLFKYNNIVYKVLEDTPFA DIEESDLELALQIAIVLLKVRLFSD AASTSKFESSDSEIADARFQINK WQTAVKSRKLKTGITVELAQDLE ANGFDAPNFLEDLLATEMADEIN KDILQSLITVSKRYKVTGITDTGFI DLSYASAPEAGRSLYRMVCEMV SHIQKESTYTATFCVASARAAAIL AASGWLKHKPEDDKYLSQNAYG FLANGLPLYCDTNSPLDYVIVGV VENIGEKEIVGSSIFYAPYTEGLDL DDPEHVGAFKVVVDPESLQPSIG LLVRYALSANPYTVAKDEKEARII DGGDMDKMAGRS | 410 | Gp24 precursor of head vertex subunit [Enterobacteria phage RB14] | YP_0028545 09.1 | 0.0 (410/410) | precursor of head vertex subunit | Major capsid protein Gp23 | pfam0706 8 | 5e-13 |
| 2 | 2881 | 1316 | 225 | MTIKTKAELLNKWKPLLEGEGLP EIANSKQAIIAKIFENQEKDFQTA PEYKDEKIAQAFGSFLTEAEIGG DHGYNATNIAAGQTSGAVTQIGP AVMGMVRRAIPNLIAFDICGVQP MNSPTGQVFALRAVYGKDPIAS GAKEAFHPWYGPDAMFSGQGA AKKFAALKASDTLEVGTIYTHFFQ ETGTVYLQATAAKQIDSGASDAD KLDAEIKKQMEAGVLVEIAEGMA TSIAELQEGFNGSTDNPWNEMG FRIDKQVIEAKSRQLKAAYSIELA QDLRAVHGMDADAELSGILATEI MLEINREVVDWINYSAQVGKSG MTLTPGSKAGVFDFQDPIDIRGA RWAGESFKALLFQIDKEAVEIAR QTGRGEGNFIIASRNVVNVLASV DTGISYAAQGLATGFNTDTTKSV FAGVLGGKYRVYIDQYAKQDYFT VGYKGPNEMDAGIYYAPYVALTP LRGSDPKNFQPVMGFKTRYGIGI NPFAESAAQAPASRIQSGMPSIL | 521 | Major capsid protein (g23) [Enterobacteria phage T4] | AAA32503.1 | 0.0 (503/521) | major capsid protein | Major capsid protein Gp23 | pfam0706 8 | <1.0e-180 |

Fig. 6A

| | | | NSLGKNAYFRRVYVKGI | | | | | |
|---|---|---|---|---|---|---|---|---|
| 3 | 3709 | 2900 | 226 | MLKEQLIAEAQKIDASVALDSIFE SVNISPEAKETFGTVFEATVKQH AVKLAESHIAKIAEKAEEEVEKNK EEAEEKAEKKIAEQASKFLDHLA KEWLTENKLAVDKGIKAELFESM LGGLKELFVEHNVVVPEESVDVV AEMEEELQEHKEESARLFEELNK RDAYINYVQREVALSESTKDLTE SQKEKVSALVEGMDYSDAFSSK LSAIVEMVKKSNKDESTITESINT PDTEAAGLNFVTEAVEDKSAQG AEDIVSVYAKVASRF | 269 | Gp22 prohead core scaffold protein [Enterobacteria phage RB51] | YP_0028541 29.1 | 9e-147 (268/269) | prohead core scaffold protein | No putative conserved domains have been detected | |
| 4 | 4378 | 3740 | 227 | MNEPQLLIETWGQPGEIIDGVPM LESHDGKDLGLKPGLYIEGIFMQ AEVVNRNKRLYPKRILEKAVKDYI NEQVLTKQALGELNHPPRANVD PMQAAIIIEDMWWKGNDYYGRA RVEGDHGPGDKLAANIRAGWIP GVSSRGLGSLTDTNKGYRIVNE GFKLTVGVDAVWGPSAPDAWVT PKEITESQTAEADTSADDAYMAL AEAMKKAL | 212 | Prohead core protein protease [Enterobacteria phage T4] | AAA32501.1 | 1e-120 (212/212) | prohead core protein protease | Peptidase _U9, prohead core protein protease | pfam0342 0 | 1e-104 |
| 5 | 4803 | 4378 | 228 | MLLIPETHELVENVEALIPEAQG RFDELSSALNKDDINTIVENMLD DETDLAVALASINENMPLNEFIVK HVSARGEITRTKDRKTRERNAFQ TTGLSKAKRROIARKATKTKIANP AGQSRAQRKRKKALKRRKALGL S | 141 | Gp68 prohead core protein [Enterobacteria phage T4] | NP_049784. 1 | 8e-75 (141/141) | prohead core protein | No putative conserved domains have been detected | |
| 6 | 5042 | 4803 | 229 | MEGLIEAIKSNDLVAARKLFAEA MAARTTDLIKEEKIAIARNFLIEGE EPDDEDDDEDEDSDDKDDKKDK DSDEDEDDE | 79 | Gp67 prohead core protein [Enterobacteria phage RB51] | YP_0028541 26.1 | 2e-19 (50/51) | prohead core protein | No putative conserved domains have been detected | |
| 7 | 6616 | 5042 | 230 | MKFNVLSLFAPWAKMDERNFKD QEKEDLVSITAPKLDDGAREFEV SSNEAASPYNAAFCITFGSYEPG MKTTRELIDTYRNLMNNYEVDNA VSEIVSDAIVYEDDTEVVALNLDK SKFSPKIKNMMLDEFSDVLNHLS FQRKGSDHFRRWVVDSRIFFHKI IDPKRPKEGIKELRRLDPROVQY VREIITETEAGTKIVKGYKEYFIYD TAHESYACDGRMYEAGTKIKIPK AAVVYAHSGLVDCCGKNIIGYLH RAVKPANQLKLLEDAVVIYRITRA | 524 | Gp20 portal vertex protein of head [Enterobacteria phage T4] | NP_049782. 1 | 0.0 (524/524) | portal vertex protein of head | Bacteriop hage T4- like capsid assembly protein (Gp20) | pfam0723 0 | <1.0e-180 |

Fig. 6B

| | | | | | | | | |
|---|---|---|---|---|---|---|---|---|
| 8 | 7191 | | PDRRVWVYDTGNMPARKAAEH MQHVMNTMKNRVVYDASTGKIK NQCHNMSMTEDYWLQRRDGKA VTEVDTLPGADNTGNMEDIRWF RQALYMALRVPLSRIPQDQGG VMFDSGTSITRDELTFAKFIRELQ HKFEEVFLDPLKTNLLLKGIITED EWNDEINNIKIEFHRDSYFAELKE AEILERRINMLTMAEPFIGKYISH RTAMKDILQMTDEEIEQEAKQIE EESKEARFQDPDQEQEDF | 6700 | 231 | MFVDDVTRAFESGDFARPNLFQ VEISYLGQNFTFQCKATALPAGIV EKIPVGFMNRKINVAGDRTFDD WTVTVMNDEAHDARQKFVDWQ SIAAGQGNEITGGKPAEYKKSAIV RQYARDAKTVTKEIEIKGLWPTN VGELQLDWDSNNEIQTFEVTLAL DYWE | Gp19 tail tube protein [Enterobacteria phage T4] | NP_049781.1 | 1e-91 (163/163) | tail tube protein | T4-like virus tail tube protein gp19 | pfam0684 1 | 1e-83 |
| 9 | 9287 | | | 7308 | 232 | MTLLSPGIELKETTVQSTVVNNS TGTAALAGKFQWGPAFCIIKQVT NEVDLVNTFGQPTAETADYFMS AMNFLQYGNDLRVVRAVDRDTA KNSSPIAGNIEYTISTPGSNYAVG DKITVKYYSEDVETEGKITEVDAD GKIKKINIPTAKIIAKAKEVGEYPT LGSNWTAEISSSSSGLAAVITLG KIITDSGILLAEIESSAETAMTAVDF QANLEKYGIPGVVALYPGELGDK IEIEIVSKADYAKGASALLPIYPGG GTRASTAKAVFGYGPQTDSQYAI IVRRNDAIVQSVVLSTKRGEKDIY DSNIYIDDFFAKGGSEYIFATAQN WPEGFSGILTLSGGLSSNAEVTA GDLMEAWDFFADRESVDVQLFI AGSCAGESLETASTVQKHVSIG DARQDCLVLCSPPRETVVGIPVT RAVDNLVNWRTAAGSYTDNNFN ISSTYAAIDGNYKYQYDKYNDVN RWVPLAADIAGLCARTDNVSQT WMSPAGYNRGQILNVIKLAIETR QAQRDRLYQEAINPVTGTGGDG YVLYGDKTATSVPSPFDRINVRR LFNMLKTNIGRSSKYRLFELNNA FTRSSFRTETAQYLQGIKALGGIY EYRVVCDTTNNTPSVIDRNEFVA TFYIQPARSINYITLNFVATATGA | Gp18 tail sheath monomer [Enterobacteria phage RB51] | YP_002854123.1 | 0,0 (654/659) | tail sheath monomer | Phage tail sheath protein | pfam0498 4 | 8e-95 |

Fig. 6C

| | | | DFDELTGLAG | | | | | | |
|---|---|---|---|---|---|---|---|---|---|
| 10 | 11151 | 9319 | 233 | MEQPINALNDFHPLNEAGKILIKH PSLAERKDEDGIHWIKSQWDGK WYPEKFSDYLRLHKIVKIPNNSD KPELFQTYKDKNKRSRYMGLP NLKRANIKTQWTREMVEEWKKC RDDIVYFAETYCAITHIDYGVKV QLRDYQRDMLKIMSSKRMTVCN LSRQLGKTTVVAIFLAHFVCFNK DKAVGILAHKGSMSAEVLDRTKQ AIELLPDFLQPGIVEWNKGSIELD NGSSIGAYASSPDAVRGNSFAMI YIDECAFIPNFHDSWLAIQPVISS GRRSKIIITTPNGLNHFYDWTA AVEGKSGFEPYTAIWNSVKERLY NDEDIFDDGWQWSIQTINGSTLA QFRQEHTAAFEGTSGTLISGMKL AVMDFIEVTPDDHGFHRFKGPE PDRKYIATLDCSEGRGQDYHAL HIIDVTDDVWEQVGVLHSNTISHL ILPDIVMRYLVEYNECPVYIELNS TGVSVAKSLYMDLEYEGVICDSY TDLGMKQTKRTKAVGCSTLKDLI EKDKLIIHHRATIQEFRTFSEKGV SWAAEEGYHDDLVMSLVIFGWL STQSKFIDYADKDDMRLASEVFS KELQDMGDEYAPVIFVDSVHSAE YVPVSHGMSMV | 610 | Gp17 terminase subunit [Enterobacteria phage RB51] | YP_0028541 22.1 | 0.0 (608/610) | terminase large subunit | Terminas e_6, terminase -like family | pfam0323 7 | 1e-67 |
| 11 | 11629 | 11135 | 234 | MEGLDINKLLDISDLPGIDGEEIK VYEPLQLVEVKSNPQNRTPDLE DDYGVVRRNMHFQQQMLMDAA KIFLETAKNADSPRHMEVFATLM GQMTTTNREILKLHKDMKDITSE QVGTKGAVPTGQMNIQNATVFM GSPTELMDEIGDAYEAQEAREK VINGTTD | 164 | Gp16 terminase DNA packaging enzyme, small subunit [Enterobacteria phage T4] | NP_049775. 1 | 1e-91 (164/164) | terminase DNA packaging enzyme, small subunit | No putative conserved domains have been detected | | |
| 12 | 12456 | 11638 | 235 | MFGYFYNSSFRRYATLMGDLFS NIQIKROLESGDKFIRVPITYASK EHFMMKLNKWTSINSQEDVAKV ETILPRINLHLVDFSYNAPFKTNIL NQNLLQKGTTSWSQYNPSPIKM IYELSIFTRYEDDMFQIVEQILPYF QPHFNTTMYEQFGNDIPFKRDIKI VLMSAAIDEAIDGDNLSRRRIEW SLTFEVNGWMYPPVDDAEGLIR TTYTDFHANTRDLPDGEGVFES VDSEVVPRDINPEDWDGTVKQT | 272 | Gp15 tail sheath stabilizer and completion protein [Enterobacteria phage T4] | NP_049774. 1 | 1e-157 (270/272) | tail sheath stabilizer and completion protein | No putative conserved domains have been detected | | |

Fig. 6D

| | | | | FTSNVNRPTPPEPPGPRT | | | | | |
|---|---|---|---|---|---|---|---|---|---|---|
| 13 | 13268 | 12498 | 236 | MATYDKNLFAKLENRTGYSQTN ETEILNPYVNFNHYKNSQILADVL VAESIQMRGVECYYVPREYVSP DLIFGEDLKNKFTKAWKFAAYLN SFEGYEGAKSFFSNFGMQVQDE VTLSINPNLFKHQVNGKEPKEGD LIYFPMDNSLFEINWVEPYDPFY QLGQNAIRKITAGKFIYSGEEINP VLQKNEGINIPEFSELELNPVRNL NGIHDINIDQYAEVDGINSEAKEY VEPYVVVNNRGKSFESSPFDND FMD | 256 | Head completion [Enterobacteria phage RB32] | YP_803104. 1 | 3e-146 (255/256) | head completion protein | No putative conserved domains have been detected | |
| 14 | 14199 | 13270 | 237 | MSGYNSQNPKELKDVILRRLGAP INVELTPDQHYDCIGRALELYGEY HFDGLNKGFHVFYVGDDEEKYK TGVFDLRGSNVFAVTRILRTNIGS ITSMDGNATYPWFTDFLLGMAGI NGGMGTSCNRFYGPNAFGADL GYFTQLTSYMGMMQDMLSPIPD FWFNSANEQLKVMGNFQKYDLII VESWTKSYIDTNKMVGNTVGYG TVGPQDSWSLSERYNNPDHNLV GRVVGQDPNYKQGAYNNRWVK DYATALAKELNGQILARHQGMM LPGGVTIDGQRLIEEAARLEKEALR EELYLLDPPFGILVG | 309 | Gp13 neck protein [Enterobacteria phage RB14] | YP_0028544 96.1 | 0.0 (309/309) | neck protein | Superanti gen-like protein | PRK13345 | 0.004 |
| 15 | 15688 | 14231 | 238 | MIELKDLPFVDSVPDEGQERISW IKNGEEILGASTKYGNDGSMNRP IVSVFKNVEVLDENIGILKTAIETS QKDIKTIQGVLDVSGDIEALSQIS VNKNDISNLKTLTNEHTDILTGTN NTVDKIHADIGPFNDEENSVYRTI RNDLLWIKQELGQYSGQDINGLP VVGNASTGMKHRITNSTLSSQ GIRLSELENKFTESDVGSLTVEV GKLRDELGNKPVDFGPNIYNRLN TIDDKQTLINSDIAEIKSSIGYPEN VSIITEINNNKSSIESISNNELNQSE GVKQRLTAIETSIGSDDIPSSIKG KIKNHTTSIESLNGIVGENTSSGL RANVSWLNQIVGTDSSGGQP3P SGSLLNKVSVLEGEVSVLNNNV QNIQVEIGNNRTGIKGQVIELTSLI NGNNPDGSTVEERGLTNSIKTNE TNIAAVTHEVNTAKDNISSLQSSV QALQEAGYIPEAPKDGQAYVRK | 485 | Fibritin neck whiskers [Enterobacteria phage RB14] | YP_0028544 95.1 | 0.0 (480/485) | fibritin neck whiskers | Fibritin C-terminal region | pfam0792 1 | 6e-25 |

Fig. 6E

| | | | DGEWVLLSTFLSPA | | | | | |
|---|---|---|---|---|---|---|---|---|
| 16 | 17248 | 239 | MSNNTYQHVSNESKYVKFDPVG SNFPGTVTVQSALSKISNIGVN GIPDATMEVKGIAMIASEQEVLD GTNNSKIVTPATLATRLLYPNATE TKYGLTRYSTNEETLEGSDNNSS ITPGKLKYHTDDVFRNRYSSESS NGVIKISSTPAALAGVDDTTAMT PLKTQKLAIKLISQIAPSEDTASES VRGVVQLSTVAQTRQGTLREGY AISPYTFMNSVATQEYKGVIRLG TQSEINSNLGDVAVTGETLNGRG ATGSMRGVVKLTTQAGIAPEGD SSGALAWNADVINTRGGQTING SLNLDHLTANGIWSRGGMWKNG DQPVATERYASERVPVGTIMMF AGDSAPPGWIMCHGGTVSGDQ FPDYRNVVGTRFGGDWNNPGV PDMRGLFVRGAGTGGHILNQRG QDGYGKDRLGVGCDGMHVGGV QAQQMSYHKHAGGWGEYNRSE GPFGASVYQGYLGTRKYADWD NASYFTNDGFELGGPRDALGTL NREGLIGYETRPWNISLNYIIKVH Y | 516 | Gp12 short tail fibers [Enterobacteria phage RB14] | YP_0028544 94.1 | 0.0 (509/516) | short tail fibers | Phage short tail fibre protein gp12, middle domain | pfam0908 9 | 9e-29 |
| 17 | 17245 | 240 | MSLLNNKAGVISRLADFLGFRTK KNDISVMNNQPVGAVTISQIAKG FYDSNVESAINDVRNMAEQOVG AVLINISGVSPTGVQQTDYWSFE GTVTDTSAKPGDPVIVNMFGIPV KATNGMTSIEFTSAVRTALQEMV VKFIAIDSFEDHPTIGNKIQVKYLD NQEHILEQYSDKGITFKQEIISPS KPGYGTWQLLGAQTVTLDSHTQ PTVFYYFERIA | 219 | Gp11 base plate wedge completion tail pin [Enterobacteria phage RB14] | YP_0028544 93.1 | 3e-124 (217/219) | base plate wedge completion tail pin | GP11 baseplate wedge protein | pfam0867 7 | 1e-89 |
| 18 | 19709 | 241 | MKQNINIGNVVDDGTGDYLRKG GIKINENFDELYYELGDGDVPYS AGAWKTYNASSGQTLTAEWGK SYAINTSSGRVTLQLPKGTVNDY NKVIKARDVFATWNNPVTLVAA SGDTIKGSSSSVEINVQFSDLELV YCAPGRWEYVKNKQIDKIISSDIS NVARKEFLVEVQGQTDFLDVFH GTSYNVNNIRVKHRGNELYYGD VFSENSDFGSPGENEGELIPLDG FNIRLRQPCNIGDTVQIETFMDG VSQWRSSYTRRQIKVLDSKLTSK | 601 | Gp10 base plate wedge completion tail pin [Enterobacteria phage RB14] | YP_0028544 92.1 | 0.0 (590/601) | base plate wedge completion tail pin | Bacteriop hage T4 gp9/10-like protein | pfam0788 0 | 3e-79 |

Fig. 6F

| | | Sequence | | | | | | |
|---|---|---|---|---|---|---|---|---|
| 19 | 20575 | TSLEGSIYYTDLSAMKSIPFSAFG LIPGEPINPNSLEVRFNGILQQQA GTAGYPLFLCEGANSDTQEGCIS LGGEWKESNTDYSIEYEDGKPV SLLFDRKFESGDIIVTWFNNDLG TLLEKDDIIELTDDRYVSKGSSTE VTGDVALTDFDKIGWPNVEKVD SYTRTYNSISSIFDSIYPVGSIYEN AINPNNPVTYMGFGSSWKLFGKG QVLVGWNDDVTDPNFALNNNDL DSSGNPSHTAGGTVGTTSVTLE NANLPATKTDERVLIEDENGSVIt GGCYDPDETGPIYTKYREDYA TTNSSHTPPTNISNIQPSITVRW IRIA | | | | | | |
| | 19709 | 242 | MFIQEPKKLIDTGEIGNASTGDIL FDGGNKINSDFNAYNAFGDQRK MAVANGTGADGQIIHATGYYQK HSITEYATPVKVGTRHDIDTSTV GVKVIIERGELGDCVEFINSNGSI SVTNPLTIQAIDSIKGVSGNLVvT SPYSKVTLRCISSDNSTSVWNYS IESMFGQKESPAEGTWNISTSGS VDIPLFHRTEYNMAKLLVTCQSV DGRKIKTAEINILVDAVNSEVISSE YAVMRVGNETEEDEIANIAFSIKT NYVTATISSSTVGMRAAVKVIAT QKIGVAQ | 288 | Gp9 base plate wedge completion tail fiber socket [Enterobacteria phage RB14] | YP_0028544 91.1 | 2e-165 (287/288) | base plate wedge completion tail fiber socket | Bacteriop hage T4 gp9/10- like protein | pfam0788 0 | 9e-95 |
| 20 | 21643 | 20639 | 243 | MNDSSVIYRAIVTSKFRTEKMLN FYNSIGSGPDKNTIFITFGRSEPW SSNENEVGFAPPYPTDSVLGVT DMWTHMMGTVKVLPSMLDAVIP RRDWGDTRYPDPYTFRINDIVvC NSAPYNATESGAGWLVYRCLDV PDTGMCSIASLTDKDECLKLGGK WTPSVRSMTPPEGRGDAEGTIE PGDGYVWEYLFEIPPDVSINRCT NEYIVVPWPEELKEDPTRWGYE DNLTWQQDDFGLIYRKANTIRF KAYLDSVYFPDAALPGNKGFRQI SIITNPLEAKAHPNDPNVKAEKDY YDPEDLMRHSGEMIYMENRPPII MAMDQTEEINLFTF | 334 | Gp8 baseplate wedge subunit [Enterobacteria phage T4] | NP_049766. 1 | 0,0 (332/334) | baseplate wedge subunit | Bacteriop hage T4, Gp8 | pfam0921 5 | 5e-162 |
| 21 | 24734 | 21636 | 244 | MTVKAPSVTSLRISKLSANQVQV RWDDVGANFYYFVEIAETKTDS GENLPSDQYRWINLGYTANNSF FFDDADPLTSYIIRVATAAQDFEQ | 1032 | Gp7 base plate wedge initiator [Enterobacteria phage RB14] | YP_0028544 89.1 | 0,0 (1022/1032 ) | base plate wedge initiator | Fibronecti n type 3 domain | cd00063 | 0,009 |

Fig. 6G

| | | | | | | | | | | | |
|---|---|---|---|---|---|---|---|---|---|---|---|
| | | | | SDWVYTEEFETFATNAYTFQNMI<br>EMQLANKFIQEKFTLNNSNYVNF<br>NNDTIMAALMNESFQFSPSYVDV<br>SSISNFIIGENEYHEIQGSIQQVC<br>KDINRVYLMESEGILYLFERYQP<br>VVKVSNDKGQTWKAVKLFNDRV<br>GYPLSKTVYYQSANTTYVLGYDK<br>IFYGRKSTDVRWSADDVRFSSQ<br>DITFAKLGDQLHLGFDVEIFGTYA<br>TLPANVYRIAEAITCTDDYIYVVA<br>RDKVRYIKTSNAPIDSDPLSPTYS<br>ERLFEPDTMTITGNPKAVCYKMD<br>SIGDKVFALIIGEVETLNANPRTS<br>KIIDSADKGIYVLNHDEKTWKRVF<br>GNTEEERRRIQPGYANMSTDGK<br>LVSLSSSNFKFLSDNVVNDPETM<br>VKYQLIGAVKYEFPREWLADKHY<br>HMMAFIADEKSDWETFTPQPMK<br>YYAEPFFNWSKKSNTRCWINNS<br>NRAVVVYADLKYTKVIENIPETSP<br>DRLVHEYWDDGDCTIVMPNVKF<br>TGFKKYASGMLFYKSSGEIISYY<br>DFNYRVRDTVEIIWKPTGVFLKA<br>FLQNQEHETPWSPEEEHGLADP<br>DLRPLIGTMMPDSYLLQDSNFEA<br>FCEAYIQYLSDGYGTQYNNLRNL<br>IRNQYPREEHAWEYLWSEIYKR<br>NIYLNADKRDAVARFFESRSYDF<br>YSTKGIEASYKFLFKVLYNEEVEI<br>EIESGAGTEYDIIVQSDSLTEDLV<br>GQTIYTATGRCNVTYIERSYSNG<br>KLQWTVTIHNLLGRLIAGQEVKA<br>ERLPSFEGEIIRGVKGKDLLQNNI<br>DYINRSRSYYVMKIKSNLPSSRW<br>KSDVIRFVHPVGFGFIAITLLTMFI<br>NVGLTLKHTETIINKYKNYKWDS<br>GLPTEYADRVAKLTPTGEIEHDS<br>VTGEAIYEPGPMAGVEYPLPDDY<br>NAENNNSIFQGQLPSERRKLMS<br>PLFDASGTTFAQFRDLVNKRLKD<br>NIGNPRDPENPTQVKIDE | | | | | | | | |
| 22 | 26713 | 24731 | 245 | MANTPVNYQLTRTANAIPEIFVG<br>GTFAEIKQNLIEWLNGQNEFLDY<br>DFEGSRLNVLCDLLAYNTLYIQQ<br>FGNAAVYESFMRTANLRSSVVQ<br>AAQDNGYLPTSKSAAQTEIMLTC<br>TDALNRNYITIPRGTRFLAYAKDT<br>SVNPYNFVSTEDVIAIRDKNNQY | 660 | gp6 base plate wedge [Enterobacteria phage RB14] | YP_0028544 88.1 | 0,0 (657/660) | base plate wedge | No putative conserved domains have been detected | | |

Fig. 6H

| | | | | | | | | |
|---|---|---|---|---|---|---|---|---|
| | | | FPRLKLAQGRIVRTEIIYDKLTPII YDKNIDRNQVKLYVDGAEWINW TRKSMVHAGSTSTIYMRETIDG NTEFYFGEGEISVNASEGALTAN YIGGLKPTQNSTIVIEYISTNGAD ANGAVGFSYADTLTNITIININENP NGDPDFVGADGGGDPEDIERIR ELGTIKRETQQRCVTATDYDTFV SERFGSIIQAVQTFTDSTKPGYA FIAAKPKSGLYLTTVQREDIKNYL KDYNLAPITPSIISPNYLFIKTNLK VTYALNKLQESEQWLEGQIIDKID RYYTEDVEIFNSSFAKSKMLTYV DDADHSVIGSSATIQMVREVQNF YKTPEAGIKYNNQIKDRSMESNT FSFNSGRKVVNPDTGLEEDVLY DVRIVSTDRDSKGIGKVIIGPFAS GDVTENENIQPYTGNDFNKLANS DGRDKYYVIGEINYPADMIYWNI AKINLTSEKFEVQTIELYSDPTDD VIFTRDGSLIVFENDLRPQYLTIDL EPISQ | | | | | |
| 23 | 27015 | 26722 | 246 | MSGLSYDKCVTAGHEAWPPTVV NATQSKVFTGGIAVLVAGDPITE HTEIKKPYETHGGVTQPRTSKYY VTGKKAVQMADPISCGDTVAQA SSKVFIK | 97 | Gp5,4 conserved hypothetical protein [Enterobacteria phage T4] | NP_049763. 1 | 9e-50 (97/97) | | No putative conserved domains have been detected |
| 24 | 27510 | 27016 | 247 | MEGSSIDVVTFTAQLETGETLVSIN ITSYEETPGVLVEENRLYGTYES VFGFGNDALKYRLGDEFKTAAS WEELPTDSDTQLYLWKAPQNLQ KTFTYEVTLIYDYQEQSESGGSG SNSRSSSDTTEPTDPPAPVRKTL VKNYTKTIVGNWSRWANKLRSY VYERS | 164 | Hypothetical protein RB32ORF151w [Enterobacteria phage RB32] | YP_803093. 1 | 9e-90 (163/163) | | No putative conserved domains have been detected |
| 25 | 29272 | 27545 | 248 | MEMISNNLNWFVGYVVEDRMDPL KLGRVRVRVVGLHPPQRAQGDV MGIPTEKLPWMSVIQPITSAAMS GIGGSVTGPVEGTRVYGHFLDK WKTNGIVLGTYGGIVREKPNRLE GFSDPTGQYPRRLGNDTNVLNQ GGEVGYDSSSNIIQDSNLDTAIN PDDRPLSEIPTDDNPNMSMADM LRRDEGLRLKVYWDTEGYPTIGI GHLIMKQPVRDMAQINKVLSKQV GREITGNPGSITMEEATTLFERD LADMQRDIKSHSKVGPVWQAVN | 575 | Bacteriophage T4 Cell-Puncturing Device | 1K28 | 0.0 (572/575) | baseplate hub subunit and tail lysozyme, cell-puncturing device | Bacteriop hage_T4-like_lysoz yme | cd00735 | 1e-74 |

Fig. 61

| | | | | | | | |
|---|---|---|---|---|---|---|---|
| 26 | 29846 | 29256 | 249 | RSRQMALENMAFQMGVGGVAK FNTMLTAMLAGDWEKAYKAGRD SLWYQQTKGRASRVTMIILTGNL ESYGVEVKTPARSLSAMAATVA KSSDPADPPIPNDSRILFKEPVSS YKGEYPYVHTMETESGHIQEFD DTPGQERYRLVHPTGTYEEVSP SGRRTRKTVDNLYDITNADGNFL VAGDKKTNVGGSEIYNMDNRL HQIDGSNTIFVRGDETKTVEGNG TILVKGNVTINVEGNADITVKGDA TTLVEGNQTNTVNGNLSWKVAG TVDWDVGGDWTEKMASMSSIS SGQYTIDGSRIDIG | | | | |
| 26 | 29846 | 29256 | 249 | MLTFFDPIEYAAKTVNKNAPTIP MTDIFRNYKDYFKRALAGYRLRT YYIKGSPRPEELANTIYGNPQLY WVLLMCNDNYDPYYGWITSQEA AYQASIQKYKNVGGDQIVYHVNE NGEKFYNLISYDDNPYVWYDKG DKARKYPGYEGALAAVNTYEDA VLENEKLRQIKIIAKSDINSFMNDL IRIMEKSYGNDK | YP_803091.1 | 3e-109 (193/196) | base plate wedge completion | No putative conserved domains have been detected |
| 27 | 29894 | 30346 | 250 | MAYSGKWVPKNISKYRGDPKKIT YRSNWEKFFFEWLDKNPEIIAW GSETAVIPYFCNAEGKKRRYFM DIWMKDSSGQEFFIEIKPKKETQ PPVKPAHLTTAAKKRFMNEIYTY SVNTDKWKAAQALAEKRGIKFRI LTEDGLRALGFKGA | YP_803090.1 | 5e-83 (150/150) | head completion | No putative conserved domains have been detected |
| 28 | 30346 | 31170 | 251 | MAIFQIINESTPQVPKVKQSLNEK KWIQIGLEYKKAKAKGMTGKQFA EERGIKYSTFTSAMSKYASGIKT AEKIQKLESKPMNKLNKQERQLL MINSFRQTLRDKIRNEGAAINNKT RKWFAETKQVKGHKVVRPQPG RIYAFAYDAKHKETLPYWDKFPLI IYLGLGKHNLMYGLNLHYIPPKA RQQFLEELLKQYANTPTITNKTKL KIDWSQVKGFRGADQMIKAYIPG NIMGSLVEIAPKDWANVVLMPLQ QFVSKGKRFSANKVWSNI | NP_049754.1 | 3e-158 (274/274) | DNA end protector protein | No putative conserved domains have been detected |
| 29 | 31277 | 31807 | 252 | MSQALQQIFNQANTTNFVVSIPH SNTTSAFTLNAQSVPIPGIRIPVT DTVTGPFGLGRAORPGATFEYD PLIVRFIVDEELKSWGMYEVML GTSNYLTGENTAQKTGPEYITLYI | NP_049753.1 | 2e-98 (175/176) | tail completion and sheath stabilizer protein | No putative conserved domains have been detected |

Fig. 6J

| | | | | | phage T4] | | | |
|---|---|---|---|---|---|---|---|---|
| 30 | 31857 | 32582 | 253 | LDNSKTEIVMSINFYKPWVSDLS EVEFSYTEDSDPALVCTATIPYTY FQVEKDGKIIAEV | | | | No putative conserved domains have been detected |
| | | | | MKLIFLSGVKRSGKDTTADFIMS NYSAVKYQLAGPIKDALAYAWG VFAANTDYPCLTRKEFEGIDYDR ETNLNLTKLEVITIMEQAFCYLNG KSPIKGVFVFDDEGQESVNSVAF NKIIDVINNIEDQWSVRRLMQALG TDLIVNNFDRMYWVKLFALDYLD KFNSGYDYYIVPDTRQDHEMDA ARAMGATVIHVVRPGQKSNDTHI TEAGLPIRDGDLVITNDGSLEELF SKIKNTLKVL | 241 | dNMP kinase [Enterobacteria phage RB32] | YP_803086. 1 | 2e-139 (240/241) | dNMP kinase | |
| 31 | 32582 | 32812 | 254 | MSEQTIEQKLSAEIVTLKSRILDT QDCAARLMEESKILQGTLAEIAH AVGITGDTIKVEEIVEAVKNLTAE SADEE | 76 | Chaperone long and short tail fiber assembly [Enterobacteria phage RB32] | YP_803085. 1 | 1e-32 (75/76) | chaperone long and short tail fiber assembly | No putative conserved domains have been detected |
| 32 | 32819 | 33267 | 255 | MEFKDFSTGLYVAAKFSELTLDA LEELQRSLRVPNPVPREKIHSTIC YSRVNVPYVPSSGSFEVASSGH LEVWKTQDGSTLVLVLDSEY.RC RHMYARALGATHDFDDYTPHITL SYNVGPLSFSGDVQIPVVLDREY KEP.KLDWADDLK | 151 | Hypothetical protein RB32ORF142c [Enterobacteria phage RB32] | YP_803084. 1 | 5e-84 (151/151) | | No putative conserved domains have been detected |
| 33 | 33341 | 33598 | 256 | MKTFKEFATKTITESSHGMEVK LGMALAEAERLFSRIKELAAAVD PSSFKGDQTKVKALLALCSDAGE IAKNGSKMKKRLEDLK | 85 | Hypothetical protein RB32ORF141c [Enterobacteria phage RB32] | YP_803083. 1 | 1e-40 (85/85) | | No putative conserved domains have been detected |
| 34 | 33663 | 33908 | 257 | MEIKMKTYQEFIAETADVKVEFIY TGKKDKMGEMPHGVLRDALDNF GQLAAEDYGDKIVVTGPAAVIEK WAAENKSIFRKK | 81 | Ip6 [Enterobacteria phage T6] | CAA84458.1 | 2e-37 (76/77) | | No putative conserved domains have been detected |
| 35 | 33967 | 34152 | 258 | MKRCELIRNVAIASASAFSFSMF VGFICGLLTTAENVFSLVVAFLIG LIAIVMDKISKGE | 61 | Trna.4 conserved hypothetical predicted membrane protein [Enterobacteria phage T4] | NP_049748. 1 | 2e-25 (61/61) | | No putative conserved domains have been detected |
| 36 | 34152 | 34550 | 259 | MNVEYYVYADYENNPSKDEDNR LGVDAFDSPAAAWQWVERTDIP YRYIEVVDHAGNKYPKEAYVASG KVNFLLFAGDNYYPRGGYTDLIA KAFSEDELRDIIKENENKPMDSN | 132 | Trna.3 conserved hypothetical protein [Enterobacteria phage JS10] | YP_0029224 85.1 | 3e-67 (127/133) | | No putative conserved domains have been detected |

Fig. 6K

| | | | | | | | | |
|---|---|---|---|---|---|---|---|---|
| 37 | 34553 | 34840 | 260 | MILYAKVSSIENGYKYDQDAAKA LIDDYGILTCFEVEKVYIDRSSSQ VKLVKEERKFNTVNFDFFIETEK GPLEYDIFKNPLGLECIVNMYYY KW | 95 | tRNA.2 hypothetical protein [Enterobacteria phage RB51] | YP_0028540 96.1 | 1e-46 (91/95) | |
| | | | | RFDWWGIVNANTHTIVDEG | | | | | |
| 38 | 34938 | 35010 | 261 | UGGGAAUUAGCCAAGUUGGUA AGGCACUGGAUUUGAUUCCA GGAUgCAAAGGUUCGAGUCCU UUAUUCCCAG | | | | | tRNA1-Gln |
| 39 | 35012 | 35095 | 262 | GCGAGAAUGGCCAAAUUGGUa AAGGCACGACACUUAAAAUGC UGCGGAAUGAUUUCCUUGUGG GUUCGAGUCCCACUUCUCGCA | | | | | tRNA2-Leu |
| 40 | 35104 | 35174 | 263 | GCGGAUAUCGUAUAAUGGUAU UACCUCAGACUUCCAAUCUGA UGAUGUGAGUUCGAUUCUCAU UAUCCGCU | | | | | tRNA3-Gly |
| 41 | 35188 | 35261 | 264 | CUCCGUGUAGCUCAGUUGGU AGAGCGCUCGCUUUGGGAGCA GAAUGUCGUAGGUUCAAAUCC UGCCACGGAGA | | | | | tRNA4-Pro |
| 42 | 35264 | 35350 | 265 | GGAGCGCUGGCAGAGUGGUU UAAUGCACCGGUCUUGAAAAC CGGCAGUCGCUCCGGCGACU CAUAGGGUUCAAAUCCUAUCGC CUCCG | | | | | tRNA5-Ser |
| 43 | 35359 | 35431 | 266 | GCUGAUUUAGCUCAGUAGGUA GAGCAACUCACUUGUAAUGAG AAGGUCGGGGUUCGAUUCC GUCAAUCAGCA | | | | | tRNA6-Thr |
| 44 | 35436 | 35507 | 267 | GGCCCUGUAGCUCGGAAGGUU CAAGCAAGCGACUCAUAAUCG CCAGAUGGUGUGGUUCAAUUCCA CCCAGGGCCA | | | | | tRNA7-Met |
| 45 | 35520 | 35603 | 268 | GGGGAGUUAUcCCGUAGAGGU AGCGGUGUGGACUGUAAAUCC AUUGUCAUUGcGACUcGGGUG GUUCGACUCCACUCCCCCA | | | | | tRNA8-Tyr |
| 46 | 35611 | 35682 | 269 | GGAUGUGUAGCUCAAUGGCAG AGCGAUCGCCUGUUAAGCGAU UGGUUAUAGGUUCGAAUCCUA UCACGUCCG | | | | | tRNA9-Asn |

Fig. 6L

No putative conserved domains have been detected

| | | | | | | | |
|---|---|---|---|---|---|---|---|
| 47 | 35800 | 35872 | 270 | GUGGCCGUAGUUCAGUUGGU AGAACUCGAGAUUGUGAUUCU CGUAGUCAUGGGUUCGACUCC CAUCGGUCACC | | tRNA10-His | |
| 48 | 35880 | 35952 | 271 | CGGGGCAUAGCUCAGAAGGAA GAGCAAGGACCUCUAAGUCC UAGGUCUAGGGUUCGACCCU ACUGCCCUCGA | | tRNA11-Arg | |
| 49 | 35974 | 36324 | 272 | MKGNVYLVVHDLTFYFNHNDTVI SERVINLLYQHADYVYVENEYGH WQFLKNRSFGLDGYEYFDRKDL LDTIPLSTQYQNHKSLHKCRLIRN AESAYEAIDLWRKRREYIDSLKE Y | Hypothetical protein RB51ORF141 [Enterobacteria phage RB51] | YP_0028540 94.1 | 8e-60 8|111/116) | No putative conserved domains have been detected |
| 50 | 36708 | 37181 | 273 | MKSYTQFLNEAVLNEASSTEIQA VAKAAIAAGKYSYKDASDESRFQ FARDMKAEGFTGNAVSMAWKSL VATGAAFAKASGKPAPKADPKA AQEKNIVKGIIAKYEAILKELLVIKT EGCKLARAYSFKDNPHVHSLEY VEDIQKIIKDRIWSAKQIK | Hypothetical protein RB51ORF140 [Enterobacteria phage RB51] | YP_0028540 93.1 | 1e-83 (154/157) | No putative conserved domains have been detected |
| 51 | 37307 | 37870 | 274 | MKTYAEFLTEAAKLPSEADLTKV FFQLDPKDRGDFLKWKAKAIEM YNIDNSSFTMSQENKFNKAFFKI SKKLASGAQVPKSVLATPERAPV KISKNMFDTKKYVNALNKALDAL DDAKKAARDLQDVYTDFDRKTK GSISNSERNSVSVYSDSLDVLGD AYTEIKNRINTASKLKAAAEAIISK LGK | Hypothetical protein RB14ORF136 [Enterobacteria phage RB14] | YP_0028544 72.1 | 5e-100 (183/187) | No putative conserved domains have been detected |
| 52 | 38100 | 38363 | 275 | MDNYGELFNFFMKCVSEDFGRT VNDIKVIGPDHPMFETYAVMGNE DGQWYTVKVVINMFTAEGYVKL SSKVYHDNDEIAEEYFNNMK | Hypothetical protein RB32ORF131c [Enterobacteria phage RB32] | YP_803073. 1 | 2e-44 (87/87) | No putative conserved domains have been detected |
| 53 | 38465 | 39058 | 276 | MNTLKKIVEFIRTKLGSAMAKNLS VEEQYTAAAAKLLDKIKDLKTASV KSINEEKRIRELVIEKNRQAESKE REIRKLLSEGQDVTMHAKLGLLY RRTAEQLTTKADGYAEMRIEIAK KVVELDDARQELAVKLEYIRETR AANALGISTADDVVEIAALTKVDI EDTLARVETFNGNISGVETTSAD VQEYINSLK | Conserved hypothetical protein e.6 [Enterobacteria phage T4] | NP_049742. 1 | 6e-105 (194/197) | No putative conserved domains have been detected |
| 54 | 39106 | 39714 | 277 | MKMQSDFNSMFEEFQRQVDVP DQLLNALKRMAEGRNYYWGSSY | Hypothetical protein RB32ORF128c | YP_803070. 1 | 4e-112 (197/202) | No putative conserved domains have been detected |

Fig. 6M

| | | | | | | | | |
|---|---|---|---|---|---|---|---|---|
| | | | | ETDESLSGRFSRGKKSLIRPGILI NSIESIHSLTCDFDVEFTDFISPE WTVCYLNDDFDYLGVYSLSDAW FKRNLQKSNLFYID'TYKFQGKK YFFTLIVDSETKHENKRILSKKNIL TIVDDLFDKFVENPNFESDLLLEK FVKECREYVKTITIPSK | [Enterobacteria phage RB32] | | | |
| 55 | 39683 | 40075 | 278 | MSKPSLYLPSKPVKYEPKRQIIST DVLIGPVILISFVILLIIGGVLDVMT DIDSGEILVLMLILPLIVPLLLVPVN WVGYWYQGRHYRKRVRDWKA QCKKIKKEHQLKLDMYEFDEIMK FVKESRCKSQN | Hypothetical protein RB32ORF127c [Enterobacteria phage RB32] | YP_803069.1 | 2e-64 (123/130) | | No putative conserved domains have been detected |
| 56 | 40057 | 40419 | 279 | MQKPKLNKVKYSFPEALLILAVS VFTALAGSLIGLLIDCFILNIDGTVI ITEVWSELRFTIAISLFSFFGTMLY FHYDNFKINWQRKKDYKIQLKEY NSYMSYIEKESMEEFVSDCRKIK | Conserved hypothetical, predicted membrane protein e.3 [Enterobacteria phage T4] | NP_049739.1 | 1e-49 (98/120) | | No putative conserved domains have been detected |
| 57 | 40416 | 40904 | 280 | MILKTRWVDLDDGDDGISVDRV DWSGCSEDTKKRLIREFRMGYQ AVKPSTVTDDKFVCIHNGRAKLT NAEWFTDKIMILWYIISLPVSSFV FYFFIKNPMDRIGDWILLTILVNIF TASILSGIWYTFIEMPVWRLRRQQ KIFDEKKYTQNLNNFITECRKLK | Hypothetical protein e.2 [Enterobacteria phage RB51] | YP_0028540 86.1 | 3e-85 (152/162) | | No putative conserved domains have been detected |
| 58 | 40901 | 41341 | 281 | MKTLSAGIIFMTEDKDLFMGRVT GSRKPGMMAHRWDIPKGRVES SDLNALEAAKRECLEETGFSNYN PDLLEDLGVFKYSSNKDLQLFYY TIPVEHEMFRNCHCESYFENKD GVMIPEMDAFALIPRTQWQYVM GPSLYRIMNSLF | Nudix hydrolase [Enterobacteria phage RB51] | YP_0028540 85.1 | 1e-83 (144/146) | nudix hydrolase | NUDIX domain | pfam00293 | 5e-10 |
| 59 | 41378 | 41872 | 282 | MNIFEMLRIDEGLRLKIYKDTEGY YTIGIHLLTKSPSLSVAKSELDK AIGRNCNGVITKDEAEKLFNQDV DAAVRGILRNAKLKPYYDSLDAV RRCALINMVFQMGETGVAGFTN SLRMLQQKRWDEAAVNLAKSR WYNQTPNRAKRVIATFRTGTWD AYKNL | Soluble lysozyme [Enterobacteria phage RB32] | YP_803066.1 | 2e-92 (164/164) | soluble lysozyme | Bacteriop hage T4-like_lysoz yme | cd00735 | 7e-64 |
| 60 | 41932 | 42348 | 283 | MTRINLTLVSELADQHLIAEYREL PRVFGIVRKHVANGKRVKDFKIS SKFILGSGHVTFFYDKLEFLRKR QSDIITECLKRGFSIKDTEVPDISD IPVEWKNDYNPCKSAIKLSQQRL | Endonuclease V [Enterobacteria phage RB51] | YP_0028540 83.1 | 1e-74 (135/138) | endonuclease V | Pyrimidine dimer DNA glycosyla | pfam03013 | 2e-69 |

Fig. 6N

Fig. 60

| | | | DEKILMKPHWYKYGKNIYI | | | | se | |
|---|---|---|---|---|---|---|---|---|
| 61 | 42494 | 43033 | 284 | MRTFLTGPYLSLMNAFTHHSDA RVEEICKNEYIPPFEDLLKQYCTL RLDGGRQSGKSTAVTNFAANWL YDGGTVIVLSNTSAYAKISADNIK KEFSRYSNDDIRFRLFTDSVRSFI GNKGSKFRGLSLSRILYIIDEPVK SPDMDKIYSVHIDTVHCCCNIKC CIGGTRPQFFVIGMQ | 179 | Hypothetical protein RB32ORF122c [Enterobacteria phage RB32] | YP_803064. 1 | 1e-100 (176/179) | Endoribo nuclease RegB T4-bacteriop hage encoded | pfam1071 5 | 4e-11 |
| 62 | 43030 | 43359 | 285 | MMTDTQLFEYLYFSPKTIKNKLV NHFEILAKNNILSEFYPKGYKLQK GVFKGCRVLCTAPNARLMNKIPY FTMEFIDGPFKGLITQSLMAYDS EPFLIKEQSWINLFFN | 109 | Unnamed protein product [Enterobacteria phage T4] | CAA28221.1 | 3e-57 (108/109) | REGB_T 4, Endoribo nuclease RegB T4-bacteriop hage encoded | pfam1071 5 | 1e-12 |
| 63 | 43366 | 43728 | 286 | MKAYQILEGTHKGTIYFEDGIQA RIIVSKTFKEDSFVDPEIFYGLHA REIEIEGQOPTVKIEGGQHLNVNVL RRETLEDAVKHPEKYPQLTIRVS GYAVRFNSLTPEQQRDVIARTFT ESL | 120 | Hypothetical protein vs.6 [Enterobacteria phage RB51] | YP_0028540 79.1 | 2e-63 (119/120) | Autonom ous glycyl radical cofactor GrcA | PRK11127 | 1e-41 |
| 64 | 43728 | 43949 | 287 | MAKIIIEGSEDVLNAFAEWFSNS GEQQFNEAWNMGDINGIYPTEI SVQGYGIHEPIRLVEYDLGTGEE VKYD | 73 | Hypothetical protein RB32ORF119c [Enterobacteria phage RB32] | YP_803061. 1 | 1e-33 (70/73) | | No putative conserved domains have been detected | |
| 65 | 43942 | 44208 | 288 | MIEDKGYKPHTDDKISKVNAIKD AEVRLGLIFDALYDEFWEAFDSC EDDELAKNYAESLDQLTIAKMKL KEASMWACRAVFCPEEKY | 88 | Hypothetical protein vs.4 [Enterobacteria phage RB14] | YP_0028544 57.1 | 4e-42 (84/88) | | No putative conserved domains have been detected | |
| 66 | 44208 | 44486 | 289 | MACLSAGFGYEYYTAPRRVSVA PKKIQSLDDFQEVVRNAFQDYAR YLKEDSQDCLEEDEIAYYEQRLE QLKNLHEVRAEVSKSMNKLIRFK E | 92 | Conserved hypothetical protein vs.3 [Enterobacteria phage T4] | NP_049727. 1 | 3e-46 (91/92) | REGB_T 4, Endoribo nuclease RegB T4-bacteriop hage encoded | pfam1071 5 | 3e-05 |
| 67 | 44546 | 45007 | 290 | MTINTEVFIRRNKLRRHFESEFR QINNEIREASKAAGVSSFHLKYS QHLLDRAIQREIDETYVFELFHKI KDHVLEVNEFLSMPPRPDIDEDF IDGVEYRPGRLEITDGNLWLGFT VCKPNAKFKDPSLQCRMAIINSR | 153 | Site-specific RNase [Enterobacteria phage RB32] | YP_803058. 1 | 8e-86 (153/153) | REGB_T 4, Endoribo nuclease RegB T4-bacteriop | pfam1071 5 | 2e-39 |

| | | | RLPGKASKAVIKTQ | | | | | hage encoded | | |
|---|---|---|---|---|---|---|---|---|---|---|
| 68 | 45015 | 45560 | 291 | MRKALLAGLLAISMMAHSSEHTFSNVQLDNMRYAYQFGEQFSKDGKYKTHKNIIHKSGLGHIMAAILWQESSAGVNLKSKPKHHAYGMFQNYLPTMRARVKELGYNMTDAEIKRMLNKRSNSASWAYIELSYWLNIHKGDIRKAISSYNSGWNVKAGSKYASEVLEKANYLKNNKLLEIVND | 181 | Conserved hypothetical protein vs.1 [Enterobacteria phage T4] | NP_049725.1 | 6e-101 (180/181) | | REGB_T4, Endoribonuclease RegB T4-bacteriophage encoded | pfam10715 | 2e-27 |
| 69 | 45553 | 45894 | 292 | MTKILVLCIGLISFSVLADTSYTEIREYNRTAADYCGKNKACQAEFAQKLIYAYKDGERDKSSRYKNDTLLKRYAKKWNTLECSVAEEKDKAACHSMVDRLVDSYNRGLSTR | 113 | Modifier of valyl-tRNA synthetase [Enterobacteria phage RB51] | YP_0028540 073.1 | 5e-59 (112/113) | modifier of valyl-tRNA synthetase | No putative conserved domains have been detected | | |
| 70 | 45891 | 46370 | 293 | MIVKYIKGDIVALFLQGNIIAHGCNCFHTMGSGVAGQLARAYPKILEIDKTTTEYGSRDKLGDMSIVFKHSPTGFGICYNLYTQYEPGPNLDYGALVNCMIELNLQAETLLFKPVIYPRIGCGIAGGDWDKVSKLIDMFTPDIDLIVVDYESTLPASV | 159 | Tk.4 conserved hypothetical protein [Enterobacteria phage JS98] | YP_0015952 33.1 | 5e-84 (148/159) | | Macro domain, Poa1p_like family | cd02901 | 5e-21 |
| 71 | 46342 | 46554 | 294 | MKVHYPHPFDPKNKVEIIRQWERICRTKCPINSPHDVDKDYIGTFVEYTFIDRKGRKGHVEEYCLKVTWL | 70 | Hypothetical protein tk.3 [Enterobacteria phage RB51] | YP_0028540 71.1 | 6e-33 (67/70) | | No putative conserved domains have been detected | | |
| 72 | 46551 | 46757 | 295 | MSQTSILKNAHCEKCEWPVVFALCNDEMACDFDYWCYCSNKGCINHKGEGFYSGFYPYPDFVKEGKPK | 68 | Hypothetical protein RB32ORF111c [Enterobacteria phage RB32] | YP_803053.1 | 6e-33 (67/68) | | No putative conserved domains have been detected | | |
| 73 | 46754 | 46927 | 296 | MNSFELQYEVLRELDNLIELAVNKGFAIGIGQKDTGHLTMEIFKGKRIILKLIEINI | 57 | RB32ORF110c hypothetical protein [Enterobacteria phage RB32] | YP_0028540 69.1 | 2e-23 (56/57) | | No putative conserved domains have been detected | | |
| 74 | 46924 | 47109 | 297 | MSLSKEQKDKLFELIHELLDEHTEANTFYDEYGPLSPEQQEEFADRFDKKENELIAYVNML | 61 | Hypothetical protein tk.2 [Enterobacteria phage RB51] | YP_0028540 68.1 | 2e-26 (60/61) | | No putative conserved domains have been detected | | |
| 75 | 47119 | 47700 | 298 | MASLIFTYAAMNAGKSASLLTAAHNYKERGMGVLVLKPAIDTRDSVCEVVSRGIKQEANITDDMDIFEFYKWAEAQKDIHCVFVDEAQFLKTEQVHQLSRIVDTYNVPVMAYGLRTDFAGKLFEGSKELLAIADKLIE | 193 | Thymidin kinase [Enterobacteria phage RB32] | YP_803049.1 | 5e-110 (192/193) | thymidine kinase | Thymidine kinase | PRK04296 | 2e-77 |

Fig. 6P

| | | | | Sequence | | | | | |
|---|---|---|---|---|---|---|---|---|---|
| 76 | 47743 | | | LKAVCHCGKKAIMTARLMEDGT PVKEGNQICIGDEIYVSLCRKHW NELTKKLG | | | | | No putative conserved domains have been detected |
| 77 | 47968 | 47955 | 299 | MLQLTEKQLRNLTVLQLDEIRRE VGNIISALRREVSLNQSPADYTRL RNFEKYLDKVKAVHRHKVNTGQ K | 70 | Conserved hypothetical protein rI.1[Enterobacteria phage T4] | NP_049718. 1 | 1e-32 (70/70) | | No putative conserved domains have been detected |
| 78 | 48258 | 48261 | 300 | MALKATALFAMLGLAFALSPPIEA NVDPHFDKFMESGIRHVYMLFE NKSVESSEQFYSFMRTTYKNDP CSSDFECIERGAEMAQSYARIMN IKLETE | 97 | Membrane protein, rI lysis inhibition regulator [Enterobacteria phage T4] | NP_049717. 1 | 2e-49 (94/97) | lysis inhibition regulator, membrane protein | No putative conserved domains have been detected |
| 79 | 48740 | 48644 | 301 | MKFSDFSQSGKPSKADEYLGLL MAAQAYFHSAHFETKSYARHKA YDFIFSELPDLIDKFGEQYLGYSG RKYTPSIPDASKLPTDTIKMIDRIL DQSNSIYKEMPPAIQSTIDDITGM FYQSKYLLSLE | 128 | MobD.6 hypothetical protein [Enterobacteria phage T4] | NP_049716. 1 | 5e-68 (128/128) | | No putative conserved domains have been detected |
| 80 | 48928 | 48929 | 302 | MKIEALNQEGNIYVIINGDFFVDM DEVTSEELVELLKKRYDMCDEAA THMACAIFSLSYVVE | 62 | MobD.5 hypothetical protein [Enterobacteria phage T4] | NP_049715. 1 | 4e-27 (60/62) | | No putative conserved domains have been detected |
| 81 | 49134 | 49131 | 303 | MTRIEQADKIKELVALIRKADEEL SDFAWFSAGIANKGIEKFEAKVD NALEALDMFLDEIIDHNTRV | 67 | Hypothetical protein RB32ORF102c [Enterobacteria phage RB32] | YP_803044. 1 | 1e-26 (61/67) | | No putative conserved domains have been detected |
| 82 | 49318 | 49328 | 304 | MLTREQFEKIIKLARDIEIDSYQLA VEHCEGYSYDGIEAAKKDLDKSK AKLVQYLEMIRWNNEN | 64 | MobD.3 hypothetical protein [Enterobacteria phage RB14] | YP_0028540 61.1 | 2e-29 (64/64) | | No putative conserved domains have been detected |
| 83 | 49656 | 49491 | 305 | MKTEKQMFLMKLIEEYANAVSDY ECSSRERGTAFAKEELKIMVDAH TKLQNFIENVI | 57 | mobD.2a hypothetical protein [Enterobacteria phage RB14] | YP_0028544 39.1 | 5e-25 (56/57) | | No putative conserved domains have been detected |
| 84 | 49843 | 49841 | 306 | MTSEQAFKLKELIETYSKAVHTA TVIDESAFSGHANKIKYKTLMEEA KVNLDSYIETLIGE | 61 | Hypothetical protein RB14ORF101 [Enterobacteria phage RB14] | YP_0028544 37.1 | 1e-25 (59/61) | | No putative conserved domains have been detected |
| 85 | 50111 | 50109 | 307 | MGFPKLEVGDLVLTKLWNGVQS VEICQYRGATGNLMYTIYNPEILL ECHLERFKDTDSMPYSVSIVRK SDTKEYSKILEQIRANKKD | 88 | Hypothetical protein RB14ORF100 [Enterobacteria phage RB14] | YP_0028544 36.1 | 7e-42 (83/88) | | No putative conserved domains have been detected |
| | | 50644 | 308 | MKRLVLEVSPLFGELAIEKVNNM YRLTQEDDMLYFTPSEIIHLTQIE | 177 | Hypothetical protein RB32ORF098c | YP_803040. | 1e-96 (169/177) | | No putative conserved domains have been detected |

Fig. 6Q

| | | | | | | | | |
|---|---|---|---|---|---|---|---|---|
| | | | | YPYTDKIVSINDEHKIHFYSSCPG FNIKSESMCLSVIHWDSFIDKIKY FYSNERKHSLKWLKNCNAIITN ACNQNDETLNVSKCYEEGDVL TIRQIDDFRSHIVTFTKDEAIALKT YLDSVIPTMISK | | [Enterobacteria phage RB32] | 1 | | have been detected |
| 86 | 50651 | 51172 | 309 | MFISSGSGLIRVEFKNDIFLSQGD DIIKMSYDEIKKICHALESHGKEN ATIDIGDLWVTLYEVSEGFNIEDE NNILAIDKRSDLFDVLKVYEQSN GGRKAVLVYQKPHSCGTASIISNI EDETDTYMCVLKAGGDRHPDFI SIRQNNGEISLSKSEAEAMIKYLT TVTPSMKG | 173 | Hypothetical protein RB32ORF097c [Enterobacteria phage RB32] | YP_803039. 1 | 4e-93 (166/173) | No putative conserved domains have been detected |
| 87 | 51175 | 51636 | 310 | MIINENSWHYKLFKMFNDEWKR PKTLCAYFWSVIPTFFVSFFGCT ILAGLTIICAEIIQKWLIFGSLWTLI PSAFILAILLVLLIIGSFVIPAQLHE KYKDYKWKKDYALHVENIDRAY KGLPPIQPKKSIIVEFLKARKAKV CPVIEYKAE | 153 | RB32ORF096c hypothetical protein [Enterobacteria phage RB51] | YP_0028540 56.1 | 8e-63 (139/153) | No putative conserved domains have been detected |
| 88 | 51636 | 52646 | 311 | MKTVMKSYFGSHLYGTSTPESD VDFKEIFVPPARDILIGNVKEHMS KNTNNTSSKNTKDDIDHELYSLK YFFKLAADGETVALDMLHTPPEL VVKSDLPDVWKFIQDNRSRFYTT NMKSYLGYVRKQASKYGVKGSR LAALRDVLKVVNQIPEGWVDYQ EDGSIKQRRTKVEDIKHRLPENE FCEWVFHNHEKTGPQTFYTVLG RKYQTTLSLIELKQSLNKLDAEY GERARKAEANEGIDWKALSHAC RGGLQLLEIYKTGDLVYPLQDAP FILDVKLGKHPFKTVQEFLEDVV DQVEAASTEASKNGMQQKVDM SFWDDFLEKVYLENHRSYYK | 336 | Hypothetical protein RB32ORF095c [Enterobacteria phage RB32] | YP_803037. 1 | 0,0 (335/336) | Nuc- transf. Predicted nucleotidy l- transferas e | pfam1012 7 | 2e-06 |
| 89 | 52764 | 52913 | 312 | MKITPIEVKKLIDTEEISECFESFL EDATEDNAVYLAQKIIETYLEKNQ | 49 | No significant similarity found. | | | |
| 90 | 52910 | 53173 | 313 | MTYVYDVLMNHGWKLRGHPTK NCHMFTDGDIEELHEMAEAIGMK RSWFQDKRIKHYDLHARRRQKA VELGAVEVSRREAVKIWRTLK | 87 | No significant similarity found. | | | No putative conserved domains have been detected |
| 91 | 53243 | 54211 | 314 | MKTVTINKGIYFGKEISGTFELLG EWFPDNAPVDAQGDGKVFVEID GKRRGVWVYKSDISYDGVKVEE VKESYEDMKTRINKRFNVMGMM | 322 | Hypothetical protein RB32ORF094c [Enterobacteria | YP_803036.1 | 0,0. (319/322) | No putative conserved domains have been detected |

Fig. 6R

| | | | | | | | |
|---|---|---|---|---|---|---|---|
| | | | TNGIINGNIRSLIISGAAGIGKTYS LDKALNKANDNGYIEYKSINGKIS GIGLYEQLWNNREENSVLIIDDV DVFSDMDILNLLKAALDTGETRK VCWSTASSYLEEKGIEREFEFKG TIVFITNVDIDRELDRGTKLAPHL QALVSRSVYLDLGVHTNEEIMVR VEDVILSTDMMQKRGLSDEETYK ALSWMKVNVNRLRNVSLRTALY LADFIMTDKNGWEEIAEVTLLK | | | phage RB32] | | |
| 92 | 5413 | 54615 | MLYSKAREIYETKIKEAVFKFATT MRWTNDWEYSKNHKKPMVTRK AHMLVLIDREQIKAREALQNHKK AAFEWFMDNTAPETKKAVSAWF SGKNCERSFF | 315 | 100 | NrdC.9 conserved hypothetical protein [Enterobacteria phage T4] | NP_04970.1 | 8e-52 (98/100) | No putative conserved domains have been detected |
| 93 | 54676 | 55203 | MNAKDIFNLVNYNDGKFKSEAQ SKFFNDISIGGEITVDGGQIYKSR WNWIVIIDEIGIVEIYKNTNKNRTL HWSRDTNEQYKKDKASKLSRVT QEDIEFIKKDILMYDNLIAEEQAVI DKFDEIKASREIPDFMKESVNER YTLISERIETYKKQRAERQNTLRK FEERLKTVLA | 316 | 175 | NrdC.8 hypothetical protein [Enterobacteria phage RB14] | YP_0023544 28.1 | 9e-96 (175/175) | No putative conserved domains have been detected |
| 94 | 55259 | 55666 | MKQLIIKRLNLLICCLCIAAAYGYY AINDYMHYKDYDVTVVNTITGTQ GKGSSLSFIAVYELKDGYRFSEYI SPEMYSSIEKGDNITVSLRPFDV KQTLFDNIVWFFGMVLVQSVCG AYIVCSILFCIFSKIEIE | 317 | 135 | NrdC.7 conserved hypothetical, predicted membrane protein [Enterobacteria phage T4] | NP_049705. 1 | 9e-66 (122/133) | No putative conserved domains have been detected |
| 95 | 55674 | 56561 | MSVVINNVNAVIKSLVNKKLNEW TVLRRGEPDKFFHRFNPTLDLNV IDRDVHAEILDKFKVDIGFGLDKH LQRTNGSGMGLSNRIMKALNKIG ALSRINASEILRNYNKGYDLYGRL MPKLSFDQMIADLWENQRRLLA LGARLAKGLDKQMIFKTNNTEDL KCFKFSTRGDDYYIRARSTDYVN MGHHLCLAFEVLKEAGTLEYVS GAKCPIGSNCILYRPDESSSTKL PTKPVFVRSNEKHSEQIAYFNKQ IEELNISIQQYDDEIFRLSGLSSKA KSEREKLIKIVDLLKS | 318 | 295 | NrdC.6 hypothetical protein [Enterobacteria phage RB14] | YP_0023544 26.1 | 8e-170 (291/295) | No putative conserved domains have been detected |
| 96 | 56570 | 57598 | MKTRSQIEDMVRNASYTRDVMT FLCENNLDPDKVNRVIHHFKYTN SSEWVRNFSKAGYITQMTAREQ LTDFCKTIDYKNPLIVQGVGQSK | 319 | 342 | Hypothetical protein RB32ORF088c [Enterobacteria phage RB32] | YP_803030.1 | 0.0 (335/342) | No putative conserved domains have been detected |

Fig. 6S

| | | | | | | | | |
|---|---|---|---|---|---|---|---|---|
| 97 | 57656 | | VDLSSGFFNPNHYRIEWRFIALF RKQLKQILSTASRLKGSDINLKNL KFDGYTLQMEVRPLKENNRTARI SFKPNTKNSLSICECLKSQLTEAF KYMDVVAAVQSKILPRFERNWE HTTTYELDMIVSFKYEFLRKDEIV QEKKQEVQDTLNLNLSNYLSND PKFWMYSSSNIDACKLNKVSFLP TENSNFKPVEKWHADAIEKSLKA VDDELVKATNEVLEAEKALEQAQ SRVQNLTKQRSKLNNALNALN | | | | | |
| | 58657 | 320 | MTRNEYIKSFNSVIDDKAIPMFG QNSVLSIINQWLNSVDASIVSSTK FIHEIRKISSRVDKDVIKKTFKESR LLSYLVNRDILGNFGKEIKRTKDV VGYNWFGDVNSYHLNIKEDPENI FTRRWISNFRLFKKQILKSASKLC YGDYRQIHPLASDMIIIKEYELDK NKVSIFVNYGFFTPETNQKNINKF FSIASTITRQLETALLCMETVENIH TYPFKNICGWEGYKLVISLREVK CAYSPTDKEIYQQKCDEIVNTPK EETTLEELMECLDDSPEPIEIRPE VIALEKAYKEVLEISNKAQKEYEQ AKRIWEESVNRLDRLEGALQLIK | NrdC.4 conserved hypothetical protein [Enterobacteria phage T4] | NP_049702.1 | 0.0 (330/333) | | No putative conserved domains have been detected |
| 98 | 58710 | 321 | MKTRKHYIDYFDSLITKHRNYQIG HRAVINNILRDFLDYIGWENHICK DTQNAYSHSLGSLLEWFKRSRL LSSVIAVNNVKKFMYPSYIETNVS NASVVTFNIINDVKRTYLEEWFS KDSKEKFASEFSHEFNNNVNML FKHSRRLFCHGDNRTINVNVKD WVTAKFTPSSQNGQFELSIIICAP HEIYKNLPYMKPREANKHNETIS SLAYNLRVLLSDMDVVKSFDDNT NYGLSLFETKFVIKLKDPSEFKPT PKSNHGNDTMKEEREYLSARLIE VEKQIEEHTKVLKALTAKANGLR NAIEVLK | Hypothetical protein RB32ORF086c [Enterobacteria phage RB32] | YP_803028.1 | 1e-180 (307/308) | | No putative conserved domains have been detected |
| 99 | 59633 | 322 | MKKRLLEDIAASSNSSLIKIIMAGE EDDMEMRGKIHGCDDLDFKPPA WDAIMAMVERRERASKNVPNCP ECGTEQVQLINWRKPELEYKCR QCKHKFSKHAPEMVKLPDSTEF FKELVSVQPMPNNILD | NrdC.2 hypothetical protein [Enterobacteria phage RB14] | YP_0285442.1 | 1e-70 (129/129) | tRNA synthetases class I (K) | pfam0192 1 | 0.002 |
| 100 | 60025 60267 | 323 | MTKRKEYMEAAEKAVRELAIAYY NEHGKFPDRYSVLKSALTRSYK | NrdC.1 hypothetical protein | YP_0028544 | 2e-39 | | No putative conserved domains |

Fig. 6T

| | | | | | | | | | | |
|---|---|---|---|---|---|---|---|---|---|---|
| 101 | 60269 | 60532 | 324 | NMLSEVSDIIYKHKEQTGQSLDY DETFKQVLGIKE | | | 21.1 | (80/80) | | have been detected |
| | | | | | | [Enterobacteria phage RB14] | | | | GRX_GR Xb_1_3_li ke, Glutaredo xin (GRX) family | cd03418 | 2e-07 |
| 101 | 60269 | 60532 | 324 | NMLSEVSDIIYKHKEQTGQSLDY DETFKQVLGIKE | 87 | [Enterobacteria phage RB14] | 21.1 | (80/80) | | GRX_GR Xb_1_3_li ke, Glutaredo xin (GRX) family | cd03418 | 2e-07 |
| 102 | 60529 | 60744 | 325 | MFKYYGYDSNIHKCVYCDNAKR LLTVKKQPFEFINIMPEKGVFDDE KIAELLTKLGRDTQIGLTMPQVFA PDGSHIGGFDQLREYFK | 87 | NrdC thioredoxin [Enterobacteria phage T4] | NP_049698. 1 | 8e-45 (87/87) | NrdC thioredoxin | No putative conserved domains have been detected |
| 103 | 60747 | 60917 | 326 | MMLEGTDYIHDYRGSAVYVGDE VAVYYGYGTLMTAKVIQIKNNRA KLEVYYSNGEKSISKWKYGDCM VKLG | 71 | RB32ORF082c hypothetical protein [Enterobacteria phage RB51] | YP_0028540 42.1 | 2e-33 (71/71) | | No putative conserved domains have been detected |
| 104 | 60883 | 61056 | 327 | MIYDINVSRTPSMVTIPAEELDRL QKIEELLWEIESDLPSGLESWIDY EELNKLRG | 56 | Hypothetical protein RB32ORF081c [Enterobacteria phage RB32] | YP_803023.1 | 6e-23 (55/56) | | No putative conserved domains have been detected |
| 105 | 61040 | 61525 | 328 | LIMKNLISFGVKPWWAARWETV EPEPEEPVYIDEETVYNEPTINDL IDMEMGHDYSR | 57 | Hypothetical protein RB32ORF080c [Enterobacteria phage RB32] | YP_803022.1 | 6e-24 (54/55) | | No putative conserved domains have been detected |
| 106 | 61562 | 61738 | 329 | MITVDKWFRINRVDTGLCNYWP ELSAGTVFKVRELAKECEDDIEP DTGIIEIELSDGKIINYDKPITYWC LWNTESVENGEIEEVVERTSQD VQKPKAAFQGERISYALAKLAAQ ENNDGYEGNLMQAAAEYIEWLE TQISFSDQKIRQYKRLHQMFYNT | 161 | Inhibitor of host Lon protease [Enterobacteria phage RB51] | YP_0028540 38.1 | 4e-86 (155/161) | protease inhibitor | PinA peptidase inhibitor | pfam1046 5 | 3e-66 |
| 107 | 61782 | 62255 | 330 | MKTELVYTEKLNGGKVWKLFIKG HSTDPHMTTCVGTYSRPTKKMI RQYKRLHRMFYNT | 58 | Hypothetical protein RB32ORF078c [Enterobacteria phage RB32] | YP_803020.1 | 9e-27 (58/58) | | No putative conserved domains have been detected |
| 108 | 62252 | 64069 | 331 | MLLTGKLYKEEKQKFYDAQNGK CLICQRENLPDVQANHLDHDHEL NGPKAGKVRGLLCNLCNAAEGQ MKHKFNRSGLKGQGVDYLEWLE NLLTYLKSDYTQNNIHPNFVGDK SKEFSRLGKEEMMAEMLQRGFE YNESDTKTQLIASFKKQLRKSLK | 157 | Gp49 EndoVII packaging and recombination endonuclease VII [Enterobacteria phage T4] | NP_049692. 1 | 1e-87 (157/157) | EndoVII packaging and recombination endonuclease VII | Recombin ation endonucl ease VII | pfam0294 5 | 3e-20 |
| | 62252 | 64069 | 331 | MTIEKEIEGLIHKTNKDLLNENAN KDSRVFPTQRDLMAGIVSKHIAK NMVPSFIMKAHESGIIHFHDIDYS PALPFTNCCLVDLKGMLENGFKL GNAQIETPKSIGVATAIMAQITAQ VASHQYGGTTFANVDKVLSPYV KRTYAKHIEDAEKWQIADALNYA | 605 | Anaerobic ribonucleotide reductase subunit [Enterobacteria phage RB14] | YP_0028544 13.1 | 0.0 (599/605) | anaerobic ribonucleotide reductase subunit | RNR, class III. Ribonucle otide reductase (RNR) catalyzes | cd01675 | 2e-159 |

Fig. 6U

| | | | | | | | | |
|---|---|---|---|---|---|---|---|---|
| 109 | 64066 | 64536 | 332 | QSKTEKDVYDAFQAYEYEVNTLF SSNGQTPFVTITFGTGTDWTER MIQKAILKNRIKGLGRDGITPIFPK LVMFVEEGVNLYKDDPNYDIKQL ALECASKRMYPDIISAKNNKAITG SSIPVSPMGCRSFLSAWKDSTG NEILDGRNNLGVVTLNLPRIALDS YIGTQFNEQKFTELFNERMDLCF EALMCRISSLKGVKATVAPILYQE GAFGVRLKPDDDIIELFKNGRSS VSLGYIGIHELNILVGRDIGQEILT KMNARLKQWAERTGFAFSLYST PAENLCYRFCKLDTEKYGSVKD VTDKGWYTNSFHVSVEENITPFE KISREAPYHFIATGGHISVVELPD MKNNLKGLEAVVDYAAQHLDYF GVNMPVDKCFTCGSTHEMTPTE NGFVCSICGETDPKKMNTIRRTC GYLGNPNERGFNLGKNKEIMHR VKHQ | Anaerobic nucleotide reductase subunit [Enterobacteria phage RB32] | YP_803017.1 | 3e-87 (155/156) | anaerobic nucleotide reductase subunit | the reductive synthesis |
| 110 | 64529 | 64642 | 333 | MNYDRFYPCDFVNGPGCRTVLF VTGCLHKCEGCYNKSTWNARN GIPFTGETLEQLECLNNDYIEGL TITGGDPLYPDNRDVIHCIVQTVK NLYPNKSIWLWTGYKFEDIKQLE MLKYVDVIIDGKYEKNLPTKKLW RGSDNQRLWSNTDGVWKHD | Hypothetical protein RB32ORF074c [Enterobacteria phage RB32] | YP_803016.1 | 4e-13 (37/37) | | NrdG, anaerobic ribonucle oside-triphosph ate reductase activating protein | TIGR0249 1 | 4e-55 |
| 110 | 64529 | 64642 | 333 | MIKLNYIMDTINDMIFHFGPEFYS QYSLVLINAWLIN | | | | | No putative conserved domains have been detected | | |
| 111 | 64652 | 64867 | 334 | MYKFRKGLADFLTTVTFFLFMAV GAIFLIPEIAIFFVISLISPEKGLSSS EFNERLDKITNKLNAVLDKKA | Gp55.8 hypothetical protein [Enterobacteria phage RB14] | YP_0028544 11.1 | 8e-32 (71/71) | | No putative conserved domains have been detected | | |
| 112 | 64870 | 65181 | 335 | MISFERYVVESWNGFDMFGNDY YFYECSLNPSFWAGREQDLEEIN ARADLLGELPTTYFTFDESGFVI QVYFPEENSGEDSVNPPYWAYQ GIISRGTKLELKE | Hypothetical protein RB51ORF079 [Enterobacteria phage RB51] | YP_0028540 32.1 | 6e-54 (103/103) | | No putative conserved domains have been detected | | |
| 113 | 65153 | 65476 | 336 | VEQNSNLKNKIEVVGIPDEVGRC PGCQSVTKLLKELNAPFTFYKVL TNNGKIEYDRPLIVSLAKRAGFTS LNIRYPVIFINDSRQKNIKHFKETL | Glutaredoxin [Enterobacteria phage RB51] | YP_0028540 31.1 | 1e-55 (106/107) | glutaredoxin | Glutaredo xin | pfam0046 2 | 7e-04 |

Fig. 6V

| | | | ISLGYDRDIIED | | | | | | |
|---|---|---|---|---|---|---|---|---|---|
| 114 | 65634 | 65816 | 337 | MVVVDKEIKKGQYYFINGNVVRV TYVNGFEVYYLILKLHKQMICDR AVFSSVAKEIKLHG | 60 | Gp55.6 hypothetical protein [Enterobacteria phage RB14] | YP_0028544 07.1 | 2e-26 (60/60) | | No putative conserved domains have been detected |
| 115 | 65809 | 66102 | 338 | MGKTYRRKDLKVRDYDFGKRK APDGVSHKDMVENIFRSDKWRR MKGIDSEVKDELNRQLRSEVRKL KKSVMDDDFDYNTSQRVAKRKS NECYRYS | 97 | Gp55.5 conserved protein of unknown function [Enterobacteria phage T4] | NP_049684. 1 | 6e-48 (96/97) | | No putative conserved domains have been detected |
| 116 | 66110 | 66241 | 339 | MNIKRMLFKQGLYTLNATPKGDT TKWSNDWIKFIDENGNWEI | 43 | Gp55.4 conserved hypothetical protein [Enterobacteria phage T4] | NP_049683. 1 | 2e-16 (42/43) | | No putative conserved domains have been detected |
| 117 | 66242 | 66442 | 340 | MNPESKLSQRIAEERAKFFQNM KHNGIEDEVFLNWFWNNKYAAC EGALSLSVAMMYEGWKGAKKFS | 66 | Gp55.3 hypothetical protein [Enterobacteria phage T4] | NP_049682. 1 | 1e-31 (66/66) | | No putative conserved domains have been detected |
| 118 | 66495 | 66821 | 341 | MTIQIKNAINSYAYDKVVSLLEKG DIVTPQILDKWEKELHQTMKQND QKIGRNTVRELLYVQYILSEFDVKA FGVESKAYQKHEISDKTIRRMKN QRKKKFADLKITKV | 108 | Gp55.2 hypothetical protein [Enterobacteria phage T4] | NP_049681. 1 | 6e-56 (108/108) | Hypotheti cal protein | PHA02100 | 0.003 No putative conserved domains have been detected |
| 119 | 66824 | 67039 | 342 | MNEALINDLRLAGYEVNTNGIGL TQIEGNGFILEYEFSQWMLYANY GELIEYVDQFDSLDAALEAAKLM NV | 71 | Gp55.1 hypothetical protein [Enterobacteria phage RB14] | YP_0028544 02.1 | 2e-32 (71/71) | | No putative conserved domains have been detected |
| 120 | 67036 | 67305 | 343 | MKLINISIAIENFGIFYVDQYMKIS FFPNKTGVGYWESHVSELNESE YVSTHKKFLDFLYRADINDHYIDI HEFKKMMEKVFQAYCLLR | 89 | Hypothetical protein RB14ORF65 [Enterobacteria phage RB14] | YP_0028544 01.1 | 2e-41 (81/89) | | No putative conserved domains have been detected |
| 121 | 67384 | 67941 | 344 | MSETKPKPKYNYNYNNKELLQAIIDW KTELANNKDPNKVVRQNDTIG_A IMLIAEGLSKRFNFSGYTQSWKQ EMADGIEASIKGLHNFDETKYKN PHAYITQACFNAFVQRIKKERKE VAKKYSYFVHNVYDSRDDDMVA LVDETFIQDIYDKMTHYEESTYRT PGAEKKSVVDDSPSLDFLYEAN D | 185 | Gp55 Sigma factor for T4 late transcription [Enterobacteria phage T4] | NP_049679. 1 | 7e-106 (185/185) | | No putative conserved domains have been detected |
| 122 | 67925 | 68143 | 345 | MRLTINLSGFLEEIPEVEAIPYLK MYLREVLALDIDIDPENPYDTAFK SNGVELNYRYHLTDDDFYFILEK | 72 | A-gt.5 hypothetical protein [Enterobacteria phage T4] | NP_049678 | 2e-33 (72/72) | | No putative conserved domains have been detected |

Fig. 6W

| | | | | | | | | |
|---|---|---|---|---|---|---|---|---|
| 123 | 68145 | 346 | MTDKPEINDEVEKLISSIEEKNRL EAERKANKLLSKNKRELNRLYKH AQIAAENNNFAQYEYAIKKSRDIL KQPYNDELISILWKTTRSQIEDMI DAYTRKIQAS | 105 | A-gt.4 conserved hypothetical protein [Enterobacteria phage T4] | NP_049677 1 | 8e-53 (105/105) | | No putative conserved domains have been detected |
| 124 | 68431 | 347 | MLTHVKFKRLKINAGFTESLNGH LCVKISEKEYHDSSIKEVNPPIVR ADPNMKVVWDSYQVKKWWQL | 67 | Hypothetical protein RB32ORF062c [Enterobacteria phage RB32] | YP_803004.1 | 2e-32 (67/67) | | No putative conserved domains have been detected |
| 125 | 68638 | 348 | MNTQTSEIDYNKIRSSKEEMMRR FKESHDKAKAEGTIKYKRIKFKSS NEPLYGVLCG | 57 | A-gt.2 hypothetical protein [Enterobacteria phage RB51] | YP_0028540 19.1 | 2e-24 (55/57) | | No putative conserved domains have been detected |
| 126 | 68878 | 349 | MKVCIFMARGLEGCGVTKFSLE QRDWFIKNGHEVTLVYAKDKSFT RNCAHDYKSFSIPVLLAKEYDKT LKLVNDCDILIINSVPATSVEEDTI NNYKKIIDNIKPSVRVVYQHDHS SLSLRRNLGLEETIRRADVIFSHS DNGDFNKYLMKEWYPETVSLFD DIEEAPTVYNFQPPMDIAKVRST YWKDVSEINMNINRWIGRTTTW KGFYQMFDFHEKHLKPAGLSTIM EGLERSPAFIPIKEKGIPYEYRL HQVDQIKIAPNLPTQILDRYVNSE MLERMSKSGFGYQLSKLDKKYL QRSLEYTHLELGACGTIPVFWKS TGENLKFRVDNTPLTSHDSGIIW FDENDMESTFERIKELSSDRTLY DREREKAYEFLYQHQDSSFCFK EQFDIITK | 400 | Alpha-glucosyl-transferase [Enterobacteria phage RB51] | YP_0028540 18.1 | 0.0 (399/400) | alpha-glucosyl-transferase | No putative conserved domains have been detected |
| 127 | 70257 | 350 | MKILNLGDWHLGVKADDEWVQS IQLDGIKQAIEYSKKNGITTWIQY GDIFDVRKAITHKTMEFAREIVQ MLDDAGITLHTIVGNHDMHFKNT LTPNASTELLAKYPNVKYYDKPT TVDFDGCLIDLIPWMCEENTGEIL EHIKTSSASFCVGHWELNGFYFY KGMKSHGLEPDFLKTYKEVWSG HFHTISEAANVRYIGTPWTLTAG DENDPRGFWMFDTETERMEFIP NNTTWHRRIHYPFKGKIDYKOFT NLSVRVMTEVDKNLTKFESELEK VVHSLRVVSKIDNSVESDDSEEV EVQSLQTLMEEYINAIPDITDSDR EALIQYANQLYVEATQ | 339 | Gp47 recombination endonuclease subunit [Enterobacteria phage RB51] | YP_0028540 16.1 | 0.0 (337/339) | recombination endonuclease subunit | Exonucle ase SbcD | TIGR0061 9 | 5e-05 |

Fig. 6X

| | | | | | | | |
|---|---|---|---|---|---|---|---|
| 128 | 71273 | 71536 | 351 | MTFDEFKNVMMSQHFECEVKDD IGHKEIIEYWFEPLEVEDNCIKKV TVCTDWAVSFNFNILDNDTPKSL RDMAVSCIKDAYCEVFDI | 87 | Hypothetical protein RB32ORF057c [Enterobacteria phage RB32] | YP_802999.1 | 1e-43 (87/87) | | No putative conserved domains have been detected |
| 129 | 71517 | 71723 | 352 | VKFSTFDINDEFIANIDYTEEDSR YVGIIYITSKTAQGVVCMAEFDEY FLDYDDMIEWSKRYIKRNLL | 68 | Hypothetical protein RB32ORF056c [Enterobacteria phage RB32] | YP_802998.1 | 9e-32 (68/68) | | No putative conserved domains have been detected |
| 130 | 71762 | 73402 | 353 | MSVGGNPIDIQLDKVQKTLITGR NGGGKSTMLEAITFGLFGKPFRD VKKGQLINSTNKKELLVELWMEY DEKKYYIKRCGOKPNVFEITVNGT RLNESASSKDFGAEFEQLIGMSY ASFKQIVVLGTAGYTPFMGLSTP ARRKLVEDLLEVGTLAEMDKLNK ALIRELNSQNQVLDVKKDSIIQQI KIYNDNVERGKKLTGDNLTRLQN MYDDLAKEARTLKSEIEEANERL VNIVLDEDPTDAFNKIGQEAVLIK SKIDSYNKVINMYHEGGLCPTCL SQLSSGDKVVSKIKDKVSECTHS FEQLSTHRDNLKVLVDEYRDNIK TQQSLANDIRNKKQSLITTVDKA KKYKAAIEKASSEFIDHADEIALL QEELDKIVKTKTNLVMEKYHRGIL TDMLKDSGIKGAIIKKYIPLFNKQI NHYLKIMEADYVFTLDEEFNETIK SRGREDFSYASFSQGEKARIDIA LLFTWRDIAEKVSGVKINTLILDE VFDSATDVEGVKAISTILDSLKNT NVFVISHRDHDPQAYGQHLQMK KVGRFTVMV | 546 | Gp46 recombination endonuclease subunit [Enterobacteria phage RB14] | YP_0028543 90.1 | 0.0 (545/546) | recombination endonuclease subunit | ABC_sbc CD, SbcCD and other Mre11/Ra d50 (MR) complexe s are implicated in the metabolis m of DNA ends | cd03279 | 6e-08 |
| 131 | 73458 | 73646 | 354 | MEYSTGQHLLTIPEIKRYILRNNF SNEEHIVTESMLRNAFKAEYTKI MSNRNEAWTVTDYD | 62 | | NP_049668. 1 | 4e-29 (62/62) | | No putative conserved domains have been detected |
| 132 | 73656 | 74045 | 355 | MTKITVNYTVDVKDIQPKHVRSE SNPQNQNKIRRAVVVLSLSDNAM EVIQNKIKSAPARHAYYEAIDREV SNKWIELMRKHTTESLNAGAKFI MTSCGERLEDEYCGNADERLIV AAQIVAETIAADFNR | 129 | RNA polymerase binding [Enterobacteria phage RB14] | YP_0028543 88.1 | 5e-71 (129/129) | RNA polymerase binding protein | Phage RNA polymera se binding, RpbA | pfam10789 | 5e-35 |
| 133 | 47101 | 74787 | 356 | MKLSKDTTALLKNFATINSGIMLK SGGFIMTRAVNGTTYAEANISDVI DFDVAIYDLNGFLGILSLVNDDAE ISQSEDGNIKIADARSTIFWPAAD | 228 | Gp45 sliding clamp DNA polymerase [Enterobacteria phage RB32] | YP_802993.1 | 2e-129 (228/228) | sliding clamp DNA polymerase | Gp45 sliding clamp, C terminal | pfam09116 | 5e-46 |

Fig. 6Y

| | | | Sequence | Length | Description | Accession | E-value/Identity | Function | Conserved Domain | | |
|---|---|---|---|---|---|---|---|---|---|---|---|
| 134 | 74839 | 357 | PSTVVAPNKPIPFPVASVVTEIKA EDLQQLLRVSRGLQDTIATVKE GKIVINGFNKVEDSALTRVKYSLT LGDYDGENTFNFINMANMKMQ PGNYKLLLWAKGKQGAAKFEGE HANYVVALEADSTHDF | | | | | | | |
| | 75798 | | MITVNEKEHILEQKYRPSTIDECIL PAFDKETFKSITSKGKIPHILHSP SPGTGKTTVAKALCHDVNADMM FVNGSDCKIDFVRGPLTNFASAA SFDGRQKVIVIDEFDRSGLAESQ RHLRSFMEAYSSNCSIIITANNID GIIKPLQSRCRVITFGQPTDEDKI EMMKQMIRRLTEICKHEGAIAD MKVVAALVKKNFPDFRKTIGELD SYSSKGVLDAGILSLVTNDRGAI DDVLESLKNKDVKQLRALAPKYA ADYSWFVGKLAEEIYSRVTPQSII RMYEIVGENNQYHGIAANTELHL AYLFIQLACEMQWK | 319 | Gp44 clamp loader subunit, DNA polymerase accessory protein [Enterobacteria phage T4] | NP_049665.1 | 0.0 (319/319) | clamp loader subunit, DNA polymerase accessory protein | The AAA+ (ATPases Associated with a wide variety of cellular Activities) superfamily | cd00009 | 5e-06 |
| | | | | | | | | | Rfc, replication factor C small subunit | PRK00440 | 1e-24 |
| 135 | 75800 | 358 | MSLFEDDIQLNEHQVAWYSKDW TAVQSAADSFKEKAENEFFEIIGA INNKTKCSIAQKDYSKFMVENAL SQFPECMPAVYAMNLIGSGLSD EAHFNYLMAAVPRGKRYGKWAK LVEDSTEVLIIKQLLAKRYQVNTND AINYKSILTKNGKLPLVLKELKGL VTDDFLKEVTKNVKEQKQLKKLA LEW | 187 | Gp62 clamp-loader subunit [Enterobacteria phage RB51] | YP_0028540 07.1 | 2e-105 (187/187) | clamp-loader subunit | No putative conserved domains have been detected | | |
| 136 | 76365 | 359 | MIEITLKKPEDFILKVKETLTRMGI ANNKDKVLYQSCHILQKKGLYYI VHFKEMLRMDGRQVEMTEEDE VRRDSIAWILLEDWGLIEIVPGQR TFMKDLTNNFRVISFKQKHEWKL VPKYTIGN | 122 | RegA translational repressor protein [Enterobacteria phage T4] | NP_049663.1 | 5e-66 (122/122) | RegA translational repressor protein | Translat_r eg, bacteriophage translational regulator | pfam01818 | 6e-46 |
| 137 | 76735 | 360 | MTAITPQEYMASLKEKYNLSATE TLFDLPENLQLKFQVEFQKLVHP EQKHFTAVVKSINADGMIIFTRQI VLI | 73 | RB32ORF047c hypothetical protein [Enterobacteria phage RB14] | YP_0028543 83.1 | 5e-34 (71/73) | | No putative conserved domains have been detected | | |

Fig. 6Z

| | | | | | | | | | |
|---|---|---|---|---|---|---|---|---|---|
| 138 | 77035 | 79731 | 361 | MKEFYISIETVGNNIVERYIDENG KERTREVEYLPTMFRHCKEESK YKDIYGKNCAPQKFPSMKDARD WMKRMEDIGLEALGMNDFKLAYI SDTYGSEIVYDRKFVRVANCDIE VTGDKFPDPMKAEYEIDATTHYD SIDDRFYVFDLLNSMYGSVSKW DAKLAAKLDCEGGDEVPQEILDR VIYMPFDNERDMLMEYINLWEQ KRPAIFTGWNIEGFDVPYIMNRV KMVLGERSMKRFSPIGRVKSKLI QNMYGSKEIYSIDGVSILDYLDLY KKFAFTNLPSFSLESVAQHETKK GKLPYDGPIINKLRETNHQRYISY NIIDVESVQAIDKIRGFIDLVLSMS YYAKMPFSGVMSPIKTWDAIIFN SLKGEHKVIPQOGSHVKQSFPG AFVFEPKPIARRYIMSFDLTSLYP SIIRQVNISPETIRGQFKVHPIHEY IAGTAPKPSEEYSCSPNGWMYD KHQEGIIPKEIAKVFFQRKDWKK KMFAEEMNAEAIKKIIMKGAGSC STKPEVERYVKFSDDFLNELSNY TESVLNSLIEECEKAATLANTNQL NRKILNSLYGALGNIHFRYYDLR NATATIFGQVGIQWIARKINEYLN KVCGTNGEDFIAAGDTDSVYVC VDKVIEKVGLDRFKEONDLVEFM NQFGKKKMEPMIDVAYRELCDY MNNREHLMHMDREAISCPPLGS KGVGGFWKAKKRYALNVYDME DKRFAEPHLKIMGMETQQSSTP KAVQEALEESIRRILQEGEESVQ EYYKNFEKEYRQLDYKVIAEVKT ANDIAKYDDKGWPGFKCPFHIR GVLTYRRAVSGLGVAPILDGNKV MV_PLREGNPFGDKCIAWPSGT ELPKEIRSDVLSWIDYSTLFQKSF VKPLAGMCESAGMDYEEKASLD FLFG | Gp43 DNA polymerase [Enterobacteria phage RB14] | YP_0028543 82.1 | 0,0 (898/898) | DNA polymerase | DNA polymerase family B | pfam00136 | 4e-70 |
| 139 | 79913 | 80293 | 362 | MKIAILVIALGLTGCVAQGPVVNQ SDVGKIVNCSSKFYNPNVKCYKE APKQTVEQMQANFDEAIRPDES AQAYRNSDVTREEKIENYCAEL WANWANNYQWRTGKNAPMEY VVNSYNSCVKNLTK | Imm.1 hypothetical protein [Enterobacteria phage RB51] | YP_0028540 02.1 | 3e-68 (126/126) | | No putative conserved domains have been detected | | |
| 140 | 80301 | 80552 | 363 | METLVAGSIFMVLVSGVLAIIIYML | Immunity to | YP_802986.1 | 1e-38 | immunity to | No putative conserved domains | | |

Fig. 6AA

| | | | | | | | | |
|---|---|---|---|---|---|---|---|---|
| | | | PWFIALMRGSKSTVGIFFTSLLFN WSINGWFITFIWSIAGETKKSAQP NQVIIIREKE | | | superinfection membrane protein [Enterobacteria phage RB32] | (83/83) | superinfection membrane protein | have been detected |
| 141 | 80706 | 81446 | MISDSMTVEEIRLHLGLALKEKDF VVDKTGVKTIEIIGASFVADEPFIF GALNDEYIGRELEWYKSKSLFVK DIPGETPKIWQQVASSKGEINSN YGWAIWSEDNYAQYDMCLAELG QNPDSRRGIMIYTRPSMQFDYN KDGMSDFMCTNTVQYLIRDKV NAVVSMRSNDCWAGYRNDYAW QKYVLDKLVSDLNAGDPSRQYK AGSIIWNVGSLHVYENQFYLVDH WWNTGETHIAKKDYTGKWK | 246 | Gp42 dCMP hydroxymethylase [Enterobacteria phage RB51] | YP_0028539 99.1 | 2e-136 (235/246) | dCMP hydroxy- methylase | TS_Pyrim idine_HM ase, Thymidyl ate synthase and pyrimidin e hydroxy- methylas e | cd00351 | 2e-16 |
| 142 | 81437 | 82078 | MEVNPHVYYKYHPKTKKWYIG SHDGHNPNYDGSGVWWQHVKK KYGIKSFNKEILYEGPMFRQVEEI ILTCLDAANCPDSYNLKNEAWG GSFPGKLNGMYGKKLSPEERYK CGNAFRGIKRPDHSKRMKGEGN PMYGKNEQAYGIINRAKENSGKT YEEIFGVEKAKIIKETMSKNRKGK PHNLIEKICPHCGLKGRGPNMTR YHFDKCKALK | 213 | Endodeoxyribonucl ease [Enterobacteria phage T4] | CAA93271.1 | 7e-66 (51/147) | endodeoxy- ribonuclease | No putative conserved domains have been detected | | |
| 143 | 82075 | 82917 | MIQFVIPSYQRYGAVSALDMFPT DYEPHIVVREHEEKAYYDAYGSK AKIVTIPDDVVNGIAGTRKAITDMY AGQRIWMIDDDTIIRMSSMRKR DDRRCVDKVNQLTREQFYELIQY VEDAMDCGYYHGHARLPIFKITS SWGNYRENSYGFTNTWYDLGK LTTEQIGYGKIDLCEDMYAFLNLI NQGYPHLALFKYLVVSGKAQAP GGCSSIRSNSKHNRALEQINREF PEQARWKTSNIEKRKSLGEEDE PLKVLRMCVSRKEKSEAFHKFN AIHPIAVD | 280 | RB32ORF041c hypothetical protein [Enterobacteria phage RB14] | YP_0028543 77.1 | 5e-167 (278/280) | | No putative conserved domains have been detected | | |
| 144 | 82996 | 84177 | MSIADLKSRLIKASTSKMTAELTT SKFFNEKQVIRTKIPMLNIAISGAI DGGMOSGLTIFAGPSKHFKSNM SLTMVAAYLNKYPDAVCLFYDSE FGITPAYLRSMGVDPERVIHTPIQ SVEQLKIDMVNQLEAIERGEKVIV FIDSIGNMASKKETEDALNEKSV ADMTRAKSLKSLFRIVTPYFSIKN | 393 | RecA-like recombinase protein [Enterobacteria phage RB32] | YP_802982.1 | 0.0 (393/393) | RecA-like recombinase protein | RecA is a bacterial enzyme which has roles in homologo us recombin | cd00983 | 1e-13 |

Fig. 6BB

| | | | | | | | |
|---|---|---|---|---|---|---|---|
| 145 | 84170 | | IPCVAVNHTIETIEMFSKTVMTGG TGVMYSADTVFIIGKRQIKDGSDL QGYOFVLNVEKSRTVKEKSKFFI DVKFDGGIDPYSGLLDMALELGF VVKPKNGWYAREFLDEETGEMI REEKSWRAKDTNCTTFWGPLFK HQPFRDAIKRAYQLGAIDSNEIVE AEVDELINSKVEKFKSPESKSKS AADLETDLEQLSDMEEFNE | | | | ation, DNA repair, and the induction of the SOS response. |
| | 84508 | 368 | MSKDDLDLEIIDESPSSEGEEER KERLFNESLKIIKSAMENVIQIEVI KLEDGSTHIVYVTKLDWDGKVV MDFAVLDQERKAELAPHVEKCIT MQLQDAFNKRSKKKFKFF | 112 | Gp40 head vertex assembly chaperone [Enterobacteria phage T4] | NP_049655. 1 | 7e-45 (104/107) | head vertex assembly chaperone | No putative conserved domains have been detected |
| 146 | 84518 | 369 | VVEIILSHLIFDQAYFSKVWPYMD SEYFESGPAKNTFKLIKSHVNEY HSVPSINALNVALENSSFTETEY SGVKTLISKLADSPEDHSWLVKE TEKYVQQRAMFNATSKIIEIQTNA ELPPEKRNKKMPDVGAIPDIMRQ ALSISFDSYVGHDWMDDYEARW LSYMNKARKVPFKLKILNKITKGG AETGTLNVLMAGVNVGKSLGLC SLAADYLQLGHNVLYISMEMAEE VCAKRIDANMLDVSLDDIDDGHI SYAEYKGKMEKWREKSTLGRLI VKQYPTGGADANTFRSLLNELKL KKNFVPTIIIVDYLGICKSCRIRVY SENSYTTVKAIAEELRALAVETET VLWTAAQVGKQAWDSSDVNMS DIAESAGLPATADFMLAVIETEEL AAAEQOLIKQIKSRYGDKNKWNK FLMGVQKGNQKWVEIEGDSTPT EVNEVAGSQQIDAEQNRYQRNE STRAQLDALANELKF | 475 | Gp41 DNA primase-helicase subunit [Enterobacteria phage T4] | NP_049654. 1 | 0.0 (473/475) | DNA primase-helicase subunit | DnaB, replicative DNA helicase [DNA replicatio n, recombin ation, and repair] COG0305 6e-13 |
| 147 | 86004 | 370 | MELVKVVFMGWFKNESMFTKEI TMMKDDVQWATTQYAEVNKALV KAFIDDKKVCEVDCRG | 60 | Dmd discriminator of mRNA degradation [Enterobacteria phage T4] | NP_049653. 1 | 7e-27 (60/60) | discriminator of mRNA degradation | No putative conserved domains have been detected |
| 148 | 86188 | 371 | MHIVLFKPTPYNVRKNTQFKALIA DTWELVLDIPAEESPPFGRVEFIK FAVRPTKRQIRQCKRYFRKIVKL EKQLLMLVK | 80 | Gp61.4 hypothetical protein [Enterobacteria phage RB14] | YP_0028543 72.1 | 4e-36 (74/76) | | No putative conserved domains have been detected |
| 149 | 86494 | 372 | MMLVNREYQFKSEEDLEKFASG CELNRRTAKVIGLKPFTVLDCEV | 84 | No significant similarity found. | | | | No putative conserved domains have been detected |

Fig. 6CC

| | | | | | | | | | |
|---|---|---|---|---|---|---|---|---|---|
| | | | SKFRRGCSISGHALVDGNTFFFV FSVRELLLINELEEIK | | | | | | |
| 150 | 86813 | 86995 | 373 | MSKVSGYQLLTQEQRSEMDSLQ ERCQHRNNALDSFLLVEYENLC SRLEKEYVHQHEGGEE | 60 | No significant similarity found. | | | No putative conserved domains have been detected | |
| 151 | 87099 | 87392 | 374 | MKKFIFAAIFALSSCAAQPAMAG YDKDLCEWSMTADQTEVETQIE ADIMNIVERDRPEMKAEVQKQLK SGGVMQYNYVLYCDKNFNNKNII AEVVGE | 97 | Sp spackle periplasmic protein [Enterobacteria phage T4] | NP_049651. 1 | 2e-49 (94/97) | spackle periplasmic protein, lysis regulation | |
| 152 | 87661 | 87762 | 375 | MLSDEINDLLNDAEKVAIPSIDDQ IFNAFMNRG | 33 | RB32ORF033c hypothetical protein [Enterobacteria phage RB51] | YP_0028539 90.1 | 1e-10 (33/33) | | No putative conserved domains have been detected |
| 153 | 87764 | 87928 | 376 | MKTFKEFIKEDMVAGDSGGNPE NISTGTTSGAVVNKGPEQIPKKK KEESKEKEE | 55 | Orf 61.1 [Enterobacteria phage T4] | AAB25712.1 | 2e-21 (54/54) | | Major capsid protein Gp23 | pfam0706 8 | 3e-04 |
| 154 | 87931 | 88959 | 377 | MSSIPWIDNEFAYRALAHLPKFT QVNNSSTFKLRFRCPVCGDSKT DQNKARGWYYGDNNEGNIHCY NCNYHAPIGYLKEFEPDLYREYI FEIRKEKGKSRPVEKPKELPKQP EKKIIKSLPSCIRLDKLAEDHPIIKY VKARCIPKDKWKYLWFTTEWPK LVNSIAPGTYKKEIPEPRLVIPIYN ANGKAESFQGRALKKDAPQKYT IKAYPEATKIYGVERVKDGDVYV LEGPIDSLFIENGIATGGQLDLEI VPFKDRRVWVLDNEPRHPDTIK RMTKLVDAGERVMFWDKSPWK SKDVNDMIRKEGATPEQIMEYM KNNIAQGLMAKMRLSKYAKI | 342 | Primase [Enterobacteria phage RB32] | YP_802973.1 | 0,0 (340/342) | primase | Toprim_N , DNA primase catalytic core, N-terminal domain | pfam0827 5 | 4e-05 |
| 155 | 89156 | 88956 | 378 | MVQKLMALVNAIKGNKKRIAFTIS AMIGILLWNFVLSPVAIAHGVSIP VITLDTFVDLAFALVGLI | 66 | RB32ORF030w hypothetical protein [Enterobacteria phage RB51] | YP_0028539 87.1 | 3e-27 (61/66) | | No putative conserved domains have been detected | |
| 156 | 89228 | 89746 | 379 | MAYFNECAHLIEGVDKANRAYAE NIMHNIDPLQVMLDMQRHLQIRL ANDKPETNRHPDSLETAGEVLA WLRNQDDYIADETRELYTSLGG MSNGEKEASAVVWKPWKKRYSE MQSKKIQDLSPEDQLEIKFELIDQ FHFFMNKFIALGMSAEEIFKLYYL KNAENFARQDRGY | 172 | dCTPase [Bacteriophage LZ5] | AF374621_1 | 6e-98 (171/172) | dCTP pyro-phosphatase | dUTPase _2 | pfam0876 1 | 2e-18 |

Fig. 6DD

| | | | | | | | |
|---|---|---|---|---|---|---|---|
| 157 | 89746 | 89946 | MARLNKRQLKKAHKKRIDQLFKN YDKELVCELLSNQLRAVDWVVE EGPDEIFVSEEALKLIIEHSK | 66 | Hypothetical protein RB14ORF29 [Enterobacteria phage RB14] | YP_0028543 65.1 | 1e-26 (61/66) | No putative conserved domains have been detected |
| 158 | 89943 | 90116 | MKISKEEFIRRQKALINLHEWYAY QLKVDSSNINAVMALYKQIQDEH EFLAQVFIED | 57 | No significant similarity found. | | | |
| 159 | 90156 | 90392 | MGGFVNIKTFTHPAGEGKEVKG MEVSVPFEIYSNEHRIADSHYQIF PSEKAAYSTVVSDAADWKTKNA AMFTPTQIGG | 78 | Small outer capsid [Enterobacteria phage RB14] | YP_0028543 64.1 | 6e-38(76/78) | small outer capsid protein |
| 160 | 90491 | 90697 | MLNRWIKPNEDLDIIISRHVMKKY ELQPWSTEVVVHSFMMYADGSV EFNAEIRYDYGEKQVEFKRGFL | 68 | Mrh.2 hypothetical protein [Enterobacteria phage RB14] | YP_0028543 63.1 | 4e-33 (68/68) | No putative conserved domains have been detected |
| 161 | 90697 | 91038 | MFIFNWFKSFFTDFFSTTPGEGV VPISNDYLPLTVVEYVYMGDGTV EAVTMTYEEAQEYYKNPWRWS TPITSSNTQNTQSSSDSYDTNVP VHVWTGDSCGSSCDSSCSSTS CD | 113 | Hypothetical protein RB32ORF026c [Enterobacteria phage RB32] | YP_802968.1 | 1e-58 (112/113) | No putative conserved domains have been detected |
| 162 | 91047 | 91532 | MEAILFEMYISSNSMSFAKDVPIT VAVMIDKGYCDPMYLVENFVSM PVPEDAEIKLKKIGIIETVPNIPFR AIEAFTKSEYINVSAEQYNDKPIS FYSYDSVYSWKDKGNKFIIVSED ALSYFISSWNSLHPNLLKIHEFD DAPTVVLGKTNESSEENV | 161 | Mrh [Enterobacteria phage RB32] | YP_802967.1 | 2e-86 (157/161) | affects phosphorylati on of host sigma32 |
| 163 | 91507 | 91710 | MKVLKKMFEWFSRPNSMYIDDG WVEQANKEMQNESEEWMKSMI SVEKEKKLERSALKLMRDIYGDK S | 67 | Postulated decoy of host sigma32 [Enterobacteria phage RB32] | YP_802965.1 | 2e-29 (65/67) | postulated decoy of host sigma32 |
| 164 | 91707 | 91871 | VNRDMTLEEAKANEALDLLLK IGSKMMEENEKYIQENKIPDGPL VGKRKSHD | 54 | ModA.4 hypothetical protein [Enterobacteria phage T4] | NP_0496539. 1 | 1e-21 (51/54) | |
| 165 | 91864 | 92346 | MIEVAKHYSIEFMSKEGKSVNTL DKKCSLIIPLAENPDILKDIKERKY PENVILIKHTEDILQNTDSPFSSS EALTIKGYKRAHEYGLFDLFEDD KVKLALNLAGQSKSKTFIIEDIK DINAFVKMVWAHFDVGLRWRMS EEERKIIEANRYFGFYR | 160 | ModA.3 hypothetical protein [Enterobacteria phage RB51] | YP_0028539 79.1 | 7e-86 (156/160) | No putative conserved domains have been detected |
| 166 | 92355 | 92537 | MDLFEMLEDNHSTNIQNDSSDY | 60 | ModA.2 | YP_0028539 | 2e-27 | No putative conserved domains |

Fig. 6EE

| | | | | | | | | |
|---|---|---|---|---|---|---|---|---|
| 167 | 92605 | | KKEYRIVLQNYGIEAPDALLEELASYHLDPPPWAPWAK | | hypothetical protein [Enterobacteria phage RB51] | 78.1 | (60/60) | | have been detected |
| | | 390 | MIINLADVEQLSIKAESVDFQYDMYKKVCEKFTDFEQSVLWQCMEAKKNKALHRQLNKIIKKHLTKSPYQLYRGISKSTKELIKDLQVGEVFSTNRVDSFTTSLHTACGFSYVEYFTEIIFRLKTDKAFNYSDHISDIILSSPNTEFKYTYEDTDGLDSERTDNLMMIVREQEWMIPIGKYKITSISKEKLHDSFGTFKVYDIEVVE | 207 | Adenylribosylating enzyme [Enterobacteria phage RB14] | YP_0028543 56.1 | 2e-117 (205/207) | adenyl-ribosylating enzyme | No putative conserved domains have been detected |
| 168 | 93225 | 391 | MKYSAMQLKDFKIKSMDASVRASIREELLSEGFNLSEIELLIHCITNKPDDHSWLNEIIKSRLVPNDKPLWRGVPVETKQVLNQGIDIITFDKVVSASYDKNVELHFASGLEYNTCVIFEFKAPMVFNFQEYAIKALRCKEYSPSFKFPDSHRYRNMELVSDEQEWMIPAGSVFRIADRYEYKKHSTYITYTLDFEGFNL | 200 | Adenylribosylating enzyme [Enterobacteria phage RB51] | YP_0028539 76.1 | 3e-112 (194/200) | adenyl-ribosylating enzyme | No putative conserved domains have been detected |
| 169 | 93943 | 392 | MKLSKNQIRKITRRLEHTQASAKRRSKDFNLDFNYIKNILDQKVCAYSGEPFDNRIEGEKLSLERFDNNVGYIKGNWAVKKKYNTFRSDYTLEELIEKRDLFALRIGRSSAKKVHKLNLDEKKWAKIIKKTYNQIKAIQKKRENRIEHISOLSKSKQTSDVKLTIIALKARIDGSRIAEGAEVVKLNVLLKGSDWKTVKKLSEAEMQYDMCDKIIQGVERYQNLSFIDKLKLKRGYPLNCSIFKLIRG | 248 | Postulated decoy of host sigma70 or sigmaS [Enterobacteria phage RB32] | YP_802959.1 | 9e-137 (243/248) | postulated decoy of host sigma70 or sigmaS | No putative conserved domains have been detected |
| 170 | 94691 | 393 | MFYYAIVYRDKDGFAVPVPLDEHRPAVFFEREIADKVFTTLKEQYQLALGMGIPRLVETPRKFWFNKIEVKHVKPDVDTQRLYRRILDTGRIVSIPIAGNLR | 103 | Hypothetical protein RB32ORF016c [Enterobacteria phage RB32] | YP_802958.1 | 5e-49 (96/103) | | No putative conserved domains have been detected |
| 171 | 94999 | 394 | MTFDDLTEGQKNAFNIVMRAIKEKKHHVTINGPAGTGKTTLTKFIIEALISTGETGIILAAPTHAAKKILSKLSGKEASTIHSILKINPVTYEENVLFEQKEVPDLAKCRVLICDEVSMYDRKLFKILLSTIPPWCTIIGIGDNKQIRPVDPGENTAYISPFFTHKOFYQCELTEVKRSNAPIIDVATDVRNGKWMYDKVVDGHGVRGFTGDT | 439 | DNA helicase [Enterobacteria phage RB14] | YP_0028543 52.1 | 0.0 (438/439) | DNA helicase | RecD_rel, recD/TraA family | TIGR0144 8 | 3e-24 |

Fig. 6FF

| | | | | | | | | |
|---|---|---|---|---|---|---|---|---|
| 172 | 96325 | 96585 | 395 | ALRDFMVNYFSIVKSLDDLFENR VMAFTNKSVDKLNSIIRKKIFETD KDFIVGEIIVMQEPLIKTYKIDGKP VSEIFNNGQLVRIIEAEYTSTFVK ARGVPGEYLIRHWDLTVETYGD DEYYREKIKIISSDEELYKFNLFLG KTAETYKNWNKGGKAPWSDFW DAKSQFSKVKALPASTFHKAQG MSVDRAFIYTPCIHYADAELAQQ LLYVGVTRGRYDVFYV | | | | | |
| | | | | MININSKYLNRLIDGIRKHTNKQD NLDVMVTGAELLHKLYLISDTILAI KRIEKQSYHSNTDTVITLDESVCK LLIKFEEAIRGNN | 86 | Hypothetical protein RB51ORF017 [Enterobacteria phage RB51] | YP_0028539 72.1 | 7e-42 (86/86) | | No putative conserved domains have been detected |
| 173 | 96572 | 96817 | 396 | VEITKDQFYLLQDKVSEIYEIAYS KNRETVKIESSKLMLQLEEIERDL IALEFFCGEVKTVTISDYVLGEISY LYKAIIND | 81 | DexA.2 hypothetical protein [Enterobacteria phage RB14] | YP_0028543 50.1 | 2e-36 (77/81) | | No putative conserved domains have been detected |
| 174 | 96810 | 97052 | 397 | MIELSWCQFKSLMTNVKAVIEKN SGPENITIREKALKIIYSLEEMQKD IESMAKFIDEPINKVYIQDYTVGQI RDLARKI | 80 | Hypothetical protein RB32ORF013c [Enterobacteria phage RB32] | YP_802955.1 | 5e-39 (80/80) | | No putative conserved domains have been detected |
| 175 | 97052 | 97735 | 398 | MFDFIIDFETMGSGEKAAVIDLAV IAFDPNPEVVETFDELVSRGIKIK FDLKSQKGHRLFTKSTIEWWKN QSPEARKNIAPSDEDVSTIDGIAK FNDYINAHNDPWKSQGWCRGM SFDFPILVDLIRDIQRLNGVSENE LDTFKLEPCKFWNQRDIRTRIEA LLLVRDMTTCPLPKGTLDGFVAH DSIHDCAKDILMMKYALRYAMGL EDAPSEEDCDPLSLPTKR | 227 | DexA exonuclease A [Enterobacteria phage T4] | NP_049629. 1 | 1e-130 (226/227) | DexA exonuclease A | DEDDh exonucle ases, part of the DnaQ-like (or DEDD) exonucle ase superfami ly | cd06127 | 0.001 |
| 176 | 97799 | 98299 | 399 | MKIYRVESSFSILDYEDAITIRRNL CVQITPYRSIIDSWSEEWLLHVG YDRPNFMHHSDNNKRIPLPHED KLLVKNANIVINTKFKKDYVGVEY HIPGWFIALYHFAFASEYDMMR WFTREERELASKGFYLAVYEV PDDQVIVGGHQVMFRKSHAELV DFIEMR | 166 | Hypothetical protein RB32ORF011c [Enterobacteria phage RB32] | YP_802953.1 | 4e-93 (163/166) | | No putative conserved domains have been detected |
| 177 | 98302 | 98847 | 400 | MKFNYNPEYTPNPAAKLIDFDVV STYVCPVKPLEIKEPTMTTAIEIG KTYKLVEPKIKTNALISGHKTLTD VFGEGEFIVEEFAKSEWFDKSYV IHGRRLDNNKIKKNLVYEDEFILF | 181 | MotB.1 hypothetical protein [Enterobacteria phage JS10] | YP_0029223 58.1 | 8e-94 (168/182) | | No putative conserved domains have been detected |

Fig. 6GG

| | | | | | | | |
|---|---|---|---|---|---|---|---|
| | | | QEVEEQDPTDLLCAAVSIRRPFD NPICGWVTDQWIEDGVELLNVV HAGDFSVVPRSAVVAILN | | | | |
| 178 | 98924 | 401 | MIINGEIARVSDKSRSKAAGKLV EVVSIQLKHGVKDEDSEVVKRIIA KDGMSKPQFGYVRWKFLEPAFL KAVPAKGIETIDTSHVGVDFKWK LGQAIKFIAPCEFKFIKDDGKAVY TRAMCGYITDQWVEDGVKLYNV VFLGTYKVIPESWIKHYSNALYA | 162 | MotB modifier of transcription [Enterobacteria phage T4] | NP_049626.1 | 2e-84 (154/162) | MotB modifier of transcription | No putative conserved domains have been detected |
| 179 | 99587 | 402 | MKRKIVQNCTNDEFEDVLFDPDL VVVQKEHTIKFTHLTSVYVYEKV GDKQPIYGVFREITEDGTTYWKE IY | 71 | Modifier of suppressor T4 tRNAs [Enterobacteria phage RB14] | YP_0028543 44.1 | 5e-34 (71/71) | modifier of suppressor T4 tRNAs | No putative conserved domains have been detected |
| 180 | 99802 | 403 | MAIKFEVNKWYQFKNKQACENFI KDHTDNGIYARRLGMHPFKILDV DALGRPIKIMSFAGNLVLSSGKDI LDEDFIWLSSNEAEFFNEVENPY QAAEEQEESAPITDQSKFPVMKV TIENDEQAWSLYQMLKAHFKE | 137 | RNA metabolism moderator [Enterobacteria phage RB32] | YP_802949.1 | 7e-61 (112/137) | RNA metabolism moderator | No putative conserved domains have been detected |
| 181 | 100218 | 404 | MPLYDYKCQSKDCAKEYEKIKKI SERDTDVCPDCHRIAIRLVSAPK HVNGGFYDLLKG | 58 | Hypothetical protein RB32ORF006c [Enterobacteria phage RB32] | YP_802948.1 | 2e-26 (58/58) | | No putative conserved domains have been detected |
| 182 | 100397 | 405 | MFKIGKKYRIREGEEKKYLFSAIY RNGSINAVISTSEFIVEDMKGNN VTMISTASGNDGKILHSFQSNVLI YDEEFDFFEEVPEGFAFECTITM KSGDPLSFTVKDEGSRLRIISLLQ AIKFK | 123 | Hypothetical protein RB32ORF005c [Enterobacteria phage RB32] | YP_802947.1 | 2e-58 (114/123) | | No putative conserved domains have been detected |
| 183 | 100774 | 406 | MKYINRSIAALVLAVSLVGCTDAD NATKVLSSSGFTNIEITGYNWFG CSENDFQHTGFRAIGPTGQKVE GTVCSGLFFKDSTIRFK | 86 | Gp39.1 hypothetical protein [Enterobacteria phage RB14] | YP_0028543 40.1 | 2e-43 (85/86) | | No putative conserved domains have been detected |
| 184 | 101104 | 407 | MIKNEIKILSDIEHIKKRSGMYIGS SANEMHERFLFGKWESVQYVPG LVKLIDEIIDNSVDEGIRTKFKFAN KINVTIKNNQVTVEDNGRGIPQA MVKTPTGEEIPGPVAAWTIPKAG GNFGDDKERVTGGMNGVGSSL TNIFSVMFVGETGDGQNNIVVRC SNGMENKSWETIPGKWKGTRVT FIPDFMSFETNELSQYYLDITLDR LQTLAVVYPDIQFTFNGKKVQGN | 605 | Gp60plus39 DNA topoisomerase subunit [Enterobacteria phage RB51] | YP_0028539 58.1 | 0.0 (603/605) | DNA topoisomerase subunit | GyrB, type IIA topoisomerase (DNA gyrase/topo II, topoisomerase IV), B subunit | COG0187 | 8e-81 |

Fig. 6HH

| | | | | | | | | | |
|---|---|---|---|---|---|---|---|---|---|
| 185 | 102976 | | FKKYARQYDEHAIVQEQENCSIA VGRSPDGFRQLTYVNNIHTKNG GHHIDCVMDDICEDLIPQIKRKFK IDVTKARVKECLTVMFVRDMKN MRFDSQTKERLTSPFGEIRSHIQ LDAKKISRAILNNEAILMPIIEAALA RKLAAEKAAETKAAKKASKAKVH KHIKANLCGKDADTTLFLTEGDS AIGYLIDVRNKELHGGYPLRGKV LNSWGMSYADMLKNKELFDICAI TGLVLGEKAENLNYHNIAIMTDA DHDGLGSIYPSLLGFFSNWPELF EQGRIRFVKTPVIIAQVGKKQEW FYTVAEYESAKDALPKHSIRYIKG LGSLEKSEYREMIQNPVYDVVKL PENWKELFEMLMGDNADLRKE WMSQ | | | | | | |
| 185 | 103179 | 408 | MKSYKVNLELFDKAVHREYRIIQ RFFDMGEAEEFKNRFKDIRDKIQ SDTATKDELLEVAEVIKRNMN | 67 | Hypothetical protein RB32ORF002c [Enterobacteria phage RB32] | YP_802944.1 | 1e-30 (67/67) | | TOPRIM_TopoIIA_li ke: topoisom erase-primase (TOPRIM ) nucleotidy l transferas e/hydrola se domain | cd01030 | 8e-24 |
| 186 | 103190 | 409 | MIITTEKETILGNGSKSKAFSITAS PKVFKILSSDLYTNKIRAVVRELIT NMIDAHALNGNPEKFIQVPGRL DPRFVCRDFGPGMSDFDIQGDD NSPGLYNSYFSSSKAESNDFIGG FGLGSKSPFSYDTFSITSYHKG EIRGYVAYMDGDGPQIKPTFVKE MGPDDKTGIEIVVPVEEKDFRNF AYEVSYIMRPFKDLAIINGLDREI DYFPDFDDYYGINPERYWPDRG GLYAIYGGIVYPIDGVIKDRNWLS IRNEVNYIKFPMGSLDIAPSREAL | 725 | Membrane-associated affects host membrane ATPase [Enterobacteria phage RB32] | YP_802943.1 | 0.0 (717/725) | membrane-associated affects host membrane ATPase | HtpG, molecular chaperon e, HSP90 family [posttrans lational modificati on, protein turnover, chaperon | COG0326 | 6e-05 |

Fig. 6ll

| | | | | | | | |
|---|---|---|---|---|---|---|---|
| 187 | 105379 | | SLDDRTRKNIIERVKELSEKAFNE DVKRFKESTSPRHTYRELMKMG YSARDYMISNSVKFTTKNLSYKK MQSMFEPDNKLCNAGVVYEVNL DPRLKRIKQSHETSAVASSYRLF GINTTKINIVIDNIKRVNIVRGLA RALDDSEFNNTLNIHHNERLLFIN PEVESQIDLLPDIMAMFESDEVNI HYLSEIEALVKSYIPKVVKSKAPR PKAATAFKFEIKDGRWEKEELFT LTSEADEITGYVAYMHRSDIFSM DGTTSLCHPSMNILIRMANLIGIN EFYVIRPLLQKKVKELGQCQCIFE TLRDLYVDAFDDVDYDKYVGYS SSAKRYIDIKIIKYPELDFVMKYFS VDEVSEEYTRLANMVSSLQGVY FNGGKDTIGHDIWTVTNLFDELS RNASKNSDKMVAEFTKKFRIVSD FIGYRNSLSDDEVSQIAKTMKAL AA | | | | |
| 188 | 106317 | 410 | MYNIKCLTKNEQAEIVKLYSSGN YTQQELADWQGVSVDTIRRVLK NAEEAERSKVTISGDITVKVNSD AVIAPVAKSDIWNASKKFHSITVD GVTYNATPNTHSNFQEILNLLVA DKLEEAAQKINVRRAVEKYISGD VRIEGGSLFYQNIELRSGLVDRIL DSMEKGENFEFYFPFLENLLENP SQKAVSRLFDFLVANDIETEDGY FYAWKVVRSNYFDCHSNTFDNS PGKVVKMPRTRVNDDDTQTCSR GLHVCSKSYIRHFGSSTSRVKV KVHPRDVVSIPIDYNDAKMRTCQ YEVVEDVTEQFK | 312 | Protector from prophage-induced early lysis rIIB [Enterobacteria phage T4] | NP_049889. 1 | 0.0 (310/312) | rIIB protector from prophage-induced early lysis |
| | 106346 | 411 | MLGYQARVKEEYDQLMLKINALS NFLESTKFLTVSAVEQELLLSQFI SMKSYADCLEKRIAQFK | 64 | Hypothetical protein RB32ORF269c [Enterobacteria phage RB32] | YP_803211.1 | 3e-27 (62/64) | No putative conserved domains have been detected |
| 189 | 106540 | | | | | | | |
| | 106604 | 412 | MQKTNPGLQRLFQIPSFTLSNSD LTSEMKVKIADTARYSLKQNPNQ DKAEVIERCRIAVYAEFFVADWL RGYVNKGQEDVNDPYTYAWDV LAHPKYCGLRVEVKTHQTDSRW ISVTTGCSGEYPYGSGINLGPILN HQVADCIIFNTKEIHPGVIQYTPK FIGDREDLRKVVRKSNYNGWYL SI | 185 | Endonuclease IV [Enterobacteria phage RB14] | YP_0028546 07 | 4e-106 (183/185) | endonuclease IV |
| | 107161 | | | | | | | No putative conserved domains have been detected |

Fig. 6JJ

| | | | | | | | |
|---|---|---|---|---|---|---|---|
| 190 | 107235 | 107498 | 413 | MKFKFYYAKHKITGEFIAFTTSTT DEGDIFTAVFLSKWESDQPYLSS REDLQRLVNGEYNDSWSYLVHD CVKKAIKQKHLEIVEIEL | 87 | Hypothetical protein RB51ORF272 [Enterobacteria phage RB51] | YP_0028542 25.1 | 9e-22 (49/87) | | No putative conserved domains have been detected |
| 191 | 107578 | 107676 | 414 | MKILNSVLIACAWWVAQVSAVVV GIHIYYEYF | 32 | Ndd.5 hypothetical predicted outer membrane protein [Enterobacteria phage T4] | NP_049885.1 | 2e-09 (32/32) | | No putative conserved domains have been detected |
| 192 | 107742 | 107855 | 415 | MKKIVKAIWNVVIILVLSIFPIVLMI DVLNAYFGFM | 37 | Ndd.4 hypothetical protein [Enterobacteria phage RB14] | YP_0028546 03.1 | 1e-10 (37/37) | | No putative conserved domains have been detected |
| 193 | 107863 | 108060 | 416 | MKRKRSAFTFIEWFFDNIFPALFI FMLIFALGSVVVGIYLMTVVGIDIH QNGLKSVVETIWNGVK | 65 | Ndd.2a hypothetical protein [Enterobacteria phage RB51] | YP_0028542 22.1 | 3e-29 (65/65) | | No putative conserved domains have been detected |
| 194 | 108057 | 108167 | 417 | MMNLLSGWFYILMFYIGANFPY WMGWSTTAFGFYTP | 36 | Hypothetical protein RB32ORF262c [Enterobacteria phage RB32] | YP_803204.1 | 6e-12 (36/36) | | No putative conserved domains have been detected |
| 195 | 108176 | 108391 | 418 | MKIFKDVKVGEIFCLDNGDQLRI SPLKSTSEKPTVNATLANNSNER FCIENDTETYVEEFWELSVDCD D | 71 | Ndd.1 hypothetical protein [Enterobacteria phage RB14] | YP_0028546 00.1 | 4e-33 (70/71) | | No putative conserved domains have been detected |
| 196 | 108452 | 108910 | 419 | MKYMTVTDLNNAGATVIGTIKNG EWFLGVPHKDILSKPGFYFLVSK LDGRPFSNPCVSARFYVGNQRS KQGFSAVLSHIRQRRSQLARTIA NNNVPYTVFYLPASKMKPLTTGF GKGQLALAFIRNHHSEYQTLEEM NRMLADNFKFVLQAY | 152 | Disrupts host nucleoid [Enterobacteria phage RB32] | YP_803202.1 | 3e-84 (149/152) | nucleoid disruption protein | No putative conserved domains have been detected |
| 197 | 108998 | 109156 | 420 | MNIAKLLGVISFICWIVACVLTICID VSSVFSQALAQGMCAYLTFVLLS TND | 52 | Acridine resistance protein [Enterobacteria phage RB14] | YP_0028545 97.1 | 3e-20 (51/52) | acridine resistance protein | No putative conserved domains have been detected |
| 198 | 109294 | 110622 | 421 | MQLNNRDLKSIIDNEALAYAMYT VENRAIPNMIDGFKPVQRFVIAR ALDLARGNKDKFHKLASIAGGVA DLGYHHGENSAQDAGALMANT WNNNFPLLDGQGNFGSRTVQK AAASRYIFARVSKNFYNVYKDTE YAPVHQDKEHPPAFYLPIPTVLL NGVSGIATGYATYILPHSVSSVK | 442 | Gp52 DNA topoisomerase subunit [Enterobacteria phage RB51] | YP_0028542 15.1 | 0.0 (442/442) | DNA topoisomerase subunit | No putative conserved domains have been detected |

Fig. 6KK

| | | | | | | | |
|---|---|---|---|---|---|---|---|
| 199 | 110619 | 110768 | 422 | KAVLQALQGKKVTKPKVEFPEFR GEVVEIDGQYEIRGTYKFTSRTQ MHITEIPYKYDRETYVSKILDPLE DKGFITWDDACGEHGFGFKVKF RKEYSLSDNEEERHJAKIMKDFGL IERRSQNITVINEKGKLQVYDNVV DLIKDFVEVRKTYVQKRIDNKIKE TESAFRLAFAKAHFIKKVISGEIVV QGKTRKELTEELSKIDMYSSYVD KLVGMNIFHMTSDEAKKLAEEAK AKKEENEYWKTTDVVTEYTKDL EEIK | | | No putative conserved domains have been detected |
| | | | | MSPFIGTSAALVSGGILLAGLGV VPAVAGGLLAFGIQRVIMTVITVM Q | 49 | MotA.1 hypothetical predicted periplasmic protein [Enterobacteria phage T4] | NP_049874. 1 | 4e-16 (48/49) | | No putative conserved domains have been detected |
| 200 | 110903 | 11130 | 423 | MKFKIENEIVKAKNALTANKLVVD GIEYDICGVREEKPGVLTFFTMIF KFKGDTEFKQFDFAHEDEIEVRN LNIK | 75 | Hypothetical protein EpJS10_0253 [Enterobacteria phage JS10] | YP_0029226 02.1 | 5e-34 (74/75) | | No putative conserved domains have been detected |
| 201 | 111236 | 111871 | 424 | MSKVTYIIKASNDVLNEKTAAILITI AKKDFITANEVREVHPDLGNAVV NSNIGVLIKKGLVEKSGDGLIITG EAQDIISNAATLYAQENAPELLKK RATRKAREITSDMEEDKDLMLKL LDENGFVLKKVETYRSNYLAILEK RTHGIRNFEINNNGNMRIFGYKM MEHHIQKFTDIGMSCKIAKNGNV YLDIKRSAENIEAVITVASEL | 211 | Activator middle promoter [Enterobacteria phage RB32] | YP_803196.1 | 7e-117 (210/211) | activator middle promoter | Transcript ion factor MotA, activation domain | pfam0911 4 | 5e-34 |
| 202 | 111882 | 112211 | 425 | MNKLEIVNELRRCVEPTQEGWDI WYHGAYLGTIVKIKTGKYMIIRES KDAPVGIRNNFMAAISSFTDAAY EIYLADYKEFQESQPVIRSIGVNK AQQKTLWQRIKGWFK | 109 | Arn.4 hypothetical protein [Enterobacteria phage RB14] | YP_0028545 92.1 | 8e-58 (107/109) | | No putative conserved domains have been detected |
| 203 | 112208 | 112669 | 426 | MNPFINRLKMLNVPLSRETPESL VEKFKAHGYKCTEEDILKEVPEIC WQTAYWDENGKYQRRIVCAAN RFKLKDGRTLIIPGARHYSKDMA EVLDVVKPQLVTQQVCDDDQGF IDQYSNVWTREEAMIIATYAGQV RIERGGSEKELYSEDLY | 153 | Arn.3 conserved hypothetical protein [Enterobacteria phage T4] | NP_049871. 1 | 4e-84 (151/153) | | No putative conserved domains have been detected |
| 204 | 112669 | 112965 | 427 | MNIIKFQIDGITNQIKALEYANKM MSTNWGIYANEPAFKFCDMEFT KKLVGKDHVCPFSSPVNGMLKP ALRDLYIAMNEEMIKELKRQLKVI | 98 | Arn.2 hypothetical protein [Enterobacteria | YP_0028542 10.1 | 8e-50 (95/98) | | No putative conserved domains have been detected |

Fig. 6LL

| | | | QFGQGN | | phage RB51] | | | | |
|---|---|---|---|---|---|---|---|---|---|
| 205 | 112949 | 428 | LAREINSKSDYFNSLNDKDKNLIR HFIVEMGYTDTHDLREHIFECGV AKKFSFTCKLCREVIQHYEQFSR KT | 72 | Arn.1 conserved hypothetical protein [Enterobacteria phage RB69] | NP_861950. 1 | 1e-22 (52/72) | | No putative conserved domains have been detected | |
| 206 | 113251 | 429 | MIIDSQSVVQYTIKIDILEKLYKFL PNLYHSIVNELVEELHLGNNDFLI GTYKDLSKAGYFYIPAPGKSIDD VLKTIMVVHDYEIEDYFE | 92 | Inhibitor of MrcBC restriction nuclease [Enterobacteria phage RB51] | YP_0028542 08.1 | 8e-44 (90/92) | inhibitor of MrcBC restriction nuclease | No putative conserved domains have been detected | |
| 207 | 113526 | 430 | MSHNLEKVIEHNVAQERKSFKEF VEKIFEENTTDQFTNQASDDIITK STN | 50 | AsiA.1 hypothetical protein [Enterobacteria phage T4] | NP_049867. 1 | 9e-19 (48/50) | | No putative conserved domains have been detected | |
| 208 | 113691 | 431 | MNKNIDTVREIITVASILIKFSREDI VENRANFIAFLNEIGVTHEGRKL NQNSFRKIVSELTQEDKKTLIDEF NEGFEGVYRYLEMVTNK | 90 | AsiA anti-sigma 70 protein [Enterobacteria phage T4] | NP_049866. 1 | 5e-44 (90/90) | AsiA anti-sigma 70 protein | AsiA, anti-sigma factor A | pfam0901 0 | 3e-30 |
| 209 | 113964 | 432 | MAAPRISFSPSDILFGVLDRLFKD NATGKVLASRVAVVILLFMMAIV WYRGDSFFEYYKQSKYETYSEII EKERNARFESVALEQLQVHISSE ADFSAVYSFRPKNLNYFVDIIAYE GKLPSTISEKSLGGYPVDKTMDE YTVHLNGRHYYSDSKFAFLPTKK PTPEINYMYSCPYFNLDNIYAGTI TMYWYRNDHISNDRLESICAQAA RILGRAK | 218 | Holin [Enterobacteria phage RB32] | YP_803187.1 | 7e-125 (216/218) | holin | No putative conserved domains have been detected | |
| 210 | 114651 | 433 | MAVVGPGWIGSSAANETGQR WMSQAAGQLRLGVPCWMSQFA GRSREIIHTVGANHNFNGQWFR DRCFEAGGAPIVFNIVGDIVSYSK DVPLFFMYGDTPNEYVQLNIHGV TMYGRGGNGGSNSPGSAGGHC IQNDIGGRLRINNGGAIAGGGGG GGGGYYSPFSQMRLTFGGGGG RPFGAPGGSIDMQGSATGGTIS APGSGSVNGIYNGGNGGEVGSA GGRCNIRGQGSEYNGGAAGYA VIGSAPTWQNVGAIYGPRV | 260 | Tail fiber protein [Enterobacteria phage KEP10] | BAF95751.1 | 2e-107 (254/260) | tail fiber protein | Phage tail fibre adhesin Gp38 | pfam0526 8 | 2e-76 |
| 211 | 115433 | 434 | MATLKQIQFKRSKTAGQRPAASV LAEGELAINLKDKTIFTKDDSGSV IELGLKYGGTINGSLEVTENITGT LIGNSSTATKLQTPRKINGISFDG SKDITLTPSDINVNSTTFIKNNGE LPTDANLDTYGPIEEYLGWSKS | 982 | Tail fiber protein [Enterobacteria phage KEP10] | BAF95750.1 | 0,0 (921/982) | tail fiber protein | No putative conserved domains have been detected | |

Fig. 6MM

| | | | | | | | | |
|---|---|---|---|---|---|---|---|---|
| 212 | 119077 | 118427 | 435 | TSTNAQPANKFPEENAVGVLEVF VAGQFAGTQRYTVRSGNVYIRS LSAKWNGVDGPWGVWRNVQAS TRPLSQTIDLDSLGELEHCGLWR NSSSAIASFDRHYPEEGSAAQGF LEIFEGGLYTRTQRYTTRMGMVY TRCLAAAWDASAPKWEEWKQV GHGTPATFYDGDLNDFKTPGLY NILGTDAVINCPTGEGLPTVIVGL LEVKQRASGGAIFQRFTTAGTGA TTRDRIFERAYTGGAWGAWNEV YTSYSLPITLGMGGIKAQLAELD WQTFDFVPGSMFSVPLNKIKNM PANMDWGTIDGNLVMFSVGPSE HTGTGRTVQVWRGTVSQANYR YFVVRIAGNPGSRTNTCRRVVLE DGSHWTAQQNFRGLLNITAAV NLGANQKISLAPGAYIQAPASGS GSNTYANQNTTIAPLYQAIDDSN KNQFAPIVKQKNTVTNITMASGM DIASSEYRIVAQGDLSATGTTATE LATWRFLPSGRFMSQSRVYAGA AFLNTDGNIAGSWKKYNDATNL DAALNTRLGKGGDTMTGRLTINA PNDSIVLSTTASNSLHIRGDIDGT GNWYIGKGGADNSLAFYSYASQ AAVHITNNGEIALNPQNTAMVNV NRDRVHINGSGWIARQPGDWG NQWRVEAPLFVDHGYVGQDSY YPILKARSVITNQGYSTAVDFGM RRIPSQWGQAIIRVGSTEASPDA GHPQAVFEFHHDGFFYTPGNGS FSDVYIRSDSRLKINKEELEYGAV EKVCRLKVYIYDKVKSIKDRSVIK REVGIIAQDLEKELPEAVSKVEVD GSDVLTISNSAVNALLIKAIQEMS EEIKELKTPLFTKIARKISKYFKF | 216 | Hinge connector long tail fiber [Enterobacteria phage RB32] | YP_803184.1 | 4e-120 (216/216) | hinge connector long tail fiber | Phage T4 tail fibre | pfam03903 | 4e-83 |
| | | | | MADLKVGSTVGGSVIWHQGNFP LNSAGDDVLYKSFKIYSEYNKPQ AADNDFVSKANGGTYAGPITINY GVNSYLQLSNNETPIRIRSGGGT GNTLVVGGSSGGISFRPAGSEIT TGQITITPEGLTTFTRAVTAPSVT VTSTPSAASDVTRKDYVDGAINT VTANANSRVLRSGDTMTGNLTA PNLFSQNPASQPSHVPRFDQIVI KDSVQDFGYY | | | | | | | | |

Fig. 6NN

| | | | | | | | |
|---|---|---|---|---|---|---|---|
| 213 | 120255 | 119140 | 436 | MEKFMAEFGQGYVQTPFLSESN SVRYKISIAGSCPLSTAGPYVKF QDNPVGNQTFSAGLHLRVFDPS TGALVDSKSYAFSASNNTTSAAF VSFMNSLSNNRLVAILTSGKVNF PPEVVSWLRGAGTSVFPSDSVL SRFDVSYAAFYTSSKRAIALEHV KLSNRKSTDDYQTILDVVFDSLE DVGATGFPKRTYESVEQFMSAV GGTNNEIARLPTSAAISKLSDYNL IPGDVLYLKAQLYADADLLDLGTT NISIRFYDASNGYISSTQAEFTGQ AGSWELKEDYVVPENAVGFTIY AQRTAQAGQGGMRNLSFSEVS RNGGISKPAEFGVNGIRVNYVCE SASPPDIMVLPTQASSKTGKVFG QEFREV | 371 | Tail fiber hinge [Enterobacteria phage RB32] | YP_803183.1 | 0.0 (365/371) | tail fiber hinge | No putative conserved domains have been detected |
| 214 | 124133 | 120264 | 437 | MAEIKRKFRAEDGLDAGGDKIIN VALADRTVGTDGVNVDYLIQENT VQQYDPTRGYLKDFVIIYNNRFW AATDNIPKPAGNFNRIRWKALRT DAVYTTVSSGPYQLKSGEAISVD TSVGNDIEFTLPPSPLDGETVIIQ DIGGKPGINQYKINSSNQSIVNFR GEQVRSVLMTHPKSQMIFIFNNR LWQMYVADYSREAAVTPSTAY QAQSNDFIVRRFTSAAPINVKLP RFANH-GDIINFVDLDKLNPLYHTI VTTYDETTSVQEVGTHSIEGRTSI DGFLMFDDNEKLWRLFDGDSKA RLRIITTNSNIRPNEEVMVFGANN GTTGTIELQLPTDISVGDTVKISM NYMRKGGTVKIKAAGEDKIASSV QLLQFPKRSEYPPEAEWWTVQE LVFNGETNYVPVLQLAYIEDSDG KYWVVGQNVPTVERVDSLNAST RARLGVIALATQAQANADLENSP QKELAITPETLANRTATETRRGIA RIATTAQVNQNTTFSFADDLITP KKLNERTATETRRGVAEIATQQE TNTGTDDTTIITPKKLQARQGSE SLSGIVTFVSTAGATPASSRELN GTNVYNKNTNNLVVSPKALDQY KATPTQQGAVILAVESEVIAGQS QEGWANAVVTPETLHKKTSTDG RIGLIEIATQSEVNTGTDYTRAVT PKTLNDRRATESLSGIAEIATQVE FDAGVDDTRISTPLKIKTRFNSTD | 1289 | Gp34 proximal tail fiber subunit [Enterobacteria phage RB14] | YP_0028545 78.1 | 0.0 (1280/1289 ) | proximal tail fiber subunit | No putative conserved domains have been detected |

Fig. 600

| | | | | | | | | |
|---|---|---|---|---|---|---|---|---|
| 215 | 124238 | 125155 | 438 | RTSVVALSGLVESGTLWDHYTL NILEANETQRGTLRVATQVEAAA GTLDNVLITPKKLLGTKSTESQE GVIKVATQSETVTGTSANTAVSP KNLKWIVQSEPTWAATTLIRGFV KTSSGGLTFVGNDTVGSTQPLES YEKNGYAVSPYELNRVLANYLPL KAKAVDSNLLDGLDSLQFIRRDIA QTVNGSLTLTQQTNLGAPLVSSS TATFGGSVSANSTLTISNTGTAT RLIFEKGPQTGTNPAQTMTVRV WGNQFSGESDTTRSTVFEVSDE TSSHFYSQRNKAGNITFNINGTV TPINVNASGTLNANGVATFGNSV TATGEIISRSANAFRAINGNYGFI VRNDGSVTNFMLTASGDQTGGF NGLRPLAINNASGQVTIGESLIIAK GATINSGGLTVNSRIRSQGTKTS DLYTRAPTSDTVGFWSIDINDSA TYNQFPGYFKMVEKTNEVTGLP YLERGEEVKSPGTLTQFGNTLDS LYQDWITYPTTPEARTTRWTRT WGKTKNSWSSFVQVFDGGNPP QPSDIGAIPSDNGIIGNLTIRDFLR IGNVRIIPDPVNKTVKFEWVE MDLEMVILDEDYKEGICFIDFSQI ALSTALVNFPDKEKINLSMVRHLI LNSIKFNVKKAKTLGYTKIVLCIDN AKSGYWRRDFAYYYKNRGKA REESTWDWEGYFESSHKVIDEL KAYMPYIVMDIDKYEADDHAVLV KKFSLEGHKILIISSDGDFTQLHK YPNVKCWSPMHKKWVKIKSGSA EIDCMTKILKGDKKDNYASVKVR SDFWFTRVEGERTPSMKTSIVEA IANDREQAKVLLTESEYNRYKEN LVLIDFDYIPDNIASNIVNYNSYK LPPRGKIYSFVKAGLSKLTNSIN EF | 305 | RNaseH [Enterobacteria phage RB32] | YP_803181.1 | 4e-178 (305/305) | ribonuclease H | RNaseH_ C, T4 RNase H, C terminal | pfam0929 3 | 9e-40 |
| 216 | 125164 | 125433 | 439 | MAKKEMVEFDEAIHGEDLAKFIK EASDHKLKLSIGYNELIKIDIRIRAKD ELGVDGKMFNRLLALYHKDNRD VFEAETEEVVELYDTVFSK | 89 | DsbA dsDNA binding protein, late transcription [Enterobacteria phage T4] | NP_049858. 1 | 5e-43 (89/89) | dsDNA binding protein | No putative conserved domains have been detected |
| 217 | 125411 | 125749 | 440 | MTQFSLNDIRPVDETGLSEKELSI KKKEDEIAKLLDRQENGFIIEKMV EEFGMSYLEATTAFLEENSIPET | 112 | Gp33 late promoter transcription accessory protein | NP_049857. 1 | 4e-57 (112/112) | late promoter transcription accessory | No putative conserved domains have been detected |

Fig. 6PP

| | | | | | | | | |
|---|---|---|---|---|---|---|---|---|
| 218 | 125746 | | QFAKFIPSGIIEKIQSEAIDENLLR PSVVRCEKTNTLDFLL | | | | | |
| | | 441 | MIKLRMPAGGERYIDGKSVYKLY LMIKQHMNGKYDVIKYNWCMRV SDAAYQKRRDKYFFQKLSEKYK LKELALIFISNLVANQDAWIGDISD ADALVFYREYIGRLKQIKFKFEED IRNIYYFSKKVEVSAFKEIFEYNP KVQSSYIFKLLQSNIISFETFILLD SFLNIIDKHDEQTDNLVWNNYSIK LKAYRKILNIDSQKAKNVFIETVK SCKY | 217 | Gp59 loader of gp41 DNA helicase [Enterobacteria phage T4] | NP_049856.1 | 4e-121 (217/217) | loader of Orf146 DNA helicase | T4-helicase_C, T4 gene 59 helicase, C terminal | pfam08994 | 3e-35 |
| | | | | | | | | T4-helicase_N, T4 gene 59 helicase, N terminal | pfam08993 | 3e-34 |
| 219 | 126500 | 442 | MFKRKSTAELAACMAKLAGNKG GFSSEDKGEWKLKLDNAGNGQ AVIRFLPSKNDEQAPFALLVNHG FKKNGKWYIETCSSTYGDYDSC PVCQYISKNDLYNTDNKEYSLVK RKTSYWANILVVKDPAAPENEGK VFKYRFGKKIWDKINAMIAVDVE MGETPVDVTCPWEGANFVLKVK QVSGFSNYDESKFLNQSAIPNID DESFQKELFEQMVDLSEMTSKD KFKSFEELSTHKFSQVMGTAAMG GAAATAAKKADKVADDLDAFNV DDFKTKTEDDFMSSSSGSSSSA DDTDLDLLNDL | 302 | ssDNA binding, DNA repair, recombination and pre-synthesis [Enterobacteria phage RB32] | YP_803177.1 | 4e-172 (296/302) | ssDNA binding, DNA repair, recombination and pre-synthesis | Gp32 DNA binding protein like | pfam08804 | 6e-41 |
| 220 | 127553 | 443 | MAKVDIDVDFEYIEEIIRNRYPEL SITSIHDDPNYCNFSIVIEGPLEDL TRFMANEYCDGMDSEDAEFYM GLIEQ | 76 | Frd.3 hypothetical protein [Enterobacteria phage RB51] | YP_002854194.1 | 1e-36 (76/76) | | Bacteriophage FRD3 protein | pfam05798 | 3e-33 |
| 221 | 127829 | 444 | MYIGKKYELVPRLIDTFINYRPRS NSSIVKIQENGGWFEVKEAFFV DGFRVIKHIECANGKHFYFNVCE DEFHCFREYKEPTSEEDGAEDIV SGVTKIHCIVDENNVDEIIELLRKT FKK | 121 | Frd.2 hypothetical protein [Enterobacteria phage RB14] | YP_002854571.1 | 6e-62 (118/121) | | Bacteriophage FRD2 protein | pfam03197 | 2e-36 |
| 222 | 128333 | 445 | MRLQRQSIKDSEVRGKWYFNIIG KDSELVEKAEHLLRDMGWEDEC DGCPLYEDGESAGFWIYHSDVD | 80 | Frd.1 conserved hypothetical protein [Enterobacteria] | NP_049851.1 | 3e-39 (79/80) | | No putative conserved domains have been detected | | |

Fig. 6QQ

| | | | | | phage T4] | | | | |
|---|---|---|---|---|---|---|---|---|---|
| 223 | 128586 | 128918 | 446 | MSGIHVTGIAQVNIRCQFKTVPG VTHITLSHDPYSRGRQLTGVIKFF GGIGGSEFTIGDDEIVGCKLKVQ KGVLELFSDEVFDEISRAVNKGM LTLIKMIKASGYVTDPF | Hypothetical protein RB51ORF237 [Enterobacteria phage RB51] | YP_0028541 90.1 | 2e-34 (78/116) | | No putative conserved domains have been detected |
| 224 | 128930 | 129175 | 447 | MIFVFEFMNDEFDYAIFNALHNP DLSEFNEMFSDALSMSEEYCGE CQRVCVTVFENKEKTYEELFFDA NKATEWFVERGFA | Hypothetical protein RB32ORF231c [Enterobacteria phage RB32] | YP_803173.1 | 7e-39 (79/80) | | No putative conserved domains have been detected |
| 225 | 129175 | 129756 | 448 | MIKLVFAYSPTKTVEGFNELAFG LGDGLPWGRIKKDLQNFKARTE GTILIMGAKTFQSLSTLLPGRSHI VVCDLARDYPVTKDGDLAHFYIT WEQYITYISGGEIQVSSPNAPFE TMLGQNSKVSVIGGPALLYAALP YADEVVVSRIVKRHRVNSTVQLD ASFLDDISKREMETHWVYKIDEV TTLTESVYK | Dihydrofolate reductase [Enterobacteria phage RB14] | YP_0028545 68.1 | 8e-109 (190/193) | dihydrofolate reductase | DHFR_1, dihydrofol ate reductase; pfam0018 6 | 2e-30 |
| 226 | 129753 | 129959 | 449 | MSNKLKVKDVPNAMALFICRQM HQGPMTPKQYLKGERSLGFTRK AKQMVKLGYKPNFAKYPSTYSW MN | No significant similarity found. | | | | |
| 227 | 129959 | 130510 | 450 | MKQYQFLIKDILENGYETDDRTG TGTIALFGTKLRWDLTKGFPAVT TKKLAWNACISELLWFLSGSTNV NDLRLIQHNSLIQGKTVWDENYE NQAKDLGYHSGELGPYGKQWR DFGGVDCQIIEVIDRIKKLPNDRRQ IVSAWNPAELKQMALPPCHMFY QFNVRNGYLDLQWYQRSVDVFL G | Thymidylate synthase [Bacteriophage RB23] | AAP86753.1 | 2e-101 (177/183) | thymidylate synthase | Thymidyl ate synthase, thyA; PRK01827 | 6e-67 |
| 228 | 130639 | 131376 | 451 | MKSGIYQIKNTLNNKVYVGSAKD FEKRWKRHFKDLEKGCHSSIKL QRSFNKHGNVFECSILEEIPYEK DLIIERENFWIKELNSKINGYNIAD ATFGDTCSTHPLKEEIIKKRSETV KAKMLKLGPDGRKALYSKPGSK NGRWNPETHKFCKCGVRIQTSA YTCSKCRNRSGENNSFFNHKHS DITKSKISEKMKGKKPSNIKKISC DGVIFDCAADAARHFKISSGLVT YRVKSDKWNWFINA | I-TevI homing endonuclease [Enterobacteria phage T4] | NP_049849. 3 | 3e-141 (245/245) | I-TevI homing endonuclease | Group I intron endonucl ease, grpIintron_endo; TIGR0145 3 | 5e-39 |
| 229 | 131521 | 131835 | 452 | MLPFNIASYATLVHIVAKMCNLIP GDLIFSGGNTHIYMNHVEQCKEI | Thymidylate synthase | AAP86755.1 | 7e-55 (103/103) | thymidylate synthase | Thymidyl ate; PRK01827 | 8e-26 |

Fig. 6RR

| | | | | | | | | | |
|---|---|---|---|---|---|---|---|---|---|
| 230 | 131859 | | LRREPKELCELVIGGLPYKFRYL STKEQLEYILKLRPKDFVLKDYQ SHGVLKGKMAV | | | | | synthase, thyA | |
| 231 | 132122 | 453 | MILRFKDTSGAVLFTLPNPSELEV PGPNQPIIYGKKYYTHKMTREYF DNKISTVKTSSDCYYDITVLTEKQ YDELSPRGPSMPGSE | 87 | NrdA.2 [Bacteriophage RB3] | AAP78917.1 | 2e-43 (86/87) | | No putative conserved domains have been detected | |
| 232 | 132076 | 454 | MTNYHRAGRLCQVVNKYKSDFD VNIHRGTFWGNYVGKDAGSREA AIELFKKDFHRRIKSGEITKAHLEP LRGMRLGCTCKPKPCHGDIIAHI VNRLFKDDFQVEDLCN | 108 | NrdA.1 [Enterobacteria phage T6] | ABI48941.1 | 5e-57 (106/108) | | No putative conserved domains have been detected | |
| 233 | 132393 | 455 | MQLINVIKSSGVSQSFDPQKIIKV LSWAAEGTSVDPYELYENIKSYL RDGMTTDDIQTIVIKAAANSISVE EPDYQYYVAARCLMFALRKHVYG QYEPRSFIDHISYCVNEGKYDPE LLSKYSAEEITFLESKIKHERDME FTYSGAMQLKEKYLVKDKTTGQI YETPQFAFMTIGMALHQDEPVD RLKHVIRFYEAVSTRQISLPTPIM AGCRTPTRQFSSCVVIEAGDSLK SINKASASIVEYISKRAGIGINVGM IRAEGSKIGMGEVRHTGVIPFWK HFQTAVKSCSQGGIRGAATAY YPIWHLEVENLLVLKNNKGVEEN RIRHMDYGVQLNDLMMERFGKN DYITLFSPHEMGGELYYSYFKDQ DRFRELYEAAEKDPNIRKKRIKA RELFELLMTERSGTARIYVQFIDN TNNYTPFIREKAPIRQSNLCCEIAI PTNDVNSPDAEIGLCTLSAFVLD NFDWQDQDKINELAEVQVRALD NLLDYQGYPVPEAEKAKKRRNL GVGVTNYAAWLASNFASYEDAN DLTHELFERLQYGLIKASIKLAKE KGPCEYYSDTRWSRGELPIDWY NKKIDQIAAPKYVCDWSSLREDL KLFGIRNSTLSALMPCESSSQVS NSTNGIEPPRGPVSVKESKEGSF NQVVPNIEHNIDLYDYTWKLAKK GNKPYLTQVAIMLKWVCQSASA NTYYFGGKNFYYHNTRDGSGT DDYEIETPKAEDCSSCKL | 754 | Ribonucleotide reductase A subunit [Enterobacteria phage RB51] | YP_0028541 83.1 | 0,0 (753/754) | ribonucleotide reductase A subunit | Ribonucle otide-diphosph ate reductase subunit alpha | PRK09103 | <1,0e-180 |
| 233 | 134709 | | | | | | | | |
| | 135887 | 456 | MSTVFNTNPVDVLKEPMFFGSG LGIARYDIQRHKVFEDLTEKQLSF | 392 | Ribonucliase B subunit | YP_0028545 | 0,0 | ribonucleotide reductase B | Ribonucle otide- | PRK09101 | 4e-141 |

Fig. 6SS

| | | | | | | | | |
|---|---|---|---|---|---|---|---|---|
| | | | FWRPEEVNLMMDAAQFNKLPQY QQNIFTNNLKYQSLLDSIQGRAP SAVLMSLISDPSLDTWVATWTFS ETIHSRSYTHIMRNLYTDPSKVF DEIVLDEAIMKRAESIGRYYDDVL IKTRYWENAKADIEYQKEINADE DVIEDAIEHETYWKRELMKSLYL CLHVINALEAIRFYVSFACTFNFH KNMEIMEGNAKIMKFIARDEQLH LKGTQYIIRQLQLGTDGDEWVKI AQECEQEAVDIFMEVNRQEKDW AVHLFKDGDVPGLNTNSMWSFI DYLTVSRMKQCGLPCPITDAPVK HPYPWIREYLNSDNVQSAPQEV ELSSYLVAQIDNDVDDKVMMSFK KYF | | [Enterobacteria phage RB14] | 62.1 | (387/392) | subunit | diphosph ate reductase subunit beta | |
| 234 | 135915 | 136325 | 457 | MKEIATEYSFIKYTELELDYNGSI KQLSIPNKYNVIYAIANDELVYIG KTKNLRKRINYYRTAINRKDKTS DSTKSALIHAALKEGSKVEFYAR QCFNLSMTNELGTMTATIDLEEP LFIKLFNPPWNIQHKKK | 136 | Endonuclease II [Enterobacteria phage RB51] | YP_0028541 81.1 | 7e-73 (135/136) | endonuclease II | GIY-YIG type nucleases (URI domain) | smart0046 5 | 1e-05 |
| 235 | 136378 | 137502 | 458 | MQELFNNLMELCKDSQRKFFYS DDVSASGRTYRIFSYNYASYSD WLLPDALECRGIMFEMDGEKPV RIASRPMEKFFNLNENPFTMNID LNDVDYILTKEDGSLVSTYLDGD EILFKSKGSIKSEQALMANGILMN INHHRLRDRLKELAEDGFTANFE FVAPTNRIVLAYQEMKIILLNVRE NETGEYISYDDIYKDAALRPYLVE RYEIDSPKWVEEAKNAENIEGYV AVMKDGSHFKIKSDWVYSLHST KSSLDNPEKLFKTIIDGASDDLKA MYADDEYSYRKIEAFETTYLKYL DRALFLVLDCHNKHCGKDRKTY AMEAQGVAKGAGMDHLFGIIMS LYQGYDSQEKVMCEIEONFLKN YKKFIPEGY | 374 | RNA ligase [Enterobacteria phage RB51] | YP_0028541 80.1 | 0.0 (373/374) | RNA ligase | RNA ligase, T4 RnlA family | TIGR0230 8 | <1.0e-180 |
| 236 | 137567 | 138070 | 459 | MDLQLITTEMVVEAYGDTTDGIS VFKGNRRVGYITDLKKDLAKQVK RKTTIKEYRNRRLEQARDMLPDA VEEMKVFLENQLAKYDCDVFINQ TOPNVHINSCKCYIIVNPLTGKHR LGISNPNRSASDMAEDVEACFKI SKSPAEHHILINGLSQDDIIEVIKT LCM | 167 | Alc inhibitor of host transcription [Enterobacteria phage T4] | NP_049838. 1 | 3e-93 (164/167) | inhibitor of host transcription | | | No putative conserved domains have been detected |

Fig. 6TT

| | | | | | | | | | |
|---|---|---|---|---|---|---|---|---|---|
| 237 | 138061 | 138414 | 460 | MHVSNFTAGLLLLVIAFGGTSIILK NKVERLETSVTEITKTANENALAL NNLRIQYNYIDAMNNKNREAIAAI ERENEKLRKDAKKADVVAHKPG LVEKQINNSFNKFAEDIQDLSK | 117 | PseT.3 conserved hypothetical predicted membrane protein [Enterobacteria phage T4] | NP_049837.1 | 2e-59 (116/117) | | No putative conserved domains have been detected |
| 238 | 138411 | 138710 | 461 | MIKLSAVILSIGLLVGCSTKPLEVK KETVHPNWPVQIKSYDEAKLSW QVKVIDGKAWVGMPFEDSQEFR IWLNDVKRYVHDQKTMICYRQ ELKEDKCK | 99 | Hypothetical protein RB32ORF219c [Enterobacteria phage RB32] | YP_803161.1 | 1e-51 (99/99) | Outer membrane assembly lipoprotein YfiO | TIGR03330 2 | 0.002 |
| 239 | 138707 | 138937 | 462 | MISWYQFEHLKGLIYESEMAAMI YGRQIQRLESLPPTNDVLLAQSR ANLKNEYQNKWGKASKDLHDYI QSLVEKNK | 76 | PseT.1 hypothetical protein [Enterobacteria phage RB51] | YP_0028541 76.1 | 2e-37 (76/76) | | No putative conserved domains have been detected |
| 240 | 138934 | 139236 | 463 | MKTLLERYIECSDRYIDVCHDNA SSISEDIEHAKALDDAGKALRKEA KARGFDMYQLKNHMIKFISSNVQ SKSVNQSTAELYKGRREHINRIL EVFLGIK | 100 | RB32ORF217c hypothetical protein [Enterobacteria phage RB14] | YP_0028545 55.1 | 3e-49 (96/100) | | No putative conserved domains have been detected |
| 241 | 139233 | 140138 | 464 | MMKKIILTIGCPGSGKSTWAREFI AKNPGFYNINRDDYRQSIMAHEE RDEYKYTKNKEGIVTYMQHDVA NMILCQDATKGVIVSDTNLNPER RKVWEEFAKELGHQIEYKVFDVP WTELVKRNSKRGTKAVPIDVLRS MYKSMREYLGLPVYKGTPGKPK AVIFDVDGTLAKMNGRGPYDLEK CDIDIINPMVVELSKMYALMGYQI VVVSGRESGTEEDPTKYYRMTR KWVEDIAGVPLVMQCCQREQGDT RKDDVVKEEIFWKHIAPHFDVKL AIDDRTQVVEMWRRIGVECWQV ASGDF | 301 | dN 3'phosphatase [Enterobacteria phage RB51] | YP_0028541 74.1 | 1e-170 (290/300) | dN 3'phosphatase | COG4639 | 8e-12 |
| 242 | 140158 | 140334 | 465 | LGFVIVNSGLVGTSNGQFCVFTS ENRAWEECLKLREKNPDVELVV KKTKLPLPWKTYE | 58 | Cd.5 hypothetical protein [Enterobacteria phage T4] | NP_049833.1 | 2e-24 (55/57) | | No putative conserved domains have been detected |
| 243 | 140327 | 140527 | 466 | MNNLEKIYRLCDKIEKEKKYLFCL WPIVDGRVGLDVLDYETEDKVD GATFDNALDVIDWLEENYVR | 66 | Hypothetical protein RB51ORF219 [Enterobacteria phage RB51] | YP_0028541 72.1 | 2e-29 (64/66) | | No putative conserved domains have been detected |
| 244 | 140530 | 140805 | 467 | MFPTYSKIVEVVFSQIIANNMFEK LDNAAELRIHAQVTHVLNALLPD | 91 | Hypothetical protein RB32ORF215c | YP_803157.1 | 2e-45 (91/91) | | No putative conserved domains have been detected |

Fig. 6UU

| | | | | | | | |
|---|---|---|---|---|---|---|---|
| 245 | 140868 | 141395 | 468 | QVDSIAITLYPGSAHIIVVFGLDAE LVIKGDIRFESQTSEFKAI | | | No putative conserved domains have been detected |
| | | | | MSEWFEEDKVYRFKAGYKDIFN ETCGANKRIAQFIGENSFKVKIDP AKNVISIKREIDDCWYKAVDVMG ESYKVSPLFSIAYMLEYSFFEEV QKDDSVSKFEIKTDKEIKWKVVGI TGCMFYIYAQTDTKEEAKKKALE YLEEHEEGPVMITQDAELVSVKL VKNVESKELGSTC | 175 | [Enterobacteria phage RB32] | YP_803156.1 | 5e-95 (173/175) | |
| 246 | 141389 | 141625 | 469 | MLSEKPITVKEFQEKVKLFAQEL VNKVSERFPETSVRVITETPRSV LVIVNPGDGDQISHLKLDFDGLV EAQRVYGVL | 78 | Hypothetical protein RB32ORF214c [Enterobacteria phage RB32] | YP_803155.1 | 5e-37 (78/78) | No putative conserved domains have been detected |
| 247 | 141622 | 141960 | 470 | MMNLTDIIDNCLENDTGDHRALD SETAQFIRITLMNDTLVNSIHPSV YDAIIVTKYPVELHKKMTGAVFID KKNRFKDGQNITSSVIKSITKLRH EIYRVETAKSAYLVIMK | 112 | Cd.1 hypothetical protein [Enterobacteria phage T4] | NP_049829.1 | 2e-58 (111/112) | No putative conserved domains have been detected |
| 248 | 141957 | 142538 | 471 | MKASTVLQIAYLVSQESKCCSW KVGAVIEKNGRIISTGYNGSPAG GVNCCDYAAEQGWLLNKPKHTII QGHKPECVSFGSTDRFVLAKEH RSAHSEWSSKNEIHAELNAILFA ARNGSSEGATMYVTLSPCPDCA KAIAQSGIKKLYCETYDKNKPG WDDILRNAGIEVFNVPKKNLNKL NWENINEFCGE | 193 | dCMP deaminase [Enterobacteria phage T4] | YP_803153.1 | 3e-110 (193/193) | Deoxycyti dylate_de aminase | dCMP deaminase | cd01286 | 1e-37 |
| 249 | 142538 | 142774 | 472 | MKFRLVKLTAISSYSNENISFAVE YKKYFFSKWKQYYKTDWTSIDR PYSWKSDLEKCQKLLSTLKERG TTHIKTVIGK | 78 | Gp1.2 hypothetical protein [Enterobacteria phage RB51] | YP_002854167.1 | 1e-37 (78/78) | No putative conserved domains have been detected |
| 250 | 142775 | 143083 | 473 | MKLTTEQKVAIREILKTKLSMGIS NVVFEKSDGTIRIMKCTRDADFM PTMQTGKLTESTRKESTDMIPVF DVELGAWRGFSIDKLISVNGMKV EHLLQFIGK | 102 | Gp31.1 conserved hypothetical protein [Enterobacteria phage T4] | NP_048826.1 | 2e-50 (99/102) | No putative conserved domains have been detected |
| 251 | 143140 | 143475 | 474 | MSEVQQLPIRAVGEYVILVSEPA QAGDEEVTESGLIIGKRIQGEVP ELCVVHSVGPDVPEGFCEVGDL TSLPVGQIRNVPHPFVALGLKQP KEIKQKFVTCHYKAIPCLYK | 111 | Gp31 head assembly cochaperone with GroEL [Enterobacteria phage T4] | NP_049825.1 | 1e-56 (110/111) | head assembly cochaperone | Chaperon in 10 Kd subunit | pfam00166 | 8e-06 |
| 252 | 143623 | 143871 | 475 | MIKQLQHALELQRNAWNNGHEN YGASIDVEAEALEILRYFKHLNPA | 82 | rIII lysis inhibition accessory protein, | NP_049824. | 6e-40 | rIII lysis inhibition | No putative conserved domains |

Fig. 6VV

| | | | | | | | | | |
|---|---|---|---|---|---|---|---|---|---|
| | | | QTALAAELQEKDELKYAKPLASA ARKAVRHFVVTLK | | | | (82/82) | accessory protein | have been detected |
| 253 | 144226 | 144444 | 476 | MPISPAFSFKREFIMAKQVKAKK AVEKKVGDSKRAGYKRGSNSRI NQTVEKIMRRARAVLRDDASRF GKQKA | | rapid lysis phenotype [Enterobacteria phage T4] | CAA35653.1 | | No putative conserved domains have been detected |
| | | | | | 72 | Unnamed protein product [Enterobacteria phage T4] | CAC42995.1 | 2e-32 (71/72) | No putative conserved domains have been detected |
| 254 | 144555 | 144920 | 477 | MNYINFERKYVSNGIAGSIDTICL WKHQNGSVCEIDQYMTPNYVY MRFENGITVSITKEGSNFKIALDD DFRERDLGTHPCWNGVHRKLLI KTWIRHILSNKAKPEHLEAIFDVV LNEFDI | 121 | Protein gp30.7 [Bacteriophage K3] | | 2e-64 (116/121) | Phage_T 4_Gp30_ 7_Phage Gp30.7 protein / pfam0691 9 / 3e-66 |
| 255 | 144949 | 145236 | 478 | MFMTTYFDTRKNFCEVVFSKAP KDLPAHLQPTSESIKNYVNVCP LEFRTVNGRDTLATKLNREIDID PSIAREINSSDINGGNVKSHGFQ MRF | 95 | Gp30.6 hypothetical protein [Enterobacteria phage RB14] | YP_0028545 39.1 | 1e-47 (91/95) | No putative conserved domains have been detected |
| 256 | 145236 | 145433 | 479 | MKFFLGQTVELKGVGIPGLISKVL PPFKWSGIQIKEAYIVSWVDGNE DLRMGDELSPIYGLKELV | 65 | Gp30.5 hypothetical protein [Enterobacteria phage T4] | NP_049819. 1 | 5e-29 (65/65) | No putative conserved domains have been detected |
| 257 | 145430 | 145636 | 480 | MNIINKIFGIQYIKVTYKVTDKNPY TDEHEEPQVKSIILEKGSDWPVE FRLPNYGHWADVEIISIENV | 68 | Gp30.4 hypothetical protein [Enterobacteria phage RB51] | YP_0028541 58.1 | 5e-29 (64/68) | No putative conserved domains have been detected |
| 258 | 145629 | 146087 | 481 | MSELEIRSNFKWPSCALSNFAQ WPFVMDGIQFGGLEGFLQGCKV KNVEQQRRIFGLSGLAAQQAGR SYARAQDRGTLFWLGVPFSRYS PAWKELYTNAYFEAAIQNKGFRD ALHASKGKVLKHSMASGLTKDD TILTEAEFIDVLNLLRDSL | 152 | Gp30.3 protein [Bacteriophage Pol] | CAD30242.1 | 5e-85 (152/152) | Bacteriop hage protein GP30.3 / pfam0801 0 / 6e-71 |
| 259 | 146084 | 146923 | 482 | MKPTILTDIDGVCLSWQSGLPYF AQKYNLPLEHILKMIQDEKFISPG KLFNCDEELGVKLIEKYNRSDFIR YLSPYKDALCVINKLKEDYNFVA VTALGDSIDALLNRQFNLNALFP GAFSEVLMCGHDSSKEELFKKA KEKYNVICYIDDLAH-HCDHASEIL NVPVYWWARGERDSIPKTAQRV YTWNDVENKLFSPKENKESFDS EKAIKDVIEKMIKNDSFPWNTTW RTPGFNPYNHLYHPYQTHPFQT | 279 | Hypothetical protein RB32ORF199c [Enterobacteria phage RB32] | YP_803141.1 | 2e-183 (276/279) | No putative conserved domains have been detected |

Fig. 6WW

| | | | | | | | | |
|---|---|---|---|---|---|---|---|---|
| 260 | 146923 | | WNYIKPGGIEYLYNRPTSGDNIFQGAF | | | | | No putative conserved domains have been detected |
| | 147192 | 483 | MFVVHTIYENEGNTTRDYGHVN QFFRCNPEFRAQKDERIFKKCVE QGFIYVKHWMQGNKVRTTYHRS LTELNDELIYNRAVNQTLKDEQ | 89 | Hypothetical protein RB32ORF198c [Enterobacteria phage RB32] | YP_803140.1 | 1e-46 (89/89) | | |
| 261 | 147189 | 484 | MILKILNEIASIGSTKQKQAILEKN KDNELLKRVVRLTYSRGLQYYIK KWPKPGIATQSFGMLTLTDMLDF IEFTLATRKLTGNAAIEELTGYITD GKKDDVEVLRRVMMRDLECGAS VSIANKVWPGLIPEQPQMLASSY DEKGINKNIKFPAFAQLKADGAR CFAEVRGDELDDVRLLSRAGNE YLGLDLLKEELIKMTTEARQIHPE GVLIDGELYYHEQVEKEPEGLDF LFDAYPEISKAKEFAEVAESRTA SNGIANKSLKGTISEKEAQCMKF QVWDYVPLVEIYGLPAFRLKYDV RFSKLEQMTSGYDKVILIENQYV NNLDEAKVITYKKYIDQGLEGIILKN TDGLWENARSKNLYKFKEVIDVD LKIVGIYPHRKDPTKAGGFILESE CGKIKVNAGSSGLKDKASVKSHEL DRTRIMENQNYYIGKILECECNG WLKSDGRTDYVKLFLPIAIRLRED KTKANTFEDVFGDFHEVTGL | 487 | Gp30 DNA ligase [Enterobacteria phage RB51] | YP_002854154.1 | 0.0 (482/487) | DNA ligase | DNA_liga se_A_M, ATP dependent DNA ligase domain | pfam01068 | 3e-26 |
| 262 | 148649 | 485 | MKAYLETIVVAQKEGGDVSTSVS QVILEFVDAYAYNKFTETFDAYE KGPKFEIYRTLLPLDY | 62 | Alt.1 conserved hypothetical protein [Enterobacteria phage T4] | NP_049812.1 | 1e-26 (57/62) | | No putative conserved domains have been detected |
| 263 | 148890 | 486 | MELITELFDEDTLPITNLNPKKKI PQIFSVHVDDCAIEQPGFRLCTYT SGGDTNRDLKMGDKMMHIVPFT LTAKGSIAKLKGLGPSPINYINSV FTVAMQTMRQYKIDACMLRILKS KTAGQARQIQVIADRLIRSRSGG RYVLLKELWDYDKKYAYILIHRKN VSLEDIPGVPEISTELFTKVESKV GDVYINKDTGAQVTKNEAIAASIA QENDKRSDQAVIVKYKISRRAIA QSQSLESSRFESELFQKYESTAA NFNKPATAPLIPEAEEMKIGINSL ASKTKAAKIIAEGTADELHYDYKF FPMSQVGEVSEKIKEVIFNAIKNE PTTSIKCLEKYAAAANQLFEEYK DNWLDKHNKTRKGQPDEVWEE | 697 | Adenosylribosyl- transferase packaged protein [Enterobacteria phage RB14] | YP_002854531.1 | 0.0 (682/697) | adenosylribos yl-transferase packaged protein | VIP2: A family of actin- ADP- ribosylating toxin | cd00233 | 1e-36 |

Fig. 6XX

| | | | | | | | | | |
|---|---|---|---|---|---|---|---|---|---|
| 264 | 150987 | 153044 | 487 | MTKNSWNAAKTKFLKRMIYSFS GIGAGPMIDTIARDGSKYTPSQK RGIREYCGSGYTDINNLLLGRYD PERYEVMSEKEIEAAITNLDSAFE NGDRIPEGITVYRAQSMTAPIYE ALVKNKVFYFRNFVSTSLTPIIFG RFGITHAGICLLEPEARNELTVDK NEEGITINPNEIRAYKENPEYVKV QIGWAIDGAHKVNVVYPGSLGIA TEAEVILPRGLMVKVNKITDASN NDGTTSNNTKLIQAEVMTTEELT ESVIYDGDHLMETGELVAMTGDI EIEDRVDFASFVSSNVKQKVESS LGIIASCIDITNMPYKFVOG<br><br>MELITELFDGASAPVVNLNPKHKI PQIFAIQAGEESVLPGFRFCTYTS GGDTNKNVKPGDKMMHIVMIGV NEKLSLVKLRNLGGNPIGVINAVF DTALQTMIKQYKIDACLFRVLKSK TNGAARQMQVIADRLVRTKGAG RYVLLKEIWGVDKKYAYIMVYRK NANLEDIPGVPPISTELFTKVESK VGDVVYDVKTGN

| | | | | | | | | | |
|---|---|---|---|---|---|---|---|---|---|
| 265 | 153105 | 153395 | 488 | MKSSLRFLGQELVVEGVIPADNA FNEAVYNEFIKFGTDKKFGIFPS ENFSKPEQTESIFQGVVTGKFES EAPVKIEVYIEDSLVASVAAFISFR K | 96 | Alt.-3 conserved hypothetical protein [Enterobacteria phage T4] | NP_049808 | 3e-46 (95/96) | | No putative conserved domains have been detected |
| 266 | 154389 | 153424 | 489 | MYSLEEFNNQAINADFQRNNMF SCVFATTPSTKSSSLISSISNFSY NNLGLNSDWLGLTQGDINQGITT LITAGTQKLIRKSGVSKYLIGAMS QRTVQSLLGSFTVGTYLIDFFNM AYNSSGLMIYSVKMPENRLSYET DWNYNSPNIRITGRELDPLVISFR MDSEACNYRAMQDWVNSVQDP VTGLRALPQDVEADIQVNLHSRN GLPHTAVMFTGCIPISVSAPELSY DGDNQITTFDVTFAYRVMQAGA VDRQAALEWLESAAINGIQSVLG NSGGVTGLSNSLSRLSRLGGTA GSISNNTMTGIVNSQSKILGAI | 321 | Base plate-tail tube initiator [Enterobacteria phage RB32] | YP_803134.1 | 0,0 (320/321) | base plate-tail tube initiator | |
| 267 | 155483 | 154389 | 490 | MAIVKEITADLIKKSGEKISAGQS TKSEVATKTYTAQFPTGRASGN DTTGDFQVTDLYKNGLLFTAYN MSSRDSGSLRTMRSNYSSSSSS ILRTARNTISNTVSKLSNGLISDN NSGTISKVPVANILLPRSKSDVDT SSHRFNDVQDSLITKGGGTATG VLSNMASTAVFGALESITQGIMA DNNEQIYTTARSMYGGAENRTK VFTWDLTPRSTEDLMAIINYQYF NYFSYGETGKSQYAAEIKGYLDE WYRSTFIEPLTPEDAVKNKTLFE KMTSSLTNVLVSNPTIWMVKNF GATSKFDGKTEIFGPCQIQSIRFD KTPNGNFNGLAIAPNLPSTFTLEI TMREITLNRASLYAGTF | 364 | Gp48 base plate [Enterobacteria phage RB51] | YP_0028541 48.1 | 0,0 (358/364) | base plate | |
| 268 | 157264 | 155492 | 491 | MKKPQEMQTMRRKVISDNKPTQ EAAKSASNTLSGLNDISTKLDDA QAASELIAQTVEEKSNEIIGAIDN VESAVSDTTAGSELIAETVEIGNN INKEIGESLGSKLDKLTSLLEQKI QTAGIQQTGTSLATVESAIPVKV VEDDTAESVGPLLPAPEAVNND PDADFFPTPQPVEPKQESPEEK QKKEAFNLKLSQALDKLTKTVDF GFKKSISISDKISSMLFKYTVSAAI | 590 | Gp29 baseplate hub subunit, tail length determinator [Enterobacteria phage T4] | NP_049805. 1 | 0,0 (567/590) | baseplate hub subunit, tail length determinator | |

Fig. 6ZZ

| | | | | | | | | |
|---|---|---|---|---|---|---|---|---|
| | | | EAAKMTAMILAVVVGIDLMVHF KYWSDKFSQAWDLFSTNFTKFS SETGTWGPLLQSIFGSIDKIKKLW EAGDWGGLTVAIVEGLGKVLFNL GELIQLGMAKLSAAILRVIPGMKD TADEVEGRALENFQNTTNASLSK EDQEKVANYQYKRMNDDLGPIA KGLDKIANWKTRASNWIRGVDN KEALTTDEERAEEEEKLKQLSPE EAKIALMKANEARAAMNRFDEYA NSADMSKDSTVKSVEAAYEDLK KRMDDPDLNNSPAVKKELAARF SKIDATYQELKKNQPNAKPQTSA KSPEAKQVQVIEKNKAQQAPIQQ ASPSINNTNNVIKKNTVVHNMTP VTSTTAPGVFDATGVN | | | | | | |
| 269 | 157794 | 492 | MNLKLILPLKKVVLPISNKEVSIPK MGLKHYNILKDYKGPDENLKLLID SICPNLSPAEVDFVSIHLLEFNGK IKSRKEIDGYTYDINDVYVCQRLE FQYQGNTFYFRPPGKFEQFLTV SDMLSKCLLKVNDEVKEINFLEM PAFVLKWANDIFTTLAIPGPNGPI -TGIGNIIGLFE | 177 | Base plate distal hub subunit [Enterobacteria phage RB32] | YP_803131.1 | 9e-97 (176/177) | base plate distal hub subunit | No putative conserved domains have been detected |
| 270 | 158914 | 493 | MSMLQRPGYPNLSVKLFESYDA WSNNRFVELAATITTLTMRDSLY GRNEGMLQFYDSKNIHTKMDGN EIIQISVANANDINNVKTRIYGCKH FSVSVDSKGDNIIAIELGTIHSIEN LKFGRPFFPDAGESIKEMLGVIY QDRTLLTPAINAINAYVPDIPWTS TFENYLSYVREVALAVGSDKFVF VWODIMGVNMMDYDMMINQEP YPMIVGEPTLIGQFVQELKYPLAY DFVWLTKSNPHKRDPMKNATIY AHSFLDSSLPMITTGKGENSIWVS RSGAYSEMTYRNGYEEAIRLQT MAQYDGYAKCSTVGNFNLTPGV KIIFNDSKNQFKTEFYVDEVIHEL SNNNSVTHLYMFTNATKLETIDP VKVKNEFKTDTTTEESSSSDK | 390 | Gp27 base plate hub subunit [Enterobacteria phage RB51] | YP_0028541 45.1 | 0.0 (390/390) | base plate hub subunit | Phage-tail_1, Baseplate structural protein, domain 1 | pfam0909 7 | 2e-98 |
| | | | | | | | | | Phage-tail_2, Baseplate structural protein, domain 2 | pfam0909 6 | 9e-86 |

Fig. 6AAA

| | | | | | | | | |
|---|---|---|---|---|---|---|---|---|
| 271 | 159663 | 158911 | 494 | MANIIRCKLPDGVHRFKPFTVED YRDFLLVRNDIEHRSPQEQKEIIT DLIDDYFGDYPKTWQPFFLQVF VGSIGKTKVPVTFVCPKCKKEKT VPFEYQKELKEPVFDVANVKIKL KFPSEFYENKAKMITENIHSVQV DENWYDWKEISESSQIELVDAIEI ETLEKILDAMNPINLTLHMSCCDK YIKKYTDIVDVFKLLVNPDEIFTFY QINHTLVKSNYSLNSIMKMIPAER GFVLKLIEKDKHQ | 250 | Gp51 base plate hub assembly catalyst [Enterobacteria phage RB14] | YP_0028545 23.1 | 3e-141 (247/249) | base plate hub assembly catalyst | No putative conserved domains have been detected |
| 272 | 159714 | 160340 | 495 | MYEYKFDVRVGSKIINCRAFTLK EYLELITAKNNGSVEVIVKKLIKD CTNAKDLNRQESELLLIHLWAHS LGEVNHENSWKCTCGTEIPTHIN LLHTQIDAPEDLWYTLGDIKIKFR YPKIFDDKNIAHMIVSCIETIHANG ESIPVEDLNEKELEDLYSIITESDI VAIKDMLLKPTVYLAVPIKCPECG KTHAHVIRGLKEFFELL | 208 | Gp26 baseplate hub subunit [Enterobacteria phage T4] | NP_049801. 1 | 7e-118 (208/208) | baseplate hub subunit | No putative conserved domains have been detected |
| 273 | 160340 | 160738 | 496 | MANINKLYSDIDPEMKDMWNKD VSRSLGLRSKNSLLGITTRKGS RPFDPEFGCDLSDQLFENMTPL TADTVERNIESAVRNYEPRIDKLA VNVIPVYDDYTLIVEIRFSVIDNPD DIEQIKLQLASSNRV | 132 | Gp25 baseplate wedge subunit [Enterobacteria phage T4] | NP_049800. 1 | 2e-70 (132/132) | baseplate wedge subunit | Baseplate wedge subunit gp25 PHA00415 3e-54 |
| 274 | 160805 | 161218 | 497 | MRLEDLQEELKDKVFIDSTKLQY EAANNVMLYSKWLNKHSSIKKE MLRIEAQKKVALKAKLDYYSGRG DGDEFSMDRYEKSEMKTVLSAD KDVLKVDTSLQYWGILLDFCSGA LDAIKSRGFAIKHIQDMRAFEAGK | 137 | UvsY [Enterobacteria phage RB51] | YP_0028541 41.1 | 3e-73 (137/137) | recombination, repair and ssDNA binding protein | No putative conserved domains have been detected |
| 275 | 161218 | 161442 | 498 | MRYNIDDAFNYEEEFETEIQFLM KKHNLKRQDIRILADHPCGEDVL YIKGKFAGYLDEYFYSKDMGIDM HMRVV | 74 | UvsY.-1 conserved hypothetical protein [Enterobacteria phage T4] | NP_049798. 1 | 1e-35 (73/74) | | No putative conserved domains have been detected |
| 276 | 161471 | 161638 | 499 | MSDKICVVCKTPIDSALVETDK GPVHPGPCYNYIKELPVSESSEE QLNETQLLL | 55 | UvsY.-2 conserved hypothetical protein [Enterobacteria phage T4] | NP_049797. 1 | 1e-23 (55/55) | | No putative conserved domains have been detected |
| 277 | 161924 | 161694 | 500 | MLLEFKQFLYEASIDEFMGKIASC QTLEGLEELEAYYKKRVKETELK DTDDISVRDALAGKRAELEDSDD EVEESF | 76 | UvsW RNA-DNA and DNA-DNA helicase, ATPase [Enterobacteria phage T4] | NP_049796. 1 | 2e-35 (76/76) | RNA-DNA and DNA-DNA helicase, ATPase | No putative conserved domains have been detected |

Fig. 6BBB

| | | | | | | | | | | |
|---|---|---|---|---|---|---|---|---|---|---|
| 278 | 163461 | 161950 | 501 | MTDIKVHFYDFSHVRIDCEESTF HELRDFFSFEADGYRFNPKYKY GHWDGRIRLLDYNRLLPFGLVG QIKKFCDNFGYKAWIDPQINEKE ELSRKDFDEWLSKLEIYSGNKRI EPHWYQKDAVFEGLVNRRRILN LPTSAGKSLIQALLARYYLENYE GKILIVPTTALTTQMADDFVDYR LFSHAMIKKIGGGASKDDKYKND APVVVGTWQTVVKQPKEWFSQ FGMMMNDECHLATGKSISSIISG LNNCMFKFGLSGSLRDGKANIM QYVGMFGEIFKPVTTSKLMEDG QVTELKINSIFLRYPDEFTTKLKG KTYQEEIKIITGLSKRNKWIAKLAI KLAQKDENAFVMFKHVSHGKAIF DLIKNEYDKVYVSGEVDTETRN IMKTLAENGKGIIIVASYGVFSTGI SVKNLHHVVLAHGVKSKIIVLQTI GRVLRKHGSKTIATVWDLIDDCG VKPKSANTKKKYVHLNYLLKHGI DRIQRYADEKFNYVMKTVNL | 503 | RNA-DNA and DNA-DNA helicase [Enterobacteria phage RB51] | YP_0028541 37.1 | 0.0 (503/503) | RNA-DNA and DNA-DNA helicase | SSL2, DNA or RNA helicases of superfami ly II | COG1061 | 8e-27 |
| 279 | 163512 | 164192 | 502 | MIDKDYIAELKALDDNKEAKAKLA EYAEQFGIKVKKNKSFDNIVNDIE EALQKLASEPMPETDGLSIKDLID AADAAEGLKYDDEEVNPEAALLI DSPVKSDIKIEVVETDKIPENTDV LIEDTPFVEEKFEQAVAEIIESEKP SVFTLPENFSPNLQLIGKNPGFC TVPWWIYQWIAETPDWKSHPTS FEHASAHQTLFSLIYYINRDGSVL IRETRNSSFVTLK | 226 | Minor capsid protein inhibitor of 21 protease [Enterobacteria phage RB14] | YP_0028545 14.1 | 4e-125 (224/226) | minor capsid protein | Ferrous iron transporte r, FeoB | TIGR0043 7 | 2e-04 |
| 280 | 164202 | 165620 | 503 | MTFTVDITPKTPTGVIDETKQFTA TPSGETGGGTITYAWTVDDAPQ EETSATFSYVLKGPAGQKTIKVV ATNQVAESEPETAEISTTTVQNK TQTTTLAVTPGSPDAGVIGTPIEF TAALASQPSGANATYQWYVDGS PVGEATSTFNYTPDASGVKTIK CVAQVTATDYDTKEVTSNEVSLT VNKKTQTTTLAVTPDSPPAGVIG TPVQFTAALASQPDGASATYQW YVDDSQVGGETNSTFSYTPTTS GVKRIKCVAQVTAENYNEKEVTS NEVSLTVNKKTMNPQVTLTPPSI NVCQODASATFTANVTGAPEEAQI TYSWKKDSSPVEGSTNVYTVDT | 472 | Outer capsid protein Hoc [Bacteriophage RB30] | AAM52483.1 | 0.0 (428/472) | outer capsid protein Hoc | PKD domain | pfam0080 1 | 0.001 |

Fig. 6CCC

| | | | | | | | |
|---|---|---|---|---|---|---|---|
| | 165722 | | SSVGSQTIEVTAVVTATDYDSKTITAEGQVQVTDKVAPEPEGELPYVHPLPHRTSAYIWCGWWVMDEIQKMTEEGKDWKTDDPDSKYYLHRYTLQKMMKDYPEVDVQESRNGYIIHKTALETGIIYTYP | | | | |
| 281 | 165925 | 504 | MRTEVVFTLHESGKSFIEIARELNLQAKEVAVLWARAMTAKNKFETREKVVYRKRHINKKVKNGTV | 67 | Hypothetical protein RB32ORF177c [Enterobacteria phage RB32] | YP_803119.1 | 4e-30 (57/67) | | No putative conserved domains have been detected |
| 282 | 166190 | 505 | MECYDLYENESFANQLREKALKSKQFKLECFIKDFSELANKAAEQGKTHFSYYCIARDKLITEEIGDWLRKEGFSFKVNSDQRDGDWLEITF | 92 | Gp24.2 conserved hypothetical protein [Enterobacteria phage T4] | NP_049791.1 | 3e-46 (91/92) | | No putative conserved domains have been detected |
| 283 | 167204 | 506 | MFKKYSSLENHYNSKFIEKLYSLGLTGGEWWAREKIHGTNFSLIIERDKVTCAKRTGPILPAEDFFGYEIILKNYEDSIKAVQDIMETSAVVSYQVFGEFAGPGIQKNVDYGDKDFYVFDIIVTTESGDVTYVDDYMMESFCNTFKFKMAPLLGRGKFEELJKLPNDLDSVVQDYNFTVDHAGLVDANKCVWKAEAKGEVFTAEGYVLKPCYPSWLHNGNRVAIKCKNSKFSEKKKSDKPIKAKVELSEADNKLVGILACYVTLNRVNNVISKIGEIGPKDFGKVMGLTVQDILEETSREGITLTQADNPSLVKKELVKMVQDVLRPAWIELVS | 334 | RniB RNA ligase 2 [Enterobacteria phage T4] | NP_049790.1 | 0.0 (329/334) | RniB RNA ligase 2 | RNA ligase | pfam09414 | 4e-132 |

Fig. 6DDD

Table 7 - Features of phage F510/08 gene products and assignment of putative functions.

| ORFs | Start position | Stop position | SEQ ID NO.: | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 1 | 1 | 124 | 507 | LLNEAVASKVLNSRLG WSAVGEYVELFNRTQ SRVAGLIPE | 40 | Hypothetical protein PPLUZ19_gp49 [Pseudomonas phage LUZ19] | YP_0016 71995.1 | 1e-14 (40/40) | | No putative conserved domains have been detected | | |
| 2 | 641 | 432 | 508 | MLSRQDRGERAWHQ QDAAWQRQIATWAAQ DHRHYAAPWRKRQAS QEYAVALTKHREALER SRHYGQPKG | 69 | No significant similarity found. | | | | No putative conserved domains have been detected | | |
| 3 | 1175 | 1528 | 509 | VGSRSVEFALSSRNNA STGSLETGLTHCQGIG RVRSQNDGRLQPSKR GTSHRRKGHGKLLGQ EPQCVRPAGITEGIDTV QDTRYSSHHLMATQQ KGLCQRTGRTNPRQRI DKTSASL | 117 | Hypothetical protein PT2_gp01 [Pseudomonas phage PT2] | YP_0021 17780.1 | 4e-31 (68/73) | | No putative conserved domains have been detected | | |
| 4 | 2012 | 2296 | 510 | MAHFKAKAPKSPFAAQ VAYWRDWEAKRTKLIA QDNVEGRKELRKMRD VRYATDPEPAPGRYHN PEQKAFVKGSEGKAR NILKGWNAKKSQGKGL | 94 | Hypothetical protein PPLUZ19_gp1 [Pseudomonas phage LUZ19] | YP_0016 71943.1 | 5e-48 (94/94) | | No putative conserved domains have been detected | | |
| 5 | 2296 | 2523 | 511 | MPRVNELTPRQRKAAK ARRDKARRIDLAHRMP KGADCPIFRKAECAQA KQPRVDTLTPRSAGY LAAAAYLNKSI | 75 | Hypothetical protein PPLUZ19_gp2 [Pseudomonas phage LUZ19] | YP_6016 71944.1 | 3e-35 (75/75) | | No putative conserved domains have been detected | | |
| 6 | 2534 | 3073 | 512 | MTNAISKTVIAFRGTEEI NRAIDAIRVRGKELDEA IQLTGLSIIHHIDQCGDV TVVKALYEAMPKGSRR NALVEWLVLHGKVQVN TDKKSNKQLPFLYNKF GKTDLVGATNSPWYSF KPEKALDQEFNLAAAL ATIKKQVLQAQTKGKVI VGMELLGDLEALAAKA APIAEQSKRAAAH | 179 | Hypothetical protein PT2_gp04 [Pseudomonas phage PT2] | YP_0021 17783.1 | 3e-100 (179/179) | | Hypothetical protein | PHA017 82 | 3e-72 |

Fig. 8A

| | | | | | | | |
|---|---|---|---|---|---|---|---|
| 7 | 3441 | 3809 | 513 | MQALNTLLAIPKDPTA GMHAADKVLCAHGFR MGDLNTAHVLTPGGFV VVGAGVTVNRYDEAY RMSRNLDSEGFDVLLV CGSPLSGRVTCQAYG WINAEYHKGCANGRPI FDIAGTSYHVIA | 122 | Hypothetical protein PPLUZ19_gp4 [Pseudomonas phage LUZ19] | YP_0016 71946.1 | 2e-65 (120/122) | No putative conserved domains have been detected |
| 8 | 3796 | 4020 | 514 | MSSRDPYRIGHRVGLV NYSDRYLGADAAGTK GIIEAITRPSRCMTVYH VRCERTLRLIEAEARNV RFIRQRAER | 74 | Hypothetical protein PPLUZ19_gp5 [Pseudomonas phage LUZ19] | YP_0016 71947 | 2e-34 (72/74) | No putative conserved domains have been detected |
| 9 | 4199 | 4459 | 515 | MTLVATVVDSAHNLEV DDLTAGNLYAASSPSG NMFIVVVGNHNGRRLP VVLSSTDTRTIGDVISN TGFRYSEIAGFSVNLA QGDYD | 86 | Hypothetical protein PPLUZ19_gp6 [Pseudomonas phage LUZ19] | YP_0016 71948.1 | 9e-42 (86/86) | No putative conserved domains have been detected |
| 10 | 4459 | 4749 | 516 | MVTRTVYVTPEDPTPPI LSVGRLAPGELYKVVA PSSAEGIIVLATKQTPA LAQAAVVLHSMNPAQY PAGSAILNTAWKCRRL GVGEYVKLVQGEED | 96 | Hypothetical protein PPLUZ19_gp7 [Pseudomonas phage LUZ19] | YP_0016 71949.1 | 3e-48 (96/96) | No putative conserved domains have been detected |
| 11 | 4749 | 4988 | 517 | MAVAILILAVWLIGGALL FLPFDLVVSPRLPLSDE ALNRTALYTVLWPVTL PTLIAITVVVMLHSAYR GAIELYQEMKS | 79 | Hypothetical protein PPLUZ19_gp8 [Pseudomonas phage LUZ19] | YP_0016 71950.1 | 1e-27 (66/69) | No putative conserved domains have been detected |
| 12 | 4985 | 5278 | 518 | MIRTHTHNVERTPHRL YRHTELASGELYRVVQ PDSKRGTLVVGVAAW DSQGRPAVLPVVIHDD GDAKVTCARPTVLRND GWRMVLADKGTQVTL TAE | 97 | Hypothetical protein phiKMvp09 [Pseudomonas phage phiKMV] | NP_8774 48.1 | 9e-39 (80/97) | No putative conserved domains have been detected |
| 13 | 5357 | 5773 | 519 | MTNVNTTTETTTAAVL GAKLIKKPATVEDFRN NVVFHHSALTKLTEVY NEAVAALQTAERLSSL VAGDWITFDHGKGEKA EVLSGEVISVVAGVYQ VLVRFSDSAPAKLLDV KASAIRAVQSSAAQAA TLDEAIAQGE | 138 | Hypothetical protein PPphikF77_gp11 [Pseudomonas phage phikF77] | YP_0027 27830.1 | 1e-58 (114/123) | No putative conserved domains have been detected |

Fig. 8B

| 14 | 5842 | 6201 | 520 | MSKRNPEHINGTVRSV SVQKLAATQELEDRLE AALAVCQQRAEDIDLL SRRLQAAERARRWEID EIRNHQATIRLLQNDLN AAHDAHEAQERRARK ATIMAWVCLLTAGLAV TLKLAGV | 119 | Hypothetical protein PPLUZ19_gp11 [Pseudomonas phage LUZ19] | YP_0016 71953.1 | 2e-60 (119/119) | | No putative conserved domains have been detected | |
|---|---|---|---|---|---|---|---|---|---|---|---|
| 15 | 6204 | 7013 | 521 | MQCKDLYTNLASGMF NVPCSQVTPEMRRVA KSRAFAHAYTPKKQAS GGTYARVSGVTCDG GKVEVRLDNVERVSTF DYAELETRVAASLCQA DAKRAAEYEKLLLKAF PSVSPKDGPLSAKDFE LRLHDLCSTKLVVLRAL RDAGIEMDGPLRSRVR KLADRNNVMCAELFSL KQELAQLVAVGQKAGL NWDGAETQRLLTVAPT KALCRLISALTGVRYTH HTVVAKAEAERERAK AEAKDSLQAATFAAAIA GGVVGSALMFLLG | 269 | Hypothetical protein PPLUZ19_gp12 [Pseudomonas phage LUZ19] | YP_0016 71954.1 | 3e-145 (260/268) | DNA polymerase | DNA_pol_A, DNA polymerase family A, 5'-3' polymerase domain | cd06444 | 5e-05 |
| 16 | 7284 | 7826 | 522 | MSKTSLYPLNLHPGLIQ IRTIHVFSIQAPSNAEN WWQWFLWQRKYHPL RESLSPAGELSASIAEC VLHLRRNGWQDSDIW RKKGGVLALGAFDLSG LMVGSCLVVGGELKAL CVDDRHSRQGIGAELV RAAELAGAEYLTCFEF LEPFYADLGWSTTHRE ANWTAGEPDVLHMRA PGHDV | 180 | Hypothetical protein PT5_gp14 [Pseudomonas phage PT5] | YP_0021 17736.1 | 6e-102 (180/180) | | No putative conserved domains have been detected | | |

Fig. 8C

| | | | | | | | | | |
|---|---|---|---|---|---|---|---|---|---|
| 17 | 8012 | 8836 | 523 | MALRRDSWLKQAGSL AVGQAGRFRHVLGCQ SMSRGGTNMTCKNLP DRWVAYCYSCQEGGV VEKTHVRRVQCADQE RFMPWPEDASDWTQA DCYQSLYGLLLSKGIDY NVMTPGLPLLYSERQH RLIFPTDAGWIGRATAD QNPKWVGYPAPDY HGWPQELSMGRPWVL TEDYLSALKVRWACPE VFAVGLNGTRLRDRLA AIMLQQTCKRAFIFLDG DRAGVRGSAGVMRRL RSILIEGQVIPTDGFD PKDLTREQIRSLVIGRI DASRTE | 274 | Primase [Pseudomonas phage LUZ19] | YP_0016 71958.1 | 2e-158 (271/274) | primase | | Putative DnaG-like primase | PHA02031 | 6e-148 |
| 18 | 8805 | 10073 | 524 | LDVLTLHALSDRDRFR TLRSVVPEGMMGPET CFVIDWIEQYWKVYPA HQKVDPQALRELIKLR GGYQPEQLAVVLNLVN QLDKPVDPDSLQGVVS QLNELDFSGRVDALLA QYNQGEDIDLAYELRR LSDEALRRGGVSTPTD YVTDDVFDILAEEQGD HGIKLPGLVLPAYMKG LHAGASVLVAAPPDAG KTSFMAWIAVHIAPQLK RYFDPGRPILWLNNEG KGRRIKPRLYSAALGM TVGEILALDPEEVRRM YAEKIGGDSELIRIKDF HGGSLAQAEQVIDAMK PSVVFWDMMAHVKGG QRKDQNRTDEMEYKV AEVREMAVRHDFISFM TWQISNDGHDQLFPPQ SCLKDSKTAVQGAVDV QIHLGRLNGADQQVM RGLSLPKNKFQMDGK PSNVEAMINFDAARCR FFESVDHAS | 422 | DNA_B Helicase [Pseudomonas phage LUZ19] | YP_0016 71959.1 | 0,0 (395/397) | DNA_B helicase | | DnaB helicase C terminal domain | cd00984 | 2e-06 |

Fig. 8D

| | | | | | | | | |
|---|---|---|---|---|---|---|---|---|
| 19 | 10063 | 10683 | 525 | MQAKHSRVLEGTKEIP LGSIEPLLGSVAGLLLC LYSDATHEEGVALAGG FPRDLMHGATPKDVDV ALYSMTWGRAEHLIQK ALPVLNPIFVRDGGWR SDYADGGDGGIFKGV MSLVGCRGLNGMDLD FNYYDADSLGRVMESF DFTINQVGIAYNWPDP EGGPRLGAYLHKDVT WGVNKEVGAGSRLPE RCEKMRAKAAYYGWE NV | Hypothetical protein PPLUZ19_gp16 [Pseudomonas phage LUZ19] | YP_0016 71960.1 | 7e-111 (196/206) | | Hypothetical protein | PHA01806 | 7e-92 |
| 20 | 10683 | 11630 | 526 | MSKRDVVLDIEKGIWR GVDQNDKAVEAIIKKN GYVIVEPKIDGCRAIVG AHGVVSRSGRRFPALD GLEDRIIERLARPGLDS GLVLDCEMYLAGMPFS EATGRMSSKTPLTEEE LECLHFAVFDATHIDVL RKARTSHLVVEERRAM ASSLLAACRLSDTPTFF QVGFTVCRRMSDVYR QYKFNREVGYEGSME KDPSLVYRNGKVAGCY KRKPGITVDGRIVGYV MGKTGKNVGRVVGYR VELEDGSGTVAATGLS EEHIQLLTYAHLNAHID EAMPNYGRIVEVSAME RSANTLRHPSFSRFRD LASNPGVKV | ATP-dependent DNA ligase [Pseudomonas phage phikF77] | YP_0027 27838.1 | 5e-159 (275/315) | ATP-depende nt DNA ligase | ATP-dependent DNA ligase | PHA00454 | 1e-99 |
| 21 | 11627 | 11911 | 527 | MKIRKSRNRNYPEDMV YHATNRDSLLYPKYVM GSVFISQDGTFRICVM AGTWDHVGSEVLHHA RDIQSLGAGRRKLHRV MRRLRRNLQQVGVKV | Hypothetical protein PPphikF77_gp20 [Pseudomonas phage phikF77] | YP_0027 27839.1 | 1e-46 (91/94) | | No putative conserved domains have been detected | | |
| 22 | 11908 | 12243 | 528 | MRMPTEEERTIRCLLA DIHEPLNLLFPGIRVKA ETMPLGWGDSICALVL RVSYEHLTLGRLEYMH EVPILHLSQWGRDGLL QHLMNEIPRRVLDGML RQAQKYSQSNWYSK | Hypothetical protein PT2_gp22 [Pseudomonas phage PT2] | YP_0021 17801.1 | 4e-58 (109/111) | | No putative conserved domains have been detected | | |

Fig. 8E

| 23 | 12240 | 14663 | 529 | MTTIRILDLETESYEHK GRKASPFDPRNYIVMA GWRDDVDGKVGQKVE HRFRSRAEAEDPNNR WFNLDGVDVIVAHNAM FESNWFFTRYRDEYLA FLRRGGRVWCTQQAE YLLSHQTWLYPALDEL APKYGGTHKVDGIKML WDQGVLTSEMDQDLL SEYLSGPCGDIENTAL VFYGQLMKLQARGMW AGYLERCEALIGFSAM ECAGLKVDLEVAKVNH AKQLEEVAGIEAELKKL MPDFPEYFEFKYTSLY HMSAWLYGGEVRYKG RVPYEDGRMEKADFV RFGTAKRGTPIESTSV RVPIHEVTDQGEWHW PTITELATKHGPVITFSA GKNKGSVKVFREDTDI PATKWDDDQRFRFPG LINLTNLPEVVREKFLG KRPEFQCALTLADGSP VFSTSGDALKALEKQG FEAAKLLMRLAELHKD NSSFYITHTYNKDGTIK DTKGMLQYVDDDGIIH HSLNTTATATTRLSSS RPNLQQLPSKDEDDPE AGSRVKEMFVSRFGA DGMIGETDYTALEVVM LAALSKDRNLLAKLMA GTDMHLYRLAGKHNN WNGFDYDQLVAIKKDP NHPWHGRMMQARKNI KPKAFSAQYGASAAGI AFNTGCTVEEAQEFLD NEAALFPESIAFRQIVR DSAEATSLVMYKAEDQ MPAGAFSEMGPDGNW RQYRRGFWQAPGGTC YSFRQQERWDKEQRK TVMDFKDTQIANYWNQ GEAGFMMTVSVGRIFR VMLHRPGFMVTEFLIN NVHDAVYTDCHKDTAA EVNKGVRDIMADAARY MSERLGYDIADVPFPA | 807 | Putative DNA directed DNA polymerase [Pseudomonas phage phiKMV] | NP_877458.1 | 0.0 (806/807) | DNA polymerase | DNA polymerase family A, 5'-3' polymerase domain | cd06444 | 2e-20 |

Fig. 8F

| | | | VAEMGPNMFNMEVIQ | | | | | | |
|---|---|---|---|---|---|---|---|---|---|
| 24 | 14660 | 14971 | 530 | VKELHPLHTPEFVKTFL DQTGCLPGVRRTGRT TGIALQAIGMALSHPRE TLTFVDHPDGSAAALV ASIETILATLGYKNVLVR PTTRADGRSVSIVFKTL PNA | 103 | Hypothetical protein PPphikF77_gp23 [Pseudomonas phage phikF77] | YP_0027 27842.1 | 2e-52 (102/103) | | No putative conserved domains have been detected |
| 25 | 15026 | 16075 | 531 | MTQQLNLQAAALALAN KAAETATIDMSETSTG GGGGRIFPAGTAMGR FCIYIELGDHAKEFQGK LKNPAPQIRLGFALWG DVNPQAGNPQSRPDD LFHTYEADGSIKPGLFR TFEMTLGNNEKSKTKL AFDKMNWSGQHTHFA QMLGGQAFIIPIKRTKITK GNNAGKERNDIDWGGI MKPYNPVDGSPYNVP ELPMDLLQYFFFDAPT KETWDALYIEGTSDNG KSKNFLQETIRSATNFP GSALHMLGGGDDLIIK PTSQAAGSNLPAVPNV AADAGVAAAPAVPAVP QAVAQTAPSVPQVANV AAPVVGTAEAQNVLPD VPQVAQTAAPAAVEVP AVPVVPAVPQV | 349 | Hypothetical protein PPLUZ19_gp21 [Pseudomonas phage LUZ19] | YP_0016 71965.1 | 0.0 (347/349) | | Hypothetical protein | PHA02030 | 4e-138 |
| 26 | 16075 | 17016 | 532 | MRLPSEEFLAGLSAQF DRSMAGGTLVCDADG PAYVAAATAKTLDTAL RRFWKLILEQFLAHC TGTRVHLTAAGGAKAY RDTYPTMKPYQGGRK GKAKPALLEPLRRAVA DVHERGGAPEGIDVIL HTFFEADDGMMMDAY AMQDKAIIRSDDKDLR MTIYPYWEIDTACVSRI EGGFGYLKEAYTPSGQ FKLKGHGRKFFLAQWL GGDTADNIRGIDRFNG KLCGMKTAFDILHPITD EDEAIDMILEAYAKIKQ NPLAEAEVLWMRRTPT DNAAQYLLSRDLRPAF | 313 | 5'-3' exonuclease [Pseudomonas phage LUZ19] | YP_0016 71966.1 | 0.0 (313/313) | 5'-3' exonucle ase | 53EXOc, 5'-3' exonuclease | cd00008 | 0.006 |

Fig. 8G

| | | | | | | | | | |
|---|---|---|---|---|---|---|---|---|---|
| 27 | 17006 | 17446 | 533 | RQWIIELDAYHEALLQK RRESDYDE MTSEPKVYQIPRSQQR TFTLKLWAEQNKLCPL CGKPIDISVKGEAVMD HDHETGLVRGVLHRSC NTAEGKITNAAGSWGC KSMKYSDIPYLRALLT YLEGPKHPLIYPLHKTD EEKHEAKLAKRRQAAA KRKAAMAVAKHNARN V | 146 | Putative DNA endonuclease VII [Pseudomonas phage phikF77] | YP_0027 27845.1 | 8e-81 (144/146) | DNA endonucl ease VII | Endonuclease_7, Recombinatio n endonuclease VII | pfam02945 | 8e-10 |
| 28 | 17443 | 18489 | 534 | MSKLRKQFTNEYLRNV YVELGLKKGAEHLTEH SRFGEVSRQCFRNWCI KLGFHDSRTRGMYAK KGAMHWLGRKAAEVV RKFPGAVGNVVGQGP KVLSLDIETSPIEGWVW SLWKQNVGLNQIKRD WTILSFCAKWMHSDEV IYMDCQGDPLDDMHLL VALHKLLDEADIIVQNG KRFDVPKINARFFLNK MPPPRPFKVIDTLIIAKQ QFAFTSRKLEYMTHKA CTIKKRLHGKFPGFDL WAACLQDNPEAWEEM RLYNIDDVRSMEELYIL MRPWFVGHPNVAVYF NDAEPTIRCPKCGDTD VKQEGWVHTQTGKYE HYHCGCGGWSRGR YTRNTSEQRKALLSN | 348 | Hypothetical protein PPLUZ19_gp24 [Pseudomonas phage LUZ19] | YP_0016 71968.1 | 0,0 (346/348) | 3'-5' exonucle ase activity | DEDDy exonucleases, part of the DnaQ-like (or DEDD) exonuclease superfamily | cd06126 | 3e-04 |
| 29 | 18499 | 18870 | 535 | MSLAFPDSYESTITTEP YRKGASLEERKVGKLP MHLVVEGFPLLKRELA RMMQWAAEVKGYLPH DWKKMTVGEFKSAQH RHESKRLIDGPLDDES NLMHLVHEAFNAMAAA EVALMDREKGNE | 123 | Hypothetical protein PPLUZ19_gp25 [Pseudomonas phage LUZ19] | YP_0016 71969.1 | 2e-66 (123/123) | | No putative conserved domains have been detected | | |
| 30 | 18863 | 19213 | 536 | MSKICWCTRPHETDEG VRVWAFNERGIGVNY VTAYITPAMVSHRDWS DVILPDILREMAERLER EVKLVELRWFRAEILSC GEWRDYRAMTLEGAV | 116 | Hypothetical protein PPLUZ19_gp25.1 [Pseudomonas phage LUZ19] | YP_0016 71970.1 | 2e-60 (116/116) | | No putative conserved domains have been detected | | |

Fig. 8H

| 31 | 19222 | 21672 | 537 | SLAEAEWGPEDIGRVI ERR MDLIQQQIAHEEALVG AAQNDARIALEKAIAQG SIDRIPRARIMLMRMLPI VTEAIFAHQEAKAAGP AAKLRHLLRIIDAQDLA VMALRAGLSMLINYPTI TATKYTHMGKILCREI EVRLAFKVNQPYYDRT LDYLKTSRTRSVRHIQK TMDALLDAVLPEEARID LPDGDYLRLGKFIGDPL IQCGLFEPNRFTGRGG TSVHLEPSPEAKEFLQ DPSAAMTWGPGRSV MLAPPRPWNDWCDG GYYSAKAQKHHVLVRR TKHQTKRARQMQLRH LGRDKMPRVYEAVNAL QSVAYEINHDVYEIIER VFTSGGGVLGIPQRTY PDKPEFPLGDEWAKE NASEQELEAFNRWKR SVHRWYTGEREHTAK LREFAALYRVVREHHG KAVYFPMHVDSRGRM YYWGTPNPQGSDIAKA CLRFHEKRALGKRGLY WLKVHVANSLGCDKV YFDDRAAWVDERWDD FQRALDEGPENYPNLF PEDESPLCAIAGLLELR AAYASGMPEGYASGFI VHMDATCSGLQHYSAI LRDEIGGAYVNLLPPGL AKADIYSRVLGLVNESL ERDRAEGADGEARGY AILWDKAGLTRSLTKKP CMTLVYGTTFKGVVDH CLDYLDESGVEIPEGV PSYRLGSYMATLILDAI RETVPSAVFAMEWLQ RLARALPDASKDLHWT TPLGMQVFQSYPKTEE VRVRLRAEAVEYVTLY EAKDELDPVRNANGIA PNFVHGLDSSHLGLTA LACAAEGIPIQAIHDSM | 816 | Putative phage-specific RNA polymerase [Pseudomonas phage phiKF77] | YP_0027 27849.1 | 0.0 (799/816) | RNA polymera se | T3/T7-like RNA polymerase | PHA00452 | <1.0e-180 |

Fig. 8l

| | | | | | | | | |
|---|---|---|---|---|---|---|---|---|
| | | | | GTYAADVDRMHVHIRE QFIAMYSGPCVLVELA KQLGIEATPPRRGSLN LEAVRDSWAFFC | | | | |
| 32 | 21845 | 22096 | 538 | MATMKTHRPTVMSPT VEGSRTGKGTARPVTF TSQQIEWLEQTFPEHQ IGPGTTMEDIQFQAGR RDVVRAVRLRRRDAIA VELK | 83 | Hypothetical protein PPLUZ19_gp27 [Pseudomonas phage LUZ19] | YP_0016 71972.1 | 1e-40 (83/83) | | No putative conserved domains have been detected |
| 33 | 22096 | 22569 | 539 | MNKSIWRVHAKAGTPS ELQGLCWLAIQELEEF TLFRSKDDALNAMLDSI EGNDRTELLVFRDGQL AGGACIVFEDDPHVGP CVTAQWQYVLPRYRN TGVVREFIRELHRQAG WGQIPLVCWSHRESD SRYTIHYRRAKPYGQE SKEGAGQDHHRQTR | 157 | Hypothetical protein PPLUZ19_gp28 [Pseudomonas phage LUZ19] | YP_0016 71973.1 | 5e-88 (154/157) | Hypothetica l protein | PHA01807 | 2e-70 |
| 34 | 22514 | 22810 | 540 | MGKVKKVLGKTIIGKL ADGLLGTDLSGAQSDA RKMEEQNRLMQQOAD QLARNQQVDLTAENVA QVDLGAMADATGTGT RRRRNQAGTGVSQTL GINY | 98 | Hypothetical protein PT2_gp34 [Pseudomonas phage PT2] | YP_0021 17813.1 | 2e-47 (98/98) | Putative structural protein | PHA01808 | 8e-14 |

Fig. 8J

| | | | | | | | | | |
|---|---|---|---|---|---|---|---|---|---|
| 35 | 22822 | 24354 | 541 | MKTTAAMLWEKLRDG SVESRAIEFAKTTLPYL MVDPMSGSRGVVEHD FQSAGALLVNNLAAKL ARSLFPTGIPFFRSELT DAIRREADSRDTDITEV TAALARVDRKATQRLF QNASLAVLTQVIKLLIVT GNALLYRDSAAATVVA WSLRSYAVRRDATGR WMDIVLKQRYKSKDLD EEYKQDLMRAGRNLS GSGSVDLYTHVQRKK GTAMEYAELYHEIDGV RVGKEGRWPIHLCPYI VPTWNLAPGEHYGRG HVEDYIGDFAKLSLLSE KLGLYELESLEVLNLYD EAKGAVVDDYQDAEM GDYVPGGAEAVRAYE RGDYNKMAAIQQSLQA VVVRLNQAFMYGANQ RDAERVTAEEVRITAE EAENTLGGTYSLLAEN LQSPLAYVCLSEVDDA LLQGLITKQHKFAIETG LPALSRSAAVQSMLNA SQVIAGLAPIAQLDPRI SLPKMMDTIWAAFSVD TSQFYKSADELEAEAE CQRQQAAQAQAAQET LLEGASDMTNALAGV | Head-tail connector protein [Pseudomonas phage LUZ19] | YP_0016 71975.1 | 0,0 (510/510) | head-tail connector protein | Head-tail_con, bacteriopha ge head to tail connecting protein | pfam12236 | 5e-103 |
| 36 | 24358 | 25326 | 542 | MTQPNDQQLPPGLAN LVANVPPAAAPTPSHV QVLPNPVIQPQAPVQP GQVGAPQQLAIPTQQP QPVPTSAMTPHYQPVA VPVAGQPVVPQAPAQ PAPVAPPAAGAVLPEN LEVPPPPAFTPNGEIVG TLAGNLEGDPQLAPSIS YLEAFSDKLDTVRAFG KAAENRDPRFIDEHYL KEVLGPAQAQHVINVA KGVLTYVDAQTKAVLN QTYAAVGGEAVLKQAA GVFNQHADPATKAAIG RLMDSGDAQAMQYAA KQIVAFAQGSGAVVQA TGQPLGAAAPALAALS | Hypothetical protein PT2_gp37 [Pseudomonas phage PT2] | YP_0021 17816.1 | 4e-174 (316/322) | scaffoldin g protein | Putative scaffolding protein | PHA01929 | 2e-92 |

Fig. 8K

| | | | | | | | | |
|---|---|---|---|---|---|---|---|---|
| | | | AEQYRLEVSKLPLNAS EAEMAALRERRKAGM AQGI | | | | | |
| 37 | 25379 | 26386 | 543 | MSFLNDLTRPNYAGKN ADVDIHLEEHLGIVDKH FAYTSKFAPLMNIRDLR GSNVVRLDRLGNVEAK GRRAGEELERSRVVN DKWNLTVDTLLYLRHQ FDHQDEWTQSFDMRK EVAELDGQELARKFDQ ACLQVIKAAAMDAPVD LEDAFSPGVLEKLDLT GLTAKQAADKIVRMHR RVVETFIDRDLGDAVY SEGLTPMSPRVFSLLL EHDKLMNVEYQATGAT NDYYKSRVAILNGVKV LETPRFATKAIAAHPLG RHFNVSAEESERQIAL FLPSKTLITAQVAPVQA KLWEDNEKFSWVLDTF QMYNIGARRPDTAGAI ELKGKGAFDITA | Major capsid protein [Pseudomonas phage LUZ19] | YP_0016 71977.1 | 0.0 (335/335) | major capsid protein | Capsid protein | PHA02004 | 3e-177 |
| 38 | 26483 | 27037 | 544 | MLLLDAVNVILRKIGEL PIPSMDETYPTMAIALP ELEDQRIQLLTQGWWF NTWWKHKLTPDPQGR INLPKDTLAFYPDSPDL QWDGLGVRDANTGDD RIGKSVEGRLVLSREW DRIPEIAQRVIAHQAAL AVYTHEIGPDETAQVIA QELQAYQNELSRMHT RSRPLNTQAKRSFSR WRRSLRT | Putative tail tubular protein A [Pseudomonas phage LKD16] | YP_0015 22825.1 | 2e-102 (183/184) | tail tubular protein A | Tail tubular protein A | PHA00428 | 7e-66 |
| 39 | 27040 | 29520 | 545 | MSYKQSAYPNLLMGV SQQVPFERLPGQLSEQ INMVSDPVSGLRRRSG IELMAHLLHTDQPWPR PFLYHTNLGGRSIAML VAQHRGELYLFDERDG RLLMGQPLAHDYLKAD DYRQLRAATVADDLFIA NLSVKPEADRTDVKGV DPNKAGWLYIKAGQYS KAFSMTIKVKDNATGT TYSHTATYVTPDNAST | Tail tubular protein B [Pseudomonas phage LUZ19] | YP_0016 71979.1 | 0.0 (821/826) | tail tubular protein B | | No putative conserved domains have been detected | |

Fig. 8L

| 40 | 29520 | 30065 | 546 | NPNLAEAPFQTSVGYI AWQLYGKFFGAPEYTL PNSTKKYPKVDPDANA ATIAGYLNQRGVQDGY IAFRGDADWVEVSTDM GNNYGIASGGMSLNAT ADLPALLPGAGAPGVG VQFMGGAVMATGSTK APYYFEWDSANRRWA ERAAYGTDWVLKKMP LALRWDEATDTYSLNE LEYDRRGSGDEDTNPT FNFVTRGITGMTTFQG RLVLLSQEYVCMSASN NPHRWFKKSAAALND DDPIEIAAQGSLTEPYE HAVTFNKDLIVFAKKYQ AVVPGGGIVTPRTAVIS ITTQYDLDTRAAPAVTG RSYYFAAERALGFMGL HEMAPSPSTDSHYVAE DVTSHIPSYMPGPAEYI QAAASSGYLVFGTSTA DEMICHQYLWQGNEK VQNAFHRWTLRHQIIG AYFTGDNLMVLIQKGQ EIALGRM-HLNSLPARE GLOYPKYDYWRRIEAT VDGELELTKQHWDLIK DASAVYQLQPVAGAY MERTHLGVKRETNTKV FLDVPEAVVGAVYVVG CEFWSKVEFTPPVLRD HNGLPMTSTRAVLHRY NVNFGWTGEFLWRISD TARPNQPWYDTTPLRL FSRQLNAGEPLVDSAV VPLPARVDMATSKFEL SCHSPYDMNVRAVEY NFKSNQTYRRV MAFWLPLLAAGGMSAL QQGLANKEERNKIKAE NKARLKTDLDNLGAAA RDIANLGVMAASYRKQ AVASQVEAKRQGMLA GGSAEAQAGAFGVKG ASVDAVALDIEREVGE ALIQIDDNLDNQMWNL AEQAHSIQAQAKAGLL GQKSTTAGQRSPLVA | 181 | Internal virion protein [Pseudomonas phage LUZ19] | YP_0016 71960.1 | 2e-97 (181/181) | Internal virion protein | Putative internal virion protein A | PHA01547 | 2e-66 |

Fig. 8M

| 41 | 30065 | 32761 | 547 | GLMSAGSLYASQYFKF GATPKGGN | 898 | Internal virion protein [Pseudomonas phage LUZ19] | YP_0016 71981.1 | 0.0 (895/898) | internal virion protein, T4-like lysozyme | Bacteriopha ge_T4-like_lysozy me | cd00735 | 2e-10 |
|---|---|---|---|---|---|---|---|---|---|---|---|---|
| | | | | MAESQRASQELGINVG QTQLQPGQSARRGVR DSEVNYSGPSVGSGIL DGILGAGQOIAGKWFE HNVQQEVLRGERARM AGEAEEAVDSNVLAKP FVKGGWRKQDYRIAQ ADFSLKMQRFIANKGR EMTPEEFRKYLSQEAT HVLDSTEGMNPNDAL QALAQQOKAEEQLFG MQAKAYMDWSIDQAA RGFRTQGNSILAKAVQ AQATGDELSRQLSLEE AGLFYTNIMTSEDIPLE VRDKVGMQFLAASLD MNQRGIYEGLRDAGFL DSMSFDDRRALNGLYE KSKAQTRAKESMATLR ADADFCQRVANGAITD LAEVEAYSRGMVEEG RWSDAQAISFMTKAMT GLGNAQRMQGIMAAL EAGDINALHTLGTNVTE ALEQWDKMQAANGSS LTDRLVQGTQLGLRLG TFPKTYGESVGSAVRM IQAAKEGEANPELVNTL NSIFEQVASAQEINPSA GNVMLSGIPEAECGAV AWALKQMKMGIAPAQ ALREFSANAEVVKQMD EFEKGGNTKAFKDNLG KQVNDKFVNNIFGRAW NMLTGESDLSNNEAVL SMYRRATIDEANWLAS DRKHAGLLTSDTGREA LLEIAAANVRNRTIQVG EGRNLKEGDLFSRRDS APLILPRGTTAEQLFGT NDTETIGTVLAEQHKP HVEGLLGYKSVVAFEY DRTRGSLLAVEYDENG VALDRTRVDPQAVGNE VLKRNADKLNAMRGAE YGANVKVSGTDIRMNG GNSAGMLKQDVFNWR | | | | | | | |

Fig. 8N

| 42 | 32765 | 36778 | 548 | KELAQFEAYRGEAYKD ADGYSVGLGHYLGSG NAGAGTTVTPEQAAQ WFAEDTDRALDQGVR LADELGVTNNASILGLA GMAFQMGEGRARQFR NTFQAIKDRNKEAFEA GVRNSKWYTQTPNRA EAFIKRMAPHFDTPSQI GVDWYSAATAE | | | | | |
|---|---|---|---|---|---|---|---|---|
| | | | | MAKQFKGRMTPKYPL DQVQLDEAQVQGQLD AVPTVGFDALTGGEIG ERNVAACQRANAREL ERIVADQELPALDRAS ALWNQSTLVGRMVDA LQLDADLAANSTGEVD PNFDAGTYGVQALQAA GIQPTDNYLQIMARAG NAEDAAYLLSRIQRYE QDEQIVRDNPYWNFAV GMLDPAALAVDAVTFG AGRALRLGRAGMAAA GGAGQVGYVAGLDAA GADVDAGTYIVAGALG AGVGALLGSGAGRIAA EAPTQPHVPEVSAPTV GLPEVAMTAEEAAARG FKAGDVVDLLDEGTVL SRVSARVEQAEIPAIPR RDTAFGDELHSLSGRK LSEVLDHIKTHAEVPKP LQGIAAKVADTIRTLEG LGQRTAFRVVQGGDT ASSAFLKPGTAGIHST QGLDTLVQVRGSTAPG RVGTNPVTVLHEAVHA ATVGVMNAALRNPGA MSPKVAQAMQTLENV RGNVLNALKQDRAAG RQLSEFEETLLAGNSN TLANVKELVAWGLTDT RFQRTLNRLRYSDGGP GLWSRFVEGIRTLLGL RSDADTALSRVLAASE TIMEAMPGYTKAQAKW ANKGAPVTEEASLETTV RSTRERAREGAGFVN RFFSEADLLAQPGEGA RRLLSRLIDDPVRRDG | 1337 | Internal virion protein [Pseudomonas phage LUZ19] | YP_0016 71982.1 | 0,0 (1327/1337) | internal virion protein | Virion protein | PHA02006 | <1,0e-180 |

Fig. 80

| 43 | 36780 | 37535 | 549 | FSTNDNAASYLRRYRN EFEGYVKSYDEMMAK AMAEQGVGLTARALNS RRAMAVRDQLNECVT RELLRRDREWTAYGS VRVDPNLPPTKALADR SDEIHGLMGQRAREAG VRGFENFAPRPGYFHR SWNWSKMAQMDEAA PGLARRAISEAVFRGIP GLERADADTIAQAIVQR ARDRATGIRSEFMGAM GVADTAFIRQALEEAN VSQAKFDSIMAKIEQK QSDQGTVKYGKGRLS LDMTAEINHNGTVYRV QDLIDRDLDRLMENYA GSMSGRSALARAGMP GDSEIEAFIREYQREAA HLGTDKVQELTGQLRG VFGDFTGNVPREHQL GPVAQRASGLTSATML GFSGVYQLAELATMAH RQGVFNVMKAMLNSR LGDFVGAMRRDPDLA DEMQTVLGLNLANDIR M

| | | | | | | | |
|---|---|---|---|---|---|---|---|
| 44 | 37535 | 37975 | 550 | QGIPFLPRYIDANNKQL LYAVQEGINTANLALD GVLDAIRIAEEARRLAQ EALDAANEALRRALGF AEIRTVTEDSDIDPSWR GYWNRCITSEQSLTLT MQMEDPDEPWIEFSE VHFEQAGIRDLNIVAGP GVTINRLQNTTMQLYG ENGVCTLKRLGPNHWI IFGAMEDD | | | | |
| | | | | MRGIIAGVVASQIRRPK PVLTITYPQSSSDRG GMTFHAIAGIIQDTVKF ADSKDLGSYEMLVRDA TLKSMVITLTEVKDSSV WSMGVLSAAIKSVVQF LTPVEEKSSLDMSIIHG EHKQSVIPYSRWAEAG SLSMGITEGKVYVP | 146 | Hypothetical protein phiKMVp39 [Pseudomonas phage phiKMV] | NP_8774 78.1 | 3e-76 (142/146) | | No putative conserved domains have been detected |
| 45 | 37965 | 38843 | 551 | MYHSSTIRGEFDLEIVR PDGTVRQHLHFKNLIT DLALEAMSSKGVPSGG WTNMFAGTGNRTPVP ADVSLVAPVANASASL NYGNRAVWDSTTGEK VHTGTGTFRAGSFOG QSLAEVGIGRVVSELY SRSLIKDANGDPTTITV LVDEELRVTYTLRIAPP ASSEVKITMKGIEYTLS MRDRRTFRDLSPEPAA EFGTRGSLSWSAISAP DSNGQTKTANLSGDA GTGIIQVPAQSAQIMRI QPADANWTEGIQYLR WETPAGRELEIKLDPP LVKNSLERVDITVTHIF NRV | 292 | Putative tail fiber protein [Pseudomonas phage PT2] | YP_0021 17825.1 | 4e-164 (284/292) | tail fiber protein | |
| 46 | 38840 | 39430 | 552 | MIQFKFGDYRTRVPFQ GARDRRDINDRSDYVD GGVAIQDPSQGLLYQE WHAELLEDGIYLTPEK ERVTTRIGPGINEGVAS MAVTFDQNMNYVLVYT KQGEGFIDFFDSATEE RNVMNLGPVDYIKTDL DDRRPEGSAWAQVLV CYTRQGNFYVRASSTR | 196 | Hypothetical protein phiKMVp41 [Pseudomonas phage phiKMV] | NP_8774 80.1 | 1e-70 (129/130) | | No putative conserved domains have been detected |

Fig. 8Q

| | | | | | | | |
|---|---|---|---|---|---|---|---|
| 47 | 39430 | 39735 | 553 | FTEEELIVGTGKVTRPI VKCGWAANWRFQVLF RGRM | | | |
| | | | | MSKKQTASAERLGLLH ELVCTAIERNFKWYMD NDIPIPASDIAAATKFLK DNEITCDPSDTINIDRL REEMRQAQAENRRIAL EGFIAGETDDEMERLY TH | 101 | Terminase small subunit [Pseudomonas phage LUZ19] | YP_0016 71987.1 | 2e-53 (101/101) | terminas e small subunit | Hypothetica l protein | PHA02046 | 9e-36 |
| 48 | 39745 | 41550 | 554 | MTPQERFQIAHEVRDM YPRFRDFCLDAMLFLG FKMTWMQLDIADFMQ DSPNKAMVAAQRGEA KSTIACIYVWWCITQNP ATRAMLVSGSGDKAEE NGQLITKLIMHWDLLAY LRPEARMGDRTSATSF DVNWALKGVEKSASIN CIGITAALQGYRADILIP DDIETTKNGLTATERAK LTRQSQEFTSICTHGKI LYLGTPQSRESIYNGLP ARGFLMRIWPGRFPTL DEQERYGDWLAPSILA RIARLEEKGHNPRTGK GLDGTRGWAADPQRY NEEDLLDKELDQGPEG FQLQYMLDTSLADEQR MQLKLRDLLFIDATHES VPEQVAWAADERFKLK FDAHRFPVIKPELYLPA LMAGGWAPLQQMTMF VDPAGDGDELSYAV GGTLGPYIHVVSIGGW KGGFAEENLEKCIALAA RYGVKVIYVEKNLGAG AVGQLFRNHMRSIDPD TNKPRYEGIGVEDRQK SGQKERRIIDTLRPIMQ RHRLIFHVSAMDSDHV ACQQYPADKRNERSV FHQIHNITTDRGSLPKD DRIDALEGLVRELAPTL VKDDEAATRAREEAAK KEWLNNPMGYTKSVL RSLGMGRERRKGRPK GRRL | 601 | Putative DNA maturase B [Pseudomonas phage PT5] | YP_0021 17769.1 | 0,0 (597/601) | DNA maturase B | No putative conserved domains have been detected | | |
| 49 | 41547 | 41747 | 555 | MMLDTATEAGKGTLAV | 66 | Holin [Pseudomonas phage | YP_0016 | 2e-29 | holin | No putative conserved domains have | | |

Fig. 8R

| | | | | | | | | | been detected | |
|---|---|---|---|---|---|---|---|---|---|---|
| 50 | 41744 | 42226 | 556 | TGVGIAVVSPYEIASLC AAVLTALYVGAQLITIL PKMLDSIAELRRRFKK | | | | | | |
| 51 | 42184 | 42513 | 557 | VNKPLRGAALAAALAG LVALEGSETTAYRDIAG VPTICSGTTAGVKMGD KATPEQCYQMTLKDY QRFERIVLDAIKVPLNV NEQTALTFFCYNVGPV CTTSTAFKRFNQGRAT EGCQALAMWNKVTIN GQKVVSKGLVNRRNA EIKQCLEPSSQYSSLL W | 160 | Endolysin [Pseudomonas phage LUZ19] | YP_0016 71990.1 | (66/66) 2e-89 (159/160) | endolysin | Endolysin_ autolysin | cd00737 | 5e-34 |
| 52 | 42603 | 42917 | 558 | MPRTIVAILVLVVALG ASYGFVQSYRALGIAQ EEIKRQTARAEALEVR YATLQRHVKEVAARTN TQRQEVDRALDQNRP WADRPVPAAVVDSLC NRPGARCAVRTPTD | 109 | Rz protein [Pseudomonas phage LUZ19] | YP_0016 71991.1 | 2e-55 (108/109) | lambda Rz1-like protein | Phage lambda Rz1-like protein | PHA020 47 | 3e-32 |
| 53 | 42967 | 43212 | 559 | MANTREQYLAGRNTG LTFYQVCQPGTDNRIA LHDMDEADVKAKATAV IAAATALGGEGGATPP DPLTAYKVKNGDTLPV DGGGSVKVTVANGAIT KVVYTAPAG | 104 | Hypothetical protein PT2_gp53 [Pseudomonas phage PT2] | YP_0021 17832.1 | 2e-52 (104/104) | | No putative conserved domains have been detected | | |
| | | | | MATFAAATQKDLRAFA GAIENLIRPLEEAALGS GFTEVITITKGTDGNET RTSERKVRPELVANLD ALMAAVETAKAAVYK | 81 | Phage particle protein [Pseudomonas phage LUZ19] | YP_0016 71994.1 | 1e-36 (79/81) | phage particle protein | No putative conserved domains have been detected | | |

Fig. 8S

Table 9 - Features of phage F44/10 gene products and assignment of putative functions.

| orf | Start position | Stop position | SEQ ID NO.: | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 1a | 467 | 1 | 561 | MKKIYILEEEIEEMDYDLWEEDT VYTTSYEVLGYTDSLEDAEYIK NNYGTSNPIFINEYPYLTKDKLI EEQRYYRYNSAIELKRVDGYFE VYEINDLNVTECFSNKDDISFD CPFSIDMFSSDRNSIFIEFMMY SEYDNKKDTIEKEKNSFLMK | 155 | hypothetical protein KgORF8 [Staphylococcus phage K] | YP_024439.1 | 2e-62 (131/155) | | PHA02241, hypothetical protein | PHA022 41 | 8.06e-17 |
| 2 | 689 | 471 | 562 | MKKIINFLVDYNINFSYSEDSLN VMGNSYLVDKHGTQDYEIIGNY GHITGVFSYQTEEEVIAKLKNLI GVWE | 72 | ORF201 [Staphylococcus phage G1] | YP_241058.1 | 3e-31 (68/72) | | No putative conserved domains have been detected | | |
| 3 | 884 | 690 | 563 | MRDKRIHSELLYNIIGKHIQEEE NITPYIEAIYVDIMNIIVVEYTFYN ENGTRMLGQYPIGEVM | 64 | ORF218 [Staphylococcus phage G1] | YP_241059.1 | 7e-28 (62/64) | | No putative conserved domains have been detected | | |
| 4 | 1611 | 874 | 564 | MNLEKSFLLSTIEFGSTYQGTS DEYSDKDYMSLVVQPLSDTIFR NSEKASKHTEVSRYYAVERFIS LVLKSGFDNVLNLCAQLEQAKN TRFNKTVLDLFYDDFIFLTYVRA NFKPIAYSVIGNINNILKKEELAG KDLVKFYTFYNHLEYYNDLLDD LDNLNVSYKDFAKVKYMPKEVL DNKRSNVSIENKKDLVTKVEPLI QEVKDKLKSNESNIKHYKDAM ELVEKSLKDKTVSFLTEVYNER | 245 | hypothetical protein KgORF9 [Staphylococcus phage K] | YP_024440.1 | 1e-124 (238/245) | | No putative conserved domains have been detected | | |
| 5 | 1778 | 1674 | 565 | MKYILGLITLGVILFKIYEYFKYIQ DEVDTTEDI | 34 | ORF437 [Staphylococcus phage G1] | YP_241061.1 | 9e-08 (29/34) | | No putative conserved domains have been detected | | |
| 6 | 2027 | 1800 | 566 | MDFYQFLNHENVRVNSITPSQ KNFIRENIDYTNILDTVDIDFMNS KQAKKEIEKIIRTKNEEEYDMA MDALSGWEG | 75 | gp ORF020 [Staphylococcus phage A5W] | ACB89011.1 | 4e-29 (61/73) | | No putative conserved domains have been detected | | |
| 7 | 2415 | 2029 | 567 | MFGKAPEHIMEIIDKEDNILGED LTLNIDYKGINLTVKRHPHSGHL NGYINVPTNITKEQFNSIEDCSH GGITYDEHEGDYRVLGFDCAH YSDMTPYAVISFSDSYYRDLKY VLNTLKDMADCLKEGE | 128 | gp ORF021 [Staphylococcus phage A5W] | ACB89012.1 | 4e-39 (79/130) | | No putative conserved domains have been detected | | |
| 8 | 2685 | 2512 | 568 | MEKVNHEFLAELAKSNSPVLNS | 57 | ORF245 | YP_241064.1 | 3e-26 | | No putative conserved domains | | |

Fig. 10A

| | | | | | | | | have been detected | | |
|---|---|---|---|---|---|---|---|---|---|---|
| 9 | 3208 | 2726 | 569 | KPLQDGDYNIEFDYDGHFEFS QKNGYWQWKYNAK | | [Staphylococcus phage G1] | | | | |
| | | | | MANEKELIRMVNYLIDNMSMW HINYARAVLIPSEVEKIIKEHEKF DDLLKKRGEWLVKGSDTDNID DLETYNQIMNNQKDEMMIQEID IYTQGKTIKVDNKHYSSNELNE VINKEQSEDIKIKSNYKLLCIDY TKVIGYEVTYASSYEEKFKNDL EKDL | 160 | hypothetical protein KgORF11 [Staphylococcus phage K] | YP_024442.1 | 5e-78 (144/160) | | PHA0224, hypothetical protein | PHA022 43 | 5.15e-24 |
| 10 | 3800 | 3258 | 570 | MDRIIGKHNLTQDLRLGDKVEV YDAHKFKENEDGTIELGDKVTE GIVVDYKGDFTGNTSGLVTLDS SEEELIIGEHNFKLIEEGNLQAV YDSVSKNKVESLSEDYDMYRK LLGVKSGELEDISYELERLIMEY NKKVDNYNGLLTLSKEKARELS LLTGDRKMIPHMKNKRLELGTE ADF | 180 | hypothetical protein KgORF12 [Staphylococcus phage K] | YP_024443.1 | 1e-188 (166/180) | | No putative conserved domains have been detected | | |
| 11 | 4333 | 3800 | 571 | MVYDSIISRTMAVSILNKWIAELI TDVDLDKCKFTEEEYGKVVTN SINKQDVLIEKNYEVTDGELYDI VCTELINPIKNNTEEEKHNEKN DLLEHLEDLAFRHDIDLGYVSD GSYNLTVTHWLMQDEFTDVNI KVNKDEDFYTITPESKYFWLPI TKENLEMFLTQDPINKGEIE | 177 | hypothetical protein KgORF13 [Staphylococcus phage K] | YP_024444.1 | 1e-95 (173/177) | | No putative conserved domains have been detected | | |
| 12 | 4500 | 4336 | 572 | MKNLIKFLSMVVVTILTFSLTYVI LKKETNNKRNGVAPFDFSLED HIHLNKEIK | 54 | hypothetical membrane protein MbpP [Staphylococcus phage A5W] | ACB89017.1 | 5e-20 (50/54) | Membrane protein MbpP | | | |
| 13 | 4781 | 4503 | 573 | MVNNIWAVVLSIIILLIILLWFLF RKKYNGGSSKNVEIQKAEEGN DNKEQEVEEAQYRELNEEKE KNENSSKDYKYDKEKVKNKLK ELE | 92 | hypothetical membrane protein MbpR [Staphylococcus phage A5W] | ACB89018.1 | 5e-24 (89/92) | Membrane protein MbpR | | | |
| 14 | 5626 | 4781 | 574 | MGRRLIDNSELNVIKYDGLPDF FSALKKNRVSGRENSSDTGSY DFTGTHSFQEAYNLMVKGDRE SYDMVVKLKKMTDALFRMDKS VKRKPVVAPEGYQPHVPNAIK GLPNSMMSQQRYKAEKKVIDV FYNSSISWMEDPENLAYRGAIM LSAIQTLETKGYSINLYLGKLSN SEYENKLTGFVVNIKHSYQRLN VFKSSFYLVNPSFLRRISFRVLE | 281 | hypothetical protein KgORF14 [Staphylococcus phage K] | YP_024445.1 | 5e-160 (277/281) | | No putative conserved domains have been detected | | |

Fig. 10B

| | | | | | | | | | |
|---|---|---|---|---|---|---|---|---|---|
| 15 | 6756 | 5638 | 575 | VEPDMVDLTNHGYGSVVSKSS YGNKLTEHILDNAVIFDSSIGIDI NNDSSENLRAVKKLFGGRL MAKQDTIERLERLVEQQMETT ADLAKKLGEKNSNPYEQAIVDA IVEKAGTESREIIITDVKKQIEEY VEEQLSNLPVKIELQQEGKTIK DISGIFHYRYQDILKLVNQNIPV FLKCGAGSCKNHVLEQVAEAL DLDPFYFSNAITQEFKLTGFIDAN GKFHETQFYKAFTKGGLFFLDE MDASIPEVLLLNSAIANKYFDF PIGRVTAHEDFRVVSAGNTMG TGADHIYVGRQQLDGATLDRF AQVEFDYDTKVEHQLSSNEDL VNFVQQLRHENDEKGLPVVFS MRAIINGSKLDGVMEDEFVVES IIFKSVPKDEINQFISSLPEGNRY TEATRKLLGMQQEPKQEPRKS NSTSKDSMDFDTIMDKLGLE | 372 | ORF15 [Staphylococcus phage K] | YP_024446.1 | 2e-109 (193/194) | ATPase | ATPase-like protein | PHA022 44 | 2.63e-175 |
| 16 | 7233 | 6907 | 576 | VSKRTDNFIYFCKYYFSEYLPS LGVEVLNHNETSHGTMEGVRK YYIANILYEGQELTVTIDLEEFN NATSMHNMLEIMNSHTYNCMF MYDMDTHGTKDIDDFFKLMYF | 108 | ORF134 [Staphylococcus phage G1] | YP_241072.1 | 3e-55 (105/108) | | No putative conserved domains have been detected |
| 17 | 7642 | 7226 | 577 | MNAKEFMKTQAQVEDYLDKLK VTIIEDALSVSKEWSNDSNDLG YALSSLGESIGILLEDYYNIQVDA HLPEHYKGSKDVISFLEEHFSY DGFVDSMIFNIVKYTTRLGRKD AVDKEVQKIKTYYVRLERNIKY GDSTRV | 138 | hypothetical protein KgORF16 [Staphylococcus phage K] | YP_024447.1 | 2e-74 (138/138) | | No putative conserved domains have been detected |
| 18 | 8077 | 7775 | 578 | MEKVELIKQWAKDRNLQTGKP EGQMLKLLEEAGELASGIAKSN DHVTRDSVGDIFVVLTVLCLQL DIDIIEECIDMAYDEIKERKGKLIN GVFVKEEDLKK | 100 | hypothetical protein KgORF17 [Staphylococcus phage K] | YP_024448.1 | 2e-49 (99/100) | Pyrophosph o-hydrolase | MazG | pfam03 819 | 4.19e-03 |
| 19 | 8265 | 8077 | 579 | MEKFQEDYVNIDIRVKAYVRVG YRYEEDITNNLHELVEDNLNVT SDSDNLIIKDTEIKGDIE | 62 | ORF228 [Staphylococcus phage G1] | YP_241075.1 | 2e-26 (62/62) | | No putative conserved domains have been detected |
| 20 | 8470 | 8309 | 580 | MVKPVITLEPEDVKVLLDYLSFL EDDMRNYEGMRELYEELHKKY QLAKGNYSD | 53 | ORF259 [Staphylococcus phage G1] | YP_241076.1 | 3e-22 (53/53) | | No putative conserved domains have been detected |
| 21 | 10518 | 8470 | 581 | MAITYKQKGLTEQEIINLPKVNK GCIYIGEEDVFLKKKKNNIINLG | 682 | hypothetical protein KgORF18 | YP_024449.1 | 0.0 (639/682) | | No putative conserved domains have been detected |

Fig. 10C

| | | | | | | | | |
|---|---|---|---|---|---|---|---|---|
| | 10596 | | SKELFRDIHNIFSFDTATEIHLFL ALCGNKEVTNFEGDPYETVEK LVEGVIGNNKGRNYKEYIEADR GERKDFPLYGSRRRKQIQSKG YVEEKIKELENENRLWGYEAR QLDEYKEAVDSLNNDIMDVLD QGKYVLINSSIIVMNEDIEKGSS EYYKEMSDSLYSRVWYMHPST ENNSSFGLKVRHIRDKHNMGN KWVLENKSSFDVKTGAVKVFL TDSLVNKEIALNLYKDDISKSEY KNELTLSVLLNVILKNYSQPNLN RGIIIKIIEQTLEHHNFDFSSWCP DNIDVYGHINYRGDKYRIFGEN STSNYLITLTDIVKNIDKINNLEE FGLFERNALLFHIPKNPKWKVH EAFNLTKQTYKKLLTLNKFEQG NYLRFANTLYKNYNHLHNEVNL HQLFDDTFLMVRDSRDVTNAL KVKPIVNEILSISFANYKKMTHY LDVDAQDRQRITGYALDNYYLD YLHDLSILIREGYRTLESVNLTP FSLKLEHDIVTDEKGSIQQQLD DAELKAKYDNKLEKIIDKTYKLK DGRKVKFLPADTVSKLKDEGK MLSHCVGGYANRILKNSCLILL ARLEEDLDNSWFTVEIRITDNG YVLGQQQSIDAYKLPNELKEAL EKDIKKINKEEFKEVA | [Staphylococcus phage K] | | | | |
| 22 | 10859 | 582 | MSIEKKEEIIAHNEVVFRSLTQG LYVKEVDIYSDVVSYTKDVDEA LAMPNTINFKNSRKYEKLIRNLD LEPLNKIQKVIYETHLEEL | gp ORF038 [Staphylococcus phage A5W] | ACB89029.1 | 8e-41 (85/87) | | No putative conserved domains have been detected |
| 23 | 10876 | 583 | LNDLIKEGNKYYHKVRAGETLW TISKNYDVEIKKLQELNNIKSVS LTNLEYLVCVE | gp ORF039 [Staphylococcus phage A5W] | ACB89030.1 | 9e-24 (56/57) | Peptidoglyc an binding protein | LysM | pfam01 476 | 5.26e-06 |
| 24 | 11056 | 584 | MDNLSHYLSILYAILVTVGYIPG LIALVKSDSVKGVSSYFWVLIVA TVGISFYNILLTDATMFQVVSV GLNLTGLVCLLVASYRKKDYF SIPFIIVFSLLLFLLSDFTALTQTV ATITILAVYTQITTFYKTKSAEG TNRFLFLIIGLGLASLIVSMVLTH TYVHIIATEFVNFVLILICYLQAN YYSRR | gp ORF040 [Staphylococcus phage A5W] | ACB89031.1 | 13-93 (183/192) | | PHA02246, hypothetical protein | PHA022 46 | 6.35e-42 |
| 25 | 12250 | 585 | MVNKIKDKVIYMGGHILNEAMV DYRDKQHKEVDGIVGVTPYSP | hypothetical protein KgORF20 | YP_024451.1 | 6e-92 | | No putative conserved domains | | |

Fig. 10D

| | | | | | | | | | have been detected | | |
|---|---|---|---|---|---|---|---|---|---|---|---|
| 26 | 13139 | 13139 | 586 | HKDKSINDKANAEQTKLAERILT NDFKAMQESDIFVFDVLNEGLG TIAELGILLGMKHQAQETIKQLK EQSELFKFNEIDELSETYDILQG QIGEQEYILKKPVLIYCSDIRQG HGKPYNDPDRAEFSTNQFVYG MVLELTNGEGFHSWEEVTNRLE KLGEQDG | | [Staphylococcus phage K] | (172/209) | | | | |
| | | 12243 | 586 | MKSYTKVKNKGIVLDKFKERGL VVQEKLDGSNASFTVENGELV CFSRRKLNENETLNGFYDWV HENINVRNTYVSALEKYIIFGEW LVKHKIQYKEEFYNNFYVFDVY DKENEVYLSIEDMNVIAHHLGL KTVKTLLVAKPSHYLNDLKPEEI QELVGKSDMTVKPDKGEGIVIK YLDGKSEYDDYFKLVSNEFKEF SRQKMKTEVKKNESVADYAITR ARMEKMIFRAIEEDRLSEDDLE LENFGLIMKQVGGNFVDDIMEE EKENILKIVDKQIKKKMPHILREI LEEKGDTIDG | 298 | putative DNA ligase [Staphylococcus phage K] | YP_024452.1 | 5e-169 (296/298) | DNA ligase | ATP-dependent DNA ligase | COG14 23 | 9.05e-03 |
| 27 | 13363 | 13139 | 587 | MNYLAKVFINNNWLVKLITVLL TLFLSGLVVVISAISLFLSTVLNL PGLVLAFLASVSLILFSIVHNS KEDN | 74 | | | | | No significant similarity found. | No putative conserved domains have been detected | |
| 28 | 14172 | 13432 | 588 | MAIQLKELDFKLKDYPNVRYNM GEHLIFNEFLEKATTEQLDFCE DFFNDNVEILWNESQAGTGKT MCSVACAYADYLNKNRKLVFII SPVSEDLGSRPGNQTEKEMAY FMGLHDALIELNMINPEQGITEM LMMEDNVKEDKLGDCWVSQIS HLFLRGGNLRDATIIIINEAQNFK RSELKKVLTRVHTKNSTVIVEG NFKQIDLKNESKSGFGDYMEY FKNYEGAVFHNFTVNFRSKLA QYADNFKW | 246 | putative PhoH-related protein [Staphylococcus phage K] | YP_024453.1 | 8e-144 (245/246) | ATPase | PhoH-like protein | pfam02 562 | 1.46e-21 |
| 29 | 14838 | 14224 | 589 | MKKINSVIKGEGKKVQTADVRK ISYVKDYNPCMTVDDANDYN ATSQYLVSDNGKFIAKYNKDM NAVGFYEESGDTVKHLTHTTP ERLEGTVFTIEEETEIDLINDTLP QGDILIKFSDGSIYLPDNESVLD SVNYLADNDWDSVDIIIYTGLS KGNSENCIVDFNYNNYDIGYDD VEDEDVCDNYPECECSNYCSS | 204 | hypothetical protein KgORF23 [Staphylococcus phage K] | YP_024454.1 | 3e-113 (204/204) | | PHA02248, hypothetical protein | PHA022 48 | 9.28e-98 |

Fig. 10E

| | | | TGEVIGN | | | | | | |
|---|---|---|---|---|---|---|---|---|---|
| 30 | 15279 | 14854 | 590 | MQDSVNIYTDGSSSYNKGKVG SGAVLVSKEGNIISEISKSVDKP GLIKYNNVAGEILACCYGIEEAI KLGYNQAIVYIDYIGLIHWYEGT WSARNILSKTYINMIREYQKVID INFVKYKSHSNDKWNDYADNL AKKSIDI | putative ribonuclease [Staphylococcus phage K] | YP_024455.1 | 5e-74 (141/141) | Ribonuclease | RnaseH | cd06222 | 4.11e-18 |
| 31 | 15460 | 15269 | 591 | MKKGVFTVIADGFKFNVIAKDK KEVQEHCFKCFDFNYISVSFCR EVYSDCEFPQFMEDYKYAG | ORF222 [Staphylococcus phage G1] | YP_241086.1 | 1e-28 (63/63) | | No putative conserved domains have been detected | | |
| 32 | 16124 | 15483 | 592 | MENNNLVNFLMTTDDIDDTIEM VDSFELQDINKVLGEDTFLTIME ITDSLPDNQYKIVLLSSLDKLLN TDRKELVEYDEEFPTIRKHNVS ELKRDTVNSVIDSYMNTNIEILY TEYPTISNYSVVDSVKVLNTL YLIESKNGKIEATLSEDGEDLHE YISEEGYSVTDILNKFDDVEDLF DEDDSLINFFSDIDEGKNKTIKS FIELVINLK | hypothetical protein KgORF25 [Staphylococcus phage K] | YP_024456.1 | 7e-113 (212/213) | | No putative conserved domains have been detected | | |
| 33 | 16344 | 16114 | 593 | MDEKKESKPLNLQKIRVEKGHT LRSLASEIGVHYSLISYWEYGK KKPRSANLMRLEKALNTPGKEL FKELEEDDGE | ORF187 [Staphylococcus phage G1] | YP_241088.1 | 5e-36 (76/76) | DNA binding protein | HTH_XRE helix-turn-helix XRE-family like proteins | smart00530 | 4.91e-08 |
| 34 | 16574 | 16347 | 594 | MNKFKRWFRINVLKKETLLFKV YWRYESPSLKKPHVFHIELYAK SKAEARNKSQEYILKNAKESED FKFLKVEEK | ORF190 [Staphylococcus phage G1] | YP_241089.1 | 6e-34 (74/75) | | No putative conserved domains have been detected | | |
| 35 | 17375 | 16683 | 595 | MKKTIFATLALGTAITFGGIATN EASADEIDYNKLAEGAKSNSAE VNTKPIQEGNYDFSFSDGEFTY HFYNYNGNFGYEYHSGSTQVD NTVSRLAGEEQTPEQKVDQQQ AQFDTQNKQDTKKEVQTTSAP VQKETKQPTQSTSSTGGSVAE QIRQAGGDEAMIEIAMRESTMN PNAVNASSGAQGLFQGLGKS WSGGSIAEQTKGAKQYMDRY GSTSGALAYHNAHNSY | hypothetical protein KgORF26 [Staphylococcus phage K] | YP_024457.1 | 1e-130 (229/230) | | LT_GEWL - lytic transglycosylase and goose egg white lysozyme domain | cd00254 | 4.34e-03 |

Fig. 10F

| | | | | | | | | |
|---|---|---|---|---|---|---|---|---|
| 36 | 18367 | 17573 | 596 | MRKSVVISGVLGFLAIIGFIILLM CITKIPQGHVGVVYSVNGVKED TKSPGWHLTAPFDKVNKYPTK TQTHKYKDLNVATSDGKNLQM DIDVSYKVDATKAVDLFNRFGS ADIEELEKGYLRSRVQDNVRQ AVSKYSVIDAFGVKTGEIKKDTL DSLNDNLEKQGFVIEDIALSSPK ADKNTQKANDSRVKANQELERT KVDKQIAEQNAKKKEVEANGD KRANEIRESSLSDKILRQQLIEK WDGKQPIQIQGDGTIVDVTGK | hypothetical protein KgORF28 [Staphylococcus phage K] | YP_024459.1 | 2e-133 (229/261) | | Band_7 domain of flotillin (reggie)-like proteins | pfam01145 | 5.79e-24 |
| | | | | | | | HflC, membrane protease subunits | COG0330 | 1.86e-13 |
| 37 | 18675 | 18367 | 597 | MALLLTYFAIFIVFLVLVGFGISY LFDFLSMKEKKSNIRKQYRELV RQGTLDEYGLEQYVKYKKQFL NDRRQSIVTRADKQEIDQEEKA LNSLIKEIEKGEM | hypothetical protein KgORF29 [Staphylococcus phage K] | YP_024460.1 | 1e-50 (102/102) | | No putative conserved domains have been detected | | |
| 38 | 20276 | 18789 | 598 | MAKTQAEINKRLDAYAKGTVDS PYRVKKATSYDPSFGVMEAGAI DADGYYHAQCQDLLTDYVLWL TDNKVRTWGNAKDQIKQSYGT GFKIHENKPSTVPKKGWIAVFT SGSYEQWGHGIVYDGGNTST FTILEQNWNGYANKKPTKRVD NYYGLTHFIEIPVKAGTTVKKET AKKSASKTPAPKKKATLKVSKN HINYTMDKRGKKPEGMVIHND AGRSSGQQYENSLANAGYARY ANGIAHYYGSEGYWEANDAK NQIAWHTGDGTGANSGNFRFA GIEVCQSMSASDAQFLKNEQA VFQFTAEKFKEWGLTPNRKTV RLHMEFVPTACPHRSMVLHTG FNPVTQGRPSQAIMNKLKDYFI KQIKNYMSNGTSSSTVVKDGK TSSASTPATRPVTGSWKKNQF GTWYKPESATFVNGNQPIVTRI GSPFLNAPVGGNLPAGATIVYD EVCIQAGHIMIGYNAYNGNRVY CPVRTCQGVPPNGIPGVAWGV FK | putative lysin [Staphylococcus phage K] | YP_024461.1 | 0.0 (491/495) | Endolysin | CHAP | pfam05257 | 1.22e-15 |
| | | | | | | | SH3_5, bacterial SH3 domain | pfam08460 | 2.54e-14 |
| | | | | | | | N-acetylmuramoyl-L-alanine amidase | COG5632 | 7.60e-05 |
| 39 | 20779 | 20276 | 599 | MANETKQPKVVGGINLSTRTKS KTFWVAIISAVALFANQITGAFG LDYSAQIEQGVNIVGSILTLLAG LGIIVDNNTKGLRDSDIVQTDYV KPRDSKDPNEFVQWQTNANN ASTFEIDSYENNAEPDTDDSDE | putative holin [Staphylococcus phage K] | YP_024463.1 | 6e-89 (162/167) | Holin | Phage_holin_1 | pfam04531 | 3.49e-25 |

Fig. 10G

| | | | | | | | | |
|---|---|---|---|---|---|---|---|---|
| 40 | 21049 | 20864 | 600 | MASAKQLYYTESLVGKAIINNK VSNKEEVWDKLELLPETKLEDL DNKQMSEVIKKLNQINE | 61 | ORF233 [Staphylococcus phage G1] | YP_241098.1 | 9e-26 (61/61) | | No putative conserved domains have been detected |
| 41 | 21282 | 21211 | 601 | ACACCCUUAGUAUAAUUAGU AGUACAAGGGUCUCCAAAAC CCUUAGUCUUUGUGCAAAUC AAAGAGGUGUG | | | | | tRNA4-Trp | |
| 42 | 21361 | 21289 | 602 | GGUUCUUAGCUCAGAUGGU AGAGCACUAGAUUGAAGCUC UAGGUGUCAUUGGUUCAAAU CCAAUAGAAACCA | | | | | tRNA3-Phe | |
| 43 | 21441 | 21368 | 603 | GGCCAUUGGUGUAACGGGU UAACACUGCCCGUCACG GCAGAGAGUACGAGUUCGAG UCUCGUAUGGGUCG | | | | | tRNA2-ASP | |
| 44 | 22812 | 22594 | 604 | MKRQKMFYSSLICKECGNVFK VPRKRANKREEG-HIKDIYCIKC CKTTKHIEDNRSEAERRWDAIQ EELTKDN | 72 | ORF200 [Staphylococcus phage G1] | YP_241099.1 | 8e-35 (72/72) | | No putative conserved domains have been detected |
| 45 | 23499 | 23290 | 605 | MSKHIETMSSGAKYFLVSTDE KSYNRQDIDYMLRGMDETSIKV YTESAITSPQVYINPNRIESFKIV F | 69 | ORF207 [Staphylococcus phage G1] | YP_241100.1 | 1e-32 (69/69) | | No putative conserved domains have been detected |
| 46 | 23844 | 23512 | 606 | LDKEINNLVSQVETIKSKIQEGN YIDRGTFKDLEVEVAELRKMIV SIDKDVAVNSEKQSAIYVQLER LDEKISELAGSTKTKDTKKKDT TEKVLLVLGAILSFVFNKFA | 110 | ORF209 [Staphylococcus phage G1] | YP_241101.1 | 3e-52 (107/110) | | PHA02414, hypothetical protein | PHA024 14 | 1.54e-30 |
| 47 | 23857 | 24183 | 607 | LTKYKDILKLEFKDALAHFKRDR RYFHVYRIDRVLINGSIIYFDYY YLPSDDPNIVIKELDLQSFGKLR FEIDTKTSYGKVVTDNYMEIIND FLENYDIH-SESETVRP | 108 | hypothetical membrane protein MbpC [Staphylococcus phage A5W] | ACB89047.1 | 4e-53 (105/108) | Membrane protein MbpC | No putative conserved domains have been detected |
| 48 | 24623 | 25009 | 608 | LNNNIAIFIFKTLVIIIFLLLLSVIN SLSLYSIRPSVVMTYFIFGGIVS NVALTVTDKFLLKKEDPLPEYV LKKVEINDKEIRIKKIIESNYGIT AEEIKVRAKAQRRIEEDSKKED YDENKERN | 128 | hypothetical membrane protein MbpD [Staphylococcus phage A5W] | ACB89048.1 | 4e-48 (125/128) | Membrane protein MbpD | No putative conserved domains have been detected |
| 49 | 24987 | 25265 | 609 | MKTKKEIKEQRKELKDGATSVS LVKKGDKRIASPSRICSLCGQQ LSGMNYTKGKALSKVNHFHLQ | 92 | ORF161 [Staphylococcus | YP_241104.1 | 5e-47(92/92) | | No putative conserved domains have been detected |

Fig. 10H

| | | | | | | | | | |
|---|---|---|---|---|---|---|---|---|---|
| 50 | 25262 | 25672 | 610 | YSKYIYFDICADINNCYKNLRKRGEMD<br>LSAENIRDIINKKKLEEEDTRKYIADGFMNGIGKLMYEFNKKVDNKEIEVKDPNDLYKLFVIFSQMQNMVNETSEGGAIPQLSRPQQELFDEITTEDSNGESTVDLQKISEMSAEDITAMISEKEKVMNEENSETF | | | | No putative conserved domains have been detected | |
| 51 | 25687 | 27504 | 611 | 136 | ORF-133 [Staphylococcus phage G1] | YP_241105.1 | 2e-71 (135/136) | | |
| | | | | MDGKELIKIAQETFQTEKITREQIDHIINMLNPSTYMLKYHTLRGHPITFSIPNRDRSKAQAHRPWQTRIVNDTHPNKAVIKSRQLGLSEMGVMEMVHFADMHSYANAKCLYTFPTNEQMKKFVQSRLNPVLEKEYFRDIVDWDKDSLGFKKIRNSSLFFRTSSKASTVEGVDIDYLSLDEYDRVNILAESSALESMSSSPFKIVRRRWSTPSVPGMGIHKLYQQSDQWYYGHRCQHCDYLNEMSYNDYNPDNLEESGNMLCVNPEGVDEQAKTVQNGSYQFVCQKCGKPLDRWYNGEWHCKYPERTKGNKGVRGYLITQMNAVWISADELKEKEMNTESKQAFYNYILGYPEEDVKLRVNEEDVYGNKSPIAETQLMKRDRYSHIAIGIDWGNTHWITVHGMLPNGKVDLIRLFSVKKMTRPDLVEADLEKIIWEISKYDPDIIIADNGDSGNNVLKLINHFGKDKVFGCTYKSSPKSTGQLRPEFNENNNRVTVDKLMQNKRYVQALKTKDISVYSTVDDDLKTFLKHWQNVVIMDEEDEKTGEMYQVIKRKGDDHYAQASVYAYIGLTRIKELLKEGNGTSFGSTFVSTDYNQEGNKQFYFDE | 605 | gp74 [Listeria phage A511] | YP_001468454.1 | 0.0 (308/503) | Terminase large subunit | Terminase_GpA | pfam05876 | 4.8e-22 |
| 52 | 27497 | 28318 | 612 | MNRGEIDLTDKLFYGTISNEEINKSVLNLLLGEELSLDYVSKNSDTLDYKYEHYYKSLGFDNFFDCFLYANREPEIVHKGGDKNLGGLNKVKRTVIRNGKEMEMTVYEDGNKENDSKEKQEGKEEVSRSAVGARAISNGEEGKYNPKKVANSLSNLSKKGVDVSHINTNSSLYKEFVDDNGDTLGITSFKRTENDIILESYASSHDSDGVGARAIMEL | 273 | hypothetical protein KgORF36 [Staphylococcus phage K] | YP_024466.1 | 3e-153 (273/273) | | No putative conserved domains have been detected | |

Fig. 101

| | | | | | | | | |
|---|---|---|---|---|---|---|---|---|
| 53 | 28296 | 28478 | 613 | LRLSIKENKNAVVYDIELPEAVE YLKTLGFKPNKDGYILRKKDVK QFLGDYSDFI | 60 | ORF235 [Staphylococcus phage G1] | YP_240894.1 | 3e-23 (59/60) | | No putative conserved domains have been detected | |
| 54 | 28475 | 28954 | 614 | VIIVILFSTIVIYSIVFILYIVLKTIYI KSNMSRIDNTTELLKILQEDIEG KIKKEGRNK | 159 | hypothetical protein KgORF37 [Staphylococcus phage K] | YP_024467.1 | 5e-86 (159/159) | | No putative conserved domains have been detected | |
| | | | | MTLEENKLTLEESITPLSKEEKE DSIKEFSSLLCEMVNRLYKSYN VFRQDPMDETQRLDGSLMVFQ SRLNDPLTGDLHDKMYKLAFS KRIDIFEANKQFRKDVEAGKAIE LGDVAIIDTALSNILSGNEFQGSI SFMLRKDFEEKERIRKEEEEKL NNL | | | | | | | |
| 55 | 28996 | 29322 | 615 | LKKKPQGNEVIITITVMIAVFVVI MTIFFNKYQDAKEDKDRYQRL VEIYKKADDNDGETKKKYVKRL NKAEEELKKVKKKQIIKIIIRSQV KKDKKKIKKLERKYMM | 108 | hypothetical protein KgORF38 [Staphylococcus phage K] | YP_024468.1 | 4e-26 (68/69) | | No putative conserved domains have been detected | |
| 56 | 30117 | 30221 | 616 | VDEEDKNEDTTDDKQPTEQPD DNNIDNEDKTEEE | 34 | hypothetical protein KgORF38 [Staphylococcus phage K] | YP_024468.1 | 2e-08 (34/34) | | No putative conserved domains have been detected | |
| 57 | 30306 | 30647 | 617 | MNIITSLSVVFTCLSLLTLMIFVH SKFSSKNVFVLYVIIYAIIGIGTYI VLTMFQTTSVLIKNDVIDSIENT EHYIGFNDPIIFTISFIGAILGGI WYKMMKIIKKSNFKDKK | 113 | hypothetical membrane protein MbpE [Staphylococcus phage A5W] | ACB89055.1 | 5e-56 (113/113) | Membrane protein MbpE | PHA02256, hypothetical protein | PHA022 56 | 6.49e-28 |
| 58 | 30665 | 31036 | 618 | LIFSKDKKWDEAKDFIKGQGM QDNWIEIVDYYRQIGGKHVAVF IALNKVKYMILEATKDNKVILVD KDNNILLEDYDIVMESKKMFYYI EEPFEVKINPQHIRDVTYNNTV VLTTVRGSRGD | 123 | hypothetical protein KgORF40 [Staphylococcus phage K] | YP_024470.1 | 2e-64 (122/123) | | No putative conserved domains have been detected | |
| 59 | 31040 | 32731 | 619 | LADLFKQFRLGKDYGNNSTIAQ VPIDEGLQANIKKIEQDNKEYQ DLTKSLYGQOQAYAEPFIEMM DTNPEFRDKRSYMKNEHNLHD VLKKFGNNPILNAIILTRSNQVA MYCQPARYSEKGLGFEVRLRD LDAEPGRKEKEEMKRIEDFIVN TGKDKDVDRDSFQTFCKKIVR DTYIYDQVNFEKVFNKNNKTKL EKFIAVDPSTIFYATDKKGKIIKG GKRFVQVVDKRVVASFTSREL | 563 | putative portal protein [Staphylococcus phage K] | YP_024471.1 | 0.0 (562/563) | Portal protein | Phage_port al | pfam04 860 | 1.13e-13 |

Fig. 10J

| | | | | | | | | |
|---|---|---|---|---|---|---|---|---|
| 60 | 32925 | 33698 | AMGIRNPRTELSSSGYGLSEVE IAMKEFIAYNNTESFNDRFFSH GGTTRGILQIRSDQQQSQHALE NFKREWKSSLSGINGSWQIPV VMADDIKFVNMTPTANDMQFE KWLNYLINIISALYGIDPAEIGFP NRGGATGSKGGSTLNEADPGK KQQQSQNKGLQPLLRFIEDLVN RHIISEYGDKYTFQFVGGDTKS ATDKLNLILKLETQIFKTVNEARE EQGKKPIEGGDIILDASFLQGTA QLQQDKQYNDGKQKERLQMM MSLLEGDNDDSEEGQSTDSSN DDKEIGTDAQIKGDDNVYRTQT SNKGQGRKGEKSSDFKH | | | | | |
| 60 | | | LEEIKFNAFVPMDLKKSVSTAS DTNEYSIVSGWASTPSMDLQN DIVNPKGIDIEYFKSGYINYEH QSDKVVGIPTENCYVDIEKGLFI EAKLWKNDENVVKMLD-AEKL EKSGSGRRLGFSIEGAVKKRNI NDNRVIDEVMITGVALVKNPAN PEATWESFMKSFLTGHGTSPD TQVDAGALRKEEIASSITNLAYV TKIKDLKEFNDVWNGVVEDLSK SNSMGYEEESVLTLQLAKGLSR KDAELAVMDINKQKLE | 257 | hypothetical protein KgORF42 [Staphylococcus phage K] | YP_024472.1 | 9e-147 (256/257) | Prohead protease | Peptidase_U35 | pfam04 586 | 8.72e-05 |
| 61 | 33717 | 34667 | MSKEMQNILEEYDKLNAQEAV SKSVEDDEKNTVESTEEQVAE TTEEPAKEPEKYSEEDAKEAQ EQGEKVESEEVAEGNEDEEVE KSAKESKDPVDQKDTKTENKD NEKRKNKKDKKEDSDDEDKDT DDDKDKKEDKKEKTSKSISDED ITTVFKSILTSFENLNKEKENFA TKEDLSEVSKSINELSAKISEIQ AEDVSKSVDTDEEAVEKSVTST NGEQEKVEGYVSKSVDTEEQA ETGEAKSEEAEEVQEDNTFKG LSQEERTKFMDSYKAQAKDPR ASKHDLQSAYQSYLNINTDPTN ASEKDIKTVKDFAQI | 316 | hypothetical protein KgORF43 [Staphylococcus phage K] | YP_024473.1 | 4e-170 (316/316) | | No putative conserved domains have been detected | | |
| 62 | 34783 | 36174 | MTIEKNLSDVQQKYADQFQED VVKSFQTGYGITPDTQIDAGAL RREILDDQITMLTWTNEDLIFYR DISRRPAQSTVVKYDQYLRHG NVGHSRFVKEIGVAPVSDPNIR | 463 | putative capsid protein [Staphylococcus phage K] | YP_024474.1 | 0,0 (463/463) | Capsid protein | No putative conserved domains have been detected | | |

Fig. 10K

|    |       |     | Sequence | SEQ ID NO | Name | Accession | E-value (identity) | Notes |
|----|-------|-----|----------|-----------|------|-----------|--------------------|-------|
|    |       |     | QKTVSMKYVSDTKNMSIASGL VNNIADPSQILTEDAIAVVAKTIE WASFYGDASLTSEVEGEGLEF DGLAKLIDKNNVINAKGNQLTE KHLNEAAVRIGKGFGTATDAY MPIGVHADFVNSILGRQMQLM QDNSGNVNTGYSVNGFYSSR GFIKLHGSTVMENELILDESLQP LPNAPQPAKVTATVETKQKGA FENEEDRAGLSYKVVVNSDDA QSAPSEEVTATVSNVDDGVKL SINVNAMYQQQPQFVSIYRQG KETGMYFLIKRVPVKDAQEDGT IVFVDKNETLPETADVFVGEMS PQVVHLFELLPMMKLPLAGINA SITFAVLWYGALALRAPKKWAR IKNVRYIAV | | | | |
| 63 | 36266 | 36562 | MLYYKKLLDKKMATVYGTVEID KDGVVKGLTKEQEKEFANVPG FEFEEEKKTTRKQSASTSKEEE PKEEEKKASTRKTTSTTRKSTA RKTTAKKDENK | 623 | ORF151 [Staphylococcus phage G1] | YP_240904.1 | 7e-46 (97/98) | No putative conserved domains have been detected |
| 64 | 36575 | 37483 | MVNSMFGGDLDPYEKSLNYEY PYHPSGNPKHIDVSEIDNLTLA DYGWSPDAVKAYMFGIVVQNP DTGQPMGDEFYNHILERAVGK AERALDISILPDTQHEMRDYHE TEFNSYMFVHAYRKPILQVENL QLQFNGRPIYKYPANWWKVEH LAGHVQLFPTALMQTGQSMSY DAVFNGYPQLAGVYPPSGATF APQMIRLEYVSGMLPRKKAGR NKPWEMPPELEQLVIKYALKEI YQVWGNLIIGAGIANKTLEVDGI TETIGTTQSAMYGGASAQILQI NEDIKELLDGLRAYFGYNMIGL | 624 | hypothetical protein KgORF45 [Staphylococcus phage K] | YP_024475.1 | 2e-177 (302/302) | No putative conserved domains have been detected |
| 65 | 37497 | 38375 | MEKPYMIGANSNPNVINKSTTY TTTQADEQDKPKYYTRLEFDT IDMIRFINDRGIKVLWEEAYFCP CLNPDTGHPRVDCPRCHGKGI AYLPPKETIMAIQSQEKGTNQL DIGILDTGTAIGTTQLEKRISYR DRFTVPEVLMPQQMIYFVNKD RIRKGIPLYYDVKEVTYIATQDG TVYEEDYEIKNNRLYLNEKYEN HTVTLKILMTLRYVVSDILKESR YQYTKFNQPKSKFENLPQKLLL | 625 | hypothetical protein KgORF46 [Staphylococcus phage K] | YP_024476.1 | 2e-170 (290/292) | No putative conserved domains have been detected |

Fig. 10L

| | | | | | | | | |
|---|---|---|---|---|---|---|---|---|
| 66 | 38375 | 38995 | 626 | KREDVIVLQDPYKVNDGIEEDL EIQVDDPKASASNPSNLGGFF GGAFK | | | | No putative conserved domains have been detected |
| 67 | 39014 | 39850 | 627 | MPVHGKRPNLFKNKNYKQVGK RTIDGMRSEVLDKLQATAQQV ENTSIKRMPTYLQITEKKLEKEG VVDLKKAFAHSSKKKTSKDGG WYLTVPIRKTSRMNNSTYQDM RTLKVDKGTGSVSKITDYLEGR RKNVSHPSMKPEPMTHNMTKV KRGKQSSYFIFRTVSSKSPASS WILNRDKVNEDNFSKTTLKTVK QLMNWKMKNLN | 206 | hypothetical protein KgORF47 [Staphylococcus phage K] | YP_024477.1 | 1e-116 (206/206) | | No putative conserved domains have been detected |
| 68 | 39852 | 40067 | 628 | MAITSVDSYLLSEIKPRLNTVLE NCYIIDEVLKDFDYQTRESFKE AFCGKNAQHEVTVGFNFPKFK NNYEAHYLIQLGQGQETKNSL GSIQSSYFEATGDTLVESSTAIR EDDKLVFTVSKPIGELIKVEDIE FAKYDNLQVEGNKVSFKYQTN EDYENYNANIIFTEKKNDSKGL VKGFTVEEQVTVVGLSFNVDV ARCLDAVLKMILISMRDSIEEQQ TFQLQNLSFGDIAPIIEDGDSMI FGRPTIIKYTSSLDLDYTITQDIN KLTFKERKDWK | 278 | hypothetical protein KgORF48 [Staphylococcus phage K] | YP_024478.1 | 3e-160 (278/278) | | No putative conserved domains have been detected |
| 69 | 40094 | 41857 | 629 | MARKKTPENNTPKFNGYVHIDT FLDTAKTLFNMKDSQVAGFKA YMEGSHYLFSEQEFLPSLEKYL GRKLDI | 71 | ORF202 [Staphylococcus phage G1] | YP_240909.1 | 2e-34 (70/71) | | |
| | | | | MAVEPFPRPITRPHASIEVDT SGIGGSAGSSEKVFCLIGQAEG GEPNTVYELRNYAQAKRLFRS GELLDAIELAWGSNPNYTAGKI LAMRIEDAKPASAEIGGLKVTS KIYGNVANNIQVGLEKNTLSDS LRLRVIFQDDRFNEVYDNIGNIF TIKYKGEEANATFSVEHDEETQ KASRLVLKVGDQEVKSVDLTG GAVYDYTNAIITDINQLPDFEAKL SPFGDKNLESSKLDKIENANIK DKAVYVKAVFGDLEKQTAYNGI VSFEQLNAEGEVPSNVEVEAG EESATVTATSPIKTIEPFELTKLT GGTNGEPPATWADKLDKFAHE GGYYIVPLSSKQSVHAEVASFV KERSDAGEPMRAIVGGGFNES | 587 | major tail sheath protein [Staphylococcus phage 812] | ABL87117.1 | 0.0 (583/587) | Major tail sheath protein | Phage_she ath_1 / pfam04 984 / 6.04e-09 |

Fig. 10M

| | | | | | | | |
|---|---|---|---|---|---|---|---|
| 70 | 41930 | | KEQLFGRQASLSNPRVSLVAN SGTFVMDDGRKNHVPAYMVA VALGGLASGLEIGESITFKPLRV SSLDQIYESIDLDELNENGIISIE FVRNRTNTFFRIVDDVTTFNDK SDPVKAEMAVGEANDFLVSEL KVQLEDQFIGTRTINTSASIIKDF IQSYLGRKKRDNEIQDFPAEDV QVIVEGNEARISMTVYPIRSFKK ISVSLVYKQQTLEA | | | | |
| | 42334 | 630 | MASEAKQTVHTGNTVLLMIKGK PVGRAQSASGQREYGTTGVYE IGSIMPQEHVYLRYEGTTIVERL RMKKENFADLGYASLGEEILKK DIDILVVDNLTKQVIISYHGCSA NNYNETWQTNEIVTEEIEFSYL | 134 | capsid protein [Staphylococcus phage 812] | ABL87118.1 | 3e-73 (134/134) | Capsid protein | No putative conserved domains have been detected |
| 71 | 42754 | 631 | MGKNQYTFNIKENKNKWYEW CKLQNVKPLVEYENACQIFYFE FLEGKFKGLIGKTYWASINRGS NMRMSCLTSESKDKYLKNLGK RKGIEVVEDYKGGRKLKHKFIV LEGKYQGCEGYITLNDLENLGR VDNRSLSEKGRKQYFDKQARL RDCIILEYPKDYRIKTKDKIVVKD KEGHVHNIVQDFFEKSSLLELS CASEGEKIVKEILTKNSIKFEKE KSFRNKEGKVQRFDFYINENN KEYAIEYNGAQHYIDSTGYLKD TLETTQKRDKLKKEYSKDKGIN LLIIPYTITDKKEMEKIILNFLNK | 309 | ORF018 [Staphylococcus phage Twort] | YP_238556.1 | 2e-19 (79/239) | | No putative conserved domains have been detected |
| 72 | 43741 | 632 | MNNRQAKLGYNQFHYYDFPT TKGKFKDIMKRKSRTELKKDLQ KERKYYLDK | 52 | ORF245 [Staphylococcus phage Twort] | YP_238558.1 | 3e-11 (37/52) | | No putative conserved domains have been detected |
| 73 | 43889 | 633 | LTNKRKTIGKMSNTRATWNINP VTKVKKDKTKYSRKNKHKGLD NYN | 46 | ORF293 [Staphylococcus phage G1] | YP_240912.1 | 1e-10 (44/46) | | No putative conserved domains have been detected |
| 74 | 44074 | 634 | MRIYISNDYNKELLDKCLSDINK DKSNINYSINYGEGNIKEADVEI IKLDKNLLETESRAFAYSKFVED CIFLFPYKIALLRGGKIELRFDW NEIL | 96 | No significant similarity found. | | | | No putative conserved domains have been detected |
| 75 | 44385 | 635 | MSTFWSERRTTNKDRQVKKHY TQMSMYERKKCVELLQETITEN RIINFTRHSAKKVKGKPTTNIPK LIGFIFKNKFAYENIIEYNNTDYN GNIERRIVVKHPKVITVEGKLSY | 152 | hypothetical protein KgORF51 [Staphylococcus phage K] | YP_024481.1 | 2e-83 (151/152) | | PHA02264, hypothetical protein | PHA022 64 | 2.05e-29 |

Fig. 10N

| | | | | | | | | | | |
|---|---|---|---|---|---|---|---|---|---|---|
| 76 | 44856 | 45050 | QFLTISLEDARVITVWYNSVDD THRTLDLNYYSKDLTIQ MGLTIVNGYFFLSSIIFIVVSILN GKGTVTRESLAMSQALVIITSIQ FLAFLIINGIYYSLKYM | 64 | ORF215 [Staphylococcus phage G1] | YP_240914.1 | 4e-19 (49/64) | | No putative conserved domains have been detected | | |
| 77 | 45066 | 45218 | MEIYIVIDLRGSTEEETSMDFKA FRKLQDAITYDGNGNRDLHIIP LELE | 50 | No significant similarity found. | | | | No putative conserved domains have been detected | | |
| 78 | 45286 | 45597 | MSQDKLRAIYTEMKVELHKFPK EVDVTSKSTAIAINQILDKFKTLT EQAGKITRKYLEGQEILTIDYEY YDSLQEYYIYLLRNSEKIEQSLQ EITKRTGEYVK | 103 | hypothetical protein KgORF52 [Staphylococcus phage K] | YP_024482.1 | 3e-51 (102/103) | | PHA02265, hypothetical protein | PHA022 65 | 2.51e-17 |
| 79 | 45730 | 46188 | MAEEIKEQDVQETTKEEKDV SKMTPEEIDKLKYQDKQEKEQ VINKVIKGVNDTWEKEYNFEEL DLRFKVKIKLPNAREQGNIFALR SAYLGGMDMYQTDQVIRAYQM LATLQEVGIEVPKFEFQDPDDIY NLYPLTVMYEDWLGFLNSFRY | 152 | hypothetical protein KgORF53 [Staphylococcus phage K] | YP_024483.1 | 2e-82 (152/152) | | No putative conserved domains have been detected | | |
| 80 | 46232 | 46768 | MESIVKQPLSRNLWAIMKEFNV LPTEQRFKDLDDYQIEFIIGNMN RDVYEHNKQLKQAQKGGKFDS QFEDDDSSWWNESHEDFDPV PDFLDADDLAQQMEAKLSDRD KEERAKRNDAELNDETEGLTT QHLAMMEYIRQKQELDDEVG NGKTSEDDATISQDSVNKALED LDDDWYM | 178 | hypothetical protein KgORF54 [Staphylococcus phage K] | YP_024484.1 | 8e-99 (178/178) | | No putative conserved domains have been detected | | |
| 81 | 46821 | 50879 | MMAMNDDYRLVLSGDSSDLEN SLKAIELYMDSLESKNIDAPLDN FLKKLKVIAKEVKNVQNAMDKQ DGKSVISSKOMDESIKSTQSAT KNINELKKALDDLQKENISKGIA PDPEVEKAYAKMGKVVDETQE KLEKMSSOKIGSDASIQNRIKE MKTLNQVTEEYNKISKDSSATK DYTKRLRANRNMTRGYMERSE GTGRLTYDQGARVRSELGKVS SYESQRKQNQRNLGQAREQY SNYRNQQQDLTKRRASGQINK AQYEQELASIKQEMKAREELIS NYEKLGAELDKTVQYYKGSVQ KDFQSRDVDQQRGTFGRMVQ ERLPSIGSHAMMGTTAMATGL YMKGASLSETNRPMVTSLGQN | 1352 | hypothetical protein KgORF55 [Staphylococcus phage K] | YP_024485.1 | 0,0 (1343/1351) | | Smc, chromosome segregation ATPases | COG11 96 | 8.71e-06 |

Fig. 100

| 82a | 50957 | 52159 | 642 | MKRLRRPKVRIEVTDDNTFTL SDNMDIDSVRNAYGDLSIDNKL GYNSTDMLKMATSYEASVGHK SDEDTMAGTKQLAIGGRSLGIK DQEAYCESMGQIMHTGGVNS DNMKEMQDAFLGGIKQSGMV GRQDEQLKALGSIAEQSGEGR TLTKDQMSNLTAMQSTFAESG SKGLQGEQGANAINSIDQGLKN GMNSSYARIAMGWGTQYQGL EGGYDLQKRMDEGISNPENLT DMADMATQMGGSEKEQKYLF NRSMKEIGANLTMEQSDEIFKD SKEGKLSKEELAKKAKKMEKE GKKEGEDNATDYKESKSGKND QNKSKTDDKAEDTYDMAQPLR DAHSALAGLPAPIYLAIGAIGAF TASLIASASQFGAGHLIGKGAK GLRNKFGRNKGGSSGGNPMA GGMPSGGGSPKGGGSPKGG GTRSTGGKILDSAKGLGGFLVG GAGWKGMFGGESKGKGFKQT SKEAWSGTRKVFNRDNGRKA MDKSKDIAKGTCSGLKDIYNDS IFGKERRQNLGEKAKGFGGKA KGLYGKFADKFGDGGKNGILS QSPKAGGSGIGKLGKLAGGLG KGAGVLGVATSALSLIPALASG DSKAIGGGIGSMGGGMAGASA GASIGALFGGVGAIPGALIGGAI GSFGGGAVGEKVGDMAKKAN TKEGWNLGWTNGDKDGKNKF QDSLLGKPISKAWSGITGLFDN DAEASEENSKDKKKGVKGVKG DTKKKEKMTAEQLREKNNQSE TKNLKIYSDLLDRAQKIESAKGI NIDGGTSDSGSDSGGSASDVG GEGAEKMYKFLKGKGLSDNQV GAVMGNLQCESNLDPNAKNPS SGAFGIAQWLGARKTGLDNFA KSKGKKSSDLDVQLDYLWKEM QSDYESKNLKNAGWSKGGSLE QNTKAFATGFERMGANEAMM GTRVNNAKEFKKKYGGSGGG GGGGAMSSTYQEAMSNPVLT GSNYRGSNDASNASTTNRITV NVNVQGGNNPEETGDIIGGRIR EVLDSNMDIFANEHKRSY | 400 | hypothetical protein | YP_024486.1 | 0,0 | Tail lysin | No putative conserved domains |
|---|---|---|---|---|---|---|---|---|---|

Fig. 10P

| | | | | | | | |
|---|---|---|---|---|---|---|---|
| | 52258 | 52368 | 643 | RFEDTRDYNGDEFGAKLLGFQ TKNSMEDDSSVFQINMAGDTY WDKLVMANDIRIFITPNDDPND KEGRQERLIQVGMVSQVSKVG SYGNDCTQFRITGQSFVKPFM KFGLGVIQEVGAVLPEVGWLID GDGDNEVKFTGSSAHEVMTGII RRFVPYMKYNYTEKTYNTIDSY LDYDDLSSWDEFENLTEVSAFT NFDGSLKQLMDMVTARPFNEL FFKNSEKTPGKAQLVLRKTPFN PTEWRALDMIKVPTEDFIEEDV GKSDVETYSIFTATPAGMLKEL NGDVFSKPQFHPELTDRYGYT KFEVENIYLSTKSGSATEDSDS SGDDNGTERGTYSKIMKDLSN YGRDNISKGIDKYTSKLSSKYK NLKKPKLKKL | KgORF56 [Staphylococcus phage K] | | (390/400) | have been detected |
| 82b | | 52368 | 643 | LTKDKLKSILKEKFKTQDDFNN SKKRKKLKQMHLKN | | | 7e-04 (23/23) | No putative conserved domains have been detected |
| 82c | 52365 | 53381 | 644 | LTTKYRFGNKTHATTLLDEYIKY KGEPPNDEAFDKYLKAIEGVSN IATDTGSDASDSPLVMFSRMLF NWYHGNPNFYAGDIIVLGDPKY DLGKRLFIEDKQRGDTWEFYIE SVEHKFDYKQGYYTTVGVTRG LKDAILEDGKGSPHRFAGLWN QSSDFMGGLMGEDTSKELKEK GVSEKQSSGDKDGGSDSGGA QDGGSLDSLKKYNGKLPKHDP SFVQPGNRHYKYQCTWYAYN RRGQLGIPVPLWGDAADWIGG AKGAGYGVGRTPKQGACVIW QRGVQGGSAQYGHVAFVEKV LDGGKKIFISEHNWATPNGYGT RTIDMSSAIGKNAGFIYDKK | | | 0.0 (334/338) | CHAP | pfam05 257 | 2.48e- 13 |
| 83 | 53395 | 54282 | 645 | MATDKEAKQVIDKFIDNVFNFD VLTMERVKEKDEEIKKITTDDM YEKVVYIRPYYGVIQSLNPQHV QYESFSNNGYDIEAELSFRKVS YLVDKGSIPTDSLSTLTVHLVER NQELLIDYFDEIQDVLYGEYME EEYVFDEDVPLSTILADLNDNL KSLSNIKYMFKGAPKENPFGTD KDVYIDTYNLLYWLYLGEDEEL AYPMNINYFFTEGRFFTFGKG HKYKVDVSKFIVGDILFFGRSD | hypothetical protein KgORF57 [Staphylococcus phage K] | YP_024487.1 | 9e-166 (292/295) | No putative conserved domains have been detected |

Fig. 10Q

| | | | | | | | | |
|---|---|---|---|---|---|---|---|---|
| 84 | 54282 | 56828 | 646 | TNIGIYVGDGEFISMIGKFPKDE TPIGKYKLDDYWNEFNGRVMR FDEEVYI MVVRFQSSMGRSLKRVDSDDL NVKGLVLATVSKINYKYQSVEV KVNNLTLGSRIGDDGSLAVPYP KSFIGRTPEGSVFGTKPLITEGS VVLIGFLNDDINSPIILSVYGDNE QNKMINTNPLDGGKFDTDSVY KYSSALYEILPSLNYKYDDGEG TSIKTYNGKSFFSMTSGEEEKP QATDFYTGTEYQDLFTSYYGN KTLIEPRIQKAPNMLFKHQGVF YDDGTPDNHITTLFISERGDIRA SVLNTETQKRTTQEMSSDGSY RVIKQDDDLMLDEAQVWIEYGI SEDNKFYIKNDKHKFEFTDEGI YIDDKPMLENLDESIAEAMKNL NEIQKELDDINYLLEGVGKDNL EELIESTKESIEASKKATSDVNR LTTQIAEVSGRTEGIITQFQKFR DETFKDFYEDASTVINEVNQNF PTMKTDVNTLKTKVDNLEKTEI PNIKTRLTELENNNNNADKIISD RGEHIGAMIQLEENVTVPTRNY MPIPWSKVTYNNAEFWDSNNP TRLVVPKGITKVRVAGNVLWDS NATGQRMLRILKNGTYSLGLPY TRDVAISTAPQNGTSGVIPVKE GDYFEFEAFQDSEGDRQFRAD PYTWFSIEAIELETETMEKDFM LIGHRGATGYTDEHTIKGYQMA LDKGADYIELDLQLTKDNKLLC MHDSTIDRTTTGTGKVGDMTL SYIQTNFTSLNGEPIPSLDDVLN HFGTKVKVYIETKRPFDANMDK ELLTQLKAKGLIGIGSERFQVIIQ SFARESLINIHNQFSNIPLAYLT STFSESEMDDCLSYGSYAIAPK YTTITKELVDLAHSKGLKVHAW TVNTKEEMQSLIQMGVDGFFT NYLDEYKKI | 848 | putative glycerophosphoryl diester phosphodiesterase [Staphylococcus phage K] | YP_024488.1 | 0.0 (838/848) | Glycero-phosphoryl diester phospho-diesterase | GDPD_SaG lpQ like, glycerophos-phodiester phospho-diesterase domain | cd08601 | 1.70e-60 |
| 85 | 56935 | 57726 | 647 | MPQSDGISNLHRIALRFPKEGG GYDMYRFKVNPENYTIDSPQR TTAIKTKSDIMEDYGKDIEVINF TGTTGFRPVREADGLKTGKQK MEELQSRVSEYAMQGGSGNV | 263 | hypothetical protein KgORF59 [Staphylococcus phage K] | YP_024489.1 | 1e-150 (262/263) | | No putative conserved domains have been detected | | |

Fig. 10R

| | | | | | | | | |
|---|---|---|---|---|---|---|---|---|
| 86 | 57726 | 58250 | 648 | SGSYLQFFNFTDDSYYKVHLAP QGLKITRSKDEPLLFRYEITLVI GSLTEADRSAVTTEEFGNVKP NASQRVDEGIKELDKNARKTR DRNNQEISKRENTPKSTGDNT NEGNRLKQSFPSSSIYNPRQST NGLKGNIDNMALIIGYGDGGVS S | | | | No putative conserved domains have been detected | |
| 86 | | 58250 | 648 | MNNFIPQPQGLLRFLNALDADL TSSHMNLLDEEVSFVSKFYTPQ LQLSELAKKVLTNIKTDDIPVLE REFNDNTIIHKANDTLLKVQAP RMYMILQSIVLEAYAIWNCFVEN PSSLKYLTEEDVSITRENLNYV ADYLGNYDDYNSVVLDRLDLD LCFSAIELQLPLIKKEANV | 174 | ORF078 [Staphylococcus phage G1] | YP_240925.1 | 8e-95 (173/174) | | No putative conserved domains have been detected | |
| 87 | 58250 | 58954 | 649 | MRFKKHVVQHEETMQAIAQRY YGDVSYWIDLVEHNNLKYPYLV ETDEEKMKDPERLASTGDTLIP IESDLTDVSAKEINSRDKDVLVE LALGRDLNITADEKYFNEHGTS DNILAFSTNGNGDLDTVKGIDN MKQQLQARLLTPRGSLMLHPN YGSDLHNLFGLNIPEQATLIEM EVLRTLTSDNRVKSANLIDWKI QGNVYSGQFSVEIKSVEESINF VLGQDEEGIFALFE | 234 | putative bacteriophage baseplate protein [Staphylococcus phage K] | YP_024491.1 | 2e-134 (234/234) | Baseplate protein | DUF1371, Protein of unknown function | pfam07 115 | 7.96e-04 |
| 88 | 58969 | 60015 | 650 | MKTRKLTNILSKLIDKTMAGTSK ITDFFTPGSASRSLLEAVSLEIEQ FYILTKENIDWGIQEGIIEAFDFQ KRQSKRAYGDVTIQFYQPLDM RMYIPAGTTFTSTRQEYPQQFE TLVDYYAEPOSTEIVVEVYCKE TGVAGNVPEGTINTIASGSSLIR SVNNEYSFNTGTKEESQEDFK RRFHSFVESRGRATNKSVRYG ALQIPDVEGVYVVEETGHITVF AHDRNGNLSDTLKEDIIDALQD YRPSGIMLDVTGVEKEEVNVSA TVTISNKSRIGDTLQKHIEGVIR SYLNNLKTSDDLIITDLIQAIMNI DDVLIYDVSFDNLDENIIVPPQG IIRAGEIKVELK | 348 | hypothetical protein KgORF62 [Staphylococcus phage K] | YP_024492.1 | 0,0 (347/348) | | XkdT, Un-characterized homolog of phage Mu protein gp47 | COG32 99 | 3,44e-05 |
| 89 | 60036 | 62600 | 651 | VANFLKNLHPLLRRDRNKKDN QDFNFALIDALNEEMNQVEKD AIESKLQSSLKTSTSEYLDKFG DWFGVYRKTDENDDVYRARIIK | 854 | hypothetical protein KgORF63 [Staphylococcus phage K] | YP_024493.1 | 0,0 (498/545) | | No putative conserved domains have been detected | |

Fig. 10S

| | | | | | | | | | |
|---|---|---|---|---|---|---|---|---|---|
| | | | YLLLKRGTNNAIIDAIKDYLGRD DIDVSVYEPFTNIFYTNKSHLNG EDHLMGYYYRFAVINVSIGDYF PVEIIDVINEFKPAGVTLYVTYD GASTIRGGAIIKWLDGLPKIETY QEFDRFTGYDDTFYGHINMNQ SKDTDNSTSDIFKTNHSLINSLD VLTGSSSVGRQYVNYGYITSYV YNPGMTSSVNQISASTEGRGQ EVPTDYYMYTSTKNNNTVELS MQTTSGVSYLYNNFNFRDYMS KYRPQVNLQSDEARRIVSDYIK ELSIDYYLSAVIPPDESIEIKLQV YDFSINRWLTVSINNLSFYEKNI GSNIGYIKDYLNSELNMFTRLEI NAGKRDSVDIKVNYLDLMFYYY ERGIYTIKPYKALVENYLDISRE TYVEAFKISSLSNGDIITKTGYL PIGYLRVSGDIDNLSNHIEITID NNTNSITSTLLEDDSNSLILSYG NVKTNIHSFELNSDASISNIKFE YSYYGDAWEELTVLTEISEGET IVPNILIDLYGLQTVDYSNINPM SKVSLRSIWNVKLGELNNKEGS LSNMPNDYFNAVWQDIDKLSDI DLGSMRMIKDTEGGVFDGATG EIIKATLFNVGVVTDLDMLAYTL TNYTEPITLGSSRLISELKEELLT SESFNVDNRIKVIDSISEQLPNN NILSNSYQTQTITQNGFAKYNL KEPIEQRKQYNLRIHGDFKEGL ERLAIGNSNGSFNEVFVYPENI KDGIVDDITYTSRDDNYAEGKQR LNNDYRVYAQPYDSEVVTIYSL ELIKV | phage K] | | | | | | |
| 90 | 62711 | 63232 | 652 | MAIATYNSHVELAKYLVSKADS VYLTIGKSTPWSNETNPPCQPDE NATVLQEVIGYKKATKVTLVRP SKSPEDDNKNLISYGNKSWVE VTPENAKDEGAKWVYLESSIV GDELPLGTYRQVGFVMDLVAK SGISKFNLVPSEVESTGTLLFFD NKQFQNRSEQTTAKERFIVEV | 173 | hypothetical protein KgORF64 [Staphylococcus phage K] | YP_024494.1 | 3e-95 (172/173) | Baseplate structural protein | Phage-Gp8, bacteriopha ge T4 baseplate structural proteins | pfam09 215 | 6.79e-04 |
| 91 | 63253 | 66711 | 653 | MAINFKGSPYLDRFDPSKDRTK VLFNPDRPLQQAELNEMQSID QYYLKNLGDAIFKDGDKQSGL GFTLSEDNVLTVNPGYVYNGK | 1152 | hypothetical protein KgORF65 [Staphylococcus phage K] | YP_024495.1 | 0.0 (1147/1152) | | No putative conserved domains have been detected | | |

Fig. 10T

IRYDNDDSVKGTGVGKETIGIK
LTERIVTPDEDASILLDQTSGVP
SYFSKGADRLEEKMSLTVNDP
TSATIYTFMDGDLYIQSTNAEM
DKINKVLAERTYDESGSYKVNG
FELFSEGNAEDDDHVSVVVDA
GKAYVKGFKVDKPVSTRISVPK
SYDLGTAENESTIFNKSNNSISL
ANSPVKEIRRVTGQVLIEKERV
TRGAQGDGQDFLSNNTAFEIV
KVWTETSPGVTTKEYKQGEDF
RLTDGQTIDWSPQGQEPSGGT
SYVVSYKYNKRMEVGKDYEVT
TQGEGLSKKWYINFTPENGAK
PIDQTVVLVDYTYYLARKDSVFI
NKYGDIAILPGEPNIMRLVTPPL
NTDPENLQLGTVTVLPDSDEAV
CISFAITRLSMEDLQKVKTRVD
NLEYNQAVNALDDGAMEGQN
PLTLRSVFSSEGFISLDKADITHP
DFGIVFSFEDAEATLAYTEAVN
QPKIIPGDTTAHIWGRLISAPFT
EERTIYQGQASETLNVNPYNIP
NKQGVLKLTPSEDNWIDTENVT
ITEQKTKVTMKRFWRHNESY
YGETEHYLYSNLQLDAGQKWK
GETYAYDREHGRTGTLLESGG
QRTLEEMIEFIRIRDVSFEVKGL
NPNDNNLYLLFDGVRCPITPAT
GYRKGSEDGTIMTDAKGTAKG
KFTIPAGIRCGNREVTLKNANS
TSATTYTAQGRKKIVQDIIIRTR
VTVNLVDPLAQSFQYDENRTIS
SLGLYFASKGDKQSNVVIQIRG
MGDQGYPNKTIYAETVMNADD
IKVSNNASAETRVYFDDPMMA
EGGKEYAIVIITENSDYTMWVG
TRTKPKIDKPNEVISGNPYLQG
VLFSSSNASTWTPHQNSDLKF
GIYTSKFNETATIEFEPIKDVSA
DRIVLMSTYLTPERTGCTWEM
KLILDDMASSTTFDQLKWEPIG
NYQDLDVLGLARQVKLRATFE
SNRYISPLMSSSDLTFTTFLTEL
TGSYVGRAIDMTEAPYNTVRFS
YEAFLPKGTKVPKYSADDGK
TMKTFTKSPTTTRANNEFTRYV
IDEKVKSSGTNTKLQVRLDLST

Fig. 10U

| | | | ENSFLRPRVRRLMVTTRDE | | | | |
|---|---|---|---|---|---|---|---|
| 92 | 66760 | 654 | MPREVRDPYSQAKLFIPTVEEK SIKELEKTYKEKIDEATKLINELK KERGEK | 52 | ORF262 [Staphylococcus phage G1] | YP_240931.1 | 3e-20 (52/52) | | No putative conserved domains have been detected | |
| 93 | 66919 | 68838 | 655 | MAFNYTPLTETQKLKDMYPKV NDIGNFLKTEVNLSDVKQSQP DFNNILASIPDSGNYYVTNSKG APSGEATAGFVRLDKRNVNYY KIYYSPYSSNKMYIKTYANGTV YDWISFKLDEGNLYNEGNTLNV KELTESTTQVYTLVNPPKENLN TGWVNYKESKNGVSSLVEFNP VNSTSTFKMIRKLPVQEQKPNL LKDSLFVYPETSSSNIKTDNWN TPPFWGYTANSGRSGVRFRG ENTIQIDDGSSTYPTAMTNRFK MGNELSVGDTITVSVYAKINDP ALLKDNLVYFELAGYDMVDRT DNPYTGGRREITASEITTEWKK YSFTFTIPENTIGASGVKVNYVS LLLRMNCSSSKGNGAVVYAL PKLEKSSKVTPFITHATDVRKY DEWSNWQEVISKDELKGHSP VDIEYNDYFKYQWWKSEVNEK SLKDLAMTVPQGYHTFYCQGSI AGTPRGRSIRGTIQVDYDKGDP YRANKFVKLLFTDTEGIPYTLYY GGYNQGWKLLKQSETSTLLWE GTLDFGSTEAVNLNDSLDNYDL IEVTYWTRSAGHFSTKRLDIKN TSNLLYIRDFNISNDSTGSSVDF FEGYCTFPTRTSVQPGMVKSIT LDGSTNTTKVASWNEKERIKVY NIMGINRG | 639 | hypothetical protein KgORF66 [Staphylococcus phage K] | YP_024496.1 | 0.0 (617/640) | PHA01818, hypothetical protein | PHA018 18 | 6.90e-04 |
| 94 | 68862 | 69236 | 656 | MAVKYDIGNNEIVLHLREGKYIT GFTTVGGYDKELGQVKVNREIL PAYFFDNFAYERYLYYSKPEEV IENKNYVPPQINNGDEESQCNT VPKEQYDSLKEELELMRKQQE AMMEMLQKLLGQKG | 124 | hypothetical protein KgORF67 [Staphylococcus phage K] | YP_024497.1 | 3e-63 (121/124) | DUF2977, Protein of unknown function | pfam11 192 | 2.94e-12 |
| 95 | 69243 | 70619 | 657 | MALNFTTITENNVIKDLTTQVNN IGEELTKERNIFDITDDLVYNFN KSQKIKLTDDKGLTKSYGNITAL RDIKEPGYYIGARTLATLLDRP DMESLDVVLHVVPLDTSSKVV QHLYTLSTNNNQIKMLYRFVSG NSSSEWQFIQGLPSNKNAVISG | 458 | hypothetical protein KgORF68 [Staphylococcus phage K] | YP_024498.1 | 0.0 (445/458) | PHA01818, hypothetical protein | PHA018 18 | 0.0 |

Fig. 10V

| | | | | | | | | |
|---|---|---|---|---|---|---|---|---|
| 96 | 70709 | TNILDIASPGVYFVMGMTGGMP SGVDSGFLDLSVDANDNRLAR LTDAETGKEYTSIKKPTEVYTA WKKEFPKDMEKYLLSSIRDD GSASFPLLVYTSDNKTFQQAIID HIDRTGQTTFTFYVQGGVSGS PMSNSCRGLFMSDTPNTSSLH GVYNAIGTDGRNVTGSVVGGN WTSPKTSPSHKELWTGAQSFL SVGTTKNLADDISNYSYVEVYT KHKTVEKTKGNDDSGTICHKFY LDGSGTYVCSGTFVSGDRTDT KPPVTEFYRVGVSFKGSTWTL VDSAVQNSKTQYVTRIIGINMP | | | | | | |
| | 72457 | 658 | MRLRIKNLYTYVEFEEDDKYLK DIFLKRVHTTIGARQEGFQYSP AYKRGSWDGYVDFYVYEEDKF PTGLLFKIELLLGELQSRYNFQF ETIDERDESFLSEEDIDDEITLL DNNVGQITLRDYQYEAVYNSLT FYNGIAHLATNGGKTEVASGIID QLLPQLEKGERVAFFTGSTEIF HQSADRLQERLNIPIGKVGAGK FDVKQVTVVMIPTLNANLKDPT QGVKVTPKQNISKKIAQEILPKF EGGTNQKKLLKVLLDNTTPKTK VEQNVLSALEIIYQNSKTDAEVL LNLRNHNAHFQKIVREKNEKKY DKYQDMRDFLDSVTVMIVDEA HHSKSDSWYNNLMTCEKALYR IALTGSIDKKDELLWMRLQALF GNVIARTTNKFLIDEGHSARPTI NIIPVANPNDIDRIDDYREAYDK GITNNDFRNKLIAKLTEKWYNQ DKGTLIIVNFIEHGDTISEMLNDL DVEHYFLHGEIDSETRREKLND MRSGKLKVMIATSLIDEGVDIS GINALILGAGGKSLRQTLQRIGR ALRKKDDNTTQIFDFNDMTNR FLYTHANERRKIYEEEDFEIKDL GK | YP_024499.1 | 0,0 (582/582) | putative helicase [Staphylococcus phage K] | 582 | Helicase | HELICc, helicase superfamily c-terminal domain | cd00079 | 1.80e-12 |
| 97 | 72469 | 74082 | 659 | MATKTQRKLYQYLEENATENK FHISTKKELADSLGVSISALSNN LKKLEEENKVVTVSKRGKNGG VIITLVREYDTEELKEFNNSTDN IITSDLQYAKALREKHFPSYRYE RKEQRRRTKIEMAQYNAIKDEK | YP_024500.1 | 0,0 (531/537) | putative Rep protein [Staphylococcus phage K] | 537 | Transcription regulator protein | HTH_ARSR subfamily of helix-turn-helix bacterial transcription | cd00090 | 4.28e-03 |

Fig. 10W

| | | | | | | | | |
|---|---|---|---|---|---|---|---|---|
| 98 | 74075 | RRIIADMNFYSEGLPYPSKDIFN MSYDPEGFYKAYILCKLYDQYA ISHMDAKHTSHLKAMSKATTKD EYDYHQHMSEYYRNKMIQNLP RNSVSDNFFGSKMFNTFYNFY LKIKDKNINVFKYMKNVFKNVTF YYENGMQPNPIPSPNFFSSDK YFKNYNNYIKGIKKGINSTNRHL GDTDSIINSSDYYKNPAVLHLH QLYTTGLNSTLHDIDTMFEQAL DLENASYGLFGDMKHIILLQYN SMIEEEIKNLPIEEKDIINKYYKQ CIINNYSPTSISPSARLSMFTMQ KEHIVYNKQLNKGIKREDLLPLS LGGIVNKDSLSSMDIQNLEQNG NEYLYMRQHTSTYYILRMFGD YLGYEVNLREVKYIVEKYNLIDK IPLTKEGMLDYNKLIIHLVEEEVN NYE | | | | | | |
| | 75517 | 660 | MSKKIKELLIHKSMKDIHFAREV LDNLPKNLFSAESEDMGYLFTA IKRTAHISDKMSNEALAIKVEQL MGNNKEDEEKVTKTLTYLEDLY KVDVNEKDESVNYEIEKYIKTE MSKEVLVKFIAENKQEDSDNLH ELVDKLKQIEVSDISGGNGEFID FFEDTEKKQELLSNLATNKFST GFTSIDNHIEGGIARGEVGLIIAP TGRGKSLMASNLAKNYVKSGL SVLYIALEEKMDRMVLRAEQQ MAGAEKSQIVNQDMSLNNKVY DAIQNHYQKNRKLLGDFYISKH MPGEVTPNQLEQIIVNTTIKKDK NIDVVIIDYPHLMRNPYAKYHSE SDAGGKLFEDIRRLSQQYGFV CWTLAQTNRGAYGSDVITSEH VEGSRKIVNAVEVSLAVNQKDE EFKSGFLRLYLDKIRNSSNTGE RFVNLKVEPTKMIVRDETPEEK QEHIQLLSDNGKEDTSKFQNK DNKIEAINNTFGGLPGV | 480 | putative helicase [Staphylococcus phage K] | YP_024501.1 | 0.0 (480/480) | Helicase | 41 helicase | PHA025 42 | 1.06e-05 |
| 99 | 75596 | 76621 | 661 | MKFVFFTDSHFHLFTNYAKPDN EFVNDRFKEQIEALQKYFDIAK KEEATVIFGGDLFHKRNSVDTR VYNKVFSTFAKNNEVPVLLLRG NHDATTNSLYTDSSIDTFEYLP NVNVIKSLNTILKDNVNIVFTAY | 341 | putative exonuclease [Staphylococcus phage K] | YP_024502.1 | 1e-172 (294/345) | Exonuclease | MPP_Mre11_N nuclease, N-terminal metallo-phosphatas | cd00840 | 3.56e-21 |

Fig. 10X

| # | ID | Sequence | Len | Description | Accession | Match | Function | Domain | PHA | E-value |
|---|---|---|---|---|---|---|---|---|---|---|
| | 76621 | GDETKEIKTYINSNYDKDMVNIL VGHLGVEGSLTGKGSHRLEGA FGYQDLLPDKYDFILLGHYHRR QYFQNPNHFYGGSLMQQSFS DEQEANGVHLIDTDKMTTEFIPI HTRRFITIQGEDIPDNFEQLIEE DNFIRVIGTANHAKVLEMDDSM KDKNVEVQIKKEYTVEKRIDSD VSDDPLTIASTYAKQYSPESEQ EILECLKEVL | | | | | | e domain | | |
| 100 | 76998 | 662 | MKKYREYLNKTDAENLAEDWE KVTEDLWKVFKDMKPKINTLDI SNVGSKDLDKSKPILQFQDSD GVIENICNVEGELEDGLSKMKKIF DDSNFEKHYNRVDHDGYY WIDYGSHHCFFRVTKGDK | 125 | hypothetical protein KgORF73 [Staphylococcus phage K] | YP_024503.1 | 3e-65 (123/125) | | PHA02275, hypothetical protein | PHA022 75 | 2.14e-21 |
| 101 | 76998 78917 | 663 | MVVFKQVEVNNFLAIKEATLEL DNRGLLIEGENKSNESFHSNG SGKSTLISAITYALYGKTEKGLK ADDVVNNIEKKNTSVKLKFDIG EDSYLIERYRKDKENKNKVKLF VNEKEITGSTNDVTDKQIQDLF GIEFNTYVNAIMYGQGDIPMFS QATDKGKKEILESITKTDVYKQ AQDVAKEKVKEVEEQQNNIRQ EIYKLGYQLSTKDEYFQREIEQ YNQYKEQLVQIENSNKEKDRL REQEEKQIEAQIEQLASQIPTIP EDEFKHSEEYNKASQSLDLLSN KLTELNQVYSEYNTKEQVLKSE IATLSNSLNQLDINDHCPVCGS PIDNSHKLKEQENMSNQIENKK QEITSVLEMKDTYKEAIDKVKD KSQEIKDKMSQEDQQEREHNN KINSIIQEASRIKSDISSLENNKT YLKVKYQHGSVQGLEREEPSK EKHEEDKKELQESIDKHEENIV QLETKKGKYQQAVDAFSNKGI RSVVLDFITPFLNEKANEYLQTL SGSDIEIEFQTQVKNAKGELKD KFDVIVKNNKGGGSYKSNSAG EQKRIDLAISFAIQDLIMSKDEIS TNIALYDECFDGLDTGCENVIK LLKDRLNTVGTIFVITHNTELKP LFEQTIKIVKENGVSKLEEK | 639 | putative exonuclease [Staphylococcus phage K] | YP_024504.1 | 0.0 (636/639) | Exonuclease | 46 endonuclea se subunit | PHA025 62 | 1.68e-26 |
| 102 | 78917 79513 | 664 | MKLKILDKDNATLNVFHRNKEH KTIDNVPTANLLVDWYPLSNAYE | 198 | hypothetical protein KgORF75 | YP_024505.1 | 2e-111 (197/198) | | No putative conserved domains have been detected | | |

Fig. 10Y

| | | | | | | | | |
|---|---|---|---|---|---|---|---|---|
| | | | YKLSRNGEYLELKRLRSTLPSS YGLDDNNQDIIRDNNHRCKIGY WYNPAVRKDNLKIIEKAKQYGL PVITEEYDANTVEQGFRDIGVIF QSLKTIVVTRYLEGKTEEELRIF NMKSEESQLNEALKESDFSVD LTYSDLGQIYNMLLLMKKISK | | [Staphylococcus phage K] | | | |
| 103 | 79528 | 80595 | 665 | MRFEDFLTQELGEPKENTIGEL RYCCPFCGEKSYKFVVKQALD SSNGQYHCKKCDETGNPITFM KTYYNITGKQAFDLLESKNIDIE RAPLLTTNNKDLTESEKLLMLR GVHQDKGTTSIKPPRLPEGYKL LKDNLNNKEIIPFLKYLKGRGITL EQIINNIGYVINGSFYKVDGES KVSLRNSIIFFTYDNNGNYQYW NTRSIEKNPYIKSINAPAKQDEV GRKDVIFNLNIARKKKFLVITEG VFDALTFHEYGVATLGKQVTEN QIKKIIDYVSIDTSIYIMLDTDALD NNIDLAYKLKTHFNKVYFVPHG DEDANDMGTRKAFELLKQNRV LVTPESIQSYKIQQKLKL | 355 | putative primase [Staphylococcus phage K] | YP_024506.1 | 0.0 (352/355) | DNA primase | DnaG, DNA primase (bacterial type) | COG03 58 | 1.08e-12 |
| 104 | 80661 | 80999 | 666 | MSNSKKDILEFVDEYITALRVG NEQRQHQLEEMGKEETATLTD VAKAITNLMLGVNEQMTDLEYN NELNLNIJIDALYKAELINEDVLD YIQESIDKSQEEPKNEEEKGEQ E | 112 | ORF127 [Staphylococcus phage G1] | YP_240943.1 | 2e-55 (111/112) | | No putative conserved domains have been detected | | |
| 105 | 80999 | 81451 | 667 | MEKNISTHTKGISQADMEKWIE AVVQGTVDGKQVDEKTAKQLD RIGSRSVSLEEATRIAKVLNAVT AQEVTGDFNDAFNAIDLMMIIM EDELGVTQEKVGKAKDKLNEK REAYLKEKQEELRQKQQEEAQ KETESDSNEKVIQLKKNDEQ | 150 | ORF098 [Staphylococcus phage G1] | YP_240944.1 | 2e-78 (149/150) | | PHA02277, hypothetical protein | PHA022 77 | 9.45e-43 |
| 106 | 81438 | 82046 | 668 | MTNSKKKGDTFERKIAKELTAW WGYQFNRSPQSGGASWGKD NNAVGDIVVPQEANFPLVVECK HREEWTIDNVLLNNREPHTWW EQVINDSSKVDKTPCLIFTRNR AQSYVALPYDEKVYEDLRNNE YPVMRTDFIIDNIRKDKFFYDVLI TTMNGLTSFTPSYIISCYDKKDI KPYKKVESNLSEVSKHEDELIN DLLSDI | 202 | ORF064 [Staphylococcus phage G1] | YP_240945.1 | 2e-115 (201/202) | | No putative conserved domains have been detected | | |

Fig. 10Z

| 107 | 82063 | 82455 | 669 | MTSKERPLIVYFSGTCQTERLV NKININNSFETFRVKSGKEKVN KPFILITPTYMKGAIPKQIERFLE INGSPKEVIGTGNKQWGSNFC GASKKISEMFKIPLIAKVEQSGH FNEIQPILEHFSNKYKVA | 130 | putative NrdI protein [Staphylococcus phage K] | YP_024509.1 | 4e-68 (129/139) | Ribonucleotide reductase protein | Flavodoxin_NdrI | pfam07972 | 2.44e-29 |
| --- | --- | --- | --- | --- | --- | --- | --- | --- | --- | --- | --- |
| 108 | 82470 | 84584 | 670 | MATYGKWIELNNETQLDDNGK NKLYKDQEALDEYLKYIEDNTR KFNSEVERIRVLTKEGTYDKIFD KVPDTIIDEMTKLAYSFNFKFPS FMAGQKFYESYASKQYDENKK PIFVEDYEQHNVRVALYLFQND YVKARELLVQLMEQTFQPSTPT YNNSGGANRGELSSCYLFVVD DSIESLNFVEDSVANASSNGG GVADLTRIRPKGAPVRNRPNS SKGVIAFAKAIEHKVSIYDQGGV RQGSGAVYLNIFHNDILDLLSS KKINASESVRLDKLSIGVTIPNK FMELVKEGRPFYTFDTYDINKV YGKYLDELNIDEWYDKLLNNDS IGKVKHDAREVMTDIAKTQLES GYPYVFYIDNANDNHPLKNLGK VKMSNLCTEISQLQEVSEIYPY SYSNQNVINRDVVCTLGSLNLV NVVEKGLLNESVDIGTRALTKV TDIMDLPYLPSVQKANDDIRAIG LGSMNLHGLLAKNMISYGSRE ALDLVNSLYSAINFQSIKTSMLM AKETGKPFKGFEKSDYATGEY FVRYIRESNQPKTDKAKKVLDK VYIPTQDDWDELAKAVKVHGL YNGYRKAEAPTQSISYVQNATS SIMPVPSAIENRQYGDMETYYP MPYLSPITQFFYEGETAYKIDN KRIINTSAVVQKHTDQAVSTILY VESEIPTNKLVSLYYYAWEQGL KSLYYTRSRKLSVIECETCSV | 704 | putative ribonucleotide reductase large subunit [Staphylococcus phage K] | YP_024510.1 | 0.0 (701/704) | Ribonucleotide reductase large subunit | RNR_I, ribonucleotide reductase | cd01679 | 3.18e-130 |
| 109 | 84598 | 85647 | 671 | MDITQKVKQHNKNAVLKATNW NIEDDGMSDIYWEQGISQFWT PEEFDVSRDLSSVVNSLTESEK NTYKKVLAGLTGLDTKQGGEG MNLVSYHEPRPKYQAVFAFMG GMEEIHAKSYSHIFTTLLSNKET SYLLDTWVEENDFLKVKAQFIG YYYDQLLKPNPTVFDRYMAKV ASAFLESSALFYSGFYYPLLLAG | 349 | putative ribonucleotide reductase minor subunit [Staphylococcus phage K] | YP_024511.1 | 0.0 (347/349) | Ribonucleotide reductase minor subunit | RNRR2, ribonucleotide Reductase | cd01049 | 1.74e-63 |

Fig. 10AA

| | | | | | | | | |
|---|---|---|---|---|---|---|---|---|
| 110 | 85665 | | RGQMTQSGAIIYKITQDEAYHG SAVGLTAQYDYNLLTEEEKKQA DKETYELLDILYTNEVAYTHSLY DPLELSEDVINYVQYNFNRALQ NLGREDYFNPEPYNPIVENQTN VDRLRNVDFFSGKADYEKSTNI KDIKDEDFSFLDSKEYNTAKEF L | | | | | |
| 110 | 85994 | 672 | MDRKEAMDLLSKAEILFKKHDE FSCVSDINDPMKLFSSSKDAKA DDTSKSFEQLEFMHDMTMYTLS YGSGGLKLIDLAEGYEAQKATV VNSFPEIIKTLEKCDSEDGKNE | 109 | hypothetical protein KgORF82 [Staphylococcus phage K] | YP_024512.1 | 4e-55 (106/109) | | No putative conserved domains have been detected |
| 111 | 85978 | 673 | MEKMNSLVDLNTAIRQKKDVIV MITQDNCGKCEILKSVIPMFQE SGDIKKPILTLNLDAEDVDREKA VKLFDIMSTPVLIGYKDGQLVK KYEDQVTPMQLQELESL | 106 | thioredoxin-like protein [Staphylococcus phage K] | YP_024513.1 | 8e-54 (106/106) | Thioredoxin-like protein | PHA02278, thioredoxin-like protein | PHA022 78 | 1.12e-45 |
| 112 | 86505 | 674 | MDELISKSRRYIMRDENHYMLF NEKYNNDRLIEKVCKHGGKVT YYTDSVLPYYVLKDLSSHPDSE VVYRMRNGFTAKEVDNIALSF MGT-KVIIDISVVFPYVNPYDIRS LHDIKTNVDEVHLSFPRILEVDE KQEKFYFFDGEAYDLKPEYKV DFADKIRVSLSVWKMYYILTSS RDFEDVDNVITKLKQQRKIKI | 198 | hypothetical protein KgORF84 [Staphylococcus phage K] | YP_024514.1 | 5e-109 (196/198) | | No putative conserved domains have been detected |
| 113 | 87111 | 675 | MSTANRRDIARKISENTGYYIQ DVEEILSAETDAISDLLEEGYTK VKNHKFMQIEVIERKGKKAWD GLNKEYFHLPNRKAIKFKPLKE LEEVIDRLNEEEK | 101 | putative integration host factor [Staphylococcus phage K] | YP_024515.1 | 2e-51 (101/101) | DNA binding / bending protein | Bac_DNA binding | pfam00 216 | 4.22e-12 |
| 114a | 87492 | 676 | MKVLILFDHIREEHFSVSKDGS VKSNVLNTPNGKTLKLLLEKCS NLKRDKTNRDYDIDFLYNAVPT PIRNDYGKIIKYQDVKQAEVKP YYERMNNIIIDNSYDWVIPVGKL GVKYLLNVTAIGKVRGVPSKVTI ENETSSHDVWVLPTYSIEYTNV NKNSERHVVSDLQTVGKFVEQ GEEAFKPKEVSYELVDNIERVR EIFNKEVKNDNYDGVDITAWDL ETNSLKPDKEGSKPLVLSLSW RNGQGVTIPLYKSDFNWENGQ DDIDEVLELLKNWLASKEDIKVA HNGK | 290 | putative DNA polymerase [Staphylococcus phage K] | YP_024516.1 | 6e-167 (289/290) | DNA Polymerase | DNA_polA_I Ecoli_like exonucleas e | cd06139 | 3.30e-09 |

Fig. 10BB

| | | | | | | | |
|---|---|---|---|---|---|---|---|
| 115* | 88530 | 89042 | 677 | VYQLNRGGTVKKDYMTSVKNN KKVCRRCNEELDLSNFKTYKK NDKIYYQSMCIPCRKEYNKLDK TKNTIKKCYDKNGDKYRKQGN EYNTSDRGRELNKKRSRKYRE NNSLKAKARNSVRTALRNGSLL RPSKCSECNKECIPEAHHPDY NKPLEIKWLCKSCHEDTHHKK | hypothetical protein KgORF87 [Staphylococcus phage K] | YP_024517.1 | 4e-79 (145/156) | | No putative conserved domains have been detected |
| 114b | 89178 | 91508 | 678 | MSTENFKDFESIQDTKVGWYL AVTQEVKESLRLSDLAYEVTDV GGYDKPLEDFKLWFVTKLLRFF SDKIKEIQKENKKIAKKEYDVKA PEYKEWLENKLNETVVELDDT EKKFRVSELEKKYIQLGLSPEIV NMNLVMNNDEFISIAEQSPEYM GLSDYAKSYTLNTAINLINEYRD VKDVVNDIDGGNFNYDWFPIEL MHPYASGDTDVCRRIHCDVVK KLKEQDRPKSMHLLEVNYPRL TKSLARIESNGLYCDLDYMKEN DESYESEMAKNHATMREHWA VKEFEEYQYNLYQMALEEHEK KPKDRDKDIHQYRDKFKDGKW MFSPSSGDHKGRVIYDILGIQL PYDKEYVKEKPFNANVKEADLT WQDYKTDKKAIGYALDNLELKD DVRELLELLKYHASMQTKRNSF TKKLPNMINKQKRTLHGSFSET GTETSRLSSSNPNLQNLPAHTS DVNKFDYKHPIKRSFVSRFENG VLLGADYSALEMRIIGLFTKDPD MLQSFLNGEDIHKATASIVYNK PVEEVTKEERQATKAVNFGLAF GESPSFAGKNNMEVSEAEEIF EKYFQTKPSVKTSIDNVHEFVQ QYGYVDTMHGHRRFIRSAQST DKKIKNEGLRQSFNTIIQGSGSF LTNMSLTYLDDFIQSRNLKSKVI ATVHDSILIDCPPEEAKIMAKVTI HIMENLPDFLKAEIDGKEVQY PIEADMEIGLNYNDMVEYDEEE IDTFNSYQGYIKYMMNLQTLED YKESGKLTDEQFEKATNVVKS EKHIYQEI | putative DNA polymerase [Staphylococcus phage K] | YP_024516.1 | 0.0 (770/776) | DNA Polymerase | DNA_pol_A pol_I_C | cd08637 | 8.00e-72 |
| 116 | 91577 | 91819 | 679 | VNTGEIRFNRSMDEWIITSMYQ DELGDMNIVVTFYNREENKHG STVLPTESSTGEVTEELANLEE | ORF181 [Staphylococcus phage G1] | YP_240959.1 | 7e-37 (77/80) | | No putative conserved domains have been detected |

Fig. 10CC

| | | | EYPLALPLSSISVNI | | | | |
|---|---|---|---|---|---|---|---|
| 117 | 91836 | 92318 | 680 | MEIHIDSLDFTNFTIKDRNGNSQ EFDITDELRITEYTIQEDFMQQS AKYAFWASILEKVRAYSEMEQ RNLETIGSKKLNLTIRQEYEQQG KKPTKDMIESSVYIHDSYQQQL KVVEAWNYKVKQLQYVVKAFE TRRDMMIQLGAELRQTNKNGG ITNPFSH | hypothetical protein KgORF91 [Staphylococcus phage K] | YP_024519.1 | 5e-90 (160/160) | | No putative conserved domains have been detected |
| 118 | 92405 | 93676 | 681 | MDFNQFINNEASKLESNNSSFN NNVESYKPKNFVLRLGNIKDAN GNKVVKENAFVRVLPPAQGTN VFFKEFRTTGINYSKKDGSQGF TGLTLPAEEGSSVLDPYIQDWI TNGVQFSRFPNKPGVRYYIHVI EYFNNNGCIQPKTDAQGNVMI QPMELSNTGYKELLANLKDTM LKPSPNAPHSFISANEAFLVNIV KAKKGEMSWKVSVYPNAPLGA LPQGWEQQLSDLDQLAKPTEE QNPNFVNFLINNVNNTELSHDN FKNRETNVLGEEFSEPKQAP TQQDVDSCMPSNMGGQPNQP QQGQVGQYAQGQSNGQGQ QLQGTQQPINNTQFGCGTPSG QQPSNTGSVDWDNLAQQQSQ PDSNPFNDFDVSSVDDSQVPF ETQPQNTQQAPEPHQTTQEPP KQKQTQSIDDVLGGLDLDNL | hypothetical protein KgORF92 [Staphylococcus phage K] | YP_024520.1 | 0.0 (421/423) | | No putative conserved domains have been detected |
| 119 | 93736 | 94992 | 682 | MARAKKGKEVDLTDLNTIDLGK ELGLTLLSDTNRADIKNVIPTMV PQYDYILGGGIPLGRLTEVYGL TGSGKSTFAVHLSRIATQLGVIT IWIDIEGTADNNRMEQLGVDVS KLFSIQSGEGRLKNTVELSVEQ VGKELEYWIDTFNEKIPGVPIVF IWDSLGATRTQKEIDGGIDEKQ MGLKASATQKVINAVTPKLNDT NTGLIVINQARCDMNAGMYGD PIKSTGGRAFEHSASLRIKVHK ASOLKQKSELTGKDEYHGHIM RIETKKKSKLSRPGQKAEADLLS DYMVGKEDDPILLNGIDLEHTV YKEAVERGLITKGAWRNYVTLN GEEIKLRDAEWVPVLKDNRELY LELFSRVYGEHFPNGYSPLLNN KVIVTQLEEYQALENYYKEWAT | putative DNA repair protein [Staphylococcus phage K] | YP_024521.1 | 0.0 (417/418) | DNA repair protein | recA | cd00983 | 1.99e-34 |

Fig. 10DD

| | | | DNKQEEQEEELKGESQEKDSE | | | | | |
|---|---|---|---|---|---|---|---|---|
| 120 | 94996 | 95349 | 683 | MDNLIDKNMSQVKESLGNANS SDVLPLPYKDIAKKFEEVKEKG ESIIIEEGGFPYTDSTVMYIEHV TDRWAGGYSLIRHEGEEVKVP KTIHFSDIYVKDKSHKVRIIFEGA NPYEES | 117 | ORF121 [Staphylococcus phage G1] | YP_240963.1 | 3e-61 (116/117) | | No putative conserved domains have been detected |
| 121 | 95336 | 95998 | 684 | MKKANNGNRYVIDIDGIPVDFE RDLDSLLNRYKNLRWSLYHRY AGILSNDFERQELRYEIDEQFIK LVKEYNIRSKVDFPGYIKAKLTL RVQNSYVKKNEKYKRTEIIGKK DYTVESLTEDLNEDFEDNQIMS YVFDDIEFTEVQSELLKELLINP EREDDAFIVSQVAEKFDMKRK EVASELTELRDYVRFKINAYHE YYAKKELNNHRVNTENHIWEN | 220 | putative sigma factor [Staphylococcus phage K] | YP_024522.1 | 1e-122 (220/220) | Sigma factor | No putative conserved domains have been detected |
| 122 | 96126 | 96758 | 685 | MAKKNVNDVLQCESVTVADKY LQVKVNRDGYTRTHEGQYAYK VVSEGEELFLYPVQTDGKGTL NVMKKSPIAYTDGDNIHFVVNT VVDPYNHSFIRTEDIKGLDKGK QLIQAFLAFVEDRFKFGVYNVF VANNKEDVLSIVDPTDNDADEV KDSLEHAHEDVIADFPASPARK DVKGVDSGEGQGDTSEPSAPK NVQVTPKEDGADVSAE | 210 | hypothetical protein KgORF95 [Staphylococcus phage K] | YP_024523.1 | 1e-117 (210/210) | | PHA02283, hypothetical protein | PHA022 83 | 5.30e-71 |
| 123 | 96781 | 97293 | 686 | LAKLNLYKGNELLNSVEKTEGK STITIENLDANTDYPKGTFKVSF SNDSGESEKVDVPQFKTKAIKV ISVTLDVDSLDLTVGDTHQLST TITPSEASNKNVSFESDKSGVA SVTSEDLIEAVSAGTANVTVTT EDGSHTDIVAVTVKEPIPEAPA DVTVEPGENSADITV | 170 | putative major tail protein [Staphylococcus phage K] | YP_024524.1 | 3e-88 (168/170) | Major tail protein | No putative conserved domains have been detected |
| 124 | 97308 | 97535 | 687 | MEKTLKVYSNGEVVGSQVANN DGATTVSITGLEAGKTYAKGDF KVAFANDSGESEKVDVPEFTT KTPTEEPSGDA | 75 | ORF189 [Staphylococcus phage G1] | YP_240967.1 | 1e-34 (75/75) | | Big_2 bacterial surface proteins containing Ig-like domains | pfam02 368 | 1.61e-03 |
| 125 | 97631 | 97891 | 688 | MDIPTILFRNPYDYTKVKKLME NKEQYIVVKFDSVSVHNLNVQ GMMNVIQDYLHIYGYRVKEYG QENSSKDDERDVKGYLYERVG E | 86 | ORF174 [Staphylococcus phage G1] | YP_240968.1 | 2e-42 (86/86) | | No putative conserved domains have been detected |
| 126 | 97895 | 98650 | 689 | MGIIVNSNHIQSDTLYEYDSFFD | 251 | hypothetical protein | YP_024525.1 | 1e-141 | | PHA02284, | PHA022 | 1.74e- |

Fig. 10EE

| | | | | | | | | |
|---|---|---|---|---|---|---|---|---|
| | | | IEKVDTFEEGLLSIQDEPTVLAG FIYDDITFNKVINSNSDIDDYIKN NDIYYVSDIGLLPDTFITVDSDR KYYSLLQQITELSKDPFPKWVE DDAKGLTKYYNFQDFEDVFDL NSFYKKEVDMVREKCYNNGNV YLLYEVLPDYKLPLAYSLLSNK EHGIVIIGSQTRSNNDILTFYK GMDAKAIASMFNVEHDYDSNIF HTFVNSHINILGNQITKFIREKG SSYE | | KgORF97 [Staphylococcus phage K] | | (251/251) | hypothetical protein | 84 | 41 |
| 127 | 98643 | 99893 | 690 | MSNYKTIEEVQAVIIGVLFKDEG KIITSKFNIKITKEFGLDRIGKDDL KEIVEDIRQDAYLNELKNKAIKG KVTLGDLKDVADNQVFEGNNY HEEVSTYVVAKEKELSHLREQ RKHNRHTAYPQIMFDELKEHM VKELQGETLVEHHGSKANINDT ELIVLLSDFHIGSIVSDMTNGKY DFEVLKARLNHFINTTVKEIEDR EISNVTVYFVGDLVEHINMRDV NQAFETEFTLAEQISKGTRLLID ILNVLSNVVSGELRFGIIGGNHD RMQGNKNQKIYNDNIAYVVLDS LLLFQEQGLLNGVDIIDNREDIY TIRDTFGGKSIIINHGDGLKGKG NHINKFILDSHIDLLITGHVHHFS VKQEDFNRMHIVASSPMGYNN YAKELHLSKTKPSQQLLFINKE NKDIDIKTVFLD | hypothetical protein KgORF98 [Staphylococcus phage K] | YP_024526.1 | 0.0 (413/416) | No putative conserved domains have been detected | | |
| 128 | 99907 | 100275 | 691 | MDTIFIIGVAFITFATFNIVFRLFD LWTTEKKMVSQGQOPPLSNFEY YHVIVPYLVGVIVIILSIIFRDSLY SAQSGFGVIITSFIYMLVYVIIGL VGSFVLTIFQARKARQYQTQED NNEVQ | hypothetical protein KgORF99 [Staphylococcus phage K] | YP_024527.1 | 5e-63 (122/122) | No putative conserved domains have been detected | | |
| 129 | 100262 | 100573 | 692 | MKFNDIYEQLIKNDTVQNIHES QDDKGNIYTIQFDKGNDKYLFN VINDGFLKEMTNGMVDHPEGQ PYSVSLINKETPSMSVKQYLTD VEDIVPTIRKMEKDFL | hypothetical protein KgORF100 [Staphylococcus phage K] | YP_024528.1 | 5e-53 (103/103) | No putative conserved domains have been detected | | |
| 130 | 100637 | 101173 | 693 | MDFNFSAFDNSSLAMRISEGV YYFNDTPYYFIEHVEEEMSEYV IVYDIHDREEKENPQKKYRIEPY QRTIPGGTPLSNLIKSMMPQRK YPKKYTEDPIFVANVIP.LGTDTV TGKTGKGFFERDKDRTIYSQKE | ORF075 [Staphylococcus phage G1] | YP_240973.1 | 8e-100 (178/178) | No putative conserved domains have been detected | | |

Fig. 10FF

| | | | | | | |
|---|---|---|---|---|---|---|
| 131 | 101166 | 101933 | 694 | PTKVVHGQYTGVFIGLTSVKW NRTYTPLESVVEYYKRVKGDR LNV MSNDVVKFYEKDIKDLIRTKKH MFKDDEITSDINDIRIFNEKVICQ GKCRTDCLVLDRNGTVMGIEIK TERDSTQRLNNQLKYYSLVCK YVYVMCHDKHVPKVEGILKRY KHNHVGIMSYISFKGKPVVGKY KDATPSPHRSPYHTMNILWKT NLMITLRLIRDPHTYRTGYSYN ASGRYSGGEGNFSQTTQSKR MKKPAIINQIIHYVGVDNTYKLF TRGWYGYNNRWEVIEEDFFNT MKNGVRVINECRQTK | hypothetical protein KgORF101 [Staphyloccocus phage K] | YP_024529.1 | 5e-149 (255/255) | No putative conserved domains have been detected |
| 132 | 101911 | 102357 | 695 | MSKDKPNRRKEIQHQPVNFAP TNTLTGANNSFFAKNPSEPKDA TSVIEYRILFIKRFDNVTSTDVKL QKKYALNLISEALDVKETYLSLK QKGKKTESILHTDRVYVYVHRGK KLIGKCSIREQRTFKGKHLIFIFK TRHRVKAERKDK | hypothetical protein KgORF102 [Staphyloccocus phage K] | YP_024530.1 | 2e-80 (147/148) | No putative conserved domains have been detected |
| 133 | 102357 | 103220 | 696 | MLKGFSEHVDKPTTSKTLYKTL TSGKVELLGVSYDSDYFPSGV TVQSYIEDIGNEDEGLQFVNKV NVVESMKQAVVGMNNQLGSS GLGYVRTEQLKKELEETGLMT DLLARGTNLTSTKKVDIVSTFIE PEVTYQNITIAKDIKLRLYKVEE ESPLNGYTHIVYLLTTEKLYDG QTLFGMILSKKDKLSKGDTDKLL AFFRNNSLISKSVFCVKLLSKD YYFNLYNTHETGIFFLEDTDVITI ACGGSYVKVNTKDIKSSYVKIE DKTHKLTELVINLKGDDTLTILF | ORF036 [Staphylococcus phage G1] | YP_240976.1 | 1e-160 (286/287) | No putative conserved domains have been detected |
| 134 | 103592 | 104323 | 697 | MARKKNLRNKNSDIKVVPDKE KESILSKLYHNKLLRSKVDNAL DEDMSYDDIIELCKEYDLELSK SAITRYKSKRKEAIENGWDLGE LIDKRKKTSVKDIKEKETPILEEE QLSPFEQSKHHTQTIYDDIQVL DMIISKGAKGLEFVETLDPALMI RAMETKDKITGNQLKGMSFIGL RELQLKQTAQDTAMSEVLLEFI PEEKHEEVLQRLEELQNEFYK NLDLDEESRKLKEALDRVGYTI | hypothetical protein KgORF103 [Staphyloccocus phage K] | YP_024531.1 | 6e-136 (243/243) | No putative conserved domains have been detected |

Fig. 10GG

| 135 | 104341 | 104799 | 698 | MADEISLNPIQDAKPIDDIVDIMT YLKNGKVLRVKQDNQGDILVR MSPGKHKFTEVSRDLDKESFY YKRHWVLYNVSVNSLITFDVYL DEEYSETTKVKYPKQTIVEYTR EDQEKDVAMIKEILTDNNGNYF YALTGEIMLFDENKLNKVKD | 152 | ORF094 [Staphylococcus phage G1] | YP_240978.1 | 3e-82 (151/152) | | | No putative conserved domains have been detected |
| 136 | 104864 | 105307 | 699 | MFISLNQEEKELLTKEESKYTPL ETSREFNTPKEEFIVTSYNEGK PLDYIAKEAKVSMGLIYTVLNVY KVGKRNKKSPVEERIAHILKDK NLVKEIIKDYQYMNLQDIYSKYN LHKNGLYYILDLYHVERKSELK DKALEEDNIVVE | 147 | hypothetical protein KgORF105 [Staphylococcus phage K] | YP_024533.1 | 2e-77 (147/147) | | | No putative conserved domains have been detected |
| 137 | 105324 | 106028 | 700 | MRNKKSFQEQLNDMRNKEKW VSEEEFTEEVAPSEEPEVEEEK LYTLNELKENLLDAQGLKDVVA DFPASKDLYEPNKLYICTIPKGY RSTEVQPGQYIGISTGLLSESE DFSHLRGQMPRNLYETSHVLK PLVRINNTNLEYQQHELLEDIKD DKKIYDVELEDLRLVTGEEISHL EIVDSKFFESRINEILDRYTELT DSDDLIYYSKLRELVGSDKMIY CSLLDKCVKIID | 234 | ORF105 [Staphylococcus phage K] | YP_024534.1 | 3e-118 (223/234) | PHA02290, hypothetical protein | PHA022 90 | 4.62e-30 |
| 138 | 106091 | 106489 | 701 | MSRKASIFYILVVIVLAFSISSYYI SSFMYHDKAKNEVSTELSNTG KIKEEKNVEFVGDYTLKKVENN KAYFMETLPTYLPGRTGDNSID MRYYKTSRFKEGVNFKLIRVYT EDGEDNPIHKYRFEAVPTKK | 132 | hypothetical protein KgORF107 [Staphylococcus phage K] | YP_024535.1 | 5e-70 (131/132) | PHA02291, hypothetical protein | PHA022 91 | 7.32e-18 |
| 139 | 106636 | 106878 | 702 | MEMADLERFDTFVRLVSDDEL SEERALELSVDLLNPILEGGTA YQAKKRIRSKFGKIEAKNFKRN YKFLLKSIAQIDQRR | 80 | ORF182 [Staphylococcus phage G1] | YP_240982.1 | 2e-35 (74/80) | | | No putative conserved domains have been detected |
| 140 | 106883 | 107440 | 703 | MIEREKLVKEIEDANRDIQLRLK EVDDYKDSIRSKGTRNYVSTKV LDSVMVGLIISFFLVMLRVLEYF VTGNAVYSPLAPAVIIMFVLALG TWKVSKMNKIVSYRGTIKMYW ELSNAEQNQAKVFKYPNDEVDI VSKHNLRQITFSEINLHLKYMR YNKAVEQHTKLSKELFKKDKET VDKNK | 185 | hypothetical protein KgORF108 [Staphylococcus phage K] | YP_024536.1 | 1e-66 (120/135) | | | No putative conserved domains have been detected |
| 141 | 107476 | 107652 | 704 | MVIPSIKAQNKFKNELEYYKQG | 58 | ORF240 | YP_240984.1 | 8e-25 | | | No putative conserved domains |

Fig. 10HH

| | | | | | | | |
|---|---|---|---|---|---|---|---|
| 142 | 107645 | 107893 | 705 | HISESKMLELAFDYIQELEQNN EYVTNLLEEERYGE VSKFIGVYLFNLLVVALIYTVGF LFFYGVASLVIILTHATIDPFVLA TFLGIGFLVIRTAHRIMARVIND AVAKAIKDKENE | 82 | [Staphylococcus phage G1] No significant similarity found. | | have been detected No putative conserved domains have been detected |
| 143 | 107886 | 108119 | 706 | MNKGEFIMDKTLPKFSVVEVIV KTVIMTPEGSSDLESFYFSTR ELAERFVEENTVETKNGKRVSF AVKERKVNQPG | 77 | No significant similarity found. | | No putative conserved domains have been detected |
| 144 | 108200 | 108688 | 707 | MKVSEEVKQSYLENRANTKMD KISWSELRSSPLGTLGDIIFYSV VIIDNIIAIILTLTLIGTITDSIESTL AQIIVGMFIIITIYGILSALIPILVHK AVSPGWSYTEWNESYYIRLPG EENYKYYSKWYLDLLGVKEFY YKRDNGEEVKEKIYHGLFKLK | 162 | ORF076 [Staphylococcus phage G1] | YP_240985.1 | 2e-52 (104/112) | | No putative conserved domains have been detected |
| 145 | 108724 | 108843 | 708 | LLTNRPLTILEYKKLKKLDKESEI RKQEDLEEYKQYNSN | 39 | ORF076 [Staphylococcus phage G1] | YP_240985.1 | 5e-13 (39/39) | | No putative conserved domains have been detected |
| 146 | 108858 | 109106 | 709 | MISSFDSILLVIYIIIAFAVAMAIIY LVFKGMTILLDKLMMLLSKTTL DVEACSMIMAVISTIVFGIIVLLI WLAVNNILL | 82 | No significant similarity found. | | No putative conserved domains have been detected |
| 147 | 109118 | 109294 | 710 | MDFNDFINSESDRVGKPKQKK KVENKLPSSTPIEDKEKKLKEIR KKSLYIDLRRKRND | 58 | ORF241 [Staphylococcus phage G1] | YP_240986.1 | 1e-23 (58/58) | | No putative conserved domains have been detected |
| 148 | 109287 | 109583 | 711 | MTKETNVLYKDKYRDYTIVVRL AGNIVTEVDKKHKTAFTPIIFDN GVEGVELVMRIGSVELSMTDL REFTKEVSTAQKALEYFNKKLY IKGLTDEAF | 98 | ORF152 [Staphylococcus phage G1] | YP_240987.1 | 1e-48 (97/98) | | No putative conserved domains have been detected |
| 149 | 109631 | 109813 | 712 | MLLGILWFIWGFVSYFVLMFGI EFWKDRWMPGVIGAGALLLFL FWIMKSIHNAMTVVYLY | 60 | hypothetical membrane protein MbpK [Staphylococcus phage A5W] | ACB89144.1 | 3e-25 (60/60) | Membrane protein MbpK | No putative conserved domains have been detected |
| 150 | 109826 | 110197 | 713 | MIDILVIHYEETNKRVLKETIQTI QNHLNDEHGLVKMTATKLSRE NIEKRFNNYNIVIAEDDPDNSYH YGEAVEDADFIIDIPISYLDIHAGI EWDVDNPVDMLDRNPDFIEAV NKLNEDLML | 123 | ORF119 [Staphylococcus phage G1] | YP_240989.1 | 9e-63 (119/122) | | No putative conserved domains have been detected |
| 151 | 110210 | 110557 | 714 | MLNEKLKNLEDTKVYMINSIASL LSASTGKSSKVFFDEGTIKIVSG | 115 | ORF124 [Staphylococcus | YP_240990.1 | 9e-60 | | No putative conserved domains |

Fig. 10II

|     |        |        | Sequence | | | | | |
| --- | --- | --- | --- | --- | --- | --- | --- | --- |
|     |        |        | ETKAVEVIDNLVHPSGRLPIKT TERIALGRLTDSLQFVISEIEVV KDQIIDEENEAYIDFVMEDWNW D | | phage G1] | | (115/115) | have been detected |
| 152 | 110557 | 110835 | MPMDLLTIASVAFIAVVIIDLIND DMSYMLTGTAILINWAGFYGW FFLLQAGMLLFLLLARKVKDDK ESILYSSASLICALGMINLLSFS | 715 | 92 | ORF162 [Staphylococcus phage G1] | YP_240991.1 | 1e-43 (92/92) | No putative conserved domains have been detected |
| 153 | 110905 | 111210 | MSKETIRRQFSNAIEIMATTKE WWNFPKSFDTNKEFIKTFKN DTLVFEVREGSRNLGSFVVFTN IDFDYDKLEGTSTQYMINVFAK KLTKDMFNYHKLQL | 716 | 101 | ORF140 [Staphylococcus phage G1] | YP_240992.1 | 4e-52 (101/101) | No putative conserved domains have been detected |
| 154 | 111225 | 111575 | MREELKPFNRKQVNVKGYLDD VKYSKRRRHKGNQHGCVKITV TDVKINGIPIDHVNIEVGISFYEK LKELQGKRIQFVGTVYKYVKHA RGRKGRIKGFYKEDYSVTLDKK LQKEEK | 717 | 116 | ORF122 [Staphylococcus phage G1] | YP_240993.1 | 2e-59 (116/116) | No putative conserved domains have been detected |
| 155 | 111575 | 111754 | MTEWYALCYYDKVGKKKIPRQ VRAHRDISVLEELKERLEERNP NTEYSIKTTKEFDEER | 718 | 59 | ORF237 [Staphylococcus phage G1] | YP_240995.1 | 6e-21(46/59) | No putative conserved domains have been detected |
| 156 | 111980 | 112390 | VKLEDKVLERIDSLGGKLGDIS QHAWEALVKYQIIYGIIDLIVGIV VIALTLFLWKVFINQHKKVNDM DRDDDYSLLFEDCEDLSGIGLF YVIVTSLISLFAFIYMLYGIPMDIIK ILNPEVFAVKDLIEQAKGGN | 719 | 136 | ORF107 [Staphylococcus phage G1] | YP_240996.1 | 3e-34 (81/136) | No putative conserved domains have been detected |
| 157 | 112392 | 112685 | MKQRDFEFEEDFVLTYECEDC KHFEDWGHDEEPEECSECGS SDLINNTSHEDTECDMCKGYID MWQDGYRYMGDNKAYLEKED SGLICEDCYEKLDI | 720 | 97 | gp ORF160 [Staphylococcus phage A5W] | ACB89153.1 | 4e-47 (93/97) | No putative conserved domains have been detected |
| 158 | 112701 | 112988 | MNKAVEQASNAVGQGFSAMV WHQVLVGLGFILLGLILSLLVWV LVKKFHVPFNHPTAFVVYSIML VSIVASFIWGGLHVINPEYYAL ELKGFIK | 721 | 95 | ORF157 [Staphylococcus phage G1] | YP_240999.1 | 3e-37 (93/95) | No putative conserved domains have been detected |
| 159 | 112999 | 113112 | MTKEELEQRVKELEAENKELKK QIERFEDEGGKTKDE | 722 | 37 | ORF362 [Staphylococcus phage G1] | YP_241000.1 | 6e-10 (36/37) | No putative conserved domains have been detected |
| 160 | 113105 | 113371 | MNSRQKKILTLTVSNFLILALDT VALIRYKKGKIKQENYNTGQITR MHATTANSLGILYLEEQERKEVK | 723 | 88 | ORF170 [Staphylococcus phage G1] | YP_241001.1 | 2e-31 (68/86) | No putative conserved domains have been detected |

Fig. 10J

| | | | | DIKVGTFEIGALKRFTNNK | | | | | |
|---|---|---|---|---|---|---|---|---|---|
| 161 | 113449 | 113754 | 724 | MKGIIFYKEETKEDLGYFLGFIN FKLEGLSYTTEGTLVDNDVVL KDNQINEDNLEQFSMSNNNLVI GILGHSSLSVRIYEKGIRQEFDR VEEYLEELRQ | 101 | No significant similarity found. | | | | No putative conserved domains have been detected |
| 162 | 113754 | 114155 | 725 | MIFILIFGLLFILSLLGIFIYSIVLR KKKQLIEERESFGIYNRTKEKL GDVTRLGYEEDVYKLIHNQSNK TIIEDKKSKVVDTIKKMYELELT SVDVSKVEGLSPLDTEPMTNM KLLSYKLDREGLYSLSKFI | 133 | No significant similarity found. | | | | No putative conserved domains have been detected |
| 163 | 114166 | 114402 | 726 | MEFIDKNNVIKAYDIPNVYLKGY VLQACDKNGDTTAYDGYDQIH YKEGRVLTFPFDKPLRKINVLS GYYKLFKKEDII | 78 | No significant similarity found. | | | | No putative conserved domains have been detected |
| 164 | 114399 | 114926 | 727 | MIYFVSDLHFGHDNIREFEAPT RSHWNSVEEMNEGLIELWNNT ITNNDIVYNIGDFFFNMKPSKYE DILNRLNYKEMILIAGNHDHKKL IKLYERNGITVKYADMIKKDGKR FYLSHYPTLIGRKNMFNIHGHIH SQLMGTEYHINVGYDVEGKIAY SFDDIISRAGEYNGEIQR | 175 | phage protein [Staphylococcus aureus subsp. aureus TW20] | CBI49957.1 | 1e-66 (124/165) | Phospho-esterase or phospho-hydrolase | MPP_AQ15 75, metametallo-phosphatas e family | cd07390 | 2.83e-37 |
| | | | | | | gp43 [Listeria phage A511] | YP_001468613.1 | 2e-18 (65/174) | | | | |
| 165 | 114907 | 115218 | 728 | MEKFKGKDLYKTRIRKQTIKNL VIKTEKLHNKHGKYRPIGHVYY YPKTKEFTLSKPEQKIFIEYMKA LGFSVKHKRRKKIIVYKNVLDE YLSMYQEAIESTC | 103 | No significant similarity found. | | | | No putative conserved domains have been detected |
| 166 | 115264 | 115443 | 729 | MKHFILILGIVILVIALGIVLPAWIL QLVLSAFGVKVSIWVCIGIFILIS AVGSMFSRN | 59 | ORF236 [Staphylococcus phage G1] | YP_241002.1 | 3e-22 (58/59) | | | No putative conserved domains have been detected |
| 167 | 115458 | 115721 | 730 | MAKYESNINGENYIATPSQALR EALAELIREEKNFAEYQTKGEE QYESQLQLRHFDSMISQYEEAI RVLEDRYSPQIFIPKDNKEEK | 87 | ORF171 [Staphylococcus phage G1] | YP_241003.1 | 3e-39 (80/86) | | | No putative conserved domains have been detected |
| 168 | 115724 | 116041 | 731 | MKAESIARFFQDKVLQIEGYKV RFTCASSSYILDTMDESVLFL DTVVFTLSGKYLLDTHITINKPE TLSSNELYTEISNKLQEIVGDQT KTDIELSKYFKEVK | 105 | ORF137 [Staphylococcus phage G1] | YP_241004.1 | 4e-42 (88/105) | | | No putative conserved domains have been detected |

Fig. 10KK

| | | | | | | | |
|---|---|---|---|---|---|---|---|---|
| 169 | 116042 | 116722 | 732 | MSSEAITNHLLNLNQIKIKEYNIH AYIKKSVCSGIENADFEVRINYI ADKDPNYIRTINSIIFVDYSNRN PKEILLQFKEKILSIVKEQVEIDN DFIEAIKDINTNHELEKLEPFINK EYYSMFKSSIEKLVPVALSSEV LNRCTGKTSTLAYLAIEKDLI'LI VSNNSMNKMLKKDYPSVKVSS VEDFSNYNIKGEIVLIDEVDVDQ LYSADRVSVDAILVGIIKN | 226 | ORF055 [Staphylococcus phage G1] | YP_241006.1 | 4e-84 (158/226) | No putative conserved domains have been detected |
| 170 | 116800 | 116958 | 733 | MVGIIILVGLILFLASGYKLVLGK YDDIDLKMLFTIFGIGAILLLTG FIL | 52 | ORF263 [Staphylococcus phage G1] | YP_241007.1 | 4e-12 (38/52) | No putative conserved domains have been detected |
| 171 | 116974 | 117198 | 734 | MNYKEVLEVIKKNKPCKVRFTG SILAIVNKENADTI0KCILQIIVVS NINKNDYIKLQQYCLERDDYTV AGAILF | 74 | No significant similarity found. | | | No putative conserved domains have been detected |
| 172 | 117211 | 117411 | 735 | MNYRDFITDCISCGYKVIISVITE KRVHIISEMTSASYPKKEINLDE LQAYVYYMNNFGSQITTEGL | 66 | ORF211 [Staphylococcus phage G1] | YP_241008.1 | 5e-30 (64/66) | No putative conserved domains have been detected |
| 173 | 117412 | 117702 | 736 | MFLVINIIAVIIGMYGIYFYVTKF STGLSGILIVLGMAVGLYFYLDY LNVRENVIRLVSVMFGAFLFSIE MIYNKIMFEIKKSKYDKTVRTYR GDQ | 96 | hypothetical membrane protein MbpO [Staphylococcus phage A5W] | YP_241009.1 | 3e-40 (85/96) | No putative conserved domains have been detected |
| 174 | 117853 | 118206 | 737 | MNARKARKNTKNHKDSSVVTK EQHLTYYNKINYLIANSSSQCK TYVVMNLRTGYPDFFSLSKIKY LKEIKQHYKDLGFTVQTQVRKS RWSEKSIIRYYFNLGYIDSVLVP IIHISW | 117 | hypothetical protein KgORF115 [Staphylococcus phage K] | YP_024543.1 | 4e-57 (107/117) | No putative conserved domains have been detected |
| 175 | 118225 | 118398 | 738 | MDNPNLNKKTLRAVIREMDKDI EERAEALRREETRLSIARDNRK RLYIELESILEEE | 57 | No significant similarity found. | | | No putative conserved domains have been detected |
| 176 | 118401 | 118625 | 739 | MDFNLKDYAVRPITDKEGNMV VRTVYVCLKREYSDWVVDKVY GRCESSETWLKFMQEIRNIERA KLRVEKWQVN | 74 | No significant similarity found. | | | No putative conserved domains have been detected |
| 177 | 118652 | 118810 | 740 | MSLSELLEYHKNSGKERAEYIS DNGNCRVAIMHYDKWAVVGDL ENAVITIEK | 52 | No significant similarity found. | | | No putative conserved domains have been detected |
| 178 | 118816 | 118917 | 741 | MYLFAKIIISIDVIPLMSIIVVQLIT DYNDRII | 33 | ORF445 [Staphylococcus phage G1] | YP_241021.1 | 2e-04 (24/33) | No putative conserved domains have been detected |

Fig. 10LL

| # | | | | | | | | |
|---|---|---|---|---|---|---|---|---|
| 179 | 119523 | 119693 | 742 | MIIPLILMMTFGTFAFSYVAHDA YRVDEKGIMYAMVVGIVVINVIG LEMIIVECL | 56 | No significant similarity found. | | No putative conserved domains have been detected |
| 180 | 119709 | 120002 | 743 | MIDYLHSEYDKDKLKFILKAIRD FSPRELTYDFRNPKADVSIQEL LGDDIDIFESIALDYPNDINILVG DSGYSIVYQNDFLTISGLSTAM KEVIG | 97 | gp ORF182 [Staphylococcus phage A5W] | ACB89175.1 | 2e-08 (38/92) | No putative conserved domains have been detected |
| 181 | 119999 | 120184 | 744 | MIGFTILSTIMVILVIAMYTQVLV DMIQSIRYDRFDKVLNIVTFIVM TVVLVSGILMFDI | 61 | ORF231 [Staphylococcus phage G1] | YP_241023.1 | 7e-11 (37/61) | No putative conserved domains have been detected |
| 182 | 120293 | 120607 | 745 | MKAIVYCAKRYSKHTLKHILEEL EAENSDLTFSTEISDLGEVDIVS QHTKLPFSELMDLCSKVSKGS DRFYVFVGNHSGYYINGDLYIN EIGKFITSRETNVMM | 104 | No significant similarity found. | | | No putative conserved domains have been detected |
| 183 | 120621 | 120938 | 746 | MIEIRLVEGYDKSQLKFMLKKIK RVAPRELTYDIEAGIDSVDVNIE DVLPHKSPQEYERYSMLLEED LWIVILESGYIAYWDGKKYGGE ALDDIIYNMFKGRGRL | 105 | hypothetical protein KgORF117 [Staphylococcus phage K] | YP_024545.1 | 1e-22 (56/99) | No putative conserved domains have been detected |
| 184 | 120938 | 121234 | 747 | MEVFLSKDYDKDLLKAYLEYIR KSASRELKYNTNHTKGTDVNIE NIISYTNQEVHHFSSYGMYRDD LCVFIDNTRVSEYLNGEPVGVD TIYKYIKEM | 98 | gp ORF185 [Staphylococcus phage A5W] | ACB89178.1 | 6e-19 (48/98) | No putative conserved domains have been detected |
| 185 | 121238 | 121495 | 748 | MFKVYTVYHRQSMKTIKDKLD RSGLIYFLYETWYKDINNVCPS NYNPEFGSLNKDIDIDRLIEAVN EEGILLINHGNYVTVEEW | 85 | ORF175 [Staphylococcus phage G1] | YP_241027.1 | 2e-33 (70/85) | No putative conserved domains have been detected |
| 186 | 121593 | 122201 | 749 | MIDIEIKIWDETLRMQVEEEDVL SFLSKFKNKTTGDKEESYGVGL DESKWKVHPFYTRYEVHPEGY VRLKDTKTPVIFTKYRKELHHK PQFISSNIMDDEGKHTVALHKL VADTFIPIPWYLQGYNYTDLSV GLKDGDYENKEAVKAYNLAWY VGRIRGNAPMIKLMDLEDDRVL YFASIPQIENFIRDNKLDPKRFN YKTE | 202 | No significant similarity found. | | | No putative conserved domains have been detected |
| 187 | 122667 | 122413 | 750 | MEFKFEGTKEELNKEVHNLLKK VNYVYQVNIFENELRNLIDVKE KDYLFSLSVDYNWLMEEKQKD GYNDLASAIYEEYIETYLN | 84 | No significant similarity found. | | | No putative conserved domains have been detected |

Fig. 10MM

| | | | | | | | |
|---|---|---|---|---|---|---|---|
| 188 | 123008 | 123316 | 751 | MDVKEIANTIMELWQMDGYRC TEPPLYESTLNHTRTYTALIVSI KGNYDTVQMFRKTPIMSMRGQ AQPASMLVNVIDDVIIIVYENVV YGVQNKEIKFIEEI | 102 | ORF145 [Staphylococcus phage G1] | YP_241031.1 | 5e-52 (99/102) | No putative conserved domains have been detected |
| 189 | 123520 | 123807 | 752 | MTNKNYLYEEAHTVQGNEITAF RIPNDANGNPRYVVHFMDLNIK LADYDNINKLYGFNKYRAKWF GGGVVFQSYNIEDTLNFALDKV KEIEAVKN | 95 | ORF159 [Staphylococcus phage G1] | YP_241032.1 | 1e-38 (76/88) | No putative conserved domains have been detected |
| 190 | 123857 | 124048 | 753 | MKFKIEKNNSDIKTLWNLAKNG YMSYQTVHNIFKNESDEFIIFNS KQTYNKFMELRYNRSAIQ | 63 | ORF221 [Staphylococcus phage G1] | YP_241033.1 | 6e-28 (62/63) | No putative conserved domains have been detected |
| 191 | 124566 | 124724 | 754 | MLKFKWKNKTIKSTQKTDNILLL IIGGLVATITPKLVNWFLLLQDNI NFLR | 52 | ORF253 [Staphylococcus phage Twort] | YP_238667.1 | 0.012 (21/38) | No putative conserved domains have been detected |
| 192 | 124794 | 124925 | 755 | MKKITTTLNLIGMKNNERFTEEL KNYRQDVTFLKANKIVKYSK | 43 | ORF297 [Staphylococcus phage G1] | YP_241036.1 | 1e-15 (43/43) | No putative conserved domains have been detected |
| 193 | 125091 | 125414 | 756 | MKFIKTIENLLTKAENKGQAILN GRYYDGYRNGELEEKYAIEIEG NKLVMRHWGTQTIEIDLGMKEI VSYYGESNSDRDSLNTLVYCL GIAPNFRYL_PSKDLFIYEN | 107 | ORF135 [Staphylococcus phage G1] | YP_241037.1 | 2e-50 (97/107) | No putative conserved domains have been detected |
| 194 | 125514 | 125915 | 757 | MFKLQNKVEIIVPKYTNSGKEIS SPAIKEAVNNATKICGGCTITEI KGGWWSDDEQRIMEDDNLNL EWYYDKGMQDMNDQQGLLQA LSKIARQLIVFEYEQEAISIKINGT LYIIDYEDLDLLSYDLYELMFKN | 133 | No significant similarity found. | | | |
| 195 | 126409 | 126630 | 758 | MNRLEIVKDTAMEYILMMDNSV MDGVMTQEEYNEAVSFEKYYD YTLSEANQECKFLGGKVLTFLV HEAIEEYA | 73 | No significant similarity found. | | | No putative conserved domains have been detected |
| 196 | 126711 | 126848 | 759 | MRYEIVTLVNGELFMFATFKKA EAENKYQEWCDLYGQENVSM EKN | 45 | No significant similarity found. | | | No putative conserved domains have been detected |
| 197 | 126919 | 127083 | 760 | MTKTIKQLESQLERLERKSDEQ LANGYYEAFERTCAQIRELDLQ IELKKNSETV | 54 | No significant similarity found. | | | No putative conserved domains have been detected |
| 198 | 127321 | 127557 | 761 | MKLLNRDNEIVISIATLESVKQA LIWEYIDHIDNNILDSEIYDQEAV WTSKTLQSIKFADTMEDLQEYI | 78 | gp ORF194 [Staphylococcus phage A5W] | ACB89187.1 | 1e-30 (66/78) | No putative conserved domains have been detected |

Fig. 10NN

| | | | ADINWKLV | | | | |
|---|---|---|---|---|---|---|---|
| 199 | 127649 | 762 | MTNTIKGFLQTEEASTVKDVAT HGVQSGAIGRLIYTSDVVKFFD RHYSDIEAVVLDFLEGFTGQRY YDLLDYDLMRELEEHANVEFE DEDEYNNIQFDLAENIASDEIEG FEDMDEAEQADAVIEAMDDVE LEILDTDKVQFVNLAVEIVAQQ MQEA | 157 | ORF092 [Staphylococcus phage G1] | YP_241038.1 | 3e-63 (120/154) | No putative conserved domains have been detected |
| 200 | 128202 | 763 | MTIKEIINQLQAVENKELELFVC DKEGNNISIKDITLFDSEAEHTE NNPLGINY | 54 | hypothetical protein EFP_gp130 [Enterococcus phage phiEF24C] | YP_001504239.1 | 0.001 (23/55) | No putative conserved domains have been detected |
| 201 | 128378 | 764 | LNIREVHNVVKSAKSKLLQEQN NINNVMIDDYITEELHRRTQRS GTIQMNNNTASYSNGSYGSLE EIREAYDLSSLSTNEIKELLETF V | 89 | ORF166 [Staphylococcus phage G1] | YP_241041.1 | 7e-33 (70/89) | No putative conserved domains have been detected |
| 202 | 128732 | 765 | MRDLQERKRELKTLLFNLAIEK NRATDETLRSVLEEAHQEVGN QLRKVRKEIEILVEEKEREFWN DFDFNGLD | 73 | gp ORF003 [Staphylococcus phage A5W] | ACB88994.1 | 2e-28 (64/73) | No putative conserved domains have been detected |
| 203 | 131537 | 766 | MPHLKAYDKEGNILAIGYNVYT EQGSVIIPNLKPHTKYPQGEFY VSWEGDNYESEKTVVPEFTTL ESSYKEITFYAKDILTVKPKTAY DIAVDNGFTGTEEEWVKSIKGE PGEPGKPGEPGKPGEPGKTG EPGKDFTFDRFTEEQLDSLRVF VNPSDSNLQEVNKTMEDSLIVY PDNGEDIRLYPSTVDKTYFSNIT IRNSIPENTMNPDGSFTLNSNG WLFYTVKAVEKLAPGKTFSAKII TDDVPDPKASFEYSIQDSDGSY IQTITQLNKINDTTFAININNIPEN SSKISLRIDTRQVTSPVNIKQFL LFDGSSTKKIQTVNNEEFIKGLI KEIDNMKISMKKETSYKIPVFTP VDYLIKDHPLVNNIFTDGLGKFS TSLNMENFKLRGGKSYYVDGE NGNDTNDGLSQSTPFKTFKKA QGIINNGDTLYVSDGDYFRVGG TLLPPISNKSINIIGLGSNVNLFM ADEPTWTKTSGRDSTYEFTRS AVRRVVDFNNDREFTNVTSLD KVDTTLFSWYSDGTKVYVNNG | 759 | ORF002 [Staphylococcus phage 37] | YP_240100.1 | 4e-105 (251/690) | No putative conserved domains have been detected |

Fig. 1000

| # | | | Sequence | Length | Match | Accession | E-value (identity) | Notes |
|---|---|---|---|---|---|---|---|---|
| | | | SIEPNKKVVPLLSSQHLIVSSVP TDFYIENLNLYGGARPARFELN QDNSVYINNCVLSYASQVNGN GLEIVGGKEVIVNNSVANNNYM DGFNYHIGADSSKPLVIENCTA LENGFEKGTAGTKSNNGSTTH DGLKAIRVNGIYARNDGGNVAD VNEGTESWNLGCTAFESYQGK DFQTSSGSHMWLDSCIAYGST NSINSSDPNSKIYTRLGSYQNK LILGEEIKY | | | | | |
| 204 | 131859 | 131602 | 767 | MKLYQVEHDNCEPYEDNFHFR EDNVYTNKEKLIKRIKEEGYRE ETNYRGEQEFIKGDPRGFDGM DMITIHELNIVDCDINIKKGN | 85 | gp ORF004 [Staphylococcus phage A5W] | ACB88995.1 | 8e-31 (65/76) | No putative conserved domains have been detected |
| 205 | 132119 | 131874 | 768 | MEFFIDRTSTINKKPIEGAYIKKL ELVDQKGNPFTLERWCVEINSL EELTEISKHEGEVIINTRGDSPF SPYLEIYDYYRE | 81 | No significant similarity found. | | | No putative conserved domains have been detected |
| 206 | 132289 | 132119 | 769 | MERFKVKRIITTEEVRYIDAETE EDAWYSVEYEDEGTDTAHFNA EYGEWSYEKEEN | 56 | gp ORF005 [Staphylococcus phage A5W] | ACB88996.1 | 1e-19 (49/56) | No putative conserved domains have been detected |
| 207 | 132773 | 132291 | 770 | MNKTFFKAIGKNTLEYSKQGLG FLVALLIMLIILSVFLAFIIGIPAGII YGLYALDINNYFITMLVTVEWFII LYGIVRTQDNKKPFVKLKLKDY LLTLYLTTITATSVLESVLLFKVL PFTGDTRAVITLLSFLLFLAVNR GICKIVIKSYKEYKEEN | 160 | ORF087 [Staphylococcus phage G1] | YP_241049.1 | 4e-65 (129/160) | No putative conserved domains have been detected |
| 208 | 133017 | 132766 | 771 | MIFKKHKEEVKKDINFIRIHDV SGTSTIIKQKDTKTNLNSFIGGL VFNGVKFLESNKGDTSIWFKD NIIHIDTVYYKEVADE | 83 | No significant similarity found. | | | No putative conserved domains have been detected |
| 209 | 133262 | 133017 | 772 | MAYEYKNKIQDIITDNENYWCID NEKELEELQEVYQKAEAFDEIV NEFHYQLQNLESWNTLDQKDC QTLKQILEENIKEE | 81 | ORF103 [Staphylococcus phage G1] | YP_241047.1 | 3e-17 (46/51) | No putative conserved domains have been detected |
| 210 | 133682 | 133266 | 773 | MNIKYIDLVLENCDVVRLEPKD VKRFHVDGITEGIDYYGTSHISR TRRCTYFGILIDNPKEISQVGFA YPDNTNAYEMITAYSDITAIDIIY DDDTNEYTYVDFNEYNDYYNIN QKNEYYNNMLEVTITESNSIEE EG | 138 | hypothetical protein KgORF2 [Staphylococcus phage K] | YP_024433.1 | 2e-61 (121/141) | No putative conserved domains have been detected |

Fig. 10PP

| 211 | 134191 | 774 | MKETKEYIMFWGKEDIYSNFYP ITFKHKGRTFNNSEQAFMWRK AQYFKDWQIAGEILNAKHPNHA KSLGRKVRNFNEEQWNKVRY DIMVEVVKDKFMTTHLKQKILD TDLRKDFVEASPYDKIWGVGIK ANDPKILDESNWKGQNILGKV MEDVRVHCVYNRFK | 164 | hypothetical protein KgORF4 [Staphylococcus phage K] | YP_024435.1 | 1e-84 (146/162) | | Riboflafusio n conserved hypothetical protein, ribA/ribD-fused | TIGR02 464 | 2.80e-55 |
| 212 | 134602 | 775 | MKKRYFKGLKLNDFEKEVFGL KKNKRYKKMNKELGRNEPKYW NYDMSFFIQLYADLNAFVESSN HVDMEYHTFTDIEGKERTQIDM IKHILSLIQFYHESMDSFDVDNE DEIEQVQNKILDNFKIVLPSLWN | 132 | hypothetical protein KgORF5 [Staphylococcus phage K] | YP_024436.1 | 2e-55 (114/132) | | No putative conserved domains have been detected | | |
| 213 | 135306 | 776 | MAIYVVPDIHGEYQKLLTIMDKI NNERKPKETIVFLGDYYDRGKR SKDVVNYIFDLMSNDDNVVTLL GNHDDEFYNVMENVDRLSIYDI EWLSRYCIETLNSYGVSTVTLK YSSVEENLRSNYDFIKSELKKL KESDDYRKFKILMVNCRKYYKE DKYIFSHSGGVSWKPVEEQTID QLIWSRDFQPRKDGFTYVCGH TPTDSGEVEINGDMLMCDVGA VFRDIDLPFFIKLEGNS | 235 | putative protein phosphatase [Staphylococcus phage K] | YP_024437.1 | 1e-130 (227/232) | Phosphatas e | Putative protein phosphatas e | PHA022 39 | 6.31e-126 |
| 214 | 135957 | 777 | MVNVLPSVYDAEKGEWVTLLA KPIAEEVFKIMKADYLEHKGNIG FFISKYKDGDSSIEQHNVVVFY NEKDYDTMELTESELTDALNEY IDYTLDGKYKPFSLNNFINYLED YGYRLPVNFEVDVTIILSDGQK FTYPRTSSITNNASIVDALKSED QYIEVKYIYNDHAIDDKKLAHGN DTLK | 183 | hypothetical protein KgORF7 [Staphylococcus phage K] | YP_024438.1 | 6e-99 (180/183) | | No putative conserved domains have been detected | | |
| 215 | 136293 | 778 | VERTLNLYDSKGKLLKSSEKIT GASAKIIIEKLTPNTVYSQGSFKI SWTINGKESILTDVPEFTTKSN EDKQEIVFNTLNIDSNSFVVSET EPSDKSKLWFKPIN | 105 | ORF138 [Staphylococcus phage G1] | YP_241056.1 | 1e-51 (104/105) | | No putative conserved domains have been detected | | |
| 216 | 136999 | 779 | GGACUCUUAGCUUAAAGGUA AGCCAACCGCUCAUAACG | | | | | tRNA1-Met | | | |
| 1b | >137359 | 780 | KYLLKHSKEADIRSTSKIMDSID KLT | 26 | hypothetical protein KgORF8 [Staphylococcus phage K] | YP_024439.1 | 2e-14 (25/26) | | No putative conserved domains have been detected | | |

Fig. 10QQ

| orf | Putative function | orf | Putative function | orf | Putative function |
|---|---|---|---|---|---|
| 29 | tail completion and sheath stabilizer protein | 127 | EndoVII packaging and recombination endonuclease VII | 192 | DNA topoisomerase subunit |
| 30 | deoxynucleoside monophosphate kinase | 128 | anaerobic NTP reductase large subunit | 196 | rIIA protector from prophage-induced early lysis |
| 38 | tRNA1-Tyr | 130 | anaerobic NTP reductase small subunit | 197 | rIIB protector from prophage-induced early lysis |
| 39 | tRNA2-Lys | 133 | glutaredoxin | 199 | endonuclease IV |
| 40 | tRNA3-Asn | 142 | sigma factor | 202 | nuclear disruption protein |
| 41 | tRNA4-Asp | 147 | alpha-glucosyl-transferase | 205 | topoisomerase II medium subunit |
| 43 | tRNA5-Met | 148 | recombination endonuclease subunit | 207 | activator middle promoter |
| 44 | tRNA6-Gln | 149 | recombination endonuclease subunit | 217 | AsiA anti-sigma 70 |
| 46 | tRNA7-His | 151 | RNA polymerase binding | 218 | holin |
| 47 | tRNA8-Ser | 152 | sliding clamp DNA polymerase | 219 | distal long tail fiber assembly catalyst |
| 48 | tRNA9-Ile | 153 | clamp-loader subunit | 220 | L-shaped tail fiber protein |
| 49 | tRNA10-Trp | 154 | clamp-loader subunit | 221 | hinge connector of long tail fiber distal connector |
| 50 | tRNA11-Gly | 155 | translation repressor protein | 222 | hinge connector of long tail fiber proximal connector |
| 51 | tRNA12-Pro | 157 | DNA polymerase | 223 | long tail fiber proximal subunit |
| 56 | tRNA13-Met | 159 | immunity to superinfection membrane protein | 224 | RNaseH ribonuclease |
| 60 | tRNA14-Leu | 160 | thymidylate synthase and pyrimide hydroxymethylase | 225 | dsDNA binding protein |
| 61 | tRNA15-Arg | 161 | beta-glucosyl-HMC-alpha-glucosyl-transferase | 226 | late promoter transcription accessory protein |
| 62 | tRNA16-Thr | 163 | RecA-like recombinase protein | 227 | loader of DNA helicase |
| 71 | nudix hydrolase | 164 | head vertex assembly chaperone | 228 | ssDNA binding protein |
| 73 | lysozyme | 165 | DNA primase-helicase ATPase | 235 | dihydrofolate reductase |
| 75 | internal head protein | 167 | protein spackle precursor | 237 | thymidylate synthetase |
| 79 | autonomous glycyl radical cofactor | 170 | DNA primase subunit | 240 | aerobic NDP reductase large subunit |
| 81 | RegB site-specific RNA endonuclease | 172 | dCTPase pyrophosphatase | 241 | homing endonuclease |
| 83 | valyl-tRNA synthetase modifier | 174 | small outer capsid protein | 242 | aerobic NDP reductase small subunit |
| 87 | thymidine kinase | 178 | ADP-ribosylase | 243 | endonuclease II |
| 90 | putative lysis inhibition regulator | 179 | Srd anti-sigma factor | 244 | RNA ligase A |
| 92 | putative lysis inhibition regulator | 181 | DNA helicase | 245 | inhibitor of host transcription |
| 120 | thioredoxin | 183 | exonuclease A | 250 | polynucleotide 5'-kinase and 3'-phosphatase |
| 125 | protease inhibitor | 186 | cef modifier of suppressor tRNAs | 254 | dCMP deaminase |

Fig. 11B

| orf | Putative function |
|---|---|
| 257 | head assembly cochaperone with GroEL |
| 258 | lysis inhibition accessory protein |
| 268 | DNA ligase |
| 270 | RNA polymerase ADP-ribosylase |
| 272 | baseplate tail tube initiator |
| 273 | baseplate tail tube cap |
| 274 | baseplate hub subunit, tail length determinator |
| 275 | base plate distal hub subunit |
| 276 | baseplate hub subunit |
| 277 | baseplate hub assembly catalyst |
| 278 | baseplate hub subunit |
| 279 | baseplate wedge subunit |
| 280 | recombination, repair and ssDNA binding protein |
| 282 | RNA-DNA and DNA-DNA helicase, ATPase |
| 283 | RNA-DNA and DNA-DNA helicase, ATPase |
| 284 | minor capsid protein |
| 285 | outer capsid protein |
| 286 | DNA primase-helicase subunit |
| 289 | RNA ligase |
| 291 | precursor of head vertex subunit |
| 292 | precursor of major head subunit |

Fig. 11C

| orf | Start position | Stop position | SEQ ID NO: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 1 | 1321 | 2 | 782 | MKKNKLIEKWQPLLENEALPEIV GASKKALIAKIFENQEADINQAP EYRDEKIAEAFGSFLSEAEIGGD HGYDAQNIAAGQTSGAVTQIGP AVMGMVRRAIPNLIAFDICGVQ PMSNPTGQVFALRAVYGKDPL AAGAKEAFHPMYAPDAMFSGQ GATEKFEAVKAGAALTVGDIVV HDFAQTGRAHLQVVEDFTVDA GATDAAKLDAAVTAALEAGKVV EIAEGMATSVAELQEAFNGSKD NPWNEMGFRIDKQTIEAKSRQL KAQYSIELAQDLRAVHGMDADA ELSSILATEIMLEINREVVDWINY SAQVGKSGMTQTVGSKAGVFD FQDPIDIRGARWAGESFKALLF QIIDKESAEIARQTGRGEGNFIIA SRNVNVLAAVDTNVSPAAQG LGRGYNTDTTKAVFAGVLGGR YRVYIDQYARQDYFTIGYKGAN | 440 | gp23 major head protein [Enterobacteria phage IME08] | YP_00373431 4.1 | 0,0 (379/400) | major head protein | Major capsid protein | PHA025 41 | 0,0 |
| 2 | 2154 | 1342 | 783 | MLKELLMTEAKTIDASVALDSIF ESVQLSPEAKANFSTVFEATVK KHAVALAESHIEKIAEKAEEKVE EEKEKAKEEAREELKEAASKYF DHIAAEWMAENQLAVDRGIKAD LFESMFVGMKELFVEHNVVIPE ESVDVVAEMEEELAEQKAETA RLFEEVSKRDEYINYAQREYAI QEATRELTDTQKEKVVSLTEGM DYSDAFSTKLKAIVEMVQGSVE QSVTESADINTIDKEADGLNFTT EAVEETPATKTPSVMDAYVAQA ARLS | 270 | gp22 prohead core scaffold protein [Enterobacteria phage IME08] | YP_00373431 3.1 | 1e-89 (187/272) | prohead core scaffold protein | Prohead core protein | PHA025 57 | 5,11e -58 |
| 3 | 2837 | 2187 | 784 | MENLNEQLLIEHWGQPGDVIDG KPMLLESIIVEGENESGLKPGLYI EGVFMQAEVVNRNKRLYPKRIL ETAVSRYIKEQVATRQALGELN HPPRANVDPMQAAIIEDMWWK GNDVYGRARIIEGDHGPGDKLA ANIRAGWIPGVSSRGLGSLKDS GKGYNIVQEGFRLTVGVDAVW GPSAPDAWVQPKQISENTSAQ VANSADDAFMALAEKLKAL | 216 | Prohead core scaffolding protein and protease [Enterobacteria phage RB69] | NP_861875.1 | 4e-95 (175/212) | prohead core scaffolding protein and protease | Peptidase_U 9 | pfam03 420 | 2,86e -88 |

Fig. 12A

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 4 | 3262 | 2837 | 785 | MLILPENHELVIDTVEALLPEAQ ARFDKLSAALSKODINKIVENLV VSEPDLAIALGSINESLQLNEFIV KHVDSKGTITRTKDRKTRERNA FQTTGLSKAKRRQIARKAVKSK RANPSAQTRGLRKRKKALKRR QALGLS | 141 | gp68 prohead core [Enterobacteria phage RB51] | YP_002854127.1 | 8e-48 (105/141) | prohead core protein | Prohead core protein | PHA02586 | 2,69e-42 |
| 5 | 3486 | 3262 | 786 | MENYISAIESRDLVAAKKAFGAI MAERTSGLIEERKKFIAASVMIE GEEPEDEDEDEDEDKSDKD EDDEDE | 74 | gp67 prohead core [Enterobacteria phage RB51] | YP_002854126.1 | 2e-05 (29/50) | prohead core protein | Prohead core protein | PHA02608 | 2e-07 |
| 6 | 5054 | 3486 | 787 | MAFHILDLFAPWEKRDEAEYKQ QINNDLESITAPKFDDGAREVE SNENEIQYNSFNQMMFGSNEP GMKTTADLINTYRSLMNNYEVD NAVEEIVSDAVYYEDGHPVVSL DLDSTDFSQAIKDRILEEFNTVL TCLNFERKGADHFRRWYVDSR IFFHKIVNTKKMKDGIQELRRLD PRNLQFIREIVTADDAGTKIVKG YKEYFIYDTGKESYYADGRLYS AGTKIKIPRDAIVYAHSGLVDCS GQNIGYLHRAVKPANQLKLLED ALVIYRITRAPDRRVFYIDTGNM PSRKAAAHMQHIMNTIVKNRVV YDASTGKIKNQQHNMSMITEDY WLQRRDGKAVTEVDTLPGMSG MSDMDDVRYFRTALYMALRVP LSRMPDANNQGVQFDAGTAI TRDELDFAKFIRRLQHKFEEIML DPLRTNLILKKVLSKDEWEDEIN NIKIVFHKDSYFTELKDAEVMER RINMLTMAEPFIGKYISHKTAMK DFLQMSDEEIEQEAKQIELESK EARFQDQENEEDF | 522 | gp20 portal vertex protein of head [Enterobacteria phage JS10] | YP_002922513.1 | 0,0 (404/502) | portal vertex protein of head | Portal vertex protein | PHA02531 | 0,0 |
| 7 | 5672 | 5085 | 788 | MFCTYLTIYTGNKLPRRYIGSTS VSRIIDENYHGSVKSKKYKDLW KSEQHDNPHLFKTRILNTYETR EEASKAELELQIKYDVVKSSSYI NMALAQPNGFFGMSTKGRKMS EESKEKQRHQRLGIKRPDHSIK LSGRKRPDHSKAMSGERNPMF GKEHPNKGKKINQPRMTCPVC | 195 | No significant similarity found. | | | | No putative conserved domains have been detected |||

Fig. 12B

| orf | Start positi on | Stop positi on | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | GVESTRSAIMRYHKACLSSI | | | | | | | | |
| 8 | 6203 | 5712 | 789 | MELTDITRAFESGDFARPNLFE VEIPYLGRNFSFKCKAAPMPAG IVEKVPVGYMNRKINVAGDRTY DDWTVTIYNDDKHEVRKAIIAW QAQAHAQGNDISGMTPADYKK VATVRQFSRDGKTITNEHTITGL WPTNVGEVQMDWDSNNEIETF ETTFAIDWWE | 163 | Tail tube protein gp19 [Klebsiella phage KPP95] | ASS46617.1 | 2e-92 (162/163) | tail tube protein | Tail tube protein | PHA025 51 | 5,59e -72 |
| 9 | 8304 | 6331 | 790 | MPLVSPGIELKETSVQSTVVLN ATGRAAIVGKFQWGPAYQVTQI TNEVELVDMFGGPNNQTADYF MSAMNFLQYGNDLRTVRVNR EAAKNASPLVDNIEWTITTAGS NYEVGDKITVKYADQTVDDTGS VTEVDSDGKIKSVFIPTSKIIAYA KSINQYPDLGSSWTTTITSQSS GVSAVITLGKIISESTVLLTEHET AHEEMTKTEFQTALAQYKMPGI VAAYPGELGNQLEIEIVSKAAFD KGEQLTIYPSGGQRASTAKAVF GYGPQTDTQYAIIVRRDGAVVE SAVLSTSRQDKDIYGNNIFMDD YFSKGSSRYVFATAQGWPEGF SGVIRLGGGVSANESVTAGDLI QGWDLFGDREALRVNLLIAGAC AGETDEIASTVQKHVSSIADER QDCLALISPPRSTIVNIPLTRAVD NLIDWRQGDGTYDSANMNINTT YAAIDGNYKYQYDKYNDVNRW VPLAADIAGLCARTDDIAQPWM SPAGYRRGQILNCIKLAIEPRQA HRDRMYQAGINPVTGQGTGEG FILFGDKTATTVPTPFDRINVRR LFNMLKNNIGDSSKWQLFELND NFTRSSFRMETSQYLAGIKALG GVYDFRVVCDTTNNTPAVIDRN | 657 | Tail sheath protein gp18 [Klebsiella phage KPP95] | ASS46616.1 | 0,0 (645/657) | tail sheath protein | Tail sheath protein | PHA025 39 | 0,0 |

Fig. 12C

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | EFVASFYIKPARSINYITLNFVAT ATGADFDELIGPQ | | | | | | | | |

Fig. 12D

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 10 | 10176 | 8338 | 791 | MEQTQPFNVLSDAHPLNDGKL TVIRHPSEMETKIENGVRFFKS QWDDKWYPEKFEDYLKLHGIV KIRLQGEDPAHFQTFKDKNNKR TRYMGLPNLKRANIKMQLTREI VAEWKKCRDDIVYFAETYCAIT HIDYGTIKVQLRDYQRDMLEIM AAKRMTCCNLSRQLGKTTVVAI FLAHFVCFNKDKAVGILAHKGS MSAEVLDRTKQAIELLPDFLQP GIVEWNKGSIELDNGSSIGAYA SSPDAVRGNSFAMIYIDECAFIP NFIDAWLAIQPVISSGRRSKIIIT TPSGLNHFYDIWTAAVEGKSGF TPYTAIWNSVKERLYNDEDMFD DGWQWSLQTISASSLEQFKQE HCAEFHGTSGTLISGMKLANMD WIEVTPDSHGFYKFKEAEADHK YIATLDSAEGRGQDYHALNIIDV TTSEWEQVGVLHSNTISHLILPD IVIKYLMEYNEAPIYIELNSTGVS VAKSLYMDLEYENVICDSIVDLG MKQTKRSKAVGCSALKDLIEKD KLIIHHRATVQEFRTFSEKGVS WAAEDGYHDDLIMSLVIFAWLT TQQKFADFVDKDEMRLASEVF KRELEDMNDDYAPVVFVDAVN SAEYAPQEHGLSFV | 612 | gp17 terminase DNA packaging enzyme, large subunit [Enterobacteria phage T4] | NP_049776.1 | 0,0 (506/608) | terminase DNA packaging enzyme, large subunit | Large terminase protein | PHA02533 | 0,0 |
| 11 | 10663 | 10154 | 792 | MSELQLDMAKLLDIEGIPGIEGQ EIPVYEKLELVEVKSNPNDRKP DLEDDYSVVRKNMHFQQOML MDAAKIFLETAKNADSPRHMEV FATLMGQMTTTNKEILKLHKEM KDITSEQVGTGKGANPQQGMN IQNATVFVGSTADMMDEFGDA YEAQEAREKIVNGTDSTV | 169 | gp16 terminase DNA packaging enzyme, small subunit [Enterobacteria phage T4] | NP_049775.1 | 0,0 (130/160) | terminase DNA packaging enzyme, small subunit | Small terminase protein | PHA02585 | 2,22e-59 |

Fig. 12E

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 12 | 11484 | 10660 | 793 | MFGHWYNSSLRRYIVLLGDLFS HVQIARWREDTGLKYIKVPITYA SKEKFLSQLGKWTAIQSTENKA KIETVLPRMNLHLVDMQYNAMY KTSQLNRTKSYKTPSKITSQYN PTPIKMIFELGIYTRNQDDMYQII EQIVPYFQPHFNTTITELYDKDT SFNRDVRIVLQSFSQDEAVDGD NITRRRLEWSLMFEVNGWLYP PVAEIDGEIRTIYLDFFANSKELT PEGNFESVDSEVTPRDVQHEN WDGSSKQTYSHDIPIPVNPEAP GPRGEK | 274 | gp15 tail sheath stabilizer and completion protein [Enterobacteria phage JS10] | YP_002922250.1 | 4e-113 (194/273) | tail sheath stabilizer and completion protein | Tail sheath stabilizer and completion protein | PHA02556 | 3.5e-117 |
| 13 | 12302 | 11526 | 794 | MSTFDSRLFAKLEDYRGYNKTN ETEILNPYVNFYNHRNSQTLAD ALSAEAIQMRGIEFYFLPREYNN PDLLFGEDPSSKFTKAWKFAAY LDSFEGYSGDNTFFSKFGMMV NDEVNLTINPNLFKHQTNNSEP KAGDLIYFPMDNSLFEINWVQP YDPFYQLGQNVQRKITAQKYIY SGEQLQPELQRNEGINIPEFSE LDLEPIKNIDALADISDIQYAESD EINKEASEYV-HPYVVNNGRGLE SPPKADSFDDGFFE | 258 | gp14 neck protein [Enterobacteria phage JS98] | YP_001595290.1 | 4e-115 (199/258) | neck protein | T4_neck-protein | pfam11649 | 7.29e-94 |
| 14 | 13247 | 12306 | 795 | MSYNTYNPKTLKDAILRRLGAP VINVEVTEDQIYDCIQRALELYG EYHFNGLNKGYQVFYIGKDEAD NARFLNGVFDLRGRNVFAVTQI VRTNVGSLTSMDGNATYPWFT DFLMGMAGINGGMGSSCNKSY GPNAFGADLGYFTCLMTYWSM MODLLAPLPDYWYNSDNEMLK VMGNFMKGDIIVCECWTKSFM NTDAMVGNTAGYGFAGPQTAD HWGLGDRYQNPDLRNNGQYA GEGNTNREGAYNNRWVKDYA TALTKKLWGEILFKHQGLQLAG GVTVDGQTLKVEAQEEIERLRE ELDLILDPGCPILLG | 313 | gp13 neck protein [Enterobacteria phage JS98] | YP_001595289.1 | 2e-123 (223/314) | neck protein | Neck protein | PHA02554 | 9.45e-117 |

Fig. 12F

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 15 | 15071 | 13305 | 796 | MTKLVDSLPFVDGIPDDFQQRI NWIKNTEPLNGASTRYGNDGE LNRASVQIQKNVVQVHNDLNNV GTAVENIQVDVDQIKKSLEITGS SDAIEQVYINKKNIEKHDGQILKL EEDTEKLRTDLDFLEEDVGVYD SSKDDYYRTVRDNIWVKREIG AYPGQDINGQPKQDSPGSGMK YRIINNASAIVKHDERIQALEDAY NDSDVGSLTIEVNDLRKEVGPK SGATSASIYARLVNNADAISAAN NEIFAINQAIDFTNPVKIGARTTR LENDYRIVDATLNFAQTGLVPR VNNIDARLGSSDKPDTIEGKISS LSTDQGYISDVVGRDTSSGLQG QVAWINQQVGIVPSEQPIPPGSI LARMTNVEGMQNSQQSAIQDI QVELGNNNEGLKGSVFTLQTQ MNGDFSSENPVQRDGVYATW ELQDKFVTAVTDVEQAGAYLRK QGEWFKKPSSIGEFSKEDFTVD LSSDALVNPNSLVAAPFNAGIRI VDDIVDDDGVFCVETDTVIEA SDSDKGVKIVILVNNIEVFSYGL GVKAVTGEQLIKTKKLIEFSSGD AIKIVYRAASEESQVLVKIKSLDI TIHPAV | 588 | Fibritin [Klebsiella phage KPP95] | ABH10666.1 | 3e-124 (221/225) | fibritin | wac, fibritin | PHA026 07 | 3.25e -111 |

Fig. 12G

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 16 | 16426 | 15080 | 797 | MAQNNYNHYSDLAKYTIFDPTN TQWPVAIKDVQSALELIGSWAR TDTGLPVASPTVAGVIRTATQA EVDAGTIGNAAVTPATLKSTVT RPEATTTVLGLTRYATNTEAAA LTAGNRTTAAALGHVFKTVKA QENVDGTVRLTTAAQAQAGTD ETTAVTPKRVVEMIGKFSVSPP SYTSATESNLGLVRVATQAQVA AGAVHDGYAVTPKTFMASKAS DSVFGIVKFAKDSDVASATSNN LAVTPKSLQALKSTKDKYGLTR LSGSPTTDASLAAAATDAVFKT RRINGKTLDNDITITNNDINCYT RQESDGRYMPAGTRVGNVTW VEGQSWISRGATFTCNAPWEA SSRLALNVNVKFERNNDGYDN RIFRFVVIVNGSQWGGELTLNIE NTKGGRNGHSWRFEAYASSNF FFNNIPPNATVGIRPTEDSRIIFY DCMLTFCTNRP | 448 | gp12 short tail fibers [Klebsiella phage KP15] | YP_00358004 3.1 | 2e-52 (123/310) | short tail fibers | Long tail fiber, proximal subunit | PHA025 84 | 3,81e -17 |
| 17 | 17097 | 16426 | 798 | MTIETKTREGAKVNSRLAAFSE YRVDPQNIAVGNTAPIGSLTFE QMDLGVWYPNTEAAINDLMSL QSAEIGTIICNDTGISPQPAQQIT RATFSGVVALEPKEDGSVGDP VIIHILGLPIRIANGDDFAAVATR WYDKVKELEAVGKVVQQVTQS PATPQYVDIIHLDYQNHNFETYK KYGLTVEFTITSPAKAGYGQWD AIGNESKTFGANTFTFHYFRRM G | 223 | gp11 base plate wedge completion tail pin [Enterobacteria phage RB51] | YP_00285411 5.1 | 5e-27 (68/215) | base plate wedge completion tail pin | Baseplate wedge subunit and tail pin | PHA025 8 | 4,15e -49 |

Fig. 12H

| orf | Start position | Stop position | SEQ ID NO: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 18 | 18922 | 17099 | 799 | MKQNLIVGQSVDDGSGDYLRK GGLKINNNFDDLYSELGDGSVP FAAGAWKTFKASPTGTTLNAKF GQAFAINTQAARVNVQLPKGTA NDYNKVIKLRDVWSTWRLSPIT VIPAQGDTLKGSASPKIFNTNFQ DLELVYCAPGRWEYIENKTVDK LTNGNLSTVAKKSIIATAGQTDF LNIFDGVEYNEDSLNVYRRGNIL YYGETSVMDKANADYGSPGTV AGQLVELNGKDIRLKVPCVEGE VITFETFLDGIGVYRSSYNKLAI QIRDSAQTTSQTIPGSIIVDNLTA LRRITLDDMGVLPGVGVNPNSL EISLNGKELLEAGTAGLPLFYCE GAEGGYAEDCINNGGQWVNS NQDYRLEFDSTGTNVEAIIFGEA FEDKDLLTVRWFNNNIGTTMDI DDIMAETDQVYMNAEQLVTLKN RIEYTNYDEPNQKNMRPVADDI MIKVNNIAAFFDVIYPIGTIYENA HNHANPADYMGFGVWKLYSQ GRVTAGWNNDSSDPYFSRNN NNLNENGQPSLTAGGTVGDLT FTLGKEHIPELMSRDKVLISDPE HGSVVIGGCQLDPDAQGPGYS KYREDTVAVNNGVVPNDITKIQ PTITVYRWIRVG | 607 | gp10 baseplate wedge subunit and tail pin [Klebsiella phage KP15] | YP_003580041.1 | 0,0 (323/611) | baseplate wedge subunit and tail pin | Baseplate wedge subunit and tail pin | PHA02582 | 0,0 |
| 19 | 19833 | 18922 | 800 | MYTDKGKKIIDVGEIGNASTGDI LYDGGVKINDNFDAIYNAFADQ RLFAAGGGALNQKIHATSYYQK IKFGDANSAGTVPMGSCIDADC SEGAVQIRLSKGKAGEAVFVVN SNGSASKARSIKITTNGEGVAD AFKDGSRELIINTPRCRIELWCV EVKANGAAVWDYSISSMFGST YSPLEATYNLTSSPINIRLGYND DYSTVKLLLSFSANPGGQTIKR QSSEVMLMDPTITSSAPNGRV FDTEYAVLRSGESSENEKMYSI SYSINAQKDLICTASTSYGNARL AYKVIATQTVGVSQ | 303 | gp9 baseplate wedge tail fiber connector [Enterobacteria phage JS98] | YP_0015952841 | 6e-60 (134/302) | baseplate wedge tail fiber connector | Baseplate wedge tail fiber connector | PHA02581 | 6,6e-67 |

Fig. 12I

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 20 | 20924 | 19899 | 801 | MSNSTRASSTRSTIYRAIITSKF RTEKMYTFYKSIGPGTDQNTLY VSFGKSTPWSDNESEPGFAPP YPADNGDGVVDVWTNMMGAV KIESSMLDCVVPRRDWGDTRY PNPRTFLIGDIVVANSAPYNRTD AGFGWMVYRCIDVPKDGMCSI GNLTSKEECIKLGGKWTPSTIS GSAPRGRGDANGTVDLGDGYL WEYLYEIPADVSINRCTNEYIVV PWPEEIEESPARWGFQNNLTW QQNDFNLIYRMKCNTIRFKAYL DAVYFPEFSLPGNTGFRQLSIIT NPLEVKPMPNSPNVKAEKGWY SASGLERQSGEMIYMENRQPII RSMDQTEELNLIFEF | 341 | gp8 baseplate wedge subunit [Enterobacteria phage JS98] | YP_001595283.1 | 9e-146 (238/330) | baseplate wedge subunit | Baseplate wedge subunit | pha025 80 | 1,08e -164 |
| 21 | 24015 | 20917 | 802 | MTIAPFVTSLRIHKLSANQVNIR WDDVGANFYYFVELAETRNRA GEIIPADNLSWSSLGYTADNDW FEQNRIEPLTYYKMRVQTTSAG FEPSEWVETEEFQTFEENAYTF EHMQEFSLVKEFIKQKFSLNNM SYVNFNTSAMMASLMTESFQF SPEYSHLSAIENFVVGESGYHEI QGPIEAVCVDKNRTMLGEIDGIL YLFERFQHMVKVSNDKGQNW QYVQLFNDRVGNPVSRVVIYQS STTSYVLGYDKIFYGRKSSDVR LKLGFEVELFGTYASLPADVTK YAEAFTCNDDHLYVVAKDTVRR VKLKDAPIDTDPLSPTFGEKVFE KEASHITGNPKSVCFKMDSVG GKIFALITGEVKTLGLDPTDPRN VVDSATKGVYVYQEDTNTWKR VFGNTDEEKRRIEHLWTSMSTD GKEIFFSSANFKTTEYTQDIELE TKYPELISTAVKNVNPIQYHSDK HYHMMSFRADEFSRWETFVPG PMRFYAEPWFVWMAREGNRC WISTADHAVVIYNDILYQKRVDA AAQGTTERVLSEVWDKGDATF YCPPVSFNGFLQYASGIMFHEP | 1032 | gp7 baseplate wedge initiator [Enterobacteria phage IME08] | YP_003734295.1 | 0,0 (667/1029) | baseplate wedge initiator | Baseplate wedge subunit | PHA025 79 | 0,0 |

Fig. 12J

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | DGKLIGYYAFDYRVRDQVTLN WKPTDVMFKAFLQNQTREEDW TPEHTPGLRDPDLRPYLTKMM PDSYLLQDSNFEQFCKYYLQFL SDGNGTHYNSLVNLVKNKYPR EENAWEYLWSEVYKRNIYLSKD ARDAVVRFFEARKNDFYATKGI EDSYKFLFKLLYNEDVEIDIESK NTTEYDIIVESTNISDDLVGRTIY TASGRSNVTYIEREYRDGRLLW RITIHNLSGRFIEGQEIKSERTDF EGIIVQGVRGKDMLSNNIDYINR SRSYYVMKIKSQLPTSRFRDDV LRFVHPVGFGFIGITLLTMFINS GLNMKHVETIINKLKNYKWDAG LPSVYPDRVAIIASDDTIERDPIT NEPRYSSRAQAGEPFPLPANY NQENNNSIIAGQNPGQRRKPLS PTFDQSAVTFANYRDLVNQRLK DDAGNPRDPENPTQVKIDE | | | | | | | | |

Fig. 12K

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| 22 | 25970 | 24012 | 803 | MAIKEPLNYQLTRTANAIPDAFT GATFDEIKNQLINWLSGQKEFQ DFDFAGSRLNVLLDDLLAYNTLYI QQFSNTALYESFIGTANLRSSV VQAAQQNGYLPSSKSAATASIM LEVTHMNPSSTLRVVIPRGTKF LAYSKSDKANPYNFVVTENVVA IRDNDQKYWPIVNLAQGRIIRTQ LSYDPKKPIVIRDQSIDRKQVKL WVDGAEWTNWTDRSMVHASS ISTIYYMRETVDGNTEFFFGEG VAEASVAGGVLESNFIGGLKPT KGAQVVIEYIRTDGEAANGATE FSYADTLQYVVNRIIENWSDSP DYVGADGGGEPEDIERIRELAQ IKRESQMRCVSKTDYESFVSSR FGSIVQAVQCFTDQDKPGYAFI AIKPKSGLOLTAVOREDIQDYLK PFCLAPITPSVMSPDYLFIRHNI KASYALNKLQESEQWLQSKIID SINRYYVDEVEMFNKNFSKSKL LTYIDDTDHSIIGSSVDIQMVREI VNYFTLPSAGIKYYNTITPRTLR SGDLVFTVTPTAEPYSVNIVGT DPDKNGKGNMVIGPFKPGDIKE NTHIQPYTENDFDRTTIGERTR WYKIGEVDYYGDNIYWSLGAIG ADPLQFEDQSIELYSTPTQDIVF ARDGTLIVFENDLRPQYTTIKLE PITQ | 652 | gp6 baseplate wedge subunit [Enterobacteria phage JS98] | YP_00159528 1.1 | 0,0 (443/650) | baseplate wedge subunit | Baseplate wedge subunit | PHA025 53 | 0,0 |
| 23 | 26263 | 25997 | 804 | MAGLSFNKCLTAGHSAYPPTEV NATQSKVFTGGIAVLVDGDSITP HTKTVDPHDTHGGVVQPRTSK VFVTGKKAVQMADPISCGDTVA QSSSKVFIH | 97 | gp5.4 conserved hypothetical protein [Enterobacteria phage JS98] | YP_00159528 0.1 | 9e-39 (76/76) | | No putative conserved domains have been detected ||
| 24 | 26767 | 26264 | 805 | MADILPINTTLREVIEGEYVEQY FTAQLSTNETLKSINIDYQPVSD ISVSETHYGKNYNSVFTFGNDV LKYREGDELKSASAWEDLPNP KTADLYLWKAPRTLEKTFTYTV EIIYTVTEESSGGSSGGSSAPIIT EHKKQKIYSQTVKGNWSRWGD QLRAYVYAGN | 167 | Hypothetical protein EME08_gp142 [Enterobacteria phage IME08] | YP_00373429 2.1 | 2e-40 (86/177) | | Hypothetical protein | PHA026 06 | 4,54e -48 |

Fig. 12L

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 25 | 28500 | 26770 | 806 | MIEMNDSLKWFTGVVEDRQDP LKQGRVRVRVYGLHPFEKVQG AITGLPTEDLPWMSVIQPTNSA GISGVGSSITGMVEGTSVFGLW LDEFKTAGLVIGTYSAHRKTKP NYTEGFSDPTGQYPRQVGSDT NPLVQGDETGYSAIPNIIQDRNL DIGINPDDADLSDIPEDPNPAITI TDMLNRDEGLRLKYYWDTEGY PTVGIGHLIMAQKVRDMSVINKT LSNQVGRTVTGNPGIITMDEAV ALFKKDRDKMLSDIKTNSRVGP VYAKVNKSRQMALENMSFQMG VGGLAKFGKMLDAMLIGDWKT AYTEARNSVWFNQTKGRASRV SMIILTGNMESYGVPAPKPEGK NLSAAYVEPKSGGNPEDPWTP EDSRILFKEPESSYNGQYPYVH TMETESGHIQEFDDTPGYERYR IVHPTGSYEEVAPDGRRTRKTV ADLYDMTQGDGNILISGDKKVN VGGNETYYNMYNRRQQIDGDN TLYVRGNETKTIEGNGTIFVKGN IKIVVEGNADIQVNGDATTKVDG NHDVTVGGNLTWQVAGTVNW NVGGAWTETMASMSSIAQGQY TVDGSRIDVG | 576 | Base plate hub subunit and lysozyme [Enterobacteria phage RB32] | YP_803092.1 | 0,0 (391/576) | base plate hub subunit and lysozyme | Bacteriophage T4-like_lysozyme | cd00735 | 4,39e -65 |
| 26 | 29135 | 28497 | 807 | MLFSFFSPIDYSAKTVKGAKAK AIPTADIFRNYRKYFDTVAENYL LQTYYISGAPRPEELAYILYGNS QLYWILLMCNNVYDPFRDWIKT QDACYQFAQQKYADVGGDQIL YHVDAYGNRYYNLEQYPENSG VWYDKGDFNHQYPQYTGALAG VDIYEDSIIENEKLRQININPSDI EAFLSDIIREMEKAPDSEYESG RYKSQTTIGEVL | 212 | gp53 baseplate wedge subunit [Enterobacteria phage JS98] | YP_001595277.1 | 1e-66 (121/199) | baseplate wedge subunit | Baseplate wedge subunit | PHA02578 | 4,62e -75 |
| 27 | 29185 | 29634 | 808 | MAYSGKFMPQNLHKYKGDFRK ITYRSTWEQYMMRWLDNHPDV VQWNSEEVVIPYFSNADGKKR RYFMDFWAKFSNGQQFFFEVK PKKETRPPVKPTKLTTSAKKRYI DEIYTWSVNVDKWKAAQATAS | 149 | gp4 head completion protein [Enterobacteria phage JS98] | YP_001595276.1 | 2e-67 (122/149) | head completion protein | Head completion protein | PHA02552 | 1,15e -63 |

Fig. 12M

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | KMGIEFRLITEDSLKKLGWKG | | | | | | | | |
| 28 | 29634 | 30461 | 809 | MAIFEFITEAAESPKAKSRSENQ WVALGVEYSAARKKGMTSKSF AESKGINPATFSKAMARHASRI KTAIKVAEIEKKPANKMTKQERA LVMVNSFRSSIKDKIRNEGAAV NNKSAKWFAETIKKNIRGHSVT KPQPGKLYAYMYDAKHKDTLP FWDKFFLIVYLGLGKQGTTTLM YGLNLHYIPPKARQQFLEELLK QYANTPVISNKTRLKINWSQVK GFAGADKMIKAYIPGNIKGALIEI KPADWANVVMLPLQQFMSKGK RYSATSVWKS | 275 | gp2 DNA end protector protein [Enterobacteria phage IME08] | YP_003734288.1 | 1e-188 (200/277) | DNA end protector protein | DNA end protector protein | PHA025 77 | 7.34e -107 |
| 29 | 30461 | 31063 | 810 | MSTGLFNQTNTTNFILEVPDGG LTQAFKANLQTAVVPGIHIPATD TVGSPQGMHRAKLPGSTFEFD AVPVRFLVDENLDSWVQMYKW MLSCQNYIDRDKSGWNNGGE GFPGAVLMHVLDNDKHDIVLTV RYIGGWVSDLSEIEYSLTEESD PAMVCVATLQYKYIEVEKDGIIT GRPSVNDTRESQYQQKVMGM HPSMR | 200 | gp3 tail completion and sheath stabilizer protein [Enterobacteria phage JS98] | YP_001595274.1 | 2e-61 (111/197) | tail completion and sheath stabilizer protein | Tail completion and sheath stabilizer protein | PHA025 76 | 7.95e -65 |
| 30 | 31068 | 31811 | 811 | LKLLFLIGKKRSGKDTTADYIMD NYNATKHQLAGPIKDALADAML TEWYRDTSREFPRITRSMEGID YDREQDLNLSTKDVIRIMANAIE YVHHDLPLPGVVYDNKRKILDG DTMEVIRKVVINKPVEPWSIRRL MQTLGTDIVCDKLDRMYWVKR FTLVMADTFGDYDYFIVPDTRQ DHELDVARAMGATVIHVVRPEQ EGSKKDTHVTERGLPIREGDIVI TNDGSLEELYSKINTILGIQNDY | 247 | gp1 dNMP kinase [Enterobacteria phage RB14] | YP_002854480.1 | 3e-69 (140/252) | deoxy-nucleoside monophosphate kinase | Deoxy-nucleoside monophosphate kinase | PHA025 75 | 2.45e -65 |
| 31 | 31801 | 32034 | 812 | MTTEQLQAQVDTLKVRVFDLSE TIQGLSALRAQYEEVLQKLIAVS GVEIGEDGQVKLDDLVAKIEAQ | 77 | No significant similarity found. | | | | No putative conserved domains have been detected | | |

Fig. 12N

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | FAEETTEESE | | | | | | | | |
| 32 | 32034 | 32489 | 813 | MKFSDFSTGLYVAAKFSEKTLD AIEDLQRELKVPNPVPRHKIHTT ICYSRVHVPYVCASGSFEVATS GKLEWDTQDGRTLVLKLDSE YLKFRHQYARALGATHDFPDYS PHITLSYNVGPAHFEGEVQVPV VLDREYQEPLKLNWSEDLK | 151 | gp57B conserved hypothetical protein [Enterobacteria phage T4] | NP_049750.1 | 6e-67 (120/151) | | Hypothetical protein | PHA025 74 | 4,25e -65 |
| 33 | 32486 | 32869 | 814 | MKSYQEFLMETEALLESTLPDY MIVKSFNVKNGYVIKFPIASVKP GADMSNDAGISVKVNVQFINYN SAKKSYDAKMTFSGGEKVVKNI KLDYDESAESVKKRFGDKLVKS IMVHPTFKRDFTELYK | 127 | No significant similarity found. | | | | No putative conserved domains have been detected | | |
| 34 | 32935 | 33114 | 815 | MKRCELIRNVASAICLTAVGTSI FGAIFMGAKEIMVVLVAAFLMG SISFIMDKISHEKD | 59 | Tma.4 conserved hypothetical predicted membrane protein [Enterobacteria phage JS98] | YP_00159527 0.1 | 5e-07 (31/59) | | No putative conserved domains have been detected | | |
| 35 | 33101 | 33280 | 816 | MKKIKQWFVKTYDLGREEVTKY DYVTLGVGLGALLAALHSSLLAI AVLLILAHYSWKRK | 59 | No significant similarity found. | | | | No putative conserved domains have been detected | | |
| 36 | 33280 | 33465 | 817 | MYALLTWSNYYPAPGSDQIRG VYSTVEECYEALQGTYQDYFEI LNSRFETVAKGSTEAYKD | 61 | No significant similarity found. | | | | No putative conserved domains have been detected | | |
| 37 | 33482 | 33832 | 818 | MNIRAAFNTFYQENYKLLSHEY YDAQGVPIPSDLVTPKHVKTDS LDNEIQPGDLVSYYCGGSLSAA SVGILLGFTPKGYRVVPFHTSPI PEHRVLLSHMDSPHRVFLVKSK SSPIV | 116 | No significant similarity found. | | | | No putative conserved domains have been detected | | |
| 38 | 33915 | 33998 | 819 | GGGGAGUUAGACCGUAGGGG UAGCGGGACAGACUGUAAAU CUGUUGCUCAAAAGGCUCGA GUGGUUCGACUCCAUUACUC CCCA | 84 | | | | tRNA1-Tyr | | | |
| 39 | 34009 | 34082 | 820 | GGGAUACUAGCUCAGUUGGU UAGAGCACCGGACUUUUAAU CCGGUGUACGAAGUUCGAA UCUUCGGUGUCCCA | 74 | | | | tRNA2-Lys | | | |

Fig. 120

| orf | Start position | Stop position | SEQ ID NO.: | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 40 | 34091 | 34172 | 821 | GGGUCGUUGGCUGAGAGGG UAAGCGACGGACUGUUAAUC CGUGUCAGAAAUGACUAGGC AGGUUCGAUACCUGCACGGC CCG | 82 | | | | tRNA3-Asn | | | |
| 41 | 34429 | 34502 | 822 | AGUGCUGUAGUCGAGAUGGU UAAGACACUCCCCUGUCACG GGAGAGAUCGCGGGUUCGAC ACCCGUCAGCACUG | 74 | | | | tRNA4-Asp | | | |
| 42 | 34586 | 34984 | 823 | LTFDEWLSWWKATGKYHLRGR ASDNYCMCRKGDVGPYSLDNI YCATNAQNAKDAGANGRIISTG FTGHNHSDETKIKISENHAHKLN ADEISLRIDLYNSIDFTQRGALV KFANKLGISHTOARKFINKFIK | 132 | PHG31p119nc [Aeromonas phage 31] | YP_238848.1 | 2e-31 (67/134) | | No putative conserved domains have been detected | | |
| 43 | 35138 | 35211 | 824 | UGCGGAGUAACUUCAGUUGG UAGAAUGUUGGGCUCAUAUC CCGACACGCGCAGGUUCGAG UCCUGCCUCCGCCU | 74 | | | | tRNA5-Met | | | |
| 44 | 35221 | 35292 | 825 | UGAAUCAUAGCCAAGUUGGU AAGGCAGUAGGUUUUGAUCC UACGAUCCCUGGUUCGAGUC CAGGUGGUUCAG | 72 | | | | tRNA6-Gln | | | |
| 45 | 35367 | 35540 | 826 | MMDGVNIDVVVVQLVEPEVVIL DVTDSNSVGHPNNEGMVEKYT ARKTLWLSLSELCL | 57 | No significant similarity found. | | | | No putative conserved domains have been detected | | |
| 46 | 35391 | 35463 | 827 | GUGGUCGUAGUUCAGUUGGU AGAACCCGAGGUUGUGAUCC UCGAUGUCACGGAUUCGAAU UCCGUCGGCCACC | 73 | | | | tRNA7-His | | | |
| 47 | 35564 | 35645 | 828 | GGAGAGUAGCGCUAGUGGUA GCAAACCGGACUUGAAAUCC GGGCACCGGAAACGGUGAG GGUUCAACACUCCUUUACUCUC CG | 82 | | | | tRNA8-Ser | | | |
| 48 | 35715 | 35787 | 829 | GGGGAUAUAGCUCAUUUGGU AGCGCUCUCGACCGAUAAUC GAGCGGUGACUGGUUCGAGU CCAGUACUCCCA | 73 | | | | tRNA9-Ile | | | |

Fig. 12P

| orf | Start position | Stop position | SEQ ID NO.: | Aminoacidic sequence | Size (aa) | Homologous/similar proteins Name[organism] | Homologous/similar proteins Acc No | Homologous/similar proteins E value and identity | Predicted function | Conserved Domains Name | Conserved Domains Acc No | E value |
|---|---|---|---|---|---|---|---|---|---|---|---|---|
| 49 | 35797 | 35868 | 830 | AGGUUCUUAGUAUAAUGGCU AUUAUGCUGGGCUCCAAACC CAGUGAUGAGGGUUCGAUUC CUUCAGGGCCUG | 72 | | | | tRNA10-Trp | | | |
| 50 | 35877 | 35948 | 831 | GCAUCCAUCGUAUAGCGGAU AUUAUGCUCGGCUUCCACCC AGAAGAUGGGAGUUCGAUUC UCCCUGGAUGCU | 72 | | | | tRNA11-Gly | | | |
| 51 | 35957 | 36030 | 832 | CUCCGUAUAGCUCAGCCUGG UAGAGCGCUCCAUUUGGGAU GGAGAGGUCCGAAUGUUCGAG UCAUUCUAUGGAGA | 74 | | | | tRNA12-Pro | | | |
| 52 | 36209 | 36361 | 833 | MKYYGFKTSHFGKAYRTENIDR RRAYYESLHKAGRSRARQEGQ KQAKEIE | 50 | Hypothetical protein RB43ORF088w [Enterobacteria phage RB43] | YP_239064.1 | 5e-13 (35/48) | | No putative conserved domains have been detected | | |
| 53 | 36358 | 36723 | 834 | MNIFIGVANNVNAITVKLQWNR PTNFALGLCKSERDLMLHADFA YTFDERKGMWVWIKCRYEALIK YEYFSERDIQEVIAYHSGCKVS KLRQVIPFTNASNVEELITDFKRI YQAKYDERF | 121 | No significant similarity found. | | | | No putative conserved domains have been detected | | |
| 54 | 36707 | 36940 | 835 | MMKDSKGRDVQVGDIVFYGER TYNKGGRGSMRCGRITDIASGL AKVDNDYVAMRSKSFVKVSPM FATMWENGTIFEI | 77 | Hypothetical protein Ea21-4_gp102 [Erwinia phage phIEa21-4] | YP_002456125.1 | 7e-04 (25/72) | | No putative conserved domains have been detected | | |
| 55 | 36995 | 37219 | 836 | MKRIALIVDQEAMFAATGKFHP VSKFVARSEKIVGLVETVAGDVI VSIKTSEISPVVKVAVENDFWEV ADFMCE | 74 | No significant similarity found. | | | | No putative conserved domains have been detected | | |
| 56 | 37298 | 37371 | 837 | GGCCCUGUAGCUCAAUUGGU AGAGCGUUCCCCUCAUAAGG GAUUGGUUGCAUGUUCGAGU CUUUGCCAGGGUCA | 74 | | | | tRNA13-Met | | | |
| 57 | 37394 | 37594 | 838 | MMRLVKVVVEESEYMGDSRMI EEFVTVEADSESEIVDKVYRHF DNMSDSYGTMYSIYRLDVIVHIN | 66 | No significant similarity found. | | | | No putative conserved domains have been detected | | |

Fig. 12Q

| orf | Start position | Stop position | SEQ ID NO: | Aminoacidic sequence | Size (aa) | Homologous/similar proteins ||| Conserved Domains ||| 
| | | | | | | Name[organism] | Acc No | E value and identity | Predicted function | Name | Acc No | E value |
| --- | --- | --- | --- | --- | --- | --- | --- | --- | --- | --- | --- | --- |
| 58 | 37605 | 38162 | 839 | MHIRFGQVIPKGLAMAITTWEN DADRYSTQMVYGLEKEEINQVI HVLEWFSSNGRRGEYLGNNDY NHEAILEKLHTEQKYVTPEFSKK FFGVDVPAYDCTDEEFDAYLDN HYSCSNEVMYAIQAWLGNPIEY DYDFMRVFEKVEIFDIKEEIRIPD APVAFHVGIITYKQKESPLKVDW LKYVKEK | 185 | Hypothetical protein EpJS98_gp138 [Enterobacteria phage JS98] | YP_0015952 7.1 | 2e-20 (63/162) | | No putative conserved domains have been detected |||
| 59 | 38162 | 38611 | 840 | MDIGSGSSYPSCALSNFAPHKF IYDGVECASMEGFLQSLKFSSP EMQAHVCTLVGKSAKFKGKKK RWWPTQTLYWKGVPIHRASEA YQNLLTGAYDALSKNEGFRKAL AATRNATLTHSMGKNKISETILT EREFCNQLYRLRNAINNQ | 149 | Hypothetical protein KP-KP15p076 [Klebsiella phage KP15] | YP_0035799 2.1 | 4e-57 (114/146) | | Phage_30_3 proteins | pfam08 010 | 4.60e -65 |
| 60 | 38757 | 38840 | 841 | GCGUCGAUGUUGGAAUUGGU AGACAAAGGAGACUUAAAAUC UCCCGGGAUUAAACCCGUAC GAGUUCGAGUCUCGUUCGAC GCA | 84 | | | | tRNA14-Leu | | | |
| 61 | 38846 | 38918 | 842 | GCCCUUAUAGUGUAAUGGAU AGCACACGAUCGUUCUAAGG UCGGUAGUCCGGGGUUCGAGU CCUGGUGGGGGUA | 73 | | | | tRNA15-Arg | | | |
| 62 | 38923 | 38995 | 843 | GCCGAUUUAGCUCAGUUGGU AGAGCCCUUCACUUGUAAUG AAGAUGCCGCGGGUUCGACU CCUGCAAUCGGCA | 73 | | | | tRNA16-Thr | | | |
| 63 | 39268 | 39852 | 844 | MKFKDFLTEEELFEAAPGRMTK SKWRDALVLVPRGERHDFSKF AASVEKIYGIGISDPKDYAKVAA AFESLGGKVTTPARGASPAQA PAAKPAPVKAKPKNPGLKISGD HGDIIGSGELFKAIDKALPLVRD NGPLYKAVQFYFDNLVMKYRES QGAKPSARETQHIGEVKTLLAK LNHHLVELSRQTELSYNV | 194 | No significant similarity found. | | | | No putative conserved domains have been detected |||
| 64 | 40040 | 40330 | 845 | MSKFNFIQIERGYNNYGTPDRY RAIWIKGEHEHAVFNVAETREL KDLIKHVRKDWPAVEEYYVRVY HEEAPTETVQIKFAKTASALTKR IEAVINC | 96 | Hypothetical protein RB51ORF009 [Enterobacteria phage RB51] | YP_0028539 4.1 | 7e-08 (40/93) | | No putative conserved domains have been detected |||

Fig. 12R

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| 65 | 40378 | 40971 | 846 | MSILKKLVEFIRSKFGTFVAQNT SVEDQYTMAANRIIDEITKLRTT HVKSVNEEKRLLKLADEKDQAG ASKEREIRRLMAEGMNVETHAK LGLLYRRTAKALRDKAAEYKEM RAQIEETVVKLDDQRLDLAVKL EYIRETRNASALGITSADDVIEIA ELAKVDVQDIMMKVETFSGTQP GIETTTADVQEYLESLK | 197 | Hypothetical protein EME08_gp126 [Enterobacteria phage IME08] | YP_003734276.1 | 7e-68 (128/197) | | No putative conserved domains have been detected | | |
| 66 | 41042 | 41602 | 847 | MATPQIKELIAAGFPTEITDILGK FAYPDTRPENWKTRYNGYNTT VLPRAIVLKDYSKLKNLISNISSI SDGVKLVDIFALRYGIYSFNDSP SNLKSARTNAGEYSTSGSTTYT IVIEIIHNKNSYRLGINLVKYVTS QDDYSNYLNYCVNELPSKVMS MFDSNNMVGKQLIIDEFIKYCRE RVQK | 186 | No significant similarity found. | | | | No putative conserved domains have been detected | | |
| 67 | 41599 | 41958 | 848 | MSNLYLPSEPPVYNYYKFDQI DYALVPGIGATVGAMCTFAAIDI MHLTDITPAVLFGILLAWWGTSL LIMGLIECSRWVKWSRNNYKRK AEWKEQCKNLTLEWNRKKSFE FIKEVRRK | 119 | No significant similarity found. | | | | No putative conserved domains have been detected | | |
| 68 | 41955 | 42251 | 849 | MNEYKPDGFWNQDGLAPGFGI VTWLLYCAFVIVGGTFFGLNVS EFMIMLFLGVFAFSLMWMLIIA LINCCTFLAYRMKYKWKEKED FNTWIRSCRK | 98 | No significant similarity found. | | | | No putative conserved domains have been detected | | |
| 69 | 42248 | 42574 | 850 | MIKTCYRGMIKSDEPGYFLFLL IWFSLSAFVGFGTFWGFYFFSP VFGDALYYIGWMSGVGTWFAIL ARWLQFVSQRQRGVFDKPKVK KEKSKQDSRSETLSWIKEMK | 108 | No significant similarity found. | | | | No putative conserved domains have been detected | | |
| 70 | 42574 | 42810 | 851 | MAVAVHVKFENGDTRLLCYSD NESLSGIEISLKEELLGINGPICD FSVEGSDNCNDDLESMVYTAM EDILEESWNECQ | 78 | No significant similarity found. | | | | No putative conserved domains have been detected | | |

Fig. 12S

| orf | Start position | Stop position | SEQ ID NO: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 71 | 42801 | 43253 | 852 | MPMKELSAGILFFTDDKRLLMG RMTNTYVQGRGSRWDIPKGHV EPGETPKEAARECKEETGFTE FDQDLLYDLGRHDYASNKDIHL FGYMLPVSPEMFRNCRCTAYH KDENGINFPEIDAFALIKPSQWK YVMGPSLYKIMTQMYSTAQ | 150 | NudE nudix hydrolase [Enterobacteria phage RB69] | YP_861819.1 | 6e-47 (89/144) | nudix hydrolase | Nudix_Hydro lase | cd02883 | 3.28e-15 |
| 72 | 43261 | 43569 | 853 | MEEAVELGIPHIYKHELRFIHDG KWISIFHPRDKMSRILMKSRYVF SDSEYIKSAYYIAEQLYPGFSEL PEDDKRDYVWWKDKWTPYEK CSLELFIAKCRAK | 102 | No significant similarity found. | | | | No putative conserved domains have been detected | | |
| 73 | 43599 | 44093 | 854 | MDIFGMLRIDEGYDSKIYKDSE GYWTIGIGHLLTKDPSKSLAISN LDKLVGRSTGGQITQAEAEVIFA KDVEKAIKGIVANATLSPVYNIL DDVRRAALINMVFQMGVSGVA GFPASMKLLLAKKWDAAAKELA NSRWYRQTPNRARRVIETMRT GTWAAYQGK | 164 | Chain A, E108v Mutant Of T4 Lysozyme | 1QUG A | 3e-57 (108/162) | lysozyme | Bacteriophag e_T4-like_lysozym e | cd00735 | 5.01e-45 |
| 74 | 44094 | 44573 | 855 | MKTYQEFLNESRLATVGVMTE SVGSNLLKFKGQKMTATLED GTEIEMDVVGYNYVVDGKLYNK SHAKFDSFDDFVSSVEDESSRK AVASGDARSLMAHGHMRIKSK QNKPGEDNFALVGYOSGKTSN GYQRTVTMYMRNGKIAFVNDR GAIRYAKSIK | 159 | Hypothetical protein RB32ORF123c [Enterobacteria phage RB32] | YP_803065.1 | 3e-60 (111/159) | | No putative conserved domains have been detected | | |
| 75 | 44766 | 45068 | 856 | MKTYKEFITEARVSAGKLEAAIN KKAHSFHDLSDKDRKKLVSLYI DKERILALPGANEGKQAKPLNA VEKKIDNFASKFGMSMDDLQQ AAIEAAKVIKGK | 100 | IpII internal head protein [Enterobacteria phage IME08] | YP_003734259.1 | 4e-47 (93/100) | internal head protein | No putative conserved domains have been detected | | |
| 76 | 45272 | 45805 | 857 | MKYLTPIYLTLMHAFKDAADRR LNNPNYSFYEPSCLMREYGTLR LDGGRQTGKTAALCQFATDWL LEDGSVIILSTRYTQSSELMEGI LREYNSSHLINKLPANEIAKSIVP MTIREFLSNDSSYKFRGRKLGR ALIIIEEPMKVPDMMKFYDMYQ EAIRWSMPNDTLPLFFVIGMQ | 177 | Vs.8 conserved hypothetical protein [Enterobacteria phage JS10] | YP_002922458.1 | 3e-40 (91/180) | | Terminase_6 | pfam03 237 | 1.09e-03 |

Fig. 12T

| orf | Start position | Stop position | SEQ ID NO.: | Aminoacidic sequence | Size (aa) | Homologous/similar proteins ||||  Conserved Domains |||
|---|---|---|---|---|---|---|---|---|---|---|---|---|
| | | | | | | Name[organism] | Acc No | E value and identity | Predicted function | Name | Acc No | E value |
| 77 | 54802 | 46113 | 858 | MMTQTEIVDMITVMENTGFADM KQLITMVTAGNLLEYKRYKFLS GPFKGAEFISNAPNTKWMNRY PNFRIEFISGKLKGVISSSLITYD QRIQEKTMQWLKLL | 103 | Vs.7 conserved hypothetical protein [Enterobacteria phage JS10] | YP_00292245 7.1 | 2e-10 (29/54) | | No putative conserved domains have been detected | | |
| 78 | 46095 | 46439 | 859 | MAEIVIRCPPHLVESFCEWFSN SGEQDFYEAHQNGTWNETTKQ WEEATTYIGTRGYGVNEPIEIVE YDKETDEEVTYHEDKITYLEAA AKFHSDEWNKMSVITAYMRGW NKESN | 114 | Vs.5 conserved hypothetical protein [Enterobacteria phage RB69] | NP_861809.1 | 2e-10 (36/77) | | No putative conserved domains have been detected | | |
| 79 | 46448 | 46810 | 860 | MKAYQILEGELKGTIYIEDGDDA RVIVSKVLKEDTITDAETFYGYK AREVEIEYQPTVKIEGGQHLNV NVLRRETLLDAVEHPEKYPQLTI RVSGYAVRFNSLTPEQQRDVIA RTFTEAL | 120 | Autonomous glycyl radical cofactor [Enterobacteria phage AR1] | BAI83131.1 | 2e-51 (100/120) | autonomous glycyl radical cofactor | Autonomous glycyl radical cofactor GrcA | PRK111 27 | 1,37e -40 |
| 80 | 46810 | 47091 | 861 | MAIEDIKGYKPHTDEKIGKVNAI KDAEIRLGLIFKALEEEHVEKYM NLDVSTMSDKEFDLAHERITQIR NAIQHLKEASMWACRSVFQPE EKY | 93 | Vs.4 conserved hypothetical protein [Enterobacteria phage JS98] | YP_00159523 7.1 | 1e-35 (72/91) | | No putative conserved domains have been detected | | |
| 81 | 47155 | 47613 | 862 | MSTNPEVFIRRTIKLRRKFEEAF RSLNLSVRARAKAEGKEPFFTK YSDHLLDRAIQREIDEEYVFSVL SKIPNHLKEINEFLAMPWLPIDP KDIDENIEYKPMRLEITDGNLWL GFTMDIPRPGKGPSIKCRMAFV NDKRLKGKISTKVIHIN | 152 | RegB site-specific RNA endonuclease [Enterobacteria phage JS98] | YP_00159523 6.1 | 2e-43 (90/148) | RegB site-specific RNA endonuclease | REGB_T4 | pfam10 715 | 1,91e -20 |
| 82 | 47621 | 48166 | 863 | MKKALIGLMALCSTAFGSEPTF SNVQLDNLHYAYNFGEQYQKS GKEKSPHNRYDNNGLGYIMAAI SWKESSAGANLKAGKGHHSYG VFQNYLPTVYKARAKLEGKNLSD SEIRKMLKSRQNSAEWAYIELS YWLNIHNGNMRKALASYNAGW NVKRGNSYASDVLEKANFLKKH KMLHTKVE | 181 | Vs.1 conserved hypothetical protein [Enterobacteria phage RB69] | YP_861805.1 | 5e-59 (115/180) | | | REGB_T4 | pfam10 715 | 1,00e -18 |
| 83 | 48166 | 48486 | 864 | MVKYAALLGLVLAFSANAENSM TDSLRIAKTFCNTNSECVDILAL ELDSAFSDGVKDSRSPAQWTT LINRKAKSMKDLCVNAPNENICL MYRDQLMARYMSGLSSK | 106 | Vs valyl-tRNA synthetase modifier [Enterobacteria phage Phi1] | YP_00146943 6.1 | 4e-13 (34/80) | valyl-tRNA synthetase modifier | No putative conserved domains have been detected | | |

Fig. 12U

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 84 | 48483 | 48875 | 865 | MKKAALLCCAFSVNAWEKLPG YPETVLAAQGTKIESNGPFKNNI EIAFVPSSRKLLMSFYNYQDKD DQVIVPLVEYNARGCGMQSDG VSVDGVMHPKEQGVLNPILNC NNAIFLRVYNNLNEYATYKIP | 130 | No significant similarity found. | | | | No putative conserved domains have been detected |||
| 85 | 48884 | 49351 | 866 | MITGYIKGNIVELFMKHECDIAH GCNCFTTMGAGVAGQLAKAYP PILDIDIDEDRYYDNNLAKLGTH TRAIHKKGTAYCYNLYTQYAPG PNVDYGAIFNAFHELNSGRIVY NRPLYIPKIGAGIAGGDWELIEK LINLATPDIDIMVVEYEEAKS | 155 | Tk.4 conserved hypothetical protein [Enterobacteria phage JS10] | YP_00292245 1.1 | 3e-41 (89/157) | | tk.4 | PHA025 95 | 6,30e -49 |
| 86 | 49375 | 49542 | 867 | MITEEQKTKLWQLIDDYAGAEQ VVAISAIYGNGLPEEYDELIRSK NAISDFMETL | 55 | No significant similarity found. | | | | No putative conserved domains have been detected |||
| 87 | 49542 | 50141 | 868 | MAQLYFNYASMNAGKSANLLT AAHNYKERGMGTLILKPAIDTR DSATEVTSRIGLRHEANTVDESI DILEFFKWAQTQRDIHCVFVDE AQFLTAEHVLQLCKIVDLYDVPV MAYGLRTDFRGELFEGSKALLS VADKLVELKGVCHCGRKATMV ARIDENGNAITDGEVVELGGED KYVSLCRKHWCELVGVYNEAK NV | 199 | Tk thymidine kinase [Enterobacteria phage RB69] | YP_861801.1 | 3e-81 (137/192) | thymidine kinase | Thymidine kinase | PRK042 96 | 3,20e -80 |
| 88 | 50122 | 50316 | 869 | MKPRTYNTILMLVLSMLFIWMG VAASIQSDRREELQNRLDSGCK VLAQGKDFIANTNGCYIKYE | 64 | No significant similarity found. | | | | No putative conserved domains have been detected |||
| 89 | 50600 | 50983 | 870 | MSRTIRRKGWHVVKSSKWNDQ NNNEFAYIKSYNEYYKTQKDKE NQQKYVELRISENSERPLEAKK LIAKSKRDGFWKTLRWTRYAM PVPRLFHKAEIKRALKYDEEYN WDEAGARTIEQGICEWLWD | 127 | No significant similarity found. | | | | No putative conserved domains have been detected |||
| 90 | 51030 | 51242 | 871 | MQHLSEKQLRNLTVEQLDELR REIGHGISHLQEEIRQHSSKADY TRKRTLEKYLKEVKAVLQHKRN TGQK | 70 | rI.1 conserved hypothetical protein [Enterobacteria phage RB69] | NP_861800.1 | 1e-20 (51/69) | putative lysis inhibition regulator | No putative conserved domains have been detected |||

Fig. 12V

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 91 | 51254 | 51541 | 872 | MAFNHICLALVLGCGISFPAASH DDISDYNSYVEGALQVYAKFKE PSKQESEQFYAFVQSKWKSES CSKDCDSLGRSAGEEYANRMR IQFDNEVQ | 95 | Hypothetical protein Acj133p120 [Acinetobacter phage 133] | ADJ19435.1 | 4e-13 (36/82) | | Hypothetical protein | PHA02054 | 3,47e-06 |
| 92 | 51528 | 51914 | 873 | MKFNDFVKDGKLTPQDEFIGLL MVSQAYFHSAHFDTKSYARHK AYEVFFNEIPDLIDAFGEQWLG FSGKSYTPALPSQKELPKDTIE MLDFILAKADGIYKSVPAALQSV LDDITGLCYKTKYLLSLQ | 128 | MobD.6 hypothetical protein [Enterobacteria phage T4] | NP_049716.1 | 2e-43 (79/128) | putative lysis inhibition regulator | rI.-1 hypothetical protein | PHA02604 | 6,38e-44 |
| 93 | 52019 | 52507 | 874 | MIKLTTELQPGKIFYHVCGVNRT ETKPGEITRYIVASGTYDVELGL SGVYSRKSPFFQVICEYENYAG QTESYSTERSAHDMGIFKPGEK RSVHNLNRGFWTREEAEQFIKE LQENKFSDPDDQAYADRLTPS EDFRRQQEFMDSYLDSCDYDY YDFDDGEE | 162 | No significant similarity found. | | | | No putative conserved domains have been detected | | |
| 94 | 52599 | 52865 | 875 | MNGWGPSDDGFATREATIADG IEWARLQKQLQEQRESEEFCV DCDEEIPVARRLLVKGCQRCVE CQGKWDTVMTSAYNRRGSKD SQLR | 88 | Conserved hypothetical bacterial protein [Acinetobacter phage 133] | ADJ19431.1 | 1e-24 (54/88) | | Hypothetical protein | PRK11019 | 4,8e-16 |
| 95 | 52868 | 53059 | 876 | MESILDSTNLDNPYSDVHVKVV NSYFTKKLSRVVLKQGNDIIHLD TKQIDSLIQFLIEAKDGE | 63 | No significant similarity found. | | | | No putative conserved domains have been detected | | |
| 96 | 53049 | 53282 | 877 | MASKLVWDGKPRKGDAVIEDE SPHVIDLYLTVFHTYEHNTIEIE RDGDCVAIDKSDAIELVKYLTA MIPTMKQDNL | 77 | No significant similarity found. | | | | No putative conserved domains have been detected | | |
| 97 | 53282 | 53782 | 878 | MNINKNSWHFKMNLWFKSGNI WKMPKTLCGYFWTTVLHILFSS AIAIFIGSVAWMFGWPLIAQTGIL AWIGVSLSSAFWLNVVAVPVGAV FIATFVLAFVAIVFGFIFGLEKFK EYRKNKQFTKKLARVKAGLPAE SEPLVFIQYLKARKRKVCPMIDY VEGKTSEE | 166 | RB69ORF104c hypothetical protein [Enterobacteria phage RB69] | NP_861794.1 | 2e-14 (55/163) | | No putative conserved domains have been detected | | |
| 98 | 53772 | 53996 | 879 | VKNDQVYIVNGRKAVFRAKTER GIISTYPIAEFTFEDGEQIKIKVV PLSQTYRFIGGEIDLDIYYEGGV WKLKS | 74 | No significant similarity found. | | | | No putative conserved domains have been detected | | |

Fig. 12W

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 99 | 53978 | 54400 | 880 | MEIEIVTTKKKLSMSLLKQMKM ASSSEIKFAMFDRVHRVLGYVN AFKWNKMDIQVAIINTGNDWAL VPMYDTHVIKTARREPHPDGQ EYHFHDVVYYHTMQKIGNVHR NSKKSTDKEHVEACAKASNDLI KFAKGNHIYL | 140 | No significant similarity found. | | | | No putative conserved domains have been detected | | |
| 100 | 54397 | 55407 | 881 | MKTIVKSYFGSHLYGTSTPESD VDFKEIFVPHPRDILMCQAMNH TNCNTNNSATKNTKDDVDHELF SLKYFFKLAADGETVALDMLHT PPELVVASDLPEVVKFIQDNRA RFYTTDMKAYLGYVRKQAGKY GVKGSRLADLHKVLDVIRDVPE WKYDDRPQQKGINERWKVQDI AEKLPLGEFLEWTTFVDHKSGE QKFYNVLGRKFQTTITIKEMKYS LEKLDAEYGERARKAEANEGV DWKALSHALRAGLQLQEIYMTG DLQFPLTHAKMVKMVKAGELPF KEVQELLESVVDEVEILAHTAEK NGMPKKVDMKFWDDFVEKVYL ENHNSYYK | 336 | NrdC.11 conserved hypothetical protein [Enterobacteria phage JS10] | YP_00292243 8.1 | 7e-132 (241/336) | | nrdC.11 hypothetical protein | PHA026 03 | 8.18e -142 |
| 101 | 55412 | 55600 | 882 | MKVFLNYGRPHKGRRWYLEAV CRETGRRENAKFSARPTRKQIH QFMSWAGETLRFSLYWAEI | 62 | No significant similarity found. | | | | No putative conserved domains have been detected | | |
| 102 | 55597 | 55836 | 883 | MILLWSVVVPIVVAIIYFIVGWSV CKHLIKNGTIEKVGEYWFYLIFW FPAFIVGAIIMFFRWAGKLPKRI AENAINKHA | 79 | No significant similarity found. | | | | No putative conserved domains have been detected | | |
| 103 | 55955 | 56170 | 884 | MKTLEIVVNNIDKAFKAAEAHGV EFEPMMVGEAFSKLAIIRGETD NLIDFVDDFYLGSKVRPYYINEIL EK | 71 | No significant similarity found. | | | | No putative conserved domains have been detected | | |

Fig. 12X

| orf | Start position | Stop position | SEQ ID NO: | Aminoacidic sequence | Size (aa) | Homologous/similar proteins ||| Conserved Domains |||
| --- | --- | --- | --- | --- | --- | --- | --- | --- | --- | --- | --- |
| | | | | | | Name[organism] | Acc No | E value and identity | Predicted function | Name | Acc No | E value |
| 104 | 56248 | 57225 | 885 | MSTTTIKKGIYFGKEISGTYELLG EWFPDSLSAEDSRQGDGKVFV ELNGKKRGVWWFKDDITIDGVA AKIEVVESVDEMKERIKKRFNV MGLMTNGLIHGNIRSLIISGAAGI GKTYSLDKALQHAHDTNAIDYK SVNGKISGIGLYCRLWESREAN SVLIDDVDVFSDMDILNLLKAA LDSGEKRKVCWSTASSFLEDK GIPNEFEFEGTVVFITNVDIDRE LERGSKLAPHLQALVSRSVYLD LGVHTNEEIMVRVQDVIMTTSM LQNRGLRNSEVIEVLEFMKDNV NRLRNVSLRTALYIGDFVATDR KNWRTIAEVTMLK | 325 | Hypothetical protein T4Tp097 [Enterobacteria phage T4T] | ADJ39814.1 | 2e-138 (243/325) | | No putative conserved domains have been detected | | |
| 105 | 57268 | 57414 | 886 | MATLISNDVKRVLFKGGMYIVD TPKGDTSSWTINEWINYIDENG AWVQ | 48 | Hypothetical protein [Enterobacteria phage AR1] | BAI83080.1 | 6e-07 (23/40) | | No putative conserved domains have been detected | | |
| 106 | 57411 | 57836 | 887 | MSLAAIKDIECWLNDIKVYPPGH IFAGKPKGKAEKACEAICEKLYK FNFGDKKNVLAEVHSSYHELRV MVNVFRAPPFIELRKEYANKVF DTFLANVQDAVKHLDEMHKQH QDLNAYYKPWRKSYQELKNRIE LIRYEVLK | 141 | No significant similarity found. | | | | No putative conserved domains have been detected | | |
| 107 | 57833 | 58171 | 888 | MKNWWMTESEAYAAYVSPDDR RSELFGYYGSYCVAEEAVKGQ SWWGSDGTVNRKPTELITFTD ENGESWTFPKSAAISVQEETPE AKRKRLEKIKESALAKLNPDER EALGL | 112 | Hypothetical protein Aeh1p086 [Aeromonas phage Aeh1] | NP_943964.1 | 1e-07 (36/107) | | No putative conserved domains have been detected | | |
| 108 | 58168 | 58488 | 889 | MSKEFSTTRMVDAFGYPCNGY REFIHPEVENQFKEVVRNILLNA FKTQGTNPRDLGIYLEEAIRDV QKSVSAKLHWAEENIAWSNKK RSDLNWPADREQIVNYAKG | 106 | No significant similarity found. | | | | No putative conserved domains have been detected | | |
| 109 | 58492 | 58782 | 890 | MFNTIVSIHAYYEGQLNAARTK YKRGMEESVECLKDIQTFAQKT QNLILMDRKQVSLAEELKASKMI IEDNRKHQLKLLKRRQHQSPW FNSDFRSF | 96 | No significant similarity found. | | | | No putative conserved domains have been detected | | |

Fig. 12Y

| orf | Start position | Stop position | SEQ ID NO: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 110 | 58863 | 59027 | 891 | MKAPTWNELQEMFNTEEAFGTI SEMVENLVDSPSEDNLLCLAQF IIETYIENQK | 54 | No significant similarity found. | | | | No putative conserved domains have been detected | | |
| 111 | 59024 | 59290 | 892 | MTVYVDVLMNHGWKMRGHQV KNCHMFSDNLDELHAMAEAIG MKRSWFQDKRVPHYDLRDVR RKQAVALGAVEVSRRDAVLLW RKFFTK | 88 | Bcep22gp48 [Burkholderia phage Bcep22] | NP_944277.1 | 4e-07 (31/79) | | No putative conserved domains have been detected | | |
| 112 | 59348 | 60136 | 893 | MKTLTEIISALVEENRVARQAHR AKVEKRAEELNAGWAKTRFGR EYFDKVVAPTWGKDDRPHAPF DGYLWENELGEVEAYHAGSYL PYVTELDSLDKPEYTGDHGWW KIRLTQEEYKELREYGYPLEVRI PYKEWKLQDGTNVVMAEVRAH KSILEAIQEHSKEVFDNIFNELN KNKGDAPEGRVTVSGTVTSVK VYEDYYGVQCKMMVVLENGAT VYGSLPKSIPFEYRGKVQFTAT FELAKDDKTHAFYKRPSKVIML DE | 262 | No significant similarity found. | | | | No putative conserved domains have been detected | | |
| 113 | 60207 | 61181 | 894 | MNKNELKMFVEAEFNKLKDKTL TKREKHVKVLSALHDLNPRAYD VAIAGNVARRVLNSMASHEANY AGFVVENIRRSRWLGAMSAEK QLKKFAIGNAKIYGQRYSFAAG AFKTEERHDRSAAQIFCSEFNA NLRRILNRSICLLKGDDRVKYQA SSTSSRNPKGVSFIRAEELDNV TVRIHINSHLSSGKYPARALLAQ VRTALDHMDVVKKSCCKQQGE NSSVLEVHLDPFKIFPKTLSTTP VIDEDVAHMYLNVVKPLPLTPV NHIEIAKNSITAEMESVKRFIDTK EAELAKHELTMADLVKSLNEYK ERYESLEYARSLL | 324 | No significant similarity found. | | | | No putative conserved domains have been detected | | |
| 114 | 61178 | 61438 | 895 | VKNQLKEDMVVDDNDLEIEFEY PPVPEFKIDWDACLEMVDRRE AAAKQVVPCEKCGSIQVQLVD WTTDILKMKCRTCKHRFERKLK | 86 | NrdC.2 conserved hypothetical protein [Enterobacteria phage T4] | NP_049700.1 | 2e-11 (34/78) | | No putative conserved domains have been detected | | |

Fig. 12Z

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| 115 | 61435 | 61749 | 896 | MITKTITGANTKFFVEYANNLIK DKNFDNIIADMILDAYESGIDPM QLKEYLRATMDFTVLNMMLRT DTEFNEMIARRNEGKFNLTDDE VLACAAHEAWKKVIK | 104 | No significant similarity found. | | | | No putative conserved domains have been detected | | |
| 116 | 61746 | 62081 | 897 | MKTTGALWKEFYNDEAFWEGY YHDDTLILFDDVEVEEYEDPSP DAVVKIESGYVYKTDDDSFTSH DLSLETFFKRWKKKQTTRTMVV TVDKDDFAKVFETISNIPGVKKV K | 111 | Hypothetical protein phiSboM-AG3_gp129 [Shigella phage phiSboM-AG3] | YP_0033586 1.6 | 7e-09 (41/115) | | No putative conserved domains have been detected | | |
| 117 | 62078 | 62590 | 898 | MIDIKLDTYAVRQLFPEGTAARA QLQQSVINNIVKEMVLKDSQNK LKQAVQSEVNIAAVTIPDVRAEV KKQVQQMFHTRGWNDMSAKE EMSQMMRNAAQSCAKNAIDDM VRQTIDDAVKQAEGRIKMSIER ANLRIQEIIVNAMNKNFADQINA AIAAKLAEHFPVTANG | 170 | Hypothetical protein KP-KP15p225 [Klebsiella phage KP15] | YP_00358010 1.1 | 1e-05 (43/173) | | No putative conserved domains have been detected | | |
| 118 | 62583 | 62756 | 899 | MDKIDFSKLNIPRMGIPDDIAKQ LASVQPMPDNCIKDIFDALDGK TLVITTKAENGS | 57 | No significant similarity found. | | | | No putative conserved domains have been detected | | |
| 119 | 62746 | 63036 | 900 | MARKRYMEEAERVMLLMYSVY YNETGQIVDSSKLKGAMTRGR GFAQAAIDKEIISRLGIKYSSKM YLHPGWNQVQAQVFKEIEEDV HSFWLRQQHP | 96 | No significant similarity found. | | | | No putative conserved domains have been detected | | |
| 120 | 62999 | 63268 | 901 | MFTVFGYDSNIHKCVFCDNAKR LLDVKKQEYAFINVMPEKGVFD EVVISDLLRRLGRESQVGLTMP QIFAPDGTHIGGFDELRKFKFN A | 89 | NrdC thioredoxin [Enterobacteria phage JS98] | YP_00159521 1.1 | 2e-34 (68/85) | thioredoxin | GRX_GRXb_1_3 like | cd03418 | 1.52e-08 |
| 121 | 63261 | 63449 | 902 | MHDYRGTLLREGDIVALYYGYG GLETGEIKQIKNHRAKVEVTYS NGVKVMSKWKYGECMVKL | 62 | Hypothetical protein RB32ORF082c [Enterobacteria phage RB32] | YP_803024.1 | 9e-16 (42/62) | | No putative conserved domains have been detected | | |
| 122 | 63468 | 63638 | 903 | MSYDIGDLKAPCTVTISAEEFIR LQAIEELLWEIECALPSGLESWI DDEDLQKLRG | 56 | RB32ORF081c hypothetical protein [Enterobacteria phage RB14] | YP_00285441 8.1 | 6e-15 (42/56) | | No putative conserved domains have been detected | | |

Fig. 12AA

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 123 | 63640 | 64029 | 904 | MTNAELVKEIKHIAGVTGEWDD NYDFEYPPNAPDDDAEEIFVLV EDDEWTQDHKYQSRSQIWYYP ARGVHFMVSESRSGSYHTDWY YNPPEVDIVTRHEKVVTRTEVE WRIEYDSVNDSAPAPCKAAKA | 129 | Hypothetical protein RB51ORF087 [Enterobacteria phage RB51] | YP_002854040.1 | 2e-12 (39/90) | | No putative conserved domains have been detected |||
| 124 | 64008 | 64166 | 905 | MQSSKGIKPWYTARWETVEPE EDAIPEEDYNTSEPTINELLDYE DKVNGTYW | 52 | No significant similarity found. ||| | No putative conserved domains have been detected |||
| 125 | 64150 | 64602 | 906 | MELIGKQFEVIENDDELTEQFP QFVPGFKFQVINAVNEDDLETC GITAVIDLLTNKIITNDPTPFGES WFWCFYSEDTMHQIKEIGQGE DVPNISEIKLDHFHGKIVPITKAL YAFAGQENCDSEEYDLMQKAA DYIVALETRLGVQYV | 150 | Pin protease inhibitor [Enterobacteria phage RB69] | NP_861778.1 | 1e-10 (50/144) | protease inhibitor | Inhibitor_I24 | pfam10465 | 4.84e-11 |
| 126 | 64595 | 64903 | 907 | MSKSCVTKTITVKILDFCDIHRIA REILRSHGYKIGDIIKFSNGYYD DDIGGMAWPKMSIIHKETNSYIE FNADDYEGIYAFCTSFCIKESNH NIYSSYSLI | 102 | No significant similarity found. ||| | No putative conserved domains have been detected |||
| 127 | 64940 | 65413 | 908 | MLLTGKLYKEEKEKLYQAQNGL CPCCKRPLDEDIQKNHLDHDHA LEGDNAGKVRGLLCNLCNAAE GQMKHKFNRSGLKGQDIDYLE WLENLLVYLRQNRKDSNIHPQY VADMAKRFSRLGKPEMAEMEL HGFTYEESDGKSQLASKYKKQ LRKSLK | 157 | gp49 EndoVII packaging and recombination endonuclease VII [Enterobacteria phage JS98] | YP_001595204.1 | 6e-61 (115/157) | EndoVII packaging and recombination endonuclease VII | Endonuc-dimeriz | pfam09124 | 1.60e-16 |
| | | | | | | | | | | Recombination endonuclease VII | PHA02565 | 2.43e-62 |

Fig. 12BB

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 128 | 65410 | 67248 | 909 | MNIELEIQGLINKTNKDLLNENA NKDSRVFPTQRDLMAGIVSKHI ANQVIPFSVMEAHKEGVIHFHD MDYSPALPFTNCCLVDLKGML QNGFKLGNAQIETPKSIGVATAI MAQITAQVASHQYGGTTFANV DLVLAPYVEKTFAKHVRDARKY QVALVKDYAISKTEKDVFDAFQ AYEYEVNTLFSSNGQTPFVTITF GMGTSWEEKLIQRAILDNRIRG LGRDGITPIFPKLVMFVEEGINL RKEDPNYDIKQLALECAAKRMY PDIISARNNRAITGSSETPVSPMG CRSFLGAWRDSSGKPVLDGRN NLGVVTLNLPRIALDANYKSSD DSNKLFKLLDERLDICKEALLTRI KSLEGVTASVAPILYQEGAFGV RMKPDEILELFKNGRSSISLGY IGIHEFDMLTFKGSGKLVLKYIN TKLNKWTEETGYAFSLYSTPAE SLCYRFCKIDQAKFGDVKGVTD KGWYTNSFHVSVEENLSPFEKI DREAPYHSIAKGGHISYVELPD MKRNLEGLEVVWDYAIEKLDYF GVNMPVDKCLSCGSTHEMTPT ENGFTCSICGETDPKKMNTIRR TCGYLGNPSERGFNLGKNKEIM HRVKHVRETNEAS | 612 | NrdD anaerobic NTP reductase, large subunit [Enterobacteria phage AR1] | BAI83088.1 | 0,0 (478/604) | anaerobic NTP reductase large subunit | Anaerobic ribonucleoside triphosphate reductase | PRK09263 | 0,0 |
| 129 | 67220 | 67453 | 910 | MLEKPMKQVDWNQLSEWGLI WKINKEVLHPLGIAITRDPESGL SAGAIQTDEPWKYDAEVEARN EVRFNEFRQNLPF | 76 | Hypothetical protein RB16p170 [Enterobacteria phage RB16] | YP_003858470.1 | 1e-13 (37/66) | | No putative conserved domains have been detected |||
| 130 | 67425 | 67895 | 911 | MNFDRIYPSDFVNGPGCRVVLF VTGCLHKCEGCYNKSTWNARN GQLFTMNITVKEIASHLSKSYIQ GLTLTGGDPLYPQNREEISNLV SWVKARFPEKDIWMMWTGYKFE DIKDLDLLQHIDVIIDGKYEKSLP TTKNWRGSDNQRLWVRNGST WTHD | 156 | NrdG anaerobic NTP reductase, small subunit [Enterobacteria phage T4] | NP_049688.1 | 1e-77 (135/156) | anaerobic NTP reductase small subunit | nrdG, anaerobic ribonucleotide reductase-activating protein | PRK11121 | 8,77e-46 |
| 131 | 67870 | 68004 | 912 | MVLPGHMIEEIYMLTYKIMFTLN HMATELFGPEFLAMTAFILTI | 44 | No significant similarity found. | | | | No putative conserved domains have been detected |||

Fig. 12CC

| orf | Start position | Stop position | SEQ ID NO: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and Identity | | Name | Acc No | E value |
| 132 | 68013 | 68225 | 913 | MKFINAIRKFISNVIALVALTAGA FVAIPFIVLIIADWINPTKKDEKL SNEEFQKRVNTLTAKLQQVMK | 70 | No significant similarity found. | | | | No putative conserved domains have been detected | | |
| 133 | 68222 | 68524 | 914 | MIEIYGIPEEVWRCPGCKAVRD LLDKLQLPYEFYNVINEVDGQP VYDRPLIESLAKRIGCYPSLAIR YPVIFMDNVKQYDIPTFKTNLIA AGHDPDIIED | 100 | NrdH glutaredoxin [Enterobacteria phage IME08] | YP_003734220.1 | 7e-26 (62/99) | glutaredoxin | Glutaredoxin | pfam00462 | 6.62e-03 |
| 134 | 68710 | 68898 | 915 | MNWLNWQEALEAMSKGCKVK HVHFTDDEYFLMKNKVICDENG YDMTRWYKGESWQNEHWYIA | 62 | Hypothetical protein AGC_0014 [Enterobacteria phage EPS7] | YP_001836934.1 | 3e-04 (26/59) | | No putative conserved domains have been detected | | |
| 135 | 68895 | 69137 | 916 | MKTFAVGDIVRTRIWDGLQFEV VYVVGSDGVLLHRINNLIKWHL ERFVKYHEFNSYHCTVAPVASK EYYDMLEELKSLKD | 80 | Hypothetical protein RB14ORF100 [Enterobacteria phage RB14] | YP_002854436.1 | 7e-04 (28/81) | | No putative conserved domains have been detected | | |
| 136 | 69202 | 69534 | 917 | MSQAIKNALNAFAYYKVSAMLE EGRCVTPSLLDQWEVELHGTM KEEGQKIGKARIRELVVAYLLSE FGIKAFGVEPIVVGVGEISESAIR KMKNQRKKGFRDVKAVKAAK | 110 | gp55.2 hypothetical protein [Enterobacteria phage T4] | NP_049681.1 | 4e-29 (61/107) | | No putative conserved domains have been detected | | |
| 137 | 69531 | 69806 | 918 | MKLNQNGCPSRVRFCILELRSN IVVIDEYTTIVGVQQYLDRRFDT RTHMKYGFPGKCKFYPMSADH QSVVNDEYKWAEGLTLKELEE YLDA | 91 | No significant similarity found. | | | | No putative conserved domains have been detected | | |
| 138 | 69799 | 70080 | 919 | MRKVILYTEIFTSRWVFDSVRIS NASKEDVRNAQRLAYDEAGKS PAFVKIEYIITDSALIHNVSESVL KKFCVDRINKGTSMEYFLLARE LKW | 93 | No significant similarity found. | | | | No putative conserved domains have been detected | | |
| 139 | 70074 | 70298 | 920 | MVEEQIAEIGLLGWFVSKTKDG RNLIETPEGEFIIEEDFDAFWIYE RSGENEYTSVDAFSKFEDAIDS VKAWLK | 74 | No significant similarity found. | | | | Formyl-methanofuran-tetrahydro-methanopterin formyl-transferase | PRK02114 | 1.51e-03 |
| 140 | 70286 | 70564 | 921 | MAKVNQIMIVVEGIGGFTIDSYM GVWFDNEEGMYWETHASMLN ETHYESLYSSFMEMMHEVDES DWFELSLVEFKRIMEQLFQCYR | 92 | Hypothetical protein RB14ORF65 [Enterobacteria] | YP_002854401.1 | 3e-08 (32/89) | | No putative conserved domains have been detected | | |

Fig. 12DD

| orf | Start position | Stop position | SEQ ID NO: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | IMKGEL | | phage RB14] | | | | | | |
| 141 | 70561 | 70806 | 922 | MKIQLTLTHENIKGVFCLENSQI TFAQDGTYWYAESDDIAGYGM ERVFEDFEAVIDVPLDFTYNDF YRIMMKLIACAELIK | 81 | No significant similarity found. | | | | No putative conserved domains have been detected | | |
| 142 | 70873 | 71421 | 923 | MSNYVNNKELYKSICSWKEKC RESEAGGPRVVKQNDTIGLAI MLIAEGLSKRFNFSGYTQSWK QEMISDGIEAAIKGLINFDETKY DNPHAYITQACFNAFVQRIKKE RKEMAKKYSYFVHNVYDSRDD DMVALADETFIQDIYDKMTQYE STAYKAPGSAKKSEPTSDGPNL EFLYEAED | 182 | gp55 Sigma factor for T4 late transcription [Enterobacteria phage T4] | NP_049679.1 | 4e-76 (139/180) | sigma factor | RNA polymerase sigma factor | PHA02547 | 1,38e-71 |
| 143 | 71405 | 71635 | 924 | MRLKINLDGFLEDVQDLDAIPYL LKMYLREVLDLDIHDPKNPHDA DFRSDSAIIEHSYNWTDTEFTFE INYHPKE | 76 | a-gt.5 hypothetical protein [Enterobacteria phage T4] | NP_049678.1 | 2e-15 (40/68) | | No putative conserved domains have been detected | | |
| 144 | 71637 | 71939 | 925 | MNNITQEERDELQQKLMEAAE EQAIARANKIVRKNRREIERLKA HAGDAVLDNNFPAYKYAIEKLR TILKQPFTDEIILTCWNTSRKSV WDILNAGTSKI | 100 | a-gt.4 conserved hypothetical protein [Enterobacteria phage JS98] | YP_001595190.1 | 2e-20 (51/99) | | a-gt.4, hypothetical protein | PHA02571 | 1,02e-22 |
| 145 | 71917 | 72114 | 926 | MLVQVKFKRVRKDAGFTLNTAT GTMAVKVADNQYRVLGSTEGC KLIDKNSLVWVDTFQVKRWYE W | 65 | a-gt.3 conserved hypothetical protein [Enterobacteria phage RB69] | NP_861758.1 | 7e-08 (31/66) | | No putative conserved domains have been detected | | |
| 146 | 72146 | 72391 | 927 | MGSNPGHDWPEGNYACRCSN CSERYTGPKRSYFCYKCDTAR REAPAPDYEAIRNAKIDMLKRF EEAKRICEAAGYVYKKI | 81 | No significant similarity found. | | | | No putative conserved domains have been detected | | |

Fig. 12EE

| orf | Start position | Stop position | SEQ ID NO: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 147 | 72461 | 73657 | 928 | MKINILMARGLEGCGVTKFSLE HREWLVKHGHEVNIIYAKDKAF TRNRAHSYKDVTIPVSLADDYD KTLSLLNACDILIINSVPAVNAPE AAIDNYKKLIENIKPEVRVVVYQ HDHRALSLRRNAGLEETVKRA DVLFSHSSNGDFNTVLMEEYFP SGGLSFFDDSDSAPPVYNFQP AMNIKAIRDKYWKDFSAIDFDIH RWIGRTTTWKGYFLMFDFHES HLRPAGKTTILEGLERSPAFINIK ERYEIDYCRHYHQVKTGPGLNP QVLDRYVNSEMLERMSQSGFG YQLSRLPDKFLERSLEYTHLEL GACGTIPVFHKATGDALKFRVD GKPLTSHDSGILWLNDENKNEV FERMKHLSSDQKLYDKERNKA FEFLVEHQDSEHCFKEQFELMT K | 398 | Alpha-glucosyl-transferase [Enterobacteria phage RB32] | YP_803002.1 | 6e-164 (273/401) | alpha-glucosyl-transferase | AGT, alpha-glucosyl-transferase | pfam11440 | 1.80e-143 |
| 148 | 73728 | 74750 | 929 | MKIIHSGDWHLGVRADDPWVQ DVQRHGIKQHIDYAKKHGIKTII QYGDIFDVRKAITHKTMEFAREI AESLEKEGINLITIVGNHDMHYK NTLTPNASTEVLGKYKHTVIEK PVTMDFDGTLIDLCPWMCEEN TSEIMKHIKESSAEYCIGHWELN GFYFYKGMKSHGLEPDFLKKY KQVWSGHFHTISSAANVKYIGT PWTLTAGDENDPRGFWVQDTE LSTFDFVPNEITWHRKLIYPVTG QVDFEEFRNLAVRIIITAVDEDL PKFESELEKVVHELRTVSKVDN SVESEDGEEVEVKSLLDLMEEY IQALEDLSADDIKALKVMSKQLY IEAQNQ | 340 | gp47 recombination endonuclease subunit [Enterobacteria phage RB32] | YP_803000.1 | 6e-144 (237/337) | recombination endonuclease subunit | Endonuclease subunit | PHA02546 | 2.02e-136 |

Fig. 12FF

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 149 | 74747 | 76429 | 930 | VKTFKLNRVKYKNIMSVGQAAI DIQLDKCQKTLITGKNGGGKST MLEAITFALFGKPFRDIKKGQLI NSFNKKDSVVELWMEYDGHSF YIKRGQKPNVFEILRDGNKLDE AASSKDFQSYFESLIGMSYTSF KQIVLGTAGYTPFMGLSTANR RKLVEDLLEVSLLADMDKLNKT QIREINQQIQVNDVQREALTNEI KTHHEYAEKQKKLSGDNVARL QAMYDEQVNEARGYKAELETL QRELLELVIGDDPAESIQEVQG KTFKIRSKIESYSKVLGLYDKGG HCPTCLQDLHSNDTLITKINHHV EECNTILGELKTRQSELDELAR EYNTVRARARDIKTQMGSLKQ MTITAVEKARRIKAAIDKASQEFI DNSDKIKLLQEELDKIILVKTNLV MEKYRRGILTEMLKDSGIKGAII KKYIPMFNKQINSYLKIMEADYS FTLNEEFSETIKSRGREEFSYAS FSQGEKARIDIALLFTWRDIAEK VSGVKINCLFLDEVYDSATDAE GYKAITAILNKMVDANVFIISHRD HDPQAYGQHLQMKKVGRFTV ME | 560 | gp46 recombination endonuclease subunit [Enterobacteria phage RB14] | YP_00285439 0.1 | 0.0 (382/563) | recombinatio n endonucleas e subunit | Endonucleas e subunit | PHA025 62 | 0.0 |
| 150 | 76426 | 76620 | 931 | MNEFTTGQHLLAFPELKRYVLV NLFSDERHLVTEEMLRDAFTGN EYNRVMSNRNPGWMVEDYYD | 64 | gp45.2 hypothetical protein [Enterobacteria phage RB51] | YP_00285401 1.1 | 3e-17 (41/64) | | No putative conserved domains have been detected |||
| 151 | 76631 | 77008 | 932 | MINFVDVKDIQVKNVRADSNPN NQNRIRKSWVLALTEETKQAIK DKIKDSEARFAFYKSIDDEVAEK WIELMRKHYNESIKAGAKIVTDR HGGERLENDYCVDADEQLVAA GQIVAEELTATFAA | 125 | RNA polymerase binding [Enterobacteria phage RB32] | YP_802994.1 | 5e-35 (71/123) | RNA polymerase binding | Phage_Rpb A | pfam10 789 | 1.19e -28 |

Fig. 12GG

| orf | Start position | Stop position | SEQ ID NO: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 152 | 77044 | 77745 | 933 | MKFSKETLNILKNFSTINSGIML KPGNFIMTRAVNGTTYAEATIS DTIDTDVAIYDLNSFLSILSLVGD DADIIMQEDGNLAIKDARSTIFW PAADPSTIVFPTKPIPFPVANVII DFKGEDLQQLMRVSRGMQIDTI AITNVDGKIVLRGYNKVEDAALT RPKYSLTLGDYEGEGNFNFIIN MSNMKMTIGDYKLMLWAKMNG SKKQTAAKFEGASASYVVAME ADSTFDFE | 233 | gp45 sliding clamp DNA polymerase [Enterobacteria phage RB32] | YP_802993.1 | 1e-94 (173/232) | sliding clamp DNA polymerase | Sliding clamp | PHA025 45 | 1,26e -86 |
| 153 | 77794 | 78756 | 934 | MKLTVNEADFMWEQKYRPGTI SECVLPAEDKEIFSALVAKGKIP HLILHSTSPGTGKTVAKALCN DINAEMMFVNGSDCKIDFVRGP LTAFASSASIAGKGKIIVIDEFDR AGLAESQRHLRSFMEAYSTNC TIIITANNLDGIIKPLQSRCRVINF GKPSPSDVKPMQIEMLKRCLAI CENEGVVVEDKKVVAALVKKNF PEFRKTINMLDHYSSKGVIDAGI LSIVLNDRGSIEDVIEAIKTKNIKE LRALAPKYAADYTWFVDKLSSE LYTMVTGPSIIRMYEIIGENNQY HGIAASIELHLVYMLIQLVVEMQ WK | 320 | gp44 clamp-loader subunit [Enterobacteria phage RB32] | YP_802992.1 | 1e-140 (231/318) | clamp-loader subunit | Clamp loader, small subunit | PHA025 44 | 3,56e -154 |
| 154 | 78756 | 79322 | 935 | MSLFEDDQYNEHQIAWLGKD WTKVQELSDSYKEKAENQFFTII GSINEKQEHLNISTMDYSKFMV ENALSQHPDCMPSYVVMNLVG QGLSDQAHYNYMMASVPRGR RYGKWAKLTENIQODALILQVIMT YYKVNAIDARMYRETLEAKNKL KPALKKMKGLVTDELVKTITKNV KEQKNLKKTALEW | 188 | gp62 clamp-loader subunit [Enterobacteria phage RB51] | YP_002854007.1 | 2e-65 (118/188) | clamp-loader subunit | Clamp loader small subunit | PHA025 93 | 4,34e -63 |
| 155 | 79316 | 79687 | 936 | MVKMIETLKQPEDFLKVKETLT RMGIANNKDKVLYQSCHILQKQ GRYYIVHFKEMLKLDGRPVTIDL EDEIRRDSIAQLLADWGLLSINR GQTLAQMQNNFRVITFKQKHE WTLKSKYTIGA | 123 | Translation repressor protein [Enterobacteria phage RB69] | YP_861747.1 | 4e-48 (96/124) | translation repressor protein | regA, translation repressor protein | PHA025 43 | 1,68e -55 |

Fig. 12HH

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and Identity | | Name | Acc No | E value |
| 156 | 79687 | 79887 | 937 | MTDQEFYDKLKLKNIRITAPEWFS LPIDEQIQYQVKETLEKYPGRKV MMCFTYDKNRVPRIQKQVIEV | 66 | No significant similarity found. | | | | No putative conserved domains have been detected | | |
| 157 | 79980 | 82688 | 938 | MKEFYISVESLGNDIVERYIDST GEERMRRVPYSPVMFSHCMEE TRYKDIYGKYCKKNTFPTMKDA RDWMRRMEDMGMEAMGMDD FKLAYISDTYGSEIVYNKKFIRIA NCDIEVTASQFPDPMKAEYEID AITHYDSVDDKFYVFDLLHSLY GSVSEWDKKLAARLDSEGGDE VPQHILDRVVYMPFNSEKEMML EYINLWEQKCPAIFTGWNIEGF DIPYIMNRVKQILGERAMKRFSP LNKVSSKIITNMYGDKEIYSIMG VTILDYMDLYKKFSFTNQPTYKL DFIAYYETKKGKLAYDGPINKLR ETNHQRYISYNIIDVESVQAIDA VRGFIDLAISMSYYAKMPYQGV MSPIKTWDAIIFNSLKEQDKVIP QSRSHVKQSYPGAYVKEPVPA AYRYIMSFDLTSLYPSIIRQVNIS PETIVGQFKLHPLGEYINKTAPR PSDEYSCSPNGWMYRKDVDG VIPVEIAKVFYQRKEWKNKMMG AKRNQELIKKVLNDKKFGTIDKF AEVNVYEDFSDDMKAELLTYTE ECLDKLMFECKHAEILGNTNQL NRKILINSLYGALGNIYFRYDL RNASAITLFGQMAIQWIERKVN EYLNKVCCGTEGHSFVVAGDTD SIYVCVDKVIEKVGLERFKETND LVEFLNQFGKKKMEPWIDQSY REMCEYMNNKEHLMFMDREAI SCPPLGSNGIGGFWKAKKRYA LNVYDMEGTRYAEPHLKIMGM ETQQSSTPTAVQNALEESIRRM LQEGEESLQQYYKQFESEYRE LDYKVIAEVKTANNIGKYDDGA GYPDKGTPYHVKGALAYNRAT AGFEGITPIMEGEKVMVIPLREG NPYGEKCMAWPSGTELPQEIR QEVLVWLDHSVLFQKSFVKPLT | 902 | gp43 DNA polymerase [Enterobacteria phage T4] | NP_049662.1 | 0,0 (675/900) | DNA polymerase | DNA polymerase | PHA025 28 | 0,0 |

Fig. 12II

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | GMSEAAGLDYEEKSSLLDMFDF | | | | | | | | |
| 158 | 82758 | 83201 | 939 | MKSLLAVIVALTLTGCCMPQGD IVPASSVGQVRANGGTVGYYRA SNQVSAESLAVERRLAKEKANP NRQLSAMELDMIEQNKHELEEI KRLRKTQKERTCTAQAAAVND QIRLTDFANGGLSYNEHKQRM EQLKSLQNHIYNKCMSN | 147 | No significant similarity found. | | | | No putative conserved domains have been detected | | |

Fig. 12JJ

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 159 | 83212 | 83418 | 940 | MEAVFGLILFFIYFLPTFVACSR KHKSRGGIFITNLVFGWSIIGWLI ALIWSASNAQONTIIIQQVK | 68 | Immunity to superinfection membrane protein [Enterobacteria phage RB32] | YP_802986.1 | 9e-08 (31/61) | immunity to superinfectio n membrane protein | No putative conserved domains have been detected | | |
| 160 | 83427 | 84161 | 941 | MIVTPMTVQDIRQEFADALLNK EFVIDKTGVKTIEIVGASFIADEN LIFGAVNDGYIARELEWYKSQS LFVKDIPGETPAIWKAIASKHGEI NSNYGWAVWSTQNYSQFANC AKELINNPDSRRGIMIYTRPQM QYDFERDGMSDFMCTNNVQYL IRDNRVHAVVNMRSNDVVFGY RNDYAWQLYVLEQLTKLLNAS GKNYSVGDIIWNVGSLHVYSRH FYLVDNYAHTGETHIAKKDYKG EWK | 244 | gp42 dCMP hydroxymethylase [Enterobacteria phage RB51] | YP_002853999.1 | 2e-103 (177/246) | thymidylate synthetase and pyrimidine hydroxy-methylase | Thymidylat_s ynt | pfam00 303 | 1,55e -21 |
| 161 | 84158 | 84994 | 942 | MIQFVIPSYKRAGAVTALTMFPE GYVPHLVVRESEKEAYETWHG HAAKIVTVPDDVDGIAGTRRLIT EMYAGQRIWMLDDDTTIHLTEI RERDDRRVPLGVGEAMSQEVF DDMVKYVETAMDCGYYHGHA RLPIFKITSSWGHYRENSFGFT NTFYDLTKLTAEDIGYGIIDLNED AYAFLKLINMGHPHLALFKYLVK SGKVQSPGGCSTQRDTARQN RALEQLHAAFPNQARWKSKDG ERRGLFGDDEPLKSIRMCINTR VKSQAFHEFGKVEPYL | 278 | Beta-glucosyl-HMC-alpha-glucosyl-transferase [Enterobacteria phage AR1] | BAI83052.1 | 4e-106 (180/277) | beta-glucosyl-HMC-alpha-glucosyl-transferase | No putative conserved domains have been detected | | |
| 162 | 84991 | 85242 | 943 | VRAKALQGPLMNIYDKSDVAGN IFKAEEFRCFVCKSDEFVHEGT TGSDGMHCWWHGMCVGCKIH YEIDMETVVYNTKKKWNFC | 83 | No significant similarity found. | | | | No putative conserved domains have been detected | | |

Fig. 12KK

| orf | Start position | Stop position | SEQ ID NO.: | Aminoacidic sequence | Size (aa) | Homologous/similar proteins |  |  | Predicted function | Conserved Domains |  |  |
|---|---|---|---|---|---|---|---|---|---|---|---|---|
|  |  |  |  |  |  | Name[organism] | Acc No | E value and identity |  | Name | Acc No | E value |
| 163 | 85325 | 86500 | 944 | MSDLKSRLIKASTSKMTAELTK SKFFNEKDVVRTKIPMLNIAISG ALDGGMQSGLTIFAGPSKHFKS NMSLTMVSAYLNKYPDAVCLFY DSEFGITPAYLKSMGVDPDRVI HTPVQSVEQLKIDMVNQLEAIE RGEKVIVFIDSIGNMASKKETED ALNEKSVADMTRAKSLKSLFRI VTPYFSIKNIPCVAVNHTIETIEM FSKTVMTGGTGPMYSADTVFII GKRQIKDGSELEGYQFVLNAEK SRTVKEKSKFFIDVKFDGGIDPY SGLLDMALDIGFVVKPKNGWYA REFLDVETGEMIREEKSWRAK DTSSTEFWGPLFKHEPFRDAIK ARYQLGAIDSNAAVDEAVAEMI NSKVSTKVDGVKLPESGSVSAA EVEDELENFMNED | 391 | RecA-like recombinase protein [Enterobacteria phage RB32] | YP_802982.1 | 0.0 (342/387) | RecA-like recombinase protein | recA | cd00983 | 4,14e-13 |
| 164 | 86490 | 86840 | 945 | MKTEFDLESELEKFEQESPSEE GDFERQERVFKKSHEIIQEAMK TVIQEIVIKLNGQSHLYVVHKLNI SPSGEVTIEFSTPSEAHKDELY PHVEACVKQQIQSALKTKKKSL WKIF | 116 | gp40 head vertex assembly chaperone [Enterobacteria phage IME08] | YP_003734187.1 | 1e-13 (47/108) | head vertex assembly chaperone | Phage_head_chap | pfam11113 | 2,81e-12 |
| 165 | 86850 | 88289 | 946 | VVETILANLIYNQAFFTKVWPYM DKEYFEQGPAQTVFNIIKKHVN EYTAIPSKTALCVALDNSSITET EHEGAKKLIDKLSDAPEDLNWL VKETEKYVQEKAMYNATSRIIEI QTNAQLEPNKRDKRLPDIGAIP DIMREALSVSFDSYIGHDWMED YEARWLSYQNKARKVPFKLSIL NKITKGGAETGTLNVLMAGVNV GKSLGLCSLAADYLQMGHNVL YISMEMAEEVCAKRIDANLLDV SLDDIDDGCVSYAEYKGKMEK WRSSSTLGRLIIKQYPTGGANA NTFRALLNELKLKKNFKPTVIIID YLGICASCRIRQYTENSYTLVKA IAEELRALAVESETVLWTAAQV GRSAWDASDMDMSDIAESAGL PATADFMLAVIETPELAQMKQQ LIKQIKSRYGDKNINNKFSMGVH | 479 | 41 helicase [Enterobacteria phage RB69] | NP_861732.2 | 0.0 (386/484) | DNA primase-helicase ATPase | Helicase | PHA02542 | 0,0 |

Fig. 12LL

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | KANQRWVEIEQQNDPTKPNPSNTVREGAGAQNRVAESNRQERVSRSKLDALAEELKF | | | | | | | | |
| 166 | 88300 | 88533 | 947 | MIFVFSVIRDQSGRSFVVTASDSVHRGVIAYNKADLSSYDYGEVKAYNDEGIWVNSAIYLPTKNLTSDEVLEKLFKR | 77 | No significant similarity found. | | | | No putative conserved domains have been detected | | |
| 167 | 88594 | 88887 | 948 | MKKIVLALIFAVSSCSAVPALANYDKDLCEWSMTADEKDVAEQIRADVGHIIDNTDPSKMKEVQAEISNDGAAIKLNYALYCDANFDNFTIASWILG | 96 | Protein spackle precursor [Enterobacteria phage AR1] | BAI83046.1 | 6e-21 (47/96) | protein spackle precursor | | | |
| 168 | 88884 | 89102 | 949 | MITYVLVMAIMTGAGGVSTEKLSFTGMNESSLAQKCEDAGKQFTGIKADSGFGSPSVYTTYKCIRIDGGNNK | 72 | No significant similarity found. | | | | No putative conserved domains have been detected | | |
| 169 | 89115 | 89282 | 950 | MKTFKEFVKLNEEMVAGDAGGNPQNIASGTTSGAVVNKGPETLPKKKRDKSKPET | 55 | gp61.1 hypothetical protein [Enterobacteria phage JS98] | YP_001595156.1 | 6e-13 (38/48) | | Gp23 | pfam07068 | 3.47e-05 |

Fig. 12MM

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 170 | 89322 | 90344 | 951 | MSWVDNEFAIRAISHLPKFRHV TTSSTFKLNCRCPICGDSQKDI NKARFWIFDACGQLRCHCFNC EYNKWLSQYLKDNEPDLYREY LLEKRREQVFDKPKTVEPSEKI NAKLPVIEKLNFCERLDRLPKEH PIVKYVTARCIPSTSWKRLWFT NQWPSLVNSVNPGTYKNETNE PRLVIPIFNKKGEIESFQGRALR KNAPQKYITIKAHEHATKNYGLD TIDESKLVFVMEGPIDSLFIDNAI AITGGSLDLAQVPCHDNRAWIM DHEPRHPDTIKRMKRLVDAGEK VVFWDKSPWKSKDINDMIMKE GATASEITDYINQNISQGLMAKL RLDKYAKI | 340 | gp61 DNA primase subunit [Enterobacteria phage JS98] | YP_00159515 5.1 | 2e-143 (243/344) | DNA primase subunit | DNA primase | PHA025 40 | 9,49e -155 |
| 171 | 90554 | 90363 | 952 | MSEVKRECKDKGGFGRYLYVG IATAALAAWNYVVVPLASTHGL VLPPMPLEKVVSFIMTGGLL | 63 | No significant similarity found. | | | | No putative conserved domains have been detected |||
| 172 | 90621 | 91142 | 953 | MPHFNECSQLIAGADKAEARYA GIVRKVGGDPLQVMLDMQKSL QVRLANDKPGTNMHPDELAQA GDIVQWLRNQKDYIDDEFRELL TSLGGMSNGEKAASAVWKPW KSDHVKMQETYIKDLSDKDQLE IKFEMIDILHFVLNMFMALGLDS EEIFKLYYLKNAENFARQDSGY | 173 | gp56 dCTPase [Enterobacteria phage JS98] | YP_00159515 4.1 | 1e-73 (136/173) | dCTPase pyro-phosphatase | dCTP pyro-phosphatase | PHA026 02 | 1,24e -79 |
| 173 | 91142 | 91279 | 954 | MAKRISKRRLKIIRKQKERALVL ALREEITREIDKEILKALTAAI | 45 | No significant similarity found. | | | | No putative conserved domains have been detected |||
| 174 | 91310 | 91546 | 955 | MAYVNIKTFDHTTADGEVKGTE VSVAFKVYSDSHRIANAQYQIF PSEKAAYSTVVDDAATWATTN AKMFEAVPSDAEV | 78 | Soc small outer capsid protein [Enterobacteria phage RB69] | NP_861717.1 | 2e-19 (48/73) | small outer capsid protein | No putative conserved domains have been detected |||
| 175 | 91625 | 91816 | 956 | MICYTKPWYQSSLKKSHFDCW YRGVRAAALLLKAAPALIKAND KWFEDNNMTEGALCGKRKNL | 63 | No significant similarity found. | | | | No putative conserved domains have been detected |||
| 176 | 91794 | 92318 | 957 | VANAKIYNAKIYKVSLQRAVQS RSDANGVLRLDQDRIFTVALYS TFDKDFKDLVNKFEAFGWCPS EDYGIIKTAHVFDVDTVPGSPVA ILRALHLKGYTNVCHETSLYEYE NDIISRGKKIIIDSTDSLIEFTKLV WLYMGADFIKLTPSPLLQKAAD | 174 | No significant similarity found. | | | | No putative conserved domains have been detected |||

Fig. 12NN

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | GYNSSSCLYRNNEWFM | | | | | | | | |
| 177 | 92318 | 92506 | 958 | MDLFEMMEEPQEEVQVHPVIS KDIKDEYRIIIOKYGIKAPEAALLD ELASIWSDPPPWSPWAK | 62 | ModA.2 hypothetical protein [Enterobacteria phage T4] | NP_049637.1 | 7e-12 (36/62) | | No putative conserved domains have been detected | | |
| 178 | 92578 | 93267 | 959 | MAISLNPSISVKLSKVIPIEKPIRS IDVLNFARESKGLPLYDLSVWE ALANRFDCKEQSILWQCMNNKI GEEFHKKLDSIVRRHQIDNSDIL YRGLSCRESKAFYDALIKGEKF GFGKVASFTTDETIAREFAGKW HYSTFVVIEVNNCHQSFDYHTN MKSLLITAPDSEFMRPNDVIDNI AQRRSADIEMIDKEQERMLPM GTKFKVVGHNKVEKSGLLMDY FSVTIA | 229 | ModB ADP-ribosylase [Enterobacteria phage RB69] | NP_861709.1 | 5e-19 (59/178) | ADP-ribosylase | No putative conserved domains have been detected | | |
| 179 | 93345 | 94103 | 960 | MMKFTAETAKIYTRLITTLGSAQ RRNKEFNLTPEYLFNIMQQTHC AYSGEKFGTVKGNHPDSMTLE RWNNDLGYVMGNVIPVKQKYN TLRGNNTIEGLERKANEIAARIV RSSDSVKPTSDKEASRLEKIRE YEKTITSIKTNLHNRENHLSQFV QKEKNGTATSADLELINALRTRI SGGKSELAKVERKLSAILASVP NRPSDAEIRVQSIRLIVSSLRRL EECSMLDKLKLKKGLPLTASFF QLLRGKM | 252 | Putative Srd anti-sigma factor [Enterobacteria phage RB69] | NP_861707.1 | 3e-34 (96/246) | Srd anti-sigma factor | Seryl-tRNA synthetase | PRK054 31 | 1,55e -04 |
| 180 | 94103 | 94417 | 961 | MQHYGYVVAYKDKDGFDHPVT TDMYDGERCVVFTNEESANKA RIRTMSVLTDKLAKGNFTGKSK TKGMLWWWKTTELVYEPLSDVE REKLKAKIKNLHVRVKVA | 104 | No significant similarity found. | | | | No putative conserved domains have been detected | | |

Fig. 120O

| orf | Start position | Stop position | SEQ ID NO: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 181 | 94414 | 95745 | 962 | MITFDCLKESQKAIFNKVIEMVK QGAKGQHTINGPAGTGKTTLT KFIIDALISQGISGIALAAPTHGA KKVLSKLSGMQASTIHSLLKINP TTYEENVLFEQKKVPDMASIRV LICDEASMYDRKLFKILMATIPA WCIVIAIGDKAQIRPVEPGSSNEP ALSPFFTHKDFLQLHLTEVMRS NAPIIEVATEIRNGGWIRDCVVD GHGVRGFTKGTALKDFMLNYF NLVKTPEDLFENRMLAFTNKSV DKLNEIIRRRIYETERPFVVGEIV VMQEPLTKELKFEGKKFSEILFN NGOFVRILDAIETTSFLGARGVP GEYLVRHWVLDIETYGDDEEYA REKICVISSEEEMNKFQFFLAKT ADTYKNWNKGGKAPWSEFWD AKRKFHKVKALPASTFHKAQGI SIDRSFIYTPCIHMADASLAQQL LYVGTTRGRYDVFYV | 443 | DNA helicase [Enterobacteria phage RB14] | YP_002854352.1 | 0.0 (323/442) | DNA helicase | DUF889, PIF1 helicase | pfam05970 | 5,03e -08 |
| 182 | 95752 | 96006 | 963 | MFELKLEDLQTMIVGLQESKFE APDNVKRAINIKIDIVLNELRDIA DNANAITWFTGYDPKVYLSEYI GCCLREIKFMLEAQNG | 84 | No significant similarity found. | | | | | | 4,61e -15 |
| | | | | | | | | | | recD | TIGR01447 | |
| | | | | | | | | | | No putative conserved domains have been detected | | |
| 183 | 95999 | 96688 | 964 | MAKDFIIDFETFGNVSSSVIDL ALITFDSDPEVLESFDELVKRGH RIKFDLKSQKGHRLFGKSTLEW WKKQSAEARANLASTPDDLSVI AGIKEAQQYLIDNGIHPWDSFG WCRGQSFDFPIFVDCLRDVQR AQGISEEEIDTFKEEPCKFWNQ RDIRTAIESLLLTRGLTTTPLPKG TLNGFIAHDSIHDCAKDILMLKY AQRYALGLSEAPSPEDTDPLSL PKGRG | 229 | Exonuclease A [Enterobacteria phage RB32] | YP_802954.1 | 8e-89 (154/225) | exonuclease A | dexA, exonuclease | PHA02570 | 4,05e -86 |
| 184 | 96688 | 96855 | 965 | MEEFEFDENFEEWFNREILPKI SPTMVLVAKALMAKGWDAGYM FGVDVGCEISHR | 55 | No significant similarity found. | | | | | No putative conserved domains have been detected | | |

Fig. 12PP

| orf | Start position | Stop position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 185 | 96916 | 97359 | 966 | MMKNLVVGENVKVIGGKHIGKE GVIVGIFNRSNKMSSYLLQLEN EDKAVYSLQKFVVALESRDLLD SMFNESYLRKWVHVNSLDNVIT QSVSSTNSATNLSLHKNVLVTD EWEEDGKTLVNVVFQGNYAVL PKADVEPTESQRQGLV | 147 | No significant similarity found. | | | | No putative conserved domains have been detected | | |
| 186 | 97424 | 97639 | 967 | MKTENTVKITAEAFEDILFNPDLI VVQKEKTFGKEEHWTWLYVFA NHGDIVPVRTFARVITVDGPEY MEIV | 71 | Cef modifier of suppressor tRNAs [Enterobacteria phage JS10] | YP_00292235 6.1 | 3e-07 (32/64) | cef modifier of suppressor tRNAs | No putative conserved domains have been detected | | |
| 187 | 97639 | 98004 | 968 | MNFKEGVQYKFVNDEAEEEFS SRYEVNEDFVYELYENGGSFTV TKVDRQNNRVSGIMWANGTEC DEVGGEDLVIFDSEFKYFTEVG TSANVIPTDLVMNLSIHNRGQAI AAIAALQSAYQC | 121 | No significant similarity found. | | | | No putative conserved domains have been detected | | |
| 188 | 97998 | 98333 | 969 | MLNLAPIFEASKLSYPIPNRSIG NVMLQLSSETGEMCDWINRPW RQKEEFEGECADVINCVVDAL WLHFRNRHKNDTHVSDDEISM MVTRALNEQIMVKTQKWKDAV NANV | 111 | Hypothetical protein 44RRORF011c [Aeromonas phage 44RR2.8t] | NP_932366.1 | 3e-10 (37/102) | | No putative conserved domains have been detected | | |
| 189 | 98320 | 98496 | 970 | MPMYDYKCEVCGKKIEIMRKIS HRDYTVNCFNPKCEGQMKRVV SAPAVHYDGLKSGDY | 58 | No significant similarity found. | | | | CxxC_CxxC _SSSS | TIGR02 605 | 5,16e -07 |
| 190 | 98582 | 98830 | 971 | MKKILITALAFMMIGCTDADNAT RVLENAGFTEVDITGYKFFSCS EDDFQHTGFKAVGPTGKTVKG TVCSGIFLKNSTIRFE | 82 | Hypothetical protein T4Tp006 [Enterobacteria phage T4T] | ADJ39724.1 | 8e-26 (52/81) | | No putative conserved domains have been detected | | |
| 191 | 98913 | 99110 | 972 | MKYIILTLIALVISIGVLVSLADST ESSNEVQKSSIGIGVNGQVGVK ISDNLCVNPSTGAAEVCF | 65 | No significant similarity found. | | | | | | |

Fig. 12QQ

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| 192 | 99151 | 100989 | 973 | MIKNEIKILSDREHIIKRSGMYIG SSACEAHDRFLFGKFQSVKYVP GIIKLIDEIIDNSVDEAIRTNFKHA NKISVDIKGNKIIVTDNGRGLPQ APVVTPEGETIPGPVAAWTRPR AGGNFGDDAERKTGMNGVG SALTNIFSVSFTGATCDGKNEII VRCSNGSENSWEEHPAKDKE FIKDKTGTVVSFIPDFSHFESTG LTDVDQSIIHDRLMTLAVVYPDI EFKFMGKRVQGKFKAYAQMYD ENAVVQDSDTCAIAIGRSDDGF RQLSYVNNIHTKNGGTHVDLVL DELSNELIPALKRKYKLEVNKAR IKECLTVIMFIRDMSNMRFDSQT KERLTSPWGEIRSHIDIDYKKLA NAIMKSEDIHMPIIEAMLARKLA AEKAAETKAAKKAQKAKVAKHI KANKYGKDADTTLFLTEGDSAI GYLLTTRDRELHGGYPLRGKF MNTWGMSAADAMKNKEVFDIC AITGLTIGEPAENTNYRNIAIMTD ADVDGVGSIFPSLLAFFSNWPE LFEQGRIRFVKTPVIILTKGKEQ RWFYSLGEYEDHKDDFKGWKL RYIKGLGSLEEDEYERVIQDPV YDVVSLPENWKELFELIMGNDA APRKTWMSE | 612 | gp60plus39 DNA topoisomerase subunit [Enterobacteria phage RB51] | YP_002853958.1 | 0.0 (441/612) | DNA topoisomerase subunit | DNA topoisomerase II large subunit | PHA02569 | 0.0 |
| 193 | 101030 | 101182 | 974 | MQRYWITLVSGDYGYMFAEKK PLPGTWVTIWVENSDGSKHEV YGRVSRVH | 50 | No significant similarity found. | | | | No putative conserved domains have been detected | | |
| 194 | 101223 | 101471 | 975 | MKSTIISILRTEALKYSVDPSNEY QELLIKRLLNSIADRLESNQSVPI NHSLFAMKVIRFLRPDIKIADMV KVIKSSGAVKC | 82 | No significant similarity found. | | | | No putative conserved domains have been detected | | |
| 195 | 101465 | 101674 | 976 | MLKKSYVPNIKELFDDAIYREYRI IQRFFDIQAAEEFKDRFKQISDKI FTTNTATAEELLEVAEIIKRHN | 69 | Conserved hypothetical protein [Enterobacteria phage AR1] | BAI83010.1 | 7e-16 (45/65) | | No putative conserved domains have been detected | | |

Fig. 12RR

| orf | Start position | Stop position | SEQ ID NO: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| 196 | 10168 5 | 10386 2 | 977 | MKIKCDDEVIIGSSDAEDSTFTIK ASGKAFDILSNKLYKYKVRAVV RELSTNCDDAHKLNGNENRPF YIKAPTRLDPRFVIRDYGPGLNH NDMMTMYKTFFESTKNNSNDFI GALGLGSKSPLSYTSTFNVVSY HNGKATGYTVMKNRGEPTIRP MFVDDMKEDEETGLEITVPVKV EDIDTWHYEIAYILRTFGAVPPK VDSLRREIEYFPVDKTDWFSVN SSYESYGLYAVYGKIVYPISGV DVKADWLLNRYGKVYVHFPLG ELDITPSREELSLDEETIANIQKR VNALEEEVITADIKAFEAYESDR EFLREFNKLSSKERSILQSRGITI GNRDIKQVVAKYNLDKIRSYYV DNEVSVYVSCDEPARRKVSSS SWHRHNQVNISDICGVDRTKAF VLIDDKAGKRIATVRALCKSGLV PIWAHITVIKDNEDELHVIDELKK IMDTDEVVVFRVSELEAQRKAL PDYDTGPKEKRPKSPNVSLHWI DKDGYWEEDRQTLLSSEITELE GYAIGRNRDEIHTFPDNVWWW NMSITDMRSLAEACGIKKFYAIR PSAMKAAAKADGLLSFDRFIIDQ YIKCIDKVDYDQYMPSNATGNR ICGNIAHYDKLNFLSSKFTASGM KNPFLTKLNKIAKVCRTSKIKDE NDENNDLALCNKIYNKLSSDAE TIFYKKIEQFKDDYPVIASVLDT WRTDSKLVDDIVKIMELLDGAS TQNSENKGE | 725 | rIIA protector from prophage-induced early lysis [Enterobacteria phage IME08] | YP_00373415 1.1 | 5e-99 (250/754) | rIIA protector from prophage-induced early lysis | HSP90 family protein | PRK140 83 | 1.11e -03 |

Fig. 12SS

| orf | Start position | Stop position | SEQ ID NO.: | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 197 | 103863 | 104774 | 978 | MAVTCLSEIQKDAIVKNFKNGLY TKKELAENYGVSRDTIRRVFKE REARAAAAVPAKVEAPVEREF KWAASSKFISITEGRTTYNADS QHPGFKSALQKLVDGDIAGAID HINLEQGIKKFVQGNVRIEDGTL FYKDIELKSGLTERIVRAMEDGE DFKRYLPFLENLMLNPSRRAVY RLFDFLNANDIDITDDGHFIGWK VVRSNYFDCASNTFDNSPGKT VTMPRNQVDEDDQRTCSTGLH VCSKSYIGHFGSGSDRIVSVKV HPRDVVSIPVDYNDAKMRTCG YVVLEDVTDRWGSELR | 303 | rIIB protector from prophage-induced early lysis [Enterobacteria phage JS98] | YP_001595395.1 | 3e-93 (169/318) | rIIB protector from prophage-induced early lysis | No putative conserved domains have been detected | | |
| 198 | 104817 | 105113 | 979 | MINPFNVSHSKVVNLRGTHHAA TVFCHHVVKHEGDVHYAWLHC DELVELGDDFVVEPDTCNHDD RVYFGELHIRGIYGIDEQSPAEI EPTPDIYPRFE | 98 | RB69ORF272c hypothetical protein [Enterobacteria phage RB69] | NP_861962.1 | 1e-20 (52/96) | | No putative conserved domains have been detected | | |
| 199 | 105046 | 105633 | 980 | MALMNKALQRLNQLRTFTLDLN KLRGEAKVKIIDTARYSLDIDPS QDRIDVLKRCRIAIPAEYVVADF LDGYVNDQVVDHNNNDPYEW AWDVLAHPHYQGVRVEVKTHF VHDRANHKPWINVTTGKDGPF PDGSGINLGPMFKHKVADCIIIF VAEEVSQNVIRYTPMFAGGIEQ LMEVVKPSRVGAGGYIMHKF | 195 | Endonuclease IV [Enterobacteria phage RB14] | YP_002854607.1 | 2e-49 (104/183) | endonuclease IV | No putative conserved domains have been detected | | |
| 200 | 105698 | 105937 | 981 | MSYLELKSLRAKRGNASIKAEL LKEYRILESMNWHYAIIACDNG DSTYGGLYPNGAAAARDEHKD KVKALEEKIRNLCI | 79 | No significant similarity found. | | | | No putative conserved domains have been detected | | |
| 201 | 106126 | 106317 | 982 | MIRSSFDRRFNLMRTVVLSFIVA VALGIVAIFGFGIYFAICAVDIIQT DGLKSLVETVWEGQK | 64 | No significant similarity found. | | | | No putative conserved domains have been detected | | |
| 202 | 106462 | 106917 | 983 | MRNIMTFADLDNAGAELIGSIRN GDWAAGAPSREITEREGFYFL MFNDGKAGYIGASARFFVAKQ RSKAGFESVLSHIRSGRSQLGR TLRSNCVTYGVFWIPANKMKPL TTGYGKGQLALAFTRQHSSAA QTYSELNRILNDNFIFTLQKY | 151 | Nuclear disruption protein [Enterobacteria phage AR1] | BAI83281.1 | 1e-42 (87/148) | nuclear disruption protein | Phage_T4_N dd | pfam06591 | 7.83e-46 |

Fig. 12TT

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 203 | 107087 | 107230 | 984 | MIKGIAGGIWAALCVSTLTTGET SVISQALAQGTLSIILIIAAFSNID | 47 | Hypothetical protein EpJS98_gp256 [Enterobacteria phage JS98] | YP_001595385.1 | 5e-05 (24/47) | | No putative conserved domains have been detected ||
| 204 | 107223 | 107363 | 985 | MIKKILIGAALVAALLLILYYGMIY GMIYIVLFISDVIVQIGSLIW | 46 | Hypothetical protein RB32ORF257c [Enterobacteria phage RB32] | YP_803199.1 | 5e-04 (28/47) | | No putative conserved domains have been detected ||
| 205 | 107369 | 108757 | 986 | MDIFDTLLKQAGSIDDLAKASNL RHRDLKSIIDNEAKEYAIYTVEN RAIPNLIDGFKPVQRFVIARALD LARGNKEKFHKLASVAGGVADL GYHGETSAQDAGALMANTW NNNYPLLDGQGNFGSRLVQSA AASRYIFCRISDNFRKIYKDTEIA PVHKDKEHVPPAYYLPVIPTVLL NGVRGIATGYSTSILPHSFESVL ECTKAALRGEMMEPEVQFPKF NGKIVQTEDGSVELHGVYKETS RNSIYISEIPYKFERASYVEKVL DPLEDAGYITYDDDCSKTGFGF KVKFRKDYALSEDPEQRHAKIM KDFKLIEKMSQYIVIDENGKLN DKFKTSGELIRHFVEVRKTFTAK RIEHKIAETKQAFNLAQAKAQFI KEVIAGNIVIQGKTRKQLTKEIE QNELFKDHSEKLVSMNIYHITD DEAKKLAQEAKRLAQEVKYWE KTTPEAEYLKDLEEL | 462 | gp52 topoisomerase II medium subunit [Enterobacteria phage IME08] | YP_003734396.1 | 2e-175 (304/462) | topoisomerase II medium subunit | DNA topisomerase II medium subunit | PHA02592 | 0.0 |
| 206 | 108985 | 109248 | 987 | MITSLKSDIKNILYISTQADGTRL SHYVKGNIVVLDEFEVNREYPM RQVIQASNYEDGEEYQVVLCVY DDFWVLKLENGDKFLIFNV | 87 | No significant similarity found. | | | | | | |
| 207 | 109373 | 110017 | 988 | MSKVTYIIKASEDALNEKTAAILV QVAKKDFITSSELREILEETMNA SSVNSNIGVLIKKGLIEKSGDGLI ITGEAQDIISKAAVIYAEENKPEL LKKRNTRKARPLTEDMNEHKDL MMKLLGEMEDILPLKELTVYRS NYIAVLEKRTFGIRSLEVNNKGT FRIFGYKISEEHQKHFTDLGMS | 214 | Activator middle promoter [Enterobacteria phage RB32] | YP_803196.1 | 3e-76 (145/214) | activator middle promoter | MotA_activ | pfam09114 | 3.76e-32 |

Fig. 12UU

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | CRVAATGNTYLDIARTAENIETII RSIKEL | | | | | | | | |
| 208 | 110017 | 110187 | 989 | MELWEIIYEDDVNIRGSIFIKALD KYHAIELFEQLQQQTYINESRYL IKLAMFLVE | 56 | No significant similarity found. | | | | | | |
| 209 | 110187 | 110528 | 990 | MNKFKVLNELQRCVEKVNLNA NIPTDCWDVWFRGHFIGYIDKK FTKCYAIYNADGKHIMDVDNYQ KALAKFVPLAEAVNSMEWLEKI QGEPVIRQIGIREKKSLWQKIKG FFK | 113 | Arn.4 conserved hypothetical protein [Enterobacteria phage JS98] | YP_0015953 8.0.1 | 3e-13 (43/117) | | No putative conserved domains have been detected | | |
| 210 | 110525 | 110950 | 991 | MSKFSEQMNKFVDASRHGALI NEPEEVSIPEICFKVADWWDGR LLQRRIVCAANRFELKSGGTIVV PGTRHYSVDMANVLDMFRDKL VSDHVHGDNQGFVDQWGEYF TREEALIIATHAGQVNTVRPKSG PANELFSEDLY | 141 | Hypothetical protein EME08_gp240 [Enterobacteria phage IME08] | YP_0037343 9.1.1 | 1e-36 (73/113) | | No putative conserved domains have been detected | | |
| 211 | 110950 | 111252 | 992 | MISTLKNNITLLKIQRKSLQRSLE MMDDNWGTYTNEAGFKMADS KFMKTLMDKEYICPFSHPFNGG AKPFLAEMYKIMTEEMIKDIDYYI KELECKEDKV | 100 | Hypothetical protein RB32ORF250c [Enterobacteria phage RB32] | YP_803192.1 | 6e-15 (38/80) | | No putative conserved domains have been detected | | |
| 212 | 111249 | 111461 | 993 | VRAISAKADYFNSLNRSEKAQIK RFILELGYVHAGDLKAHIQECGI AKRFDITRNCLNEVIAHVQPSSE E | 70 | Arn.1 conserved hypothetical protein [Enterobacteria phage RB69] | NP_861950.1 | 3e-14 (37/67) | | No putative conserved domains have been detected | | |
| 213 | 111436 | 111561 | 994 | MYNPVAKNDFNKGGAHKDKKR AAKESKRKQKHKGKDNAHSE | 41 | Hypothetical protein RB43ORF288c [Enterobacteria phage RB43] | YP_239264.1 | 7e-05 (24/35) | | No putative conserved domains have been detected | | |
| 214 | 111701 | 111823 | 995 | MVHDWNNGTFTVAIIANVEPEE VLEQFQKCVDAYDIGDYL | 40 | No significant similarity found. | | | | | | |

Fig. 12VV

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 215 | 111820 | 112146 | 996 | MNTETLRREDEAKAYHKRVELL SAIKVEYTLQVRLKVLNSWAND LEVKHLEQAVMFTFTQEASKPF SLSADFHTYGIITIKAKDRGDIIS GVEYIESILGNRGEVVLA | 108 | No significant similarity found. | | | | No putative conserved domains have been detected | | |
| 216 | 112143 | 112409 | 997 | MSHNLESVIESQRYLEALMNKI ALGSLIDLSFQEAMDVCHWMN RRVRPIGKEWYLTAKVKDGRY GLWMSSGAEYITTKEDLNSRW ELA | 88 | No significant similarity found. | | | | No putative conserved domains have been detected | | |
| 217 | 112477 | 112749 | 998 | MTKFEIVQEIVTVASILTKFNAEH IMEKRDEFIAFLNEIGIKNEQGR QLNQSNFRKMVSELTDEEKRIL VEEYNEGFESIYRTMAMHSNK | 90 | AsiA anti-sigma 70 protein [Enterobacteria phage RB69] | NP_861947.1 | 2e-22 (53/85) | AsiA anti-sigma 70 | AsiA, Anti-sigma factor A transcriptional inhibitor | pfam09 010 | 1,02e -19 |
| 218 | 113406 | 112750 | 999 | MASKQSIPFFDMFLGLLELLFKD GATGRVLFSRVFVVILLALLAFA GYKSDSLITAYVDSTYDKYDKL VQKDRDTRFDNTALEQLQIVHI SSGADFSAVFTFRPKNLNYFVD LIAYEGTLPSTVDSKNLGGYPID KTSAEYSTHLSGRYFWTDKEFV FLPTKRKPPEISYMFSCPYFNL DNVYAGTVEMYWYNSKPALSN ERLTSICGQAVRALGRAK | 218 | t holin lysis mediator [Enterobacteria phage RB69] | NP_861946.1 | 4e-75 (132/217) | holin | Phage_holin_T | pfam11 031 | 8,03e -75 |
| 219 | 113974 | 113435 | 1000 | MAVTGPWVGSSAKAETGEPW MAQAGAKLRLGTPFWMSNMIG RSVFNFSLTVQYRNWNNIYR GSWQVGGWNWSPKPTTKNTV QGNFEGKEVTLFVSVSGQGGV NYWNGDPQGTTLGIRNGDAINL RVMMSDGTTFDFTPGKMDGDV RNYQIASNDEANKLKNWFSDR TDQYWQGLITRR | 179 | gp38 distal long tail fiber assembly catalyst [Enterobacteria phage RB16] | YP_00385856 0.1 | 8e-23 (73/183) | distal long tail fiber assembly catalyst | GP38 | pfam05 268 | 8,30e -12 |

Fig. 12WW

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 220 | 118588 | 114011 | 1001 | MADQNLKQIQFKRTSTENKAPG ADVARGEIVLNTHGRTLAIYTK DEADNVVQLAGKGVPFLDTAG NLNVDGITTLKDNVTISPNKAIN FEATDLSGAIVRHIVGKCATND GWYIGAGGTSNSGILEIGTIDDG AETIQFVQRGSGNVEARKLVLL DGSGNTTLPGDLRLSTNKTVKI NNGSTLVLEMGVGSNDAYIKN QRGVGVLQLTNDSNLTFRNSQ VYYAMNGRGPGKSGTLLTNVE NNRQAWQYVISAATAGTPRWV KVATIKHPGDASSQLDLMITGGI DSGHGRHYVDFITLSGRNLTS WSTSNLDNWVEWRRIGSPNKG NVPEYYVVKNDAATDSEASFDF YAKVPRYGNGLYVTVLNTAEYN GQDSGKVIIYETGQDTGATTPS GSILVSMKQVFDSISKPDFSDTT GTLPVNRGGTGATNVGDARNN LGLRTAAVRDVGESSGNVMEV GAFGIGGNGKSLVDITSDVDLM TRLKALGGTTFRANVASGYTGA PYYSHGAGFFSRTGDTMSALNI DYATGNVRVFAINDSGLASGRV NSNVLYGTANKPSKADVGLGN LTNDTQVKKAGDTMTGDLTVP NLHASGTGTASVYYNAGSGNA HVWFRTGGNERGVIWATPNTA DLGQINIRAKTTGDVSAGDFSF RSDGRLDVPVAVKVGGAAMLT KDGNITSCSSMFGGNLNNYLTSI KNDITTGDSKQVSKTGDTMTG NLTINANLKVENPNGSMVDLGS ENSDKYSRLTLARKVGSGAAVA MLKITPEGYVQFGYQDAVATPA PSKYIRVKPDGLDVEGDLVFNQ TYRGTEDAINITDKTNDLNNMVI KGSDLGTRQLYKCVSSGGGSN ISNKPTSDGNFVLEVLSLRKISD SDWTCKQTFTTKNGNVEGTYV RYCQNGTWSAWKEVVAGVQPI NLGGTGATSVAAARNNLGVGE GQSVKFGWLVVNGVGTSDPTI | 1525 | L-shaped tail fiber protein [Klebsiella phage KP15] | YP_0035801 1.1 | 6e-137 (386/1138) | L-shaped tail fiber protein | No putative conserved domains have been detected |||

Fig. 12XX

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | TFKNGAVVREAQGGSTGALIMS ASATAAASAKYIAFRPFGDSSG SEIRVKANGSEPLLEWSYGPGI RSNDSGAFVIYAKTGQALHLRP NGDDSNQATVIDQKGKMTVGG EFEAQNSKITGNLNVSEDNRMI VLGKNSDIGLVKKNGMPGKMAI GKSNSFTVMVSANTNNQINPAD TFSDIFKVDASGNQTVYGNAQI NRQLTVTSNTNLNSDLIVKGNS RFSGVINADGNINVASGKFVIAG QAPTDNSHLTNKKYVDDKVAS AISNAGDTYLPLAGGTVTGTLIV TGNQLKTTSLWTTGDAAVNGV LTVDGKARFNQEFSYSTSVNV QNTGNSHVFFRKADGTEKGLL WADEPGNVSIRAGGASGPVWN FWASGSCQFPGAISNYNGISST TNYPAGQPNGTYNNTAGLVSR FSNGAYASLYFQEYVGNFHQAI INVNGFGRDDSFYFRAGGDFIC TRNGSFDNVEIRSDRRAKSDIK VIENALEKVETLSGNTYELHNTS GGTTRSAGLIAQEVQEVLPEAV TQDIEADGGLLRLNYNSVIALLV ESVKELSAEVKGLKAEIEELKSK | | | | | | | | |
| 221 | 119260 | 118598 | 1002 | MADLKAGSTVGGNPIWHAGTF PLVPAGNSLTYRGKKVYTEIDK PQAADNDFVSKANGGSYSRTV TFETGLRVQTTGSGGMELVNG GVDGATLNGVNAKIKTWWGLG FESNSGSNGITIAFDLRSGNITT KGGITSNNQVSVAAAAPTANSH LTRKDYVDELINTVSNVANAAV KKAGDTMTGVLRANAGVVVNK ATSGEYAPRLDQVISRGVTIDF GTY | 220 | Hinge connector of long tail fiber distal connector [Klebsiella phage KP15] | YP_003580109.1 | 1e-59 (120/223) | hinge connector of long tail fiber distal connector | Phage_T4_g p36, phage T4 tail fibre | pfam03903 | 9.26e-51 |

Fig. 12YY

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 222 | 120454 | 119318 | 1003 | MADPILMAAFGEDFVETRILSEA NSVKYWLKAYATHSNAVPNKP ELNINGAFDMTSSLRRGINVVQ VNGDRFINFKTFDVTTDDNNAN NKAFVEYANGLTSGLYIIMTHER FQSSPLIDRWFKNKWSASWPG SDFSKSFPNSAYVGVLGAAKG RILIESFYGNDGKVKEDSRAKV DTVYDNVGDVGYTGCPYRSIE DTNEYSDSTGYEYKRYPVQNE SISKIADYGLSPGDSVFLVCDM YASKSLLDAGSTTRASLRWFKG TSLLSSNVSLEVPKNGADRWLR FERFTAVPTDADGFTIVVSRYP KTSVVGDSKIKNLVFVQTSHGE QLNSVIQEFGVNGIRMNKGVEG GTTMIMELPNSKVDPSGVIPVQ SFRETSD | 378 | gp35 hinge connector of long tail fiber proximal connector [Klebsiella phage KP15] | YP_00358010 8.1 | 9e-110 (203/371) | hinge connector of long tail fiber proximal connector | No putative conserved domains have been detected | | |

Fig. 12ZZ

| orf | Start position | Stop position | SEQ ID NO.: | Aminoacidic sequence | Size (aa) | Homologous/similar proteins | | | Conserved Domains | | | |
|---|---|---|---|---|---|---|---|---|---|---|---|---|
| | | | | | | Name[organism] | Acc No | E value and identity | Predicted function | Name | Acc No | E value |
| 223 | 124299 | 120454 | 1004 | MSDLLKQHFRATNGLDAGGNK VINVALADRNVKTDGVSVEYVI QENTIQKYDPTRGYLTDFAVTY GRRIWIANKDIPKPAGEFNQAN WTSLRVDPNWIYTVRKGEFEIQ SGQFINVDSNAAGNATLLLPLA PDEGDTIVVRDIGGRPGYNGILI KAQDTGASIVFGESRLREVRLT RPYSQIMLTFSNGAWRASLTDF GDTAKMVVPNGIVPTQVQSGD NVVRRYTSNSEIFITLPLFANSN DIINFTDLDGTSPINHMTVRTFD PTISIGTPGQTEIQVRTSGSGFL VYDAIDKIWRIFENDLRTRVRIIT SDVTLMPNEHISVFGADNSTVK TINITLPTDVAVGDTVKIAMNYM RKGQTVVIKASDGDTIASNLNLL QFPKRSEYPPDAAWVQSSSITF NGTTSYVPVLELAYIEDKASGK SYWIVTESDPTVERVDAKDNTT RARLGVIALATQAQANAESNPE KELAITPETLNGRRSTETQTGIA RIATSGEVNQATTASYLDNVIVT PKKLNERSATETRRGLAEIASN AKMDAGTDDFTIVTPKKLLYRT TSDSRLGVIQLVKTGGAPNTTA DRSSAGTGIFDHSDYKNAVTPK TLREYKATVNQSGIVWLASDSE VRNGTPASSNIPTVVTPESLHK KVATDCAICLIQIATQTEVNAGG VTNKAVTPKTLNDRTATNDRTG IARFATPCAQGEFEAGTSSTVM VNPKLLFDKFANTSRICVNTSS GLTITGNLWDHYTINIQEASTSQ RGTTTLATAAEVRTGTDAKKIVT AATLHAKTATEGAIGLAQYATQ AQVDAGTLSDRIVPPAYLKQTIQ VTESWQATDSVRGTVRLSTGD GTWKGNDTNGSTLPDNGYASK GVAVSPYELNLTLKHYLPRLGK AYDTGMLGGQTPDKYARRDIA QTISGAWTFSQDTVFNNNISVQ NILYANGGEVKISPTADTGNAH VRFQNRDGTERGIIYAETQTAS | 1281 | gp34 long tail fiber proximal subunit [Klebsiella phage KP15] | YP_0035801 07.1 | 0,0 8596/130 9) | long tail fiber proximal subunit | Long tail fiber, proximal subunit | PHA025 84 | 0,0 |

Fig. 12AAAA

| orf | Start position | Stop position | SEQ ID NO.: | Aminoacidic sequence | Size (aa) | Homologous/similar proteins ||| Predicted function | Conserved Domains ||
|---|---|---|---|---|---|---|---|---|---|---|---|
| | | | | | | Name[organism] | Acc No | E value and Identity | | Name | Acc No | E value |
| | | | | AGNLKVRVKNGTGTTAASQTY TFGGNGTLDVPNEVSTKTLRSS GNTIVGGTVMVKDTVLLTIETQN AIIGARSHSAFIDTRDADTQIFAR DNTNSYPILTTKNYARLADGRY VKKAGDTMTGNLNINSSAIVITG SESWYVPTNDTVLRQGSWTAE IKDATKLKGLRGYMVPIRTPIDP ANPSTLVVTGYEEKTAAGGVLT QVGVTTNNTYQLWTPYPPTE TADKRFAHTVWMRIYNPNLNKF DDWMRVFTSATPPTAADIGAPS SVSTQVKTLEVLEWIKLGPVKI WPDRPNQTLKFEWVGD | | | | | | | | |
| 224 | 12437 5 | 12530 1 | 1005 | MSDLNCLFAEEDQVKEGVLIDL SQIAMATILHTYKEGDKLTTPMV RHLILSTLKFNAFKWKKDGYTKI VICVDNAVNGVWRRDVAYYYK KNRAKAREESNWDWEGYFEG LRTVIDEFKQYMPYYVIDIDKAE ADDSIAVLTKKFSLEGHPVMIVS SDGDFTQLHKYPNVKQWSPM QKKLVKSKTGSPALDCMVKIIK GDKKDNVASIKVRSDFWYTHV DGERTPSTKMTFVEECLDAGE NIKDLLTEEQYKRFLENRVLIDF DYIREDIVANILDCYNNYQLPGR GKIYSYFVKSGLSKLMKEINNF | 308 | RNaseH ribonuclease [Enterobacteria phage T4] | NP_049859.1 | 2e-114 (202/306) | RNaseH ribonuclease | rnh, RnaseH | PHA025 67 | 4,40e -127 |

Fig. 12BBB

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 225 | 125312 | 125584 | 1006 | MAKKEKEQVVFDEAVHGGALR DMIKEASGNKLKAESYLELNKDI KDRAKKELGVEGKLFNQLLALF HKGTRDRFETEKDEVVEAYDSI FA | 90 | DsbA dsDNA binding protein [Enterobacteria phage IME08] | YP_003734380.1 | 1e-21 (54/86) | dsDNA binding protein | Double-stranded DNA binding protein | PHA02599 | 1,94e-24 |
| 226 | 125665 | 125864 | 1007 | MTLFSLKDEGDTSPSESINQLL DKQANGFAIESMVTELGMGYLE ATTQWLEENSIPEGNFSRYIPP AIIEKIMSEALEENMLRPSFSQT HKTNSLDFLL | 99 | gp33 late promoter transcription accessory protein [Enterobacteria phage RB69] | NP_861938.1 | 5e-25 (54/84) | late promoter transcription accessory protein | No putative conserved domains have been detected | | |
| 227 | 125861 | 126523 | 1008 | MIRLRMPQNNNRYVNGKSVYL LYLMLKQHFAGRYDVVKYNWV MRVSDKAYQKRDKYFFEKLA EKYTLKELTLIFMSNLVANQDA WIGDISDADALIFYREYIGKLKQI KTTFSEDVKNIYYFAKKVNVDKL HDIFEYNEKVGTSYVFKLLQSN VISFETFIMLDSFLDIINTHDTAT DNLVWSNYSTKLKAYKKLLNVD GAEAKKLFISIIKSCKEISI | 220 | gp59 loader of gp41 DNA helicase [Enterobacteria phage JS98] | YP_001595365.1 | 8e-95 (166/216) | loader of DNA helicase | T4-helicase_N | pfam08993 | 2,06e-36 |
| | | | | | | | | | | T4-helicase_C | pfam08994 | 2,67e-28 |
| 228 | 126591 | 127508 | 1009 | MFKRKNPAQLQQQLAGLKGGS SFSNEDKNEWKLKTDNAGNGQ AVIRFLPGKDENSLPFVKLINHG FKHAGKWYIENCTSTHGDFDS CPVCAHLSKNDSYNSNPAEYKL LKRKTSFWSNILVIKDPANPENE GKYFKFRFGQKIMDKINAMVEV DVDMGETPVDVTCVYEGANFV MKVKKVGGFQNYDECKFLGQS EIANINDEETQKFLTENMADLSE IVAPSQFKSFEVNEAKFKQIMG TAALGGAAAKAAAQADKIGDDL DSFDKDLSDFESKPTSSRSADD IMGDAGDSVGDDDLNDILNDL | 305 | gp32 single-stranded DNA binding protein [Enterobacteria phage JS98] | YP_001595364.1 | 9e-104 (202/284) | ssDNA binding protein | Single-stranded DNA binding protein | PHA02550 | 5,68e-109 |
| 229 | 127634 | 127891 | 1010 | MGKLNIDIVAEPYINKSGFCTDLI FEDGSRFYDTDHGIDFDLVIKE GPGGWPNIDLRGSKEAVRAW LEANEWEDIDLMMEDWKE | 85 | No significant similarity found. | | | | No putative conserved domains have been detected | | |

Fig. 12CCC

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 230 | 127933 | 128154 | 1011 | MAQVTVEIYDYEHFIETIEKYGLI EVSNKSAPWGGNEITVEGDTP TLWLWLEQEYFPGMDDECRED TLTTFSG | 73 | No significant similarity found. | | | | No putative conserved domains have been detected | | |
| 231 | 128158 | 128523 | 1012 | MKLNTEYRIIPSLAAEWDLSSS GNRRMRLMIEEHGGSFFPTKM LDEDNSFITEVKFKDGTTADAE GFGDAYFEISDYEFKYFEPVYEI GSAIQPGPTRLDLIVTPENAEE MIDLIKKVFKK | 121 | Frd.2 conserved hypothetical protein [Enterobacteria phage RB69] | NP_861934.1 | 3e-08 (45/130) | | Bacteriophage FRD2 protein | pfam03197 | 3,59e-11 |
| 232 | 128580 | 128858 | 1013 | MKLQRQSIKLGSEYRGKWNFCI CDKNPEELERVEEVLCQMEAP FTMGGETVYWNDYCDNCPCY EDGYGSGFWIPVEDVEEFKKAF KLAKAKK | 92 | Frd.1 conserved hypothetical protein [Enterobacteria phage RB16] | YP_003858463.1 | 4e-25 (53/89) | | No putative conserved domains have been detected | | |
| 233 | 128937 | 129257 | 1014 | MSKFSVTGYPRVNIRCQFDEIP GVTHELVFDPHSRCNQVSGKI DSAYGEFLINDQVVVSAISGEQ AGSLYILKREVFEEISEAIKEGFK TLQSMKASEYKSCGF | 106 | Hypothetical protein RB51ORF237 [Enterobacteria phage RB51] | YP_002854190.1 | 6e-06 (39/114) | | No putative conserved domains have been detected | | |
| 234 | 129340 | 129504 | 1015 | MENFAVDDYDDLIWWDGREW VTICAMSNIDSAIKRLQELQQK WEDGNVERVEFY | 54 | No significant similarity found. | | | | No putative conserved domains have been detected | | |
| 235 | 129512 | 130111 | 1016 | MIQIVYAFAPTKTVDGKNENAF GLGDGLPWKHISQDMKNFANR TRDTILICGAKTFMSFPEPLPGR KTIVVQDMSRALATAKNGFFAD AYVSELEFIGFLGGDIMAAHTSY NSTITFNRDLNYSIIGGAGIIQKA YPYADRVIQTIIRKSHRVNSDVT LPAEFVTAPTWPESGFITKENH WYHIDEVTNISEVVYERKL | 199 | Frd dihydrofolate reductase [Enterobacteria phage IME08] | YP_003734372.1 | 4e-44 (91/197) | dihydrofolate reductase | DHFR_1, Dihydrofolate reductase | pfam00186 | 2,29e-14 |
| 236 | 130095 | 130412 | 1017 | MSANYDITQLSEDKVQKRWKR FPFKHGIHLLVFSYNGLSTYNG STTVYNRNGNIPIEIERDYKKMF IGMSHGNVTVNDDVVSIIGRFE KRGDQLFFTPLQEKFNA | 105 | RB32ORF229c hypothetical protein [Enterobacteria phage RB14] | YP_002854567.1 | 1e-06 (36/116) | | No putative conserved domains have been detected | | |

Fig. 12DDD

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 237 | 130405 | 131265 | 1018 | MREYQELIKDIFENGYETDDRT GTGTIAKFGTQHRFDLQEGFPA VTTKRLAWKACIAELIWFMCGS TNVHELRLIQHDSLLEGKTVWD DNYENQAKDMGYSSGELGPVY GKQWRDFMGVDQLKLIIDRIKQ LPYDRRQIVTAWNPVDLDKMAL PPCHLLYQFNVRQGHLDLQWY QRSVDVFLGLPFNIASYAALVHII AKMTNLKPGHLVFTGGNTHIYL NHEEQCKEILRREPKELCELEIA FPDTYETWQTSSQIRWLEQFA RPHHFELVGYKSHPTIKGKMAI | 286 | Thymidylate synthetase [Enterobacteria phage RB32] | YP_803170.1 | 3e-134 (217/286) | thymidylate synthetase | thyA, thymidylate synthase | PRK01827 | 3,21e-96 |
| 238 | 131262 | 131468 | 1019 | MNIRFVRKGHQSKTVLGEMQD AFSSDLPEVNDTIVFDGTEQRV LSVIKSYEWSIGKTQLICWFEVD IT | 68 | No significant similarity found. | | | | No putative conserved domains have been detected | | |
| 239 | 131465 | 131770 | 1020 | MKICRVVNKYHSDFDVNIQRGT MWGNYVGKDCDNRPDAIAAFK DDFIAKIRNGEIKREHLETLRGM RLGCTCKPLPCHGDIIALVVNKL FKDTFELEDLCK | 101 | NrdA.1 conserved hypothetical protein [Enterobacteria phage T4] | NP_049846.1 | 2e-36 (71/99) | | No putative conserved domains have been detected | | |
| 240 | 131761 | 134007 | 1021 | MQVIKSSGVSQEFDMQKIIKVLE WACEGTKVDPYELYEIIKSHLR DGMSTADIQKTIVKVAANSISID EPDYQYVASNAAMFEIRKRVYG QFEPPAFIDHISRCVNANKYDK EILSKWSAEEITLLDSYIKHERD FTMTYAGTMQLIEKYLVKDRHT GELYETPQFAFMLIGMCLHQDD GENRLANVIRFYDAVSTKKISLP TPIMSGVRTPTRQFSSCVVIEG GDSLNSINEAAASITKYISKRAGI GINAGMIRAEGSKIGFGEVKHT GVIPFWKHFQTAVKSCSQGGV RGGAATLYYPIWHLEVENLLVL KNNKGVDENRIRHLDYGVQINN LMIERLIKNDYITLFSPDVCLGAL YTEYFRDAQAFRTLYEELEKNP DIRKKRIKARELFELFLTERAGT ARIYPYMVDNVGEYGPFIRDVA TVKQSNLCLEIALPTSDVGQED GEIALCTLAAFVLDNFNWQDQE | 748 | NrdA aerobic NDP reductase, large subunit [Enterobacteria phage JS10] | YP_002922571.1 | 0,0 (572/751) | aerobic NDP reductase large subunit | nrdA, ribonucleosid e-diphosphate reductase subunit alpha | PHA02572 | 0,0 |

Fig. 12EEE

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | EVNEIAEVMVRALDNLLDYQDY PVDKALKAKDRRALGVGITNYA AWLASNFASYADANDITHEMM ERIQYALIKASVKLASEKGPCAL YKETRYGRGELPIDWYNKRIDQ LAAPNYVCDWELLREDLKRYGI RNSTLSALMPCESSSQVSNST NGIEPPRGPVSVKESKEGSFNQ VVPNVEHNASLYDYAWQLAKQ GNKPYLNQVLIMQKFVDQSISA NTYYDPANFPKGKVEMSVMMD DLLYFWYFGGKTLYYHNTRDG SGNDDMIQDSADCAACKL | | | | | | ATP_cone | pfam03 477 | 3,83e -12 |
| 241 | 13400 7 | 13464 8 | 1022 | MNYQNVYNSLISRARARESLLG YKETHHIPRCIGGSDDKENLVE LTGREHFIAHWILLCKIYEAPGLK KAFGLMCLTGKNRSYKVSSQL YELGKRRLSEAATGRKASIETR EKISKSLKGREFTEEHLANMRK PKTEETKKNIAAAKVGVLNPMY GKISPTRDVPHTKETRDVISLRT KQGTEYPPCPHCGKKVNKGNA | 213 | Putative homing endonuclease [Enterobacteria phage LZ7] | ABA03236.1 | 4e-113 (193/213) | homing endonuclease | HNHc, HNH nucleases | cd00085 | 2,82e -04 |

Fig. 12FFF

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | LRWHYDKCKFKDPK | | | | | | | | |
| 242 | 134645 | 135787 | 1023 | MSTVFNKEPVDIMNEPMFLGS GLGIARYDVQRHKVFEELIEKSL SFFWRPEEVNVMMDRGQFEKL PEHQRNIFTDNLKYQSLLDSIQ GRAPAAVLSALISDPSLDTWNQ TWTFSETIHSRSYTHIMRNLYV DPAKIFDEIVLDEAIMKRAESIGV YDDVIAKTRAWENAKNRCFN QDNIEIKEAKRDLMKSLYLCLHV INALEAIRFYVSFACTFNFHKNM EIMEGNAKIMKFIARDEQLHLKG TQYILRQLQTGTDGEEWVEIAK ECEQEAIEIFMEVNRQEKDWAI HLFRNGGLPGLNVKILHDFIDYL TVSRMRSCCGLPCPITDAPTRHP IPWIREYLNSDAVQSAPQEVEIS SYLVAQIDNDVTDDVLIGFKRYL | 380 | NrdB aerobic NDP reductase, small subunit [Enterobacteria phage T4] | NP_049841.1 | 0.0 (306/388) | aerobic NDP reductase small subunit | nrdB, ribonucleotid e- diphosphate reductase subunit beta | PRK0910 1 | 3,79e -147 |
| 243 | 135815 | 136231 | 1024 | MNDIANEFSFIKYVQLELEPDFS IKPVLVANKLNVVYAIAVDDELV YIGKTKNLRKRINYYRTAINRKD QTSDSAKSAKIFEALMAGKKVE FYARQCFNLLINNELGEMSIST MDLEEPMFIKKFNPPWNTQHK VKKC | 138 | DenA endonuclease II [Enterobacteria phage JS98] | YP_001595351 .1 | 1e-58 (108/137) | endonucleas e II | denA, endonucleas e II | PHA0259 8 | 3,38e -49 |

Fig. 12GGG

| orf | Start position | Stop position | SEQ ID NO: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 244 | 136225 | 137376 | 1025 | MLELYKNLMNLCESSEVAKFFY KDFTGPMDGKFRVFSYHYASY SEWLKPDALECRGIMFEMDGD TPIRIASRPMEKFFNLNENPLTM GIDISDVEYIMDKADGSLVSSYV DDGYLYLKSKTSLYSDQARQAS ALLNSEEYSSLHQVILELALDGY TVNMEFVSPNNRVVLAYQEPQ LFVLNVRNNTTGEYIKYDDLYA NAKIRPYLINAYGISDPTTWVEG VRELEGVEGYIAVLNTGQRFKV KTEWYSALHHTKDSITSNERLF ASVVSANSDDLRSLFAGDEYTI KKISAFEQAYLDYLGKSLELCQ SFYDEYRGRARKDYAIAAQKAT VNQRHLFGVIMNMYEGTVDVD KLLKDLERVFLKYWAGYVPKEY EKEIEISEE | 383 | RNA ligase A [Enterobacteria phage RB69] | NP_861926.1 | 8e-109 (188/376) | RNA ligase A | mlA, RNA ligase A | PHA025 89 | 6.98e -147 |
| 245 | 137439 | 137948 | 1026 | MDMQAITLDMVVNKYGTHSDGI FWWNGTKKVGFVTDLRTHMAR KEAARKKQKEYTNRVNEQRAE ALPEAVDEMIDFLDNHLAKYGA EVFKNITQPNVHANGCKCYVIV DPIYGKHRLGIMHRELNYSEMA EYVEACFKCSPSESSDRHILISG LSRDDIVEVILKLCSK | 169 | Inhibitor of host transcription [Enterobacteria phage T4T] | ADT39948.1 | 2e-46 (94/167) | inhibitor of host transcription | | No putative conserved domains have been detected ||
| 246 | 137936 | 138289 | 1027 | MLKINTTWLLIGVLALSAGGLKY LSWRVENLKADLKVVQDESDR QAKEIENIGVSIKNLQTTYKGYQ ENRAARDTSNAKMNKDSKRGN VVAAKPGLVEKQINASFNKFAE DIQEATR | 117 | PseT.3 conserved hypothetical predicted membrane protein [Enterobacteria phage RB69] | NP_861924.1 | 1e-12 (47/119) | | Hypothetical protein | PHA021 41 | 3.41e -03 |
| 247 | 138286 | 138573 | 1028 | MKRSLLAMCIISLLAGCSSSAPD VPVLHPEWPDPIQKWEGHWEV KVIDGKAWVGMPFEESGEYRI WMNDILRYTKDANGMICYRSE LKEPRCVK | 95 | PseT.2 conserved hypothetical protein [Enterobacteria phage JS10] | YP_002922565.1 | 4e-24 (53/95) | | OM_YfiO | TIGR03 302 | 6.31e -03 |

Fig. 12HHH

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 248 | 138595 | 139080 | 1029 | MEPSHFYSYFVKDASHLLSIKN TQLRNMLAVGSCOLTPLAKKAT VIPENISNGYVYTVRVSVPGALK ERLFELNDQTRISFDVWFKLFM VEFMYPDFLKFVQRKEALKEAI SELEDASIEFGKALQFVESGGV EQDAVNGFLKKYGKRRSLAHR NLSKMVM | 161 | No significant similarity found. | | | | No putative conserved domains have been detected |||
| 249 | 139080 | 139292 | 1030 | VNQEQYETLKGLIAENELACIVF GRAAENYDKNDILSMNKPLRAI KEKYRANWGEKSKALHDFIDTL KDV | 70 | PseT.1 conserved hypothetical protein [Enterobacteria phage T4] | NP_049835.1 | 2e-05 (26/71) | | No putative conserved domains have been detected |||
| 250 | 139292 | 140185 | 1031 | MKKLVLTQGAPGSGKTTWANE YVAANPGWYVLSRDDLREGIF GLDKRNDYKYSKLREKSVSVC QFSMAKTLLEMETTKGVIIADTN LNPTTIKKWQELAYEIDGVKWEI KRFDVPWTELVKRNLYRGANA VPIEVLRSFYSKMHPYDLYIPDE SLPKAVIFDLDGTLADNNHRSP YDLAKCGKDHPKEMVIEFLKML RNKGYKILTVSGRESGTKEDPT VYQRITKKWLLDHVGETGEHFQ RKQGDSRKDDVVKEEIFWDRIA DRYNVKLAVDDRAQVVEMWR RIGVECWQVAHGDF | 297 | Polynucleotide 5'-kinase and 3'-phosphatase [Enterobacteria phage AR1] | BAI83237.1 | 4e-92 (175/301) | polynucleotide 5'-kinase and 3'-phosphatase | HAD_like, Haloacid dehalogenase-like hydrolases | cd01427 | 3,38e-08 |
| | | | | | | | | | | pseT.poly-nucleotide kinase | PHA02530 | 2,64e-105 |
| 251 | 140197 | 140481 | 1032 | MFPKYSEVVKVSFTQVVANHLT DEFTPAEVAKMHAEFLSAMNAL IPNGEVVKFSIDRLGGSSEIKISC GEGEHDWFIVGIIANFETQQVE TYVV | 94 | Cd.3 conserved hypothetical protein [Enterobacteria phage RB69] | NP_861916.1 | 2e-06 (34/90) | | No putative conserved domains have been detected |||
| 252 | 140471 | 140707 | 1033 | MLSDAKFSHDEFISKVKIFAQEV ANRVPGSKVTLRRESSFNYVD AYIITVNNGKSNQHTQLALTGT | 78 | No significant similarity found. | | | | No putative conserved domains have been detected |||

Fig. 12III

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | GQVEMTNILGHI | | | | | | | | |
| 253 | 140707 | 141051 | 1034 | MTLREAVEALLIEHARGIKAEIS PNGIRLISAVIGSDQGVWSIPRE EYDAILYSNVNVKEGQPMYGYV FSDSLERGNHPFPDGTGIRTSR VESFASPTDELKLVKTNNTTYL VI | 114 | No significant similarity found. | | | | No putative conserved domains have been detected | | |
| 254 | 141052 | 141621 | 1035 | MKASTVLQIAYLVSQESKCCSW KVGAVIEKNGRIISTGYNGSPSG GVNCCDHAAEQGWIGEIPYKST GLRQDGFQVKKVGLLKEHRAA HSAWSKVNEIHAELNAILFAAR NGSSIDGATMYVTLSPCPDCAK AIAQSGIKKLVYCETYDKNEPG WDDILRSAGIEVFNVPKRNLDK LNWYNIKEFCGIE | 189 | dCMP deaminase [Enterobacteria phage RB32] | YP_803153.1 | 7e-83 (155/193) | dCMP deaminase | cd, deoxycytidyl ate deaminase | PHA025 88 | 1.13e -81 |
| 255 | 141621 | 141821 | 1036 | MKLRIVEINKLNLSGDVVISYSV ERRYWFKWKPLATFKFEDQAV RLLKELSKRKSVIIKTIKETSK | 66 | gp5 [Enterobacteria phage N4] | YP_950483.1 | 3e-06 (29/63) | | No putative conserved domains have been detected | | |
| 256 | 141818 | 142126 | 1037 | MKLTTEQNIHIRETLKAVLSMGE SQIVFEKADGTIRTLRCTRDKDII PSDLVESTTKSARAESTTSLPV YDTEKEGWRSFAFDKLISVNG MKVEHLLQMIGK | 102 | gp31.1 hypothetical protein [Enterobacteria phage RB14] | YP_002854545.1 | 2e-29 (65/102) | | DUF2693 | pfam10 902 | 2.25e -22 |
| 257 | 142184 | 142507 | 1038 | MELPIKALGEYVILVSEPAQQG DEIVSPSGIILGKEEQGQLPDMC EIYSIGDDVPKGFVEVGDLTPLP VGNIRNVPHPLVAAGVKKPKEI RQKFVTCHYKSLACVYK | 107 | gp31 head assembly cochaperone with GroEL [Enterobacteria phage IME08] | YP_003734352.1 | 3e-40 (78/107) | head assembly cochaperone with GroEL | Cpn10 | pfam00 166 | 2.77e -03 |
| 258 | 142623 | 142871 | 1039 | MNKQLTKALELQRNAWNSGHE NYGASIDIYAEALEVLKGFKHLN PAQAEFRDTLEAMDELKYAKHL GSAARKAVRHFVVTLK | 82 | rIII lysis inhibition accessory protein rapidlysis phenotype [Enterobacteria phage IME08] | YP_003734351.1 | 6e-29 (63/82) | lysis inhibition accessory protein | | No putative conserved domains have been detected | |
| 259 | 143224 | 143415 | 1040 | MEDDKMAKOAKAKTAVKEVVG TSKRAGYKRGSNKRINQTVEKI MRRARAVLRDDASRFGKPKA | 63 | Uncharacterized 11.1 kDa protein in Gp30-rIII intergenic region | PI7310.1 | 1e-14 (41/44) | | No putative conserved domains have been detected | | |

Fig. 12JJJ

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| 260 | 143537 | 143896 | 1041 | MNFTNFNRKYYQNNAWDVSTT LLWEHNNGTVAQIDMYWEDNY VFFSFENGPTLDIQFNGSEIKVG FHDEVRKRDLSSHPSWNTNRQ LLVKIYLRHILGRKTTEEQREAI WDIVSNEIKF | 119 | gp30.7 conserved hypothetical protein [Enterobacteria phage T4] | NP_049821.1 | 3e-26 (58/118) | | Phage_T4_Gp30_7 | pfam06919 | 2,72e-27 |
| 261 | 143936 | 144418 | 1042 | MEKGKFYKLKKTPSLSPGALIK GVFEQIGNNPKITRTFKYAENT GLVEFEIIKPDGEYKRVSIDEVR FSRMWCIITNQEFQHYFEETH KEPEPKTDDGSNDWGVWTSN KGNDTYKGGLTKEEAVNLAKV QRLNATKDTKVVIMQPFAVPVV HVNIRPF | 160 | No significant similarity found. | | | | No putative conserved domains have been detected | | |
| 262 | 144431 | 144709 | 1043 | MIVSAFYDSRKKKVETIISDTRD GTPANKNGVKAYIDKYCPPEFR MIDGVDSLSINIINAKIEFINETVP IGYSDGDGSNAKMPKEKFITKF | 92 | Hypothetical protein EME08_gp196 [Enterobacteria phage IME08] | YP_003734347.1 | 7e-05 (24/66) | | No putative conserved domains have been detected | | |
| 263 | 144720 | 144890 | 1044 | MIVSVPKSKDGIFSCGLKNHPM VDIMSANVKQHTVEYEIDAPDF FELPEWAVRLDA | 56 | No significant similarity found. | | | | No putative conserved domains have been detected | | |
| 264 | 144887 | 145087 | 1045 | MKYHIFNTVRLANGIPGVVCDT APAIKAYSVEPWYEVNWVDGN RSIHAESELYPITQLRAANDDYY | 66 | No significant similarity found. | | | | No putative conserved domains have been detected | | |
| 265 | 145077 | 145286 | 1046 | MSINPHFGHMVARRITREMLKT AEYYNIELIDIEPSDAPGLIWFNF TGAANSVAKFKQALRNFPECQ NQ | 69 | No significant similarity found. | | | | No putative conserved domains have been detected | | |
| 266 | 145271 | 146113 | 1047 | MSKPVIATDVDGIIVKWQSGLP YFAQKYNLPVEHILDMMTTEKFI KPAELFDCEEDLAVKLLLKYNN SDFIRYLAPYADALATVNKLKEK YDFVAITALGNSVDANLNRRFN LNALFPDAFTEIMVCDYDESKD ALLEKAKVKYGDRIVCYVDDLP KHIAAASKVFEDTETRVFYMPR GEREGSVTAPGIMVEDWHQIVT CLESLESVKKPQKSLSRLWEEA IKDQIRKEQHPFNWPRQVPG DWWKQPIIPFSPSPHVPPGND WWNNGRITCDNHQINC | 280 | gp30.2 protein [Bacteriophage Ox2] | CAG29240.1 | 5e-62 (132/267) | | 30.2 hypothetical protein | PHA02597 | 8,07e-59 |

Fig. 12KKK

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 267 | 146155 | 146361 | 1048 | MFVVHTKVGKRWLSCDYGHVN QFYRWNPIWREAKACPIWNECI NNGFVYIDGLTYHRSVSELSKE LGE | 68 | gp30.1 conserved hypothetical protein [Enterobacteria phage T4] | NP_049814.1 | 2e-08 (34/75) | | DUF3045 | pfam11243 | 3.18e-12 |
| 268 | 146361 | 147833 | 1049 | MIFDIIKAIEDAKGSKAKTQILIDN KDNVDLKRAYLLAYSGRFKFFIK KVPEYTPVKYPNVPSKTFSDGL DYLQDILAARVLTGNMAIQGLV DLLSKMNEGDASVLVRVLLKDM RCGASGSIANKVWKKLIPEMPQ MLASAYSEKALSYIKFPAFAQLK ADGARCFAEIRGDDLDDVTLLT RSGNEYLGLDKLKRQLIEMTKE ARERHPNGVMIDGELVYHVEV KEEENDLFDMFKEPELPELSKA KEFQQTARTESNGLANKAIKGTI SAEEAEGMRFQVWDYVPLDVV YSEGKVPGFAYDVRFRALEMM SKGYDKIILIENHVVHNIHEARAI YKTYVDQGLEGIILKNIGAYWED KRSKNLVKFKEVITVDLKCVGS YEHRKQPGKMGGLMFVSECG RIRVNAGSGLKDKPEELHELDR THLWKIRDSLPGTIWELECNGW VTAEGRDDGTVGLFLPIIKQRR YDKEVANTFEAAFGVNFTEATG IK | 490 | gp30 DNA ligase [Enterobacteria phage T4] | NP_049813.1 | 1e-147 (287/503) | DNA ligase | DNA ligase | PHA02587 | 8.32e-169 |
| 269 | 147830 | 148009 | 1050 | MKVLYEVIAKTDDGRGGISVHT EVLDFDNIDVFKNFKENIEEYES VNGLQVWRTATIIN | 59 | No significant similarity found. | | | | No putative conserved domains have been detected || |

Fig. 12LLL

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| 270 | 148062 | 150188 | 1051 | MELLNEVFDEENSKIYPVENVK PKLKVPQVFLIKVPGNNNLMIRL VHGSGQGDAVKNIIKMGDKFIQ VYVFSVSEKGNIGALKGGLGQD PIGAINTIFETVNKVVKQIKADAV MFRFNPKKMQGGDKAIQRILAR LITTRTGGRFNLMKDMAYYKGK YAYSIMVHKGKKLEEIEGIPEISD ELYTKVESKVGEIYVSKETGES VTKAEALANSIGEKEDKKSELA VMSKMKVSRKDLIRAQYGKFVS YVDEDWPENKRERWYELTTNT PVLNAEGDTVDLQKDIKAGLEK SIPFYVDDIKHYRVRGGYGSNF GDAVERLFVGQMSRMHDDWK VFIPSGSDKMKIAEQRISDVADV IAQAKNPASMETMRKIVEVATR GFDMPPADDFGALRQYQNLVN YMISAYVSIVGDSISKAIEYNRE MQSRLSEEERDAIHHYCGSGY SFVNNYLIGMESLGDPIIDKKIRP LDSAFEKGLRLEPGTLLYRGQR GKYEDFKDNIESKMFYFQNYVS TSLSPIIFGAYSNAGDSLMPDAP SSDLENKETTANAVSSVIGTDN LERVDRGEEVAYGDEFKFGFVI HGADKVKVVIPGVLSSFSDEAE VILPRGLAMKVNKVWGTPFRN GVGVANNKTFMVEMTVVPPEQ IDESVHLYDGDILMEQGKVEPL EESKFKGFLNEIYFSPDRSTDK VSYTRTMELLAGAINLDGIPEKL A | 708 | Alt RNA polymerase ADP-ribosylase [Enterobacteria phage JS10] | YP_002922542.1 | 4e-115 (261/745) | RNA polymerase ADP-ribosylase | alt. ADP-ribosyl-transferase | PHA02566 | 1,89e-145 |
| 271 | 150252 | 150530 | 1052 | MKHVFRFNGIEWSADVKDAEK FNEEVLIMLEGFNEGTPTVLIQD IFRKPTEPSFVEAVLNGKAEGII PVKVVWTTKEMKLLRTEPGFIG CIA | 92 | No significant similarity found. | | | | No putative conserved domains have been detected | | |

Fig. 12MMM

| orf | Start position | Stop position | SEQ ID NO: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 272 | 151478 | 150552 | 1053 | MFTLEEFKSQAADIDFQRTNMF SVVFATVPSSKTQALLNDFGGE LYNNMGLDGNWLGLTPGEFNQ GITTIVTQGTRQVVRKSGVNTF MIGAMTQRVVQSLLGEFTVGTY LLDFFNMAFPTAGLMVYSAKIP ENRLSYEMDKFHNAPNIKITGR DMEPLVLSFRMDPEASNYRAM QDWVNAVEDPVTGLRGLPQDV ECDIQVNLHARNGLPHTVCLFS GAMPVACGAPEFTYDGENTIAV FDVTFAYRSMQTGSVGKQAAM DWLEDKTIQKIETINPNQGLSTS ASRLSRLGGAGGGISNITTSTS RII | 308 | gp54 baseplate tail tube initiator [Enterobacteria phage JS98] | YP_001595320.1 | 1e-117 (190/303) | baseplate tail tube initiator | 54, baseplate subunit | PHA02605 | 4,28e -126 |
| 273 | 152530 | 151478 | 1054 | MIFEELADGLENIKKSGTRISQG KSKLTNAPTTKVAQFPAERSAG NDSAQDMRVHDLYRNGLLFTA YDFKGRTTPDLRSFRRDVMLS SVFDSPMSALANSSSSTTSTAP VANILLPRSKSDVDSVSHKFND VGDSLVTRGSGTATGVLSNVA STAVFGSIESLTQGLMADNGEQ IYNTARSMYAGPDNRTKVFTW DLTPRSADDLIQIIRIYEIFNYYSY GVTGNSSYAKEVKAAIDEWYK GTLKSAAPDGAKVENTVFEQIT SFLSNVIVVSNPTIWTVRNFGYS TSMDGREDIFGPCQIQSIRFDK TPNGHFNGLAIAPNLPSTFTLEI TMREILTLNRGNVYIGGIE | 350 | gp48 baseplate tail tube cap [Enterobacteria phage JS98] | YP_001595319.1 | 2e-126 (225/363) | baseplate tail tube cap | Baseplate subunit | PHA02613 | 2,88e -137 |

Fig. 12NNN

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 274 | 154273 | 152540 | 1055 | MTKKSEMNSMRRRVIADSAPQ KKAESQADAQINTLEDIGRRLD DQQASTDLISDVIETKSNEIIKSV EDVSAGVELTAEASERTTDAVS KLNDTASLINDKLTKLADLLSKK HDVQQDVQKTGTGTSLETITEQ VPDAPVQQPLEELLERLIPPQD DRRPDADFFPNTEEQEERKEP NKETEDKNKKFLGLKFGELIKSV KSGFGKTISLTDKISSMLFSYTV SALAQMAKTAAMVLGVIMLIDLI KVHFNYWTKLFEKNFVEFNKQ AKEWGPLLTAISEMSNEIVKSFV KGDWGGLAKAIGSGLVDVIDKL GETIMLGMSKLLAGMLRALGFN DSADNIEGAALDRFQTVTGAEL DEEDAKMRAKYVDRQEREYDE QPEWKRKLSAKFQKFTGQIDD DEYNKLLSGEKKQSAYADLPED ERLKIITARNNAEAELKRTKAYV EKTDASDSTRLDSAKDAVQSTT TRYKELEKLSPEVAKDLKVELD QLQKLLDSKISEPAPTAEAIPAT EQPEVKQSASIKAAADSREAAR TRESNTQSQPIQVNTAVNKNST YVYRTPPQTSTAAPGMQGAMK TS | 577 | gp29 baseplate hub subunit, tail length determinator [Enterobacteria phage RB69] | NP_861896.1 | 2e-77 (225/613) | baseplate hub subunit, tail length determinator | BAR_Vps5p | cd07627 | 8.94e-03 |
| 275 | 154797 | 154270 | 1056 | MNLNVILPIKKIVINEKTISIPKLG LKHHNLMKDVKGPDENMNLLL DSICPGLTAAESDIVVLHLLAFN NRIKETVVKDDFTYDLNKVYICQ RLTQRLDGKEFKFRAPPRYSKL GSVDSILSEFLESVDGKPMDINF MKLPAFVTKWADDLVNTIAIDG PEGPIKGMLNVMEIFE | 175 | Base plate distal hub subunit [Enterobacteria phage RB32] | YP_803131.1 | 2e-48 (93/177) | base plate distal hub subunit | Phage_hub_GP28 | pfam11110 | 3.47e-53 |

Fig. 12OOO

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 276 | 155911 | 154769 | 1057 | MTAQRLGYPNISIKLYSGYDAW LANRFVELAATFITLTMRDSLRG TNEGLLQFYDSKNMHTRMNGD ELVQISVANSNTSRTQTRIYGIK HFTVGVDDKGDSIITLQLGTLHD IMNLKFSRAFFSSAYETIKEMIG AMYVDQPLIAPPINGINAYVPRV PWTSTLKDYLRYVRNVGISTDN DQFIFAWEDITGINMMDYESMIS QNPNVFMFGAPQTIGQFAAGL KYPLAWDFEWLVKSNRYNRNP MKNATFYAHSFVDKDVTRIING EGQNSVFINRSGGYSDMIFRNG YEEALRISTMAQYDGYAQTKCY GNFELTPGMKINFVDLKDQFRT DFYVDEVIHEISNNTSITNLYMF TNGSALEPVDLIKVKNELKRDS SY | 380 | gp27 baseplate hub subunit [Enterobacteria phage IME08] | YP_003734332.1 | 1e-145 (236/377) | baseplate hub subunit | baseplate hub subunit | PHA02612 | 1.76e-159 |
| 277 | 156666 | 155908 | 1058 | MANIVRCELPDGVQRFKPFTVE DYRDLLLVRNDMNTKSEEEQK QLIAELMDDYFHDHPAEYRPYIF LKVFLSSIGKTKIPVRMKCPKCG KYKQYLFNLNQPPLVNPKVEVA GLTLKFKKPIEIIDDTGKMILDNII SVKDSSGEYAWNELSDSNKLT VIDAIDVETLEKILSQMKPFNFEL KTSCCDTTTILKYDNIVDIFKLL HPDEIFTFYQINHRLVSQGKYDL NSIMKMLPIERGITLSLIEKDLKS | 252 | gp51 baseplate hub assembly catalyst [Enterobacteria phage JS10] | YP_0029225 3.1 | 3e-81 (145/251) | baseplate hub assembly catalyst | Baseplate hub assembly protein | PHA02611 | 7.69e-87 |
| 278 | 156718 | 157347 | 1059 | MNITYKFETRINGKNIQCRAFTL EEYANLIAAKKNGTIDECIKALLR ECTNATELNKQESELLIVILWAH SIGEVNHEVTWNCTCGRKIPVP LNYTHAQIDPPEDLWYDLKGFK IKFKYPSLFDDSDIPMMISKCIDY IVVGNEQIYFNDLNDAEIDDLYS AITTEDVVNIKNMLLKPQVQLAV PITCECGISHIHVIKGLKEFFKIM S | 209 | gp26 baseplate hub subunit [Enterobacteria phage JS10] | YP_0029225 4.1 | 4e-54 (103/207) | baseplate hub subunit | T4_baseplate | pfam12322 | 5.28e-51 |

Fig. 12PPP

| orf | Start position | Stop position | SEQ ID NO.: | Aminoacidic sequence | Size (aa) | Homologous/similar proteins ||||  Conserved Domains |||
|---|---|---|---|---|---|---|---|---|---|---|---|---|
| | | | | | | Name[organism] | Acc No | E value and identity | Predicted function | Name | Acc No | E value |
| 279 | 157344 | 157754 | 1060 | MSNIDKLYSDLDPEMRLAWDT DVSKTVGARSVKNSLLGIITTRK GSRPFDPAFGCDITNELFENMT PLTGDTIKRNIVSAVRNYEPRIN RLSVDVLPLYDDNAIIVTVQFSIV DDPDTLERIRIQMRSNANSSSR V | 136 | gp25 baseplate wedge subunit [Enterobacteria phage JS98] | YP_001595313.1 | 2e-52 (98/128) | baseplate wedge subunit | Baseplate wedge subunit | PHA00415 | 3,87e -46 |
| 280 | 157796 | 158212 | 1061 | MRLEELQDELDNDLIIDQTKLQY EAANNPVLYGKWVRKHSTCRK EMLRDALKKQNLKARLDYYTG RGEVGGEVCMDVYEKSEMKTV LSADKEILGVDTKLQYWGILLEF CSDAMDAIKSRGFSIKHIIDLRQ FEAGA | 138 | UvsY recombination, repair and ssDNA binding protein [Enterobacteria phage T4] | NP_049799.2 | 6e-51 (99/137) | recombination, repair and ssDNA binding protein | UvsY | pfam11056 | 4,75e -42 |
| 281 | 158243 | 158410 | 1062 | MSNTVCVVCKGPIDEALVVQTD KGPVHPGACYNYAIELPVTEDT EEQLQETQLLI | 55 | UvsY.-2 conserved hypothetical protein [Enterobacteria phage T4] | NP_049797.1 | 1e-16 (41/55) | | uvsY.-2, hypothetical protein | PHA02610 | 3,92e -10 |
| 282 | 158712 | 158470 | 1063 | MIKFEDIYEATIREATIDNFMSKI NACQTLDGLKELEKYYDKRSKE TTLADSDDIIVRDALAGRRQALE ADSEDDEDEDF | 80 | UvsW RNA-DNA and DNA-DNA helicase, ATPase [Enterobacteria phage T4] | NP_049796.1 | 2e-15 (44/73) | RNA-DNA and DNA-DNA helicase, ATPase | uvsW.1 | PHA02609 | 7,25e -18 |

Fig. 12QQQ

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 283 | 160211 | 158709 | 1064 | VHDIQVKFKDFSHVHIECDDSIF YELRDYFSFEADGYRFNPKYRY GHWDGRIRLLDYNRLLPFGLVG QIRKFADQFGYKVYFDPAIFEQ ETLSREDFDNWLSTKEIYSGLT KIEPHWYQKDAVYEGLVNRRRI LNLPTSAGKSLIQALLARYYVEN YEGKVLIIVPTTALVDQMIDDFC DYRLFPRNAMLGIRGGTARDS NALVYVSTWQTAVKQPKEWFS QFGMMMNDECHLATGKSISTII AGLTNCMFKYGLSGSLKDGKA NIMQYVGMFGEIFRPVSTSKLM EDGQVTELKINTIFLRYPDAAAN ALKGKTYQEEIKFITNVKKRNR WIANLATKLAARDENAFVMFKH VAHGKELFEMKAAGHEHVYYV SGEVNTETRNALKAMAENGKGI IIVASYGVFSTGISVKNLHHVILA HPVKSKIVLQTIGRVLRKHKDK SLATVWDIIDDLGVKPKSSANAK KKYTHLNYCLKHALERIQRYAD EKFNYVMKTVNL | 500 | UvsW RNA-DNA and DNA-DNA helicase, ATPase [Enterobacteria phage JS10] | YP_002922529.1 | 0.0 (392/497) | RNA-DNA and DNA-DNA helicase, ATPase | UvsW helicase | PHA02558 | 0.0 |
| 284 | 160269 | 161063 | 1065 | MLDKDYIKEIQALDKKEAKDKLD EYAQTFGIKLKKTRSFDNMVAD LEKELAKLANEPMPEDNDGLSI ADLIQADDEIEGKAVFKDEASD EAKLLFDAPVNVGIKIHDIDPGF YKETPKVNDPGFEVKTPSINDK GFYAEAPIGDSVIHIDDEGQVTN IPVSITDPEEFSKAMDKVVKIIKT DEIIELPENFSPNMQLLGKNPG YITLPWWIYQWIKDNPDWKSRP TSFEHPSAHQTLFSLIYYIKRNG SVMIRETRNSSFVTLK | 264 | Minor capsid protein inhibitor of 21 protease [Enterobacteria phage RB51] | YP_002854136.1 | 2e-64 (144/265) | minor capsid protein | No putative conserved domains have been detected |||

Fig. 12RRR

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| 285 | 161073 | 162482 | 1066 | MAYSVSIAPLAASAVIGATTNFT ATTSGAAAEGTETFVWTVNGV KQSSVTAAMNYVTAGPAGSKT VKVVATVTPAEGEVETAEAETT LTVKNKTMPAITLTLSPTSVSKEI GQSQVVTADVTGAPSGASIAYV WKRGSSVISGQTGKTITLTEST ETSYTLNCEVTVSAPDYNNGTA TKGIAVAFTKKTMSGVSVTLSP TSVSKEIGQSQVVTANVVGAPE GASIAYVWKRGTVVIEGQTAKTI TITESAEANYTLNCEATVSAPDY NPVTVSKGASVTITKKTMSGVS VTLTPESITVEQGSDASFKADVI GSPEGASGTYSWTKDGSPVEG STSTLVIDTSDIGSQVIGVSVEV SAEDYNSVTVTTTGNVTITKRV APTPNGELPYIHPLPFRETAYIW CGWWVMDEIQRMTVEGKDWK LDDPDSDYYLHRYTLAKMLDDY PEVDVQESRNGYIVHRTALEAG IIYP | 469 | Hoc head outer capsid protein [Enterobacteria phage JS10] | YP_002922527.1 | 1e-164 (295/468) | outer capsid protein | No putative conserved domains have been detected | | |
| 286 | 162561 | 162788 | 1067 | MKAIQAHLMHESGKDFQEIARA LDITPAEAAKLWSVEKAHERF KQKEKVVYRKRLTNVGIKSRHK KLVKHMRTL | 75 | DNA primase-helicase subunit [Klebsiella phage KPP95] | ABH10667.1 | 8e-35 | DNA primase-helicase subunit | DUF2774 | pfam11242 | 6,15e -16 |
| 287 | 162785 | 163111 | 1068 | MWSKVDPIVVEREFEEMLSKKFT PAANGVNVWLFASKFVSKMMA VQSSYYYKSGARKITDLINERY GKIDWMLMDKDIPLVLEVGSKS QFEIMLTKSGYIMYRFVPSGY | 108 | No significant similarity found. | | | | No putative conserved domains have been detected | | |
| 288 | 163226 | 163483 | 1069 | MNLADRMANTAINVATEELSAA KEEVLTQIEKTALAGKRELIMYP SSLVKKHITNVLNYLHDEGFVT NYTSAQRNGDTDFMKITF | 85 | No significant similarity found. | | | | No putative conserved domains have been detected | | |

Fig. 12SSS

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 289 | 163494 | 164501 | 1070 | MFAKYSSLENHYNNKFIEKIRG AGFDMHTVEWVAREKIHGTNF SVIITPTEIVPAKRTGPILEGESF FGHEIIMKKYKDSFVKMQNMLN TMDLVSVQIFGEFAGGGIOKGV DYGDKDFYVFDILSDSGNEKVY WDDYVVESFATGLGLKLAPLLG RGSFAELSQYVNDFKSIVNYYN ELVDTTDLEHANKHVFGPQASS ETGVAEGYVLKPVNPKFFNNGT RVAIKCKNSKFSEKAKSDKPIKA KVELTDTDKRVLEIFSEYVTWN RVSNVLSHIGTVTAKDFGRVMG LTMKDIINEAAREGHDMLFADN PSAVKKELTTLIQNTIRSKWHEV LE | 335 | RNA ligase [Enterobacteria phage RB14] | YP_002854510.1 | 1e-104 (195/336) | RNA ligase | RNA_lig_RN L2 | TIGR02 307 | 1,30e -77 |
| 290 | 164501 | 165049 | 1071 | MRLALIGSREAPRRVLSLMTIIG QRLSEEGHFSYSGGAPGSDEA WLAKYDRSNSCRIIPYSGFCGH VPDTGVVWNSELSNEAKIKSIIK AREVTSYWDECSKIVQTLFARN SMQVLGLECTEPVDKVLYWAP EKRCGSVSGGTRVAVDIARRH GIECVNLYDKNVFKSLEEEYSP RFDIFSL | 182 | Hypothetical protein KP-KP15p208 [Klebsiella phage KP15] | YP_003580084.1 | 5e-25 (64/116) | | No putative conserved domains have been detected | | |
| 291 | 166359 | 165079 | 1072 | MAKINELLRESTTTSSNLIGRPN LVALTRATTKLIYTDLVATQRTK QPVAALYGIKYLNPNGDLTFNT GATYAGQIGAPERESIEELTMA NKDSFNKDDMFKYQNVVFKVL KDSPFTDTAETDEFGIVSEAVA ANNIRMLSDAAVTEKFEGPDSD PITEASFKIDKWQTQVKSRKLKT DLTVELAQDLEANGFDAPELID DLLATEMAEDINKDILQSLITVSS RFKVAGVSDKGVLDLTKQDSA PEQGRTLYRFICEMNSAVQRNT SYSGTYAVASTRCAAVLAASG WLTQKNDGSIPENAYGMLNNG LPLYCDTNSPDYVIVGVKAEF GGKETVGGSLFYAPYTEGLDLDD PEHVGAFKVIVDPASLOPSVAL LVRYALSVNPYTVGLDEDEARV | 426 | gp24 precursor of head vertex subunit [Enterobacteria phage RB51] | YP_002854131.1 | 2e-163 (293/428) | precursor of head vertex subunit | Capsid vertex protein | PHA025 48 | 1,38e -178 |

Fig. 12TTT

| orf | Start position | Stop position | SEQ ID NO.: | Aminoacidic sequence | Size (aa) | Homologous/similar proteins ||| Predicted function | Conserved Domains |||
| --- | --- | --- | --- | --- | --- | --- | --- | --- | --- | --- | --- | --- |
| | | | | | | Name[organism] | Acc No | E value and identity | | Name | Acc No | E value |
| | | | | INAADMDKMAGRSKMSVLLGV KLPKLIAD | | | | | | | | |
| 292 | 16667 7 | 16644 1 | 1073 | MDAGIYYAPYVALTPLRGSDPK NFQPVMGFKTRYGIGINPFADS AAQQPKGRITSGMPSIVNSVGK NAYFRRVWVKGI | 78 | gp23 precursor of major head subunit [Enterobacteria phage RB51] | YP_00285413 0.1 | 6e-35 (70/78) | precursor of major head subunit | Major capsid protein | PHA025 41 | 7.51e -38 |

Fig. 12UUU

Fig. 13B

| orf | Putative function |
|-----|-------------------|
| 183 | tail lysin |
| 185 | glycerophosphoryl diester phosphodiesterase |
| 188 | baseplate protein |
| 197 | helicase |
| 198 | transcription regulator protein |
| 199 | helicase |
| 200 | exonuclease |
| 202 | exonuclease |
| 204 | DNA primase |
| 208 | ribonucleotide reductase protein |
| 209 | ribonucleotide reductase large subunit |
| 210 | ribonucleotide reductase minor subunit |
| 212 | thioredoxin-like protein |
| 214 | DNA binding / bending protein |
| 215 | DNA polymerase |
| 219 | DNA repair protein |
| 221 | sigma factor |

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 1b | 2 | 310 | 1075 | FVQIPIFSLIPILRYKLEEQ GIGLIETEESYTSKTSFIDN EKPIKHNVYKGKRVKRGL FKTEEGRILNADVNGAFQI MKKVFPDVEIPRDNGFVY NPFLINC | 102 | IS element Dka2 orfB [Hyperthermophilic Archaeal Virus 2] | YP_003773391.1 | 5e-18 (109/405) | Transposase | orfB_IS605, probable transposase | pfam01 385 | 2.87e-36 |
| 2 | 475 | 1107 | 1076 | MAKNVNDVLQQESVTV ADKYLQVKVNRDGYTRT HEGQYAYKVVSEGEELFL YPVQTDGKGTLNVMKKS PIAYTDGDNIHFVVNTVV DPYNHSFIRTEDIKGLDKG KQLIQAFLAFVEDRFKFG VYNVFVANSKEDVLSIVD PTDNDADEVKDSLEHAHE DVIADFPASPARKDVKGV DSGEGQGDTSEPSAPKNV QVTPKEDGADVSAE | 210 | hypothetical protein KgORF95 [Staphylococcus phage K] | YP_024523.1 | 6e-177 (209/210) | | PHA02283, hypothetical protein | PHA02 283 | 4.55e-71 |
| 3 | 1121 | 1642 | 1077 | MVNLAKLNLYKGNELLN SVEKTEGKSTITIENLDAN TDYPKGTFKVSFSNDSGE SEKVDVPQFKTKAIKVISV TLDVDSLDLTVGDTHQLS TTITPSEASNKNVSFESDK SGVASVTSEGLIEAVSAGT ANVTVTTEDGSHTDIVAV TVKEPIPEAPADVTVEPGE NSADITA | 173 | putative major tail protein [Staphylococcus phage K] | YP_024524.1 | 1e-88 (168/169) | Major tail protein | Big_2, bacterial Ig-like domain (group 2) | pfam02 368 | 2.14e-04 |
| 4 | 1657 | 1884 | 1078 | MEKTLKVYSNGEVVGSQ VANNDGATTVSITGLEAG KTYAKGAFKVAFANDSG ESEKVDVPEFTKTPTEEP | 75 | ORF189 [Staphylococcus phage G1] | YP_240967.1 | 3e-33 (73/75) | | No putative conserved domains have been detected | | |

FIG. 14A

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | SGEA | | | | | | | | |
| 5 | 1979 | 2239 | 1079 | MDIPTILFRNPYDYTKVK KLMENKEQYIVVKFDSVS VHNLNVQGMMNVIQDYL HTYGYRVKEYGQENASK DDERDVKGYLYERVGE | 86 | ORF174 [Staphylococcus phage G1] | YP_240968.1 | 5e-42(86/86) | | No putative conserved domains have been detected | | |
| 6 | 2243 | 2998 | 1080 | MGIIVNSNHQSDTLYEYD SFFDIEKVDTFEEGLLSIQ DEPTVLAGFIYDDITFNKV INSNSDIDDYIKNNDIYYV SDIGLLPDTFITVDSDKKY YSLLQQVVELSKDPFPKW VEDDAKGLTKYYNFQDF EDVFDLNSFYKKEVDMV REKCYNNGNVYLLYEVL PDYKLPLAYSLLSNKEHGI VIIGSQTRSNNDLTFYVK GMDAKAIASMFNVEHDY DSNIFHTFVNSHINILGNQI TKFIREKGSSYE | 251 | hypothetical protein KgORF97 [Staphylococcus phage K] | YP_024525.1 | 2e-140 (248/251) | | PHA02284, hypothetical protein | PHA02 284 | 5,61e-42 |
| 7 | 2991 | 4241 | 1081 | MSNYKTIEEVQAVIIGVLF KDEGKIVTSKFNKITKEFG LDRIGKDDLKEIVEDIRQD AYLNELKNKAIKGKVTLG DLKDVADNQVFEGNNYH EEVSTYVVAKEKELSHLR EQRKHNRHTAYPQIMFDE LKEHMVKELQGETLVEH HGSKANINDTELIVLLSDF HIGSIVSDMTNGKYDFEV LKARLNHFINTTVKEIEDR EISNVTVYFVGDLVEHIN | 416 | hypothetical protein KgORF98 [Staphylococcus phage K] | YP_024526.1 | 0,0 (415/416) | | No putative conserved domains have been detected | | |

FIG. 14B

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | MRDVNQAFETEFTLAEQI SKGTRLLIDILNVLSNVVS GELRFGIIGGNHDRMQGN KNQKIYNDNIAYVVLDSL LLFQEQGLLNGVDIIDNRE DIYTIRDTFGGKSIIIHHGD GLKGKGNHINKFILDSHID LLITGHVHHFSVKQEDFN RMHVASSPMGYNNYAK ELHLSKTKPSQQLLFVNK ENKDIDIKTVFLD | | | | | | | | |
| 8 | 4255 | 4623 | 1082 | MDTIFIIGVAFITFATFNIV FRLFDLWTTEKKMVSQG QPPLSNFEYHVIVPPYLV GVIVITLSIIFRDSLYSAQS GFGIIITSFIYMLVYVIIGL VGSFILTIFQARKARQYQT QEDNNEVQ | 122 | hypothetical membrane protein MbpG [Staphylococcus phage A5W] | ACB89126.1 | 5e-62 (119/122) | Membrane protein MbpG | No putative conserved domains have been detected | | |
| 9 | 4610 | 4921 | 1083 | MKFNDIYEQLIKNDTVQN IHESQDDKGNIYTIQFDKG NDKYLFNVINDGFLKEMT NGMVDHPEGQPYSVSLIN KETPSMSVKQYLTDVEDI VPTIRKMEKDFL | 103 | hypothetical protein KgORF100 [Staphylococcus phage K] | YP_024528.1 | 5e-53 (103/103) | | No putative conserved domains have been detected | | |
| 10 | 4985 | 5521 | 1084 | MDFNFSAFDNSSLAMRIS EGVYYFNDTPYYFIEHVE EEMSEYIVYDIHDREEK ENPQKKYRIEPYQRTIPGG TPLSNLIKSMMPQRKYPK KVTEDPIFVANVIPLGTDT VTGKTGKGFFERDKDRTI YSQKEPTKVVHGQYTGV | 178 | ORF075 [Staphylococcus phage G1] | YP_240973.1 | 1e-99 (178/178) | | No putative conserved domains have been detected | | |

FIG. 14C

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | FIGLTSVKWNRTYTPLES VVEYYKRVKGDRLNV | | | | | | | | |
| 11 | 5514 | 6281 | 1085 | MSNDVVKFYEKDIKDLIR TKKHMFKDDEITSDINDIR IFNEKVICQGKCRTDCLVL DRNGTVMGIEIKTERDST QRLNNQLKYYSLVCKYV YVMCHDKHVPKVEQILK RYKHNHVGIMSYISFKGK PVVGKYKDATPSPHRSPY HTMNILWKTNLMTILRLI RDPHTYRTGYSYNASGRY SGGEGNFSQTTQSKRMKK PAIINQIIHYVGVDNTYKL FTRGVIYGYNNRWEVIEE DFNTMKNGVRVINEQRQ TK | 255 | hypothetical protein KgORF101 [Staphylococcus phage K] | YP_024529.1 | 6E-149 (255/255) | | No putative conserved domains have been detected | | |
| 12 | 6259 | 6705 | 1086 | MSKDKPNRRKEIQHQPVN FAPMNTLTGANNSFFAKK PSEPKDATSVIEYRILFIKR FDNVTSTDVKLQKKYAL NLISEALDVKETYLSLKQ KGKKTESILHTDRVYYVH RGKKLIGKCSIREQRTFKG KHLFIFKTRHRVKAERKD K | 148 | hypothetical protein KgORF102 [Staphylococcus phage K] | YP_024530.1 | 3e-80 (147/148) | | No putative conserved domains have been detected | | |
| 13 | 6705 | 7568 | 1087 | MLKGFSEHVDKPTTKTL YKTLTSGKVELLGVSYDS DYPSGVTVQSYIEDIGNE DEGLQFVNKINVVESMKQ AVVGMNNQLGSSGLGYV RTEQLKKELEETGLMTDL | 287 | ORF036 [Staphylococcus phage G1] | YP_240976.1 | 1e-159 (283/287) | | sepiapter_re d. sepiapterin reductase | TIGR01 500 | 8.02e-03 |

FIG. 14D

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | LARGTNLTSTKKVDIVSTF IEPEVTYQDITIAKDIKLRL YKLEEESPLNGYTHIVYLL TTEKLYDGQTLFGMLSKK DKLSKGDTDKLLAFFRNN SLISKSVFCVKLLSKDYYF NLYNTHETGIFFLEDTDVI TIACGQSYVKVNTKDIKS SYVKIEDKTHKLTELVINL KGDDTLTILF | | | | | | | | |
| 14 | 7940 | 8671 | 1088 | MARKKNLRNKNSDIKVV PDKEKESILSKLYHNKLLR SKVDNALDEDMSYDDIIE LCKEYDLELSKSAITRYKS KRKEAIENGWDLEELIDK RKKTSVKDIKEKETPILEE EQLSPFEQSKHHTQTIYDD IQVLDMIISKGAKGLEFVE TLDPALMIRAMETKDKIT GNQLKGMSFIGLRELQLK QTAQDTAMSEVLLEFIPEE KHEEVLQRLEELQNEFYK NLDLDEESRKLKEALDRV GYTI | 243 | hypothetical protein KgORF103 [Staphylococcus phage K] | YP_024531.1 | 6e-135 (242/243) | | No putative conserved domains have been detected | | |
| 15 | 8689 | 9147 | 1089 | MADEISLNPIQDAKPIDDI VEIMTYLKDGRVLRVKQ DNQGDILVRMSPGKHKFT EVSRDLDKESFYYKRHW VLYNVSVNSLITFDVYLD EEYSETTKVKYPKDTIVE YTREDQEKDVAMIKEILT DNNGNYFYALTGETMLF | 152 | ORF094 [Staphylococcus phage G1] | YP_240978.1 | 7e-81 (148/152) | | No putative conserved domains have been detected | | |

FIG. 14E

Table 11 - Features of phage F125/10 gene products and assignment of putative functions.

| orf | Start position | Stop Position | SEQ ID NO. | Aminoacidic sequence | Size (aa) | Homologous/similar proteins ||| | Conserved Domains |||
|---|---|---|---|---|---|---|---|---|---|---|---|---|
| | | | | | | Name[organism] | Acc No | E value and identity | Predicted function | Name | Acc No | E value |
| | | | | DENKLNKVKD | | | | | | | | |
| 16 | 9212 | 9655 | 1090 | MFISLNQEEKELLTKEESK YTPLETSREFNTPKEEFIV TSYNEGKPLDYIAKEAKV SMGLIYTVLNYYKVGKR NKKSPVEERIAHILKDKNL VKEIIKDYQYMNLQDIYS KYNLHKNGLYYILDLYH VERKSELKDKALEEDNIV VE | 147 | hypothetical protein KgORF105 [Staphylococcus phage K] | YP_024533.1 | 3e-77 (147/147) | | No putative conserved domains have been detected | | |
| 17 | 9672 | 10376 | 1091 | MRNKKSFQEQLNDMRNK EKWVSEEEFTEEVAPSEEP EVEEEKLYTLNELKENLL DAQGLKDVVADFPASKD LYEPNKLYICTIPKGYOST EVQPGQYIGISTGLLSESE DFSHLRGQMPRNLYETSH VLKPLVRINNTSIEYQQHE LLEDIKEDKNVYDVELED LRLATGEEISYLEIVDSKF FESRINEVLDFYHELTDSD DLLEYYNKLRELVGNDR MIYCPLLNKCVKIID | 234 | hypothetical protein KgORF106 [Staphylococcus phage K] | YP_024534.1 | 2e-113 (215/234) | | PHA02290, hypothetical protein | PHA02 290 | 2,24e-29 |
| 18 | 10522 | 10836 | 1092 | MYHDKAKNEVSTELSNT GKIKEEKNVEFVGDYTLK KVFDNKAYFMETLPTYLP GRTGDNSIDMRYYKTSRF KEGVNFKLJRVYTEDGED NPIHKYRFEAVPTKK | 104 | hypothetical protein KgORF107 [Staphylococcus phage K] | YP_024535.1 | 2e-54 (104/104) | | PHA02291, hypothetical protein | PHA02 291 | 2,86e-15 |
| 19 | 10983 | 11225 | 1093 | MEMADLERFDAFVRLISD DELSEERILELSVDLLNPIL | 80 | gp ORF144 [Staphylococcus phage | ACB89137.1 | 6e-37 | | No putative conserved domains | | |

FIG. 14F

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | EGGTAYRAKKRIKSKFGK LEAKNFKRNYKFLLKSIA QIDQRR | | [ASW] | | (79/80) | | have been detected | | |
| 20 | 11230 | 11787 | 1094 | MTEREKLIKEIEEANRDIQ LQLKEVDNYKDSIRSKGT RNYISTKVLDSITVGFIVSF LILIIMRVLEYFVTGNAVY SPLAPAVIIMFVLALGTW KVSKMNKIVSYRGTIKMY WELSNAEQKQAKVFKYP NDEVDIVSKHNLRQITFSE INILHLKYMRYNKAVEQH TKLSKELFKKDKETVDKN K | 185 | hypothetical protein KgORF108 [Staphylococcus phage K] | YP_024536.1 | 1e-71 (133/135) | | No putative conserved domains have been detected | | |
| 21 | 11823 | 11999 | 1095 | MVIPSIKAQNKFKNELEY YKQGHSESKMLELAFDY IQELEQNNEVTNLEEE RYGE | 58 | ORF240 [Staphylococcus phage G1] | YP_240984.1 | 1e-24 (58/58) | | No putative conserved domains have been detected | | |
| 22 | 11989 | 12240 | 1096 | MVSKFIGVYLFNLLVAL VYTVGFLFFYGVASLVIIL THATIDPFVLATFLGIGFL VIRTAHRIMARVINDAVA QAIKDKENE | 83 | No significant similarity found. | | | | No putative conserved domains have been detected | | |
| 23 | 12233 | 12466 | 1097 | MNKGEFIMDKTLPKFSVY EVIVKTVIMTPTEGSSDLE SFYFSTRELAERFVEENTV ETKNGKRVSFAVKERKV NQPG | 77 | No significant similarity found. | | | | No putative conserved domains have been detected | | |
| 24 | 12548 | 13192 | 1098 | MKVSEEVKQSYLENKAN TKMDKISWSELKASPLGIT | 214 | hypothetical membrane protein MbpJ | ACB89141.1 | 4e-88 | Membrane | No putative conserved domains | | |

FIG. 14G

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | LGDIFYSVVIIDNIIAIILTL TLIGTITDSIESTLAQIIVGV FIIITYGILSALIPILIHKAV SPGWSYTEWNESYYIRLP GEENYKYYSKWYLDLLG VKEFYYKRDSGEEVKEK NISWAFQAEVKRPEDVNH WKNQLLTNRPLTILEYKK LKKLDKESEIRKQEDLEE YKQYNSN | | [Staphylococcus phage A5W] | | (162/173) | protein MbpJ | have been detected | | |
| 25 | 13207 | 13455 | 1099 | MISSFDSILLVIYIIAFAVA MAIIYLVFKGMTILLDKL MMLLLSKTTLDVEACSMI MAVISTIVFGIIVLLIWLAV NNILL | 82 | No significant similarity found. | | | | No putative conserved domains have been detected | | |
| 26 | 13467 | 13643 | 1100 | MDFNDFINSESDRVGNPK QKKKVENKLPSSIPEDRE KKLKEIRKKSLYIDLRRKR ND | 58 | ORF241 [Staphylococcus phage G1] | YP_240986.1 | 5e-22 (55/58) | | No putative conserved domains have been detected | | |
| 27 | 13636 | 13932 | 1101 | MTKETNVLYKDKYRDYT IVVRLAGNIIVTEVDKKH KTAFTPIIFDNGVEGVELV MRIGSVELSMTDLREFTK EVSTAQKALEYFNKKLYI KGLTDEAF | 98 | ORF152 [Staphylococcus phage G1] | YP_240987.1 | 1e-48 (97/98) | | No putative conserved domains have been detected | | |
| 28 | 13980 | 14162 | 1102 | MLLGILWFIWGFVSYFVL MFGIEFCKDRWMPGVIGA GALLLFLFWIMKSIHNAM TVVYLY | 60 | hypothetical membrane protein MbpK [Staphylococcus phage A5W] | ACB89144.1 | 3e-24 (59/60) | Membrane protein MbpK | No putative conserved domains have been detected | | |

FIG. 14H

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 29 | 14175 | 14543 | 1103 | MDILIHYKETNKRVLKET IQTIQNHLNDEHGLVKMT ATKLSRENIEKIFNNYNIV IAEDDPDNSYHYSEAVEE ADFIIDIPISYLDIHAGVEW DVDNPVDMLDRNPDFIEA VNKLNEDLML | 122 | ORF119 [Staphylococcus phage G1] | YP_240989.1 | 1e-62 (119/122) | | No putative conserved domains have been detected | | |
| 30 | 14556 | 14903 | 1104 | MLNFKLKNLEDTKVYMI NSIASLLSASTGKSSKVFF DEGTIKIVSGETKAVEVID NLVHPHSGRLPIKTTERIA LGRLTDSLQFVISEIEVVK DQIIDEENEAYIDFVMED WDWD | 115 | ORF124 [Staphylococcus phage G1] | YP_240990.1 | 5e-59 (114/115) | | No putative conserved domains have been detected | | |
| 31 | 14909 | 15181 | 1105 | MDLLTIASVAFIAVVIIDLI NDDMSYMLTGTAILINIW AGFYGWFFLLQAGMLLF LLARKVKDDKESILYSS ASLICALGMIINLLSFS | 90 | hypothetical membrane protein MbpI [Staphylococcus phage A5W] | ACB89147.1 | 8e-42 (90/90) | Membrane protein MbpI | No putative conserved domains have been detected | | |
| 32 | 15251 | 15556 | 1106 | MSKETIRRQFSNAIEIMAT TKEWWNFPKSFNTSKEFK IKTFKNDTLVFEVREGSR NLGSFVIFTNIDFDYDKLE GTSTQYMINYFAKKLTKD MFNYHKLQL | 101 | ORF140 [Staphylococcus phage G1] | YP_240992.1 | 8e-51 (98/101) | | No putative conserved domains have been detected | | |
| 33 | 15571 | 15921 | 1107 | MREELKPFNRKQVNVKG YLDDVKYSKRRRHKGNQ HGCVKITVTDVKINGIPID HVNIEVGISFYEKLKELQG KRIQFVGTVYKYVKHAR GRKGRIKGFYKEDYSVTL | 116 | ORF122 [Staphylococcus phage G1] | YP_240993.1 | 2e-59 (116/116) | | No putative conserved domains have been detected | | |

FIG. 14I

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | DKKLQKEEK | | | | | | | | |
| 34 | 15921 | 16523 | 1108 | MIKRRKHLDHSLQPEKG WRTVPFNGYYEAHPTGLJ RNKVTKLIKGTQTRKNH PKWTAHEIVYLINPKKTS YSRGVVIAHTFPEMISQSR GDLKNGHVCFKDGDRSN CHVDNMFIGKGNVNKNI YKLNDSYLTRKDIEEDVN NLVNERLFSQLELLIKKNF PERLTPSNHFIKRDNNVFSI TDLSKNSLVEFFLEIKNIK | 200 | ORF065 [Staphylococcus phage G1] | YP_240994.1 | 2e-113 (200/200) | | No putative conserved domains have been detected | | |
| 35 | 16537 | 16716 | 1109 | MNEWYALCYYDKVGKK KIPRQIKAHRDVSVLEDL KDRLEEQNPKEEYKIKTT KEFDKER | 59 | ORF237 [Staphylococcus phage G1] | YP_240995.1 | 2e-25 (57/59) | | No putative conserved domains have been detected | | |
| 36a | 16943 | 17218 | 1110 | MKLEDKVLERIDSLGNKA GNLSNQAMESLVKYQITY GIIDIVVSILVIALTIFLGKV YLKEYKKVKMDLKESLL YDDYDILSLRNSCRYTN | 91 | hypothetical membrane protein MbpM [Staphylococcus phage A5W] | ACB89152.1 | 1e-35 (81/87) | Membrane protein MbpM | No putative conserved domains have been detected | | |
| 36b | 17223 | 17291 | 1111 | MRLINPEVYAVKDLIEQV KGGN | 22 | | | 2e-12 (22/22) | | No putative conserved domains have been detected | | |
| 37 | 17293 | 17586 | 1112 | MKQRDFEFEEDFVLTYEC EDCKHFEDWGHDEEPEEC SECGSSDLINNTSHEDTEC DMCRGYIDMWQDGYRY MGDNKEYIEKEESGLICE DCYEKLDI | 97 | gp ORF160 [Staphylococcus phage A5W] | ACB89153.1 | 2e-48 (97/97) | | No putative conserved domains have been detected | | |

FIG. 14J

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 38 | 17603 | 17890 | 1113 | MNKAVEQASNALGQGFS AMVWHQVLAGLGFILLG LVLSLLVWVLVKKFHVPF NHPTAFVVYSIMLVSIVAS FIWGGLHVINPEYYAILEL KGFIK | 95 | hypothetical membrane protein MbpL [Staphylococcus phage A5W] | ACB89154.1 | 2e-45 (94/95) | Membrane protein MbpL | No putative conserved domains have been detected | | |
| 39 | 17901 | 18017 | 1114 | MTKEELEQKVKELEAEN KELKKQIERFEDEGGKTK DEQ | 38 | ORF362 [Staphylococcus phage G1] | YP_241000.1 | 1e-10 (38/38) | | No putative conserved domains have been detected | | |
| 40 | 18007 | 18273 | 1115 | MNSRQKKILTLTVSNFLIL ALDTVALIRYKKGKIKQE NYNTGQITRMIATTANSL GILYLEEQERKEVKDIKV GTFEIGALKRFTNNK | 88 | ORF170 [Staphylococcus phage G1] | YP_241001.1 | 3e-31 (68/86) | | No putative conserved domains have been detected | | |
| 41 | 18351 | 18656 | 1116 | MKGHFYKEETKEDLGYF LGFINFKLEGLSYTTEGTL VDNDVVVLKDNQINEDN LEQFSMSNNNLVIGILGHS SLSVRIYEKGIRQEFDRVE EYLEELRQ | 101 | No significant similarity found. | | | | No putative conserved domains have been detected | | |
| 42 | 18656 | 19057 | 1117 | MIFILIFGLLFILSLLGIFIYF IVLRKKQLIEERESFGIY NRTKEKLGDVTRLGYEED VYKLIHNQSNKTIIEDKKS KVVDTIKKMYELELTSVD VSKVEGLSPLDTEPMTNM KLLSYKLDREGLYSLSKFI | 133 | No significant similarity found. | | | | No putative conserved domains have been detected | | |
| 43 | 19068 | 19304 | 1118 | MEFIDKNNVIKAYDIPNV YLKGYVLQACDKNGDTT AYDGYDQIHYKEGRVLTF | 78 | No significant similarity found. | | | | No putative conserved domains have been detected | | |

FIG. 14K

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | PFDKPLRKINVLSGYYKLF KKEDII | | | | | | | | |
| 44 | 19301 | 19828 | 1119 | MIYFVSDLHFGHDNIREFE APTRSHWNSVEEMNEGLI ELWNNTITNNDIVYNIGD FFFNMKPSKVEDILNRLN YKEMILAGNHDHKKLIK LYERNGITVKYADMIKKD GKRFYLSHYPTLIGRKNM FNIHGHTHSQLMGTEYHIN VGYDVEGKIAYSFDDIISR AGEYNGEIQR | 175 | phage protein [Staphylococcus aureus subsp. aureus TW20] | CBI49957.1 | 2e-66 (124/165) | | MPP_AQ15 75, Aquifex aeolicus AQ1575 and related proteins, metallophos phatase domain | cd07390 | 2,83e-37 |
| 45 | 19809 | 20129 | 1120 | MEKFKGKDLYKTRIRKQT IKNLVIKTEKLHNKHGKY RPIGHVYYPKTKEFTLS KPEQKIFIEYMKELGFNV KHRRRKKTLIIYKNAFTE YISMYHEAIEQIEGGT | 106 | No significant similarity found. | | | | No putative conserved domains have been detected | | |
| 46 | 20129 | 20359 | 1121 | MEYLFLFIGIGMIIWGFIAP YLAFVVYYKHVRENHNG FSDEESLEEATVLGMGFM FIAFIPIGLVVIEEIKILFF | 76 | No significant similarity found. | | | | No putative conserved domains have been detected | | |
| 47 | 20412 | 20618 | 1122 | MKHFILILGIVILVIALGIVI LVIALGIVLPAWILQLVLS AFGVKVSIWVCIGIFILSA IGSMFSRN | 68 | ORF236 [Staphylococcus phage G1] | YP_241002.1 | 5e-20 (59/68) | | No putative conserved domains have been detected | | |
| 48 | 20633 | 20896 | 1123 | MAKYESNNINGENYIATPS QALREALAKLITEEKSFAE YQTKGGEQYESQLQLRHF DAMISQYEEAIRVLEDKY | 87 | ORF171 [Staphylococcus phage G1] | YP_241003.1 | 1e-41 (85/87) | | No putative conserved domains have been detected | | |

FIG. 14L

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Conserved Domains Name | Acc No | E value |
|---|---|---|---|---|---|---|---|---|---|---|---|---|
| | | | | RPQIFIPKDNKEEN | | | | | | | | |
| 49 | 20899 | 21216 | 1124 | MKAESIARFFNDKVLQIE GYKVRFPQASSSYILDIDT VDESVLFLDAQVSTLSGK HLLDTAITIERPETLSAKE LYTEISNKLQAIVGDQTKT TIELSRYFKEEK | 105 | ORF137 [Staphylococcus phage G1] | YP_241004.1 | 2e-5 (102/105) | | No putative conserved domains have been detected | | |
| 50 | 21217 | 21897 | 1125 | VSNKTITNHLLNLKGINIE TYSIIARIKKQTSWGDKG DSFEISISYKADKDPRTVR YITTEITIDYSSNNPKEILL QLKDKIFSIVEEQVETDND FIESIKEINSTKALEKLKPY INNEYYSMFKSSIEKEIPV ALSSEVLNRCTGKTSTLA YLALEKDLPLVVSNEPMR KMLKNKFPHLRVSSAEDY SNYDIKGEIVLIDEVDIDQ LYSADKVSVDALLVGIIK N | 226 | ORF055 [Staphylococcus phage G1] | YP_241006.1 | 5e-116 (210/226) | | No putative conserved domains have been detected | | |
| 51 | 21975 | 22133 | 1126 | MIPIIVILIGLILFLSSGYKL VLGKYYDDVDLKILFTIF GVGIALLLGGFIL | 52 | hypothetical membrane protein MbpN [Staphylococcus phage A5W] | ACB89160.1 | 3e-17 (51/52) | Membrane protein MbpN | No putative conserved domains have been detected | | |
| 52 | 22149 | 22373 | 1127 | MNYEEVLRTKENKPCKV RFTGNILAIVNEEFNADTD KGVLQLDVSNINKEGYIR LQQYCLERDDYTVVGAIL F | 74 | No significant similarity found. | | | | No putative conserved domains have been detected | | |

FIG. 14M

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| 53 | 22386 | 22586 | 1128 | MNYRDFITDCISGGYNVH ISVTEKRVHIISEMTSASYP KKEINLDELQAYVYYMN NFGSQITTEGL | 66 | ORF211 [Staphylococcus phage G1] | YP_241008.1 | 2e-31 (66/66) | | No putative conserved domains have been detected | | |
| 54 | 22587 | 22877 | 1129 | MELVINIVAVLVGMYAIY FYVTKFSTGLSGILIVLGM AIGLYFYLDYLNVRENVI RLVSVMFGAFLFSIEMIYN KIMFEIKKSNVQKTVRVY DKEQ | 96 | ORF155 [Staphylococcus phage G1] | YP_241009.1 | 7e-46 (96/96) | | No putative conserved domains have been detected | | |
| 55 | 22971 | 23279 | 1130 | MYPEIDVEKLAYKLKSTR EYLESIKIKEVEIYEIYHLK TGKLVFKGEYIEVKELLR KMYKENLTLVDVDTMLSI GKGFIDVIKNISAENVFQI TYKKELSTK | 102 | hypothetical protein KgORF109 [Staphylococcus phage K] | YP_024537.1 | 2e-47 (99/102) | | No putative conserved domains have been detected | | |
| 56 | 23276 | 24184 | 1131 | MIKIFSEVDKEYKPIITEKF PNGEINFKYDDLKYLVEE NLRFDVFFKWENDADLM HLYMFTKYLEQLGIKDKA EFLEIAYLPYSRMDRVEE GHNNMFSLKYITEFINNL NYKSVWVVEPHSPVTEEL LTNSVAIDVTLKLLNQYIE MSEEPVTIVLPDKGAYDR YLFDVERILMESNIESYSI VYGEKKRDFETGKIKGKI IKDKNTLYDNCIILDDLTS YGGTFVGCKKALDKLKV SSVSLILTHAERAFAEGAL LSSGFKDIIVTDSMFPKNN WEKAIAKHRARINGTELQ | 302 | putative ribose-phosphate pyrophosphokinase [Staphylococcus phage K] | YP_024538.1 | 2e-172 (299/302) | Ribose-phosphate pyrophosphokinase | RibP_PPkin, ribose-phosphate pyrophospho-kinase | TIGR01 251 | 8.54e-17 |

FIG. 14N

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | IKDIERYL | | | | | | | | |
| 57 | 24202 | 25671 | 1132 | MLNPTLMCDFYKLSHRE QYPEGTEIVYSTLVPRSNK YYEHSDNIVVFGIQSLVK KYFIDMFNKEFFNRPKEE VINEYKRTVKFTLGQENP DAKHLEQLHDLGYLPIDV RALKEGTVVHPNTPVMTI ENTHSDFFWLTNYLETIIS TQTWQAMTSATLAYDMR KMLDKYAMETVGNIEAV DFQGHDFSMRGMSSLETA QLSSAGHAISFKGSDTVPV VDFLESYYNADVEKEMV VASIPATEHSVMCANGNY ETMDEYETYKRMLTEIYP TGIFSIVSDTWDFWGNMT KTLPRLKDIIMERDGKVVI RPDSGDPVKIICGDPDADT EYERKGAVEVLWDITFGG TETEKGYKVLDEHVGLIY GDSINYERAQQICEGLKE KGFASINVVLGVGSFSYQ FNTRDTHGFAIKATYAKI KNEEKLIYKNPKTDSGKR SHKGRVAVYKDGSWEDN LTLHQWLNKQNVNQLER VFEDGKLYRDQSLSEIREII KNN | 489 | nicotinamide phosphoribosyl transferase [Staphylococcus phage K] | YP_024539.1 | 0.0 (488/489) | Nicotinamide phosphoribosyl transferase | PBEF_like, pre-B-cell colony-enhancing factor (PBEF)-like | cd01569 | 2,88e-163 |
| 58 | 25750 | 25995 | 1133 | MIYKISKHNYYSRFEYSSY LPDEGFAYIDYVDVILIGV DNPRKRKVITLKADEFNP SDFKVGHKYNIIKILWFEK | 81 | ORF178 [Staphylococcus phage G1] | YP_241013.1 | 5e-35 (70/81) | | No putative conserved domains have been detected | | |

FIG. 140

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | WEWLQP | | | | | | | | |
| 59 | 26012 | 26404 | 1134 | MIIDKLNGVKLEIGGHVV SFSVSKFKTINGERQLLDY HHIKRRKQKYFRITEEFY NEYKEIKPDKNEIDEMFES LGYVDTKLEDVVRNQEK VTEILGVSEQYLNQLSYK AIFEYVDKIVTLEIKELKG EK | 130 | ORF113 [Staphylococcus phage G1] | YP_241014.1 | 3e-63 (121/130) | | No putative conserved domains have been detected | | |
| 60 | 26406 | 26603 | 1135 | MSNSWEKEGVNYWENED CPREYLEKAFIELVEYVEG VTVTSRDVQQLREDKLRE DIGFYEYVADK | 65 | ORF194 [Staphylococcus phage G1] | YP_241015.1 | 8e-26 (58/63) | | No putative conserved domains have been detected | | |
| 61 | 26668 | 26964 | 1136 | MMNGKQIYVFLSDQYSK DILSLQLGLIKEWSRRELT YSDDVGSDADVVICTDIV RDDFVKKLSKNNSNALFV FISSFYWIGYKGGEFFVAV QDYVKGM | 98 | No significant similarity found. | | | | No putative conserved domains have been detected | | |
| 62 | 26968 | 27279 | 1137 | MKKLLILFTLASTLLLAGC TPDNHEGKVLGTGEYREP TTYIKSGSVTVPVIGEMK YYVDLETDKGEDRVYLN REVYHKFDKGDDFSNVG KKVYKNDELIYKGD | 103 | hypothetical protein KgORF113 [Staphylococcus phage K] | YP_024541.1 | 2e-51 (102/103) | | No putative conserved domains have been detected | | |
| 63 | 27285 | 27584 | 1138 | MKQFIHDKKDSYNSTNRN FDIQYKGIPLQQIDRGYG QARARRFTINNTNQNIWIP MTYLKPNGTLKNNIDIDW ILVKEKCSLKKAGLVIKIK | 99 | hypothetical protein KgORF114 [Staphylococcus phage K] | YP_024542.1 | 2e-50 (98/99) | | No putative conserved domains have been detected | | |

FIG. 14P

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | ITGDVL | | | | | | | | |
| 64 | 27584 | 27823 | 1139 | MYILERTIRGFAGQTEDIL PYYFKSKKEIVNFLKLME FLKEETNYWVKKNGNYTI IIRAKRILYIEEHIQKLKEW ENDL | 79 | No significant similarity found. | | | | No putative conserved domains have been detected | | |
| 65 | 27813 | 27968 | 1140 | MTYDVYVLYKRGEPIAQ GSMEHCLDVYYWERVHG YSNKGYELLPMGYEQEE | 51 | No significant similarity found. | | | | No putative conserved domains have been detected | | |
| 66 | 27972 | 28166 | 1141 | MINIEHDYTIRTVDNRKY TYYSKHESPVTLYKNIIGK DCIEVTKYGKDKKVIIAT KYIVSIERW | 64 | gp ORF179 [Staphylococcus phage A5W] | ACB89172.1 | 5e-23 (55/64) | | No putative conserved domains have been detected | | |
| 67 | 28184 | 28537 | 1142 | MNARKARKNTKNVKDSN VVTKEQILTYIYNKLNYL IANNSSQGKTYVVMNLRT DYPDEFSLSKLKYLKEIKQ HYKDLVFNVKTQVRKAQ WSEKSIIRYYFNLGYIDSV LVPIHISW | 117 | hypothetical protein KgORF115 [Staphylococcus phage K] | YP_024543.1 | 3e-58 (110/117) | | No putative conserved domains have been detected | | |
| 68a | 28556 | 28744 | 1143 | MFFKKKKLSNVEKQIRQN RNKEDKERKEHQDKLDT DMYKTYELDKIVEEHLRK LNTISLEEL | 62 | hypothetical protein KgORF116 [Staphylococcus phage K] | YP_024544.1 | 8e-24 (58/62) | | No putative conserved domains have been detected | | |
| 68b | 28754 | 28942 | 1144 | VCLGTRLVYYYSIGKDW NKQVYSLNELEYMKKKF KKLGFETQITNEDIGFQPY IYLRLLWDA | 62 | | | 7e-29 (61/62) | | | | |

FIG. 14Q

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 69 | 29627 | 29788 | 1145 | MNLTFEDKLEDLLKKVRS GEIEPIEYSQVNDEHPNGK TTCGVTFKFDIDTPTK | 53 | No significant similarity found. | | | | No putative conserved domains have been detected | | |
| 70 | 29883 | 30188 | 1146 | MILLFTQDYDKTLMKVIL GDINTMRPNWKYSVNHP EKEEDVHIQAYEGEDIFD DIEELSDSTQDIVIGVTED DCISESPYDFNGGLRLVTK HIKEHIEKFL | 101 | No significant similarity found. | | | | No putative conserved domains have been detected | | |
| 71 | 30200 | 30499 | 1147 | MIDIYLGEGYNKEYLSKA LRLINDHAPRELSYDFNN VEADVNIHTMLYVKPEDR YVYKDISYDFPGDLIICIVE DDAIVYHQGKQVSGISILR IIEELI | 99 | gp ORF182 [Staphylococcus phage A5W] | ACB89175.1 | 5e-47 (91/98) | | No putative conserved domains have been detected | | |
| 72 | 30596 | 30889 | 1148 | MIEIYLSENYDKDLLKAE LKWIKETASRELTYDVNR NPNLDVHVSPFRYTKDEV KEISLHPQFEDDVCVFIAE TWIHEYHRGKSIGVDSME EYYKEM | 97 | gp ORF185 [Staphylococcus phage A5W] | ACB89178.1 | 5e-39 (80/97) | | No putative conserved domains have been detected | | |
| 73 | 30892 | 31149 | 1149 | MFKVYTVYHKGSMKTI KDKLDRSSLIYFLYDTWY KDISNVFPNHYNKEFGSN SDDIDKLIEAVNEEGILL INRGNYVTIREW | 85 | ORF175 [Staphylococcus phage G1] | YP_241027.1 | 6e-41 (83/85) | | No putative conserved domains have been detected | | |
| 74 | 31267 | 31506 | 1150 | MVTLTYTIIHKESDRVIAS GLDELEVINLVQRMVNTN LVTDISLDDYIRRPSGDID VLNLLVDIRRQGVFDFNH | 79 | gp ORF187 [Staphylococcus phage A5W] | ACB89180.1 | 4e-32 (69/79) | | No putative conserved domains have been detected | | |

FIG. 14R

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Homologous/similar proteins Acc No | Homologous/similar proteins E value and identity | Predicted function | Conserved Domains Name | Conserved Domains Acc No | Conserved Domains E value |
|---|---|---|---|---|---|---|---|---|---|---|---|---|
|  |  |  |  | TWHVG |  |  |  |  |  |  |  |  |
| 75 | 31517 | 31864 | 1151 | MIVIYTDVSKDYLKDEFL PWLNERDRYLEDYKDELP EDIDSSYIVSVVYCKDME GLLERKDIVIGNSYNEPVA LLGVPEFFGNYSNYFYYR GESISKHDLGEIVRLKAW QRMGGD | 115 | hypothetical protein KgORF118 [Staphylococcus phage K] | YP_024546.1 | 1e-57 (112/115) |  | No putative conserved domains have been detected |  |  |
| 76 | 32761 | 32069 | 1152 | MKHNINNIEMFSKYYIKE NKVYSKKTNKELKKDKN NFYRMTDDINKARKVKID TLLQYNLKDYNSINNLPN EKWKRIENNINNIFNYSVS NYGRIKRHGNYYMIEKLV KPHNHKQGYKIVKINYKH HSIHRLVYEYFGNDFNQD YHIHHIDGNKQNNHHNL QCISPTEHNNLHHHKDETIN NFKRGKSLTDNERKNIYK LYTEKGFTQEELSNMYNV SRITINRNIKRFK | 230 | ORF085 [Staphylococcus phage G1] | YP_241035.1 | 3e-37 (83/165) |  | HNHc, HNH nucleases | Smart00 507 | 5,48e-03 |
|  |  |  |  |  |  |  |  |  |  | Sigma 70_r4 | pfam04 545 | 6,44e-03 |
| 77 | 32902 | 33210 | 1153 | MEIKEIADTIMYLFNMDG YRCAEPPLYESTLNHTRT HTALIVSIKGNYDTVQMF RKTPIMSMRGQSQPASML VNVIDDVIIIVYENVVYGV QNKEIKFIEEI | 102 | ORF145 [Staphylococcus phage G1] | YP_241031.1 | 9e-49 (94/102) |  | No putative conserved domains have been detected |  |  |

FIG. 14S

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 78 | 33417 | 33704 | 1154 | MTNKNYLYEETHTVQGQ DITAFRIPNDTNGNPRYVV HFMDLNIKLADYDNINKL YGFNKYRAKWFGGGVVF QSYNIEDTLNFALDKVKEI EAVKN | 95 | ORF159 [Staphylococcus phage G1] | YP_241032.1 | 2e-39 (78/88) | | No putative conserved domains have been detected | | |
| 79 | 33754 | 34026 | 1155 | MILEIETKPVKTLKAIKDD TKNIKNSIAEHLGLNREQF KLSNGLITLKGYSEEFKC WYNLTSTIGNFPKYLKSE LYNEYKLYCNVELKTK | 90 | No significant similarity found. | | | | No putative conserved domains have been detected | | |
| 80 | 34550 | 34708 | 1156 | MLKFKWKNKTIKSTQKT DNILLIIGGLVATITPKLV NWFLLLQDNINIFLR | 52 | No significant similarity found. | | | | No putative conserved domains have been detected | | |
| 81 | 34875 | 35255 | 1157 | MFKLQNKVEIIVPKEDNN GVEIADKRIKEYNSITME AGGCTITEIKGQWYSEDE KRIMEDNNLNLEWYYIPD RAKFMTVELKGIVRRLIE VYGQEAISIKVNGTLYIVD QSDIEELHTTLLNIMK | 126 | No significant similarity found. | | | | No putative conserved domains have been detected | | |
| 82 | 35747 | 35968 | 1158 | MNRLEIVKDTAMEYILM MDNSVMDGVMTQEEYN EAVSFEKVYDYTLSEANK ECKFLGGKVLTFLVHEAI EEYA | 73 | No significant similarity found. | | | | No putative conserved domains have been detected | | |
| 83 | 36049 | 36186 | 1159 | MRYEIVTLVNQELFMYAT FNKQEAEAKYSEWCELY GQENVSMEKN | 45 | No significant similarity found. | | | | No putative conserved domains have been detected | | |

FIG. 14T

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 84 | 36215 | 36493 | 1160 | MILNYTKEKEMIQMKLL NQENQIVISIATLESVKQA LIWEYIDHIDYNIWNNEL DDTEAVVKISGILQSIKFA DTMEDLQEYIGDIGWKLI | 92 | gp ORF194 [Staphylococcus phage A5W] | ACB89187.1 | 3e-24 (56/78) | | No putative conserved domains have been detected | | |
| 85 | 36584 | 36823 | 1161 | MKKNVKASTIEWLELTQ GHGEFDGFDEEDMDFRK LDDEDIKWYFENWYFTEE KQEQIIDEIGQEEFEEAYS DDIKEYNN | 79 | No significant similarity found. | | | | No putative conserved domains have been detected | | |
| 86 | 36898 | 37158 | 1162 | MTKFKLIDKNSFYVNDNY NNETYLTSQIVLSGEAGR LLDDMIEDCEDEHDKDN YKKLDTNNIDDIDYILECA NVYIYPYNKTEFKY | 86 | No significant similarity found. | | | | No putative conserved domains have been detected | | |
| 87 | 37176 | 37349 | 1163 | MNTRANKALNEAVRLL DKQIEDTQKTMQELNKQL EQQIKAKQELMTLVDVM TGDDE | 57 | gp ORF002 [Staphylococcus phage A5W] | ACB88993.1 | 2e-19 (50/57) | | No putative conserved domains have been detected | | |
| 88 | 37349 | 37618 | 1164 | MNIKEAHKVVRSAKSKLL QEQEHITNHIIEDYIIEELH RRTQGSGTIQMNNNTASY SNGSYGSLEELREAYDLS SLSTGEIKELLETFV | 89 | ORF166 [Staphylococcus phage G1] | YP_241041.1 | 2e-33 (71/89) | | No putative conserved domains have been detected | | |
| 89 | 37720 | 37971 | 1165 | MKEQIKQFFKELEMAVN NLFVLHDCGVSQAKIEEQ NQKVVYLKAIVENMKAY EEIRVEPKSEEQFFKELEE ELEEEEKILKGI | 83 | No significant similarity found. | | | | No putative conserved domains have been detected | | |

FIG. 14U

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | | | Homologous/similar proteins | | | | Conserved Domains | | |
| 90 | 38522 | 38259 | 1166 | MKLYQVEHDNCEPYEDN YSYREDKVYTNKENLIKR IKAEGYEEKISGYLQDGY TYYYKDNIEDVPLFREDM ITIHELEVINNTSEEE | 87 | gp ORF004 [Staphylococcus phage A5W] | ACB88995.1 | 5e-19 (52/83) | | PRK14902, 16S rRNA methyltransf erase B | PRK14 902 | 6.40e-03 |
| 91 | 38955 | 38524 | 1167 | MENYKNFIIEEMNKAHIL VTKAEQIKGDRKLAETEL EEVYRKAEAFDEIVNELL YQLQNLESWDTLDQKDC QTLKQILEENIKEEKQME RFKVKRITTEEVRYIDAE TEEDAWYSVEYEDEGTD TAHFSAEYGEWSYEREDN | 143 | ORF103 [Staphylococcus phage G1] | YP_241047.1 | 1e-67 (129/142) | | No putative conserved domains have been detected | | |
| 92 | 39149 | 38958 | 1168 | MIEISISWTYLITFLLLWSA GTLYINYLVYRIRLTNKER KEMSKEHHRNREEIKQRI ENRRDK | 63 | ORF224 [Staphylococcus phage G1] | YP_241048.1 | 1e-26 (61/63) | | No putative conserved domains have been detected | | |
| 93 | 39394 | 39146 | 1169 | MRYDINEKCYDEKDFVL QIIYENYSDETDREVETIY NKAEAWDKLCEMLKDK DMSDGHFEEEMFKLFSRT GKSFTIDKEESQ | 82 | No significant similarity found. | | | | No putative conserved domains have been detected | | |
| 94 | 39876 | 39394 | 1170 | MNKTFFKFLGKNTLEYSK QGLGFLVALPIMLIIFSVFL AFIIGIPAVIIYALHALNID NDFIIQLVPVMWFIILYGI VRTDEHKKPFVKLKLKD YLLSILYLTITAISVLESY LLFQLLPFTGDVRAVITLL SFIVFVAVNRGICKIAIKSY | 160 | ORF087 [Staphylococcus phage G1] | YP_241049.1 | 5e-81 (153/159) | | No putative conserved domains have been detected | | |

FIG. 14V

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | KEYKEEL | | | | | | | | |
| 95 | 40300 | 39869 | 1171 | MNIKYIDLVLENCDVVRL ESKDVSRFHISGITEGIDY YGTYKETSNISRTRHCTYF GILIDKPMEIPQVGFAYPD NTNAYEMITAYSDITAIDII YENDANEYIYVDFNEYND NYNINQKNDYYNNMLEIT ITESNSREEEDE | 143 | hypothetical protein KgORF2 [Staphylococcus phage K] | YP_024433.1 | 7e-74 (139/143) | | No putative conserved domains have been detected | | |
| 96 | 40856 | 40314 | 1172 | MDKINLNKKHDGSTVVNI SNNIMLKIQCTDLRKECD DSEAPTTYTHFKAYIVYNI FIVVNDRKQKKKVKYDY YNDHVGRGNVKDLLKVK DVIFQLSTQLNTNEIIKISG ADERRYKIYKYFIEKDIRF EDNMYYSKSNIWINNFSL LQKFQWNTVVTKDGDYN KKELKKVDKEWKELLI | 180 | ORF073 [Staphylococcus phage G1] | YP_241051.1 | 8e-96 (177/180) | | No putative conserved domains have been detected | | |
| 97 | 41356 | 40868 | 1173 | MRETSEYIMFWGKEDIYS NFYPIKFKHQGRTFNNSE QAFMWRKARYFNDFQIA GEILNAKNPNHAKSLGRK VRNFNEEQWNKVRYDIM VEVVKDKFMTTHLKQRIL DTDVRKDFVEASPYDKIW GVGLKANDPKILEQSNW KGQNLLGKVMEDVRVHC IYNK | 162 | hypothetical protein KgORF4 [Staphylococcus phage K] | YP_024435.1 | 2e-90 (160/162) | | Riboflavin_ fusion, conserved hypothetical protein, ribA/ribD-fused | TIGR02 464 | 2.28e-60 |
| 98 | 41767 | 41369 | 1174 | MKKKYFKGLKLNDFEKE VFGLKKNKKYKKMKKKL | 132 | hypothetical protein KgORF5 | YP_024436.1 | 8e-69 | | No putative conserved domains | | |

FIG. 14W

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | GRNEPKYWNYDMSFFIQL YADLNAFVESSNHVDME YHTFVDVDGKERTQIDMI KHILSLIKYYHKEMDDFD MDKYDELEQVQSKILDNF KIVLPSLWN | | [Staphylococcus phage K] | | (130/132) | | have been detected | | |
| 99 | 42471 | 41764 | 1175 | MAIYVVPDIHGEYQKLLTI MDKINNERKPEETIVFLG DYYDRGKRSKDVVNYIF DLMSNDDNVVTLLGNHD DEFYNJMENVDRLSIYDIE WLSRYCIETLNSYGVSTV TLKYSSVEENLRNNYDFI KSELKKLKESDDYRKFKI LMVNCRKYYKEDKYIFSH SGGVSWKPVEEQTIDQLI WSRDFQPRKDGFTYVCG HTPTDSGEVEINGDILMC DVGAVFRNIDFPFIKLEVK K | 235 | putative protein phosphatase [Staphylococcus phage K] | YP_024437.1 | 5e-134 (234/235) | Phosphatase | MPP_PPP_family, phospho protein phospha-tases of the metallo-phosphatase superfamily, metallo-phosphatase domain | cd00014 4 | 6.21e-23 |
| 100 | 44413 | 42563 | 1176 | MTKKLKLYDYENNLLKS SENIEDSIGQIVIENLNPDT TYEAGHFKICWDINGEESI KVDIPKFVTLTSSQDKLII VTYNEVEPMNIKAENIIGL QDVIDTQFNDHIKEEFMA EINKLIADNKPTQQPSTTTI SPLKDKKVIFIGDSITEVN ARTTKNYHQFIADRTGLI NVNKGTSGTGYQDRKNV AYTITDKPDLICVMLGTN DYGLVGGKTKPLGTAKE HSYTTVAGSIYYTYYQLS KVFPTVPIVVLTPTPRIESN | 616 | lipase/acylhydrolase domain protein [Staphylococcus epidermidis RP62A phage SP-beta] | AAW54968.1 | 2e-149 (277/503) | Hydrolase | SGNH_hydrolase_like_2, SGNH_hydrolase subfamily | cd01183 4 | 2.31e-08 |

FIG. 14X

Table 11 - Features of phage F125/10 gene products and assignment of putative functions.

| orf | Start position | Stop position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | PFKEVENGQGYTLGQLVD VIKEIAKQFSFPVLDLYRE SNIRVWDNNVNKTFFAW KEGMEDGLHPNAKGHEFI SYTIQSFLESKGTVGAIAS PPSIDTSVKDLGNGVYSK LIRPTGMRWKKDTSFVM NMSTDDIDLTANKILNVS YNGKSLINPEGYTSNSPY WYTLPAYEDGNKYNRISE VQNFLNAFITIDDNAQGL EFMRDYIKVIYVDKTKTN IVGEYTQVGYKDTTASTP PTGDTSGTITPVSNGDGTY TATFTPTAIYWKEDQSFMI NIDKTKLDLTGKSVTKLE YNGKTLVNNTSLASNSPY WLTVPTATEGTTNNRTPE VKDFVSVLTLESTGTDGR KKYKNVEIKLTYK | | | | | | | |
| 101 | 45043 | 44972 | 1177 | GGACUCUUAGCUUAAAG GUAAAGCCAACCGCUCA UAACGGUUUGACUGUA GGUUCGAGUCCUGCAGA GUCCA | | | | | tRNA4-Met | | | |
| 102 | 45871 | 45323 | 1178 | MEKIYILEEIEEMDYDL WEEDTVYTTSYEVLGYT DSLEDAEYIRDNYGTSNPI FINEYPYLTKEKLEEQRY FRYNSYLELKRVNGYFEIS EINELHVTEDFSNKDDKN FDSPFSINMFSHNRNSIGIE FIMFSEYNDKEDIIEKEKN SFLMKLKYLLKHSREADI | 182 | hypothetical protein KgORF8 [Staphylococcus phage KJ] | YP_024439 1 | 4e-88 (162/169) | | PHA02241, hypothetical protein | PHA02 241 | 1,20e-23 |

FIG. 14Y

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | RSTSKIIDSIDKLT | | | | | | | | |
| 103 | 46093 | 45875 | 1179 | MKNINFLVDYNINFSYSE DSLNVMNNSYLVDKHGT QDYEIVGNYEHITGVFSY QTEEEVIAKLLKNLIGIWE | 72 | ORF201 [Staphylococcus phage G1] | YP_241058.1 | 4e-33 (71/72) | | No putative conserved domains have been detected | | |
| 104 | 46288 | 46094 | 1180 | MRDKRIHSELLYDIIGKHI QEEENITPYIEAIYVDMM NIIVVEYTFYNENGTRML GQYPIGEVM | 64 | ORF218 [Staphylococcus phage G1] | YP_241059.1 | 8e-29 (64/64) | | No putative conserved domains have been detected | | |
| 105 | 47015 | 46278 | 1181 | MNLEKSFLLSTIEFGSTYQ GTSDEHSDKDYMSLVVQ PLSDTIFRNNEKASKIITEV SRYYAVERFISLVLKSGFD NVLNLCAQLEQAKNTRF NKTVLDLFYDDFIFLTYV RANFKPIAYSVIGNINNIL KKGELTGKDLVKFYTFYN HLEYYNDLLDDLDNLNV SYKDFAKVKYMPKEVLD NKRSNVSIEKKKDLVNKV EPLIQEVKDKLKYNESNIK HYKDAMELVEKSLKDKT VAFLTEVYNER | 245 | hypothetical protein KgORF9 [Staphylococcus phage K] | YP_024440.1 | 2e-135 (243/245) | | No putative conserved domains have been detected | | |
| 106 | 47182 | 47078 | 1182 | MKYILGLITLGIILFKVYE HFKYKQDEVDTEEDI | 34 | ORF437 [Staphylococcus phage G1] | YP_241061.1 | 4e-10 (34/34) | | No putative conserved domains have been detected | | |
| 107 | 47442 | 47194 | 1183 | MSNMDFYQFLNHENVRV NSITPSQKNFIRENLELTN LEDTDIDFISSKKAKEEIEK IIRIKNEEEYDMAMDALA | 82 | gp ORF020 [Staphylococcus phage A5W] | ACB89011.1 | 6e-40 (80/82) | | No putative conserved domains have been detected | | |

FIG. 14Z

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | GWVTKHGY | | | | | | | | |
| 108 | 47824 | 47435 | 1184 | MFKKAPQYIMEKVEKEN NILGEDLSLDIYYKGVKLT VKRHPETGHLNGYITLPS DINEKEYDSLERRAHRGIT YDDYDYEGKRVLGFDCA HAWDMTPYAIIGSLDDQY RDLEYVLSILKDMAEYVK KDE | 129 | hypothetical protein KgORF10 [Staphylococcus phage K] | YP_024441.1 | 2e-69 (129/129) | | No putative conserved domains have been detected | | |
| 109 | 48096 | 47923 | 1185 | MEKVNHEFLAELAKSNSP VLNSKPLQDGDYNIEFDY DGFHFEFSQKNGYWQWK YNAK | 57 | ORF245 [Staphylococcus phage G1] | YP_241064.1 | 7e-25 (55/57) | | No putative conserved domains have been detected | | |
| 110 | 48619 | 48137 | 1186 | MANEKEIIRMVNYLIDNM SMWHINYARAVLIPSEVE KIIKEHEKFDLLKKRGE WLVKGSDTDNIDDLETYN QIMNNQKDEMMIQEIDIY TQGKTITIDNEHYSSDDLN EVLNKLEQSEDIKIKSNYK SLYVGYTNVVGYEVTYA SSYEETFKNDLEKDL | 160 | hypothetical protein KgORF11 [Staphylococcus phage K] | YP_024442.1 | 2e-85 (159/160) | | PHA02243, hypothetical protein | PHA02 243 | 2.31e-36 |
| 111 | 49211 | 48669 | 1187 | MDRIIGKHNLTQDLRLGD KVEVYDAHKFKENEDGTI ELGDKITEGIVVDYKGDF TGNTSGLVTLDSSEKELII GEYNFKLIEEGNLQAVYD SVSKNKVESLSEDYDMYR KLLGVKSGELAGIEDELE YLVRQYNSKVDNYNGLL TLSKEKARELSLLTGNKK | 180 | hypothetical protein KgORF12 [Staphylococcus phage K] | YP_024443.1 | 1e-94 (177/180) | | No putative conserved domains have been detected | | |

FIG. 14AA

Table 11 - Features of phage F125/10 gene products and assignment of putative functions

| orf | Start position | Stop Position | SEQ ID NO. | Aminoacidic sequence | Size (aa) | Name[organism] | Acc No | E value and identity | Predicted function | Conserved Domains Name | Acc No | E value |
|---|---|---|---|---|---|---|---|---|---|---|---|---|
| | | | | TIPHMKNRRLELGKEADF | | | | | | | | |
| 112 | 49744 | 49211 | 1188 | MVYDSIISRTMAVSILNK WIAELITDVDLDKCKFTE EEYGKVVTNSINKIQDVLI EKNYEVTDGELYDIVCTE LNPIKNNTEEEKHNEKND LLEHLEDLAFRHDIDLGY VSDGSYNLTVTHWLMQD EFTDVNIKVNNDEDFYTV TIPESKYFWLPITKENLEM FLTQDPINKGEVK | 177 | hypothetical protein KgORF13 [Staphylococcus phage K] | YP_024444.1 | 4e-97 (177/177) | | No putative conserved domains have been detected | | |
| 113 | 49911 | 49747 | 1189 | MKNPIKLLSIAVVTILTFSL TYVILKKETNNKRNGVAP FDFSLEDHIHLNKEIK | 54 | hypothetical membrane protein MbpP [Staphylococcus phage A5W] | ACB89017.1 | 2e-22 (54/54) | Membrane protein MbpP | No putative conserved domains have been detected | | |
| 114 | 50192 | 49914 | 1190 | MANNIWAVVLSIIILLIILLI LWFLFRKKVNGGNSKNV EIQKAEENNDNKEQEVEE AQYRELNEEEKENENSS KDYKYDKEKVKNKLKEL E | 92 | hypothetical membrane protein MbpR [Staphylococcus phage A5W] | ACB89018.1 | 2e-41 (92/92) | Membrane protein MbpR | No putative conserved domains have been detected | | |
| 115 | 51037 | 50192 | 1191 | MGRRLIDNSELNVIKYDG LPDFFSALKKNRVSGRDN SSDTGSYDFTGTHSFQEA YNLMVKGDRESYDMVV KLKKMTDALFRMDKSVK RKPVVAPEGYQPHVPNAI KGLPNSMMSQORVKAEK KVIDVFYNSSISWREDPEN LAYRGAIMLSAIQTLETK GYSINLYLGKLSNSGYED | 281 | hypothetical protein KgORF14 [Staphylococcus phage K] | YP_024445.1 | 8e-161 (280/281) | | No putative conserved domains have been detected | | |

FIG. 14BB

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | KLTGFVVNIKHSYQRLNV FKSSFYLVNPSFLRRISFR VLEVEPDMVDLTNHGYG SVVSKSSYGNKLTEHILD NAVIFDSSVGIDNNDSSE NLRAVKKLFGGRL | | | | | | | | |
| 116 | 52167 | 51049 | 1192 | MAKQDTIERLERLVEQQ METTADLAKKLGEKNSN PYEQAIVDAIVEKAGTESR EIIITDVKKQIEEYVEEQLS NLPVKIELQQEGKTIKDIS GFHYRYQDILKLVNQNIP VFLKGGAGSGKNHVLEQ VAEALDLDFYFSNAITQEF KLTGFIDANGKFHETQFY KAFTKGGLFFLDEMDASI PEVLLILNSAIANKYFDFPI GRVTAHEDFRVVSAGNT MGTGADHIYVGRQOLDG ATLDRFAQVEFDYDTKVE HQLSSNEDLVNFVQQLRH ENDEKGLPYVFSMRAIIN GSKLDGVMEDEFVVESIIF KSVPKDEINQFISSLPEGN RYTEATRKLLGMQQEPK QEPRKSDSTSKDSMDFDTI MDKLGLE | 372 | putative ATPase [Staphylococcus phage K] | YP_024446.1 | 9e-110 (194/194) | ATPase | PHA02244, ATPase-like protein | PHA02 244 | 1.23e-175 |
| 117 | 52645 | 52319 | 1193 | VSKRTDNFIYFCKYFSE YLPSLGVEVLNHNETSHG TMEGVKKYYIANILYEGQ ELIVTIDLEEFNNATSMH NMLEIMNNHTYNCMFMY DMDTHFTKDIDDFFKLM | 108 | ORF134 [Staphylococcus phage G1] | YP_241072.1 | 6e-56 (106/108) | | No putative conserved domains have been detected | | |

FIG 14CC

Table 11 - Features of phage F125/10 gene products and assignment of putative functions

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | YF | | | | | | | | |
| 118 | 53054 | 52638 | 1194 | MNAKEFMKTQAQVEDYL DKLKVTIIEDALSVSKEWS NDSNDLGYALSSLGESIGL LENYYNIQVDAHLPEHYK GSKDVISFLEEHFSYDGFV DSMFNIVKYTTRLGRKD AVDKEVQKIKTYYVRLER NIKYGDSTRV | 138 | hypothetical protein KgORF16 [Staphylococcus phage K] | YP_024447.1 | 7e-74 (137/138) | | No putative conserved domains have been detected | | |
| 119 | 53488 | 53186 | 1195 | MEKVELIKQWAKDRNLQ TGKPEGQMLKLLEEAGEL ASGIAKSNDHVTRDSVGD IFVVLTVLCLQLDIDIEECI DMAYDEIKDRKGKLINGV FVKEEDLKK | 100 | hypothetical protein KgORF17 [Staphylococcus phage K] | YP_024448.1 | 9e-50 (100/100) | Pyrophospho-hydrolase | MazG | pfam03 819 | 7,10e-03 |
| 120 | 53676 | 53488 | 1196 | MEKFQEDYVNIDIRVKAY VRVGYRYEEDITNNLHEL VEDNLNVTSDSDSLIIKDT EIKGDIE | 62 | ORF228 [Staphylococcus phage G1] | YP_241075.1 | 5e-26 (61/62) | | No putative conserved domains have been detected | | |
| 121 | 53881 | 53720 | 1197 | MVKPVITLEPEDVKVLLD YLSFLEDDMRNYEGMRE LYEELHKKYQLAKGNYS D | 53 | ORF259 [Staphylococcus phage G1] | YP_241076.1 | 4e-22 (53/53) | | No putative conserved domains have been detected | | |
| 122 | 55932 | 53881 | 1198 | MAITYKQKGLTEQEIINLP KVNKGCIYIGEEDVFLKK KKNNINLGSKELFRDIHN IFSFDTATEIHLFLALCGN KEVTNFTGNPYETIEKLVE GVIEENKGRSYKEYIASSR EERKEFPLYGSKRITQIKS | 683 | hypothetical protein KgORF18 [Staphylococcus phage K] | YP_024449.1 | 0,0 (591/683) | | No putative conserved domains have been detected | | |

FIG. 14DD

Table 11 - Features of phage F12S/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | KGYVEEKIKELENETRLR WYESRQLDEYKEVVDSL NNDIMDILYQGKYGLIKS SITSRLNEDTEKGSSKYYK EISDSLYSSTWYMHPSTE NSSSFGLKVRHIRDKYNM GNRWVLENKSSFDVKTG EVKVFLTDSLVNKEITLNL YKDDISKSEYKNELNLAV LLNVILKNYSTPNLSKNVI IKJIEETLRNDGFGLSSWC LDEVDVYGRVNYGGNKY KPLKGENSTSNYLTILTDI VKNIDKINNLEEFELFERN SLLFHPKNPKWKIHEAFN LTKQTYKKLLTLNNFEQS NYLRFSDTLYNYYNHLH NEVNLHQLFDDTFLMVQ DVRNVTDALKVKPIVNEI LSISFANYKKMTHYLDVD AQDRQRITGYALDSYYLD YLHDLSILIREGYRTLESV NLTPFSLKLEHDIVTDEKQ SIQQLDDAELKSKYENK LEKIIDKTYKLKDGRKVK FLPADTVSKLKNEGKMLS HCVGGYANRIIKNSCLILL ARLEEDLDNSWFTVEIRIT DNGYVLGQQQSIDAYKLP NELKEALEKDIKKINKEEF KEVA | | | | | | | |
| 123 | 56273 | 56010 | 1199 | MSIEKKEEVVAHNEVVFK SLTQGLYVKEVDIYSDVIS YTKDIDEALAMPNTINFK NSRKYEKLIRNLDLKPLN | 87 | gp ORF038 [Staphylococcus phage A5W] | ACB89029.1 | 5e-39 (79/87) | | No putative conserved domains have been detected | | |

FIG. 14EE

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | KIQKVIYETHLEEL | | | | | | | | |
| 124 | 56465 | 56292 | 1200 | LNDLIKEGNKYYHKVRA GETLWTISKNYGVDIKKL QELNNIKSVTLTSLEYVLV CVE | 57 | gp ORF039 [Staphylococcus phage A5W] | ACB89030.1 | 1e-21 (52/57) | Peptidoglycan binding protein | LysM | pfam01 476 | 8.09e-07 |
| 125 | 57050 | 56472 | 1201 | MDNLSHYLSILYAILVTV GYIPGLIALVKSDSVKGVS SYFWYLIVATVGISFYNLL ITDATMFQVVSVGVNLTL GIVCLLVASYRKKDYFSIP FIIVFSVLLFLLSDFTALTQ TIATTHLAYVTQTTFYK TKSAEGTNRFLFLIIGLGL ASLILSMVLSHTYVHIIAT EFVNFVLILICYLQANVYS RR | 192 | gp ORF040 [Staphylococcus phage A5W] | ACB89031.1 | 5e-92 (177/192) | | PHA02246, hypothetical protein | PHA02 246 | 2.51e-33 |
| 126 | 57636 | 57043 | 1202 | MVNYTKDKVCYMGGHL LNQAMVEYRTKQHEQVE GIVGVTPYSPIIQDKSIND KANAEQTGLAERILNNDF KAMQESDIFVFDILNEGL GTIAELGILLGMKHQAQK IIDKYEDIDFRDLEPLTQY DILEAYNIVNKPVLIYCSD IRQGHGKGYDDPDRAEFS TNQFIYGCVLSLTNGEGFI SWEEVLKRLEKLGGQDG | 197 | hypothetical protein KgORF20 [Staphylococcus phage K] | YP_024451.1 | 8e-79 (153/210) | | No putative conserved domains have been detected | | |
| 127 | 58522 | 57629 | 1203 | MKSYTKVKNKGLSLDKF KDRGFVVQEKLDGSNASF TTENGELVCFSRRKKLNE NETLNGFYNWVHENMTD | 297 | putative DNA ligase [Staphylococcus phage K] | YP_024452.1 | 8e-134 (237/298) | DNA ligase | RNA_lig_ RNL2, RNA ligase, Rnl2 | TIGR02 307 | 1.21e-07 |

FIG. 14FF

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | KLDLSILEGIIIFGEWLVKH KVNYKEECYNNFYVFDV YDKDSETYLPYSEVISLSE TLGLKTVKTLMIIEPSFYL NKLNPQEIQDLVGKSDMT VKPNTGEGIVIKYLDGKS EHDDYFKLVSKEFKEFSR KKMKSEVRSNDSVADYAI TKSRMEKMIFRAIEENRLS KDDLELENFGLIMKQVGQ NFVDDIMEEEKENMMKII EKQIKKKMPHILRGILEEK GDTIDG | | | | | | family | | |
| 128 | 58750 | 58526 | 1204 | MNYLAKVFINNNWLVKLI TIVLLTLLLGGLYYVISAV ALFLSTVLNLPGLVVLAF LASVSLILFSIVHNSKEDN | 74 | No significant similarity found. | | | | No putative conserved domains have been detected | | |
| 129 | 59558 | 58818 | 1205 | MAIQLKELDFKLKDYPNV RYNMGEHLVFNEFLEKAT TEQLDFCEDFFNDNVEIL WNESQAGTGKTMCSVAC AYADYLNKDRKLVFIISP VSEDLGSRPGNQTEKEMA YFMGLHDALIELNMNPEQ QITEMLMMEDNVKEDKL GDCWVSQISHLFLRGGNL RDSTIIINEAQNFKRSELK KVLTRVHTKNSTVIVEGN FKQIDLKNESKSGFGDYM EYFKKYDGAVFHNFTVNF RSKLAQYADNFKW | 246 | putative PhoH-related protein [Staphylococcus phage K] | YP_024453.1 | 4e-142 (242/246) | ATPase | PhoH-like protein | pfam02562 | 3.99e-21 |

FIG. 14GG

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| 130 | 60224 | 59610 | 1206 | MKKINSVIKGEGKKVQTT DVRKISYYVKDYNPCMT VDDANDYNSTSQYLVSD NGKFIAKYNKDMNAVGF YEESGDTVKHLTHTPER LEGTVFTIEEETKIDLINDT LPQGDILIKFSDGSIYLPDN ESVLDSVNYLADNDWDS VDDIIYTGLSKGNSENCIV DFNYNNYDIGYDDVEDEE VCDNYPECECSNYCSSTG EYIGN | 204 | hypothetical protein KgORF23 [Staphylococcus phage K] | YP_024454.1 | 3e-111 (200/204) | | PHA02248, hypothetical protein | PHA02248 | 2.68e-96 |
| 131 | 60665 | 60240 | 1207 | MQDSVNIYTDGSSSYNKG KVGSGAVLVSKEGNIIAEI SKSVDKPGLIKYNNVAGE ILACCYGIEEAIKLGYNQA IVVIDYIGLIHWYEGTWSA RNILSKTYINMIREYQKVI DINFVKVKSHSNDKWND YADNLAKKSIDI | 141 | putative ribonuclease [Staphylococcus phage K] | YP_024455.1 | 1e-73 (140/141) | Ribonuclease | RNase_III_bacteria_HB D | cd09277 | 8.50e-30 |
| 132 | 60846 | 60655 | 1208 | MKKGVFTVIADGFKFNVI AKDKKEVQEHCFKCFDF NYISVSFCREVYSDCEFPQ FMEDYKYAG | 63 | ORF222 [Staphylococcus phage G1] | YP_241086.1 | 2e-28 (63/63) | | No putative conserved domains have been detected | | |
| 133 | 61510 | 60869 | 1209 | MENNNLVNFLMTTDDID DTIEMVDSFELQDINKVL GEDTFLTIMEITDSLPDNQ YKIVLLSSLDKLLNTDRK ELVEYDEEFPTIRKHNVSE LKRDTVNSVIDSYMNTNV EILYTEYPTISNYSVVVDS VKVLNTLYLIESKNGKIEA | 213 | hypothetical protein KgORF25 [Staphylococcus phage K] | YP_024456.1 | 7e-113 (213/213) | | No putative conserved domains have been detected | | |

FIG. 14HH

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | TLSEDGEDLHEYISEEGYS VTDILNKFDDVEDLFDED DSLINFFSDIDEGKNKTIKS FIELVINLK | | | | | | | | |
| 134 | 61730 | 61500 | 1210 | MDEKKESKPLNLQKIRVE KGHTLRSLASEIGVHYSLI SYWEYGKKKPRSANLMR LEKALNTPGKELFKELEE DDGE | 76 | ORF187 [Staphylococcus phage G1] | YP_241088.1 | 6e-36 (76/76) | DNA binding protein | HTH_XRE, Helix-turn-helix XRE-family like proteins | cd00093 | 9.43e-07 |
| 135 | 61960 | 61733 | 1211 | MNKFKRWFRINVLKKETL LFKVYWRYESPSLKKPHV FHIELYAKSKAEARDKSH EYILKNAKASEDFKFLKV EEK | 75 | ORF190 [Staphylococcus phage G1] | YP_241089.1 | 2e-33 (73/75) | | No putative conserved domains have been detected | | |
| 136 | 62778 | 62071 | 1212 | MKKTIFATLALGTAITFGG MATNEASADEIDYNKLAE QAKSNSVEVNTKPIQEGN YDFSFSDGEFTYHFYNYN GNFGYEYHSGSTQVDNT VSRLAGEEQTPEQKVDQQ QAQFDTQNKAVEQPKQE TTTQEAPKSVEAPKVETK TTATKSTGGSVAEQIRQA GGDEAMIEIAMRESTLNP NAVNPTSGAQGLFQGLG KSWSGGSIAEQTKGAKQY MIDRYGSTSGALNFHNAN GNY | 235 | hypothetical protein KgORF26 [Staphylococcus phage K] | YP_024457.1 | 3e-110 (201/235) | | No putative conserved domains have been detected | | |
| 137 | 63768 | 62974 | 1213 | MRKSVVISGVIGFLAIIGFI ILLMCITTKIPQGHVGVVYS VNGVKEDTKSPGWHLTA | 264 | hypothetical membrane protein MbpS [Staphylococcus phage] | ACB89042.1 | 1e-137 (237/261) | Membrane protein | Band_7_Hfl C domain of flotillin | cd03405 | 3.25e-11 |

FIG. 141I

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | | | | | | | Conserved Domains | | |
| | | | | PFDKVNKYPTKTQTHKY KDLNVATSDGKNLQMDI DVSYKVDATKAVDLFNR FGSADIEELEKGYLRSRV QDNVRQSVSKYSVIDAFG VKTGQIKKDTLDSLNDNL EKQGFVIEDIALSSPKADK NTQKAIDERVKANQELER TKVDKQIAEENAKKKEVE AKGEKKANDIRSESLTDE VLQQQLIEKWDGKQPIQI GGDGTIVDVTGK | | A5W] | | | MbpS | (reggie) like proteins | | |
| 138 | 64077 | 63769 | 1214 | MALFLTYFAIFIVFLVLVG FGMSYVFDFLSMREKKSN IRKQYRFLVRQGTLEEYG LEQYVKYKKQFLNDRRQ SLVTKADKQEIDKEEKAL NSLIKEIEKGEM | 102 | hypothetical protein KgORF29 [Staphylococcus phage K] | YP_024460.1 | 3e-47 (94/102) | | No putative conserved domains have been detected | | |
| 139 | 64810 | 64190 | 1215 | MENIIGKKIEKLFVEEYVG SDKIKGKLYLCLCDCGMD RVLSKSQLYYYKSCGCM KSRNGSKKHPEYTVWRK MKERCYNKNQDSYPYYG GRGIEVCDRWKNSFESFL YDMGKRPSDKYQLDRKD NDGNYSPENCRWTTRSEN IVNRPSKLEGLKNIQERTN GKYRVSITRNNIRYQSYQ VDSIKEAINLRDRMLKEY EETKSITIFK | 206 | hypothetical protein KgORF27 [Staphylococcus phage K] | YP_024458.1 | 3e-34 (88/211) | | No putative conserved domains have been detected | | |
| 140 | 66363 | 64873 | 1216 | MAKTQAEINKRLDAYAK GTVDSPYRVKKATSYDPS | 496 | putative lysin [Staphylococcus phage | YP_024461.1 | 0,0 | Endolysin | PGRP, Peptidoglyc | cd0658 | 3,07e- |

FIG. 14JJ

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | FGVMEAGAIDADGYYHA QCQDLITDYVLWLTDNK VRTWGNAKDQIKQSYGT GFKJHENKPSTVPKKGWI AVFTSGSYEQWGHIGIVY DGGNTSTFTILEQNWNGY ANKKPTKRVDNYYGLTH FIEIPVKAGTTVKKETAKK SASKTPAPKKKATLKVSK NHINYTMDKRGKKPEGM VIHNDAGRSSGQQYENSL ANAGYARYANGIAHYYG SEGYVWEAIDAKNQIAW HTGDGTGANSGNFRFAGI EVCQSMSASDAQFLKNEQ AVFQFTAEKFKEWGLTPN RKTVRLHMEFVPTACPHR SMVLHTGFNPVTQGRPSQ AIMNKLKDYTFIKQIKNYM DKGTSSSTVVKDGKTSSA STPATRPVTGSWKKNQY GTWYKPENATFVNGNQPI VTRIGSPFLNAPVGGNLPA GATIVYDEVCIQAGHIWIG YNAYNGNRVYCPVRTCQ GVPPSHVPGVAWGVFKG | | KJ | | (492/495) | | an recognition proteins (PGRPs) | 3 | 10 |
| | | | | | | | | | | CHAP domain | pfam05 257 | 1,42e-15 |
| | | | | | | | | | | Bacterial SH3 domain | pfam08 460 | 6,49e-14 |
| 141 | 66866 | 66363 | 1217 | MANETKQPKVVGGINLST RTKSKTFWVAHSAVALFA NQITGAFGLDYSAQIEQG VNIVGSILTLLAGLGIIVD NNTKGLKDSDIVQTDYLK PRDSKDPNEFVQWQANA NNASTFEIDSYENNAEPDT DDSDEVPAIEDEIDGGSAP SQDEEDTEEHGKVFAEEE | 167 | putative holin [Staphylococcus phage KJ] | YP_024463.1 | 6e-90 (165/167) | Holin | Phage_holin_1 | pfam04 531 | 1,53e-25 |

FIG. 14KK

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | VK | | | | | | | | |
| 142 | 67136 | 66951 | 1218 | MASAKQLYYTESLVGKAI INNKVSNKEEVWDKLELL PETKLEDLDNKQMSEVIK KLNQINE | 61 | ORF233 [Staphylococcus phage G1] | YP_241098.1 | 1e-25 (61/61) | | No putative conserved domains have been detected | | |
| 143 | 67369 | 67298 | 1219 | ACACCCUUAGUAUAAUU AGUAGUACAAGGUCUC CAAAACCCUUAGUCUUU GUGCAAAUCAAAGAGG GUGUG | | | | | tRNA3-Trp | | | |
| 144 | 67448 | 67376 | 1220 | GGUUUCUUAGCUCAGAU GGUAGAGCACUAGAUU GAAGCUCUAGGUGUCAU UGGUUCAAAUCCAAUAG AAACCA | | | | | tRNA2-Phe | | | |
| 145 | 67528 | 67455 | 1221 | GGCUCAUUGGUGUAACU GGUUAACACACUGCCCU GUCACGGCAGAGAGUAC GAGUUCGAGUCUCGUAU GGGUCG | | | | | tRNA1-Asp | | | |
| 146 | 68901 | 68683 | 1222 | MKRQKMFYSSLICKECGN VFKVPRKRANKREEGHIK DIYCIKCCKTTKHEDNRS EAERRWDAIQEELTKDN | 72 | ORF200 [Staphylococcus phage G1] | YP_241099.1 | 1e-34 (72/72) | | No putative conserved domains have been detected | | |
| 147 | 69593 | 69384 | 1223 | MSKHIEITMSSGAKYFLVS TDEKSYNRQDIDYMLRG MDETSIKVYTESAITSPQV YINPNRIESFKIVF | 69 | ORF207 [Staphylococcus phage G1] | YP_241100.1 | 1e-32 (69/69) | | No putative conserved domains have been detected | | |

FIG. 14LL

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains ||||
|---|---|---|---|---|---|---|---|---|---|---|---|---|
| | | | | | | Name[organism] | Acc No | E value and identity | Predicted function | Name | Acc No | E value |
| 148 | 69939 | 69606 | 1224 | LDKEINNLVSQVETIKSKI QEGNYIDRGTFKDLEVEV AELRKMIVSIDKDVAVNS EKQSAIYVQLERLDEKISE LAESTKTKDTKKKDTTEK VLLLVLGAILSFVFNKFA | 110 | ORF209 [Staphylococcus phage G1] | YP_241101.1 | 5e-53 (108/110) | | PHA02414, hypothetical protein | PHA02 414 | 8.04e-30 |
| 149 | 70277 | 69951 | 1225 | LTKYKDILKLEFKDSLAH FKRDRRFFHMYRIDRLLIN GSIIYFDYYYLPSDDPNIVI KELDLQDFGKLRFEIDTK TSYGKVVTDNYMEIINDF LENYDIHSESETVRP | 108 | hypothetical membrane protein MbpC [Staphylococcus phage A5W] | ACB89047.1 | 6e-51 (100/108) | Membrane protein MbpC | No putative conserved domains have been detected | | |
| 150 | 70717 | 71103 | 1226 | LNNNIAIFIFKTLVIIFLLL FLSVVNSLSLIYSIRPSVV MAYFTFGGIVSDVALTMT DKFLLKKEDPLPEYVLKK VEINDKEISIIKKIIESNYDI TSEEIKVRAKAQQRLEED SKEEDNDENEERN | 128 | hypothetical membrane protein MbpD [Staphylococcus phage A5W] | ACB89048.1 | 7e-42 (112/128) | Membrane protein MbpD | No putative conserved domains have been detected | | |
| 151 | 71081 | 71359 | 1227 | MKTKKEIKEQRKELKDG ATTVSLVKKGDKRIASPS RICSLCGQQLSGMSYTKG KALSKVNHFHLQYSKYIY FDICADINNCYKNLRKRG EMD | 92 | ORF161 [Staphylococcus phage G1] | YP_241104.1 | 3e-46 (90/92) | | No putative conserved domains have been detected | | |
| 152 | 71356 | 71766 | 1228 | LSAENIRDIINKKKLEEED TRKYIADGFMNGIGKLMY EFNKKVDNKEIEVKDPND LYKLFVIFSQMQNMVNET SEGGAIPQLSRPQQELFEEI TTEDSNGESTVDLQKISE | 136 | ORF133 [Staphylococcus phage G1] | YP_241105.1 | 2e-69 (132/136) | | No putative conserved domains have been detected | | |

FIG. 14MM

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | MSAEDITEMISEKEKVMN EENSKTF | | | | | | | | |
| 153a | 71782 | 72021 | 1229 | MDGKELIKIAQETFQTEKI TREQIDHIINMLNPSTYML KYHTLRGHPITFSIPNRDR SKAQAHRPWQVRKHTMR TINLF | 79 | hypothetical protein KgORF35 [Staphylococcus phage K] | YP_024465.1 | 5e-34 (68/69) | Terminase large subunit | No putative conserved domains have been detected | | |
| 153b | 72255 | 72398 | 1230 | MIVNDTHPNKAVIKSRQL GLSEMGVMEMVHFADM HSYANAKCLYTFN | 47 | | | 2e-19(45/45) | | No putative conserved domains have been detected | | |
| 154* | 72647 | 73558 | 1231 | MGKKLTNTEFLNRVFQLV SDEYSFLEEYKGRHTKLR CKHNLCSYEWDVEPGAF LGNKNKAGSRCPSCYGN VTKTTDKFKKEIYNLTKD EYRLLSEYINAKTKVKJK HSKCGNTFSMTPNTFNGS RCPECNPQKPYNTDSAKD RINKETNGTFELVSEYKG CYELMKLKHHECGNIVEI NMQSIDSNRLNCPYCYNR SRGELLVSSFLLSKNIPFE VQKRFDGFKKYPYDFYIA DYNTVIEYHGEQHYKPIK FYGGEDRLVRQKNIDLKK KNFVEGKGINYLEIPYTLN NQNKVNEFLINYFK | 303 | ORF031 [Staphylococcus phage Twort] | YP_238727.1 | 5e-49 (119/307) | | No putative conserved domains have been detected | | |
| 153c | 73663 | 75123 | 1232 | MKKFVQSRLNPVLEKEYF RDIVDWDKDSLGFKKIRN SSLFFRTSSKASTVEGVDI DYLSLDEYDRVNLLAESS | 486 | hypothetical protein KgORF35 [Staphylococcus phage] | YP_024465.1 | 0,0 (486/486) | Terminase large subunit | Terminase_GpA | pfam05 876 | 5,63e-17 |

FIG. 14NN

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | ALESMSSSPFKIVRRWSTP SVPGMGIHKLYQQSDQW YYGHRCQHCDYLNEMSY NDYNPDNLEESGNMLCV NPEGVDEQAKTVQNGSY QFVCQKCGKPLDRWYNG EWHCKYPERTKGNKGVR GYLITQMNAVWISADELK EKEMNTESKQAFYNYLG YPFEDVKLRVNEEDVYG NKSPIAETQLMKRDRYSH IAIGIDWGNTHWITVHGM LPNGKVDLIRLFSVKKMT RPDLVEADLEKIIWEISKY DPDIIIADNGDSGNNVLKL INHFGKDKVFGCTYKSSP KSTGQLRPEFNENNNRVT VDKLMQNKRYVQALKTK DISVYSTVDDLKTFLKH WQNVVIMDEEDEKTGEM YQVIKRKGDDHYAQASV YAYIGLTRIKELLKEGNGT SFGSTFVSTDYNQEGNKQ FYFDE | | KJ | | | | | | |
| 155 | 75116 | 75937 | 1233 | MNRGEIDLTDKLFYGTIS NEEINKSVLNLLLGEELSL DYVSKNSDTLDVKYEHV YKSLGFDNFFDCFLYANR EPEIVHKGGDKNLGGLNK VKRTVIRNGKEMEMTVY EDGNKENDSKEKQEGKE EVSRSAVGARAISNGEEG KVNPKKVANSLSSLSKKG VDVSHINTNLSLYKEFVD DNGDTLGITSFKRTENDII | 273 | hypothetical protein KgORF36 [Staphylococcus phage KJ] | YP_024466.1 | 2e-150 (270/273) | | No putative conserved domains have been detected | | |

FIG. 1400

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | LESYASSPDSDGVGARAI MELLRLSIKENKNAVVYD IELPEAVEYLKTLGFKPNK DGYILRKKDVKQFLGDYS DFI | | | | | | | | |
| 156 | 75915 | 76097 | 1234 | VIVILFSTIVIYSIVFILYIV LKTIYIKSNMSRIDNTTEL LKILQEDIEGKIKKEGRNK | 60 | ORF235 [Staphylococcus phage G1] | YP_240894.1 | 4e-23 (56/60) | | No putative conserved domains have been detected | | |
| 157 | 76094 | 76573 | 1235 | MTLEENKLTLEESITPLSK EEKEDSIKEFSSLLCEMVN RLYKSYNVFRQDPMDET QRLDGSLMVFQSRLNDPL TGDLHDKMYKLAFSKRID IFEANKQFRKDVEAGKAI ELGDVAIIDTALSNILSGN EFQGSISFMLRKDFEEKER IRKEEEEKLNNL | 159 | hypothetical protein KgORF37 [Staphylococcus phage K] | YP_024467.1 | 6e-86 (159/159) | | No putative conserved domains have been detected | | |
| 158 | 76615 | 77826 | 1236 | LKKKPQGNEVIITIITVMIA VFVVIMTIFFNKYQDAKE DKDRYQRLVEIYKKADD NDGETKKKYVKRLNKAE EELKKVKKETNYKDYNK KSSKERQKEDKETREKIY DVTGDDDLILVKNNIDFS DKVDKPEILISEDGIGTITV PVDSGYEKQTVGSIITSVL GSPFLSPGSNSIDGLSVIND NVYPNTVDSIVEDTKPSIN LPMDNPIITNPVEPTIPSDT IPPIDNPSVPVFPENPVDN NQGNTDNPNPPPGYTDE DGGRGSGGGNSEPPSTE | 403 | hypothetical membrane protein MbpF [Staphylococcus phage A5W] | ACB89054.1 | 2e-163 (375/403) | Membrane protein MbpF | No putative conserved domains have been detected | | |

FIG. 14PP

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | EPSDNGNTGGGDWEEKP DPGEEPSDNGNTGGNGGE VTPEPDPTPSEPEQPNENS DEGNEEKPSEPSDNPDEN GGWETEPTEPESPSEPDD KVDEEDKNEDTTDDKQP TEQPDDNNIDNEDKTEEE | | | | | | | |
| 159 | 77969 | 78253 | 1237 | MIFVHSKFSSKNVFVLYVI YAIIGTYIVLTMFQTTS VLIKNDVIDSIENTEHYIGF NDPIIFTISFIGAILGGIWY KMMKIIKKSNFKDKK | 94 | hypothetical membrane protein MbpE [Staphylococcus phage A5W] | ACB89055.1 | 2e-45 (94/94) | Membrane protein MbpE | PHA02256, hypothetical protein | PHA02256 | 8.96e-22 |
| 160 | 78262 | 78642 | 1238 | VNRLIFSKDKKWDEAKDF IKGQGMQDNWIEIVDYYR QIGGKHVAVFIALNKVKY MILEATKDNKVILVDKDN NILLEDYDIVMESKKMFY YIEEPFEVKINIPQHIRDVT YNNTVVLTTVRGSRGD | 126 | hypothetical protein KgORF40 [Staphylococcus phage K] | YP_024470.1 | 2e-64 (122/123) | | No putative conserved domains have been detected | | |
| 161 | 78646 | 80346 | 1239 | LADLFKQFRLGKDYGNNS TIAQVPIDEGLQANIKKIE QDNKEYQDLTKSLYGQQ QAYAEPFIEMMDTNPEFR DKRSYMKNEHNLHDVLK KFGNNPILNAHLTRSNQV AMYCQPARYSEKGLGFE VRLRDLDAEPGRKEKEE MKRIEDFIVNTGKDKDVD RDSFQTFCKKIVRDTYIYD QVNFEKVFNKNNKTRLE KFIAVDPSTIFYATDKKGK IIKGGKRFVQVVDKRVVA | 566 | putative portal protein [Staphylococcus phage K] | YP_024471.1 | 0.0 (555/566) | Portal protein | Phage_porta 1 | pfam04 860 | 1.00e-13 |

FIG. 14QQ

Table 11 - Features of phage F125/10 gene products and assignment of putative functions

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | SFTSRELAMGIRNPRTELS SSGYGLSEVEIAMKEFIAY NNTESFNDRFSHGGTTR GILQIRSDQQQSQHALENF KREWKSSLSGINGSWQIP VVMADDIKFVNMTPTAN DMQFEKWLNYLINIISAL YGIDPAEIGFPNRGGATGS KGGSTLNEADPGKKQQQ SQNKGLQPLLRFIEDLVN RHIISEYGDKYTFQFVGG DTKSATDKLNILKLETQIF KTVNEAREEQGKKPIEGG DIILDASFLQGTAQLQQD KQYNDGKQKERLQMMM SLLEGDNDDSEEGQSADS SNDDKSNPEVGTDSQIKG DSNVYRTETSNKGQGKK GEKSSDFKH | | | | | | | | |
| 162 | 80364 | 81518 | 1240 | MSVIYKDNNWIDLTNVPY LQKGDSGYRKDIPRKNW KKCLNTEVSFSYKGKKGL FYTYRKEDKGKVKVEY DKYVKIIDPHDLKTLNINK IVNPPNKAKYREQEVING DTVRNIRKVKNTGIVYTM LCSEYEEEYDIRESDLLRG RGSPYKSGRKVCYNNSLY SVENLREYICDLEYAKTV TKFSHKDIKCKCPICSEEK VMKVNKLVNNGFSCHRC SSTITYPERLMIGLLELNN LNYEYQKVFKDLPNRKFD FYLPKLNMVIETHGLQHY RELNGYMNHEKTKESDL | 384 | conserved phage protein [Staphylococcus phage CNPH82] | YP_950629.1 | 6e-53 (133/332) | | No putative conserved domains have been detected | | |

FIG. 14RR

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | EKYNYCKNNNIDYIEIDCSYSDLSFILSNVENSKLNSILKNKNYDNLSNYTIRSKNDDVKYNIYLDYCKGLSKKELKDKYNKTSYYINRSIEIFKH | | | | | | | | |
| 163 | 81712 | 82485 | 1241 | LEEIKFNAFVPMDLKKSVSTASDTNEYSIVSGWASTPSMDLQNDIVNPKGIDIEYFKSQGYINYEHQSDKVVGIPTENCYVDIEKGLFIEAKLWKNDENVVKMLDLAEKLEKSGSGRRLGFSIEGAVKKRNINDNRVIDEVMTGVALVKNPANPEATWESFMKSFLTGHGTSPDTQVDAGALRKEEIASSITNLAYVTKIKDLKEFNDVWNGVVEDLSKSNSMGYEESVLTLQLAKGLSRKDAELAVMDINKQKLE | 257 | hypothetical protein KgORF42 [Staphylococcus phage K] | YP_024472.1 | 1e-146 (256/257) | Prohead protease | Peptidase_U35 | pfam04586 | 8.72e-05 |
| 164 | 82504 | 83460 | 1242 | MSKEMQNILEEYDKLNAQEAVSKSVEDDEKNTVESTEEQVAETTEEPAKEPEKVSEEDAKEAQEQGEKVESEEVAEDNEDEEVEKSAKESKDPVDQKDTKTENKDNEKRKNKKDKKEDSDSDDEDKDTDDDKDKKEDKKEKTSKSISDEDITTVFKSILTSFENLNKEKENFATKEDLSEVSKSINELSAKISEIQAEDVSKSVDTDEEAVEKSVTSTNGEQEKVEGYVSKSVD | 318 | ORF029 [Staphylococcus phage G1] | YP_240902.1 | 9e-170 (317/318) | | No putative conserved domains have been detected | | |

FIG. 14SS

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | TEEQAETGEAKSEEAEEV QEDNTFKGLSQEERTKFM DSYKAQAKDPRASKHDL QSAYQSYLNINTDPTNAS EKDIKTVKDFAQI | | | | | | | | |
| 165 | 83576 | 84967 | 1243 | MTIEKNLSDVQQKYADQF QEDVVKSFQTGYGITPDT QIDAGALRREILDDQITML TWTNEDLIFYRDISRRPAQ STVVKYDQYLRHGNVGH SRFVKEIGVAPVSDPNIRQ KTVSMKYVSDTKNMSIAS GLVNNIADPSQILTEDAIA VVAKTIEWASFYGDASLT SEVEGEGLEFDGLAKLID KNNVINAKGNQLTEKHL NEAAVRIGKGFGTATDAY MPIGVHADFVNSILGRQM QLMQDNSGNVNTGYSVN GFYSSRGFIKLHGSTVME NELILDESLQPLPNAPQPA KVTATVETKQKGAFENEE DRAGLSYKVVVNSDDAQ SAPSEEVTATVSNVDDGV KLSISVNAMYQQQPQFVS IYRQGKETGMYFLIKRVP VKDAQEDGTIVFVDKNET LPETADVFVGEMSPQVVH LFELLPMMKLPLAQINASI TFAVLWYGALALRAPKK WARIKNVRYIAV | 463 | putative capsid protein [Staphylococcus phage K] | YP_024474.1 | 0,0 (462/463) | Capsid protein | No putative conserved domains have been detected | | |
| 166 | 85059 | 85355 | 1244 | MLYYKKLLDKKMATVY GTVEIDKDGVVKGLTKEQ EKEFANVPGFEFEEKKT | 98 | ORF151 [Staphylococcus phage] | YP_240904.1 | 9e-46 | | No putative conserved domains | | |

FIG. 14TT

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | TRKQSASTSKEEPKEEEK KASTRKTTSTTRKSTARK TTAKKDENK | | G] | | (97/98) | | have been detected | | |
| 167 | 85368 | 86276 | 1245 | MVNSMFGGDLDPYEKSL NYEYPYHPSGNPKHIDVS EIDNLTLADYGWSPDAVK AYMFGIIVQNPDTGQPMG DEFYNHILERAVGKAERA LDISILPDTQHEMRDYHET EFNSYMFVHAYRKPILQV ENLQLQFNGRPIYKYPAN WWKVEHLAGHVQLFPTA LMQTGQSMSYDAVFNGY PQLAGVYPPSGATFAPQM IRLEYVSGMLPRKKAGRN KPWEMPPELEQLVIKYAL KEIYQVWGNLIIGAGIAN KILEVDGITETIGTTQSAM YGGASAQILQINEDIKELL DGLRAYFGYNMIGL | 302 | hypothetical protein KgORF45 [Staphylococcus phage KJ | YP_024475.1 | 3e-117 (301/302) | | No putative conserved domains have been detected | | |
| 168 | 86290 | 87168 | 1246 | MEKPYMIGANSNPNVINK STTYTTTTQADEQDKPKY TTRLEFDTIDMIRFINDRGI KVLWEEAYFCPCLNPDTG HPRVDCPRCHGKGIAYLP PKETIMAIQSQEKGTNQL DIGILDTGTAIGTTQLEKRI SYRDRIFTVPEVLMPQQMI YFVNKDRIKKGIPLYYDV KEVTYIATQDGTVYEEDY EIKNNRLYLNEKYENHTV TLKILMTLRYVVSDILKES RYQYTKFNQPKSKFENLP QKLLLKREDVIVLQDPYK | 292 | capsid protein [Staphylococcus phage 812] | ABL87113.1 | 1e-170 (291/292) | Capsid protein | No putative conserved domains have been detected | | |

FIG. 14UU

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | VNDGIEFDLEIQVDDPKA SASNPSNLGGFFGGAFK | | | | | | | | |
| 169 | 87168 | 87788 | 1247 | MPVHGKRPNLFKNKNYK QVGKRTIDGMRSEVLDKL QATAQQVENTSIKRMPTY LQITEKKLEKEGVVDLKK AFAHSSKKKTSKDGGWY LTVPIRJKTSRMNNSTYQD MRTLKVDKGTGSVSKITD YLEGRRKNVSHPSMKPEP MTHNMTKVKRGKQSSYF IFRTVSSKSPASSWILNRD KVNEDNFSKTTLKTVKQL MNWKMKNLN | 206 | hypothetical protein KgORF47 [Staphylococcus phage K] | YP_024477.1 | 1e-116 (206/206) | | No putative conserved domains have been detected | | |
| 170 | 87807 | 88643 | 1248 | MAITSVDSYLLSEIKPRLN TVLENCYIIDEVLKDFDY QTRESFKEAFCGKNAQHE VTVGFNFPKFKNNYEAHY LIQLGQGQETKNSLGSIQS SYFEATGDTLVESSTAIRE DDKLVFTVSKPIGELIKVE DIEFAKYDNLQVEGNKVS FKYQTNEDYENYNANIIF TEKKNDSKGLVKGFTVEE QVTVVGLSFNVDVARCL DAVLKMILISMRDSIEEQQ TFQLQNLSFGDIAPIIEDG DSMIFGRPTIKYTSSLDLD YTITQDINKLTFKERKDW K | 278 | hypothetical protein KgORF48 [Staphylococcus phage K] | YP_024478.1 | 4e-160 (278/278) | | Crotono-betainyl-CoA:carniti ne CoA-transferase | PRK03 525 | 8.14e-03 |
| 171 | 88645 | 88860 | 1249 | MARKKTPENNTPKFNGY VHIDTFLDTAKTLFNMKD | 71 | ORF202 [Staphylococcus phage] | YP_240909.1 | 2e-34 | | No putative conserved domains | | |

FIG. 14VV

Table 11 - Features of phage F 125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | SQVAGFKAYMEGSHYLFS EQEFLPSLEKYLGRKLDI | | G1] | | (70/71) | | have been detected | | |
| 172 | 88887 | 90650 | 1250 | MAVEPFPRRPITRPHASIE VDTSGIGGSAGSSEKVFCL IGQAEGGEPNTVYELRNY AQAKRLFRSGELLDAIEL AWGSNPNYTAGKILAMRI EDAKPASAEIGGLKVTSKI YGNVANNIQVGLEKNTLS DSLRLRVIFQDDRFNEVY DNIGNFTIKYKGEEANAT FSVEHDEETQKASRLVLK VGDQEVKSYDLTGGAYD YTNAIITDINQLPDFEAKL SPFGDKNLESSKLDKIENA NIKDKAVYVKAVFGDLE KQTAYNGIVSFEQLNAEG EVPSNVEVEAGEESATVT ATSPIKTIEPFELTKLTGGT NGEPPATWADKLDKFAH EGGYYIVPLSSKQSVHAE VASFVKERSDAGEPMRAI VGGGFNESKEQLFGRQAS LSNPRVSLVANSGTFVMD DGRKNHVPAYMVAVALG GLASGLEIGESITFKPLRVS SLDQIYESIDLDELNENGII SIEFVRNRTNTFFRIVDDV TTFNDKSDPVKAEMAVG EANDFLVSELKVQLEDQF IGTRTINTSASIIKDFIQSYL GRKKRDNEIQDFPAEDVQ VIVEGNEARISMTVYPIRS FKKISVSLVYKQQTLQA | 587 | major tail sheath protein [Staphylococcus phage 812] | ABL87117.1 | 0,0 (584/587) | Major tail sheath protein | Phage_ sheath_1 | pfam04 984 | 2.11e-07 |

FIG. 14WW

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| 173 | 90723 | 91127 | 1251 | MASEAKQTVHTGNTVLL MIKGKPVGRAQSASGQRE YGITGVYEIGSIMPQEHV YLRYEGTITVERLRMKKE NFADLGYASLGEEILKKDI IDILVVDNLTKQVIISYHG CSANNYNETWQTNEIVTE EIEFSYL | 134 | capsid protein [Staphylococcus phage 812] | ABL87118.1 | 3e-73 (134/134) | Capsid protein | No putative conserved domains have been detected | | |
| 174 | 91547 | 92476 | 1252 | MGKNQYTFNIKENKNKW YEWCKLQNVKPLVEYEN AQQIFYFFLEGKFKGLIG KTYWASINRGSNMRMSC LTSESKDKYLKNLGKRKG IEVVEDYKGGRKLKHKFI VLEGKYQGCEGYITLNDL ENLGRVDNRSLSEKGRKQ YFDKQARLRDCIILEYPKD YRIKTKDKIVVKDKEGHV HNIIVQDFFEKSSLLELSC ASEGEKIVKEILTKNSIKFE KEKSFRNKEGKVQRFDFY INENNKEYAIEYNGAQHY IDSTGYLKDILETTQKRD KLKKEYSKDKGINLLIIPY TITDKKEMEKIILNFLNK | 309 | ORF018 [Staphylococcus phage Twort] | YP_238556.1 | 2e-19 (79/239) | | No putative conserved domains have been detected | | |
| 175 | 92534 | 92692 | 1253 | MNNRQAKIKGYNQFHYY DFPTTKGKFKDIMKRKSR TELKKDLQKERKYYLDK | 52 | ORF245 [Staphylococcus phage Twort] | YP_238558.1 | 5e-11 (36/52) | | No putative conserved domains have been detected | | |
| 176 | 92682 | 92822 | 1254 | LTNKRKTIGKMSNTRAT WNINPVTKVKDKTKYS RKNKHKGLDNYN | 46 | ORF293 [Staphylococcus phage G1] | YP_240912.1 | 1e-10 (44/46) | | No putative conserved domains have been detected | | |

FIG. 14XX

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 177 | 92864 | 93322 | 1255 | MSTFWSERRTTNKDRQV KKHYTQMSMYERKKCVE LLQETITENRIINFTRHSAK KVKGKPTTNIPKLIGFIFK NKFAYENIIEYNNTDYNG NIERRIVVKHPKVITVEGK PSYQFLTISLEDARVITVW YNSVDDTHRTLDLNYYS KDLTIQ | 152 | hypothetical protein KgORF51 [Staphylococcus phage K] | YP_024481.1 | 2e-84 (152/152) | | PHA02264, hypothetical protein | PHA02 264 | 1.25e-30 |
| 178 | 93335 | 93526 | 1256 | MGITIVNSYFILSNIFLIILTI LNGKGTVTRESLTMSKIL VVITSIQFLACLINGIYWS LKF | 63 | ORF215 [Staphylococcus phage G1] | YP_240914.1 | 3e-25 (62/63) | | No putative conserved domains have been detected | | |
| 179 | 93599 | 93910 | 1257 | MSQDKLRAIYTEMKVEL HKFPKEVDITSKSTAIAIN QILDKFKTLTEQAGKITRK YLEGQEILTIDYEYYDSLQ EYYIYLLRNSEKIEQSLQEI TKRTGEYVK | 103 | hypothetical protein KgORF52 [Staphylococcus phage K] | YP_024482.1 | 3e-51 (103/103) | | PHA02265, hypothetical protein | PHA02 265 | 2.50e-17 |
| 180 | 94042 | 94500 | 1258 | MAEEIKKEQDVQETTKEE KKDVSKMTPEEIDKLKYQ DKQEKEQVINKVIKGVND TWEKEYNFEELDLRFKVK IKLPNAREQGNIFALRSAY LGGMDMYQTDQVIRAYQ MLATLQEVGIEVPKEFQD PDDIYNLYPLTVMYEDWL GFLNSFRY | 152 | hypothetical protein KgORF53 [Staphylococcus phage K] | YP_024483.1 | 2e-82 (152/152) | | No putative conserved domains have been detected | | |
| 181 | 94544 | 95080 | 1259 | MESIVKQPLSRNLWAIMK EFNVLPTEQRFKDLDDYQ IEFIIGNMNRDVYEHNKQ | 178 | gp ORF080 [Staphylococcus phage] | ACB89073.1 | 1e-98 (178/178) | | No putative conserved domains have been detected | | |

FIG. 14YY

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | LKQAQKGGKFDSQFEDD DSSWWNESHEDFDPVPDF LDADDLAQQVEAKLSDR DKEERAKRNDAELNDETE GLTTQHLAMMEYIRQKQ QELDDEVGNGKTSEEDAT ISQDSVNKALEDLDDDW YM A5W] | | | | | | | | |
| 182 | 95136 | 99191 | 1260 | MAMNDDYRLVLSGDSSD LENSLKAIELYMDSLESK NIDAPLDNFLKKLKVIAK EVKNVQNAMDKQDGKS VISSKDMDESIKSTQSATK NINELKKALDDLQKENIS KGIAPDPEVEKAYAKMG KVVDETQEKLEKMSSQKI GSDASIQNRIKEMKTLNQ VTEEYNKISKDSSATKDY TKRLRANRNMTRGYMER SEGTGRLTYDQGARVRSE LGKISSYESQRKQNQRNL GQARFQYSNYRNQQQDL TKRRASGQINKAQYEQEL ASIKQEMKAREELISNYE KLGAELDKTVQYYKGSV QKDFQSRDVDQQRGTFG RMVQERLPSIGSHAMMG TTAMATGLYMKGASLSE TNRPMVTSLGQNSDNMDI DSVRNAYGDLSIDNKLGY NSTDMLKMATSYEASVG HKSDEDTMAGTKQLAIG GRSLGIRDQEAYQESMGQ IMHTGGVNSDNMKEMQD AFLGGIKQSGMVGRQDE | 1351 | ORF001 [Staphylococcus phage G1] | YP_240918.1 | 0,0 (1348/1351) | | COG4372, un- characterized protein conserved in bacteria with the myosin-like domain | COG43 72 | 9,12e-03 |

FIG. 14ZZ

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name [organism] | Acc No | E value and identity | | Name | Acc No | E value |
| 183 | 99270 | 101696 | 1261 | MRRIRRPKVRIEIVTDDNT FTLREEDTRDYNGDEFGA KLLGFQTKNSMEDDSSVF QLKALGSIAEQSGEGRTL TKDQMSNLTAMQSTFAES GSKGLQGEQGANAINSID QGLKNGMNSSYARIAMG WGTQYQGLEGGYDLQKR MDEGISNPENLTDMADM ATQMGGSEKEQKYLFNR SMKEIGANLTMEQSDEIF KDAQSGKLSKEELAKKA KKMEKEGKKEGEDNATD YKESKSGKNDQNKSKTD DKAEDTYDMAQPLRDAH SALAGLPAPIYLAIGAIGA FTASLIASASQFGAGHLIG KGAKGLRNKFGRNKGGS SGGNPMAGGMPSGGGSP KGGGSPKGGGTRSTGGKI LDSAKGLGGFLVGGAGW KGMFGGESKGKGFKQTS KEAWSGTRKVFNRDNGR KAMDKSKDIAKGTGSGL KDIYNDSIFGKERRQNLG EKAKGFGGKAKGLYGKF ADKFGDGGKNGILSQSPK AGGSGIGKLGKLAGGLGK GAGVLGVATSALSLIPAL ASGDSKAIGGGIGSMGGG MAGASAGASIGALFGGV GAIPGALIGGAIGSFGGGA VGEKVGDMAKKANTKEG WNLGWTNGDKDGKNKF QDSLLGKPI | 808 | hypothetical protein KgORF56 [Staphylococcus phage] | YP_024486.1 | 0,0 (806/808) | Tail lysin | CHAP domain | pfam05257 | 1,02e-14 |

FIG. 14AAA

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | QINMAGDTYWDKLVMA NDIIRIFITPNDDPNDKEGR QERLIQVGMVSQVSKVGS YGNDQTQFRITGQSFVKP FMKFGLGVIQEVQAVLPE VGWLIDGDGDNEVKFTG SSAHEVMTGIIRRFIPYMK YNYTEKTYNTIDNYLDYD DLSSWDEFEKLTEVSAFT NFDGSLKQLMDMVTARP FNELFFKNSEKTPGKAQL VLRKTPFNPTEWRALDMI KVPTEDFIEEDVGKSDYE TYSIFTATPAGMLKELNG DVFSKPQFHPELTDRYGY TKFEVENIYLSTKSGSATE DSDSSGDDNGTERGTYSK IMKDLSNYGRDNISKGID KYTSKLSSKYKNLKKAQ AKKIIEKFVKEGKVTEKE YEKITGNKVDDELTSDNR PKLTKDKLKSILKEKFKT QDDFNNSKKKKKAKTDA LKELTTKYRFGNKTHATT LLDEYIKYKGEPPNDEAF DKYLKAIEGVSNVATDTG SDASDSPLVMFSRMLFNW YHGNPNFYAGDIIVLGDP KYDLGKRLFIEDKQRGDT WEFYIESVEHKFDYKQGY YTTVGVTRGLKDAILEDG KGSPHRFAGLWNQSSDF MGGLMGEDTSKELKEKG VAEKQSSGGKDGGSDSG GAQDGGSLDSLKKYNGK LPKHDPSFVQPGNRHYKY | K] | | | | | | | |

FIG. 14BBB

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name [organism] | Acc No | E value and identity | Predicted function | Name | Acc No | E value |
| | | | | QCTWYAYNRRGQLGIPVP LWGDAADWIGGAKGAG YGVGRTPKQGACVIWQR GVQGGSPQYGHVAFVEK VLDGGKKJFISEHNYATPN GYGTRTIDMSSAIGKNAQ FIYDKK | | | | | | | | |
| 184 | 101710 | 102597 | 1262 | MATDKEAKDVIDKFIDNV FNFDVLTKERIKEKDEEIK KITTDDMYEKVVYIRPYV GVIQSLNPQHVQYESFSN NGYDIEAELSFRKVSYLV DKGSIPTDSLSTLTVHLVE RNQELLIDYFDEIQDVLY GEYMEEEYVFDEDVPLST ILALDLNDNLKSLSNIKY MFKGAPKENPFGTDKDV YIDTYNLLYWLYLGEDEE LAYPMNINYFFTEGRFFTI FGKGHKYKVDVSKFIVGD ILFFGRSDTNIGIYVGDGE FISMMGKFPKDETPIGKY KLDDYWNEFNGRVMRFD EEVYI | 295 | hypothetical protein KgORF57 [Staphylococcus phage K] | YP_024487.1 | 4e-167 (295/295) | | No putative conserved domains have been detected | | |
| 185 | 102597 | 105143 | 1263 | MVVRFQSSMGRSLKRVD SDDLNVKGLVLATVSKIN YKYQSVEVKVNNLTLGS RIGDDGSLAVPYPKSFIGR TPEGSVFGTKPLITEGSVV LIGFLNDDINSPIILSVYGD NEQNKMNTNPLDGGKFD TESVYKYSSSLYEILPSLN YKYDDGFGTSIRTYNGKS FFSMTSGEEEKPQATDFY | 848 | putative glycerophosphoryl diester phosphodiesterase [Staphylococcus phage K] | YP_024488.1 | 0.0 (845/848) | Glycero-phosphoryl diester phospho-diesterase | GDPD_SaGlpQ_like, glycero-phospho-diester phospho-diesterase domain | cd08601 | 1.43e-60 |

FIG. 14CCC

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | TGTEYQDLFTSYYGNKTL IEPRIQKAPNMLFKHQGV FYDDGTPDNHITTLFISER GDIRASVLNTETQKRTTQ EMSSDGSYRVIKQDDDL MLDEAQVWIEYGISEDNK FYIKNDKHKFEFTDEGIYI DDKPMLENLDESIAEAMK NLNEIQKELDDINYLLEG VGKDNLEELIESTKESIEA SKKATSDVNRLTTQIAEV SGRTEGIITQFQKFRDETF KDFYEDASTVINEVNQNF PTMKTDVKTLKTKVDNL EKTEIPNIKTRLTELENN NNADKIISDRGEHIGAMIQ LEENVTVPMRKYMPIPWS KVTYNNAEFWDSNNPTR LVVPKGITKVRVAGNVL WDSNATGQRMLRILKNG TYSIGLPYTRDVAISTAPQ NGTSGVIPVKEGDYFEFE AFQDSEGDRQFRADPYT WFSIEAIELETETMEKDFM LIGHRGATGYTDEHTIKG YQMALDKGADYIELDLQ LTKDNKLLCMHDSTIDRT TTGTGKVGDMTLSYIQTN FTSLNGEPIPSLDDVLNHF GTKVKYYIETKRPFDANM DKELLTQLKAKGLIGIGSE REQVIIQSFARESLINIHNQ FSNIPLAYLTSTFSESEMD DCLSYGSYAIAPKYTTITK ELVDLAHSKGLKVHAWT VNTKEEMQSLIQMGVDG | | | | | | | | |

FIG. 14DDD

Table 11 - Features of phage F125/10 gene products and assignment of putative functions.

| orf | Start position | Stop position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | FFTNVLDEYKKI | | | | | | | | |
| 186 | 105250 | 106041 | 1264 | MPQSDGISNLHRIALRFPK EGGGYDMYRFKVNPENY TIDSPQRTTAIKTKSDIVIE DYGKDIEVINFTGTTGFRP VREADGLKTGKQKMEEL QSRVSEYAMQGGSGNVS GSYLQFFNFTDDSYYKVH LAPQGLKITRSKDEPLLFR YEITLVVIGSLTEADRSAV TTEEFGNVKPNASQRVDE GIKELDKNARKTRDRNNQ EISRRENTIPKSTGDNTNE GNRLKQSFPSSSIYNPRQS TNGLKGNIDNMALIIGYG DGGVSS | 263 | hypothetical protein KgORF59 [Staphylococcus phage K] | YP_024489.1 | 7e-151 (263/263) | | No putative conserved domains have been detected | | |
| 187 | 106041 | 106565 | 1265 | MNNFIPQPQGLLRFLNAL DTDLTSSHMNLLDEEVSF VSKFYTPQLQLSELAKKV LTNIKTDDIPVLEREFNDN TIIHKANDTLLKVQAPRM YMILQSIVLEAYAIVNCFV ENPSSLKYLTEEDVSITRE NLNYVADYLGNYDDYNS VVLDLRDLDLCFSAIELQL PLIKKEANV | 174 | ORF078 [Staphylococcus phage G1] | YP_240925.1 | 3e-95 (174/174) | | No putative conserved domains have been detected | | |
| 188 | 106565 | 107269 | 1266 | MRFKKHVVQHEETMQAI AQRYYGDVSYWIDLVEH NNLKYPYLVETDEEKMK DPERLASTGDTLIIPIESDL TDVSAKEINSRDKDVLVE LALGRDLNITADEKYFNE | 234 | putative bacteriophage baseplate protein [Staphylococcus phage K] | YP_024491.1 | 2e-134 (234/234) | Baseplate protein | COG3628, phage baseplate assembly protein W | COG36 28 | 1.50e-03 |

FIG. 14EEE

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | HGTSDNILAFSTNGNGDL DTVKGIDNMKQQLQARL LTPRGSLMLFIPNYGSDLH NLFGLNIPEQATLIEMEVL RTLTSDNRVKSANLIDWK IQGNVYSGQFSVEIKSVEE SINFVLGQDEFGIFALFE | | | | | | | | |
| 189 | 107284 | 108330 | 1267 | MKTRKLTNILSKLIDKTM AGTSKITDFTPGSASRSLL EAVSLEIEQFYILTKENID WGIQEGIIEAFDFQKRQSK RAYGDVTIQFYQPLDMR MYIPAGTTFTSTRQEYPQ QFETLVDYYAEPDSTEIV VEVYCKETGVAGNVPEG TINTIASGSSLIRSVNNEYS FNTGTKEESQEDFKRRFH SFVESRGRATNKSVRYGA LQIPDVEGVYVYEETGHIT VFAHDRNGNLSDTLKEDII DALQDYRPSGIMLDVTGV EKEEVNVSATVTISNKSRI GDTLQKHIESVIRSYLNNL KTSDDLIITDLIQAIMNIDD VLIYDVSFDNLDENIIVPP QGIIRAGEIKVELK | 348 | hypothetical protein KgORF62 [Staphylococcus phage K] | YP_024492.1 | 0.0 (348/348) | | XtdT, uncharacterized homolog of phage Mu protein gp47 | COG3299 | 2,38e-05 |
| 190 | 108351 | 111410 | 1268 | VANFLKNLHPLLRRDRNK KDNQDPNFALIDALNEEM NQVEKDAIESKLQSSLKTS TSEYLDKFGDWFGVYRK TDENDDVYRARIIKYLLL KRGTNNAIIDAIKDYLGR DDIDVSVYEPFTNIFYTNK SHLNGEDHLMGYYYRFA | 1019 | hypothetical protein KgORF63 [Staphylococcus phage K] | YP_024493.1 | 0.0 (1006/1019) | | No putative conserved domains have been detected | | |

FIG. 14FFF

Table 11 - Features of phage F125/10 gene products and assignment of putative functions.

| orf | Start position | Stop position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | VINVSIGDYFPVEIIDVINE FKPAGVTLYVTYDGASTI RGGAIIKWLDGLPKIETYQ EEFDRFTGYDDTFYGHDNM NQSKDTDNSSSDIFKTNHS LINSLDVLTGSSSVGRQYI NYGYVTSYVYNPGMTSS VNQISASTEGRGQEVPTD YYMYTSTKNNNTVELSM QTSGVSYLYNNFNFRDY MSKYRPQVDLQSDEARRI VSDYIKELSIDYYLSAVIPP DESIEIKLQVYDFSINRWL TVSINNLSFYEKNIGSNIG YIKDYLNSELNMFTRLEIN AGKRDSVDIKVNYLDLM FYYYERGIYTIKPYKALIE NYLDISRETYVEAFKIASL SNGDIITKTGFQPIGYLKL VGNYENTRPSTINIVAKDT DNNPIESSNELDVYNTVEN RNLLQSYKGANTIAREITS TKEFTVSGWAKEIYSTNY LSKVLKPGKVYTLSFDIEI TGNDLTLKSYSDNHGIYL YSNTKGIVVNGVKSMERT IGNKVSVTQTFTAPTITDH RLLIYTGRYTSDGKASTPP VFFNTVKITELKLSEGTSN LEYSPAPEDKPNVIEKGIK FNNILTNIQTLSINSDTILK NVTLYYSYYGDNWVELK TLGNISTGETTETNNLIDL YGLQTVDYSNINPMSKVS LRSIWNVKLGELNNQEGS LSNMPNDYFNAVWQDID | | | | | | | |

FIG. 14GGG

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | KLSDIEIGSMRMVKDTEG GVFDGATGEIIKATLFNV GSYTDLDMLAYTLTNYTE PLTLGSSRLISELKEELLTS ESFNVDNRIKVIDSIYEELP NTSIIKNGFVEREVTGSKY LDYGLYEPIEDGTRYKLIV EGEFKDNIEFIYLYNSNPN FNETFIYPSEIINGVAEKEF IAKPSTEDKPRLNTDVRIY IRPYDSTISKVRRVELRKV | | | | | | | | |
| 191 | 111521 | 112042 | 1269 | MAIATYNSHVELAKYLVS KADSVYLTIGKSTPWSNE TNPPQPDENATVLQEVIG YKKATKVTLVRPSKSPED DNKNLISYGNKSWVEVTP ENAKAEGAKWVYLESSIV GDELPLGTYRQVGFVMD LVAKSGISKFNLVPSEVES TGTLLFFDNKQFQNRSEQ TTAKERFIVEV | 173 | hypothetical protein KgORF64 [Staphylococcus phage K] | YP_024494.1 | 6e-96 (173/173) | | Bacterio-phage T4, Gp8 | pfam09215 | 2.26e-03 |
| 192 | 112063 | 115521 | 1270 | MAINFKGSPYLDRFDPSK DRTKVLFNPDRPLQQAEL NEMQSIDQYYLKNLGDAI FKDGDKQSGLGFTLSEDN VLTVNPGYVYINGKIRYY DNDDSVKITGVGKETIGIK LTERIVTPDEDASLLDQTS GVPSYFSKGADRLEEKMS LTVNDPTSATIYTFMDGD LYIQSTNAEMDKINKVLA ERTYDESGSYKVNGFELF SEGNAEDDHVSVVVDA GKAYYKGFKVDKPVSTRI | 1152 | hypothetical protein KgORF65 [Staphylococcus phage K] | YP_024495.1 | 0,0 (1151/1152) | | No putative conserved domains have been detected | | |

FIG. 14HHHH

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | SVPKSYDLGTAENESTIFN KSNNSISLANSPVKEIRRV TGQVLIEKERVTRGAQGD GQDFLSNNTAFEIVKVWT ETSPGVTTKEYKQGEDFR LTDGQTIDWSPQGQEPSG GTSYYVSYKYNKRMEAG KDYEVTTQGEGLSKKWYI NFTPSNGAKPIDQTVVLV DYTYYLARKDSVFINKYG DIAILPGEPNIMRLVTPPL NTDPENLQLGTVTVLPDS DEAVCISFAITRLSMEDLQ KVKTRVDNLEYNQAVNA LDDGAMEGQNPLTLRSVF SEGFISLDKADITHPDFGIV FSFEDAEATLAYTEAVNQ PKIIPGDTTAHIWGRLISAP FTEERTTYQGQASETLNV NPYNIPNKQGVLKLTPSE DNWIDTENVTITEQKTKK VTMKRFWRHNESYYGET EHYLYSNLQLDAGQKWK GETYAYDREHGRTGTLLE SGGQRTLEEMIEFIRIRDV SFEVKGLNPNDNNLYLLF DGVRCAITPATGYRKGSE DGTIMTDAKGTAKGKFTI PAGIRCGNREVTLKNANS TSATTYTAQGRKKTVQDI IIRTRVTVNLVDPLAQSFQ YDENRTISSLGLYFASKG DKQSNVVIQIRGMGDQG YPNKTIYAETVMNADDIK VSNNASAETRVYFDDPM MAEGGKEYAIVIITENSDY | | | | | | | | |

FIG. 14III

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | TMWVGTRTKPKIDKPNE VISGNPYLQGVLFSSSNAS TWTPHQNSDLKFGIYTSK FNETATIEFEPIKDVSADRI VLMSTYLTPERTGCTWE MKLILDDMASSTTFDQLK WEPIGNYQDLDVLGLAR QVKLRATFES | | | | | | | | |
| 193 | 115570 | 115728 | 1271 | MPREVRDPYSQAKLFIPT VEEKSIKELEKTYKEKIDE ATKLINELKKERGEK | 52 | ORF262 [Staphylococcus phage G1] | YP_240931.1 | 3e-20 (52/52) | | No putative conserved domains have been detected | | |
| 194 | 115729 | 117651 | 1272 | MAFNYTPLTETQKLKDM YPKVNDIGNFLKTEVNLS DVKQISQPDFNNILASIPD SGNYVVTNSKGAPSGEAT AGFVRLDKRNVNYYKIY YSPYSSNKMYIKTYANGT VYDWISFKLDEGNLYNEG NTLNVKELTESTTQYATL VNPPKENLNTGWVNYKE SKNGVSSLVEFNPVNSTST FKMIRKLPVQEQKPNLLK DSLFVYPETSYSNIKTDN WDTPPFWGYSSNSGRSGV RFRGENTVQIDDGSNTYP LVVSNRFKMGKELSVGD TVTVSVYAKINDPALLKD NLVYFELAGYDTVDDTSK NPYTGGRREITASEITTEW KKYSFTFTIPENTIGASGV KVNYVSLLLRMNCSSSKG NGAVVYYALPKLEKSPK VTPFITHENDVRKYDEIW SNWQEVISKDELKGHSPV | 640 | hypothetical protein KgORF66 [Staphylococcus phage K] | YP_024496.1 | 0,0 (633/640) | | PHA01818, hypothetical protein | PHA01818 | 5,89e-04 |

FIG. 14JJJ

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | DIEYNDYFKYQWWKSEV NEKSLKDLAMTVPQGYH TFYCQGSIAGTPKGRSIRG TIQVDYDKGDPYRANKFV KLLFTDTEGIPYTLYYGG YNQGWKLLKQSETSTLL WEGTLDFGSTEAVNLNDS LDNYDLIEVTYWTRSAGH FSTKRLDIKNTSNLLYIRD FNISNDSTGSSVDFFEGYC TFPTRASVQPGMVKSITL DGSTNTTKVASWNEKERI KVYNIMGINRG | | | | | | | | |
| 195 | 117673 | 118044 | 1273 | MAVKYDIGNNFIVLHLRE GKYITGFTTVGGYDKELG QVKVNREILPAYFFDNFA YERYLYYSKPEEVIENKN YVPPQINDDEESQQITVPK EQYDSLKEELELMRKQQE AMMEMLQKLLGQKG | 123 | hypothetical protein KgORF67 [Staphylococcus phage K] | YP_024497.1 | 2e-63 (123/124) | | DUF2977, protein of unknown function | pfam11192 | 2.73e-12 |
| 196 | 118051 | 119427 | 1274 | MALNFTTITENNVIRDLTT QVNNIGEELTKERNIFDIT DDLVYNFNKSQKIKLTDD KGLTKSYGNITALRDIKEP GYYYIGARTLATLLDRPD MESLDVVLHVVPLDTSSK VVQHLYTLSTNNNQIKML YRFVSGNSSSEWQFIQGLP SNKNAVISGTNILDIASPG VYFVMGMTGGMPSGVSS GFLDLSVDANDNRLARLT DAETGKEYTSIKPTGTY TSWKKEFEPKDMEKYLLS SIRDDGSASFPLLVYTSDN | 458 | hypothetical protein KgORF68 [Staphylococcus phage K] | YP_024498.1 | 0,0 (448/458) | | PHA01818, hypothetical protein | PHA01818 | 0.0e-00 |

FIG. 14KKK

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | KTFQQAIIDHDRTGQTTF TFYVQGGVSGSPMSNSCR GLFMSDTPNTSSLHGVYN AIGTDGRNVTGSVVGGN WTSPKTSPSHKELWTGAQ SFLSVGTTKNLADDISNYS YVEVYTKHKTVEKTKGN DDSGTICHKFYLDGSGTY VCSGTFVSGDRTDTKPPV TEFYRVGVSFKGSTWTLV DSAVQNSKTQYVTRIIGIN MP | | | | | | | |
| 197 | 119517 | 121265 | 1275 | MRLRIKNLYTYVEFEEDD KYLKDIFLKRVHTTIGAR QEGFQYSPAYKRGSWDG YVDFYVYEEDKFPTGLLF KIELLGELQSRYNFQFET IDERDESFLSEEDIDDEITL LDNNVGQITLRDYQYEAV YNSLTFYNGIAHLATNGG KTEVASGIIDQLLPQLEKG ERVAFFTGSTEIFHQSADR LQERLNIPIGKVGAGKFD VKQVTVVMIPTLNANLK DPTQGVKVTPKQNISKKI AQEILPKFEGGTNQKKLL KVLLDNTTPKTKVEQNVL SALEIIYQNSKTDAEVLLN LRNHNAHFQKIVREKNEK KYDKYQDMRDFLDSVTV MIVDEAHHSKSDSWYNN LMTCEKALYRIALTGSID KKDELLWMRLQALFGNV IARTTNKFLIDEGHSARPTI NIIPIANPNDIDRIDDYREA | 582 | putative helicase [Staphylococcus phage K] | YP_024499.1 | 0,0 (580/582) | Helicase | HELICc, helicase superfamily c-terminal domain | cd00079 | 1,74e-13 |

FIG. 14LLL

Table 11 - Features of phage F125/10 gene products and assignment of putative functions.

| orf | Start positi on | Stop Positi on | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | YDRGITNNDFRNKLIAKL TEKWYNQDKGTLIIVNFIE HGDTISEMLNDLDVEHYF LHGEIDSETRREKLNDMR SGKLKVMIATSLIDEGVDI SGINALILGAGGKSLRQTL QRIGRALRKKKDDNTTQI FDFNDMTNRFLYTHANER RKIYEEEDFEIKDLGK | | | | | | | |
| 198 | 12127 7 | 12289 0 | 1276 | MATKTQRKLYQYLEENA TENKFHISTKKELADSLG VSISALSNNLKKLEEENK VVTVSKRGKNGGVIITLV REYDTEELKEFNNSTDNII TSDLQYAKALREKHFPSY RYERKEQRRRTKIEMAQY NAIKDEKRRIIADMNFYSE GLPYPSKDIFNMSYDPEGF YKAYILCKLYDQYAISHM DAKHTSHLKAMSKATTK DEYDYHQHMSEYYRNK MIQNLPRNSVSDNFFGSK MFNTFYNFYLKIKDKNIN VFKYMQNVFKNVTFYYE NGMQPNPIPSPNFFSSDKY FKNYNNYIKGIKKGVNST NRHLGDTDSIINSSDYVK NPAVLHLHQLYTTGLNST LHDIDTMFEQALDLENAS YGLFGDMKHILLQYNSM IEEEIKNLPREEKDIINKYV KQCIINDYSPTSISPSARLS MFTMQKEHIVYNKQLNK GIKREDLLPLSLGGIVNKD SLSGMDIQNLEQNGNEYL | 357 | putative Rep protein [Staphylococcus phage K] | YP_024500.1 | 0.0 (536/537) | Transcription regulator protein | HTH_2, Helix-turn-helix domain | pfam12 840 | 2.66e-03 |

FIG. 14MMM

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | YMRQHTSTYYILRMFGD YLGYEVNLREVKYIVEKY NLIDKIPLTKEGMLDYNK LIHLVEEEVNNYE | | | | | | | | |
| 199 | 12288 3 | 12432 5 | 1277 | MSKKIKELILHKSMKDIHF AREVLDNLPKNLFSAESE DMGYLFTAIKRTAHISDK MSNEALAIKVEQLMGNN KEDEEKVTKTLTYLEDLY KVDVNEKDESVNYEIEKY IKTEMSKEVLVKFIAENK QEIDSDNLHELVDKLKQIE VSDISGGNGEFIDFFEDTE KKQELLSNLATNKFSTGF TSIDNHIEGGIARGFVGLJI APTGRGKSLMASNLAKN YVKSGLSVLYIALEEKMD RMVLRAEQQMAGAEKSQ IVNQDMSLNNKVYDAIQN HYQKNRKLLGDFYISKH MPGEVTPNQLEQIIVNTTI KKDKNIDVVIIDYPHLMR NPYAKYHSESDAGGKLFE DIRRLSQQYGFVCWTLAQ TNRGAYGSDVITSEHVEG SRKIVNAVEVSLAVNQKD EEFKSGFLRLYLDKIRNSS NTGERFVNLKVEPTKMIV RDETPEEKQEHIQLLSDN GKEDTSKFQNKDNKIEAI NNTFGGLPGV | 480 | putative helicase [Staphylococcus phage K] | YP_024501.1 | 0,0 (480/480) | Helicase | 41 helicase | PHA02 542 | 1,01e-9 |
| 200 | 12440 | 12542 | 1278 | MKFVFFTDSHFHLFTNYA KPDNEFVNDRFKEQIEAL QKVFDIAKKEEATVIFGG | 341 | putative exonuclease [Staphylococcus phage] | YP_024502.1 | 2e-172 | Exonuclease | MPP_Mre11 _N_Mre11 nuclease, N- | cd00084 | 1,01e- |

FIG. 14NNN

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name [organism] | Acc No | E value and identity | Predicted function | Name | Acc No | E value |
| | 4 | 9 | | DLFHKRNSVDTRVYNKV FSTFAKNDEVPVLLLRGN HDATTNSLYTDSSIDTFEY LPNVSVIKSLNTILKDNVN IVFTAYGDETKEIKTYINS NYDKDMVNILVGHLGVE GSLTGKGSHRLEGAFGYQ DLLPDKYDFILLGHYHRR QYFQNPNHFYGGSLMQQ SFSDEQEANGVHLIDTEK MTTEFIPHTRRFITIQGEDI PENFEQLIEEGNFIRVIGTA NHAKVLEMDDSMKDKN VEVQIKKEYTVEKRIDSD VSDDPLTIASTYAKQYSPE SEQEILECLKEVL | | K] | | (295/345) | | terminal metallo-phosphatase domain | 0 | 20 |
| 201 | 125429 | 125806 | 1279 | MKKYREYLNKTDAENLA EDWEKVTEDLWKVFKD MKPKINTLDISNVESKNL DKSKPILQFQDSDGVIENI CNVEGLEDGLSKMKKVF DDSNFEKHYYSRVVDHD EYYWIDYGSHHCFFRVTK GDK | 125 | hypothetical protein KgORF73 [Staphylococcus phage K] | YP_0245031.1 | 7e-65 (121/125) | | PHA02275, hypothetical protein | PHA02 275 | 1,65e-21 |
| 202 | 125806 | 127725 | 1280 | MVVFKQVEVNNFLAIKEA TLELDNRGLILIEGENKSN ESFHSNGSGKSTLISAITY ALYGKTEKGLKADDVVN NIEKKNTSVKLKFDIGEDS YLIERYRKDKENKNKVKL FVNEKEITGSTNDVTDKQI QDLFGIEFNTYVNAIMYG QGDIPMFSQATDKGKKEI LESITKTDVYKQAQDVAK | 639 | putative exonuclease [Staphylococcus phage K] | YP_024504.1 | 0,0 (638/639) | Exonuclease | 46, endo-nuclease subunit | PHA02 562 | 1,71e-21 |

FIG. 14OOO

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | EKVKVEEQQNNIRQEIY KLGYQLSTKDEYFQREIE QYNQYKEQLVQIENSNKE KDRLREQEEKQIEAQIEQL ASQIPTIPEDEFKHSEEYN KASQSLDLLSNKLTELNQ VYSEYNTKEQVLKSEIAT LSNSLNKLDTNDHCPVCG SPIDNSHKLKEQENINNQI ENKKQEITSVLEMKDTYK EAIDKVKDKSQEIKDKMS QFDQQEREHNNKINSIIQE ASRIKSDISSLENNKTYLK VKYQHQSVQGLEREEPSK EKHEEDKKELQESIDKHE ENIVQLETKKGKYQQAV DAFSNKGIRSVVLDFITPF LNEKANEYLQTLSGSDIEI EFQTQVKNAKGELKDKF DVIVKNSKGGGSYKSNSA GEQKRIDLAISFAIQDLIM SKDEISTNIALYDECFDGL DTIGCENVIKLLKDRLNT VGTIFVITHNTELKPLFEQ TIKIVKENGVSKLEEK | | | | | | | |
| 203 | 127725 | 128321 | 1281 | MKLKILDKDNATLNVFHR NKEHKTIDNVPTANLVD WYPLSNAYEYKLSRNGE YLELKRLRSTLPSSYGLD DNNQDIIRDNNHRCKIGY WYNPAVRKDNLKIIEKAK QYGLPVITEEYDANTVEQ GFRDIGVIFQSLKTIVVTR YLEGKTEEELRIFNMKSEE SQLNEALKESDFSVDLTY | 198 | hypothetical protein KgORF75 [Staphylococcus phage K] | YP_024505.1 | 2e-111 (197/198) | | No putative conserved domains have been detected | | |

FIG. 14PPP

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | SDLGQIYNMLLLMKKISK | | | | | | | | |
| 204 | 128336 | 129403 | 1282 | MRFEDFLTQELGEPKENTI GELRYCCPFCGEKSYKFY VKQALDSSNGQYHCKKC DESGNPITFMKTYYNITG KQAFDLLESKNIDIERAPL LTNNKDLTESEKLILML RGVHQDKGTTSIKPPRLPE GYKLLKDNLNNKEIIPFLK YLKGRGITLEQIINNNIGY VINGSFYKVDGESKVSLR NSIIFFTYDNDGNYQYWN TRSIEKNPYIKSINAPAKQ DEVGRKDVIFNLNIARKK KFLVITEGVFDALTFHEY GVATLGKQVTENQIKKIID YVSIDTSIYIMLDTDALDN NIDLAYKLKTHFNKVYFV PHGDEDANDMGTRKAFE LLKQNRVLVTPESIQSYKI QQKLKL | 355 | putative primase [Staphylococcus phage K] | YP_024506.1 | 0,0 (354/355) | DNA primase | dnaG, DNA primase, catalytic core | TIGR01 391 | 1,95e-16 |
| 205 | 129469 | 129807 | 1283 | MSNNKKDILEFVDEYITA LRVGNEQRQHQLEEMGK EETATLTDVAKAITNLML GVNEQMTDLEYNNELNL NLIDALYKAELNEDVLD YIQESIDKSQEEPKNEEEK GEQE | 112 | ORF127 [Staphylococcus phage G1] | YP_240943.1 | 7e-56 (112/112) | | No putative conserved domains have been detected | | |
| 206 | 129807 | 130259 | 1284 | MEKNISTHTKGISQADME KWIEAVVQGTVDGKQVD EKTAKQLDRIGSRSVSLEE ATRIAKVLNAVTAQEVTG | 150 | ORF098 [Staphylococcus phage G1] | YP_240944.1 | 2e-78 (149/150) | | PHA02277, hypothetical protein | PHA02 277 | 9,45e-43 |

FIG. 14QQQ

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
|  |  |  |  | DFNDAFNAIDLMMIIMED ELGVTQEKVGKAKDKLN EKREAYLKEKQEELRQKQ QEEAQKETESDSNEKVIQ LKKNDEQ |  |  |  |  |  |  |  |  |
| 207 | 130246 | 130854 | 1285 | MTNSKKKGDTFERKLAKE LTAWWGYQFNRSPQSGG ASWGKDNNAVGDIVPQ EANFPLVVECKHREEWTI DNVLLNNREPHTWWEQV INDSSKVNKTPCLIFTRNR AQSYVALPYNEKVYEDL RNNEYPVMRTDFIIDNIRK DKFFYDVLITTMNGLTSF TPSYIISCYDKKDIKPYKK VESNLSEVSKHEDELINDL LSDI | 202 | ORF064 [Staphylococcus phage G1] | YP_240945.1 | 2e-115 (201/202) |  | No putative conserved domains have been detected |  |  |
| 208 | 130843 | 131263 | 1286 | VIYKEGKISMTSKERPLIV YFSGTGQTERLVNKININN SFETFRVKSGKEKVNKPFI LITPTYKKGAIPKQIERFLE INGSPKEVIGTGNKQWGS NFCGASKKISEMFKIPLIA KVEQSGHFNEIQPILEHFS NKYKVA | 139 | putative NrdI protein [Staphylococcus phage K] | YP_024509.1 | 1e-68 (130/130) | Ribonucleotide reductase protein | Flavodoxin_NrdI | pfam07972 | 1,62e-29 |
| 209 | 131278 | 133392 | 1287 | MATYGKWIELNNEITQLD DNGKNKLYKDQEALDEY LKYIEDNTRKFNSEVERIR VLTKEGTYDKIFDKVPDTI IDEMTKLAYSFNFKFPSF MAGQKFYESYASKQYDE NKKPIFVEDYEQHNVRVA | 704 | putative ribonucleotide reductase large subunit [Staphylococcus phage K] | YP_0245101 | 0,0 (699/704) | Ribonucleotide reductase large subunit | PRK07632, ribonucleotide-diphosphate reductase subunit | PRK07632 | 0,0e-00 |

FIG. 14RRR

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 210 | 133406 | 134455 | 1288 | LYLFQNDYVKARELLVQL MEQTFQPSTPTYNNSGQA NRGELSSCYLFVVDDSIES LNFVEDSVANASSNGGGV AIDLTRIRPKGAPVRNRPN SSKGVIAFAKAIEHKVSIY DQGGVRQGSGAVYLNIFH NDILDLLSSKKINASESVR LDKLSIGVTIPNKFMELVK EGRPFYTFDTYDINKVYG KYLDELNIDEWYDKLLD NDSIGKVKHDAREVMTDI AKTQLESGYPYVFYIDNA NDNHPLKNLGKVKMSNL CTEISQLQEVSEIYPYSYS NKNVINRDVVCTLGSLNL VNVVEKGLLNESSVDIGTR ALTKVTDIMDLPYLPSVQ KANDDIRAIGLGSMNLHG LLAKNMISYGSREALDLV NSLYSAINFQSIKTSMLMA KETGKPFKGFEKSDYATG EYFVRYIRESNQPKTDKA KKVLDKVYIPTQDDWDE LAKAVKVHGLYNGYRKA EAPTQSISYVQNATSSIMP VPSAIENRQYGDMETYYP MPYLSPITQFFYEGETAYK IDNKRIINTSAVVQKHTDQ AVSTILYVESEIPTNKLVS LYYYAWEQGLKSLYYTR SRKLSVIECETCSV MDITQKVKQHNKNAVLK ATNWNIEDDGMSDIYWE QGISQFWTPEEFDVSRDLS | 349 | putative ribonucleotide reductase minor subunit [Staphylococcus phage] | YP_024511.1 | 0,0 (348/349) | Ribonucleotide reductase | NrdF, ribonucleotide-diphosphate alpha | PRK09 614 | 4,21e-80 |

FIG. 14SSS

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | SWNSLTESEKNTYKKVLA GLTGLDTKQGGEGMNLV SYHEPRPKYQAVFAFMG GMEEIHAKSYSHIFTLLS NKETSYLLDTWVEENDFL KVKAQFIGYYYDQLLKPN PTVFDRYMAKVASAFLES ALFYSGFYYPLLLAGRGQ MTQSGAIIYKITQDEAYH GSAVGLTAQYDYNLLTEE EKKQADKETYELLDILYT NEVAYTHSLYDPLELSED VINYVQYNFNRALQNLGR EDYFNPEBYNPIVENQTN VDRLRNVDFFSGKADYE KSTNIKDIKDEDFSFLDSK EYSTAKEFL | | KJ | | | minor subunit | reductase subunit beta | | |
| 211 | 134473 | 134802 | 1289 | MDRKEAMDLLSKAEILFK KHDEFSCVSDINDPMKLF SNSKDAKADDTSKSFQLE FMHDMTMYTLSYGSGQL KLIDLAEGYEAQKATVVN SFPEIIKTLEKDDSEDGKN E | 109 | hypothetical protein KgORF82 [Staphylococcus phage KJ] | YP_024512.1 | 1e-55 (107/109) | | No putative conserved domains have been detected | | |
| 212 | 134786 | 135106 | 1290 | MEKMNSLVDLNTAIRQK KDVIVMITQDNCGKCEIL KSVIPMFQESGDIKKPILT LNLDAEDVDREKAVKLF DIMSTPVLIGYKDGQLVK KYEDQVTPMQLQELESL | 106 | thioredoxin-like protein [Staphylococcus phage KJ] | YP_024513.1 | 1e-53 (106/106) | Thioredoxin-like protein | PHA02278, thioredoxin-like protein | PHA02278 | 2,95e-30 |
| 213 | 13531 | 13590 | 1291 | MDELISKSRRYIMRDENH YMLFNEKYNNDRLJEKVC | 198 | hypothetical protein KgORF84 | YP_024514.1 | 7e-109 | | No putative conserved domains | | |

FIG. 14TTT

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | 3 | 9 | | KHGGKVTYTDSVLPYY VLKDLSSHPDSEVVYRMR NGFTAKEVDNIALSFMGT KVIIDISVVFPYVNPYDIIR SLHDIKTNVDEVHLSFPRI LEVDEKQEKFYFFDGEAY DLKPEYKVDFADKIRVSL SVWKMYIYILTSSRDFED VDNVITKLKQQRKIKI | | [Staphylococcus phage K] | | (196/198) | | have been detected | | |
| 214 | 13591 9 | 13622 4 | 1292 | MSTANRRDIARKISENTG YYIQDVEEILSAETDAISD LLEEGYTKVKNHKFMQIE VIERKGKKAWDGLNKEY FHLPNRKAIKFKPLKELEE VIDRLNEEEK | 101 | putative integration host factor [Staphylococcus phage K] | YP_024515.1 | 2e-51 (101/101) | DNA binding / bending protein | Bac_DNA_binding | pfam00216 | 4.57e-12 |
| 215 | 13630 0 | 13951 8 | 1293 | MKVLILFDHIREEHFSVSK DGSVKSNVLNTPNGKTLK KLLEKCSNLKRDKTNRDY DIDFLYNAVPTPIRNDYG KIIKYQDVKQAEVKPYYE RMNNIJIDNSYDMIIPVGK LGVKYLLNVTAIGKVRGV PSKVTIENGTSSHDVWVL PTYSIEYTNVNKNSERHV VSDLQTVGKFVEQGEEAF KPKEVSYELVDNIERVREI FNKEVKNDVYDGVDITA WDLETNSLKPDKEGSKPL VLSLSWRNGQGVTIPLYK SDFNWENGQDDIDEVLEL LKNWLASKEDIKVAHNG KYDIKFLMSTENFKDFESI QDTKVGWYLAVTQEVKE SLRLSDLAYEVTDVGGYD | 1072 | putative DNA polymerase [Staphylococcus phage K] | YP_024516.1 | 0,0 (1065/1072) | DNA polymerase | DNA_pol_A_pol_I_C, Polymerase I | cd08637 | 7,32e-72 |

FIG. 14UUU

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | KPLEDFKLWFVTKLLRFF SDKIKEIQKENKKIAKKEY DVKAPEYKEWLENKLNE TVVELDDTEKKFRVSELE KKYIQLGLSPEIVNMNLV MNNDEFISIAEQSPEYMG LSDYAKSYTLNTAINLINE YRDVKDVVNDIDGGNFN YDWFPIELMHPYASGDTD VCRRIHCDVVKKLKEQDR PKSMHLLEVNYPRLTKSL ARIESNGLYCDLDYMKEN DESYESEMAKNHATMRE HWAVKEFEEYQYNLYQM ALEEHEKKPKDRDKDIHQ YRDKFKDGKWMFSPSSG DHKGRVIYDILGIQLPYDK EYVKEKPFNANVKEADLT WQDYKTDKKAIGYALDN LELKDDVRELLELLKYHA SMQTKRNSFTKKLLPNMIN KQKRTLHGSFSETGTETS RLSSSNPNLQNLPAHTSD VNKFDYKHPIKRSFVSRFE NGVLLGADYSALEMRIIG LFTKDPDMLQSFLNGEDI HKATASIVYNKPVEEVTK EERQATKAVNFGLAFGES PFSFAGKNNMEVSEAEEIF EKYFQTKPSVKTSIDNVH EFVQQYGYVDTMHGHRR FIRSAQSTDKKIKNEGLRQ SFNTIIQGSGSFLTNMSLT YLDDFIQSRNLKSKVIATV HDSILIDCPPEEAKIMAKV TIHIMENLPFDFLKAEIDG | | | | | | | | |

FIG. 14VVV

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | KEVQYPIEADMEIGLNYN DMVEYDEEIDT | | | | | | | | |
| 216 | 139588 | 139830 | 1294 | VNTGEIRFNRSMDEWITS MYQDELGEMNIVVTFYN REENKHGSTVLPTESSTGE VAEELASLEEEYPLALPLS SISVNI | 80 | ORF181 [Staphylococcus phage G1] | YP_240959.1 | 2e-36 (77/80) | | No putative conserved domains have been detected | | |
| 217 | 139847 | 140329 | 1295 | MEIHIDSLDFTNFTIKDRN GNSQEFDITDELRITEYTIQ EDFMQQSAKYAFWASILE KVRAYSEMEQRNLETIGS KLNLTIRQEYEQOGKKPT KDMIESSVYIHDSYQQQL KVVEAWNYKVKQLQYV VKAFETRRDMMIQLGAEL RQTNKNGGITNPFSH | 160 | hypothetical protein KgORF91 [Staphylococcus phage K] | YP_024519.1 | 6e-90 (160/160) | | No putative conserved domains have been detected | | |
| 218 | 140416 | 141687 | 1296 | MDFNQFINNEASKLESNN SSFNNNVESYKPKNPVLR LGNIKDANGNKVVKENA FVRVLPPAQGTNVFFKEF RTTGINYSKKDGSQGFTG LTLPAEEGSSVLDPYIQD WITNGVQFSRFPNKPGVR YYIHVIEYFNNNGQIQPKT DAQGNVMIQPMELSNTG YKELLANLKDTMLKPSPN APHSFISANEAFLVNIVKA KKGEMSWKVSVYPNAPL GALPQGWEQQLSDLDQL AKPTEEQNPNFVNFLINN VNNTELSHDNFKFNRETN VLGEEPSEPKQAPTQQDV | 423 | hypothetical protein KgORF92 [Staphylococcus phage K] | YP_024520.1 | 0.0 (421/423) | | No putative conserved domains have been detected | | |

FIG. 14WWW

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | DSQMPSNMGGQPNQPQQ GQVGQYAQQGQSNGQGQ QLQGTQQPINNTQFGQGT PSGQQPSNTGSVDWDNL AQQQSQPDSNPFNDFDVS SVDDSQVPFETQPQNTQQ APEPHQJTTQEPPKQKQTQ SIDDVLGGLDLDNL | | | | | | | |
| 219 | 14174 9 | 14301 4 | 1297 | MARAKKGKEVDLTDLNT IDLGKELGLTLLSDSNRA DIKNIVFTMVPQYDRLLGG GIPLGRLTEVYGLTGSGKS SFAVHLSRISTQLGVITIWI DIEGTADNNRMEQLGVD VSKLFSIQAGEGRLKNTV ELSVETVGKELDYWIDTF NEKAPGVPILFIWDSLGAT RTQAEIEEGVDHRKLGTK ATATQKVINAVSPKLNDT NTGLIVINQARDNLNMSN PYDDPIKSTGGRAFEHGA SLRLKITKGKESDLKQSDS MTGKPTYKGHVMRVETK KSKLSRPGQKAEADLLSG YEVGSGSDITQLNGIDPYH TIYKEAVERGLITKGTWR NYITLNGEEIKLYDKDWV PRLIDDHELYLELFSRVYG EHFPNGYSPLLNTKVIVTQ LEEYQALENYYEEWAKD NKQEEQEEESKGESQEKD SE | 421 | putative DNA repair protein [Staphylococcus phage K] | YP_024521.1 | 0,0 (351/421) | DNA repair protein | RecA | cd00098 3 | 6,13e-22 |

FIG. 14XXX

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | | | | | | | Conserved Domains | | |
| | | | | | | Homologous/similar proteins | | | | | | |
| 220 | 143018 | 143371 | 1298 | MYNLIDKNMRQVKESLG NANSSDVLPLPYKDIAKK FEEVKEKGESIIEEGGFPY TDSTVMYIEHVTDRWAG GYSLIRHEGEEVKVPKTIH FSDIYVKDKSHKVRIIFEG ANPYEEG | 117 | ORF121 [Staphylococcus phage G1] | YP_240963.1 | 2e-59 (114/116) | | No putative conserved domains have been detected | | |
| 221 | 143358 | 144020 | 1299 | MKKAKNGNRYVIDIDGIP VDFERDLDSLLNRYKNLR WSLYHKYAGILSNDFERQ ELREYIDEQFIKLVKEYNI RSKVDFPGYIKAKLTLRV QNSYVKKNEKYKRTEIIG KKDYTVESLTEDLNEDFE DNQIMSYVFDDIEFTEVQS ELLKELLNPEREDDAFIV SQVAEKFDMKRKEVASE LTELRDYVRFKINAYHEY YAKKELNNHRVNTENHI WEN | 220 | putative sigma factor [Staphylococcus phage K] | YP_024522.1 | 2e-121 (218/220) | Sigma factor | No putative conserved domains have been detected | | |
| 1a | 144114 | 144994 | 1300 | VRIEKHKIKNNKVINEMSI TANNLYNHANFILRQNFF NNKTNKGYRKFLNYNTIH RILKNMNEENYIKLPRQTS QQVLRDLINNWSSFRKSE KDYFKNPNKYRNRPKPPK YKAKGGKGTIKFTNQQCR IHKDGLIHLPTPLQDITIK PYKAKNIRELVCIPKSDYF EVLVCYKEENSNKTLNDN ENIASIDLGLDNLITMVSI VDKPIINGKGLKSKNKYF NKKIRYYQSLLQNNSYSS KRILKYWFKRHNIILDYF | 293 | IS element Dka2 orfB [Hyperthermophilic Archaeal Virus 2] | YP_003773391.1 | 5e-18 (109/405) | Transposase | orfB_IS605, probable transposase | pfam01 385 | 2.87e-36 |

FIG. 14YYY

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | HKATNEVVKYCVKNDIS KVVIGYNKQQKYKSKLK | | | | | | | | |
| | | | | | | | | | | | | |
| | | | | | | | | | | | | |

FIG. 14ZZZ

FIG. 15A

```
sequence.txt
SEQUENCE LISTING

<110> DA COSTA GARCIA, MIGUEL ANGELO
      SOUSA DE SAO JOSE, CARLOS JORGE
      RODRIGUES LEANDRO, CLARA ISABEL
      RODRIGUES PARDAL DIAS ANTUNES MARCAL DA SILVA, FILIPA MARIA

<120> ANTIBACTERIAL PHAGE, PHAGE PEPTIDES AND METHODS OF USE THEREOF

<130> 16395-105003US1

<140>
<141>

<150> 61/384,015
<151> 2010-09-17

<160> 1300

<170> PatentIn version 3.5

<210> 1
<211> 113073
<212> DNA
<213> Unknown

<220>
<223> Description of Unknown: Bacteriophage F391/08

<400> 1
attatgcaaa ctaaacgaaa tcatacactc cactaattaa aggttgacaa catgaaacgc       60
tttgtaatat catctaaacc ggcggcaaaa ttgaacaaaa tggcaagctc ggaactggtc      120
aaaatgcagc gcgatatggc gcggcgttac cgctcttatc agcgcggagg tcagcaaggc      180
ttaccgatga tttgggataa catgatgcgt tatctaaaat ctttacaaaa taacgtttga      240
caatctgccg ataacgcttt attatagaat ctcaataagc aacaccgctc tttaaaaatt      300
tggaaaagtc gattctctca gtaagggtaa ttgagttttc tgttaacact ctagcagtaa      360
aagagtgtta accggataac ccaataaact aaactggagt aagaaacatg caaaacgtta      420
aaaccccaat gatcggtgat tccgttttta ttcctttcgt tactggcgac gtaagtaagc      480
cgggcgaaaa tgaaaaaatc ggatatatca aagggcggc gatgatcccg tttgataaaa       540
ttaatgcggt atacgccgaa acggaaaaag caaaaaacag cgacgcgaag atttacagcg      600
tccgggtaga ttccggcgac gtggtgaaag tcattcgcaa agatgataaa tggttggctg      660
tcgcttaaca gccaataagt ttaaccccgg caaataatgg gatgcttccc ctatgttaga      720
cttccgatgt atattccatg cagcgcaagc aatgttatgg tgcgcaaatt aaacttatgt      780
gctggaactt atatcatgct ttgaacggca attgtgagtt aacacgaatc tatagcgtga      840
aatagacgta atagcgtaat tattaaaggc agcgtatata tacaatgccg ctttaaatag      900
ctttaaattg aaaactaaaa taaagagttt tcgttatata ttctagctag aatatatagc      960
ggctaacttt ctagccttaa cccttaaata aaactggaga tatatcatga ctgctactaa     1020
```

FIG. 15B sequence.txt

```
aaccgaaaaa ttcgcatgga acgaaacaaa cgccgctacc gccgttgaaa tgtacgaaaa      1080
gatcattgct tccgatggtc tggaggtggc taactcgcaa ggtcttattg atattgcaaa      1140
ggctgtaggt gctgaatcgc atgttaaagt gcgctctaaa ctggttagcg caaaggtgta      1200
tcagaagtcc gataagccgc gcaaagtcgg cggcggctcc tccctgcgta aagctcacta      1260
tgtgcgcgtt ctcactcagc acgccattgc tgacggcctg attgatgatg ccgatggtct      1320
ggcaagtctg gaacaaatga agctcgacca actggacgtt atcgcccgta tggttggcgt      1380
tcaggatgaa gtaaagaat cagcagaata attataatgc gcctccctag cggggcgcat      1440
aattaaatat tttgtcccc ataactggag aaataaaaat ggctttaatt aaaggctccg      1500
ttattaaatt aacgggaacc gttgtggatg aattaatcca acggggtat caggataata      1560
aggttatgac gcccccaagc gttaaagtac ctgaatatat tgttttgtgg gttaaccctg      1620
atgcggatac tttcgggatg gctattaacc gcgaagtctt taagccggaa atgctggaat      1680
tatcttcccg cgaaatttac cttctcaatt acgctttcag cgtagaagaa aaggaggttg      1740
taaaatgatc tttttcccta ctgaatcctt aattcttatc gctggctttt tcgccgccgc      1800
ttgtctctat ggttactata atttcatgga aataggcagc gaacaaacgg atttattacg      1860
ccgtgacttc tggttcaaga aagcgagtat ttgccgccgc tggtcaataa tctttattat      1920
tctagcggta actttcggaa tatcagcaag cattatcccg gcaatagttt agagtcgcaa      1980
attataacgc caccagcaac aaggcgttat atttggcaat tctgcctata tcccattaac      2040
tggagaattt agataatgat cattgcaatt gagaaacaaa aagctatttt aaccgctgct      2100
aacaacctca attttgggg taaacgcctg cgcgctaaaa agctggagat ctgcgacgaa      2160
ttgagcaaag agcattacgg gacggcgaaa cactctagcg aaatttgcga ttggctggat      2220
agtaacaagc ctgttaaacc cgctgctgaa aaacgcgccc aacgtgttgc ggtggaagat      2280
tcccgccccg ttgccgctgg tcagcttaat tccagcgtcg aaagctggaa ggtaattccg      2340
ggccgccgtt ttctgctaac gtcgattcaa aataatacct tccctcatgc taatttctgg      2400
aaaactttac aggaggccgc gaaatatctc ggcgctactc tgttagtaag caaatacgcc      2460
tacaacaaaa aaggcttcca aaacgggcaa ggcaacgatg aactgaaata tgatgatgct      2520
ttctcagatt tcatttgtga tgaaaacgtg tttttgggca accgcgaaac cggattcgca      2580
ttcatggcgg aaattaatat tctgccaact gctgattttc cgctgtccgg ctttggcgag      2640
actgcgaccg cctacggcct gaaagggctg gctattggtc acgctaaaat caccgccgaa      2700
agtgtcccgg caatgaaggg cgacactgtg cgccgtatgt attcaactgg cacagcgacg      2760
ctgaaaaatt atattcagca aaaagcgggc aaaaggccg aagcgctgca taactatggc      2820
gctttgctgg tagagatcga cgacaacggc aacttctttg ctcgccaaat cgaaacgatg      2880
```

FIG. 15C

```
                                   sequence.txt
gacgaaagcg ggatgtttta cgatcttaat cataaattta ctgttaacgg tggcgaggag    2940
gtaacgggcc acgttgccgc gctgcaatat ggtgacattc acgccgaaaa gctggatcac    3000
gctgtcgcct ttgcttcatg ggggccgtgt gatgattctc tagtgaacgt cctgcgccct    3060
cgttaccaga ttgtgcatga tgtgcatgac tttacatcac gaaaccatca taaccgcgct    3120
agtggcgttt tccttgcgaa acaatatgcc gccggacgtg acaaggtaat tgacgatctt    3180
atcgataccg ggcgcgtact agaagcaatg gaacgtgaat tcagtcaaac ggtcattgtt    3240
gaatcgaacc acgatcttgc gctttctcgc tggctggatg atagtaaagc taacattcaa    3300
caagacccgg cgaacgccca tctttattat cgcctgaatg ctgcgattta tgaagcaatc    3360
gaaaacaagg acgatacttt taacgtacta gattacgccc tgcgcaatgt tgctggctgc    3420
gattttgctg cgatcttctt aaccacggat gaatctatga aaattgcggg catcgaatgc    3480
ggttcccacg gtcacaacgg cattaacggc gctcgcggca acccgaaggg attccgcaag    3540
ctcggcaaga tgaacactgg ccatacgcat acgcccagca tttacggcgg cgtttatacc    3600
gctggcgtcg ctggttccct cgatatgggt tacaacatcg gcgcgtctag ctggtcacaa    3660
acgcatttga tcacctatga aaacgggcaa cgtaccttga ttgactttaa agacggcgtt    3720
ttctttgcat aacaaaaaag ccggggtaat tgccccggca ataataacc cataaataaa     3780
taaataagct ggagaaacaa atgaaactta ctttcatcta taacaatcgt aaatctttca    3840
ccgcgtccaa cgtcgtagaa aatagccttg ttatttcccg cgatagtgaa gggcgcccgc    3900
atgttagcta tcagaaagtt aacacggtgg acggcgacac tgttttaaaa gctctagccg    3960
ctatcctccc gcgccccgct gaatttaaag aatccggcat tgtgtcgcaa ttagtcgccg    4020
ccgattctat tctttatgag gctgatatct gcgagatcgt agagattgac gccgccgccg    4080
ctggccttat gtttatcgtc gtaagcgaaa atgattatga tgatacctat ctgctcggcg    4140
acgtgatgga ttattcttct agcgaatata cgccgccgct ggcaattgtc ccggtaatgg    4200
ctacccggat taaaccggct gaattagccg atgccttaac tttattcttc tgataattaa    4260
caaagcgagt tataatatag ctcgcttgat taattaccaa caccccgaa accggagaaa     4320
tgaaaaatgg cttttaataa actggcaatt aaggcaatta agttatggga tttagacgga    4380
actgttatta attccttttgc ccgcgtgttc ccgtgtatgg atgataaagg gaacttagat    4440
ttaaacatgt accgggaaaa ggcttgcgta catgatgcaa ttatgaccga cactctttta    4500
ccgctggttg aatatatgcg ggcatcgctt aacgatccca ctgtattaaa cattattgtc    4560
accgctcgtt atatgggtaa gagtgactac tatttcctac gcaaacaacg tatccgggcg    4620
gggcgcggtg gtaatatcca gatactgtcc cgcgatgtat tgcaccgata tattggcgat    4680
gctgattata aagaggtgta ctattcgaaa gatggtatct ataaaacgca ttatttcgaa    4740
atgcttaaag ctgaatatcc gaacgctact atcactatga ttgacgataa tagaggcgtg    4800
```

FIG. 15D sequence.txt

```
ttggctgctg ctgctgctgc tggccttcaa acgatggacg ctaccgcaat taacgatatt    4860
ctatctattg gtgtgcgcct tgcgggtgag tcattcatag atgaagcgct ggatgatgat    4920
aatgattatc aatatctttg cgagcgttta gctcattgct gggaaggtat gaccgaagaa    4980
gaaagaagcg actacggaat taagccgcaa caatttattc aatcgttagc catcgcatca    5040
taagaaagct aatagtaccc tagcgaaata gttagggtac taatagttag ctaggggggt    5100
aatcggacta ccataccacc ccccgaccct ctaagcccac ctccatgtgt aactttatga    5160
aatttggaga aaaggctaaa gggagtactt aggcaaactt agaacgagca gcccgaatca    5220
aagctactac tgctactgcc gctgtcgcaa taagaacttc ccgagtcata cccgctatac    5280
gttgcaactg ccgcagttgt agctatgatt gctgcagtcg acccatcatc gctccgagaa    5340
cttcccgagt tcgatgaagg acttcccgaa actttccgag aattatccga gcctgcccgt    5400
ttttgcttgc gtttcgcgac ctgtggtgtc actggaggga tgtagtacgg gttgctcggg    5460
tcattccgaa gatcgttcat gactcgttgg tgttttgaga tcgctacttg acgttctgcc    5520
cgagtttgaa ggatctcttg atgcagactt tgttacgaa gatctgccgc tactaccgcg    5580
ttccgcaggt catgtgcccg cacaccaaac caaactgctg ccaggaaaaa gaatgttgtg    5640
aaaattaata caatagtcat gttttacacc atacccttag taatgtagat tttgtttgct    5700
gattctagtt ctgccttgca ttcagacagg tttaactgtg ccttatgcag caaacgggtt    5760
tgattgtcat aagacttctg cagcaccccg ttagtgcgtt ctagctgttt gattgcctta    5820
ccctgcttta cggtaatgac gaatagtacg attgagagta aaacaagtgc tcctataact    5880
acttccatag tggtcctcct agatggtttt aaaaaatctg gtttacttgg cggttgattt    5940
aatttataat aatattatat tataaaagtc acttgttagc aagtgagatt ttgaggtttt    6000
tatgggcttt tatgcaggaa ggataggcga caaaaaagtg ttgtctctta cctctggcaa    6060
caataaagac gttaataacc acactaatcc aggttgggat actatattcc atagcgatat    6120
gcctcacgtt gtagttttag aaactcacga aagagacctc tgggatggtg gtgattggta    6180
tcgttgtact agaatgccag acagaattat tcaggtactg tccgcagact acgacagggt    6240
tgtcttaact gaagttgagt ttgaggatgg caccagacgt ttcatttatg gtacatccct    6300
gggtgtgggc gctaaagcgt ataacgctta ctttagtaat actgtcggtt cccaggcttc    6360
tgcaggtact atggctagta tgaagactaa cgtttgtgct tctgcagact tacacatgga    6420
tattagtttc tatttcgaag agacgccagg tactattaac gagaagctac gagacggtac    6480
tgggtgtatg tacacctggg gcgttaactc agaatgggga gacagagggc ctgggccgcc    6540
ggttggagct cctatacgtc ctaactttga gactattatt aaagctggat gggtgctcta    6600
tagggggggct tttagtggca atatagccgg ttctgtgtct ccgcccaata gacccttac    6660
```

FIG. 15E sequence.txt

```
tattggtgtt gatgctatgc gccacccgtg gatgcgtact actggtgtta acagtatatg    6720
tttgcgtggt gagactctca accgtaatat gtacggacat atggggccta gatatgggca    6780
gagctccaat cccgttggtg gtccttatgc tcataacatc cagactgagt cttatcagga    6840
ggttcagtac aaagcaggtt ttttccgtgg tccgcccaat aactttatgg ggtgggaaaa    6900
cacagataac aacaatgctg gtagtggttg gggtaacaat gccatttacc gtgacaataa    6960
cttccgtgtt cctaaacgtg ttcgctggta tattactaat atgaaataca atgggcaggg    7020
gttctacgca gagaacgtat ttggctcccg caaccaggag attaaaatca gccctagaga    7080
gttcattgta aacggtataa acctaatgaa cactgggtgg aagttcataa accagaacga    7140
tataaactac agcccaggta ataggcctga tatccgagtt attgcaacca acgtcgccag    7200
atttagtggc aaccctactg ttggtaataa tggatatgtt cactttaatc agcctctaac    7260
tcgaccagat aatggtgctg agtttggaca aggtaacgtg agtgagatgc atgtaaccac    7320
tgtagggtt tacaatttta gatctgatgc acagtggtac gtaaaatcta acccgccgga    7380
aatcggaaac cagtggggtc cagtatggtc tgaatcaact cgacctctcc gcctagtggg    7440
cggtaccggc tctgctgata ttggagggaa cctacgtact agcggtaatg ctagtcacca    7500
cctggctacc ttgtggttag gggttaataa ctcccgaaat ggggcttgcg tcgtcactct    7560
agactggaaa aatgatgagt ggattgctgc tgcagggatt ggatgttata accctctaga    7620
agatcttacc cagtggagcg aggtggatag taggctgaga attttcggaa atcacttcca    7680
gaaacgtgtg catcaaatca tgtgtttgcc cgttaacatg tgtgtgccgt tccactttat    7740
acgcgggacc gtaacccagt gtggggttat tcctgggaac aacgccatgc aaatgaaggc    7800
tatgtgggca cctactacta ccaactctgc cactcagggc gattatgcca ttatctattg    7860
gctgatagct agggctgacg gtagtgttga agtttgggtt aacgttgaga tgagcaatat    7920
catgaatatg cgagtaattc ttcctgaggt taggattgct gtgcaaaggc ttgcctaaag    7980
gaggcaatat gagcaatgat ttaattgtac cagatacaat gtctccggaa ggcatgctag    8040
ttatagaggc ctacctggag tctggcagcg acgttgcgaa agcagcgtta gctgttggca    8100
tggaggaacc taaattccgg gagattatgc gtaaacctga ggtcaaagcg taccttacgg    8160
atatcttcat ggaatctggc ttccgtaacc gtgataaatt cttcggcatt ctagacactg    8220
ttctaactat gaaaatggag gaactggatg aaactggaat gggttcagag atggatatta    8280
tggatatcct caaactcatg cacaaaatga agatggatga gatgaagatg cagatcgagt    8340
atgagaaggt gaagcaagct aaagctccaa taccaaaaa taatactcag atcaacctgg    8400
caggggtca cgactctaat tacacggacc ttctgtcacg cattgtggga gcaggtaagt    8460
aatggaaatc tcacgtagtt atattaatac gactgacgtg gtggattttg gtgttgataa    8520
acgattcttt aaattcccgg tgtccggctt gctggccacc gaggggatcg ttccaaatgg    8580
```

FIG. 15F sequence.txt

| | | | | | | |
|---|---|---|---|---|---|---|
| cccgcagtgc | gcaatcataa | acgcactgga | agacccacgt | caccgtttcg | ttacagcatg | 8640 |
| cgtatcacgt | cgtgttggca | agtcgttcat | tgcgtatact | ctaggcttcc | ttaaactcct | 8700 |
| agagccgaac | gttaaggtgc | tcgtagtagc | tccgaactac | tccctggcaa | acatcgggtg | 8760 |
| ggcgcagatc | aaaggtctga | ttaagaaata | cgggcttcaa | actgagcgtg | agaacgccaa | 8820 |
| agataaagag | attgaacttg | ctaacggttc | gctctttaag | ctggcttctg | ctgcgcaggc | 8880 |
| tgactccgca | gttggtcgtt | catacgactt | tattatcttt | gacgaagcag | cgatctccga | 8940 |
| cgttggtggg | gacgcttttg | atattcagct | ccgtcctaca | ctagacaaac | ctaactctaa | 9000 |
| agctctgttt | atctctactc | ctcgtggcgg | taactggttc | aagcgcttct | atgaacaggg | 9060 |
| attcagagag | gatcttccgc | aatgggtatc | aatccacggt | acataccgag | ataaccctcg | 9120 |
| cgtatctctt | gcagatatcg | aggaagcacg | taagactgta | tctaagaact | acttcaaaca | 9180 |
| ggagtatgag | gcggacttct | ccgtattcga | aggtcagatt | tacgacacct | tcagcgtttc | 9240 |
| cgagcacgta | caggatcttg | caggtatggg | gcacttcttt | gctgcggacc | atgagttcga | 9300 |
| aaccattcta | ggtatcgacg | ttggttacag | agacccgaca | gcagtactta | ccattaagta | 9360 |
| ccactatgac | caagatgtgt | actacatcct | tgaggagtac | cagcaggcag | agaagactac | 9420 |
| agcacagcat | gccatgtaca | tacaacactg | catagaccgg | tataacgtag | accgtatctt | 9480 |
| cgttgactcc | gcggctgcac | agttccgaca | ggacttagca | tacgagcatg | aaatatcctc | 9540 |
| tgctcctgcc | aaaaaatctg | ttctagatgg | cctggcatgc | ctagctgctc | tattccagca | 9600 |
| gggtaagatc | attgtcgacg | cctcgtgcac | tgcgttaatt | cacgcactcc | agaactacaa | 9660 |
| gtgggacttc | caagaagggg | aggaaaagct | ctccagagag | aaacctcgtc | acgatgccaa | 9720 |
| ctctcactta | tgtgacgcac | tgcgttacgg | catctactcg | atttcccgtg | gcaaataaga | 9780 |
| gctgagttgg | aacggatagt | agtgagtaca | aattccgttc | caactttata | aaattcactt | 9840 |
| tacaatttcg | tgtgtggcag | ttataatata | ttcataccct | gagagatctc | atagacatca | 9900 |
| gggtgaatga | gaggaatatt | taattgctat | acccgaagta | gtattttccc | aactaagagg | 9960 |
| aggaacactt | tggcttccaa | tgtaaaatat | aagagagatg | caatctccat | aatgcgtgac | 10020 |
| ggaatcaaag | cccagtacaa | aagaggcaac | tgttgcgcca | tttgtgactc | acaggaaaac | 10080 |
| ctggagctac | accactactc | gactgtggcc | ttactagtta | aaaactttgc | taaagaattc | 10140 |
| caactggatt | tcactgactc | agaagtcgtc | ctaagtaatc | gggataagtt | ctataaacat | 10200 |
| tattggcatg | agctagtaga | ggacacggtc | accttatgtg | tctttcatca | tcagaccttg | 10260 |
| cacaaggtct | atacgaaaga | acctccgttg | tttttcagcta | acaaacagaa | gatttgggtt | 10320 |
| gagaaacaac | gtgaaagatg | tatgaatcca | gaggcacctc | gtacaagcaa | cactggcgaa | 10380 |
| agatcaggct | ttgcgaagtg | gcttccgact | gacgtcaaga | ctgagaaatc | aggattcgca | 10440 |

FIG. 15G sequence.txt

```
aggttcctat aatggctatt cgtgactggt tagttactaa actaaaccgc ggacaacgca    10500
taatcaggga cttggaggat gttagtcacc gtactaacgt caagccattc acgactggca    10560
aagcctattc gtctattgag atccttaata gatccgcgaa catggtaatt gacagcgccg    10620
ctgagtgctc ctacaccgta ggtgaacagt ataaaacaat aacaacctat ggcacgatca    10680
ggagtaaaac tcttgagacg ctgcttaatg ttcgccctaa cccgtacatg gattccagta    10740
cttttagacg cctaatagtg tctgaccttc tattcgaagg gtgcgcgtat atccattggg    10800
acggttcgtc tctgtaccat ctgcctgctg ccctaatgga agtaaaagca gatgacaaaa    10860
aattcgttaa caaattcgtc tttaataata tgatcgacta tcgcgttgat gaaattatct    10920
tcatcaaaga taatggccag aatggtggta ttaactccca gattacgggt caatctcgtg    10980
tggctaccgt aattaactcg cttactaagc gtgagaaaat gcttgagttc aaggagaaat    11040
tcctggacaa tggtacggtt atcggtctta ttctagaaac agatgaaatc ctaaataaaa    11100
agctccgtga acgtaaacaa gaagagcttc agctggacta taaccctagt accggccaat    11160
caactgtgct cattctagac ggcgggatga aggctaagcc atactcccaa atctcctcct    11220
ttaaagatct cgatttcgag aacgatatcg ctcgttttaa taaagacgta tgtatcgctc    11280
tcggagtccc acaactattg atcgatgggg gtaacaacgc caatattcga ccgaacattg    11340
agctgttcta ctacatgact attgtgccta tgctcaataa agtatgtagc tctcttacgt    11400
tcttcttcgg ttttaaagta acgcccaata ctaaagacgt agtagcacta actcctgaca    11460
aggagaaaga ggctaaattc gtaactgcac tggtcaacaa cggtatcctt accggtaacg    11520
aaggtcgtat agagcttggt tacgaggagc tggctgacga gcagatgaag aaaattcgca    11580
tccctgccaa cgtagctgga tcagctaccg gagtaagtgg acaagaaggt ggcgctccca    11640
ataaagacga ggaaaaacaa tgattgacta taaagcatta aaagcactat tccctaatgg    11700
tctccccgag gcacataacg tgtttgcaac cgttaaggca catctcactt accagattct    11760
gcgtaaggag tatgggtacg ctgctactaa cagtaaaacc tgggatcagt ttaaggaagc    11820
ctacgcggaa gcaactaagc cagtaccggt agcttctgtt agtatcacgg gcgctcctgc    11880
atccttagac tatactaaga ctgtacagct tgccgcaact gtcctaccaa caaacgcaga    11940
taataaaact gtaacgtgga agactagtga tgctacccta gctactgtga gctcaacagg    12000
attagtaaca gccctgtcta aggcaggcac tgttaaaatt actgccactg caggtggtaa    12060
atctagtgaa gtgtctattc aggtcaaggc tcctgttgta gcagttaccg gtgtcactat    12120
gtcacctaag actattacaa tcgaagcagg taagaccggc aaacttactg gtaccgtagc    12180
cccggctaac gcaaccaata agtctgtaac ttacacttct gctgatacca ccaaagctac    12240
cgtagctgcg gacggtacgg taactgttcc tgctaacctg gctgcggata gtaccgtagt    12300
tattactgtt aaaacagctg acggcaataa gaccgacact gcaatagtaa cagttaaggt    12360
```

FIG. 15H sequence.txt

| | | | | | |
|---|---|---|---|---|---|
| tcctacagcg | ggtgtgtaat | atctgttaac | tggggagctt | cggctcccca | tttttctatg | 12420 |
| ctagtgcata | actattttca | gtgtaaccaa | tttcgactac | ctactaattc | cacacaccgt | 12480 |
| gtgggatttt | caaatatctt | ttgacattcg | cgatttggta | tgtaataata | gtatctgaaa | 12540 |
| actgaggaac | aacacgaaag | tgtttggagc | aaacgatgca | gaatattaat | cttaatgctg | 12600 |
| agattaaatc | tgttaaagct | gtcggtgagg | gtgataatcc | tcctttaaaa | atcaaagggt | 12660 |
| atgctaacac | gattaccaaa | gaccgcgccg | gcgacgttat | tctctccgaa | gcgtggacta | 12720 |
| ccagtaacgc | cctcaagaat | tttatgaaga | acccgatcat | gcttttcggc | ataaccata | 12780 |
| gccgcccaat | tggtaagatc | ctagacctgg | taccaaccga | gtccggactt | atggttgagg | 12840 |
| gtgaggtaag | tgctgctgat | ctacagattt | actcattaat | acgtgatgag | gttcttaaaa | 12900 |
| cgttctcggt | aggcttctat | attaaagacg | ccgaatggga | cgatatgact | gaaacgttca | 12960 |
| ttattaaaga | tctggagtta | ctcgagatct | ctgtagtctc | ggttccctgc | aaccaagact | 13020 |
| caacttttag | cctttcgaag | tctgtaaacc | ataatgatta | catggagctt | cgtaagtctt | 13080 |
| ttgtaaaatc | ttcgcaggtc | cagcctgttg | aacaacctga | actttctaat | ttagagaaat | 13140 |
| tcctagtagc | cgctggttac | gctaaaggat | aatggagaaa | taataatgtc | ttacgatatc | 13200 |
| gcacaactgt | ctaaagatct | gggcctgggt | gacattgctg | agcagcttaa | aggtctaacc | 13260 |
| gcctctcaga | aagctgaaga | agctcgcaaa | tttgctgctg | agcaggaagc | taaagaactc | 13320 |
| aagcgtatgg | aagacctggt | tgctaaagca | actggtgaag | accgtaaaaa | cctggcagaa | 13380 |
| gctctggagc | ttgtaaaaaa | cctggatgag | aaatccaaac | agtccgctga | agcgttcgtt | 13440 |
| aaagcaatga | actcccagca | ggaagaaatc | actggtctga | agaagaaat | caaatctctg | 13500 |
| ctggccgctc | gtgaaaatgg | tcgctctttc | gtagctgatg | gcgttgctaa | ggcaatgttt | 13560 |
| ggtaagcagg | aagatttcga | agacgaagtt | gagaaactgg | ttcttctgtc | ctacgtaatg | 13620 |
| cagaaagatg | tattcggtac | taagcgtggc | gaagcccacc | tgaaagctgt | taacggctct | 13680 |
| tcttctatcg | aagtttctac | cgaagcatac | gaaaccatct | tctccctgcg | tatcctgcgt | 13740 |
| gacattcagg | ctaaactgat | tatcggtacc | atgttcgaag | aactgccgat | gtctagcaaa | 13800 |
| ttgctgacca | tgatggttga | gccggaagct | ggtgaagcta | gctgggttga | cgcctctact | 13860 |
| tacggtactc | ctgctactgt | tggtgcggaa | gacaaaacca | agctgtctga | aatccacttc | 13920 |
| aagacctaca | aactggctgc | taaagcgtat | atgaccgacg | aaacagaaga | agatgctatc | 13980 |
| ttcactctgc | tgccgatcat | gcgtcgtcgt | ctgattgaag | ctcacgctat | cgcaatcgaa | 14040 |
| aaggcgttcc | tgaccggtac | tggtgctgcg | ggtactccga | aaggcctgat | ccagttcgct | 14100 |
| aaagacgatg | gtaaagtggt | tgctaccact | gctaaagctg | acggttctgt | taaagttacc | 14160 |
| gctaaagaaa | ttcacaagct | gcgtcgttcg | ctgggccgcc | acggtctaga | cctgaacaaa | 14220 |

FIG. 15I sequence.txt

| | | | | | | |
|---|---|---|---|---|---|---|
| ctggctctgg | ttgtttcgat | ggatgcttac | tacgatctga | tcgaagacga | agaattccag | 14280 |
| gacgttgcac | aggttaccgc | taccaccgct | atcaaactgc | agggtcaggt | tggtcgtatc | 14340 |
| tacggtctgc | cggtactggt | ttctgagttc | ttcccagcta | aggctgcaag | cgctgagttc | 14400 |
| tgtgtagttg | tttaccgtga | caacttcatc | gttcctcgtc | agcgtgcaat | cactgttgag | 14460 |
| aaagagcgtc | aggctgaacg | tcagcgcgat | gcgtactacg | ttactcagcg | tctgaacctg | 14520 |
| atgcgtttct | tcgagaacgg | cgtagttgct | ggtgcttacg | ctgcttaatt | tggctatact | 14580 |
| gccgactaaa | ggagagcttc | ggctctcctt | ttttattggg | taaaatatgc | aattcatgac | 14640 |
| agattctgat | tggagaacat | atggaggcct | taaacgtcct | gacttagagt | caaatatccc | 14700 |
| aatgttaatc | aaagcagcca | atgctctgat | tactcagctt | ctaggtattg | acgacactgc | 14760 |
| taacgttgta | gacgttctgc | ctactaaacc | agcacgcaaa | aagtacttcc | tgtcttctcc | 14820 |
| cgtgcctagc | acgatcacta | aaattacgat | taacgatcag | gagatcgata | agtcgcaata | 14880 |
| taagaactac | ccggatggta | cgctcttgct | gaaattctcc | cctccagagg | ggtatatgga | 14940 |
| agtagagttt | actcagaccg | gcttcacctc | gatccctgac | gacctggtac | tagcagcctg | 15000 |
| cttcctagtt | gatcactggg | tcaagaagga | ctaccgcgag | tctcgtacat | tcggcggaga | 15060 |
| aaccgttact | ttcaatacca | ctaaatctgg | cgtaccggaa | cacattcgta | ctataatcga | 15120 |
| agtataccgg | aggctgtagt | ggcgttgggc | gatctagctc | gacagatagt | taaagaacag | 15180 |
| ctggacatta | tgagtggtgg | tagccactct | accaagaaca | ccgtgatata | tagtgcggaa | 15240 |
| actatggata | accacaaaga | tggcaccata | ggcaaggtat | ccttccgatt | taccaagccg | 15300 |
| gtatcggagg | atttactgaa | tgttcggacg | tcctctattt | taaaagctgt | ctcgtcgtca | 15360 |
| cttaatctgg | aaggtgacgt | tggtgttatc | gataaccttc | taaatagtat | cactggtaaa | 15420 |
| aaatccaaaa | taggaagaaa | acggtctacc | ggtagggtag | aggttaactt | tggagatcct | 15480 |
| tcagatgctg | acaacggtta | cgctggtgct | atttctggcg | cttctgggcg | tttcgtctca | 15540 |
| aacacaaacc | ttagagcgtt | acttgaactc | gtagcgaaag | aatacttagt | caaggatatg | 15600 |
| aaaaaagctg | gggcacccct | taaatttaga | acggggcgtt | tcgctaattc | cttgaagatt | 15660 |
| aaagacgtgc | tgttaagaga | agacgcaggg | gcaaagactc | ctgacctcaa | catcacgtat | 15720 |
| aactacatgc | ttaagcctta | ctctgtgttc | aaccctgccg | tctctaccta | ccgcggactt | 15780 |
| tccttacggc | ctttccctgg | tgctaggaac | ccgcagaagc | tgatcggcga | ggcaatcgct | 15840 |
| aaggctgcaa | gagaccttat | ccattctaga | taccggataa | gagtaaatca | gggtacataa | 15900 |
| tgaattacag | aacaagtatt | gctgatgccc | tagtggaacg | actgaagaag | gacatggatg | 15960 |
| ggagtaatcc | cacagagttc | ttcactaata | tgtatgggaa | cgtatcccgc | cagacttatt | 16020 |
| cgtttgagca | gatcaatgag | ttcccttaca | tagcagtcca | tgtgggtacc | gaaactggaa | 16080 |
| actacctgcc | gtctgcacag | cagtgggttt | accttgaaat | tcctattctt | atctatgata | 16140 |

FIG. 15J sequence.txt

| | | | | | |
|---|---|---|---|---|---|
| aagaaaagga | tgatattaac | atgcaacttg | agaaactcat | agcggatgta | aaaacctcta | 16200 |
| ttgacactgg | aggaaattta | caatatacta | taatgaaacc | tgatggttca | actatcgatt | 16260 |
| ctgaagccac | tgacatgcag | atcacgtcgg | tgtccacaga | cgagggtata | ctgtccccgt | 16320 |
| ttggttttgc | tcaagttaac | gtaacagtcc | ggtatatgcc | tctgagaaga | gcgctggata | 16380 |
| gataagttac | agctcaggag | aaatttaaat | gtctgtacaa | ctattacgta | atacacgaat | 16440 |
| cttcgtgtca | accgttacta | cggggttcac | taaggccaac | actcaggaga | tcctagttca | 16500 |
| ggatgatgtc | tcctggagcc | aggacagtaa | ctccactgat | attaccctaa | atgaggctgg | 16560 |
| ccctaagccg | acccgcggtt | cgcagcgctt | taacgattca | ttgaacgctg | ctgagtggag | 16620 |
| cttctccact | tatatcctac | cgtatgacga | tgcaggtaaa | cagatcctgc | cggactacct | 16680 |
| actgtggcac | ggactggcaa | ctggagctgc | cgtgaatcta | gcaggtacta | ctggcgtatt | 16740 |
| ccagaatgct | actaacctgg | ttgtcaactt | taaagacaac | gggtaccacg | aactggccat | 16800 |
| gttgaacatc | tacatcctaa | ccgatagctc | ttggtctgtg | atccgtaact | gccaggttgg | 16860 |
| gcaggctgag | gttaacgtag | atattgatga | tatcgggcgt | gtaacctggt | caggtaatgg | 16920 |
| tactcgcttg | gagaccctag | cttctcagcc | gttcgaccct | aaaaccatag | ggatagacga | 16980 |
| cgctctttat | gctaagattc | agagttctta | tatcaagaac | aaactgacca | ttcttaagct | 17040 |
| gaagaacaac | gctaccggcg | gaaaaaccta | taacatcccg | atcacgggag | gttctttcac | 17100 |
| tatgaacaac | aacgtgacgt | acctgactcc | taacatcatg | tctcgtgttg | acgttccgat | 17160 |
| cggttcattc | actggttcct | tcgagctgac | tggttccttg | acagcgtata | tgaatgatgc | 17220 |
| tgccaacggc | tctatccagc | tgtacaaaga | tctggtttcc | gacctgaaag | ctgtgaacga | 17280 |
| cttcgaagtt | gcaatcatcc | tgggtggaga | gtatgatact | gctcgtccgg | cagctgttct | 17340 |
| ggtggctaag | cacgctaacc | tgaacatccc | gtcaatcgaa | actgatgacg | tgctgggtgt | 17400 |
| gtctattgag | ttcaaggcta | ttccgactca | gatggacgca | ggggatgaag | gttatctggg | 17460 |
| cttctcttcc | aagtacacca | agacttcgat | cgcgaagctg | atcagctctg | gtgacggtaa | 17520 |
| ccctgtcaca | ccataaggat | aactaatgct | atactcccta | atgcgggagt | ctagagtagt | 17580 |
| catcgagtac | gatggcaggg | cgtacggatt | tgacgccctg | tctgattaca | ctgctggaac | 17640 |
| gtcctacgaa | gagtttaaag | caaatcgtag | gacgattcac | agacgcagta | actacgccta | 17700 |
| ttcgaagata | actgctcagt | ctccttcttc | aatttctcta | actcttaact | tctctagcaa | 17760 |
| tgctctcgaa | ggtctattt | tcgagttgat | ggggtttata | gagatagacg | gaatgtatca | 17820 |
| gatgcccttg | ttcagtaata | atattgagcc | taaaatgttc | tccgtatata | ttattaacaa | 17880 |
| gaacacgagc | ttacgtttcg | ataactgttt | tgctaccacc | tgcgactttt | ctctagataa | 17940 |
| gagtgtcccg | gtgctaaacg | ttggtatcga | gtcgggatac | tttgaggaag | taggccaccc | 18000 |

FIG. 15K sequence.txt

```
actcaacagc tatacgcttg atcaaggtga ggtgctacca ttttcattac ctcaggtatc    18060
ttcgaatggg agagtgctcc caggacttat gtcagccggt atgtcattcc agcagcaatg    18120
cgaatggcga ggtgacagaa gtttattcga tatcaataag atttataata atagaagggc    18180
aatcgttaac gaattgaact catccgcttt gatatcgatg tactatgcaa agagtcttca    18240
gatagactct acgcataaca ttaaacctga tattggccta ccggtacaaa tcagaaataa    18300
atatattgtg gtggatttcc cttccactcg aatcacaaaa cgcctagact taaccgacgt    18360
gtacaagatc gattatgacg taatacctac tgagcaatca gatcctgtcc gaatcaagct    18420
aattggagaa taacaaatga gtattaacct aaaagatatt gcactggata ccaaacagat    18480
caccattgca taccctggcc taccacactt caaactgaaa gttaactacg tctcccgtaa    18540
gctctccaag aaaattctgg aagctgcaca agagaaccag tttgttaatg gtatcgctgt    18600
taaagtgcaa aacgatgaca aattcgcaga agagttcgtc aaagtggcta ttgcaggttg    18660
ggaaggtctg accgtcgcag atgttgagaa actaatgctg atcgaagttc cagaagatcg    18720
tctggaagac aaagtcgaat ttagtatcga caacgcgatg atgttggtgc gtaactccag    18780
tgccttcgag acttggatga acagcactgt cttccaccta gacactttc gtggctcaaa    18840
atcggaacct actgcttaag gaaatagatg cctttgcaga acgatgtgtc aaaggagggg    18900
actccaaaat tacacgggag cagtatctga cgatgtgcga atccctcggg gaggaaccta    18960
accccgaggt acttaaacgt ttcgtagaga tccatgactt ccctgaaatc gcacagaccg    19020
ctctaacaat atataacaac ttatcggata actatatccc cggagattat ccaacctatt    19080
taggcaagga taagagtgct ttactagttt tcttcgatat ctacggagtc gaagacgctg    19140
atgagaagag ccttatactc caaatcatca atatattcga ctcacatgcc gtggcagcct    19200
ctcgtaaacg cgttgaagca gctattaaga agtctaaaat gaagtcttct agtaggtagt    19260
gagttacagt ttcctccaac gggcgttcca cgtgaggctt ggcctagggt taatgcccta    19320
ggcctttta ttggaaaaaa tcatgacaga tagactaata cgagaattac ttgtagatat    19380
caagcagcgt ggtggatcca aagccgctaa acaaatcagg gatgttgaag ctgctttaga    19440
cggggctgct cagagctcag agggtctaaa tacaagcttg gcaaacttc ctgggtcttt    19500
cacggcgctg gaacgatctg tatcacgtac tgctaagtcg ctggagaaat tatcctcgac    19560
caccagcatt acagcattag cagcgtctat cggcatgcta agcggcaagt ttacctcgtt    19620
cgaggttgac ttggctaaat ccgtactaaa aatcaacgca aacctaaacg gggtgacttc    19680
cgccgctaac aaaatggcct ctggttttga cactgcagcc acttcttcgg ttgcggactt    19740
aaaccgcgtc aataaggctc ttcaggagtt agatgcgcac gcctcttcag tagctaaagt    19800
gttgcagacc ttgaaggcgg gggccgggtt agaatctatt agctctagtg ctgctaaggc    19860
tagtacggat cttagccacc tagtatctgg ggtggaaaag ataggtaacc aattagctag    19920
```

FIG. 15L sequence.txt

| | | | | | |
|---|---|---|---|---|---|
| aatggcggag | caagccgtgc | tggcaggcag | gtctcttcag | gggctgaaag | ccgactcctt | 19980 |
| aggggctgcc | ggagagcatc | tgagtaaggc | tgcgtccggg | atttccgtag | ctgtatcttc | 20040 |
| tatgggcgaa | gaggtgaaca | agctaaacaa | actacttctt | gagttggcag | taaaggctga | 20100 |
| tttagcgagt | aaatctatag | caaatattgc | accagggacc | aaactgaata | gtctgggaac | 20160 |
| tgaaatccag | aagattaata | ctagtttagc | cactgcagcc | aatacctcgg | tagctgagat | 20220 |
| atctaagatt | aaagcagccc | ttacgtcttt | agtatcctct | accgctacag | ctgccgcttc | 20280 |
| aatgaaaacc | gtaggaaccg | gtagtggtct | gagcaagcta | atctcagaga | tatcagcagc | 20340 |
| cacctcagct | tccacttcgg | atatctctaa | agtaacagcc | gctttaaaac | agcttaacgt | 20400 |
| agatgctacg | gcagcaggaa | aagcactgca | aagtattaaa | gcaggcgcaa | atctttcttc | 20460 |
| tgtacctaca | gttgttggaa | agataggtac | ttcaatgacg | cagttgcgtg | ctcagttaga | 20520 |
| aggatctgta | accggtatcg | agaaaagcct | aaatgatcta | tctagagctt | ttgccactat | 20580 |
| gggaggtacg | ggaaacctga | atccactggg | taactccatc | agaggtatga | tcccgtcact | 20640 |
| cacccagctg | gctaaggccg | ctgtgcaagt | taactccgct | ctgtcaaaaa | tacaggcagg | 20700 |
| caggggcgta | cttcaattac | ctacccaatt | caaagcagta | acggcctcat | taaatgccct | 20760 |
| ggagactaaa | ctggcctcta | cgtctcaaat | actagagcgc | ggattctcca | agggatttca | 20820 |
| ggatatggcg | tctaaatcaa | cctcgtcatc | tacgagaatg | attaacaact | tccagaaagt | 20880 |
| ggtaccggag | ctcaacgcta | ttgaagctgc | tgctatacgt | tctgctgctg | caatagacaa | 20940 |
| gctaatagcc | aaacgtatac | gcctcggaca | agctggggga | ggggtaacc | ctgcagcgtt | 21000 |
| caatatgggt | gccttagtag | cggaaatgaa | caggattgta | acctccattg | aagctatggg | 21060 |
| caacaaaatg | aataccacca | tggctgatat | ggcacggagt | acggacaagg | tatctgacaa | 21120 |
| attaacagat | ctaaactcgg | gagttcggga | tgttaatact | ggtttaggtg | ggttgaattc | 21180 |
| aacgttaacg | ggtacgggta | gcgctgctaa | tagggcgtcc | agagcgttgg | gaaatacttc | 21240 |
| aggatctgct | cgcggagcta | ctaggaactt | cgcagcacta | gctatggtga | ctggccctat | 21300 |
| gcctcttatc | tacggtgcta | tagcctctaa | cgtatacgtg | cttaaagcag | cgttcgatca | 21360 |
| gctaaaactt | ggagaccagc | tgaaccgctt | agaacagttt | ggatctatcg | taggagcgaa | 21420 |
| gacaggtaca | cctattcagt | cccttgctgt | ggcactgcag | gaagctaccg | gccacgcggt | 21480 |
| atcctttgaa | gaggcaatgc | gtcaggcatc | tactgcggcc | gcgtatggtt | tcgacgctaa | 21540 |
| acagattagc | gagtttgctc | tagttgcacg | tagggcagcg | gctactcttg | gcgttgatat | 21600 |
| gaccgatgca | ctcaaccgtg | taatcaaggg | tgtgtccaag | caggaaattg | agcttctaga | 21660 |
| cgaattaggt | gtaaccatcc | gtttaaatga | tgcgtatgcc | gaatacgtta | aaatacttaa | 21720 |
| tgcggctaac | actggtataa | cgtataacat | tcagggtcta | acttccttcc | agaagcagca | 21780 |

FIG. 15M

```
                                    sequence.txt
ggcatatgct aatgcggtag tagcagagtc taccaaacgc ttcggctacc ttgatgaggt    21840
actacgagca accccatggg agcaatttgc ggctaatgcg gattctgcat tacgcaaggt    21900
tcaacaagca gctgctaaat atctaggtcc agttattgca tctataaacg cagcattcta    21960
tacgtctaag gcttcggtat ctgcagaggc agctactgcc cagcaagagt cgattaagca    22020
aatggacggt aaagactcta acgcagtggt catgaacctt gaggcttctc agaaaggctt    22080
ggatgatgca gtcaaagcaa aagaggaagt aaaaaataaa ctcgcagctc ttaataagga    22140
gataatggat agagaggcga agatggatat gtccactgca ctggccacag ccgccaacta    22200
tagtgggttc ggtaatctgc ttaccctggg agcctctaaa gctaacaaag aatttacaca    22260
acagactgca gatatgcgta gacaggcgta tatgttacag caggagttag cagattctgc    22320
gggagctatc caaaaatgga aagacgccag ggactccgct ctatctaagg ctcagaaaga    22380
gaacccagaa ctggcgggga aacttaatat agggcagaac gttgaagcaa gtaatggact    22440
atacaccttt gacaacgcag cattagacgg ggcagttgct ctacggaagg agttcaataa    22500
tataaagaaa acttccggag atctgagcaa cgatatccag aactttgcac aggactctaa    22560
cactgcgtct cgagctactg cagcactggg tgatgcactt aaggcggttg agtcattggc    22620
gggtggatct acggaaaaag ccaatcaaat gaccaaggac cttaatttgg gctattccac    22680
cgtaaccgag atgaacactg cgtataaagc catgtctaac tatcagaaga tagtgaatga    22740
tgaggctaag tctaagctag atgttgagaa acgtatagcg gaggtctacg ctgccactcg    22800
taataaggat aaggcggaag aagctggtag agccctagaa atgcagcaac ttagcgcgaa    22860
gaaagaggca ttgaaagctg tgctggcgac gaacaaggac aacaaggcta ttcaaaaaga    22920
gttgaccctg ttagagacgg aagagctcaa agtgaagaac cagggcatgg aagcgactaa    22980
gaaggagaaa ttctataagg ataagatagt aggcatagat cgagaaatag cactcctaaa    23040
taatcgcact atgacagatt ctcagtataa cgtggcgaac cttaaattaa atctacaagt    23100
agagaaagat aggttagcct tactgaagac tcaggcagat aaggagaagg aagccgaaca    23160
gtctagacgt aacattgcct ctattgaaag ggaaatctgg aaagagcagc ttgaccgtaa    23220
tgccaaaact gctgagatgc gtaaagaaga attcgagcgc aatcaaagca tgaagcctct    23280
aatgggagag tcacagaaaa tgcaggagca gctagcgttc taccaagaaa tgaaggaatt    23340
cacgaaaggt aacgctgatg aacaggcgcg ttggagcaag gaaattgcta acactactgc    23400
gcaaatggcg gctctcaaag ctcagcgtac tgcacagatg atggatcgcg taggacagtc    23460
cttgggcgca gactatacgc ctactactgg cctggagggg gaggataaga aattcgccga    23520
catggaaaac cagatggcgt catacgatac cgctatcggt aagctctctc agctaaattc    23580
ggaggctact gctactgctc aaagtatggg gaacttagct aacgctatga tccagttctc    23640
tcaaggatct ctggatacta cgtccatgat tgcagcgggc atgcagacag ttagccagat    23700
```

FIG. 15N sequence.txt

| | | | | | | |
|---|---|---|---|---|---|---|
| gatcagctac | ggtactaacc | agcagatttc | agcaattgat | gcagctatag | cggcagagca | 23760 |
| gaagcgtgac | ggtaaatctg | agcagtctaa | gaacaagatc | aaaaagatgg | aagcggagaa | 23820 |
| gattaaactt | cagcaggaat | ctgctaagaa | gcaaatcatt | atccagacag | cagtagcggt | 23880 |
| aatgcaggca | gcaacagctg | ttccgtatcc | gttctctatt | cctctgatga | tcgcggctgg | 23940 |
| gcttgcaggt | gctctgtctc | tagcacaggc | gtctagtgct | accggaatga | ccgatatagc | 24000 |
| aggatctggt | ggtgaaaccg | cctcttacct | aaccttaggt | gagcgccaga | aaaacgtaga | 24060 |
| cgttagcatg | ggcgcaaacg | caggtgaact | atcttacgtt | cgcggcgata | aaggcatagg | 24120 |
| tagtgctaac | ggatttatcc | ctcgtgcaga | aggtggtaat | acctacccag | gtgtctccta | 24180 |
| taagatgggt | gaacacggaa | cggaagttgc | aactcctatg | gtgcctacca | aggtaactcc | 24240 |
| agcggataaa | gtggcttctg | aaacttcttc | tggcggtgct | agaagaccgg | ttaatctgaa | 24300 |
| catccaggca | atggacgcta | agagctttat | ggagtacgca | ttggaaaacc | ctgcggcatt | 24360 |
| ccaggcagct | gtagagttag | ccttgaatga | acaagggctg | agcttaaaga | acctgaatta | 24420 |
| actaaactaa | agggaggacg | taattgtcct | cccttctttt | tggaatttat | aaaattatct | 24480 |
| tgaaaatttt | tcttgatatg | actataatat | taacattgag | aggagaaaac | aaaacatgag | 24540 |
| attaccagat | cccttacac | atcctcagta | taacggcctt | gggtttgata | aagctacgct | 24600 |
| gatcgataat | gatccagtga | tcagagacga | gctaccaaac | ggcaaggtta | acgaagttaa | 24660 |
| aacagccact | cagtactggg | gtcttaacat | tagttatcct | gtgatgtttc | ccgacgagta | 24720 |
| tgctgtactt | tcgtcagcaa | ttctagagta | taagcgtacc | agaggctatc | tcgacgttat | 24780 |
| actcccacat | tacgagtctt | accgagtaag | aggggatgcg | aacaactgtc | gcattgccgc | 24840 |
| tggacaaaaa | ggctccacac | tggttatcac | caatacgaat | tccttatctg | gagaacctaa | 24900 |
| gccaggtgat | ttattccagt | taaccacaca | tccaaaggtg | tataagatta | catcttttaa | 24960 |
| aaacgtagca | ggagtatgga | cacttaatct | ataccctgat | ctgttgctca | ctaccaacgg | 25020 |
| ctccgagaga | ccacgtttca | atgggattct | tttccaaact | aaattaatga | acggagattc | 25080 |
| attcagcgaa | gagatcacag | ttgatggtgt | atacgacggg | gttaacctag | ttctgagaga | 25140 |
| aagtctatga | gacagatcct | tccttctgcg | aaagcctacc | ttgccaacaa | tgacaagata | 25200 |
| cgattagcgt | atcttgtctc | tatcgaactc | ccggggtcca | cgggtaataa | cgctgtttat | 25260 |
| gcttatatga | cggactatat | gagagatatc | aactatggtg | gtatactctt | ccaatcaggg | 25320 |
| aaaattaaaa | caattagcag | ccacaaacaa | aaccgtacgt | taaccgtcgg | cagtttgagc | 25380 |
| tttagtgtta | ctggtacgga | tgccaacgaa | gtcattaagc | tcgtgcaaag | tggtgtatca | 25440 |
| tttttagatc | gctctatttc | tatatatcag | gcgatcatcg | acgacaatgg | ggaaatcctt | 25500 |
| ccagtggacc | cagatactaa | tggccccttga | ctcttcttta | ggggtaagat | tgtaggtggt | 25560 |

FIG. 150

```
                                   sequence.txt
ggtatcaaag aaagtaatac agtatccgga gttggtactt ctgttataac ctggaactgt     25620
tctaatgaat tctatgattt tgagcgggtt gctggacgct tcacagatga cgcttcccac     25680
cgaggacttg agattgtaaa tggagaatta ctgccttctc acggtgccaa acgaccggaa     25740
taccaagaag actatggatt cttccacgcc aacaagagcg ttaacttcct agctaaatat     25800
caagtaaaag aagaacgata caagctagaa tctaagaaga aattattcgg tctctccaag     25860
agctacagcc ttaaaaagta ttatgagact gttactaaag aagtagacct ggacttcaac     25920
cttgcagcca aatttattcc tgtagtatac ggtactcaaa aagttcctgg tatcccggtt     25980
ttcgcggata cagagagaaa caatccaaac gttgtgtacg tggtttacgc gttctgtgag     26040
ggtgagattg aaggattcct agacttccag tttggggacg cccccatgat ctgtactgat     26100
caaactgaca gtacatctcg tacatgcttt ggacaaaaaa gggtgtcggg agatactatg     26160
gcaagaattt ccacagggct cccatcaaca tctctctcca cgcatggtca agaatacaag     26220
tataatgacg gtaacggaga tatacgaatc tggacattcc atggcaagcc agaccaaacg     26280
gtagctacgg tactaagaga cattgctgct gctaacaatt tcttccttca aggagagaac     26340
ggtaatggtc cggagtactg ggattctagg tacaagttat tagacaccgc atacgctgtc     26400
atacgtttca ctatcacgga gaacagaact gatattcctg aagtatccgc agaattaagc     26460
ggacgcaaag tgaaagtata ccaggcagat ggttctgtta aaatggataa aacgagtcag     26520
aatggtgtgt ggcaaacatt tgactaccta acctccacca cctttggtgc aagtatcccg     26580
atagacagaa tggtgattgg tgactggaga aaagaggccg atctattaaa cattatagac     26640
acctcttatc aaactagttg gcaacctttc tggagatacg ttggatggga gagctggaca     26700
gccgaaaaca gacaaataat gcaaatgaac acaatcctgg ataactccaa ctctgtgttc     26760
aaaaacgtgc aggagctatt agaatccttc caggggcgt tgaataacct atcaggtatc     26820
ttccgcatca ccgtagagaa agattcaaaa actccgctag aacttaattt cctagatact     26880
tatggggacc tggatctatc agatactaca ggccgtaata agtacaactc agttcaggca     26940
tctctgattg atcctaccct gaactggaaa accaactcta taacgttcta taattctaag     27000
tttaagaatg aagatcgtgg agttgacaag aaacttcaac tttcttttgc taacataacc     27060
aactactaca ctgctagaag cttggcagat agagagctta agaagtctcg ttactctcgc     27120
tctctgagtt tctcttttacc ttacaaattc cttggtatag aacctaacga tcctgtagta     27180
ttcacctacg atcgttatgg ctggaataag aagttcttcc tagtagatga ggtggagaac     27240
acaagggatg gtaagataaa cgtaactctt caggagtatg gtgaggatgt atttattaac     27300
tcaacgcagg tggataacag tagcgaggcc gttcctgaaa tatccaataa cgtcctgcca     27360
ccaagagact ttaagtacac ccctacacca ggtggaatgg taggtgatgt tggcaaaaac     27420
ggagagcttt catggcttcc tagcttgaca cctaacgtag tctattactc gatacgtaaa     27480
```

FIG. 15P sequence.txt

| | | | | | |
|---|---|---|---|---|---|
| tccgaccgcg | tggatcctta | tattgtgcag | cagactgctt | tcacacctaa | cgttagaatg | 27540 |
| ttccaagata | tcgtgggtga | gcctgctggc | ctgactattt | tcgagatccg | cgccgttgat | 27600 |
| attaatggtc | gtcgtagctc | tccagtaaca | atttctgtag | atttgaactc | agctaaaaac | 27660 |
| cttagtatgg | tggaaaactt | ccgagtgctt | aaccttgccc | ctgaccctgc | tgaatgggta | 27720 |
| ggacctgact | tagagttagg | gtgggacaag | ctgcaagaag | aggggctgat | ttcagggatt | 27780 |
| ttctacacgc | ttgaaataag | gacaacact | aataaactgc | ttagatccgc | aaagatcacc | 27840 |
| agtttatata | actacagcta | cctgttgggc | tataataagc | tcgactacaa | ggccaacaac | 27900 |
| tcgaatactt | tggggattta | cagagcactt | cagccaagaa | ttcaggcgga | gggaccaaag | 27960 |
| ggcgagaagt | cggttgcatg | ggcatatatc | taaatgattt | caaacatagc | accagctaaa | 28020 |
| atggtactgc | agaatatcgt | gaccggctat | acgattgcga | gtattcagca | ctcaatcttt | 28080 |
| tccgattacg | acgtaattgg | tagaactttc | tggctaacta | cgggtggggt | aactacccgt | 28140 |
| agggacttta | ccggcgttga | tacattcatt | gccacaatta | acaatctaat | cgctggcgct | 28200 |
| acctactctg | cccagggtgc | tttctatgac | tcgatggttg | atgcagagct | gatggctgct | 28260 |
| aaagtaggta | tgaacctctc | tagcaccatt | aacttcaaga | tgaaaactgc | tccgaagatt | 28320 |
| accaaagtgt | cctcttttgc | agaatctgtt | gacgtgggtg | tgggtgctcc | tatggttgtc | 28380 |
| gtagagcttt | ctggggaggc | cgaatacgtt | accatcgaaa | tgaaacctga | gggctctagc | 28440 |
| acctggacta | aatactaccg | tggtccaatc | actgagcaga | tcatctttgg | gggtgttcca | 28500 |
| gttggcagat | acaatatccg | ggtatctggt | gttgtcacta | tgccagatgg | tgttactgtg | 28560 |
| gatgtttctg | ggtatgatac | ctggccgtca | ctgtttaacc | tgacctacaa | cttcactcca | 28620 |
| ccgtctgccc | caactaacct | gcgtttcaaa | actgcccaca | tccaagatgg | tatggagcgt | 28680 |
| tttgacgttc | gcctggaatg | ggattggact | cgtggtacgg | gtgctaacgt | tcgtgaattt | 28740 |
| atcatccagt | atattagtaa | cgatgagttt | gcaaaaactg | gatggactaa | ggccaacaag | 28800 |
| ctaaacgtgg | gtgcagctaa | agctggtact | atcactagct | tcccttacaa | aatccgccac | 28860 |
| cgcttccgtg | tactatcggt | tgcttgggc | ccagatactc | agtctataac | taactctaac | 28920 |
| gaggttactt | atattataga | cgagagcacc | actttcgaca | atgcattcat | taacgagacc | 28980 |
| ggtgtagaaa | tgacctacgc | aggtatcaag | ggtaaactct | ggaactctaa | caccaaacag | 29040 |
| tgggagcaga | ctttcttagt | cgatgctgct | acaggtgcag | tagttcttgg | tacactcgat | 29100 |
| gaaaatggta | aagcgccgat | ttcattcgac | cctgttaata | agattgtaaa | cgtcgatggt | 29160 |
| aaagttatca | ctaaagacat | taatgctgct | aacgtaattc | ttactaacct | gaccggtaaa | 29220 |
| gataacccgg | caatcttcac | tcagggtaag | aagtacggta | ataacgcagg | tggtgtctgg | 29280 |
| atgggtgttg | acaacgttga | cggtaaggcc | aaatttgacc | tcggtaataa | cactcagtat | 29340 |

FIG. 15Q

```
                                   sequence.txt
gtgcgctggg acggtgatac tcttcgcatt tctggtaacg ttgtaatcgg tactcctgga    29400
ggcgatgtag accttgaaac cggtatgcag ggtaagcaga ctgtatttgc ttataaactt    29460
ggtacatctc tgccaagtcg cccgcttgac caagtttatc caccagctgg atggtccgca    29520
ttcccgccta accgcactgc tcagaatcag aacgtgtacg ttgtgcaggg tactctggat    29580
cctaagaaga gtcctcctgc tctagtagac ggtaccaact actcagctgc atcccagtgg    29640
tctggtgtcc caggtactgg tggtactgat ggttctaacg gtgattacac tgttcagatt    29700
taccagatca gtgctagtaa gcccacgaaa ccaggcaata tcaatgaccc tagcggttgg    29760
agtcgtaccc caccgactgg aacccctctt tggatgtgtt ctggtagatt caatggcgat    29820
actaacgctc taactgttga ggggttggtca gacccgatcc gagtagacgg cgagaaaggg    29880
gctactggtg ctactggtgc tactggtcct caaggtcctc aaggtccggc aggtggttca    29940
gtagaagtac agtggtctaa agatggtact actaactggc atgcaaactt tactactggt    30000
gatatctaca tgcgtcagcg tgttggtaca ggtgggtgga gttcagctat ccgtgcagtt    30060
ggggaagatg gtactaatgg tactcctggg tctaagggta actacattgg gatgcgcttc    30120
cgagtggcgg ctgagaaacc tgccactccg actggccaga ccccttcagg ttggtcagat    30180
gcacctcctc agggaaaccc tctatggatg gttaaagctg agttcaacgg tcaaaccaac    30240
gccctagtag gtacgtggtc agaaccagtt cgtattgatg gcgaaggtat tggagtaaac    30300
ctgtatccgg ttaagaaaac actggatcag tggaccggaa tgagcaacgg tactatggtt    30360
aagaacccag atacctcag ctttaccata accaacacag agagcactac ctcctctacc    30420
ggaccgggtg cacatcctgt tccgttccag ggttcacaag gtcctatagt tgagattcca    30480
gtaaagccga atacagcgta catcttcact tatgaggtta gtactgatag caccagcttt    30540
gttctgagag acctgttact agagttctct agcattaccg gaagttttac caacttccaa    30600
gagttactga ctggagccaa aggtaagcag gaagctaaga ttgtcactcg tgctgatact    30660
aagttcctga gcttccgtcc aggtgtccgc actgccggag ctacggttac ttattctaat    30720
ctaaaacttg aagaaggcat taaagctacc gcttacagcg tagaggcttc cgacagtatc    30780
ggtgagaaag gagaccaagg tactcagggt ccacaagggc ctcagggtaa tcagggtcca    30840
cagggtaatc aaggcccgca aggtgctaag ggtgataatg caaaaggatt cagcctctct    30900
tctctcggtc agacgtttac gtacgacgca gaaggtaaac tgaagtccga tgcaaccatc    30960
ctgttccagg ctttccgtca gaatactact gcaaacgtta cttggtcagc caaggacgag    31020
aaaggtggga acatcactct gacaagtact agcaatactg gtgctacact gaccgccgct    31080
aacttcaaaa catcgaagtc tgtagtagtt acagccgtct gtgatggtat caccgatcag    31140
atcactattg tgcgtctaga cgatggttcc aacgctctcg tagggcttct gaccaacgaa    31200
ggttccacag ttctagcgaa ctatgctggt tacgtgcaaa actatagtac tggttctggt    31260
```

FIG. 15R sequence.txt

| | | | | | |
|---|---|---|---|---|---|
| gacttcaaag | tattctatgg | ggcgaaggat | atcacctcag | aatgcacctt | cagtactatg | 31320 |
| gagaagaata | accttgatgc | tgatattact | tcagcgggca | aatatacttt | aaaaggtatg | 31380 |
| ccggctggta | ctgatgttat | caacggctgg | gtcgacttac | gtgctgtaca | ccctacttac | 31440 |
| ggtgccgtgg | tccgcagagt | ggcaactact | aaatctatcc | ttgcaaaagg | ttatgatcgc | 31500 |
| gttattacca | cttcattcga | gaacggaaat | aagggtacct | ggtcgactgg | tagtgtccaa | 31560 |
| ggggtttctg | gtgccacaat | tgtagccgca | ggtttcagca | aggccctagt | gatctctgct | 31620 |
| agagactgta | tagaagatgc | taacgcattc | cctgtagtag | ctggtcagaa | atatagactg | 31680 |
| ggcatgtgga | taatggctag | tgagtctaaa | gtcaatatca | acatgggaat | gcgaattgta | 31740 |
| agggcggccg | acggagttgt | tgattggcaa | ggaacccta | tgattgcaca | aggtactgta | 31800 |
| gtacctggtg | gctggtccta | catcgaaaaa | gagtttactg | ttggcagttc | taataccggt | 31860 |
| atagcaatgc | cgtggatcca | gatggctggg | tcttctggta | gtgacttagg | taaagcttac | 31920 |
| gttaccgata | ttcacatttt | cgccctagaa | atggatgggg | agaaaggtga | tactggtgca | 31980 |
| actggtgcta | caggttctca | aggtccacaa | ggtccacagg | gtaataaagg | ggacaaaggt | 32040 |
| gatactggtg | caactggtgc | tcaaggccct | gctggtagct | ctgtaaacgt | ccagtggtct | 32100 |
| aaggatgggt | ctactaactg | gcatgctggt | ttccaacctg | gcgatatttt | catgcgtcag | 32160 |
| caggttaatg | gagtttgggg | cagtgctatt | cgtgcagttg | gcgaagacg | taaaaatggt | 32220 |
| gctgatggta | ctgacggtga | ctacatttca | atgaagttta | tcgttcagga | taccaaacct | 32280 |
| ggcacaccta | ctggtaacaa | cccaggtagc | tggagtgatg | ctcctccagt | tggtagccct | 32340 |
| ttatggatga | ctaagggcac | tatgaatgct | agcggtcaac | tacagggtac | gtggtctaat | 32400 |
| ccggtccgcc | tagacgggac | tatcaaccct | aacctgttcg | cagtacgtaa | gtggatggca | 32460 |
| gggatgactg | gtacggaagc | cggcacatct | aagaacgata | tcgagaagct | agcgcatacc | 32520 |
| ttgactcgta | cttccggaac | tgataatacg | gctccagggt | gctatgcgac | cccgtatcta | 32580 |
| ggtagtgggg | cgttttccca | tccagtgact | ccaggtaaac | gctacactct | aacctataat | 32640 |
| atcgacgcgg | ctagcgaggt | ccagacccga | gatactatat | tctggcaggc | taatccagac | 32700 |
| tcaggacaat | ccacctacat | agaggaactg | aataccggga | cgtctataaa | ggttaagcgt | 32760 |
| acctttgtag | ttcctacagg | tatgaactac | ctaaccctac | gcccttctgc | tctgacactt | 32820 |
| aacgtagcga | ctacgtggag | caagattaag | ctggaagaag | gcggagagaa | aactgagtat | 32880 |
| caagtagaat | actcagacag | tatcggtata | gtaggtaaat | cagttttagt | acagtggtct | 32940 |
| aaggatagct | cttctagtaa | ctggcatgat | accttccaaa | caggtgactt | gttcatgcgt | 33000 |
| cagaacgttg | acggtgtttg | gggtcctgcg | attcgtgcta | taggtgagaa | aggtgagatt | 33060 |
| ggtcctgacg | gtaagaaagg | taactacacc | aatatcatct | tccgtatttc | ggatactaaa | 33120 |

FIG. 15S sequence.txt

```
ccagctaaac ctactggtaa caaacctacg gattggtttg atgctccacc tgatggttcc    33180
cctctttgga tggcaacagc aacgtttaat ggggatacta acgctatcat tggtgcttgg    33240
tctgaccctg tgcgaatcga tgcttccggc gtaggcgaaa acttcttagc gttcaaagag    33300
tggatgatgt ctattcagag ggctgagggg acgggctctt cagttagcaa gaatccggac    33360
cagatgagat tccgggtaac agctgggcca tccagaaatg acgcgtacac tacccttac     33420
caaggaaccg gcacacattt tatagaagtg tcgcctaata ctgtgtatac tttatcattt    33480
gaaatggaaa ctgctgtgtc cactagaatg atgctgttgc agtttgataa tggtaatggg    33540
ggcacgcacg cacgtaacaa tcaggttata tcaaccagta ctggtataaa cagtctgact    33600
attactacgg gtgctaacac tacccacctg tctatgcgta tgtcaatctc taacatggga    33660
gagactaacg tactgatgaa acctaagctg gaactcgggg cgtttcctac ggcatacgtg    33720
gcgcatccta gtgatctact tggtaaagat ggtgctactg gagctactgg tcctcaaggt    33780
ccgcagggta acactggtgc tactggtgct acaggcccac aaggtagtaa aggtgacaca    33840
ggggctactg gtcctcaagg tcctcaaggt ccgaaaggta acgcaggtga aaacgctaaa    33900
ggattcgccc taacgtcaga ttatcagtca ttcgtgtatg atactgtagg gacattaaa     33960
tccgctacta ctattctgtt caagggacta aaacagaata ctactgcagg gatcacgtgg    34020
agtgctgtaa ataatacggg agctgcagta acactgatga attctggaga taaccgtcag    34080
ctaaccgctg cgaacttcgg cgcctctaag tgggttacga taacagcaac ctgtgatggt    34140
ttatcagatc aaattactgt ggttcgtttg caggacggtg agaacgtgtt gaccgctgtt    34200
atgacaaatg aggcagctac ggtacttgct aactactccg gatattgcca gagttacgaa    34260
aacgccaaag gtcagatgag agtttggtac ggaagcaccg atgttactgg tcagtgcact    34320
ttctctgagg gcggaagaag taacgtaact cctagcatca actcagcaaa tgggaactac    34380
tccgttactg gtatgttgga tgggaccgat attaccgaag gttgggtgga cgttaaggct    34440
actcatccaa aatatggagc aattaccaag cgttttgcgg taactaaggt attcctagcc    34500
aagagctatg agatggttat caccaatacc ttcgagaatg gtaacaaagg ttcatgggca    34560
ggagctctgc agagtgtttc cggcccaaca aaccagagca tctctaaggc gctgcgtatc    34620
acagctagag ataacctaga gggtaggaac accatcccag tagcagggcg gcaaaaagtc    34680
cgtatcagat tctggtacaa cccactagga ttagaggaag ccatttttag agtaggcttt    34740
attgttcacc gcaaagatgg gggcaaaggt tacccctcca gaactgtggt tacgggcccc    34800
gctcctaata gctcctgggc gtacttcgat caagagttga ctctaagtgc taacgatgag    34860
ggtattgcct ggccgtggtt ccagttagat aacaaaactt ctggttcttc attagggtat    34920
atgcttgttg ctgacataca cttcgaagat ctatccatgg atggtgcaga cggagctact    34980
ggtcctcaag gtccgcaggg taacactggt gctacaggtc ctcaaggtaa caagggggat    35040
```

FIG. 15T

```
sequence.txt
actggtccac agggtccaca aggtcctgca ggagcttcag ttggtgttca gtggtctaaa    35100
accggcaacg cgagcgattg gcacacaaac tatgctactg gcgacattta tatgcgtcag    35160
caagttaacg gtgtgtggtc ttcggcaatc cgcgcagttg gcgaggatgg gcgggttggt    35220
gctgatggta aatatacctc cctgagattc caagtagctg caactaaacc tgctagacct    35280
acagggaact ctccggctaa ctggtctgat tcacctccag aaggttcccc actctggatg    35340
gttaaaggtg agtttgactc cagcaaccaa cttcagggaa cctggtcaga tccagttcgt    35400
ctggacggtg agacggtcaa cctcaacctg tttgctaaca aagcatggat tgcgtctata    35460
acgggtgcca gtggtagtgg atctgttgta gccaaaaacc ctgacgaact acgcttacgc    35520
attaccgcag gttctggtgc aactgacgcg tataccatgc ctagtggtgg tgatggtacg    35580
ttcttcacta aagttaccgc aggtaagcgc tacactatgt cgttcgacac ggatagtgct    35640
ctggaaatga gaatgcatgt gttctttatc caggcaggag caaatactac tacctcatca    35700
ttctcttgga tagcgtcaac aactgctggc agaactagct ggtcgttcac tgttcctgca    35760
ggatgtgata gggtatctgt ccgtgtgtca ctgaacaaca acccaggtgg aaccaacgtt    35820
gtttccaata tcaagctgga agagggagat ttcgccacag cgttcattag gaacgagctg    35880
gatactattg gtgctgatgg ttcacaaggc ccacaaggtc cacagggtag taaaggtgat    35940
aaaggggaca caggagctac tggtccacaa ggtccgcagg gtccaaatgg tactagcgcc    36000
aaagcctttg ccttaacatc cgatagcctg tcctttagct tcgatactag tggtaacctg    36060
aaatctaatg gtactatcaa gatcgatagc tggagacaga ataccactgc tgcaataacc    36120
tggactgcca agaaccaagc agggagtaat ataactttag gtggcactgc tactaacaag    36180
actataacct ctgctcagtt cggaagctca gagtacgtaa cagtaaccgc gacgtgtgat    36240
ggaataaccg attccattac aatagttagg ctgcaagacg gggtgaactc tctagtcggg    36300
tacttaacta acgaagcggc taacctgtcg tgtaactcct acggttttgt gcagaattgg    36360
gatggcacta cgggtaactt taaggtgttc tacggaacgg tagatgttac cagtcagtgt    36420
accttcggag tggaggataa gagcaatctt aacggcaaca tagggtcaag cggttattat    36480
gcccctagcg ctatgccaaa cgggctggaa attacctctg ggtgggtaga ttataaggct    36540
acgcatccta agtacggaac acttattaag aggtttacac tcaaaaagag cctgcccggg    36600
attggttacg acagagtgtt cacgggggtcc tttgactctg gtaacaatgg atcgtgggga    36660
cgtacggtag ttgacatcgc tacgggcagt cccggaggac acaccaaggc tatacagtgc    36720
acctctaggg acaccatgga aagtagtaac tggttcccta ctcgtaaggg gatgcgctac    36780
cgtgtaactg catgggtgaa caactctgag ggtgagtatc agctaaggtt aggcctccat    36840
acccagaact cttctggcag cgttaacact ggttacccaa ctatgctagc cgcatcagct    36900
```

FIG. 15U sequence.txt

| | | | | | | |
|---|---|---|---|---|---|---|
| aaggattccg | agggatggaa | actagtaact | ggtattgtca | cggtaggaga | tgggtctact | 36960 |
| gcggagactg | gtagggcaag | accatttatc | cagatgaatg | gtagtgctag | cccttcggc | 37020 |
| aacgcttacg | tagctgctat | agcgatcgaa | gacctatcta | tggatggtgc | agatggggca | 37080 |
| acagggccgc | agggtccaca | aggtaatact | ggtgccactg | gtccgcaagg | tgataaaggg | 37140 |
| gatactggtc | ctcagggtcc | acagggtcct | gcaggtaact | ctgtaaacgt | tcaatggtct | 37200 |
| aaggacgggt | ctactaactg | gcacagtacg | ttcacttcag | gtgatctgta | catgcgtcag | 37260 |
| caggtgaatg | gatcctgggg | tcctgcgatc | agagcagtag | gtgagaacgg | ggctaatggt | 37320 |
| acgccaggtt | ctaagggtaa | ctatgtgagt | atgaagttcg | ccgtaatggc | tagcactcct | 37380 |
| agtaggcctt | ctggtagtaa | tccggctggc | tggtcagata | gccctcctcc | aggtaacccg | 37440 |
| ttatggatga | ttaaagcgga | gtttaatggg | gagactaatg | ctattatagg | taattggtca | 37500 |
| gatcctattc | gcctagatgg | ggatagtatt | aacgagaacc | tgttctactt | taaagcctgg | 37560 |
| ttagactcga | ttaccggagt | tgcaggcaac | ggttcatcta | taggtaagaa | ctacgagtta | 37620 |
| ctaagggcta | ggataatcgc | aggtacagga | gttaccgatg | cgtatacct | cccatcagat | 37680 |
| ggatccgcct | ccatgttcac | ctaccttcct | ccaagcacca | catatacgat | gtctttcgag | 37740 |
| actgataacg | ctgtagaagt | tcgttgtcac | gtattttggt | acgctaaggg | aagcaatacc | 37800 |
| actggaggag | tgctgaagac | tattgcatct | actactgcag | gtttgagcag | ctttaccttc | 37860 |
| accacgccgg | ctaattcgga | taggatatcc | gttaggttct | cagttaacga | atctggggga | 37920 |
| aataacgttg | taggaaggtg | taagattgaa | aagggagcct | tcgtaacgtc | atatgttcgt | 37980 |
| aaccagtatg | acgctgtagg | ggatcgtggt | ccagggttct | atactcaggc | gatcacaaac | 38040 |
| ttaaccggat | ggaacgatac | tcaggcagca | tctttcttcc | agtcaacatt | tggtggacct | 38100 |
| ccggttaagt | atgacgtact | aactcagtat | aagtcgggct | ctccgcagaa | ctcctggact | 38160 |
| cgtcaatgga | atggctcggc | atggacagct | cctgcattaa | ctgttcatgg | tgatatgatc | 38220 |
| gtctccggtt | ctatcactgc | tgataagatt | attgcaaaca | acgcgttcct | ggcgcagatt | 38280 |
| ggtgttgaca | tcctttacaa | tagggccgcc | gcactaagct | ctaacccaga | gggcacttac | 38340 |
| acaatgaaaa | tagacctggc | taacgggtac | attcatataa | ggtaacaaat | gagcacggaa | 38400 |
| aacagagtag | ttgatattat | ccttgatcaa | aacgtgtcat | acggattgat | gctacagttc | 38460 |
| atggatatcg | atgactctgc | gtacccagca | acggaaaccc | ctgtcaatct | gacaggggta | 38520 |
| acccttaagt | cttcaattaa | agactctctg | gaatccactg | gggtaaaatt | agcagatttc | 38580 |
| gtcgtaacag | tagtaaacgc | tacacaaggt | caggcgtcgc | taggattaac | tgcggctacc | 38640 |
| gtggcaacaa | tcgttagtaa | agcaagtaaa | gaacgagata | aatataatcc | tagacttcgg | 38700 |
| ttcgcaggtt | actatgatgt | aatcatgacc | aaaggaacag | gagctaccgc | tacctcttat | 38760 |
| agagtcatgg | aggggagcgt | gtacgtcagt | gatggagtaa | ccgcgtaatg | gctattacaa | 38820 |

FIG. 15V sequence.txt

| | | | | | |
|---|---|---|---|---|---|
| caagaattat | tgcacaacag | gttaccgctc | ttgacggagc | taactcaagg | gtaagtaagt | 38880 |
| acccaaaatt | taccgtacag | ctaggatact | cagttagttc | tctggctgct | acagaattac | 38940 |
| tagatgctgc | cactagatcg | gcagcatccg | ccgccgccgc | taaaacttcg | gaaaccaatg | 39000 |
| ctaaggcttc | tgaaaccgct | agtaaaaatt | cccagacagc | agctaagact | tcagaaacta | 39060 |
| acgcggcagc | atccgcccaa | gtagctcaga | atttggcagg | taaagcgtcc | ctagtaacac | 39120 |
| cactaggagt | gatgaccggc | tcggcagaag | ctaagattgc | atctataaca | atagccgcaa | 39180 |
| atcagtcttc | tagcgttcac | gtattatttg | cgctctacgc | tacaggtaat | ggagccaaca | 39240 |
| gggatgatat | atacaatatg | gagatagtat | ccctggcatt | acctggtcct | gtaacctctg | 39300 |
| taaccgcgga | caacatcggc | agcttcctta | gtcatcgagt | aataggtccg | gccaacacta | 39360 |
| atggatttat | ggtaggactt | aaatctacta | ttgagggtag | caacgtgacc | tatgatgtat | 39420 |
| acctcaaatc | tcgtagtagt | ttcagagacc | ctaagatggc | attcttatcc | ggctccatat | 39480 |
| ctgttactcc | acctaccgga | cctttggtgg | acggaacatc | ccctgcgtgg | aaaactacag | 39540 |
| gttttgatac | tgatgttatc | tatgtaaata | gggcgcaagt | aattgatgat | ggcattagtt | 39600 |
| tagcccgcat | caaacaacta | gctataacta | acggtaaaac | cgatagctct | atacttcttt | 39660 |
| tatcctattt | aaatgaaaca | ggtatactat | ctaccaataa | gaagtctatt | tccctccggc | 39720 |
| caggaggtac | gagtgactct | agtattgcag | ctacggagtt | tctacctaac | gggaatataa | 39780 |
| ttctgcctaa | tggggatact | gggaaccaaa | ctattagttg | gttaggtggt | ccccgcatac | 39840 |
| gagtcaactc | caacgggtct | tttgttctttt | ctactaataa | tcccagtaat | caaactagtg | 39900 |
| ggtttataac | tttcaggcca | caaggtgatc | aagtaacttc | cactgagctt | cagattaggg | 39960 |
| atgatggtaa | cattaagcag | acagctccac | agtcatcggc | aggcaatgca | cttatacgcc | 40020 |
| aggatgcggc | tattcaacat | atcatggata | aggctccggc | tgccggtatt | actgctaacc | 40080 |
| ccctaagcga | cttgaacgta | ataccctacgc | ctgaaggtac | agatccttgg | ggagcagacg | 40140 |
| gtgtacgtgt | attccaatca | ggggtatcaa | caaaaaatac | tccggacgga | actactggtc | 40200 |
| ggcttggaac | tatcctcaac | gttaggcaca | cccagtaccg | tataatgcag | ttcttcatgc | 40260 |
| agagtaatgc | tactgcacct | attctgcata | ttagatcatt | aagggctgat | cagggtaata | 40320 |
| ccccaccggc | atggtttaaa | gtttatacag | aatactctaa | acctaacatt | cagtctgaca | 40380 |
| tagcaggtat | tactatagac | ggcaatggtt | tcgttaagaa | agcctccccg | atcgccaagc | 40440 |
| tcatagccga | aattcctagc | aaagaggatt | cattcttctg | gacaggcgtg | gaaactgtgg | 40500 |
| gaggttacgt | agggtgtaac | gcagaggctc | aaggtgtatt | tgctgtaaaa | actggactag | 40560 |
| gcaagtatac | tattaaaggg | agtttaggct | ggaacacgga | aggatggaaa | tttgagctac | 40620 |
| caagagatga | taacggcaat | atgttgtgct | tcgtggaatc | ggattggaat | gaggaagaga | 40680 |

FIG. 15W

```
                                     sequence.txt
aagagctaaa catacaggtg ttcacccgta agtttgatat taacacaggt aatatcatcg    40740
ctggtgaacc tatggagata ccacaaggtc gttggattga tctacgtctg gaaatgccaa    40800
aagtggaaat accagaagtg gaatttccag aagatccaga agtataataa aataaaaccc    40860
cagtcggagc aatccgctgg ggtttttcta tttacatctt accagaactt ccgaagccac    40920
cttcgccacg atcagtgtcg gtcagactat cgacaatttc aatgtcattg gggttataat    40980
gaggtacgat caccaactga cacagacgct caaagttatc aatcggttgt gtctcgttgc    41040
tcatattcaa caggttcatc ttgatggttc ctcgataatc tgagtcaatc acccctgttg    41100
tattggcaat cattagccga cgtttcccta gagaacttct cggaaccacg attcctaccc    41160
agccttcggg aatctcaacc gcaactccgg tatcaatcat caatgactcc ccaggaggta    41220
tggcacgcaa taggtcggaa gcacgatctc cgaagtaggc ccgtagatcc ataccggctg    41280
cttccgagct tccaacgtga ggtttacaat cggggtgaga taatttaata cgcattatac    41340
ttctcctgtg gcaatagccg taatgtcttt aacaaattga tcgtagatat cttgtcctgc    41400
tgcggcaact gcttccccac agaaacttgg gagatctact agagttaggt tacgttccat    41460
aagttcgcct gatttattca gagcctggac gaattttttga gttcctggga gcggtagtgc    41520
atcaataatg tctagcacgc taccatgttc ccggattagg ttgtagccac gtttttcgcc    41580
gataccttca acaccacgaa tgttatcccc catatcgccc ataatggctt ttaatgagat    41640
aaactgatct acagtatcta cgttatggtt gtcgaacata tctttctcgt gatattcttt    41700
acgagtagta aacgagaagc gggagatatt cggagcaagc agggtatccc agtcaccgtc    41760
tgtggagatg agccagatat gatcgtagtg atgacctatc agctgaataa tgaaagccgc    41820
catgtcatct gcttctactc cgcggattcg gaaagtaggg aattggcttg caataagatc    41880
aaacgcatcg tctaagtatt caaagaattg acgatccgcc tctacttccg cttcggagcg    41940
atcggcgtac ttagcgtctc ggttgccctt atactccggg aaaatattgg tacggaagat    42000
actcttccct ttatccccta gaacgatagt gtgcttcgca tcgtaggagt ttgccaaaga    42060
gttgatggtg tttgcaaagg atgctgcaat aggcttacca ctatctttct tgaagcggaa    42120
gcctaagttc gtaccgtcaa caatcataag attacggcgt gaggcgaggc gttgttctgc    42180
ctctcgtttc attgttcccc aggatttact catttaacta aatctccaat ttcacatgcg    42240
tttaaccacg gctcaaaaag accgataaca atttccattc cacgtttatt aactatgaaa    42300
tgtgctctac tcatgaggtt atcaatcata gggtcgctac tatccagagc gataagccat    42360
tgaccacgat cttttcttaaa gatcagggcg ggtttcatgt tcatttgctc accttcacgt    42420
gcggcttggg cccaccattt ttctagctgg gattctccaa cgtttaggat attgctatta    42480
aattttcgt ctgcgtagtg tttgatctca aaacagtatt ggctcatttt acctacgcta    42540
ggtggcagat acacatcccc ctttagggag tgggattggc caaaagctcc tgaaccagga    42600
```

FIG. 15X sequence.txt

| | | | | | | |
|---|---|---|---|---|---|---|
| acacgttccc | agtccaagga | ggtatattta | cgcagcatat | cacggatttg | gtattccgcg | 42660 |
| cgttttcctt | tctcgcgact | atctacggcc | attaggcctc | caaaattgat | aagccagctt | 42720 |
| cgtcttgttt | aacctcaatc | ttatgtgcat | acggatgtgt | gtgcccgtga | gatacgatga | 42780 |
| ttgagttcag | ctgatcttct | tcctgtagaa | gttctacgag | ggtattaatt | ccatccgggt | 42840 |
| caatataact | tacaacttca | tcaaggaaga | gcaggttgat | attaacttta | ctaatcgttg | 42900 |
| aaagcaacat | tcgaattgct | aatagcgtgg | aaatattgat | acggctctgc | tgaccagtgg | 42960 |
| agcagttgac | catagaagtc | ctgttaccat | cattgtagat | gacaacctgt | agcttcgtct | 43020 |
| cgtctaactc | gaaccctaga | gcaaatttac | cgctggtcat | gatagagaga | taatgattga | 43080 |
| tcatctcttc | aaataccttg | acactatgct | ccagcttata | ccctaccaga | tcttttagcc | 43140 |
| cggtaattaa | gatatctaga | tccgctactt | cttctgcaac | taaggacagt | tcagcctgga | 43200 |
| tcttatcaaa | ctcctgctcg | gccttttgaa | tctgttcacg | cttagcttca | tatttcgcat | 43260 |
| tttcacgtac | aactgattcg | ttatgggttc | ttgcaagttc | taccgaggat | ctgccttgac | 43320 |
| gaatgctaga | ctcaatagct | ttgatacgct | cagctaaccc | gctagcgtct | acgatttcat | 43380 |
| cctgcgttcc | attgacctca | tcaaattcct | tgaggttttt | gcgagcctgt | tccagagcgt | 43440 |
| taaacttaga | gatataatcc | ttaaacgccc | tatcttcctt | cctaagttct | tcaacttctg | 43500 |
| cttccagctt | ttgacgttct | ttatagagcg | gatcatactc | ctccttagtt | cgtctcatag | 43560 |
| cttcttgggc | ggcggaggta | tctaagtgag | ttccgcacgc | agaacactga | gttttacctg | 43620 |
| cggcattttt | gaaatcgtag | taacgtttct | tcaaatcatc | cgctctagtt | gccacgaccg | 43680 |
| ttaggttacg | cgtaacactc | aggagttcct | cagatttcga | ggtgggcgca | ggtaaatttt | 43740 |
| cgaatggtgc | aaaagttttt | tcggcagctt | gtacggccat | gtccaaagag | ctacgttttg | 43800 |
| caatactggc | tttttgcttc | tgagccagtg | ctaccttgac | ttttgcttcg | gttaattctt | 43860 |
| cgactagtgg | ctcttcatcg | aaaacaggga | ttgggatctc | tgattgaggt | gcgccaagcg | 43920 |
| aggcttttga | ggaaagtata | gattgggcag | ttcgcaggct | accttccaat | ccggacagtt | 43980 |
| ttgccgagac | ggctttacgt | cccgctttaa | cacgttcaga | aacttcctta | tattgttcct | 44040 |
| gatcaaacag | gttaacgagg | aaagtcttgc | gctgagcatc | cgtagtcttg | aggaagtcga | 44100 |
| gactggatcc | aactgactga | tatacgagct | tagtaaatgt | cgtaaaatca | caggcgagta | 44160 |
| cctcttctat | cagcttatac | gtttgggttg | cggtgtgtcc | gctgatatct | tcaccgtttt | 44220 |
| tagtgagagt | tactttggcg | gttgacttca | caactttctt | gacgttgtac | acgtcaccgt | 44280 |
| cttttgtgaa | ctgaccttct | agcgtatagg | ccttggagcc | agtatgccag | ttaaacaggt | 44340 |
| cgtccttctt | gataccacgt | gagttcttat | tataaagaag | ctcctctaga | gctgtaccaa | 44400 |
| ttgttgattt | acccagcccg | ttacgcccga | ttaactgagt | tacgcggtga | ttatcaaatt | 44460 |

FIG. 15Y sequence.txt

```
ctatcaccac gttctcagca tatgacataa aatggctgat tgtcaattta ttaattacta    44520
tcgacatact cagcggctct ctttaatatg cgtgttctag acgcttcgtc tagtttctgc    44580
acgtttgtga aataagtatc cagctcctgt agcagtgaca tatcgtctag atctaactta    44640
gcatctttgg tgacacggtt attgatcttc ttatctaaca gttcgctgtt ctttaacgtt    44700
ttgagttgtg atacgtcgcc ggtgacttcg tatataactc tgtcatacgc atcggcttcc    44760
attggctcgc cgacttcaat agttttcgt atgagctgtg aagatctcc cagttcaatc     44820
cacgaaaggt agtgctcatg gtctcttggc aagaccgtat cgatgataaa agctccgtta    44880
gttccttttg tcctttctct gtgaaacgaa gttgtaagcg gagatccggg atagagcagg    44940
tcaacatccc cgatcttttg gctgttcttg tagctgtgga gatcgcctgc aaatactttg    45000
gagtacccat gttcgacgaa tctttcgagg tagatttctg gtacgacatg aggcgggatt    45060
gcacctctga catgcgtgaa gcaaatgtct gaaactctgg gcttccaact agctttgtga    45120
aggctgctgt aagggatgat atcgaactct ggagatcggt agtctttgac gactttccaa    45180
agtccatctg ttgcgtcgct aattgctgct gcatagtgat ccaggcaaga aatcgtttta    45240
gatttcattt cgtggttccc ggtgtaaata ataccaggat gttggagggt agctaggaat    45300
gcaaacagta gttcaacttc ttctgaagac gggtctgaaa catccatgat gtcaccacca    45360
ataatgtgaa ggtcacatcc agtagctcca aacacttcgt ccagcttttc accgagaaga    45420
ataaaccgat ttttctgcca ttcctgagga acgttcttcg ctcctagctt gatgtgatga    45480
tctgctgaga aaagtatttt catagtcaaa ataaagggga gccgaagctc cccttgtttg    45540
gattaatcga ggtcagaagc tgcttcgtga tcgatgttac cggagttcgc ggaaccttca    45600
ttacctttag attcgtcgcc ctcctcatct ttcttacctt ccagccatgc ctggattgct    45660
ttcttctgct catcatagga cggaaccggg taggtaacat ccagtttagg cacttttcg    45720
aagccttcga attcgtctgc ttcgttgtac agagcctcac caatcagagc aacgtcggct    45780
tcatgcaggg cggcctcttt agaacccggc tgattttag ccatctggaa ctgcattgca     45840
gcgatctgct gtacatcgta cttggtatcg aagccagtac cagatttgga gatagtgata    45900
tcgatctcac ccggatcttc cagattcagc tgggccatga tggagtggat accggtcagg    45960
atggttgcct taacttccat cagcttcagt ttgttatcag tacgatcgat aacaacggcc    46020
aggtagtttt tcttaggacg cagcggctga gccttaccat ctttcttctc cggatctttg    46080
aagcccatgt cgtgaaccgg atcggatgct ccacggatga aacgctcttt ttcacggtcg    46140
aaacgcaggc actcgaacgg agccggttta ccttccttat tctgaatcca gtacacataa    46200
cgcgggagaa cgccggaaac gatacgtaca acgttcttac cgttgttgaa cttcatgtag    46260
tccagtttgt cgccgttaga accgccagta gtagaacccc aagatttagt agccatattt    46320
aattttcctc gataaatgtc aattttgact tgttgattgc gattagtggg tggtgctcga    46380
```

FIG. 15Z sequence.txt

```
taactgctct aggaacccac ggtggaatat attgcatatc cagtgatgta tccttcgaga    46440
agctatattc ggcatagttt ctaaaactca aaagtcctag atactcagcc aactgtcggt    46500
ctgacagctt tcgtttatta taaacgattg tatcttcgtt caagataaat gatctacccg    46560
ttaacataac atgagcttcg ggatcttcaa ccattcgtct gataatctgt acaatcagcg    46620
atgagttacc tcgtgctaat atgtaaattt tttcgtaatc ataaaacaac atgattatta    46680
tacaccattt tgagagaatt tagcaactaa gtttttattt ttctgcttcg gactttccga    46740
agattcagtt gctgttccca ttaatttata cagatattat atcgtatttt tgaggactca    46800
gcaactgaaa tttttaacta tttgcttaac tcttctttgt aaatctgtct ctcagttcaa    46860
tataaatatt atatcaaact tgggggttct tagcaaacag aattttatct aagtttgcca    46920
tattcttctc gttaaagtca agaacttccc acccattgag acgatatacc gcttctctac    46980
ccgccgcctg cttaaatcct acacctccta gcttcagatc cacgaggatt gggtctaact    47040
tatcatctgc catacgttgg acacgacctg ccaactgttc gattagagat tcgttattta    47100
ttaaagagcc taacactaaa cacgataaag catttaatga tacaccctcc gagaagatgc    47160
tttgggaagc cgctaacaca cacggaccgt cattggtcac gtcaatctgt acttgctccc    47220
tatcatcgag cgaagttaca ccggtgatcg tgtaggtctt cacacccctg agttccaaag    47280
cattcgtaac tctctcaatt agatctatac gatcggacac aaacaggact ttatggcctg    47340
ccatcgaata tagctcgcac aagtcaacaa cctgttgaaa gtattctggc tgcgaatata    47400
catcgttagc tcttatcgcc cacggcacat tcatatttcc agaaacctgc gttttagcg    47460
caaacctatg gatagtaggt ggcatagtgt tatttaccgg aggactatat actttcgttc    47520
caaaatagtc cttaaacata acctgcaaac catccttacg ttttaatgta ccggatagcc    47580
cgattttata tcgtgccgaa gactgctcta gaaacttggt aaacgtggtg gcaacgcagt    47640
gatgcacttc gtcaacaata acggtgccga attcttttgc caaagcggct ccgtgtttgt    47700
taactgtctg tatattacta ataacgatag gagaatcgat attaaatttg ccagacccaa    47760
taactcctgg ctcaatccca aagaacttgc gtacctcctt ctcccacata gctcgaatgg    47820
tagtgttggt acatataact aacgttttct gcccaagttt atgggcgata gcaagagcaa    47880
ggattgtttt accgaaccca ggcttaccat taataataca cgtatcatta cagtcttcat    47940
atatagggag ctgatcccct ggtcgcaggg tgaacgatgg ctttggaata tccataggaa    48000
ccagagtacg tttatctacg atctctgtca cttttgccc gaaagattct agaagatcta    48060
atctggttac gggaaaccac ttgatctctt tacctaccga tcctgagttc tggaacatta    48120
gaggatactt tgccccaggt ttaaagatct ggtatgaagt gtgttttaat aagtattccc    48180
acagttcgtt gctgggttta caatagattt tattagatat aactatcttc atatcttaac    48240
```

FIG. 15AA sequence.txt

```
tctaagtcta ggagtttctg gctcctcttc gtgcgtgtca aaaataactg gtgaaccgcg    48300
aaccaacgcg tacgaaatat agttggcagg ttcactaagt aagaaaggat atggaacgtt    48360
cttgacataa cactggtact ttccgttgaa gattctagtt gatcctctaa cgcgttccgt    48420
gataatgttg taataagtcg taggtttcca tgttactatc ttacctgtgg agtcgatgaa    48480
atgctttagt ccagagttta ttatctgaga taagtacttg aactgtttct ttaaaggata    48540
gagcttataa ggtaaatttt cccgctcacc ataaagaaaa agccttcgct gagagaatgt    48600
cccaggaagg cttggattgt ccagcacata ccttgtaaat ctcgtctgga taacaatgta    48660
ctcccccctct tggaagagta catcataagc ccttaaagca tatactggta agctaaagtt    48720
aagcaccaag aaccctgcga acgttgacaa tatctttgct gatttccggc aaaaacttaa    48780
tattggcgta cttatcgtga tcagggtggt tttcatcgtt agccgcaata gcagcgtagt    48840
cgaagtcctc cataccgata atactacgta cttttctcctc aaactccttg tcctcaatgc    48900
aagcaacaga aggacgctgt ttcttgatct taccacagga gtaatcacga gaaccgccag    48960
cctcggagtc agagtcgata ccaataggac agcccggaat actaatacca cggtctacct    49020
gaatgttacg gattagcatc tcgttatact gatcaactaa atcctcacga acaatggcaa    49080
ccacggagtc gtgaaccagc atgataatct tcatttcgtc ctgcagaccc agagagcgaa    49140
tctcattatc ggtatcgata gcgcctagca ggagactatc agaagatgca gactgaatga    49200
tggcgttgaa accagaacgc agttcttcac cctgtacacc acggtcttcg gagttaatgt    49260
tgtgcagacg acgcttacga ccaaagtggc tgtaaatgaa gccgttagtt tggatctggg    49320
catgagattt atcgatccat ttcttaagct gagggaatcg gccaaagtag gtttcgatgt    49380
actctttcgc atcaccagta gtacattcag tgtacggttt accggtcttc atgtgctctt    49440
ctaggagagc ttcgtttact gacgctgcta ctttagccgg gccagaaccg taaagaatac    49500
cgaatgaaat agcttttgca gcctgtcgta gtgcaggata cagtttttta acctcagtcg    49560
gtttacacgg cagagcaaat accatgtgtg caattgaacc gtggaagtct gagtagtttt    49620
ccgggtcgtt ctgcatgttg ataaacactt gctgcatgtt aatgtcacca gacagtacag    49680
cggcgtagta aatctcagca gttgttaagt cccatgcgat aatacgataa cctacagggg    49740
caacaataca accttttaata acagactcat cacgaggtaa ctgctgaagg ttcagcttac    49800
cagacgaact cagacgaccg gatgtagtca tatggatatg gaatccagta cgaatgcaac    49860
cgtcagcatc aatactgatc agcatcttct cgatatacgt cgagagcagc ttggagatct    49920
tacgaatctc tagcagagtc ttagctatcg gatgctggtc cgaaagctct ttcagggcat    49980
ctgcgccggt ggaatctgca cccgtatctg tcatgatacc cgtcggggtt aagccaacat    50040
aatcgaacag gagcttacga agctgtacaa cagaggctgc gttaaatact gagccctgat    50100
cttcctctag cttacgaact tctggatact catacagctt agcttttgca agctgtagcg    50160
```

FIG. 15BB sequence.txt

| | | | | | | |
|---|---|---|---|---|---|---|
| cagtcattaa | ctgaacctga | gcctctttca | gacgatcttt | ggagatcggt | acaccacggt | 50220 |
| cttccatacg | ctgtaggaat | acacatcccg | gcatcagtac | atcgtaatac | agagacttca | 50280 |
| gtcgagggtt | agcttcgact | tttggcagga | agaaattgga | tagacgcagt | gttgcatcgg | 50340 |
| tatccttcgc | tgcgtaaggc | cacatgatat | caaacggaat | gagatcatac | gagaaatcct | 50400 |
| ctttcttgat | cttatgcgtc | ttgcaatacg | tctccttgaa | ctggtcgagt | tcaaaatcgt | 50460 |
| agtcccccat | atcggtatac | ttcatcgcca | aagatttcaa | accgtgtgta | ccacgtcgtt | 50520 |
| catctagggc | gtagtgcatc | agcatggtat | cgtggaggcg | tttctcttct | gctgccttat | 50580 |
| caaaggatag | acctaagtga | tagcagtaga | agtgcatatc | aaacttcaag | ttatggaaca | 50640 |
| caacgccatg | ctccgggcta | tcgaacagtt | tctgtaagta | atagacggta | ttttctgtga | 50700 |
| tgacgtctgc | atcaatatat | acgccctgat | actcttggtg | ggagattgag | atccccagca | 50760 |
| tgtaaccatc | tcggcagtat | agcgcactgg | tttcggagtc | atatgcgatc | atgccaggac | 50820 |
| acatggtata | caccatcttc | acatacgctt | cggcttcgtc | cgggcactga | atcgggcggt | 50880 |
| aatcccctgc | tttagagcgt | ttttcacgac | cattgagaat | ggcatgaatg | ctctctactg | 50940 |
| tggcttcaaa | tacaggcttc | atttccggtt | taaagtggag | ctgggccgga | ctgatacttg | 51000 |
| caatccagtt | agcataccca | tcatgctcaa | cacgtttacc | tgagtaatcg | gaaatgccct | 51060 |
| ttttagctgc | aaacttcaag | aacgggtctg | cacctaccag | aataacgtaa | tcaaaatctt | 51120 |
| ccggattgaa | cgggttctcc | ggtgttccga | tagtgatatg | tttcttgagc | agtcgcccgg | 51180 |
| ttactttctc | actagccatg | aagaaggtct | caacctcatg | gtcaaagagt | tcgaagtgtt | 51240 |
| tctgatagcg | gacgttattc | ggtgatttgt | ctacaactgc | gattttcatt | gatttctcct | 51300 |
| attaggtaag | caagtaaaac | gtcagtgttt | cttctcaaac | ttacccaatt | attatatcaa | 51360 |
| atcttgacat | gttcagcaat | caagatttct | acgtttctga | tgagttggtc | gacttcttca | 51420 |
| gcatctaggt | ctccagggtc | tttgccctct | ggaagcaaga | agttacctat | aattggtata | 51480 |
| attctagtct | tatcacggat | taatttggcc | aacttcttag | ccgcctcatt | accggactta | 51540 |
| tcattgtcca | atatgatgac | tacgtgagta | gtaccggcga | tttggaacgg | catgaattta | 51600 |
| tctgcaatgt | tatctagtga | gaactggtga | gtaccaaaac | aacatgaaac | gttatggcaa | 51660 |
| cctttatctt | ctagattcaa | catgtcgaat | ataccttcga | ctaggattag | ggctggggtg | 51720 |
| ttatagcgaa | cagggaagat | tggggggggag | accttcttag | gtctaatcat | atatttcgga | 51780 |
| ggggcagagc | tatccatatt | acggcctaag | aagaataagt | ttctccctac | ggcatccgta | 51840 |
| ataggaaaca | ctacacgacc | ttcccagtcc | tctgtttgtt | ggaatgcaaa | gtatttcttg | 51900 |
| aaagtctctg | ctttgatacc | acgaaagtct | tgatcgaata | tcatggctga | ttctggaatt | 51960 |
| tctagactgc | gaccctcagt | tcggaggtca | ctaatcattc | tgcgaactct | caggagtcta | 52020 |

FIG. 15CC sequence.txt

| | | | | | | |
|---|---|---|---|---|---|---|
| ggcgacgtcc | tgtactgttc | ttcattgaag | taatgaaaga | tgcttggtat | accacgacca | 52080 |
| aatccgcagc | ttaggcagtg | gaaaaccccg | gaatcggggt | caacacgcaa | actaggatga | 52140 |
| gcatcctcat | gatcaggatt | gagacagcgg | atgaggatgt | ccccacccgt | atctctgtat | 52200 |
| tcaatccctt | tgagatctaa | aagctcggtt | attctactca | taagtctctt | gaggattctc | 52260 |
| cggtgggatt | agtatcctca | tccgaagcct | ttttcctttt | tggtttgtct | ttcggtttat | 52320 |
| cgctttcaag | tgggataaca | aactctgctt | ccatctgacg | aatgtcctct | agcttaaggt | 52380 |
| cagaagtctg | atccatacgc | agtgagttcc | agttgatctt | cggcatgaat | gtcataccct | 52440 |
| cggagttacg | agtttttacg | aagtcgaact | tgattgcacc | gtcatgcccc | tcgttctgtt | 52500 |
| tagcagcatt | taggtttgca | gccatatcac | aggaatcgag | aatacctctt | gccatacggg | 52560 |
| cgttaccctg | ttggtcaatc | tggtaagggg | ctacaccagc | aacgttatgc | ttttggcacg | 52620 |
| tagacttgaa | tgtagaggag | acaaccatct | gctgcttcca | atcgtacata | tctagtgtct | 52680 |
| tcgtatccgg | caaacgtacc | tggttgatgt | agtctagcag | ggcgattgtt | accttatctc | 52740 |
| catacttgga | ggttagctta | gttagttcaa | catcgatggt | tgctgtacta | agttccggat | 52800 |
| catacacaat | gatcatcgga | gtgtgcaggg | gtctttcctg | cattagcata | gtctccatgt | 52860 |
| catggaaatc | actcatctcg | ttgagcgtat | aacgtgatac | aaaatcgtta | tatacttcca | 52920 |
| gaccgccttc | aaacattttt | gcacgagtct | tcgcaagttt | gttgagttca | ataccttgta | 52980 |
| aggagtcatt | gcgcatagcc | ttagcggaaa | caccggccat | aatggctagg | ttacgtctaa | 53040 |
| agacctcatt | ctctggcatt | tcgatggaga | aatatggggc | gatatcccg | ttgtaatatt | 53100 |
| gggctacttg | aatgttagaa | cagatgattg | atttacctgt | accacgccat | ccaccgagta | 53160 |
| gcagtgtttc | ttttctggca | attccgccaa | gttgagcatc | aaattcgttt | gagatgccga | 53220 |
| gagagataag | atttaacatg | gagtcttctt | ttctcttgaa | aacacgcata | gtatcggcgt | 53280 |
| tgaagacctt | accagtcgtt | gttactcgtt | cctctagctt | catgtgcaga | gccgctactc | 53340 |
| gatcaagtaa | ttctccctga | tccagtatgg | taatatcctg | caacacatca | gtttctagca | 53400 |
| gattcaggaa | tagatcctgt | gtgtattccg | actctaggac | atgaatcgca | tgcgatatgt | 53460 |
| caacgtctgg | aatctgagtg | tttgctaaaa | cagttagtgc | ttgagacaac | cttgcgtttc | 53520 |
| tgttagactc | tagcattaga | gcatctaacg | aaggcattcc | gttatgcttt | ttgtaataat | 53580 |
| tctggacagc | ttggtagatc | gcggtaaatg | cgtcattgaa | gtgatctttg | cgcagtctag | 53640 |
| agaatgtctc | tagggccacc | tgcttttgat | cggaggctag | gagcattttc | aaaactactg | 53700 |
| cttggacgtt | atacataaga | tactctctac | gccgcgttag | cgtctactta | aacgaaaaag | 53760 |
| gggagaggaa | caaaattcct | ctcccctcag | gtcaaatcaa | ttacttggcg | gatttagcgt | 53820 |
| caagtttagc | gcgcttagca | acaccatcgt | gatccttagc | agagatacca | cggcggctca | 53880 |
| gcatagactt | aacaccacgc | tcggatttac | cagttgcttc | tgcgatctca | gcaacggtca | 53940 |

FIG. 15DD sequence.txt

| | | | | | |
|---|---|---|---|---|---|
| tatcggcgat | attcagacct | tccagaacgt | cttcgcgtgc | cttagcatta | gagacttcct | 54000 |
| ggaccggcat | agcttcgata | cggccttcac | gcagcaggct | cagagcttta | ccacggatct | 54060 |
| gcttaacggt | acgttcgaac | tgagcagcga | ttgcttcaac | ggacgcgcca | ctggcaacgg | 54120 |
| cattaatgaa | agcagcttcc | tgatccgggc | taaagctacg | tacagcagcg | gccttttcag | 54180 |
| tcggcttaac | agccgcagtc | agttccaggc | tcaggatttt | accctgtact | tgtttagcgg | 54240 |
| tataagcacc | accaactaca | gcagcagcga | tttcagcgta | ggtatactga | cccggatgat | 54300 |
| cgttcaggaa | tgcaaccagt | tcatcttcct | gacccggagt | ccacggagat | tggttacgt | 54360 |
| cggatgcttt | ctgtacttcg | aagccttctt | tacgcagttt | agaaccaacc | gaacgggcgg | 54420 |
| taacttcttt | accagtttca | gcagccagtt | cagcagcgat | gttagcaacg | gcttcctgag | 54480 |
| agataacggt | cgcgttcaga | gcgttagctt | tagcggtcag | ggatgcagtg | atttcttcgt | 54540 |
| tccaggttaa | tttagccatt | tttatttatt | ctccagtaga | attttaatcg | tcaagacttc | 54600 |
| gatgcccagc | gattgtgctt | ttttgtatga | agaagaaccg | atcttggttt | catcttcgca | 54660 |
| gattaagtag | tttacagcct | tagtcacgga | ggttttcacc | gtatacccaa | gactttccag | 54720 |
| atatttggta | gcgtccgcac | gattttgaa | gtcgttgagc | ttaccagtaa | tgcaaagaac | 54780 |
| aactccgttg | gattcagtcg | ccggggtaac | ttgagcttcc | cgcgcccac | tgaatttcca | 54840 |
| tggtagatta | attacgttct | gtcctgccgg | tgtattcttc | cacgaagcta | agttttctcc | 54900 |
| agctttacct | tccgctttca | cagattggaa | atcgttgtaa | agctgggata | atttcttagc | 54960 |
| agcaacttca | ccgataagag | ggatactaag | agatccaaga | accgaaccaa | agtcaacatc | 55020 |
| ttgtctcagc | ttagtttcca | actctagctc | aagtttcgtg | gcgactttat | cacctacagc | 55080 |
| tctgaccaaa | tcttctttag | tcaggaaaaa | gagttctgaa | actttcgtga | tttccagttt | 55140 |
| agcaatcgtc | tgtgggccaa | agccctttaa | cttcatcttt | gagcagaagt | tctcgattaa | 55200 |
| tttactgctt | tgagctggac | acatagactt | gttacggcag | aacaactgat | cgttaactaa | 55260 |
| gtccagtttc | gaaccacaag | agtggcaatt | cagtggaatt | tcaattttca | ttgattttct | 55320 |
| tcctcatcaa | tttatataaa | tattatagca | agaaaatcag | gactaagcaa | tcgaaatttt | 55380 |
| tcagaattta | gctcagtctc | tcaccaaata | tttctttccc | tcaactgaat | gataatagta | 55440 |
| tacaccctgg | cgatgaaaat | gtcaataact | actttaaaaa | atcatcacgg | tgtatctatt | 55500 |
| gaatcaagtg | ttactcgtaa | acacgttcta | cgatgcgagg | gatgacccca | ccactacgaa | 55560 |
| ttacgcgaat | ctggcaaccg | atttctaggt | caagggcagt | gatataacca | acgttattca | 55620 |
| gggtagcttt | tgaaatgaca | gcgtcgtcga | tgactaccgg | ggtgaagtat | ccgacaggag | 55680 |
| taactttacc | ggaagcccca | acttgccatt | ctacccgttc | gagcgtagta | acctcgcctt | 55740 |
| catcatcttc | tttgatggcg | tacgcaccac | gcgggaactt | gttagtccaa | cctgctgcgt | 55800 |

FIG. 15EE sequence.txt

```
taaattggtt gttgccatcc atacgaacca ccacgccgtc cgttgggaac caatctactc   55860
gactggagat atccagacag gtaacaaaac catcaccctg gaggatatgc atatctccac   55920
agaaagtagc ggtcaggcca actttgccgg tttcacactg aatactatat gccgtgaaca   55980
tcaggccacc ttccgcaata cgggagagaa actctccaga atctttcagg ttaatagcac   56040
cagaggcgaa gttacgcata ttttcaactt ctttggtgat gtgtacttca ccagtaatct   56100
gcaccggagt cttttgggag atccgtttag ggatgttcag taacttcaca ttatgagtta   56160
catcattacc taagacgccg ttaccacggg ttaacgcaga aacgaacttt ccgtcaatat   56220
acagaagtga aatagcacag ccatcgagct tcggcgtttc aatgccctgg aagggtactt   56280
cttcgccgcg gcctgggtac actttctgta gggagaacat acggaatagg tgaggtacat   56340
cacctttagg gccaatttct tcctctagcg gaaaacgacg gattaaggca tcatactctt   56400
catcagagat aatcgacatg cctttgtagt acgcgtcttg gcacagctta ataaattctt   56460
taacgtgttg cattatttgg cctcgtagta atcgaacagc atctgagtct tcccttccca   56520
gtaaaagttt tcgcataccg cctggaaggt ggacattacc ctacgcttag attttggact   56580
gtacaattcg catactagta cgttcttctc ataccacatg cctagcatct ggaagcctga   56640
cattgtccgt actacaggtt tgcccttctc tttctctaac caggttagga ctagctcctg   56700
accctgaagt ggcgggctgg agtatgcgtt aagcgttatc ttttgcattc tttaatgcct   56760
cgttaacaat tctagacatg tgtgctctca gctgttgagt gtgagcatac gtcttagcag   56820
cttcggtcag cttattaact aattgagcga tttcatgatc tttcataaag atctccttta   56880
aactatgaga atattatatc aaggtttaaa acactaagca attgagattt taaagaaaaa   56940
gccagcaact tagtcgtcac tggcttgggt cttttgagat tcacggtaaa cttcatgaag   57000
aacctctgaa ttgcttagta ttttagtaaa tgcacggaat agcgtgctgg tcatttctaa   57060
cgtgtacggg aacgagaagc ctgatttagt agggaaccag ttatcttcaa tatctagtaa   57120
ccataatcgg aaaccaaagt ataaattgcc tctaaactcc gagacagtca tacgaatctg   57180
tcgcccttca tcttcaaaga taacgtggga ctgatcatca atatgtcctt cgtaatcctg   57240
acaaatgttt tgattcattt ttattgttct cagataaaca aaaagccccc gaaggggctg   57300
attgcgtctt aacgacctac tggagtagct cgatcaagtt cttggttgag ctggtgatg    57360
cgcttaatat tcgcaatcgg aatatagcgg aatttatcgc tagagcggct aaagaccagg   57420
atatgatctt tgtcagcggg ttccaggcct tcacggacga ttcgctcggc cagatattta   57480
tcttgcttag gatcgaactc agtcgtaccg tagaggtaag ttacccccctt ggtacgcagt   57540
ttggtgtatt gcatgcaaaa ctcaccgtgt ttctcacaga tagctacgac ttgtgctttta  57600
ttcattgcaa taccctctta tttagtgatt ttacggatag cttcagccag gtgagaggca   57660
gctttaccgg tcagtttgtc aacgatcgat tcgtccagga agccatcttc cagtccagcg   57720
```

FIG. 15FF sequence.txt

```
tcgttaaatg cagcgcgcag ttcagcctga gcatcagact tagaagtacg gccaccagct    57780
ttaggggcat caccaccagt tttagcggta gacttaccag cttctttctt gacgtatacg    57840
ccagctttgg acagcttcat acgaaggccg ttcggggaaa caccgtgctc tttggcgatc    57900
tcagctacga tctccatgga aacgccagga cgctcatctt ccgggaagag ttcgattttg    57960
gcgacgtagg cagaagtcag ttcagcttcg agttcaggag accattgagt tggagtagac    58020
atatttatta cttccttatt tattgttaaa aagagttttt aagttttgtt tcagactatg    58080
agaatattat aacaagttac tgagctgcaa agcaaacaga attttctagg atttggttaa    58140
cagctaccaa accattaggg gacaaacgat acatcttcag caaaccacga tcgtatttgg    58200
taagccagcc attatcttct gcttcgtcca tgggaagtgc atagtgcaga tcccggatag    58260
ctgtagcacc ctcggaatag atctgaaata agttcaggag ttgatattta ctcacctta    58320
cctctctttt ctagtttcag ggctgctttt acagcgttat taaccagttc agctacgtct    58380
tctttacccc acttgaaccc cagggacttg atatcaacac caagtgctac cagatgttcg    58440
acagacgcca gatcccaata catgtagtta acatactgct ggcgggcttc ggacagcagg    58500
taaacacgat acgcgcctac cggattatcc agagcttttt taacttcgcc aatacactga    58560
tagccaggaa cccaaacgtg ttcgcctact tcgaatacct cttttcattga ttcttctgga    58620
atcgcaggtg gaaagagcgg gtcaacctcg ccattaacac gaagcagagc accgtgagca    58680
gacagaacca ttctgatcat gtttgcggaa cggtagaaac gctcggcaat tgcctcaaaa    58740
ctatcacctg acaggtacga atcgataacg ttggccagtt cagccccttc gattttagta    58800
ccacgtttct ttttacgcat ttcagcggaa acacgctggt tatctttcca ttcctcgata    58860
aggcgttcca tcgtggagtt agacgctacg ccgaggattt cgcaagcgcc tttcttggtt    58920
ttgccttcct ctagccactg aatcgcttcc ttaaactttt cgtccgggat gctattagca    58980
tgaagttttt tgcggattgc catgttcttt atcctctctc gaatttatga aactattata    59040
atacagattt agcttctaag caatcgcgat tttcatagaa cgtagggtcg aaagtaacgt    59100
gcatgaattc agatagactc ttgtacccca tgttaagttc catgttgatg cgtatagaaa    59160
ggcgtgtctt tcgctgagcc tctagccaat catagatatt tggcatctgt gctaagcgaa    59220
taggtattac tctacacaat tctatctctt tagctttccg tgctttcgta tcgcgtttgg    59280
gaaacttcct tgtttcccag cgggcatcac gcttgctcat tacgtactcc aagttcgttt    59340
tgcgcttcat cggccagcgc cttctcctcg tccgtcataa actcatacgg tacagagata    59400
ccctcgatag aacagtacgt gcgataccag tctacgatct gctccgtctc catttcctta    59460
ttaataccca tttgggttaa gtacatacgg gcatatttag ggttggcaga ctgtcccgtc    59520
ctaataaaga agtccttctt gtgtttcttc agggcttcaa taaaggggct aatcgtcacg    59580
```

FIG. 15GG

```
                                sequence.txt
ttagaacact tcttaatatc cttccagaat atatcttgaa gtttatggaa gaactccgcc    59640
cgcttgtgtg gtttcttact aatccacatc tccgcatgtt cctgtgtgat actcttgata    59700
gagtccaggt ggaagtactt gaccaacatt agcttggctt cgtatgcgtc cgcatgacgt    59760
ggtgcacacc aatccggggt actactcaaa atagcagaga ctcgttcagc agtatactct    59820
gcggccgagc tatcaatctt accccagctt tcactgaaga tatcgatagt tgctccctga    59880
tccagcagat aataccgcag agtactgata aagttacggg actctagttc acgacgttta    59940
acatacagct gctgagctaa ttctagccaa ccctcatcga tgttatactg ctccgaaccc    60000
gcagagaatc cgctggtgga cttatcgatg aaatagaaga tattcttagc tccccggtcg    60060
cgcctgattg cctggaagcg catgtttggc gcctggttag cggtacgagt aataacgaat    60120
acgttgtcga agtaattaaa gtcaacacca ctcgttactg acggactgca cagtagacaa    60180
tcaatctgct gttcaattaa ctcattcgtt gtataatcca agatacgacg aatatctata    60240
tcagatgtag agtttgagtg aatctcttta acaatcgcac ctgtattgtt tcttagcgtc    60300
aggcctttct cgtttaactc atccggccca cagtcggaca ccagaataga tttctctccc    60360
atctctaggg acgtttggag ggcaacccaa atactggatt catcagggaa ctcatacgcc    60420
tgagcatccg agagcatctt acgatggtgt ttataataag agaccggctt gtcaaaatct    60480
atgagagatc catatgcctc aatggtttct gcgctgatat ccccgtcaga caggataacg    60540
acttttgcag atagcagaat ttcacgaaga actgagatac actcacgacg ttgtttaaca    60600
actggagcaa ataacaggtc attcataact gcgtcgcact catcgataaa gataacatcg    60660
atctgcccaa caaagttttt aaacttgtgg attgagtgaa tagtagtaga catacgatca    60720
atggcaccgc gcttgaagtt taacatatct acggacttat catactgtcc ggcttcaaac    60780
ttcttagcgt tagatgaaac cagggcacgg gtgttagtaa ctgcaaggaa attacctttc    60840
agctgatcac gttctagcca cttcgtcact gcggtggttt tacccgtacc tagagaagcc    60900
ttgataaacg ttaaatgccc ttccggtggt ggacggttga tcttcaaata attcatcccg    60960
tctgggctat cagaggtcaa cttgtgtaca ggaacgcctt taacattcga ctcaggaata    61020
tctcgcatcg agttgttcac aaacgctttt aatgcctgct tacgaccgtt attgaagtaa    61080
tcctgaagac tgcgggaatt atccttcgtg ttgatataat cggacaaagc tgaggtaatt    61140
tctttctcaa gccaggcgaa atcaacaccg tcctccagag ctctgtggta cagtttagga    61200
ataatacgca gataaacacc atcctctgct tcttccagct ctgcaatggt ttgttccact    61260
ttctcagagg ctacgcgctt gcctttaatc tgattaagta gggatagaaa ctcttcttta    61320
aattccccac gagtggcttc ataatctggc atagtattgg gcagttcaat cctagcaccg    61380
ttaactttaa ccagacgtgg cttaccctcc gctttaaacg gatcggtaaa ctgatcccgg    61440
aaaatcgggt cagcgaaata gtgtagctgt acagatgaat aataagctaa gtcggcaata    61500
```

FIG. 15HH sequence.txt

| | | | | | |
|---|---|---|---|---|---|
| tcaaaaccat | acttctgccg | agagctatca | ttgagggacg | taaatagaaa | ctttaactga | 61560 |
| ccctgagtaa | cgggaatatt | actctctaat | agcatgtgca | tacgaatccc | cggcttaatt | 61620 |
| ccagccgaag | acgacgcatg | ggcaataaac | cctgcgttaa | gcgggaacat | gtcctcgctg | 61680 |
| atgctattta | ataacttaat | gacatgacgt | cccataccca | caatgtcaaa | cctgtcgcat | 61740 |
| cctccggtat | cagagattcc | atcgacgtcc | atagcaataa | tattgctctt | atggtcgatt | 61800 |
| ttgaagttag | tacgtttacg | acgcacggcc | ttctctgcaa | ctaagcatgt | acctcgtact | 61860 |
| gctacgagat | gtggatcttg | agtgagctga | accatcagct | catacgcttc | attaagattt | 61920 |
| ttggggtcaa | ctgtatccac | tacgttaaat | ttgtagggca | ttgaggctgg | cttaccttct | 61980 |
| ggatgctcgt | tagaaaactc | cttcgcaaaa | aggtaatcag | ttgtcttcac | ttccttccag | 62040 |
| tttccggaag | cgggatcgcg | ggaaaaaccc | gcgtgtcctt | ctagaataga | aaacattacg | 62100 |
| ttttctccta | tgttgaagaa | taaagcgatc | tcgaactatc | aaggatagaa | cagcttaaaa | 62160 |
| gtccactgac | tcaacaaatt | tccttataga | tggaggggtg | gtcacttcct | cattgctaga | 62220 |
| actggccgct | tcgcacaact | cccacacagc | atgtaatcgc | cgctaagctc | catgtggttg | 62280 |
| accccctattc | gtcgctattg | cgcagaggta | cgttgctact | tacagcttca | cttcttggtc | 62340 |
| atttcagacc | gcggtgctat | ttgctccaca | tgactaacga | acaaatatct | gagagcctcg | 62400 |
| cgatgccaac | ctctcttacc | cgcattctag | atcaattatc | tataattccg | ttcggaatca | 62460 |
| atttcccaat | aagccaaacc | caaccaagca | tgtagcagcc | ggactgttct | gtatgctcgg | 62520 |
| aagtgaatga | gaggaattat | gtcagttttg | taactcacat | catttctctc | aacctatgaa | 62580 |
| tatattatat | aaaaatcgtg | gcgagattgc | aagtaaaata | tttaaatacg | tggtaggtaa | 62640 |
| ctgggtttaa | gcatagaaaa | gaccagagga | taatcccctg | gtctaagcgt | tcaactaggc | 62700 |
| attccaaccc | ataatattaa | ttgagttaga | agaggcattt | tgtttgccct | cacgaagaac | 62760 |
| ctctggagca | tacgtccaag | gctcatcagc | taccaagaac | cccggagaaa | tacctgcccc | 62820 |
| cggttcccgg | aatgctgcaa | aattagaggg | gtggaacaca | acgttgttca | ccagaaccat | 62880 |
| tagccccaga | tccgagaggt | catcccaatc | aaagaggatc | tcataatcct | gggccaaact | 62940 |
| accctttggac | aaaccaacac | acacgtcatg | ctggatgatg | aagcaaagct | cctcgtccct | 63000 |
| caacgcggct | cgcagcagat | tctctgctac | atcaatcaat | tccttgggga | tatccgccca | 63060 |
| ggagatacgt | tccattttag | gaatactcat | ttagttaacc | cttcaacttg | gaaaccgaag | 63120 |
| cgacgcagca | cctggatcca | accgttaata | ttttccggag | cataataatc | ttcattacgt | 63180 |
| ccgacccaaa | tacctgctga | aacacctgta | accccaaccg | ggatatagga | ctcacgcagc | 63240 |
| agacacacgt | agcctagtgc | aaacaccagc | cccatctcag | tcagatcgcc | ccagtctagg | 63300 |
| acttcatctt | gatcttcgtc | cataggaacc | catagcccca | ggtgcatgtt | gtcataatcg | 63360 |

FIG. 15II

```
                              sequence.txt
aagtagacct ccatattatc gcaccacaca cgaagatggt ccagcagaga ctcttttacg    63420
tccagaggaa tttcagccca gggaactagc ccaaccccct gattaacaac cttttcattg    63480
accagcatat tcttccccca tttggatgaa ttcgtgccac tgctcagagt ccgctcgtaa    63540
aacctgatag tcgtccgata ggtgactcat atcttgtaca tcactgcgat aacaccaact    63600
accgttgggc cataacagga tatcatcggg atggtacata aatttctcc tccagccaag     63660
cctcaacttg acctatgaaa tgtttgttgc taaatacatt ggcagcagta tcataccaaa    63720
cggggatccc gcgttcttcg tacaaactct gctccaggta gttaataccg ttgttcacta    63780
cccacacctt agtacctcga ctatgggctg ggaatagttc ccaattaaag tcgattactt    63840
ggttactagc accaacaacg attaccagat cctgggttgt cagggtatca aacaggttga    63900
tctgccccat ataccacgga gcggtttccc cgaagaacgt aattgcaggc ttaacccact    63960
catacttacg gtaatcaacc gcagtgtacc cgatatcttc cacgatcaca tccttacctc    64020
ggcgatacat tatctccgta aggtagccat gagcatggat cacatcatca tggggaatgc    64080
cagcacgctc tagtagatca tccacgttag tagtaaagtt aacgacttga ccagggaagc    64140
gctcatacca ctcagcaatt ctcaagtgag caatgttagg ctccaccgta cccagctcct    64200
gtcgccgcat gttgtagaac tcatgggtta gctcgtacag gttgcgacta ggctcatcat    64260
cagatccctc agaaagggct tctaacgggg gcatagggtc gttcagatag tgaaacccct    64320
tatcgaacgc ctgaatattg catacttcgg ttagtttgta tttatcccac aggggagtga    64380
tggcacccct acggaacgtt ggcactcaat ccagcaccac ttacgataat caatctacgc    64440
attacaggaa ctccatatag tttctcattt cttcttttccg caactgctca gccttttcgg   64500
acaagcactc agaggttctg ggatcgactt tatctttcca caagtggtta cggcatcgca    64560
gaagttttac cacgtcttct cgggaaatag atccgtatgc tccagagtcc atcataaagt    64620
agatacgctt ttcatcagtt ttatggattt tcataaatcc tccgtttctc aattacaact    64680
atcttatcaa aaacggaggt atttagcaag tgatttattt caaattcatg tgtttgaccc    64740
tttgcattac ttcctgttgc ttaccagggt taaagggtct actaccagga ctacctaagt    64800
acccacaaac gcgacgggta accgagatat tccccgaccc acattgagga catacaaagc    64860
cgtgctctcc ggatacagac tctcctagat atccgcactc ttcacattca tcaactggaa    64920
tgttaacccc tatgtagtga gatttactta atccataatc aacaacccac tctagtgcag    64980
ggataaactt acgcatctcc ggaagttcca caaggatat attaccccca ttggcgatgg     65040
tggtaaaatt agcctcatag tcaaacttca cgttaggggc aacttttgta cggacatcca    65100
ggtggtggct attagtcagg tatcccttat ccgttagcca gtcgtactca gggtactgtt    65160
cggcaatttt agtattgaac ctattgcaca gagactcact aggggtagca taaaggctga    65220
atccaagatt agtttcctca gcttttttgt tacaacggtc tttcatgtgg ttgagaacct    65280
```

FIG. 15JJ

```
sequence.txt
gtacagcaaa ttcaatcgca ggtggggaca tggggtcggt atcctcaaac attacttcaa    65340
ccagctcgtt aataccgata tatcccaaag acactgatgc cctgccttca aagatgggcc    65400
atacaagatc attggctttc aaccgtaccc caaaagctcc gtgcatatag agaattggtg    65460
cctgtttagc acgcacacgc ttcaaccgct caatagccca atcgtgggca gccatcgctt    65520
tatcaatgta ttcgtccaac aacttccaga acctatcgaa gtatccctca gactctacag    65580
caactagcgg caggttaatg gatacaaccc ctaggttatt gcgccccgca gtctccccgg    65640
actcaatagc tgaaaggaaa gaccgacaac ccatagggaa cttaaaatca cctgtaacag    65700
ccgttactct ttcataactc acgtaatccg ggtacatcct cttagaagtg caggtgagcg    65760
ccagctgttt gatatcgtag ttgggatcgc tgggagattt attaagcccc tctttaactg    65820
cgaaaataag tttaggaaat acagcagtat gccctgaagc acccaggcct cttatacgaa    65880
cttccagcat agctttctgc aacatgcgtg cctcccagga ttctcctaga ccaaacccaa    65940
atgtcacaaa tggctgctga ccattagagt tgaacaacgt attaacttcg tactctagcc    66000
cctggcacgc atcatatact tcttttctg tcatttcagt agcatacact gctgccttct      66060
tactatcgtg aagccaacgc tggccaatag ctaagtgctt atcataggac ttacggacat    66120
acggggcaaa gacctcgtca atacgatcga tagacgtacc cccatactga cacgagctta    66180
cctgggcaat aacttgggca gttactgcag ctgcagtaga gatagatttt ggagtttcaa    66240
tctctgctcc accaattta gttccattct taaacatccc cgctaaatct accaggcagc      66300
agttagtata cccctgcgct cggtagtcca tatcgtgaat gtgtatctct cctctattat    66360
gagccgccaa taggtatgct ggaagctcct gtgctaccac atacttagag acttccccag    66420
ctatcatgtc cctctgtgta gggaattgct cgcttgcctt attggcatta ttaaacataa    66480
ggtcttcttc accctcgtta tcaaggatac tatagatatt atcaatcagg tctaattcgt    66540
tcatatattc ctccagttag gcatatatta taccaaatag acacaactat gtcaacctta    66600
ttttattata atcaacagta acttgatctg gatcatcaaa acaataaaaa ctggaaaatt    66660
ttatttgctt attcacccta ttttatatta ttcgtgtgcg cccgcgcatc gcgcgaataa    66720
aggaaaggat ccgtcctcca tatcatccta gaaatttca gttgcaatcc acgccaaaac      66780
ttggtatact ggtattctaa attgataaac atggtcgaaa tttgaccctc tgtagacctc    66840
taaggagatc gcaatgagaa aagcagcacg tcgtaaggag tcgcgccgta acggtagcgc    66900
aaaacgtgaa cgtcacgaaa acgtcatccc cgttgatttt gaagcacggg aacgttttca    66960
accaaccgca aaagaactca agccgaagaa cgctgagcaa aagcactata ttagcaccat    67020
ccgtaacttt acggtgacag ttggtattgg agaagcaggt acgggtaaaa cgtttatccc    67080
atctgttctc gctgctcaag agttagcaac gcctggttct gtgtacgaga agttcatcct    67140
```

FIG. 15KK

```
                                sequence.txt
agtccgtccg aacgaacctc ttggtaaatc cctagggatg ttgccaggag atctgaacga    67200
gaagatggca ccgtggttag aaccaatcgc tgacggcttc aagtgggcct taggggaacg    67260
ttcttatcag gggctggttg aacgcaaggc aatccaatac cttgctatcg aacatgcacg    67320
cggtcgtacc ttcaacaatt cttatgtaat tgttgacgaa gctcaaaata tctccgtaga    67380
agcaatgaag tgtattctaa cccgcgtagg tcaggattgc aaattagtaa tctgtggcga    67440
cgtagcgcag aaagacatta aatccgactc tggtctgcaa ctgatcatgg atatctacga    67500
tcagtacgaa catgtgcctt tctccttagt agagttgcat gataacgtgc gttccgctga    67560
atccaaagca ttccaggcaa tctttaacga tatgggaatc taatatggtt actgaactga    67620
tcattggtta tggtgagggt attacctctg aagaaaactg gggctttgta ggcttcggtg    67680
aaggtatcac ttctcacgac gaacgtcctg acctctaact ctaggagcgc gtatgaacaa    67740
cgtatttaca ctgaacaact tccgcactcg taaaacgaaa gtgcatccag tatccctggc    67800
aacagtcaat aaatacaatg ctaactatcc tgaggatgag cggcgacacc atgccgcttt    67860
caagatagca aacgaatttc ctaaccaacc cctcggtact aaagagttag ttagtcgaat    67920
gaaaaaatta cacttttatt aaagtagacc gacacacagg cagcctcgaa aggggttgcc    67980
tgttttttgtc tgtaaaatct catttgcaaa atggccgaaa acaaagtaga atatctttta    68040
aatcctgaca acttccaaaa ggagttacca atgacccaac gtattgaata cgttatcaag    68100
cgtgacggta caaaagaacc gttcatggcc cagaagctga atgactgggc aaaatacatc    68160
ggaatccgaa gcgatgttcc gtggtctccg gtagcggtag ccgcagttaa gaacctgccg    68220
aaaggtgatg tacactcaga cgatctgcaa acaatgctga ttaagtctgc cgaatcaatg    68280
atcgagcgtg atcatcgtta cgaccgattc gccctagagc tgcgtttagc ccagctccgt    68340
aagaacctgt ttgattctta cacccgccg tctctgcgtt tcttccacga ccacatggta    68400
gagctgggag cgtgggaaga tatgagcggc tggatctctg acgaccagtt cgaagctcta    68460
aacgaagtta tcgaccacag ccgtgacgaa ctattcacta atgctggtct gaagcagttc    68520
atggataaat actctagacg taatatctat acggaagaga tctatgaaac tccgcagttt    68580
gcctacatgg gtatggcaat ggcaatgctt tctcaacctc actggagtat gctcgatgca    68640
atcgaccttt ataacgcgct gtcgctacag aaaatcaacg tcccaactcc gccgctcgtg    68700
ggccttcgga gtgctgacag gggcttcgct tcttgctgtc ttgttgatgg tactgacacc    68760
ctggactcca ttgacgcagc agagcacgtc gtcttcaaaa tggtcgctgc ccgagcaggg    68820
atcggctatc atcttgagag tagatcaatt gctgatccgg tgcgaaaagg cgcgttccca    68880
cactctggaa aactgccata ttatcgacac atcgaccgct ccgtaaaagc taacactcag    68940
cagtcccgtg gcggttctgc aaccgtttac actgcgttct tcgatccgga aatcattcag    69000
gtaatggaag ctaagagcaa ccgttcccct gatgaaaaga aaatcgataa gatggactac    69060
```

FIG. 15LL sequence.txt

| | | | | | |
|---|---|---|---|---|---|
| aacctgaagt | ttaacagtat | tctcctgaaa | cgcttcctgc | gtaaagagaa | catcacactg | 69120 |
| atgagcttcc | tgtacgctcc | agaagtatac | gcagcattcg | actctggtga | tgtagcagaa | 69180 |
| tttgaacgcc | tgtacatcgc | agccgaaaaa | cgtctagcgg | gcgttaccaa | acgtggtttc | 69240 |
| aagggtgaag | ttctccctgt | agcccagtg | attcctgccg | cagaactgat | tgagttctgg | 69300 |
| aaaactgtac | gtatggaaac | tggccgcctg | tacactatgg | acgctggtga | agtgaaccgc | 69360 |
| aacagccgtt | acaaagatcc | ggtgcgtatg | tccaaccttt | gtgttgagat | tgtacagcca | 69420 |
| acgttcccga | tccctcacgt | agtagatctg | taccgtacag | acgaagaact | ggataaaatg | 69480 |
| gatgtttcag | agtatgggga | agtatctctg | tgcaacttag | gcgggttcgc | cctaggtcgt | 69540 |
| atcaaaactc | tggaagagtg | ggagaagatc | tcttacatcc | tgttgaagtt | cgttgatacc | 69600 |
| atcatcgaga | ttcagcacta | tccgttccca | gctatgaagt | acacggcatt | acgccgccgt | 69660 |
| aacgtaggta | ttgggctgat | gaacgccgca | ggagcgatgg | ccgctgaagg | cctggcattc | 69720 |
| gaaggcgaag | aagcccgtaa | ctggattcac | cgtgaagcag | agaaggcatc | attcttcctt | 69780 |
| cataaagcgt | ctgtacgtct | ggcaaaagag | atcggcccat | gtgaatggtt | ccatcgtact | 69840 |
| cacacttctg | atggtacact | gttaatcgat | acttacaaga | agactgtgga | tgacctggtt | 69900 |
| tccgtaggtc | tggaaatgga | ctgggagagc | ctccgtgaag | agatcaaaac | tcacggtatg | 69960 |
| cgcaactctg | ttctgacggc | aagtatgccg | ggagagtcca | gctctgttct | gattggtgtt | 70020 |
| accaacgcag | tagagcctcc | tcgcagtgcg | gtaactatca | agacttcggg | cgttaacaaa | 70080 |
| gtaattactg | tagctccggg | tctagacgat | tgggacacca | tgcagtccta | taagtatgcg | 70140 |
| ttcgatattg | accgtactga | gcacattaag | tggttagcag | ttctgcagaa | gttcacggat | 70200 |
| caggctatta | gtgccaacct | gtactacgac | tttaacaaat | atcctggagg | tattattccg | 70260 |
| ggtactgaga | ttatcaaaga | tctccttaac | tccactaaat | atgggattaa | gaacctctac | 70320 |
| tacgcaaact | ttgacgtaga | taccggaggc | tctgcagcag | agcagggttg | ttccagtggc | 70380 |
| ggttgtactc | tgtaattaag | ctcgatccaa | ccgaaagcaa | aattttattt | gcaagtaggt | 70440 |
| tggatttttt | gttataatat | tcgtatatta | aatgagagag | gaaattaaac | aatggcaaca | 70500 |
| gtatttaacc | gcgaatggga | tcacactgag | tctaaactat | tcctgggcca | agacctggga | 70560 |
| atcgccgact | atgtaaacgt | tcgctatcct | cgtttagagg | aacttgcatt | actgcaacgc | 70620 |
| tcgcagttct | gggttgagac | tgagatctcc | ctggaagccg | ataagaaaca | atggcctaat | 70680 |
| ctgccacaac | atattaaaaa | caaaaccctg | ctgaacttag | cctggcaaac | ccaagccgac | 70740 |
| tccattatca | cccgtgctcc | ggaagatgcc | attctgaaac | tggtatctcg | ccctgaactg | 70800 |
| gaaggtatgc | ttattcagtg | gagctacttt | gagaatattc | atagccgtgc | gtattccaac | 70860 |
| attattcgta | acgttctccc | taatccgggt | gagttcattg | caaccgtaca | ggctaacgac | 70920 |

FIG. 15MM

```
                              sequence.txt
gaagcattcg cacgtctagc actgccggtt tctgttattg atgagttggc cgaaattgcc      70980
gacatttggc tggacgctag agccaatctg gaaatcgctg agaaggaagg tactctggaa      71040
tacaccgaag aggcagactt cttagcactt actgaacaag tacagcagaa gattctggag      71100
ttctactacg ctgtatacgc tctagaagcc attatgttct acgcgtcgtt tgcgtgcacc      71160
tttgctctgg cagaaaacga tatcctaacc ggtattgcaa agaacttaca gctgatcgct      71220
aaagatgagg cactccatac cgttatggct atggaagttc tccgtattct tcaaaatggg      71280
gaaattcccc cacatgtagt ggcagcagct caggctaacg ccccgaagat cctgcgcagt      71340
attctggaga cagaaattaa ctgggcgcat tatattttcc cggaaggcga agatattcca      71400
ggcctgaacg ccgatttgct ggtagagtac ctgtactaca acgcacgcct ggcatttatg      71460
gcgatcaaca ttccgtggcc ggaagatctc ccggtaatta tggaagaccc gattggctgg      71520
atgaaaggtt ggctgaacac caagaaccag caagtagctc cgcaagaagc acagattacc      71580
aactatcgtg ttggtgcaac ctctcaggct aacccggacg atctgtctga tgaatttgga      71640
gagttcctgt aatgattaca gctttatacg caatgcgagt tgacgccgcc ttcgggattt      71700
ttaatccggc tacaatggat gcctacgggg aacttccctg gggctccatt cccgaggagc      71760
tagaacagtt ctacagaatc ctggatacct atcaggttgt tatagtgggc cataatacct      71820
acgaaacagc ccctccacga ctgaaaaagg cactggagaa gaaatccatg gtgtacgtag      71880
taggttctaa ggctccagtt ctgataaaaa accctccccg taatgtgcgg tttattaccc      71940
acttgggttc caaaattcgg gacttctgta atgaagttga ggtagtctgc ataggaggga      72000
aagctctgct agaaaccta gcaactatgg gctgtctgga tgcgatttat cgctccacca      72060
tttatcctaa ggccggtaca gtaccaagcc tagaccacat catgtatctg aacacccga      72120
tacttacgtc cactcctccg gatgctgtag taactcatat agcttctggg gaaaatgagc      72180
gctatcgttt tgttatggaa ggagtctatc tgtgattcac tatattaatg aaggcaaacg      72240
cattcttgaa gaaggtgtat ggctggagaa ccctcgaacg ggggttcgtt gtttaaccgt      72300
aatagggtca aactttgaat atgatgtact cggaaagaaa ttcccactta tcacaactcg      72360
taaagcgtat gctcttcagg ccatcatgga gcttatcgga tatctgcgag gatatgattc      72420
cgcagagcaa ttccgtgcta tcggctgcaa tacgtggaac gctaacgcca acgaaaacga      72480
ggcgtggttg gtcaacccta acagaaaggg aaccgacgat atgggtagag tctatggagt      72540
acagggcaga acgtggcttc gaccggatgg ttcccacttt gaccaactct ataagatcta      72600
tgagaattta cgacgaggca ttgatgaccg cggagagatt ctcaccttct ggaaccctgg      72660
cgaatttgat caaggatgct tacgaccgtg catgcatacc caccagttct cgctgctcaa      72720
tggaaatctg tatctcgact ccttccagag atccaatgac ttcctattgg acaagccttt      72780
taacatggtc caatgctaca cgtttcttgc gcttatggcc cagatcacag ggaaccgggc      72840
```

FIG. 15NN sequence.txt

```
aatcagagca aaccaacgta tagtaaatat gcacatctac gagaatcagt acaaggttct    72900
catggaacat gggcaatttg accgcaaacc tttcccggct cctcgtctag agatcaaccc    72960
ggagataaaa accctagagg acgtactcac ctgggtttct aaggacgact ttaaaatcgt    73020
ggggtataag tctcatgacc ctattgcata tccgttcact gcgtgaggac ttatgggatt    73080
atttaacaga cgccccaaaa taaccttctc cgaaagggag gagtctcagc tgaagtttct    73140
ggttcaatcc tcgggattac acatagatgt tatcctaggg atggtaaagt acaagggcat    73200
ggacgcacta atgcgtcagt ttgcccctaa accacctaaa gaaaaccctc cagccaagcg    73260
ggactataac agtaatttac tggttcctcc agctaaatta ctataactaa ggtggccttc    73320
gggccactta tattaaaaat tcatttgcaa accacgtgaa tttctaatat aatagattca    73380
taaatttgag agaggaaata aatatgtctt ttactgatgc aaaagcaatg gcagctaaag    73440
ccaaaaggtc taacgatatg gcagttatag cagctcgcag atctattata tcaaatattg    73500
atggatcagc ttcttcaggt aaaacagaag tagattctta cgcattgaat ggcctgccta    73560
tcgccgcacg gtctcagatt atggaagacc taaggacgc gggctatgaa gtaaaagtaa    73620
atcatccgtt tgaccaacgc gatactgaat caattaccat ttcctggggg cacgcataat    73680
gtttcatgtt tatactgatg gtggttgccg cggtaatacc cgtggggtag acaacgttgg    73740
tgcttgggct atggtagttt acaactccag cgaagagcaa atcggcacca agtctgctcc    73800
caaacgcaac acaactaaca acgagatgga gcttcaagca gtcctagagg ctctgctatg    73860
gtctaacaaa aaccctggcc gaccaatgac aatctatctg gactcaacct acgttaagaa    73920
tggttgtgag tcctgggttt ggggctggga acgtaaaggc tggaagaagg cagatggtga    73980
tacacctctg aacttagacc agtggaagtg gattatcgac gaactcaaga agtatcgtct    74040
aaaccacaat gagatcccaa ctttcgttaa ggttaagggc cactctggtg tagaaggtaa    74100
tgaggccgca gataacctgc taaatgttcg aatgaccgaa ctggaaatgg aggatatgtg    74160
atgttggaga atttacgccg cctagttagt gaaatgaaat atgaagtgct cctgatggag    74220
cctggtgtgg atcgagtagt aatgaaattg cgaatcgcac gtatggaagc ccaaatcttt    74280
gaagcggagt ggaaagctct gaggggtgga gatgaattat aatggcacca gatttgaggg    74340
atttgttccc aaacgtacca cagtaccagc tcgatctcta cgccgcgttt ctggaagcgt    74400
caaaatcggg gaaccctcta cgcgtctacc gccaagaccg caggcacggg aaatcctgga    74460
tcctgagatg gctgaaagag aacgagccgc tcttaaagaa attgagcgaa agaaactctg    74520
tacagcaccg gcatacaaca aaggtgggta ccagtacatc agctcagaag agcaggcaaa    74580
acatatcggg cggtaacaga tacgagttca tcatcttcga tgatcttgta gatgaaaatg    74640
aaaaaacgca gttgctaaac gctaaaaatt aacgtataat agattcataa attaacgaaa    74700
```

FIG. 1500

```
                              sequence.txt
ccaatcaaaa caaaggaaat aaatcatggc taagcagacc tctaaaaaag cagtagaaac    74760
caaagttgca acttttccca aaactgaagc gaatcgcaaa gcacgtctgg agcgtcatct    74820
gcgtaaacat ccggctgata ctcaagcagc atcagctgta ggcaaaccgg ccccgcgtcg    74880
taagaaaccg gtaactaagg gttctacctc cggctacgtc tccaagatcg tcggttggag    74940
tacgccggat aaggcagaca ccaaagaagt cctgcgcaag acccagggcc gtttcggtag    75000
cgtcaagccg aatatcttcg gttgcgaata cagccgtgag aatgttcgcg ctctgtgcta    75060
cggcgtaggt attaaattta cgggcaaggc aaataagccc cgtaatcaaa aacgcaaacc    75120
agctaagaag gcataatgcg aaatttgta gctaaaaacg atttcaatcg tgcagcgaca    75180
cataagtcgg ccctagatta ttctagggtc aactcccggg aactgatgga ttcgtgctac    75240
gaagaactcg aagattgggc ggctgactgg ccgtcgatgg aagaaaactg ggatgtgtcc    75300
gaagatatga ctaagccacc accggaggtg gcttctaaat gtgataacac atctagaagc    75360
aactttaata acaaaggaaa caatatgcaa aacttacaag accgctggat ctctgtttgt    75420
gatatcgaat ccctgggaac tccgggagat tgcaagagca cctttatcgc tatgccgttt    75480
ttcgctttcg tactgatgaa agatctatcg ttagatccgt atatcgttct aggcactcct    75540
aacgttgccc agcagttggc cctcggtgct aaagtctccg ccggaactat tgcattctgg    75600
atgaatgagg ctcgtgctgg tagtgctccg tcgctgtcca ttattgaagc tctgaacgct    75660
aaagacggtg agtctactgt tctggtctgc aatccgactc atgaatcacc ggtatccaag    75720
catacgttca tggatctgat ctgcccgttc gtagaggcaa aacaggtaat cgaaggcatt    75780
atcgatgagc aaggtatcga cactcgttcc ctgcgccact acggtaatgg cccgcagttc    75840
gatatgtcta tttacgaaac agtggcggct caggctaatg tcttctctcc gtctgatcct    75900
gcaatcgttc cgtggaaatt ctgggatatc tccagcgccc gtaacccgcg tgactatttc    75960
gaggctctcg gaggagactg gaaagcattg gtacgttgtg ctgaaatcta cgcacacgac    76020
gtaatcgagc gttacaacct gattcctgag ggggtctatc cgtcgaaaca tgatccggtg    76080
tttgacgccc tggtagaagc gtactgtatt aaaactatcg aatcgaaatt gaaaatttga    76140
tttgactaaa tggctgattt cttgatatac tattattctt gaatcaaaga gtaaaggaga    76200
aataatgaaa gcagccattc taatgatctc catcctcact agcttccatg cgcaggcaaa    76260
gattgatgcg catgagatag agtgcatagc taaaaatgcg tactttgaag ctagagggga    76320
aggagttaaa ggaatgaccg cagttgcaca agtaacgaaa aatcgtgtta actatggaaa    76380
attcccgtcc acatattgta aagtagtcta tcaaccaggg cagttcagct gggttggtaa    76440
gaagaaacat aaactcgatc gtaaagacga agagtggaaa caagctaaag agatagctag    76500
actagtttac tatatggatc ttccagtaga tccgacgaag ggagctttgt actttcacag    76560
taaagatact aaaccttact ggacaaaaga caaggacttc aaaagaacaa gtaaaattgg    76620
```

FIG. 15PP sequence.txt

| | | | | | |
|---|---|---|---|---|---|
| caaccatgtg | ttctataaat | taaaatctca | gttgcctaat | gcttaaaaag | ttgatataat | 76680 |
| agtttcataa | attagagaga | acagcgggcc | gattacgctg | aacttgtttt | aatgtaagac | 76740 |
| tcgtcgagca | ttaagattcg | ttgaatagaa | tcggtgagtt | aagagtgatc | acctgacaaa | 76800 |
| gttcgtgcat | ccagtccgga | taccggccag | ggagcgtatt | ggacgggcgt | aggttagaga | 76860 |
| tctcttgtaa | aactcgggag | ctgtcccgga | gtctcgtaaa | ctcttctcct | gatttataga | 76920 |
| aaatggtgga | atctcacttt | aacctgttcg | accagaatga | agcatggtgc | gtggcctgcc | 76980 |
| ggagaggtgg | ggagctgagc | ctgagaaact | cgtatagctc | ccacactgac | ctgcctaggc | 77040 |
| cgcaaattgg | agacatgtgt | atagcgtctg | gtgctagtta | ttgccaccat | agtggggtgt | 77100 |
| cgaaatcact | tatgtagcaa | cactgccgtc | ctaagttaat | tggtagactt | ctgcacgcgg | 77160 |
| gggagctatc | cccagatgcg | gaaagtgcag | gttcgaatcc | tgcggtcgga | aagagttaga | 77220 |
| taactgatgg | ttctattggc | gaaccactcg | ctgctggagt | acctcctccc | ctcccaggga | 77280 |
| aagacttggg | agactcgcgg | gaacgaaaca | gctaaaccac | gaaggactag | gatgctgatt | 77340 |
| tggctaccct | tacctgatat | atgcccaaat | caaaagaaga | actttaggcg | gtagcctaga | 77400 |
| tagtgaagtt | tttcctccac | gaggagtcgt | ttttcaagct | atcaaaactt | cacatcgaaa | 77460 |
| attcggaggt | gtgattttaa | cagaccgcgt | ggaggatggc | tctccagaag | tgccaaagtt | 77520 |
| agtccttaaa | tacggcatga | tgatcgtatg | aactttggcg | aggtgggatc | tcgcctgatt | 77580 |
| ctaagtggga | aagagtattc | ggatagccgt | tcgtacaaac | ggtggctccg | agacctaagt | 77640 |
| gggacacggt | tgagtataca | gctccgcgga | agctcgtata | ccctgtgtaa | gcatgtgaca | 77700 |
| atggagtcat | gaccggagtc | accccgagcg | aaagcataac | cactatttat | agcacccta | 77760 |
| cacaggctag | aagtgcccct | gtttggagtg | tgccctcgcc | tagaccgcat | tagccgacgg | 77820 |
| atatccgttg | gccgggatct | ggcaaggtat | attagtcacc | ttgactataa | ctggaagata | 77880 |
| cgtctgacag | aagggccgca | tagcttaaac | aggggaaggc | ccctacctac | tggcggtatc | 77940 |
| tttaagagct | ttcacgagag | ttcttaaaga | tactaattga | cgaggtctat | atgaacgatt | 78000 |
| taagtatgtt | aactaagata | cgctctgata | ttgagtctat | ggtctctcgt | cgtagtgagc | 78060 |
| tgactaaggc | taaacagatc | atcagcggtg | gtacacagaa | acgcttcaca | ttgcaagccg | 78120 |
| gggatattaa | gtttgaccta | tgtggcagcc | agactcgaga | ttacactttc | gaaatgaaac | 78180 |
| cgtgttacga | tatggtgaag | ctgggcttaa | tcaaagctct | agacaaacaa | atagatcagt | 78240 |
| gtacggacgc | aatcaaaacc | ctaaacgtcc | agttcgccgc | tgaatgcgat | cgtctcaaaa | 78300 |
| actctatcaa | ggtataataa | tggtggcatc | tgtgcatact | cctccgtatg | aacgtccagc | 78360 |
| acctaatctg | acacctgaac | agaaacagct | aatcgccagg | cgcactctag | agtttaaaga | 78420 |
| gtcgctgcat | aagagcgttg | gccggtattc | tgaacaggtt | catgatctgg | ttgtcaaaac | 78480 |

FIG. 15QQ sequence.txt

```
acttaaactt tattaatgct tccttagctc agaggataga gcaacggtct tctaaaccgt    78540
gggtcacagg ttcgaatcct gtagggagta ccactttaat cgctgcccac acgtaatatt   78600
cagtgggcag cggcagaaag cccgcagggc gcagattaag attgattcta caaaattttt   78660
cttgcaattt tgtcagaaat tttgtataat agttctttaa atcaaagaga aagtagagga   78720
taaaatggct tacaaaattg aatatttaaa gaaaggggtt ctcactgagc tggttatcga   78780
tgcgaacatg gctcgcaacg agggcactaa atccgtattc tataaagacg gtagcgtagc   78840
tcgtatgatc aataccgaag acattcagga tctgtacgtg atctccgacg aagaagcagg   78900
tttcgtaaaa gatcctgagc cggctgaaga tactccaact gaagacactc cggtagcgga   78960
taccactact gaagaacctc cggtggaagg cactccggaa gatgaagcag cagtataaat   79020
aactaagggc tagaaatagc ccttctcctt gggccggtag cttaaagtta aagcagtggc   79080
ctcataagcc aacgagtggg agttagagtc tcccctggcc caccaatttc ataacaggag   79140
actaaaatgt ctactaaaaa cgcaatcgta tccttcgtgg atgacagtgg tatcgtccta   79200
gagtccacag taacagatat cagtcctaaa cgtctgctcc atcgtgatgg ggatatcctg   79260
gaaatcctta ataaacggtc tgagactatg ctggtcattc ctgtaaatcg tctttctctcg   79320
attaaaatcg tgtgggagga ctaatggacg ctcaattaca aacccagtac tatatgcttt   79380
taggcatgtt agaggatgct ggcccgacag tcagagggca ctatgagcgt cacaaagcag   79440
cttttgaagc cctactaaaa gaagttaatg agaacgaagg tggtaaaggc tctgactcct   79500
atgccgcatt cattatcgcg ctacaagttt tcctaatcaa tcaactcaag taataggcta   79560
aatatgctga atattaaacg taaaggtttt ttctacaagt ggcttaattt ctcttccgcg   79620
tctttcacct accggctgaa cgacaacaga gtcaccttgt gtagcctatt ttggcactca   79680
gtgtggtatt tcctgctaca gattggcgta actgctattg ctgtactctt ctccttgggg   79740
atgggaagta tcttatctac gttcttgggt ctcacctttg agctgggaat tactccctgg   79800
tacatgcttg tagggttaag tctagcagga ctatctacga taatagcgat tctgctggcg   79860
atagctggga tcggctgggc ctgcgctaag ataggggatc ggatccagga atggaacgcg   79920
agtaaatcct ttgaaagggc acagaaagag tataatgctc gcgatgaaga gctccgcttc   79980
ggtaatatct accagaagat gcgaatctat aagaaggaca aactttgtcc gctcattcgt   80040
gtagaccacg gcgagtagtt tgcatagtga cctgcgttgc cgggtcacta ccaaaatact   80100
tgaaaaattc aattgctaaa tgctctagaa tttgagataa tatttatatt gaaagggaat   80160
agccaagtgg ttacggcatc ggcctttgac tccgagatcg gtaggttcaa ctcctccttc   80220
ccttgccaaa tttaaaatgc tcctgtcgtc taagctggtt aggacaccac tctttcacag   80280
tgggaacacg ggttcgaacc ccgttgggag taccaaattt actgaaaaat tcagttgcta   80340
aatgcttaac aaattgatat aatatttata tagtttgtta aggaattaat ctgatactga   80400
```

FIG. 15RR sequence.txt

| | | | | | | |
|---|---|---|---|---|---|---|
| gccggaacca | aaaaacacgc | ttgcagcttg | ctcggtcatt | gtactgaggg | ttcgcaagaa | 80460 |
| tagcggagtg | gctctccgaa | acgcctggta | agcgtagagt | gtatcgtatt | tgtgaagagc | 80520 |
| gggtatcctc | gcatggctaa | ttgcttaggg | tattacgcgc | accggattaa | ttgccttaac | 80580 |
| aaattattgg | gggatgggtc | tgctgggagt | ggacaccgca | cttgcaatgc | gggaatcaga | 80640 |
| acggttcaaa | tccgttatcc | tccaccaaac | aaatggggat | gtggcgaaat | tggcagccgc | 80700 |
| gctagattta | ggttctagtg | gtgaaatatc | cgtgtgggtt | cgaccccctc | catccctacc | 80760 |
| aaataacggg | agttcgtgat | gaacatagaa | atcatgcagt | tggatcgtaa | gaaaaatgag | 80820 |
| ttccgtaagg | tccatacctt | tccgagtaaa | gaagctctag | agtttcatat | taagtgtatg | 80880 |
| ggactggtgc | taccggaaag | cgagatcttc | gacttagcat | gtgctaacgg | agttctgtac | 80940 |
| gtctgggaaa | tcacgtatca | tgctgatcct | gatgaactcc | gtaaagaagt | agagcaaata | 81000 |
| ctaactggag | agtagtgctc | atgggagcaa | gctgacttga | aatcagtcgc | catcggaaac | 81060 |
| ggtgagggtt | cgattccttt | attctccgcc | aaacaacagg | aaagctggtg | aaatggtagc | 81120 |
| cacgcatcac | tgctaatgat | gagtccgcaa | gggcatgaag | gttcaagtcc | ttcgctttcc | 81180 |
| gccaaacaat | ggcccgacga | gtaacggttg | cccctttcta | gagaattttc | tgggcgaaaa | 81240 |
| tccagaagta | atcaactagt | tgtaagtggg | aagagtttct | tagggccgcc | aaatttgagt | 81300 |
| atcattggta | ttgtaggagt | cgtacgctgg | gactacgtag | tacactgagt | gtcctatgcc | 81360 |
| cagtacgcgg | tctaaccaaa | tacggtgtgc | gatgtgcatt | ttatttgtgg | aggtctgatc | 81420 |
| agccctcgat | ggtactcaaa | tttgggatat | tatcataact | ggataatgac | ctcgattgtg | 81480 |
| gatcgagtct | atcttggttc | gaatccaaga | tatccctcca | gattactgca | ccattagttt | 81540 |
| aatggataga | atatagagct | acgaactcta | tggttgaggt | tcgattcctc | gatggtgtac | 81600 |
| cataaaatct | ctgctgagag | tgacgaggtt | agccctctgg | gtcacatccc | tcttctagcc | 81660 |
| gcctcccata | aatgcaagca | tttatgttct | ggccctagac | acaacgttgt | actcagcaga | 81720 |
| gtgcgcataa | ttggggtata | gctcagtagg | tagagcggag | gtctctgaag | ccttaggtca | 81780 |
| caagttcgat | tcttgttgcc | cctgccaatt | gcaccgtaga | ggagaggccg | tcctcgccag | 81840 |
| tctcataagc | tggagatcgc | aagttcgaat | cttgccggag | catccaattc | taggagaaga | 81900 |
| tgatgagaat | ctctttcaca | gaacgagtac | taggtactgg | agtaatgcta | atcacttcct | 81960 |
| gggatggaga | tagctggtgt | aacgtgacag | gcttacgtaa | gtcagaacaa | acacccgaga | 82020 |
| atatcgctaa | aatcaagaaa | cgaatggcag | aagctgctag | tcgtcctgga | gcacctcgta | 82080 |
| atggtaaacg | ttgaggtaac | tatgactcgc | tatcaaggta | tgctaattaa | tacccacaca | 82140 |
| aaagagattg | tattcttggc | accggctttt | cacgacacct | acaatgaagc | cgaggaagac | 82200 |
| gctaggatcg | ctaaaataca | cccggacgag | gaaatctgcg | tccgtcagca | agaacaataa | 82260 |

FIG. 15SS sequence.txt

```
tgcttcaata gctcagttgg tagagcaaac gaccgataat cgttaggtca ctggttcgag    82320
tccagttcgg agtaccaatt tttgccccct ataggatatt tcatcggaat atcctccagc    82380
gatggtacgt agtatagtac ttacctgtta agcctagaca aagttacttt gtgggcaaaa    82440
taggtataga taggagaaga atagtagcgt aagattcttg aggcaaattc tttaggtcag    82500
ttggcagaga tggtttatgc actcgcttca tacgtgagac tacagtggtt cgagtccact    82560
attgaccacc aaatacttgc ttagctcaat cgggagagca tcgtctttac acggcgaggg    82620
tagctggttc gaaaccagca gcaagtacca atttacagtg agacttcggt cagggccgtc    82680
aaacgtccga gaagctgtaa tttctgatgg ggatgatccc agattcgtaa gaatacccca    82740
tccttacctt cacaggtttt agcgcaatgc tgagtaaaag tctagggaat cgactccatg    82800
ccatccagga gtataaatgg cgaatctagg gacttagacg gtcattgccc tagcgcgttg    82860
atgccgtgcc ggaatcggta tacggggctt cctaaagggc gtaagcagaa catccactct    82920
gcataagata cccgaaaacg aggctgagat aaatggtcta tcttgtgaag gttcgatccc    82980
ttccggggtt agcgtgtagt ggggctaatc aatccccacg ttaaacgttc aagttaagat    83040
ttgttagttg cagaagcggg gaggctatca accttcagtc cctgaaagct ctcagcgctt    83100
ggaactcttt cgtccgtaag gaatagatcc cctttcgctt tgactcgcaa acttcaaacc    83160
aagtgtaact aacagctgca agcctggatt accgctctcc ggagcggata attcaaaaat    83220
ttatttgcta aacgctctta tttactgtat aatagttaca taaattaatg agaggagtta    83280
gcaaatggaa aagattactg caactggtat tgaatctgca ctggtggttg attgggccgg    83340
atgggacgga gatcacgaat ggatggtctt ttatagctgt acgcttcagc cagaactatg    83400
gactaggctt accgatgagc atgctatgcc ctacggtatc atagatgtag aaattgagat    83460
taacaaactg gttggcacca ttatggtgca tcgagccgaa ggcgatcaca aggaaatctt    83520
ccgtaaaagc attaaactgg tagtttctac cggtgacttt atttaacaat taactgagga    83580
aatactatgt acacacgtcc tactaatgga aattctgctg tagtccgcct gatgattgtt    83640
caggacaacc tgtccaacaa catcgagtct ctagaccgtc gtattgagga gtatcgcact    83700
gagatgctgt ctctgatgcg cgaacgtgag gccaagatcg aagagcagct agaggtttgc    83760
gaagctatcg accgcctggt tgacggaacc gcagtattta tggcggaagc tcccgcagag    83820
cctaccttca ccccggtagc accagctgac atgcagtatg ctattctgcc tttccatctg    83880
gaagaagaag atggcgaagg cccgtcgctg gaagacgttg ttcgcttcct gcttgcctcc    83940
ggtttcccga acggaggtcg ttaatggatt ttatcgttgt ttgcggagcg aatactgact    84000
gcttcgagct gttaaacgac gccctagaca aggttgatga acacatgcag gaaggcagaa    84060
ctcctacatt cattgacctg tctcaaggta aaacttactt ctacccgtct cttgacgtag    84120
agcctacagt tctacctatc ttcatgcact ccctctcgtg ggacgaagaa gacgattaat    84180
```

FIG. 15TT sequence.txt

| | | | | | |
|---|---|---|---|---|---|
| gaaaaaattc | atttgcctag | tactctgaaa | tttagtataa | tatttatatt | gaaacgaaag | 84240 |
| aggaaaagca | aatggaagat | gaagttaaat | tgtacatttg | ttcagattgc | ggtgagttaa | 84300 |
| gtgaatgtca | ttgggagtgt | ccgacttgtg | agtcagacga | cttaatggaa | tacgaaccgg | 84360 |
| aataacaaat | taagcggcta | tggtgttcag | cggtcaacat | accggcctgt | cacgtcggag | 84420 |
| ccacgggttc | gaatcccgtt | agccgcgcca | aattctctct | gggctaagag | atatgaccgt | 84480 |
| ctagaggtat | cctcggacac | aagggtcagc | cctagacaca | ataagttagc | aaatatctcg | 84540 |
| tttcgacgag | gtatttgaag | aggttcttac | gagagcttct | tcaaatacgg | gggaatattc | 84600 |
| tgtaagtggt | agcagagcgg | tctgtaaaat | cgttgccatt | gcggctcggg | tggttcgact | 84660 |
| ccatcttccc | ccaccaattt | tgacaatcaa | agagatccgg | gttcgaatcc | cgcgtacgca | 84720 |
| acaggcggca | taaaggcctt | gtagcttaaa | tggacaaaag | cgctttggtt | gttaaatcta | 84780 |
| tttgggagag | aagcagtaag | tggtataggc | ggtcgcctgt | taagcgaatg | acagtgagtt | 84840 |
| cgaatctcac | ctctcccgcc | aattttactg | aaaaggttat | ttaattaacc | taggcacgcg | 84900 |
| taggaatact | gccaccgcaa | ttgaaagatg | tggcccggtt | tggagaggta | tgccgctaca | 84960 |
| cgctacggtg | ctaactccgt | ctaggtgaaa | atcctagtca | gtaatacagt | attagggtaa | 85020 |
| gaacagcgac | ttaggttgca | gtgaagcgtt | agcaatcggt | ggaactccgg | tgcgccctaa | 85080 |
| ttaaacaatg | catcattggc | cgagtgacta | ggcagaggct | tgcaaaccct | cgaagcatgg | 85140 |
| ttaaaatcca | tgatggtgct | ccaattacca | gaggtactca | tgattaagta | taaggcgttt | 85200 |
| gtaacaagag | agtcccaaac | aggagattca | agtattaaat | tcgaaggtac | aacgttacat | 85260 |
| gatacatttg | aagccgcttt | aacagaggcg | gaaacccata | tagtatcgaa | aagctgctat | 85320 |
| gctcatgtat | gggaagtaaa | cactatttta | gatcgctagc | tcaatggtta | gagcactcgc | 85380 |
| cttttaagcg | ataggttccg | ggttcgagtc | ccgggcggtc | taccacatta | tgggacttca | 85440 |
| gctaatcggc | taagcatcat | agatagcggg | gaatcccggt | ctgtgagggg | agtaacacgt | 85500 |
| agtctcccaa | gttccaccaa | acatcagagc | agcgtgatgt | actgcaaaga | cccaaagacc | 85560 |
| ggggtggact | tcttgattca | aaggagcagg | cacgaattac | gcaactgtag | ctcagcgagg | 85620 |
| tgagagcact | ggtttgaaag | tccaggggtc | gttcgttcaa | atcgaaccgg | ttgcaccaaa | 85680 |
| ttaatagtat | caatagctta | tggagctgaa | tagtcctaaa | gctcacggta | aagcagctgg | 85740 |
| ccgttagtga | gcagacttgg | aaacgtctgg | tgatctctag | gttagccggt | gcgttggttc | 85800 |
| gaatccaact | gatacttcca | aatcccaagt | agcccgttac | aggctctctg | attaaactca | 85860 |
| gacaagcagg | taatgggtga | caggataaaa | taagccactg | atttccggcc | gtttgacgtg | 85920 |
| gtaaagtcct | ccagtcaaga | agaatttctg | cgtgcagaaa | tcactgaaag | caatggggca | 85980 |
| gacaacttga | gatagattgc | ctataacgtc | tcaagtagtg | gcattgactt | agggtggcat | 86040 |

FIG. 15UU sequence.txt

| | | | | | | |
|---|---|---|---|---|---|---|
| tttcccgaaa | gttcgaaaaa | ttcatttgct | aaacgctctt | atttataata | taatatttat | 86100 |
| ataaattaat | gagagggctt | acctaatgaa | tcaaaaaatt | cttatgcgat | ataatccacg | 86160 |
| agctttatgg | ttccgctggg | aagtgattgt | atcgtaccag | atacgagtgc | gtaacggtga | 86220 |
| tcctgagaac | aacattatcg | tgctggagac | attctctaat | agagatgcgg | cagttaagtt | 86280 |
| cctgaacacc | atcgacaata | ctttaatcaa | ggtatattaa | taatggatat | ctttactact | 86340 |
| cctgctatca | acttggtcgg | tgtcggccta | ttccaggcaa | cggtctatcg | tattgatgat | 86400 |
| agcactgacg | ttgtaacgtt | cattgtaccg | gagttcttcc | ttgagaagtt | ctttgaagag | 86460 |
| tttgagcaat | tccgtgaaga | gcatgatgct | tactccaata | tggaagatct | agcagcgatg | 86520 |
| ttcccaactg | tatacggcta | catctttgaa | ggcaatgatc | tgcttttgga | taagtcagag | 86580 |
| ctggtggaac | tcaactgggg | cattagcttt | gaagtgggct | ctccgttccc | gcggtatttc | 86640 |
| caaggtctgg | agattcgata | atgggcggct | actctaattt | catcgagaat | tacattaatt | 86700 |
| ccgtagattc | ctggaatcag | gaaactctag | tggtagtgct | taaagagaga | ttcaatatct | 86760 |
| ctactctgga | agccctagag | gctatagaag | cctacttgga | taacgattaa | cacccacttg | 86820 |
| gtccaatctg | gtagaggcat | gaggcttaag | acttcagggt | tcccggttcg | agtccgggag | 86880 |
| tgggtaccaa | attatggggc | acgactgatg | gggaagtcgg | cctggctagg | gttgagatac | 86940 |
| ggttcgattc | cgtaggcaaa | tggtctcgta | attccgcaca | ggtgatggaa | ggttcgagtc | 87000 |
| cttctcccat | aactatacaa | attcccctta | gctcagtctg | gcagagcggg | cgctttggga | 87060 |
| gcgtcaggtc | aagtgttcaa | atcacttagg | ggagaccaat | cttgcctcaa | tagctcagcc | 87120 |
| gggagagcaa | ccgccttgta | agcggtaggt | cgtgggttcg | attcctactt | ggggcaccat | 87180 |
| tttcgctggt | tatggttaca | gtgtgattaa | gtttacattg | tcattaaatt | ccggttcaat | 87240 |
| tccggaagcc | agcaaaccta | aaaggtaagc | atatgaggat | tctttccata | gaagatgtta | 87300 |
| tgtgtgacag | atgctacggc | tccatattct | ctggtggctg | tagttgtaag | taatctatct | 87360 |
| aatgaccttc | tgtagatgta | aaataaatat | gaagggtcga | tgctcgcggc | taccgacaga | 87420 |
| tcgtaatgat | caagtagtag | tctgaggtga | agagactagc | ccattaattc | cgcgactaac | 87480 |
| tgtacgggtt | acagcgtccg | ccttccaagc | ggtactgagt | ggggttcgat | tcccctagt | 87540 |
| cgctccaaat | tcggtaaaat | gaccgtcccc | tgacgttacg | gggaattaaa | caaggaactg | 87600 |
| ggagccggta | aggccatttt | atcgatacta | cttgagaggt | acaacaatga | aagcctttga | 87660 |
| tgcagaacta | gtgttctcac | tcttagctga | gatggaagcc | tgcgtagatc | gtgtacgtgc | 87720 |
| gctgcgtctt | agtatgttta | gctcttaaat | tatttgctgt | tctagagcca | atgtagtccg | 87780 |
| gggtgccgac | gtctgcctgg | aactcgactc | taggatagtc | aggacgtcac | ttaacagcca | 87840 |
| gagatggcaa | actataggag | aagcaaatgt | taacagttaa | ggtaatgtca | cctaacggtg | 87900 |
| gcgaagaaat | tcacgatggt | tcaagcgttg | ggtttaatcc | taagcagaag | agcatctcta | 87960 |

FIG. 15VV sequence.txt

| | | | | | | |
|---|---|---|---|---|---|---|
| ttgctggtct | tgatcagcat | atcttcctga | aagaagatga | ggtagcctac | gttatgaatc | 88020 |
| agaatggtaa | gacagtatcc | gtctaccacg | gtagctaatt | ttattccccg | agtgttactg | 88080 |
| gacagcacgc | cggtctccaa | aaccgtgcag | taggagttcg | agtctcctgg | ggtttgccag | 88140 |
| tttaaaggag | tgatcatgat | cacttatagc | accaatttta | tggggccagt | ctccaacaat | 88200 |
| tggtacatcc | gtatgggtat | tccgtatacg | gaagtaaccg | agccgaatcg | ttttgcagat | 88260 |
| ggcgggcaac | taactcgaaa | agtatttgcc | aaacgatatg | ccggtggtcg | cattgacgtt | 88320 |
| cgtggtactg | atgactattt | cggccaggaa | atcggtgttc | cgattatgga | ggccgagtct | 88380 |
| tggaatgaac | tacagcagtt | tctctggaca | ttctcgtccg | ataaggttct | gacattggag | 88440 |
| caaattgtac | aggctctaga | ggacgagaca | ggttttcgca | ttgtttggtt | taaggagcca | 88500 |
| gcatgtacat | agatcgtaac | caactgttca | agttcctaga | gcttgacctt | cgttggcctc | 88560 |
| tatcagtcaa | tccgggacga | gctactggca | agacgttcga | ggctattaat | acagcctatg | 88620 |
| agtttgcagt | atttaaaggt | attcaagcag | tatacgtagc | atccggtgtc | cgtgaaatgg | 88680 |
| cacgcctaga | gaagaagtat | aacgagcttc | aacctcatgt | taaaattaca | acgtatagca | 88740 |
| tgttagaacc | ctaccgtata | ggtcgtcgat | tcagctgcat | catgtttgac | gaacctagct | 88800 |
| tggctattaa | gtacggcgta | aacgcttacg | tggttcgtat | agccagagaa | aaccagtgtc | 88860 |
| ctgtaattat | ttttggagag | taaagtggaa | caagaatttc | aagtcttcgt | agacgcctct | 88920 |
| aagagagttt | tattcataca | agccaccgat | gaaggtcatg | gcctgcaact | ttccttcgac | 88980 |
| tctctggagc | aaataaacca | gattgttctg | agggcacaaa | aatcattaga | aaagaacact | 89040 |
| gaggcacctc | ctgacctcta | aacaaaagcc | ccttgtctct | ttgagcgagg | ggcttttttct | 89100 |
| ttataaattc | acttgcaaaa | atgccaattt | tgccgtataa | tagatttata | aattgatgag | 89160 |
| agagatttcc | aagatgaaag | taacaatgga | aaacacagaa | gagtttattg | ctatctgtac | 89220 |
| tgcgtatgca | gatacgcttc | cacctgaggg | tatggacgac | catacaatgc | agttagtggc | 89280 |
| ggatatctac | agattagcag | agttagctaa | agaacaacac | aacaggctgg | tgtacgtcaa | 89340 |
| agaacgcctc | gaaatgatgg | ataaggagta | atcaatgaac | gaactcaatg | aactgaatga | 89400 |
| attgcattac | gctgaacgtg | ctattgacga | gctggatttc | gctggtggtt | attatacccg | 89460 |
| acacgtcaac | gcaatgaccg | ccgaagggct | taatagtaag | tctgcgattg | ctgcggagtt | 89520 |
| agcagttcgg | gactttgtta | ttgatagtct | ccagaagact | attagcaact | tgagcgaaaa | 89580 |
| caacaaagct | gctctggaag | ccctggataa | gctgtccaac | catcttctcg | cattggggat | 89640 |
| caaataatga | ataagcaatc | tctacgtggt | atccgagtat | ttcgctctag | ccttgttgat | 89700 |
| tccttctata | tctggggcaa | ggcaactcga | cgcactgttg | agcaagcact | agacggtacg | 89760 |
| ttctatgatt | ggcgagaaaa | agagcgaaac | cccgtattca | gccgcccagg | gctgtatcac | 89820 |

FIG. 15WW sequence.txt

```
gatcgtgtat ctaagacagc gtggtacgaa attgaagtaa ctcctggcgt tatcagagcg    89880
ttctatacgg attgggagca cgaaaagtgg gtttgggaca atcagattgc tcccggtgat    89940
cgtattatga actatgccga atataaagaa atgaagcgca tgttcgagct atacgatgtt    90000
cctaggctgt ctcgcccggc tatcttcatt gctagccaag agtactggca tactgttcgt    90060
atgaagcgtg attttaacaa gcatcacctg cgctatgaga agaacacgg cacactgcgg     90120
gaacgtgtgg ccaagagaaa agccgaactg cgtgaaaaac gcctggagaa gaaatatggt    90180
gaaagctagt ctcttacgct tcactcctgg agttggcctc cagtataaaa ttgttggggg    90240
ccacaagttc caatacttca ccccgggtaa gctctacttc gtcgagctac acgatagtag    90300
agcaggctac aaattacgaa gcgacgcaaa tgagggcatt tgggtgagct tcacacaagt    90360
taaacgctgg tttacagttg aaggatataa tgattatgag taaagttgta tatttcgtaa    90420
aatgctgccg tgacacctta gagttggtcg accacaaaat gcagacctgt aaatgtggtg    90480
cttcctccat agatggtgta gccggagcct acgtccgttt tctaggcgac aaaagtaact    90540
tcatgcgtct gaatgagttc cagctcgaag ttgaaaagaa tcgaccggct ctagaggcag    90600
aggctgagcg tctcaaagat ttcgatggga acatcgtagc atataacatg gtaagcggta    90660
aagacttctg gtctgaactg gctgaaaaac ttaacatgcc gcggcaggcg gctaaggctt    90720
tatatcatgg cttcaactac tcgccacgtt ggaattaagt tttccaacag taacagaact    90780
tacgtttacc gagtacctag ttattggaaa tactccccgg agataggtga tgtagtagtc    90840
ataccgggga atgttatgtt taataatcct cgtcgcgcca aagtagtaga agtgcatggt    90900
atgtatggta agccagagta taaagaaaga aagaacatct cttatgtaga gctgcatgat    90960
tacttaccga aggaggaacg taatggacga taaaattgct cgggaagcaa tagaacttgt    91020
tcgtaaacga ctggaagaac gtaatgtcga ggtgccgaaa ataatgctta ttggctacgg    91080
cggcatcggc ggatttccca gcttcactga cctagaaaga atggaacgag agtcccaagc    91140
cagctttcta gagttagaat cctacgctcg ggaaatggaa cacgaacatc cgattggtaa    91200
taactttatg ccacgtagct cccgccagga ggttactcac ggcaagacta attcctggcc    91260
cactccgaaa cgcagaggta gaaaatgatt actacaggat ttggatattc tcacgaagaa    91320
ttgtgcaaaa tggttgaaag cgctccgttt attaagaagt tagtcgaaga gcaacgaccg    91380
gtgtgtttac atgctgcctg taccaagtgt cacggtactg gtgttgataa aaacggcaag    91440
atgtgcgtac atgcactgtc ctgcccgtgt cctaaatgta gctggagctg ttaatatgga    91500
tctaggatat tgtgtagtac atgaattcat ggagcagggg ttgccggatc gtatttgcgt    91560
tgtaacctct cgtaatctgg aagcagccca atcactagtg gagcgactct ctggctacta    91620
tcgtgaccat gaacgttacc agcagaaagt atttgacctg acaaaactgt accatcaaaa    91680
agctctggat atgccaactc cacagctgga cgatctcaag cagtttagtc ctgaggcctg    91740
```

FIG. 15XX sequence.txt

| | | | | | |
|---|---|---|---|---|---|
| gtatagcgtc | aaagacgcca | gtccggtaga | ctataccgta | caggtattct | cgcattatgg | 91800 |
| tactcgtcac | tggataaacc | gtaaatggga | ttccatggtt | gactacctta | attcggaact | 91860 |
| cgaaaagggg | gctgccgaat | acaaaagaaa | gcgtgccgaa | gccaaagtat | tgaaaaattc | 91920 |
| agttgcattg | taggcgattt | ttcgatataa | tagttacata | aattgatagg | gagagcttca | 91980 |
| tgagcaaact | aagtattgaa | agcattatcc | gcccgttaat | gcacgggtat | gtacaaggtt | 92040 |
| cctgtgtaag | cgaaactgaa | gctctcaatg | ttatcgaaga | agagctggtg | gctaacgggt | 92100 |
| ataatcttca | cgaaggtgtt | atcgaggatc | tcttctggca | gaccgcggaa | gatatggaga | 92160 |
| tctttcggtg | cgtgaattgc | gggtggtggt | gtcctgcttt | tgaaagggcg | gagaaccaaa | 92220 |
| tagaggaaat | ctgccgggac | tgcgagccag | acctcgaagg | tgaagtggat | gaacaagata | 92280 |
| acgaaggtga | agactatgag | taagcgttca | attgcagcaa | tcatcgcatt | cagtatgatg | 92340 |
| tactctggag | tatctctggc | cgcagagcgt | aacaaagtag | agatctctga | taacgggcgg | 92400 |
| gttcgtgtaa | caacgaatgg | gattactaaa | ggagctggta | agtttcgtaa | atctgaaacc | 92460 |
| cgttttgggg | aaactaagat | ctacacgaac | aaaacctatg | gcaagcccgc | tgtgacactg | 92520 |
| gaccgctatg | gtcgtcaggt | agaagacgag | gatgatagcg | atgagtaatc | ttcaccccaa | 92580 |
| acttcaagag | accctagact | ggattaatga | agagtgtgct | tttgaggaag | ctccttactg | 92640 |
| tgtctgggca | agagctggtg | cagcccctc | ggagtggtgt | actgtgtttg | ataatcgcta | 92700 |
| ccggataaca | gttgaactaa | gcctaaaaga | ggacaaagta | tacgctaaag | cctctatgac | 92760 |
| cgcgctagga | ttatccgggt | tcgtggagat | gcaagagctc | tgtatgccta | acactcacct | 92820 |
| tcgggttcag | atcgagcagt | tggcaacaat | tcgtttgatg | ttgccggaag | ataacatcaa | 92880 |
| tgaccatttc | cataaggtta | ttgaaaatga | atacaaacta | cggcggcaac | gtcgcaaagc | 92940 |
| acgacgggaa | gtagagaaga | ctcggatgat | gtgtaacatg | aatccacacg | tataacggta | 93000 |
| gggccgttat | aggagtcacc | ttcctgttcc | tatccggagt | cgtgcccgcg | atgaacgaag | 93060 |
| tggtgagttg | gtcgccgacc | actaactaat | tcaaagacaa | actgaggaag | caaaatgttt | 93120 |
| actttattta | tactggcagt | atcggcgtgg | atggcagttg | gtatcaatca | tggtctggac | 93180 |
| tctgctaagc | tgctgtcagc | taaagccttc | gagttcctgg | ctaagtttgc | cacccgtaaa | 93240 |
| gatatcgagg | ccatcatcgc | aaaaggcggt | gccaaagatg | catcgagtgt | cctgaagtcc | 93300 |
| ttcgataaga | tcctagagct | tcgtaacggt | aagcatgccg | cagagctacg | ctgtatgagt | 93360 |
| cgcaagacca | taggcagact | gtgtaaggcc | atcttcatcg | tacaggggc | gttgaaaggc | 93420 |
| ccattcgcta | agtataaacc | ggatagtatc | aagcgagcca | agatctttaa | cgattactgt | 93480 |
| gtggaacacc | acccgttaaa | tcgctaacta | cccaagccca | gcatcgaaag | gtgttgggct | 93540 |
| tttctttttt | aaaaattact | tgcgctctcg | cttaaaatgt | tgtataatag | ttttataaat | 93600 |

FIG. 15YY sequence.txt

| | | | | | | |
|---|---|---|---|---|---|---|
| gagaggagaa | ctaacatgcg | tattatctct | aaattaaagg | acgtatatga | tctacaaggt | 93660 |
| actatgtatg | atgcagaaag | agcatggtat | cgcgaagaag | tgaaagaggt | tgtaaacgta | 93720 |
| tccgctgatt | tcgaacaaat | tatttctac | gctgaaatct | tgcgtaaccg | cacttcctct | 93780 |
| ggatatgggg | gtgttaatat | gggaactctg | gaagttcgtc | cagtattgat | ttgtggtaca | 93840 |
| ctacgctggc | tgtacggtta | tcacactggc | ctaggagcag | atgctgtgca | tatccagact | 93900 |
| ttcgatccag | ttaaggtaaa | agaggtactg | gaagaacaag | gatactacct | gcggatgggt | 93960 |
| tgggacatga | atacgattga | gaagatcgac | gctcatgttc | gtaacgcaac | cgccacggct | 94020 |
| tctgcgttcc | tggagacttt | caacaagccc | attgcgatgg | catgggatgc | cgcaaagtct | 94080 |
| aagacagacc | caacggttaa | tattaccgtt | aaaactgatt | tcaacttcca | tgcggaagat | 94140 |
| ttcccgtggc | aggaaattga | tccaaacctg | tatcgctggc | accagacctt | agaatcatat | 94200 |
| atcttcggtg | tgctgggtca | aggggaacca | aagaccgagt | ctacgtctga | tcgtgatcgg | 94260 |
| ttaattgcta | agggcttcga | tgctaaagtt | tctttcagga | atatggagcg | gtaagactgg | 94320 |
| agcaattctg | tttctggcaa | ttgcagcagg | caccttcggg | ggtgcctact | acattaccaa | 94380 |
| taagctaaca | gatatgtcca | gttctttaca | gtccctatca | aaccgtaatg | aacaactaga | 94440 |
| aaagacagtt | ggtaatctcc | aaacagagat | tcgaaatcga | gatcgcaata | ccactaccta | 94500 |
| cataaccaac | ctagctaaga | accaggaaga | tctggatggg | cgtattaata | aactggatgc | 94560 |
| agctagagcc | aaagagggcg | tggttgccgc | taaacctaaa | cttgctacca | aagtggcaaa | 94620 |
| agacaaagtt | aatgagttcc | aggagagact | ttcatgcgta | actggaaata | tggactcctg | 94680 |
| ctctcggctg | caattatcgc | atccgggtgt | gcagaacggc | cagacccaag | tagcacagta | 94740 |
| acggggttg | agccacagca | cctaccgtgg | ccagcaagcc | tacagacttg | cccgtttaat | 94800 |
| tttgagttca | taaacgaaga | agggaaagtg | tatgttcgca | taccttacca | agattggatc | 94860 |
| acgatgggca | agtgtaatga | gcaggtctac | acctacattg | ccaatctgac | tgcattaacg | 94920 |
| tgtacctatc | gcgtgtcact | taatgaatat | cgttgcaaac | cgttcaataa | ggaaacaaaa | 94980 |
| tgaaatacgt | tttaggatta | attggtgatg | ccggcgcagg | caaagacacc | tttgctgaca | 95040 |
| tggctaaggt | ttgggcctgg | gaagtcctcg | gtccggagta | ttctatcagt | aaatttagtt | 95100 |
| ttgcagctcc | agtttacgaa | ctcgcggctg | taatccttgg | agtcacgcca | gaaaagctgg | 95160 |
| cagagcgcag | gacaaaagag | attaagcagt | ggttttgggt | gactcaggaa | gcccttgagc | 95220 |
| gtactgctaa | cgtctggaag | cgttttggga | tcgacaagta | cgccgatttc | tcttacgttt | 95280 |
| ggcctcagtt | tgaagcgtca | gcactatatc | cgttgattgc | taagactgcc | ccagactttt | 95340 |
| atcaaggtcg | tgagaccccg | ttgtacccat | tatacacgtc | ccctcgtaaa | atgctagaat | 95400 |
| ttgttggcac | ggagttagga | cgcgctctgg | tggatgagaa | cttgtggttg | aatattgtgg | 95460 |
| tagatcgtat | cactgctacc | aaagctgaca | ttagtattat | ttctgatgtt | cgtttgata | 95520 |

FIG. 15ZZ sequence.txt

| | | | | | |
|---|---|---|---|---|---|
| atgaagccgc | gctagttcgg | aacttccccg | gtgcgcagaa | ctctagtatt | cttaaagttc | 95580 |
| acgcccctaa | caacatccac | gctatccaat | ctactcatgc | ctccgctaga | ggtgttgcac | 95640 |
| ctgagtttat | tgatgatgtg | gtaacaaata | actttgacgg | actggaaaat | ttccgtaaaa | 95700 |
| atgtaaacgc | attttgcgac | gagaggattc | tctttatata | aggtaacaat | atgggacaaa | 95760 |
| ttaataacgt | agagcagaaa | ggtggcaata | agactcctaa | ttacttcgcc | tccctagtgg | 95820 |
| cgactaaggc | agagtataat | atttaccact | atcatctcga | tgggccgata | gtcgatgtag | 95880 |
| actactaccg | cgacctatca | gtcactctgg | caactatgca | agagggagac | actcttaatc | 95940 |
| tttatattaa | tagtcccggc | gggtacgttg | atacagcagt | tcagttgtgc | aaccttatca | 96000 |
| tgaactgcca | gggaaccgta | attgggcacc | tggttgggcc | atcagcatca | gctgcctgct | 96060 |
| caatcttcct | agcatgtcat | ggttggctgg | tgcaccctta | cgttatgttg | atgggtcata | 96120 |
| cctatcgtgg | tgcgcactat | ggtaagggca | aaaatgagat | ccagcactat | gctgatcagt | 96180 |
| ttaactcgtt | cttcgaggat | atgatgctag | acctgtacta | cccgttcttc | tctctagaag | 96240 |
| agatcactga | gatgatagaa | ggtggtaagg | atatttggct | gacctccaaa | gaaatcaacg | 96300 |
| aacgtgtaga | tcgtatggct | gcgcaccgag | aacaagaagc | tcgtaaggct | gcgggtcaat | 96360 |
| aaaactaagt | aggccagggc | tttttagctc | tggccttttt | ctttatctaa | attctacttg | 96420 |
| acatttgtct | caaagtatga | tccgagcaat | aactataaat | ttttattgca | acttcctcca | 96480 |
| ataagggta | taattataaa | tggttagagg | aggttcttaa | tggataaatt | tatacagttg | 96540 |
| atatcgctgt | tactacaaga | agcgaaggat | ccagcttctc | ttcttaaacg | tttgctaacc | 96600 |
| ttactggttg | gtctagttat | ctacctcttt | atagctaata | cgagtgaagt | catgtcgtac | 96660 |
| ttaaagactt | tctctacttc | ggcggtccta | caagatgtta | aagtacaacg | cacactagag | 96720 |
| tttccaaatg | tggcacgaga | gaaggcaatg | atcctattct | cacagactcg | agctgatgcc | 96780 |
| gtcttcgtgg | ttaaatacaa | gcctgaggct | ataatgatt | accaaactat | catagcttgg | 96840 |
| gaaagcaacg | ttcagttgga | taaatccgat | gtatccgaca | aagcagttga | caagacgtct | 96900 |
| atgctctacc | gagcgcattt | agacggtctg | aactttgcaa | ttgatgcaag | ggaaaaacga | 96960 |
| ggtttatcga | agtggtctgg | aacgggtttg | ccaccgttca | agagtgcaaa | tttcgagtat | 97020 |
| gtgtacacgt | gcccatattt | taaccttaat | aacatctact | ctggatatgt | tgccgtcgcg | 97080 |
| tgggagaagt | atcccctaca | agacgaagac | atgggtatgt | taatgacta | tatggcaaaa | 97140 |
| atctgcgcat | cgccgcagag | atcattaggg | agatcaatat | gagtttcaga | tttggaaacc | 97200 |
| gtagtctcca | gcagctcgat | actgtagatc | ctaaactcaa | ggctctagct | attcgtgctc | 97260 |
| tggaactctc | accgcacgat | tttaccatca | ttcagggcaa | acgtaccgta | caacagagtg | 97320 |
| cccagaacat | tgctaatggt | acttcatttt | tgaaagaccc | tagcaagtct | aaacacgtta | 97380 |

FIG. 15AAA sequence.txt

```
cgggcaaagc cattgacttc gccccatata tcaatggtaa gattgactgg aatgacttag      97440
aagcattctg ggctatcgtc ggtgcattta aaaaggccgc aaatgagatg aacattgccg      97500
ttcgtttcgg agcggattgg aataactctg gcgactaccg tgatgaaatc caacgtggta      97560
cttatgacgg cggacacgta gagttactgt aacattaagg ggagctttta ggctcccctt      97620
ctttgtatgg agcaagcaaa taggaggtgg ttatgtttgc aagtttagta actataatgc      97680
tactcaagat atttcaattc ggtatagtat tcttttccgc aacatggatt ttaatacgcg      97740
gtgccattta ttttcgcaga acacgcttag ctagggttgc tagatggctt ctacacttcg      97800
tatttggtat tttcggtgtg ttccgctgcc catgtgagaa aaagagggga acagggttct      97860
gctggctctg gttaggtcta gagaattgct tctcattgtc cttagcgcta ctatttggta      97920
tgatagtcct agctataacg ctagcattta taccactaat gtacgcaggt ggggtgacgt      97980
ctatcctaac ccttacttct cctgtgttga tgtactcagt atacccatt acactatttt      98040
tcgtaagacg aggcaagcac tgcaattaat gaaaaattca attgactttc cgctcgattt      98100
agcgtataat atatttataa attcgagaga ggagatacaa aatgtcagac agattctaca      98160
ctcaaatgtg cgagcatttt aaagtatctc cctacgagtt aaatatagct ttgtgggatc      98220
gtgaatcacc ggagtttaag aaaattgcta agaaatcgga gggtgttatg tccaacggta      98280
agaaaatgac ccgaattgac cttaacaatg cgctaaccaa actgctcggc gttaacattg      98340
agggccagaa gctctctatg ccaactttga ctactatttt ggagaaagtc aaggctggag      98400
atgttaaaaa agtagcagtg cctgagggtc gtctgaaaaa gccgtatcag gaggctataa      98460
ttgaggcttt cggagaaaag ctagacctgg ataccgcaac cgtaaaaaca atgaaagcac      98520
tactggagag tattaataat gtctaagaaa attgtattcc ttaaaggttc tagctgcgtt      98580
ccttgcaagc aatttgaacc agtttttgat aaactcaccg ctgagttcaa cctgcccgtt      98640
gaaaaacgca cggacgacgt agattcccta cgtaagttcg gccttcgcac tgtacccgca      98700
gtagtcctgg tggatgtgga aacggacgt gaagaagcac atcacattct tagtggtgcc      98760
acgcttcgct ctgcagtagt tagtaaagct atccaagact ttatcgacta cgtagaagaa      98820
taatacctaa ccccggctca atacgagacc ggggtttttt attatttgct aaacgcttaa      98880
aattttgata taatatttat attgaattga gagaggatta cacaatgact aagcaagcat      98940
atcttatcct gaataatggt tttgcagttg gtactacctt cgttgatctg gggtatacaa      99000
aagaagagtg gcaagctctc gatgctgccc agaagaatca gcttgttaat gaagccgcct      99060
gggagtatgc agaggcttac gtggaggcgg tagatgacga gttagttatt gtcgtttccc      99120
ttggtgccgt aggttgtgat gctcatgtac atacagactt ccagagcgaa gaagagtggg      99180
atgagttaga tctaacccac caaaatgctc tgattaacga agcgttctgg gaagttgtag      99240
actgctacgt tgcgttctgt aaggacgatg atgaagctaa cacctgcact aactatggct      99300
```

FIG. 15BBB sequence.txt

| | | | | | | |
|---|---|---|---|---|---|---|
| atgaacacga | cgatgtggag | tgtgcataat | gcaaaaattc | tctagagact | ggtcttctga | 99360 |
| tatggcccgt | aaaaatcgag | ctgctgccta | ctataataag | aaaatacagc | tcgataagtt | 99420 |
| aataaagggt | atcacctaca | atgtagagag | gggcttttct | ggtataaaag | tagatgctag | 99480 |
| gagcctggac | tactcgtgca | tactgtgggc | taagcagaat | gggtacgcgt | ttaaacgaat | 99540 |
| aggcaatgag | atactgattg | cctgggaacc | cgaaggtcta | gtgcaatacg | taatatacga | 99600 |
| cccttatcga | ggggaatatg | taagagatca | caggcagcag | cccacagact | tctcgctgcc | 99660 |
| aaaacgttac | tatttagaga | cgaggtatta | atgaacgtac | atgaaacagt | taccgtgccc | 99720 |
| gacaatgcta | atatcttctt | cattggggat | attcatggcg | agtacgacat | gatgatgggt | 99780 |
| gccctgaaac | ttgcagggta | cgaggaaggt | cgtgactacg | tgttctgtgt | aggggatctt | 99840 |
| atcgaccgtg | gcccgaaaaa | cttacaggtt | ctagcgaagt | tcctgtacaa | cccgaaattc | 99900 |
| cgctctgttc | gcgggaatca | tgacgaattc | atgatccaag | acgactacgc | taactggatg | 99960 |
| tataatggcg | gtagctggac | tatcacggaa | ggtttcgata | cggataccat | gaaaggtatc | 100020 |
| gcggaagaca | tggacagcaa | gatgccatac | attatgaccg | ttgaacaccg | tggcaagcgt | 100080 |
| tacggggtag | ttcatgctgg | tatccctctg | cgctaccagg | ctcaaggtat | gggtgtaact | 100140 |
| gtaccggtgt | gggacgacat | tgtgcacgaa | cacgaatcta | caccagattt | acgtcgtttg | 100200 |
| ggtgtactgc | tgtgggatcg | tgatgtaatc | caagaagttg | ggtttaatct | gtatcgtagt | 100260 |
| ggggagaagc | atccgtactt | cgatcgctac | gccagcttct | ccgaggagtg | cgcagtcgat | 100320 |
| gtgcctgaaa | tcgtgggagt | agactacacg | tttcatggcc | atactggtgt | cccgttcccc | 100380 |
| attcgctgga | agaaccgtgt | ctatttggac | acaggtggca | cctttaacgg | tcgtatgacc | 100440 |
| gtggcgtcgc | cggttctagg | tcaattatac | acattcacca | cagatcgtga | tgatccttgt | 100500 |
| ggttccgctg | acattattta | ataggtgaaa | catgaaactt | ttcaaagatc | tggaagaagg | 100560 |
| tgaagtattc | gtagttgctg | gtggcttcga | gttgcagaaa | tgtgtagcaa | tgctggacaa | 100620 |
| cggaaactcc | gtgtttacag | acgacgcgaa | tatctcggtt | actattgccc | cggacactga | 100680 |
| aacctggaaa | cccaaagaat | tctgggagat | ccataaagat | cgtccattgg | acgacctact | 100740 |
| ggacgacatt | ctattcacag | cctgaggtaa | atcatgaaac | tcgaatctcg | ttatattgta | 100800 |
| tttaagcagt | cagatgccgc | taagtatcta | accagcactg | ctattcggga | gataaacgac | 100860 |
| agcttatccc | tgatctataa | aggccgagag | gctgacggca | aggtaggatt | cccgaactat | 100920 |
| atcgttctag | aagaggattg | gccggagtat | cctatcgcta | aagaagctct | agaaggacgt | 100980 |
| atcgtgctgg | aagagtttaa | taaagggcg | gagaagaaac | gtggggctaa | ggctgcagaa | 101040 |
| gatcactata | agcagcacca | gtctacggaa | ctactccggg | gtatttctcc | attctgtgca | 101100 |
| gggtggaacg | actacatgag | aagactggta | atcgaggagt | aaccatgtat | actggaatgg | 101160 |

FIG. 15CCC sequence.txt

| | | | | | | |
|---|---|---|---|---|---|---|
| gaaatgatat | ggccaagatg | tttattggcc | tcttaatcct | ggctgcgtta | gtcggtgcag | 101220 |
| caattgtagg | cggaatctgg | gcgctcgtag | catttgtatt | ttaaattcag | ttgcttccga | 101280 |
| gccaattttt | ctgtataata | gctgtataaa | ttgatgagga | agcaaatatg | aaaaacgcaa | 101340 |
| tgatcgaact | gaatgcaaat | atggaatccc | ttcgccacgc | agttaacacc | gcccgtgctt | 101400 |
| cttttaacct | gctgatgcgc | gatgagagca | taccgctgtc | cgctcgtgtc | aaggcatttg | 101460 |
| aggagttcgc | cgatgagctt | cttcatatgg | gagactatct | cagcgactcc | ccgtttaatg | 101520 |
| aagatcgccg | ggattatcaa | cacgcctact | gcaatcgtgg | ggaaatagtt | tacctgaccg | 101580 |
| atgttctgga | gagtgtgctg | gagtatgcga | actctttcat | gcgaactcct | gacgaatggg | 101640 |
| aagacgcttc | gaacgactat | gttctagacg | agattcaaaa | gaactggcca | gaaattaaga | 101700 |
| aactggtaga | agaacacatt | cattctgaag | tttacgctta | ccggatcgat | tggtaaaaag | 101760 |
| tttaaaaatt | cacttgctaa | gtagttagaa | tttcggtata | atatacgcat | aaattaacga | 101820 |
| aacggacgga | aatcattatg | gctaagaaca | ctatctctta | caccactggt | aaaactgctg | 101880 |
| acgaacaagc | taacaccctg | accaaagacg | aaatggttgc | ggtactggta | atcctgctgg | 101940 |
| atatgagtgg | gttcgaaggt | cagcttgcta | aactgtctct | cccggcactt | cgtgctctgt | 102000 |
| acgaaggcac | taacaaaaat | gctgcggcct | acaacctcgc | taaaaatgaa | gcgcgctggg | 102060 |
| ccaaggaaca | ccagcaggtt | gctgaacgtc | gtgctgagag | tttcgaacgt | gacctgaaac | 102120 |
| gtgaaaaggc | gaagaaaaag | taatggtact | agaaattctc | tccgggctgt | taatagcagc | 102180 |
| cctagtaact | ggaacgggtc | tggcggtttg | ggtatcgata | ctgcgggaaa | ataaccggag | 102240 |
| aatgagatta | accaacaacg | ggctacacga | gaagttgatg | gatcaagtac | aagatgctga | 102300 |
| tgaattctct | gctgcggctg | agcgactttt | agttcgcctg | gcgaagattg | aagagattat | 102360 |
| cggccaagat | tccacaatgt | cgaagacaac | caaaatgcgg | ttgatcacgg | agattaagaa | 102420 |
| atgatctcac | caattgtagc | ggcactttac | ttagtagttg | ttggctacct | gtccgggaag | 102480 |
| taccacggct | tcggtttaaa | aggtactatt | aaggcagcaa | tgctggttcc | tctgtatcct | 102540 |
| ctggcaattc | tgttaaccgg | gtactacgcc | tgtgttttaa | gaatctttgg | ccggggcaaa | 102600 |
| gttaactacg | ataactgcac | agcgttgctg | gacgatattg | aaaacaccat | taagaaggaa | 102660 |
| gaaaaatgaa | ccttaactcc | aaagaacgcc | aagtgttagt | agatgctctg | cgtcaggtag | 102720 |
| tagaccacga | tttgctttgt | gatgaagata | tcgttgagtc | aattgcccta | atcgccaaga | 102780 |
| ttgagcttgc | tgagaaggac | tcatggcgtc | ctttgagtga | gcttcctcct | ctaggcttgg | 102840 |
| caatcgtagt | acaacgtgct | gatggcgctc | cgtttaacac | tgtgatggtt | cgcagagatc | 102900 |
| tggcaaagtc | ctactccccg | gatatcatca | cgttgcacac | taagatcacc | aacgaacctt | 102960 |
| tcgagtttaa | tactcgtcac | tattactgga | gactgaccaa | tgcttaatca | gcttcgaatc | 103020 |
| tataatttcc | tggattgcaa | cttccaggtc | tggcgagaac | tccccagccg | tttcctaggc | 103080 |

FIG. 15DDD sequence.txt

```
tgggcattat tcctctccat ggtggtttca gtcttccata acgtcccagc gacgttctat    103140
atggaagcaa ttcaaccagt cactgtattc atttacgaga tgtacctcgt agcaattaac    103200
gggtggaaag atggccgcat caactgaagt tttaaatcaa tattttaatc gtgagcacca    103260
agagttcagc gatctgttca tccagatgtt cgtcaacgct aataacgctc tggactatcg    103320
tttcttcaac gagttccatg agaccacgtt cagccatcag gatattaact ccgctctgaa    103380
agaactcatt ggctctaaag tgataccatt ccgacagact gcaaatgcag agacactaga    103440
gcttagtgtc gtttggggct tgttcaagaa agcatatgag tttggcaagt atcagaacgc    103500
acgtcactgg atttacgagg tgtatctaaa cactgaagtc attctacctc gccaaatgat    103560
gttgggctgg attgcaaaac aacgtcctga acgcaatgca aaatcattcg caccaattaa    103620
cgacgggaac ttataccatg caagtgaaaa atttgatgct ccaaaatccg tggcttgatc    103680
gcctggcgca agtagagaag atgcttctgg ttgaaggtct gaccgaagaa gacatttgtc    103740
tgaactcctt ctacaactgc aaaactcatg taatgcaggc gctagacgaa gaacgtgttg    103800
aactgagtaa gtttatggtg aacatcgcca cagctcaagt tcactggcaa acccagggct    103860
tatccgccga cgatatcctg aaacataccc tgaacgctat tgcagagtat gggaaagctc    103920
gtggtgaagc tctcttggct tcaaagaaag agtttgataa atcggagtca atgctgaaaa    103980
tggcaatcga tatccatatg gaaggcatcg acggtactat tcactaagag ggtgacaaat    104040
ggctaagaaa cgcgttgtgg taaacttcct agaggaagat tctggggact gcgagtacgg    104100
ttgctggaat actggctacg gtgttgaggt tatggtggat ggcaaatgcg tccaccgtca    104160
ggaagcctgg gcaagctgca ctaacaacag cagcgtagac tttgacgtat tggcccatgt    104220
tcttcagggc atcaagacga aagaaggcta cccggtcaaa gcagatcaca tcgactttgg    104280
agatccttcc gattatccag aggagtttct ggatctgttc acctaacaaa gaggccaggg    104340
ctaattgctc tggcctttcg tggtttaagg atattaaatg aaatctatag acaactattt    104400
gcgcggggaa aaccctgtag atcaagcagc agttactgtt gaaaaggtca ggaaagagtg    104460
ttttatactt actcaacgtg gaggtggtaa tcggcctaat cgagtgtatc ttaattggac    104520
tcagtccaaa gacctgtatg agaggttgaa aagggaattt gagtagtgga agaattaaga    104580
cagaagataa atcaagagct agtatgggaa gctaaatcct tccccattaa tcaattcctt    104640
aaacgtgacg gttcgatcaa ccataataag ataaagcaac ttaggccaga tttcaggcaa    104700
gatgctaaga acctcatctt tattaaccgt gctctagacg ctcatggagt attcttcgga    104760
tatgagaagc tagtgttcca cagcctaaat cagctggtgg aaatatggtg tcccgaccat    104820
caagattact ttatgcaaac tgctagaagc caccttgagg gtaacggttg ccaaaaatgc    104880
aggcaccgca tggttaccag agttacggat tatggaagtt acaccgtgcc agcatactat    104940
```

FIG. 15EEE sequence.txt

```
cacaaatttt caattgacgg agactccatt atttggtata ataactccag taaattgata    105000
aaacctttgg aggttaaaga tgaaatacga ttccctgaat aatccgagca ccaactatct    105060
gactgaccag tcagtttctg agatcaagtt ccatccgaac tactccccgg actctagcaa    105120
gccgagtgta gcagctatct ccttccgctt ccgcaatctg cgctttacgt tcgttggaga    105180
ggaagacaag atgatctcta taattgacaa ggttaaagca gtaagcgagc tgtccggtag    105240
cgataccgtt aagttcgaag cattaacctc gttgctgctg actagtgggg ctaccgttgg    105300
taagttcgaa cttattcagc cgcatgtttc tgcactgacc aataccagaa acttctggga    105360
tcaagccaat gtcgagagtc tcataaaatg ggatagtgct actgagttct acaacaagta    105420
agagggctag gatatgttat tctgtacagt tgattttgaa gaagctaacg aaacgtatat    105480
tgtctacggt atgtctgaaa gcaaagtacg tatcctctgg aatcagttcc aattagaagt    105540
accggacgac atatccaaga ctccgaaaga cttctttcat ttaatagata ttaaggcagt    105600
aaaagctcgt aagaagctaa ctccttatgt gttcccaggt gcagtattcg tccatgagtt    105660
aacagcgtat actaacgtgg ttctcaaaaa gtctcgacag cacccaggct atctcacgat    105720
gttgacgtac aaagttggag ctattcacga cggtgagctg gtggttcggg tagatgcacg    105780
cttgcagcaa gaagtcgaag aaatgattag gcagtgccaa aataaagcag aattaaaaca    105840
aagagcacgc ctattcgaca tggcagcacc tagcgaggca gttgccgcat atcacggctt    105900
ttataaagaa atagctgaat ccgatgaaga tttctttatg taagaggata acacaatgaa    105960
cgagaaatat gaagtatgga ctccggttgg ggagaattgt agctatcttc ttcgtaccct    106020
gtgtactcgg gaagatggca catctttctc agaatacttg agtgaatgcc acgctaaggc    106080
ccagcaggac aacccgctat ttaagatcag aggagaggat atcctcaaag ttaacggcgt    106140
gccgtacacg ccagtggaca gtttcgccgc tcttcaggtg tttaaggaac acagagagcg    106200
ggagcaccgg aggatgattg aacgcttgac aggtagagag ccgttttcac atcctaggtg    106260
gaatgaggag acataatgag cagagttgaa aagctacaac atatctataa cctggttaag    106320
aaagctgacc aaaagaaact ctcagagctg agtgaagaag agtatcaagc agtcctcttc    106380
tgttgttcgg caatgccagc gaagctcgat ggagtactgg caaagtcaga catccacaac    106440
ggtaaggaaa caactttcca gccgccgtat aaatggctag cgtccaacat ccagcaaatg    106500
gtgggtaaag ttacgggatt ctcaaataga aagacgccta acatctttat tgacattact    106560
cctagaaccc ctgagtttac gaaggactgg agagacgcat tggattcatt tccgtcatgg    106620
aaagtctttt ataaacctga cgatgaaacg tatgcacatc ttcccttttt gaagcaccca    106680
ggctacacag ttgaagaccc aagttctggg gttaatttca aagacttcaa gtgtactgac    106740
gagaacattg cttacggact catgagaaca tccgtgagga ttgcaatgga tcatgaacta    106800
gacaaacaag atctagcagt cattgcactt tgtaaggatc gttatattaa agttaagagg    106860
```

FIG. 15FFF sequence.txt

| | | | | | |
|---|---|---|---|---|---|
| atcgcagaga | aactttccgt | actttcttgc | tttgaaacaa | tccgagattg | tgaaccagag | 106920 |
| ggtgaatatc | ctaaaggttc | cctctactgg | aaagatgtta | aacatctagg | actatcagaa | 106980 |
| gaagccgtat | tcctaggctt | agtagttacg | ggaagattcc | tgaggctaca | ggagaaataa | 107040 |
| tttgtacttc | gtctatattt | tcgctaatga | agatcagcgg | cttatcccta | ggcggaccaa | 107100 |
| ggtgggttac | tcgcgtgacc | cattttatcg | tctaaattcg | cttcaacttc | acagactacc | 107160 |
| tcatcgtgga | ttacaggata | tcgttattca | ttctgtctat | ataatagatg | acgccagcga | 107220 |
| gttctcagca | aagttgctag | agaaggccgc | gcataaaaag | tttaagccta | tgcgagttaa | 107280 |
| tttcggtgac | aagtttgatg | ggcatacaga | atggtttgat | gttgaacctc | acgttattga | 107340 |
| gaagttcttc | ctgtcagttg | gggcaaaaca | agtacctatt | gacaaactca | tagcccaaga | 107400 |
| acaaaagatt | cgtaaatcca | cgaaaaagta | gttgaaaaaa | aataaaacgc | atgttataat | 107460 |
| aatctcatag | attacataca | atttgaaaaa | tttatgaagc | taggcggatt | atgaaccaga | 107520 |
| atcctggact | cggggcgacc | aagcctacga | tgtcacagag | actttctggt | ctcacataat | 107580 |
| ccgcatgcct | agcgcttcgt | aatctcacat | gaacgatgga | gaacctataa | ctataataaa | 107640 |
| actaaggaga | aaatagggaa | acgtgggaat | gaactcacga | ttactcacgt | ttaaaagtag | 107700 |
| gtaatcctta | cacaccatcg | tttcgcggct | ctagggttga | actctagtca | tctttctata | 107760 |
| cagggcggtt | ctttctacac | acctaagggg | agggcggtta | ttttccaacc | ctaaaaatcc | 107820 |
| ataaccattt | tctggaattg | cacaaatttt | cacaccgtct | cacatatccc | acgaagccct | 107880 |
| cacacatctc | acgcaatccc | tctagtacgc | ccaagttcta | agcgtcactc | cacaaagtcc | 107940 |
| tcacgaagtc | cccacacaaa | cccacgtcat | tcacccaagt | tctaagcgtc | aaacattatc | 108000 |
| ggatttgcac | attgctccta | gatattaaag | aagccaagca | tttctagatt | tctagcaatt | 108060 |
| gtcggatttg | cacatgacaa | aacgattgtc | ggaaatgcac | attaactctg | aatccaaaaa | 108120 |
| cacggtcgaa | tttgcacata | taaaaactac | tatcggattt | gcacatactc | aaacgcttgt | 108180 |
| cggaaatgca | cattattact | gaagtacggt | agctgtggat | caaaatcttc | gattctgcga | 108240 |
| atataaaata | tctcctgaaa | tttcaagcct | ttttacacgg | tgtgtcaccg | tgagttcgct | 108300 |
| tgttttttag | agccacagga | attttttctg | tgtcaacccc | tttaccccca | tttaactcat | 108360 |
| aatattttcc | cttatctgcc | ccctgccccc | atcatcccg | aattgcccca | attaccccc | 108420 |
| tttatccctc | ccccaaaaat | acccatcgga | tttgcacata | ctcacccaaa | ctcgcgccca | 108480 |
| ccgctgcgct | gcagcaaact | gcgcgccttc | cccctaaaaa | ttattatcgg | ttttgcacat | 108540 |
| attagtatcg | gatttgcaca | tgcccctagg | gcggtaaaaa | taaatttttca | tcggatttgc | 108600 |
| acataccccta | gcagcctcac | gtaatatttt | gcttgacaca | ttgtcggatt | cgcacataag | 108660 |
| cgcaggaagg | gccggggtc | ggaaatgcaa | atacgaatga | gagtgattcg | catttgagaa | 108720 |

FIG. 15GGG

```
                                    sequence.txt
gttgaatgcg aatgataatt attctcgttt gataagctga atacgaatga gaatgattcg   108780
cattccggaa aggaagtgag aaacactatc atttaagtta tcaccagagt tatacaaaat   108840
tgtaaattag cttgacgctt gagaaggtcg cagacgagtt atccacagac ttattaacag   108900
gttatcctac tggttattta tacagtagtt cccggcaaca ctttctgcta atgtcgattt   108960
taagcgccct aggaagcgtt ctaagcgatt taaatttcgt ggggtatttt tagtaagggg   109020
tcacgcggtg gaggagggcg gcgacactct tacatatcgc cgtggaaaca ctcaggccaa   109080
aagtgattta caactgaaac tattagcagg gtaatgattg cgctaataac tatcatgccc   109140
aaaaacatta ggccgctcat tattggcagc tctgcaaaaa gactagggtc ataataataa   109200
ccatgatgac acgaaaaccc cactcaccgc cgccaccgtc accgcctttc ttctgaccgt   109260
cacgaataac gttcaattgg taagtattgt ggctacggct tttgggacta ccaccgcgta   109320
aagttcgcat taaaaagcct ccttattaaa caaggtatca tagagggcat agccgcaaaa   109380
agcgataaaa cccaaaacca tcatagaacc aactaaaccg agcgccaaca ttgaaaaagc   109440
cattttcga tctcctatat gggtgagtca taataataac ataactctag cgggaagcaa   109500
ctactatttt tagtagtaga caagcaaatc cgatttccct atagtttgat ctcccggcaa   109560
gcatagaaaa attttgcttg ctaaaaagcg gagaatcttg ctataataga ttctcagcca   109620
aacaaaggag taacagaaga tgttacagaa atttaccccc gttgcaaatt tgcctatggt   109680
tcgcggtggc gctcgcaacc tgttagatgg tagtaaatgc gcctctatcg gtcatatttt   109740
aggcgtttac cgctcgaata tggaaagtag aaccagccgc gcttttgaac atagccgcga   109800
ctacgttcta gccaaccccg gcgctgcgat tgttattttt cacgacgatc aatatttagt   109860
tgacagccag cctattgatc tgatagtatc taccactacg gacgcttatt tgtataaggc   109920
atccgaaggt aagcaagcgt caagacgttt ttgctaccat gaaagcgaac tgctcgcttt   109980
caccgatgcc cgcgcatgga ttaaaaacct gtgcgatcat ctggaactac caccagcacg   110040
aatttctagc gaaatgatga ttttgtgct tgacaaagac ggaagcatcc tgctaccatg   110100
tgacccttac gatattgata tcgaagaagg ggcaaggact ggaaattatc gttatgatgg   110160
cgagctagaa gaagtcgccc cggctgttac tgaaaatgta gttaacccta ataatttga   110220
gactggagca ttacaaatga atactatcaa atctaccgct accgctatcg ttgccgctaa   110280
caaaaacgct gctgtaaacg ctgctaaact ggaagccggt tctatcgtcc tgaaaaaagt   110340
ttccggcatc gccgccagca aagcgccgtt tatggttcgc ggttatgttg acacggcggt   110400
aggtcgtgtg gtaattgcta acctgctgaa tttcgcggtt agccagtatg cgccgaacaa   110460
ccgcaaagcg gtgattgcgg ctgacgctgc aatgcaagcc gccatgttgg aactggtaca   110520
aagtttcaat gtaggcgaaa tgattgacga agtattgaaa ggcgtcaatc tttctagcct   110580
gattgaaagc gacgtagcag aataattata tctagcgcct ctataatggg gcgctataat   110640
```

FIG. 15HHH sequence.txt

```
aattaccctg ctaactaact ggagacaaaa aatggaacgg ctaaccgcta ctttcgaagg   110700
cgaaaagatg acgatcgcta atgtatggca gcgcctgcgc cagaatggcg atcgtggcaa   110760
ttttgctatt ttcatcgagc caaaaaactt ggataatctg gctcgccaga ttgaccgccg   110820
ggactgctac ccggatacag atgatatgct gggaatcccc ttgcggatta tcggggtata   110880
tggttacggc tttgatatct gtattggtga tagtagcttt gaaatcgact gcgaatccgg   110940
cgctaccgaa atcgaagtat tcctaattaa tttaggctcg ctaacgtttt tggatacgcc   111000
accagcggaa ccggaaccgg aaaagctgga ggtgaaaacg tccgttattg ttagttcgct   111060
aactatggat gagctggcgg atatcgtgtc aacgtatgac gaaattcacg ccgacgcgat   111120
taaagagcta acaaccggc ttgatacttt ccgcgataag ctgtaaaatc cctcccggcg   111180
gctaaatctc tagccgcccc cattattgga gaaaaccatg tttcatgtga aatcttgcgt   111240
accgggcatt aattatacgg tagaagcgga agaaggttta tatttagagg gcgggcgaat   111300
tgagtctcag gaagtcgccg ccgtcctcaa atgtgacact aacgtttgcg gtacgtcctg   111360
gactgacctt catttttag gtcgtggaat tgacgtcgat tccctttcct gggaaaaggc    111420
ttgcgaacat gctgaaagta tgctaaacga ggatgattgg gatgatgacg acagcgacga   111480
aaaatacgcg aatgctgggg tagaagggtc gttttatatg tactggcccg gtcattcctg   111540
caacctcgtt aatggtggtt cgcccctcca ttccgttcta gagcgggcaa tctatttggg   111600
ctatatccag atagttgacg gaaaggcagt cattaatctg cgcgaattga aaacgtttat   111660
ctatatcccg gatgctgaaa ctatccttca tattgaggaa ggtttaaaat ccggttggaa   111720
ggttagcggg gtcgtatacc tatgatttac atctatgtca acaaatattt tctggcgcac   111780
tataaaacga tggaatctgt gatccagtac gttagccgcc agaatgcaag gcatattgat   111840
gaagtggcta ccctcaaaat cggattgcgg ggcgatgcta tcaatattag ctggcctttg   111900
ctaattctga tttgccgtga tcttgtagcg ggtaaacctg tttccgtttc cgcgctgggg   111960
gaatcttacc cgctttccga tgatctggat ctctatgatc tgctaaccaa atataaaact   112020
gaacgcctgt tttatcgtgg cgggtcggta tgctctagcg gcgaaacaat agaaacggta   112080
ttccgctaat agttagctaa ctaatgataa gcctgcttat aatgagcggg cttttttattt   112140
ttctgcgccc ctctagcaat ggcctttaat atggcctcta aatttaaagc gcttagaatg   112200
cgttatagag cgttctagag gcatattaga gtattaccgc tgccggaata tactgtataa   112260
atatacagta ggataacctg tgggataagtc tggggatatc tcgttatacc gcttctcagc   112320
ttgtcaagtc aaaacgtgct gtggataact tgcccggaaa acaggagtgc agcataaaat   112380
aaacgcaagc attattttgc gttttcataa aaataatcgt ttgtctagtg gataactaat   112440
taaatttcat ttttgctttt tgtataagtt attaacaggg tctaaaacgc cctagaatcg   112500
```

FIG. 15III

```
                                     sequence.txt
attctaagcg gttttagata aaagccgatg aatcataccg ggtatgaggc gatctcctca    112560
cctcgtgtga aatagatttt gtcaacccct tttgaagaaa aatagtaaaa atattcgttg    112620
actttcttta aatattgtgt cacgtgcgcg cgcttcctat ctatcgtggg cctgttttct    112680
ctttacgctt ctttacaatt ctccgcttgc ggctaaacgc cattgtgtta ttatttatct    112740
cgtagggcgg caagacgaaa cggaaacacg aaagcgtttc actagtagtt aggtatctgg    112800
aggcggcaac attgccccga ctaccgcgaa aggaaaggcc gaaacgatat agtctgcccc    112860
cgccctacac tgctctttaa aaatttggga ttctataaaa agcgttatcg gctttctta    112920
cttaataagg gaaccgaaaa catgttaaaa gaaaacgtaa tgagtagcga gattgtaaac    112980
gagtttacag tagcagacgc cgaacatttt atagagactt atttaaatgt gtacgacgta    113040
gatttagcct tcattcataa agacggccaa atc                                113073
```

FIG. 16A sequence.txt

<210> 2
<211> 31078
<212> DNA
<213> Unknown

<220>
<223> Description of Unknown: Bacteriophage F394/08

<400> 2

| | | | | | | |
|---|---|---|---|---|---|---|
| aaacccggag | caaggccaag | cagcagccgc | agaaagtacg | ccagcagatc | cggcggctaa | 60 |
| tgtttcacgt | gaaacgaagc | ccgaagattt | aataaaaaac | gacgtggccc | cggctgaatt | 120 |
| aacccggct | ttttatgtgg | tggctgaagg | tcgcgcgatt | acgtcaaaac | gtggcatttt | 180 |
| ggccgctggt | gaagcagtag | aggcccgcga | ctttgtaggc | ggtgaagaaa | cgctaaacag | 240 |
| ccttttagag | cgtggtttag | ttgaatgaat | atccgagatt | tagcggccca | agatttcctt | 300 |
| aatatcgtga | atgataaaaa | tagcggtttt | ggcgttcccg | tggtgttaat | tgccccggat | 360 |
| ggtaacgcgc | agccgttaag | cggattaacc | acggatatat | cgagctatat | tgatccggaa | 420 |
| acgggcgttt | tagttgcggg | ccgtgttgca | tcggtcacat | tcgcaaacaa | ggcaatccgt | 480 |
| gccgctggat | tcgcagaaat | gcccgtagcg | gtggccgatt | caaataaacg | cccgtgggtg | 540 |
| gtgtgctttc | gtgatcctga | aggcatcccg | tatttgttca | aagtggttaa | ggctatgccg | 600 |
| gatcgcgcga | ttagtggcat | agttttagaa | ttggaagttt | ataagcgttc | tatttacttc | 660 |
| aatggggctt | ataaatttga | tgggacgacg | ttatacgatg | gagttttaga | cttgttatga | 720 |
| atatagaagg | ctttaaaaaa | ctgcaaagcc | cgattaacaa | gctagatagt | tttgaaatag | 780 |
| tccgcgacca | gatcgcggct | attttatttc | ttgagcttga | aaatcaaaaa | gccattgctg | 840 |
| ggcgcgcgca | gattgacccc | gctagatttg | atatgaaagt | ttataaagag | cgttctaatc | 900 |
| cgtgggatct | attcgacgat | ggcgaaaata | agcccattat | taacgtgtgg | tttagtaata | 960 |
| gcgatttcga | ttacaccaat | agcagcacag | tcgataagca | gaaaaccacg | gctattttta | 1020 |
| atattgattg | catagcgacg | gctataagcc | aagaaacagc | gaccgggcaa | acgctgggcg | 1080 |
| atgaaatggc | atctttagag | gtgcagcgcg | tggctaaagt | gatccgaaat | attttaatgt | 1140 |
| cagatacaaa | tacatatttg | caattgcgcg | ggcttgtttg | gtcgcgccgt | gtgctgtcat | 1200 |
| taaacatatt | tcagcccagc | gcagaaaatg | gaatgatgca | aatctatgc | gcggcccggc | 1260 |
| ttgtacttca | ggcgacgttt | agcgagtttt | cgccgcagta | tgaaccccaa | gagctagaga | 1320 |
| ttttgtccgt | aactgtccat | aattgcgatg | gacaaatttt | atttaacaag | gagattgcta | 1380 |
| agaatggcaa | ttagtaccgc | tgttgatata | agcgcggtgg | cccgcgtttt | aggtatcaaa | 1440 |
| acaaattta | aaaatttgcg | ggatggtcgt | gtggtgattt | tgccgcagcg | gatcgcctta | 1500 |

FIG. 16B

```
                                sequence.txt
attggtcaag gttccacggg gatggtgttt gcaacgtcaa aacgacaagt aacaagcgcc    1560
aatgaggtgg gttcgctata tggttatggt tcaccgcttc acttagcagc taaacaacta    1620
tttccgaata atggcgacgg agtggggacg atcccggtaa cggtttaccc gttaagtgat    1680
gcggacggat cgcaagcggc gaccggatca attgagcttc tagggacgca attagaatcc    1740
ggggcttata gagttgttgt gaacggtatc cgttcggaac aattttcaat tttgattaat    1800
gaggccgggc aaactgttct aaatcgagtt gcggcggcta ttaactccgt tttagatatg    1860
ccagtacgtg cgacggcaga ttcggaactt caaaaagtaa cgcttgtttc aaaatggaag    1920
ggtttaagcg ctaatgctat ttctgtccaa gttgatgggg atttagggca aggtatcgaa    1980
tttgcagtaa cgcagccagc gggcgggctt attaatccga gtgtttccgg tgcgctttcg    2040
cagtttggca acgtatggga aacaatggtt ttaaactgtc ttaatattca ggataccgaa    2100
gcattaagcg cttattctga ttttggggaa gggcgctggg gtgcgttggt gcgtaaaccg    2160
cttattgtat ttacggggaa tactgaagcc gacgtaaata gcgccgtttc agtcccggac    2220
gcgcgaaaac gtgatcggac aaatgttcaa cttgtggccc cggattctat cgatttgccg    2280
ttcgttgttg cgtcccgtca attggcccgt attgtaaaaa ttgcaaacga aaacccggct    2340
tgtgattacg gcagccaagt agccgacggc attaaccccg gcgaagatgg gaaacaatgg    2400
ctttataacg tgcgtgatat ggccgttaaa aaaggcagtt caactattga aattcgggac    2460
aatcaagtat ttatcgggga cgttgtaacc ttctatcatc ctgaaggtga agaaaatccg    2520
ccgtatcgtt acgtttgcga tattgtgaag ctgcaaaaca ttattttaa cttaaatcta    2580
atttttgccg tgccggaatg ggacggagcg ccgttaattc caaacgatca gccgaccaca    2640
aacccacgcg ccaaaaagcc ttctatggcc gttgccgcta ttgccagcct tgtggatagc    2700
ttgggcctaa atgccattat tagcgatgcg gcatttacca agaaaaacac gtttgcacaa    2760
attaatgaac aaaatccgaa gcgtttagac gtttcgacga ctgtaaaact tagcggaaat    2820
acaaacattt taagtgtgga tcttaatttt ggtttctatt tcggtaattc ggtaattgtg    2880
gggtaaataa cttatgtcag ttggtggcag cattgagagc ttaactttag acggccgaac    2940
cttcagcgta gcagcggacg cggattcaac gcgcaattta ggcggcacgg ataacgaagt    3000
agaaatgaac ggggatggta cttatcgaat tgtaaaaacg cgcgtaccgt caaaactaga    3060
cggtatcacg gttgcaattg atgacgtgcg cggggatgca gaatacttgc aagagctaaa    3120
agatcgaaaa gagggctttc cctattcgat tacatacgcc agcggtgtga tttatcaagg    3180
tacggggaca atcgtaggag aaacgggaat ttctagccaa aacgcgaccg cttcgattac    3240
tatttcggga tcggctttaa ctaagcagta atttacagcg cggccataag attggccgcc    3300
ctttcttaat catttagggg gtttcacgtg gaacatatcg aaaatactga aaatcaaact    3360
ttgtggggct tgcctgttaa ggttgcgcgt gaagttgcgg aggctgaatt tatccgcttt    3420
```

FIG. 16C sequence.txt

| | | | | | | |
|---|---|---|---|---|---|---|
| tgtgatgcta | tggacgtgga | ttacaacacg | gatcgaatga | cggacgaaga | tgcaaaagac | 3480 |
| tttaacgaaa | gtaaagggct | tttgcttgat | gcgctgcaaa | ttggcgtttt | ggaaattgat | 3540 |
| agcgacggca | tggccgttgt | ttacccgaaa | aaaggcgata | ttaagcaaat | taaatttaat | 3600 |
| gagctttgcg | gggcggatta | cgtggcaatg | gacaataaaa | aggatacgca | aagtttcgct | 3660 |
| aaaatgttcg | caatgatggg | atctattacc | aagttaccgc | ccgcgacttt | ctcaaaactt | 3720 |
| aaaaagtttg | atgcaaaagt | ttgtttgtcg | attgctaaac | ttttttttggt | ctagtcgata | 3780 |
| ccgtttttaat | cataaagggg | ggcgaggttc | gcctatcccc | ttcgagagat | tcggatggta | 3840 |
| tcgagcgcgg | gaataatacg | agatttcaag | tttattcaac | gatgcttatg | cagatcctaa | 3900 |
| gagattataa | cttgccgaat | tttagaacct | taacaagttc | agaaattcgg | tttttttatga | 3960 |
| cggattgcgg | gccgagttga | aagaaacaac | aaaaccgagg | aattaatgag | ccgttacagc | 4020 |
| gtagaaacaa | tatttagggc | cgtggatcgc | atgacggccc | ccatatcccg | gatgcaatcg | 4080 |
| ggaattagtc | gatttactcg | ccgggctgaa | agcggactta | ggcgcgtttc | agatatgacg | 4140 |
| tggaatatat | ccaaagtatc | aggcgcagca | gccgcggcca | ttggtggcgc | atttatggcg | 4200 |
| gccgctggtg | gtattgccct | ctttgtcgca | gaaacaaacc | gggccaattc | agaaataaat | 4260 |
| gaaatgtcca | aagctatggg | ggtttccgcg | ttatccgcaa | gggccgcaga | ttccttgctt | 4320 |
| acaccgcttg | ggatgaattg | ggaaaattac | acggatctta | ttgaagaatt | gggaaataag | 4380 |
| atgggtgaat | taaaaaacac | ggggggaaatg | aaaacatttc | aagaggctat | tggacttact | 4440 |
| aatattaaaa | tgaaggaatt | aaaagcctta | aagccggagc | agcaatttac | aagaattatg | 4500 |
| gattctttgg | caaaaatgga | ggatcagcaa | aaagcccaat | ttattgcaga | tgaaattttc | 4560 |
| gggggtgagg | gtaataaatt | cgtttcagcg | ttaaaggcgc | gcggcttgac | tatgacgagc | 4620 |
| ttgattgaaa | attataaaaa | gtacaatttt | tataatgagc | aaggcgaaaa | agcaacggcc | 4680 |
| gcttttaatg | cagctttaac | cccgctaacc | acgacggcaa | attcggcaaa | atcgcagatc | 4740 |
| gcggccttaa | ctggtggcgc | gatggttcca | tatattcaaa | aggcgacgga | atgggctgcg | 4800 |
| gcaaataagg | aattaattaa | tagcaaaatc | gaagtattcg | ccaaaggctt | ggcggattcg | 4860 |
| cttgtttggg | tggtggttaa | ttttttccgag | attgtgacgt | gggttaaacg | tgtcgctatt | 4920 |
| ggtatcggca | tattcttagc | gcttacagcc | gttttaaaaa | ctttcgtttt | gattatgacg | 4980 |
| gccgttaatt | tagtaatgat | gatgaacccg | atagggctaa | tcattatcgc | cgtggtcgcg | 5040 |
| cttattgctg | tcattgcgta | tctgattaat | aagttttttg | ggttgcaagg | tgtcattgcc | 5100 |
| gcggctaatg | gtgtgcttat | ggggattggg | gccgctattt | tggtggcgat | ggggccaata | 5160 |
| ggctggctaa | ttgggccgc | tgtcttgatt | tggaaaaatt | ggggcgtttt | aagtggtttc | 5220 |
| tttagtggtt | tatgggcggg | tatcgtttca | gttttcagg | gcgcgcaaaa | tattattatg | 5280 |

FIG. 16D

```
                                sequence.txt
gggatcatta acgggattat gggcgcaatt gataacgtga ttaataaagc ggtttcgatg    5340
ggttcggctg ttaagggctt ttttagcttt ggcggcggtg gtggtgatca aaagcaagca    5400
gcagcagcgg gcggacgtgt ggcaagccca caagagcgaa ccgcaaaaag cgtaacggaa    5460
aataatagcc attcaacggt aacgatccaa gacaaaaccg gacgcgcgaa aatgtcaggt    5520
aaaccgggga atggggttcg attggttaaa acggggacta tgtaaacaat gagttgggaa    5580
gatcgtttaa aggaggcggc ttacaccgcc cccggaggta cacgggccac gttcttagtt    5640
gaggacgttt cccgtagttt tgataaaaaa acaaatggtt tcacgttccc ggatgcgtcc    5700
gggacttatg ttcaagattc aggcgtaagc gggtttaaat atccgctgac tatctatttt    5760
agtgggccgg attgcgatgt ggaggccgaa gcgtttgaag cgcttttgag agaaacggga    5820
atagggcgtt tagagcatcc gctttatggc gttattaacg tggttccgtt cggtacgatt    5880
acccgtaccg atgcaattaa aaccgaggca aaccaaacaa aaatagagct ggaattttgg    5940
gaaacaaacc ttttaattta cccattaccg caagccgacc aattaagcgc cgtatttgag    6000
gctatttccg acgttaaggc ggctttaagc ggtgatgtgc tagatagtat cgacgtaacc    6060
gacgcgagcg ccctagcgcg atttaaaaac aaaataacgg gggctttaag caaggtaaaa    6120
accgctttag ggaaaattaa gaatttagcg gacttgccgg ggcaattaat ggacaaggta    6180
aacggcttaa tttcgcccgg ccttgagttt atttccgatg ttaaagccca gcttggcgat    6240
gtggttaatt catttttga gcttgccacg ttgcccgaac aaattgtcga ttcattcaaa    6300
gagaaaatag cggtctataa ggatctcttt agcgaattaa cttcattcga gggcatattc    6360
cccagcaatg aagaatacga ggcagcttgt accggggtaa cggtgacttt atccggctta    6420
gtagtggatt tggttgaatc tgaatttaat acacaaagcg aagcattgga ggcggccgag    6480
gatctattag ccatttttga tgatgtaacg ggatggattg aagaaaaggc gcaaggcttg    6540
ggccgtaccg attcaaacgc ggtttatcag cgcttacata gcgccgtgat gaccgcggcc    6600
agctatttgg ttcagcaatc ttttacctta aaaaagagc gtaaattggt tttaaaccgt    6660
agccgtacaa ttattgattt atgcgcggag ttatacgggg aagtcgatag cgctttagat    6720
ttctttatta cgtcgaatga tttaagcggg gctgaaatat tggaaattcc gaaagggcgc    6780
gaggttttt attatgtctg acgtttctat gatgatccac gggacgcgct ttcatttttg    6840
gagtggtgta aggatctctt taaatattga cgcggtggca acgattagtt ttaacgcccc    6900
gtttgaccat gaggccccg gatttaagcg caatttcgcg ccgtttggat ttccccggt    6960
tgctatcgac gtggacgatc agcgcttatt taccggaacc atgttggacg tttccccggt    7020
gattagtgaa gatggtaaaa aagagatttc cgtaaatgct tatgcaaaat gcggagtgct    7080
tcaggattgc accgccccgc ctgaatccat gccattagag ttcaataaat taaacctgtt    7140
ggatattgct agaaaaatgg cctcttattt tggggtgggt gtggtattta atgcagatcc    7200
```

FIG. 16E sequence.txt

```
gggaccggct tttgatcgcg tggcgtgtga cccggataag aaagttttag aatttttagc    7260
ggatctcgca aaacaacgcg gctttgtgat cggtagcgat gaaaacggca atttactttt    7320
ttctaaaagt tcaatcggcg gcattgttgc taagttggag caaggcgtat ccccgctttt    7380
aagtgtatcc cctacttta  acccgcagga atattattcg catattacgg ggctatcccc    7440
tgtcgaagtg gcaaagcccg cggccaaaag cacggccaaa gtaaaaaagg acgctgcaac    7500
gcctgaaaaa gcagggcagg ggagcgaaaa ggcgaccgat aaggcgggcc aagccgaaat    7560
taaaaggaa  ccaaaaaaag aggaaaaaac caaaaggaa  aagcaaaaac caaagcccac    7620
gacttataaa aagtttacag ctatcgacga ggccccgta  tatcggccat tggtttttaa    7680
aattgatgat gcagaaggcg cgaccgatgt agaaacggcc acaaaagcaa aaatggcccg    7740
aatgcttggc aatatgtgta cttatgcaat tacggtttcg acgtggttcg atgcgtccgg    7800
ggatttatgg cggcccaata ctaaaattaa actcaaggcc ccggattcaa tgatttatga    7860
tttttcgag  tttgatatta aaagcgtgga attgtcggcc gatgaaaaca gccaacaagc    7920
aaatttaact ttatgtttac cgggttcgtt tacgggcgaa ccccggaga  ttttcccgtg    7980
ggaattgtag cgactgtatt aagtaatgat ggtaaggatt taaaagtaga tcggggcaac    8040
ggggacaacg taacggccca gcagttcggc ccgtccggtg atgatgctcc cccgcttaaa    8100
aatgattatt cggttttagg atcggccaaa ggttcaggca atgccagcgc cgtggcctat    8160
cgtgaccaaa aggccgaaaa ctacatagcc aaagcagggg aaaaacggat ttattcgcgg    8220
gatgaatcgg gggcggtaaa agctgaagtt tatttaaaag cggacggaac cgcggagatt    8280
aaaaacgcca gcgggctttt tgttatggag ccgggcggtg atgtggtaat aaatgggtt    8340
agaattacta aagccggagt tattcaaacg ccggcgggg  cttcaatgag ttctgatttc    8400
acaaacgcgg gcggaataac tttgggcgac catgcggccg atacaagttt acataagcca    8460
taaggggga  tagttttaa  tgtctttttt tgatgtgcat ttatttgatt cagtcgatgg    8520
cggcaatgta acggatgatt tagaaacgcg ggacggccta gaaacggctg tttatctaag    8580
tcttttggc  ggtaatgcct tagatgatgg aaggccccaa aacctttcga cgtggtgggg    8640
gaatattggg gagaatgaag cggcaaagca atataaaagc gaagccgctt ttttgcttcg    8700
cacggttccg ccgaatacag ccaatttaaa gcgaatcgaa gcggctgcat cgcgggatct    8760
tgcttggttg attcctgaat atgtgaataa gattcaagtt aaggcgttta tgcctaaatt    8820
gaatgcggtt aatttaacgg tttctttgga tggtttagat ccgttgcaat tccgtacaaa    8880
ttggggcgaa aaggttaaag agcctgttta tagactattg ccgcctaaag tttcccgaaa    8940
taatgggtt  aatttagaag gcacagcaga aacaaaaact aaactaattc ttatccgtgc    9000
cgatggatca agattaagta cgctggttga tggttcaggg aattggaaat ttgattttta    9060
```

FIG. 16F sequence.txt

| | | | | | |
|---|---|---|---|---|---|
| ccctttatat | ggtggtgaac | gtgcccggat | gtatgttgag | ggtgtagggg | gtaaaatatc | 9120
| cgctattgtt | acagttatcg | gggttttacc | gcttcgctat | gatgggatgg | caatttatga | 9180
| cggtacgcac | aaatataacg | gagttagatt | aaattaatga | gtacgccaac | gactaaagaa | 9240
| atatcgaacc | gtattttatc | caagttagaa | acgacattcg | ggcaaagttt | gcctaagtct | 9300
| tttacacgtg | ttttatccac | ggttttgggg | ggtgtgtttg | taattttata | taaatacggt | 9360
| ggttttattg | ctttgcaaat | gtttgtttca | acggccagcg | ctaaagatac | ggactttaac | 9420
| ggcaaaacaa | ttaacccatt | acgcgaatgg | ggccgcctca | ttggggcggg | tgatcctaat | 9480
| ccagccgtta | atgccattat | tttaacgcgg | attgtagtag | aaaagccggg | cgagatattg | 9540
| cccgcaggga | cgcagctagt | aaacagcggc | aacggtgtta | catacattac | ccaagaagat | 9600
| attgagctag | tcgaaggggc | gcaagatatt | gaagttttag | cggcttcgga | tacttcggga | 9660
| aattcaggcg | caggcaaagc | gggcaattta | aatgcggggg | atgttttgac | ttttgcgaac | 9720
| ccgcttggat | cggttggccg | ttattcgact | gtggtaacta | caattcggga | aggcctggac | 9780
| gctgaagcta | tcgaaacata | tcgcgcccgt | gttgtttcac | gtttccaatt | gcgcgctcaa | 9840
| ggcggggcaa | tggtggatta | taagatttgg | ggcgaatctg | tttccggggt | tagtcgaatt | 9900
| tatccttata | cgtccgattt | gccgggccaa | gtggatattt | atgtagatgt | tttggagggc | 9960
| gtagcaagtc | aagcgatttt | aaatcaggtt | aaaaacgccg | tcgaatttga | tgcaaataac | 10020
| gggcttgcac | aaaaccgccc | tttaaatgcg | ctggtaaatt | atttaccgat | ggagtttgta | 10080
| gaatttaacg | taacgattag | cggtttaagt | gttgagggcg | cgctatctgt | tagggctgaa | 10140
| attagagcag | ctttagaaca | ttattttaat | atccgtgcgc | cgtatattgt | gggcctttct | 10200
| actgattcgc | gcgcggaccg | aatcacattg | gcggccgcgt | ccggtgttgt | ggacgatgtt | 10260
| gttaataaag | ctggggggcat | ttttaacgat | atgcagttat | ttaaggggca | aacgccaatt | 10320
| tctttttata | tgttggggat | tggtgaaaag | gcgactttgg | taaacgtcga | gtatctataa | 10380
| tatgaatatg | tttaagcact | tgttacccag | cggccgcgct | tggaacctaa | ccgcggaaaa | 10440
| gccactaaag | gcttttttcc | gttgcttgga | tgttttgaga | acggacgcag | taaattattt | 10500
| taatttgctt | tttttagata | taaacccaaa | aacaacgcgc | ttacttgatc | aatgggagca | 10560
| gcaattcggc | attaaccgag | gattttttaac | cgaggcccag | cgccgggaac | gtgtcgcggc | 10620
| cgcttggcgt | gatgtgggcg | gacaatcccc | ggcctacatt | caagaagttt | taagaaataa | 10680
| tggctttgat | gtttatattc | acgaatggtt | cgatccggca | gatcgcgggg | aagtaggtga | 10740
| aaaacagcct | ataacgccac | gtaacccgct | gtcgattatg | tcggcccaat | atgccgaggt | 10800
| tttgcccgtt | gtggattgtg | gcgaaccgct | ggcgctatgt | ggtgaagaat | ttgcacatgc | 10860
| cggaaattat | ttgggccttg | ttgggtatcc | gcttgttaat | aagttcgttt | atgacgcgga | 10920
| taaatacggc | tacactgtcc | ccgttgatcc | ggcttattgg | tatcactttt | tttatgtttg | 10980

FIG. 16G sequence.txt

```
tggccctaat tttggcgatg tggcccaagt tgaagcaacg cgacgcgctg aatttgaagc    11040
gctaattttg agaattaaac ccgcgcactt atgggcgggc gttattgtga gatacgttta    11100
atatgtcttt agtgtttaat gagaaatttc ccggaaaaac ggcaggggct acacaaaatt    11160
acccgtatgg cgaagcgcgt aacgtatcag gccccggaaa tggtgacggt acgccgtggg    11220
atgcggccct agtgaatgat attttggat tacttcaagg gcttttagtt cgtgccaata     11280
ttcagccgaa cggccagtcg gacacggctt taaactcgca atatttacaa gccttgcttg    11340
ccctgtttat gccgaaacaa acgccaattt ccggaaagtt agagcaaaac ggatatttaa    11400
ctatccctt ccctgttgta ataaacggcc aaacggtaga gcgtgaattt acaattcaat     11460
ggggttctaa ggattggtct agttatccgg gtgaaattca agattctatt gtttttgaaa    11520
agcctttaa aacagcctgt tttggtgttt ttccaatccg aaaaatgtcg cagcattccg      11580
cttatggtga tggtggtgtt aagcctattt ctgtttctaa aaccgggttt acagtttctt    11640
tgcaagccta cgggggttct gtgggccact tgttgggtta ttattggttc gctgttggtg    11700
tttaagttag ttctgatttt atggggtaaa tgatgaatct atttatacaa ggcatttatt    11760
tactatggaa ccaatttcaa cgggtggcac agccgctttt ttaaaggttt atggggtgtg    11820
gttggcggtt gttaccgctt tggtgtttgt tgctactgtc gttttaatga tgcgtttacc    11880
acgtagccca caagagttcc ttgtgggcat tattacgact gtcgtttcaa gtctaatggg    11940
cggatctttt ttaattcttt attttgattt acagatttgg gccaattcag cttatggcct    12000
tatggtaatt ggtgggcttt actttgtggc gggtattccc ggctgggctt tggttcgctg    12060
ggtgtttaat tttattgatg cgcgggaagg ttccacacta ttggacattt tccgcgaatt    12120
taatgaagaa tttagaggcg ggaaaaaatg agtaaaatta ttgcgatttg cgcggggcat    12180
agtgataaag atccgggcgc ggtaaatggt aaacgtaccg aggcggccat tgttttagat    12240
atgcgtaaga tggttgccag ttatttggaa aaagcgggcg tgaaatattt aacagacggc    12300
aaaggcgggg ttaatcagcc attggccgaa gctatcaaag tggcaaaaca agccagtatt    12360
gctgttgaat ttcactgtaa tgccgctaca tcgaaaaaag cgaccggggt ggaggtttta    12420
tccgctgaaa aaaataaggc cctagcgaag caaatagcgg ccaaaattaa cggggtttta    12480
aatattccgt tacgtgggga aagtggttgg aagtctgaag gatcagggca gcatagccgc    12540
ttaggtttta ttagttccgg gggcggttta attgttgaat tgttctttat ttccaatgat    12600
gacgatttag cgaaatggga cgcgaaaaaa tggcttgttg ccaaagaagt ggcggccgta    12660
ttgattgaac aagtaaaaaa ggcggaggcg gcataaatgg cagcattaac gatatttaac    12720
gcgatttcag aagttacaag ttttgcaggg gtggcccgtg agattttcga cacagcagcc    12780
aatgcaatgg acgcggccca aaatgagaaa aaaggcggag gaaataaaaa agtttgggta    12840
```

FIG. 16H

```
                                         sequence.txt
atggcttaca tggaatcatt tattaatgat ttgggcgaaa attgggaacg atgggccaaa    12900
gctattttt ctttattga ttttgccaag tcgattttta atagtaagcg ctaataaaaa    12960
agccccgtat taattcgggg ctttttatg gttccacgtg gaacggttta gcttttcttt    13020
ttgcttgccg ggtttcttaa taaacgatct tttttgatct cgcttacaat cccgtcgatt    13080
aaaaattcca tgcttgttcc tttggttggt gggttggttc agatgattta attcgagttc    13140
ttagggccgc ttttacaatc ttatccgcca tgcgccctat ttgcgccttg tggcagttat    13200
tacacgcgca tccggcctta tatccccgaa cggttccgca gcctttaacg gcttatatg    13260
cgtcccctgt cgttcttca ataaaatcta tggttgattt gtccgccgtg tttcgcatcc    13320
tttaccccta agccgcagcg ggagcaacgg ccattttaa ataaggtgaa tgtttggcaa    13380
ataaaacaaa agttagtcat ttttgccgtt tgccttagcg attcgcatta cattaagggc    13440
cttttgcttt agatccgcgt atagctcatt agtaaggtaa ctttgtgcta catcgtgaaa    13500
agtagataaa aaatgcgtgt cttgttttac cttgctttgt ttaagttccg cttggtttac    13560
ctgaattaag ccaatagctt tgtttgcctt tttgattaag ttattcacgt cgcttaattg    13620
cgcgtttatt ttggcctctt tttcgccttt tatgtgtgct ggggccttat ccatcaaaag    13680
ggcttcacgt tggccgttta ggtgggtttt taggcccgtt aattcctcta ttgagaattg    13740
ccccgccact tgcaaagtgg ttaatgctga aaattcaatg attgcggttt taagttctgt    13800
tttagtcatg ggtagcactt catttaaaaa gtattaagcc cagcagcagc cggcaatgg    13860
tgggttagat ttcggttaag ccgtgttttt tcatttttctt aataacggtt aatcggttaa    13920
tgcctaatat tcgggatact tcggcaatat tatattttga atatttaagc gcttttcca    13980
aaacgcactt ttcaatagga tctaatgcag ccgctagagc ttggccggaa ttttcataaa    14040
aaaaattcgc gtccaaagca tccgggttaa ataaattagt ggtttcgctc attcggatat    14100
tccttaaatt gcgcgttata ttcagcgaca aattccgctt gtttgtcgat ttcatcggct    14160
tgtttgataa tgaacatata agacaaagcc gcaagcataa aacagaaaaa caacgtgctt    14220
aaaatctctt ttatttttgc gccgtggttc gctgtttctt gtgaaaaatt gcttaattgt    14280
tgacgctgaa taactggctg tttcataata atcggactcc atgaaattag aaaaaagccc    14340
cgtagccgtc caaagttccg gggcttttg ctgtctatgt gttgcataat atacaatata    14400
aataaaaagt aaatagagaa attatagata ataaataaaa taaataaaat agataaaag    14460
tattagtttt aattgtggca tgaatatttg ataagtgtta aaatttgttc taagcaatca    14520
tgctgaaaat aaaaaacccg ccggacgggg cgggtttag tttgtcttga gggtataaga    14580
cgtgaaaaag tttaacacga aatttaagca aaatcttgat gatgcaaata acaacgcatt    14640
tattccgaac agctttcaaa ttacaaatgc tttcgttgat aacatcatgg ataaaatttc    14700
ggatgcagca gtaaagatct atttaattac agtgcgtaaa acaacgggct ggggtaagca    14760
```

FIG. 16I sequence.txt

| | | | | | |
|---|---|---|---|---|---|
| gatagattcg | atttctttaa | gccaatatga | agcgtatagc | ggcaagtcgc | gccctactgt | 14820
| tgttaagtgt | ttaaaagagt | tggttaaggt | gggtttattg | gtagagcata | ccgggacacg | 14880
| gtacggtaat | tcgtattcgg | tggcgcttgt | aaatagcatc | ggtttcgagc | ttttatctgc | 14940
| tagtaaaaaa | attttactag | taaaaagttt | taactacact | agtaaaaaat | ctttactgcc | 15000
| actagttaaa | atttttaaca | cacaaaaaca | actatcaaaa | aacactaatc | aaaaacaaat | 15060
| aaataagcgc | gattggtttt | ctttaaaaac | tttaaagat | gaattgttta | aaaccgggtt | 15120
| gcaaattgag | gctgaagatc | taacagcggc | taaatggttc | gatagagaga | aaacagcctt | 15180
| tgaaaactat | gcacctaatc | aaaacctttc | agatccgcaa | aaaatgtatt | acttcgttga | 15240
| ttggctttta | aaagcaaagc | gcaagtacga | cgcagcagag | cgccagcaag | cagctaaggc | 15300
| aaaagcggaa | ggcaaaaacc | aaaatcaaaa | ccctgaagat | acaaaaacag | aaaacgaccc | 15360
| ttttaaactt | tctactaaac | aaatttcatt | ctttgctagt | cagttagccc | atttaccatc | 15420
| atttgcaaaa | tattgcactg | gtaacaaagg | ctttaaagaa | tttgaaatgt | ggattgcttc | 15480
| aatgttgaac | aatcctgaaa | atgttaaaaa | gtggaataaa | tatttaaatg | aattgggtta | 15540
| tttgatcggg | taatcagggg | gattaaaaac | aatgaagatt | tcaaactttc | attttcaaat | 15600
| gcaaattta | cttttgattt | ctaaaaacac | ggttttagat | tttgagggat | taaaagagaa | 15660
| gttagcgccg | tcgattacag | acaacgcatt | aacggaatgt | ttagaagaat | tattgatgtg | 15720
| gggatgggta | caagtacaaa | agggcccttta | catggtttca | ggcgttgctt | atcagatcat | 15780
| gggggatatt | tgccaatgct | gatagacaaa | tatttctatt | aatcggcttc | gatacggatg | 15840
| caatggaaaa | atacaagtat | tcagaatcaa | acgccgtatt | aagcccgcat | ttaaattgcg | 15900
| gcctaacttc | agttagtcgc | gttggatctt | caggccaagc | aaagcataaa | ccgcataagc | 15960
| gaagtgaaat | agcagatcag | gcagaaaaag | agatttgcaa | gaattgggcg | ttaagacaac | 16020
| aagcatttt | aaataacagc | gtaagcaacg | cggtactagg | gggctaatat | gaacaagttt | 16080
| attcacattg | agggcaaacc | aacggcccag | caagtacgcg | aagcgctggc | aatgtatgca | 16140
| aaagacatta | aacgcccgga | attttctta | attgttcagc | gtgagcttat | cgaatcattc | 16200
| cgcaacgata | cggcccacgc | ccttaaatcc | gcagttgcct | tttatttaa | aaatcgtgtg | 16260
| atccaacgcc | ccggccttgt | gttggcaagt | ggtaaagatc | aagcgcttat | tgttgagagt | 16320
| tgcgaaaata | aggcattaaa | gcgccacttg | gtcgcggtgt | cggggtattc | atcgcaattt | 16380
| ctgcaaatgg | tgatagatca | taaaacgcca | ctttcagccg | ttgccgcgcg | ggatctaaag | 16440
| caggcattac | caaaagcgga | aaaactctat | aaggccgaat | gcaaggaaaa | agatgcaaaa | 16500
| ttaaaaaaga | atatttgcgg | ttttgtcgct | tgctatagaa | atggctgtca | ttgcacaaaa | 16560
| tgcaccacgg | catataagaa | atatcgctaa | aagcaagcct | atcttttaaa | gagaaaaagc | 16620

FIG. 16J sequence.txt

```
gcagttcgcg ccgtggccgc ttagtgtttc acgtggaacc aaacaacgcc ccggattaaa    16680
cgtccgggga tctaaaaaag agtaaggaaa aggaataaaa atgggtgttt cgattattaa    16740
tttagtttta ttggttggtg tttgcttatt gctaacaaat atcgccttaa attgtttgtt    16800
tcataccgaa aataaaacat atctagtcta tgcgtgtggt tttagtgcgg cttcggtggc    16860
gggtgccatt gctggcgtta ttggttgttt ggcttatggg gtaacagtgt aatgaaaaat    16920
aaatcaattc ttatgggcct attcgttgcg gccgctggtg tggtgtttta tatggggcg    16980
gatagtgctt gcaatcaaaa ggctgttata gatccgggcg cgcttatgtc gcttggtggt    17040
atcactgttg aaaataaaaa agcctcattg gttcgcgtat gtgatacgcc agtaaaagaa    17100
aaccttgtga gctttgtttt gattaaagac ggcttgcgcg tgggtggtgt ggtcgataaa    17160
agccatgttg cgctcatagg tgaataaatg agtttaggaa aacgccccgc aggtgcgacg    17220
catatagaga gcgacggcac atattggaaa aatgaggacg cggattggta ttttggcgt    17280
gacttgtggg gctggtgtca atatgtcggg ccaaagaata gaaatttttt aaataagttt    17340
tcggtgttgg ggtgatggat ttatatattg gtcagattgt cgggcatagt tcgcccactt    17400
gggttgttca gggaaaattg aagataacca aaattaacga gggtaagcga agcggtttaa    17460
agattattac ggctacagat gaatcgggta aggaatttac cgcagtttat ggcgtgtttt    17520
ttagtgttga tagatattaa ttaaaatttt ggggtaatac gtgagaaacg aaaactttga    17580
agattattta aaacaaacgg atgattacgc cgtattactg aataattacg gatctagtct    17640
atttatccat gaaaatggcg tttatcgcgc tttgcctgtc cgggtggctt atgccgcttg    17700
ggtatcgggc ggggatcgct ggggagaggt gcagcacttg aaaggcaaaa ttaagaaaat    17760
ggccgaacgt gcagcagaaa cagcggattt ttaccatacc aaaatagaaa aattggaaag    17820
tagcacggtt aaaaaggcgg gtttattgga tatggccgaa caatgggacg gtttagagtt    17880
gcgcggacgt gatttggaat taaaccgggt gcaagaatca atttataagc gttgtgctta    17940
tttgttgcgg gtggctgtta atgggtaatc ggtggacgtt aagcggaaag gtaaagggt    18000
taaaagattt gcccgaaagt ataaccgcgg cacaattcag ggaaatgata gaacgggggc    18060
aagtcaaaaa cacgccacaa gccccaaaaa agcgccgtag cggaaaagta agtagtccgg    18120
gggaggctac attagcccaa gccttaaaag cgcttaaaat cgaatttgtg caagagtatc    18180
gcttttgtga atatcgcaaa tggcgcgcag atttccatat accggggaca aaccttttaa    18240
ttgaggtaga aggggcgta agatccggcg ccgccacgt gcgaccacaa ggctatataa    18300
acgacacgga aaaatataat gaggcggcta agttgggctt tgttgtattg cgctttgata    18360
cggaaacggt ttcacgtgga accgcaataa acgaaataga aagttatta gaaaggcgcg    18420
gatatttcca aaataagggg cttacttgtg aagaaagtta aaaagtttaa atacgattgg    18480
cgcgccgtgc cggatcatat taattggctt gcaacgtatg aaggcgggga aatggcctgg    18540
```

FIG. 16K

```
sequence.txt
gggtatgtga ataaaccata tagaaaagaa aacgcgggga tatggtacga aacgggcgga    18600
gagtggcggc atcgtgtacc tgttgcccca tatcgcggcc attggacgca atcattagaa    18660
aaacgaccta gcaaggccca gctagtcgag tgggttttaa atggggctgt agtggtttaa    18720
tattcacgaa ccctcataga gtgttttata acattctgtt ttacaagcct cattgcctat    18780
agtgaggctt tttttgctt  tgcggtttga ttggattttt aattgttctg tgaatttgg     18840
gctaatatta gaaaaccgca taggcggcaa cgattgataa attagagagt aaataatggc    18900
tgaaaatagt tttattcaac caattgcaag aaaggacgcg attgcccta  ttggccgtga    18960
tgagcttgtg gaaggtgggc cggaaggggc agcgaataaa caagcaattg cacttgcaaa    19020
taatattaag tatttaatgg gcttaattcc tgaaaattgg ggggtggaaa aaaccgaata    19080
tggtttagat gaagttgtaa ggctttcaaa tggtgacgtt gttaaatctg ttattgatga    19140
aaatatcaat aatccgaacg agaatttgtc gggttggtct tttgttacaa gtaattcagt    19200
aaatactatt tctgatttat taagtattaa aaatccgaaa aatggaatga agtttatgt     19260
tcttggatac cataaaccgg ataattttgc tcttttaagc ccgtatgaag ggggcgggct    19320
tttcatatat agcgggaata aggcagcgga aaatgatggc ggcgtggttt taaatggctg    19380
gattcgtcaa tatgttggcg atgtggatat ttcttggttc ggagcaaaac aaggtcaaga    19440
cgcttcgccg tttattgaag cagctttaaa agtgaaaatg tcaattgtga ttcgtggaga    19500
atacaagtta gaaacaattt gcggcatacc aagacaaaat aactatgcgg caaaagttat    19560
tagaattaag ggggaaaatc aggcttcgct tactgtaaat tgcccggatg gtgctgtttt    19620
tacttcgtta gatgcaaaag caaaccctac aagtttatcc aatattttta ccgcaaaaat    19680
tgacgtattc gggattaact ttgtaggtac aacggttgca aattctgttc tgtttaatgg    19740
tgatcgttta tacaatatta atattcatca caataatttc aaaacaaata ttacaattgt    19800
taaagcgtat ttaaagcgcg aggcatcaag acaatatacg caaagcgttt ctattaatca    19860
taatcactta gcggaaattc accgggttat tgagtcggac aagtcttata acttcgattt    19920
tgcatacaat atgtgtgaag cgtgtaaagg tggcatgtat atcggtgttg atgcgcctta    19980
tgatccttca ggtatttcta taacaattca tcgaaattta tgggaagcca gcgggttt     20040
attaaaaaca aatggcggga ttattgctgg tagtgtttca aaaaactatt ttgaagctaa    20100
cgtatatcaa gatgcagcaa ttgataaatg cttaatatat atcaaccgaa gcggaacggg    20160
ggcgggttat tccggtggtt aactttga  aaataattta ttttcaggga cttcgtcgat    20220
tccggattat gttgatgtgc gcgttttggg tcaaagtaca gaaacatcgg gaaattcaaa    20280
atctgctact acgcgaccgc ctgtatttat tggtaactgg tcaaatagtt acatgctaac    20340
aaatatggcc caagctattt tgatcggtaa taagtgttct aaccgcgaaa aaatgctgaa    20400
```

FIG. 16L sequence.txt

```
tgcttacagc ccgcaagaag cgcgcgttac ttactattcc ggctatttta ctaagcaatt    20460
ggctaatatt ttaaccgata aaaagttaaa tttattaaag gtgaatactt cagcagttca    20520
tgctattggt tcctctcaag ctaactttaa aactacatta gacgttattg tattctttaa    20580
aacatccggc gcagttggaa cagcaatggc gacttttaaa ttagatttat ttgtttacga    20640
atcagtcgga cttggcgctg gcaatgttcc aaaagcaaac ttaaaagccg tgatgtataa    20700
ttttatgcaa tccaccgcag acgacaaaat tacaccaacg gttaatatgt tttcggctat    20760
ttctgatccg ttaattaatg ttgttgataa ctcagacgga acgtatagca ttgagctttc    20820
gagttttact aataaatcat cgccaaactg ggggtttgtt tctgaattgc atattgaata    20880
cacggcccaa gcgacgctta tagcttcgca tacatccagt tattcagcgg ctaacttatt    20940
aaccatttca taaacttaat taatagctaa ctaaggggga gcgccaattt tgttttaag    21000
attggcgctt tttttattgg ggttttatgt ttgatataga tacaaagcaa ttgcacggcc    21060
tggagaggcg tttagagcga ttaaaccgcc gtggcttgcc ttatgccact aggcaaacaa    21120
tgaacgatct agcgtttgaa tctcgcgccg tggcccgtgc cgagttacca acgcgcatgg    21180
ttttaagaaa taaacacgcg attaatagca ttcaagtaac taaagcaaca tcgctaaaca    21240
tttcccagca agccgcgcat gttggatcta cagccgacta tatggcaacg caagaaacgg    21300
gaggcattaa aaccaaacaa ggcggggccg ccgtgtctat tccgaccacg acggcagcag    21360
ggcagggcag aaacgcaaag ccccgaaccc gtttaccacg tgcagcgctc aaaatgggcg    21420
ctattcacct aaagcgtata gcggcaagcc gtaacgctaa gaatcgtaaa caacgcaatg    21480
ccattgctat ggctacatcg gataaatatg tatttctcga tttgggccgc cgtaaaggta    21540
tttttagaaa ggacaagggg ggaggggtaa caatgttgca tgatcttaca cgcgcatcgg    21600
tgcagatccc taagaatgaa tggctgaagc ccgcgaccga ggcagccgaa cggaagttac    21660
cgggattcta tggccgtgct ttagagttcc aattaaggcg cttttaatta accaaaaact    21720
taacttcggg cggttcgggc gggtagccgc ccgcggttaa gttaaagaat ttttcgcaca    21780
aaaagccacg gttcgcgccg tggtttttat ttgtctttat cattcacgtg atgaatggat    21840
ttatttttaa aatcaatagt ctgaaataaa aaaaggtact gtgccgaccc cccacccccct   21900
tgccgttttg attgcgacgc gcgggccgcg cacaaattca gaattttttaa cttgtcttaa    21960
cttcgggcgg gttaaatgtt aaatttcgca tcatggttaa aaagttaatt tctcgcagcg    22020
attttgctgc taaggcgggg gttagcgggg cggcaatcag taaggcatgt aaagggccgt    22080
tattagatgc tgttgagggt aaattcatcg acttaaacca taagtcggct atcgcttact    22140
tagaatcaaa gaaaaacggc aagacaacgc cagcacttga ggggattgat tcgctatatg    22200
aggaagcatt agaagtttgc agagaagcgg gccgatgctc gcaaacattg ttgcgtgaca    22260
aattaatgat aggcagcgac cgggctagaa agttggtcgc tttaattcaa aacgcaaata    22320
```

FIG. 16M sequence.txt

| | | | | | | |
|---|---|---|---|---|---|---|
| tccaagattt | tgaaaaacca | gcagccgaaa | aggtaaaaag | agaggagaaa | gcgcgcccgc | 22380 |
| atacccgcgg | gacggctgca | aaaaaacagc | aagcaattca | agaggacgac | gaagaattat | 22440 |
| ttgagctgtt | agatcggaac | gtagcgcaat | atgcagatat | gacgctaagg | gacattgtta | 22500 |
| ggaaattcgg | gacggcaacg | cgatttgcgg | aatatcttag | agcaatgaaa | gaaatatcaa | 22560 |
| tgattgaaga | tcgggaaatt | aaaatagccc | aaacaaggg | cgagctagtc | catagggatc | 22620 |
| tagttagtca | attgatcatt | gagccgatag | attcggccca | tgtaaaactt | atgcgggacg | 22680 |
| gatctaaaac | aatagccgtg | cgaatggcag | caatgcacgg | cagcggggcg | gacattaacg | 22740 |
| aaatgcagtt | agtcacatca | gaattaattg | caagtttcat | taaacccgta | aaagccaaag | 22800 |
| taaataaaat | cgcaacggaa | ttaaaacgag | gggctgaagc | gtgaatatga | attttatagg | 22860 |
| tatggattgg | ctttgcgata | aagtcgagaa | tctaaccgag | tatattaagc | acgtaacgcc | 22920 |
| cagccaattt | aatgaagaaa | atagatattt | gcccgaatct | gtgaccagta | ttccgggctt | 22980 |
| tatccgttac | gacgtaaacc | cgtttatgcg | tgaaattgtc | gattgctttg | atattaattc | 23040 |
| acctgtccgg | gaagtgaatt | taaaaaaggg | cgtacaaatt | acatattcca | cggttttaga | 23100 |
| atccggggct | ttgtactata | tgggccacgt | taaaaccttg | cccattatgt | atatgacggc | 23160 |
| cgacaaggaa | ttagcaaagg | cccgtattga | aaacaacttt | atcccaatgc | tggcacagtc | 23220 |
| ggacatggcc | cacattgtcc | gatcaagcga | cgaaggtaac | agcagaaaaa | cgggtaaaac | 23280 |
| cgataatcat | atccaatttg | agggcggcgg | ctatttggtt | ccattcgggg | ccattaatgc | 23340 |
| aaataaaatg | cgttcgtttt | ctattgctgt | catgctcaag | gatgagattg | acgcgtggcc | 23400 |
| ggatcgcgtc | ggaaaagatg | gcgacccgga | taagttgagt | gatgaccgtt | gtagcgccta | 23460 |
| ttgggaacgt | cgaaagattt | tccgaggttc | cacgcccta | atcaaaggat | cttcaaaaat | 23520 |
| tgaaaaagca | tacttgcgcg | gggatcaaag | aaaatatcac | gtactttgta | aaaaatgcag | 23580 |
| tttcccgcag | gaattgcgat | ggagtacgcc | ggacggtgta | ggcggtttta | aatgggacac | 23640 |
| ggacgaggac | ggaattttaa | aacttgattc | ggtgcgctac | tgttgccagc | aatgcgggga | 23700 |
| gccacatttc | gagcatgaca | aagagcgcct | atttagtgag | aaattcgggg | caaaatggat | 23760 |
| accaacggcc | cgccctgttg | agccggggat | tcgttcctat | catttacccg | cgttatattc | 23820 |
| gccgtttggg | atgcaaccgt | ggtacaagtg | cgtgattgct | tatttagacg | cattcgaccc | 23880 |
| ggtagagcgc | aaagtaaaag | acatagagct | ttaccaagta | ttttataaca | acgtattggc | 23940 |
| ggaaccgttc | gagattcaag | gtgctaaggt | tcgctttgaa | acggtttcgc | atcatcgccg | 24000 |
| cacagtgtac | cgattgggcc | atattccgaa | ccgttacgcg | gttcaatatg | ctggatcgcc | 24060 |
| tatcctattt | ctaacctgtc | aagtggacgt | acataaatca | ttcttagccg | tttccgtgat | 24120 |
| gggttgggcc | aaagatgcta | aatgttttgt | tattgattat | ttgcggatcg | agggcgagga | 24180 |

FIG. 16N sequence.txt

```
cttttccgat agcgcggaac cgggttgggg taaattgcgc gagctaatcg aagaaaagca    24240
atatattgcc gatgacggta aaaaataccg cgttgctttg accttcatag attcgggtta    24300
tgctaacgat accgtcgtta aattttgttc tgaatattcg agttcagtct atccaatttt    24360
gggccgtgac cgaccaagta aaaaccaagc aattaaagaa tttgccgact ttaaaacgca    24420
agaagggaca acgggcttta gaattattgt cgatcattat aaggatcgtt tggccccggt    24480
gttgcgtcgt gaatgggacg agatgggcgg aggtttacag cctgtttatc attttaatgc    24540
gcctgtcgat ttgtctgata agtcattaaa agaattgacc gtagaaacgc gcaaggagaa    24600
aaccgacgca agcggcaata cttcatattt ttggcatcgc cccggcaatg cacgaaatga    24660
gctttgggat ttgctttgct atggacatgc agccgtcgag attttcgcgt ggtcgctatg    24720
cgttaaaaat atggaacaaa aggaagtgga ttgggcttgg ttttgggaat ttttggaaac    24780
agaagcccg tattttgagc aaggcgaacc cgtcgccagt gagtaacaaa aagcccgcta    24840
aattagcggg ctttgtttca cgtggaacct tataaaacgg ctataaaatc gaaatgcttt    24900
aggtttaagt gatccggggt aaaccaagtt ttaacccaca taatgcgatt gaaggttagc    24960
aagcggcctt tttgttcagc ctccttaaaa taggcgattc gatcccctt tactgcgacg    25020
atggtcgcgc cttcgggttt atttcccttc agcttttcta aattattttc atattgcatt    25080
ttgttagatc cttaaaaaat gtttaaacct tgattattaa aattaggcgt ttggcattgc    25140
ggcatatttt tagcgatgct gttgtaagtg ttttgcgtca tgtaaatttt accgtcaaaa    25200
gcaatcgtgt tttgatcggt gatttgcacc gggtagccgt gttgctggat cgttgcgcca    25260
gcttgtacga tttcgatttt atggccgcgc caattgttaa aagattggtt attcatgagt    25320
ttggttcctt aaattaattt gttgctggta ggttatattt accgtttgtt tgtgggccta    25380
atttaataag attgtgattc tcattaagcc cataaggtaa atgggttcgc gggtttaatt    25440
cggttttatc agtaataaaa atacattcat gcggattcac gttgtaaaga taggcgacca    25500
tgcgcggggc tacataatgg gattgcttat catgttttga gcgaacccag ccgccgaaaa    25560
ctaaatattt tttatctatc attttttgga aacagcctca ttttttaagt gttggttaag    25620
cagatcccgg acaagatcgc ccacgtttgg cactgtttca atgtattcga ttaaatgctt    25680
atcgcgttcc ttgagtagag aaaaatttt aattacgcgc ttttttctcat aatcgctttt    25740
ttgcttttgc cttgcttcgc tttggcccat tatttacacc gttttacagc ttggttatat    25800
tgatttcttg caatgttgga gagcgttgta gttttggaat tattccgacc cgcttggcgt    25860
gatgaaccaa gcgggctttt ttttacattt cttcagccat aaacacggtt aagaagccac    25920
ccatatcatt ggcaaaaagg ccgatagatt caataatgcg ctttgcttcg tttagatttt    25980
taccttcaac cataagccaa acatcgcgtt tcactttata ttcagggcct agaattttt    26040
taagtggctt ggtcaattcg cgtggtgttt ttacttgagt gtttccgatc attaacattt    26100
```

FIG. 160 sequence.txt

| | | | | | |
|---|---|---|---|---|---|
| tgcaaaactc | ttatttatct | atttgatgtg | tcaattatgt | cgtattacga | caagcaaggc | 26160
| aatagggaat | gtataaaaaa | tatatatttt | ttaaaatggt | tccacgtgga | accgtggcgg | 26220
| gcgtttatgt | tgcgctttcg | ctttattgat | atactaaaaa | caacatagcg | ggagtattta | 26280
| aaaaattgga | tcaagcattt | ttaaaagaaa | ggatcgaagc | gacaaagcgg | caaattgtgg | 26340
| cctatgagga | tgcagtaaac | cagctttcaa | gcggtgcggt | tcaatcgtac | tcattaaaca | 26400
| cggggcagac | gacgcaaaac | gtgacgcgct | ttgatgttgc | gcgcctaaat | ggggatattg | 26460
| acgggcttta | taatcgcttg | gcgacgcttg | aggcgcgttt | aaatggttcg | ggttctactt | 26520
| tggttcgtcc | gggatggtaa | tagatgaatt | atgattttag | ccgtgggctg | gtaaaggttc | 26580
| cgacggtggg | tttaaaaacc | gagtttaaat | attcaggggc | tacaattgca | ccgccgccaa | 26640
| tgcagggcgc | aaaatccgac | gctatcgaaa | taaacgcgct | gggcggtggg | ttcaatcatt | 26700
| ccgcttttac | cggggaaaaa | tttataggcg | gtttcgggcc | tacaagttta | tttactatgg | 26760
| attattggac | gttacgcaaa | agatccgagc | agctatttag | cgaaaactta | tacgcggccg | 26820
| gattaatcga | gcgtttagta | acaaatgaaa | taaacacagg | attaaccccg | gaggcttgtc | 26880
| ccgatgaacg | gattttggga | ttaaagccgg | gtgatttaga | agattggacg | gaattagtag | 26940
| aaaaccgatt | ttctatttgg | gccaatagtt | cggaatattg | cgacttttac | ggacaaaaca | 27000
| gcttagggga | aattcagcgg | atcgcaagac | gcgaagccct | tatttgtggt | gatgtgctgg | 27060
| tggtgttacg | ccaaaaccaa | agtaccaaaa | tgccgcaagt | tcagcttgta | agcggatctt | 27120
| taatccgaac | cccgccggat | atcccgcgca | aaggccacaa | aattaaacac | ggtgtcgaat | 27180
| tagatacgca | aggccgccag | tgtgcttatt | gggtttttaca | agacgatgga | acctataagc | 27240
| gtttgcccgc | gtttggtgaa | aaatcaaagc | gccgcattgc | gtggatggtg | tacggagcgc | 27300
| aaagacgttt | aggcgaattg | cgcggccagc | cgcttttaag | tatcgttttg | cagagcttaa | 27360
| aagaaattga | ccgataccgc | gacgcggccc | agcgtaaagc | cgttgtaaat | tctattttgg | 27420
| caatgtttat | tgaaaaaacg | caggataaaa | tgtccacgtt | gccaattacc | ggggcgcaa | 27480
| tccgacgtga | taaggttacg | gataattcaa | acaccgcggc | cccgcgtagc | tttgaaatag | 27540
| cttcgcaagt | tccgggcgtg | gtattgcaag | aattacaagc | gggagaaaag | cccgtaggtt | 27600
| tccatagtca | aggcacagat | attaactttc | ccgcgtttga | ggaggccgtg | attagtgcgg | 27660
| ttgcttggtg | caagcagatc | ccgccggaga | ttctaaaact | gtcgtttagt | tctaattatt | 27720
| cggcaagtca | ggcagccatt | aacgaattta | aaatttattt | aaatatggtc | tggaatgaat | 27780
| ggggcgctaa | cttttgccag | ccgatctata | ccgagttttt | aattagtgag | gcgcttttag | 27840
| ggaaaattga | cgcgccgggc | ttttggacg | catggcgcga | cccggtaaaa | atggatattt | 27900
| ttggggcttg | gttgtggtgc | gactggttcg | gcagtattaa | accgagtaca | gacatgcgta | 27960

FIG. 16P

```
                                    sequence.txt
aaatggggca aggcttggcg cttgccgtgg aacaaggttg gacgaccaac gcccaagcat    28020
cgcggcaaat gttcgggact aagttcacta aaaacattgc aagacaacgc cgcgaacgtg    28080
aattacaagc cagccttttta aggccaatgc ttgagctgca aaaagaatac ggcataagcg    28140
cggagcattt agtaaatgta gcccatgcga ttggcgggac aatttcggca caaactgaag    28200
aaacagagga aatttaatgg attggttttt aacgcctgaa gccctaaaag aaattcagga    28260
attacacgcc cgcggcttgg ttttgaccgc ggagcaaatg acggaattta acgcgcttta    28320
ttcggatgat ttccccggat cgcgtatttt tcaaaaagtg gggacggttg cacaagtaaa    28380
cattgccgga gttctaacaa aggaacctaa ttggatgtat cgctattacg gtggcggtaa    28440
tacagcatat agcgaaatta tttccgcgat taatgaggcg gagcgcgacc cagccattaa    28500
agaaattatt ttggcgattg atagccccgg cggacaaaca aacgggcttt gttcagcgat    28560
ggacgcaatt aaaaacacga aaaaaaccgt tttggccgtg gtggaaggtc aggcagcaag    28620
cgccgcttat ggccttgcat cgcaagcaaa taagattatt gccgcggatc gcggttgcat    28680
ggtcggaagt gtaggcgcgg ccgcttcgat tgttgttagc gaaaatgttg tcgatattgc    28740
cagtaccaac gcgccaaaga aacgcccgga cgtgaccaca gacgcgggta aagcggtaat    28800
acgtgaaaca ttagatcaaa ttgaaagtat ttttattgct gatattgccg ccgggcgcaa    28860
ggtaacggcc gataaagtta aacttgagtt tggtcagggt ggtatgtatg ttgcggccca    28920
tgcccttgag cgtggtatga ttgacgaaat taaaacggct gattctagcg ctacaacaaa    28980
cgcgaaaagt tcagcaactt acacagcaag cgaggaaaat tcaacaatgg atgcagcaac    29040
tttaaaggcg caattcccag cagtttacac agcaatttat aacgaaggca aaaccgcaga    29100
aaatgagcgc gtatccgcgc atttaacgct gggcgaggct tcaggcgata tgcaaacggc    29160
tatttctgca attaacgacg gttcagaatt aaccgcaagc attcaagcca agtatatggc    29220
ggcaaatatg aagcgcggcc aagttgctgg gcgtgaaaca gacgacacgg ccgcggctaa    29280
tgctttggat ggtgttaaac cgggcgcgac tgctacagat gcgaatgcag ttacaaacat    29340
ggttgctaaa aatttgggcg ttgcataagc ccaaaccgta aagacatttt agaaataaag    29400
gggtaacagt tgcatgatgc aggtaacgca gcacacaaac agttcaatta attggggtga    29460
agtagcttgt caggatgaca cgctaacttt aggcgcaaac gcaacgctaa aagaaggcac    29520
aattttagcc cgtgcagcaa cgggaaaact tatcccgttt gttaagggtg gcgcagatgg    29580
ggcgggggtt cctgttgcta ttgctatgca cgaaattaaa accgtggccg ctggtgatgt    29640
ttcagtacgt gcgggcattt ccggccaagt gcgtaaaaat aacttagtga tccatgccga    29700
tggaaacgcg accaatatcg acggagcagt aacagacgct ttgcgtagtt atggcattgt    29760
cgctttcaca gtaaacagca caaacaaacc ggataaccaa taaggaattt ttgatttatg    29820
actactagca caattgccgg ggtatataca caagttgcac caaagccgct atttttatcg    29880
```

FIG. 16Q sequence.txt

| | | | | | |
|---|---|---|---|---|---|
| ggcttttttca | aagcaccgcc | acagaatcat | tttaatactg | aatctgtcga | gctggacatt | 29940
| gagcgcgatt | cgcagcaagt | ggccgcggtt | gttcaatcgc | ttggcagcga | ctacaacaaa | 30000
| aacgaaacgg | gtgaatttac | caataagaaa | tttacgccgc | cagtttataa | agaaggcttt | 30060
| tcgcttaatg | cgttcgattt | gcttaaacgt | gaagcgggcc | aaagcggttt | taatacgcct | 30120
| agcgaacaga | tccgcggcaa | tttgattacc | cgctttatta | aaggcgcgcg | aaaagttgaa | 30180
| gcaaagattt | tacgcggtat | tgagttgcaa | gcatcgcaaa | ttttgcaaac | gggtaatttg | 30240
| ttgctgaagg | atcaagaagg | caaagacgct | tttaaaattg | attacaagcc | aaaagcaacg | 30300
| cattttgtga | atgttgcgaa | tgtttggacg | ggtgcgaatg | ccgacccgat | gaaagatctt | 30360
| gaatcattgt | ccgaagtaat | ccaaaccgac | ggccttgtaa | ttcccgatat | tatcattatg | 30420
| ggcgcttcag | cactggcagc | ggctaagggt | aacgagaagt | ttattaaaaa | ctttgattct | 30480
| cgcaatattt | cgggcaatgt | tttagctgat | atgcaaatta | cggcccgcgg | tggtatctat | 30540
| caagggacgt | tgcgcgtagg | taatgccgtt | tgtgagcttt | acacttatgg | cgtgggttat | 30600
| caggcttcat | cttcagcagt | tgcaacgccg | ttttaaaata | ccaataaagt | gcttatgctt | 30660
| agttctgaat | cgcaattaga | cgcgcttttt | ggtgcggttc | caaacattgc | ggacatttttg | 30720
| ggcgtgagct | tgcgcgaaca | gcttttaccg | gaattgccga | cgcgctttga | ttcaaacagt | 30780
| accgatttat | ttacaaatgt | gtatttgtcg | gcaagtggtg | agcagcttat | gggcggggtt | 30840
| gctagtcgcc | ctattcttgt | cccgacggct | attgattcat | tcggctgttt | aactgttgca | 30900
| taaaaattaa | aatgaaccccc | cttcaatggg | ggttttttct | tttaaatttg | gagatattcg | 30960
| acgtgactaa | aaccgattta | attaacgcaa | ttaaagccat | tgattcaaac | gcgaaaacgt | 31020
| ccggccttga | taaagacgaa | ttacaagccc | ttttaacaga | attacaagcc | aaagcgac | 31078

FIG. 17A sequence.txt

<210> 3
<211> 167285
<212> DNA
<213> Unknown

<220>
<223> Description of Unknown: Bacteriophage F488/08

<400> 3

| | | | | | |
|---|---|---|---|---|---|
| tctgaacgac | ctgccatttt | atccatgtct | ccaccgtcaa | ttattcttgc | ttcttttta | 60 |
| tcttttgcta | cagtgtaagg | atttgctgat | aaagcatatc | taactaataa | accgatagat | 120 |
| ggctgcaaac | tttctgggtc | aactacaact | ttaaatgcac | ctacatgttc | agggtcatct | 180 |
| aagtcaagac | cttctgtata | cggagcatag | aaaattgatc | caacaatttc | tttttcaccg | 240 |
| atattttcta | ctacaccaac | gattacataa | tctaatgggc | tgttagtatc | gcaataaagc | 300 |
| ggtaaaccat | tagctaagaa | cccataggca | ttttgtgaaa | gatatttatc | atcttctggt | 360 |
| ttatgtttta | accacctga | tgcagcaaga | atcgcagcag | cacgagctga | agcaacacag | 420 |
| aacgttgctg | tataagttga | ttcttttgg | atatgcgaaa | ccatttcaca | taccattcgg | 480 |
| tataatgaac | gaccagcttc | aggtgcagat | gcataactca | aatcgatgaa | tccagtatca | 540 |
| gtaattcctg | taactttata | gcgttttgac | actgtaatca | aagactgcag | aatatcttta | 600 |
| ttgatttcat | ctgccatttc | agttgcaagc | aaatcttcca | agaaattagg | agcatcgaat | 660 |
| ccatttgctt | ctaaatcttg | tgctaattca | actgtgatac | cagttttaag | tttacgagat | 720 |
| ttaactgcgg | tttgccattt | attaatctgg | aatctagcat | ccgcaatttc | actatcagag | 780 |
| ctttcaaatt | tgcttgttga | cgctgcgtca | gaaaatagac | gaacctttaa | aagaacaatt | 840 |
| gcaatctgaa | gagctaattc | taaatcgctt | tcttcaatat | cagcaaatgg | tgtatcttct | 900 |
| aatactttat | aaacgatatt | attatatttg | aataaatcgc | ccttattgag | agttaattta | 960 |
| gactcttctg | ttaattctgt | gatttgttct | cggtctacat | atccagcttc | gccggcgtaa | 1020 |
| gtagcaccag | ttttaaatgt | aaattcgtta | tccgggttaa | ggtatttgat | accataaaaa | 1080 |
| gcagcaacag | gttgattagt | tctttgcgtt | gctacaatgt | cagaatatat | taatttagtg | 1140 |
| gtagcgcgag | tcaaagcaac | gagatttggg | cgaccgattg | agttgctatt | cgttgtggtt | 1200 |
| gattcgcgca | gaagttcgtt | gattttagcc | attcgctttt | cctttcagtt | tatatgattt | 1260 |
| atttatacca | taaaaacaac | taaagggacc | cgaaggtccc | ttaaatcgtc | aaagattaga | 1320 |
| tacctttaac | atatacacgg | cggaagtaag | cgtttttacc | aaggctattc | agaatagaag | 1380 |

FIG. 17B

```
                            sequence.txt
gcataccgct ctggatgcga gaagccggag cctgagcagc ggattctgca aatgggttga    1440
taccgatacc gtaacgagtt ttgaatccca ttaccggttg gaagttcttc ggatcagaac    1500
cacgcagcgg agtcagagct acatatggag catagtaaat accagcatcc atttcgttcg    1560
gacctttata acctacggtg aaataatcct gtttagcata ctggtcgata tatacacggt    1620
atttaccacc cagaacacca gcaaatactg acttggtagt atcagtgtta aagccagtag    1680
ccagaccttg tgcagcataa gaaatgccgg tatcaactga agccagaacg ttaactacgt    1740
tacgggaagc gataatgaag ttaccttcgc cgcgaccagt ctgacgagca atttcaactg    1800
cttctttgtc aatctggaac aacagagctt taaaggattc acctgcccag cgagcaccac    1860
gaatatcgat tgggtcctgg aagtcaaata caccagcttt agaacccgga gtcagggtca    1920
taccagattt accaacctga gcggagtagt taatccaatc aacaacttcg cggttgattt    1980
ccagcataat ttcggtagcc agaataccag acagttcagc atcagcatcc ataccgtgaa    2040
cagcgcgaag gtcttgtgct aattcaatag agtaagcagc tttcagctga cgagatttag    2100
cttcgataac ttgtttatcg atacggaagc ccatttcatt ccatgggtta tcggtagaac    2160
cgttgaaacc ttcctgaagt tcagcgatag aagtagccat accttcagcg atttctacca    2220
gtacaccagc ttccatttgt ttcttaattt cagcatctaa tttgtctgcg tcagatgcgc    2280
ctgaatcaat ttgtttagct gctgtagctt gcagatatac tgtaccagtt tcctggaaga    2340
agtgagtgta aatagttccg acttcaagag tatcacttgc tttcaaagca gcgaatttct    2400
tagcagcacc ctgaccagag aacattgcat ctggaccata cattgggtgg aatgcttctt    2460
tagcgccgga agcgattgga tctttaccat atactgcgcg cagcgcgaat acctggccag    2520
tcgggctgtt cattggctga acaccacaaa tatcgaaagc aatcaggtta ggaatagcac    2580
gacgtaccat acccataaca gctgggccaa tctgagttac tgcgccagaa gtctgacctg    2640
cggcgatgtt ggtagcattg taaccgtggt caccaccgat ttcagcttct gttaagaaag    2700
aaccgaatgc ctgagcaatt ttttcgtctt tatattccgg agctgtctgg aaatctttt     2760
cctggttttc aaagattta gcgataatcg cttgttgct attagcaatt tccggtaaac     2820
cttcaccttc cagtaatggc ttccatttgt tcaaaagttc agctttagtt ttgatagtca    2880
tttgtgttaa cctttaaaat tagaaacgag atgcgacttt cgcatataca cttacaatat    2940
cttctgcacc ttgtgcagat ttatcttcta cagcttcagt gacgaaattc agtccggctg    3000
cttcagtatc aggagtattt atactctcag taatagtgct ttcatcttta ttagatttct    3060
tcaccatttc tacgattgca ctcaatttac ttgagaatgc atctgaataa tccatacctt    3120
cgaccagagc agagactttt tcttttttgag actcagtcag atctttagta ctttcgctca    3180
atgccacttc acgctgcaca taattgatat atgcgtcacg cttattgagt tcttcgaaca    3240
gacgagctga ttcttcttta tgttcttgca gttcttcttc catttcagct acaacatcaa    3300
```

FIG. 17C sequence.txt

```
ctgattcttc tggaacaaca acgttgtgtt caacgaagag ctctttcaat ccaccaagca    3360
tggattcaaa cagttcggct ttgatacctt tatctactgc taatttattt tcagtgagcc    3420
attctttgc  aagatggtca aggaatttag aagcttgctc agcgattttc ttctcagctt    3480
tttcttctgc ttcttcttta ttttttttcta cttcttcttc tgcttttttca gcaattttag   3540
cgatatgaga ttcagctaat ttaacggcgt gctgcttgac ggtagcttcg aatacagtgc    3600
cgaaagtttc ttttgcttcc ggagaaatat taactgattc gaaaatacta tcaagagcaa    3660
cggaagcatc aatttttctgc gcttcggcaa tcagttgttc tttaagcatt ttgtagtcct    3720
gttgtttaga taataatatt tataacgctt ttttcatggc ctctgcgaga gccatatagg    3780
cgtcatcggc acttgtatcg gcttccgccg tctgtgattc ggtaatttcc ttaggagtta    3840
cccatgcatc tggagcactt ggaccccata ctgcatcaac acctacagtt aatttgaatc    3900
cttcgtttac gatacgataa cctttatttg tgtcagtcaa tgaacctaat ccacgagaag    3960
aaactcctgg aatccatccg gcacgaatat tagctgctaa tttatctcca ggaccgtggt    4020
caccttcaat aacacgagct cgtccgtata cgtcatttcc tttccaccac atatcttcta    4080
taatgatagc ggcttgcatc gggtcaacat tagcgcgtgg aggatgattt aattctccga    4140
gagcttgttt agttaaaact tgctcattaa tatagtcttt taccgctttt tctaatatac    4200
gttttggata aagacgttta tttctattga cgacttccgc ttgcatgaat attccttcga    4260
tgtataaacc cggttttaaa cctaagtctt ttccatcatg agattcaagc attggtacgc    4320
catcaataat ttcgccaggt tgacccccaag tttcaattag taattggggt tcattcatta    4380
gcttaatcct aatgctttac ggcgtttaag agctttttta cgcttacgct gagcacgaga    4440
ttgacctgct ggattggcaa tcttcgtttt ggtagcttta cgagcaattt gtctacgttt    4500
tgctttagac aacccggtag tttgaaatgc attacgttcg cgggttttgc gatctttagt    4560
gcgagtaatt tcaccacggg cagaaacatg tttaacgata aattcattta acggcatatt    4620
ttcattaata gaagctaatg caaccgctaa atcagtttca tcatcaagca tattctcgac    4680
aattgtattt atatcgtctt tatttaaagc agaagacaat tcgtcaaagc gacctgtgc    4740
ttcaggaata agtgcttcga cattctcgag aactaattca tgagtttcag ggatcagaag    4800
cattattcat catcctcgtc ttcgtcagag tctttgtctt ttttgtcgtc tttatcatca    4860
ctatcttcgt cttcgtcatc atcctcgtca tcaggttctt caccttcgat taagaaatta    4920
cgagcgatag cgattttttc ttctttaatt aaatcagtcg ttcttgcagc catggcttca    4980
gcaaataatt tacgagcggc tacgaggtcg tttgatttaa tagcttcaat taaaccttcc    5040
attaaaaatc ctcttgttct tggtcggggt cttggaaacg agcctcttta gactcttctt    5100
caatttgctt ggcttcttgt tctatttctt catcagtcat ctgcaaaata tctttcatag    5160
```

FIG. 17D sequence.txt

```
cagttctgtg agaaatatat ttaccaataa atggttctgc catggttagc atattaattc    5220
ttcgttccaa aatttctgct tctttgagct cagcaaagta gctatcccga tgaaattcta    5280
tcttaatatt atttatttca tcattccact catcttctgt gattatacct ttaagcaaaa    5340
gatttgtttt aagtggatct aggaaaactt cttcaaactt gtgctgtaac tcacgaataa    5400
atttagcaaa cgttaattca tcacgtgtaa tgctagttcc agaatcaaac atcacaccgc    5460
cttgttggtc ttgtggaatg cgtgaaagag gaacacgtaa tgccatgtaa agagcttgtc    5520
taaaccaacg aatatcttcc atattgccag tattatcagc accaggaaga gtatcaactt    5580
ctgtcacagc tttaccatca cggcgctgca accaatagtc ttcggtcata gacatattat    5640
gttgttgatt ttttatttta cctgttgatg catcatatac tacacggttt ttcatcgtgt    5700
tcataacatg ttgcatgtgc tcagcagctt tacgagcagg catattacct gtgtctacat    5760
accaaacacg acggtcagga gcacgagtaa tgcgataaat gactacagca tcttctaata    5820
attttaattg gttagcaggt ttaacagcac gatgtaaata cccgatgata tttttgccac    5880
agcaatcgac taatccagaa tgggcataaa caacagcagc ttttggaatt tttatttttg    5940
tgccagcttc atacattcta ccatcacatg catatgactc atgggcagta tcatatataa    6000
aatattcttt gtaacctttta actatttttg tgccagcttc agtttctgtt ataatttcgc    6060
gaacatactg aacttggcga gggtctaatc tacgtaattc ttttatgcct tcttttggac    6120
gttttggatc aatgatttta tgaaagaaaa ttcttgaatc aacataccaa cgtctaaaat    6180
gatcagaacc ttttcgttga aacgatagat gatttaatac atcactaaat tcatctaaca    6240
tcatattttt aattttggga ctaaatttag atttatccaa atttaacgct acgacttcag    6300
tatcatcttc gtagacgata gcatctgaaa cgatttctga aactgcatta tctacttcat    6360
agttattcat gagattacga tatgtatcaa taagctcacg agtagttttc attcctggtt    6420
catatgaacc aaaaattgtt tggaatgcag cattataagg agaagcagct tcattcgagc    6480
ttacttcaaa ttctcttgct ccatcatcaa gctttggggc tgtaatggaa acaagatctt    6540
cttttttctg gtctttaaaa tttcgttcgt ccattttagc ccatggagca aacaaactta    6600
atacattaaa tttcattgta ttctccaaat gggaattata gttatattta taatggactt    6660
ctctgcttta agcaggatgg ggatttctcc ccattcattt tattcccaat aatcgagagc    6720
aagagttact tcaaaggttt ggatttcatt gtttgaatcc caatctaatt gaagttcacc    6780
cacgttagta ggccacagac ctttaatttc aatttctttt gttactgttt tagcatcacg    6840
agcatattga cgaacaatag cgctcttttt atactctgca ggttttccac cagtaatttc    6900
gtttccttga ccagcagcaa tgctttgcca atcaacaaac ttctggcgag catcatgagc    6960
ttcatcgttc attactgtaa cagtccagtc atcgaatgta cgatcgcctg ctacgttaat    7020
tttacggttc ataaatccga ctggaatttt ttctacaata ccagctggta aagcagtggc    7080
```

FIG. 17E sequence.txt

| | | | | | |
|---|---|---|---|---|---|
| tttacattgg | aatgtaaaat | tttgtccaag | ataagaaatt | tctacttgga | ataagttagg | 7140 |
| tcgagcaaaa | tcaccagatt | caaacgctcg | tgttacatca | tctacaaaca | tattagcctc | 7200 |
| tgtagtattt | atatccctat | gtttaaccta | gggcatatag | aattaaagaa | ttaaggatat | 7260 |
| agtgtattta | tatggcctgc | cgaaacaggc | ctttagaatg | caccgtatta | accagcaaga | 7320 |
| ccagttaact | catcgaaatc | tgcaccagta | gcagttgcta | cgaagttcaa | ggtaatgtag | 7380 |
| ttaatgcttc | tagccggttg | aatgtagaat | gttgcaacaa | actcatttct | atcaattact | 7440 |
| gacggagtgt | tatttgttgt | atcgcaaact | acacgatatt | cataaattcc | accgagagct | 7500 |
| ttaattccct | gtaagtattg | ggcagtttct | gtgcggaatg | atgaacgagt | aaacgcgttg | 7560 |
| tttaattcga | acaaacgata | ttttgaacta | cgtccgatat | tcgttttcaa | catattaaac | 7620 |
| agacgacgaa | cgttaatacg | atcaaatgga | gaaggaacag | aagtagctgt | tttatcacca | 7680 |
| tacaatacgt | aaccatcgcc | acctgtacca | gttactggat | taatagcttc | ttggtataaa | 7740 |
| cggtcgcgct | gagcttggcg | agtttcaata | gcaagtttaa | taacgttaag | aatctggcca | 7800 |
| cgattataac | cagctggaga | catccaagtc | tgagatacgt | tatcagttct | tgcgcataaa | 7860 |
| ccagcaatat | cagctgctaa | tggaacccaa | cgattcacat | cattatattt | gtcatactga | 7920 |
| tatttgtagt | taccatcaat | tgctgcgtag | gttgaactga | tattaaagtt | attatcagtg | 7980 |
| tatgaacctg | ctgcagttct | ccagttaact | aaattatcta | ctgcacgagt | tacaggaatt | 8040 |
| ccaactacag | tttcacgcgg | aggtgagcac | aatactaagc | aatcttgacg | agcatcacca | 8100 |
| attgaaacaa | catgtttttg | gacagtagat | gctgtttcaa | gagattcacc | ggcacaagaa | 8160 |
| cccgcaataa | acaactgaac | gtcaacagat | tcgcggtcag | caaagaagtc | ccaagcttcc | 8220 |
| atcaaatctc | ctgctgttac | ttcagcattt | gatgataatc | caccagacag | agttaaaatt | 8280 |
| ccagagaagc | cttctggcca | gttttgcgca | gttgcgaaaa | tatattctga | accacctttt | 8340 |
| gcgaaaaagt | catcaatata | gatgttacta | tcgtaaatat | cttttttcacc | acgcttagtt | 8400 |
| gaaagaacaa | cgctttgaac | aatagcatca | tttcgacgaa | ctataatagc | gtactgtgag | 8460 |
| tcagtctgcg | gcccatatcc | aaatactgcc | ttggcagtag | atgcacgagt | accaccacct | 8520 |
| ggataaattg | gcagtaatgc | agaagcgcct | ttcgcatagt | cagctttaga | tacgatttca | 8580 |
| atttcaattt | tatcgcctaa | ttcgcctgga | tagagagcta | ctactcctgg | aattccatat | 8640 |
| ttttcaagat | ttgcctgaaa | atcaactgct | gtcatagcag | tttcagcgct | ctcgatttca | 8700 |
| gctaataaaa | taccggaatc | agtaataatt | tttccaagag | ttattactgc | agctaaaccg | 8760 |
| gaagaagatg | aagaaatttc | tgcagtccag | ttagaaccta | atgttgggta | ttcgccaact | 8820 |
| tctttagctt | tagcaataat | ttttgcagta | ggaatattaa | ttttcttaat | ttttccatca | 8880 |
| gcatctactt | cggtaatttt | accttctgtt | tcaacatctt | ctgaaacata | tttgaccgtg | 8940 |

FIG. 17F

```
                                    sequence.txt
attttatctc caaccgcgta gttactacct ggggtagaaa ttgtgtattc aatattacca    9000
gcaatcggag atgagttttt agcggtatct ctatcgacag cgcgcacaac tcgcaaatca    9060
tttccatatt gtaagaaatt cattgcagac ataaaatagt cagcagtttc agctgtaggt    9120
tgaccaaaag tattaactaa atctacttcg tttgtaacct gtttaatctg aaaagcagga    9180
ccccactgga atttaccggc caaagctgct gtaccagtag agttattaac cacggtgctt    9240
tgaaccgtag tttctttgag ctcaatgccc ggagataata aagtcatttt taatcctctt    9300
taatatgctt taatatattt ataccattga cataccatga gatactggaa catactcagc    9360
agaatgaacc gaatcaacaa ataactgg agcgtattca tcccccatat cttgaagctc      9420
ttttgaaaac acttcagatg ctaatcgcat gtcatctttg tcggcataat caataaattt    9480
tgattgtgtt gataaccatc caaaaattac taaagacatt actaaatcgt catgataacc    9540
ttcttcagcc gcccaagaca cgcctttttc actaaacgtt ctaaattctt gaatagttgc    9600
acggtgatga ataataagct tatcttttc aataaggtct tttaatgtag agcatcctac     9660
tgctttcgtt cgtttagttt gcttcattcc taaatcagta tatgaatcgc aaataacgcc    9720
ttcgtattct aaatccatgt aaagtgattt cgcaactgac acaccagtac tatttaattc    9780
aatataaact gggcattcat tatattctac taaataacgc ataacgatgt caggcagaat    9840
taaatgagaa atggtatttg aatgtaaaac accaacctgt tcccacacat catcggtaac    9900
atcaataata tgtaaagcgt ggtaatcttg cccacgacct tctgaacagt ctaaagttgc    9960
aatgtatttt ctatctggtt caggtccttt aaatcgatga aaaccatgat catctggagt   10020
tacttcaatg aaatccataa cagccaattt cattcctgaa attaatgtac cagaagtccc   10080
ttcaaacgct gcggtatgtt cttgacggaa ttgtgctaaa gtagaaccat taatggtttg   10140
tatgctccat tgccatccat cgtcaaaaat atcttcatca ttataaagac gttctttaac   10200
tgaattccaa atagcagtgt atggttcaaa tcctgattta ccttcaacag cagcagtcca   10260
aatatcataa aaatgattta atccattagg agtcgtagta ataataattt ttgaacgacg   10320
accagatgaa attactggtt gaatagcaag ccaggaatca tggaagtttg gaataaatgc   10380
acattcgtca atataaatca ttgcgaatga gttaccacga actgcgtcag gagaggaagc   10440
ataagcgcca attgaagaac cattatctag ttcaatagac cctttattcc attcaactat   10500
accaggctgt aaaaagtcag gaagcagttc aattgcttgc ttagtacggt ctaaaacttc   10560
cgcagacatt gagcctttgt gcgcaagaat acctacagct ttatccttgt taaaacatac   10620
aaagtgtgca agaaaaatag ctactacagt tgttttacca agctgacgtg atagattaca   10680
aacagtcata cgtttagatg acattatttt gagcatatca cgctgatagt cacgtaattg   10740
aacctttatg acaccatagt cgatatgagt aatggcgcag tatgtttctg caaaatatac   10800
aatatcatct cggcatttt tccattcctc aaccatttca cgagtccatt gtgttttaat   10860
```

FIG. 17G sequence.txt

| | | | | | |
|---|---|---|---|---|---|
| attagctcgt | tttaagttag | gaagacccat | ataccgagat | cttttattat | tcttatcttt | 10920 |
| ataagtttga | aataattcag | gcttatcaga | attatttggg | atttttacta | ttttgtgtaa | 10980 |
| acgaagataa | tcactgaatt | tttcaggata | ccattttcca | tcccactgtg | attttatcca | 11040 |
| atgaattcca | tcttcatctt | ttctttctgc | taagcttggg | tgttttatta | aaattttttcc | 11100 |
| agcttcattt | aatggatgga | aatcatttaa | tgcattaatc | ggttgttcca | tttatcacct | 11160 |
| tctcacgagc | ttcttgagcc | tcgtaagcat | caccaatttc | gtccattaat | tctgttggtg | 11220 |
| aacccatgaa | tactgtcgcg | ttctgaatat | tcatttgacc | tgtaggaaca | gcgcctttag | 11280 |
| tgccaacctg | ctcagatgta | atatctttca | tatctttatg | aagcttcagt | atttctctgt | 11340 |
| tcgtcgtagt | catttgcccc | ataagagttg | caaatacttc | catgtgacga | ggagaatcag | 11400 |
| cattctttgc | cgtctcaaga | aaaatcttgg | ctgcgtccat | tagcatttgt | tgttgaaaat | 11460 |
| gcatatttcg | acgaactact | ccataatcat | cttctaagtc | aggagtacgg | ttttgaggat | 11520 |
| tgcttttaac | ttctactaat | tgtagaggtt | catatacttt | aatttcctcc | ccgtcgattc | 11580 |
| cggggaggtc | agaaatatct | aaaagtttgt | ttatatcaag | accttccata | ataacctcta | 11640 |
| tgttcttggg | ccaggaggtt | ctggcggtgt | tggtctattt | acattgctag | tgaaagtttg | 11700 |
| ttttactgtt | ccatcccagt | cctctgggtt | aatatctcga | ggaacaactt | cgctatcaac | 11760 |
| agattcaaaa | acaccttcgc | catcaggcaa | atctcttgta | ttggcgtgaa | aatctgtata | 11820 |
| agtagtacga | attaatcctt | ctgcatcatc | tactggagga | tacatccatc | cgtttacttc | 11880 |
| aaatgttagt | gaccattcga | ttctacgacg | agataaatta | tctccatcta | tagcttcatc | 11940 |
| tatagcagca | gacatcagta | caattttaat | atccctttta | aatggaatat | catttccaaa | 12000 |
| ctgttcgtac | atagttgtat | taaaatgagg | ttgaaaatat | ggaagaatct | gttcaactat | 12060 |
| ttgaaacata | tcgtcttcgt | aacgagtaaa | gatactcaat | tcataaatca | ttttaatagg | 12120 |
| agatggatta | tactgcgata | ctacagaagt | tgtacctttt | tgcagtaaat | tctgatttaa | 12180 |
| aatgtttgtt | ttaaatggag | cgttatagct | aaaatcaact | aaatgcaaat | ttatacgagg | 12240 |
| tagaatagtt | tcaaccttgg | ccacatcttc | ttgtgaattt | atcgatgtcc | atttattcaa | 12300 |
| tttcatcata | aagtgttcct | ttgatgcata | cgtaatagga | acacgtataa | acttatcacc | 12360 |
| agattctaac | tgacgtttga | tttggatatt | tgaaaacaaa | tcgcccatca | aggtagcata | 12420 |
| tcgtctaaaa | gacgaattat | aaaaataacc | aaacatgatt | tctcctaatc | tgggctttaa | 12480 |
| ttagtttata | atatttatta | atccatgaaa | tcattatcaa | atgggctaga | ttcaaaagat | 12540 |
| ttgcctctgt | tattgacaac | aacataaggt | tcaacatatt | ctttagcttc | agaattaatt | 12600 |
| tgatctactt | cagcatattg | atcaatatta | atatcatgaa | taccgttaag | attgcgaaca | 12660 |
| ggatttagtt | ctaattcact | aaattctgga | atgttaattc | cttcattttt | ctgtagaact | 12720 |

FIG. 17H

```
                                    sequence.txt
ggattaattt  cttctccaga  ataaatgaat  ttacctgctg  taattttacg  aatagcgttt    12780
tgacctaatt  gataaaatgg  atcatatggt  tcaacccagt  taatttcaaa  taagctgtta    12840
tccataggaa  aatatatcaa  atcgccttct  ttcggttctt  ttccattaac  ttggtgttta    12900
aacaagtttg  gattaatgga  caaagtaact  tcatcctgta  cttgcatacc  aaagttacta    12960
aagaacgatt  tagctccttc  atatccttca  aatgaattta  aatatgcagc  gaatttccaa    13020
gctttagtaa  atttattttt  taagtcttcg  ccaaatatca  aatcagggga  aacatactct    13080
cttggaacat  aatagcattc  tacacctcgc  atttgaatgc  tttcagctac  taatacatca    13140
gctaatattt  gactgttttt  ataatgattg  aaatttacat  aaggatttag  tatttcagtt    13200
tcattggtct  gagaataacc  agtgcggttt  tccaatttag  caaaaagatt  tttatcataa    13260
gtagccatat  taacctacca  aaattccaaa  tggaggatcg  agcaagtata  attcttcacg    13320
taatgcttct  ttttctaatc  gagcttcttc  tattaagcgt  tgtccatcaa  tcgtaacacc    13380
gccaggaagc  atcatacctt  ggtggcgtgc  taaaatttga  ccattcaatt  ctttagctaa    13440
agcagtagca  tagtctttca  cccaacgatt  attataagca  ccctgtttaa  catttgggtc    13500
ttgaccaaca  acacgaccaa  ctaaattgtg  gtctgggtta  ttatatcgtt  cagataatga    13560
ccagctatct  tgtggaccga  ctgttccata  tcctactgta  ttttccaacca  ttttattagt    13620
atcaatgtat  gatttagtcc  agctttctac  gataattaaa  tcatattttt  ggaagtttcc    13680
catgactttg  agctgttcat  ttgctgaatt  aaaccaaaag  tctggaatag  gagagagcat    13740
atcttgcatc  attcccatgt  aactggtaag  ctgggtaaaa  tatcctaaat  cagctccaaa    13800
ggcatttggt  ccataaaatc  tattacaaga  agtccccata  ccgccattaa  taccagccat    13860
tcctaaaaga  aaatcagtaa  accatggata  tgtagcgttt  ccgtccattg  acgttattga    13920
tccaatattt  gttcgcaaaa  tgcgagttac  tgcgaataca  tttgaacctc  ttaaatcgaa    13980
gactccagtt  ttatattttt  cttcgtcatc  tcctacataa  aatacatgaa  aacctttgtt    14040
aagtccatca  aaatggtatt  caccgtataa  ttctagggca  cgctggatac  aatcataaat    14100
ttgatcgggt  gttaactcaa  cattaataat  tggagcccct  aaacgtctta  gaatgacatc    14160
tttgagttcc  tttggattct  gagaattata  tcctgacatt  taaaatcctt  tggggccttg    14220
cggccccatg  ttatgctggt  gataaaaagg  tagaaagtag  tacccattcg  ccgtctttac    14280
gaacgtaagc  ttggccatct  tttggagctt  caggaatata  acccgcttct  tgtagagctt    14340
gaacgctgct  ctgtaaagag  gatatattgt  ctttagctgt  atttacttca  tgcgtgactg    14400
ccgcaatgtt  agtttcattc  gtttttatag  aattagttaa  tcctcgttct  tcaacagttg    14460
atccgtcagg  attatttcca  tttataagtg  aagtaagttc  aataacttga  cctttaattc    14520
ctgttctatt  atttcctatt  tcaacttgta  tattttgaac  attattgttt  aaaactgaaa    14580
cttctccttc  aagcactgaa  actttatttta  atagagatcc  agaaggagac  ggttgtcctc    14640
```

FIG. 17I sequence.txt

| | | | | | |
|---|---|---|---|---|---|
| cgctggagtc | agttccaaca | atttgattta | accacgaaac | attcgctctt | aaaccagacg | 14700
| aagtgttttc | accaacaatt | ccgtttaaag | actcaataga | agttgtgtga | tttttaattt | 14760
| ttcctttaat | actagaagga | atatcatctg | aacctataga | agtttcaata | gccgttaagc | 14820
| gctgtttaac | accttcactc | tgatttaatt | cattattaat | agattcaatg | ctactttgt | 14880
| tattattaat | ttctgttatt | atagaaacat | tttctgggta | tccaatagaa | gatttaattt | 14940
| ctgctatatc | agaatttatt | aaagtttgtt | tatcatctat | agtgtttaat | ctattataaa | 15000
| tatttggtcc | aaaatctact | ggtttattac | caagttcatc | gcgtaattta | ccaacttcaa | 15060
| ccgtcaatga | tcctacgtca | gattcagtaa | atttattttc | taattcactt | aaacgaatgc | 15120
| cttgtgaaga | taataatgta | ctatttgtta | ttattctatg | tttcattcct | gtgctagcat | 15180
| taccaacaac | aggaagaccg | ttaatgtctt | ggccagaata | ttgccctagt | tcttgtttaa | 15240
| tccacaataa | atcatttcta | attgttctat | aaacagagtt | ttcttcatca | ttaaatggac | 15300
| ctatatcagc | aataattttg | tcaactgtat | tattagttcc | agttaatata | tcagtgtgtt | 15360
| cattagtaag | tgtctttaaa | tttgatatgt | cattttatt | aacactgatc | tgcgatagtg | 15420
| cttctatatc | tcctgataca | tctaaaactc | cttgaattgt | tttaatatct | ttctgcgatg | 15480
| tttcaatggc | agttttaaga | attcctatat | tttcgtcaag | aacctcaaca | tttttaaaca | 15540
| cggaaacaat | tggtctattc | attgatccat | cgtttccata | cttagtgcta | gctcctagta | 15600
| tttcttcacc | atttttaatc | catgaaatac | gttcctgacc | ttcatcagga | acgctatcaa | 15660
| caaaaggtaa | atctttaat | tcaatcattt | gtaatcctta | gtaatgaact | ttaataatat | 15720
| agtttaatga | tatattccat | ggtctagttt | cataaccaat | taatccttca | cgattaagtg | 15780
| taccaagggc | atctctcggt | ccgcctaatt | caaatccatc | attagtgaag | tatgaagcat | 15840
| tatcccagtc | ggcatatttt | ctagttccaa | gatatccttg | ataaacagac | gcgccaaatg | 15900
| ggccttcact | tctgttatat | tcccccaac | caccggcgtg | tttatggtat | gacatttgtt | 15960
| gtgcttgaac | accaccaaca | tgcattccgt | cacatcctac | gccaagtcta | tcctttccat | 16020
| aaccatcttg | tcctcgttga | tttaaaatat | gaccgcctgt | gccagctcct | ctgacgaaaa | 16080
| gacccgcat | atcaggaacg | ccaggattat | tccaatcgcc | accaaatctt | gttccaacta | 16140
| cgtttctata | atcaggaaat | tggtcacctg | acacggttcc | accatgacac | ataatccaac | 16200
| ctggaggtgc | tgaatcaccc | gcaaacatca | taatagttcc | aaccggaact | cgttcggacg | 16260
| catatctttc | agtggcaaca | ggttgatcgc | cattttcca | cattccaccg | cgtgaccaaa | 16320
| ttccatttgc | tgtaagatgg | tctaaattta | agaaccatt | aatagtttgt | ccaccacgcg | 16380
| tattaattac | atctgcgttc | cacgctaatg | ctccagaact | atcaccttca | ggggcaatac | 16440
| cggcttgcgt | cgttaattta | actactccac | gcatagaacc | agtagctcct | cgaccattta | 16500

FIG. 17J

```
                              sequence.txt
gtgtttcacc tgttactgca acatctccta aattactgtt aatttccgat tgtgttccta    16560
aacgtataac acccttatat tcttgtgttg caacagaatt cataaaggta tacggagaaa    16620
ttgcatatcc ttcgcggaga gttccttgac gagtttgcgc aacagttgat aattgaacca    16680
cacctctcac agattctgat gcagtatctt cggaaggagc tatttgtgaa attaatttta    16740
ttgcgagttt tgggttttt agcggagtca tcgccgtagt atcatcaaca ccagccaaag     16800
ccgcaggcgt agatgatatt ttaataaccc cgtttgatga ctcagatgaa tatctatttc    16860
ggaacacatc atcagtatgg tatttcagtt tttgcggcgt tattgatgaa ttattatctg    16920
agccttctaa tgtttcttca tttgttgaat agcgcgttaa accatattta gtttcagtag    16980
catttggata caataatctt gttgctaatg tagctggtgt aacgattta gaattatttg     17040
ttccatctaa aacctcttgc tctgatgcaa tcattgctat tcctttaact tccatagttg    17100
catcaggaat accatttacg ccgatattac ttatttttga taatgcagac tgtactgtcg    17160
taacagtgcc aggaaaattc gatcctactg gatcgaattt aacatatttt gattcatttg    17220
atacgtgctg atatgtattg ttactcatgc tattctctca aaataataaa atactgtagg    17280
ttgtgtgtga ctatctagcg taacagtttg cgcacctaat aattgccaag ttccataccc    17340
gggtttagaa ggagaaatta tttcttgttt gaaagtaatt cctttatcag agtattgttc    17400
taagatatgt tcttggttat ctaaatactt aacttgtatt ttattcccta tggtaggatg    17460
gtcttcaaat gaatcaattg caataaattt tacaaccatt tcctgtagag ctgttctaac    17520
agcactagta aattcaattg aagtcattcc attagtagct ttaactggaa taccaaacat    17580
gttaacaata actgggtcac ctggtttggc tgaagtatca gtaacagttc cttcaaatga    17640
ccaatagtcg gtttgttgca cgccagtagg agatacgccg cttatattaa ttaatacagc    17700
tccaacctgt tgctctgcca tatttctaac atcattgata gcagattcta catttgagtc    17760
ataaaaacct tttgctattt gtgaaattgt tacagcgcct accggctgat tattcataac    17820
cgaaatatca ttttcttag ttctaaaacc aagaaaatct gctaagcggg aaataactcc     17880
cgctttatta ttaagtaaac tcattatgca atccttatcc aacggtatac agtaatagac    17940
ggttgaatat tactaatatt agtaggagga gtatgtgaag agtttgttgt tgcgtagtct    18000
tcacgatatt ttgtatatat aggaccagtt tcgtctgggt catattgaca tcctccaata    18060
ataactgatc cattttcgtc ttcaattaaa actctttcat cagttttagt cgcaggaaga    18120
tttgcgtttt caagcgttac tgatgttgta ccaactgttc caccggcagt atgtgaagga    18180
tttccgctag aatctaaatc attattgttt aaagcaaagt ttggatccgt aacatcatca    18240
ttccatccta ctaaaacttg tcctttacca aataatttcc atgaaccaaa tcccatataa    18300
gtcaccggat tatttggggtt tatagcattt tcataaattg aaccaacagg ataaatgctg   18360
tcgaaaatag atgatattga attatacgtt ctagtataag aatcaacttt ttcaacattt    18420
```

FIG. 17K sequence.txt

```
ggccaaccga ttttatcaaa atctgttaag gctacatccc cagtaacttc agtagatgat    18480
cctttactaa cataacggtc atcagttaat tcaataatgt catcttttc taaaagagtt     18540
cctaaatcat tattaaacca tgttataacg attatatcac ctgattcaaa ttttctatca    18600
aataaaagac tgacaggttt tccatcttca tattctatag aataatctgt gtttgattct    18660
ttccattcgc caccaagaga tatacatcct tcttgcgtat ctgaattagc gccttcgcac    18720
aaaaacagag gatacccagc tgttccagcc tgttgctgta aaattccatt aaaacgaacc    18780
tcaagagaat taggattaat gggttcgcca ggaattaatc caaaagctga aaatggaatt    18840
gatttcatcg ccgataaatc agtaacataa atgcttcctt ctaaagaagt ctttgatgtt    18900
agttttgaat ctagcacttt tatttggcgt cttgtatatg aacttctcca ttgtgataca    18960
ccatccataa acgtttcaat ttgaacagtg tcgccaatat tacaaggctg tcttaaccta    19020
atattaaatc catcaagagg aattaattct ccttcatttt cccccggaga gccaaagtca    19080
ctgttttcac taaatacatc gccgtaatat aattcgttac cgcggtgttt tactctgatg    19140
ttattgacat tataactagt tccatggaaa acatctaaaa agtcagtttg tccttgaact    19200
tctactaaaa attctttgcg agctacatta ctaatatctg aactaataat tttatcaatt    19260
tgtttgtttt tgacatattc ccaacgtcct ggagcacaat aaactaactc taaatcgcta    19320
aattgaacat taatttcaac tgatgacgat gatcctttaa tagtatcacc agaagcggct    19380
actagagtaa ctggattaac attccatgtt gcaaatacat ccctagcttt aattacttta    19440
ttataatcat taacggttcc tttaggaagt tgtagagtta ctcttccaga tgaagtgtta    19500
atagcatatg attttcccca ttctgctgtt aatgtttgtc ctgatgaagc attataagtt    19560
ttccaggcac cggctgaata tggaacatct ccatcaccaa gctcgtaata aagctcatca    19620
aagttttcat ttattttat accacctta cgcaggtagt caccggtacc atcatctaca     19680
acattaccga tattaatatt ttgtttcatt attgagccac cccgattttc tgcgtagcga    19740
taactttaac tgctgctctc ataccgacag ttgaagaact tatagtcgct gttacataat    19800
ttgttttaat actaaatgca atattagcga tttcgtcttc ttcagtttca ttcccaactc    19860
gcatgacagc atattcagaa gaaatgactt ctgaattaac agcatctaca agaatattta    19920
tttctgccgt tttaattttt cttccatcta ccgattggca cgtaactaac aatttagcca    19980
tattgtattc agtgcgatga aatagtggaa tatcaactga tccggatgta gaaatattcc    20040
atgtaccttc agctggtgat tccttttgtc caaacatact ttcaatagaa taattccaaa    20100
ccgatgtaga attatcagat gaaatacagc gtaaagttac tttactatat gggctagtta    20160
ctactaaatt acctgaaaca cctttaattg aatcaatagc ttgaattgtt aaaggattag    20220
taactgatat tgatccatta gagttaatga attcaacaca atcgccgagt tcgcctcttt    20280
```

FIG. 17L

```
                              sequence.txt
caataataac tttaacacct acagtagagg tatcaatatc atgtctagtg ccaactttca      20340
ctggagttgc gtactctgta atagagtgtt tttgataata cccagtagca tggataattt      20400
gaccatctgc tccagtgcca tttgctactg ccattttacg ctgatcgcca aacgcattat      20460
aaattgcgtt aaaatcacta ttaattttat taccaccgtc gaataagata tcaccagtag      20520
aagcgttacc aatttcgccg gtatcaatca atttctttgg ttcttgaatg aacatagcgg      20580
tttccttatg agtttatagt atttataaag aaaaagggag cccatgggct cccttaattt      20640
aaaatgtaaa cagaatattg atttcttctg tttgatccat tgccataata ataggtggcc      20700
tattttccat ataaatcatt tcgcccgaat gcctcattaa atcttctggg tcataataat      20760
ccttttcagc tttaacgttt gggtcatttg gatgagcttt agcttcaaga ggattcgtga      20820
ttattgatat ttgtctaaat cctttatttc ctggcaatgc agcatcagga aaataaactg      20880
aatctaaata tgctttaaaa cggatagtat ttgccttaac ccggtaaatt aatccaaaat      20940
catcttgttg ccaagtgaga ttatcttcat atccccatct agtcgggtct tctttaatt      21000
cctcaggcca aggaaccaca atatattcat tcgtgcatct atttatagat acatcgggtg      21060
gaatctcaaa aagatattcc catacatacc cgtccccagg ttcaattgtt ccttcagcat      21120
ctcctcgacc ttcaggagga gtcattgacc taacagaagg tgtccatttt ccgcctaatt      21180
taaggcattc atccttatca gttaaagatg caattgaaca cattccagta tcaggaacat      21240
ctaaacaacg atatactaac cagcctgcgc ctgattcagt agcgttgtaa ggagctgagt      21300
tacacactac aatatcgtta attctaaatg tgtatggatc cggatatcta gtatctcccc      21360
aatctcgacg aggaataact gcgtcaagca ttgatggaag aacctttact gttcccatca      21420
tatgcgtcca catgtcagtt acgcctaata cagaatcggt tggataaggt ggggcaaagc      21480
ccacctcatt ttcatttgat gaccacggtt ctgatcttcc aaatgtgata aagatagtgt      21540
ttttatccgg accacttcca attgaattat aaaaattcaa catttttct gttctaaatt      21600
ttgaagtaac tatcgcacga tagataacac ttgaatcatt catctatttt aacctgtgtt      21660
ggattttcag ggtctcttgg atttcctata ttatctttta gacgttatt aactaaatct      21720
ctaaattgcg caaatgttgt tccagatgca tcaaataaag gactcattaa tttacgtcgt      21780
tcagacggca attgaccttg aaatattgaa ttattatttt cagcattata gtcatcagga      21840
agaggatatt ctacaccagc cattgggcca ggctcataaa ttgcttcgcc tgttactgaa      21900
tcatgctcaa tttcaccggt tggagttaat ttagctactc tatcagcata ttcagtaggc      21960
aatccagaat cccatttata gttttatat ttattaatta ttgtctctgt gtgtttaaga      22020
gttaaaccaa cattaataaa catcgttaaa agggtaattg ctataaatcc aaatcctact      22080
ggatgaacaa aacgaataac gtcagatttc cagcgggaag aaggtaaatt ggatttaatt      22140
ttcattacat agtatgatct acttctatta atatagtcta tattgttttg aagcaaatcc      22200
```

FIG. 17M sequence.txt

| | | | | | |
|---|---|---|---|---|---|
| tttcctttaa | ctccacgaat | aatttcgcct | tcaaaactag | ggagtctttc | tgctttaact | 22260 |
| tcttgaccag | caattaatct | tcccaaaaga | ttatgaatag | ttacggtcca | ttgcaattta | 22320 |
| ccattagaat | aacttctttc | tatataagta | acattacatc | ttcctgttgc | cgtataaatc | 22380 |
| gtttgtccta | ctaaatcttc | agtcaaagaa | tcagattgaa | cgattatgtc | atattcagta | 22440 |
| ccggccccag | attcaatttc | aatttcaact | tcttcattat | aaagaacttt | aaaaagaaac | 22500 |
| ttgtatgatg | cttcaattcc | tttagtagaa | taaaaatcat | agctacgtga | ttcaaagaat | 22560 |
| ctcgcaacag | catcacgttt | atcagcattt | aaataaatgt | ttctttata | tatctctgac | 22620 |
| cacaaatatt | cccacgcatg | ctcttctcgt | ggatattggt | tacgaattaa | atttcgtaaa | 22680 |
| ttgttatact | gagttccata | tccatcagaa | agatactgaa | tatatgcttc | gcaaaatgcc | 22740 |
| tcaaaattcg | aatcctgcaa | caaataagaa | tcaggcatca | ttgtgccaat | taatggtctt | 22800 |
| aaatcaggat | cagctaatcc | atgctcttct | tctggtgacc | aaggagtctc | atgctcttgg | 22860 |
| ttttgtaaaa | atgcttttaa | aaatactcca | gtcggcttcc | aaataatttc | tactgtatct | 22920 |
| ctcacacgat | agttaaaatc | atagtaagaa | attatttcac | cagaagattt | ataaaaaagc | 22980 |
| atcccagacg | catatttttt | aaatcccgtg | aatttaacat | ttggcattac | tatcgtacaa | 23040 |
| tcaccatcat | cccagtattc | atgaactaat | ctatctggtg | atgtttccgg | aatattttct | 23100 |
| ataactttag | tgtattttaa | atcagcataa | actactacag | ctctattaga | gttgtttatc | 23160 |
| caacagcgtg | tgttagattt | tttagaccaa | ttaaagaacg | gttctgcgta | gtatttcatt | 23220 |
| ggttgaggag | taaaagtctc | ccaatcagat | ttttcatccg | ctataaatgc | catcatatga | 23280 |
| taatgcttat | cagctaacca | ttcacgggga | aattcatatt | taacagcacc | gattaactga | 23340 |
| tatttcacca | tagtttcagg | gtcattaaca | acattatcac | ttaaaaattt | aaaattactc | 23400 |
| gaagacagag | aaactaattt | accgtcagtt | gacatgtttg | cgtatccagg | ttgaatacgt | 23460 |
| cttcttcttt | cttcggtatt | accgaaaact | cttttccatg | tttttcgtc | atgatttaaa | 23520 |
| acatatattc | ctttatcagc | agaatcaatt | attttgaag | ttctcggatt | ggcatttaat | 23580 |
| gtttcaactt | caccaataat | aagagcaaaa | actttatcac | cgatagaatc | catttatag | 23640 |
| catactgctt | taggatttcc | agttatagtc | attgtatcag | gttcaaaaag | tctttccgag | 23700 |
| tatgttggtg | ataacgggtc | agaatctata | ggtgcattac | tcgttttat | atatctaact | 23760 |
| ttatctctgg | caacaacata | gatataatca | tccgtacaag | taatggcttc | agctatacga | 23820 |
| tatacattcg | ctggtaaagt | cgcataagta | ccaaagattt | ctacatcaaa | tcctaaatgt | 23880 |
| aactggtcgc | caagtttagc | aaatgttata | tcctgcgaac | tgaatctgac | atcatctgct | 23940 |
| gaccatctaa | cgtcagtcga | tttacggcca | tagaaaatct | tgtcgtatcc | tagaacgtat | 24000 |
| gttgtgttcg | cagattggta | atatactgtc | ttagataaag | gatatcctac | acggtcattg | 24060 |

FIG. 17N

```
                              sequence.txt
aagagcttca cagcttttcca ggtttgtcct ttatcattag atactttaac cacgggttga    24120
taacgctcaa aaagatatag aatcccttct gattccatca aataaactcg gttaatatcc    24180
ttacatactt gctgaatgga accttgtatt tcatgatact cattttcacc aataataaaa    24240
ttactgattg atgaaacatc aacatatgat gggctgaatt ggaacgattc attcatcaat    24300
gcagccatta tagtgtcatt attaaaattg acataattag aattgttaag agtaaatttt    24360
tcctgaatga atttattggc taattgcatt tcaatcatgt tttgaaatgt gtaagcattc    24420
gtagcaaaag tttcaaactc ttccgtataa acccaatcag attgctcaaa atcttgtgca    24480
gctgtagcta ctctaatgat gtatgatgtt agtggatcag catcatcaaa aaagaaacta    24540
ttgtttgctg tatatcctaa attaatccaa cgatattgat cactcgggag attttccccc    24600
gagtctgttt ttgtctcagc gatttctaca aaatagtaga aattagcacc aacgtcatcc    24660
cagcgtactt gcacctgatt tgcggataac ttggaaattc tgagactagt gactgaaggt    24720
gcttttactg tcattgtgat ataggctcca aatcgatagt taagtattgc ggacgtaaat    24780
cattttcaaa tacaatcagt gaaccatcac gggtaaagat aacatcatcg gttgggtcag    24840
aatataattc aatagtctga acctcaaatt tttcagatgt taaattaatt ttagcgatat    24900
tccaataaat catgtcagcc ggataattta tttcaccgat aacatagtat ttgtcgcgtc    24960
catcagaatt tgctaattta ttaaaatcat tgcctgtata tggctgaatg ttttcatttt    25020
ctgtaacatc gccagaagca aatggaccaa taataacttt accaattcct ttagaatctc    25080
ggtctgttga tactatacga acatcatata atacatcttc ttctaaacca gtatcaggat    25140
ttacaaccTt tcgtccagaa ttaaatgaaa acgtattaga ttccatagaa cgatctttta    25200
tttgattatt gtatttaata cctgcttcag gtgttttata gaagttttgt acttcacgaa    25260
ccatttgaat agtcgctgat gaaccaatga cagaatgatc tgcatcatct acataagtta    25320
acatcttaga tttagcgaaa gacgagttaa aaatttctac atcttcggta taatagcgat    25380
caattttatc aattatttga ccttcaagcc actgctcgga ttcttgtagt ttatttaaag    25440
catatgtgac ttttaaatta gtcttaataa aaagataatt aggagaaata attgatggcg    25500
taataggagc taaattatag tctttgagat aattttaaat atcttcacgc tgtacagtag    25560
ttaaatacag acctgattta ggtttagcag caataaatgc atacccaggt ttagtagaat    25620
cagtgaaagt ctgaactgcc tgaataatag aaccaaatct ctctgaaacg aatgtatcgt    25680
agtcagtcgc agttacgcat cgttgctggg tttcgcgttt aatagtaccc aattcgcgaa    25740
tacgctcaat atcttctgga tcaccgcctc catctgcccc aacaaaatct gggtcaccgt    25800
ttggattttc attaatattg atgatagtta tatttgttaa tgtatctgcg tatgaaaatc    25860
cgactgctcc gttcgcgtca gcaccattag tactaatgta ctcaataaca atcgtagagt    25920
tctgagtagg tttgagacct ccgatataat tagcggtcaa agctccttca gaagcattaa    25980
```

FIG. 170 sequence.txt

```
cagaaatttc accttcacca aaatagaatt cagtgtttcc atcaatagtt tcacgcatgt    26040
agtaaattgt tgatgtagaa ccagcatgaa ccattgactt tcttgtccag ttaatccatt    26100
ccgctccatc aacgtataat ttaacctggt ttctatcaat attttatca taaatgataa    26160
taggtgtcaa tttatcataa atgatttcag ttcttactat acgtccttgg gccaatttta    26220
atcgtggaaa atattggtta ttttatcac gaatagcaat aacatcttcg gtagatacaa    26280
agttatatgg attaacagaa gtatcttttg catatgctaa aaagcgagtt ccgcgaggaa    26340
ttgtaatgta attcctattc aatgcgtcgg tgcatgttaa cataatttcg gtctgcgcag    26400
cggattttga agtaggtaaa tatccgttat cttgtgcagc ttgaacaact gaacttcgta    26460
agttagcagt acgcataaag ctttcataca cagcagcatt accaaactgc tgaatgtaca    26520
atgtattata agccaaaagg tcacacagaa cgtttaatct tgagccttca aaatcataat    26580
ccaaaaattc attttggcca ttaagccatt caatgaggtt ttgttttatt tcagcaaacg    26640
tacccccgac gaatatctcg ggaatagcat ttgctgttct tgttaattga taatttacag    26700
gggtatttgc cattttaaat cctatttaat gaatacttta gatgatgcct gagccacagt    26760
atcaccgcat gatattggat cagccatttg aacagctttc tttccagtga catataccct    26820
agaagttctg ggttgtgtca ctccgccatg tgtttcatat ggcttttta tttctgtatg    26880
ttctgtaatt ggatcacctg ctacgagaac agcaattcct ccagtgaata ctttactttg    26940
tgtggcattc acaactgttg gaggccatgc ttcatggcca gcagtaacac acttatcata    27000
acttaatcct gacatctatg acctctcata cacatagctt cttaatttat tagcccaacg    27060
actccaattt ccaactatag tttttgtgta attttaact agagttttttc ttactggagc    27120
aggaggatcc gtcggttcag tagtatcaga ggatgaccta gaattactgc cagaacctcc    27180
agattcactt tgttcttggt agtcatatat taatgttact tcgtaagtga atgtcttctg    27240
gaggttttga ggagcttttcc ataaatacaa ctgagtatca gaatcagtag gaagttcttc    27300
ccatgaagca gcagttttaa attcatcgcc taaacgatat ttcaacgcgt catttccaaa    27360
tccaaacaca gattcatatg ttccgtataa gcgattttct tctactaaaa ccccaggagt    27420
ttcttcgtaa ctagttatat ttatagatac taacgtttca cctgtttcta attgagcggt    27480
aaaggtgacg tcgatagaag aaccttccat ggattctcct aaatcagcgc tcattggaag    27540
tatattagcc aatgtcaatc ctcgatccat caattgtgta ttgaccagat gaaatagaac    27600
tcatagatgc cattttttct gtccaatcac caccaacgtc ccaatcaact gtcccagcaa    27660
ctttccaaga aagatttcca tttactgtgt tagtttgatt tccttcaact aaagtggtag    27720
catctccttt aactgtaatg tcagcattac cttcaactac aatagtaaca ttacctttaa    27780
ctaggatagt tccattgcct tcaactgtct tagtttcatc gccacgtaca aatattgtat    27840
```

FIG. 17P sequence.txt

```
tgcttccatc tatttggtga agacgattat ccatgttgta ataaatttct gatccaccga    27900
cgttagtctt tttatcaccg gctaccaaaa aattaccatc agcgttggtt atatcataca    27960
aattatcgac agttttcttt gttcttcttc ctgacggtga tacttcttca taagttccag    28020
tcggatgaac taatctgtat cgttcttgcc caggagtatc atcaaattcc tgaatatgtc    28080
cgctttcagt ttccattgta tgcacataag gatattcacc tttatatgaa gaaactggtt    28140
ctttgaataa aattctcgag tcatttggaa taggagggtc agccgggtca gaagatttag    28200
ctacagtagc agccattgct gatagagacc tagctggggt tttcacttca acaccatatg    28260
attccaaatt ccccgtaaga ataatcatgg taacacggga tgcacggcct tttgtttgtt    28320
gataccacaa tgaatcacga ccggctttat atgcttttcc ccaatctccg gctaacatag    28380
cagttaacat tgtgttaaat ttagctacac cgccaacacc catttgaaat gccatatttt    28440
ctaacgccat ttgacgagaa cggttgacag cttgccagac tggtcctact ttagaatgtg    28500
atttaatgtc ccgttgcata tcagccaaat cacgttcaaa taaagtcgtc gcctcttcca    28560
tcgtaataga acctgggttt ccagtaattt cacgaccaac ttgttttgat aaaactttat    28620
taatttgagc catatcacga actggctgct tcatgataag atgaccaata ccaattgtcg    28680
gatatccttc agtatcccaa taaacttta gtcttaatcc ttcatcacgg cgaagcatgt    28740
cagccattga catatttgga ttatcatcgg ttggaatctc tgatagtggt ctatcatcgg    28800
gatttattgc agtgtctaag ttactatctt ggataatgtt agaagacgaa tcatatccta    28860
cttctccgcc ttggtttaat acattagtat catttcctaa acgtctagga tattgcccag    28920
ttgggtcaga aaatccttca agtctattcg gttttcgcg aactattcca ccatacgtgc    28980
caaggacaat tccgttagtt ttccatttgt ctaaaaaatg accataaact ctagttcctt    29040
ctaccggtcc agtaacagaa cctccaattc cagacattgc tgcagaagtt ataggttgaa    29100
taactgacat ccatggtaat ttttcagttg gaatacccat tacatcgcct tgtgctcttt    29160
gaggtggatg cagaccaacc acacgaacac gaacacgacc taattttaat gggtccattc    29220
tatcttcaac aacaccaaca aaccaattaa ggttattact tatcatttcc ataagatttc    29280
tccattatac gtataaggtc gttcataaat gaattaatgt ctgattttgc tattatttt    29340
atttgacgaa gtttttcatt ttcaagaaca gcatcttcat acgtattaac agcagcaagt    29400
gctccttcat attgaggata ttttctagct ttatcacctt tatcatacca aacatatgga    29460
ttatcatcgt atgatattaa attataaaat ttttcaccgt tctcattcac atgatatact    29520
atttggtctc cacctacatt tttgtatttt tgtatagatg cttgataagc tgcttcttgt    29580
gaagtaatcc atccataata cgggtcataa ttatcattac acatcaataa aacccaatac    29640
aactgtggat ttccatatat agtatttgct aattcttccg ggcgtggtga acctttgata    29700
taataagtac gtaagcggta tcccgcaaga gcgcgtttaa aatagtcttt atagtttcta    29760
```

FIG. 17Q sequence.txt

| | | | | | | |
|---|---|---|---|---|---|---|
| aaaatatctg | tcataggaat | agtcggcgcg | tttttattca | ccgttttggc | cgcatattca | 29820 |
| atcggatcaa | aaaatgtaaa | gagcatgggc | cctcctgttt | ataaatatat | tatctattta | 29880 |
| taaggagaat | ccaatggcat | attctggaaa | atgggttcct | aaaaatatat | caaagtatag | 29940 |
| aggtgaccct | aaaaaaatta | cgtatagatc | aaattgggaa | aaattctttt | ttgaatggtt | 30000 |
| agataaaaat | ccagaaatta | ttgcatgggg | tagtgaaaca | gcagtaattc | cttatttttg | 30060 |
| taatgcagaa | gggaaaaaac | gtagatactt | catggatatt | tggatgaaag | attcttctgg | 30120 |
| acaagaattt | tttattgaaa | taaaacctaa | aaaagaaaca | caaccaccag | ttaaaccagc | 30180 |
| acatctaaca | actgcagcga | agaaaagatt | tatgaatgaa | atttatacat | attccgttaa | 30240 |
| tactgacaaa | tggaaagcag | ctcaagcttt | agctgaaaag | cgtggaataa | aatttagaat | 30300 |
| tttaacagaa | gatggattac | gagctcttgg | ctttaagggg | gcataatggc | tatttttcaa | 30360 |
| ataattaatg | aaagcactcc | ccaagttcca | aaggttaagc | aatcattaaa | cgaaaagaaa | 30420 |
| tggattcaga | taggtcttga | atataaaaag | gccaaagcaa | aaggaatgac | cggaaagcaa | 30480 |
| tttgctgaag | aaagaggaat | caaatactct | acgtttactt | cagcaatgtc | aaaatatgct | 30540 |
| tcaggaatta | aaacggctga | aaagattcaa | aagcttgaat | caaaaccaat | gaataaactc | 30600 |
| aataagcaag | aaagacaact | gcttatgata | aattcattca | gacaaacatt | gcgcgataaa | 30660 |
| attcgtaatg | aaggcgcagc | aattaataat | aaaaccagaa | agtggtttgc | tgaaactatt | 30720 |
| aagcaagtaa | aaggacataa | agttgttcgc | ccgcagccgg | gacgaatata | tgcttttgct | 30780 |
| tatgatgcta | aacacaagga | aactcttcct | tactgggata | aatttccttt | gataatttac | 30840 |
| cttggtttag | gtaagcataa | tttaatgtac | ggattgaact | tgcactatat | tccacctaaa | 30900 |
| gctcgtcaac | agtttctaga | agagctttta | aagcaatatg | caaatacacc | tactattact | 30960 |
| aataaaacga | aattaaaaat | tgattggagt | caagtgaaag | gatttagggg | tgcagaccaa | 31020 |
| atgattaagg | catatatacc | tggtaatatt | atgggtagcc | ttgttgaaat | cgccccgaaa | 31080 |
| gactgggcga | acgttgtgtt | aatgccactt | cagcagttcg | tttcaaaagg | aaaacgtttc | 31140 |
| tctgcaaaca | aagtctggtc | aaatatctaa | ttctattatc | ttccattctt | ttctgttgtt | 31200 |
| tgttctaaat | ggaattgaat | ggaagggact | tagacccatt | ataccaccaa | cagttataaa | 31260 |
| gcattatgag | gaatatatgt | cgcaagcact | gcaacaaatt | tttaaccaag | caaatacaac | 31320 |
| taactttgta | gtatcaatac | cacatagtaa | tactacatct | gcttttactt | taaatgctca | 31380 |
| gtcagttcct | attccaggaa | ttagaatacc | tgttactgat | accgtgactg | ggccgtttgg | 31440 |
| actgggccga | gcacaacgtc | caggtgctac | atttgagtac | gatccactca | tcgtgagatt | 31500 |
| tatagttgat | gaagaactta | agtcatggat | aggaatgtat | gaatggatgc | taggaactag | 31560 |
| caactatctt | acaggtgaaa | atactgccca | aaaaacaggt | cctgaataca | ttacgcttta | 31620 |

FIG. 17R

```
                              sequence.txt
cattttagat aatagcaaaa ctgaaatcgt gatgtcaata aatttttata agccttgggt      31680
ttctgacctg tctgaagtag aatttagcta cacagaagat tcagacccgg ctttagtatg      31740
tacagcaacg attccttata cgtattttca agtagaaaaa gatggaaaaa ttatagcgga      31800
agtttaatgc ttcagtttca tgtgttataa tcttaactaa atttgaggag aaacatatga      31860
aactaatctt tttaagcggt gtaaagcgta gtggaaaaga tactactgct gattttatca      31920
tgagcaatta ttctgcagtt aaataccaac ttgctggtcc tattaaggat gcattggctt      31980
atgcatgggg agtatttgca gcaaataccg actatccttg cttaactcgt aaagagtttg      32040
aaggaattga ctatgatcgt gagactaatt taaatctaac taaattagaa gtaatcacga      32100
ttatggaaca agcattttgc tatcttaatg gtaaaagccc aattaaaggt gtgtttgttt      32160
ttgatgacga aggacaagaa tcagttaatt ccgtagcatt taacaagatt attgacgtta      32220
taaataatat tgaagatcaa tggtcagtcc gtcgtctgat gcaagcccta ggtacggatt      32280
tgattgttaa taacttcgac cgcatgtact gggtaaaatt atttgcttta gattatcttg      32340
ataaatttaa ctcaggttat gattattata tcgttcctga tacccgtcaa gatcatgaaa      32400
tggatgcggc tagggcgatg ggtgctacag taattcatgt agttcgtcct ggtcaaaaat      32460
ccaatgatac acatattaca gaagctggat tgccaattcg tgatggcgat ttagtaatta      32520
caaacgatgg ttctcttgaa gaactttttt ctaaaattaa aaatacacta aaggtactat      32580
aatgtctgaa caaactattg aacaaaaact gtctgctgaa atcgtaactc tgaaatctcg      32640
tattcttgat acgcaggacc aagcggctcg tctgatggaa gaatccaaaa ttctgcaagg      32700
aactttggct gaaattgctc atgcagtagg tatcactggc gatactatta agttgaaga      32760
aatcgttgaa gctgtcaaga atcttactgc tgaatctgca gatgaagaat gatggaattt      32820
aaagactttt caacgggtct ttatgtagca gctaagtttt cagaattaac acttgacgcg      32880
ctggaagaac tccagcgctc tttacgtgtt cctaatccag ttcctagaga aaaaattcat      32940
tcgactatat gttattcaag agtaaatgtt ccatatgttc catcgagtgg aagttttgaa      33000
gtagcttctt ctggacattt agaagtgtgg aaaacacaag atggatcgac tcttgtactt      33060
gtgctagatt ctgaatatct gcgctgtcga cacatgtatg cgcgggcact aggtgctaca      33120
cacgattttg atgattacac accgcatata acattgtctt ataatgttgg gcccttatca      33180
tttagcggtg atgtacaaat tccggttgta cttgaccgtg aatacaaaga gcctcttaaa      33240
ctcgattggg cagatgattt aaaataattt cacaaagttg tttacatact gatgaggtag      33300
tgatactatt acctcatcaa aattaattag gaaaataaaa atgaaaactt tcaaagagtt      33360
tgctacaaaa actactatca ctgaatcttc ccacggtatg gaagtaaagc ttggaatggc      33420
tttagctgaa gctgagcgtc ttttctctcg tattaaagaa cttgctgctg cggtcgatcc      33480
ttcatctttt aaaggagacc aaactaaagt taaagcactt ttagcattat gctccgatgc      33540
```

FIG. 17S sequence.txt

```
aggagaaatt gctaaaaatg gttctaagat gaagaaacga ttagaagatt taaaataatt    33600
tcacaaagtt gtttacatag ggttttagtt gtgatactat taccctatca aaacaaaacc    33660
aaatggaaat caaaatgaaa acttaccaag aatttattgc tgaaactgct gatgtaaaag    33720
ttgagtttat ttacactggc aagaaagata aaatgggtga aatgcctcat ggagttcttc    33780
gtgatgcatt agataatttc ggtcaactcg ccgcagaaga ttacggtgat aaaattgttg    33840
ttactggtcc tgctgcagtt attgaaaaat gggcagcaga aaataaatca attttcgta    33900
aaaaataagt ttacttttag atagggtagt gatactatta ccctatctac tactgaggag    33960
aataaaatga aacgttgtga attaattcga aatgttgcta ttgcaatttc tgcttccgct    34020
ttcagttttt caatgtttgt tggatttata tgcggattat tgactacggc agaaaatgtt    34080
ttttcacttg tagtagcatt tttaattggt ttaattgcta ttgttatgga taaaatttct    34140
aaaggtgaat aatgaacgtt gaatattatg tatatgcgga ttacgaaaat aatccgtcta    34200
aagatgaaga taatcgttta ggtgtagatg cttcgattc ccctgcggcg gcatggcaat    34260
gggttgaaag aaccgatatt ccttaccgtt atattgaagt ggttgaccac gcaggaaaca    34320
agtatcctaa ggaagcatat gttgcttccg ggaaggtaaa tttccttttg tttgcaggtg    34380
ataattatta tccccgtggt gggtataccg atttaattgc taaagcattc tctgaagatg    34440
aactccgtga cattatcaaa gaaaatgaaa acaaaccgat ggattctaat cgctttgatt    34500
ggtggcaaat cgtaaatgct aatactcaca ctattgttga tgaaggctga taatgattct    34560
ttatgcgaaa gtatcatcca ttgaaaatgg atataaatat gatcaagacg cggctaaagc    34620
tttgattgat gattatggca ttttaacatg ttttgaagtt gaaaaggttt acattgaccg    34680
ttcatcttct caagttaaat tagtgaagga agaacgtaaa tttaatacag taaattttga    34740
tttctttatt gaaacagaaa aaggtcctct tgaatatgat attttcaaga atcctttggg    34800
tcttgaatgc atcgtaaata tgtattatta taaatggtaa atatgcttta agaattattt    34860
gttattatta actcatatcg cactgattaa taccctctat catcaagggt tcttgcttaa    34920
gagccttttgt taataattgg gaattagcca agttggtaag gcactggatt ttgattccag    34980
gatgcaaagg ttcgagtcct ttattcccag cgcgagaatg gccaaattgg taaaggcaca    35040
gcacttaaaa tgctgcggaa tgatttcctt gtgggttcga gtcccacttc tcgcaccaaa    35100
tttgcggata tcgtataatg gtattacctc agacttccaa tctgatgatg tgagttcgat    35160
tctcattatc cgctccaatt taatttactc cgtgtagctc agtttggtag agcgtctgct    35220
ttgggagcag aatgtcgtag gttcaaatcc tgccacggag actggaggcg tggcagagtg    35280
gtttaatgca ccggtcttga aaaccggcag tcgctccggc gactcatagg ttcaaatcct    35340
atcgcctccg ccagttttgc tgatttagct cagtaggtag agcaactcac ttgtaatgag    35400
```

FIG. 17T

```
                                  sequence.txt
aaggtcggcg gttcgattcc gtcaatcagc accaaggccc tgtagctgga aggttcaagc    35460
aagcgactca taatcgccag atggtggttc aattccaccc agggccacca aattaatttg    35520
gggagttatc ccgtagaggt agcggtgtgg actgtaaatc cattgtcatt gcgactcggg    35580
tggttcgact ccaccactcc ccaccaattt ggatgtgtag ctcaatggca gagcgatcgc    35640
ctgttaagcg attggttata ggttcgaatc ctatcacgtc cgccaaattt gtgacaactg    35700
tcacattaat atctacttga cgcgattata ggggttgaac tgatcactct tctcttaatt    35760
tcgtgtgaag acatcttgat tgttggagta ggtattaatg tggccgtagt tcagttggta    35820
gaactcgaga ttgtgattct cgtagtcatg ggttcgactc ccatcggtca ccccaattac    35880
ggggcatagc tcagaaggaa gagcaaggac cttctaagtc ctaggtcgta ggttcgatcc    35940
ctactgcctc gaccaattat aagtgaggaa aatatgaaag gtaatgttta tttagtagtt    36000
catgatttaa cattctattt taatcataat gatactgtta tttctgaacg tgtaattaat    36060
ttgctttatc agcatgcaga ttatgtttat gtcgaaaacg aatatggtca ttggcaattt    36120
ctcaaaaatc gttcatttgg tttagatggt tacgaatatt tgatcgtaa agaccttta     36180
gatacaattc cgttatctac acaatatcaa aatcataagt ctttacataa atgccggcta    36240
attcgaaatg ctgaatccgc gtatgaagca attgatttgt ggcgtaaacg ccgtgaatat    36300
attgattctt taaagaata ttaagaaacc gggtcgctac cggtaagtcg tcggactgat    36360
gttccctgga gtatagtttc ctcccacagt tttactgtgt tctggctctt tactatcaca    36420
gcagaaacgg cgcaccgaat tatcgattcg aggaaatatc tttgccgtaa gccgagtagc    36480
gttttttgacg gaacgttcgg atatggtcga gatatggcct tttaaaaata ttgagtagcg    36540
tcaactactt aataaccggg ttcgaatccc ggcgtttcgt acaaacactt gccttagcag    36600
gtggaaccccc gacaaggttg ccgcaaggct tagccccgac cgaaaggttg gggcttttttg   36660
gtataaatat tagtatatta aatctacaaa ttaaacagg aataagatg aaatcatata     36720
ctcaattttt aaatgaagcg gtgttaaatg aagcatctag caccgaaatt caagctgttg    36780
caaaagctgc cattgccgcg ggtaaatatt cctataaaga tgcttctgat gaatcgcgat    36840
tccagtttgc acgcgacatg aaagcggaag gatttacggg aaatgcagtt agtatggcct    36900
ggaaaagttt agttgctact ggcgctgctt ttgcaaaggc ttcgggtaaa cctgctccta    36960
aagcagatcc taaagcggca caagaaaaaa atatcgttaa aggaattatc gctaaatatg    37020
aagctatcct taaagagctt ttagtaatca aaaccgaagg ccaaaagtta gcccgtgctt    37080
atagtttcaa agataatcca catgttcact ctcttgagta tgttgaagac atccaaaaaa    37140
ttattaaaga ccgcatttgg tctgctaaac aaatcaaatg acattcttag ccccgaccga    37200
aaggttgggg cttttttagtt tgaatcactc ggataacgct gttacggata gtaacaaagt    37260
aataaataat taataaccaa ccgataaatt atttcaagga ttttaaatga aaacctatgc    37320
```

FIG. 17U sequence.txt

```
cgaattttta accgaagcag caaaattacc atctgaagca gatcttacta aagtattctt    37380
ccaattggac ccaaaagacc gcggcgattt tcttaagtgg aaagctaaag ctattgaaat    37440
gtacaacatc gataatagtt cttttacaat gagtcaagaa aataaattca ataaagcatt    37500
tttcaaaatt tctaagaaat tggcatctgg cgctcaggtt cctaaatctg tgttagctac    37560
tcctgaacgc gcacctgtta aaatttctaa gaatatgttc gacactaaaa aatacgttaa    37620
tgctttgaat aaagctcttg atgcattgga tgatgcaaag aaggcagccc gcgatcttca    37680
agacgtgtac accgattttg accgcaaaac taaaggttct atttcaaata gcgaacgcaa    37740
tagtgtaagt gtttattctg atagccttga tgttcttggc gatgcgtata ctgaaattaa    37800
aaatcgtatt aacactgcat ctaagctaaa agctgctgca gaagctataa taagtaaact    37860
aggtaaataa ttttaaatcc ctatctaaat gatagggctt tttggtatct aggcctttct    37920
ggacctctct aggcatcatt tagtttatac cctttataat atattatcct atcctttaat    37980
tgcccatccc tgccctagaa ttccctaaaa attttttcac aaaactgttt acatctctgt    38040
tcttccatgg tactatacaa ctatcaacta ctgatacaga aaacaacttg gagaatgaaa    38100
tggataatta cggcgaactg ttcaacttct ttatgaaatg cgtttcagaa gatttcggtc    38160
gtacagtgaa tgatattaaa gttatcggtc ctgatcatcc gatgtttgaa acttacgcag    38220
taatgggtaa tgaagacggt cagtggtata ctgtaaaagt tgtgattaat atgttcacag    38280
cagaaggtta tgttaaactg tcttctaaag tttaccatga taacgacgaa atcgcggaag    38340
aatatttcaa taatatgaaa taagtttacg caggctcatg attgagatat tatgagccta    38400
taatttgacg atagagtatt atactcctac ggattttaaa tctcaattaa cctaaggaaa    38460
tactatgaac acactgaaga aaattgttga gttattcgc actaaacttg gttctgctat    38520
ggctaaaaat ctatctgtcg aagaacagta tactgctgca gcagcaaaac tacttgataa    38580
aattaaagat ctaaaaactg cttctgttaa atctattaac gaagaaaaac gtattcgtga    38640
acttgttatc gaaaagaatc gacaggccga atcaaaagag cgtgaaattc gtaaacttct    38700
ttccgaaggc caagatgtaa caatgcatgc taaactcggt ttactatatc gtcgaacagc    38760
tgagcagttg actactaagg ctgacggtta tgctgaaatg cgaattgaaa tcgccaagaa    38820
agtagttgag ttagatgatg ctcgtcaaga acttgcggtt aaattggaat atatccgtga    38880
aactcgtgca gcaaatgccc ttggaattag tactgctgat gatgtagttc aaattgcagc    38940
actgactaag gttgatattg aagataccct tgctcgagtt gaaaccttta acggtaatat    39000
ttctggggtt gaaactacct ctgccgatgt tcaggaatac attaattctc tgaaataatg    39060
ataaggggct tcggcccctt atacttggag taaataggaa tgaaaatgaa aatgcaaagt    39120
gatttcaatt caatgtttga agagttccaa agacaggttg atgttccaga ccaattacta    39180
```

FIG. 17V sequence.txt

```
aatgctctta aacgcatggc agaaggacgt aattactatt gggggtcttc atatgaaact   39240
gatgaaagcc tttccggaag attttctaga ggtaaaaagt ctttaatacg tcctggaata   39300
ctcattaaca gtattgaatc aattcattca ttgacgtgtg attttgatgt tgaatttact   39360
gatttcattt ctcctgaatg gacggtttgt tatttaaacg acgattttga ttatctcggt   39420
gtttatagtt taagtgacgc atggtttaaa cgtaatttac aaaagtcaaa tttattttat   39480
attgatacta ctgtaaaatt tcagggcaag aaatatttct ttactcttat agttgattct   39540
gaaacgaagc atgaaaataa acgtattctt agtaaaaaga atatcttaac tattgttgat   39600
gatcttttg  ataaatttgt agaaaatccc aattttgaaa gtgatttatt actagaaaaa   39660
tttgttaagg aatgtagaga atatgtcaaa accatcacta taccttccaa gtaaacctgt   39720
gaagtatgaa ccaaagcgtc agataatttc tactgatgtg ttaataggtc ctgttatact   39780
catatcattt gtaattctat tgattattgg aggtgtttta gatgttatga ctgatattga   39840
ttctggcgaa atacttgtgt taatgctaat tcttccatta atagttccac ttttattagt   39900
acccgtaaat tgggtaggat actggtatca aggaagacat tatcgtaaac gtgtacgtga   39960
ttggaaagct cagtgtaaaa agattaaaaa ggaacaccag cttaagctag atatgtatga   40020
atttgatgaa attatgaaat ttgttaagga atcacgatgc aaaagccaaa actaaataaa   40080
gtcaaatatt cgtttcctga ggcactatta attcttgctg tatcagtatt tacagctctt   40140
gcgggtagtc ttattggatt gttaattgac tgttttattt taaatatcga cggcacagta   40200
attataacag aggtttggag tgaacttcgt tttactatag cgatttcatt attttcattc   40260
tttggtacca tgttatattt tcattatgat aattttaaaa taaattggca agaaaaaaag   40320
gattacaaaa tacaattaaa ggaatataat agctatatgt cttatattga aaaagaatca   40380
atggaagagt ttgtgagtga ttgtaggaaa attaaatgat tttaaaaact cgctggtatg   40440
atttagatga tggggacgat ggcatttcag ttgatagagt tgactggagc ggctgttctg   40500
aagatacaaa gaaacgatta attagggagt ttagaatggg atatcaagca gttaagccat   40560
ctactgtaac agatgataaa ttcgtgtgta ttcataatgg tcgtgctaag ttaacgaatg   40620
ctgaatggtt cacagataag attatgattc tgtggtatat cattagtctt cctgtgtcat   40680
cattcgtatt ttacttttt  ataaaaaatc caatggacag aataggagat tggattcttt   40740
taaccatact tgttaatatt tttacagcat caatattatc tgggatatgg tacacgttca   40800
ttgaaatgcc atggcggcta cgcagacaac aaaagatttt tgatgaaaag aaatatactc   40860
aaaatttaaa taactttatc actgaatgca ggaaattaaa atgaaaacat tatcagctgg   40920
tattatcttc atgacagaag ataaagattt atttatgggt cgggttactg gttctcgtaa   40980
gcctggaatg atggcacatc gctgggatat tccaagggga cgtgtagaaa gttctgattt   41040
gaatgcactg gaagctgcaa aaagagaatg cttagaagag accggttta  gcaattataa   41100
```

FIG. 17W sequence.txt

| | | | | | |
|---|---|---|---|---|---|
| tccagacctt | ctagaagacc | taggtgtatt | taaatattct | agtaataaag | acttacagtt | 41160 |
| attttattat | acgattccag | tagagcatga | gatgtttaga | aattgccatt | gcgagtctta | 41220 |
| ttttgaaaat | aaagatggcg | ttatgattcc | agagatggat | gcttttgctc | ttattcctcg | 41280 |
| tactcagtgg | caatatgtga | tgggtccttc | actttaccga | ataatgaaca | gcctctttta | 41340 |
| atttataaat | accttctata | aatacttagg | aggtattatg | aatatatttg | aaatgttacg | 41400 |
| tatagatgaa | ggtcttagac | tcaaaatcta | taaagacaca | gaaggctatt | acactattgg | 41460 |
| catcggtcat | ttgcttacta | aaagtccatc | actaagtgtt | gctaaatctg | aattagataa | 41520 |
| agctattggg | cgtaattgta | atggtgtaat | tacaaaagat | gaggccgaaa | aactctttaa | 41580 |
| tcaggatgtt | gatgctgctg | ttcgcggaat | tctgagaaat | gctaaattaa | aaccagttta | 41640 |
| tgattctctt | gatgctgttc | gccgctgtgc | attgattaac | atggtcttcc | aaatggggga | 41700 |
| aaccggcgta | gcaggattta | ctaattcttt | acgcatgctc | cagcaaaaac | gctgggatga | 41760 |
| agcagcagtt | aacttagcta | aaagtagatg | gtataatcaa | acacctaatc | gcgcaaaacg | 41820 |
| agtcattgca | acgtttagaa | ctggcacttg | ggacgcgtat | aaaaatctat | aaagttgttt | 41880 |
| actttctcct | agaattgtga | tagtatattc | acagttactt | ggagggataa | aatgactcgt | 41940 |
| attaatttga | ctttagtatc | tgaacttgct | gatcaacatt | taatcgcaga | ataccgtgaa | 42000 |
| ttgccgcgtg | tttttggtat | agttcgtaag | catgtggcaa | acggtaagcg | cgttaaagat | 42060 |
| tttaaaatat | cttctaaatt | tattttaggt | tctggtcatg | ttactttctt | ttacgataag | 42120 |
| ttagaatttt | tgcgaaagcg | tcaatcggac | attataacgg | aatgcttaaa | acgcgggttc | 42180 |
| agtataaaag | atactgaagt | tcctgacatc | agcgatattc | cagtagaatg | gaaaaatgat | 42240 |
| tataatccat | gcaaatcagc | tattaagttg | agtcaacaac | gactcgatga | aaaaatttta | 42300 |
| atgaagccac | actggtataa | gtattacggc | aaaaatattt | acatttaaat | aacatgggaa | 42360 |
| taacctggac | ctcatgattc | tgtgagggat | tcccgccaac | ctgtaataag | gtcgagccca | 42420 |
| agtgcggtaa | tgggtaaata | cagaaatgga | caattcatgc | gccatggaat | ggcccaaacc | 42480 |
| tagagagaac | aaaatgagaa | cattttttaac | tggtccttat | ctatccctga | tgaatgcttt | 42540 |
| tacacaccat | tctgatgcta | gagtagaaga | aatttgtaaa | aacgaatata | tcccgccatt | 42600 |
| tgaagactta | cttaaacagt | attgtacact | tcgactagat | ggtgggcgtc | aatctggtaa | 42660 |
| atcaactgca | gtaactaatt | ttgccgctaa | ttggttgtat | gacggtggaa | cagttattgt | 42720 |
| tctttctaat | acttcagctt | acgctaaaat | ttccgcagat | aatattaaaa | aggaattttc | 42780 |
| gcgttattct | aatgatgata | tacgttttcg | tttatttact | gattctgtgc | gcagttttat | 42840 |
| tggtaataaa | ggaagcaagt | tcagaggttt | atcgcttttcg | cgaattttgt | atataattga | 42900 |
| tgagcctgtc | aaatctcctg | atatggataa | gatttatagt | gtccatattg | acactgtaca | 42960 |

FIG. 17X sequence.txt

```
ctgctgctgt aatattaaat gttgcattgg tggtattact cgtccacagt ttttcgtaat    43020
cggaatgcaa tgatgacaga cactcagctt ttcgaatatc tttattttc gccaaaaact     43080
attaaaaata aattggtgaa tcattttgaa attttggcaa aaaataacat tttgagcgaa    43140
ttttatccca agcaatacaa attacaaaaa ggcgtattca aaggatgcag agttttgtgc    43200
acggctccta atgcacggct aatgaataaa attccatatt ttaccatgga atttattgat    43260
gggccttta aaggactaat cacacagagt ttaatggcat atgattctga gccatttta     43320
attaaagaac aatcttggat aaatttattt tttaattgag gttatatgaa agcatatcaa    43380
attcttgaag gcacacataa aggtactatt tattttgaag atggtattca agcacgaatt    43440
attgtctcta aaacctttaa agaggactct tttgtagacc cagaaatttt ctatggtttg    43500
catgcccgtg aaattgaaat tgagcaacag cctacagtta aaattgaagg tggtcaacac    43560
ctgaacgtta acgttctgcg tcgtgaaact ctggaagatg cagttaagca tccggaaaaa    43620
tatccgcagc tgaccatccg tgtatccggt tatgcagttc gctttaactc tctgactccg    43680
gaacagcagc gcgacgttat cgctcgtacc ttcaccgaga gtttgtaatg gcaaagataa    43740
ttattgaagg ttctgaagat gtgctaaatg ctttcgccga gtggtttagt aattcaggcg    43800
aacagcaatt taacgaagca tggaacatgg gtgatattaa tggaatttat cctacgacag    43860
aaatttctgt tcaaggatat ggcattcatg aacctattcg tttagttgaa tatgatttgg    43920
gaacaggtga ggaagtaaaa tatgattgaa gacattaaag gttataaacc acatactgac    43980
gataaaatca gtaaagtgaa tgctatcaaa gatgctgaag ttcgtttagg cttatctttt    44040
gatgctttat atgatgaatt ctgggaagca tttgatagct gtgaagatga tgaactcgcg    44100
aagaattacg ccgaaagcct cgatcagtta actattgcta aaatgaaact caaagaagcc    44160
agtatgtggg cttgtcgcgc agtgttccaa ccagaggaaa aatactaatg gctcaattaa    44220
gcgcagggtt tggttatgag tattatactg ccctcgtcg tgtatctgtt gctcctaaga    44280
aaattcaaag tcttgatgac ttccaggaag tagttcgtaa cgctttccag gactatgcac    44340
gttatcttaa agaagattca caggactgtc tcgaagaaga tgaaattgct tactatgagc    44400
agcgtcttga acagctcaaa aatctacatg aggttcgtgc agaagtttca aagtctatga    44460
ataaattgat tagatttaaa gaataactgt ttacttttcc tcttgactgt ggtataattt    44520
ttctatcagt taagaggaga ataacatgac tatcaataca gaagttttta ccgtcgaaa    44580
taagcttcgt cgtcactttg agtcggagtt tcgtcaaatt aacaatgaga ttcgtgaggc    44640
atcaaaagca gcaggagtct catcgtttca tctaaaatat tctcaacatc ttcttgatcg    44700
tgcaattcaa cgggagattg atgagacata tgttttgaa ttattccata aaataaaga     44760
ccatgtttta gaagttaatg aattcctgag tatgcctccg cgtcctgaca ttgacgagga    44820
ttttattgat ggggttgaat atcgtcctgg acgtttagaa atcacagatg gaaatctttg    44880
```

FIG. 17Y sequence.txt

| | | | | | |
|---|---|---|---|---|---|
| gcttggattt | acagtttgta | aacctaacgc | gaagttcaaa | gacccgtcac | ttcaatgtag | 44940 |
| gatggcaatt | atcaacagtc | gtcgtttacc | aggaaaggct | tctaaagcag | taattaaaac | 45000 |
| tcaatgaggt | aagcatgaga | aaagcactac | tcgctggtct | attggccatt | tcaatgatgg | 45060 |
| cacatagctc | cgagcatact | ttcagtaatg | tccaactcga | taacatgcgt | tacgcgtatc | 45120 |
| aattcgggga | acaattttct | aaggatggaa | aatataaaac | acacaaaaac | atccataaga | 45180 |
| gcggattggg | tcatataatg | gctgctattt | tgtggcaaga | aagctctgcc | ggagttaatt | 45240 |
| taaaatctaa | accaaagcat | catgcctatg | gaatgttcca | aaattatttg | cctactatgc | 45300 |
| gagcgagagt | caaggaactt | ggttataata | tgaccgatgc | tgaaataaaa | agaatgttga | 45360 |
| ataaacggtc | caattcagct | tcctgggcgt | acattgaact | ttcttattgg | ttaaatatac | 45420 |
| ataagggtga | tataagaaaa | gcaatatcat | cttataattc | gggatggaat | gttaaagcag | 45480 |
| gttctaaata | tgcttctgaa | gtcctagaaa | aggctaatta | ccttaaaaat | aataaacttt | 45540 |
| tggaaatagt | aaatgactaa | aattttggtt | ttatgtatag | gattaatttc | attttctgtg | 45600 |
| ttagcagata | catcatatac | tgaaattaga | gagtatgtaa | accgtactgc | agcggattat | 45660 |
| tgcgggaaaa | ataaagcatg | ccaagctgaa | tttgcgcaga | aattaatata | tgcatataaa | 45720 |
| gacggagaaa | gagataaatc | aagcagatac | aaaaatgata | cattgttaaa | acgatatgct | 45780 |
| aaaaagtgga | ataccttaga | atgttcagtt | gcggaggaga | aagataaagc | cgcttgtcat | 45840 |
| tcaatggttg | accgtttagt | agattcttat | aatcgaggat | tgagtactag | atgattgtaa | 45900 |
| aatatatcaa | gggcgatatt | gtcgccctat | ttcttcaagg | taatattatt | gcgcacgggt | 45960 |
| gcaattgctt | ccacacaatg | ggctctggcg | tagcgggtca | attagcaaga | gcctatccca | 46020 |
| aaatttaga | aatagataaa | accactaccg | agtacggttc | tcgtgataaa | ttaggcgata | 46080 |
| tgtctattgt | ttttaaacat | agtcctacgg | gatttggtat | atgctataac | ctgtatacac | 46140 |
| aatacgaacc | gggtcctaat | cttgattatg | gtgctttagt | aaactgcatg | atagaattaa | 46200 |
| atctacaggc | agaaacccctt | ttgtttaaac | cagtaattta | cattccacgc | ataggttgcg | 46260 |
| gtattgctgg | cggcgattgg | gataaggttt | ctaaattaat | cgacatgttt | actcctgata | 46320 |
| ttgatttaat | agtggtggat | tatgaaagta | cattacccgc | atccgtttga | tcctaaaaac | 46380 |
| aaagtggaaa | ttattcgtca | atgggaacgc | atttgccgta | ctaaatgccc | aattaatagt | 46440 |
| ccacatgatg | tagataaaga | ctatattgga | acattcgttg | aatataccttt | tattgatagg | 46500 |
| aaaggtcgta | aacaacatgt | agaagaatat | tgtttaaagg | ttacatggtt | atgagccaaa | 46560 |
| ctagtattct | taaaaatgcc | cactgcgaaa | agtgtgaatg | gccagttgtt | tttgctttat | 46620 |
| gtaatgatga | aatggcttgt | gatttcgatt | attggtgcta | ttgttctaat | aaaggatgca | 46680 |
| tcaatcataa | aggtgaagga | ttttattcag | gattttatcc | ttatcctgat | ttcgttaaag | 46740 |

FIG. 17Z sequence.txt

```
aaggtaaacc gaaatgaata gttttgagtt acagtatgaa gtgttacgtg agcttgataa    46800
tttaattgaa ctcgctgtca ataaaggttt tgccattgga atcggtcaaa aagatactgg    46860
tcatttaact atggaaatat ttaagcaaaa gcgaattatt ttaaaactcc tggaaattaa    46920
tatatgagtc tgagtaaaga acaaaaagat aaattgtttg agcttatcca tgaacttcta    46980
gatgagcata cagaagcaaa caccttttat gatgaatacg gcccgctatc tcccgaacag    47040
caagaagaat ttgctgatcg gtttgataag aaagaaaacg aattaatagc ttatgtgaat    47100
atgctttaag aaggtgatat ggcgagttta attttactt acgcagcaat gaatgctgga    47160
aaatctgctt ctcttttgac tgctgcacat aattataaag aacgcggaat gggtgtatta    47220
gttcttaagc ctgctattga tactcgcgat tctgtctgtg aagtcgtttc tcgcattgga    47280
attaagcagg aagcgaatat tattacggat gatatggata ttttgagtt ctataaatgg    47340
gctgaagcac aaaaagatat tcattgtgta tttgtagatg aagctcagtt tttaaaaact    47400
gaacaggtgc atcaattaag tcgaattgtt gatacatata atgttcctgt tatggcttat    47460
gggctaagga ctgatttcgc tggaaaatta tttgaaggtt ctaaagaact tttggcgatt    47520
gcagataaac ttattgaact aaaggcagtt tgtcattgtg gtaaaaaagc tattatgaca    47580
gctcgattaa tggaagatgg aacaccagtt aaagaaggta atcaaatctg tattggtgat    47640
gaaatttatg tttctttgtg tagaaaacat tggaacgaat taactaaaaa gctcggttag    47700
tgcaaaagtt ataataggt ttatctaact aaagggtat atatgctaca attaactgaa    47760
aagcaacttc gcaatcttac tgttcttcaa ttagatgaaa ttcgtaggga agttggaaat    47820
atcatttcag ctttgcgtcg agaagtatca ctcaaccaat ctccggcaga ctatactaga    47880
ttgcgaaatt tgaaaaata ccttgataaa gttaaggccg tgcatcggca taaagtaaat    47940
acaggacaaa aatgatagga ggcctttatg gccttaaaag caacggcact atttgccatg    48000
ctaggattag cgtttgcttt atctccacca attgaagcga atgtcgatcc tcattttgat    48060
aaatttatgg aatctggtat tagacacgtt tatatgcttt ttgaaaataa aagcgtagaa    48120
tcatctgaac agttctatag ttttatgcga acgacttata aaaatgaccc gtgctcttcc    48180
gattttgaat gtatagagcg aggcgcggag atggcacaat catacgctag aattatgaac    48240
attaaattgg agactgaatg aaattcagcg acttttcaca aagtggaaaa ccttcaaagg    48300
cagatgaata cttaggttta ttaatggctg cacaagctta ttttcattct gcgcatttg    48360
aaactaaaag ttatgctaga cacaaagcat acgattttat tttctctgag ttgccagatt    48420
tgattgataa atttggtgag caatatttgg ggtattctgg tagaaaatac acgccttcta    48480
ttccagatgc cagtaaactt cctaccgaca caattaaaat gattgatcgc atactagacc    48540
aatctaacag catttataaa gaaatgcctc cagccattca aagcacgata gatgatatta    48600
ctgggatgtt ttaccagagt aaatatcttc tttccctcga ataacattag tctccttcgg    48660
```

FIG. 17AA sequence.txt

| | | | | | |
|---|---|---|---|---|---|
| gagactttt | tcattttacc | ggtttacttt | ccatttgagc | tgtgatacta | tacaactatc | 48720 |
| ggataaagag | gagaacatca | tgaaaattga | agcacttaat | caagaaggaa | atatctacgt | 48780 |
| catcattaat | ggtgattttt | tcgtcgacat | ggatgaagtt | actagtgaag | aacttgtaga | 48840 |
| acttcttaag | aaacgttatg | atatgtgtga | tgaagctgca | actcatatgg | cgtgtgcaat | 48900 |
| attctctctt | tcatatgtgg | tggaataatg | actagaattg | aacaagcaga | taaaattaaa | 48960 |
| gaattggtag | ctttaattcg | caaagcagat | gaggaactta | gtgactttgc | ttggttttcg | 49020 |
| gcaggcattg | caaataaagg | tattgaaaaa | tttgaagcta | aagttgataa | tgctttagaa | 49080 |
| gcgttagata | tgtttcttga | tgaaattatc | gatcataata | cgagagtgta | agtatgctaa | 49140 |
| cacgcgaaca | gtttgaaaaa | atcattaaat | tagcacgtga | tattgaaata | gattcatatc | 49200 |
| aattagcagt | tgagcattgt | gaaggatatt | catacgatgg | tatagaagca | gctaaaaagg | 49260 |
| atttggataa | atctaaagct | aagttagttc | aatatcttga | aatgattagg | tggaataatg | 49320 |
| aaaactgaaa | agcagatgtt | tttaatgaag | ctaattgaag | aatatgctaa | tgcagtttct | 49380 |
| gactatgaat | gttcttctcg | tgaaagaggt | acagctttcg | ctaaagaaga | attgaaaatc | 49440 |
| atggttgatg | ctcatacaaa | gcttcagaat | tttattgaaa | acgtcattta | atggtttaca | 49500 |
| agttggcaag | gttatggtat | agtaatcttg | tcaactgcca | aggagaagag | aatgaaagtt | 49560 |
| ttgtttgttg | tgtatgtgat | gattcaatat | aattacccaa | tgtttactta | taatctggtg | 49620 |
| aacaacatta | ttgatattat | tcaaaggagt | atgtaatgac | aagtgagcag | gcttttaaat | 49680 |
| taaagaatt | aattgaaaca | tatagcaaag | ctgttcatac | agcaacagtt | attgatgaat | 49740 |
| cagctttctc | cggacatgct | aacaagatta | aatacaaaac | tcttatggaa | gaagctaaag | 49800 |
| taaatcttga | ttcttatatt | gaaactttaa | ttggtgaata | acatgggctt | tcctaaatta | 49860 |
| gaagtaggtg | atttagtttt | aacaaaatta | tggaatggtg | ttcaatcagt | agaaatctgc | 49920 |
| caatatcgtg | gagcaacagg | taatttgatg | tacacgattt | ataatccaga | aattttgtta | 49980 |
| gagtgtcatt | tggaacgctt | tataaaagac | accgatagta | tgccttatag | tgtatcaatt | 50040 |
| gtacgtaaat | ctgatacaaa | ggaatattct | aaaattttag | aacaaattcg | tgccaataaa | 50100 |
| aaggattaat | atgaaacgat | tagtattaga | agttagtccg | cttttggtg | aattggctat | 50160 |
| agaaaaagta | aataacatgt | atcgtttgac | gcaagaagac | gatatgctat | attttacgcc | 50220 |
| tagtgaaatc | attcatttaa | cccaaattga | atatccttat | actgataaaa | tagtaagcat | 50280 |
| caatgatgag | cacaaaattc | atttttattc | ttcatgccca | ggatttaata | ttaaaagtga | 50340 |
| gtcaatgtgt | ttatcagtta | tccattggga | tagttttata | gataagatta | aatattttta | 50400 |
| ttattctaat | gaaagaaaac | atagtttaaa | atggctcaaa | aattgcaatg | ctattattac | 50460 |
| taacgcttgc | aatcagaatg | atgaaactct | tttaaatgta | tcaaatgtt | atgaagaggg | 50520 |

FIG. 17BB

```
                              sequence.txt
agatgtctta actattcgcc aaattgacga ttttcgatca catattgtca catttaccaa    50580
agacgaagct attgcgttaa agacttatct tgattctgtc attccaacta tgatttcaaa    50640
gtgaggaaat atgtttattt caagtggaag cggtttaatt cgtgttgaat ttaaaaatga    50700
catctttctt agtcaaggag atgatattat taaaatgagt tatgacgaaa tcaagaaaat    50760
ttgtcatgct cttgaaagtc atggaaagga aaatgctact atcgatatag gtgatttatg    50820
ggtgacactt tatgaagtat ccgaaggatt taacattgaa gatgaaaaca acatttagc    50880
tattgataaa agaagtgatt tgtttgatgt attaaaagtt tatgaacagt caaatggtgg    50940
aagaaaagct gtattagttt atcaaaaacc acattcatgt ggaactgctt caatcatttc    51000
aaatattgaa gatgaaactg atacttatat gtgtgtttta aaagctggtg gtgaccgtca    51060
tccggatttt atttctattc gtcaaaataa tggagaaatt tcattatcaa aatcagaagc    51120
tgaagctatg attaagtatt taacaactgt tacaccttca atgaaaggat aattatgatt    51180
attaatgaaa actcttggca ttataaatta ttcaaaatgt ttaacgacga atggaaacga    51240
cctaagacac tttgtgcata ttttggtct attgttatcc ctacattttt cgtttctttt    51300
ttcggatgta ctatactcgc aggtctaact attatctgtg cagaaatcat acagaaatgg    51360
cttatttttg gtagtttatg gactcttatt ccatcagcat ttatacttgc catttgctt    51420
gttttactta ttatcggttc atttgttatt cctgcacaac tacatgaaaa atataaagat    51480
tataaatgga aaaggatta tgctttacat gtagaaaata ttgatagggc gtataaaggt    51540
ttacctccta ttcaacccaa gaaatctatt atcgtcgaat ttttaaaagc gcgtaaagct    51600
aaagtatgtc ctgttattga atataaggct gaatgatgaa aacagtaatg aaaagctatt    51660
ttggtagtca tctttatgga acttctactc cagaatctga tgtagatttt aaagaaatct    51720
ttgttcctcc tgctcgcgat attcttatcg gaaatgttaa agagcatatg agtaaaaaca    51780
ctaacaacac atcatctaaa aacactaaag atgatattga ccatgaacta tacagtctta    51840
aatatttctt taaattagca gcagatggtg aaactgtagc gttagatatg cttcacactc    51900
cacctgagtt agtggttaaa tctgatttgc ctgatgtgtg gaagtttatt caagacaacc    51960
gttctcgttt ttatacgact aacatgaaat cctatttagg atatgtccgt aagcaagctt    52020
ctaaatacgg cgttaagggt tctcgtttgg ctgcattacg tgatgtattg aaagtagtta    52080
atcaaatccc tgagcagtgg gttgattacc aagaagatgg ttctattaag cagcgtcgta    52140
ctaaagttga agatattaag catcgtcttc cagaaaacga attctgtgaa tgggtgttcc    52200
ataatcatga gaaaacaggc ccacagacgt tctacacagt gttgggtcgt aaatatcaga    52260
caacgctttc tcttattgag cttaagcagt cactgaacaa attagatgct gaatatggtg    52320
aacgcgctcg taaggccgaa gccaatgaag gtattgactg gaaagctctg agtcatgctt    52380
gccgtggtgg actccaacta ttggaaattt acaaaactgg tgacttggtt tatccactcc    52440
```

FIG. 17CC sequence.txt

| | | | | | |
|---|---|---|---|---|---|
| aagatgctcc | atttattctc | gacgtgaagt | tgggtaaaca | tccatttaaa | acggttcaag | 52500 |
| agtttttgga | agatgtggtc | gatcaagtag | aagcagcatc | tactgaagct | tctaagaacg | 52560 |
| gtatgcagca | aaaagtagac | atgagtttct | gggatgactt | ccttgagaag | gtctatcttg | 52620 |
| aaaaccatcg | aagttattat | aaatgatagg | gagccttcgg | gctcccttttt | ttatttaaa | 52680 |
| aatttttca | caaaactgtt | tacaagcata | aagctttatg | gtactataca | actatcaaaa | 52740 |
| caaacactta | aacggaaaac | aaaatgaaaa | ttacaccaat | tgaagtaaaa | aagttgattg | 52800 |
| atacagaaga | aatttcagag | tgttttgaaa | gtttcttaga | agacgcaact | gaagataacg | 52860 |
| cggtttatct | cgcccagaaa | attatcgaaa | cttatttgga | gaagaatcaa | tgacagttta | 52920 |
| cgtagatgtt | ttaatgaatc | atggatggaa | acttcgcggt | catccaacta | aaaattgtca | 52980 |
| tatgttcact | gatggagata | ttgaagagct | tcatgaaatg | gcagaagcaa | taggaatgaa | 53040 |
| acgttcttgg | tttcaagata | aacgcattaa | acattatgac | ttacacgctc | gccgacgcca | 53100 |
| aaaagctgta | gaacttggag | ctgtagaagt | atctcgccgt | gaagcagtaa | aaatttggcg | 53160 |
| aacgttaaaa | taaattgttt | acagaagggt | agtagtgtga | tactattacc | ctatcaaaac | 53220 |
| aaatgtgaga | ttggagaata | aaatgaaaac | tgtaactatc | aataagggta | tctacttcgg | 53280 |
| taaagaaatc | tctggaactt | ttgagctctt | aggtgaatgg | ttcccagata | atgctccggt | 53340 |
| agatgcacaa | ggagatggta | aagttttttgt | tgaaattgac | ggtaagcgtc | gcggtgtttg | 53400 |
| ggtttacaaa | tcagacattt | catatgatgg | tgtaaaagtt | gaagaagtta | aagaatcata | 53460 |
| tgaagatatg | aaaacccgca | ttaataaaag | atttaatgtt | atgggaatga | tgacgaatgg | 53520 |
| tattattaac | ggaaacattc | gttcattaat | tatctctggt | gcggcgggta | ttggtaaaac | 53580 |
| gtattcttta | gataaagctt | tgaataaagc | aaatgataat | ggatacattg | aatataaaag | 53640 |
| cattaacggt | aaaatctccg | gtatcggtct | ttatgaacaa | ctttggaata | atcgtgaaga | 53700 |
| gaattctgtc | cttttgattg | atgatgtgga | tgttttctct | gatatggaca | ttcttaatct | 53760 |
| tctgaaagct | gctctggaca | ctggagagac | ccgtaaagtc | tgctggagca | ccgcatcttc | 53820 |
| ttacttagaa | gaaaaaggca | ttgagcgtga | gtttgaattt | aaaggaacga | ttgttttttat | 53880 |
| cacaaacgtt | gacattgacc | gcgaattaga | ccgtggtact | aaacttgctc | cacatttaca | 53940 |
| agcattagtg | tcccgctcgg | tttatttgga | tttgggtgtt | cacactaatg | aagaaattat | 54000 |
| ggtcagggtt | gaagatgtta | ttcttttcaac | tgacatgatg | caaaagcgcg | gtctttctga | 54060 |
| tgaagaaact | tataaagcat | tatcatggat | gaaagttaat | gttaatcgtt | tacgcaatgt | 54120 |
| ttcactgcgt | actgctcttt | atcttgctga | ctttattatg | accgacaaaa | acggttggga | 54180 |
| agaaattgct | gaggttactc | ttctgaaata | attcataaga | ggacttctat | gacaaaaagg | 54240 |
| cagttcagaa | atagattata | tggactgcca | ttaaaaagat | gactagaatt | aaactggtga | 54300 |

FIG. 17DD

```
                                     sequence.txt
atggaggtaa tgatgttata ctcaaaggct cgtgaaattt acgaaactaa aattaaagaa    54360
gcagtattta agttcgcaac gacaatgcga tggacaaatg actgggagta ttcaaaaaat    54420
cataagaagc ccatggtgac aagaaaggct catatgttag tgttaataga ccgtgagcag    54480
attaaagccc gagaagccct ccagaatcat aaaaaggctg cctttgaatg gtttatggat    54540
aacactgctc ctgagactaa gaaagcggta agcgcatggt tcagtggaaa aaattgtgaa    54600
agaagtttct tttagtggtt tacaagactg ttcctctgtg gtactataca actatcaact    54660
acggaggaac acaaaatgaa cgctaaagat attttcaacc tggtaaatta caacgatggt    54720
aaatttaaat ctgaagcaca aagtaagttc tttaatgaca tctcaatcgg aggtgaaatc    54780
acggttgacg gaggacaaat ttacaaatct cgttggaatt ggatcgttat tatcgatgag    54840
attggtattg tagaaattta caagaatacg aataaaaatc gtacattaca ctggtctcgt    54900
gatactaacg aacagtacaa aaaggataaa gcatctaaat tatctcgtgt aactcaagaa    54960
gatattgagt tcatcaagaa agatattttg atgtatgata acttaattgc tgaagagcaa    55020
gctgttattg ataaatttga tgagattaaa gcttctcgtg aaattcctga ttttatgaaa    55080
gaatcagtaa atgaacgata cactctcatt tcagagcgta ttgaaactta caaaaagcaa    55140
agagctgaac gccagaatac tcttcggaag tttgaagaac ggttaaagac ggtactcgca    55200
taaccgcttt ataccaagga tggtataatg gttctaagcc cttttaattg agattattat    55260
gaaacagttg ataattaaaa gattgaattt attgatatgt tgtttatgta tagcaattgc    55320
atatggttat tacgcaatta atgattatat gcattataaa gattatgatg ttactgtagt    55380
taataccatt acaggaacac aaggaaaagg gtctagttta tcgtttattg ccgtatatga    55440
actcaaagat ggttatagat ttagtgaata tatttcccca gagatgtatt catcaataga    55500
aaaaggtgat aatattactg taagtttacg tccttcgac gtaaaacaga cattgtttga    55560
taatattgtt tggttctttg gaatggtatt agttcaatct gtgtgtggtg cttatatagt    55620
ctgttccatc ttattctgta tatttagtaa aattgaaatt gagtgaggaa aatatgtcag    55680
tagtaattaa taatgtcaat gcagtaatta atctttagt taataaaaaa ttaaatgaat    55740
ggactgtact tcgtcgtgga gagccagata aatttttttca tagatttaac ccaactttgg    55800
atttgaatgt tattgacaga gatgttcatg ctgaaatttt agataaattt aaagttgata    55860
ttgggtttgg gttagataaa catttgcaac gaacaaacgg atctggaatg ggtttatcta    55920
atcgcatcat gaaagccctt aataaaattg gagcgttgtc tcgtattaat gcgagtgaaa    55980
tccttcgcaa ttataataaa ggatatgacc tttatggtcg actaatgccg aaattatcat    56040
ttgaccaaat gattgcggat ttgtgggaaa atcaacgacg attattagca ttaggcgctc    56100
gattagctaa aggtctagat aaacaaatga ttttaagac caataataca gaagacctta    56160
aatgctttaa atttagtact cgtggagatg attattacat cagagctcgc tctacagatt    56220
```

FIG. 17EE sequence.txt

```
atgttaatat ggggcatcat ctctgtttag cttttgaagt tttaaaagaa gccggaacat    56280
tagaatatgt gtctggtgct aaatgtccga ttggttcaaa ttgcatttta atttatcgcc    56340
cagatgaatc cagttcaact aaattaccta caaaacctgt accagttcgc agtaatgaaa    56400
aacattctga acaaattgct tattttaata agcagattga agagctaaat atttctattc    56460
agcaatatga tgatgaaatt ttcagactat ctggattgag tagtaaagct aaatctgagc    56520
gtgaaaaatt aattaaaatc gttgatttac ttaaatctta aggaacacca tgaaaactcg    56580
ttctcaaatt gaagatatgg ttcgtaatgc cagctatact cgtgatgtta tgacattttt    56640
gtgtgaaaat aatttagacc ctgataaagt taatcgtgtt attcatcact ttaagtatac    56700
gaatagcagt gaatgggtgc gtaattttag taaagcaggg tatattacac aaatgactgc    56760
tcgtgaacag ctcaccgatt tctgtaaaac tattgattat aaaaatcctt tgattgttca    56820
aggcgttggt caaagtaagg tcgatttatc atctggattt ttcaatccaa atcattatcg    56880
tattgaatgg agatttattg ctctattccg taaacaatta agcaaattt tgtctactgc     56940
tagtcgatta aaaggctctg atattaactt aaagaacctg aaatttgatg ttatactct    57000
tcagatggaa gtaagaccgt taaaagaaaa taatagaact gcacgaatta gctttaagcc    57060
taatactaaa aattctcttt caatttgtga atgtcttaaa tcacagctga cagaagcatt    57120
taagtatatg gatgttgttg ctgctgttca atctaagatt ttacctcgtt ttgagcgaaa    57180
ttgggaacat acaacaacat atgaacttga tatgatcgtt tcatttaaat atgaattttt    57240
gagaaaggat gaaattgttc aagagaaaaa gcaggaagtg caagatacct taaatttaaa    57300
tttatccaat tacttatcaa acgatcctaa attttggatg tatagctcaa gcaatataga    57360
tgcatgtaaa cttaataaag tgagttttct tcctactgaa aattcaaatt ttaaacctgt    57420
agaaaaatgg cacgctgacg cgattgagaa gtctcttaag gcagtagatg atgaactcgt    57480
taaagcgacc aatgaagtgc tagaagctga aaaggcgtta gaacaagctc agtcaagggt    57540
tcaaaatctg acaaagcaac gttctaaact gaacaatgca ctaaatgcac tgaactagtt    57600
tactttgcca caaggatgtg gtataatgtt tttacttttct actgaggaga ttattatgac    57660
tcgtaacgaa tatatcaaat cattcaatag cgttattgat gataaagcta taccgatgtt    57720
tggccaaaat agcgttcttt ctattatcaa tcaatggctc aatagtgttg atgcaagtat    57780
tgtttcttct actaaattta ttcatgaaat tcgtaaaatt tctagccgtg tagataaaga    57840
tgttatcaag aaaacccttta aagagtctcg tcttctttca tatttggtta atcgggatat    57900
tcttggtaat tttgggaaag aaattaaacg aactaaagat gtagtaggat acaattggtt    57960
cggtgatgtt aattcttatc atcttaatat taaagaagac cctgagaata tttttactcg    58020
tcgttggatc agtaatttca gactttttaa gaaacaaatt ctaaaatcag cttctaaatt    58080
```

FIG. 17FF sequence.txt

```
atgttatggc gattatcgtc aaattcatcc tttggcttct gatatgatta tcataaaga   58140
atatgaactt gataaaaata aagtatctat ttttgtgaat tatggatttt ttacaccaga   58200
aactaaccaa aagaatatta ataaattttt ctcaattgct agcactataa ctcgtcaatt   58260
agagaccgca ttactttgta tggaaacagt agaaaatatt catacatatc cttttaagaa   58320
tatatgcggt tgggaaggat ataaactcgt aattagcctt cgtgaagtga aatgtgctta   58380
ttcacctact gataaagaaa tttaccaaca aaaatgtgat gaaattgtga atactcctaa   58440
agaagaaact acccttgagg aactaatgga atgtcttgat gattcacctg aaccgataga   58500
aattcgtcca gaagttattg cactagaaaa agcttataaa gaagttctag aaatttctaa   58560
taaagcgcag aaagaatatg agcaggctaa aaggatttgg gaagaatctg ttaatcgtct   58620
tgatcgtctg gaacaagctt tacagttaat taagtaattt aaagccaagg atggctcgga   58680
gtataaatca ttaaccaagt gagaagaaca tgaaaactcg taaacattat attgattatt   58740
ttgacagtct tattactaaa catcgtaatt atcagatagg acacagagca gtaatcaata   58800
atattcttcg tgattttta gactatattg gatgggaaaa ccatatttgt aaagatacac   58860
aaaatgcgta ttcacattct cttggttctt tgctcgagtg gttcaaacgt tcccgattac   58920
tatcttctgt gatagctgtt aataatgtta aaaaatttat gtatccaagc tacattgaga   58980
ctaatgtatc aaatgctagt gttgttacat ttaatattat taacgacgtg aaaagaactt   59040
atttagaaga atggttttct aaagatagta aagaaaaatt tgctagtgaa ttttcacacg   59100
aattcaataa taacgtgaat atgctttta agcattctcg tagactgttt tgtcatggtg   59160
ataaccgtac tattaatgtg aatgtaaaag actgggttac ggctaaattc actccatcgt   59220
cccagaatgg gcaatttgaa ttgtcaatta tcatttgtgc tccgcacgag atatataaaa   59280
accttccgta tatgaaacca cgcgaagcta ataaacacaa tgaaactatt agttctttgg   59340
cttataattt acgcgtgtta ttatctgata tggatgtagt caaatccttt gatgataata   59400
cgaattatgg tctttcgctg tttgaaacta aatttgttat taaattaaag gaccctagtg   59460
aatttaaacc tacaccaaaa tccaatcatg gaaatgatac tatgaaagaa gaacgcgaat   59520
atctcagtgc ccgtttgatt gaagttgaaa aacagattga agagcatact aaagttctta   59580
aggctttaac cgccaaagca aatggtttac gtaatgctat tgaggtattg aaatgaaaaa   59640
gcgtttatta gaagacattg cagcttcaag taattccagt ttaattaaaa ttattatggc   59700
tggtgaggaa gatgatatgg aaatgcgtgg aaagattcac ggctgcgacg atttagattt   59760
taaacctcca gcatgggatg ctattatggc tatggttgaa cgacgtgaaa gagcttctaa   59820
aaacgttcct aattgccctg aatgcggtac tgaacaagtt caattgatta actggcgtaa   59880
accagagctt gaatataaat gccgtcaatg taaacataaa ttcagtaagc atgctccgga   59940
aatggttaaa ttgcctgact ctactgagtt ctttaaagaa cttgtgagtg ttcaaccaat   60000
```

FIG. 17GG sequence.txt

```
gcctaataat attttggatt aaaaatgacc aagcgtaaag aatatatgga ggctgctgaa      60060
aaggcagtcc gtgaattagc aatagcttat tataatgaac atggtaaatt tcctgataga      60120
tacagcgtgc ttaaatctgc tttaactcgt tcatataaaa atatgctatc agaagtaagt      60180
gatattatat acaaacataa agaacaaacg ggccaaagtc ttgattacga cgagactttt      60240
aaacaagtac taggaattaa ggaataatat gtttaaagta tatggttatg atagcaacat      60300
tcataaatgt gtgtattgcg ataatgcaaa acgtcttttg accgtgaaga aacagccgtt      60360
tgaatttatc aacattatgc cggaaaaagg tgttttttgat gatgagaaaa ttgctgagct      60420
tctgactaaa ctaggtcgtg atactcaaat cggcttgaca atgccccagg tatttgctcc      60480
tgatggaagt catattggtg gatttgacca actgcgagaa tattttaaat gatgctcgaa      60540
ggaactgact atattcatga ttaccgcgga agcgcggtat atgtaggtga tgaagttgca      60600
gtttattatg ggtatggaac tttgatgaca gccaaggtta ttcaaattaa aaataatcgt      60660
gctaaactcg aagtttatta ttctaatggt gaaaagtcta tttctaagtg gaaatacggc      60720
gattgtatgg ttaaattggg gtaaatatga tttacgatat taatgtatca agaactccgt      60780
caatggttac tattccagcc gaagaactag atcgtcttca gaaaattgaa gagcttcttt      60840
gggaaattga atctgatttg ccatcaggat tagaatcctg gattgattat gaagaactta      60900
ataagcttcg gggttaaacc ttggtgggcg gctagatggg aaactgtaga gccagagccg      60960
gaagaaccgg tttacattga tgaagaaaca gtatataatg aaccaacgat aaatgactta      61020
attgatatgg agatgggaca tgattacagt agataagtgg tttagaatta atcgtgttga      61080
tacagggcta tgtaattact ggccggaact tagtgcaggt actgtcttta aagttcgtga      61140
acttgcaaaa gaatgcgaag atgatataga acctgatact ggaattattg aaattgaact      61200
ttccgacgga aagattatta acatctatga taagccaatt acatactggt gtttgtggaa      61260
tactgaatcc gttgaaaatg gcgaaattga agaagttgta gagagaacta gccaagatgt      61320
tcagaagcct aaagccgctt ttcaaggtga acgtatttca tacgcattag ctaaattagc      61380
tgcgcaagaa aataacgatg gctatgaagg taacctgatg caagctgccg cagagtacat      61440
tgaatggctt gaaactcaaa tttctttttc tgaccaaaag attcggcaat ataagcgatt      61500
gcatcaaatg ttttacaata cttgaaaaaa ctcaaaattc tttttctgac aggacatttt      61560
aatgaaaacc gaattggttt atactgaaaa gttaaatggc ggtaaggttt ggaaactttt      61620
tattaaagga cattctacgg accctcatat gaccacttgc gtaggaacct attctcgtcc      61680
tactaaaaag atgattcgac agtataaacg attgcatcga atgttttaca atacttaaaa      61740
ataataaata cccttatcta tttaaggtaa gggtatttat tatgttattg actggcaaat      61800
tatacaaaga agaaaaacaa aaatttttatg atgcacaaaa tggtaaatgc ttaatttgcc      61860
```

FIG. 17HH

```
                              sequence.txt
aacgagaact aaatcctgac gttcaagcta atcatcttga tcatgaccat gaattaaatg    61920
gaccaaaagc aggaaaggta cgtggattgc tttgtaatct ctgcaatgct gcagaaggtc    61980
aaatgaagca caaatttaat cgttctggct taaagggaca aggtgttgat tatcttgaat    62040
ggttagaaaa tttacttact tatttaaaat ccgattacac ccaaaataat attcatccta    62100
actttgttgg agataaatca aaggaatttt ctcgtttagg aaaagaggaa atgatggccg    62160
agatgcttca aagagagatt gaatataatg aatctgacac caaaacacaa ttaatagctt    62220
catttaagaa gcagcttaga aagagtttaa aatgacaatt gaaaaagaaa ttgaaggatt    62280
gattcataaa actaataaag acctttaaa cgagaatgct aataaagatt ctcgtgtttt     62340
tccaactcaa cgggaccta tggctggtat tgtgtctaaa cacattgcca aaaatatggt    62400
cccgtctttt attatgaaag cgcatgaaag cggaattatt catttccatg atattgatta    62460
ttcccctgct cttccatta ctaattgttg tttagtagat ttaaaaggaa tgcttgaaaa    62520
cggatttaag cttggtaatg cacagattga aactcctaaa tcaattggcg ttgctactgc    62580
aattatggcg caaattactg cacaggttgc ttctcaccaa tacggcggaa cgactttgc    62640
taatgtagat aaagtacttt ctccttatgt taaacgcacc tatgcaaaac atattgagga    62700
tgcagaaaaa tggcaaatcg ctgatgcgtt aaattatgct caatctaaaa cagaaaaaga    62760
tgtatacgat gcattccaag cttatgaata tgaagtaaat actctcttta gttcaaacgg    62820
acagactcct tttgtaacaa ttacatttgg tacgggaact gactggactg aacgaatgat    62880
tcagaaagca attctgaaaa atcgtattaa aggtctcggt cgtgatggga taactcctat    62940
tttcctaag cttgttatgt tcgttgaaga aggcgttaat ctttataaag acgatccgaa    63000
ctatgatatt aagcagcttg ctttagagtg tgcaagcaaa aggatgtatc ctgatattat    63060
ttcagctaag aacaataaag ctatcaccgg ctcatctatt cctgtttctc caatgggttg    63120
ccgcagtttc ttgagcgcgt ggaaagattc aaccggtaat gaaattcttg atggacgtaa    63180
taatcttggt gttgtaacac tgaatcttcc tcgtattgcg ttggattctt atattggaac    63240
acagttcaat gaacagaaat ttactgaatt gttcaatgag cgaatggatt tatgttttga    63300
agctttgatg tgtagaatta gttccttaaa aggagttaaa gcgactgttg ctcctattct    63360
ttaccaagaa ggtgcattcg gggttcgtct taaacctgat gacgacataa ttgagttatt    63420
taaaaacggt agaagttcag tgtctttagg atacattggt attcatgaat tgaatattct    63480
tgtcggtcgt gatattggac aagaaatttt aactaaaatg aatgctcgtc ttaaacagtg    63540
ggctgaaaga actgggtttg cttttagttt gtattcgact cctgctgaaa acctttgtta    63600
tcgcttctgt aaacttgata cagaaaaata tggaagtgta aaagatgtta ccgataaagg    63660
atggtacact aacagtttcc atgtttcagt agaagaaaat attactccgt ttgaaaagat    63720
ttctcgcgaa gccccatatc atttcattgc gacaggtggt cacatttctt atgttgaact    63780
```

FIG. 17II sequence.txt

| | | | | | |
|---|---|---|---|---|---|
| tcctgatatg | aaaaataacc | taaaaggtct | tgaggctgtc | tgggattatg | ctgcacaaca | 63840 |
| tttagattat | tttggtgtta | atatgccagt | agataagtgt | tttacatgcg | gaagtaccca | 63900 |
| tgaaatgact | cctactgaaa | acggatttgt | ttgttctatt | tgtggagaaa | ctgatcctaa | 63960 |
| aaagatgaac | acaataagaa | gaacatgtgg | ttatttggga | aatccgaacg | aacgcggatt | 64020 |
| taatctcggc | aaaaataaag | aaatcatgca | tagggttaag | caccaatgaa | ttatgataga | 64080 |
| ttttatcctt | gcgattttgt | taatggtcct | ggctgcagga | ccgttctttt | cgttacaggt | 64140 |
| tgtttgcata | aatgtgaagg | gtgttataat | aaatcaacat | ggaatgctag | aaatggtatt | 64200 |
| ccattcactg | gtgaaacact | agaacaatta | attgaatgtt | tgaataatga | ttatatagaa | 64260 |
| ggattaacta | taaccggagg | tgaccctctt | tatcctgata | acagagacgt | gattcattgc | 64320 |
| atcgttcaaa | cagtaaaaaa | tctttatccc | aataaaagca | tttggttgtg | gacaggatat | 64380 |
| aagtttgaag | atattaaaca | actagaaatg | cttaaatatg | ttgatgttat | tattgatggg | 64440 |
| aagtatgaga | aaaatcttcc | gactaaaaag | ctgtggcgag | gatcagataa | tcagcgactt | 64500 |
| tggtcaaata | ccgatggggt | gtggaaacat | gattaaattg | aattatatta | tggatactat | 64560 |
| aaatgatatg | atttttcatt | ttggtccaga | attttattcc | caatatagtt | tagtgcttat | 64620 |
| caatgcttgg | ttaattaatt | aagggtaaaa | tatgtataaa | tttcgtaaag | gtttagctga | 64680 |
| ttttcttaca | actgtaacat | tctttctgtt | tatggcagtt | ggagctattt | tccttattcc | 64740 |
| ttttattgct | atattttcg | tgattagttt | aatttctcca | gaaaagggct | tatcttctag | 64800 |
| tgagtttaat | gagcgtctgg | ataaaattac | taacaagctg | aatgctgttc | ttgataaaaa | 64860 |
| ggcttaatta | tgattagttt | tgagcggtat | gtagtagaga | gttggaatgg | ttttgatatg | 64920 |
| ttcggtaatg | actattattt | ctatgaatgt | agtctgaacc | caagcttctg | ggctggacgt | 64980 |
| gaacaagacc | tcgaagaaat | caacgctcgt | gccgatttgt | taggtgaact | gcctactact | 65040 |
| tatttcacct | tgatgaatc | cggcttcgtt | atccaggttt | attttcctga | agaaaactct | 65100 |
| ggtgaggatt | ctgttaatcc | tccttattgg | gcttaccaag | gaattatttc | tcgtggaaca | 65160 |
| aaactcgaac | ttaaagaata | agattgaagt | ctatggaatt | ccagatgaag | taggtcgttg | 65220 |
| tcctggatgt | caatcagtta | caaaacttct | aaaggagctc | aatgctcctt | ttactttcta | 65280 |
| taaagttctt | acaaataatg | gtaagattga | gtatgatcgt | ccactgattg | tatctcttgc | 65340 |
| taaacgcgct | ggattcacat | ctcttaacat | tcgttatcca | gtcattttca | ttaatgattc | 65400 |
| tagacaaaag | aacattaaac | acttcaaaga | aactctcatt | tcacttggat | atgatagaga | 65460 |
| tatcatagaa | gactaagacg | ggccctctgg | gccttctttt | ctcacattct | gtatattacc | 65520 |
| attctaagct | atcgttccct | tcttatcatt | ccctaaaata | atttcacaaa | gttgtttaca | 65580 |
| acaagttcaa | actgtggtat | tattaacata | tgaattgcct | ttgaggattt | gatatggttg | 65640 |

FIG. 17JJ sequence.txt

```
tggttgataa agagattaaa aagggacaat attattttat taatggtaat gttgttcgtg    65700
ttacttatgt aaacggtttt gaagtttatt atcttatact caagttacat aaacagatga    65760
tttgtgatcg tgctgtattt agttcagttg ctaaggaaat taaactccat gggtaaaacg    65820
tatcgtcgta aagatttaaa agtacgtgat tatgactatt tcggaaagcg taaagctcct    65880
gatggtgtaa gtcataaaga tatggttgaa aacattttc gctctgataa atggcgtaga     65940
atgaaaggca ttgattcaga agttaaagat gagctaaatc gtcaattacg tagtgaagta    66000
agaaagttga aaaaatcagt ttacattgac gatgattttg attacaatac ttctcaacga    66060
gttgctaagc gcaaatcaaa cgagtgttat cgttatagct gaggaaaata tgaatatcaa    66120
acgcatgctt tttaagcaag ggctatatac tttaaatgct actccaaaag gcgatacaac    66180
taagtggtca gtaaatgact ggattaaatt tattgatgaa aacggtaatt gggaaattta    66240
aatgaatcct gaatctaaat tatcgcagcg aattgctgaa gaacgcgcca aattttcca     66300
gaacatgaaa cacaatggta ttgaggatga agttttcta aattggttct ggaataataa     66360
gtatgcagca tgcgaaggag ccttgtcatt gtcagtcgca atgatgtacg aaggctggaa    66420
gggtgccaaa aagtttagct aagggcttcg gccctttttg gataataaaa ttttaatgca    66480
attgaggata atgtatgact attcaaatta aaacgccat caattcttac gcatatgata     66540
aagtagtttc tctgctagaa aaaggcgata ttgtaactcc tcaaattttg gataaatggg    66600
aaaaagagct tcatcagacg atgaaacaga atgatcagaa gattggacgc aatactgtcc    66660
gtgaattgtt ggttcaatat atcttgtcag aatttgatgt taaagctttt ggtgtagaat    66720
ctaaagctta tcaaaagcat gaaatttccg ataaaactat tcgtcgtatg aaaaatcaac    66780
gcaagaaaaa atttgcagac ctgaaaatta ctaaggtata attatgaacg aagctcttat    66840
taacgatttg cgtcttgccg gatatgaagt aaatacaaat ggcattggtt taactcaaat    66900
tgaaggaaac ggattcatcc ttgagtatga atttagccaa tggtggttat atgccaatta    66960
cggcgaattg attgaatatg ttgaccaatt tgattcacta gatgcagctc ttgaagcggc    67020
taagttgatg aatgtatgaa attaattaat atttctattg ctattgaaaa ttttggtatt    67080
ttctatgttg accaatacat gaaaatttca tttttcccaa ataaaactgg tgttggatat    67140
tgggaaagcc atgtttctga attaaatgaa agtgaatatg ttagtacaca taaaaagttt    67200
ttagactttt tatatcgcgc tgatattaat gatcattaca tagatattca tgaatttaaa    67260
aagatgatgg agaaagtgtt ccaagcatac tgcttactta gataactgat atcctctatg    67320
ctttaagata gatcttcaaa tattatgata taatagatct atgaattgag ctaagaggtg    67380
aaaatgtcag aaactaagcc taagtataat tacgtaaaca ataagagct tttacaagct     67440
attattgatt ggaaaacaga attagcaaat aataaagacc caaataaagt agttcgtcag    67500
aatgatacta tcggattagc cattatgctt attgcagaag gcttatctaa acgtttcaac    67560
```

FIG. 17KK sequence.txt

| | | | | | |
|---|---|---|---|---|---|
| ttttcaggat | acacccagtc | ttggaaacaa | gaaatgattg | cagatggtat | agaagcttct | 67620 |
| attaaggggc | ttcacaattt | tgatgaaacg | aaatataaaa | acccacatgc | gtatataact | 67680 |
| caagcttgtt | ttaatgcatt | tgtccaacgt | attaaaaaag | aacgtaagga | agttgcaaag | 67740 |
| aaatatagtt | acttcgttca | caatgtctat | gacagtcgtg | acgacgatat | ggttgcgtta | 67800 |
| gtagatgaaa | cttttattca | agacatctac | gataaaatga | cgcattacga | agaatcaacc | 67860 |
| tatagaacac | cgggggctga | aaagaaaagt | gttgtagacg | attctcctag | tttggatttt | 67920 |
| ttatatgagg | ctaacgatta | acctctccgg | attcttggaa | gaaatacctg | aagttgaagc | 67980 |
| tattccctat | ttacttaaaa | tgtatctcag | ggaagtttta | gctcttgaca | ttgatattga | 68040 |
| tccagaaaat | ccgtatgata | ccgcttttaa | atctaatggt | gtagaattaa | actatcggta | 68100 |
| tcatttaaca | gatgatgatt | tttattttat | attagagaaa | taatatgact | gataaacccg | 68160 |
| aaattaatga | tgaagtggaa | aagcttattt | cttctattga | agaaaagaac | cgtcttgaag | 68220 |
| cagaaagaaa | agcaaataag | ttattgtcta | aaaacaaacg | cgaactgaat | cgtctttata | 68280 |
| agcacgctca | gatcgcagct | gaaaacaata | attttgctca | atacgaatat | gctatcaaga | 68340 |
| aaagtcggga | tattctgaaa | cagccatata | acgatgaact | catcagtatt | ctttggaaga | 68400 |
| ctactagatc | gcagattgag | gatatgattg | atgcttacac | acgtaaaatt | caagcgtctt | 68460 |
| aaaattaatg | caggatttac | tgaatctttg | aatggtcatc | tttgtgtgaa | aatttctgaa | 68520 |
| aaagaatacc | atgatagttc | aattaaagaa | gttaatcctc | ctattgtaag | agcagacccc | 68580 |
| aatatgaaag | tgtgggttga | ttcttatcaa | gtcaaaaaat | ggtggcagtt | atgaaagatg | 68640 |
| aacacccaga | cttctgaaat | agattataat | aaaattcgtt | cctctaaaga | ggaaatgatg | 68700 |
| agacgcttta | aagagtctca | tgataaagct | aaagcagaag | gaactataaa | atataagcgc | 68760 |
| ataaaattta | aaagttctaa | cgagcctctg | tatggcgtat | tatgtggata | ggagcttcgg | 68820 |
| ctcctatatt | gctttataaa | tttttggtaa | aataaaccaa | aacaaagagg | atattaaatg | 68880 |
| aaagtatgta | tttttatggc | tcgaggtctt | gaaggttgcg | gtgtaactaa | attttctctt | 68940 |
| gagcagcgtg | attggtttat | taaaaatggt | catgaagtaa | ctttggttta | tgctaaagat | 69000 |
| aaatcattta | ctcgtaattg | tgcgcatgat | tataaatcat | tttcaattcc | ggttttatta | 69060 |
| gcaaagaat | acgataaaac | acttaagctg | gtaaatgatt | gtgatattct | aattatcaat | 69120 |
| tcagttcctg | ctacttcggt | tgaagaagac | actattaata | actataaaaa | aattattgat | 69180 |
| aacattaaac | cttctgttcg | tgttgtagtt | tatcaacatg | accattcttc | tctttctttg | 69240 |
| cgccgaaatt | tgggattaga | agaaactatt | cgtcgagctg | atgttatttt | tagccattct | 69300 |
| gataatggtg | attttaataa | agttctgatg | aaagaatggt | atcctgaaac | agtttctctg | 69360 |
| tttgatgata | ttgaagaagc | accgacagta | tataactttc | agcctcctat | ggatattgcg | 69420 |

FIG. 17LL sequence.txt

| | | | | | | |
|---|---|---|---|---|---|---|
| aaggttcggt | caacctactg | gaaagatgtt | tctgaaatta | acatgaatat | caaccgttgg | 69480 |
| attggtcgta | cgactacatg | gaaaggtttt | tatcagatgt | ttgattttca | tgaaaaacat | 69540 |
| cttaaacctg | caggactaag | tactattatg | gaaggtctgg | aacgttctcc | agcgttcatt | 69600 |
| cctattaaag | aaaaaggaat | tccatacgag | tattatcgtc | ttcatcaagt | agaccaaatt | 69660 |
| aaaattgctc | ctaatttgcc | aacgcaaatt | cttgaccgtt | atgtaaatag | cgaaatgctt | 69720 |
| gaacgcatga | gtaaatccgg | atttggttat | cagctgagta | agttggacaa | aaaatatcta | 69780 |
| caacgttctt | tagaatatac | tcatctcgag | cttggtgcat | gtggaacaat | tccggtattt | 69840 |
| tggaaatcta | ctggcgaaaa | tttaaaattc | cgtgttgata | atactccttt | gacctcgcat | 69900 |
| gatagcggta | tcatttggtt | tgatgaaaat | gacatggaat | caacatttga | acgtattaaa | 69960 |
| gaactgtcat | ctgaccgaac | tctttatgac | cgtgaacgcg | aaaaagctta | tgaattttg | 70020 |
| tatcagcatc | aagattcaag | cttctgcttt | aaagaacagt | ttgacattat | tacaaaataa | 70080 |
| agggcttcgg | ccctttagct | ttatacggag | tttgatataa | tgatatttct | tggatatgtg | 70140 |
| atactttttc | ttgcatttta | tctattcact | agagcatgtt | ggattgggtt | ctttagcacg | 70200 |
| ccagatgggt | ttatttcaat | aattttattt | tgcatttcaa | tgacggttct | tgatatatga | 70260 |
| aaattttaaa | tttaggtgat | tggcatttag | gcgttaaagc | cgatgatgag | tgggttcaat | 70320 |
| ccattcagtt | ggatggaatt | aaacaagcaa | tagaatattc | taagaaaaat | ggaattacta | 70380 |
| cctggattca | atacggtgat | attttgatg | tgcgaaaagc | aatcacacac | aaaactatgg | 70440 |
| agttcgcccg | tgaaatagtt | caaatgcttg | atgatgctgg | tattacccta | catactattg | 70500 |
| taggaaacca | tgatatgcac | tttaaaaata | ctttaactcc | aaatgcctct | actgagcttt | 70560 |
| tggctaaata | tcctaatgtt | aaagtatatg | ataagcctac | tacagtagat | tttgacggat | 70620 |
| gtttaattga | tttaattcct | tggatgtgtg | aagaaaatac | tggtgaaatt | cttgagcata | 70680 |
| tcaaaacttc | atctgcttct | ttttgtgttg | gtcactggga | actgaatgga | ttttattttt | 70740 |
| ataaaggaat | gaaatctcac | ggtcttgaac | ctgatttcct | taagacttat | aaagaggtgt | 70800 |
| ggtctggtca | cttccatact | atctctgagg | ctgctaacgt | cagatatatt | gggacaccat | 70860 |
| ggacactaac | tgcaggtgac | gagaatgacc | ctcgtgggtt | ctggatgttt | gatacagaaa | 70920 |
| cagaacgaat | ggaatttatt | ccaaacaata | ctacctggca | tcgtagaatt | cattatccat | 70980 |
| ttaaaggaaa | aattgactat | aaagatttta | caaatctatc | agtacgtgtt | atagtaactg | 71040 |
| aagtagacaa | aaatctgacg | aagttcgaat | ctgaactaga | aaaagttgtg | cattcattac | 71100 |
| gagttgtgtc | aaagattgat | aactctgtcg | agtcagatga | cagtgaagaa | gttgaagttc | 71160 |
| aatctcttca | gacgttgatg | gaagaataca | ttaatgcaat | tccagacatc | actgattctg | 71220 |
| accgtgaagc | acttattcaa | tatgcaaatc | agttatatgt | agaggcaaca | caatgacttt | 71280 |
| tgatgaattt | aaaaatgtta | tgatgagtca | gcattttgaa | tgcgaagtaa | aagatgatat | 71340 |

FIG. 17MM sequence.txt

```
tggtcataaa gaaattattg aatattggtt tgaaccgcta gaggttgaag ataattgtat    71400
taaaaaagtt acggtctgta cagattgggc tgtatctttt aacttcaaca ttttagataa    71460
tgacacacct aaatcattgc gagatatggc cgtatcttgt attaaggatg catactgtga    71520
agttttcgac atttgacatt aatgatgaat tcatagcaaa cattgattat accgaagaag    71580
attctagata tgttggaata atttatatta catcaaaaac agcacaaggt gttgtttgca    71640
tggctgaatt tgatgaatac tttttagatt atgatgatat gatagaatgg tctaaaagat    71700
acattaaaag gaatcttttg tgaagaattt taaactaaac cgagttaggt accaaaatat    71760
aatgtcagta ggtggaaatc ctattgacat tcaattagat aaggttcaaa aaactcttat    71820
tactggacga aatggtggtg gtaagtctac tatgttagaa gccatcacat ttgggctttt    71880
tggcaagcca tttcgtgatg taaagaaagg tcaattaata aacagcacaa ataagaaaga    71940
acttttagtt gaactgtgga tggaatatga tgagaaaaag tactatatca aagaggaca     72000
aaaccgaac gttttcgaaa tcaccgttaa cggtacacgt cttaatgaat ctgccagcag     72060
taaagatttc caagcagaat ttgaacagct tatcggaatg tcatatgcca gtttcaagca    72120
gattgttgtc cttggtacag cagggtatac cccttcatg ggtttgtcga cccctgcgcg     72180
aagaaagctt gtggaagact tgcttgaggt aggaacatta gctgaaatgg ataagcttaa    72240
taaagcacta atacgcgaat taaattcaca aaaccaagtg cttgatgtta aaaagatag     72300
tattatccaa caaattaaaa tatataatga taacgttgaa cgccagaaaa aattaacggg    72360
tgacaacctt actcgtctgc aaaatatgta tgatgatttg gcaaagaag ctagaacgct     72420
aaaatcggaa atagaagaag ctaatgaaag attagttaat attgttttag acgaagaccc    72480
gactgatgca tttaataaaa tcggtcaaga agcagtttta attaaatcaa aaattgactc    72540
gtataataaa gtcattaata tgtatcacga aggtggatta tgcccaacct gtttgtcaca    72600
attaagttcc ggtgataaag ttgtttctaa aattaaagat aaagtttctg aatgcacaca    72660
ttcatttgaa cagcttttcaa cgcatcgtga taatttaaaa gttcttgttg atgaataccg    72720
agataatatt aaaacccaac agtcgttggc aaatgatatc cgcaataaaa agcaatctct    72780
aatcacgacg gtagataaag ctaaaaagt taaagcggct atagaaaaag catcttctga    72840
gtttattgac catgctgatg aaatagcact gcttcaagaa gaacttgata aaattgttaa    72900
gacaaaaact aatttagtaa tggaaaaata ccaccgagga attttgactg atatgctcaa    72960
agattctggt attaaaggtg ctattattaa aaagtacatt ccattattta ataagcagat    73020
taaccattat cttaaaataa tggaagcgga ttatgtgttt acattagatg aagaatttaa    73080
tgagacaatt aaatcccgtg gtcgtgaaga ttttagttat gcttcattca gtcaaggtga    73140
aaaagcacga attgatattg ctcttttatt tactggcgt gatattgctg aaaaagtttc     73200
```

FIG. 17NN sequence.txt

```
aggtgttaaa ataaacacac taattcttga tgaagttttt gattcagcga ccgacgttga    73260
aggtgtaaaa gctatttcaa ctatttaga  tagtttaaaa aatactaacg tttttgttat    73320
ttcgcataga gaccatgacc cgcaagcata cggtcagcat cttcaaatga agaaagttgg    73380
tcgatttact gtaatggttt aatttataag agattatgct ttaatttatt agagtataat    73440
ctctatggag gaaaaacatg gaatattcaa ccggacagca tctattaact attcctgaaa    73500
taaaacgata tattctgaga aataatttt  ctaatgaaga gcatatagtt actgaatcta    73560
tgcttaggaa tgcatttaaa gcagaatata caaaaataat gtccaataga aatgaagctt    73620
ggactgttac tgattattat gactaaaggt gtattatgac taaaattact gtgaattata    73680
ctgttgatgt aaaagatatt cagccaaaac acgtgcgttc tgaatcaaat ccacaaaacc    73740
aaaataaaat tcgtcgagca tgggttttgt ctctttctga taacgcaatg gaagttattc    73800
agaacaaaat taaatctgca cctgctcgtc atgcgtatta tgaagctatc gatcgtgaag    73860
taagtaataa atggattgaa ctaatgcgca aacatactac agaatcccta aacgctggtg    73920
ctaaatttat tatgacttca tgtggtgaac gccttgaaga tgaatattgt ggcaatgcag    73980
atgaacgtct gattgttgcc gctcaaattg ttgccgaaac aatcgcagct gattttaatc    74040
gttaattgct ttattaaatt agttataaaa ttaaatctca tttgaattga aggaaattac    74100
atgaaactgt ctaaagatac tactgctctg cttaaaaatt tcgctactat taactctggt    74160
attatgctta aatccggtca atttattatg actcgcgcag ttaatggtac aacttatgcg    74220
gaagcaaata tttctgacgt tattgatttt gatgtagcaa tttacgattt gaacggtttt    74280
ctcggtattc tgtctctagt taatgatgat gcagaaattt cccagtcaga agatggaaat    74340
attaaaattg ctgatgcccg ctcaacaatt ttttggccag cagccgatcc gagtacagta    74400
gttgctccta ataaaccaat tccattcccg gtagcatctg ttgttactga aattaaagct    74460
gaagaccttc aacaactgtt gcgtgtatct cgtggtctgc aaattgatac aattgctatc    74520
acggtaaaag aaggtaaaat cgtaattaac ggttttaata agtagaaga  ttctgctttg    74580
actcgtgtta aatattcttt gactcttggt gattatgatg gtgaaaacac atttaatttc    74640
attatcaata tggcaaatat gaaaatgcaa ccaggaaatt ataaacttct gctttgggca    74700
aaaggtaaac aaggcgctgc taaatttgaa ggtgaacatg cgaattatgt agtagctctt    74760
gaagctgatt ctaccatga  ttttaatag  agggcttcgg ccctttataa tttacactaa    74820
aacttgaatg aggaaattat gattaccgta aatgaaaaag aacacattct tgaacagaaa    74880
tatcgtccat ctactatcga tgaatgtatt cttcccgcct ttgataaaga aacctttaaa    74940
tctattacaa gtaaaggtaa gattccacat attattcttc attctccttc tccaggaaca    75000
ggtaaaacaa ctgtagcaaa agcattgtgt catgatgtaa atgctgatat gatgtttgtg    75060
aatggatcag actgtaaaat tgatttcgtt cgtggtcctt tgactaattt tgctagtgca    75120
```

FIG. 1700 sequence.txt

```
gcttcatttg atggtcgtca aaaagtaatc gttattgatg aatttgaccg ttcaggttta    75180
gcagaatctc agcgacatct tcgttccttt atggaagctt atagttcaaa ctgtagtatt    75240
attattactg ctaacaatat tgatggtatt attaaaccac ttcagtcacg ctgccgagtt    75300
attacgttcg gtcaaccgac cgatgaagat aaaattgaaa tgatgaagca gatgattcgt    75360
cgattgactg aaatctgtaa gcatgaagga attgctatag ctgatatgaa agttgtagca    75420
gctttggtta aaagaatttt tcctgatttt cgtaaaacta ttggcgagct cgatagttat    75480
tcatctaaag gtgttttgga tgctggtatt ttatcactgg ttactaacga tcgtggtgct    75540
attgatgatg ttcttgagtc tctcaaaaat aaagatgtta acaactcag agctttagca     75600
ccaaaatatg cagccgatta ttcgtggttc gtgggtaaac ttgccgaaga aatctattca    75660
cgtgtaactc cacagagtat tattcgtatg tacgaaattg tcggcgaaaa taatcagtat    75720
catggtattg cagctaatac tgaattgcat ctagcttatc ttttcattca gttagcatgt    75780
gaaatgcagt ggaagtgata tgagcttatt tgaagatgat attcaattaa acgagcatca    75840
agttgcttgg tattcaaaag attggacagc cgtccaatcc gctgctgatt cttttaaaga    75900
aaaagctgaa aatgagtttt ttgaaataat tggagctatt aataataaaa ctaaatgctc    75960
tattgctcaa aaagattatt caaaattcat ggttgaaaat gcattatcac aatttccaga    76020
gtgcatgcca gctgtatatg caatgaattt aatcggttct ggattaagtg atgaagctca    76080
ttttaattat ctaatggctg ctgttcctcg tggtaaaaga tatggtaaat gggcaaaact    76140
ggttgaagat tccaccgaag tattgattat taagttactt gctaagcggt atcaagttaa    76200
tacaaatgat gcaattaact ataaatcaat tcttactaaa aatggaaaac ttcctttagt    76260
attaaaagaa ctaaaaggtt tagtcacgga tgattttttg aaagaagtga ctaagaacgt    76320
aaaagaacag aaacaactca aaaaactagc attggaatgg taaaatgatt gaaattactc    76380
ttaaaaaacc tgaagatttt ctgaaagtaa aagaaacttt gactcgtatg ggaattgcta    76440
ataataaaga taaagttctg tatcagtcct gtcatattct tcagaaaaaa ggactatact    76500
atatcgttca ttttaaagaa atgcttcgta tggatggccg tcaagttgaa atgacagaag    76560
aagatgaagt tcgtcgtgat tcgattgcat ggctgttaga agattggggg ctgattgaaa    76620
tcgttcctgg tcaaagaact tttatgaaag atttaactaa taacttccga gttatttctt    76680
ttaaacaaaa acatgaatgg aaactcgttc ctaaatatac gattggtaat taatatgact    76740
gctataactc cacaagaata catggcgtct cttaaagaaa aatataatct ttctgcaaca    76800
gaaacacttt ttgatttacc agaaaacctc caattaaaat ttcaggtaga atttcaaaaa    76860
ttagttcacc cagaacaaaa acattttact gcagtcgtta agtcaattaa tgcagatgga    76920
atgataattt tcacccggca aatagtacta atttaagcaa ggggcttcgg cccccttattt   76980
```

FIG. 17PP sequence.txt

| | | | | | | |
|---|---|---|---|---|---|---|
| ggagtataat | atatcaagag | cctaataact | cgggctataa | actaaggaat | atctatgaaa | 77040 |
| gaattttata | tctctattga | aacagtcgga | aataacattg | ttgaacgtta | tattgatgaa | 77100 |
| aacggaaagg | aacgtactcg | tgaagtagaa | tatcttccaa | ctatgtttag | gcattgtaag | 77160 |
| gaagagtcaa | agtacaaaga | catctatggt | aaaaactgcg | ctcctcaaaa | atttccatca | 77220 |
| atgaaagatg | ctcgagattg | gatgaaacga | atggaagaca | tcggtctcga | agctctcggt | 77280 |
| atgaacgatt | ttaaactcgc | ttatatcagt | gatacatatg | gttcagaaat | tgtttatgac | 77340 |
| cgaaaatttg | ttcgtgtagc | taactgtgac | attgaggtta | ctggtgataa | atttcctgac | 77400 |
| ccaatgaaag | ctgaatatga | aattgatgct | atcactcatt | acgattcaat | tgatgatcgt | 77460 |
| ttttatgttt | tcgaccttt | gaattcaatg | tacggttcag | tatcaaaatg | ggatgcaaag | 77520 |
| ttagctgcta | agcttgactg | tgaaggtggt | gatgaagttc | ctcaagaaat | tcttgaccga | 77580 |
| gtaatttata | tgccattcga | taatgagcgc | gatatgctca | tggaatatat | caatctttgg | 77640 |
| gaacagaaac | gacctgctat | ttttactggt | tggaatattg | agggatttga | cgttccgtat | 77700 |
| atcatgaatc | gcgttaaaat | ggttctcggt | gaacgcagta | tgaaacgttt | ctctccaatc | 77760 |
| ggtcgagtaa | aatctaaact | tatccaaaat | atgtacggta | gcaaagaaat | ttattctatt | 77820 |
| gatggcgtat | ctattcttga | ttatttagat | ttgtataaga | aattcgcatt | tactaatttg | 77880 |
| ccgtcattct | ctttggaatc | agttgctcaa | catgaaacca | aaaaaggtaa | attaccatac | 77940 |
| gacggtccta | ttaataaact | tcgtgagact | aatcatcaac | gatacattag | ttataacatc | 78000 |
| attgacgtag | aatcagttca | agcaattgat | aaaattcgtg | ggtttatcga | tctagtttta | 78060 |
| agtatgtctt | attacgccaa | aatgcctttt | tctggtgtaa | tgagtcctat | taaaacttgg | 78120 |
| gatgctatta | tttttaactc | attgaaaggt | gaacacaagg | ttattcctca | acaaggttcg | 78180 |
| cacgttaaac | aaagttttcc | gggtgcattt | gtatttgaac | ctaaaccaat | tgctcgtcga | 78240 |
| tatattatga | gttttgactt | gacgtctctg | tatccgagca | ttattcgtca | ggttaacatt | 78300 |
| agtcctgaga | ctattcgtgg | gcaatttaaa | gttcatccaa | ttcatgaata | tatcgcagga | 78360 |
| acagctccta | agccaagtga | agaatattct | tgttctccga | atggatggat | gtatgataag | 78420 |
| catcaagaag | gtatcattcc | aaaggaaatc | gctaaagtat | ttttccagcg | taaagactgg | 78480 |
| aaaaagaaaa | tgttcgctga | agaaatgaat | gccgaagcta | ttaaaaagat | tattatgaaa | 78540 |
| ggcgcagggt | cttgttcaac | taaaccagaa | gttgaacgat | atgttaagtt | cagtgatgat | 78600 |
| ttcttaaatg | aactatcgaa | ttatactgaa | tctgttctca | atagtctgat | tgaagaatgt | 78660 |
| gaaaaagctg | ctacacttgc | taatacaaat | cagctgaacc | gtaaaattct | cattaacagt | 78720 |
| ctttatggcg | ctcttggtaa | tattcatttc | cgttactatg | atttgcgaaa | tgctactgct | 78780 |
| atcacaattt | tcggccaagt | tggtattcag | tggattgctc | gtaaaattaa | tgaatatctg | 78840 |
| aataaagtat | gcggaactaa | tggtgaagat | ttcatcgcag | caggtgatac | tgattcggta | 78900 |

FIG. 17QQ sequence.txt

| | | | | | | |
|---|---|---|---|---|---|---|
| tatgtttgtg | tagataaagt | tattgaaaaa | gttggtcttg | accgattcaa | agagcagaac | 78960 |
| gatttagttg | aattcatgaa | tcagttcggt | aagaaaaaga | tggaacctat | gattgatgtt | 79020 |
| gcatatcgtg | agttatgtga | ttatatgaat | aaccgcgagc | atctgatgca | tatggaccgt | 79080 |
| gaagctattt | cttgccctcc | acttggttca | aagggtgttg | gtggattttg | gaaagcgaaa | 79140 |
| aagcgttatg | ctctgaacgt | ttatgatatg | gaagataaac | gatttgctga | accgcatcta | 79200 |
| aaaatcatgg | gtatggaaac | tcagcagagt | tcaacaccaa | aagcagtgca | agaagctctc | 79260 |
| gaagaaagta | ttcgtcgtat | tcttcaagaa | ggtgaagagt | ctgtccaaga | atactacaag | 79320 |
| aacttcgaga | aagaatatcg | tcaacttgac | tataaagtta | ttgctgaagt | aaaaaccgcg | 79380 |
| aacgatatag | cgaaatatga | tgataaaggt | tggccagggt | ttaaatgccc | gttccatatt | 79440 |
| cgcggtgtgc | taacttatcg | tcgagctgtt | agtggtctgg | gtgtagctcc | aattttggat | 79500 |
| ggaaataagg | taatggttct | tccattacgt | gaaggaaatc | catttggtga | caagtgtatt | 79560 |
| gcttggccgt | cgggcacaga | acttccaaaa | gaaattcgtt | ctgacgtact | gtcttggatt | 79620 |
| gactactcaa | ctttgttcca | aaaatcgttt | gttaaaccgc | ttgcgggtat | gtgtgaatcg | 79680 |
| gctggtatgg | actatgaaga | aaaagcttcg | ttagacttcc | tgtttggctg | atagaataaa | 79740 |
| tctagggacc | tccgggtccc | ttttttcatac | aagtaatata | aatctatact | tatgaaaaac | 79800 |
| agatgattct | ggacctttag | aattccctaa | aaaattttc | acaaaactgt | ttacaagact | 79860 |
| gttcctctgt | ggtactatac | aactatcaac | taatacggat | ttggagaatg | aaatgaaaat | 79920 |
| cgctattttg | gttattgcat | taggtcttac | tggttgtgta | gctcaaggac | cggtagtaaa | 79980 |
| tcagtctgat | gtaggaaaaa | ttgtaaactg | ttcaagcaaa | ttttataatc | ctaatgtcaa | 80040 |
| gtgttataaa | gaagctccaa | agcaaacagt | agaacaaatg | caggcgaatt | ttgacgaagc | 80100 |
| tattcgtcca | gatgaatctg | ctcaagcata | tcgtaattct | gatgtaatta | cacgcgaaga | 80160 |
| aaaaattgaa | aactactgcg | cagagctttg | ggcaaattgg | gctaataatt | accaatggcg | 80220 |
| tactggtaaa | aatgctccga | tggagtatgt | agtgaattct | tataattcat | gcgtaaaaaa | 80280 |
| tttgactaag | tgaggaaaag | atggaaactt | tagtagcagg | ttcaattttt | atggttttag | 80340 |
| tttcaggcgt | gttggctatt | attatataca | tgcttccatg | gttcatcgcc | ttgatgcgtg | 80400 |
| ggtcaaaatc | gacagtagga | atcttttttca | cgtctttact | gtttaactgg | tcaattattg | 80460 |
| gttggtttat | tacatttatt | tggtcaattg | cgggtgaaac | taaaaagtct | gcacaaccaa | 80520 |
| accaggtaat | tatcatcaga | gagaaggaat | gaaaagcaaa | attataacag | tgttgctttt | 80580 |
| aatcttgatg | attataataa | gtatatacta | tagtgtaacg | gttcctctta | tgattccaac | 80640 |
| tattatttta | ggttggggtt | tattactgtt | acaagttaaa | tatgaatgta | tcaattgagg | 80700 |
| tttaaatgat | tagtgactct | atgacagttg | aagaaatccg | tcttcatttg | gggcttgcat | 80760 |

FIG. 17RR sequence.txt

```
taaaagaaaa agatttcgta gttgataaaa ctggtgttaa aactattgaa attattggcg   80820
catcatttgt agcagatgaa ccgtttattt ttggcgctct taatgatgaa tacattcagc   80880
gtgaacttga atggtataaa tctaagagct tgtttgttaa agatattcca ggtgaaacac   80940
caaagatttg gcagcaggta gcatcttcta aaggcgaaat taactcgaat tatggttggg   81000
ctatttggtc agaagataac tatgcccagt atgatatgtg tttagctgaa cttggtcaaa   81060
atcctgattc tcggcgtggt atcatgattt atactcgtcc atccatgcaa tttgactaca   81120
ataaagatgg tatgtcagat ttcatgtgta ctaatacagt acagtacctg attcgtgata   81180
agaaagtcaa tgcggttgtt agcatgagaa gcaatgattg ctgggcaggc tatcgtaatg   81240
attatgcttg gcaaaaatac gtactagata aattagtatc tgatttgaat gcaggcgacc   81300
catcgcggca atataaagca ggttctatta tatggaacgt tggaagtctt catgtgtacg   81360
aaaatcagtt ttatttagtt gaccattggt ggaacaccgg tgagactcat attgctaaaa   81420
aggattatac tggaaaatgg aagtaaatgt gccgcatgtt tataagtata aacatcctaa   81480
aactaaaaag tggtatatag gaagtcatga tggtcacaac ccgaattatg atggttcggg   81540
tgtagtttgg caacatgtta aaaagaaata tggaataaaa tcctttaata aagaaatatt   81600
atatgaagga ccaatgttta gacaggttga agaaattatt ttaacttgtt tagatgctgc   81660
taattgtccg gattcatata atttaaagaa tgaagcatgg ggaggaagtt ttccaggcaa   81720
attaaatgga atgtacggta aaaaactatc tccagaagaa agatataagt gcggaaatgc   81780
cttttcgtgga atcaagcgtc ctgatcattc taaaagaatg aaaggcgaag gtaatccaat   81840
gtatggtaaa aatgagcagg catatggaat tataaatcga gccaaggaaa attctggtaa   81900
aacttatgaa gaaatttttg gcgtagaaaa agctaaaata attaaagaaa cgatgtctaa   81960
aaatcgtaaa ggaaaacctc ataatttgat agaaaaaata tgtccgcatt gcggactaaa   82020
aggacgtggg ccaaatatga caagatacca ttttgataaa tgtaaggcac ttaaatgatt   82080
caattcgtaa ttccgagcta tcaacgtgta ggggcagttt ctgcccttga tatgtttccg   82140
actgattatg aacctcatat cgtagtacgt gaacatgaag aaaaagctta ttatgatgcc   82200
tatgggtcta aagctaaaat tgtaactatt cctgatgatg ttaatggaat tgccggtact   82260
cgtaaagcaa ttactgatat gtatgcaggt caacgaatct ggatgattga cgatgatact   82320
actattcgta tgagttcaat gcgaaaaaga gatgatcgtc gttgtgtgga taaagtcaat   82380
caattgactc gtgaacagtt ctatgaattg attcaatacg tcgaagatgc catggattgt   82440
gggtattatc acggtcatgc tcgcctacca atttttaaaa ttacttcatc ttggggtaat   82500
tatcgtgaaa attcatatgg attcacgaat acatggtatg accttggaaa acttacgaca   82560
gaacaaattg ggtatggaaa aattgatttg tgcgaagata tgtatgcatt tctcaattta   82620
attaatcaag gttatccgca tttggccttg ttcaaatatc tggttgtatc tggaaaagca   82680
```

FIG. 17SS sequence.txt

| | | | | | | |
|---|---|---|---|---|---|---|
| caagctcctg | gagggtgcag | ttcaattcgt | agtaattcta | aacataatag | agcgcttgag | 82740 |
| caaatcaata | gagagtttcc | agagcaagct | cgttggaaaa | cttctaatat | tgaaaaacga | 82800 |
| aaatcgttgg | gtgaagaaga | cgagccatta | aaggttcttc | gcatgtgcgt | ttcgcgtaaa | 82860 |
| gaaaaatcag | aagcatttca | taagtttaat | gctattcatc | caatagcagt | tgattaatgc | 82920 |
| ctaaatttat | tgtgttataa | ttactctatc | tttaaccagt | gaggaaaata | taatgatgcc | 82980 |
| tatggaaaaa | aatgaatgtc | tattgcagat | ttaaaatccc | gtttgattaa | agcttccact | 83040 |
| tctaaaatga | ctgctgaact | gactacatct | aaattcttta | atgaaaagga | tgtaattcgt | 83100 |
| acaaaaattc | caatgcttaa | tattgctatt | tctggtgcga | ttgatggcgg | tatgcagtct | 83160 |
| ggtttaacta | ttttcgcagg | gccttctaaa | cactttaaat | caaatatgtc | tttgactatg | 83220 |
| gttgcggcat | atttgaacaa | atatcctgac | gcggtttgtc | tattctatga | tagtgaattt | 83280 |
| ggtattactc | cagcttattt | gcgatccatg | ggagttgacc | cggaacgagt | aattcatacg | 83340 |
| ccaatccagt | cagttgaaca | gctgaaaatt | gatatggtga | atcagcttga | agctattgag | 83400 |
| cgtggtgaaa | aagttattgt | attcatcgac | tcaatcggta | atatggcttc | taagaaagaa | 83460 |
| acggaagatg | ccttgaatga | aaaatctgtg | gcagatatga | ctcgtgctaa | atcactgaag | 83520 |
| tcattattcc | gtattgttac | tccttacttt | agcattaaaa | atattccatg | tgttgcggtt | 83580 |
| aaccatacaa | ttgaaacaat | tgaaatgttt | agtaaaaccg | tgatgacagg | tggtacaggc | 83640 |
| gtaatgtatt | cggctgatac | tgtattcatt | atcggtaagc | gtcagattaa | agatggttct | 83700 |
| gatcttcagg | ggtatcaatt | tgttctaaat | gtagaaaaat | ctcgtaccgt | taaagaaaaa | 83760 |
| agtaaattct | ttattgatgt | taaatttgac | ggtggtattg | atccttattc | tggattgtta | 83820 |
| gatatggctc | tagaattagg | atttgtagta | aaacctaaaa | atggttggta | tgctcgtgaa | 83880 |
| tttcttgatg | aagaaaccgg | cgagatgatt | cgcgaagaaa | atcttggcg | tgcaaaagat | 83940 |
| accaactgca | ctacattctg | gggtccttta | tttaagcatc | aaccattccg | agatgctatt | 84000 |
| aaacgtgctt | atcagttagg | tgctattgat | agtaatgaaa | ttgttgaagc | tgaagttgat | 84060 |
| gaattgatta | actcaaaggt | tgaaaaattt | aaatctccag | aaagtaaaag | taaatcagca | 84120 |
| gctgatttag | aaactgacct | cgagcagtta | agtgatatgg | aagaatttaa | tgagtaaaga | 84180 |
| tgatttagat | ttagaaatta | tcgatgaatc | ccctcttcg | gagggggaag | aagaaagaaa | 84240 |
| agaacgtctt | tttaatgagt | ctcttaagat | aattaaatcc | gctatggaaa | atgttatcca | 84300 |
| ggagattgtc | attaaactag | aagatggttc | tacacacatt | gtgtatgtga | caaaattaga | 84360 |
| ttgggttgat | ggaaaagtcg | taatggactt | tgctgttctt | gaccaagaaa | gaaaagctga | 84420 |
| gttagctcct | catgtagaaa | aatgtattac | aatgcaacta | caagatgcat | ttaataaaag | 84480 |
| gtcaaagaaa | aaatttaaat | tcttttaagg | agtaagtgtg | gtagaaatta | ttcttttccca | 84540 |

FIG. 17TT sequence.txt

| | | | | | | |
|---|---|---|---|---|---|---|
| tctcatattt | gatcaagctt | attttttcaaa | agtttggcca | tatatggatt | cagaatattt | 84600 |
| tgaaagtggt | ccagctaaaa | atacattcaa | attaattaaa | tctcatgtta | atgagtacca | 84660 |
| tagcgttcca | tctattaatg | cgttaaatgt | tgcattagaa | aatagttcat | ttactgaaac | 84720 |
| agaatattct | ggtgtaaaaa | cacttatttc | aaaactagcc | gattctccgg | aagaccacag | 84780 |
| ctggttagta | aaagaaacag | aaaaatatgt | tcagcaaagg | gcgatgttta | atgctacgtc | 84840 |
| taaaataatt | gaaattcaaa | ctaatgctga | gcttcctccg | gaaaaacgaa | ataagaaaat | 84900 |
| gccagatgta | ggtgctattc | ctgacatcat | gcgccaagca | ttatcaattt | catttgatag | 84960 |
| ttacgttggt | catgattgga | tggatgacta | cgaagcacgt | tggctatctt | atatgaataa | 85020 |
| agctcgtaag | gttccattta | aactcaaaat | tctaaataaa | attactaaag | gcggagctga | 85080 |
| gactggaaca | ctgaacgttt | taatggctgg | tgttaacgtt | ggtaagtcat | taggattgtg | 85140 |
| ttcattggca | gcagattatt | tacagctcgg | tcataatgtt | ctttacattt | ccatggaaat | 85200 |
| ggcagaagaa | gtctgtgcta | aacgtattga | cgctaatatg | cttgatgttt | ctcttgatga | 85260 |
| cattgatgat | gggcatattt | cttacgctga | gtataaagga | aaaatggaaa | aatggcgtga | 85320 |
| gaaatctact | ctcggtcgtt | taatcgttaa | gcaatatcct | actggtggag | cagacgctaa | 85380 |
| tacatttcga | tctcttttaa | acgaattgaa | gctcaagaag | aattttgttc | caacaatcat | 85440 |
| tattgttgac | tatctgggta | tttgtaaatc | ttgccgcatc | agagtttatt | cggaaaatag | 85500 |
| ttacacaact | gttaaagcta | tcgcagaaga | attgcgtgct | ctggctgttg | aaactgaaac | 85560 |
| tgttctttgg | actgcagcac | aggttggtaa | gcaagcttgg | gattcttctg | atgttaacat | 85620 |
| gagcgatatt | gcggaatctg | ccggtcttcc | agcaacagcc | gattttatgc | ttgcggtcat | 85680 |
| tgaaaccgag | gagttagcag | ctgctgaaca | acaactcatt | aagcaaatca | aatcacgata | 85740 |
| tggtgataag | aataaatgga | ataagttttt | gatgggtgtt | caaaaaggaa | atcagaaatg | 85800 |
| ggtagaaatt | gaacaagatt | ctactccaac | tgaagtgaac | gaagtagcag | gttcacaaca | 85860 |
| gatacaagct | gaacagaacc | gctatcaaag | aaacgaatcc | actcgagctc | agttagatgc | 85920 |
| tttggcgaat | gaattaaaat | tttagtttac | aagctgacaa | gactatggta | tagtagtctt | 85980 |
| gttggttaaa | tgaggagatt | gttatggaat | tggtaaaggt | agtttttatg | gggtggttta | 86040 |
| agaatgaaag | catgtttact | aaagaaatca | caatgatgaa | agatgacgtt | caatgggcta | 86100 |
| ctactcaata | tgctgaagtt | aataaagcgc | tagttaaagc | tttcattgat | gacaagaaag | 86160 |
| tatgtgaagt | ggattgccga | ggataatatg | cacattgttt | tatttaaacc | tactccgtat | 86220 |
| aatgtcagga | aaaatactca | attcaaagca | cttatcgcag | atacgtggga | attggtgtta | 86280 |
| gatattccag | cagaagaaag | tcctccattt | ggtcgagtgg | aatttattaa | gtttgctgtg | 86340 |
| cgccctacga | agcgacagat | tcgccaatgc | aaaagatact | ttcgtaaaat | cgtcaagtta | 86400 |
| gagaaacagt | tattgatgct | agtaaaatag | tagtttacaa | gctgatagag | ttgtgttata | 86460 |

FIG. 17UU sequence.txt

| | | | | | | |
|---|---|---|---|---|---|---|
| gtaattctat | cagctaatcg | cggagaaaag | aaaatgatgc | tagttaatag | agaatatcag | 86520 |
| tttaaatcag | aagaagattt | ggaaaaattc | gcgagtggtt | gtgaactgaa | tagacgcaca | 86580 |
| gctaaagtca | taggattaaa | acccttttaca | gttctagatt | gtgaagtttc | taaattccgc | 86640 |
| agagggtgtt | ctattagcgg | tcatgctctg | gttgatggaa | acacattttt | ctttgttttt | 86700 |
| agcgtcagag | aactttatt | gattaacgaa | cttgaggaaa | taaaatagtt | tacttttgtt | 86760 |
| ttaaacatgt | tattatagac | ctatcaaaac | aaacgagtaa | atggagaaca | aaatgtctaa | 86820 |
| agtatcaggt | tatcaattat | taacacaaga | acaacgttca | gagatggatt | ctttacaaga | 86880 |
| acggtgtcag | catagaaata | acgcacttga | ttcattttta | ttagttgaat | atgaaaactt | 86940 |
| gtgctctaga | cttgaaaaag | aatatgttca | tcaacatgaa | ggaggagaag | aatgaaactg | 87000 |
| aaatcaccaa | ttattgcaat | ttgtctgttt | gcttctacta | gtgtttactt | ttgttgaaaa | 87060 |
| ttgagatact | ataaacataa | actactgagg | agattatcat | gaaaaatttt | atctttgctg | 87120 |
| caattttgc | tttatcttct | tgcgctgctc | agcctgctat | ggcgggttat | gacaaagatt | 87180 |
| tgtgtgagtg | gtctatgact | gcagatcaga | ctgaagttga | aactcaaatt | gaagcggata | 87240 |
| ttatgaatat | cgttgagcgt | gatcgtcctg | aaatgaaagc | tgaagtgcaa | aaacagctca | 87300 |
| agtctggtgg | tgtaatgcag | tataattacg | ttctgtattg | tgataaaaac | ttcaataata | 87360 |
| aaaatatcat | cgctgaagtg | gtaggtgagt | aattagaggt | taatatgtat | agttctgaat | 87420 |
| tttcatattt | aaaaatggaa | aaaaatttca | tacgatttta | tagatgaaaa | ggtttattac | 87480 |
| agtttccatg | aaccacgttt | taatagtgag | gttgggttta | ttgcagtaaa | agacaatttc | 87540 |
| attttaaaaa | tatattcggc | attaaaggat | tttcactacg | aaaatattaa | cctaaaattt | 87600 |
| gataaagaaa | acgttcgtaa | ttgcgcagta | acaattacag | gaaataaagg | tacatgcgtt | 87660 |
| atgctatctg | atgaaattaa | tgatttgcta | aatgatgccg | aaaaggttgc | tattccatcg | 87720 |
| attgatgacc | aaatttttaa | tgcttttatg | aatagaggtt | aatatgaaaa | cgtttaaaga | 87780 |
| atttatcaaa | gaagatatgg | tcgctggaga | ttcaggtggt | aatcctgaaa | atatctctac | 87840 |
| tggaacaacg | tcaggcgctg | tagtaaataa | aggtcctgaa | cagattccta | aaaagaaaaa | 87900 |
| agaggaatct | aaagaaaaag | aagagtaaaa | atgtcatcga | taccttggat | tgataatgag | 87960 |
| tttgcatatc | gtgcattagc | tcatttacct | aaattcacac | aagtaaataa | tagttcaact | 88020 |
| tttaaattgc | ggtttagatg | ccctgtttgt | ggagattcaa | aaaccgacca | aaataaagcc | 88080 |
| cgtggatggt | attatggtga | taataatgaa | ggaaatattc | attgttataa | ctgtaactat | 88140 |
| catgcaccaa | tcggaatata | tttaaaggag | tttgaacctg | atttatatcg | tgagtatatc | 88200 |
| tttgaaataa | gaaaagaaaa | aggtaaaagt | cgtccagtag | aaaaacctaa | agaacttcct | 88260 |
| aaacaacctg | agaagaaaat | aattaaatct | cttccgtcat | gcattagatt | agataaattg | 88320 |

FIG. 17VV

```
                              sequence.txt
gcggaagacc atccaattat aaaatacgta aaagctcgct gtattccaaa ggataaatgg    88380
aaatatcttt ggtttacaac tgaatggcct aaattagtta atagcatagc accaggaaca    88440
tataaaaagg aaataccctga gcctcgtctt gttattccaa tttataatgc taatggaaaa    88500
gctgagtctt ttcaagggcg tgcattaaag aaagatgctc cccaaaaata tatcaccatc    88560
aaagcttatc ctgaggcaac aaaaatctat ggtgttgaac gggttaaaga tggtgatgta    88620
tatgttctag aaggacctat agattcgctt tttattgaaa atggtatagc tattacgggt    88680
ggtcaattag acctagaaat tgttccattt aaagatagac gtgtatgggt tttagataat    88740
gaacctcgtc accctgacac tattaaacga atgactaaat tagttgatgc aggagaaagg    88800
gttatgtttt gggataaatc tccctggaaa tcaaaagatg tcaatgatat gattagaaag    88860
gaaggtgcaa ccctgaaca aattatggaa tatatgaaaa ataatattgc ccaagggttg    88920
atggctaaaa tgcggctatc taaatatgct aagatttaaa ttaacccaac caaagcaaat    88980
gctaaatcta cgaatgtatc aagagtaatt actggaatac taacgccatg agcaatagca    89040
actggcgata aacaaaatt ccaaagtaaa attcctatca tagcagaaat agtaaaagct    89100
atacgttttt tattacctt gatggcatta acaagtgcca ttaattttg taccatatgt    89160
cctccttatt gctttatata tttattgtat aattaatcta ctaatccatg aattgaaagg    89220
aaaaataatg gcatacttta atgaatgcgc tcatttgatc gaaggtgttg ataaagcaaa    89280
tcgtgcatat gctgagaata ttatgcacaa tattgacccg ctgcaggtta tgcttgatat    89340
gcagcggcat ttacaaattc gtttggctaa cgataaacca gaaacaaatc gtcatcccga    89400
ttcacttgaa actgcgggag aagttcttgc ttggctgcga aaccaagacg attatatcgc    89460
agacgaaact cgcgagctat atacttctct tggtggtatg agtaatggtg aaaaagaagc    89520
ttctgctgta tggaaacctt ggaagaaacg ttattctgaa atgcaatcca agaaaattca    89580
agatttatct cctgaagatc agcttgaaat taaattgaa ctgattgatc aatttcactt    89640
tttcatgaat aaatttattg ctcttggaat gtcagctgaa gaaatcttta aactttatta    89700
tctgaaaaat gctgaaaatt tcgctcgtca agatcgaggt tattaatggc tcgtttaaat    89760
aaacgccagc ttaagaaagc ccacaagaaa cgtattgacc agctatttaa aaattatgac    89820
aaagagctcg tgtgtgagct cttatctaat cagcttcgtg cggttgattg ggttgtagaa    89880
gaaggtcctg atgaaatttt tgtcagcgaa gaagccttaa aattaattat agagcattca    89940
aaatgaaaat atccaaagaa gaatttatta gacgacaaaa agctttaatt aatttacacg    90000
agtggtatgc ttaccagctt aaagtagata gctctaatat aaatgctgta atggctttat    90060
ataaacaaat tcaagatgaa cacgaattcc tggcacaagt tttcattgaa gactgatata    90120
aatacacctg taattaaaca ataaaggagt ttattatggg tggtttcgtt aacatcaaga    90180
cctttactca tccagcgggt gaaggcaaag aagttaaagg tatggaagtt tctgttccgt    90240
```

FIG. 17WW sequence.txt

| | | | | | | |
|---|---|---|---|---|---|---|
| ttgaaattta | ttctaacgag | catcgtatcg | cagattctca | ttatcagatc | tttccgtcag | 90300 |
| aaaaggcagc | atattctact | gtagtttctg | atgcagctga | ttggaaaact | aagaatgctg | 90360 |
| caatgtttac | gcctacacaa | ataggtggtt | aataattcaa | ggactcctcc | gggagtcctt | 90420 |
| ttttcatttt | actggtttac | tttccaaaat | gagtatggta | taataaaatt | atcttataga | 90480 |
| ggagagcact | atgttaaatc | gttggattaa | accaaatgaa | gatttagata | ttatcatttc | 90540 |
| acggcatgta | atgaagaaat | atgaactgca | gccatggtct | acagaagttg | ttgtgcattc | 90600 |
| atttatgatg | tacgcagatg | gttctgtcga | atttaatgca | gaaattcgat | atgattatgg | 90660 |
| cgagaagcaa | gtcgaattca | agagaggctt | tttgtaatgt | ttatctttaa | ttggtttaaa | 90720 |
| agcttcttta | cagattttt | ctctacaact | cctggagaag | gtgtagttcc | tatttcaaat | 90780 |
| gactaccttc | ctttaactgt | agttgaatat | gtttatatgg | gagatggaac | agtagaagca | 90840 |
| gttactatga | cttatgaaga | agcccaagaa | tattataaaa | atccttggcg | ctggtcaaca | 90900 |
| cctattacat | catctaatac | acagaataca | cagtctagtt | ctgattcata | tgacactaat | 90960 |
| gttcctgttc | atgtatggac | gggcgattcg | tgtggaagtt | cttgtgattc | tagttgttca | 91020 |
| tctacatctt | gtgattgagg | aaaattatgg | aagcgatttt | gtttgaaatg | tatattagca | 91080 |
| gtaatagtat | gtcgtttgct | aaagacgttc | caattaccgt | agcagtaatg | attgataagg | 91140 |
| gttattgtga | cccaatgtat | ctcgtagaaa | atttcgtttc | aatgccagtt | ccagaagatg | 91200 |
| ctgaaataaa | acttaaaaag | attggtatta | ttgaaactgt | accaaatatt | ccgtttagag | 91260 |
| caattgaagc | atttactaaa | tccgaataca | ttaatgttag | cgcagaacaa | taatgata | 91320 |
| aacctatatc | tttctattcg | tatgattcag | tatatagttg | gaaaatagat | aaaggaaata | 91380 |
| aatttataat | tgtgagtgaa | gatgctttat | catactttat | ttcttctata | tggaatagtt | 91440 |
| tacatccaaa | tttgctaaaa | attcatgaat | tcgatgatgc | tcctactgtt | gttttaggta | 91500 |
| aaacaaatga | aagttctgaa | gaaatgttt | gaatggttca | gtagaccaaa | ctcaatgtac | 91560 |
| attgatgatg | gttgggttga | acaagcaaat | aaagaaatgc | agaacgaatc | agaagaatgg | 91620 |
| atgaaatcaa | tgattagcgt | tgagaaagaa | aagaaattag | aacgctcagc | gcttaaattg | 91680 |
| atgagagaca | tttatgggga | taaatcgtga | acagagatat | gacgctagaa | gaggctaaag | 91740 |
| ctaaagcaaa | tgaagcttta | gatttgcttc | ttaaaattgg | cagtaaaatg | atggaagaaa | 91800 |
| atgagaaata | tatccaggaa | aacaaaattc | ctgatggtcc | attagtaggc | aaaaggaaat | 91860 |
| cgcatgattg | aagtagcaaa | acattattca | atagaattta | tgtctaaaga | aggtaaatca | 91920 |
| gtaaatacac | ttgataaaaa | gtgctcatta | attattcctt | tagcagaaaa | tccggatatt | 91980 |
| ttaattaaag | atataaaaga | aagaaaatat | ccagaaaatg | ttattctaat | tataaagcat | 92040 |
| actgaagata | ttttgcagaa | tactgattca | ccgttttctt | cttctgaagc | tttaactatt | 92100 |

FIG. 17XX sequence.txt

| | | | | | | |
|---|---|---|---|---|---|---|
| aaaggctata | aaagagctca | tgaatatggt | cttttgacc | tgtttgaaga | cgataaagtt | 92160 |
| aaattagcac | ttaatttagc | aggtcaatct | tctaaaagta | aaacattcat | tattgaagat | 92220 |
| attaaagata | taaatgcatt | tgttaagatg | gtctgggctc | attttgacgt | tggactacgc | 92280 |
| tggagaatgt | ccgaagaaga | aagaaaaatt | attgaagcta | atcgttattt | tggtttttat | 92340 |
| cgctaggaat | taatatggat | ttatttgaga | tgttagaaga | taatcattct | acgaatatcc | 92400 |
| agaatgattc | tagtgattat | aagaaagagt | accgtatagt | attacagaat | tatggaattg | 92460 |
| aagccccaga | tgctcttcta | gaagaactag | cttcatacca | tcttgaccct | ccgccctggg | 92520 |
| ctccctgggc | aaaataattc | aaaaagttgt | ttactttcct | tcctaacaat | gatatgatag | 92580 |
| cttctgaagt | atatggaggc | tatcatgatt | attaatcttg | cagatgttga | acagttatct | 92640 |
| ataaaagctg | aaagcgttga | ttttcaatat | gatatgtata | aaaaagtctg | tgaaaaattt | 92700 |
| actgactttg | aacaatcagt | tctttggcaa | tgtatggaag | ccaaaaagaa | taaagctctt | 92760 |
| catcggcagt | tgaataaaat | cattaaaaag | catttaacta | aatcaccta | tcagctatat | 92820 |
| cgtggtatat | caaaatcgac | aaaagaactc | attaaagatt | tacaagttgg | agaagtgttt | 92880 |
| tcaacgaaca | gagtagattc | atttactact | agtttgcaca | cagcgtgcgg | tttttcttat | 92940 |
| gttgagtatt | tcactgaaat | aatatttcgc | ttaaaaactg | ataaagcttt | taattattct | 93000 |
| gaccatatca | gcgatattat | actttcttct | cctaatactg | agtttaagta | tacatatgaa | 93060 |
| gatactgatg | gattagattc | agaacgtact | gataacttaa | tgatgattgt | gcgtgaacaa | 93120 |
| gaatggatga | ttccaattgg | aaagtataaa | ataacttcta | tttcaaaaga | aaaattacac | 93180 |
| gattcatttg | gaacatttaa | agtgtatgat | attgaggtag | ttgaatgaaa | tattcagcaa | 93240 |
| tgcaattaaa | agattttaaa | atcaaatcaa | tggatgcatc | ggtgcgtgct | tctattcgtg | 93300 |
| aagaattact | ttctgaagga | tttaatttat | ctgaaattga | actttaatt | cattgtatta | 93360 |
| ctaataagcc | agacgatcat | tcttggttaa | atgaaataat | caaatctcgt | ttggttccaa | 93420 |
| acgataaacc | tctttggaga | ggtgttccag | ttgagactaa | gcaggtgtta | aatcaaggaa | 93480 |
| ttgatattat | tacatttgat | aaagtagtat | cagcttcata | tgataaaaat | gtagagctac | 93540 |
| attttgcttc | tggattagaa | tacaacacgc | aagttatttt | tgaattcaaa | gctcctatgg | 93600 |
| tatttaattt | ccaggagtat | gctataaaag | ctctacgttg | taaagaatat | agtccgagtt | 93660 |
| ttaagtttcc | agatagccat | cgttatcgta | atatggaatt | agtttcagat | gaacaagaag | 93720 |
| taatgatacc | agctggaagt | gtatttagaa | ttgcggatag | atacgagtat | aaaaagcatt | 93780 |
| caacatacac | tatctatact | cttgactttg | aaggatttaa | tctataatgg | aaggacttag | 93840 |
| attcattata | ccatgaaagt | tttaaagcat | ttttcataaa | gttgtttaca | agctgaagta | 93900 |
| aaaatgttat | agtataagta | gttaaccgtc | cgtgagaaaa | atatgaaact | gtctaaaaat | 93960 |
| caaattcgta | aaattacacg | tcgtttagag | catactcagg | catctgctaa | aagacgttct | 94020 |

FIG. 17YY sequence.txt

| | | | | | |
|---|---|---|---|---|---|
| aaagattta | acttagactt | caattacatt | aagaacattt | tagatcagaa | agtttgcgct | 94080 |
| tactcgggag | aacctttga | taatcgtatt | gaaggagaga | aattatcatt | agaacgtttt | 94140 |
| gataataacg | ttggatacat | taaagggaat | gttattgcag | taaagaaaaa | gtataataca | 94200 |
| tttcgttctg | attatactt | agaagagttg | attgaaaagc | gtgatttatt | tgctttgcga | 94260 |
| attggtcgtt | catctgcgaa | aaagttcat | aaactaaatt | tagatgaaaa | gaaatgggct | 94320 |
| aaaatcaaaa | agacttataa | tcaaattaaa | gctatacaga | aaaaacgtga | aaaccgaatt | 94380 |
| gagcacattt | ctcagctttc | taaatcaaaa | caaacttctg | acgttaagct | aacgattata | 94440 |
| gcacttaaag | ctcgtattga | tggttctcgt | atagcagaag | gcgctgaagt | tgttaaattg | 94500 |
| aacgttcttc | ttaaaggctc | ggattggaaa | actgtgaaaa | agctgtcaga | agcagaaatg | 94560 |
| caatatgata | tgtgtgataa | aattattcaa | ggtgtagagc | ggtatcaaaa | cttgtctttt | 94620 |
| attgataaac | ttaaactgaa | aagaggatac | ccgctaaatt | gttcaatttt | taaacttatc | 94680 |
| cgaggataat | atgttttatg | tatatgcgat | agtgtataga | gataaagatg | gatttgcggt | 94740 |
| gcctgttcct | cttgatgaac | atcgccctgc | tgtatttttt | gaaagggaga | ttgctgataa | 94800 |
| agtatttaca | actcttaaag | agcagtatca | actagcttta | ggtatgggaa | ttccgagatt | 94860 |
| agttgagact | ccacgcaagt | tttggtttaa | taaaatagaa | gttaaacatg | ttaagcctga | 94920 |
| tgtagacacg | caaagattat | atcggcgaat | tttagatact | gggcgtattg | ttagtatacc | 94980 |
| aattgcaggg | aatttacgat | gacatttgat | gatttgacag | aaggccagaa | aaatgccttt | 95040 |
| aacatcgtta | tgagggctat | caaagaaaag | aaacatcatg | taactattaa | tggacctgcc | 95100 |
| ggtactggta | aaactactct | tactaagttc | atcattgaag | ctttaatatc | tacgggcgaa | 95160 |
| actggcatta | ttttagcagc | tcctacacat | gcagctaaaa | agattctttc | aaaactgtca | 95220 |
| gggaagaag | cgagtactat | tcatagtatt | cttaaaatta | accccgtaac | atacgaagaa | 95280 |
| aacgttcttt | ttgaacaaaa | agaagtaccg | gatttagcca | aatgtagagt | attaatctgc | 95340 |
| gacgaagtgt | caatgtatga | tagaaagcta | tttaaaattc | tgctttcaac | tatcccgcca | 95400 |
| tggtgtacta | taattggaat | aggcgataat | aagcaaatta | gacctgttga | cccaggggaa | 95460 |
| aacactgctt | atatcagtcc | attctttaca | cataaagatt | tttatcagtg | tgaactcact | 95520 |
| gaagttaaac | gcagtaatgc | tcctattatt | gatgtagcta | ctgatgttcg | caacggtaag | 95580 |
| tggatttatg | ataaagttgt | tgacggacat | ggagtacgtg | gatttactgg | tgataccgct | 95640 |
| ttacgcgatt | ttatggtaaa | ttatttttca | atcgttaaat | cactagatga | tttgtttgaa | 95700 |
| aatcgcgtaa | tggcatttac | gaataaatct | gttgataagt | taaatagcat | tattcgtaaa | 95760 |
| aagattttg | aaactgataa | agattttatt | gtcggtgaaa | ttattgtaat | gcaggaaccg | 95820 |
| ttaattaaaa | catataaaat | tgatggaaag | cctgtgtcag | aaattatttt | taataacgga | 95880 |

FIG. 17ZZ sequence.txt

```
caattagttc gtattataga agcagaatat acatcaacat ttgttaaagc tcgtggcgtt    95940
cctggagaat atctaattcg tcattgggat ttaacagtag aaacttacgg cgatgatgaa    96000
tattatcgtg aaaagattaa aataatttca tctgatgaag agctgtataa gtttaactta    96060
tttttaggta aaacagcaga aacttataaa aactggaata agggtggaaa agctccatgg    96120
agtgattttt gggatgctaa atcacagttt agtaaagtga aagcacttcc tgcatcaaca    96180
ttccataaag cgcagggtat gtctgtagac cgtgctttca tctatacacc ttgtattcat    96240
tatgcagatg ctgaattggc tcaacaactt ctttatgttg gtgttacccg tggtcgttat    96300
gacgtatttt atgtgtgagg atatatgatt aacatcaatt caaaatattt aaatcgtcta    96360
atagatggta taaggaagca tactaataag caagataatc tcgatgttat ggtaacagga    96420
gctgagctcc ttcataagct ttatcttata agtgatacta tattagcaat taaacgaatt    96480
gaaaaacaat catatcacag taatacagat acggtaatta cactagatga agtgtctgt    96540
aaattactaa ttaaatttga ggaagctatt cgtggaaata actaaagacc agttttatct    96600
gcttcaagat aaagtgagcg aaatttatga aatagcttat agtaaaaatc gtgaaactgt    96660
aaaaattgaa tctagtaagt tgatgcttca attagaagaa attgaacgag atttaattgc    96720
gttagaattc ttttgtggtg aagtgaaaac tgtcacaatc agtgattatg ttttaggtga    96780
aattagctat ctttataagg cgattattaa tgattgaatt aagttggtgt cagtttaaat    96840
ctcttatgac aaatgttaaa gctgtcattg agaaaaattc tggtcctgaa aatattacta    96900
ttcgcgaaaa agctttaaag ataatataca gtcttgaaga gatgcaaaaa gatattgaat    96960
ctatggcaaa atttattgat gaacctatta ataagtttta tattcaagac tatactgtag    97020
gccaaattcg cgatttagcg aggaaaattt aatgtttgat tttattatag attttgaaac    97080
aatgggaagt ggtgaaaaag cagctgttat tgatttagct gtaattgctt ttgaccctaa    97140
cccagaagta gttgaaacat ttgatgaatt agtttcacgc ggcattaaaa tcaaatttga    97200
tttaaaaagc caaaaaggac atcgtctttt tactaaaagc actatcgaat ggtggaaaaa    97260
tcagtctcct gaagctcgaa aaaatattgc accgtccgat gaagatgtaa gcactatcga    97320
cggtattgcg aaatttaatg attacatcaa tgcacataat atcgatcctt ggaaatctca    97380
aggctggtgc cgtggaatgt cgtttgattt tccaatttta gtcgatctca ttcgtgatat    97440
tcaacgtctt aatggtgttt ctgagaatga acttgacaca tttaagttag aaccatgtaa    97500
attctggaat cagcgtgata ttcgtaccag aattgaagca cttctgcttg ttcgtgatat    97560
gaccacgtgt cctcttccaa aaggaacttt agatggattc gttgcgcatg attctattca    97620
tgactgcgcg aaagacatcc tgatgatgaa gtacgctttg cgatatgcta tgggtcttga    97680
agatgctcca tcagaggaag attgcgatcc tctatctctt ccaacaaaac gataaaaagt    97740
tgtttacttc ctcggttagt tgtggtatta taacaccata gctactgagg ataataaaat    97800
```

FIG. 17AAA sequence.txt

| | | | | | |
|---|---|---|---|---|---|
| gaaaatttat | cgtgttgaat | catcgtttag | tattcttgat | tatgaagatg | ctataacaat | 97860 |
| acgtcgaaat | ctttgtgttc | aaataacgcc | gtacaggagt | ataatagatt | catggagcga | 97920 |
| agagtggcta | ttacacgtag | gttatgacag | acctaattt | atgcatcata | gcgataataa | 97980 |
| taaaagaatt | cctttaccac | acgaagataa | actattagtt | aaaaacgcta | atatagtaat | 98040 |
| taatactaag | ttcaagaaag | attatgttgg | agtagaatat | catattccag | gatggtttat | 98100 |
| agctctttat | cattttgctt | tcgctagcga | atatgatatg | atgagatggt | tcacacgaga | 98160 |
| agagcgtgaa | gaattagctt | cgaaaggatt | ttatcttgct | gtatacgaag | taccagatga | 98220 |
| ccaagttatc | gttggcgggc | atcaagtaat | gttccgtaaa | tcccatgctg | aacttgtaga | 98280 |
| ttttattgaa | atgagataat | tatgaaattt | aattataatc | ctgaatacac | accgaatccg | 98340 |
| gcagctaaac | tgattgattt | tgacgttgta | agtacttatg | tatgccctgt | taaaccactg | 98400 |
| gaaattaagg | aacctactat | gactaccgct | attgaaatcg | gcaaaaccta | caaactggtt | 98460 |
| gaacctaaaa | ttaaaactaa | tgccttgatt | tctggtcata | aaactctgac | tgatgttttt | 98520 |
| ggcgaaggcg | aatttattgt | tgaagaattt | gccaaaagtg | agtggtttga | caaatcttac | 98580 |
| gtcatccacg | gtcgccggtt | agataataac | aaaataaaga | aaaacctggt | ttatgaagat | 98640 |
| gagttcatcc | tgttccaaga | agttgaagaa | caagaccta | cagacctgtt | gtgtgctgct | 98700 |
| gtgtctatcc | gtcgtccttt | tgataatcct | atctgtggtt | gggtaacaga | ccagtggatt | 98760 |
| gaagatggtg | ttgagcttct | gaacgttgtc | catgcaggag | attttagtgt | agtacctcgt | 98820 |
| agtgcggtgg | tagctatttt | gaattaatag | tttacaaact | cttgggacca | gagtataatg | 98880 |
| gtcctgtgga | gtataaaatc | tttttaacaa | gtgagagata | actatgatta | ttaatattgg | 98940 |
| tgaaattgct | cgtgtatctg | ataaatcccg | ttctaaagca | gcaggaaaat | tggtcgaagt | 99000 |
| tgtaagcatt | cagcttaaac | acggtgttaa | agatgaagat | tctgaagtaa | aagtacgtat | 99060 |
| cattgctaaa | gatggaatgt | ctaagcccca | gtttggttat | gttcgatgga | aatttcttga | 99120 |
| gcctgcgttt | ttgaaagctg | ttcctgctaa | aggaattgaa | acgattgata | cttcgcatgt | 99180 |
| aggtgtagac | tttaagtgga | aactcggtca | agctatcaag | ttcattgctc | cttgtgaatt | 99240 |
| taaatttatc | aaagatgatg | gaaaggctgt | ttatactcgc | gctatgtgtg | gatacattac | 99300 |
| cgatcaatgg | gtagaagatg | gcgttaagtt | gtacaacgtg | gtattttag | gaacatataa | 99360 |
| agtcattcct | gaaagttgga | ttaaacacta | cagcaatgct | ctctatgcat | aaagtttaaa | 99420 |
| attttttcat | aaaactatat | acatcagtag | ttgattatgg | tactatatca | atatcaacta | 99480 |
| ctgatacaga | aaacaacttg | gagaataaaa | tggataattc | gttaaaggtg | cgctgatact | 99540 |
| cttctgaaac | gcatcgctcc | aatgttcaat | taatgaggaa | attatgatga | aacgtaaaat | 99600 |
| tgttcagaat | tgcactaatg | atgaatttga | agatgtatta | ttcgatccag | atttggtagt | 99660 |

FIG. 17BBB sequence.txt

| | | | | | | |
|---|---|---|---|---|---|---|
| agttcaaaag | gaacacacta | tcaagtttac | tcacttgact | tcggtttatg | tgtatgaaaa | 99720 |
| ggttggggat | aaacaaccaa | tttacggtgt | atttcgtgaa | atcactgaag | atggtacaac | 99780 |
| ttactggaag | gaaatttatt | aatggctatt | aaatttgaag | ttaataaatg | gtatcaattt | 99840 |
| aaaaataaac | aagctcaaga | aaattttatt | aaagaccata | ctgataacgg | aatctatgca | 99900 |
| cgccgtttag | gtatgcatcc | ttttaaaatt | ttagatgtgg | atgctcttgg | gcgtcctatt | 99960 |
| aaaattatgt | catttgctgg | aaatttagta | ctatcttctg | gtaaagatat | tttggatgaa | 100020 |
| gattttattt | ggctttcatc | gaatgaagct | gaattcttta | atgaagttga | aaatccatac | 100080 |
| caggcagctg | aagagcagga | agaatctgca | ccgataactg | atcaatctaa | attccctgta | 100140 |
| atgaaagtta | ctattgaaaa | tgatgaacag | gcatggtcct | tgtatcagat | gttgaaagct | 100200 |
| cactttaagg | aataattatg | ccgctttatg | attataaatg | tcaatcaaaa | gactgcgcaa | 100260 |
| aagaatacga | aaaaatcaag | aaaatttctg | aaagagatac | tgatgtatgt | cctgattgtc | 100320 |
| atcggattgc | tattcggtta | gtctctgccc | ctaagcatgt | gaatggcgga | ttttacgact | 100380 |
| tacttaaagg | gtaattatgt | ttaaaatcgg | taagaaatat | cgcattcgcg | aaggtgaaga | 100440 |
| aaagaaatat | ctattttctg | ctatttatag | gaatggttct | attaatgctg | taatatctac | 100500 |
| aagcgaattt | atcgttgaag | atatgaaagg | taataatgtt | acaatgatta | gtacagcatc | 100560 |
| tggaaatgac | ggaaaaattc | ttcacagttt | tcagagtaat | gttctaattt | atgatgaaga | 100620 |
| atttgacttc | ttcgaagaag | ttcccgaagg | ttttgctttt | gaatgcacta | tcactatgaa | 100680 |
| atctggtgac | cctctttctt | ttacagttaa | agatgaagga | agtcgcttga | gaattattag | 100740 |
| tcttcttcaa | gccattaaat | ttaagtgaaa | attatgaaat | atattaatcg | ttctatcgcg | 100800 |
| gcattagtat | tagcagtgtc | tttagtagga | tgtactgatg | ctgataatgc | aaccaaagtt | 100860 |
| ttgtcttcaa | gcggttttac | taatattgaa | atcactggat | ataactggtt | cggttgttct | 100920 |
| gaaaatgatt | tccaacatac | tggatttcgt | gctattggac | ctactgggca | gaaagtagaa | 100980 |
| ggaacagtat | gttctgggct | gttctttaag | gattcaacta | ttcgttttaa | ataaaaggcc | 101040 |
| ttcgggcctt | tagctttatg | attaccggag | tataatattc | ccgaaaccaa | acgaggataa | 101100 |
| gtgatgatta | agaatgaaat | taaaattctg | agcgatattg | aacatatcaa | aaagcgtagc | 101160 |
| ggcatgtata | ttggctcttc | tgctaatgaa | atgcatgagc | gctttctgtt | tggtaaatgg | 101220 |
| gaaagtgttc | agtatgtacc | tggtcttgtt | aagcttattg | atgaaattat | cgataactca | 101280 |
| gtagatgaag | gtattcgtac | taagtttaaa | ttcgcaaata | aaattaatgt | tactattaaa | 101340 |
| aacaatcaag | taacagttga | agataacggt | cgcggtattc | cacaagcgat | ggttaaaaca | 101400 |
| cctactggtg | aagaaattcc | tggtccagtt | gctgcgtgga | ctattccaaa | agcaggtggt | 101460 |
| aactttggtg | atgataaaga | acgcgtcacc | ggtggtatga | atggtgttgg | ttctagttta | 101520 |
| actaacattt | tttctgtgat | gtttgtcggt | gaaactggcg | atggtcaaaa | taatattgta | 101580 |

FIG. 17CCC sequence.txt

```
gttcgttgtt caaatggcat ggaaaataaa tcatgggaaa ctattcctgg aaaatggaaa    101640
ggaactcgtg ttactttcat tccagatttt atgtcatttg aaactaatga attatctcaa    101700
gtttatcttg acattacatt agatcgtctc cagacacttg ctgttgttta tcctgatatt    101760
caatttacct ttaatggtaa aaaggttcag ggcaatttta agaaatatgc acgccaatat    101820
gatgagcatg ctatcgttca agaacaagaa aactgttcta ttgcagttgg tcgttcaccg    101880
gatggttttc gtcaattaac atacgttaat aacattcata ctaagaatgg tggccatcac    101940
attgactgtg ttatggatga tatttgtgaa gaccttattc cacaaatcaa acgtaagttc    102000
aaaattgatg tgactaaagc acgcgttaaa gaatgtttga caatcgttat gtttgttcgt    102060
gatatgaaaa acatgcgatt tgattctcaa actaaagagc gtttgacttc tccatttggt    102120
gaaatccgta gtcatattca gcttgatgct aaaaagattt cacgtgctat tttgaataat    102180
gaagcaattc tgatgccaat tattgaagct gctttggctc gtaaattggc ggcagaaaaa    102240
gcagcagaaa ctaaagcagc taaaaaggca tctaaagcta aggttcataa acatatcaaa    102300
gcgaatcttt gtggtaaaga tgctgatact acattgttct tgactgaggg tgattctgct    102360
atcggatatc ttattgatgt tcgtaataaa gaacttcatg gtggttatcc attacgtggt    102420
aaagttctca acagttgggg tatgtcatat gctgacatgc ttaaaaacaa agaactgttt    102480
gatatttgcg caatcactgg attagttctc ggtgaaaaag ctgaaaactt gaattatcat    102540
aatattgcta ttatgactga tgctgaccat gatggtctag gaagcattta tccttctctg    102600
cttggatttt ttagtaattg gccagaactg tttgagcaag gaagaattcg cttcgtcaaa    102660
actcctgtaa tcatcgctca ggtcggtaaa aaacaagaat ggttttatac agtcgctgaa    102720
tatgagagtg ccaaagatgc tctacctaaa catagcatcc gttatattaa aggacttggc    102780
tctttggaaa aatctgaata tcgtgagatg attcaaaacc cagtatatga tgttgttaaa    102840
cttcctgaga actggaaaga gcttttgaa atgctcatgg gagataatgc tgaccttcgt    102900
aaagaatgga tgagccagta gtttacttta ccacaaggat gtggtataat taattgggca    102960
aatgaggata ttgaaatgaa atcatataaa gtaaatttag aacttttga taaagcagtt    103020
catcgagaat atagaatcat tcaacgcttt ttcgatatgg gagaagctga agagtttaaa    103080
aaccgcttta aggatattag agataaaatt caatccgaca ccgcaactaa agatgaacta    103140
ctagaagttg ctgaagttat taaacgcaat atgaattaat gaggaaatta tgattatcac    103200
cactgaaaaa gaaacaattc ttggtaatgg ttctaaatca aaagcattta gcatcacagc    103260
atctcctaaa gtatttaaaa ttctatcatc tgatttgtac acaaacaaga ttcgcgcagt    103320
agtccgtgaa ttgattacca acatgattga tgcccatgct ctcaatggaa atcctgaaaa    103380
atttatcatt caagttcctg gacgtttaga cccacgattt gtttgtcgag atttttggtcc    103440
```

FIG. 17DDD

```
                                         sequence.txt
gggtatgagt gattttgata ttcagggtga tgataattct cctgggttgt ataattcata    103500
cttcagttca tctaaagctg aatctaatga ctttattggc ggatttggtt taggttctaa    103560
atctccgttt agttatactg atacgtttag tattacttcg tatcataaag gtgaaattcg    103620
tggttatgta gcttacatgg atggtgatgg cccacagatt aaacctacat tcgtaaaaga    103680
aatgggtcca gatgataaaa ctggtattga aatcgtagtt ccagttgaag aaaaagactt    103740
tagaaacttt gcttatgaag tttcttatat catgcgacca ttcaaagatt tggctatcat    103800
taatggtctt gaccgcgaaa ttgattattt tccggatttt gatgattatt acggcataaa    103860
tccagaaaga tactggcctg atcgtggtgg attatatgct atctatggcg gtattgttta    103920
tcctatcgat ggtgttatta aagaccgtaa ctggctaagc attcgtaatg aagtgaatta    103980
cattaagttt ccaatgggtt cgcttgatat tgctccatca cgcgaagctc tttcactaga    104040
tgatcgtact cgtaaaaata ttattgaacg agttaaagaa ctcagtgaga aagcatttaa    104100
tgaagatgta aaacgattta agaatctac atctcctcgt cacacatatc gtgaattgat     104160
gaagatggga tattctgctc gagattatat gattagtaat tcagtcaaat tcacgactaa    104220
aaatctgtca tataaaaaga tgcagagcat gtttgaacct gacaataagt tatgtaatgc    104280
aggagttgtg tatgaagtaa atcttgatcc tcgactgaag cgcattaagc aaagtcatga    104340
aacttcagcc gttgcatcaa gttatcgtct gtttggtatt aatacaacaa aaattaatat    104400
cgttattgat aatattaaaa atcgtgttaa tattgttcgt ggattagcac gagcgttaga    104460
tgatagtgaa tttaataaca ctttgaatat tcatcataat gagcgtcttc tgtttattaa    104520
tccagaagta gaatcgcaga ttgatttgct tcctgatatt atggcgatgt tgaaagtga    104580
tgaagttaac attcattatt tgtcagaaat tgaagcttta gttaaaagct atattccaaa    104640
ggtagttaaa agtaaagctc ctcgtcctaa agctgctaca gcatttaagt ttgaaattaa    104700
agacgggcgc tgggaaaaag aggaattatt tacgctcaca tcagaagcag atgaaattac    104760
tgggtatgta gcgtatatgc atcgttctga tattttctct atggatggta ctacatctct    104820
ttgtcatcca tctatgaata ttttgattcg tatggctaat cttattggca ttaatgagtt    104880
ttatgttatt cgtccgcttt tgcagaaaaa ggtaaaagaa ctcggtcagt gccaatgtat    104940
ttttgaaact ctgcgtgatt tatatgtaga tgcttttgat gatgtagatt atgataagta    105000
tgtaggttat tcaagttcag ctaaacgata tattgataaa attattaagt atcctgaact    105060
agatttatg atgaagtact tcagtgtaga tgaagtttct gaagaatata cacgactcgc     105120
taatatggtt agttcattac agggtgtata tttcaacggt ggaaaagata ccatcggtca    105180
tgacatctgg acagtaacta atcttttga tgaattatca cgtaatgctt caaaaaacag     105240
tgataaaatg gttgctgagt ttaccaagaa attccgtatt gtttccgact tcatcggata    105300
tcgcaactct ttaagtgatg atgaagtttc ccaaatcgct aaaactatga aggcccttgc    105360
```

FIG. 17EEE sequence.txt

| | | | | | | |
|---|---|---|---|---|---|---|
| ggcctaataa | ggaaaattat | gtacaatatt | aaatgcctga | ccaaaaacga | acaagctgaa | 105420 |
| attgttaaac | tgtattcaag | tggtaattac | acccagcagg | aattggctga | ttggcaaggt | 105480 |
| gtatcggttg | acacaatccg | tcgtgttttg | aaaaatgctg | aagaagcaga | acgctctaaa | 105540 |
| gttactatta | gcggtgacat | tacagttaaa | gttaatagcg | atgcagttat | tgctccagtt | 105600 |
| gctaaatctg | acattatttg | gaatgcatct | aaaaaattca | tttcaattac | tgttgacggt | 105660 |
| gtaacttata | acgcaactcc | taatactcat | tcaaacttcc | aggaaattct | taatctgctt | 105720 |
| gtagcggata | agttggaaga | agcggcacaa | aaaattaatg | ttcgtcgcgc | tgttgaaaaa | 105780 |
| tatatttccg | gcgatgttcg | aattgaaggt | ggaagcttat | tctatcaaaa | tattgaattg | 105840 |
| cggtctggtt | tggttgatcg | tattcttgat | tcgatggaaa | aaggcgaaaa | ctttgaattt | 105900 |
| tattttccgt | tcttggaaaa | tctgctggaa | aacccaagcc | agaaagcggt | atctcgactc | 105960 |
| tttgatttct | tggtagcaaa | cgatattgaa | attacagaag | atggttactt | ctatgcttgg | 106020 |
| aaagtagttc | gtagcaatta | ctttgattgt | cactcaaaca | cttttgataa | cagtcctggt | 106080 |
| aaagtagtta | aaatgccgcg | tactcgtgtg | aatgacgatg | atacgcaaac | ttgttcccgc | 106140 |
| ggtttgcatg | tatgttctaa | atcttatatt | cgtcactttg | gcagttcaac | cagccgagtc | 106200 |
| gtaaaagtta | aagtacatcc | gcgtgatgta | gtatcaattc | cgattgatta | caacgatgct | 106260 |
| aaaatgcgta | cctgccaata | cgaagtagtt | gaagacgtta | ctgaacaatt | taaataaggg | 106320 |
| cttcggccct | taactaagga | aaattatgtt | aggttatcaa | gcacgagtaa | aagaagaata | 106380 |
| cgatcaatta | atgctcaaaa | ttaatgcact | tagcaatttt | ttagaaagca | caaagtttct | 106440 |
| aacggttagt | gcagttgagc | aagaattgct | actttcgcag | tttatctcaa | tgaaatctta | 106500 |
| cgcagattgt | ttagaaaaaa | gaattgcaca | attcaaataa | aataagggct | tcggcccttt | 106560 |
| tgttttaagg | gaaattatga | ttccgacata | aggaaagtt | taaatgcaga | aaacgaatcc | 106620 |
| gggtttgcag | agactatttc | agattccgtc | atttacccta | tcgaacagtg | acttgactag | 106680 |
| tgaaatgaag | gtcaaaattg | ctgatactgc | aagatactct | ttaaaacaaa | acccgaacca | 106740 |
| ggataaagca | gaagttatcg | aaagatgtcg | tatcgctgtg | tacgcagagt | tttttgtggc | 106800 |
| agattggcta | agagggtatg | ttaacaaagg | ccaagaggat | gttaatgacc | cgtatacata | 106860 |
| cgcatgggat | gtactggcgc | atccaaaata | ctgcgggctt | cgtgtagaag | ttaagacaca | 106920 |
| tcaaactgac | tcacgttgga | tttcggtaac | aacaggatgc | agcggagagt | atccatatgg | 106980 |
| ttctggaata | aatctagggc | ccattctaaa | tcatcaagtc | gctgactgta | taattatatt | 107040 |
| caacactaaa | gaaattcatc | caggtgtcat | ccagtacact | ccgaagttca | tcggtgacag | 107100 |
| agaagacctt | cgtaaggttg | taagaaaaag | caactacaat | ggatggtatc | tttccattta | 107160 |
| aaaattttca | caaacggtt | tacataccac | aaggactgtg | gtactataca | actatcagct | 107220 |

FIG. 17FFF sequence.txt

```
acggaggagt aaaaatgaaa tttaaattt attacgctaa acataaaatt accggtgaat    107280
ttattgcatt tacgacttca actacagatg aaggagatat ttttactgca gtatttttat    107340
caaaatggga atcagatcaa ccttacttat catcacgtga agatctccaa cgattagtta    107400
atggagaata taatgattca tggtcatatt tagtccatga ttgtgttaaa aaggcaataa    107460
aacaaaaaca cttggaaatc gttgagattg aactatgagt tcattatggt ggtgtttcgt    107520
ttggttaatt agtattccat taatttgttt aacatttact tttgtgatga ggttattatg    107580
aaaattttga attctgtgct tattgcttgt gcgtggtggg ttgcgcaagt ttcagcagta    107640
gtagttggta ttcacattta ttacgaatat ttttaaaaaa gttgtttaca agactgttct    107700
tccgtggtat tattaccta tcaactacgg aggaacagaa aatgaaaaag attgttaaag    107760
ctatatggaa tgtagttata atactaatag ttttgagtat attcccaatc gttttaatga    107820
ttgatgtatt aaacgcttac tttggattta tgtgaggaaa atatgaagcg taaacgcagt    107880
gcttttacat ttattgaatg gtttttcgat aatattttc cggctttatt cattttcatg    107940
ctgattttg ctttaggttc agttgtagtt ggaatctatt tgatgacagt agtcggaatt    108000
gatattcatc aaaatggttt aaaatccgta gttgaaacaa tttggaacgg tgtaaaatga    108060
tgaatttgct gagcggttgg ttttatattc ttatgtttta cattggcgca aattttccat    108120
attggatggg atggtcaaca actgcgtttg gattttatac tccttgaggt gaattatgaa    108180
aatctttaaa gatgtaaaag ttggtgaaat tttctgttta gataacggtg atcagttaat    108240
tcgtatttca cctcttaaga gcactagcga gaaaccgaca gttaacgcta ctttagcaaa    108300
caatagtaat gaacgttct gtattgaaaa tgatactgaa acttataccg tagaagagtt    108360
ttgggaattg agcgtcgact gcgacgatta atttaatggc cgtgtgtatt catgcggcct    108420
tggagtagaa aataatttag aggaaattaa tatgaaatac atgactgtta ctgatctgaa    108480
taatgcaggc gctaccgtta ttggtacaat caagaacggt gaatggtttt tgggagttcc    108540
acataaagat attttatcta aacctggatt ttactttta gtaagtaaat tagatggtcg    108600
tccatttagt aatccatgtg tgtctgcacg attttatgta ggtaatcagc gttctaagca    108660
aggatttagt gcggttctaa gtcatattcg tcaacgtcgg tctcagcttg cgcgtactat    108720
tgcaaataac aatgttccat acacagtatt ttatctgcct gcttctaaga tgaaacctct    108780
gactacggga tttgaaaaag gtcagttagc tttggcgttt attcgtaatc atcattctga    108840
gtatcaaaca cttgaagaaa tgaaccgtat gttggctgat aactttaaat tcgttttgca    108900
ggcatattaa tgagtaattt ccacaacgaa catgtgatgc agttctatcg taataatttt    108960
aaaactaaag gcgtcttcgg acgccagtga ggaaaatatg aatattgcaa aattattagg    109020
agttatttca tttatttgtt ggatagtagc atgtgtttta actatctgta ttgatgtcag    109080
cagtgtgttt tcgcaagctt tagctcaggg tatgtgtgca tatttaacat ttgtgttgtt    109140
```

FIG. 17GGG sequence.txt

| | | | | | | |
|---|---|---|---|---|---|---|
| atctactaat | gattaagaaa | atcttgggct | attcattagc | ccttgctatt | ttattgatag | 109200 |
| cattatatta | cggaataatg | ttcggattaa | ttcaagtcgt | gcttttcatt | tctgatgtta | 109260 |
| ttatggcact | acattcacta | gtatggtaaa | tttatgcaac | tgaataatcg | tgatttaaaa | 109320 |
| agtatcattg | ataatgaagc | attggcttat | gctatgtaca | cggttgaaaa | tcgtgccatt | 109380 |
| ccaaatatga | ttgacggatt | taagccagtt | caacgatttg | ttattgctcg | agctcttgat | 109440 |
| ttggcacgag | gaaataaaga | taagtttcac | aaactcgctt | ctatcgcagg | cggtgtagcg | 109500 |
| gaccttggat | atcatcatgg | tgaaaactct | gcgcaagacg | caggtgcttt | gatggctaac | 109560 |
| acttggaata | ataactttcc | tctgttagac | ggtcaaggaa | actttggttc | tcgtactgtc | 109620 |
| caaaaggcag | cagcaagtcg | ttatatttt | gctcgtgtaa | gtaaaaattt | ctataacgta | 109680 |
| tataaagata | ctgaatatgc | tccagtacat | caagataaag | aacacattcc | gcctgctttc | 109740 |
| tatttgccta | ttattcctac | tgttcttctt | aatggcgttt | ccggtattgc | aactggttat | 109800 |
| gcaacttaca | ttcttcctca | tagtgtttct | tctgtcaaga | aagctgtact | gcaagctctt | 109860 |
| caaggaaaga | aagtaactaa | accgaaggta | gaattcccag | aatttcgtgg | tgaagtcgtt | 109920 |
| gaaattgatg | gcaatatga | aattcgtgga | acatataagt | ttacttcacg | aactcaaatg | 109980 |
| catatcactg | agattccata | taagtatgat | cgtgaaactt | atgtgagtaa | aatcttagac | 110040 |
| ccgcttgaag | ataaaggctt | cattacatgg | gatgatgctt | gtggtgagca | tggctttggc | 110100 |
| ttcaaagtta | aattccgaaa | agaatactct | ttgagcgata | atgaagaaga | acgccatgca | 110160 |
| aaaattatga | aagacttcgg | gttgattgag | cgtcgttccc | agaatattac | cgtcattaat | 110220 |
| gagaaaggaa | agctgcaagt | ttacgataat | gtagttgatt | taatcaaaga | cttcgttgaa | 110280 |
| gttcgtaaaa | cttatgtcca | aaaacgaatt | gataacaaaa | tcaaagaaac | tgaatcagca | 110340 |
| tttcgtttag | cttttgccaa | ggcacatttc | attaagaaag | taatttcagg | tgaaattgtt | 110400 |
| gtacaaggta | aaactcgcaa | agaactgacc | gaagaacttt | ctaaaattga | tatgtattct | 110460 |
| tcttatgttg | ataaactagt | tggaatgaac | atttttcata | tgacttccga | cgaagcaaag | 110520 |
| aaacttgctg | aagaagctaa | agccaaaaaa | gaagaaaacg | aatattggaa | aactactgat | 110580 |
| gtagttacag | aatacaccaa | agatttagag | gaaatcaaat | gagtccattc | attggtatca | 110640 |
| caagcgctgc | attagtatct | ggtggcattt | tactggcggg | tttaggtgtt | gttcctgccg | 110700 |
| tagcaggagg | tcttcttgcg | ttcggaattc | aacgtgttat | catgacagtt | atcacagtca | 110760 |
| tgcagtaatt | ttagggagag | cctcggctct | ccctttttat | ttcaaaaatt | ttttcacaaa | 110820 |
| acggtttaca | accaaagcat | actgtggtac | tatacaacta | tcaaataaat | gaactgaaac | 110880 |
| aaacaacccg | gagatacaaa | aaatgaaatt | taaaatcgaa | aacgaaatcg | ttaaagctaa | 110940 |
| aaatgctctg | actgctaaca | aactggttgt | agatggtatt | gaatatgata | tctgtggagt | 111000 |

FIG. 17HHH sequence.txt

| | | | | | | |
|---|---|---|---|---|---|---|
| tcgtgaagaa | aaacctggtg | ttctgacttt | cttcacaatg | attttaaat | ttaaaggtga | 111060 |
| cacagaattc | aaacagtttg | attttgccca | tgaagacgaa | atcgaagttc | gtaatctgaa | 111120 |
| cattaagtaa | gtactttatt | agagctcttg | aaaaagagtg | caaaaagtg | tttacttctg | 111180 |
| cttaaacat | gatactatag | acctatcaaa | taatgaact | gaaacggaga | ttaaaatgtc | 111240 |
| taaagtaact | tacatcatca | aagcttctaa | cgatgttctg | aatgaaaaaa | ctgctgcgat | 111300 |
| tttaattacc | attgctaaga | aagatttcat | tacagccgca | gaagttcgtg | aggtgcatcc | 111360 |
| agatttaggt | aacgcagtag | ttaatagtaa | tattggggta | ttgattaaaa | aaggcctggt | 111420 |
| ggagaaatct | ggtgatggat | taatcattac | tggtgaagct | caagatatta | tttcaaacgc | 111480 |
| agcaacttta | tacgcgcagg | aaaatgctcc | ggaactactg | aaaaaacgtg | ctactcgtaa | 111540 |
| agctcgtgag | attacttctg | atatggaaga | agataaagac | ctcatgttaa | aacttttaga | 111600 |
| tgaaaatgga | tttgttctta | aaaaggttga | aacttatcgt | agtaattatc | ttgccatttt | 111660 |
| agaaaaacgc | actcacggaa | ttcgtaattt | tgaaattaac | aataatggaa | atatgcgaat | 111720 |
| ttttggatac | aaaatgatgg | aacatcatat | tcagaaattt | actgatatcg | gaatgtcatg | 111780 |
| taaaatcgct | aaaaacggta | atgtgtatct | tgacattaaa | cgctcggcag | aaaacattga | 111840 |
| agctgtaatc | actgtagcat | ctgaactgtg | aggaataaat | aatgaacaag | ttagaaattg | 111900 |
| tcaatgaact | tcgtcgttgt | gtagaaccta | ctcaagaggg | ttgggacatc | tggtaccatg | 111960 |
| gagcttatct | tggaactatc | gtaaagatta | agactggtaa | atacatgatt | attcgtgaaa | 112020 |
| gtaaagatgc | tccagtaggt | attcgcaata | attttatggc | agcgataagt | tcatttacag | 112080 |
| atgcagctta | cgaaatttac | cttgccgatt | ataaagaatt | ccaggaatct | caaccggtta | 112140 |
| ttcgttcaat | tggtgttaac | aaagctcagc | agaaaacttt | gtggcagcgt | attaaaggat | 112200 |
| ggtttaaatg | aacccattta | ttaatcgttt | aaaaatgctg | aatgttcctt | tatctcgtga | 112260 |
| aactccagaa | agtcttgttg | aaaaatttaa | agcgcatggt | tataaatgca | cagaagaaga | 112320 |
| tattctgaaa | gaagttcctg | aaatctgttg | gcagactgcg | tactgggatg | aaaaccaaaa | 112380 |
| gtatcaacga | cgaattgtct | gcgcagctaa | tcgttttaaa | ttaaaagatg | gacgaactct | 112440 |
| tattattcca | ggtgctcgtc | attattctaa | agatatggca | gaagttttag | atgtagttaa | 112500 |
| acctcaatta | gttactcaac | aagtttgtga | tgatgaccaa | ggatttattg | accaatatag | 112560 |
| taattattgg | acacgtgaag | aagcaatgat | tattgcaact | tacgccggac | aagtacgtat | 112620 |
| tgaacgtggt | ggtagtgaaa | aagaacttta | ctctgaggac | ctttactaat | gaatattaaa | 112680 |
| aagtttcaaa | ttgatggaat | tacgaatcaa | attaaggcat | ggaatatgc | caataaaatg | 112740 |
| atgtcaacta | attggggaat | ttatgcgaat | gagccagcat | ttaaattttg | tgatatggaa | 112800 |
| tttaccaaaa | agcttgtagg | aaaagatcat | gtatgcccat | ttagttctcc | ggtaaatgga | 112860 |
| atgctaaaac | ctgctttacg | cgatctttat | attgcgatga | acgaagaaat | gataaaagag | 112920 |

FIG. 17III sequence.txt

| | | | | | |
|---|---|---|---|---|---|
| ctaaaacgtc | aactgaaggt | gattcaattt | ggccagggaa | attaattcaa | aatcagatta | 112980 |
| ttttaactct | ctcaatgata | aagataaaaa | tctaatacgg | cattttattg | ttgagatggg | 113040 |
| atataccgat | acacacgatt | taagagaaca | tatatttgaa | tgtggtgtag | ctaaaaagtt | 113100 |
| ttcattcacg | tgcaaatgtt | taagagaggt | aattcaacac | tatgaacaat | ttagtcgcaa | 113160 |
| aacataattt | taataaagct | tctgtccata | aagataagaa | gaaagcgttt | aaagaatcta | 113220 |
| atcgcaaaca | gaaacataag | gggaaggtct | atgattattg | attctcaatc | tgtagttcaa | 113280 |
| tatacaatca | aaattgatat | tctagaaaag | ctatataagt | ttctaccaaa | tttataccac | 113340 |
| tcaattgtta | atgaattagt | tgaagaactg | catcttggga | ataatgattt | cttgattgga | 113400 |
| acttataaag | acctctcaaa | agcaggatat | ttttacataa | ttccagctcc | aggaaaaagt | 113460 |
| attgatgatg | tattaaaaac | tataatgatt | tatgtccatg | attatgaaat | tgaagattat | 113520 |
| ttcgaatgag | tcataatctt | gaaaaagtaa | tcgagcataa | tgtagctcag | gaacgtaagt | 113580 |
| cgttcaagga | attcgtagaa | aaaattttg | aagaaaatac | cacagaccag | tttacaaatc | 113640 |
| aagcgtctga | tgatattata | acaaagtcaa | ctaattgagt | ggtatagtta | atgaataaaa | 113700 |
| atattgatac | agttcgtgaa | attattactg | ttgcgtctat | tttgattaaa | ttttccagag | 113760 |
| aagatattgt | tgagaatcgc | gctaatttta | ttgcatttct | gaatgagatt | ggagtaacgc | 113820 |
| atgaaggtag | aaagttaaat | cagaattcat | tccgtaaaat | tgtttctgaa | ttaactcaag | 113880 |
| aagataagaa | aaccctcatc | gacgaattca | acgagggttt | tgagggtgta | tatcgatatc | 113940 |
| tagagatgta | tacgaacaaa | taattattta | gcccttccta | atattctggc | cgcctgagca | 114000 |
| catattgatt | caaggcggtc | attacttata | tgatcatttc | tataccagta | catggttatt | 114060 |
| gttccagcat | agatattatc | caaattaaaa | tatggacaac | tgtacatgta | gtttatttcg | 114120 |
| ggagtaggct | ttttagttgg | taaaaaagca | aattttgagt | cggaataata | atgacgtcca | 114180 |
| tttaaatgaa | ctgtatattc | atccatagtt | ttatcaacag | gatatcctcc | aagtgattt | 114240 |
| tcacttattg | ttgaaggtaa | ttttccttca | tatgctataa | tatcaacaaa | atagtttaag | 114300 |
| tttttagggc | ggaaagaata | caccgcacta | aagtctgcct | cagatgatat | atgaactatc | 114360 |
| tggagttgtt | ccagggcgac | agattcaaag | cgtgcatttc | tttccttttc | aataatttca | 114420 |
| ctgtatgttt | catactttga | ttgcttatag | tactcaaaga | aactatctcc | cctataccaa | 114480 |
| acaatcgcca | tcataaataa | aagaattacg | acagctaccc | gggaagcaag | aactttcccg | 114540 |
| gtagcgttat | ctttgaacaa | gcgatctaga | acaccaaaca | gaatatcaga | gggcgaaaat | 114600 |
| gatattctag | gtgctgccat | agaccctcct | tttaagggta | tttattcaca | ttatactctt | 114660 |
| ggaccatata | ttgctccaac | attttgccat | gttggagcgg | accctatgac | agcataacca | 114720 |
| gcagcgccgc | cattatattc | agatccttga | ccgcgaatat | tgcatctacc | tcccgcggaa | 114780 |

FIG. 17JJJ

```
                                sequence.txt
cctacttcac caccgtttcc accattatag ataccattca cggatcctga gccaggtgca    114840
gaaatagtac cgccagtcgc gcctgattgc atatcaatag atcctcctgg cgcaccaaaa    114900
ggacgaccgc caccaccacc aaaggtcaat ctcatttgtg aaaaaggaga ataatatccg    114960
ccgccgccac cgccgccacc gcctgcaata gctccgccat tattaattct tagtctccca    115020
ccaatatcgt tttgaataca atgacctcca gctgagccag gactattgct accgccatta    115080
cctccacgac catacatcgt tacgccatgt atatttaact gaacatattc atttggtgta    115140
tctccgtaca tgaagaataa aggaacatct ttagaataag aaacgatatc accaacaata    115200
ttgaatacaa taggtgcacc gccagcttca aagcatctat cacggaacca ctgaccatta    115260
aaattgtggt ttgctcctac agtatgaata atttctcgtg agcgacctgc aaattgactc    115320
atccagcaag gaacacccaa tcttaattga ccagctgctt gactcatcca gcgctgtcct    115380
gtttcatttg cggctgaact tccaatccaa ccaggaacac caactactgc cataatttat    115440
actccaaagg gggcatttcc cccttgttgt tagaatttaa aatatttact aattttgcga    115500
gcaattttag taaagagagg cgttttcaat tctttaattt cttcactcat ttcctgaata    115560
gccttaatta aaagagcatt cacagcagag ttagaaattg tcagaacatc agatccatca    115620
acttcaactt tagatacagc ttccggtaat tccttttcaa ggtcctgagc aataatacca    115680
acttcacgtt taataacact acggtcttta atagacttaa ctttatcgta aatataaact    115740
ttcagtcggc aaacttttc gactgctcca tattctaatt cttctttatt aatcttgaga    115800
cgggagtcag aacgaatata cacatcgcta aagctaccat ttcctggtgt ataaaagaat    115860
ccatcatgat ggaattcaaa cacagcttgt gggtgtccag catcaggaga agcctccgtg    115920
gatccgacac gaatgattgc ttgcccccac tgtgatggaa tacgacgcat accaaagtca    115980
acagcggtgc tatatccttg attggttata acgcttcttg ctttaagaat aggataataa    116040
ctatcttgac caacataacc atgatcaacg aataatggag cttctactcg ccattggttg    116100
ccccaatcac ccggttgtct agcaatccat ccagaaccgt taatgtgtac acggtcacgg    116160
ttaacgttaa ccattgcggt attttgcggg tttaacgcaa tctcaccatt gtttgtgata    116220
tgtactgccg cctgagaagc atagctataa aatgctagcg aattatcagc accaccctg    116280
ccaatatacc agttaccagt cccgtctatg tcaccgcgaa tatgcaaaga attactagca    116340
gttgttgata atacaataga atcattaggt gcattgattg ttaaccgacc tgtcatcgta    116400
tcaccgcctt tacctaggcg agtattcaag gcagcatcta aattggttgc atcgttgtat    116460
ttcttccaga ttgaaccagc aatgttacca tcagtgttca agaatgctgc gccagcataa    116520
actcggcttt gtgacatgaa tcggccagac ggcaagaaac gccatgtagc taattcagtg    116580
gctgtagttc cagtagcgga taaatcaccc tgagcaacga tacgatattc tgaactagca    116640
atatccatac cagaagccat agtaatattt gttacagtgt ttttctgttt aacaattggc    116700
```

FIG. 17KKK sequence.txt

| | | | | | |
|---|---|---|---|---|---|
| gcaaactggt | ttttatttga | atcgtcaata | gcctgatata | atggcgcaat | ggtagtattc | 116760 |
| tgatttgcgt | aagtattaga | accagaaccg | ctagcagggg | cttgaatata | tgctcctgga | 116820 |
| gcaagtgaaa | ttttctgatt | agcaccaaga | ttaacagcag | cagtgatatt | cagcaatccc | 116880 |
| ctaaagtttt | gttgagcagt | ccaagtatgt | gatccgtctt | caagaacaac | acgacgacaa | 116940 |
| gtattagtcc | tacttcctgg | attaccagcg | atacgaacaa | cgaaataacg | atagttcgcc | 117000 |
| tgagatacag | taccgcgcca | cacttgaaca | gttcgacccg | ttccggtatg | ttcgctagga | 117060 |
| ccgacagaaa | acataaccag | gtttccatca | atcgtgcccc | aatccatatt | tgctggcata | 117120 |
| ttctttattt | tgttcaaagg | aacactaaac | atactaccag | ggacaaaatc | aaaggtttgc | 117180 |
| caatctaact | ccgctaattg | agctttaata | ccacccatac | ccaaagtaat | tggcagagaa | 117240 |
| taagatgtat | atacttcgtt | ccatgcaccc | cacgcaccac | cagtatatgc | acgctcaaaa | 117300 |
| atacgatcgc | gagtagttgc | acccgttcct | gcggtagtga | aacgttggaa | aatagcaccg | 117360 |
| ccagaagcac | gctgtttaac | ttccagcaaa | ccaacaataa | cagtcggcaa | accttcacct | 117420 |
| gtaggacagt | taataacggc | atcagtgcct | aaaatattat | ataacccggg | agttttaaaa | 117480 |
| tcattcagat | ctccatcata | gaaagtcgct | ggtgtgccat | gaccaacctg | cttccattcc | 117540 |
| tcccacttag | gtgcactagc | atcccatgca | gcagcgagac | aacgagtata | aaccatacac | 117600 |
| atgcgggtag | tataacgctg | agttctcgtg | tataaaccac | cttcaaatat | ttctaaaaat | 117660 |
| ccttgtgcgg | ctgatccttc | ttctggataa | tggcgatcaa | atgatgcgat | tgcgcttgaa | 117720 |
| ctgtttcgcc | ataagccaca | atgttctaat | tctcccaagc | tatcaaggtc | aatcgtttgt | 117780 |
| gaaagtggac | gagttgacgc | ttgaacatta | cgccacacac | cccatggacc | atcgacgcca | 117840 |
| ttccatttag | cagataagga | acgaatatag | acgttaccag | atcttacagt | ataacgctga | 117900 |
| gtgccagcaa | attggccggc | cacaaacact | tctagtacac | ctacggcatt | ttcttctggg | 117960 |
| aatttatttg | ctggttgcgc | atttgttgaa | gtagatttcg | accaaacacc | aagatattct | 118020 |
| tcaatgggcc | catacgtatc | taaattagca | tcagtaggta | attcgccatt | atttttata | 118080 |
| aatgttgtgc | tattgacatt | tatgtcagat | ggagttaagg | taatgtcctt | tgacccatca | 118140 |
| aaagatatac | cattaatttt | cctaggtgtt | tgcaatttag | tagctgtgct | agaatttcca | 118200 |
| attaaagttc | cagttatatt | ttctgtaacc | tctaaagacc | catttatagt | tcctccatat | 118260 |
| tttaaaccta | attctataac | actacctgag | tcatcttttg | tgaaaattgt | tttatctttt | 118320 |
| aagtttatag | ccaattcacc | ttcggctaat | actgaagcag | caggacgttg | acctgcagtt | 118380 |
| ttgcttcttt | taaattgtat | ttgttttaaa | gtagccataa | gtcctcttaa | taatagccga | 118440 |
| aatcttgaac | agaatcctta | attacgattt | ggtcaaatcg | tggaacgtgt | gaaggttgag | 118500 |
| atgcaggatt | ctgtgaaaaa | aggtttggcg | cagttaaatt | tcctgtcata | gtgtctccag | 118560 |

FIG. 17LLL sequence.txt

```
agcgtaatac cctagagttt gcatttgctg taacagtatt tattgctcca tcaacataat     118620
ctttgcgagt aacatcagat gctgcggaag gagtagatgt aacagttacc gatggagccg     118680
ttacagccct ggtaaatgtt gtcaaacctt ctggcgtaat agtaatttgt ccagtagtga     118740
tttcactacc tgcaggtcta aaactaatac caccggaaga gccgccaact acaagagtat     118800
taccagtgcc gccaccagaa cgaattcgga tagggtttc attattactt aattgaagat     118860
aactatttac cccgtaatta atagtaattg gaccggcgta agtaccacca ttagctttag     118920
aaacgaaatc gttatcagct gcctgcggtt tattatattc tgaatatatt ttaaatgatt     118980
tgtagagtac atcgtcaccg gctgaattca atggaaaatt tccttgatgc caaatgacag     119040
atccacccac agttgaacct acttttaaat cagccattat atgccccttt attttaatat     119100
tatttataaa gaaaaaggga acccgaaggc tccctcagtt taaacttctc taaattcctg     119160
tccaaacact ttgccagttt tagaagaggc ttgtgtagga agtaccatta tatctggagg     119220
tgaagccgat tcacagacat aattaacgcg aataccgttg acgccaaatt cggcaggttt     119280
tgaaatgccg ccatttcttg atacttcaga aaaacttaaa tttctcatgc cgccttgacc     119340
tgcttgagca gttctttgtg catatatcgt aaatcctacg gcgttttctg gaacaactac     119400
atagtcttct tttaattccc aagacccagc ttgcccagta aactcagctt gggtcgagga     119460
aatatatcca tttgatgcat cataaaaacg aatggatatg tttgtagttc caagatcaag     119520
taaatcagca tcagcatata actgtgcttt aagataaaga acatcaccag gaattaaatt     119580
atagtcagaa agtttactta tagcagctga agttggcaat cgcgcaattt cgttattagt     119640
tccaccaact gctgacatga attgctctac actttcataa gttctttttg gaaatcctgt     119700
cgctccgacg tcttctaaac tatcaaatac aacatctaaa atagtttgat aatcatctgt     119760
gcttttcta ttacttagtt taacatgctc taatgcaata gctcttttag aagaagtata     119820
aaaagcagca tatgatacgt caaatcttga caatactgaa tctgatggaa aaactgaagt     119880
tcctgctccc cttaaccaag ataccacttc aggaggaaaa ttaacctttc cgctagttaa     119940
tatagcaaca agtctattgt ttgacaaaga attcatgaaa ctgacaaaag cggcagatgt     120000
tgtattgttt gaagcagaaa aagcatatga cttgctatca actaatgctc ccgtagaagg     120060
gtcaaaaact cttaaatgaa gacctgcact aaatgtttga tttccaacgg gattatcctg     120120
aaatttaaca tatggccccg cagtagaaag cgggcaagaa cccgctatgc ttattttgta     120180
tcttactgaa ttactttccg ataaaaatgg cgtttggacg tatccttgtc caaactctgc     120240
cataaatttt tccataatac ctcttattca acccattcaa atttaacagt tttattcact     120300
gggtcaggaa taatgcgaac attaccaatt cgtaagaaat cacgaatagt aagattacct     120360
attattccat tatcagatgg gattgctcct atatccgaag gttgaggagg gttacctcca     120420
tcaaatacct gaacaaaact tgaccaagaa tttttagttt tctgccatgt acgcgtccag     120480
```

FIG. 17MMM sequence.txt

| | | | | | | |
|---|---|---|---|---|---|---|
| cgagtggtac | gtgcttctgg | ggtcgttgga | taagtaatcc | aatcttggta | aagcgaatca | 120540 |
| agtgtgttac | caaactgagt | caatgtacca | ggagatttaa | cttcttcgcc | acgttctaag | 120600 |
| tatggaagcc | cagtcacttc | attagttttt | tcaaccattt | taaaataacc | cgggaactgg | 120660 |
| ttataagtgg | ctgaatcgtt | aatatcaatt | gaccagaatc | ctacagtatc | agatgttgga | 120720 |
| gcgcgggtgt | ataaatcaga | tgttttagtg | ccctgagaac | gaattctcga | gttaacagtc | 120780 |
| aaaccgcctg | aatttatagt | agcacctttg | gcaatgatta | agctttcacc | aatcgttact | 120840 |
| tggccagatg | cattattaat | agctaaagga | cgtaatccat | taaatccacc | agtctgatca | 120900 |
| cccgatgcag | taagcataaa | attcgttact | gatccatcat | tgcgaacaat | gaaaccataa | 120960 |
| tttccgttaa | tagcacggaa | agcatttgcg | cttcgagaaa | taatttcacc | agttgcagtg | 121020 |
| actgaattac | caaatgttgc | tacaccattt | gcattcaatg | ttcctgaagc | attaacattt | 121080 |
| atcggtgtta | ctgtaccgtt | gatattaaat | gttatatttc | cagctttatt | acgctgagaa | 121140 |
| taaaaatgac | tagacgtttc | atcactaact | tcaaatacgg | tagaacgtgt | tgtgtctgat | 121200 |
| tccccgctaa | attgatttcc | ccacactctg | actgtcatcg | tttgagccgg | gtttgttcca | 121260 |
| gtttgaggtc | ctttctcaaa | aatcagacga | gttgccgttc | cagtattaga | aatagttaat | 121320 |
| gtactatttg | ctgaaactga | tccaccgaat | gtagcagtac | tagatgatac | aagaggggca | 121380 |
| cccagattcg | tttgttgggt | taaggttagt | gaaccattaa | ctgtttgtgc | aatgtcccta | 121440 |
| cgaatgaact | ggagcgaatc | tagaccatct | aataaattac | tatctacagc | ttttgctttt | 121500 |
| aatggcaaat | aatttgctaa | tacgcgattt | aattcatatg | gtgatactgc | ataaccattt | 121560 |
| ttctcatatg | attctaatgg | ctgtgttgaa | cctaccgtat | cattaccaac | aaacgttaat | 121620 |
| gaaccagaag | aagttttaac | aaaccctctt | atcagagtag | ttgctgccca | agttggttca | 121680 |
| ctctgcacaa | tccattttaa | attttttgga | gatacagcag | tatttgctga | cgttccagtc | 121740 |
| acagtttcag | actgagttgc | aactttaata | acaccttctt | gcgattcggt | agatttagta | 121800 |
| cctaaaagct | ttttaggagt | tattaaaaca | ttatctaatg | ttcctgcagc | agcttcaact | 121860 |
| tgtgtagcta | cacgaagtgt | accacgctgt | gtctcatttg | cttcaagaat | attaagggta | 121920 |
| taatggtccc | agagagttcc | tgattcaact | aatccagata | gagcaacaac | agaagtacga | 121980 |
| tcagtactat | taaatctggt | tttaattttt | aatggtgtag | agatacgagt | atcgtcgacg | 122040 |
| cctgcgtcga | attcaacttg | cgtagcaatt | tcagctatac | cacttaaact | ttcagttgct | 122100 |
| ctacggtcat | ttaaagtttt | aggagtgact | gcgcgagtat | aatcagttcc | tgtattaact | 122160 |
| tcgctttgcg | tagcaatttc | aattaaacca | attcttccat | cagttgatgt | ctttttatgt | 122220 |
| aacgtttctg | gtgttacaac | cgcatttgcc | catccttctt | ggctttgtcc | agcaattact | 122280 |
| tcactttcaa | ctgctaaaat | tactgcgcct | tgttgcgttg | gagtagcttt | atactgatcc | 122340 |

FIG. 17NNN sequence.txt

```
aaagctttag gtgaaacaac taaattatta gtgttttat tataaacatt cgtaccattt    122400
aattcacgac tagaagctgg agtagctcct gcggtagata caaaagttac aataccagat    122460
aatgattcag aaccttgacg agcttgaagc tttttaggag tgatgattgt agtatcatca    122520
gtacctgtat tagtttcctg ctgcgtagca atttcagcga cacctctacg agtttctgta    122580
gcagttcttt cattcagctt tttaggagtg atgataaggt catctgcaaa agagaatgtg    122640
gtgttctgat ttacttgagc agtagttgct attcttgcaa tacctctgcg agtttcagta    122700
gcagtacgat tagctaacgt ttctggagta attgccaatt cttttgcgg agaattttct     122760
aaatcagcat ttgcttgagc ttgtgtagct aaagcaatta cgcctaatct tgctctagta    122820
gaagcattta aagagtctac tctttctaca gttggaacgt tttgctgtac aacccagtat    122880
tttccatcag aatcttctat ataagcaagt tgtaaaactg aacataatt agtttcaccg      122940
ttaaaaacta attcttgaac tgttacccat tcagcttcag gcggatattc tgaacgtttt    123000
gggaattgca gcaattgaac tgaagaagca attttatctt caccagcagc tttgatttta    123060
actgtttgtc cttttctcat gtaattcatg gaatttttaa cagtatcacc aacagaaata    123120
tcagtcggaa gctgaagttc aattgtttgg gttgttccat tattcgcgcc aaataccatg    123180
acttcttcat ttggacgaat atttgaatta gttgttataa tgcgtaaacg tgctttacta    123240
tccccgtcaa acaatctcca caatttctca ttatcgtcaa acatcaagaa accgtcaatc    123300
gatgtacggc cttcaatgga atgagttcca acttcttgta ctgaagtcgt ttcatcgtat    123360
gtagtaacaa ttgtatgata aagtggattc agtttatcta aatcaacgaa attaataata    123420
tcgccatgat tagcaaatct cggaagttta acattaattg gtgcagcaga agtaaatcta    123480
cgtacgataa aatcattaga ttgtgcttga tacgcagtcg atggagtaac aatcgcagct    123540
tctctgctat aatcagcaac atacatttgc cacaaacgat tattaaaaat gaatatcatc    123600
tgtgactttg gatgagtcat taaaactgaa cgtacttgtt cacctctaaa attgacaata    123660
ctctgatttg aagaatttat tttaacctga tttatgccag gttttccacc gatatcttga    123720
attattacgg tttctccatc aagcggagaa ggtggtaaag taaactcaat gtcattgcca    123780
actgatgtat ctactgaaat tgcttctccg gattttaatt gatatggtcc agatgataca    123840
gttgtatata cagcatcagt acgtaatgct ttccaacgaa ttctattaaa atttccagca    123900
ggttttggaa tattatccgt tgctgcccaa aaacgattat tataaatgat tacaaaatct    123960
tttaaatatc cacgagttgg atcatattgc tgaactgtgt tttcttgaat taagtaatca    124020
acgttaacac cgtcagttcc tacggtacga tcagctaaag ctacgttgat tattttatcg    124080
ccacctgcgt ccagaccatc ttctgctctg aactttcttt taatctcggc cattctcccg    124140
ggctcctatt gtgttttcaa taataagtat ttatacctgt ttactttaag atttagatag    124200
tatataatag aaatctcact aattgaacga ggttcatatg gatttagaaa tgatgctgga    124260
```

FIG. 17000 sequence.txt

| | | | | | |
|---|---|---|---|---|---|
| tgaagattac | aaagaaggaa | tttgctttat | tgactttagt | caaattgctc | tttcaactgc | 124320 |
| tctggtaaac | ttcccagata | aagaaaaaat | taatttatcg | atggttcgtc | atttgatatt | 124380 |
| gaactcaatt | aagtttaatg | tcaaaaaagc | aaaaacgctt | ggatacacta | aaattgtgct | 124440 |
| gtgtattgat | aacgcgaaat | ctggatactg | gcgtcgtgat | tttgcttact | attacaagaa | 124500 |
| aaaccgtgga | aaagcacgag | aagaatctac | ttgggactgg | gaaggttatt | ttgaatccag | 124560 |
| tcataaagtt | atagatgaat | tgaaagctta | tatgccatac | attgttatgg | atattgataa | 124620 |
| gtatgaagca | gatgaccaca | ttgctgttct | tgttaaaaag | ttctctttag | aaggacataa | 124680 |
| gattttaatc | atttcatcgg | acggtgactt | tacacagctt | cacaaatatc | caaatgttaa | 124740 |
| gcaatggtca | ccgatgcata | agaaatgggt | taaaattaaa | agcggttctg | ctgaaattga | 124800 |
| ctgtatgact | aaaatcctta | aaggcgacaa | aaaggataac | gttgcttcag | ttaaagtacg | 124860 |
| atctgacttt | tggtttacca | gagttgaagg | tgaacgaacc | ccttcaatga | aaacttcaat | 124920 |
| cgttgaagct | attgctaatg | accgtgagca | agctaaggtg | cttctcacag | aatctgaata | 124980 |
| taatcgttat | aaagaaaatt | tagttctaat | tgattttgat | tatattcctg | ataatattgc | 125040 |
| ttcaaacatt | gtgaattact | ataattcata | taaattacca | ccgcgtggca | aaatttattc | 125100 |
| atattttgta | aaagcgggtc | tttctaaatt | aactaatagc | attaatgaat | ttgaggtga | 125160 |
| ataatggcta | aaaagaaat | ggttgaattt | gatgaagcta | tccatggcga | agacttggct | 125220 |
| aaatttatta | aagaagcatc | tgatcataaa | ctgaaaattt | ccggttataa | tgaactgatt | 125280 |
| aaagatattc | gaattcgtgc | taaagatgaa | cttggcgttg | atggtaagat | gtttaatcgt | 125340 |
| ctattagctt | tgtatcataa | agataaccgt | gatgtgtttg | aagctgaaac | tgaagaggta | 125400 |
| gttgaacttt | atgacacagt | tttctctaaa | tgatattcgc | ccggtcgatg | agaccggtct | 125460 |
| ttcagaaaaa | gaactttcaa | ttaagaaaga | aaaggatgaa | attgcaaagc | ttcttgaccg | 125520 |
| ccaagaaaat | ggatttatta | ttgaaaaaat | ggtagaagaa | tttggaatga | gttatcttga | 125580 |
| agctacgaca | gcattcttgg | aagaaaactc | tattcctgaa | actcaatttg | ctaaatttat | 125640 |
| tccttcgggt | ataattgaaa | aaattcagtc | agaagccatt | gacgaaaatc | ttttacgtcc | 125700 |
| ttctgttgtt | cgttgtgaaa | aaactaatac | attagatttt | ctgctatgat | taaactccgc | 125760 |
| atgcctgctg | gtggtgaaag | atacattgat | ggtaaatcag | tttataaatt | atacttaatg | 125820 |
| ataaaacagc | atatgaatgg | aaagtatgat | gtaattaagt | ataattggtg | catgcgggtg | 125880 |
| tctgatgccg | cttatcaaaa | gcgaagggat | aagtattttt | tccagaagtt | atcagaaaaa | 125940 |
| tataaattaa | aggaacttgc | tttaattttt | ataagtaatt | tggttgctaa | ccaagatgct | 126000 |
| tggattggtg | acatctctga | cgctgatgca | cttgtgtttt | atcgtgaata | tatcggacgc | 126060 |
| ttaaagcaaa | ttaaatttaa | gtttgaagaa | gatattcgca | atatttacta | ttttagtaaa | 126120 |

FIG. 17PPP sequence.txt

```
aaagttgaag tttctgcttt taaagaaatc tttgagtata atccaaaagt tcaatcaagt    126180
tatattttta aactacttca atcgaatata atttcgtttg aaacgtttat cttgcttgat    126240
tcgtttttaa ataatattga taaacatgat gaacagactg ataatttagt ctggaataat    126300
tattctataa agttaaaggc ttatagaaaa attttaaata ttgattcaca gaaagctaaa    126360
aatgttttca ttgaaactgt gaaatcttgc aagtattaat tgcttattat aaataagatt    126420
ataattatct cactgaccag ctatgaggtc atacatcgtc atagcaccaa ctgttaatta    126480
aattaaaaag gaaataaaaa tgtttaaacg taaatctact gctgaactcg ctgcgcaaat    126540
ggctaaactg gctggaaata aggtggttt ttcttctgaa gataaaggcg agtggaaact     126600
gaaactcgac aatgcgggta acggccaagc agtaattcgt tttcttccgt ctaaaaatga    126660
tgaacaagca ccattcgcac ttcttgtaaa tcacggtttc aagaaaaatg gtaaatggta    126720
tatcgaaaca tgctcatcta cctacggtga ttacgattct tgtccagtat gtcagtacat    126780
cagtaaaaat gatttgtaca acactgacaa taaagagtac agtcttgtta aacgtaaaac    126840
ttcttactgg gctaacattc ttgttgtaaa agacccagct gctccagaaa acgaaggtaa    126900
agtatttaaa tatcgtttcg gtaagaaaat ctgggataaa atcaatgcaa tgattgcagt    126960
tgatgttgaa atgggtgaaa ctccggttga tgtaacttgt ccgtgggaag gtgctaactt    127020
tgtactgaaa gttaaacaag tttctggttt tagtaactac gacgaatcta aattcctgaa    127080
tcaatctgcg attccaaaca ttgacgatga atctttccag aaagaactgt tcgaacaaat    127140
ggttgacctt tctgaaatga cttctaaaga taaattcaaa tcatttgaag aactgagcac    127200
taagttcagt caagttatgg gaactgctgc aatgggtggt gccgctgcaa ctgccgctaa    127260
gaaagctgat aaagttgctg atgatttgga tgcattcaat gttgatgact caaaacaaa    127320
aactgaagat gatttttatga gctcaagctc tggcagttca tctagtgctg atgacacgga    127380
tctagatgac ctttgaatg accttaaca gattatatta ctaattaatt ggggacccta      127440
gaggtcccct ttttatttca aaaatttttt cacaaaactg tttacatcct tgtccttcca    127500
tggtactata caactatcgg caatactgct gataattaaa gaggaaaata atatggctaa    127560
agttgatatt gacatcgttg attttgaata tattgaagaa attattcgta atcgttatcc    127620
tgaacttagt atcacaagta ttcacgatga tcccaattat tgcaatttt ctattgtcat     127680
tgaaggtcct cttgaagacc tcacccgctt tatggctaat gaatattgtg atggtatgga    127740
ttctgaagac gcagaatttt acatgggatt gattgaacaa taattatcaa ggggctatta    127800
caagcccgt taaatgagg aaaacgtaat gtatattggc aaaaagtatg agcttgttcc      127860
aagcttatt gatacattta ttaattatcg cccacgttct aattcatcga tagttaaaat     127920
tattcaagaa aatggtggat ggtttgaagt taaagaagct ttctttgttg atggatttag    127980
agtaataaaa cacattgaat gcgcaaatgg aaagcatttt tactttaacg tttgtgaaga    128040
```

FIG. 17QQQ sequence.txt

| | | | | | | |
|---|---|---|---|---|---|---|
| cgaatttcat | tgttttcgtg | agtataaaga | accgacttct | gaagaagatg | gagccgaaga | 128100 |
| catagtttct | ggcgtaacaa | aaattcactg | cattgttgac | gaaaataatg | tagatgaaat | 128160 |
| cattgaactt | ttgcgaaaaa | ctttcaaaaa | gtagtttaca | acagggtagt | agtgtgatac | 128220 |
| tattaccta | tcaaaactaa | tggagaaaag | aaaatgttcg | cacctttat | tatggcagca | 128280 |
| gttatgttgg | tctgtttata | tcttttgatt | aaagcttgct | aaggagaata | aaatgagatt | 128340 |
| acaacgccag | agcatcaaag | attcagaagt | tagaggtaaa | tggtatttta | atatcatcgg | 128400 |
| taaagattct | gaacttgttg | aaaaagctga | acatctttta | cgtgacatgg | gatgggaaga | 128460 |
| tgaatgtgat | ggatgtcctc | tttatgaaga | cggagaaagc | gcaggattct | ggatttatca | 128520 |
| ttctgatgtt | gatcagttta | aagctgattg | gaaaattgtg | aaaaagtctg | tttgaggaaa | 128580 |
| ataatatgtc | tggcattcat | gtaactggaa | ttgctcaagt | aaacatccgc | tgccaattta | 128640 |
| aaactgtacc | tggggtgact | catattactt | tatcacacga | cccatattct | cgtggaagac | 128700 |
| agttaactgg | cgtaattaag | tttttcggcg | gaattggcgg | aagcgaattt | actataggag | 128760 |
| atgacgaaat | tgttggctgt | aaattaaaag | ttcagaaggg | cgtgttagaa | cttttagtg | 128820 |
| atgaagtttt | tgatgaaatc | tcacgagcag | ttaacaaagg | aatgttaacg | ttaattaaaa | 128880 |
| tgattaaagc | tagcggatat | gttactgatc | cttttaata | ggaggcaata | tgattttgt | 128940 |
| atttgaattt | atgaatgatg | aattcgatta | tgcaattttt | aacgcattgc | ataatcctga | 129000 |
| tttaagtgaa | tttaatgaaa | tgttttctga | cgctttgagt | atgtcagaag | aatactgtgg | 129060 |
| agaatgtcaa | cgtgtttgtg | tgacagtctt | tgaaaacaaa | gaaaagacct | atgaagaatt | 129120 |
| attctttgat | gctaataaag | ccactgaatg | gtttgttgaa | agaggttttg | cgtaatgatt | 129180 |
| aaattggtat | tcgcttattc | tccaactaaa | acggtcgaag | gctttaatga | attagcattc | 129240 |
| ggtttaggtg | atggtttacc | atggggacga | attaaaaagg | acctccagaa | ttttaaagct | 129300 |
| cgtacagaag | gtacaatttt | gattatgggt | gctaaaacgt | tccagtcatt | atctacatta | 129360 |
| cttcccggtc | gtagccatat | tgtggtgtgt | gaccttgcgc | gtgattatcc | tgtaactaaa | 129420 |
| gacggcgatt | tagcacattt | ctatattact | tgggaacagt | acataactta | catttctggc | 129480 |
| ggcgaaattc | aagtttcaag | tcctaatgca | ccattcgaga | ctatgcttgg | tcagaattcc | 129540 |
| aaagtaagtg | taattggcgg | gcctgctctg | ttatatgctg | cgttaccta | tgcggatgaa | 129600 |
| gtagttgttt | ctcgcatcgt | taaaaggcat | cgtgttaatt | caacggttca | attagacgca | 129660 |
| agttttcttg | atgatataag | caagcgtgaa | atggttgaaa | cgcattggta | taaaatagat | 129720 |
| gaagtaacaa | cccttacgga | atcagtatat | aaatgagcaa | taaattaaaa | gttaaggatg | 129780 |
| ttcctaatgc | tatggcccctt | tttatttgta | ggcagatgca | tcaagggcct | atgacaccaa | 129840 |
| aacaatatct | taaaggtgag | cgttctttag | gatttactcg | caaagcaaaa | caaatggtta | 129900 |

FIG. 17RRR sequence.txt

```
aattaggata taagcctaac tttgccaaat atccttctac atattcttgg atgaactaat    129960
gaaacaatac caatttttaa ttaaagatat cctggaaaat ggctacgaaa ccgatgaccg    130020
aacaggcaca ggaacaattg ctttgttcgg tactaaatta cgctgggatt taactaaagg    130080
ttttcctgca gtaacaacta agaagctcgc ctggaatgca tgtatttctg agttattgtg    130140
gttcttatca ggaagtacta acgtaaatga tttgcgatta attcaacata attcattaat    130200
tcaaggcaaa acagtttggg atgaaaatta cgaaaatcaa gcaaaagatt taggatacca    130260
tagcggtgaa cttggtccaa tttatggaaa acagtggcgt gattttggtg gtgtagacca    130320
aattatagaa gttattgatc gtattaaaaa attgccaaat gataggcgtc aaattgtttc    130380
agcatggaat ccagctgaac tcaagcagat ggcattaccg ccttgtcata tgttctatca    130440
gtttaatgtg cgtaatggct atttggattt gcagtggtat caacgatcag tagatgtttt    130500
cttgggttaa ttgaggcctg agtataaggt gacttatact tgtaatctat ctaaacgggg    130560
aacctctcta gtagacaatc ccgtgctaaa ttgtaggact gcccttttaat aaatacttct    130620
atatttaaag aggtatttat gaaaagcgga atttatcaga ttaaaaatac tttaaacaat    130680
aaagtatatg taggaagtgc taaagatttt gaaaagagat ggaagaggca ttttaaagat    130740
ttagaaaaag gatgccattc ttctataaag cttcagaggt cttttaacaa acatggtaat    130800
gtgtttgaat gttctatttt ggaagaaatt ccatatgaga aagatttgat tattgaacga    130860
gaaaattttt ggattaaaga gcttaattct aaaattaatg gatacaatat tgctgatgca    130920
acgtttggtg atacatgttc tacgcatcca ttaaagaag aaattattaa gaaacgttct    130980
gaaactgtta aagctaagat gcttaaactt ggacctgatg gtcggaaagc tctttacagt    131040
aaacccggaa gtaaaaacgg gcgttggaat ccagaaaccc ataagttttg taagtgcggt    131100
gttcgcatac aaacttctgc ttatacttgt agtaaatgca gaaatcgttc aggtgaaaat    131160
aattcattct ttaatcataa gcattcagac ataactaaat ctaaaatatc agaaaagatg    131220
aaaggtaaaa agcctagtaa tattaaaaag atttcatgtg atgggggttat ttttgattgt    131280
gcagcagatg cagctagaca ttttaaaatt tcgtctggat tagttactta tcgtgtaaaa    131340
tctgataaat ggaattggtt ctacataaat gcctaacgac tatccctttg gggagtaggg    131400
tcaagtgact cgaaacgata gacaacttgc tttaacaagt tggagatata gtctgctctg    131460
catggtgaca tgtagctgga tataattccg gggtaagatt aacgaccttta tctgaacata    131520
atgctaccgt ttaatattgc atcatatgct acgttagttc atattgtagc taagatgtgt    131580
aatcttatcc caggagattt gatattttct ggtggtaata ctcatatcta tatgaatcac    131640
gtagaacaat gtaaagaaat tttgcgtcgt gaacctaaag agctttgtga actggtaata    131700
ggcggattgc cttataaatt ccgctatctt tctactaaag aacaattgga atacattctt    131760
aaactcaggc ctaaagattt cgttctcaaa gattatcagt cccacggcgt cttgaaagga    131820
```

FIG. 17SSS sequence.txt

| | | | | | | |
|---|---|---|---|---|---|---|
| aaaatggcgg | tgtaatttca | atttaattgc | gaggatatat | gattttacga | tttaaagata | 131880 |
| cttctggtgc | agttcttttt | acacttccta | atccaagtga | gctagaagtt | ccaggaccaa | 131940 |
| atcagcctat | tatcatttat | ggcaaaaaat | attatactca | taaaatgact | cgtgagtatt | 132000 |
| ttgataataa | aatttctaca | gttaaaactt | cttctgattg | ttactatgat | attactgttt | 132060 |
| taacggaaaa | acaatatgac | gaattatcac | cgcgcgggcc | gtctatgcca | ggtagtgaat | 132120 |
| aaatataaat | ccgactttga | tgtcaatatt | caccgcggta | cattttgggg | aaattacgtc | 132180 |
| ggtaaagatg | ctggcagccg | ggaggctgcc | attgaattat | tcaaaaaaga | ttttatacgt | 132240 |
| cgaattaaat | ccggagaaat | aactaaagca | catttagagc | ctttacgtgg | aatgaggcta | 132300 |
| ggatgcacat | gtaaaccaaa | gccgtgtcat | ggtgatataa | tagctcatat | agttaaccga | 132360 |
| ttgtttaaag | acgattttca | agttgaggac | ttatgcaatt | aattaatgtt | atcaaaagta | 132420 |
| gtggtgtttc | tcagagcttt | gacccacaaa | aaattattaa | agttttatct | tgggcagctg | 132480 |
| aaggaacatc | agtagatcct | tatgaattat | atgaaaatat | taaatcatat | ctccgtgatg | 132540 |
| gaatgacaac | tgatgatatt | cagactattg | tcattaaggc | cgctgcgaat | tctatttcgg | 132600 |
| ttgaagaacc | tgattatcaa | tatgtagctg | cacgttgttt | aatgtttgct | cttcgtaagc | 132660 |
| atgtttacgg | gcagtatgaa | ccgcgttcat | ttattgacca | tatttcttac | tgtgtaaatg | 132720 |
| aaggtaaata | tgaccctgaa | ttgttgtcaa | aatattcagc | agaagaaatt | acatttttag | 132780 |
| aatcaaaaat | taagcacgag | cgggatatgg | aatttactta | ttccggggcg | atgcaattaa | 132840 |
| aagaaaaata | tctcgttaaa | gataaaacca | ctggtcaaat | ttatgaaact | ccgcagtttg | 132900 |
| catttatgac | tattggaatg | gcattgcatc | aagatgaacc | tgttgataga | ttaaaacatg | 132960 |
| ttattcgttt | ttatgaagca | gtatctactc | gacagatttc | attaccaact | cctattatgg | 133020 |
| ctggttgtcg | tactccgact | cgacagttta | gttcatgtgt | tgttattgag | gcaggtgatt | 133080 |
| cgctgaagtc | tatcaataag | gcttccgctt | cgattgttga | atatatctct | aaacgcgctg | 133140 |
| gaattggtat | taacgttggt | atgattcgtg | ccgaaggttc | taagattggc | atgggtgaag | 133200 |
| tacgccatac | tggtgttatt | ccttttttgga | aacatttttca | gactgcagtt | aaatcatgtt | 133260 |
| cacagggtgg | aattcgtggc | ggcgctgcta | ctgcttatta | tcctatttgg | catttggaag | 133320 |
| ttgaaaatct | tctcgttttg | aaaaataaca | aaggcgtaga | agaaaaccgc | attcgtcata | 133380 |
| tggattatgg | tgttcaactg | aatgatttga | tgatggaacg | attcggaaag | aacgattaca | 133440 |
| ttactttgtt | cagtccgcat | gaaatgggtg | gagagctttta | ttattcttat | tttaaagacc | 133500 |
| aagaccgttt | ccgtgaatta | tacgaagcag | cagaaaaaga | ccctaatatt | cgtaaaaagc | 133560 |
| gtattaaagc | ccgtgaacta | tttgaattgc | tcatgactga | acgttcagga | acagcaagaa | 133620 |
| tttatgtaca | gttcattgat | aatacgaata | actatactcc | gtttattcgt | gaaaaggcac | 133680 |

FIG. 17TTT sequence.txt

```
ctattcgtca gagtaacttg tgctgtgaaa ttgctattcc aacaaatgat gtgaatagtc    133740
ctgatgctga aattggattg tgtactctct ctgcattcgt actagataat tttgactggc    133800
aagaccaaga taaaattaat gaattggcag aagttcaagt tcgtgctctt gataatcttt    133860
tggattacca aggatatcca gttcctgaag cagaaaaagc taaaaagcgt cgtaacctcg    133920
gtgtaggtgt taccaactat gcagcttggc tggcaagtaa cttttgcttct tatgaagatg   133980
ctaacgattt aacacatgaa ctatttgaga gattacagta tggactcatt aaagcatcca    134040
ttaagctcgc caaagaaaaa ggaccttgcg aatattattc agacactcgt tggtctcgag    134100
gcgaattacc tatcgactgg tacaataaaa agattgacca aatcgcagct ccaaaatacg    134160
tttgtgactg gtcgtcgctg cgggaagacc ttaagctctt tggcatccgt aatagcacac    134220
tatcagcact tatgccatgt gagtcatctt cccaagtttc taacagtaca aacggtatcg    134280
agcctccacg tggaccagtc tctgttaaag aatcaaaaga gggttccttt aatcaagtcg    134340
tgcccaatat tgaacataac atagacctat atgattatac atggaaatta gctaagaaag    134400
gtaataaacc ttatcttacg caagtagcta ttatgctgaa atgggtatgt caatcagctt    134460
cagcgaatac atactatgac ccgcagattt ttccaaaagg aaaggttcca atgtcaataa    134520
tgattgatga ccttttgtat ttttggtatt ttggcggaaa aaatttctat tatcataata    134580
cccgtgatgg ttctggtact gatgattatg aaatagaaac tccaaaagct gaagattgtt    134640
catcctgtaa attatgatat aatttgactc acggacgagt caccaactat taactaagcg    134700
gaaaatttat gagcacagtt tttaatacaa atccagttga tgttttaaaa gaacctatgt    134760
tttttggttc aggtcttggt attgcgcgtt atgatattca acgccataaa gtttttgaag    134820
atttgaccga aaagcaatta tcatttttct ggcgtcctga agaagtaaac ttaatgatgg    134880
atgctgcaca gtttaataag cttcctcaat atcagcagaa tatttttact aataatctga    134940
agtatcaatc acttctagat agcattcagg gtcgtgcacc gtctgctgta cttatgtcat    135000
tgatttcaga cccaagcctt gatacatggg ttgctacatg gacttttagt gaaactattc    135060
acagtcgttc atatactcat atcatgcgaa atctttatac tgatccatcg aaggtatttg    135120
atgaaattgt attagatgaa gctattatga aacgtgctga atctattgga cgttattatg    135180
atgatgttct gattaaaact cgttattggg aaaacgctaa agctgatatc gaataccaaa    135240
aagaaattaa tgcagacgaa gacgttattg aagatgctat tgagcatgag acatattgga    135300
agcgtgagct aatgaaatct ctttacctct gtttgcatgt aatcaacgca ttggaagcta    135360
ttcgttttta tgtatctttt gcatgtacct ttaacttcca taagaacatg gaaatcatgg    135420
aaggtaatgc caagattatg aagttcattg cacgtgatga gcagcttcac cttaaaggca    135480
cccaatatat tattcgtcaa cttcaacttg gcactgatgg cgatgaatgg gttaaaattg    135540
ctcaagagtg tgaacaagaa gcagttgata ttttcatgga agttaaccgc caagaaaaag    135600
```

FIG. 17UUU sequence.txt

```
attgggcagt tcatttattt aaagatggtg atgttcctgg attaaataca aatagcatgt    135660
ggagctttat tgattactta actgtatctc gtatgaagca gtgtggtctt ccatgcccaa    135720
ttaccgatgc tccggttaaa catccatatc cttggattcg tgaatatctt aattctgata    135780
atgttcaatc tgcgccacaa gaagtagaat tgtcatctta ccttgttgca cagattgata    135840
atgatgttga tgataaagtt atgatgagtt ttaaaaaata cttttaagga gtgggccgca    135900
aggcccattt tattatgaaa gaaattgcaa cagaatattc atttattaaa tatactgagc    135960
tagaattaga ctacaacgga agtataaaac aattatctat tccaaacaag tataacgtaa    136020
tttatgctat tgctataaat gatgaacttg tttatattgg aaaaactaaa aatttacgca    136080
aaagaataaa ctattataga actgctatta accgtaaaga caaaacgtct gattctacta    136140
aatctgcatt aattcatgct gcgctaaagg aaggaagcaa agttgaattt tacgcccgcc    136200
aatgttttaa tctttctatg acaaatgagt taggtacaat gacaatcgcg acgattgacc    136260
tagaggaacc actattcatt aagctgttta acccgccttg gaatattcaa cataagaaaa    136320
aatgatgctt ccacatggag tgtggtacta tattcaaaac acaaagagg atacacaatg    136380
caagaacttt ttaacaattt aatggaacta tgcaaggatt cacagcgtaa gttttttac    136440
tcggatgatg taagtgcgtc tggaagaact tacagaattt tctcatataa ttatgcatct    136500
tattctgatt ggttacttcc agacgcattg gaatgtcgtg gaatcatgtt tgaaatggat    136560
ggagaaaaac cagtaagaat tgcttctcgt cctatggaaa agtttttttaa cttgaatgaa    136620
aatccattca cgatgaatat cgatttaaat gatgttgatt acattctaac aaaagaagat    136680
gggtctttgg tatcaactta tttagacggt gatgaaattc tgttcaaatc aaagggttca    136740
atcaaatccg aacaggcttt aatggctaat ggtattttga tgaatattaa tcaccatcgg    136800
ttgcgtgata gacttaaaga attagctgaa gatggattta ctgctaactt cgaattcgtt    136860
gctccgacga atagaatcgt tcttgcttac caagaaatga aaattatttt actgaatgtt    136920
cgtgaaaacg aaacgggtga atacatttca tatgatgata tttataaaga tgctgctctt    136980
cgtccatatc tagttgaacg atacgaaatc gatagcccta aatgggtaga agaagctaaa    137040
aatgcggaaa acatcgaagg ctatgttgct gtgatgaaag atggttctca ttttaaaatt    137100
aagtctgact ggtatgtgtc tcttcatagc acaaaaagtt cattagataa tccagaaaaa    137160
ttgtttaaga ctattattga tggtgcatca gatgatctta agcaatgta tgctgacgat    137220
gaatattcat acagaaaaat tgaagcattt gaaacgactt atctgaagta cttagaccga    137280
gctctgtttt tagttcttga ctgtcataat aagcattgtg gtaaggatag aaagacttat    137340
gcgatggaag cgcaaggtgt tgctaaaggt gctggaatgg atcacttgtt cggtatcatc    137400
atgagcttat accaggggta tgatagtcaa gagaaggtta tgtgtgaaat cgaacagaat    137460
```

FIG. 17VVV sequence.txt

| | | | | | | |
|---|---|---|---|---|---|---|
| tttttgaaaa | attataaaaa | atttatccca | gaaggatact | aagctgttta | caagtccctc | 137520 |
| gtgttgtgtt | acagtagtct | tactgacata | acatgaggac | tttatgatgg | atttgcagct | 137580 |
| cattactact | gaaatggtcg | ttgaagcata | cggtgatact | acagatggga | tttctgtatt | 137640 |
| taaaggaaac | cgtcgagttg | gatatatcac | cgatcttaag | aaagatttag | ctaagcaagt | 137700 |
| caagcggaaa | acgaccatta | aagaatatcg | aaatcgtcgt | cttgagcaag | cccgtgatat | 137760 |
| gcttcctgat | gcggttgaag | agatgaaagt | cttttagaa | aatcagcttg | cgaaatatga | 137820 |
| ttgtgatgta | tttattaatc | agactcaacc | taatgttcat | atcaatagtt | gtaaatgcta | 137880 |
| tatcatcgtt | aatcctttga | ctggaaagca | tcgtcttgga | attagtaatc | caaatcgtag | 137940 |
| tgcatcggat | atggcagaag | atgttgaggc | atgctttaaa | atttctaaat | ctccagctga | 138000 |
| acatcatatt | ttaattaacg | gtctttctca | agacgatatt | atagaggtta | ttaaaacttt | 138060 |
| atgcatgtaa | gtaattttac | agctggattg | ctattacttg | taatagcatt | tggcggaaca | 138120 |
| tctattattt | taaaaaataa | ggtagaaaga | ttagaaacat | cagttactga | aattacaaaa | 138180 |
| acagccaatg | aaaacgcctt | agcattaaat | aatttgcgaa | ttcagtataa | ttatattgat | 138240 |
| gcgatgaata | ataaaaatcg | tgaggcaatt | gctgctattg | agcgtgaaaa | tgaaaaactg | 138300 |
| cgcaaagacg | caaagaaggc | ggatgtggtg | gctcataagc | caggattggt | tgaaaaacaa | 138360 |
| atcaacaact | ccttcaacaa | gttcgcagaa | gacatccagg | acctttctaa | atgattaaac | 138420 |
| tatcagcagt | aatattatct | attggtcttc | tagttggttg | ttcgacaaag | cctctagaag | 138480 |
| taaagaaaga | aacagttcat | cctaattggc | ctgtgcaaat | aaagtcatat | gacgaagcta | 138540 |
| aactatcttg | gcaagttaaa | gttattgatg | gtaaagcttg | ggtaggtatg | ccatttgaag | 138600 |
| attctcagga | atttcgtatt | tggcttaatg | atgtaaaacg | atatgtacat | gaccagaaaa | 138660 |
| ctatgatatg | ttattatcgt | caagagctaa | aagaggataa | atgtaaatga | tttcatggta | 138720 |
| tcaatttgaa | catctaaaag | gattaattta | tgaatccgag | atggctgcaa | tgatttatgg | 138780 |
| acgacagatt | caacgattag | aatctttacc | tccaactaat | gatgttttat | tagctcaatc | 138840 |
| acgtgctaat | ctcaaaaatg | aatatcaaaa | taagtggggt | aaagcatcta | aagacttgca | 138900 |
| tgattatatt | caatcattag | ttgagaaaaa | taaatgaaaa | ctctgctaga | acgttatatt | 138960 |
| gaatgctcgg | accgttacat | tgatgtatgc | catgacaatg | catcaagcat | tagcgaagac | 139020 |
| attgaacatg | ctaaagcttt | agatgatgct | ggtaaagccc | tacgaaaaga | agcaaaagct | 139080 |
| cgtgggtttg | atatgtatca | gcttaaaaat | cacatgataa | aatttatttc | atctaatgtt | 139140 |
| cagagcaaat | cggtgaatca | atcaacagct | gaattatata | aagggcggcg | tgagcataat | 139200 |
| attcgtattc | ttgaagtttt | cttaggaatt | aaatgatgaa | aaagattatt | ttgactattg | 139260 |
| gctgtcctgg | ttctggtaag | agtacttggg | ctcgtgaatt | tattgctaaa | aatccagggt | 139320 |
| tttataatat | caatcgtgat | gactatcgcc | aatctattat | ggcacatgaa | gaacgcgatg | 139380 |

FIG. 17WWW sequence.txt

| | | | | | | |
|---|---|---|---|---|---|---|
| agtacaagta | taccaaaaat | aaagaaggta | tcgtaactta | catgcagcat | gatgttgcta | 139440 |
| acatgattct | ctgccaagac | gcaacgaagg | gtgtaattgt | ttcagatact | aatctgaatc | 139500 |
| ctgaacgacg | taaggtttgg | gaagagtttg | ccaaagagct | tgggcatcaa | attgaatata | 139560 |
| aagtgtttga | tgttccttgg | actgaattgg | ttaaacgtaa | ctcaaaacgc | ggaactaaag | 139620 |
| cagtaccaat | tgatgtttta | cgctcaatgt | ataaaagcat | gcgagagtat | ctcggtcttc | 139680 |
| cggtatataa | agggactcct | ggtaaaccaa | aagcagttat | ttttgatgtt | gatggcacgt | 139740 |
| tagcaaaaat | gaatggtcgt | ggtccttatg | accttgaaaa | atgcgatatc | gatattatta | 139800 |
| atccaatggt | cgttgaacta | tccaagatgt | atgctcttat | gggttatcaa | atcgtagtcg | 139860 |
| tttcaggccg | tgaaagtgga | accgaagaag | atccaacgaa | atattatcgt | atgacccgta | 139920 |
| aatgggttga | ggacattgct | ggtgttccat | tagtcatgca | gtgtcaacgc | gaacaaggcg | 139980 |
| atacccgtaa | agatgatgta | gttaaagaag | aaattttctg | gaaacacatc | gcaccacatt | 140040 |
| ttgatgtgaa | attagctatt | gatgaccgaa | ctcaagtagt | tgaaatgtgg | cgccgcatcg | 140100 |
| gtgttgaatg | ctggcaagtc | gcttcgggag | attttttaatg | gcttggcacc | atgaaacttg | 140160 |
| ggctttgtta | ttgtaaatag | cggtttagtt | ggtactagta | atgggcaatt | ttgtgtattt | 140220 |
| actagtgaaa | atagagcatg | ggaggaatgc | cttaaattaa | gagaaaagaa | tcctgatgtt | 140280 |
| gaactagtag | taaagaaaac | taaactgcct | ttaccatgga | aaacgtatga | ataacctaga | 140340 |
| aaagatttat | cgtctttgtg | ataaaattga | aaaagaaaag | aaatatctat | tttgtctatg | 140400 |
| gcctattgtt | gacggaagag | taggcctaga | tgttcttgat | tatgaaacag | aagacaaagt | 140460 |
| agatggcgca | acttttgata | cgctttgga | tgttattgat | tggctcgaag | aaaattatgt | 140520 |
| gaggtaaata | tgtttccgac | ttactctaaa | atcgtagaag | tagtgtttag | ccaaattatc | 140580 |
| gctaataaca | tgtttgaaaa | gcttgataat | gcagctgaac | ttcgaatcca | cgctcaagtg | 140640 |
| actcatgtat | tgaacgcttt | gcttccagac | caggtggatt | ctattgccat | tacgttgtat | 140700 |
| ccaggttccg | cgcatatcat | tgttgtattt | ggtcttgatg | ctgagctagt | tatcaaaggc | 140760 |
| gacattcgct | ttgaatcaca | gacatcagaa | ttcaaagcaa | tttaatagtt | tactttacgg | 140820 |
| tagagttgtg | atattatagc | tctaccaaaa | caaatgagga | aattgaaatg | agcgaatggt | 140880 |
| ttgaagaaga | taaggtttat | cgctttaaag | ctggatataa | agatattttt | aatgaaactt | 140940 |
| gcggggctaa | taacgaatt | gcccagttta | ttggggaaaa | ttcatttaaa | gtaaaaatag | 141000 |
| atcctgcgaa | aaatgttatt | agcattaaac | gtgaaattga | tgattgttgg | tataaagctg | 141060 |
| ttgatgtaat | gggtgaatcc | tataaagtta | gcccgttatt | ttcaattgct | tatatgttag | 141120 |
| aatattcttt | tttcgaagaa | gttcaaaaag | atgattctgt | aagtaaattt | gaaattaaaa | 141180 |
| ctgataaaga | aattaagtgg | aaagtagtag | gtattactgg | ttgtatgttc | tatatctatg | 141240 |

FIG. 17XXX

```
                                    sequence.txt
ctcaaactga tacgaaggaa gaagctaaaa agaaagctct agaatatctt gaagagcatg    141300
aagaaggtcc ggtaatgatt acccaagatg ctgaattagt ttctgtcaaa ttagttaaaa    141360
atgttgaaag taaggagcta ggatcaacat gctaagcgaa aaaccaatta ctgttaaaga    141420
attccaagaa aaagttaaac tatttgctca agaattggta aataaggttt ctgaacgatt    141480
tcctgaaacg tcggttcgtg ttattaccga aactcctcgt tcagtattag taattgtgaa    141540
tccaggtgat ggcgatcaaa tatcgcatct taaactggat tttgatggat tagttgaagc    141600
acaaagggtg tatggcgtac tatgatgaat ttaactgata taattgataa ttgtcttgaa    141660
aatgatactg gcgatcatag agcgcttgat tctgaaacag cacagttcat tagaataact    141720
ttaatgaatg atactctggt gaatagtatt catccttctg tgtatgatgc tattattgtg    141780
acgaagtatc cggttgagct tcacaaaaag atgactggcg cagtttttat tgataagaaa    141840
aaccgcttta aagatgggca gaatataact agttctgtta ttaaaagtat aactaaactt    141900
cgtcacgaaa tttatcgtgt tgaaactgct aaatctgctt atctggtgat tatgaaatga    141960
aagcgagtac agtacttcaa attgcatatt tagtatcaca ggaatcaaaa tgttgctcct    142020
ggaaggtagg agcagtaatt gaaaagaatg gacgtattat ttctactggg tataatggtt    142080
cacccgcagg cggtgtgaac tgttgtgatt atgctgctga gcaaggttgg ttgctgaata    142140
agcctaaaca cactatcatt caaggccata agcctgaatg cgtatcattt ggttcaactg    142200
atcgctttgt cttggcgaaa gaacatcgta gtgctcactc ggaatggtca tctaaaaatg    142260
aaattcatgc tgaactaaat gcaattttgt ttgctgcacg aaatggttct tctattgaag    142320
gcgctactat gtatgtaaca ctttctcctt gtccggattg cgcaaaagcg atagctcaat    142380
ctggtattaa aaagctggtt tattgtgaaa catacgataa aaataaacct ggctgggatg    142440
atattctgcg aaatgcaggt attgaagtgt ttaatgttcc taagaaaaac ttgaataagt    142500
taaactggga aaatatcaac gaattctgtg gtgaataatg aaatttcgtt tggtaaagct    142560
cacagcaatt agttcttatt ctaacgagaa catctcattt gctgtagagt ataagaaata    142620
tttttttctct aaatggaaac agtattataa aactgattgg actagtattg ataggccata    142680
tagttggaaa tctgatttag aaaaatgcca aaaattactt tccactctta agaacgtgg     142740
aacaactcat attaaaactg taataggtaa atgaatgaaa ctgacgactg aacagaaagt    142800
agcaattcgt gaaatttga aaactaaatt gtccatgggt atttcaaacg tagtttttga     142860
aaagtctgat ggtactattc gtattatgaa atgtactcgt gatgcagact ttatgccaac    142920
catgcaaact ggtaaattga ctgaatctac tcggaaagaa tctactgata tgattccagt    142980
atttgatgtt gaacttggtg cgtggcgagg ttttttctatt gacaaattga tttccgttaa   143040
tggtatgaaa gttgagcatt tgctccaatt tattggtaaa taaatgcttt aagaattatt    143100
tgttattatt aattcatctg ttaacaaaaa ggaaaaacga tgtctgaagt acaacagtta    143160
```

FIG. 17YYY sequence.txt

| | | | | | | |
|---|---|---|---|---|---|---|
| ccaattcgtg | ctgtcggtga | atatgttatt | ttagtttctg | aacctgcaca | agccggtgat | 143220 |
| gaagaagtta | cagaatcagg | acttattatt | ggtaaacgta | tccaaggcga | agttcctgaa | 143280 |
| ctgtgtgtag | ttcactctgt | cggtcctgat | gttcctgaag | gtttctgcga | agttggtgat | 143340 |
| ttgacttctc | ttccagttgg | tcaaattcga | aatgttccgc | atccttttgt | agctctgggt | 143400 |
| cttaagcagc | caaaagaaat | taaacaaaaa | tttgttacct | gtcactataa | agctattccg | 143460 |
| tgtcttata | agtgatataa | ataataatat | gaattgggtg | tcggaataat | aagttaaccg | 143520 |
| aacaattcta | tgtggtagtc | tacaactgag | agatctgtcg | aaagaagatg | aaattcagaa | 143580 |
| gaacgtgact | accgagtttt | aatctctaac | gagaattttt | aaatgattaa | acaattacaa | 143640 |
| cacgctcttg | aactgcaacg | aaacgcatgg | aataatggtc | acgaaaacta | tggcgcatct | 143700 |
| attgatgttg | aagccgaagc | tcttgaaatc | ctgcgttatt | tcaaacatct | gaatcctgct | 143760 |
| caaactgcat | tagctgctga | gcttcaggaa | aaagatgaac | ttaaatatgc | taagcctctg | 143820 |
| gcttctgctg | cacgaaaagc | agttcgtcat | tttgtggtaa | cactgaagta | atttattgga | 143880 |
| gattcactgc | cttagtgtga | gctaaatcga | ggagccgtcg | aactgtctga | ttaatgattt | 143940 |
| gcgaatcatt | atagtttaa | daccccggca | gttttacggt | gtacctcttg | aatgttattt | 144000 |
| tatagcggca | agtgcatgct | accccgaggt | gatggccaat | cgggagtacg | cctcaaggcc | 144060 |
| tatatatcca | tcagtatata | tcttatcctc | gagtaatcgg | acccggaacc | tttaagctaa | 144120 |
| cggtgtgcaa | cagataagag | ctataaggta | tgttgacgag | gtttatggtt | atcctgtcgg | 144180 |
| taaatattca | aaacctaagt | accccctttga | gggattgcgc | aggcaatgcc | aataagtcct | 144240 |
| gcattttcat | ttaaaagaga | atttataatg | gcaaaacaag | ttaaagcaaa | gaaagcagtt | 144300 |
| gaaaagaaag | ttggtgattc | taaacgcgct | ggctacaagc | gtgggtcgaa | ctctcgtatc | 144360 |
| aatcaaactg | ttgagaagat | catgcgccga | gcacgtgcgg | ttcttcgaga | tgatgcttct | 144420 |
| cgttttggta | agcagaaagc | ataagttgag | gactccttcg | ggagtccttt | tttattttcc | 144480 |
| aaagattgca | caaagttgtt | tacagtacgg | ttcctttgtg | atagtattat | cttacacaaa | 144540 |
| caaaggagaa | taaaatgaac | tacatcaact | ttgaacgtaa | atatgtttct | aatggtattg | 144600 |
| caggttctat | tgatactatt | tgtctctgga | aacatcaaaa | cggatcagta | tgcgaaatcg | 144660 |
| atcagtatat | gactcctaat | tacgtttata | tgcgatttga | aaatggcatc | acggtttcaa | 144720 |
| tcactaagga | aggttccaac | tttaaaatcg | ctctagatga | tgatttccgt | gaacgcgatt | 144780 |
| tagggactca | tccttgttgg | aatggcgttc | atcgcaagct | tctgattaaa | acttggattc | 144840 |
| gtcatattct | gagtaacaaa | gctaaacctg | agcatcttga | agcaatcttt | gatgtagttc | 144900 |
| ttaacgaatt | tgatatttaa | gcttcggccc | cttactgagg | aaaatattat | gtttatgact | 144960 |
| acttattg | atacccgcaa | aaatttctgt | gaagttgttt | tctcaaaggc | gcctaaagac | 145020 |

FIG. 17ZZZ sequence.txt

```
cttcctgcac atttgcaacc taccagtgaa tcgattaaaa actacgttaa tgtagtctgc    145080
cctttagagt tccgtactgt aaatgggcgc gatactttag ctatcactaa actcaatcgc    145140
gaaattgaca ttgatccctc aattgcacgt gaaattaata gttctgatat taatggcggt    145200
aatgttaaat cgcacggttt tcagatgagg ttttaatgaa attcttttta ggtcaaactg    145260
ttgaattaaa gggagttggt atacctggat taatttctaa ggttctacct ccgtttaaat    145320
ggagtggtat tcaaataaaa gaggcttata ttgtttcttg ggtagatgga aatgaagacc    145380
ttcgtatggg cgatgaatta tctcctatct acggattaaa ggaattagta tgaatataat    145440
taataagatt tttggaattc agtacattaa ggtcacatat aaagtaacag ataaaaatcc    145500
gtatactgat gaacacgaag aaccgcaagt taagtctatt atattagaaa aaggcagtga    145560
ctggccagtt gaatttcgtc taccaaacta tggtcattgg gctgatgttg aaattataag    145620
cattgaaaat gtctgagtta gagattagaa gcaattttaa atggccatca tgtgcattaa    145680
gtaatttcgc ccaatggcct ttcgttatgg atggtattca atttggaggt cttgaaggat    145740
tcctccaagg atgcaaggtg aaaaatgttg aacaacaacg tcgtatattt gggttatccg    145800
ggcttgccgc ccaacaagct ggaaggtctt atgctagagc tcaggaccgt gggaccctct    145860
tctggcttgg agttccgttt tcaagatact ccccagcatg gaaagaatta tacacaaatg    145920
catattttga agcagcgatc caaaacaagg gctttcgtga tgcattacac gcctcgaaag    145980
gaaaagtttt gaagcacagc atggctagtg gtctaacaaa agatgataca atattaaccg    146040
aagctgaatt tattgatgtg ttaaacctat taagagactc tctatgaagc ctactatttt    146100
aactgatatt gatggagtat gtttaagctg gcaatcaggc cttccttatt ttgctcagaa    146160
atataatctt ccgttagaac atattttaaa aatgatccaa gatgagaaat ttatttctcc    146220
aggtaaactc tttaattgtg acgaagaact tggcgtcaag ttaattgaaa aatacaatcg    146280
ttcagatttt attcgttact tgtctccata taaagatgct ctgtgtgtaa ttaacaaatt    146340
aaaagaagat tataattttg tagctgttac agcattgggt gattctattg acgctctgct    146400
gaatcgtcaa tttaatttga acgctctttt tcctggtgcc ttctcagaag tactgatgtg    146460
tggtcatgat tcttcaaaag aagagttgtt taaaaaggca aaagagaaat ataacgtgat    146520
ttgttatatt gacgatctcg ctcaccattg cgatcatgcg agtgaaatat taaatgttcc    146580
tgtttattgg atggctcgag gggaacgtga cagtattcca aaaactgcac agcgagttta    146640
tacatggaat gatgtagaaa ataagctttt ttcaccaaag gaaaataaag aaagttttga    146700
tagtgaaaaa gctataaaag atgtaattga gaagatgatc aaaaacgatt cttttccttg    146760
gaacactacc tggagaactc ctggatttaa tccttataat catctatatc atccatatca    146820
gacacatccg tttcagacat ggaactatat taaacctggt ggcatagagt atttgtataa    146880
tagacctact agtggtgata atattttcca aggagcattc taatgtttgt tgttcatact    146940
```

FIG. 17AAAA sequence.txt

| | | | | | | |
|---|---|---|---|---|---|---|
| atttatgaaa | atgaaggtaa | tactacacgt | gattacggtc | acgtaaatca | attttttaga | 147000 |
| tgcaatccag | aattccgagc | tcaaaaagac | gaacgaattt | ttaaaaaatg | tgtagagcaa | 147060 |
| ggtttcattt | acgtcaagca | ctggatgcaa | ggaaataaag | ttagaaccac | gtaccacagg | 147120 |
| tctttgactg | agcttaatga | tgaattgatt | tataatagag | ctgtaaacca | aactctaaag | 147180 |
| gatgaacaat | gattcttaaa | attctgaacg | aaatagcatc | tattggttca | actaagcaga | 147240 |
| agcaagcaat | tcttgaaaag | aataaagata | atgaattgct | taaacgagta | tatcgtctga | 147300 |
| cttattctcg | tgggttacag | tattatatca | agaaatggcc | taaaccgggt | attgctaccc | 147360 |
| agagttttgg | aatgttgact | cttaccgata | tgcttgactt | cattgaattc | acgttagcta | 147420 |
| ctcggaaatt | gactggaaat | gcggcaattg | aggaattaac | tggatatatt | actgacggta | 147480 |
| aaaaagatga | tgttgaagtt | ttgcgtcggg | tgatgatgcg | agaccttgaa | tgcggtgctt | 147540 |
| cagtatctat | tgcaaacaaa | gtttggccag | gtttaattcc | tgaacaacct | caaatgcttg | 147600 |
| caagttctta | tgatgaaaaa | ggcattaata | agaatatcaa | atttccagcc | tttgcccagt | 147660 |
| taaaagctga | tggagctcgg | tgttttgctg | aagtcagagg | tgatgaatta | gatgatgttc | 147720 |
| gtctttatc | acgagctggt | aatgaatatc | taggattaga | tcttcttaag | gaagagttaa | 147780 |
| tcaaaatgac | tacagaagct | cgccagattc | atccagaagg | tgtgttaatt | gatggcgaat | 147840 |
| tggtatacca | tgagcaagtt | gaaaaggaac | cagaaggcct | agattttctt | tttgatgctt | 147900 |
| atcctgaaat | tagtaaagct | aaagaattcg | ccgaagtagc | tgaatcacgt | actgcatcta | 147960 |
| atggcatcgc | caataaatct | ttaaagggaa | ccatttctga | aaaagaagct | caatgcatga | 148020 |
| agtttcaggt | ctgggattat | gtcccgttgg | tagaaatata | cggtcttcct | gcatttcgtt | 148080 |
| tgaaatatga | tgtacgtttt | tctaaactag | aacaaatgac | atcaggttat | gataaagtaa | 148140 |
| ttttaattga | aaaccaggta | gtaaataacc | tagatgaagc | taaggtaatt | tataaaaagt | 148200 |
| atattgacca | aggtcttgaa | ggtattattc | tcaaaaatac | cgatggattg | tgggaaaatg | 148260 |
| ctcgttcaaa | aaatctctat | aaatttaaag | aagtaattga | tgttgattta | aaaattgtag | 148320 |
| gaatttatcc | tcaccgtaaa | gaccctacta | aagcgggtgg | atttattctt | gaatcagagt | 148380 |
| gtggaaaaat | taaggtaaat | gctggttcag | gcttaaaaga | taaagccagt | gtaaaatcgc | 148440 |
| atgaacttga | ccgtactcgc | attatggaaa | accaaaatta | ttatattgga | aaaattctag | 148500 |
| agtgcgaatg | caacggttgg | ttaaaatctg | atggccgcac | tgattacgtt | aaattatttc | 148560 |
| ttccgattgc | gattcgttta | cgtgaagata | aaactaaagc | taatacattc | gaggatgtat | 148620 |
| ttggtgattt | tcatgaggta | actggtttat | gaaagcttac | ttagaaacaa | ttgtcgtggc | 148680 |
| tcaaaaagaa | ggtggagatg | tttctacttc | tgtatcacaa | gtcattctcg | aatttgtaga | 148740 |
| tgcatacgct | tataataaat | ttacagaaac | atttgatgcc | tatgaaaaag | gaccaaagtt | 148800 |

FIG. 17BBBB

```
                                     sequence.txt
tgaaatatat cgtactctct taccactaga ttactaaagg ccttcgggcc tttaattta    148860
taaatagaat aaacactaga gaggctatga tggaacttat tacagaatta tttgacgaag   148920
atactactct tccgattaca aacttaaatc caaagaagaa aataccgcaa attttttcag   148980
ttcatgttga tgatgcaatt gaacagccag gctttcgttt atgtacatat acatctggag   149040
gtgatactaa tcgcgattta aaaatgggcg ataaaatgat gcatattgtt ccttttacat   149100
taactgctaa aggttcaatt gctaaattaa aaggtcttgg tccaagccca attaattata   149160
tcaattcagt ttttactgtt gcaatgcaaa caatgcgcca gtataaaatt gatgcttgta   149220
tgcttcgtat tcttaagtct aaaaccgctg gtcaagctcg acaaattcaa gttattgctg   149280
atagacttat ccgtagccgt tcaggtggca gatacgtcct tcttaaggaa ctctgggatt   149340
atgataaaaa gtatgcatat attcttatac atcgcaaaaa tgtatcacta aagacattc    149400
caggagttcc ggaaattagt accgagctct ttactaaagt tgaatcgaaa gtcggcgatg   149460
tttacatcaa taaagatact ggagctcaag taactaaaaa tgaggcaatt gcagcatcta   149520
ttgcacaaga aaatgataaa cgttctgacc aagctgtaat cgttaaagtt aaaatttccc   149580
gtagagcaat tgcgcaaagt caatcattgg aatcttctag atttgaaagt gaattattcc   149640
agaagtatga atctacagca gctaatttta ataaaccagc tactgcacct ttaattcccg   149700
aagcagaaga aatgaaaatt ggaattaatt cattagcttc taaaacaaag gcagcaaaaa   149760
ttattgctga aggaacggca gatgaacttc actatgatta taaattcttt ccaatgagtc   149820
aagtcggtga agtttcagaa aaaattaaag aagtaatttt taatgcaatt aaaaatgaac   149880
caactacttc aataaaatgt ttagagaaat acgcagcagc tgctaatcaa ctctttgaag   149940
aatataaaga taattggctt gataaacata ataaaactcg taaagggcag ccagatgaag   150000
tctgggaaga aatgactaaa aattcctgga acgcagcaaa aactaaattc ctcaaaagaa   150060
tgatttatag tttttctgga attggtgcag gtccaatgat tgatattact attgcccgtg   150120
atggttctaa atatactcca tcacaaaagc gcggcattag agagtattgt ggttcagggt   150180
atactgacat caataatctt cttttgggtc gttatgatcc agaacgttat gaagtaatga   150240
gtgaaaaaga aattgaagct gctataacta atttagattc tgcttttgaa aatggtgatc   150300
gtataccaga aggcattaca gtttatcgtg ctcaaagtat gactgctcct atatacgaag   150360
cactagttaa aaataaagta ttctatttca gaaattttgt atctacttct ttaactccta   150420
tcattttgg acgttttgga attacacatg ctggtattgg tcttttagaa ccagaagctc    150480
gcaatgaatt aacagttgat aaaaatgaag aaggaataac tattaatcca acgaaataa    150540
gagcgtataa agaaaatcct gaatacgtta agttcaaat aggatgggca attgatggag    150600
ctcataaagt taatgttgta tatccaggaa gtctcggaat agcaacagaa gctgaagtta   150660
ttctaccgcg tggattgatg gtcaaagtta ataaaataac tgatgcttct aataatgacg   150720
```

FIG. 17CCCC sequence.txt

| | | | | | |
|---|---|---|---|---|---|
| gaacaacatc | taataataca | aaactcattc | aagctgaagt | tatgaccacg | gaagagctca | 150780 |
| ccgaatcggt | aatctatgat | ggagaccatt | taatggaaac | tggtgaattg | gttgcaatga | 150840 |
| caggtgatat | tgaaatagaa | gacagagttg | actttgcatc | atttgtttca | tcaaacgtta | 150900 |
| aacagaaagt | agaatcatct | cttggaatta | ttgcgtcttg | catagatatt | acaaacatgc | 150960 |
| cttacaagtt | cgttcaagga | taaatcatgg | aacttattac | agaattattt | gacggcgctt | 151020 |
| cggcgccggt | tgttaactta | aatcctaagc | ataaaatacc | tcaaattttt | gctattcaag | 151080 |
| ccggtgaaga | aagcgtgctt | cctggattta | gattttgtac | atacacctct | ggcggtgata | 151140 |
| caaataaaaa | cgttaagccg | ggcgataaaa | tgatgcatat | cgtaatgata | ggtgtcaacg | 151200 |
| agaaattatc | gttagtcaag | cttagaaact | tgggtggaaa | tccaattggc | gtcattaatg | 151260 |
| ctgttttga | tactgctctt | caaacaatga | aacagtataa | aatcgacgca | tgcctattcc | 151320 |
| gcgtactaaa | aagtaaaaca | aatggcgcag | ctcgtcaaat | gcaagttatt | gctgaccgtt | 151380 |
| tagtacgtac | taaaggagca | ggtcgatatg | ttcttttaaa | ggaaatctgg | ggctatgata | 151440 |
| agaaatatgc | atatattatg | gttaccgta | aaaatgccaa | tttagaagac | attccaggtg | 151500 |
| tacctcctat | ttcaactgag | ttattcacaa | aagttgaatc | aaaggttggt | gatgtttatg | 151560 |
| tagacgttaa | aacaggtaat | gctgttccta | aagctgtcgc | tgttgctgct | tctattgctt | 151620 |
| tagaaaatga | taagcgcacg | gatcaagctg | ttattcagaa | aactaaaatt | agtcgtcgat | 151680 |
| tagcagcaca | agctcaatat | tctactgttg | atgcttcact | tcagggtgat | agcttcgctg | 151740 |
| ctaagaaata | tcaagagttt | gaatctaaag | ttccggtata | taaagcagaa | ggtccgatga | 151800 |
| actctggcgt | tattcagatt | ggttcaaact | ttagcaaagg | agctatcggt | ggtatgagaa | 151860 |
| gtgcttctcg | ttttaaatct | aacgattatg | aactagaaag | tttccgaaat | catattgcat | 151920 |
| tagcccatgc | acgtttacgt | gatccatcta | tcaagttgca | gagcgatata | acatatcaag | 151980 |
| gttctcaaga | atatttaaag | aataaagaat | tctttgatta | taaaactgat | aaaattttaa | 152040 |
| gcgatcttgc | tgacattaat | atttctaata | gctttgatgt | tattaagaaa | attatcaatg | 152100 |
| atttagttaa | aggttctaaa | gctacaccag | atgaaaagac | agctattatt | caatttgtca | 152160 |
| tgaatggcat | ttataaattg | attaatgaat | ctgccgctca | ggcatatgaa | tacgcaagca | 152220 |
| ctgaagtaac | tccaaaagga | ttaactcagg | ctgagtctga | tgtaattgaa | gattattgtg | 152280 |
| cagattcata | tgttgaaatg | aactcgttcc | ttttaggtaa | acctgattct | acccgtgaag | 152340 |
| aatatatgga | acgagctatt | aaacacatcg | agacgttgga | ttctgcattt | gctaaaggtt | 152400 |
| cagttcttcc | tccaggaact | actctttatc | gtgggcaaga | agttaccttt | aaaactttgc | 152460 |
| gtcataacat | tgaaaataaa | atgttctatt | tcaagaactt | cgtatccaca | tcgcttaaac | 152520 |
| caaatatctt | cggtgagcat | ggtaaaaact | atatggctct | agatgattct | ggcgcagtat | 152580 |

FIG. 17DDDD

```
                                    sequence.txt
tttctggtga aggagaaggt tccattgatg cagaagattt gatgcatatg ggtagtcatt    152640
ctacatatgt taatgaagat gctgaaacta gcgtgggtat ggtaattaaa ggagctgagc    152700
gaatcaaagt tatcgttcca ggtcatttat caggatttcc atcagaagct gaagttattc    152760
taccacgtgg aattttactg aagattaata aagtaagtac ttactttatg aaagaaactg    152820
cttataacaa gtatctaatc gaaggtacaa tcgttcctcc ttctgaacaa ttagaggaat    152880
cagtatatga tggcgatcat ttgatggaaa ctggtgaagt tcgtccaatg actggattta    152940
atcaattcct tgtagaagaa tcaaagaag aggaaaacga agtttctcaa atcttagctt    153000
ctttggttaa catcaacgga atgtctaaaa agttcaaaat gtagtttaca agtccctcat    153060
gttgtgttat agtagtctta ctgacataac atgaggaaca caaatgaaa tcttctttgc    153120
gctttttggg tcaagaactt gtagttgaag gcgttattcc tgctgataat gcttttaatg    153180
aagcagttta caatgaattt atcaaaattt ttggaacaga taaaaagttc ggaatttttc    153240
cttctgaaaa tttttcaaag ccagaacaga ctgaaagtat tttccaaggt gtagtaacag    153300
gtaaatttga gtcagaagct ccggtaaaaa ttgaggttta tattgaagac agtttagttg    153360
cttcagttgc tgcttttatt tcattccgta aataaaaata tggggaccga aaggtcccca    153420
ttgttatatt gctcctaata ttttactttg cgaattgaca attcctgtca tagtattaat    153480
gtttgaaatg cttcctgcag ttcccccctaa tctactgagt cgtgaaagcg aattagatag    153540
tccagtaaca cctccactat ttccgagaac gctttgaata ccatttatag cagcagattc    153600
aagccattca agcgcagctt gcctatcaac tgctccagcc tgcatcactc tatacgcaaa    153660
agtaacgtca aatgtagtta tttggttatc tccatcatat gataactcag gagcgctcac    153720
tgatattgga atgcatccag tgaacatcac cgcagtatga ggcaatccat tacgagaatg    153780
aagattaacc tgaatatctg cctcgacatc ctgtggcaaa gcacgcagtc cagttactgg    153840
gtcttgaacg gagttaaccc agtcttgcat tgcacgatag ttacaagctt ctgaatccat    153900
tctaaatgaa ataaccaaag ggtctaattc tctcccagtt atacgaatat taggagaatt    153960
atagttccag tcagtttcat aggataatct attctctggc attttacag agtatatcat    154020
caatccagat gagttatatg ccatgttaaa gaagtcaatt aaatatgtac caactgtaaa    154080
tgagcctaat aaactttgaa ctgtacgttg actcatggca ccaataagat atttactaac    154140
ccctgatttt cttatcagtt tttgtgtgcc agcagtaatt agcgtggtaa ttccctgatt    154200
aatatcacct tgagtcaatc ctaaccaatc tgaatttagg cccaagttat tataagaaaa    154260
gttgctaatt gaacttatca acgaagagct tttagttgat ggagttgttg caaaaacgca    154320
gctaaacata ttattacgtt ggaaatctgc gtttattgct tgattattaa attcctctaa    154380
agaatacatt aaaaagtccc cgcatataaa gaagcacggt ttaacgtgat aatttctctc    154440
atagtaatct cgagagtaaa tgtactaggg aggtttggag caatagctaa tccgttaaag    154500
```

FIG. 17EEEE sequence.txt

```
ttaccattag gtgttttgtc aaatctgata ctctggattt gacatggacc gaatatttcc   154560
gttttttccat caaacttaga tgttgcacca aagttttca ccatccaaat tgtcgggttt    154620
gaaactacaa gaacgttagt taaactcgat gtcattttct caaataacgt cttattttta   154680
actgcatctt ctggagttaa cggctcaata aaagtagaac ggtaccactc atctaaatat   154740
ccttttattt cagcagcata ttgagattta ccagtttcac cgtaagaaaa atagttaaaa   154800
tactgataga tattaataat agccattaaa tcttctgttg agcgcggagt caaatcccaa   154860
gtgaacactt tagttctatt ttcagcaccg ccgtacatgc ttctggctgt cgtataaatc   154920
tgttcattat tatcagccat tataccttgt gttatacttt ccagcgctcc aaatactgcg   154980
gttgaagcca tattgcttag cacaccagta gcagtacctc cacctttgt aataagacta    155040
tcttgaacat cattaaatct atgtgatgac gtatcgacgt cagatttaga tctaggtaaa   155100
agaatatttg caacaggaac tttacttatt gttcctgaat tattatctga tattagtcca   155160
tttgatagtt ttgatactgt attactgata gtgtttctgg ctgtacgtaa aatactcgaa   155220
gatgaagaag agtagttaga tctcatcgtt ctaagacttc cagaatccct agatgacata   155280
ttgtatgcag taaataataa tccattctta tatagatctg ttacctggaa gtcccctgta   155340
gtgtcattac cactagcacg cccagttgga aactgggcag tgtatgtttt agttgctact   155400
tctgatttag tactctgtcc ggctgaaatt ttctcaccgg acttttaat taaatcagca    155460
gttatttctt taacaattgc catattattc cttaattaac tccagtcgca tcaaatacac   155520
caggagcagt cgtgctcgtt acgggtgtca tattatgaac gacagtattt ttcttaataa   155580
cattattagt attattgatt gaaggagatg cttgttgaat aggagcttgc tgtgctttgt   155640
tctttctat tacctggact tgttttgctt ctggcgattt agcagaagtt tgaggtttgg    155700
cattaggctg attttttcttg agctcttgat aagtagcatc aatttagaa aatctagcag    155760
caagttcttt tttaactgcc ggtgaattat ttaaatccgg gtcatccatt cgttttttaa   155820
ggtcttcata ggcagcttca actgatttaa ccgttgagtc tttactcata tcagctgaat   155880
tagcgtattc atcaaaacga ttcatagcag cacgagcttc attagctttc attaaagcaa   155940
ttttagcttc ctccggagaa agttgcttta atttttcttc ttcctctgct ctctcttcat   156000
cagtcgttag tgcttcttta ttatcaacac cacgaatcca gttagatgca cgagttttcc   156060
agttcgcaat tttgtctagc ccttttgcta ttggaccaag atcgtcattc attcttttat   156120
attgataatt tgcaacttt tcttggtctt ctttgctaag agaagcattt gtagtatttt    156180
ggaaattttc tagtgctctt ccttctactt catcagcagt atccttcata ccaggaataa   156240
ctcgaagaat tgccgcagat aatttagcca ttccaagttg aataagctct cctaaattaa   156300
aaagaacctt tccaagtcct tcgacaatag ctactgtcaa tccgccccag tctccagctt   156360
```

FIG. 17FFFF sequence.txt

| | | | | | | |
|---|---|---|---|---|---|---|
| cccacagctt | cttaatttta | tcaatagaac | caaagatgct | ctgtaataaa | ggaccccacg | 156420 |
| ttccggtttc | gctagagaat | ttggtaaagt | ttgtactaaa | caaatcccat | gcctgcgaaa | 156480 |
| atttatctga | ccaatatttg | aagtgaacca | tcaacagatc | tattccaaca | acaacagcca | 156540 |
| atatcattgc | agtcatttta | gcagcttcaa | tagcagcact | aacggtatac | ttaaataaca | 156600 |
| tgcttgatat | tttatcacta | attgaaatag | atttcttaaa | tccaaaatca | acagtctttg | 156660 |
| ttaatttatc | taaagcttga | gataatttta | agttaaatgc | ttcttttttc | tgtttttctt | 156720 |
| ctggcgattc | ttgtttaggt | tcaactggct | gaggggtagg | gaaaaaatca | gcatcaggat | 156780 |
| cattattaac | tgcttcagga | gctggtaata | aaggacccac | ggattcagct | gtatcgtcct | 156840 |
| caacaacttt | aacaggaata | gcgctttcaa | ccgtagctaa | actagttcct | gtttgttgaa | 156900 |
| ttccggctgt | ctggattttt | tgctcgagta | aactcgttaa | tttatctaat | ttacttccga | 156960 |
| gcgattcacc | gatttcttta | ttaatattat | tgccaatttc | gacagtttca | gcaattaact | 157020 |
| cagaaccagc | agtagtatca | ctcactgcgc | tttctacatt | gtcaattgct | ccaattattt | 157080 |
| cattcgattt | ttcttcaaca | gtttgagcaa | ttaattcaga | agcagcttga | gcatcatcca | 157140 |
| atttcgtaga | tatatcgtta | agtccagata | aagtgttaga | agcggattta | gccgcttcct | 157200 |
| gtgttggttt | attatctgaa | ataacttttc | tacgcatcgt | ttgcatttct | tgtggctttt | 157260 |
| tcattcaaat | aatccaataa | tattgccaat | tccggttatt | ggaccattag | ggccaggaat | 157320 |
| tgctaaagtt | gtaaaaatat | catttgccca | ttttaaaacg | aatgctggca | tctcaagaaa | 157380 |
| attaatttct | ttaacttcat | cattgacctt | aagcaagcat | ttggataaca | tatcgctcac | 157440 |
| cgttaaaaat | tgttcaaatt | ttccaggagg | tctaaaataa | aatgtatttc | cttggtattg | 157500 |
| aaattctaat | ctttggcaca | cataaacatc | attaatgtca | taagtataac | catctatttc | 157560 |
| tttacgagat | ttaatctttc | cattaaattc | caataaatga | atggaaacga | atcaacttc | 157620 |
| tgccggtgat | aaatttggac | aaatagaatc | aataagaagc | tttaaatttt | catcaggacc | 157680 |
| tttaacatct | tttaaaatgt | tataatgttt | aagacccatc | ttaggaatag | aaacttcttt | 157740 |
| attacttatc | ggaagaacta | ctttcttcag | tggtagtatc | agttttaaat | tcatttttaa | 157800 |
| ccttaactgg | gtcgattgtt | tccagtttcg | ttgcattagt | gaacatatat | agatgagtta | 157860 |
| cggaattatt | atttgataat | tcgtgaataa | cttcatcaac | gtaaaattct | gttttaaatt | 157920 |
| ggttttact | atcattaaaa | ataattttaa | cgccaggagt | caagttaaaa | ttaccgacag | 157980 |
| tagaacattt | agcatagccg | tcatattgcg | ccatagtctg | aagacgaata | gcttcttcat | 158040 |
| atccatttct | ataagtcatt | tcagaataag | cacctgacct | tgacactaca | atagagtttt | 158100 |
| caccctttcc | tgtagtaatc | attggtaatg | aagaatctaa | aaatgaatga | gcatagatag | 158160 |
| tagcattttt | cattggatca | cgtttatgcg | ggtttgattt | agtcaaccaa | acaaaatcat | 158220 |
| atgctaatgg | atatttcaat | tcttggacga | attgacctat | taaagttggc | tcacctacaa | 158280 |

FIG. 17GGGG sequence.txt

| | | | | | | |
|---|---|---|---|---|---|---|
| tcattggata | tggttcttga | tttatcatca | tatcatagtc | catcatgtta | actcccatga | 158340 |
| tgtcttgcca | tacaaatacg | aacttatcgc | ttcctaccgc | tagagcaact | tctcttacat | 158400 |
| atgacaaata | gttttcaaat | gtgctagtcc | atggaatatc | aggaacataa | gcattaatag | 158460 |
| catttatcgc | tggagttaat | aatgtacgat | cttgataaat | tacgccaagc | atttccttta | 158520 |
| tagattcacc | ggcatcaggg | aaaaatggtc | taccaaattt | aagatttcct | atagaatgaa | 158580 |
| tagttcccaa | ttcaatagca | atgatgttat | cacctttga | atctacagat | acagaaaaat | 158640 |
| gcttacatcc | ataaattctt | gttttaacat | tattaatatc | gtttgcatta | gctacagaaa | 158700 |
| tctgaattat | ttcatttcca | tccattttg | tatggatatt | tttagaatca | taaaattgta | 158760 |
| gcattccttc | atttcgacca | taaagagaat | cccgcatagt | taatgtggta | atagtagcag | 158820 |
| ctaattcaac | aaatctatta | ttactccaag | cgtcataact | ctcaaataat | ttaacgctga | 158880 |
| gatttggata | tccaggacgt | tgtaacatac | tcattgatgt | ttatccttct | caatcagttt | 158940 |
| taatacgaat | ccgcgctcgg | caggaatcat | tttcattatt | gaatttaagc | tataattact | 159000 |
| ttttacaagc | gtgtgattaa | tttgataaaa | agtaaatatc | tcatctggat | taactaatag | 159060 |
| cttaaacaca | tctactatat | cagtgtattt | tttaatgtac | ttatcacaac | acgacatgtg | 159120 |
| caatgttaaa | ttaataggat | tcattgcatc | gagaattttt | tctaatgttt | ctatctcgat | 159180 |
| ggcgtcaact | agttctattt | gactggactc | gctaatttcc | ttccaatcat | accatatttc | 159240 |
| atctacttga | acagaatgaa | tattttcagt | aatcatcttt | gctttatttt | cataaaactc | 159300 |
| agaaggaaac | tttaatttaa | ttttaacatt | agctacatca | aaaacaggtt | cctttaattc | 159360 |
| ttttgatat | atttcaaatg | gaactgtctt | ttctttttta | cattttggac | atacaaatgt | 159420 |
| gactggtact | ttagttttac | ctattgaacc | tacaaatacc | tgcaaaaata | taatggttg | 159480 |
| ccaagtcttc | ggatagtctc | caaaataatc | atcaattaaa | tcagtaatta | tttcttttg | 159540 |
| ttcttgtggt | gaccgatgtt | ctatatcgtt | tcgaactaac | aaaaaatctc | gataatcttc | 159600 |
| taccgtaaat | ggtttaaaac | gatgaacacc | atctggtaat | ttacaacgaa | taatgtttgc | 159660 |
| catagatgct | ccttttattc | tatttataaa | tatgataaat | aaaggagcta | aatatgtatg | 159720 |
| aatacaaatt | tgatgtgaga | gttggttcta | aaataatcaa | ctgtcgcgca | tttactctta | 159780 |
| aagaatatct | agaacttatt | actgccaaaa | ataatggttc | tgtagaagta | attgttaaaa | 159840 |
| agctaatcaa | agactgtaca | aatgcaaaag | atttaaaccg | ccaagaatca | gaactattac | 159900 |
| tgattcattt | atgggcgcat | tctcttggtg | aagttaatca | cgaaaactct | tggaagtgca | 159960 |
| cctgtggaac | tgaaatacca | acccatataa | atctattaca | tacacaaata | gatgcaccag | 160020 |
| aagacctctg | gtatacactg | ggtgacatta | aaattaaatt | ccgatacct | aaaattttg | 160080 |
| atgataaaaa | tatagcccac | atgatagtat | catgcataga | aacgattcat | gctaacgggg | 160140 |

FIG. 17HHHH sequence.txt

| | | | | | |
|---|---|---|---|---|---|
| aaagcattcc | agttgaagac | ttaaatgaaa | aggaactaga | agatttatat | tctatcatca | 160200 |
| cagagtcaga | tattgtagct | ataaaagata | tgcttttaaa | acctaccgtt | tatttggctg | 160260 |
| ttccaattaa | gtgtccagag | tgtggaaaaa | cccatgctca | tgtaataaga | ggcctcaaag | 160320 |
| agttctttga | gttactataa | tggcaaatat | taataagctt | tattctgaca | ttgacccaga | 160380 |
| aatgaaaatg | gattggaaca | aagatgtttc | cagatcgctt | ggattaaggt | caattaaaaa | 160440 |
| cagtcttttg | ggaattatta | caacaagaaa | aggttcaaga | ccgtttgacc | ctgaatttgg | 160500 |
| atgtgattta | tcagaccagc | ttttttgaaaa | tatgactcct | cttactgctg | atactgttga | 160560 |
| gcgtaatatc | gaaagcgcag | taagaaacta | tgagccacgt | attgataaat | tagcagttaa | 160620 |
| tgtaataccg | gtttatgatg | attatacttt | gatagtagaa | atacgctttt | cagtcatcga | 160680 |
| taaccctgat | gatattgagc | agataaaact | acaactggct | tccagtaata | gagtataatg | 160740 |
| cttcacgtat | aaacgtggta | taatgaatct | aagtccatcc | aataacaatt | gaatagagaa | 160800 |
| caatatgaga | ttagaagatc | ttcaagaaga | attgaagaaa | gatgtgttta | tagattcgac | 160860 |
| taaattacag | tatgaagcag | ctaataatgt | gatgttatat | agtaaatggc | ttaataagca | 160920 |
| ttcaagtatt | aaaaaggaaa | tgcttagaat | tgaagcacag | aaaaaagttg | ctcttaaagc | 160980 |
| taaattagac | tactactcgg | gacgaggaga | tggtgatgaa | tttagtatgg | atcgttacga | 161040 |
| gaaatcagaa | atgaagacag | ttctatcagc | tgataaggat | gttttaaagg | ttgatacctc | 161100 |
| gttacagtat | tgggggattt | tattagattt | ctgtagcgga | gctcttgatg | ctattaaatc | 161160 |
| acgtggattt | gctattaagc | atattcaaga | catgcgagca | tttgaggctg | gaaaataatg | 161220 |
| agatataaca | ttgatgatgc | ttttaattat | gaagaagaat | ttgaaacgga | aattcaattc | 161280 |
| ttaatgaaaa | agcataatct | taagcgtcag | gatattcgta | tcctggccga | ccacccgtgc | 161340 |
| ggtgaagatg | ttctttatat | taaaggaaaa | tttgccggat | atcttgatga | atatttttat | 161400 |
| tctaaagata | tgggcattga | tatgcatatg | agagttgtat | aaatagatat | ataattcaga | 161460 |
| ggagacaatc | atgtcagata | agatttgtgt | tgtctgtaaa | actccaatcg | attctgcatt | 161520 |
| ggttgttgaa | acagacaaag | gtcctgtaca | tcctgggcct | tgctataatt | acattaaaga | 161580 |
| actaccagtt | tcagaaagtt | cggaagaaca | attaaatgaa | acgcaacttt | tgctatagtg | 161640 |
| tgacctttag | tctatagttt | tggcccttcc | tttttggttg | ggcttttttt | aatttaaaag | 161700 |
| ctttcttcta | cttcatcgtc | tgaatcttct | aattcagctc | tttttcctgc | caaagcatct | 161760 |
| ctgactgaga | tgtcatcagt | atctttttaat | tcagtttctt | taactctttt | cttataataa | 161820 |
| gcttcaagtt | cttctaaacc | ttctaatgtt | tgacaagagg | caattttacc | cataaattca | 161880 |
| tcaatagaag | cttcataaag | aaattgttta | aattctagta | acatcttttt | ctccaaaggg | 161940 |
| ccgaagccct | tataaattaa | ctgttttcat | tacgtaatta | aattttttcat | ctgcgtagcg | 162000 |
| ctgaatacga | tcaatgccgt | gttttaaaag | atagttcaag | tgaacatatt | tcttttttagt | 162060 |

FIG. 17IIII sequence.txt

```
attagcagat tttggcttga caccacagtc atctatgagg tcccagactg ttgcgattgt  162120
tttagaacca tgcttacgta atacacgacc gattgtttgt aatacaatga ttttgatttt  162180
aacaccgtgc gctaaaacaa cgtgatgcag attttaact gaaataccag tagaaaatac   162240
accataacta gctactataa ttattccttt accatttca gctaaggttt tcattatatt    162300
gcgggtttcg gtatcaactt ccctgatac gtaataaact ttatcgtatt cattttaat    162360
taaatcgaaa atagctttac catgtgatac atgtttaaac atgacaaaag cgttttcatc   162420
tttttgtgca agcttaatag ccaatttagc gatccattta tttcttttac taagccccgt   162480
aataatttt atttcttctt gataagtttt tcccttaat ttagtagtga actcatcggg    162540
atagcgaaga aaaatactat taatttag ctcagttact tgtccatctt ccattaactt    162600
agaagtcgtt actggcttaa atatttcacc aaacattcca acatactgca tgatattggc   162660
tttgccatca cgtaatgaac cagatagacc aaatttgaac atgcagttat ttaaacctga   162720
tatgatagat gaaatacttt ttcctgtagc aagatggcat tcatcattca tcatcattcc   162780
aaactgtgag aaccattctt tcggttgttt tactacagtt tgccatgtac caacaacgac   162840
tggtgcatca ttttatatt tatcatcttt tgatgctccg ccaccaattt tctttatcat   162900
tgcatgactg aataaacgat agtcaacgaa gtcatcagcc atctgagttg ttagagcagt   162960
tgttggaaca atgataagaa ttttaccttc ataatttcc aaataatatc gcgcaagcaa    163020
agcttgaatt aacgatttac cagcggatgt tggaagatta agaattctac gacgattaac   163080
taatccttcg aacactgcat cttttgata ccaatgcggt tcaattcttt tatttcctga    163140
atagatttct aatttagaaa gccattcatc aaaatctttt cttgataatt cttcttttc    163200
gttaatctgt gggtcaatcc aggctttata gccaaagtta tcgcagaact ttttaatttg   163260
cccgactaaa ccgaatggaa gaaggcgatt ataatctaaa agacgaattc gtccatccca   163320
gtggccatat ttgtacttcg gattaaaacg atacccatca gcttcaaagc taaagaaatc   163380
acggagttca tgaaatgtac tttcttcgca atcaattctc acgtgactaa aatcataaaa   163440
atgtacttta atgtcagtca tgtctaaata ccatgtaata aatatatcta tatttatact   163500
gaggaaatat tatgatagat aaagattata ttgcagagct gaaggctctt gatgataata   163560
aagaagctaa agctaaatta gctgaatatg ctgaacagtt tggtataaag gtcaaaaaga   163620
ataaatcttt tgataatatc gttaatgata ttgaagaagc tctccagaag ctcgctagtg   163680
aacctatgcc ggagactgat gggttatcta ttaaagactt aattgatgct gctgatgctg   163740
cagaggggtt aaaatatgac gatgaagaag tcaatccaga agcagcactt ttgattgatt   163800
ctccggttaa atctgacatt aaaattgaag tagtagaaac agataaaatt cctgaaaata  163860
ccgatgtttt gattgaagat actccatttg ttgaagaaaa atttgaacag gctgtagctg  163920
```

FIG. 17JJJJ sequence.txt

```
agattattga atctgaaaag ccgtctgtat ttactcttcc ggaaaacttt agcccgaatc   163980
ttcagttgat tggaaaaaat ccaggattct gtactgttcc ttggtggatt tatcaatgga   164040
ttgctgaaac tcctgattgg aaatctcacc caactagttt tgaacatgcg tcagcacacc   164100
aaactttatt tagcttaatt tattatatta accgtgacgg atcagttcta attcgtgaaa   164160
cacgcaactc ttctttcgta acattaaaat aaggataact tatgactttt acagttgata   164220
taactcctaa aacaccgaca ggggttattg atgaaactaa gcagtttact gctacaccca   164280
gtggtgaaac tggaggcgga actattacat atgcttggac tgtagacgac gctccacagg   164340
aagaaacgtc agcaactttt agttatgtac taaaaggacc tgccggtcaa aagactatta   164400
aagtagttgc aaccaatcaa gttgcagaat ctgaacctga aacagctgaa attagtacaa   164460
ctatcacagt tcaaaataag acacaaacaa ctactttggc agtaactcct ggtagccctg   164520
atgctggagt gattggaact ccaattgaat ttaccgctgc cttagcttca cagccatcag   164580
gtgcaaacgc tacgtatcaa tggtacgttg acggttctcc tgtgggcgaa gcaactagca   164640
ctacattcaa ttacactcct gacgcaagcg gagttaaaac aattaagtgc gtagctcaag   164700
taaccgcgac agattatgat acaaaggaag ttacttccaa tgaagtgtca ctgactgtta   164760
ataaaaagac gcagacaact actttggcag taactcctga tagtcctcca gcgggagtaa   164820
tcggaacccc agttcaattt actgctgcct tagcttctca acctgatgga gcgtctgcta   164880
cgtatcagtg gtatgtagat gattcacaag ttggtggaga aactaactct acatttagct   164940
atactccaac tacaagtgga gtaaaaagaa ttaaatgcgt agcccaagta actgctgaaa   165000
attacaatga aaaggaagtt acttctaatg aagtatcatt gacagttaat aagaagacaa   165060
tgaatccaca ggttacattg actcctcctt ctattaatgt tcagcaagat gcttcggcta   165120
catttacggc taatgttacg ggtgctccag aagaagcaca aattacttac tcatggaaga   165180
aagattcttc tcctgtagaa gggtcaacta acgtatatac tgtcgatacc tcatctgttg   165240
gaagtcaaac tattgaagtt actgctgtcg ttactgcaac tgattacgat agcaaaacta   165300
ttacagcaga aggtcaagtt caggtaactg ataaagttgc tccagaacca gaaggtgaac   165360
taccttatgt tcatcctctt ccacatcgta cttcagctta tatctggtgc ggttggtggg   165420
ttatggatga aatccaaaaa atgaccgaag aaggtaaaga ttggaaaact gacgacccag   165480
atagtaaata ttacctacat cgttacactc ttcagaagat gatgaaagac tatccagaag   165540
ttgatgttca agaatcgcgt aatggataca tcattcataa aactgcttta gaaactggta   165600
tcatctatac ctatccataa tcataagggg cttcggcccc tttcttcatt ttgaaagcac   165660
acaaaacaca atcagaaaat gatgtatata atggcaccaa ctcgataaca tgagattgat   165720
tatgagaact gaggttgtgg tgtttactct tcatgagtct ggaaagtcat tcattgaaat   165780
tgctcgtgaa ttaaacttac aggcaaaaga agtggctgta ttatgggctc gagctatgac   165840
```

FIG. 17KKKK sequence.txt

```
tgctaaaaat aaatttgaaa ctcgagaaaa agtcgtctat agaaaaagac atatcaataa    165900
aaaggtgaaa aatggaacag tatgatcttt atgaaaatga atcttttgct aatcaattgc    165960
gcgaaaaagc acttaaaagt aaacagttta agctagagtg ttttattaaa gatttttcgg    166020
aacttgctaa taaagcagct gaacaaggta aaacacattt tagttattat tgtattgctc    166080
gtgataaatt gattactgaa gaaattggtg attggctgag aaaagaagga ttcagcttta    166140
aagtcaatag tgatcagcgt gatggtgatt ggttagaaat tacattttga ggattaatta    166200
tgtttaaaaa gtatagcagt cttgaaaatc attacaactc taaatttatt gaaaaacttt    166260
atagcttggg attgactggt ggggagtggg tagctcgtga aaagattcac ggcacaaatt    166320
tctcattgat tattgagcgt gataaagtaa cttgcgctaa acgtactgga ccgattcttc    166380
ctgctgaaga tttctttggg tatgaaatta ttctaaagaa ttacgaagat tctattaaag    166440
cagtacaaga tattatggaa acctcagcgg ttgtatctta tcaagtcttt ggcgaattcg    166500
ctggacctgg cattcagaag aatgtcgatt atggcgataa agatttttat gtatttgaca    166560
ttattgtcac tacagaaagt ggtgatgtga cttatgtcga tgattatatg atggaatcat    166620
tttgtaatac atttaaattt aaaatggctc cacttttagg tcgcggtaaa tttgaagagc    166680
ttattaaatt gccaaatgat ttagattctg tcgtccaaga ttataatttt acagtagacc    166740
atgctggatt agttgacgct aacaaatgtg tttggaaagc tgaagccaaa ggcgaagtat    166800
ttaccgctga aggatatgta ttgaaacctt gttatccttc ttggcttcat aatggaaatc    166860
gtgtagccat caaatgcaag aattccaaat ttagtgaaaa gaaaaagtct gataagccta    166920
ttaaagctaa agttgaacta tcagaagctg ataacaaatt ggtgggaatt ttagcttgct    166980
acgttacact gaaccgagta ataacgttta tttctaaaat tggtgaaatt ggtccgaagg    167040
atttttggaaa ggtgatggga ctaactgttc aagatatttt ggaagaaact tctcgtgaag    167100
gtattactct aactcaagca gataatcctt cttttggttaa aaaggaatta gttaaaatgg    167160
tacaagatgt acttcgtccg gcttggattg aattggtaag ttaaataaaa agggaccgaa    167220
aggtcccttt gttttattca tcaacgataa ttttggtag cttaacacct aataaaacag    167280
acaaa                                                                167285
```

FIG. 18A sequence.txt

```
<210> 4
<211> 43313
<212> DNA
<213> Unknown

<220>
<223> Description of Unknown: Bacteriophage F510/08

<400> 4
cctactcaac gaggccgtgg ctagcaaggt gctaaactcc cgcctgggct ggtccgcagt        60
cggcgagtat gtcgaactgt tcaaccgcac gcaatcccgc gtggccgggt tgattcccga       120
gtagctcaag ccgagtacct gcatagtcgg gtgctccact ggaactactg gaatttttat      180
tgagattggc tggaggttgg ctgtctgtgg ctgggggggg tagttactcc gggtctaatt      240
ttggtatcgt cgtgtgagaa ccctcccgac tctgatcagc ccaccccttcc cccgtaggcc    300
ctccgcctgg tgggccatcc ctcgcattgc ctgggtgttg cttcctagcc tcctgggagc     360
ttccagctcc gctgggtggc gtgggcttcc ctgccctgtc gccgaccatt ctacgcatcc     420
tgtcgggagt gtcaacccct gggctggccg tagtgcctgg agcgctccag cgcttccctg    480
tgcttggtca gcgctaccgc gtactcctgg gatgcctggc gcttccgcca cggtgctgcg    540
tagtgccggt ggtcctgcgc tgcccacgtc gctatctgcc tctgccatgc tgcgtcctgc    600
tggtgccagg ctcgctcgcc tctgtcctgt ctgctcagca tcctgtgcct cctgtggcct    660
ctgctggtcc tgtcgggtgg tggtgcggga gtggctggcc ttgcctcttg tggtattgcc    720
tcctggctgt acctggcgtt gcctgggtgg tcccggctct gcctggggcc tacctggcca    780
ctccctctag gccacgtact ctacccgcct gcctctgcct tgtctagtcc ctcctggctg    840
gtgcctgggt gctggtctgt ctcaccctgg ctcactctgt ctctacctgt gccctgcctg    900
gctctgtcct ggctaccgct ggtcctgctg tcttgcctcg ccgctccctc gcatgctcgg    960
tcgcacctgc ggcgctgatg gactcctgtt tgtccattgt gtgtgacata accgcagccc   1020
tagtgccacg cggggttccag ggcggtgggt cgggtgcctg ggtggcggct gtcgctccct  1080
```

FIG. 18B sequence.txt

```
ggtaacgcaa atcctggcta gctagactaa gcctcgcacg tgggtctcta tacgtgtggg    1140
aaggctccag ggagcgccct gggagggttg acacgtgggc agtaggtctg tagagttcgc    1200
cctgtcttca cgcaacaacg cctctacagg cagcctggag acggggttga cacactgcca    1260
gggcatcggt agagtacgca gccagaacga cgggagattg caaccttcca agcgcggcac    1320
aagccatagg cgcaagggac acggcaaact cttagggcag gaaccgcagt gtgtaaggcc    1380
ggcaggcatc actgagggga ttgacacggt gcaggacacg cggtacagtt cgcaccacct    1440
gatggccact cagcaaaagg gcctatgcca gagaactgga cgaactaatc cccgacagag    1500
gattgacaag acaagcgcaa gtctctaaca tgcgcagcaa gacgaaagga tggttcagcc    1560
atctggcggt agaggttcga agcttcacca gcggtacatg gactggtgcg gtaggttgac    1620
cgaagctgca actggttagg cagggtccca gggaatacct gtcgggtgct gaagactcac    1680
ccaaaagagt ctgagcggga agcctcaccg tccacggtta agcaaaggca cgttagtgcc    1740
ggtgggaacg aacagagtgt cagtgggatc gagaactaga aacctcggtt aatcgcgact    1800
gacagtatgc tgggtagtat cggcgggccg attgaacaag gccaggcaga tagcgcaaag    1860
ggtacggggg atgagtgctg acgatcccga agagtatgcg caggacaagc cagaaccgct    1920
gatactacag ggactatgcc aatgccaagg tttgtccctt gaggcccttc caccgagggg    1980
attcaagaga cagacctagt gaggattgcc gatggcacac ttcaaggcta aggctcccaa    2040
gtcgcccttt gctgctcagg tagcgtactg gcgggactgg gaagccaaac gtactaagct    2100
catcgcacag gataacgtcg aagggcgtaa agagcttcgc aagatgcgtg acgtgcgcta    2160
cgccaccgac ccggagccag cgccaggacg ctaccataac cctgaacaga aggctttcgt    2220
gaagggtagc gaaggcaagg cgcggaacat cctgaaggga tggaacgcta agaagtcgca    2280
agggaagggt ttgtaatgcc acgtgtgaat gaactgacgc cgcgtcaacg caaggccgcc    2340
aaggctcgcc gcgacaaggc tcgccggatt gatctagcgc acaggatgcc gaaaggtgcc    2400
gactgcccga tcttccgcaa ggctgagcag gcgcaagcta agcagccacg agtcgatacc    2460
ctgaccactc cccgcagtgc tggctacctg gccgccgctg cttacctgaa caaatccatc    2520
tgaggtacat accatgacca acgcaatctc caaaaccgta atcgcattcc gtggcaccga    2580
agagatcaac cgcgctatcg acgccatccg tgtccgtggc aaggaactcg acgaagccat    2640
ccaactgacc ggcctgtcga tcatccacca catcgaccag tgcggcgacg tgaccgtagt    2700
caaggcgctg tatgaagcca tgccgaaggg cagccgccgc aatgcgctgg tcgagtggct    2760
ggtgctgcac ggcaaggtac aggttaacac tgacaagaaa tcgaacaagg acctgccctt    2820
cctgtacaac aagttcggca agaccgatct cgtcggcgcc accaacagcc cgtggtacag    2880
cttcaagcct gagaaagcgc tggaccagga gttcaacctg gctgctgccc tggccacgat    2940
```

FIG. 18C sequence.txt

| | | | | | |
|---|---|---|---|---|---|
| caaaaagcag | gtgctccagg | ctcagaccaa | gggcaaggtg | atcgtcggta | tggaactgct | 3000 |
| gggtgacttg | gaagcgctgg | ccgccaaggc | tgcacccatc | gccgagcaga | gcaagcgcgc | 3060 |
| tgccgcccat | tgactcaagt | cgaacgcctg | ctaagcgggc | gttccgctgg | aatcaatgac | 3120 |
| aactggagaa | acacgatgag | cttcaaacaa | cgcctgcaac | gtcaaatcgc | cctggcacag | 3180 |
| tacagccgcc | cggctcagtt | cccgtatggc | gagcaagccg | tccaggcgaa | ggggagtga | 3240 |
| ccatggactt | ctggatcgcc | cttccttcc | tcgaactcgg | cctcaacctc | ggcgaggatg | 3300 |
| aactgcgcat | gttgtggttc | agcggcctga | cgatattctt | catccacctc | ctgaagcggt | 3360 |
| gactcaagtc | atggccctgg | cgggcgaccc | tcgcctactc | cggggccatc | gctggactca | 3420 |
| tcacaagcga | gaactaaacc | atgcaagctt | tgaataccct | gttgattgca | atccccaagg | 3480 |
| acccgaccgc | aggcatgcac | gccgccgaca | aggtgctgtg | cgcccacgga | ttccgcatgg | 3540 |
| gtgacctgaa | taccgcgcac | gtcctgaccc | caggcgggtt | cgtggtagtg | ggcgccggcg | 3600 |
| tgactgtgaa | ccgctatgac | gaagcgtatc | gtatgagccg | gaacctcgac | tccgaaggct | 3660 |
| tcgacgtgct | gctggtccag | ggcagcccgc | tgtccgggcg | tgtcacctgc | caggcgtacg | 3720 |
| gatggatcaa | cgccgagtac | cacaagggct | gtgcgaatgg | ccgtcccatc | ttcgacatcg | 3780 |
| caggaacctc | gtaccatgtc | atcgcgtgac | ccgtaccgca | tcggccaccg | cgttgggctg | 3840 |
| gtgaactaca | gcgaccgcta | cctgggtgcc | gacgcggcag | gcaccaaggg | catcatcgag | 3900 |
| gccataaccc | gaccgtcgcg | ctgtatgacg | gtctaccacg | ttcgctgcga | gcggaccctg | 3960 |
| cgcctgatcg | aggcagaggc | ccgcaacgtg | cgattcatcc | gacagcgggc | ggagcggtga | 4020 |
| gctggcgcat | cgtggtagtg | acgccaggca | acgggtgcgc | cttcgtgtgg | acccgtcgca | 4080 |
| agcgcgtccg | gcctctgaga | ttctactccc | gcaaggccgc | taaacgctgg | ctccgtaggc | 4140 |
| accgccgccc | ggcgatcctc | ggtagccagt | acctgatcgt | gaactggagc | aaacgtatat | 4200 |
| gaccctcgtg | gccaccgtag | tagacagcgc | gcacaacctg | gaagtcgacg | acctcaccgc | 4260 |
| cggcaacctg | tatgccgcca | gctcgcccag | cgggaacatg | ttcatcgtgg | tagtgggtaa | 4320 |
| tcacaatggg | cgcaggcttc | ccgtagtcct | gtcatccacc | gatacccgca | ccatcgggga | 4380 |
| cgtgataagc | aacactgggt | tccggtacag | tgagatcgcc | gggttctccg | taaacctggc | 4440 |
| acagggagat | tatgactgat | ggtcacccgt | actgtatacg | tcacgcctga | agacccgacg | 4500 |
| ccgccgatct | tgtccgtggg | ccgactggct | ccgggagaac | tctacaaggt | ggtggcaccc | 4560 |
| agctcggcgg | aagtatcat | tgtgctggcg | accaagcaga | cgccggcgct | agcccaagca | 4620 |
| gccgtcgtac | tgcacagcat | gaaccctgcg | cagtatcccg | caggttcggc | tatcctcaac | 4680 |
| acggcctgga | agtgccgccg | cctgggagtg | ggcgagtacg | tcaagctcgt | ccaaggggag | 4740 |
| gaggactgat | ggccgtggca | atactcatcc | tggccgtgtg | gttgatcggc | ggcgccctgc | 4800 |
| tattcctgcc | gttcgacctt | gtggtctcac | cgcgcttgcc | gctatcagac | gaggccctca | 4860 |

FIG. 18D sequence.txt

| | | | | | |
|---|---|---|---|---|---|
| accgaaccgc | actgtacacc | gtgctttggc | cggtaaccct | acctaccctg | atcgccataa | 4920 |
| ccgtggttgt | catgctgcat | tccgcgtaca | ggggcgccat | cgaactctac | caggagatga | 4980 |
| aatcatgatc | cgtacccata | cccacaacgt | cgagcgcaca | ccgcaccgac | tgtaccggca | 5040 |
| cactgagctg | gcgtctggcg | agctgtaccg | tgtagtgcag | cccgactcca | agcgcggcac | 5100 |
| gttggtggtc | ggcgtagcgg | cctgggacag | ccagggccgg | cccgcagtgc | tgcccgtggt | 5160 |
| catccatgac | gatggtgacg | ccaaggtgac | ctgcgcacgt | cctaccgtac | tgcgcaacga | 5220 |
| cgggtggcgc | atggtcctcg | ccgacaaggg | gacccaggtg | acactcaccg | ccgagtgacc | 5280 |
| aaggcgaagg | ctggtgcgcc | agccttccac | cgtggccatt | ccctgccgcg | aaccaactca | 5340 |
| actgaggagc | tacaacatga | ccaacgtcaa | caccaccacc | gaaaccacca | ccgctgctgt | 5400 |
| cctgggtgcc | aagctgatca | agaagccggc | caccgtcgag | gacttccgca | acaacgtggt | 5460 |
| cttccaccat | agcgccctga | ccaaactgac | cgaggtctac | aacgaagcgg | tcgccgccct | 5520 |
| gcaaaccgcc | gagcgcctgt | ccagcctcgt | cgccggtgac | gtgatcacct | tcgaccacgg | 5580 |
| caagggcgag | aaagccgaag | tgctgagcgg | cgaagtcatc | agcgtggtcg | ccggcgtcta | 5640 |
| tcaggtgctg | gtccgcttca | gcgacagcgc | accggccaag | ctgctggacg | tgaaggccag | 5700 |
| cgccatccgc | gccgtccagt | cgtcggcagc | ccaggctgca | accctcgacg | aagccatcgc | 5760 |
| ccagggcgag | taaggcccgc | acgtaatagg | cccggccctc | cgggcctatt | gcgagctagc | 5820 |
| cataccatag | gaggaatcac | catgagcaag | cgcaaccccg | aacacatcaa | cggcaccgtt | 5880 |
| cgtagcgtca | gcgtccagaa | gttggcggcc | acccaggaac | tggaggatcg | tctggaggct | 5940 |
| gccctggccg | tgtgccagca | gcgggcagag | gacatcgacc | tgctgagccg | ccgtctccag | 6000 |
| gccgccgagc | gcgcccgtcg | ctgggagatc | gacgagattc | gcaaccacca | ggcgaccatc | 6060 |
| cgcctgttgc | aaaacgatct | gaacgctgcg | catgatgccc | acgaggcaca | agagcgccgc | 6120 |
| gctcgcaagg | caaccatcat | ggcctgggta | tgcctgctga | ccgcaggttt | ggccgtcacc | 6180 |
| ctgaagctgg | caggagtctg | accatgcagt | gcaaagacct | ttacacgaac | ctcgcgtcgg | 6240 |
| gcatgttcaa | cgtgccgtgc | tcccaggtga | ccccggagat | gcgacgggta | gccaagagcc | 6300 |
| gggcattcgc | ccacgcctat | acgcccaaga | aacaggcttc | gggcgggact | tacaccgccc | 6360 |
| gtgtgagcgg | cgtcacctgt | gacggtggta | aggtggaggt | gcgcctggat | aacgtggagc | 6420 |
| gcgtcagcac | cttcgactat | gccgagctgg | agacgcgggt | agcggccagt | ctgtgccagg | 6480 |
| ccgacgcgaa | gcgcgccgct | gaatacgaaa | agctactgct | gaaagcgttc | ccgtcggtat | 6540 |
| ccccgaagga | tgcccgctg | tccgccaagg | acttcgaatt | gcgcctgcat | gatctgtgct | 6600 |
| caaccaagct | ggtagtgctt | cgtgccttgc | gtgatgccgg | gatagagatg | gacggtccgc | 6660 |
| tgcgcagccg | ggtacggaag | ctggcggatc | ggaataacgt | gatgggtgct | gagttgttca | 6720 |

FIG. 18E sequence.txt

| | | | | | | |
|---|---|---|---|---|---|---|
| gcctcaagca | ggagttggca | caactggtcg | cggtcggcca | aaaggctgga | ctgaattggg | 6780 |
| acggggcgga | gactcagcgc | ctgctgacgg | tggccccgac | caaggctctc | tgtcgactca | 6840 |
| tcagcgcgct | gaccggcgtg | cggtataccc | accacaccgt | cgtagccaag | gccgaggctg | 6900 |
| aggcgcgcga | gcgggcaaag | gccgaggcca | aggattcatt | gcaggcggca | accttcgcag | 6960 |
| ccgccatcgc | tggtggcgtc | gtcggcagcg | ccctgatgtt | cctgctcggc | tagggcgacc | 7020 |
| agggcctact | ccggggtcaa | atccgagggc | gttcctagag | cgccctctcg | tgtgagtctg | 7080 |
| gaggatcacg | aacatgcaat | accacttcac | gcattacaac | ggataccgct | tcggcgtcga | 7140 |
| gctggaggac | gaggctgtct | tcccgtgcat | cgacggtaag | cgggcgacct | gggacaaggt | 7200 |
| ggcggcatgt | gccggtagcc | ttgtgcatta | catggcgcag | gacctgatcg | actttggcca | 7260 |
| gcgcaagtta | agggagtttg | aagatgagca | agacgagcct | gtatccgctg | aacctgcatc | 7320 |
| ccggcctgat | tcaaatcagg | acgattcacg | tattcagcat | ccaagccccg | agcaacgccg | 7380 |
| agaactggtg | gcagtggttc | ctctggcagc | ggaagtacca | cccgctccgg | gaaagcctga | 7440 |
| gtccagccgg | ggagctgagt | gcgagtatcg | ccgagtgtgt | gctccacctc | cgccggaatg | 7500 |
| gctggcaaga | tagcgacatc | tggcgcaaga | agggaggcgt | gctggccctc | ggtgcctttcg | 7560 |
| acctgtccgg | cctgatggta | ggttcctgcc | tcgtagtagg | tggtgagctg | aaggccctgt | 7620 |
| gcgttgatga | ccggcacagc | aggcagggta | tcggcgctga | gctggtgcgg | gccgctgagc | 7680 |
| tggctggtgc | cgagtatctg | acctgcttcg | agttcctgga | gccgttctac | gccgacttgg | 7740 |
| gctggagcac | cacccaccgc | gaggcgaact | ggacagcagg | agagccggac | gtgctgcaca | 7800 |
| tgagggcacc | cggtcatgac | gtatgaggtg | atgacatggc | ttatcgagaa | caaaccgctg | 7860 |
| gtcatcggag | tcgccttcag | tctggtggcc | ctgggcgtgc | tgctcacaca | gaacaacggc | 7920 |
| ggcccgccta | cggcgcccgc | atgacctggc | acctccagga | catgttcgag | gcccgaggcg | 7980 |
| ggctgcggcc | tttgtgggag | gaatggtacc | aatggcactg | cgccgtgact | cctggctaaa | 8040 |
| gcaagcgcaa | tccctggcgg | tcggtcaggc | gggtcgattc | cgccacgtcc | tgggatgcca | 8100 |
| gagcatgagc | cggggcggga | ccaacatgac | ctgcaagaac | cttcctgacc | gctgggtggc | 8160 |
| ttactgctac | tcctgtcagg | agggtggcgt | ggtcgagaaa | acgcatgtgc | ggagggtaca | 8220 |
| atgcgcggat | caagaacgct | tcatgccctg | gcccgaggat | gcctcggact | ggacgcaagc | 8280 |
| cgactgctat | caatcgcttt | atggtttgct | gctgtccaag | ggcatagact | acaacgtgat | 8340 |
| gacgccaggg | ctgccgctgc | tgtacagcga | aaggcagcat | cggcttatct | tccctaccga | 8400 |
| cgcgggctgg | attgggcgcg | ctactgccga | ccaaaatccc | aagtgggtgg | gttacgggta | 8460 |
| tcctgccccg | gattaccatg | gatggcccca | ggaattatca | atgggcaggc | catgggtgct | 8520 |
| gacggaagac | tacttgtcgg | cgctgaaggt | gcggtgggcc | tgtcccgaag | tctttgctgt | 8580 |
| cggtctgaac | ggtacaaggc | tgcgcgacag | gctggcggcg | atcatgttgc | agcagacctg | 8640 |

FIG. 18F sequence.txt

| | | | | | |
|---|---|---|---|---|---|
| caagcgcgcc | ttcatcttct | tggatggcga | ccgggcaggt | gtccgtggta | gtgcaggcgt | 8700 |
| gatgcgccgg | ctccggtccc | tgcttatcga | aggccaagtc | ataccaacgc | cggacgggtt | 8760 |
| cgaccccaag | gacctgaccc | gcgagcagat | aaggagccta | gtaattggac | gtattgacgc | 8820 |
| ttcacgcact | gagtgaccgg | gaccgcttcc | gcacattgcg | gagtgtggtg | cccgaaggaa | 8880 |
| tgatggggcc | ggagacgtgc | ttcgtcatcg | actggatcga | gcagtattgg | aaggtctacc | 8940 |
| cggcgcatca | gaaggtagac | ccgcaggcac | tgcgcgaact | gatcaagctg | cgaggtggct | 9000 |
| accagccgga | gcaactggcg | gtggtcctga | cctcgtcaa | ccaactggac | aagccggtgg | 9060 |
| acccggactc | gctacagggc | gtcgtgtccc | agctcaacga | actggatttc | tcagggcggg | 9120 |
| tggatgccct | cctggcgcag | tacaaccagg | gcgaggacat | cgacctggcg | tatgagctgc | 9180 |
| gccggctgag | cgacgaggcc | ctgcgccgcg | gaggggtcag | cacgccgacc | gactacgtga | 9240 |
| cggacgacgt | gtttgatatc | ctcgcggagg | agcagggtga | ccacggcatc | aagctgccgg | 9300 |
| ggctggtgct | accggcgtac | atgaagggcc | tccacgccgg | ggcctcggtg | ctggtggcag | 9360 |
| cgccgccgga | tgcgggcaag | acctcgttca | tggcctggat | cgctgtccat | atcgcgccgc | 9420 |
| agctcaagcg | gtacttcgac | cccggacgac | ccatcctgtg | gctgaacaac | gagggcaagg | 9480 |
| gccggcggat | caagccgcgc | ctgtactcgg | cagccttggg | catgaccgtg | ggcgagattc | 9540 |
| ttgccctgga | cccggaggaa | gttcgcagga | tgtacgccga | gaaaatcggc | ggcgactctg | 9600 |
| agctgatccg | catcaaggac | ttccacggcg | ggtccctggc | ccaggccgag | caggtcattg | 9660 |
| acgcgatgaa | gccgtcggtg | gtgttttggg | acatgatggc | tcacgtcaag | ggtggacagc | 9720 |
| gcaaggacca | gaaccgcacc | gacgagatgg | agtacaaggt | ggccgaggtc | cgcgagatgg | 9780 |
| cggtgcgcca | cgacttcatc | agcttcatga | cgtggcagat | tagcaacgac | ggccacgacc | 9840 |
| agttgttccc | accgcagtcc | tgcctcaagg | attcgaagac | agcagtgcag | ggtgcggtag | 9900 |
| atgtgcaaat | ccacctgggc | cgtctcaacg | gtgcggatca | acaggtcatg | cgtggcctgt | 9960 |
| ccctgccgaa | gaacaagttc | cagatggacg | ggaagccttc | gaacgtggag | gctatgatta | 10020 |
| acttcgacgc | cgcacggtgt | cgattcttcg | agagtgtaga | ccatgcaagc | taagcatagc | 10080 |
| cgggtgctcg | aaggcaccaa | agaaattccg | ctgggtagca | tcgagccgtt | actgggcagc | 10140 |
| gtcgcgggcc | tgctgttgtg | cctgtactcc | gacgcaactc | acgaggaggg | cgtcgccttg | 10200 |
| gccggtgggt | tccctcgcga | cttgatgcac | ggcgccactc | ccaaggacgt | ggatgtggcc | 10260 |
| ctgtatagca | tgacctgggg | gcgggcagag | cacctgatcc | agaaggcact | cccggtcctg | 10320 |
| aaccccatct | tcgtccggga | tggtgggtgg | cgctcggact | acgctgatgg | tggtgacggt | 10380 |
| ggtatcttca | agggcgtgat | gtccctcgtg | ggctgccgtg | ggttgaatgg | catggacttg | 10440 |
| gactttaact | actacgacgc | cgacagcctc | ggtcgagtga | tggagtcgtt | cgacttcacc | 10500 |

FIG. 18G sequence.txt

```
atcaaccagg taggcatcgc gtacaactgg cccgaccccg agggtgggcc gcgcctgggt    10560
gcgtacctgc acaaggacgt tacctggggc gtgaacaagg aagtcggtgc cggctcacgt    10620
ctgccggaac gatgcgagaa aatgcgagcc aaggccgcgt actacggatg ggagaacgtg    10680
tgatgagcaa gcgcgacgtg gtactggata tcgagaaagg catctggcgt ggtgttgacc    10740
agaacgacaa ggccgtcgag gccatcatca agaagaacgg gtacgtgatc gtcgagccta    10800
agatcgacgg gtgccgtgcc atcgtcggtg cgcatggcgt ggtgtcccgc agtgggcgcc    10860
gcttcccggc cctggatggc ttggaagacc gcatcatcga gcgactggcc cgaccggggc    10920
tggactccgg cctggtgctg gactgcgaga tgtacctggc cggcatgccc ttcagcgagg    10980
cgactggccg catgtcgagt aagacccgc tgaccgagga agagctggag tgcctgcact    11040
tcgcggtatt cgacgccacc catatcgacg tgctccgaaa ggcgcgcacc tcacacctgg    11100
tatacgaaga gcgccgagcc atggccagca gcctcctggc agcctgtcgg ctcagcgaca    11160
ctccgacgtt cttccaggtg gggttcaccg tctgccggag aatgtctgac gtttaccgcc    11220
agtacaagtt caaccgggag gtgggctacg agggatcaat ggagaaagac cccagcctgg    11280
tctaccgcaa cggcaaggtc gccggctgct acaagcgcaa gccgggcatc accgtagatg    11340
gccgcatcgt cgggtacgtg atgggcaaga ctggcaagaa cgtgggccgc gtcgtgggct    11400
accgcgtgga gctggaagat ggttccggca ccgtggccgc caccggcctg agcgaggagc    11460
acatccagct cctgacctac gcccacctca acgcccacat cgacgaggcc atgccgaact    11520
acggtcgtat cgtcgaggtc tccgcgatgg agcgctcagc caacaccctc cgccatccca    11580
gcttcagtcg cttccgcgac ctggccagta atccaggagt caaggtatga agattcgaaa    11640
gtcccgtaac cgcaactacc cggaagatat ggtgtaccac gccaccaacc gggattcact    11700
gctgtatccg aagtacgtca tgggttccgt gttcatcagc caggacggaa cattccgcat    11760
ctgcgtcatg gcagggacct gggaccacgt tgggtccgaa gttctgcatc atgcacggga    11820
catccaatcc cttggcgccg gtcgccgtaa gttgcaccgg gtcatgcgac ggctgcgccg    11880
caatctgcaa caggtaggag tcaaggtatg agaatgccaa ccgaagaaga acgcacgatc    11940
cgctgcctgc tggcagatat ccacgaaccc ttgaacctgc tgttccccgg tatccgtgta    12000
aaggccgaga caatgccctt gggctgggga gatagtatct gtgccctggt actccgggtg    12060
agctacgaac atctcacgct ggggcgcctg gagtacatgc acgaggtccc catcctgcac    12120
ctgtcgcagt ggggccggga cggcctgcta cagcacctga tgaacgagat tccccgtcgg    12180
gtgctggatg gcatgctacg tcaggcacag aaatacagcc agagtaactg gtacagcaaa    12240
tgacgactat ccgaatcctc gacctcgaaa ccgagagcta cgagcacaaa gggcgcaagg    12300
cgtcgccctt tgaccccgc aactatatcg tcatggccgg ctggcgtgac gatgttgacg    12360
gcaaggtcgg ccagaaggtg gagcatcgct tccgcagccg ggccgaagcc gaagacccga    12420
```

FIG. 18H sequence.txt

```
acaaccgctg gttcaacctc gacggcgtgg acgtgatcgt agcgcacaac gccatgttcg    12480
aatcgaactg gttcttcacc cgctaccggg acgagtacct ggccttcctg cgacgtggtg    12540
gccgggtctg gtgtacccag caggccgagt atctgctgag tcatcagacg tggctgtacc    12600
cggcgctcga cgagctggcc ccgaagtacg gcggcaccca caaggtggac ggcatcaaga    12660
tgctgtggga ccagggtgtg ctcacctcgg agatggacca ggacctgctg agcgaatacc    12720
tgtctggccc gtgcggcgac atcgagaata ccgccctcgt attctacggt cagttgatga    12780
agctccaggc ccgtggcatg tgggctggtt acctggagcg ctgcgaggcc ctgatcggtt    12840
tctcggcgat ggagtgcgcc ggcctgaagg tggacctcga agtcgccaag gtgaaccacg    12900
ccaagcaact ggaagaggtg gccgggatcg aggccgagct gaagaagctg atgcccgact    12960
tcccggaata cttcgagttc aagtatacca gcctctacca tatgagcgca tggctatacg    13020
gtggcgaggt gcggtacaag ggccgggtgc cctacgaaga tggccggatg gagaaagccg    13080
acttcgtgcg cttcggcaca gccaagcggg ggactcctat cgagagtacc tcggtacggg    13140
tcccgatcca cgaagtgacc gaccagggtg aatggcactg gcccaccatc accgagctgg    13200
cgaccaagca cggtccggtc atcacgttct ccgccggcaa gaacaagggc agcgtcaaag    13260
tgttccgtga ggatacggac atcccggcga ccaagtggga cgatgaccag cgattccggt    13320
tccccggcct gatcaacctg accaacctgc cggaagtagt gcgtgagaaa ttcctgggca    13380
agcgcccgga gttccagtgc gccctcaccc tggcggatgg atcgcccgtg ttcagcacca    13440
gcggcgacgc cctcaaggct ctggagaaac agggcttcga ggcggccaag ctgttgatgc    13500
gcctggccga gctgcacaag gacaactcct cgttctacat cacccacacc tacaacaagg    13560
atgggacgat taaggacacg aaggggatgc ttcagtacgt ggacgatgat ggtatcatcc    13620
accactcgct gaatacgacg gcgacggcga caacgcgtct gtcgtccagc cgcccgaacc    13680
tccagcagct cccgtcgaag gacgaggacg acccggaagc cggcagccgc gtgaaggaga    13740
tgttcgtgtc tcgcttcggc gcagacggga tgatcggcga gaccgactat accgccctgg    13800
aggtggtgat gttggcggcc ctgtcgaagg accggaacct cctggcgaaa ctgatggccg    13860
gcactgacat gcacttgtac cgcctggcag ggaagcacaa caactggaac gggttcgact    13920
acgaccagct cgtggccatc aagaaggacc ccaaccaccc gtggcacggt cgcatgatgc    13980
aggctcgaaa gaacatcaag cccaaggcat tctcggcgca gtacggcgcg agtgcggctg    14040
gtatcgcatt caacaccggc tgtaccgtgg aagaggccca ggaattcctg gacaacgagg    14100
cggccctgtt cccagagtcc atcgcattcc ggcagatcgt ccgagacagt gcagaggcca    14160
ccagcctcgt catgtacaag gccgaggacc agatgccggc aggcgccttc agcgagatgg    14220
ggccggatgg caactggcgc cagtaccgcc ggggattctg gcaagcgccg ggtggcacct    14280
```

FIG. 18I sequence.txt

```
gctacagctt ccgccaacag gagcgctggg acaaggaaca gcgcaagacg gtcatggact    14340
tcaaggacac gcagatcgcc aactactgga accagggcga ggctgggttc atgatgaccg    14400
tgagcgtagg gcgcatcttc cgttggatgc tgcatcgccc aggattcatg gtcaccgagt    14460
tcctgatcaa caacgtacac gatgccgtgt acaccgactg ccacaaggac accgccgccg    14520
aggtcaacaa gggcgtgcgc gacatcatgg ccgacgctgc ccgctacatg agcgagcgcc    14580
tgggctacga catcgccgac gttccgttcc cagcagtggc tgagatgggg ccgaacatgt    14640
tcaatatgga ggtgatccag tgaaagaact gcacccgctg cacacgcctg agttcgtcaa    14700
gacattcctg gaccagaccg ggtgcctgcc gggagtacgc cgtacgggtc gcaccaccgg    14760
cattgctcta caggccattg gcatggcgct gtcccatccg agggaaaccc tgacgttcgt    14820
ggaccacccg gacggcagcg cggcagcact ggtggccagc attgaaacca tactggcgac    14880
cctgggctac aagaacgtcc tcgttcgacc cacaacccgt gcggatgggc gcagcgtgag    14940
catcgtcttc aagacgctgc cgaacgcctg acgacccttc cctactccgg ccttaaatct    15000
tcatccgaca cgagagagac cacgcatgac tcaacaactc aacgctctgc aagccgccct    15060
cgccctggcc aacaaggctg ccgagaccgc aaccatcgac atgtccgaaa cctccaccgg    15120
cggtggcggc ggtcgcatct cccggcggg caccgccatg ggccgcttct gcatctacat    15180
cgagctgggt gaccacgcca aggaattcca gggcaagctc aagaacccgg cgcctcaaat    15240
ccgcctgggc ttcgcactgt ggggcgacgt gaacccgcag gccggtaacc cgcagagccg    15300
cccggacgac ctgttccaca cttacgaggc cgacggctcg atcaagcccg gcctgttccg    15360
taccttcgag atgaccctcg gcaacaacga aaagtccaag accaagctgg ccttcgacaa    15420
gatgaactgg agcgggcagc atacccactt cgctcagatg ctcggccagg cgttcatcat    15480
cccgatcaag cgcaccaaga tcaccaaggg caacaacgcc ggcaaggaac gcaacgacat    15540
cgattggggc ggcatcatga agccctacaa cccggtcgat ggcagcccgt acaacgtgcc    15600
ggaactgccg atggacctgt tgcagtattt cttcttcgac gcgccgacca aggagacctg    15660
ggacgccctg tatatcgagg gcacctcgga caacggcaag tccaagaact tcctgcaaga    15720
gaccattcgc tcggccacca acttccccgg ctcggccctg cacatcatgt tgggcggcgg    15780
cgacgatctg atcatcaagc caacgagcca ggccgcaggc agcaacctgc cggcagtgcc    15840
caacgtggcc gccgatgcag gcgtagcagc agcccctgcc gtcccggcag tcccgcaggc    15900
agtggctcag acggccccca gcgtgcccca ggtggcgaat gtggctgccc ctgtggtagg    15960
tactgccgag gcgcagaacg tgctgcctga cgtgcccag gtggctcaga cggcggctcc    16020
ggcagcggtc gaagtcccgg cggtcccggt agtgccggca gtaccgcagg tctaatgcgc    16080
ctgccatcgg aagagttcct ggcaggacta tccgcgcagt tcgaccgcag catggcaggc    16140
gggacgttgg tgtgtgacgc cgatggaccc gcctacgtgg ctgcggccac tgctaagacc    16200
```

FIG. 18J sequence.txt

```
ctggacactg cactccgaag attctggaag ctcattttgg agcagcagtt cctagcgcac      16260
tgcacaggga cacgggttca cctcacggca gcaggtgggg cgaaggcgta ccgcgacacg      16320
tatccgacca tgaaaccgta ccagggccag cgcaagggca aggcaaagcc cgcgctgctg      16380
gagccactgc ggcgggccgt ggcggacgtg catgagcgag gcggggcgcc ggaggggatc      16440
gatgtcatcc tgcacacgtt cttcgaggcg gacgacggca tgatgatgga cgcctacgcc      16500
atgcaggaca aggccatcat ccggtccgac gacaaagacc tgcggatgac gatctacccg      16560
tattgggaga tcgatacggc gtgtgtgagc aggatcgaag gcggcttcgg ctacctcaag      16620
gaagcgtaca cgccttccgg ccagttcaag ctcaagggcc atggacggaa gttcttcttg      16680
gcgcagtggc tcggcggcga caccgctgac aacatccgag ggatcgatcg attcaacggt      16740
aagctctgcg gtatgaagac ggccttcgac atcctccatc cgatcacgga tgaggacgag      16800
gccatcgaca tgatcctgga ggcgtacgcc aagatcaagc aaaacccgct ggcagaggcc      16860
gaggtgctgt ggatgcgccg aacgcctacc gacaacgcag cgcagtacct gttaagccgc      16920
gaccttcgtc cggccttccg ccagtggatc atcgagctgg acgcctacca cgaggcgctg      16980
ctccagaagc ggagggagag cgattatgac gagtgagccg aaggtctacc agataccgcg      17040
cagtcaacag cgcaccttca ccctgaagct atgggccgag cagaacaagc tgtgcccgct      17100
ctgcggcaag cccatcgata tcagcgtgaa gggcgaagcg gtgatggacc acgaccacga      17160
aacggggctg gtgcggggcg tcctgcaccg gtcctgtaac accgcagaag gcaagataac      17220
gaatgcggca ggttcctggg gatgcaagtc gatgaagtat tcagacatca tcccctacct      17280
tcgtgccctc ctgacgtatc tggaggggcc gaagcatccg ctgatctacc ccctgcacaa      17340
gaccgacgag gagaaacacg aagcgaagct ggccaagcgc cggcaggcag ccgccaaacg      17400
caaggcggcg atggccgtcg caaagcacaa cgcgaggaac gtatgagcaa actccgcaag      17460
caattcacca atgagtacct gcgaaacgtc tatgtcgagc tgggcctcaa gaagggtgcc      17520
gagcacctga ccgagcattc gcgcttcggt gaggtgagcc gccagtgctt ccgcaactgg      17580
tgcatcaagc tgggcttcca cgacagcagg acgcgcggca tgtacgccaa gaagggcgcg      17640
atgcactggc tgggccgcaa ggctgccgag gtagtgcgca agttccctgg cgccgtgggc      17700
aacgtggtag gccagggtcc gaaggtgctg agcctggaca tcgagacctc gcctatcgag      17760
ggctgggtct ggtcgctctg gaagcagaac gtgggcctca accagatcaa gcgggactgg      17820
accatcctgt cgttctgtgc gaagtggatg cacagcgacg aggtgatcta catggactgc      17880
cagggtgatc ccttggacga catgcacctg ctggtcgcgc tgcacaagct gttggacgag      17940
gccgacatca tcatcgtcca gaacggcaag cgcttcgacg tgcccaagat caacgcccgg      18000
ttcttcctga acaagatgcc gccgccgcga ccgttcaagg tgatcgacac cttgatcatc      18060
```

FIG. 18K

```
                                sequence.txt
gccaagcagc aattcgcgtt caccagccgc aagctggagt acatgaccca caaggcatgc    18120
accatcaaga agcgactgca cggcaagttc cccggattcg acctgtgggc ggcctgcctc    18180
caggacaacc cggaggcgtg ggaagagatg cgcctgtaca acatcgacga cgtacggtcg    18240
atggaagagc tgtacatcct gatgcgtcca tggttcgtcg gccaccccaa cgtggccgtg    18300
tacttcaatg acgccgaacc gaccatccgc tgcccgaagt gcggcgacac ggatgttaag    18360
caagaaggct gggtgcatac gcagaccggc aagtacgagc actatcactg cggtggctgc    18420
ggtggctgga gccgagggcg gtacacccgc aacacctcgg aacagcgcaa agccctgctg    18480
agcaactaag gaggtagcat gagcctagca ttcccggact cttacgagtc gacgatcacg    18540
actgaaccgt accgcaaagg tgcgagtctg gaagaacgca aggtcggcaa gcttcccatg    18600
cacctggtag tcgaggggtt cccgctgctg aagcgggagc ttgctcgaat gatgcaatgg    18660
gctgccgagg tcaagggggta tctgccgcac gactggaaga agatgacggt gggcgagttc    18720
aagtccgccc aacacaggca cgagtccaag cggctgatcg acgggccgct ggatgacgag    18780
tccaacctga tgcacctggt gcatgaggca ttcaacgcaa tggccgccgc cgaggtggcc    18840
ctgatggacc gggagaaagg caatgagtaa aatctgttgg tgtacccgac cgcacgagac    18900
cgatgaaggt gttcgggtca tctgggcctt caacgagcgg ggcatcgggg tcaactacgt    18960
cacagcgtac atcacgccgg cgatggtcag ccatcgggac tggagcgatg tcatactccc    19020
ggacattctc cgggagatgg cggagcgcct ggagcgggaa gtgaagctgg tggaactgcg    19080
ctggttccgc gctgagattc tgagctgcgg ggaatggcgt gactaccgag cgatgacgct    19140
ggagggggcg gttagcctgg ccgaggccga gtggggtccc gaggatatcg ggcgcgtaat    19200
cgaaagacga taggagatgg aatggacctg atacagcagc agatcgccca cgaagaggcc    19260
ctggtcgggg cggcgcagaa tgacgcccgc attgccttgg aaaaggcgat tgcccaaggg    19320
tccatcgacc gcatcccgag ggcgcgcatc atgttgatgc ggatgctccc catcgtgacc    19380
gaagcgatct tcgcccacca ggaagcgaag gcggcggggc cggcagcgaa gcttcggcac    19440
ctgctgcgga tcatcgacgc ccaggacctc gcggtcatgg cgctgcgggc tgggctgtcg    19500
atgctcatca actacccaac gatcacagcg acgaagtatt acacccacat gggtaagata    19560
ctctgtcgag agatcgaagt gcggttggcc ttcaaggtca accaaccta ttacgaccgg    19620
acgctggact acctcaagac cagcaggact cgcagcgtcc ggcacatcca gaagacgatg    19680
gacgctcttc tggacgcggt actaccggaa gaggcacgta tcgacctgcc ggatggcgac    19740
tacctgcgcc tcggcaagtt catcggtgat ccgctgatac agtgcggcct gttcgagccg    19800
aaccgcttca caggtcgtgg aggtactagc gtccacctgg agccgtcgcc ggaagccaag    19860
gagttcctgc aagacccttc ggcggcgatg acctggggag gcccaggccg tagcgtgatg    19920
ctggcaccgc cgcgaccatg gaacgactgg tgcgatggcg gttactacag cgctaaggcg    19980
```

FIG. 18L sequence.txt

```
cagaaacacc atgtgctagt gcgccgtacc aagcaccaga ccaagcgggc gcgccagatg    20040
cagctacgcc acctgggccg ggacaagatg cccagggtgt atgaggcggt caacgcgctg    20100
caatcagtgg cctacgagat caaccacgac gtgtacgaga tcatcgagcg cgtcttcact    20160
tccggcggcg gtgtgctggg catccctcag cgcacctacc cggacaaacc tgagttcccg    20220
ctcggcgacg agtgggccaa ggagaacgcc agtgaacaag agctggaagc cttcaaccgc    20280
tggaagcgat ccgtccaccg atggtacacc ggcgagcggg agcataccgc caagcttcgc    20340
gagtttgctg cactctaccg agttgttcga gagcatcatg gcaaggcagt gtacttcccg    20400
atgcacgttg actccgtgg ccgcatgtac tattggggca caccgaatcc ccagggggtcc    20460
gacatcgcca aggcatgtct gcgattccac gaaaagcgtg ccctcggtaa gcgcggactg    20520
tactggctca aggtccacgt cgccaactcc ctcggatgcg acaaggtgta cttcgacgac    20580
cgagcagcct gggtcgatga gcgctggac gacttccagc gagcgctcga cgaagggccg    20640
gagaactatc gaatctctt ccccgaagac gagtccccac tgtgcgccat cgcaggtctg    20700
ctggagttgc gggcggccta cgcttccggc aatcccgagg gctacgccag tggtttcatc    20760
gtccacatgg acgccacctg ctccggcctc caacactact cggctattct ccgcgacgag    20820
atcggcgggg cctacgtcaa cctgctgcca cctggacttg caaaagctga tatctactcc    20880
cgagtgctcg gactcgttaa tgagtctctg gagagagacc gagcggaagg cgcggatggc    20940
gaggcgcggg gttatgccat tctatgggat aaagctggtc tgacgcggag cctgaccaag    21000
aagccctgca tgacgctggt gtacggcacc acgttcaagg gcgtcgtgga ccactgcctg    21060
gactacctcg acgagtccgg tgtggagatt cccgagggtg tgccgtcata ccgcctagga    21120
agctacatgg cgacgctcat actggacgca atccgcgaga cagtaccatc ggcagtcttc    21180
gccatggagt ggctccagcg gcttgctagg gcccttcctg acgcatccaa ggatttgcac    21240
tggaccacgc cgctcggcat gcaggtcttc cagtcctacc cgaagaccga ggaggtgcga    21300
gtacggctgc gcgccgaggc tgtcgagtac gtcaccctgt acgaggccaa ggacgagctg    21360
gacccggtac gcaacgccaa cggcatcgct ccgaacttcg tccacgggct ggacagcagc    21420
cacctgggcc tgacggcctt ggcatgcgcg gcagagggaa tcccgatcca ggccatccac    21480
gacagcatgg gcacttatgc ggcagacgtg gaccggatgc acgttcacat cagggagcag    21540
ttcatcgcca tgtacagtgg cccctgtgtg ctcgtagagc tggcaaagca gcttggtata    21600
gaggctaccc cgccccggag aggatcgttg aatctggagg ctgtacggga ctcctgggcg    21660
ttcttctgct gaggcggatt atgtcaccca cataggagca agtgcatccg tccaaggccc    21720
tcgtagaggg agcgggggag aggagaggtc agggaagacc tggtagagga gaggtgaaga    21780
tgagaatgga tgactacgaa ggattctaga tagaatagac taaccagcat aggagatatg    21840
```

FIG. 18M sequence.txt

```
atagatggct actatgaaga cccaccgccc tacggttatg tcacccacag tggaaggatc    21900
gagaacaggc aagggtacgg cccgtcctgt cacgttcacc tctcagcaga tcgagtggtt    21960
agaacagacc ttccccgaac atcagatcgg tcctggaacc acgatggaag acatccagtt    22020
ccaggccggt aggcgagacg tggtgcgagc agtacgcctg cgccgacgcg atgccatcgc    22080
agtggagctg aagtgatgaa caagtccatc tggcgagtcc acgcaaaggc cggcactccc    22140
tcggaactcc agggcctgtg ctggctggcg atacaggagt tggaggagtt caccctcttc    22200
cgctcgaaag acgacgccct gaatgcgatg ctggacagta tcgagggcaa tgatcgaacc    22260
gagctgttgg tattccgcga tggccagttg gctggcggtg cctgcattgt gttcgaggac    22320
gatccccacg tcggcccgtg cgtcacagca cagtggcagt acgtcctacc gcgctaccgc    22380
aatacaggcg tggtccggga gttcatccgc gaactccacc gtcaggccgg ctggggtcaa    22440
atcccccctcg tgtgctggag ccatcgtgaa agcgatagcc ggtacacgat ccactaccgg    22500
agagccaagc cttatgggca agaaagtaaa gaaggtgctg ggcaagacca tcatcggcaa    22560
actcgctgat ggcctgctgg gcaccgacct gagcggcgca caatccgatg cccgcaagat    22620
ggaagagcag aaccgcctaa tgcagcagca ggcggaccag ctcgcacgaa accagcaggt    22680
tgacctcacc gccgagaacg tggcgcaggt tgacctagga gcgatggccg atgccactgg    22740
caccggcacg cgacggcgcc ggaatcaggc gggcacaggc gtatcgcaaa ccctcggtat    22800
caactactga cgaggtacgc catgaaaacc accgcagcta tgctgtggga gaaacttcgg    22860
gatgggagcg tggagagtcg agccatcgag ttcgccaaga ccacgcttcc ctacctgatg    22920
gtcgatccca tgtccggcag ccggggagtc gtagagcatg acttccagtc cgccggtgcc    22980
ctcctggtga acaacctcgc cgccaagctg gcgagatcgc tgttccccac ggggattccg    23040
ttcttccgat ccgaactcac tgatgcgatc cgccgcgagg ccgacagccg ggacacagac    23100
attaccgaag tgaccgctgc cttggctcgg gtggatcgca aagcaacaca gcgcctgttc    23160
cagaacgcct ccctggcggt cctgacgcag gtgatcaagc tactgatcgt gactggcaat    23220
gctctgctgt accgagacag cgccgccgct acggtggtcg catggtcgct ccgctcctat    23280
gcggtgcgtc gagatgcgac tggccgctgg atggatatcg tcctaaagca gcgctacaag    23340
tccaaggacc tggatgaaga gtacaagcag gacctgatgc gcgcaggccg caacctatcc    23400
ggttcgggca gcgtggacct gtacacccac gtacagcgca agaagggcac ggcgatggaa    23460
tacgccgagc tgtaccacga gatcgacggc gtgcgtgtgg gcaaggaggg ccgctggcct    23520
atccacctgt gcccgtacat cgtgccgacc tggaacctcg cacctggcga gcactacggt    23580
cgaggccacg tcgaggacta catcggcgac ttcgccaagc tgtccctgct gagcgagaaa    23640
ctcggcctgt acagctgga gtcgctggag gtcctgaacc tcgtggacga ggccaagggt    23700
gcggtggtcg atgactacca agacgccgag atgggtgact acgtgccagg tggcgcggag    23760
```

FIG. 18N sequence.txt

| | | | | | | |
|---|---|---|---|---|---|---|
| gccgtccgtg | cttacgagcg | tggcgactac | aacaagatgg | ctgctataca | gcagagcttg | 23820 |
| caagccgtag | tcgtccgcct | gaaccaggcg | ttcatgtatg | gtgccaacca | gcgcgacgcc | 23880 |
| gagcgcgtta | ctgccgagga | agtccgcatc | actgcggagg | aggcagagaa | cacgctgggt | 23940 |
| ggtacatact | cgctcttggc | tgagaacctc | cagtcgcccc | tggcctacgt | ctgcctatcc | 24000 |
| gaggtggatg | acgcgctact | ccagggcttg | atcaccaagc | agcacaagcc | ggctatcgag | 24060 |
| acgggcctcc | cagctctgtc | ccgctccgcc | gctgtgcaga | gcatgctcaa | cgcttcccaa | 24120 |
| gtcatcgctg | gcttggcccc | gattgctcag | ctcgatcccc | gcatctcgct | accgaagatg | 24180 |
| atggacacga | tttgggcagc | cttcagtgtc | gatacgtcgc | agttctacaa | gagcgccgac | 24240 |
| gaactggaag | ccgaggcaga | acagcagcgc | cagcaggccg | cacaggccca | ggcagcgcag | 24300 |
| gagaccttgc | tggaaggcgc | ttccgacatg | accaatgcac | tcgcaggagt | ctgatagatg | 24360 |
| acccaaccga | acgatcagca | actgccaccg | ggcctcgcta | acctggttgc | caacgtaccg | 24420 |
| cccgccgccg | cgccgacccc | gagtcatgtg | caggtgttgc | cgaacccggt | gatccagccg | 24480 |
| caggctccgg | tccagcccgg | ccaggtaggt | gcgccgcagc | aactggccat | cccgacccag | 24540 |
| cagccgcaac | ccgttccgac | cagcgccatg | acgccccact | accagccggt | agcggtgccc | 24600 |
| gtcgccggtc | aacccgttgt | tccgcaagca | cccgctcagc | cggccccggt | agctccgccg | 24660 |
| gctgcgggtg | cagttcttcc | cgagaacctg | gaagtcccgc | cgcctccggc | cttcactccc | 24720 |
| aacggggaga | tcgtaggcac | cctggcaggg | aacctcgaag | gcgaccgcag | gttggcgccc | 24780 |
| tctatcagct | atctggaagc | attctctgac | aagctggata | ccgtccgtgc | cttcggcaag | 24840 |
| gccgccgaga | accgcgatcc | gcgattcatc | gacgagcact | atctgaagga | agtcctgggt | 24900 |
| ccggcccagg | cacagcacgt | catcaacgtg | gccaagggcg | tcctgaccta | tgtcgatgcg | 24960 |
| cagaccaagg | ccgtcctgaa | tcagacctat | gccgccgtcg | gcggtgaggc | cgtcctgaag | 25020 |
| caggctgccg | gagtcttcaa | ccagcacgct | gacccggcca | ccaaggccgc | catcggtcgg | 25080 |
| ctgatggact | cgggcgatgc | ccaggccatg | cagtacgcag | cgaagcaaat | tgtggccttc | 25140 |
| gcacaaggct | cgggtgccgt | ggtacaggct | accggccaac | ccctgggtgc | tgcggcacct | 25200 |
| gcactggcag | ctctgagcgc | tgagcagtac | cgcttggaag | tatctaagct | gccgctgaac | 25260 |
| gcatccgaag | ccgagatggc | tgcgctgcgc | gagcgtcgta | aggcaggcat | ggcgcagggt | 25320 |
| atctaacgac | cctgccctac | tccggcctta | aacccacatc | caaaagagag | agaatcgcat | 25380 |
| gagctttctg | aacgacctga | ctcgtccgaa | ctacgctggc | aagaacgcgg | acgttgacat | 25440 |
| ccacctggaa | gagcacctcg | gcatcgtcga | taagcacttc | gcctacacct | ccaagttcgc | 25500 |
| accgctgatg | aacatccgcg | acctgcgtgg | ctcgaacgtg | gtccgcctgg | atcgcctggg | 25560 |
| taacgtcgag | gccaagggtc | gccgcgccgg | tgaagagctg | gagcgcagcc | gagtcgtgaa | 25620 |

FIG. 180 sequence.txt
```
cgacaagtgg aacctgaccg tcgacaccct gctgtacctc cgccaccagt tcgaccacca   25680
ggacgagtgg acccaatcct tcgacatgcg caaggaagtc gccgagctgg acggccagga   25740
actggctcgc aagttcgacc aagcctgcct gatccaggtg atcaaggctg ccgcgatgga   25800
cgcgccggtg gacctggaag atgcgttctc gccgggcgtg ctggagaaac tggacctgac   25860
cggcctgacc gccaagcagg ctgccgacaa gatcgtccgc atgcaccgcc gcgtagtcga   25920
gaccttcatc gaccgcgacc tgggcgatgc ggtttactcc gagggcctga ccccgatgtc   25980
gccgcgtgtg ttcagcctgc tgctggagca cgacaagctg atgaacgtcg agtaccaggc   26040
aaccggcgcg accaacgact acgtgaagtc ccgcgtggcc atcctcaacg gcgtcaaggt   26100
gctggagact ccgcgcttcg ccaccaaggc aatcgcagcc cacccgctgg gccgtcactt   26160
caacgtgagc gccgaggagt ccgagcgcca gatcgccctg ttcctcccga gcaagaccct   26220
gatcaccgcc caagtggcgc cggtccaggc caagctgtgg gaagacaacg agaaattctc   26280
gtgggtcctg gataccttcc agatgtacaa catcggtgcc cgtcgtccgg acaccgctgg   26340
tgccatcgaa ctgaagggta tcggcgcctt cgacatcacc gcgtgatgcc acgaaacccc   26400
gcacttcggt gtggggtttc ttcaaagcct aacgacccgc gcagattccc tgcgtgggtt   26460
tttgcgcttt aggagaaacc ctatgctact actcgacgca gtgaatgtca tcctgcgcaa   26520
gatcggcgag ctgccgattc cgagcatgga tgagacgtat cccaccatgg ccattgccct   26580
cccggagttg gaggaccagc gcatccagtt gctgacgcaa ggctggtggt tcaacacctg   26640
gtggaagcac aagctgacac ctgacccgca gggtcgcatc aacctgccca aggatacctt   26700
ggcattctac cccgactccc cggacctcca gtgggacggc ctgggagtac gggatgccaa   26760
caccggcgac gaccgtatcg gcaagtcggt cgagggtcgg ctggtgctgt cccgcgagtg   26820
ggaccgtatc ccggagattg cgcagcgcgt cattgcgcac caagccgccc ttgcggtata   26880
cacccacgag attggcccgg acgagaccgc ccaggtcatc gcccaggaat tgcaggcgta   26940
tcagaacgaa ctgtctcgca tgcacactcg atcccgtccg ctgaacaccc aggccaagcg   27000
tagcttcagc cggtggcggc gtagcttgag gacctgagca tgagctacaa gcaatccgcg   27060
tatcccaatc tgctgatggg cgtgagccaa caggtgccct tcgagcgcct gcccggccag   27120
ctcagcgagc agatcaacat ggtatccgac cccgtgtcgg gactgcggcg gcgcagtggt   27180
atcgagctga tggctcacct gctgcatacc gaccagccct ggccgaggcc gttcctctac   27240
cacacgaacc taggtggccg cagcattgcg atgctggtgg cccaacaccg tggcgagctg   27300
tacctgttcg acgagcggga tggacgcctg ctgatgggcc agccgctggc ccacgactac   27360
ctcaaggccg acgactatcg gcagctacgg gccgctacgg tggcagatga cctgttcatc   27420
gccaacctga gcgtgaagcc cgaggccgac cgcaccgatg tcaagggtgt agaccccaac   27480
aaagcgggct ggctgtacat caaggccggg cagtattcga aggcattctc tatgaccatc   27540
```

FIG. 18P sequence.txt

| | | | | | |
|---|---|---|---|---|---|
| aaggtcaagg | acaacgccac | gggcaccacc | tacagccata | ccgccactta | cgtgacgccg | 27600
| gacaacgcca | gcacgaaccc | caacctcgct | gaggcgccat | tccaaacgag | cgtaggctac | 27660
| atcgcgtggc | agctctacgg | caagttcttt | ggtgcgccgg | agtacactct | gcccaactcg | 27720
| acgaagaagt | acccgaaggt | ggacccggac | gccaacgcgg | caaccatagc | cggctacctc | 27780
| aaccaacggg | gcgtgcagga | cgggtacatc | gcgttccgtg | gtgatgccga | tatcgtggtc | 27840
| gaagtgtcca | cggacatggg | caacaactac | ggcatagcct | ccggcggtat | gagcctcaac | 27900
| gccacggcag | acctgccagc | cttactgccg | ggcgcgggtg | ctcctggcgt | gggtgtgcag | 27960
| ttcatgggcg | gcgctgtcat | ggccaccggc | tccaccaagg | ccccggtata | cttcgagtgg | 28020
| gattccgcta | accgccgctg | ggcagagcgg | gccgcctacg | gcaccgattg | ggtcctgaag | 28080
| aagatgccac | tggccctgcg | ctgggatgag | gctaccgaca | cctacagctt | gaacgagctg | 28140
| gagtatgatc | gacgtggctc | cggcgacgag | gatacgaacc | ccacgttcaa | cttcgtcacc | 28200
| cgaggcatca | ccggcatgac | gaccttccag | ggtcgcctcg | tcctcctgtc | gcaggagtac | 28260
| gtctgcatgt | cggccagtaa | caatccgcac | cgctggttca | agaagtcggc | agccgcgctg | 28320
| aacgacgatg | atcctatcga | gatcgcagcc | caggggagcc | tgactgaacc | gtacgagcac | 28380
| gcggtcacct | tcaacaagga | cttgatcgtc | ttcgccaaga | agtatcaggc | cgtggtcccc | 28440
| ggtggcggca | ttgtaactcc | ccgcacggcg | gttatcagca | tcaccacgca | gtacgacctc | 28500
| gataccaggg | cggcacctgc | cgtgactggc | cgcagtgtgt | acttcgctgc | ggagcgtgcc | 28560
| ctgggtttca | tgggcctgca | tgagatggcc | ccgtctccgt | ccacggacag | ccactacgtc | 28620
| gccgaagacg | ttaccagcca | catcccgagc | tacatgccgg | ggcctgctga | gtacatccag | 28680
| gcggcggcct | ccagcggcta | cctggtgttc | ggcaccagca | cggcggacga | gatgatctgc | 28740
| caccagtacc | tctggcaggg | caacgagaaa | gtgcagaacg | cgtttcatcg | ctggacgttg | 28800
| cggcatcaga | tcatcggcgc | ctacttcact | ggcgacaacc | tgatggttct | gattcagaag | 28860
| ggccaggaga | tcgccctggg | acggatgcac | ctgaacagcc | tgccagcccg | tgagggtctg | 28920
| caatacccta | aatacgacta | ctggcggcgt | atcgaggcga | ccgtcgatgg | tgagctggaa | 28980
| ctgaccaagc | agcattggga | cctgatcaag | gatgcctctg | ccgtgtacca | gctacagcct | 29040
| gtggccggcg | cctacatgga | gcgtacccat | ctaggcgtga | agcgcgagac | gaatacgaag | 29100
| gtgttcctcg | acgtgcccga | ggccgtggtc | ggggcggtgt | atgtggtcgg | ctgcgagttc | 29160
| tggtcgaagg | tggagttcac | tccgccggtt | ctccgggacc | acaatggcct | gcccatgacc | 29220
| tcgacccgtg | cagtgcttca | tcggtacaac | gtaaacttcg | gctggaccgg | cgagttcctg | 29280
| tggcgcatca | gcgacacggc | tcgacccaac | cagccgtggt | acgacacgac | gccccttcgg | 29340
| ttgttcagcc | ggcaactcaa | tgccggggag | cctctggtgg | atagcgctgt | ggtgccgctg | 29400

FIG. 18Q sequence.txt

| | | | | | |
|---|---|---|---|---|---|
| ccggcacggg | tcgatatggc | cacgtccaag | ttcgagctga | gctgtcacag | tccgtacgac | 29460 |
| atgaacgttc | gggctgtcga | gtacaacttc | aagtccaacc | aaacctacag | gagggtgtga | 29520 |
| tggctttctg | gctaccacta | ttggccgctg | gcggcatgtc | cgcccttcaa | cagggattgg | 29580 |
| ccaacaagga | agagcgcaac | aagatcaagg | ccgagaacaa | ggctcgactg | aagacggacc | 29640 |
| tcgacaacct | gggcgccgct | gcccgcgaca | tcgccaacct | cggagtcatg | gctgctagct | 29700 |
| accgcaagca | agccgtggcc | tcgcaggtgg | aggccaagcg | ccaggggatg | ctagccggcg | 29760 |
| gaagcgccga | ggctcaggcc | ggggcgttcg | gcgtcaaggg | tgcatccgtc | gatgcggtgg | 29820 |
| ccctggatat | cgagcgggag | gtcggcgagg | ccctgatcca | gattgacgac | aacctggaca | 29880 |
| atcagatgtg | gaacctcgcc | gagcaggcgc | actccatcca | ggctcaggct | aaggccggcc | 29940 |
| tgctgggtca | aagagtacc | acggcggggc | aacggtcccc | gctggtggcc | ggtctgatgt | 30000 |
| cggcgggttc | cctgtacgca | agtcaatact | tcaagttcgg | cgccacgcct | aaaggaggca | 30060 |
| actgatggcg | gaatcgcaac | gtgcttccca | agagcttggg | atcaacgtcg | gacagacgca | 30120 |
| actccagccg | ggccagagtg | ctcggcgcgg | agtgcgcgac | tccgaggtca | actacagcgg | 30180 |
| tccgagcgta | ggctcgcaga | ttctcgacgg | catcctgggt | gccggtcagc | agatcgctgg | 30240 |
| caaatggttc | gagcacaacg | tgcagcagga | agttctgcgc | ggtgagcgtg | cccgtatggc | 30300 |
| cggcgaggcg | gaggaggcag | tagacagcaa | cgtactggcc | aaaccattcg | tgaagggtgg | 30360 |
| ttggcgtaag | caggactacc | gtatcgccca | ggcggacttc | agcctgaaga | tgcagcgatt | 30420 |
| catcgccaac | aagggccggg | agatgactcc | cgaggagttc | cgcaagtacc | tgtcccagga | 30480 |
| ggctacgcac | gtcctggact | cgaccgaggg | catgaacccc | aacgatgcct | acaggcgct | 30540 |
| ggcgcagcag | cagaaggccg | aggaacagct | cttcggcatg | caggctaagg | cgtacatgga | 30600 |
| ctggtccatc | gaccaggccg | cccgtggctt | ccgtacccag | ggtaacagta | tcctggccaa | 30660 |
| ggctgtgcag | gctcaggcca | ccggcgacga | actgtcccgg | cagctcagcc | tggaagaggc | 30720 |
| cggcctgttc | tataccaaca | tcatgacctc | cgaggatatc | ccgctggagg | tgcgcgacaa | 30780 |
| ggtaggcatg | cagttcctgg | cggccagcct | ggacatgaac | cagcggggca | tctatgaggg | 30840 |
| cctgcgcgat | gccgggttcc | tggacagtat | gtcctttgac | gaccggcgtg | cgctcaacgg | 30900 |
| cctctatgaa | aaatcgaagg | cacagacccg | tgccaaggaa | tcgatggcta | ccctgcgggc | 30960 |
| cgacgcggac | ttccagcagc | gggtggccaa | cggcgccatc | acagaccttg | ccgaggttga | 31020 |
| agcgtactca | cgaggcatgg | tcgaggaggg | ccgctggagc | gacgctcagg | ccatctcatt | 31080 |
| catgaccaag | gccatgaccg | gtctgggcaa | tgcccaacgc | atgcagggca | tcatggcggc | 31140 |
| cctggaagcg | ggggacatca | acgccctaca | cacgctgggg | acgaacgtta | ctgaggccct | 31200 |
| ggagcagtgg | gacaagatgc | aggccgccaa | cggctcaagc | ctgactgacc | gtctcgtgca | 31260 |
| gggcacacag | ctcggcctgc | gcctggggac | cttccccaag | acctacggcg | agtccgtggg | 31320 |

FIG. 18R sequence.txt

| | | | | | |
|---|---|---|---|---|---|
| cagcgcggtg | cgcatgatcc | aggccgccaa | agaaggcgag | gcaaacccgg | agctggtcaa | 31380 |
| cacgctgaac | agcatcttcg | agcaggtggc | ctcggcccag | gagatcaacc | cctccgccgg | 31440 |
| caacgtgatg | ctatccggca | tcccggaagc | cgagcaaggt | gccgtggcct | gggcactcaa | 31500 |
| gcagatgaag | atgggcatcg | caccagctca | agctctgcgc | gagttcagcg | ccaacgccga | 31560 |
| agtcgtgaaa | cagatggacg | agttcgagaa | aggccagaac | accaaggcat | tcaaggacaa | 31620 |
| cctcggcaag | caggtcaacg | acaagttcgt | gaacaacatc | ttcggtcggg | cctggaacat | 31680 |
| gctgaccggt | gaaagcgacc | tgagtaacaa | cgaggccgtt | ctcagcatgt | accgtcgagc | 31740 |
| aaccatcgac | gaggcgaact | ggctggccag | cgaccgcaag | catgcgggtc | tgctcaccag | 31800 |
| tgacacgggc | cgcgaggccc | tgctggagat | cgccgccgcc | aacgtgcgta | accgcaccat | 31860 |
| ccaggtaggc | gaaggtcgga | atctgaagga | aggggaccta | ttcagccgcc | gcgatagcgc | 31920 |
| gccgctgatc | ctgccgcgtg | gcaccaccgc | cgagcagcta | ttcgggacca | acgacaccga | 31980 |
| gaccatcgga | accgtcctgg | ccgagcagca | caagccgcat | gtcgaaggac | tcctcggcta | 32040 |
| caagtcggta | gtcgccttcg | agtacgaccg | caccaggggc | agcctcctcg | ccgtcgagta | 32100 |
| cgacgagaac | ggtgtggccc | tggaccgcac | gcgggttgat | ccccaggcag | tcggtaacga | 32160 |
| ggtgctcaag | cgcaacgcgg | ataagctgaa | tgcgatgcgg | ggcgccgagt | acggtgccaa | 32220 |
| cgtcaaggtc | agcggcacgg | acattcgcat | gaacgggggt | aacagtgccg | gcatgctgaa | 32280 |
| gcaggacgtg | ttcaactggc | ggaaggaact | ggctcagttc | gaggcttacc | gaggggaggc | 32340 |
| gtataaggat | gccgatggtt | atagtgtggg | cctggggcat | tacctgggca | gtggcaatgc | 32400 |
| tggggcaggc | actacagtca | cgcctgagca | agccgcgcag | tggttcgccg | aggacaccga | 32460 |
| ccgcgcactc | gaccagggtg | tgaggttggc | cgacgagctg | ggcgttacga | acaatgcctc | 32520 |
| tatcctggga | ttggccggta | tggccttcca | gatgggcgaa | ggacgtgccc | ggcagttccg | 32580 |
| taacaccttc | caggcgatca | aggatcgcaa | caaggaagcc | ttcgaggctg | gtgtacgaaa | 32640 |
| cagcaagtgg | tacacgcaga | cgcccaaccg | ggccgaggca | ttcatcaagc | gcatggcgcc | 32700 |
| ccacttcgat | acaccgagtc | aaatcggtgt | cgattggtac | agcgccgcaa | cagcggagta | 32760 |
| agacatggca | aagcaattca | agggccgcat | gacgcccaag | tatcccttg | accaagtaca | 32820 |
| gctcgacgag | gcccaagtac | agggccaact | cgacgcggtg | cctaccgtgg | ggttcgacgc | 32880 |
| cctgacgggt | ggtgagatcg | gagaacgaa | cgtggcagcg | ggccaacgag | ccaatgcgcg | 32940 |
| ggaactggaa | cgcatcgtag | cggaccagga | actgccggcc | cttgaccgtg | cttccgcact | 33000 |
| ctggaaccag | tccacccctcg | tcggacgctg | ggtcgatgcg | ctccagctcg | acgcagacct | 33060 |
| tgcggcgaac | agtaccggcg | aggtggaccc | taacttcgac | gctgggacct | atggggtcca | 33120 |
| ggcgctccag | gcggcaggta | tccagccgac | tgataactac | cttcagatca | tggcccgtgc | 33180 |

FIG. 18S sequence.txt

```
cggcaatgcc gaggacgcgg cctacctcct atcgaggatt caacggtatg agcaggacga    33240
acaaatcgtg cgggacaacc catactggaa cttcgcggtt ggtatgctgg acccggcagc    33300
cctggcagtt gatgcggtta ctttcggcgc tggccgtgct ctgcggctcg gtcgtgctgg    33360
catggctgct gctggcggcg ctgggcaagt cgggtatgtt gctgggctgg atgccgcagg    33420
ggccgatgtg gatgctggaa cctacatcgt ggcgggtgct cttggcgctg gcgtgggtgc    33480
tctgctgggg tctggtgcgg gacgcattgc cgcagaggcc caacgcaac cgcatgtgcc     33540
cgaagtatcg gcgcctactg tcgggctgcc agaagtagcc atgaccgccg aggaggccgc    33600
agcacgcggc ttcaaggcag gtgacgtggt agacctgctg gacgagggca ctgtgctatc    33660
ccgtgtcagt gcccgcgtgg agcaggctga gataccggct attccgcgac gtgacactgc    33720
cttcggcgac gagctgcata gcctgtcggg ccggaagctg tctgaggtcc tggaccacat    33780
caagacccac gcagaggtgc ccaagccgct ccagggcatc gccgccaagg tggctgacac    33840
tatcaggacc ctggagggcc tggggcagcg taccgcgttc cgtgtggtgc agggcggtga    33900
cactgccagc tctgccttcc tcaaaccggg tacggcgggg attcactcca cccagggcct    33960
cgacaccctg gtccaggtac gcggcagcac cgcacctggt cgagttggca ccaacccggt    34020
gaccgtgctc cacgaggcgg ttcacgctgc caccgtgggc gtgatgaacg ccgccctgcg    34080
caaccccggt gcgatgagtc cgaaggtggc tcaggccatg cagaccctgg agaatgtccg    34140
gggtaacgtg ctcaacgccc tgaagcagga ccgcgccgcc ggtcggcaac tgtccgagtt    34200
cgaagagaca ctgctggccg gtaactccaa caccctggcc aacgtcaagg aactggtagc    34260
ctggggcctg acggataccc gcttccagcg gaccctgaat cgcctccgct acagcgacgg    34320
cgggccgggc ctgtggtccc gcttcgtgga gggcatccgc accctgctgg gtctgcggtc    34380
cgatgctgac acggccctga gccgcgtcct ggccgcctct gagacgatta tggaggccat    34440
gcccggttac actaaggcac aggccaagtg ggccaacaag ggcgctccgg taaccgagga    34500
ggccagcctg gagaccatcg tccggtccac cagggagcgc gcccgcgagg gtgccggctt    34560
cgtgaacagg ttcttcagcg aggcagacct cctggcacag cccggagagg gcgcacggcg    34620
actcctgagc cgtcttattg acgacccggt acgtcgggat gggttcagca cgaacgacaa    34680
cgcagcgagc tatctccgcc gctatcggaa cgagttcgag ggctacgtga agtcctacga    34740
cgagatgatg gccaaggcaa tggctgagca gggtgtgggc ctgacggcac gtgcgctgaa    34800
ctcccgccgc gccatggcag tccgggacca gctcaacgag caggtcaccc gcgagctgct    34860
gcgccgggac cgggagtgga ccgcctacgg cagcgtccgc gtggacccta acctacctcc    34920
gaccatcaag gccctggccg accgctcaga cgagattcat ggtctgatgg ccagcgtgc    34980
cagggaagct ggggtgcgcg ggttcgagaa cttcgcaccg cgaccgggat acttccaccg    35040
ctcgtggaac tggtcgaaga tggcgcagat ggacgaggcc gcccctggcc tggcccgccg    35100
```

FIG. 18T sequence.txt

| | | | | | |
|---|---|---|---|---|---|
| tgccatcagt | gaggccgtgt | tccgtggcat | ccctgggctg | gagcgcgccg | acgccgatac | 35160 |
| catcgcacag | gccattgtgc | agcgggcgcg | ggatcgggcc | accggaatcc | gctccgagtt | 35220 |
| catgggcgcg | atgggcgtgg | cggacacggc | attcatccgg | caggcgctgg | aggaggccaa | 35280 |
| cgtgtcccag | gccaagttcg | acagcatcat | ggccaagatc | gagcagaagc | agtccgacca | 35340 |
| gggcaccgtc | aagtacggca | agggccggct | gtcgctggac | atgaccgccg | agatcaacca | 35400 |
| caacggcacc | gtgtatcgtg | tgcaagacct | gatcgaccgg | gacctcgacc | ggctgatgga | 35460 |
| gaactacgcc | ggcagtatgt | cgggccgctc | agcattggcc | cgcgcaggca | tgccggggga | 35520 |
| ctcggagatc | gaagccttca | tccgggagta | ccagcgagag | gcagcccacc | tgggcaccga | 35580 |
| taaggtgcag | gagctgacgg | ggcaactgcg | gggagtcttc | ggggacttca | ccggcaacgt | 35640 |
| gccgagggag | catcagctcg | gcccggttgc | tcagcgggcc | agcggcctaa | ccagcgccac | 35700 |
| catgctggga | ttctccggcg | tgtaccagct | cgccgaactg | gccacgatgg | cgcaccgtca | 35760 |
| aggcgtcttc | aacgtcatga | aggccatgct | gaactcccgc | ctgggagact | tcgtgggcgc | 35820 |
| catgcgtcgc | gacccggacc | tcgctgacga | gatgcagacc | gtcctcggcc | tgaacctcgc | 35880 |
| caacgatatc | cggatgaagc | cctggaagcg | gcagttcgac | accttcctgg | tcagccaaga | 35940 |
| caccttcatg | gatcgcttcc | tccacgcagg | taagcaggct | gtcccagtgc | tcaacggcat | 36000 |
| gaagttcatc | cacaactggc | aatcccgtat | gaacgccaac | ctcaccttga | acaaggtggc | 36060 |
| gcggcggcg | caggggggatg | aagcagccct | tcgcgtgctc | cagcagtacg | ggaaggacgt | 36120 |
| ggactggacg | ccagtcctgg | cgcgggttcg | cggttatgtc | acatacagag | gaaggaacgc | 36180 |
| ccgatccatg | aattggggcg | cctggagcca | agcagacgtg | aacactgtca | tgaacaccgc | 36240 |
| actgcggatc | atggacgact | cactcctgta | cggtagggtc | ggtcagaact | cgggcttcgc | 36300 |
| tcggtctccg | gtcggtcaaa | tcctgggcca | gttccgcagc | tttgtggcct | tcgcacacaa | 36360 |
| caagctcctc | cggggaacct | atgagaactc | cggcgtgctt | ggcgtggcct | cgctcctcgc | 36420 |
| attccagtat | ccgctcaccg | cgctgatgat | gggtgccaag | gcagcgatca | acggcaagtt | 36480 |
| cgacacctct | gatgaaggca | tccgcaagat | ggccatcgac | ggcatcggtt | acactgccgg | 36540 |
| cctcggcttc | accgccgaca | tgtgggggtgt | gatcaccggg | cactcccgga | tgtccgcacc | 36600 |
| ggtctttggc | ctggcggagc | actccaacga | ggtgttccgc | ggcgtcaagg | acctagtaac | 36660 |
| cggcgacgac | cccgcagccg | ccaccggcga | tatcgtcaac | ggcgccgcag | gggcactgcc | 36720 |
| tttcgtcaac | gtattcccgg | cgaccaagtt | gctgctggaa | tccatcaaag | gggaataacg | 36780 |
| tggctcggtt | caagaatccc | gagaccatcc | acgtcgcaga | tggggtcgag | gctgtcttca | 36840 |
| gtctcgactt | cccgttcctg | cggcgtgagg | acgtattcgt | ccaggtcgat | aagatactcg | 36900 |
| tcaccgacta | tacgtgggta | gacgacacca | acattcaatt | ggccgtggtg | ccgaagaagg | 36960 |

FIG. 18U sequence.txt

```
atcaagaggt ccgcatcttc cgcgacacac ccgcccaggt cccggacact cagttcagcc    37020
agggcatccc gttcctgcct cgatacatcg acgcgaacaa caagcagctc ctgtacgctg    37080
tgcaggaagg catcaacacc gcgaacctcg ctctcgacgg cgtactcgac gcgatccgca    37140
tcgccgagga agctcgtcgc ctggcacagg aagcactcga cgccgccaat gaggcgctgc    37200
gccgtgccct aggcttcgcc gagattcgca ccgtgaccga ggactcggac atcgatccga    37260
gctggcgtgg ttactggaac cgctgcatca cctccgagca gtccctgact ctgaccatgc    37320
agatggagga cccggacgag ccttggatcg agttcagcga ggtccacttc gaacaggcgg    37380
gcattcgcga cctcaacatc gtggccggcc ctggcgtgac catcaaccgc ttgcagaaca    37440
ccaccatgca gctctatggc gagaacggtg tgtgtaccct gaagcgcctc ggccctaacc    37500
actggatcat cttcggggcg atggaggacg actaatgcgt ggcattatcg caggtgtggt    37560
ggcgtcgcag attcgccggc ccaagccggt gctgaccacc atcacctacc cgcagtcttc    37620
ctcggatcgt ggggtatga cgtttcatgc catcgccggg atcatccaag ataccgtgaa    37680
gttcgcggat agtaaggacc tgggtagtta tgagatgctt gtgcgggacg ctaccctgaa    37740
gagcatggtc attacactca ctgaggttaa ggacagtagc gtctggagta tgggtgtgct    37800
gagtgcggca atcaaatccg tagttcagtt cttgacacca gtcgaggaga aatcctcgtt    37860
ggatatgagc atcatccacg gcgagcacaa gcaatcggtc attccatact cccgctgggc    37920
tgaggctggg tccctgtcca tgggtatcac agagggtaaa gtttatgtac catagcagca    37980
ccattcgagg tgagttcgat ctggagattg tacgtcctga cggtacagtc cgccagcacc    38040
tgcacttcaa gaacctgatc accgacttgg cccttgaggc catgagttcc aagggcgtcc    38100
cgagtggcgg ctggacgaac atgttcgccg gcactggcaa ccgtaccccg gtccccgctg    38160
acgtgtccct cgtggcgcct gtggctaatg ccagtgcctc gctgaactac ggcaaccgcg    38220
cagtgtggga ttccaccact ggcgagaaag tgcatactgg cacggggacc ttccgcgcag    38280
gttccttcca aggccagtcc ctggccgagg taggaatcgg tcgggtagtc tctgagctgt    38340
actcccgatc cctgatcaag gacgccaacg gcgatcctac cacgatcacg gtgctggtgg    38400
atgaggaact gcgtgtgacc tacactctgc ggattgctcc gccggcgtcc agtgaagtca    38460
agatcacgat gaagggtatc gagtacaccc tgagcatgcg ggaccgccgt accttccggg    38520
acttatcgcc cgagcctgcg gctgagtttg gcactcgcgg cagtctgtcg tggagcgcta    38580
tcagtgcgcc ggacagtaac ggccagacca agaccgccaa cttgagcggc gacgccggga    38640
ccgggattat ccaggttcct gcacagtctg cacagatcat gcgtatccag cccgccgatg    38700
ccaactggac ggaaggtatt cagtacctcc gctgggagac tccggcagga cgtgagctgg    38760
agatcaagct ggacccgcct ctggtcaaga acagcttgga gcgcgtggac atcaccgtaa    38820
cccacatctt caatcgggta tgattcagtt caagttcggt gactaccgga cccgtgtgcc    38880
```

FIG. 18V sequence.txt

| | | | | | |
|---|---|---|---|---|---:|
| cttccagggt | gcgcgggacc | ggcgggatat | caacgaccgc | agcgactacg | tggacggtgg | 38940 |
| cgtcgccatc | caagacccta | gtcaaggtct | gttgtatcag | gagtggcacg | ccgagctact | 39000 |
| cgaagacggc | atctacctga | cacctgagaa | agagcgagtg | actacccgca | tcggaccagg | 39060 |
| tatcaatgaa | ggcgtggcta | gtatggcggt | cacgttcgac | cagaacatga | actatgtcct | 39120 |
| ggtgtatacc | aagcaaggcg | aaggcttcat | cgacttcttc | gattccgcta | ccgaagagcg | 39180 |
| caatgtgatg | aaccttgggc | cggtggacta | tatcaagaca | gacctagacg | atcggcggcc | 39240 |
| agagggcagc | gcctgggcgc | aggttctggt | ctgctacaca | cggcagggaa | acttctacgt | 39300 |
| ccgagccagc | tcaactcgct | ttactgaaga | ggagcttatc | gtcggtacgg | gcaaagtgac | 39360 |
| ccggcctatc | gtcaaatgcg | gaatggcagc | gaactggaga | ttccaggtcc | tgttccgagg | 39420 |
| gagaatgtaa | tgagcaagaa | gcagaccgcg | agtgctgagc | ggctgggcct | gctacatgag | 39480 |
| ctggtctgca | ccgccatcga | gcgtaacttc | aagtggtaca | tggacaacga | catcccgatc | 39540 |
| cccgcatcgg | atatcgctgc | cgccaccaag | ttcctcaagg | acaacgagat | cacctgcgat | 39600 |
| ccgtccgaca | ccatcaacat | cgaccgcctc | cgcgaggaga | tgcggcaggc | gcaggcggag | 39660 |
| aatcgccgta | tcgcgctgga | gggcttcatc | gccggtgaga | cggacgatga | gatggaacgc | 39720 |
| ctgtacaccc | actaaggagg | cagcatgacg | ccgcaagaac | gattccagat | agcccacgag | 39780 |
| gtgcgggaca | tgtacccgcg | cttccgggac | ttctgcctgg | acgccatgct | gttcctcggc | 39840 |
| ttcaagatga | cgtggatgca | gctcgacatc | gccgacttca | tgcaggactc | gcccaacaag | 39900 |
| gcgatggtcg | ctgcacagcg | cggcgaagct | aagtccacca | tcgcctgtat | ctatgtggtg | 39960 |
| tggtgcataa | cgcagaaccc | ggctaccgc | gccatgctgg | tatccggttc | cggtgacaag | 40020 |
| gccgaggaga | acggccagtt | gatcacgaag | ctgatcatgc | attgggacct | gctggcgtac | 40080 |
| ctgcgccccg | aggcccgcat | gggtgaccgt | acctcggcca | ccagcttcga | cgtgaactgg | 40140 |
| gcgttgaagg | gtgtcgagaa | atcggcctct | atcaactgca | tcgggatcac | cgctgccctc | 40200 |
| cagggctacc | gggctgacat | cctgatccct | gacgacatcg | agaccacgaa | gaacggcctc | 40260 |
| accgccaccg | agcgggccaa | gctgacgcgg | cagtcgcagg | agttcacctc | tatctgtacc | 40320 |
| cacggtaaga | ttctctacct | gggcacgccg | cagtcccgtg | agtcgatcta | caacggtctg | 40380 |
| ccggcgcggg | gcttcctgat | gcgcatctgg | ccgggccgct | cccgaccct | ggatgagcag | 40440 |
| gaacgctacg | gtgactggct | cgcaccttcc | atcctagcgc | gcattgcccg | cctggaggag | 40500 |
| aaaggccaca | acccgcgtac | tggcaagggc | ctggatggca | ctcgtggctg | ggcggctgat | 40560 |
| ccgcagcgct | acaacgaaga | ggacctgctc | gacaaggagc | ttgaccaagg | ccccgagggc | 40620 |
| ttccagcttc | agtacatgct | ggacaccagc | ctcgccgacg | agcagcgtat | gcagctcaag | 40680 |
| ctgcgcgacc | tgctgttcat | cgacgccacg | catgagagcg | tgccggagca | agtggcctgg | 40740 |

FIG. 18W sequence.txt

```
gctgccgacg agcgcttcaa gctcaagttc gacgcccacc gattcccggt catcaagcct    40800
gagctgtacc tgccggcgct gatggctggc ggctgggcac cactccagca aatgacgatg    40860
ttcgtggacc ctgccggcga cggtggcgac gagctgtcgt atgccgtggg cgggactctt    40920
ggcccgtaca tccacgtcgt gagcatcggc ggctggaagg gtggctttgc tgaggagaac    40980
ctggagaaat gtattgccct agctgcgcgt tatggcgtca aggtgatcta tgtcgagaaa    41040
aacctcggcg ctggtgcagt tggccagctc ttccgcaacc acatgcgatc catcgacccg    41100
gacaccaaca agccccgcta tgaggggatc ggcgtagaag accgccagaa gtccggacag    41160
aaagagcgtc gtatcatcga caccctgcgg cccatcatgc agcggcaccg tctgatcttc    41220
cacgtatcgg cgatggattc cgaccacgtg gcctgccagc agtacccagc ggacaagcgc    41280
aatgagcgct ccgtgttcca ccagattcac aacatcacca ccgaccgagg ctcactgccg    41340
aaggacgacc ggatcgatgc ccttgagggc cttgtccgcg agctagcacc cacgctcgta    41400
aaggacgacg aagccgcaac ccgcgctcgt gaagaggctg ccaagaagga atggctgaac    41460
aacccgatgg gttacactaa gtctgtcctt cggtctctcg gcatgggccg ggagcgtcgc    41520
aagggccgcc caaaaggacg aagactatga tgctcgatac cgccaccgag gcgggcaaag    41580
gcaccctcgc cgtcactggc gtggggatcg ccgtttactc gccctatgag atcgccagcc    41640
tctgtgctgc ggtactcacc gcgctctatg tgggcgccca gctcatcacc ctgctcccga    41700
agatgctcga tagcatcgcg gagcttcgcc ggaggttcaa gaagtgaaca agcccctgcg    41760
cggcgcagcc cttgcggctg ccctcgccgg ccttgtcgcc ctggaaggta gtgagaccac    41820
tgcctaccgg gacatcgccg gcgtgcccac catctgttct ggcaccactg ccggggtcaa    41880
gatgggtgac aaagccacac cggagcagtg ctaccagatg acgctcaagg actaccagcg    41940
cttcgagcgc atcgtcctgg acgccatcaa ggtgccgctg aacgtcaacg agcagaccgc    42000
cctgacgttc ttctgctaca acgtgggtcc agtctgtaca accagcacag cgttcaagcg    42060
cttcaaccaa ggccgcgcca ctgagggctg ccaagccctg gccatgtgga acaaggtcac    42120
gatcaacggc cagaaggtcg tatccaaggg cctcgtgaat cgccgcaacg cggagatcaa    42180
gcaatgcctc gaaccatcgt cgcaatactc gtccttgctg tggtagccct gggagcctca    42240
tacggcttcg tccagagcta ccgggccttg ggtatcgccc aggaggagat caagcggcag    42300
acggcccgtg cggaggccct ggaggtgcgt tatgccacct tgcagcgcca cgtcaaggag    42360
gtcgctgcca ggaccaacac ccagcgccag gaggtggacc gtgccctgga ccagaaccgc    42420
ccgtgggctg accggcctgt tcctgctgct gtcgttgaca gcctgtgcaa ccgccccggc    42480
gcccgctgtg ctgtgcgaac acccactgat tgaccctacc acccaggctg gcctgatccg    42540
cgctgtagcg gcctatcagg acgccctgga cctatgcaac gccttgaatc aaggagactg    42600
acatggcgaa cacccgtgag caataccTcg ctggccgtaa caccggcctg accttctacc    42660
```

FIG. 18X sequence.txt

```
aggtctgcca gcccggcacc gacaaccgca tcgccctgca cgacatggac gaggccgatg    42720
tcaaggccaa ggccaccgcc gtaatcgcag cagccaccgc cctgggcggc gaaggtggcg    42780
ctactccacc ggacccgctc accgcctaca aggtgaagaa cggtgacacc ctgcccgtgg    42840
acggcggtgg ttccgtgaag gtgaccgtag ccaacggtgc tatcaccaag gtcgtgtaca    42900
ccgcaccggc gggctgagct acagcccgtc ccacctgact ccatccctaa cacaaggaac    42960
tgaaccatgg caaccttcgc cgctgcaact cagaaagacc tccgcgcctt cgccggcgct    43020
atcgagaacc tgatccgccc tctggaagaa gcggccttgg gttccggctt caccgaggtg    43080
atcaccatca ccaagggcac cgatggcaac gagactcgca cctccgagcg taaggtacgt    43140
cccgagctgg tcgctaacct cgacgccctg atggccgctg tcgagaccgc caaagccgcc    43200
gtctacaagt aaggggacac catgagcaaa gccaaactac gagtcatcgc cgacaccccg    43260
gagctggagt cagtgctaaa agcattgctg accgccacct acgctatcga gga           43313
```

FIG. 19A sequence.txt

<210> 560
<211> 137360
<212> DNA
<213> Unknown

<220>
<223> Description of Unknown: Bacteriophage F44/10

<400> 560

| | | | | | |
|---|---|---|---|---|---:|
| aatttcatta | gaaaagaatt | tttttctttt | tctatagtat | ctttcttgtt | atcgtattct | 60 |
| gaatacatca | taaattctat | aaatatacta | tttctgtcag | atgaaaacat | atctatagaa | 120 |
| aacggacaat | caaaacttat | gtcatcttta | ttaatactaa | aacattcagt | aacatttaag | 180 |
| tcatttattt | catatacctc | aaagtatcca | tcaactctt  | taagttctat | agcactatta | 240 |
| tatctataat | aacgttgttc | ctctattaac | ttatcttttg | ttagataggg | atattcattt | 300 |
| ataaatatag | gattacttgt | tccatagtta | tttttaatat | attcagcatc | ttctaaggaa | 360 |
| tcagtataac | ctaaaacttc | gtaacttgtt | gtatacacag | tatcctcttc | ccacaagtca | 420 |
| tagtccattt | cctctatttc | ttcctctagt | atataaattt | ttttcatata | ttactcccaa | 480 |
| acaccaataa | gatttttaag | tttagctata | acttcttctt | ctgtttgata | agaaaatact | 540 |
| cctgtaatgt | gtccatagtt | acctataatt | tcataatcct | gtgtaccatg | tttgtctact | 600 |
| agatatgagt | tacccataac | atttaaacta | tcctccgagt | aactgaaatt | tatattatag | 660 |
| tctactaaaa | aattaataat | ttttttcatt | tacataacct | ctcctatcgg | atattgtcct | 720 |
| aacattcttg | ttccattttc | gttatagaag | gtatattcta | ctacaataat | attcattata | 780 |
| tcgacatata | tagcttctat | ataaggtgta | atattctctt | cttcttgtat | gtgtttacct | 840 |
| ataatattat | ataataattc | agagtgtatt | cttttatctc | tcattataga | cctccgtaag | 900 |
| aaatgataca | gtcttatctt | ttaaagattt | ttctactagt | tccatagcat | ctttataatg | 960 |
| ttttatatta | gattcattag | acttcagttt | atcttttact | tcttgaatta | gaggttcaac | 1020 |
| tttagtaact | aaatctttt  | tatttctat  | actcacattg | cttcttttat | tatctaatac | 1080 |
| ttcctttggc | atatacttaa | cttttgcaaa | gtctttatag | ctaacattta | agttatctaa | 1140 |
| atcatctaat | aaatcattat | aatattctaa | atgattatag | aatgtgtaaa | acttaacaag | 1200 |
| gtctttacct | gctagctctt | ctttttttag | tatattattg | atattaccaa | taacagaata | 1260 |
| tgctataggc | ttaaaattag | ccctaacata | agttaaaaat | ataaaatcat | cataaaacaa | 1320 |
| gtctaaaaca | gttttattga | atctagtatt | tttagcttgc | tctaattgag | cacataaatt | 1380 |

FIG. 19B sequence.txt

| | | | | | |
|---|---|---|---|---|---|
| aagaacatta | tcaaacccac | tctttaatac | caaagagata | aatctttcca | ctgcatagta | 1440 |
| cctagatact | tcagtatgtt | tgcttgcttt | ttcactattt | ctaaaaatag | tatctgataa | 1500 |
| aggttgaact | actaaactca | tataatcttt | atctgaatat | tcatccgatg | ttccttgata | 1560 |
| agtacttcca | aattctattg | tagataataa | aaaactttt | tctaaattca | ttataacatc | 1620 |
| ctcctttac | ttgttattat | aatactaaca | catatgttta | ttaatgtcaa | acattaaata | 1680 |
| tcttctgttg | tgtcaacttc | atcttgtata | tacttaaagt | attcataaat | tttaaatagt | 1740 |
| ataactccta | gtgttattaa | tcctaaaata | tatttcataa | caatcctcct | taaaagtatt | 1800 |
| tatccttccc | atcctgataa | agcatccata | gccatatcat | actcttcttc | attttagtt | 1860 |
| cttataattt | tctctatttc | ttttttgct | tgtttagagt | tcataaaatc | aatatctact | 1920 |
| gtatctaaat | ttgtataatc | aatattttct | ctaataaagt | tcttttgact | tggtgttata | 1980 |
| gaattaactc | gtacgttttc | gtgatttaaa | aattgataga | agtccatact | attccacttc | 2040 |
| ttttaaacag | tctgccatat | cttttaaagt | attaagtaca | tatttcaaat | ctctataata | 2100 |
| actatcagaa | aaactaataa | cagcatatgg | tgtcatatca | ctatagtgtg | cacaatcaaa | 2160 |
| acctaatacc | ctatagtcac | cctcatgttc | atcgtatgtt | atacctccat | gggaacaatc | 2220 |
| ttctatacta | ttaaactgtt | ctttggttat | attcgtaggc | acattaatat | aaccatttag | 2280 |
| atgtcctgaa | tgagggtgac | gtttaacagt | taggtttatt | cccttataat | ctatatttaa | 2340 |
| agttaagtcc | tctcctaata | tattatcctc | tttatctata | atttccataa | tatgttctgg | 2400 |
| agcttttcca | aacatcataa | ttcctccctt | ttctttatac | tcttactata | cactactttt | 2460 |
| tctattttgt | caacaaaaaa | aggctactaa | ttaaagtagc | ctaagaatta | attatttagc | 2520 |
| attatatttc | cattgccaat | aaccattttt | ctgtgagaac | tcaaagtgaa | aaccgtcata | 2580 |
| gtcaaattca | atattatagt | ctccatcttg | aagtggtttt | gaatttagta | caggactatt | 2640 |
| actctttgcc | aattctgcta | gaaactcatg | atttactttt | tccataggg | ttattcctcc | 2700 |
| taattattct | tacagtacta | atatatcaca | ggtcttttc | taggtcgttt | ttaaatttct | 2760 |
| cctcataaga | actagcataa | gttacttcat | aacctattac | cttagtataa | tctatgcaaa | 2820 |
| gtaatttata | attggactt | attttaatat | cctctgattg | ttctatttta | ttgataactt | 2880 |
| catttagctc | attcgaagag | taatgtttat | tatcaacttt | tattgttttt | ccttgggtat | 2940 |
| agatatcaat | ttcttgtatc | atcatttcat | cctttgatt | attcattatt | tgattataag | 3000 |
| tctctaaatc | atcaatgtta | tctgtatctg | aaccttttac | taaccattct | cctctcttct | 3060 |
| taaggaggtc | atcaaatttc | tcatgttctt | taattatctt | ctctacttca | ctcggtatta | 3120 |
| gaacagctct | agcgtaattt | atatgccaca | tagacatatt | atcaataaga | taattaacca | 3180 |
| ttcttataag | ttccttctca | tttgccatat | accaacctcc | ttatatctaa | tactaatata | 3240 |

FIG. 19C

```
                                    sequence.txt
agagaaaagc agacttatta aaagtctgct tctgtaccta attctaatct tttattttc     3300
atatgaggaa tcatttttct atctcctgtt aatagagata attctctagc tttttcttta    3360
gataatgtta atagtccatt ataattatct actttcttat tatattccat aattaagcgc    3420
tctagctcat atgatatatc ttcgagttct cctgatttaa ctccaagtaa ctttctatac    3480
atatcataat cttcagaaag actttctact ttatttttag atacagaatc ataaactgct    3540
tgtaaattac cttcttcaat aagtttaaag ttatgttcac ctatgattaa ttcctcctca    3600
gaagaatcaa gcgttactaa tccgcttgta ttacctgtaa agtcaccttt ataatctaca    3660
acaataccatt cagttacttt gtcacctaat tcaatagtcc catcttcatt ttctttaaat   3720
ttatgagcat catatacttc tactttgtca cctaatctca aatcttgagt taagttatgt    3780
ttaccaataa ttctatccat tactcaatct ctcctttatt aatagggtct tgtgttaaga    3840
acatttctag attctctttt gtaataggta accaaaaata tttactttcc ggaattgtaa    3900
ttgtatagaa atcctcatct ttgttaactt taatattaac atctgtaaac tcatcctgca    3960
ttaaccaatg agttacagtt aagttatatg aaccatcact aacatacctt aaatcaatat    4020
catgtctaaa agccaaatct tctaaatgtt ctaataaatc gttcttttca ttatgttttt    4080
cttcttctgt attattttta attgggttaa ttaactctgt gcaaacaata tcgtacaatt    4140
caccatctgt aacctcatag ttcttttcaa ttaatacatc ttgtatttta ttgattgagt    4200
ttgtaactac tttcccatat tcttcttctg taaacttaca tttatctaaa tcaacatctg    4260
taattaattc tgcaatccat ttatttaaaa ttgatactgc cattgttcta gaaataatac    4320
tgtcgtatac catatttatt taatctcctt atttaggtga atgtggtctt ctaatgaaaa    4380
atcaaaaggc gctacaccat ttcttttatt atttgtttct ttttaagta taacataagt      4440
tagtgaaaaa gtcaagatag ttactacaac cattgataaa aatttaatca ggttttcat      4500
aattactcta actccttaag tttattttt actttctctt tatcgtactt ataatcttta     4560
ctagagtttt catttttttc tttctcttct tcattaagtt ctctatactg agcctcttct     4620
acctcttgtt ctttattatc attaccttct tctgcttttt gaatttctac attttacta     4680
ctaccaccat ttaccttttt tctaaaaaga aaccaaagta ttaataaaat gatgagtaaa     4740
ataataatgc ttaatacaac agcccaaata ttattaacca ttacaaccta cctccgaata    4800
gttttttac ggctcttaag ttttcagatg aatcattatt tatatcaata cctatgctag      4860
aatcaaaaat tacagcatta tcaagtatat gctctgtcaa tttattaccg taactacttt    4920
tacttaccac actaccataa ccatgattag ttaggtcaac catatcaggt tcaacttcta    4980
gtactctaaa agatattcta cgtaagaatg aaggatttac caagtaaaag gaagatttaa    5040
aaacatttaa tctttgataa gaatgtttta tattaacaac aaaccctgtt aacttatttt    5100
catattctga atttgataac ttacctaggt aaaggtttat actatatcct tttgtttcta    5160
```

FIG. 19D sequence.txt

```
atgtttgaat agcacttaac attatagccc ctctataagc aaggttttca gggtcttcca    5220
tccaactaat actagaatta taaaatacat caataacttt cttctctgct ttaactcttt    5280
gctgagacat catagaatta ggtaacccct ttatagcatt aggtacgtga ggttgatacc    5340
cttccggagc tacgacaggt tttctttta ctgacttatc cattctaaat aatgcatctg    5400
tcatttttt aagtttaact accatatcat atgattctct atcacccta accattaagt    5460
tataggcttc ttgaaaacta tgagttcctg taaaatcata gctacctgta tctgatgaat    5520
tttctctacc tgaaactcta ttcttttta aagcagaaaa gaaatcaggt agaccatcat    5580
atttaattac atttaattct gagttatcta ttaatcgtct acccattgat tttcctccta    5640
ttctaatcct aacttatcca taattgtatc aaagtccatt gaatcttttg atgtactatt    5700
agatttctta ggttcctgtt taggttcttg ttgcatacct aaaagctttc ttgttgcttc    5760
tgtatatctg ttaccttcag gtaaagagct aataaattga ttaatctcat ctttcggtac    5820
agatttaaag ataatacttt ctacaacaaa ctcatcttcc attactccat ctaatttact    5880
accattaata attgcacgca tgagaatac ataaggtaat ccttttcat cattctcatg    5940
tcttaattgt tgtacaaagt ttactaagtc ttcattgctt gatagttgat gttccacctt    6000
agtatcatag tcaaattcaa cttgagcaaa gcggtctaat gtagctccat ctaattgttg    6060
tctacctaca taaatatggt ctgctcctgt tcccatagta ttacctgctg acacaactct    6120
gaaatcttca tgagctgtta cacgtccaat agggaagtca aagtatttat ttgcaatagc    6180
tgaattaaga attaatagta cttcaggaat agatgcatcc atttcatcta agaagaataa    6240
cccacctttt gtaaatgctt tatagaattg agtttcatga aacttaccat ttgcatcaat    6300
aaatcctgtt aatttaaatt cttgagtaat tgcattacta aaatagaaat ctaaatctag    6360
ggcttctgct acttgttcca atacatggtt cttacctgaa cctgctccgc cttttaaaaa    6420
tactggaata ttttggttaa ctaactttag tatatcttga tatctgtaat ggaagattcc    6480
tgagatatct ttaattgttt ttccttcttg ttgtaattca attttaactg gtaaattact    6540
aagttgttct tctacatact cttcaatttg ttttttaaca tcagtaataa taatttctct    6600
actctcagtt cctgctttct caacaattgc atctacaatt gcttgttcat acggattaga    6660
gtttttctct cctagttttt ttgctaaatc tgctgttgtt tccatttgtt gctctaccaa    6720
tctctctaat cttccaatag tatcttgctt tgccatattt atcattctcc tttgatttgt    6780
tatacattta ttatattaca agtatttgaa tttgtcaaca actttctaaa acttttttag    6840
ttgctaataa aaaaatacct tacacctata acttaacata gggtaaggta attgtcaaca    6900
cttttgttaa aaatacatta atttaaaaaa atcatcaata tctttagttc catgtgtatc    6960
catatcatac ataaacatac aattatatgt atgactattc attatttcta acatgttatg    7020
```

FIG. 19E

```
                              sequence.txt
catagaagtt gcattattga attcctctaa atcaatagtt accgtaagtt cttgaccttc      7080
ataaagtatg tttgctatat aatatttcct aacaccttcc attgttccat gggaagtttc      7140
attatgatta agtacttcta cacctagtga aggtaaatat tctgaaaagt aatatttaca      7200
gaaatatata aaattgtctg ttcttttaga cacgagtact atctccgtac tttatatttc      7260
tttctaatcg tacataatat gttttaattt tttgtacttc tttatctact gcatcctttc      7320
ttcctaacct tgtagtatat tttacaatat taaatatcat agaatcaaca aagccatcat      7380
aagaaaaatg ttcttctaga aaagaaataa catccttact acctttataa tgttcaggta      7440
aatgtgcatc tacttgtata ttataataat cttctaaaag acctatactc tcaccaagac      7500
tagataaagc gtaacctaaa tcatttgaat cattagacca ttctttagat actgatagtg      7560
catcttctat aattgttact tttaatttat ctaaataatc ttctacttga gcttgtgttt      7620
tcataaattc ttttgcgttc atgtaatacc ctcctaaatt atataaaaaa aacaccctgc      7680
ttggatacaa gcaaggtgaa aaaggaaaga tattatggaa gtgtactatc taagtacacc      7740
tcataatata acagttttcc ttgctagtta ttacttattt tttaaggtct tcttctttga      7800
caaacactcc gttaataagc ttacctttcc tttcttttat ctcatcataa gccatatcaa      7860
tacactcttc aatatctata tctaactgta aacatagtac tgttaatact acaaaaatat      7920
ccccaacact atctcttgtt acatggtcat tacttttagc aatacctgaa gctaattctc      7980
ctgcttcttc taataatttt aacatttgac cctcgggttt acctgtttgt aagtttctat      8040
cttttgccca ttgtttaata agttctactt tttccattat tctatatctc ctttaatttc      8100
tgtatctttg ataattaggt tatcagagtc acttgttaca tttaagttat cttcaactaa      8160
ttcatgtaga ttattagtaa tatcttcttc atacctataa cctacacgaa cataagcttt      8220
aactctgata tctatattaa cataatcttc ttggaatttt tccatttcta acttcctttta     8280
ttatatcata ttattatact attgtcaatt aatctgagta gtttccttta gcaagttgat      8340
acttttgtg taattcttca tataattctc tcataccttc gtagtttctc atatcatctt       8400
ccaagaaact aagataatct aataatactt ttacatcctc aggttctaaa gttataactg      8460
gttttaccat taggcaacct ccttaaattc ttctttattt attttcttaa tatcttttc      8520
taatgcttct tttaattcat taggtaattt ataggcatca attgattgtt gttgacctaa      8580
tacatatcca ttatctgtga tacgtatttc cactgtaaac catgaattat ctaaatcttc      8640
ttctaatctt gctaataata ttaaacaact atttttaaa attctattag catacccgcc       8700
aacacaatga gataacattt taccttcatc tttaagttta cttacagtat ctgcaggaag      8760
gaatttact tttctaccat ctttttaattt ataagttta tcaattattt tttctaattt       8820
attatcatat ttagctttaa gttccgcatc atctaattgt tgttgtatag attgtttctc      8880
atctgtaact atatcatgtt ctagttttaa tgagaatggt gttaggttaa cactttctaa      8940
```

FIG. 19F sequence.txt

```
tgttctataa ccttctctta ttaatattga taaatcatgt aagtaatcta agtaatagtt      9000
atctagtgca tatcctgtta tacgttgtct gtcttgagca tctacatcta aatagtgagt      9060
catcttttg  tagttagcaa aagatataga taatatttca tttacaatag gttttacttt      9120
taaagcattt gtaacatctc ttgaatctct aaccattaaa aaggtatcgt caaataattg      9180
gtgtaaatta acttcattgt gtaaatgatt atagttctta tagagagtat tagcaaatct      9240
taagtaatta ccttgctcaa atttatttaa agttagtagc tttttataag tctgttttgt      9300
aagattgaag gcttcatgaa ctttccattt agggttttta ggtatatgga atagtaatgc      9360
atttctttca aataatccaa attcttctaa gttatttatt ttatcaatat ttttaacaat      9420
atctgttaaa gttattaagt aattagaagt tgaattttct cctataaaaa tcctatactt      9480
atccctctca taatttatat gaccataaac atctatatta tcaggacacc aactagaaaa      9540
atcaaaatta tgatgctcta atgtttgttc tattatcttt attataattc ctctatttaa      9600
gttaggttgt gaatagtttt ttaaaataac atttaataaa acagataatg tcaattcatt      9660
tttgtattca cttttactaa tatcatcttt ataggtttt  aaagctattt ctttattaac      9720
aagactatct gttaagaaaa ccttgactgc tcctgtctta acgtcaaatg aactttatt      9780
ttctaaaacc catttgttac ccatattatg cttatccctg atatgtctaa ctttaagacc      9840
aaaagatgaa ttattctcag tacttgggtg catgtaccaa acacgactat acaatgaatc      9900
tgacatttcc ttataatact cactagaacc ttttctata  tcttcattca taacaataat      9960
agatgaattt ataagaacat atttaccttg gtctagtaca tccatgatat cattatttaa     10020
actatctact gcttccttat actcatctaa ttgtctagct tcatatcccc ataaacggtt     10080
ttcattttct aattctttaa ttttttcttc aacatacct  ttagattgta tttgttttct     10140
acgtctacta ccatataaag gaaaatcttt tctttctcct ctatcagctt caatatactc     10200
tttgtaattt cttcctttat tattaccaat cacaccttca actaatttt  caactgtttc     10260
atagggtca  ccttcaaagt ttgttacttc tttattacca catagggcta aaaataaatg     10320
tatttctgta gctgtatcaa aactaaatat attatgaata tctctaaata attctttaga     10380
acctaagtta attatattat ttttcttttt cttaagaaat acatcttctt ctcctatata     10440
gatacatcct ttattaacct taggtaaatt aataatttct tgttctgtta atccttttg      10500
tttataagtt attgccattt aaaatcactc cttatttgtt atgtactaat cataccatag     10560
taaataatat ttgtcaacaa aaaagaaga  acttttaaa  gttcttctaa atgagtttcg     10620
tatataactt tttgaattt  atttaatggt tctaaatcta aattcctaat aagtttttca     10680
tactttcttg aatttttaaa attgatagta tttggcatag caagagcttc atcaacatct     10740
ttagtatagc ttacaacatc tgaatagata tctacttctt ttacatatag accttgagtt     10800
```

FIG. 19G

```
                                     sequence.txt
aaactcctaa atactacctc attatgtgct ataatttctt ctttcttttc tatgctcatt    10860
tataaacctc ctggtctact ctacacaaac aagtacgtat tctaaattag ttaaagaaac    10920
tgatttaata ttgtttaatt cttgtaattt cttaatttcc acatcatagt tcttacttat    10980
agtccataat gtctctcctg ctcttacttt gtgataatat ttatttccct ctttgataag    11040
gtcattcaat attacctacc tccttgagta ataattagct tgtagataac atataagtat    11100
aagaacaaag tttacaaatt cagtagctat aatatgaaca taggtatgtg ttaaaaccat    11160
acttacaatt aatgaagcta atcctaatcc aataataaga aatagaaatc tatttgttcc    11220
ttctgcactt ttagttttat aaaaggttgt tatctgagtt acatacgcaa ggataatagt    11280
aatagttgct acagtttgtg ttaaggctgt aaagtcactt aataaaaata gtaacagtga    11340
gaacacaata ataaaaggta tagagaaata gtcctttttt ctatatgaag ctactaataa    11400
gcaaacaata cctagagtta aattaagacc aactgatact acttgaaaca tcgtagcatc    11460
agttagaagt aaattgtaaa aactaatacc tactgtagct acaattaaat accaaaaata    11520
actactaaca cctttaacac tatctgactt aactagggct attaaacctg gtatataacc    11580
tactgtaact aatatagcat ataatatact taagtaatgt gataaattat ccatcttgtt    11640
cccctaattt ctctaatcta ttagtaactt cttcccatga aataaatcct tctccgtttg    11700
ttaattctaa aaccatacca tacacaaatt ggtttgtact aaattcagct ctgtcagggt    11760
cattgtatgg tttaccatga ccctgtctaa tatcagagca gtagattaat acgggttttt    11820
ttaaaatata ttcctgctct ccaatttgtc cttgtaaaat atcatatgtt tctgatagtt    11880
catctatctc attgaactta aataactcag actgttcttt taattgtttt attgtttctt    11940
gtgcttgatg tttcatacct aataaaatac ctagttctgc aattgttcct aatccttcat    12000
taagaacatc aaatacaaaa atatctgatt cttgcatagc cttaaagtca ttagttaaaa    12060
tacgttctgc tagcttagtt tgttctgcat tagctttatc atttattgac ttatctttgt    12120
gagggctata cggagttact cctacaatgc catctacttc tttatgttgt ttatctctgt    12180
aatctaccat agcttcattt aggatatgtc cacccatata aattactttg tctttaattt    12240
tattaaccat ctatagtatc tccttttcct tctaaaattt ctcttaaaat atgtggcatt    12300
tttttcttaa tttgtttatc tactattttc agtatatttt ctttttcttc ttccataata    12360
tcatcaacaa agttttgacc tacttgtttc ataattagac cgaagttttc taattctaaa    12420
tcatcttcag ataatctatc ttcttctata gccctaaaaa tcatttttc cattcttgct     12480
cttgtaatgg cataatctgc cactgactcg ttcttttta cttctgtttt catttttga      12540
cgactaaatt ctttaaactc attagatact aatttaaagt agtcatcata ttctgattta    12600
ccatctaagt atttaattac tataccttca cccttatcag gtttaactgt catgtcagat    12660
tttcctacta attcttgaat ttcttcaggt tttaaatcat ttaagtagtg agatggttta    12720
```

FIG. 19H sequence.txt

```
gctactagca aagtttaac  tgttttaac  cctaaatgat gtgcaattac attcatgtct     12780
tctattgata aataaacttc attttcttta tcataaacat caaatacata aaaattgttg     12840
taaaattctt ctttgtactg aatcttatgt ttgactaacc attcaccaaa aataatgtat     12900
ttttctaagg ctgatacgta cgtatttctt acatttatat tttcatgtac ccaatcataa     12960
aaaccattta aagtttcatt ctcatttaat tttttctac  gtgaaaaaca tactaattca     13020
ccatttttcta ctgtgaagct tgcattactt ccatctaatt tttcttgtac aactagacct    13080
ctttctttaa atttatctag tacaatacct ttattttta  ctttagtata cgatttcatt     13140
aattatcctc ctttgaatta tgtactatag aaaacaaaat aagacttaca ctagctaaaa     13200
atgctaatac tactaaacca ggtaaattaa gaactgttga taagaataat gatattgcac     13260
ttataacata aactagaccg cttagaaata aagttaataa tacaattgtt ataagtttca     13320
ccaaccaatt attattaata aataccttag ctaaataatt cataaaaaaa tcctccttag     13380
ttattataga ataactatac cataactaag gggatttgtc aacatattat tttaccattt     13440
aaaattgtct gcatattgtg caagcttaga gcggaaatta actgtaaaat tatgaaatac     13500
tgctccttca taattttaa  agtattccat ataatctcca aaacctgatt tactttcgtt     13560
ctttaaatct atttgtttaa aattaccttc tactattaca gtagaatttt ttgtatgaac     13620
ccttgtaaga acttttttaa gttcactgcg tttaaagttc tgtgcttcat ttataattat     13680
agtagcatct cttagatttc cacctcttag gaataaatgg gatatttgag atacccaaca    13740
atctcctagt ttatcttctt taacattatc ttccatcatt aacatttcag ttatttgttg     13800
ttcaggattc atattaagtt caataagggc atcgtgtaat cccatgaaat aagccatttc     13860
ttttttctgtc tgattacctg gtctgcttcc taaatcttct gatactggtg aaattataaa    13920
tactagcttt ctattttat  taagatagtc tgcgtaagca caggctactg agcacattgt     13980
tttacctgta ccggcttgac tctcattcca aagtatttca acattatcat taaagaaatc     14040
ctcacagaaa tctaactgct cggttgtagc tttttcaagg aattcattaa agattagatg     14100
ttctcccatg ttgtatctta cattaggata atcttttaac ttaaagtcta actcttttag     14160
ttgtattgcc atatttaaa  gttcccctat ctataaatag ttttactctc ttttaatata     14220
gtactaattt ccgatatatt ctcctgttga agagcaataa ttactacatt cacattcagg     14280
gtagttatca caaacatctt catcttctac atcatcataa ccaatatcat aattattata     14340
attaaaatct acaatacaat tttcactatt acctttagat aatcctgtat aaataatatc     14400
atccacagaa tcccaatcgt tatctgccaa gtaatttaca ctatctagta ctgattcatt     14460
atcaggtaaa taaatactac cgtctgaaaa tttaattaaa atatcacctt gaggtaaggt     14520
atcattaatt aaatcaatct ctgtttcttc ttcaatagtg aatacagttc cttctaatct     14580
```

FIG. 19I sequence.txt

| | | | | | | |
|---|---|---|---|---|---|---|
| ttccggtgta | gtatgtgtta | aatgttttac | agtatcccct | gattcttcat | agaatcctac | 14640 |
| tgcattcata | tctttattat | attttgcaat | aaatttacca | ttgtcactta | ccaaatattg | 14700 |
| actagttgca | ttatagtcgt | ttgcgtcatc | tactgtcatg | caagggttat | aatctttaac | 14760 |
| ataataacta | attttcctaa | catctgctgt | ttgtactttc | ttaccttcac | ctttaattac | 14820 |
| tgaattaatt | ttcttcataa | tattttctcc | tttttatata | tcaattgatt | ttttgcaag | 14880 |
| attatcggca | tagtcattcc | atttgtcatt | tgaatggctc | tttacttta | caaagtttat | 14940 |
| atctattact | ttttggtatt | ctcgtatcat | attaatatat | gttttactta | gaatatttct | 15000 |
| tgcagaccaa | gtaccttcat | accaatgtat | taaaccaata | taatctatat | aaactattgc | 15060 |
| ctgattgtat | cctagtttta | tagcctcttc | aataccataa | caacaagcca | atatttcacc | 15120 |
| cgcaacatta | ttatacttta | ttaatcctgg | tttgtcaaca | cttttactaa | tttccgatat | 15180 |
| tatatttcct | tctttactta | ccaagacagc | acctgagcct | actttacctt | tattatatga | 15240 |
| ggagctaccg | tctgtgtata | tatttacact | atcctgcata | cttataatcc | tccataaatt | 15300 |
| gagggaattc | acaatctgaa | tagacttctc | tgcaaaaaga | tactgagata | tagttaaaat | 15360 |
| caaaacattt | gaaacagtgt | tcttgaactt | cttttttatc | tttagcaatc | acattaaatt | 15420 |
| taaaaccatc | agctatgact | gtaaatactc | ctttttttcat | aaaacaaata | cctccactaa | 15480 |
| ttttatttta | aattaataac | taactcaata | aatgatttaa | tagttttatt | tttaccttca | 15540 |
| tcaatatctg | aaaagaaatt | aattaaactg | tcatcctcat | caaataaatc | ttcaacatca | 15600 |
| tcaaatttat | ttaatatgtc | tgtaacactg | taaccctctt | ctgatatata | ctcatgtaag | 15660 |
| tcttctccat | cttctgacag | tgttgcttct | attttaccat | ttttactttc | aattaaatat | 15720 |
| aaagtattta | atactttaac | agaatctaca | actacactgt | agttactaat | agtaggatac | 15780 |
| tctgtataaa | gtatttctat | attagtattc | ataaactat | caattacaga | gttaactgta | 15840 |
| tctcttttta | gctcagatac | attatgtttt | cgtatagtag | ggaattcttc | atcatattct | 15900 |
| actaattctt | ttctatctgt | attcaataac | ttgtctaaag | aagacaacaa | tactattta | 15960 |
| tattggttat | caggaagact | gtctgtaatt | tccattattg | ttaaaaacgt | atcttcacct | 16020 |
| agaactttgt | ttatatcttg | taattcaaat | gaatctacca | tttcaatagt | atcatctata | 16080 |
| tcatctgtag | tcattaaaaa | attaactaaa | ttattattct | ccatcgtctt | cctccaattc | 16140 |
| tttaaataac | tcttttcctg | gagtatttaa | cgctttctct | aaccgcatta | aattagcact | 16200 |
| tcttggtttc | ttttttccat | actcccaata | agatataaga | gagtaatgaa | cacctatctc | 16260 |
| agaagctaga | cttcttaacg | tatgtccttt | ttctactcta | atttttgaa | ggtttagagg | 16320 |
| tttactttcc | ttttttttcat | ccataattat | ttctcctcta | cttttaaaaa | tttaaaatcc | 16380 |
| tcagattctt | ttgcattttt | tagtatatac | tcttgtgatt | tatttcttgc | ctctgcctta | 16440 |
| cttttagcat | ataactctat | atgaaataca | tgaggttttt | ttaaagacgg | tgactcgtat | 16500 |

FIG. 19J sequence.txt

```
ctccaataaa ctttaaaaag tagtgtttct ttttttaaaa cattaattcg aaaccatctt    16560
ttaaatttat tcattcatta tcctcctcta tttatttgtt aaactaatta tagcatagtt    16620
aacttatgaa gtcaactata atatacaaaa aagactaaga aattaatctt agccttaata    16680
tattaataac tattatgtgc gttgtggtat gcaagagctc ctgatgttga accgtaacgg    16740
tcaatcatat attgttttgc acctttagtt tgttctgcta tagaaccacc actccatgat    16800
ttacctaatc cttggaatag tccttgagct cctgatgatg cattaacagc attagggttc    16860
attgtagatt cacgcatagc aatttcaatc attgcctcgt ctccacctgc ttgtctaatc    16920
tgttctgcta cagagcctcc tgtagaacta gttgattgtg taggttgttt agtttccttt    16980
tgaactggtg ctgatgttgt ttgtacttct tttttagtat cttgtttatt ttgagtatca    17040
aattgtgctt gttgttggtc tacttttgt tcaggtgttt gttcttctcc tgctaatcta     17100
gatactgtat tatctacttg agttgagcct gaatggtatt cataaccaaa gttaccatta    17160
taattataga aatgataagt aaattcaccg tcactaaatg agaaatcata attaccttct    17220
tgaattggtt ttgtattgac ttctgctgaa tttgatttag cctgttctgc taacttatta    17280
taatcaattt cgtctgcact agcttcgttt gtagcaatac ctccaaaagt aatagctgta    17340
cctaatgcta atgttgcaaa aattgttttc ttcataaatt taaaactcct taaataattt    17400
tttagaattg tttatttgta aaccgacata agtaatcata acatatatct ttaaataacg    17460
caagtataat atagcactaa ttagtgtaat attattaagg ttttattaca aacattacag    17520
ttatcagata attaaataca aaaaaaagag aggtattaac ctctctaatt tattattttc    17580
ctgttacatc tacaatagtt ccgtctccgc caatttgaat aggttgttta ccatcccatt    17640
tttcaattaa ctgttgacgt aatatcttat cagataagga agattctcta atctcattgg    17700
cttttttatc accattagcc tctacttctt ttttcttagc attttgttca gcaatttgtt    17760
tatcaacttt agtacgttct aattcttggt tagctttaac tcgactgtca attgcttttt    17820
gagtattctt atctgcttta gggctagata atgcaatgtc ctcaattaca aatccttgtt    17880
tttctaagtt gtcattcaag ctatctaaag tatcttttt aatttcccct gttttaactc     17940
caaatgcatc aattacagaa tacttagata ctgcttgacg gacattatct tgtacccgtg    18000
aacgtaaata tccttttct agttcttcga tatctgcact accaaaacga ttaaataaat     18060
ctacagcttt agttgcatct acttataag atacatcaat atccatttgt aaattcttgc     18120
catctgaagt tgctacattt aaatctttat atttatgtgt ttgtgtttta gttgggtatt    18180
tatttacctt atcaaaaggt gctgttaaat gccaacctgg tgatttagta tcttccttaa    18240
caccatttac tgagtataca actccaacat gaccttgtgg aatcttagta atacacatta    18300
ataaaataat aaaccctata attgctaaaa accctaatac tcctgaaata actactgact    18360
```

FIG. 19K

```
                                    sequence.txt
ttctcattac atttctcctt tttctatttc ttttattaag ctatttaaag cttttttcctc   18420
ttggtctatt tcttgtttat cggctctagt tacaattgat tgtctacggt catttaagaa   18480
ttgttttta tactttacat attgttctaa accgtattca tctaatgtac cttgcctaac    18540
taattccctg tattgttttc ttatgttact cttcttctct ttcattgaaa gaaaatcaaa   18600
taaataactt ataccaaaac ctacaaggac tagaaaaaca ataaaaatag caaaatatgt   18660
taaaagtagt gccatgtaat tcctccttta tttgattaca tatataacta tacactatgt   18720
atttaatttt gtcaacactt ttttgcaaaa aaaaatagac ggattttaaa tccgtctaaa   18780
tttatattct atttgaatac tccccaggca acgccaggta tttgattagg tggaacacct   18840
tgacaagttc taacagggca atatactctg ttaccgttgt aagcattata acctatccaa   18900
atatgacctg cttggataca aacttcgtca tatacaattg tagcccctgc cggtaagtta   18960
ccgcctactg gagcatttaa gaatggagaa cctattctgg ttactatagg ttggttacca   19020
ttaacaaatg ttgcgctttc cggtttatac caagttccga actggttctt tttccaagaa   19080
cctgtaactg gtctagttgc cggtgtactt gcactacttg ttttaccatc tttaactaca   19140
gtagagcttg aagttccgtt actcatgtag tttttaattt gtttaatgaa gtaatctttt   19200
aacttattca ttattgcttg tgatggtctt ccttgtgtta ctgggttaaa tcctgtatga   19260
agaaccatcg aacggtgagg gcaggcagtt ggtacaaatt ccatatgcaa tcttacagtt   19320
ttacggttag gagtaagacc ccattctta aatttctctg ctgtaaattg gaatactgct    19380
tgttcatttt taaggaattg agcatcacta gcactcattg attgacagac ttcaatacct   19440
gcaaatctaa agttacctga gtttgctcct gttccatccc ctgtgtgcca agcaatttga   19500
ttcttagcat ctattgcttc ccatacataa ccttcagagc catagtaatg agcaatacca   19560
ttagcatatc tagcataacc tgcattagct aatgaattct cgtattgttg tcctgaagaa   19620
cgacctgcat cgttgtgtat taccattcct tcaggttttt taccacgttt atccattgta   19680
tagttaatgt gattcttaga aacttttagt gttgctttct ttttaggtgc aggtgttta   19740
cttgcgcttt tcttagctgt ttcttttttta acagtagttc ctgcttttac aggtatttca   19800
atgaagtgag ttaatccgta ataattatct cacgttttg taggtttttt attagcataa    19860
ccattccagt tttgctctaa aatagtaaat gtagaagtat tacctccatc atatacaata   19920
cctatgtgac cccactgttc ataactaccg gatgtaaata ccgcaatcca acctttttta   19980
ggtacagtag aaggtttatt ttcatgtatt ttaaatccag taccataact ctgtttaatt   20040
tggtctttag cattacccca agttctaact ttattatctg ttaaccataa aacatagtct   20100
gtaataaggt cttgacattg agcgtgatag tagccatctg cgtcaatggc tcctgcttcc   20160
attacaccaa atgacgggtc ataacttgta gctttttaa ctctgtaagg gctatctact    20220
gttccttttg cataagcgtc taaacgttta tttatttctg cttgagtctt agccattact   20280
```

FIG. 19L sequence.txt

| | | | | | |
|---|---|---|---|---|---|
| taacttcctc | ctctgcaaat | actttaccat | gttcctcggt | atcttcttca | tcttgagaag | 20340 |
| gtgctgaacc | accatcaatt | tcatcttcaa | tagcaggtac | ttcatcacta | tcatctgtgt | 20400 |
| caggttctgc | attgttttcg | tagctgtcta | tctcaaaagt | actagcgtta | tttgcgtttg | 20460 |
| tttgccattg | aacgaactca | ttagggtctt | tactatcacg | aggtttaacg | taatctgttt | 20520 |
| gaacaatatc | actgtctcta | agacctttag | tattattatc | aacaataata | cctaaacctg | 20580 |
| ctaataatgt | tagtatagaa | cctacaatat | ttacaccttg | ctcaatttga | gctgagtagt | 20640 |
| ctaaaccgaa | agcacctgta | atttggttag | caaataatgc | tactgctgat | ataattgcta | 20700 |
| cccaaaatgt | tttgctctta | gttcttgtgc | taaggtttat | tcctccaaca | actttaggtt | 20760 |
| gtttagtttc | attagccatt | aaaaaaccga | cctttctatt | atatttattt | ctaacaataa | 20820 |
| tataacagta | ggtcggtcat | gtttatctat | attaatttaa | cacttactca | ttaatttggt | 20880 |
| ttagtttttt | gataacttca | gacatttgtt | tgttatctaa | atcttctaat | ttagtttccg | 20940 |
| gaagtagctc | taacttatcc | caaacttctt | ctttattaga | tactttatta | ttaataattg | 21000 |
| ccttaccaac | taaactttcc | gtataatata | attgttttgc | tgatgccatt | tgtatctctc | 21060 |
| cttttaaata | tgtaaagtat | atagctagta | tcgtatccta | ggaacaaaca | cttgcgctat | 21120 |
| atactcaatg | aaatcctacc | ctcattcgag | gacacagcaa | accggttcgt | caaccgcaca | 21180 |
| tatgaattct | aagatttcat | ttatgtaaaa | cacaccctct | ttgatttgca | caaagactaa | 21240 |
| gggttttgga | gaccttgta | ctactaatta | tactaagggt | gtttattatg | gtttctattg | 21300 |
| gatttgaacc | aatgacacct | agagcttcaa | tctagtgctc | taccatctga | gctaagaaac | 21360 |
| cttaaaacga | cccatacgag | actcgaactc | gtactctctg | ccgtgacagg | gcagtgtgtt | 21420 |
| aaccagttac | accaatgagc | caaaattata | atgctatacc | ctaaccttac | cttaatgtat | 21480 |
| agcaggtttt | ctcttaggct | cgaagcaacg | attattacca | ctcataacaa | ctatatatta | 21540 |
| agtgaaagga | ggtgaaatga | acaaaacgtg | gtaattggta | cctaagaagg | taatatgtat | 21600 |
| aatctacaag | gagtaagtta | ttggttcata | aaggagtgtg | aacaataaat | acatgaaaga | 21660 |
| gtgaaagttt | actccctgta | gattcttttt | taattatcaa | tcaaaggagg | aaactgataa | 21720 |
| ttgttaataa | taaactataa | agaggaaaat | atttatagtc | acattctgat | ataatgcaac | 21780 |
| taaatatcca | agcataaccc | gtctcacgag | gaacctacct | ataagacctg | ttattaagtg | 21840 |
| aatcactacg | attgactcta | ttaaggagct | accttaagtc | catctcacgc | aatttaaaag | 21900 |
| ggacttacaa | accgtaaaac | ggtaataagt | ttattaaata | atgtgatatt | aacatattag | 21960 |
| ttaataactt | tcacatggtc | gaagaaaagt | aaatttattt | gattaccaaa | ttatttttat | 22020 |
| caaatatagc | tcttttgaac | ctgtagattt | atgctactca | tactgataac | ctctattatc | 22080 |
| taacacattt | ctgtgctcca | actacagtta | gtcgttacag | cgtatctttc | taggattccg | 22140 |

FIG. 19M

```
                              sequence.txt
ctaagaccct agaaagaaat taaaccctag ccgttatcat actctacaga ccttataagt    22200
aagtaccaag tataccaatc gtatttaaca atactaatga cgacccatcc taccgatata    22260
tctccgataa gttttgattc gtttgattat cttgtacctt atgactacca aatcattatt    22320
cagtcactat gctcagatat ttagttgtat tatttatata ttaattataa catagttttt    22380
attacttgtc aagttaattt caaaaaaatt atagaagtag ggacgcttac ctacttccat    22440
ttaatttaca caaggatgat aacattgtta ttgttttata ctggaaaaca atgtaagaaa    22500
aacagtgatg tgtaaggtat ttgttttatt gttaattaca ttatagcata tactgatacc    22560
tttgtcaagt taatttaata cttttttaaa atattagtta tcttttgtta attcttcctg    22620
aatagcatcc catcttcttt ctgcttcact acgattatct tctatatgtt ttgtagtttt    22680
acaacatttg atacaatata tatctttgat atgaccttct tctcttttat ttgctctttt    22740
tcttggtact ttgaatacat ttccacattc tttacatatt aaacttgagt aaaacatttt    22800
ttgtcttttc ataattaatc aattcctttt ctcttttatt tgataattta actatatact    22860
atattgataa ataagtcaac agttttctaa aaataattta aattattttg aagaatcctt    22920
taatatcaag ggttacaaga gaaaagtac gtatttagaa aataaggagt actcctatta    22980
tatataatta tattctgata tagagtaata aataatatta aatatataat tataattaat    23040
aaggttggga aaattgatat aaacataact gatattgctt atagatactc agtataaaag    23100
taaaatccct tagtatcagt acttacaggc aaaaaagtac gtatttagaa aataaggaac    23160
tctcctatta tagttatata tattaattac tattattaat tactatttaa atatataatt    23220
ataattaaca atgttagaaa gtcaacaata gtataaataa aaaagtgact acttaaagtc    23280
actcaataat tagaatacta ttttaaaaga ttctattctg tttggattaa tatatacttg    23340
aggtgaagtt atagcacttt cagtatatac ttttatagag gtttcatcca ttcctcttaa    23400
catataatct atatcttgcc tattgtaact cttttcatca gtagatacta aaaagtattt    23460
agctccactt gacattgtta tttcaatatg ttttgacatc tacaatctct cctatgcaaa    23520
tttgttaaag acaaaggata atatagctcc tagaacaagt aaaagaactt tctcagttgt    23580
atccttcttc ttagtatcct tagttttgt acttccagca agtctgaaa tcttttcatc    23640
aagtctttct aattggacgt aaattgctga ttgttttca ctattgacag ctacatcttt    23700
atctatacta actatcattt ttcttagttc agctacctca acttctaaat ctttgaaagt    23760
ccctctatct atataattac cttcttgtat cttagactta atagtttcta cttgagaaac    23820
aaggttgttt atctccttat ccaactagaa tcacctctaa ggtctaaccg tttcagattc    23880
agaatggata tcataatttt ctaagaaatc attgataatc tccatataat tatccgtaac    23940
gacttttccg taagatgttt ttgtatcaat ttcaaaccta agcttaccaa aactttggag    24000
gtctaattct tttattacaa tattagggtc atcagaagga aggtaataat agtcgaagta    24060
```

FIG. 19N sequence.txt

| | | | | | |
|---|---|---|---|---|---|
| tataattgag | ccatttatta | atactctgtc | tattctatag | acgtggaaat | agcgtctgtc | 24120
| tcttttaaaa | tgggctagtg | catctttaaa | ctctaactta | aggatatcct | tatatttagt | 24180
| caaagtggta | acctccttac | tattaatttt | taaatttact | tattttgtgg | tataatagtt | 24240
| atgataaagg | cagttattat | aattatatta | agaataatga | taataattat | tttttctgag | 24300
| aaataagcc | aaatactaaa | aacagataaa | gcatagatag | ctgatagata | tactatatta | 24360
| agagttacct | tacttttatc | ttttctatag | atagaataac | ctaaagacgt | tgtaacacca | 24420
| ctaagtataa | aataatagaa | acaaaaaaga | ggtatagaca | gaaaaaaaga | tacgataatc | 24480
| attgttaaac | acctatttct | ttttgaccta | ttatttctag | aacttttaga | ttacaccact | 24540
| aatataacat | taaaagccag | tcataaaagt | caattgttag | attaataata | taataaaaaa | 24600
| agacaatagg | aggttaaagt | ggttgaataa | taacatagct | atattcatat | tcaaaacact | 24660
| ggttatcatt | atattcttac | tactaatttt | gtctgttatt | aattccttgt | cccttattta | 24720
| ctcaataaga | ccgagtgtag | ttatgacata | ctttatcttt | ggtggtattg | tttctaatgt | 24780
| cgcacttact | gtaacagata | agttcttact | gaagaaagaa | gacccctac | ctgaatatgt | 24840
| tcttaaaaaa | gtagagataa | atgataaaga | aataagaata | atcaagaaaa | tcatagaaag | 24900
| taattacgga | ataacagcag | aagagataaa | agttagggct | aaagcacaaa | gaagaataga | 24960
| ggaagatagt | aaaaaggaag | attacgatga | aaacaaagaa | agaaattaaa | gaacaaagga | 25020
| aagagcttaa | ggatggtgct | acatctgttt | ctttagtaaa | aaaaggagat | aagagaatag | 25080
| ctagccctag | tagaatttgt | agtctatgtg | gtcagcagtt | atcaggtatg | aattcacta | 25140
| aaggaaaagc | attatcaaaa | gttaatcatt | ttcatttaca | gtattctaag | tatatttatt | 25200
| ttgatatttg | cgcagatatc | aacaattgtt | ataaaaattt | aagaaaacga | ggtgaaatgg | 25260
| attgagtgca | gaaaatatta | gagatataat | taacaagaaa | aagttagaag | aagaggatac | 25320
| aagaaaatat | atagctgatg | gatttatgaa | tggtatcggt | aaattaatgt | acgaattcaa | 25380
| taaaaaagta | gataataaag | aaatagaagt | taaagaccct | aatgatttat | ataaattatt | 25440
| tgtgatattc | tctcaaatgc | aaaatatggt | caatgaaact | tctgaaggtg | gagcaatacc | 25500
| tcaactatct | agacctcaac | aggaattatt | tgatgagatt | acaacagaag | atagtaatgg | 25560
| agaatctaca | gttgatttac | agaagatatc | agaaatgtca | gcagaagata | ttacagcaat | 25620
| gatttctgaa | aaggaaaaag | taatgaatga | ggaaaattca | gaaacattct | aaggagaaag | 25680
| atataaatgg | atggaaaaga | actaattaag | atagcacaag | aaacatttca | aactgaaaaa | 25740
| ataacaagag | aacagataga | ccatataatc | aatatgctaa | accttctac | ctatatgctt | 25800
| aagtatcata | cactgagagg | tcatcctata | acttttagta | ttcctaacag | ggatagaagt | 25860
| aaagcacagg | ctcatagacc | ttggcaaact | aggattgtaa | atgatactca | tcctaataag | 25920

FIG. 190

```
                                      sequence.txt
gctgtaataa aatcacgtca gttaggtctt agtgaaatgg gtgtaatgga aatggttcat    25980
tttgcagata tgcatagtta tgctaacgca aagtgtctgt atacattccc tacaaatgaa    26040
caaatgaaaa aatttgttca gtcacgtttg aaccctgttt tagagaaaga atatttaga    26100
gacattgttg attgggataa agactcgtta ggttttaaaa agataagaaa ctctagttta    26160
ttctttagaa caagttctaa agcaagtacc gtagagggtg tggatattga ttatttatct    26220
ttagatgagt atgatagggt aaacttatta gcagaatcgt ctgcactaga atcaatgtct    26280
tcatcacctt ttaagattgt gagaagatgg agcacacctt ctgtacctgg gatgggtata    26340
cacaaattat accaacaatc agaccagtgg tattacggtc atagatgtca acattgtgat    26400
tacttaaatg aaatgagtta taatgattac aaccctgata atcttgaaga aagtggaaat    26460
atgttatgtg ttaatcctga aggtgtagat gagcaagcta aaacagtaca gaatggcagt    26520
taccaatttg tttgtcaaaa atgtggtaaa ccattggata gatggtataa cggtgagtgg    26580
cattgtaagt accctgagcg tacaaaaggt aataaagggg tacgaggata cctaataaca    26640
caaatgaacg ctgtatggat ttctgctgat gaattaaaag agaaagaaat gaatacagaa    26700
tctaagcaag cattctacaa ctatattta ggttatcctt ttgaagatgt taaacttaga    26760
gttaatgaag aagatgttta tggtaacaaa tcacctattg cagaaacaca attaatgaaa    26820
cgagatagat attctcatat agctattggt atagattggg gaaatactca ctggataact    26880
gttcatggta tgttacctaa tggtaaggta gacttaatac gattattctc tgttaaaaaa    26940
atgacaagac ctgatttagt tgaagcagat ttagaaaaaa taatttggga aatatctaag    27000
tacgaccctg atattataat tgcagataac gggactcag gtaataacgt tttaaaactc    27060
attaatcatt ttggaaaaga taagtattt gggtgtactt ataaatcttc tcctaaatct    27120
acagggcaat taagacctga atttaatgag aacaataata gggttacagt agataaatta    27180
atgcagaata aaagatatgt acaagcactt aagacaaagg atataagtgt ttatagtaca    27240
gtagatgatg atttaaaaac tttcttaaaa cattggcaga atgttgttat tatggatgaa    27300
gaagatgaaa aaactggaga aatgtaccaa gttatcaaac gtaaaggtga cgaccactat    27360
gcacaagcaa gtgtctacgc ctatatagga ttaacaagaa taaaagaact tcttaaagaa    27420
ggaaacggta caagctttgg ttctacattt gtttctactg attacaatca agaaggaaat    27480
aaacaattct actttgatga atagaggtga aatagacttg acagataaat tattttatgg    27540
tacaattagt aatgaagaaa ttaataaaag tgtattgaat ttgttattgg gtgaggaatt    27600
atccttagat tatgtttcta aaaatagtga tacttagat gttaaatatg aacatgttta    27660
taaatctcta ggattcgata atttctttga ttgttttta tatgctaata gagagcctga    27720
aatagtccat aaaggtggag ataaaaatct tggtggacta aataaggtta acgtactgt    27780
tattcgtaat ggtaaagaaa tggaaatgac agtttacgaa gatggtaata agagaacga    27840
```

FIG. 19P sequence.txt

| | | | | | | |
|---|---|---|---|---|---|---|
| tagtaaagaa | aaacaagaag | gaaaagaaga | agttagtaga | agtgcagtag | gagcaagggc | 27900 |
| tatttctaat | ggtgaagaag | gaaaggtaaa | ccctaaaaag | gtagcaaatt | cattatctaa | 27960 |
| tttaagtaaa | aaaggtgtag | atgtatcaca | tattaataca | aactcatcat | tgtataaaga | 28020 |
| gtttgttgat | gataacggtg | atacattagg | aattacatct | tttaaacgaa | ctgaaaatga | 28080 |
| tataatatta | gaatcttatg | caagttcaca | tgattcagat | ggtgtaggag | caagagctat | 28140 |
| tatggaatta | ttacgtttaa | gtattaagga | aaataaaaat | gcagttgtgt | atgatataga | 28200 |
| attacctgaa | gcagtagagt | atttaaaaac | tttaggattt | aaacctaata | aagatggata | 28260 |
| catcttaaga | aaaaaagatg | taaaacaatt | cttaggtgat | tatagtgatt | ttatttagca | 28320 |
| ctatagtcat | ctattctatt | gtatttattc | tatatattgt | attaaaaaca | atttatataa | 28380 |
| agtctaatat | gagtagaata | gataacacaa | ctgaattatt | aaaaatatta | caggaagata | 28440 |
| ttgaaggtaa | gataaaaaag | gaaggaagaa | ataaatgact | ttagaagaaa | ataaattaac | 28500 |
| attagaagaa | tcaataactc | cacttagcaa | agaggagaaa | gaagatagta | ttaaagaatt | 28560 |
| tagcagttta | ttatgtgaaa | tggtaaatag | actatataag | tcttataatg | tatttagaca | 28620 |
| agaccctatg | gatgaaactc | aacgtctaga | tggctcttta | atggtctttc | aaagtagatt | 28680 |
| aaatgaccct | ttaacaggag | atttacatga | taagatgtat | aaacttgctt | tttcaaaacg | 28740 |
| tattgatatt | ttcgaagcta | ataagcaatt | tagaaaagat | gtagaagcag | gtaaagcaat | 28800 |
| tgagttaggt | gatgtagcta | ttatagatac | agcattaagt | aacatccttt | caggcaatga | 28860 |
| gttccaagga | agtatttcat | ttatgcttag | aaaagacttt | gaagaaaaag | aacgaattag | 28920 |
| aaaagaagaa | gaagagaaac | ttaataactt | ataaaaggga | agaattatga | gactatataa | 28980 |
| aatgaggtat | cataattgaa | aaagaaacca | caaggcaatg | aggtaatcat | aaccataata | 29040 |
| acggttatga | tagcagtatt | tgtagtcatt | atgaccatat | tttttaataa | atatcaagat | 29100 |
| gctaaagaag | ataaagatag | atatcaaaga | ttagtagaga | tttataaaaa | agcagatgat | 29160 |
| aatgatggtg | agactaaaaa | gaaatatgtt | aaaagattaa | ataaggctga | agaagaactt | 29220 |
| aaaaaagtaa | aaaagaaaca | aattataaag | attataataa | gaagtcaagt | aaagaaagac | 29280 |
| aaaaagaaga | taaagaaact | agagagaaaa | tatatgatgt | aactggtgat | gatgacttaa | 29340 |
| tattagtaaa | aaataatatt | gagtttagtg | ataaagtaga | caagcccgaa | atacttatta | 29400 |
| gtgaagatgg | aattggtacg | ataactgttc | ctgtagatag | tgggtatgaa | aaacaaacag | 29460 |
| taggttctat | tattactagt | gtattaggtt | ctcctttcct | atcacctggt | tcaaatagta | 29520 |
| tagatggttt | aagtgttatt | aacgataatg | tttatccaaa | tacagtagat | agcatagtag | 29580 |
| aagatacaaa | accttctatt | aacttaccaa | cggataatcc | tattataaca | aatccagttg | 29640 |
| aaccaactat | accttcagat | attatacctc | ctattgataa | tccttcagtt | ccgatatctc | 29700 |

FIG. 19Q sequence.txt

| | | | | | |
|---|---|---|---|---|---|
| ctgagaaccc | aggagataat | aatcaaggaa | atacagataa | tccaaatcct | cccccatccag | 29760 |
| ggtacacaga | tgaagatggt | ggaagaggct | ccggtggtgg | aggaaattct | gaaccaccat | 29820 |
| caacggaaga | accttcggat | aatggtaaca | ccggaggagg | agattgggaa | gaaaaacctg | 29880 |
| acccaggaga | agaaccttca | gataatggta | atacaggagg | aaatggtgga | gaagttacgc | 29940 |
| ctgaacctga | acctgaacct | gaacctgaac | ctgaacctga | acctgaacaa | ccgaatgaaa | 30000 |
| atcctgatga | aggtaatgaa | gaaaaaccat | ctgaaccgtc | tgacaatcct | gatgaaaatg | 30060 |
| gaggatggga | aactgaacca | actgaacctg | agtccacttc | agagccggac | gataaagtgg | 30120 |
| acgaagaaga | taaaaatgaa | gatactacag | atgataaaca | gcccactgaa | caaccggacg | 30180 |
| ataacaacat | agataatgaa | gataaaactg | aagaggagta | attactcctc | ttttttgttt | 30240 |
| gctatattaa | ataagagcta | aatataaaaa | aattgaacat | tacggtggtg | aaaactttgt | 30300 |
| taggaatgaa | tattataacg | tcactatcag | tagtatttac | ttgtttaagt | cttttaactt | 30360 |
| taatgatttt | tgttcatagt | aagttctcta | gtaaaaacgt | ttttgttttg | tatgtaattt | 30420 |
| atgctataat | aggaataggt | acatacatag | ttttaactat | gtttcaaaca | acatctgtac | 30480 |
| ttattaagaa | tgatgtaata | gattccatag | aaaatactga | acattatatt | ggattcaatg | 30540 |
| accctataat | tatatttact | ataagtttta | taggtgcaat | acttggagga | atttggtaca | 30600 |
| agatgatgaa | aattattaaa | aagagtaact | ttaaagataa | aaaataaaaa | agacggtgaa | 30660 |
| taggttgata | ttctctaaag | ataaaaaatg | ggatgaagca | aaagatttca | tcaaaggtca | 30720 |
| aggtatgcaa | gataattgga | tagagattgt | agattattat | agacagatag | gtggaaaaca | 30780 |
| cgtagctgtt | tttattgctt | taaacaaagt | aaaatacatg | attctagaag | caacaaaaga | 30840 |
| caataaggta | atattagtag | ataaagataa | taatatacta | ttagaagatt | atgatattgt | 30900 |
| tatggaaagt | aagaagatgt | tttattacat | tgaagaaccg | ttcgaggtta | aaataaatat | 30960 |
| ccctcaacat | attagagatg | taacttataa | taatactgtt | gtattaacta | cagtaagagg | 31020 |
| gagtagaggt | gactagtaat | tggcagattt | atttaagcaa | ttcagattag | gtaaagacta | 31080 |
| tggtaataat | agtaccattg | ctcaagttcc | tattgatgaa | ggattacaag | ctaacattaa | 31140 |
| aaaaatagaa | caagacaata | aagagtatca | agatttaact | aagtctttat | acggacagca | 31200 |
| acaggcttat | gcagagccat | ttatagaaat | gatggatacg | aatcctgaat | ttagagataa | 31260 |
| gagaagttac | atgaagaacg | aacataactt | acatgatgtt | ttgaaaaagt | ttggtaataa | 31320 |
| ccctatcctt | aatgctatca | tacttacacg | ttcaaatcaa | gtagctatgt | attgtcaacc | 31380 |
| tgcaagatat | tcagagaaag | gtttaggttt | tgaggtaaga | ttaagagacc | tagatgcgga | 31440 |
| acccggtaga | aaagaaaaag | aagaaatgaa | acgtatagaa | gattttattg | ttaatacagg | 31500 |
| taaagataaa | gatgtagata | gagattcatt | tcaaactttc | tgtaagaaaa | ttgttagaga | 31560 |
| tacttacatc | tatgaccaag | ttaactttga | aaaagtattt | aataagaata | ataaaactaa | 31620 |

FIG. 19R sequence.txt

```
attagaaaaa ttcatagcag tagacccttc tactattttt tatgcaacag ataaaaaagg    31680
taaaattatt aagggtggta agagatttgt tcaagtagta gataaaagag tagtagctag    31740
ttttacttct agagagttag ctatgggtat aagaaaccct agaactgaat tatcttcttc    31800
aggatatgga ttatcagaag tagagatagc tatgaaagag tttattgcct acaataacac    31860
tgaatcattt aatgatagat tcttctccca cggtggtact actagaggta ttttacagat    31920
acgttcagac caacaacaat cacaacatgc attagagaac tttaagcgtg aatggaaatc    31980
tagtttatca ggtatcaacg gttcatggca ataccagtg gtaatggcag atgatattaa     32040
atttgtcaat atgacaccaa ctgctaatga tatgcaattt gagaaatggt taaattacct    32100
tatcaatatt atatctgctt tatatggtat tgaccctgca gaaattggtt tccctaatag    32160
aggaggagct acaggttcta aaggtggttc tactttaaat gaggctgacc cgggtaaaaa    32220
acaacaacaa tctcaaaata aaggtttaca acctttactt agatttattg aagacttagt    32280
taatagacat attatatcag aatatggaga taagtataca ttccaattcg taggtggaga    32340
tactaagagt gctactgata aacttaatat tcttaaacta gagactcaaa tatttaaaac    32400
agttaatgag gctagagaag agcaaggtaa gaaacctatt gaaggtggag acattattct    32460
agatgcttca ttcttacaag gaacagccca attacaacaa gataaacaat ataatgatgg    32520
taaacaaaaa gaacgtttac aaatgatgat gagtttacta gaaggagaca atgatgattc    32580
tgaagaaggg caatcaacag attctagtaa tgatgataaa gagataggaa cagatgcaca    32640
aataaaaggt gacgataatg tttatcgtac tcaaacatct aataaaggtc aaggaagaaa    32700
aggagaaaaa tcttctgact ttaaacatta attaataagc ctagaataaa tctaggcttt    32760
gtttatttt ttcgtaattt aattttgata aatgtaataa ctatgatata ctatatgtaa    32820
ttgatattaa tacataaaaa atattaatat ttcacttaca agttattatt gttatattat    32880
taacgtaaaa gtaaataaaa taacaagtgg aggtgtagac acctttggaa gaaataaaat    32940
ttaatgcttt tgtacctatg gatttgaaga aatctgtatc aacagcttct gatactaatg    33000
agtattctat cgtttcagga tgggctagta ctccaagtat ggatttacag aatgatatag    33060
ttaatcctaa aggaatagat atagagtatt ttaagtcaca agggtacatt aattatgagc    33120
atcaaagtga taaagttgta ggtataccta cagagaattg ctatgtggat atagaaaaag    33180
gtttatttat tgaagcaaag ctatggaaga atgacgaaaa tgttgttaag atgcttgatt    33240
tagctgagaa attagaaaaa tcaggtagtg gaagacgttt aggtttttct attgaaggtg    33300
cagttaaaaa acgtaatata aatgacaatc gagttattga tgaagttatg ataaccggag    33360
ttgcattagt taaaaaccct gctaatcctg aagcaacatg ggaaagcttt atgaaatcat    33420
ttttaactgg tcatggtaca tcacctgaca ctcaagttga tgcaggagct ttaagaaaag    33480
```

FIG. 19S sequence.txt

| | | | | | |
|---|---|---|---|---|---|
| aagaaatagc | atctagcatt | acaaatttag | cttacgtcac | taagattaaa | gatttaaaag | 33540 |
| agtttaatga | tgtatggaat | ggcgttgttg | aagatttgag | taaatctaat | agtatgggat | 33600 |
| atgaggaatc | agtccttacg | ttacaactag | ctaaaggttt | atctcgtaaa | gatgcagaac | 33660 |
| tagcagtaat | ggatataaac | aaacaaaaac | tagaataggt | aaggagaata | cattctatga | 33720 |
| gtaaagaaat | gcaaaatatt | ttagaagagt | atgataagtt | aaatgctcaa | gaggcagttt | 33780 |
| cgaaatctgt | agaagatgat | gaaaagaata | cagtagaatc | taccgaagag | caagtagcag | 33840 |
| aaacaactga | agaacctgct | aaagaacctg | aaaaagtatc | tgaggaagat | gctaaagaag | 33900 |
| cacaagagca | aggtgaaaaa | gttgaatctg | aagaggtagc | agagggcaat | gaagatgagg | 33960 |
| aagttgaaaa | atcagctaaa | gaatcaaaag | accctgtaga | ccaaaaagat | actaagacag | 34020 |
| aaaataaaga | caacgagaaa | cgtaaaaata | aaaagataa | aaagaagat | tctgacgatg | 34080 |
| aagataaaga | tactgacgat | gataaagata | agaagaaga | taagaaggaa | aaaacttcta | 34140 |
| aatcaatttc | tgatgaagat | atcacaacag | tatttaaatc | tatcttaaca | tcttttgaaa | 34200 |
| acttaaataa | agagaaagaa | aactttgcta | ctaaagaaga | tttaagtgaa | gttagtaaat | 34260 |
| ctattaatga | gttatcagca | aaaatttctg | aaatccaagc | tgaagatgtt | tctaaatcag | 34320 |
| tagacactga | tgaagaagct | gtagaaaaat | cagtaacatc | tacaaacgga | gagcaagaaa | 34380 |
| aagtagaagg | ttacgtttct | aaatcagtag | acactgaaga | acaagctgaa | actggtgaag | 34440 |
| caaaatcaga | agaagctgaa | gaagtacaag | aagataacac | atttaaagga | ttaagtcaag | 34500 |
| aagaacgaac | taagttcatg | gattcttaca | aagcacaagc | taaagaccct | agagcttcta | 34560 |
| aacatgactt | acaatcagct | taccaatctt | acttgaacat | taacactgac | cctactaatg | 34620 |
| catcagagaa | agatattaaa | actgtaaaag | actttgcaca | aatttaatta | atgcacaaag | 34680 |
| ttgtgttata | ttatacggtg | taactaaaga | atataaatag | ggtacatttt | actgtaccct | 34740 |
| acataaaata | aaaagaacac | aaatgaaagg | tgataaattt | atatgactat | cgaaaagaac | 34800 |
| ctgtcagacg | ttcaacaaaa | gtacgctgac | caattccaag | aagacgtagt | aaagtcattc | 34860 |
| caaactggtt | atggaatcac | tcctgataca | caaattgacg | caggagcttt | acgtagagaa | 34920 |
| attttagatg | accaaatcac | aatgttaaca | tggactaatg | aagacttaat | cttctatcgt | 34980 |
| gatatctcac | gccgtcctgc | tcaatctaca | gtagtaaaat | acgaccaata | tttacgtcat | 35040 |
| ggtaacgtag | gtcactctcg | tttcgttaaa | gaaatcggag | tagcaccagt | atctgaccca | 35100 |
| aatatccgtc | aaaaaactgt | atcaatgaaa | tacgtttctg | atactaaaaa | tatgtcaatt | 35160 |
| gcatcaggtt | tagtaaataa | cattgctgac | ccatcacaaa | tccttacaga | agatgctatc | 35220 |
| gcagttgttg | caaaaacaat | tgagtgggct | tcattctacg | gtgacgcttc | attaacttct | 35280 |
| gaagttgaag | gtgaaggtct | agagtttgat | ggtttagcta | aattaattga | caaaaataac | 35340 |
| gtaattaacg | ctaaaggtaa | tcaattaact | gagaaacact | taaatgaggc | ggcggtacgt | 35400 |

FIG. 19T sequence.txt

| | | | | | | |
|---|---|---|---|---|---|---|
| atcggtaaag | gtttcggtac | agctacagat | gcttacatgc | ctatcggtgt | acacgcagac | 35460 |
| ttcgttaact | caatcttagg | tcgtcaaatg | caattaatgc | aagacaacag | cggtaacgtt | 35520 |
| aacactggtt | acagcgtaaa | tggtttctac | tcatctcgtg | gattcattaa | attacatggt | 35580 |
| tctacagtaa | tggaaaatga | actaatctta | gatgaatcat | tacaaccatt | accaaatgct | 35640 |
| ccacaacctg | ctaaagttac | agctactgtt | gaaactaagc | aaaaaggtgc | ttttgaaaat | 35700 |
| gaagaagacc | gtgcaggatt | atcatataaa | gtagtagtta | actcagatga | cgctcaatca | 35760 |
| gctccttctg | aagaagtaac | agctacagta | tctaacgtag | acgatggtgt | taaactttca | 35820 |
| attaatgtta | acgctatgta | ccaacaacaa | ccacaattcg | tttctatcta | ccgtcaaggt | 35880 |
| aaagaaacag | gtatgtactt | cctaatcaaa | cgtgtaccag | ttaaagatgc | acaagaagac | 35940 |
| ggaacaatcg | tattcgtaga | taagaacgaa | acattgcctg | aaacagcaga | cgtatttgtt | 36000 |
| ggtgaaatgt | caccacaagt | agttcactta | ttcgaattac | ttccaatgat | gaaattacca | 36060 |
| ttagctcaaa | ttaatgcttc | tattacattt | gcagtattat | ggtatggtgc | attagcatta | 36120 |
| cgtgctccta | aaaatgggc | tcgtattaaa | aacgttcgtt | atatcgcagt | ttaatagaat | 36180 |
| aagaaaaact | gaatacaaga | gaatagggat | aaacttaggg | tttatccctt | ttttattaaa | 36240 |
| ataaacttga | agggatttaa | taaatatgtt | atactataag | aaactattag | ataaaaaaat | 36300 |
| ggctactgtt | tatggtacag | tggagattga | caaagatgga | gtagttaaag | gattaactaa | 36360 |
| agagcaagaa | aaagaatttg | caaatgttcc | aggttttgaa | tttgaagaag | aaaagaaaac | 36420 |
| tactagaaaa | caatcagctt | ctactagtaa | agaagaagag | cctaaggaag | aggaaaagaa | 36480 |
| agcctctact | agaaaaacta | caagtactac | tagaaaatct | acagcacgta | aaacaacagc | 36540 |
| caaaaaagat | gaaaataagt | aaagggtgaa | ttaaatggtt | aactcaatgt | ttggagggga | 36600 |
| cttagaccct | tatgaaaaat | cattaaacta | tgaatatcct | tatcatccta | gtggtaatcc | 36660 |
| taaacatata | gacgtaagtg | agatagataa | tttaacatta | gctgattatg | gatggtcacc | 36720 |
| ggatgcagtt | aaagcatata | tgttcggtat | cgtagttcaa | aatcctgata | caggacagcc | 36780 |
| tatgggtgat | gagttttata | accatatatt | agaaagagcg | gtaggtaaag | ctgaaagagc | 36840 |
| attagatata | tctatactac | ctgacactca | acatgagatg | agagattatc | atgagacaga | 36900 |
| gtttaatagt | tatatgtttg | tacatgctta | cagaaaacct | atattacagg | tagagaactt | 36960 |
| acagctacag | tttaatggta | gaccaatata | taaatacccct | gctaactggt | ggaaagtaga | 37020 |
| gcatctagca | ggacatgttc | aattatttcc | tacagcactt | atgcaaacag | gacaatcaat | 37080 |
| gtcatatgat | gctgtattca | atgggtatcc | tcaattagca | ggtgtatacc | cgccatcagg | 37140 |
| ggcaacattt | gcacctcaaa | tgatacgatt | agaatatgta | tcaggtatgc | ttccacgtaa | 37200 |
| aaaagcagga | agaaataaac | cttgggaaat | gcctcctgag | ttagaacagt | tagttataaa | 37260 |

FIG. 19U

```
                                sequence.txt
atatgcattg aaagaaatat accaagtatg gggtaactta atcattggtg ccggtattgc    37320
taataaaaca ttagaagtag acggtattac agagacaata ggtactactc aatcagctat    37380
gtatggtgga gctagtgcac agatacttca aataaatgaa gatataaaag aactattaga    37440
tggtttaaga gcttactttg gatataatat gataggatta taaggagggt tagaaaatgg    37500
aaaaaccgta tatgatagga gccaactcta accctaatgt tattaataag tcaacaacat    37560
atactactac aacacaagca gatgaacaag ataaacctaa gtatactact agactagagt    37620
ttgatacgat tgacatgatt aggtttatta atgaccgagg tataaaagta ttatgggaag    37680
aagcatattt ctgtccttgt cttaatcctg atacaggaca tcctagggta gattgcccta    37740
gatgtcatgg taaagggatt gcatatctac ctcctaaaga gactataatg gcaatacagt    37800
ctcaagagaa aggaactaac cagttagata taggtatatt agacacaggt actgcaatag    37860
gtaccactca attagaaaag agaatttcct atagagatag gtttactgtt cctgaggtat    37920
tgatgcctca acaaatgatt tattttgtga ataaagatag aattagaaaa ggtatacctc    37980
tatactacga tgtaaaagaa gtaacttata tagctactca agatggtaca gtctatgaag    38040
aagattatga aattaagaat aacagattgt atttaaatga aaaatatgag aaccatacag    38100
taactttaaa gatacttatg actttaagat atgtagtatc agatatacta aaagaaagtc    38160
gttatcaata tactaagttt aatcaaccta aatcaaaatt tgaaaactta cctcaaaaat    38220
tacttcttaa aagggaagat gttattgtac tacaagaccc ttataaagtt aatgatggca    38280
tagaagaaga cctagaaatt caagtagatg accctaaggc ttcagcatct aatcctagta    38340
atttaggtgg attcttcgga ggtgcattta ataatgcca  gttcacggaa agagacctaa    38400
tttatttaaa aataaaaact ataagcaggt aggtaagaga acaattgatg gtatgcgttc    38460
agaagttctt gataaattac aagcaacagc acagcaagta gagaatacta gtattaaacg    38520
tatgcctact tacctacaaa taacagagaa aaagcttgaa aagaaggag  tagtagacct    38580
taaaaaagct tttgctcact catctaaaaa gaaaactagt aaagatggcg gatggtattt    38640
aactgtacca atccgcatca aaactagtag aatgaataac agtacttacc aagatatgag    38700
aactttaaaa gtagataaag gtacaggttc agtctctaag ataactgatt acctagaagg    38760
acgtagaaag aatgtaagcc atccttcaat gaagcctgaa cctatgactc ataatatgac    38820
taaagttaaa agaggaaagc aatcttctta ctttatattt agaactgttt ctagtaagtc    38880
acctgctagt tcttggatac ttaacagaga taaagttaat gaagataact tctctaaaac    38940
aactctaaaa actgttaagc aattaatgaa ctggaagatg aaaaatttaa attaagagga    39000
gggttagtat taaatggcaa taacatcagt tgattcatat ttattatcag aaataaagcc    39060
tagacttaac actgtgctag agaattgtta tattatagat gaagttttaa aagactttga    39120
ttatcaaact agagagagct ttaaagaagc tttctgtggt aagaatgcac aacatgaagt    39180
```

FIG. 19V

```
sequence.txt
aacggtagga tttaacttcc caaaatttaa aaataactat gaagctcatt acttgataca    39240
attaggtcaa ggacaagaga caaaaaactc tttagggagt attcagtcat cttactttga    39300
ggcaacagga gataccttag tcgaatcttc tacagcaata agagaagatg ataagttagt    39360
ttttactgtt tctaaaccaa taggagagtt aataaaggta gaagatatag agtttgctaa    39420
atacgataat ctccaagttg aaggtaataa ggtatcattt aagtatcaaa caaatgaaga    39480
ttatgagaac tacaatgcta acattatatt taccgaaaag aaaaatgatt ctaaaggttt    39540
agtaaaagga ttcacagttg aagaacaagt aacagttgta ggtctttcat ttaatgtaga    39600
cgttgcaaga tgtttagatg ctgtactgaa aatgatttta atatctatga gagatagtat    39660
agaagagcaa caaacattcc aattacagaa tttgtctttt ggtgatattg caccaataat    39720
agaagatggt gactcaatga tttttggtag accaacaatt attaagtaca caagttctct    39780
agatttggat tatactatta cacaagatat taataaacta acttttaaag aaagaaagga    39840
ttggaagtag gatggctaga aaaagacac ctgaaaataa cactcctaaa tttaatggtt    39900
atgttcatat agatacattc cttgatactg caaaaaccct ttttaatatg aaggattcac    39960
aagtagcagg atttaaagct tatatggaag gtagtcatta tttgtttagt gagcaagaat    40020
tcttaccatc attagagaag tatctaggta ggaaattaga tatataataa cattcagata    40080
aggagaatta aatatggcag tagaaccatt cccaagaaga cctattaccc gtcctcatgc    40140
atctattgaa gtagatactt caggtatcgg tggctcagca ggttcaagtg aaaaagtatt    40200
ttgcttaatc ggtcaggctg aaggcggaga accaaataca gtttatgaat tacgtaacta    40260
tgcacaagct aaacgtttat tccgttcagg agaattactt gatgcaatag aattagcatg    40320
gggttctaac cctaactata cagcaggtaa gattttagct atgcgtatag aagatgctaa    40380
acctgcttca gcggaaatcg gtggattaaa agtaacatct aaaatctatg gtaatgttgc    40440
taacaacatt caagtaggat tagaaaagaa tacattaagt gattcattac gtttaagagt    40500
aatcttccaa gatgaccgtt tcaatgaggt ttatgataat atcggtaata tcttcacaat    40560
caagtacaaa ggagaagaag ctaacgcaac tttctctgta gaacatgatg aagaaactca    40620
aaaagcaagt cgtttagtat taaaagttgg agaccaagaa gttaagtcat atgatttaac    40680
tggtggagct tatgactaca ctaatgctat tattacagac attaatcaat tacctgatct    40740
cgaagctaaa ttatcacctt tcggagataa gaacttagaa tctagtaaat tagataaaat    40800
tgaaaatgca aatatcaaag ataaagctgt atatgtaaaa gcagtttttg gtgacttaga    40860
aaaacaaaca gcttacaacg gtatcgtatc tttcgagcaa cttaatgcag aaggagaagt    40920
accaagtaat gtagaggttg aagcaggaga agaatcagct acagtaactg ctacttcacc    40980
tattaaaact attgagccgt ttgagttaac taagttaacg ggcggtacta atggagaacc    41040
```

FIG. 19W sequence.txt

| | | | | | | |
|---|---|---|---|---|---|---|
| acctgctaca | tgggcagaca | agttagataa | atttgcacat | gaaggcggat | actacattgt | 41100 |
| cccattatca | tctaaacaat | cagttcatgc | agaggtagct | tcttttgtta | aagaacgttc | 41160 |
| tgatgcaggg | gaaccaatga | gagctattgt | tggtggagga | ttcaatgaat | ctaaagaaca | 41220 |
| attgttcggt | agacaagcat | cattatctaa | tccacgagta | tcattagtag | ctaactcagg | 41280 |
| tacttttgtt | atggatgatg | gacgtaaaaa | ccacgtacct | gcttacatgg | tagccgtagc | 41340 |
| tctaggtggt | cttgcaagtg | gtttagaaat | tggtgaatca | atcacattca | aaccactacg | 41400 |
| tgtaagttca | ttagaccaaa | tctatgagtc | aatagactta | gatgaattaa | atgaaaatgg | 41460 |
| tattattagt | atagagtttg | ttcgtaaccg | tactaataca | ttcttcagaa | tcgttgatga | 41520 |
| cgtaactaca | ttcaatgata | aatcagaccc | agttaaggct | gaaatggctg | ttggggaagc | 41580 |
| taatgacttc | ttagtaagtg | agcttaaagt | tcaacttgaa | gaccaattta | ttggtactcg | 41640 |
| tactatcaat | acaagtgctt | caatcattaa | agactttatc | caatcttact | tgggtcgtaa | 41700 |
| gaaacgtgat | aatgaaattc | aagacttccc | tgctgaagac | gtacaagtta | ttgttgaagg | 41760 |
| taacgaagca | agaatttcaa | tgacagttta | cccaatcaga | agcttcaaga | aaatttctgt | 41820 |
| tagcttggtt | tacaagcaac | aaacattaga | agcctagtct | aggtgatgga | gtacctggat | 41880 |
| taggtactcc | tattaatata | atttgaatac | tttaggagag | tgaatacaga | tggcatcaga | 41940 |
| agctaaacaa | accgtccata | ctggtaatac | cgtcctactt | atgattaaag | gtaaaccggt | 42000 |
| aggaagagca | caatcagcat | caggtcaacg | tgaatacggt | acaactggtg | tatacgaaat | 42060 |
| cggttctatc | atgcctcaag | aacacgtata | tttacgttat | gaaggtacaa | ttacagtaga | 42120 |
| acgtttacgt | atgaaaaaag | aaaactttgc | agatttagga | tatgcttcac | ttggtgaaga | 42180 |
| aattcttaag | aaagatatca | ttgatatttt | agtggtagat | aacttaacga | aacaagttat | 42240 |
| tatctcatat | catggttgct | ctgcaaataa | ctacaatgaa | acttggcaga | caaatgaaat | 42300 |
| tgtaacagaa | gaaatcgagt | tcagttaccct | ttaactaata | gaggctatgt | ttggtgacaa | 42360 |
| gcatagaaaa | cactttaaat | tgcgtgaaag | tcttaaagac | tagataacta | caacgtaact | 42420 |
| cgaaagggta | agcgtgaatg | ttgagaaatc | agaaaaaata | tctagtatag | tataaggtta | 42480 |
| aatcctaagt | acagtaaaat | agatgatacg | caggcaagcc | tacaaatgtg | ggaagcttca | 42540 |
| acgactataa | taggtgagtc | ttagttacac | attaagatta | tggtatagtc | tactcccttt | 42600 |
| aaaatatatc | gaaagatagg | gtacaaagga | cagcatcaga | taaagctaga | acttaaattt | 42660 |
| cttattaaga | ccaacaataa | aagttggtct | tatattttat | acttgctttg | tctgaggcag | 42720 |
| tgtgctataa | ttaaaataca | aggaggtaat | aatatgggaa | aaaatcaata | tacatttaat | 42780 |
| attaagaaa | ataaaaataa | atggtatgaa | tggtgtaaac | tacaaaacgt | aaaaccttta | 42840 |
| gtagaatatg | aaaatgcaca | acaaatattt | tattttgaat | ttcttgaagg | taaatttaaa | 42900 |
| ggactaatag | gaaaaacata | ttgggctagt | ataaatagag | gttctaatat | gcgtatgagt | 42960 |

FIG. 19X sequence.txt

```
tgtttaacat cagaaagtaa agataaatat ttaaaaaatt taggaaaaag aaaaggtata    43020
gaggtagtag aagactataa gggtggcaga aaattaaaac ataaatttat agttttagaa    43080
ggtaagtacc aaggatgtga agggtatata actttaaatg atttagagaa tttaggtaga    43140
gtagataata gaagtttatc tgaaaaagga aggaaacaat actttgataa acaggcaaga    43200
cttagagatt gtattattct agagtaccct aaagactata gaataaaaac taaagataag    43260
atagtagtaa aagataaaga agggcatgtt cataatatta ttgttcagga ctttttttgag   43320
aaatcatctt tattggagtt atcttgtgct agtgaaggag agaaaatagt taaagaaata    43380
cttactaaaa attctataaa atttgaaaaa gaaaatcat ttagaaacaa agaaggtaaa     43440
gtacaaagat ttgattttta tattaatgaa aataataaag aatatgcaat agagtacaat    43500
ggtgcacagc actacataga ttctacagga tatcttaaag atactttgga aacaacccag    43560
aaaagagata aactaaaaaa agaatacagt aaagataaag gtataaattt attaattatt    43620
ccttacacaa taacagataa gaaagaaatg gaaaaaatta ttttaaattt tttaaacaaa    43680
taaccttga cactccctca agggatatgt tattataata acaggttagg agtaataagt     43740
atgaataata ggcaagctaa actaaaagga tataaccaat ttcattatta tgattttcca    43800
acaactaaag gtaagtttaa agatataatg aaaagaaaat ctagaacaga acttaaaaaa    43860
gatttacaaa aagaaaggaa gtattatctt gacaaataag agaaaaacga taggtaagat    43920
gagtaacaca agagcaacat ggaatattaa tccggtaact aaagttaaaa aagataaaac    43980
aaaatattct agaaaaaata aacataaagg tcttgacaat tataattaac taaggtatat    44040
tattagtata acaaaaaaag gagatgttat aatatgagaa tttatataag taatgactat    44100
aacaaagagc tattagataa atgtttatca gatattaaca aagataaagg taatataaac    44160
tacagtatta attatggtga aggtaacatt aaagaagcag atgtagaaat tattaaacta    44220
gataagaatc tattagaaac agaatcaaga gcatttgctt attcgaagtt tgttgaagat    44280
tgtatatttt tatttccctta taagattgct ttacttagag ggggtaaaat agagttaaga   44340
tttgattgga atgaaatatt ataacaaaaa aaggagatgg atatatgagt acattttggt    44400
cagaaagaag aacaactaat aaagataggc aagttaaaaa acattatact caaatgagta    44460
tgtatgaaag aaagaaatgt gtagagttat tacaagagac aattactgaa aatagaatta    44520
ttaattttac acgacatagt gcaaaaaaag ttaaaggtaa accaacaaca aatataccta    44580
aattaatagg ttttattttt aaaaataagt ttgcctacga aaatatcata gagtacaata    44640
acacagatta taatggtaat attgagagga gaattgttgt taaacatccc aaagttataa    44700
ctgtagaagg aaaacttagc tatcagtttt tgacaattag tcttgaagat gctagagtta    44760
ttacggtgtg gtataacagt gtagatgata cacatagaac actagattta aattattata    44820
```

FIG. 19Y

```
                                    sequence.txt
gtaaagactt gacaattcaa taaggaggag ttataatggg attaacaata gtaaatggtt     44880
atttctttct atcaagtatt atatttattg tagtaagtat actaaatgga aaaggtacag     44940
ttacaaggga atcactagct atgagtcaag cattagtgat aataacatcc attcaatttt     45000
tagcattttt aattataaat ggcatttatt actcattaaa atatatgtaa taaaaggag      45060
tacaaatgga aatatacatt gtaatagact taagaggaag cacagaagaa gaaacaagta     45120
tggattttaa agcttttaga aaattacaag atgctataac atatgtagat ggtaatggta     45180
acagggattt acatataatt cctctagaat tagaataaaa gtattgacaa attaaaacta     45240
ataattata  ataaaggtat aacaaattaa aggagaagat ataaaatgtc acaagataaa     45300
ttaagagcaa tttacacaga aatgaaagta gaattacaca aatttcctaa agaggtagat     45360
gtaacaagta aatcaactgc aattgcaatc aatcagattt tagataaatt caaaacatta     45420
acagaacaag caggaaagat tactagaaaa tatttagaag gtcaagaaat attaactatt     45480
gattatgagt actatgattc attacaagaa tactatattt acctacttag aaatagtgaa     45540
aaaattgaac aaagtttaca agaaattact aagcgtacag gtgaatatgt aaagtaattt     45600
tgatttaaaa acaaaatatg atatactatg tttaaagtag taagcctaca ctagtccgtg     45660
ttatattaat attgaatcgg ataagcgtag gctttattaa tatttaaaaa aaggaaggta     45720
tatcatatta tggcagaaga aattaaaaag gaacaagatg tacaagaaac aactaaagaa     45780
gaaaaaaaag atgttagcaa aatgacaccg gaagaaatag ataattaaa  atatcaagac     45840
aagcaagaaa aagaacaagt tattaacaaa gttattaaag gtgttaatga tacttgggaa     45900
aaagaatata actttgaaga attagactta agatttaaag ttaaaattaa attacctaac     45960
gcacgagagc aaggtaatat atttgcgtta cgttctgctt acttaggtgg tatggatatg     46020
taccaaacag accaagtaat tagagcatat caaatgttag ctacattaca ggaagtaggt     46080
attgaagttc ctaaggaatt ccaagaccct gacgatattt ataacttata tcctttaact     46140
gttatgtatg aagattggtt aggattctta aactcctttc gttactaata gtatagaaac     46200
actagataaa gatatagaac gattgggcgg tatggaatca attgttaaac aacctttatc     46260
tagaaatcta tgggctatta tgaaagagtt taatgtttta cctactgagc aaagatttaa     46320
ggacttagat gattatcaga tagagtttat tattgggaat atgaacagag atgtttatga     46380
acataacaaa caacttaaac aagctcaaaa aggtggaaaa ttcgatagtc aatttgaaga     46440
tgatgatagt agttggtgga atgaatctca tgaagacttt gacccagtac ctgatttctt     46500
agatgctgat gatttagcac aacagatgga agctaaatta tccgatagag ataaggaaga     46560
aagagctaag agaaacgatg cagagttaaa tgatgaaaca gaaggactta ctacacaaca     46620
tctagctatg atggaataca tcagacagaa acaacaagaa ttagatgatg aagtaggaaa     46680
tggtaagact agtgaagatg acgctactat atcacaagat agcgttaata aagcactaga     46740
```

FIG. 19Z sequence.txt

```
agacctagat gatgactggt atatgtaaag ggtggtaggt gatactacca tccttatttt    46800
tttaaaatgg atggtgaata atgatggcaa tgaatgacga ttatagattg gtcttgtccg    46860
gtgatagttc ggatttagag aatagtctaa aggcaataga actttatatg gattctttag    46920
agtctaagaa tattgatgct cctttagata atttcttaaa aaaattaaaa gtaattgcta    46980
aagaagttaa aaatgtacag aacgcaatgg ataaacaaga tggtaaatct gttatatctt    47040
ctaaagacat ggatgaatct attaaatcca ctcaatctgc tacaaagaat ataaatgaat    47100
taagaaaagc tttagatgac cttcaaaaag agaatatatc taaaggtatt gcacctgacc    47160
ctgaagttga aaaagcatat gctaagatgg gtaaagttgt agatgaaact caagaaaaac    47220
ttgagaaaat gtcttcacaa aaaataggtt ctgatgctag tattcaaaat agaattaagg    47280
aaatgaaaac cttaaatcaa gtaactgaag aatacaataa aataagtaaa gattctagcg    47340
caactaaaga ttatacaaaa cgattaagag ctaatcgtaa tatgactaga ggttacatgg    47400
agcgttcaga aggaacagga cgtttgacat atgaccaagg tgcacgagtt agaagtgaac    47460
taggtaaagt aagttcttat gagagccaaa gaaaacaaaa ccaacgtaat ttgggacaag    47520
caagagaaca atatagcaac tatagaaacc aacaacaaga cttgactaaa cgtagagcta    47580
gcggtcaaat taataaggca caatatgaac aagagttagc ttctattaaa caggaaatga    47640
aagctagaga agaacttata tctaactatg agaaattagg agcagaactt gataaaacag    47700
ttcagtatta taagggttca gttcaaaagg atttccaatc tagagacgta gaccaacaaa    47760
gaggaacatt tggtagaatg gttcaagaac gtttgccatc tattggttct catgctatga    47820
tgggtactac agctatggct acaggtttat acatgaaggg tgcctcacta agtgaaacta    47880
atagacctat ggttacatca ttaggtcaaa attccgataa tatggatata gattctgtaa    47940
gaaatgcata tggagacttg tcaattgata acaaattagg ttataatagt actgacatgt    48000
tgaaaatggc tacttcatat gaagcatcag taggacataa aagtgatgag gacacaatgg    48060
caggaactaa acagcttgct attggaggac gttctttagg cattaaagac caagaagctt    48120
atcaagagtc tatgggtcaa atcatgcata ccggcggagt aaattctgat aacatgaagg    48180
aaatgcaaga tgcattctta ggtggtatta acagtcagg tatggttggt cgtcaagatg     48240
aacaacttaa agcactaggt tctatagcgg aacaatcagg agaaggaaga actctaacta    48300
aagaccaaat gagtaatctt actgccatgc aatctacttt tgcagagtca ggaagtaaag    48360
gattacaagg tgaacaaggt gccaatgcta ttaacagtat agaccaagga cttaaaaatg    48420
gtatgaatag ttcttatgct cgtatagcaa tgggatgggg aacgcaatac caaggtcttg    48480
aaggtggata tgatttacaa aaacgtatgg atgaaggtat atctaatcct gaaaacttga    48540
cagatatggc tgatatggct actcaaatgg gtggcagtga aaaagaacaa aaatacctat    48600
```

FIG. 19AA

```
                                     sequence.txt
ttaatagaag  tatgaaagaa  ataggcgcta  acctaactat  ggagcaatct  gatgaaatat      48660
ttaaggactc  taaagaagga  aaactgtcta  aagaagagtt  agctaagaaa  gctaagaaaa      48720
tggaaaaaga  aggtaaaaaa  gaaggagaag  ataacgccac  tgattataaa  gaatctaaat      48780
caggaaaaaa  tgaccaaaat  aaatctaaga  ctgatgataa  agcagaagat  acttatgata      48840
tggctcaacc  actaagagat  gctcatagtg  ctttagcagg  tcttcctgcc  cctatatatt      48900
tagctattgg  tgctatagga  gcatttacag  cttcactaat  tgcatctgca  agtcaatttg      48960
gagcaggtca  cttaattggt  aaaggagcca  aaggacttag  aaataaattt  ggtagaaata      49020
aaggtggtag  ctccggtggt  aaccctatgg  caggtggaat  gcctagtggt  ggtggttcac      49080
ctaagggtgg  aggctcacct  aaaggtgggg  gcactcgttc  tactggagga  aaaatacttg      49140
atagcgctaa  aggtcttgga  ggattcctag  taggtggcgc  aggatggaaa  ggtatgtttg      49200
gcggggagtc  taaaggtaaa  ggatttaaac  aaacatctaa  agaagcctgg  tcaggtacta      49260
gaaaagtatt  taatagagat  aatggtagaa  aagccatgga  taaatctaaa  gatatagcta      49320
aaggtaccgg  tagtggtctt  aaagatatct  ataatgatag  tatatttggt  aaagaaagaa      49380
gacaaaacct  aggagaaaaa  gctaaaggtt  ttggtggcaa  agctaagggt  ctctatggta      49440
agtttgctga  taagtttggt  gacggaggta  aaaatggtat  cctttcacaa  tcaccaaaag      49500
caggtggaag  tggcataggg  aaacttggaa  aacttgcagg  tggacttgga  aaaggagccg      49560
gagttttagg  tgttgctacg  tctgccttat  cattaatacc  tgctttagct  tccggagata      49620
gtaaagctat  cggcggagga  ataggctcta  tgggtggagg  aatggcaggt  gcatcagcag      49680
gagcttctat  aggagcttta  tttggtggtg  taggtcaat   ccctggagct  ttaataggtg      49740
gagctatagg  ttctttcggt  ggaggagctg  ttggtgaaaa  agtaggagac  atggctaaga      49800
aggctaacac  taaagaagga  tggaacctag  gatggactaa  tggagataaa  gacggtaaga      49860
ataaattcca  agattcttta  ttaggaaaac  ctatatctaa  agcatggagt  ggtataacag      49920
gtctctttga  taatgacgct  gaagcatctg  aagaaatag   caaagataag  aaaaaaggcg      49980
ttaaaggtgt  taaggggat   actaagaaga  aagaaaaaat  gacagcagaa  caacttagag      50040
aaaaaaataa  ccaatctgaa  actaagaacc  ttaaaatcta  tagtgattta  cttgatagag      50100
ctcagaaaat  tattgagagt  gctaaaggta  ttaatataga  tggaggaact  tctgatagtg      50160
gttctgatag  tggaggctct  gcatctgatt  taggaggaga  aggtgcagag  aaaatgtata      50220
agttccttaa  aggaaaagga  ctatctgata  accaggtagg  agctgttatg  gggaacttac      50280
aacaagaatc  taaccttgac  cctaatgcta  agaacccttc  aagtggagca  tttggtattg      50340
ctcaatggtt  aggtgctaga  aaaacaggat  tagataactt  tgctaagtct  aaaggtaaaa      50400
aatccagtga  tttagatgtt  caattagact  acctatggaa  agaaatgcaa  tctgattatg      50460
aaagtaaaaa  cctcaagaat  gcaggttgga  gtaaaggtgg  aagtctagaa  cagaatacaa      50520
```

FIG. 19BB sequence.txt

| | | | | | | |
|---|---|---|---|---|---|---|
| aagcatttgc | taccgggttt | gaacgtatgg | gagcaaatga | ggctatgatg | ggtactcgtg | 50580 |
| ttaacaatgc | caaggaattc | aagaagaaat | atggaggttc | cggcggagga | ggcggagggg | 50640 |
| gcgctatgtc | ctctacttac | caagaagcta | tgagtaaccc | tgtattaacc | actggttcca | 50700 |
| actacagagg | ctctaacgat | gcttctaatg | cttctacaac | taacagaata | acagttaatg | 50760 |
| ttaacgttca | aggcggaaat | aatcctgaag | aaactggaga | cattatcgga | ggaagaatta | 50820 |
| gagaagtttt | agacagcaac | atggatattt | ttgcaaatga | acataagaga | agttattagt | 50880 |
| gattttgtat | tgacacaaga | gtagtatagt | agtatactac | tcttatacat | ataaaaataa | 50940 |
| aaggaagtat | gtgtatatga | aaagattaag | aagacctaag | gtaagaatag | agatagttac | 51000 |
| agatgataat | acatttacat | taagatttga | agatacacgt | gactacaatg | gtgatgagtt | 51060 |
| tggagctaaa | cttttaggct | ttcaaactaa | aaactctatg | gaagatgata | gttctgtatt | 51120 |
| ccaaatcaat | atggcaggag | atacttactg | ggataagtta | gttatggcta | atgatataat | 51180 |
| cagaatattt | attacaccta | atgatgaccc | taatgataaa | gaaggtcgtc | aagaacgttt | 51240 |
| aatacaagta | ggtatggtat | cacaagtatc | aaaagtaggt | agctatggta | atgaccaaac | 51300 |
| tcaatttaga | ataacaggtc | aatcttttgt | aaaacccttt | atgaaatttg | gattaggtgt | 51360 |
| tattcaagag | gttcaagctg | tattacctga | agtaggttgg | cttattgatg | gtgatgggga | 51420 |
| taatgaagta | aaatttactg | gtagttcggc | acatgaagtt | atgacaggta | ttatccgaag | 51480 |
| atttgttcct | tatatgaaat | ataactatac | agaaaaaaca | tataatacaa | tagatagtta | 51540 |
| ccttgattat | gatgatttaa | gtagttggga | tgaatttgaa | aatctgacag | aagtatctgc | 51600 |
| ttttactaat | tttgatggct | cattaaaaca | gttgatggat | atggtaacag | ctagaccttt | 51660 |
| caatgagtta | ttcttttaaaa | actccgaaaa | aacaccaggt | aaagcacagc | ttgtttttaag | 51720 |
| aaaaactcct | tttaatccta | ctgagtggag | agctttggat | atgattaaag | tacctactga | 51780 |
| agactttatt | gaagaggatg | tgggtaaaag | tgacgtagaa | acatactcta | tatttacagc | 51840 |
| tacacctgca | ggtatgttaa | aagaacttaa | tggtgatgta | ttttctaaac | cacaatttca | 51900 |
| ccctgaattg | actgatagat | atgggtatac | taaatttgaa | gtagagaata | tctatcttag | 51960 |
| tactaaatca | ggttcagcta | ctgaagactc | agattcttcg | ggtgatgata | atggtactga | 52020 |
| aagaggaact | tattctaaaa | ttatgaaaga | tttaagtaac | tatggaagag | ataatatatc | 52080 |
| taaggtata | gataagtata | caagtaaatt | atcctcaaaa | tataaaaact | aaaaaagcc | 52140 |
| caagctaaaa | aaattataga | gaagtttgtc | aaagaaggaa | aagtaacaga | aaagaatat | 52200 |
| gaaaagataa | caggtaataa | ggtagatgat | gaattaacat | cagataacag | accgaagttg | 52260 |
| acaaagata | aattaaagag | tatactaaaa | gagaagttta | aaacacaaga | tgattttaat | 52320 |
| aattctaaaa | aagaaaaaa | gctaaaacag | atgcacttaa | agaattgaca | actaaatatc | 52380 |

FIG. 19CC sequence.txt

| | | | | | | |
|---|---|---|---|---|---|---|
| gttttggtaa | taaaacacat | gctacaactt | tgttagatga | atatattaaa | tacaaaggag | 52440 |
| aaccacctaa | tgatgaggct | tttgataaat | atcttaaagc | tattgaaggt | gttagtaata | 52500 |
| tagctacaga | tacaggttca | gatgcaagtg | atagtccttt | agttatgttc | tctagaatgc | 52560 |
| tatttaactg | gtatcatggc | aaccctaact | tctatgcagg | agatattatt | gttttaggag | 52620 |
| accctaagta | tgacctaggt | aaaagattat | ttattgaaga | taagcaacga | ggagacactt | 52680 |
| gggagttcta | tattgaatct | gtagaacata | aattcgatta | taaacaaggg | tattatacaa | 52740 |
| ctgtaggagt | aactagaggt | ttaaaagatg | ctattctaga | agacggtaaa | ggtagtcctc | 52800 |
| atagatttgc | aggactatgg | aaccaatcat | cagacttcat | gggaggtctt | atgggtgaag | 52860 |
| atacttctaa | agaacttaaa | gaaaaaggtg | tatcagagaa | acaaagcagt | ggagataaag | 52920 |
| acggtggctc | tgatagtggt | ggcgctcaag | atggtggctc | tttagattca | cttaaaaaat | 52980 |
| ataatggcaa | acttcctaag | catgacccaa | gttttgttca | acctggtaac | cgacattata | 53040 |
| agtatcagtg | tacatggtat | gcttataata | gaagaggtca | attaggcatt | cctgtgcctt | 53100 |
| tatgggggga | tgccgccgac | tggataggcg | gtgctaaagg | agcaggttat | ggagtaggta | 53160 |
| gaacacctaa | acaaggtgct | tgtgttatat | ggcaaagagg | agtacaagga | ggtagtgctc | 53220 |
| aatatgggca | tgttgctttt | gttgagaaag | ttttagacgg | aggtaaaaaa | atatttatct | 53280 |
| ccgaacataa | ctgggctact | cctaatggat | atggtactag | aacaatagat | atgagctcag | 53340 |
| ctataggtaa | gaatgctcaa | ttcatttacg | ataagaaata | aaggaggata | gtctatggca | 53400 |
| acagataaag | aagctaaaga | tgttattgac | aagtttatag | ataatgtatt | taattttgat | 53460 |
| gtattaacta | tggaaagagt | taaagaaaaa | gatgaagaaa | ttaaaaaaat | aactacagat | 53520 |
| gatatgtatg | aaaaggttgt | gtatatacga | ccttatgttg | gagtaataca | aagccttaac | 53580 |
| cctcaacatg | tacagtatga | atcatttct | aataatggtt | atgatataga | ggcagaatta | 53640 |
| agtttcagga | aagtaagtta | tttagttgat | aaagggtcta | tacctacaga | ttctttatct | 53700 |
| actttaacag | ttcatttagt | agaaagaaat | caagagctat | taatagatta | ctttgatgag | 53760 |
| atacaagatg | tgttgtacgg | agaatatatg | gaagaagaat | atgtattcga | tgaagatgta | 53820 |
| cccttaagta | cgatactagc | attagactta | aatgataatc | ttaaatcctt | atcaaatata | 53880 |
| aagtatatgt | tcaaaggtgc | tcctaaagag | aatccatttg | gaacagataa | agatgtttat | 53940 |
| atagatactt | ataacttatt | atactggtta | tatttaggtg | aagatgaaga | gttagcatac | 54000 |
| cctatgaata | ttaattattt | ctttacagag | ggtagattct | ttactatatt | tggtaaaggg | 54060 |
| cataagtaca | aggtagatgt | tagtaaattt | atagttggag | atatattatt | ctttggtaga | 54120 |
| agtgatacta | atataggtat | ttatgtaggt | gatggagagt | ttatatctat | gataggtaaa | 54180 |
| tttcctaaag | atgaaacacc | tataggaaaa | tataaacttg | atgattactg | gaatgaattt | 54240 |
| aacggaagag | ttatgagatt | cgatgaagag | gtgtatattt | aatggtagta | agattccaat | 54300 |

FIG. 19DD

```
sequence.txt
cttccatggg aagaagttta aaaagagtag attcagatga tttaaatgta aaaggattag    54360
ttttagctac agttagtaaa attaattata aatatcaatc agtagaagtt aaagttaaca    54420
acctaacttt gggaagtcgt ataggtgacg atggtagctt agctgtacct tatcctaaat    54480
ctttcatagg aagaacaccg gaaggaagcg tattcggtac aaaacctctt attactgaag    54540
gttctgtagt attaataggg ttcctaaatg atgatataaa tagccctata atcttaagtg    54600
tttacggtga taatgaacaa aataaaatga ttaatacgaa tcctttagat ggaggtaaat    54660
ttgatacaga cagtgtttat aaatatagta gtgcactata tgaaatttta ccatctttaa    54720
attataagta tgatgatgga gaaggtacaa gtattaagac ctataatggt aagtcattct    54780
tctccatgac atcaggtgaa gaagaaaaac ctcaggcaac agatttttac actggaactg    54840
agtatcaaga tttatttact tcttattatg gtaataagac attaattgag cctagaatac    54900
aaaaggctcc taatatgtta tttaaacatc aaggagtttt ttatgatgat ggtacaccgg    54960
ataatcatat aactacttta tttatatctg aaagaggaga tataagagct tcagttttaa    55020
atacagaaac acagaaaaga accacacagg aaatgtcaag tgatgggtct tatagggtta    55080
tcaaacaaga tgacgattta atgttggatg aagctcaagt ttggattgag tatggtatta    55140
gtgaagataa taaatttttat attaaaaatg acaagcataa atttgaattt actgatgagg    55200
gaatctatat agatgataag cctatgttag aaaacttaga tgagagtata gcagaggcta    55260
tgaagaattt gaatgaaata caaaaagaac tcgatgatat aaactacctt ctcgagggtg    55320
tgggtaaaga caatttagaa gaattaatag agtctacaaa agagtctata gaagcttcta    55380
aaaaagcaac ttcagatgtc aatagactta caactcagat agcagaagtt agtggtagaa    55440
ctgaaggtat tataacacag ttccaaaaat ttagagatga gactttttaaa gattttttatg    55500
aagatgcttc tactgttatt aatgaagtaa atcagaattt ccctactatg aaaacagatg    55560
ttaataccttt aaagactaaa gttgataacc tagagaaaac tgaaatacca aacattaaaa    55620
ctagattaac agaactagag aacaataata acaatgccga taaaataatc tcagatagag    55680
gagagcatat aggtgctatg atacagttag aagaaaatgt tactgtaccg acaagaaact    55740
atatgccaat accttggagt aaagttactt ataataatgc agagtttttgg gattctaata    55800
atcctactcg attagtagta cctaaaggaa taacaaaagt aagagttgca ggtaatgttt    55860
tgtgggactc taacgccaca ggacaacgta tgttgagaat attgaaaaat ggtacttata    55920
gtctagggtt accttataca agagatgtag ctatatctac agcccctcag aacggtacta    55980
gtggagttat tcctgttaaa gaaggagatt actttgagtt tgaagctttc caagactcag    56040
aaggtgacag acaattcaga gcagaccctt atacatggtt tagtattgaa gctatagaat    56100
tagaaactga aactatggag aaagacttta tgcttatagg acatagagga gcaaccggat    56160
```

FIG. 19EE sequence.txt

```
acacagatga gcacacgata aaaggatatc aaatggcttt agataaaggt gcagattata    56220
tagaattgga tttacaatta acaaaagata ataagttatt gtgtatgcat gattctacta    56280
tagacagaac aacaacagga acaggtaagg taggagatat gactttatct tatatacaaa    56340
ctaactttac atctcttaat ggtgagccga taccatctct tgatgatgta ttaaatcatt    56400
ttggaacaaa agttaaatat tatatagaaa ctaaacgtcc gtttgatgct aatatggata    56460
aagaattatt aactcaatta aaagcaaaag gattaatagg aatagggtca gagagattcc    56520
aagtaattat tcaatcattt gctagagaat cattaattaa tattcataat caattctcta    56580
atatacecttt agcttattta acaagtacat tctctgaaag tgaaatggat gattgtttaa    56640
gttatggttc ttatgctatt gctcctaagt atacaactat aactaaagaa ttagtagatt    56700
tagctcatag taaaggtctt aaagtacacg catggacggt aaacacaaaa gaagaaatgc    56760
aaagcttaat acaaatgggt gtagatggat tctttacaaa ctacttagat gaatataaaa    56820
agatttaata ttaaagacct attaatttag gtctttttt agttgtaatt taaactagtt    56880
cgtgatatat tagtagtatg agatttatat acatactgaa aaggagagga taaaatgcca    56940
caatcagatg gaataagtaa tcttcataga atagctttac gcttccctaa agaaggcggt    57000
ggttatgata tgtatagatt taaagttaac cccgagaact acacaataga ttcaccacaa    57060
cgtacgacag caattaaaac aaaatcagat attgtaatag aagattatgg taaagacata    57120
gaagttatta acttcacagg tacaactggt tttagacctg ttagagaagc agacggatta    57180
aaaacaggta agcagaaaat ggaagagtta caaagtagag ttagtgaata tgctatgcaa    57240
ggtggtagtg gtaatgtaag tggttcttac ttacaatttt ttaactttac agatgatagc    57300
tactataaag ttcatttagc tcctcaaggg ttaaagataa ctaggtctaa agatgaacca    57360
ttactttta gatatgaaat aacattagta gttattggtt cgttaacaga agcagataga    57420
agtgctgtaa caacagaaga gtttggtaat gttaaaccta atgcttctca aagagtagat    57480
gagggtataa aagaattaga taaaaatgct cgtaaaacga gagatagaaa taatcaagaa    57540
atatctaaaa gagaaaatac aatacctaaa tctacaggag ataatacgaa tgagggtaat    57600
agacttaagc aaagcttccc tagtagttct atatataatc ctagacaatc tactaacgga    57660
ttaaaaggga atattgacaa tatggctctg ataataggtt acggtgatgg aggtgtatct    57720
agctaatgaa taattttata ccacaacctc aaggtctact cagattttta aatgccctag    57780
atgcagattt aacttcttct cacatgaatt tactggatga agaggtatca tttgtatcta    57840
aattttacac accacagcta caattaagtg aattagcaaa aaaagtattg acaaatataa    57900
agacagatga tatacctgta ttagaaagag aatttaatga taatacaatt atccataaag    57960
ctaatgatac attactaaaa gtacaggctc caagaatgta tatgattcta cagtctattg    58020
tgcttgaagc atatgctatt gttaattgct ttgtagaaaa tccaagctct ttaaaatact    58080
```

FIG. 19FF sequence.txt

| | | | | | | |
|---|---|---|---|---|---|---|
| taactgaaga | agatgttagt | ataacacgag | aaaatttaaa | ttatgtagct | gactacttag | 58140 |
| gtaactatga | tgactacaat | agtgttgtct | tagacttaag | agatttagac | ttatgtttta | 58200 |
| gtgctataga | attacaatta | cctctaatta | aaaaggaggc | taatgtataa | tgagatttaa | 58260 |
| gaaacacgta | gttcaacatg | aagaaacgat | gcaagcaata | gcacagagat | actatggtga | 58320 |
| tgttagttat | tggatagacc | tagtagagca | taataatcta | aagtatccct | atttagtaga | 58380 |
| aactgatgaa | gaaaaaatga | aagaccctga | acgattggct | tctacaggtg | atacactgat | 58440 |
| tatacctata | gaatctgatt | taacagatgt | atcagcaaaa | gaaattaatt | ctagagataa | 58500 |
| agatgtacta | gttgaattag | ctttaggaag | agatttaaat | attactgcag | atgaaaagta | 58560 |
| ttttaatgaa | catggtacta | gtgataatat | actagcattc | agcacaaacg | gtaatggaga | 58620 |
| tttagatact | gtaaaaggca | tagataatat | gaaacagcaa | ttacaggcac | gtttattaac | 58680 |
| tcctagaggt | tctttaatgc | tacatcctaa | ttatggttca | gatttgcata | atttatttgg | 58740 |
| tcttaatata | cctgaacaag | ctacattaat | agaaatggaa | gtattgagaa | cattaacatc | 58800 |
| agataataga | gtaaaatctg | ctaatctaat | tgattggaaa | atacaaggta | atgtttattc | 58860 |
| aggtcaattt | tcagtggaaa | taaaatctgt | tgaagaatca | ataaattttg | tcttaggaca | 58920 |
| agatgaggaa | ggaatttttg | ctttatttga | ataggaaagg | attaaattat | gaaaactaga | 58980 |
| aaattaacta | acatactatc | aaaattaata | gataagacaa | tggcaggtac | aagcaagata | 59040 |
| acagacttta | ctcctggttc | agcttcccgt | tcattattag | aagctgtatc | attagagata | 59100 |
| gagcaattct | atatcctaac | aaaagaaaat | attgattggg | gtatacaaga | aggtatcatt | 59160 |
| gaagcttttg | attttcaaaa | aagacaatct | aaaagagctt | atggtgatgt | tactattcaa | 59220 |
| ttctaccaac | ccttagatat | gagaatgtat | atacctgcag | gaacaacttt | tacttcaaca | 59280 |
| cgacaagaat | atcctcagca | atttgaaaca | ttagttgatt | attatgcaga | gcctgattct | 59340 |
| actgagattg | ttgttgaagt | ttattgtaaa | gaaacagggg | ttgcaggtaa | tgttcctgaa | 59400 |
| ggaacaatta | atactatagc | atcaggttct | agtttgatta | gaagtgttaa | taacgagtat | 59460 |
| tcttttaata | caggaactaa | agaagagagc | caagaagact | ttaagcgcag | attccactct | 59520 |
| tttgtagaat | ctagaggtag | agcaactaat | aaatcagtaa | gatatggtgc | attgcagata | 59580 |
| cctgatgtag | aaggtgttta | tgtttatgaa | gaaacaggac | atattacagt | atttgctcat | 59640 |
| gatagaaatg | gtaatttatc | agataccta | aagaagata | taatcgatgc | tttacaagac | 59700 |
| tatagaccaa | gtggtataat | gttagatgtt | acaggtgtag | aaaaagaaga | agttaatgtt | 59760 |
| tctgctacag | taactatatc | taataaatct | agaattggtg | atacattaca | aaaacatatc | 59820 |
| gaaggtgtta | ttagaagcta | tttaaataat | ctaaaaactt | ctgatgactt | aataattaca | 59880 |
| gaccttattc | aagctataat | gaatattgat | gatgtactaa | tatatgatgt | gtcatttgat | 59940 |

FIG. 19GG sequence.txt

| | | | | | | |
|---|---|---|---|---|---|---|
| aacctagatg | agaacattat | agtaccacca | caaggaatta | ttagagcagg | agaaataaaa | 60000 |
| gtagaactaa | agtaaagaga | ggtgaaactt | aagtcgtggc | taattttta | aagaatcttc | 60060 |
| atccattatt | aagaagagat | agaaacaaaa | aagataatca | agaccctaac | tttgctctca | 60120 |
| tagatgcact | caatgaagag | atgaatcaag | tagagaaaga | tgctatagaa | agtaaattac | 60180 |
| aatcctctct | aaagacatct | acaagtgaat | atttagataa | gtttggggat | tggtttggag | 60240 |
| tttatcgtaa | gactgatgag | aacgatgatg | tttatagagc | aagaattata | aaatatttac | 60300 |
| tcttgaaaag | aggaactaat | aatgctataa | tagatgctat | aaaagattat | ttaggtagag | 60360 |
| atgatattga | tgtaagtgta | tatgaacctt | ttacaaatat | tttctatacg | aacaaatcac | 60420 |
| atttaaatgg | tgaagaccac | ttaatgggat | actattatag | atttgctgtt | attaatgtct | 60480 |
| ctataggtga | ttatttccct | gtagagatta | tagatgtaat | taatgaattc | aaacctgcag | 60540 |
| gtgtaactct | gtatgtcact | tatgatggag | cttctactat | tagaggtgga | gcaattatta | 60600 |
| agtggttaga | tgggttacct | aaaatagaaa | cataccaaga | gtttgatagg | tttacaggat | 60660 |
| acgatgatac | attctatggt | catattaaca | tgaatcaaag | taaagatact | gataatagta | 60720 |
| catcagatat | ttttaaaaca | aaccatagct | taattaatag | tttagatgtt | ttaacaggtt | 60780 |
| cctctagcgt | aggtagacag | tatgttaact | atggatatat | aacatcatat | gtttataatc | 60840 |
| caggtatgac | atcttctgta | aatcaaataa | gcgctagtac | agaaggtaga | gggcaagaag | 60900 |
| tacctactga | ctattatatg | tatactagta | ctaagaataa | caatacagta | gaacttagta | 60960 |
| tgcaaactac | ttccggtgtg | tcttatttat | ataataactt | taattttagg | gattatatga | 61020 |
| gtaaatatag | acctcaagta | aatttacaat | ctgatgaggc | tagaagaatt | gtatctgatt | 61080 |
| atataaaaga | attaagtatt | gattattatc | tcagtgctgt | aatacctcct | gatgaaagta | 61140 |
| tagaaattaa | attacaagtt | tatgattttt | ctattaatag | atggcttaca | gtatcaatta | 61200 |
| ataatttatc | tttctatgaa | aaaaatatcg | gtagcaatat | aggatatata | aaagattatt | 61260 |
| taaacagtga | attaaatatg | tttactagat | tagagataaa | cgcaggtaaa | agagattcag | 61320 |
| tagatattaa | agttaattac | ttagatttaa | tgtttattta | ctatgaacga | ggtatttata | 61380 |
| caataaaacc | ttataaagcc | ttagtagaaa | attatttaga | tatatctaga | gagacttacg | 61440 |
| tagaggcatt | taaaatatca | tcgttatcta | atggagatat | tataactaaa | acaggttatt | 61500 |
| tacctatagg | ttatctaaga | gtatcaggag | acattgataa | cttaagtaac | catatagaaa | 61560 |
| ttattaccat | agataataat | actaatagta | ttacaagtac | tcttttagaa | gatgactcta | 61620 |
| atagtttgat | attatcatat | ggtaacgtca | aaaccaatat | acacagtttt | gaattaaata | 61680 |
| gtgatgcttc | aatttcaaat | attaaatttg | aatactctta | ttatggtgat | gcttgggaag | 61740 |
| aactgacagt | attaactgaa | atatctgagg | gtgaaactat | agtacctaat | atactaatag | 61800 |
| atttatatgg | attacagaca | gtagattatt | ctaatataaa | tccaatgtca | aaagtatcat | 61860 |

FIG. 19HH sequence.txt

| | | | | | |
|---|---|---|---|---|---|
| tacgttctat | ttggaatgtt | aaattaggtg | aacttaataa | taaagaaggt | tctttatcaa | 61920 |
| atatgcctaa | cgattatttt | aatgctgtat | ggcaagatat | agataaacta | tcagatattg | 61980 |
| atttaggctc | tatgagaatg | attaaagaca | ctgagggtgg | agtatttgat | ggagctacag | 62040 |
| gtgaaattat | taaagctact | ttatttaatg | ttggtgtata | tactgattta | gatatgttag | 62100 |
| cctacacttt | aactaactat | actgaaccaa | taactttagg | ttctagtcga | ttaataagtg | 62160 |
| aacttaaaga | agaactatta | acatcagaat | catttaatgt | cgataataga | attaaagtaa | 62220 |
| ttgactcaat | atctgagcag | ttacctaata | acaatatatt | aagtaactct | taccaaacac | 62280 |
| aaactattac | acagaatgga | tttgctaagt | ataatttgaa | agaacctata | gagcagagaa | 62340 |
| aacaatacaa | tctaagaata | catggagatt | taaagaagg | attagaaaga | ttagctatag | 62400 |
| gtaattctaa | tggttcattt | aatgaagtat | ttgtttaccc | tgaaaatatt | aaagatggta | 62460 |
| tagtagatat | tacttacact | tctagagatg | ataattacgc | agaagggaaa | caaagactta | 62520 |
| ataatgatta | tagagtttac | gctcaaccat | acgatagtga | agtagtaaca | atttacagtt | 62580 |
| tagagttaat | aaaagtttaa | taaataagtt | gacagaaagt | taataatatg | gtatacttat | 62640 |
| aaagtaatat | ttagtgggta | taccatgtta | tattaataaa | gaaaacaaca | gatgaaagga | 62700 |
| attaaaaaat | atggcaattg | caacgtataa | ttctcatgtt | gagttagcaa | aatatctagt | 62760 |
| tagtaaagct | gattcagttt | acttaacaat | tggaaagagc | acaccgtggt | ctaatgaaac | 62820 |
| aaacccaccg | caacctgatg | aaaatgcaac | agtattacag | gaggttatag | gatacaaaaa | 62880 |
| agctactaaa | gtaactttag | ttagaccttc | taaatcacct | gaagatgata | ataagaattt | 62940 |
| aatttcttat | ggtaataaat | catgggtaga | agtaacacct | gaaaatgcta | aagatgaagg | 63000 |
| agctaaatgg | gtttacttag | aaagcagtat | tgttggtgac | gaactacctc | ttggaacata | 63060 |
| tagacaagta | ggatttgtta | tggacttagt | agcaaaaagt | ggtattagta | aatttaactt | 63120 |
| agtacctagt | gaagtagaat | caactggaac | attattattc | tttgataata | aacaattcca | 63180 |
| aaatagaagt | gagcaaacaa | ctgctaaaga | aagatttatt | gtagaagttt | aaagaaaggg | 63240 |
| agataattct | aaatggcaat | taatttttaaa | ggttcacctt | atttagatag | atttgacccg | 63300 |
| tctaaagata | gaacaaaagt | attatttaat | cctgatagac | ctctacaaca | ggcagaatta | 63360 |
| aatgaaatgc | agtctataga | ccaatattat | ttaaaaaatc | taggagacgc | tatttttaaa | 63420 |
| gacggagata | aacaatcagg | tcttggattc | acattatctg | aagataatgt | attgacagta | 63480 |
| aatcctggtt | atgtatatat | caacggtaaa | ataagatatt | acgataatga | cgattcagtt | 63540 |
| aaaataactg | gcgtaggtaa | agaaactatc | ggtattaagt | taacagaacg | tattgttaca | 63600 |
| cctgatgaag | atgctagcct | actagaccaa | actagtggag | taccaagtta | cttctctaaa | 63660 |
| ggtgcagata | gattagaaga | aaagatgtca | ttaactgtta | atgaccctac | atcagcaact | 63720 |

FIG. 19II sequence.txt

| | | | | | | |
|---|---|---|---|---|---|---|
| atttatactt | tcatggacgg | agatttatat | atccaatcaa | ctaatgctga | gatggataaa | 63780 |
| atcaataaag | tattagctga | acgtacttat | gatgagtcag | gttcatataa | agtaaatggt | 63840 |
| tttgagttat | tctcagaagg | taatgctgaa | gatgatgacc | acgtttctgt | agttgtagat | 63900 |
| gcaggtaaag | cctatgtaaa | aggttttaaa | gtagataaac | ccgtatcaac | aagaattagt | 63960 |
| gtacctaaat | cttatgactt | aggaacagca | gaaaatgaaa | gtactatctt | taataagtct | 64020 |
| aataattcta | ttagtttagc | taatagccct | gtaaaagaaa | ttagacgtgt | tacaggtcaa | 64080 |
| gtacttattg | aaaaagaacg | agttacaaga | ggagcccaag | gtgatggtca | agattttctt | 64140 |
| tcaaataata | cagcatttga | aattgtaaaa | gtttggactg | aaacaagccc | tggagttact | 64200 |
| acaaaagagt | ataaacaagg | agaagacttc | agattaacag | atggtcaaac | gattgactgg | 64260 |
| tcacctcaag | gtcaagaacc | ttcaggaggt | acttcatact | atgtttctta | taaatataat | 64320 |
| aaacgtatgg | aagtcggtaa | agattatgaa | gtaacaactc | aaggagaagg | gttaagtaag | 64380 |
| aaatggtata | ttaattttac | acctgaaaat | ggtgctaaac | ctattgacca | aacagtagta | 64440 |
| ttagtagatt | atacttatta | cttggctcgt | aaagattcag | tgtttattaa | taagtatggt | 64500 |
| gatattgcaa | tattacctgg | tgaacctaat | attatgagat | tagttacacc | accattaaac | 64560 |
| acagaccctg | agaatttaca | attaggtaca | gttacagtat | tacctgattc | agatgaagcc | 64620 |
| gtatgtattt | catttgcaat | cactagattg | tctatggaag | acttacagaa | agttaaaaca | 64680 |
| agagtagata | acttagagta | taaccaagca | gtaaatgcct | tagatgatgg | tgctatggaa | 64740 |
| ggacagaacc | ctctaacatt | acgttcagta | tttagtgaag | gtttcattag | tcttgataaa | 64800 |
| gcagatatta | cccatcctga | cttcggaata | gtatttagtt | ttgaagacgc | agaagctact | 64860 |
| ctagcttata | cagaagccgt | taaccaacct | aaaattattc | ctggagatac | aacagctcat | 64920 |
| atttggggta | gattaatttc | agcaccattt | actgaggaac | gtacaatcta | tcaaggtcaa | 64980 |
| gcatcagaaa | cattaaatgt | taacccttat | aatatcccta | ataagcaagg | tgtacttaag | 65040 |
| ttaacaccta | gtgaggataa | ttggattgat | actgaaaatg | ttacaattac | tgagcaaaaa | 65100 |
| actaagaaag | taactatgaa | acgattttgg | agacacaatg | aaagttacta | cggtgagact | 65160 |
| gaacactact | tgtactctaa | tttacaatta | gacgcaggtc | aaaagtggaa | aggtgaaact | 65220 |
| tacgcttatg | acagagagca | tggtcgtaca | ggtacattac | tagaatcagg | cggtcaacgt | 65280 |
| actttagaag | agatgattga | attcattaga | attagagatg | tatccttcga | ggttaaaggt | 65340 |
| ctaaacccta | atgataataa | cttatattta | ttatttgatg | gtgtaagatg | tcctattact | 65400 |
| cctgcaactg | gttacagaaa | aggttctgaa | gatgggacta | ttatgacaga | tgcaaaagga | 65460 |
| acagctaaag | gtaaatttac | tattcctgca | ggtattcgtt | gtggtaaccg | agaagttaca | 65520 |
| ctcaagaatg | ctaactctac | aagtgctaca | acttacacag | ctcaaggacg | taaaaaaatc | 65580 |
| gttcaagata | ttattattag | aactcgtgta | acagtaaact | tagtagaccc | gttagcacaa | 65640 |

FIG. 19JJ sequence.txt

```
tcattccagt atgatgagaa cagaactata tcatcattag gtttatactt tgcttctaaa     65700
ggagataagc aatctaacgt tgttatccaa attagaggta tgggtgacca aggttatcct     65760
aataaaacaa tctatgcaga gacagttatg aatgcagatg atattaaagt atctaataat     65820
gctagtgctg aaactagagt atactttgat gaccctatga tggcagaagg cggtaaagaa     65880
tacgctattg ttattattac tgagaacagt gattatacaa tgtgggtagg tactagaact     65940
aagcctaaga ttgataaacc taatgaggtt atctcaggta atccatatct tcaaggtgtg     66000
ttattcagtt catcaaacgc atcaacatgg actcctcatc aaaactctga ccttaaattt     66060
ggtatctata cttctaaatt taatgaaaca gcaacaattg aattcgaacc aattaaagat     66120
gtatctgcag atagaatagt tcttatgtct acgtacttaa ctcctgagag aacaggatgt     66180
acatgggaaa tgaaattaat tctagatgac atggcatctt ctacaacatt cgaccagttg     66240
aaatgggaac ctattggtaa ctatcaagac ttagatgttt taggtctagc aagacaagtt     66300
aagttaagag caactttcga atctaataga tatatctcac cattaatgag ctctagtgat     66360
ttaacattca ctacattctt aacagagtta acaggttcat atgttggtag agctattgat     66420
atgacagagg ctccttacaa tacagtaaga tttagttatg aagctttctt acctaaaggt     66480
actaaagttg ttcctaagta ttctgcggat gatggaaaaa cttggaaaac atttactaaa     66540
tcccctacaa ctactagagc caataatgag tttacacgct atgtcattga cgagaaagta     66600
aaatcatcag gaacaaatac taaactacaa gttagattag atttatcaac tgaaaatagc     66660
tttttacgtc ctcgtgttcg tagacttatg gttactacta gggatgaata aactagaggg     66720
gttgattgac ccctctttat ttaataagga gagatttata tgcctagaga agttagagac     66780
ccttattctc aagctaaatt atttatacct acagttgagg aaaaatcaat taaggaatta     66840
gaaaaaacat acaaagaaaa aattgatgaa gctactaagt taatcaatga attaaagaaa     66900
gagagaggag aaaaatagat ggcatttaac tacacgcctc ttactgaaac acagaagtta     66960
aaagatatgt atcctaaagt taatgatata ggtaacttt taaaaacaga agttaaccttt    67020
agtgatgtaa aacaaatatc acaacctgac tttaataata ttttagcatc tatacctgat     67080
agtggtaact actatgtaac taattcaaaa ggtgctccta gtggagaagc tacggcagga     67140
tttgtaagat tggataaacg aaatgtaaat tattataaaa tttattattc accatatagt     67200
agtaataaaa tgtatatcaa gacttatgct aatggtactg tatatgattg gattagtttt     67260
aaattagatg aaggtaactt atacaatgaa ggtaatactt tgaatgtaaa ggaacttact     67320
gaatctacaa ctcaatatgt aacactagtt aatcctccaa aagagaactt aaatacaggt     67380
tgggttaatt acaaagaaag taaaaatggt gtttcttctt tagtagaatt taacccagtt     67440
aactctacct caactttcaa gatgataaga aagttaccag tacaagaaca aaagcctaac     67500
```

FIG. 19KK sequence.txt

| | | | | | |
|---|---|---|---|---|---|
| ttattgaaag | atagtttatt | tgtttatcct | gaaactagct | cttcaaatat | taaaacagat | 67560 |
| aattggaata | cacctccttt | ttggggatac | acagctaata | gtggtcgttc | aggggttaga | 67620 |
| tttagaggag | agaatactat | acagattgat | gatggtagta | gcacatatcc | tactgcaatg | 67680 |
| actaatagat | ttaagatggg | taatgagctt | tctgtaggtg | atacaattac | tgtatctgta | 67740 |
| tatgctaaaa | ttaatgaccc | tgcattactt | aaagataact | tagtttactt | tgaactagcg | 67800 |
| gggtatgata | tggtagatag | aactgataat | ccttatacag | gaggacgtag | agaaataaca | 67860 |
| gcaagtgaga | taacaactga | gtggaaaaag | tactccttca | cattcacgat | acctgaaaat | 67920 |
| acaattggag | catcaggcgt | taaagttaat | tacgtatctt | tactcttaag | aatgaattgt | 67980 |
| tcatctagta | aaggtaatgg | tgctgtggta | tactatgctc | tacctaaatt | agaaaaatca | 68040 |
| tctaaagtta | caccgtttat | cacacatgca | actgatgttc | gtaagtatga | tgagatttgg | 68100 |
| tctaactggc | aagaagttat | tagtaaagat | gaattaaaag | gtcactctcc | tgtagatata | 68160 |
| gaatataatg | attactttaa | gtaccaatgg | tggaaatctg | aagttaatga | aaagagttta | 68220 |
| aaagatttag | ctatgacagt | acctcaagga | tatcatacat | tttattgcca | aggctctatt | 68280 |
| gccgggacac | ctaggggacg | ttctattaga | ggaaccattc | aggtagatta | tgacaaaggt | 68340 |
| gaccctaca | gagctaataa | gtttgttaaa | ttattgttta | ctgacacaga | aggtatacct | 68400 |
| tatacattat | actacggagg | gtataatcaa | ggttggaaac | tcttaaagca | atcagaaact | 68460 |
| tctactttac | tatgggaagg | tactttagat | tttgggtcta | cggaagctgt | taacttaaat | 68520 |
| gactcattag | ataattatga | tttaattgag | gtaacttatt | ggactcgttc | agcaggacat | 68580 |
| ttttctacaa | aaagattaga | tataaaaaat | acatcaaatt | tactgtatat | tagagatttt | 68640 |
| aatatttcaa | atgatagtac | aggttctagt | gtagactttt | ttgaagggta | ttgcactttt | 68700 |
| cctactagaa | catcagtaca | acctggtatg | gtaaaatcta | taactttaga | cgggtctaca | 68760 |
| aatacaacaa | aagtagcatc | atggaatgaa | aaggaacgta | taaaggtata | caatattatg | 68820 |
| ggaattaata | gaggataaag | aaaggtggaa | taaaaaaaac | tatggctgtt | aaatatgata | 68880 |
| taggtaataa | tgagatagta | ttacatttaa | gagaaggtaa | atatataaca | gggtttacaa | 68940 |
| cagtaggagg | gtatgataag | gagttaggac | aagtaaaagt | taatagagaa | atcttacctg | 69000 |
| cttacttctt | tgataatttt | gcctatgaaa | gatacttgta | ttatagtaaa | cctgaagagg | 69060 |
| ttatagagaa | taaaaactat | gtaccacctc | aaatcaataa | tggtgatgag | gaatctcaac | 69120 |
| aaaatactgt | acctaaagaa | caatatgata | gtttaaaaga | agaactagaa | cttatgagaa | 69180 |
| aacaacaaga | agctatgatg | gaaatgcttc | aaaaactctt | aggtcaaaag | gggtaataat | 69240 |
| aaatggcatt | aaattttact | acaataacgg | aaaacaatgt | tattaaagac | ctgactactc | 69300 |
| aggtcaataa | cattggggaa | gaattaacaa | aagaaagaaa | tatatttgac | attacagatg | 69360 |
| atttagttta | taattttaat | aaatcacaga | agattaaact | aactgatgat | aaaggattaa | 69420 |

FIG. 19LL sequence.txt

| | | | | | | |
|---|---|---|---|---|---|---|
| ctaaatcgta | tggaaacata | acagctctta | gagatataaa | agaaccaggt | tactactata | 69480 |
| taggcgctag | aacattagca | acattattag | atagacctga | tatggagtct | cttgatgttg | 69540 |
| ttttacatgt | agtacctctt | gatacttcta | gtaaggtagt | tcaacattta | tatacactat | 69600 |
| ctactaacaa | taaccaaatt | aaaatgttat | atagatttgt | ctcaggaaac | tctagttcag | 69660 |
| aatggcaatt | tattcaagga | ttaccgagta | ataaaaatgc | tgttatatca | ggaactaata | 69720 |
| ttctagatat | agcttcacca | ggtgtttatt | ttgttatggg | aatgacagga | gggatgccta | 69780 |
| gtggtgtaga | ttcaggtttt | ttagatttaa | gtgtagatgc | taatgacaat | agattagcta | 69840 |
| gactaactga | tgctgaaact | ggtaaagaat | atactagtat | taagaagcct | acagaagtat | 69900 |
| acacagcttg | gaaaaagaa | tttgagccaa | aagatatgga | gaaatattta | ctaagtagta | 69960 |
| tcagagacga | tggtagtgca | tcattcccac | tcctagttta | tactagtgat | aataaaacgt | 70020 |
| ttcaacaagc | tattatagac | catatagata | gaacaggtca | aacaaccttt | actttctacg | 70080 |
| ttcaaggtgg | tgtatcaggt | tccctatgt | ctaatagttg | tcgaggtcta | ttcatgtcag | 70140 |
| atacacctaa | cacttctagt | ttacatggtg | tctataatgc | tataggtaca | gatggtagaa | 70200 |
| atgtaacagg | ttcagtggta | ggaggtaatt | ggacttcacc | aaagacatca | ccttcccata | 70260 |
| aagaattatg | gacgggagca | caatcattcc | tatctgtagg | tactactaag | aatctagcag | 70320 |
| atgatattag | taattactct | tatgtagagg | tttatactaa | acataagaca | gtagagaaga | 70380 |
| ctaaaggtaa | tgatgactcg | ggtacaattt | gccacaagtt | ctacttagat | ggtagcggta | 70440 |
| cttacgtttg | ctcaggaact | tttgtttcag | gagatagaac | agatacaaaa | ccacctgtta | 70500 |
| cagagttcta | tagagtaggt | gtatctttca | aaggttcaac | atggacgctt | gtagatagtg | 70560 |
| cagtacaaaa | tagtaaaact | caatacgtta | caagaattat | aggtattaat | atgccataga | 70620 |
| ctaggataag | tttcctagtc | ttttttctt | gacttgaaaa | ggattctatg | gtatactata | 70680 |
| actcgtgtaa | ggatataagg | agattaaaat | gagattaaga | attaagaact | tatataccta | 70740 |
| tgtagaattt | gaggaggatg | ataaatactt | aaaagatata | tttttaaaga | gagttcatac | 70800 |
| aactatagga | gcaaggcaag | aaggttttca | gtatagccct | gcttacaaaa | gaggcagttg | 70860 |
| ggatgggtat | gtagactttt | atgtttatga | ggaagataaa | ttccctactg | gactttttatt | 70920 |
| taaaattgag | ttattattag | gtgagctaca | atcaagatat | aacttccagt | ttgaaacaat | 70980 |
| tgatgagcgt | gatgaaagtt | tcttatctga | agaagatatt | gatgacgaga | taacattgct | 71040 |
| tgataataat | gtaggtcaaa | ttaccttacg | agattatcaa | tatgaggcag | tgtacaacag | 71100 |
| cttaacattt | tacaatggta | ttgctcattt | agctactaat | ggaggtaaaa | ctgaggttgc | 71160 |
| tagtggtatt | atagaccaac | tattacctca | attagaaaaa | ggtgaaagag | tagcattctt | 71220 |
| cacaggctct | acggagatat | tccatcagtc | tgcagataga | ctacaagaac | gtttaaatat | 71280 |

FIG. 19MM sequence.txt

| | | | | | | |
|---|---|---|---|---|---|---|
| ccctattggt | aaagtgggtg | caggtaagtt | tgatgttaag | caggttacag | ttgtaatgat | 71340 |
| acctacttta | aatgcaaacc | ttaaagaccc | aacacaaggg | gtaaaggtta | cacctaaaca | 71400 |
| aaatattagt | aaaaagattg | ctcaagagat | attaccgaaa | tttgaaggcg | gtacaaatca | 71460 |
| aaaaaaatta | ctaaaagtat | tacttgataa | cacaacacct | aaaacaaaag | tagaacaaaa | 71520 |
| cgtattaagt | gccttagaga | taatttacca | aaatagtaag | acagatgcag | aagttttatt | 71580 |
| aaacttaaga | aatcataatg | cacattttca | aaaaattgtt | agagaaaaaa | acgaaaagaa | 71640 |
| atatgataaa | tatcaagata | tgagagattt | tttagactca | gttacagtta | tgatagttga | 71700 |
| tgaggcacac | cattctaaat | ctgattcctg | gtacaacaat | ctaatgacat | gtgaaaaagc | 71760 |
| tttataccga | attgcattaa | cagggtctat | agataaaaaa | gatgaattac | tttggatgag | 71820 |
| attgcaggct | ctattcggta | atgttattgc | acgaactact | aataagtttt | taattgatga | 71880 |
| aggtcattct | gctagaccaa | caataaatat | tatacctgta | gctaatccta | atgacataga | 71940 |
| tagaattgat | gattataggg | aagcttatga | taaaggtata | acaaataatg | attttagaaa | 72000 |
| taaacttatt | gcaaaactaa | cagaaaagtg | gtataatcaa | gataaaggta | cattgattat | 72060 |
| tgtaaacttc | attgaacatg | gagacacaat | atcagaaatg | ttaaatgatt | tagatgtaga | 72120 |
| gcactacttc | ttacatggag | aaatagactc | tgaaactagg | agagaaaaat | taaatgatat | 72180 |
| gagaagtggt | aaacttaaag | taatgatagc | tacatcactt | attgatgagg | gtgtagatat | 72240 |
| atccggtatt | aacgcactaa | tattaggtgc | aggaggcaag | tcattaagac | aaacattgca | 72300 |
| acgtattggt | cgtgctttgc | gtaagaaaaa | agacgataat | acaacacaaa | tatttgattt | 72360 |
| taatgatatg | acaaatagat | ttttatatac | tcacgctaat | gagcgtagga | aaatttatga | 72420 |
| agaggaagat | tttgaaataa | aagacttagg | aaaataggag | ggtaagagat | ggcaacaaaa | 72480 |
| acacaaagaa | agctatacca | atatctagag | gaaaatgcta | cagaaaataa | atttcatatt | 72540 |
| tctactaaga | aagagttagc | agattctcta | ggtgtttcca | tctctgctct | atccaataac | 72600 |
| cttaaaaagt | tagaagaaga | aaataaagtc | gttactgttt | ctaaaagagg | aaaaaacggt | 72660 |
| ggagtaataa | taactttagt | tagagagtat | gacacagaag | aattgaaaga | atttaataat | 72720 |
| tctacagata | atattattac | ttccgattta | cagtatgcta | aggcattaag | agaaaagcac | 72780 |
| ttcccttctt | atagatatga | gagaaaagaa | caacgtagac | gtactaagat | agaaatggca | 72840 |
| caatacaatg | ctattaagga | tgagaagaga | agaattatag | cagatatgaa | tttctattca | 72900 |
| gaaggtcttc | cttacccttc | taaagatatt | tttaatatgt | cttatgaccc | ggaaggtttt | 72960 |
| tataaagcat | acatcttatg | taagttatat | gaccaatatg | ctatttctca | tatggatgct | 73020 |
| aaacatacaa | gtcatcttaa | agcaatgagt | aaggcaacaa | ctaaagatga | atatgactac | 73080 |
| catcaacata | tgtctgaata | ctatagaaat | aaaatgattc | aaaatttacc | tagaaatagt | 73140 |
| gttagtgata | atttctttgg | tagtaaaatg | tttaatactt | tttataattt | ttatttaaaa | 73200 |

FIG. 19NN sequence.txt

| | | | | | | |
|---|---|---|---|---|---|---|
| ataaaagata | aaaatattaa | tgtatttaaa | tatatgaaaa | acgtatttaa | aaatgtaaca | 73260 |
| ttttattacg | agaacggtat | gcaacctaat | ccaatacctt | ctcctaactt | ctttagttca | 73320 |
| gataagtatt | ttaaaaacta | taataattat | attaaaggaa | taaaaaaagg | cattaacagt | 73380 |
| acgaatagac | acctaggtga | tacagacagc | atcattaatt | catcagacta | tgtgaaaaac | 73440 |
| cctgctgtat | tacatctaca | ccaactatat | actacaggat | taaattctac | tttacatgat | 73500 |
| attgatacta | tgtttgaaca | agccttagac | cttgagaatg | cttcttatgg | attatttgga | 73560 |
| gatatgaaac | atattatctt | actacagtat | aattctatga | ttgaagaaga | aattaagaat | 73620 |
| ttacctatag | aagagaagga | tattattaat | aaatatgtaa | aacaatgcat | aattaataat | 73680 |
| tactcaccaa | caagtatttc | accatctgca | agattatcaa | tgtttactat | gcagaaagag | 73740 |
| catatagttt | ataataagca | attaaataag | ggaatcaaga | gagaggattt | attaccatta | 73800 |
| agtctaggag | gtatagtgaa | taaagattca | ttaagtagta | tggatataca | aaacttagaa | 73860 |
| cagaatggca | atgaatacct | atatatgaga | caacatactt | caacttatta | tatactaaga | 73920 |
| atgtttggtg | actatttagg | gtatgaggta | aatttaagag | aagtaaaata | tattgtagag | 73980 |
| aaatataatt | taattgataa | aataccattg | acaaaagagg | gtatgttgga | ttataataaa | 74040 |
| cttatacatt | tagtagagga | agaggttaat | aactatgagt | aagaagataa | aggagcttat | 74100 |
| ccttcataaa | tcaatgaagg | atatacattt | tgcaagagaa | gtattagata | acttacctaa | 74160 |
| gaacttattt | tcagcagagt | ctgaagacat | gggttactta | tttacagcca | taaagagaac | 74220 |
| agcacatatt | tccgataaga | tgtcaaatga | agcattagca | attaaagtag | aacagcttat | 74280 |
| gggtaataac | aaggaagatg | aggagaaagt | aaccaagaca | ttaacttact | tagaagattt | 74340 |
| atataaagta | gacgttaatg | aaaaagatga | atctgttaat | tatgaaatag | agaagtatat | 74400 |
| taaaacagaa | atgtcaaaag | aagtttttagt | taaatttatt | gcagaaaata | aacaagaaga | 74460 |
| ctctgataat | ctacatgaac | ttgtagacaa | actaaagcaa | atagaagtaa | gtgacatctc | 74520 |
| aggaggtaat | ggggagttta | ttgacttctt | cgaagataca | gaaaagaaac | aagaactatt | 74580 |
| gagtaattta | gctacaaata | aattctctac | tggatttact | tctattgaca | accatattga | 74640 |
| aggtggtata | gcaagaggag | aggttggatt | aatcatagct | cctaccggta | gaggtaaatc | 74700 |
| attaatggct | tcaaacttag | ctaagaatta | tgttaaaagt | ggattaagtg | ttttatatat | 74760 |
| tgccttagag | gaaaaaatgg | atagaatggt | tttgcgtgct | gagcaacaaa | tggcaggagc | 74820 |
| agaaaagagt | caaattgtaa | atcaggatat | gtctttaaat | aataaagttt | atgatgcaat | 74880 |
| acaaaatcat | tatcagaaga | atagaaagtt | attaggtgac | ttttatattt | ctaaacatat | 74940 |
| gccgggtgaa | gttacaccaa | accaattaga | gcaaattatt | gtcaatacaa | caattaagaa | 75000 |
| agataaaaat | attgatgttg | ttattattga | ctatcctcat | ttaatgagaa | atccttatgc | 75060 |

FIG. 1900

```
                                   sequence.txt
taaatatcat tcagaatcag atgcaggcgg aaaattgttt gaagatattc gtagattatc    75120
acagcaatat ggatttgttt gttggacgtt agctcaaact aaccgtggtg cttatggttc    75180
agatgttatt acaagtgagc atgtagaagg ttctcgtaaa attgtcaatg ctgttgaggt    75240
gtctttagca gtaaaccaaa aagatgaaga attcaagagt ggtttcttaa gattatattt    75300
agataaaatt cgtaatagct ctaacacagg agaacgattt gttaatctta aagtagaacc    75360
aactaagatg attgtaagag atgaaacacc tgaagaaaaa caagagcata tacaattgct    75420
atcagataat ggaaagaag acacaagtaa atttcaaaat aaagataata aaatagaagc    75480
tataaataac acattcggag gattaccggg agtttaattt tttaaaatat accacttgac    75540
attttatatg ttaggtggta taattatttt ataaagaata aaggagagat taataatgaa    75600
atttgtattc tttacagata gtcattttca cctatttact aactatgcta aacctgataa    75660
tgaatttgtg aatgatagat ttaaagaaca gatagaagca ttacagaaag tttttgatat    75720
tgctaaaaaa gaagaagcaa cagttatatt tggtggagat ttattccata aacgtaactc    75780
ggtagatact agagtatata acaaagtatt tagtacattt gccaaaaata atgaggttcc    75840
tgtattatta cttagaggta atcatgatgc tacaactaat tcattatata ctgattcaag    75900
tatagataca tttgagtatc tacctaatgt aaatgtaata aaatcattaa atacaatttt    75960
aaaagataat gttaatattg tgtttactgc ttatggggat gagacgaagg aaataaagac    76020
atacattaat agtaattatg ataagatat ggtcaatata ctagtaggtc atttaggtgt    76080
agaaggttca ttaactggaa aaggctctca tagattagaa ggggcatttg gataccagga    76140
tttattacct gataaatatg atttcatttt actaggtcat tatcaccgta gacagtatt    76200
ccaaaatccg aatcattttt atggtggctc attaatgcaa caatcatttt ctgatgaaca    76260
agaagctaat ggtgttcatt taatagatac agacaaaatg actacagaat tcattccaat    76320
tcatacacgt agatttatta ctattcaagg agaagatatt cctgataact ttgaacaatt    76380
aatagaggaa gataatttta ttagagttat tggtacagca aatcatgcta aggttttaga    76440
aatggatgac agtatgaaag ataagaatgt tgaagttcaa attaaaaaag agtatactgt    76500
agagaaacgt attgatagtg atgtatctga tgaccctcta acaattgcta gtacctatgc    76560
taaacaatac tcacctgaat cagaacaaga aatccttgaa tgtttgaagg aggttttata    76620
atgaaaaaat atagagaata tctaaataag acagatgcag aaaatttagc agaggattgg    76680
gagaaagtaa ccgaagattt atggaaagtg tttaaagata tgaaacctaa aattaataca    76740
ttagatatca gtaatgtagg aagtaaagat ttagataaaa gtaaacctat actacaattc    76800
caagattcag atggagtaat agagaatatt tgtaatgttg aaggtttaga agatggtcta    76860
agtaaaaatga aaaagatttt tgatgatagt aattttgaaa agcattatta caatagagta    76920
gtagaccatg atgggtatta ctggattgat tatggttctc atcattgttt ctttagagtt    76980
```

FIG. 19PP sequence.txt

| | | | | | | |
|---|---|---|---|---|---|---|
| acgaaagggg | ataagtaatg | gttgtattta | aacaagtaga | agttaataat | tttttagcaa | 77040 |
| ttaaagaagc | tacactagag | ttagacaata | gaggtttaat | tctcattgag | ggtgagaata | 77100 |
| aatccaatga | gtcatttcat | tcaaacggct | caggtaaatc | aactttaata | tctgccatta | 77160 |
| cttatgcttt | atatggtaaa | actgaaaaag | ggctaaaagc | ggatgatgta | gtaaataata | 77220 |
| ttgagaagaa | aaatacgtct | gtgaaactta | agtttgatat | cggggaagat | agctatttaa | 77280 |
| ttgaacgtta | tcgtaaggac | aaagagaata | agaataaagt | aaaattattc | gttaatgaaa | 77340 |
| aagagattac | aggttcaaca | aatgacgtta | ccgataaaca | aatacaagac | ttatttggta | 77400 |
| ttgagtttaa | tacttatgtt | aatgccatca | tgtatggtca | aggtgatatt | cctatgttct | 77460 |
| ctcaagcaac | agataagggt | aagaaagaaa | ttcttgaatc | tattactaag | acagatgtat | 77520 |
| ataaacaagc | gcaagatgta | gcaaaagaga | aagttaaaga | agtagaagaa | caacaaaata | 77580 |
| atataagaca | ggaaatctat | aaactaggtt | atcagttatc | tacaaaagat | gagtacttcc | 77640 |
| aaagagaaat | agaacaatat | aatcagtata | aagaacaatt | ggttcagata | gaaaatagta | 77700 |
| ataaggaaaa | agatagatta | agagaacaag | aggagaagca | aatagaagct | caaatagagc | 77760 |
| aattagcttc | acagatacca | acaatacctg | aagatgaatt | taagcactca | gaggagtata | 77820 |
| ataaagcctc | tcaaagccta | gatttacttt | ctaataaatt | aacggagtta | aatcaagtat | 77880 |
| actcagaata | taataccaaa | gaacaagtac | taaaatctga | aatagctaca | ttaagcaata | 77940 |
| gtctaaatca | gttagatata | aatgaccatt | gtcctgtttg | tggctcccct | atagataatt | 78000 |
| ctcataaatt | aaaagaacag | gaaaatatca | gcaatcagat | tgagaataag | aaacaagaga | 78060 |
| ttactagtgt | attagaaatg | aaagatacgt | ataagaagc | tattgataaa | gtaaaagata | 78120 |
| aatcacaaga | aattaaagat | aaaatgtcac | aggaagacca | acaagaacga | gagcacaata | 78180 |
| ataagattaa | cagtatcatt | caagaggctt | ctaggattaa | atcagacatt | agttcattag | 78240 |
| agaataataa | aacttattta | aaagtgaaat | accaacatca | atctgttcaa | ggattagaga | 78300 |
| gagaagaacc | aagtaaagaa | aaacatgagg | aagataaaaa | agaattacaa | gaatctattg | 78360 |
| acaaacatga | agagaatata | gtacaattag | aaactaagaa | agggaaatat | caacaagctg | 78420 |
| tagatgcttt | tagtaataaa | ggtatacgtt | cagtagtgtt | agactttatt | acaccattct | 78480 |
| taaatgagaa | agcaaatgag | taccttcaaa | ctttatcagg | ttcagatatt | gaaatagagt | 78540 |
| tccaaactca | agtgaagaat | gctaaaggag | aactaaaaga | taagtttgat | gttattgtta | 78600 |
| agaataacaa | gggtggaggc | tcctacaaat | ccaattcagc | aggagaacaa | aaacgtattg | 78660 |
| atttagcaat | tagttttgca | attcaggatt | taattatgag | taaagatgag | atatctacga | 78720 |
| acattgcact | ttacgatgag | tgttttgatg | gattagatac | tatcggttgt | gaaaacgtga | 78780 |
| ttaaattatt | aaaagataga | cttaatacag | taggaacgat | atttgtaatt | actcataata | 78840 |

FIG. 19QQ sequence.txt

```
ccgaacttaa acccctattt gaacaaacaa ttaaaatagt aaaagaaaat ggagtatcaa    78900
aactggagga aaaataatga aattaaagat tttagataaa gataatgcaa cacttaatgt    78960
gtttcatcgt aataaggagc ataaaacgat agataatgta ccgactgcta atttagttga    79020
ttggtaccct ctaagtaatg cttatgaata caagttaagt agaaatggag aatacttaga    79080
attaaaaaga ttacgttcta ctttaccttc atcttatggt ttagatgata ataaccaaga    79140
tattattaga gataataacc atagatgtaa aataggttat tggtacaacc ctgcagtgcg    79200
taaagataat ttaagatta tagagaaagc taaacaatat ggattacctg ttataacaga    79260
agaatatgat gctaatactg tagagcaagg atttagagat attggagtta tattccaaag    79320
tcttaaaact attgttgtta ctagatatct agaaggtaaa acagaggaag aattaagaat    79380
atttaacatg aaatcagagg aatcacaatt gaatgaagca cttaaagaga gtgattttc    79440
tgtagactta acttatagtg acttaggaca aatttataat atgttgttat taatgaaaaa    79500
aattagtaaa tagtaaggaa ggatattatg aggtttgaag acttttttaac ccaagaatta    79560
ggagaaccaa aagaaaatac tataggtgag ctaagatact gttgtccgtt ttgtggagaa    79620
aaaagttata agttctatgt taagcaagcc ctagactcta gtaatggtca gtatcattgt    79680
aaaaaatgtg atgaaacagg caaccctatt acatttatga agacttatta taacattaca    79740
ggtaagcaag cttttgattt attagagtct aagaatatag atatagagag agcccctta    79800
cttacaacta ataataagga tttaacagaa tcagagaaac ttatattaat gcttagaggt    79860
gtgcaccaag ataaaggaac tactagtatt aaacctcctc gattacctga aggatataaa    79920
ttattaaaag ataatttaaa taataagag attatacctt ttttaaaata cttaaaaggt    79980
agaggtataa ctttagaaca aatcattaat aacaatatag gctatgttat taatggtagc    80040
ttttataaag ttgacgggga atccaaagta tcattaagga atagtattat attttttact    80100
tatgataaca atggaaacta ccagtactgg aatacaagaa gtatagagaa gaaccctttat    80160
attaaatcta ttaatgctcc tgctaaacaa gatgaagtag ggagaaaaga tgtcatattt    80220
aatttgaata tagcaagaaa gaaaagttc ttagttataa ctgaaggtgt atttgatgct    80280
ttaaccttc atgaatatgg agtagcaaca ttaggtaaac aagtaactga gaatcaaata    80340
aaaaaaataa ttgattacgt tagtatagat acatcaatat atattatgtt agacactgat    80400
gcattagata ataatataga cttagcttat aagttaaaaa cacattttaa taaagtttac    80460
tttgtaccac atggtgatga agatgcaaat gatatgggaa caaggaaagc ttttgagtta    80520
ttaaaacaga accgggtgtt agtaacacct gaaagtatac agagttacaa aatacaacaa    80580
aaacttaaac tttaggcttg accttagaga agttttatgt tatactagta attaagtaat    80640
taataaagga gaaaaaaata atgtcaaata gtaaaaaaga tattttagaa tttgtagatg    80700
aatacattac agctttaaga gttggtaatg agcaacgaca acaccaatta gaagaaatgg    80760
```

FIG. 19RR sequence.txt

| | | | | | | |
|---|---|---|---|---|---|---|
| gtaaagaaga | aacagcaaca | ttaacagatg | tagctaaagc | tattactaac | cttatgttag | 80820 |
| gtgttaatga | gcagatgaca | gacttagaat | ataataacga | gttaaactta | aatattttaa | 80880 |
| ttgacgcttt | atataaagca | gagcttatta | atgaagatgt | attagactac | attcaagaat | 80940 |
| caattgataa | atcacaagaa | gaacctaaaa | atgaagaaga | aaaaggagaa | caagaataat | 81000 |
| ggaaaaaaat | attagcacac | acacaaaagg | tattagtcaa | gcagacatgg | agaaatggat | 81060 |
| tgaagctgta | gtacaaggaa | ctgttgatgg | taaacaagtt | gatgagaaaa | cagctaaaca | 81120 |
| attagataga | attggttcac | gtagtgtttc | tttagaagaa | gcaactcgta | ttgctaaagt | 81180 |
| tcttaatgct | gtaacagctc | aagaggttac | aggagacttt | aatgatgcat | taatgcaat | 81240 |
| tgacttaatg | atgattatca | tggaagatga | gctaggagta | actcaagaaa | aagtgggtaa | 81300 |
| agctaaagat | aaactaaatg | aaaaacgaga | agcttaccta | aaagagaaac | aagaagaatt | 81360 |
| acgccaaaaa | caacaagaag | aggcacaaaa | agaaactgaa | tctgacagca | atgagaaagt | 81420 |
| aattcagttg | aagaaaaatg | acgaacagta | agaaaaaagg | ggatacattc | gaacgtaaaa | 81480 |
| tagctaaaga | attaactgct | tggtggggat | accaattcaa | taggtctcct | caatcaggtg | 81540 |
| gtgcttcatg | gggtaaagat | aataatgctg | tcggagatat | agtagtacct | caggaagcta | 81600 |
| attttccttt | agtagtagaa | tgtaaacata | gagaagaatg | gactatagat | aacgttcttt | 81660 |
| taaacaacag | agagccacat | acatggtggg | agcaagtcat | taatgatagt | agcaaggtgg | 81720 |
| ataagacacc | ttgcttaata | tttactagaa | acagagctca | gagttatgtt | gctttacctt | 81780 |
| atgatgagaa | agtatatgaa | gatttgagaa | ataatgaata | ccctgtcatg | agaacagatt | 81840 |
| ttattattga | taatattaga | aaagataaat | tttttatga | tgtacttata | actaccatga | 81900 |
| atgggttgac | ctcatttaca | ccttcttata | ttatatcttg | ctacgacaaa | aaagatataa | 81960 |
| aaccatacaa | gaaggtcgag | tctaatttat | ctgaggtaag | taagcatgaa | gatgaattga | 82020 |
| ttaatgacct | tcttagtgat | atataaggaa | ggtaagataa | gtatgacaag | taaagaaaga | 82080 |
| ccattaatcg | tatatttttc | aggtacaggg | caaacagaaa | gattagtaaa | taaaattaat | 82140 |
| attaataatt | catttgaaac | atttagggtt | aagagtggaa | aagagaaagt | aaataaacct | 82200 |
| tttatactaa | taacacctac | ttatatgaaa | ggtgcaatac | ctaaacaaat | agaaagattc | 82260 |
| ctagaaatta | atgggagccc | taaagaagtt | attggtacag | gaaataaaca | atggggctct | 82320 |
| aatttctgtg | gagcaagtaa | aaagatttca | gagatgttta | agattccttt | aattgctaaa | 82380 |
| gtagagcaat | caggacactt | taacgagata | caaccaatat | tagaacactt | tagtaataaa | 82440 |
| tataaagtag | cgtaaaggat | gagagatata | tggcaacata | tggaaaatgg | attgagttaa | 82500 |
| ataatgaaat | aactcaatta | gatgacaatg | gaaaaaataa | actctataaa | gaccaagaag | 82560 |
| ctttagatga | gtatttaaaa | tatattgaag | acaatacaag | aaagtttaat | agtgaagtag | 82620 |

FIG. 19SS sequence.txt

```
aaagaattag agtattgaca aaagaaggaa catatgataa aatatttgac aaggttcctg    82680
atactattat tgatgagatg actaagttag cttacagttt taattttaaa ttccctagtt    82740
tcatggcagg gcaaaagttt tatgaatctt acgcatcaaa acagtatgat gaaaacaaaa    82800
aacctatttt tgttgaagac tatgagcaac ataatgttcg agtagcttta tatttatttc    82860
aaaatgacta tgtaaaggct agagaattac tagtacaact tatggagcaa acattccaac    82920
catctacacc tacgtataac aactcagggc aagctaatag aggtgaacta agttcatgtt    82980
atctatttgt agtagatgat tcaattgagt ctttaaactt tgttgaggat agcgtagcta    83040
atgctagttc taatggtggc ggagttgcaa ttgatttaac tagaattaga cctaaaggag    83100
ctccagtacg taatagacct aattcaagta aaggtgttat tgcttttgct aaagctattg    83160
aacataaagt tagtatttat gaccagggcg gtgtaagaca gggtagtggt gcagtttacc    83220
taaatatatt ccacaatgat atcttggatt tattaagctc taagaaaatc aatgccagtg    83280
agtctgttag actagataaa ttatctattg gtgttacaat ccctaacaaa tttatggagt    83340
tagttaaaga aggtagacct ttctatactt tcgatactta cgacattaat aaagtgtatg    83400
gtaagtattt agatgagcta acattgatg aatggtatga taagttatta aataatgata    83460
gtatcggtaa agtaaaacat gatgctagag aagttatgac agatattgct aaaacgcaat    83520
tagaatcagg ctacccttat gtattctata ttgataatgc taatgataat cacccattga    83580
aaaacctagg taaagttaaa atgagtaact tatgtacaga aatttcacaa ttacaagagg    83640
tatcagaaat ttatccgtac tcttacagta atcagaatgt tattaataga gatgttgttt    83700
gtacattagg ttctcttaac ttggttaatg tagttgaaaa aggtttattg aatgaatctg    83760
tagatattgg tacaagagca ttaacaaaag ttactgatat tatggattta ccttacttac    83820
ctagtgttca aaaagcaaat gatgatatta gagctatcgg tttaggttca atgaatttac    83880
atggactttt agctaagaat atgattagtt atggttctag agaagcatta gacctagtaa    83940
acagtttata tagtgctatt aacttccagt ctattaagac atctatgtta atggctaaag    84000
aaacaggaaa accatttaaa ggctttgaga agtctgatta cgctacaggt gaatactttg    84060
taagatatat tagagaatcc aatcaaccta agacagataa agctaagaaa gtcttagata    84120
aggtttatat tccaacacaa gatgattggg atgaattagc taaagcagta aaagtacatg    84180
gcttgtataa tggttataga aaagcagaag cacctactca atctatatct tatgtacaga    84240
atgctacaag ttctattatg ccagtcccta gtgctataga gaatagacaa tatggagata    84300
tggagacata ttacccaatg ccttacctaa gtcctataac tcagttcttc tatgaaggag    84360
aaacagctta taagattgac aataaacgta ttattaatac aagcgcagtt gttcagaaac    84420
atacagacca agcagtgtct acaatacttt atgtagagtc agaaatccct actaataaac    84480
tagtatcatt atactattat gcttgggaac aaggattaaa atcattatac tatacacgtt    84540
```

FIG. 19TT sequence.txt

| | | | | | |
|---|---|---|---|---|---|
| cacgtaaact | ttctgttatt | gaatgtgaaa | catgttcggt | ttagaaagga | aatagatatg | 84600 |
| gatattacac | aaaaagtaaa | acaacataat | aaaaatgctg | tattaaaagc | aacaaactgg | 84660 |
| aatattgaag | atgacggtat | gtctgatatt | tattgggagc | aaggaatctc | ccaattttgg | 84720 |
| actcctgaag | agtttgatgt | atcaagagat | ttaagttctt | ggaatagttt | aactgaaagt | 84780 |
| gaaaagaaca | cttataagaa | agtccttgca | gggctcacag | gtctcgatac | aaagcaagga | 84840 |
| ggagaaggta | tgaacttagt | atcctaccat | gaaccaagac | ccaaatacca | agctgtattt | 84900 |
| gcgtttatgg | gtggtatgga | agagatacat | gctaaatcct | atagtcatat | ctttacaaca | 84960 |
| ttactaagta | ataaagaaac | aagctatcta | ttagatactt | gggtcgaaga | aaatgacttt | 85020 |
| ttaaaagtaa | aagctcagtt | tatcggatat | tactatgacc | aactattaaa | acctaaccct | 85080 |
| actgtatttg | atagatatat | ggctaaagta | gctagtgcct | ttttagaaag | tgcactattc | 85140 |
| tactcaggat | tttattatcc | tttacttctt | gcaggaagag | gtcagatgac | acaatcagga | 85200 |
| gctattattt | ataaaattac | tcaagatgaa | gcttaccatg | gttcagcagt | aggattaaca | 85260 |
| gctcaatatg | attataatct | tctaacagaa | gaagagaaaa | aacaagcaga | taaagaaact | 85320 |
| tatgaattat | tagatattct | ttacactaat | gaagtagcgt | atacacatag | tctatatgac | 85380 |
| ccactagaat | taagtgaaga | cgtaattaac | tatgttcagt | ataattttaa | tagagctctt | 85440 |
| caaaaccttg | gaagagagga | ctattttaat | cctgaacctt | ataaccctat | tgtagaaaat | 85500 |
| caaactaatg | tagacagatt | acgaaatgtt | gatttcttta | gtggtaaagc | agactatgaa | 85560 |
| aaatctacaa | atatcaaaga | cattaaagat | gaagatttct | cattcttaga | tagtaaagaa | 85620 |
| tacaatactg | ccaaggaatt | cctataaaaa | ggagaaaaga | tattatggat | agaaaagaag | 85680 |
| caatggattt | actaagtaaa | gcagaaatat | tatttaaaaa | acatgatgag | ttttcatgtg | 85740 |
| taagtgatat | taatgaccct | atgaagttat | tcagtagctc | taaggatgct | aaagctgatg | 85800 |
| atacgtctaa | gtcttttcag | ctagagttta | tgcatgatat | gaccatgtat | actttatctt | 85860 |
| atggctcagg | acagttaaaa | cttattgatt | tagcagaagg | ttatgaagca | caaaaagcta | 85920 |
| cagtagttaa | ctcatttccc | gaaattatta | aaacattaga | aaaggatgat | tcagaagatg | 85980 |
| gaaaaaatga | atagtttagt | agatttaaat | acagcaatta | gacaaaagaa | agatgttatt | 86040 |
| gtcatgatta | cacaagataa | ttgtggtaag | tgtgagattt | taaaaagtgt | aatccctatg | 86100 |
| tttcaagagt | caggtgacat | taaaaaacct | atcttaacat | taaatctaga | tgctgaagat | 86160 |
| gtagatagag | aaaaagctgt | taagttattc | gatatcatga | gtacaccagt | attaattggg | 86220 |
| tataaagatg | gtcagttagt | taaaaagtat | gaagaccaag | ttacacctat | gcaattacaa | 86280 |
| gaattagagt | cactttaatt | tggaatttcc | tactatctgt | gctatactat | aatagtacaa | 86340 |
| ggtagtagga | ttttttaatg | gaaggaagat | gacatatcgc | aaagaataaa | acattaacga | 86400 |

FIG. 19UU

```
                              sequence.txt
tatataatag tgatagatat tttaatatac acacaaaaga taaagataaa attaatgagg    86460
ctattaaagt cacacatggt aatgaagaag aaattgagaa gaatatggat gaattaatat    86520
ctaagtctag acgatatatc atgagagatg aaaatcatta catgttattt aatgagaagt    86580
ataataatga tagacttata gaaaaagtat gtaaacatgg cggtaaagtt acatactata    86640
ctgattcagt attaccttat tatgttttaa aagacttatc tagtcaccct gactcagaag    86700
ttgtttatcg tatgcgcaat ggttttactg caaaagaagt agataatata gctttatcat    86760
tcatgggtac aaaagttatt attgatattt ctgtagtatt tccttatgta aacccttatg    86820
atattattag aagtttacat gatattaaaa caaatgtaga tgaagttcat ttatcatttc    86880
cacgaatatt agaggtagat gaaaaacaag aaaagtttta tttctttgat ggtgaagctt    86940
atgatttaaa acctgaatat aaagtcgatt ttgcagataa aattagagta tctttatcag    87000
tatggaaaat gtatatctat atcttaacaa gtagtcgtga ttttgaggat gtagacaatg    87060
taattacgaa attaaaacaa caacgaaaga ttaagatata aggtgattat atgagtacag    87120
caaatagaag agatatagca agaaagatat cagagaatac aggttactat atccaagatg    87180
tagaggaaat actaagtgca gagacagatg ctatttctga cttactagaa gaaggatata    87240
ctaaagtaaa gaatcataaa tttatgcaaa tagaagttat tgaaagaaaa ggtaaaaaag    87300
cgtgggatgg tctgaataaa gaatacttcc atttacctaa tagaaaagct ataaaattca    87360
aaccactaaa agaactagaa gaggttattg atagacttaa tgaagaagag aaataattct    87420
cttctttttt tattgacaag gtttaaaata tatggtatag tattattaag ttaaaaaagg    87480
agaggaatta aatgaaagta ttaatcttat ttgaccacat tagagaagag catttttctg    87540
taagtaaaga tgggagtgtg aaatctaatg tactaaatac acctaatgga aaaacactta    87600
agaaattact tgagaagtgt tctaacttaa agagagataa gacaaacaga gattatgata    87660
ttgattttct ctacaatgca gtacctacac ctatcagaaa tgactacggt aaaatcatta    87720
aatatcaaga tgttaaacaa gcagaagtaa agccatacta tgagagaatg aacaatatta    87780
ttattgataa ttccttatgat atggtaattc ctgtaggtaa actaggtgtt aaatacctat    87840
taaatgttac agctatcggt aaagtaagag gagtcccaag taaagtaact attgaaaatg    87900
aaacatcttc tcatgacgtg tgggtattac ctacttcacg tattgaatat actaatgtaa    87960
ataaaaatag tgaacgtcat gtagtatcag atttacaaac agttggtaag tttgtagagc    88020
aaggagaaga ggcatttaaa cctaaggaag tatcttacga gttggtagat aacattgaaa    88080
gagtaagaga aatattcaat aaggaagtaa agaacgacaa ttatgatggc gtagatatta    88140
ccgcatggga cttagagact aactcattaa aacctgataa agaaggaagt aaacctttag    88200
tactatctct atcatggaga aacggtcaag gtgtaactat accttatat aaatcagact    88260
ttaactggga aaatggtcaa gatgatattg atgaagtctt agaattgctt aagaattggt    88320
```

FIG. 19VV sequence.txt

```
tagctagtaa agaagacatt aaagtagcac acaacggtaa atgatttgct gttgtaaaat        88380
ccctctcata tcgggcatag ctttaagaag ctgataagag aacctaagtc ctgtaataag        88440
gatagtggta atcccgagcc tacattattg gtgacaatag atggggtgta gagactgagc        88500
tgaggttttg tagaccaagg tgagacatag tgtatcaact taatagaggt ggtacagtga        88560
aaaaagatta tatgacatca gttaaaaata acaaaaaagt atgtagaaga tgtaatgaag        88620
aattagactt atctaatttt aaaacatata aaagaatga taaaatttat tatcagagta         88680
tgtgtatacc ttgtagaaag gaatacaata aattagataa aactaaaaat actattaaaa        88740
aatgttatga taaaaatgga gataagtatc ggaaacaagg taatgagtat aacacttctg        88800
atagaggaag agaactaaat aaaaagcgtt caagaaaata cagagaaaat aattctttaa        88860
aagctaaagc tagaaactct gtaagaactg cattaagaaa tggttctcta ttaagaccta        88920
gtaaatgttc agagtgtaat aaggaatgta ttcctgaagc tcatcatcct gattataaca        88980
aacctttaga aataaaatgg ttatgtaaat catgtcatga agatacacat cataaaaaat        89040
aatcacacta tgtaaatgag ggacatcaag cccatttagg taactacaaa caaacctaat        89100
ggtaagggct tatgaaggta tagtccgttc tgtatagaaa tatacaggct aaaacgaaat        89160
atgatattaa attcttaatg agtactgaaa actttaaaga ttttgagagt attcaggata        89220
ctaaagtagg ttggtaccta gccgttaccc aggaagttaa agaatcttta agattatctg        89280
atttagctta cgaggttacg gatgtcggag gatatgataa accattagaa gactttaaat        89340
tatggtttgt tactaagtta ttaagattct tctcagataa aattaaagag atacagaaag        89400
aaaataaaaa aattgctaag aaagagtatg atgttaaagc tcctgaatat aaagaatggt        89460
tagagaataa actaaatgaa acagtagtag aactagatga tactgagaag aaatttagag        89520
tcagtgaatt agagaaaaag tatattcaac taggtctttc acctgaaatt gtaaatatga        89580
atttagttat gaataacgat gagtttataa gtattgcaga acaatcacct gagtacatgg        89640
ggttatctga ctacgctaag tcttacacat taaatactgc aattaattta attaatgagt        89700
atagagatgt aaaagatgta gttaatgata ttgatggagg taactttaat tatgattggt        89760
tccctattga gttaatgcat ccatatgctt caggagatac tgatgtatgt agaagaattc        89820
attgtgatgt agttaaaaaa cttaaagaac aagatagacc taaatcaatg catttattag        89880
aagttaatta tccaagactt actaagtctt tagctaggat tgaatcaaat ggtttatatt        89940
gtgacttaga ttatatgaaa gaaaatgatg agtcatacga gtctgagatg gctaaaaatc        90000
atgctacaat gagagagcac tgggctgtta aagaatttga agaataccaa tacaatcttt        90060
accaaatggc gttagaagaa catgagaaaa agccaaaaga tagagataaa gatatccatc        90120
agtatagaga taaatttaaa gatggtaaat ggatgttttc cccaagttcc ggagaccata        90180
```

FIG. 19WW

```
                                    sequence.txt
aaggtagagt aatttatgat attttaggaa ttcaattacc ttatgataaa gaatatgtta    90240
aggaaaaacc atttaatgct aatgttaaag aagcagacct tacttggcag gactataaaa    90300
cagacaagaa agctattggt tatgcgttag ataatttaga attaaaagat gatgttagag    90360
aacttcttga gttacttaaa tatcatgcta gtatgcagac aaaacgtaat tcatttacta    90420
agaaattacc taatatgatt aataaacaaa aacgaacatt acatggttct ttttctgaga    90480
caggtacaga gacatcaaga ctaagtagta gtaaccctaa cttgcaaaac ttaccggcac    90540
acacatcaga tgtaaacaag tttgattaca aacatccaat taaacgttca tttgtttcta    90600
gatttgaaaa tggagtacta ctgggagccg actatagcgc cctagagatg cgtattattg    90660
gattatttac taaagacct gatatgctac aatcattctt aaatggggaa gatattcata    90720
aggctactgc aagtattgtt tataataaac cagtagaaga ggtaactaag gaagaacgac    90780
aagcaactaa agcagttaac ttcgggttag ccttcggtga atcacccttc tcatttgcag    90840
gtaaaaataa tatggaagta agtgaagcag aagaaatatt tgaaaagtac ttccaaacaa    90900
aaccaagtgt aaaaacttct attgacaatg tacatgagtt tgtgcaacaa tatggttatg    90960
ttgatacaat gcacggacat agaagattta tccgttcagc ccaatcaaca gataaaaaga    91020
taaaaaatga aggtctaaga cagtcattta acactattat ccaaggttca ggtagtttct    91080
taacaaacat gtctttaact tacttagatg attttatcca atctcgtaac ttaaaatcaa    91140
aagttattgc cacagtacat gatagtatct taattgattg tcctcctgaa gaagctaaaa    91200
ttatggctaa agtgacaatt catattatgg aaaacttacc atttgatttc ttaaaagcag    91260
aaattgatgg aaaagaagta caatacccta ttgaagctga tatggaaatc gggttaaact    91320
ataatgatat ggttgaatat gatgaggaag aaatagatac atttaattct taccaaggtt    91380
atattaagta tatgatgaat ttacagacct tagaagatta taaagagtca ggtaaactaa    91440
cagatgaaca atttgaaaag gctactaacg ttgttaaaag tgaaaaacat atttaccaag    91500
aaatttaata aaagtattga caatatattt aacttatgtt atactatata ggtaataaat    91560
ataaggagga aaaagagtga atacaggaga gattagattt aatcgttcta tggatgaatg    91620
gattataaca agtatgtacc aggatgagct aggtgatatg aatattgttg ttacattcta    91680
taatagagaa gaaaataaac acggttctac agttttaccc acagagtcat ctactggaga    91740
agtaacagag gaattggcaa atcttgaaga agaatatcct ctagctttac ctttaagtag    91800
tatctcagtt aatatttaaa aggaggaact gataaatgga aatacacatt gattccctag    91860
attttacaaa ctttactatt aaagatagaa atgggaactc acaagagttt gatattacag    91920
atgagttaag aattacagag tatacaatac aagaggactt tatgcaacaa tcagctaaat    91980
atgctttttg ggcttctata ttagagaagg taagagcata ttctgaaatg gaacaaagaa    92040
atctagaaac aattggtagt aagctaaacc ttacaattag acaagagtac gaacaacaag    92100
```

FIG. 19XX sequence.txt

| | | | | | |
|---|---|---|---|---|---|
| gtaaaaagcc | tactaaagat | atgattgaat | ctagtgttta | tattcatgat | tcttaccaac | 92160 |
| aacaacttaa | agttgttgag | gcttggaatt | ataaagttaa | acaacttcaa | tatgttgtaa | 92220 |
| aagcttttga | gacaagaaga | gatatgatga | ttcaattagg | tgcagaatta | cgacaaacaa | 92280 |
| ataaaaatgg | tggaattact | aatccatttt | cacattaaaa | aataaagtaa | agaatataat | 92340 |
| tgacaaatat | aaaaaactat | gttataataa | ataagtaaat | taattaaaag | gagaaaagat | 92400 |
| aattatggat | ttcaatcaat | ttattaacaa | tgaggcaagc | aaattagaaa | gcaataacag | 92460 |
| ttcttttaac | aataatgtag | agagctacaa | acctaaaaac | cctgtactac | gtttaggtaa | 92520 |
| tattaaagat | gcaaacggaa | ataaggttgt | taaagaaaat | gcttttgtac | gagtattacc | 92580 |
| tcctgcacaa | ggaacaaatg | ttttctttaa | agaatttaga | acaacaggta | ttaactattc | 92640 |
| taagaaagat | ggttctcaag | gattcacagg | attaacatta | cctgcagaag | aaggttcatc | 92700 |
| tgtccttgac | ccgtacattc | aggactggat | aacaaatggt | gttcaattta | gtagattccc | 92760 |
| taataaacca | ggagtacgct | attacattca | tgtgattgaa | tactttaata | acaatggtca | 92820 |
| aattcaacca | aaaacggatg | ctcaaggaaa | tgtaatgatt | caacctatgg | aattatctaa | 92880 |
| cacaggatat | aaagaattat | tagctaactt | aaaagatact | atgttaaaac | catcacctaa | 92940 |
| tgcacctcat | agctttatct | cagcaaatga | agcattctta | gttaatattg | ttaaagctaa | 93000 |
| gaaaggtgaa | atgtcatgga | aagtaagtgt | ttatcctaat | gctcctttag | gtgcgttacc | 93060 |
| gcaaggttgg | gaacaacaat | tatctgacct | agaccaatta | gcaaaaccaa | cagaagaaca | 93120 |
| aaatcctaat | tttgttaact | tcttaatcaa | taatgttaat | aacacagagt | taagtcatga | 93180 |
| taactttaaa | tttaaccgtg | aaacaaatgt | cttaggtgaa | gaaccttcag | agcctaaaca | 93240 |
| agcacctacg | caacaagatg | tagatagtca | aatgccaagt | aatatgggag | gacaacctaa | 93300 |
| tcagcctcag | caaggtcaag | taggtcagta | tgcacaacaa | ggtcaaagta | atggtcaagg | 93360 |
| acagcagtta | caaggtacac | aacaacctat | caataacacg | caatttggtc | aaggaactcc | 93420 |
| ttcaggacaa | caaccaagta | acacaggttc | tgttgattgg | gataacttag | cgcaacaaca | 93480 |
| atcacaacct | gattcaaacc | cattcaatga | ttttgatgtt | agcagtgttg | atgattcaca | 93540 |
| ggtacctttt | gagacacaac | ctcaaaatac | acaacaagca | cctgaccac | accaaactac | 93600 |
| acaagagcct | ccaaaacaaa | aacaaacgca | aagtattgac | gatgtattag | gtggtctaga | 93660 |
| cttagataac | ctataagata | tagagtgcct | tagagcactc | ttttatttga | gatataatta | 93720 |
| ctaggaggat | attaaatggc | aagagcaaaa | aaaggtaaag | aagtagattt | aacagattta | 93780 |
| aatacaattg | atttaggtaa | agaattagga | ttaacattgc | tatcagatac | aaacagagca | 93840 |
| gatattaaaa | acgttatacc | tacaatggtt | cctcagtatg | actatatttt | aggtggaggt | 93900 |
| attccattag | gtcgattaac | agaagtttac | ggtttaactg | gtagtggtaa | atctactttt | 93960 |

FIG. 19YY

```
                              sequence.txt
gcagttcact tatctagaat tgcaacacaa ctaggtgtta tcactatttg gattgatatt    94020
gaaggaacag cagataacaa tcgtatggaa caacttggtg tagatgtttc aaaactattc    94080
tctattcaat caggagaagg tagacttaaa aatacagtag aattatctgt agagcaagta    94140
ggtaaagaat tagaatactg gattgacact ttcaatgaaa agattccagg agtacctatt    94200
gtatttattt gggactcatt aggggctaca agaactcaga aagagattga tggcggtatt    94260
gatgagaagc aaatgggtct caaagcatca gctactcaaa aagtaattaa tgcagtaaca    94320
cctaaactaa atgatacaaa cacagggtta attgttatta accaagcccg tgatgatatg    94380
aacgcaggta tgtatggtga ccctattaaa tctacaggtg gtagagcttt tgaacatagt    94440
gctagtttac gtattaaggt tcataaagca tctcagttaa aacagaagag tgagttaact    94500
ggtaaagatg aataccacgg tcacattatg cgtattgaaa ctaagaaatc taaactatca    94560
cgaccagggc aaaaagctga agcagactta ctatctgatt atatggtagg taaagaagat    94620
gaccctatct tattaaatgg tatcgactta gaacataccg tatataaaga agcagttgaa    94680
agaggtttaa ttactaaagg agcatggaga aactatgtta cattgaatgg tgaggaaatt    94740
aaacttagag atgctgaatg ggttcctgta cttaaagata atagagagtt atatctagaa    94800
ttgtttagta gagtttatgg agaacacttc cctaatggtt actcaccatt acttaataac    94860
aaagtaatcg taactcaatt agaagagtat caagctcttg aaaactacta taaagaatgg    94920
gctacagata ataaacaaga agaacaagag gaagaactaa aaggagaatc tcaagaaaag    94980
gattctgaat aatagatgga taatttaata gataaaaaca tgagtcaggt aaaagaatct    95040
ttggggaacg caaattcctc agatgttctt cctttacctt ataaagatat agcaaagaaa    95100
tttgaagaag taaagaaaa aggtgaatca attatcattg aagaaggtgg attcccttat    95160
acagattcta cagtgatgta tatagaacat gtaacagata gatgggcagg aggatattcc    95220
ttaattagac atgaaggtga ggaagttaaa gtacctaaga ctatccattt ctctgatata    95280
tatgttaaag ataaatcaca caaagtaaga ataatcttcg aggggctaa tccttatgaa    95340
gaaagctaat aatggtaata gatatgtaat agatatagat ggtatacctg ttgattttga    95400
aagagattta gatagtttac ttaataggta taaaaacctt agatggtctt tatatcatag    95460
atacgcaggg attttatcta atgattttga aagacaagaa ctaagagaat atattgatga    95520
gcaatttatt aaattagtta aagaatataa tattagaagt aaagtggatt ttcctggata    95580
tattaaagct aaactaactt taagagttca aaatagttat gttaagaaga atgaaaaata    95640
taaacgtact gaaattatcg gtaaaaaaga ttatacagta gagtccttaa cagaagattt    95700
aaatgaagac ttcgaggata atcaaattat gagttatgta tttgatgata tagaatttac    95760
agaggttcaa agtgagttac ttaaagaatt acttattaac cctgaaagag aagatgatgc    95820
ctttatcgtt tctcaagtag cggaaaagtt tgatatgaaa agaaaagaag tagcaagtga    95880
```

FIG. 19ZZ sequence.txt

```
gttgacagaa ctcagagact atgttagatt taaaataaat gcataccatg agtactatgc    95940
taagaaagaa ttaaataacc atagagttaa tactgaaaat catatttggg aaaactagtt    96000
acagtgcctt ccttgtgtta tattattatc gagaattcaa taataaagca tagggaaggc    96060
tttttctat gtcttataga atgctttaaa atagattact aaaataaaga ttggagatta     96120
agcttatggc taaaaagaat gttaatgatg tattacaaca agaatctgtt acagtagcag    96180
ataagtattt acaagttaaa gttaaccgtg acggttatac tcgtacacat gaaggacaat    96240
atgcgtacaa agtagtttca gagggagaag aattattctt atacctgta caaacagatg     96300
gtaaaggtac attaaatgta atgaagaaat cacctattgc ttacactgat ggagacaata    96360
tccatttcgt agtaaacaca gtagtagacc cttataatca ctcatttatc cgtactgaag    96420
atattaaagg attagataaa ggtaaacaac ttattcaagc tttcttagct ttcgttgaag    96480
accgtttcaa atttggtgtt tataacgtat ttgttgcaaa caacaaagag gatgtattat    96540
ctattgtaga ccctacagat aatgatgcag atgaagttaa agatagttta gagcacgcac    96600
atgaagatgt aattgcggat ttccctgcta gccctgctcg taaggacgtt aaaggcgtag    96660
attcaggaga aggtcaagga gacacttcag aaccatcagc acctaagaac gttcaagtta    96720
ctcctaagga agacggagca gacgtatcag cagaataata tatagataag gatggtaaat    96780
ttggctaagt taaatttata caaaggtaat gagttactaa acagcgtaga aaaaacagaa    96840
ggaaaatcaa caatcacgat tgagaattta gatgctaata cggattaccc taaaggtact    96900
tttaaagtat cattctcaaa tgattcagga gagtcagaga aggtcgatgt tcctcagttt    96960
aagacaaaag caattaaagt tatttcagtt acccttgacg ttgatagttt agaccttaca    97020
gttggagata ctcaccaact atcaacaact atcacgccta gtgaagcatc taacaaaaat    97080
gtgtcatttg aatcagacaa atcaggtgtt gctagcgtaa catcagaaga cttaattgaa    97140
gcagttagtg caggaacagc taatgttact gtaactactg aagatggtag tcacactgat    97200
attgttgctg taacagttaa ggaacctatt cctgaagcac ctgcagacgt aacagttgaa    97260
cctggtgaaa atagcgcaga tattactgta taagaggaca ataagaatg gaaaagacat     97320
taaaagttta tagtaatggt gaagttgtgg gctctcaagt agctaataac gatggagcta    97380
ctacagtatc tattacaggc ttagaagccg gaaaaactta tgctaaagga gattttaaag    97440
tagcatttgc taatgattca ggtgaatcag aaaaagtaga tgttcctgaa tttacaacta    97500
aaactcctac tgaagaacct tcaggagacg cataataatt aagaccaact aaaaagttgg    97560
tctttttta ttgacaattt ataatatcta tgatacacta tataagaatt aagaaaagga    97620
ggggaaagta atggatattc caacaatatt atttagaaat ccatatgatt atacgaaagt    97680
aaaaaaatta atggaaaaca aagagcagta tattgtagta aagtttgatt ctgtttctgt    97740
```

FIG. 19AAA sequence.txt

| | | | | | | |
|---|---|---|---|---|---|---|
| tcataattta | aatgttcaag | gtatgatgaa | tgtcatccaa | gattacctac | acatctatgg | 97800 |
| ttacagagtt | aaagagtacg | gacaagaaaa | ttcttctaaa | gatgatgaaa | gagacgttaa | 97860 |
| aggctactta | tatgaaagag | taggtgagta | gggtatggga | attatagtaa | actccaacca | 97920 |
| tattcaatca | gacactttat | atgagtatga | tagctttttt | gatattgaga | aagtagatac | 97980 |
| atttgaagaa | ggattgcttt | caatacagga | tgagccaact | gttttagcag | gattcatcta | 98040 |
| tgatgatatc | acatttaata | aggtcattaa | ttctaattca | gatattgatg | actatattaa | 98100 |
| gaataatgat | atttattatg | tctctgatat | aggattactt | cctgatactt | ttatcactgt | 98160 |
| tgattctgat | agaaaatatt | attcattatt | acaacagata | actgagttaa | gtaaagaccc | 98220 |
| ttttcctaaa | tgggtagagg | atgatgcaaa | aggtttaact | aagtattata | actttcaaga | 98280 |
| ttttgaagat | gtatttgatt | taaatagttt | ttacaaaaaa | gaagttgaca | tggtaagaga | 98340 |
| aaagtgctat | aataatggta | atgtatattt | attatatgag | gttctgcctg | attataaatt | 98400 |
| acctctagct | tatagtttac | tttcaaacaa | ggagcatggt | attgttatta | tcggttcaca | 98460 |
| gacacgttct | aataatgata | tactgacttt | ttatgttaaa | ggtatggatg | ctaaggcaat | 98520 |
| agctagtatg | ttcaatgtag | aacatgatta | tgattctaat | attttccata | catttgtaaa | 98580 |
| cagtcacatt | aatatttttag | gaaatcaaat | aactaagttt | ataagagaga | aaggaagcag | 98640 |
| ttatgagtaa | ctataaaaca | atagaagaag | tacaagcagt | tattattggg | gtattattta | 98700 |
| aagatgaagg | taaaattata | acatctaagt | ttaataaaat | tactaaagag | tttggtttag | 98760 |
| atagaatcgg | taaagatgac | cttaaagaaa | ttgtagagga | tatccgacaa | gacgcttatc | 98820 |
| taaatgaact | taaaaacaaa | gcaattaaag | gtaaagtaac | gttaggtgat | ttaaaagatg | 98880 |
| ttgcagataa | ccaagtattc | gaaggtaata | actaccatga | agaagtatct | acttatgtag | 98940 |
| tagctaaaga | aaaagaattg | tctcacttaa | gagaacagcg | taagcacaat | aggcatactg | 99000 |
| catacccctca | aattatgttt | gatgaactta | agaacatat | ggttaaggaa | ttacaagggg | 99060 |
| aaacattagt | agaacatcac | ggaagtaaag | ctaatattaa | tgatacagag | ctaattgtgt | 99120 |
| tactatcaga | tttccatatt | ggaagtattg | tatctgatat | gactaatggt | aaatatgatt | 99180 |
| ttgaagttct | taaagcaaga | ttaaatcatt | ttattaatac | aacagttaaa | gaaattgaag | 99240 |
| atagagaaat | ttctaatgta | actgttttact | ttgttgggga | cttagtagaa | catattaata | 99300 |
| tgagagatgt | taaccaagca | tttgaaacag | agtttacttt | agcagaacaa | atctctaaag | 99360 |
| gtactcgatt | acttattgat | atcctgaatg | tactatctaa | tgtagtttca | ggagaactaa | 99420 |
| gatttggtat | tattggtggt | aaccatgacc | gtatgcaagg | taacaagaat | cagaagattt | 99480 |
| ataatgataa | cattgcttat | gtagtgttag | attcttttatt | gttattccaa | gaacaaggac | 99540 |
| tattaaatgg | tgtagatatt | attgataatc | gtgaagatat | ttatactatt | agagatacct | 99600 |
| ttggcggtaa | atctattatc | attaaccacg | gagatgggtt | aaaaggtaaa | ggtaatcata | 99660 |

FIG. 19BBB sequence.txt

| | | | | | |
|---|---|---|---|---|---|
| tcaataaatt | tatcttagat | agtcatattg | acttattaat | tacaggtcat | gtacatcatt | 99720 |
| tctcagtaaa | acaagaagat | tttaatagaa | tgcacatcgt | agcttcatct | ccgatgggat | 99780 |
| ataataacta | tgctaaagag | ttacatttat | caaaaactaa | accttcacag | cagttattat | 99840 |
| tcataaataa | ggaaaataaa | gatattgata | ttaaaacagt | attttttagat | taaggatggt | 99900 |
| taataaatgg | atacaatttt | tattataggt | gtagcgttta | taactttttgc | aacatttaac | 99960 |
| atagtcttta | gattatttga | tttatggact | acagagaaaa | aaatggtaag | tcaaggacaa | 100020 |
| cctccactaa | gtaactttga | gtactatcat | gtgatagtac | cttacttagt | aggtgttatt | 100080 |
| gttattatac | tgagtattat | ttttagggat | tccttgtatt | ccgcacaatc | agggttcggt | 100140 |
| gttattatta | caagctttat | ttacatgcta | gtttatgtta | taattggtct | tgtagggtca | 100200 |
| tttgtactta | caatattcca | agctagaaaa | gctagacagt | atcaaacaca | ggaggataat | 100260 |
| aatgaagttc | aatgatattt | atgagcaatt | aattaaaaat | gatacagtac | aaaacattca | 100320 |
| tgagtctcaa | gatgacaaag | gaaatattta | tacaatacag | tttgataaag | gtaatgataa | 100380 |
| gtatttattt | aatgttatta | atgatggatt | cttgaaagaa | atgacaaatg | gtatggtaga | 100440 |
| ccatcctgaa | ggtcagccat | attcagtaag | tttaatcaat | aaagaaacac | ctagtatgtc | 100500 |
| agtgaaacaa | tatttaacag | atgtagaaga | tattgtacct | actattagaa | aaatggaaaa | 100560 |
| ggatttctta | tagagtcaag | tctttacttg | actctttttta | ctatatatgg | tatattaata | 100620 |
| tagaggtgac | ttaaaaatgg | attttaatttt | tagtgctttt | gataatagct | cattagcaat | 100680 |
| gagaattagt | gagggtgtat | actatttcaa | tgatacgcct | tattacttta | ttgagcatgt | 100740 |
| agaagaagaa | atgtctgagt | atgttattgt | atatgacata | catgacagag | aggaaaaaga | 100800 |
| aaatcctcag | aagaaatata | gaatagaacc | ttaccaacgt | acaataccgg | gaggaacacc | 100860 |
| tcttagtaat | ttaattaaga | gtatgatgcc | tcaacgtaag | tatcctaaga | aggttacaga | 100920 |
| agaccctata | tttgtagcta | atgttattcc | tttaggaaca | gatacagtaa | caggtaaaac | 100980 |
| cggtaaagga | ttttttgaaa | gagataagga | tagaactatc | tattctcaaa | aggaaccaac | 101040 |
| taaagtcgtt | catggtcaat | acacaggtgt | ttttataggt | ctaacaagtg | ttaagtggaa | 101100 |
| tagaacatat | acccccttag | aaagtgttgt | tgagtactac | aaaagggtta | aaggagatag | 101160 |
| gttaaatgtc | taatgatgta | gttaagttct | atgaaaaaga | tattaaagac | cttatcagaa | 101220 |
| ctaaaaaaca | catgttcaaa | gacgatgaaa | taactagtga | tataaacgat | atacgaatct | 101280 |
| ttaatgagaa | agtcatttgt | caaggtaaat | gtagaacaga | ttgtttagtg | ttagaccgta | 101340 |
| atggtacagt | aatgggtata | gagataaaaa | cagaacgaga | ctctacacaa | agattaaata | 101400 |
| accaattaaa | atattatagt | ctagtatgta | agtatgtata | tgtaatgtgc | catgacaaac | 101460 |
| atgtacctaa | agtagaacaa | atacttaaaa | ggtataaaca | taatcatgta | ggtataatga | 101520 |

FIG. 19CCC sequence.txt

| | | | | | |
|---|---|---|---|---|---|
| gttacattag | tttaaaggc | aaacctgttg | taggcaaata | caaagatgct | acaccatcac | 101580
| cacatagaag | cccttatcat | acaatgaata | tattatggaa | gacaaactta | atgacaatac | 101640
| ttagattgat | tagagaccct | catacgtata | gaacagggta | tagctataat | gctagtggta | 101700
| gatatagtgg | aggggaaggt | aatttctccc | aaacaactca | aagtaaaaga | atgaaaaaac | 101760
| ctgctattat | taaccaaata | attcattatg | tagggggtaga | taatacttat | aaactcttta | 101820
| caagaggtgt | tatctatggt | tataataata | ggtgggaagt | tatagaagaa | gatttcttta | 101880
| atactatgaa | gaatggggta | agagtaatta | atgagcaaag | acaaaccaaa | tagacgtaaa | 101940
| gagatacagc | atcaacctgt | taactttgcc | cctacgaata | ctttaacagg | agctaataat | 102000
| agtttctttg | ctaaaaatcc | ttcagagcct | aaagatgcaa | catctgttat | tgaatatcgt | 102060
| atactattta | ttaaaagatt | tgataacgta | acaagtacag | atgtgaaatt | acagaaaaag | 102120
| tatgcactaa | atcttattag | tgaagcactt | gatgttaaag | aaacttactt | gtctcttaag | 102180
| caaaaaggaa | aaaaaacaga | atctattttg | catacagata | gagtttatta | tgttcataga | 102240
| ggtaaaaaac | ttattggaaa | gtgtagtatc | agagagcaaa | gaacatttaa | gggtaaacat | 102300
| ttgatattta | tattcaaaac | aagacataga | gttaaagcag | aaaggaaaga | taaataatgt | 102360
| taaaaggatt | ttcagaacat | gtagacaaac | ctacaactag | taagaccta | tacaagacct | 102420
| taacaagtgg | taaagtagaa | ttactaggtg | tatcttacga | tagtgattac | ttcccttcag | 102480
| gtgttacagt | acaatcttac | attgaggata | taggtaatga | agatgagggt | ctacagtttg | 102540
| ttaataaggt | aaatgtagta | gaatcaatga | aacaggctgt | agtaggtatg | aataatcaat | 102600
| taggttcttc | aggtcttggc | tatgtgagaa | ctgaacaact | taaaaaagag | ttggaagaga | 102660
| ctggactaat | gacagattta | cttgctagag | gtactaactt | aacctctact | aagaaagtag | 102720
| atattgtaag | tacttttatt | gagcctgagg | taacatacca | aaatattact | atagctaaag | 102780
| atattaaact | acgtttgtat | aaagtagaag | aagaatcacc | attaaatggt | tacactcata | 102840
| ttgtatactt | acttactaca | gaaaaactat | atgatggtca | aacactcttc | ggtatgctct | 102900
| ctaaaaaaga | taagttatct | aaaggagata | ctgataaatt | attagcattc | ttcagaaaca | 102960
| atagtttaat | aagtaaaagt | gtatttgtg | ttaagttatt | aagtaaagac | tactacttta | 103020
| atttatataa | tacacatgag | acagggatat | tcttttaga | agacacagat | gttattacta | 103080
| ttgcttgtgg | tcagtcatat | gttaaagtta | acactaaaga | tattaagtct | agttatgtta | 103140
| aaattgaaga | taagactcat | aaattaactg | agctagtaat | taacctaaag | ggtgacgaca | 103200
| cattaactat | tttattctag | gaaaatgtta | taaatatgtg | ataattaagt | ataaatatac | 103260
| gttatataag | aagttttcat | aatgttttta | atacagaaac | tagttaagtt | ttttctactt | 103320
| gctctagttt | ctgtgaaatt | atatttatga | aaagttaaaa | tatcttttag | gtaaaggctt | 103380
| tgtaaatagt | taaaaaatat | attaaaattt | tatacaaagt | agttaataaa | attatattac | 103440

FIG. 19DDD sequence.txt

```
atttatatat tatgaaataa taacagaaat tgtgatatat tatatagtgt aaccttgaaa    103500
cagttgatgt tgtagggttt gtttatgttc gttaaactgg tttcaaaaca tcagttacca    103560
taaataaatg acagttaagg agagctatat aatggctaga aaaaagaatt tacgaaataa    103620
aaacagtgat ataaagttg ttcctgataa agaaaaagaa agtatattat ctaagctata    103680
ccataataaa ttactacgtt ctaaggtaga taatgcatta gatgaagata tgagttatga    103740
tgatattata gaactatgta aagaatatga tttagaattg tctaaatcag ctattacaag    103800
atacaaaagt aaaagaaaag aagctattga aaatggttgg gatttaggag aattaattga    103860
taaacgtaaa aaaacaagtg taaaagatat taaggaaaaa gaaactccta tattagaaga    103920
ggagcaactt tctccattcg aacaatcaaa acatcacaca caaacaattt atgatgatat    103980
tcaagtacta gatatgatta tttctaaagg tgcaaaagga ttagagtttg tggaaacttt    104040
agaccctgct ttaatgatac gtgcaatgga aactaaagat aagattaccg gaaatcaatt    104100
aaaaggtatg tcatttattg gacttagaga attacaatta aaacaaacag ctcaagatac    104160
agctatgagt gaagtattat tagaatttat acctgaagag aaacatgaag aggtattaca    104220
acgattagaa gaactacaaa atgaattcta caaaaatcta gatttagatg aggaaagtag    104280
aaaattaaaa gaagctcttg atagagtagg ctatacaatt tagatagtga ggttagagta    104340
atggcagatg agattagttt aaatccaata caagatgcta agccaattga cgatatagta    104400
gatatcatga catacttaaa aaacgggaaa gtactgagag ttaaacaaga caaccaagga    104460
gatatccttg ttagaatgag tccagggaaa cacaaattta ctgaagtatc tagagactta    104520
gataaagaat cattctacta taaaagacat tgggttctct ataatgtatc tgttaactct    104580
cttataacat ttgatgttta tctagatgaa gaatattcag aaacaactaa ggttaagtat    104640
cctaaagata ctattgtaga atatacaaga gaagaccaag aaaaagatgt tgctatgatt    104700
aaagaaatac ttacagataa taatggtaat tatttctatg cacttacagg agaaacaatg    104760
ctctttgatg aaaataaatt aaataaagtt aaagattagg gttgacagct tctatagttt    104820
atgatatagt atatgtatac taaaaataaa ggagctaaca attatgttta tttcattaaa    104880
tcaagaagag aaagaattat taactaaaga ggaaagtaaa tacacaccac tagaaacatc    104940
aagagagttt aacacaccta aagaagaatt cattgtaaca agttataacg aaggtaaacc    105000
cttagattac attgcaaaag aagctaaggt aagtatggga ttaatttaca cagttctaaa    105060
ctactataaa gtaggtaagc gtaataagaa atcacctgta gaagaaagaa ttgcacatat    105120
cttaaaagat aaaaacttag tcaaagagat tattaaggat taccaatata tgaatttaca    105180
ggacatttat agtaaatata atcttcataa gaatggttta tattacatct tagatttata    105240
ccatgtagaa agaaaatctg aacttaagga caaagcatta gaagaggata atattgtcgt    105300
```

FIG. 19EEE sequence.txt

| | | | | | |
|---|---|---|---|---|---|
| tgagtaagta | aagaggttat | aatatgagaa | ataaaaaatc | atttcaagag | cagttaaatg | 105360
| acatgcgtaa | taaagagaaa | tgggtatctg | aagaggagtt | cactgaagaa | gtggctcctt | 105420
| ctgaagaacc | tgaagtagaa | gaagaaaaac | tatatacttt | aaatgagtta | aaagagaact | 105480
| tactagatgc | tcaaggatta | aaagatgttg | tagctgattt | tcctgcatct | aaagatttat | 105540
| atgaacctaa | taaactatat | atttgtacaa | taccaaaagg | atatcgttct | acagaagtac | 105600
| aaccaggtca | atatattggt | atcagtacag | gattattatc | agaatcagaa | gattttagtc | 105660
| atttaagagg | tcaaatgcct | agaaatcttt | atgaaacttc | tcatgtttta | aaacctttag | 105720
| tacgtattaa | taatacaaat | ctcgaatatc | aacagcatga | gttacttgaa | gatattaaag | 105780
| atgacaagaa | gatatacgat | gttgaattag | aagacctgag | attagtaaca | ggagaagaaa | 105840
| tatcccattt | agaaattgtc | gatagtaagt | tttttgaaag | tcgtattaat | gaaattctag | 105900
| accgctatac | tgaattaacg | gattccgatg | atttgcttat | atactatagt | aaattacgag | 105960
| aattagttgg | tagtgacaaa | atgatttatt | gttcactttt | agataaatgt | gttaaaatta | 106020
| tagattaata | gttagtctcc | tcttatatta | taactgtaag | aggagacatt | tttgtataga | 106080
| ggtgttaatt | atgtcaagaa | aagcaagtat | attctatata | ctagtggtta | ttgttttggc | 106140
| tttttctatt | tcatcttatt | atatatcttc | tttcatgtat | cacgacaaag | caaagaatga | 106200
| agtctctact | gagttatcaa | acacgggaaa | gattaaagaa | gaaaagaacg | tagaatttgt | 106260
| cggtgactat | acacttaaaa | aagtggaaaa | taataaagct | tattttatgg | aaacattacc | 106320
| tacttaccta | cccggtagaa | caggagataa | cagcatagat | atgaggtact | acaaaacaag | 106380
| tagatttaaa | gaaggggtaa | atttcaagct | tattagggta | tatactgaag | atggggaaga | 106440
| taatccaatt | cataagtata | ggtttgaagc | agtaccaacc | aaaaagtaat | aaggaggtga | 106500
| cttaaatgac | aacattaatt | gtcgtcatct | ttattgctat | catttattac | ttatggaaca | 106560
| gtgattgagt | caagttaatt | cttgactctc | tttttgtttt | atggtatatt | aatatataga | 106620
| aaggagagat | taattatgga | aatggcagat | ttagaaagat | tcgatacgtt | tgtaagatta | 106680
| gtttcagatg | atgagctttc | ggaggagaga | gcattagaat | taagtgtaga | cttattaaat | 106740
| ccgatactag | aaggaggtac | agcttaccaa | gctaaaaaac | gcattagaag | taagttcggt | 106800
| aaaatagaag | caaaaaactt | taaagaaaat | tataaattct | tactcaagtc | gatagctcaa | 106860
| atagaccaaa | ggagatagga | caatgataga | aagggaaaag | ttagttaaag | aaattgaaga | 106920
| tgctaataga | gacatacaat | tgaggttaaa | agaagtagat | gattataagg | atagtatacg | 106980
| ttctaaagga | acaagaaact | atgtatctac | taaggtatta | gattcagtta | tggtagggct | 107040
| aattataagt | ttctttattc | ttgtaatgtt | acgtgtactt | gaatattttg | taacaggtaa | 107100
| tgctgtttat | tcacctttag | cacccgcagt | tattattatg | tttgttttag | ccttaggtac | 107160
| atggaaagta | agtaaaatga | ataaaatagt | atcctatagg | ggaactatta | agatgtactg | 107220

FIG. 19FFF sequence.txt

```
ggaattaagt aatgctgaac agaaccaagc taaggtattt aagtatccta atgatgaagt   107280
agatattgta tcaaaacata acttaagaca aataactttt agtgagatta atatacttca   107340
tcttaaatat atgagatata ataaggcagt agaacagcat actaagttat ctaaagaact   107400
tttttaaaaaa gataaagaaa ctgttgacaa gaataaataa gtgtagtata gtattactaa   107460
aggaggagag atattatggt tatacctagt attaaagcac aaaacaaatt caagaatgaa   107520
ttagagtatt ataagcaagg tcacattagt gaaagtaaaa tgttagaatt agcttttgat   107580
tacattcaag aattagaaca aaataatgaa tacgttacta atttgctaga agaggagaga   107640
tacggtgagt aaatttattg gagtgtactt atttaattta ttagtagtag cactaattta   107700
cacagtagga tttttattct tttatggtgt agctagctta gttattattt taactcatgc   107760
tactattgac ccgttcgtat tagctacttt cttaggaata ggattcttag ttattagaac   107820
tgcacacaga atcatggcac gagtaattaa tgatgcagta gctaaagcta ttaaggataa   107880
agaaaatgaa taaaggggaa tttattatgg ataaaacatt accaaagttt agtgtatatg   107940
aagttattgt aaagactgta attatgacac caacagaagg aagttctgac ctagaatcat   108000
tttacttttc aactagagag ttagcagaaa gatttgttga agaaaataca gtggaaacaa   108060
aaaacggtaa acgtgtatct tttgctgtta aagaacgtaa agtaaatcaa ccaggctaac   108120
attaatttgt tagctttttt tattgacaaa tcattttata tagtgtatag taatattata   108180
cagaaaagga ggaattatta tgaaagtttc agaagaagta aaacagagtt atctagagaa   108240
tagagctaat actaaatgg ataagataag ttggtctgag ttaaggtcta gtcctttagg   108300
tattacctta ggtgatatta tattttatag tgtggttatt atagataaca ttatagctat   108360
tattttaact ttaaccttaa taggtactat tactgactca attgagagta ctttagccca   108420
aataatcgta gggatgttca taatcattac tatatatgga atcctatcag cgttaatacc   108480
tattctagtt cataaagctg tatcaccggg atggagctat actgaatgga atgaatccta   108540
ttacatcaga ttacctggag aagagaacta caagtactat agtaaatggt atttagattt   108600
attaggagtt aaagaatttt actataagag agacaatgga gaagaagtaa aagaaaaaat   108660
atatcatggg cttttcaagc tgaagtaaaa agacctgaag atgttaacca ctggaaaaac   108720
caattgctta ctaatagacc tttaacaatt ttagaatata aaaattaaa gaattagat    108780
aaggaaagtg aaattaggaa acaagaagat ttagaagaat ataacaata caatagtaat   108840
taaagaggtg gaaagcaatg ataagctcat ttgatagtat actcttgtc atatacatta   108900
ttatagctt tgcagtagct atggcaatta tctacttagt atttaaaggt atgactattc   108960
tactagataa gctaatgatg ttattattaa gtaaaactac attagatgta gaagcttgct   109020
ctatgataat ggcagtcatc agtacaattg tgtttggaat tattgtactt ttaatatggc   109080
```

FIG. 19GGG sequence.txt

```
tagcagtaaa taatatttta ctataaggag atttactatg gattttaatg actttataaa    109140
cagtgaatcg datagggtag gtaagcctaa acaaaagaag aaggtagaga ataagctacc    109200
ttcttctact cctattgaag ataaggaaaa gaaattaaaa gagataagaa agaaatcatt    109260
atatattgat ttaaggagaa aaagaaatga ctaagaaac aaatgtactt tacaaagata     109320
agtatagaga ttatactata gttgtaagat tagcagggaa tattattgtt actgaagtag    109380
ataagaaaca taaaacagca tttacaccta ttatatttga caatggtgta gaaggcgtag    109440
agcttgtaat gcgtataggt tctgtagagc ttagcatgac agatttacgt gagttcacaa    109500
aggaagtatc tacagctcag aaagctttag aatattttaa taaaaaactt tatattaaag    109560
gcttgacaga tgaagcattt taatatatac taaaagtata aataaaataa agaaaagagg    109620
aatgattatt atgttattag gaattttatg gtttatatgg ggatttgtat cgtactttgt    109680
attgatgttt ggaattgagt tttggaaaga tagatggatg ccaggtgtta tcggagcagg    109740
agctttacta ctattcttat tttggattat gaaatctatt cataatgcta tgacagtagt    109800
atacttgtat taggaggttg tatagatgat tgatatacta gttattcact atgaagaaac    109860
aaataaacgg gttttaaaag aaacaataca aacaatacaa aatcatttaa atgatgaaca    109920
tggtttggtt aagatgacag caacaaaact tagcagagag aatatagaga aaagatttaa    109980
taactataat atagtcattg cagaagatga ccctgataat tcttatcatt acggtgaagc    110040
tgtagaagac gcagatttta ttatagacat accaatttca tatttagata tacatgcagg    110100
aatagaatgg gatgttgata atcctgtaga tatgctagat aggaatcctg attttataga    110160
agctgtaaat aaactaaatg aagacttaat gttataagga ggaaatagaa tgctaaatga    110220
aaaactaaaa aacctggaag atacaaaagt atacatgatt aatagtattg caagtttact    110280
aagcgcaagt acaggaaaat caagtaaagt attttttgat gaaggaacta ttaaaattgt    110340
aagtggtgaa acaaaagcag tagaagttat tgataactta gttcaccctc actcaggacg    110400
tttacctatt aaaacaacag aacgtattgc gctaggtaga ttaacagatt ctttacagtt    110460
tgttatctca gaaatagaag tagttaaaga ccaaattata gatgaagaaa atgaagctta    110520
cattgatttt gtgatggaag actggaactg ggattaatgc ctatggactt attaactatt    110580
gcttctgttg cttttatagc tgtagtcatt attgatttga ttaatgatga tatgagctat    110640
atgcttactg gtactgcaat cttaataaat atttgggcgg gatttatgg atggtttttc     110700
ttactacaag caggtatgtt acttttctta ttattagcta ggaaggttaa agatgataag    110760
gagtcaatac tatattccag tgcttcatta atatgtgcac taggaatgat aataaatctt    110820
ctttcatttt cttaaaaata agtattgaca ccttttgtact tttgtattat acttagtata    110880
taacaagtac aggagatgat taatatgagt aaagaaacaa tcagaagaca attttcaaat    110940
gcaattgaga ttatggcaac aactaaagaa tggtggaact tccctaaaag ttttgatacg    111000
```

FIG. 19HHH sequence.txt

| | | | | | |
|---|---|---|---|---|---|
| aataaagaat | ttaaaattaa | aacttttaaa | aatgatacac | ttgtatttga | agttagagaa | 111060
| ggtagtagaa | acttaggaag | ctttgtagtt | tttacaaaca | ttgattttga | ttatgataaa | 111120
| ctagaaggaa | cttcaacaca | atatatgatt | aattactttg | ctaagaaatt | aactaaagat | 111180
| atgtttaact | atcataagtt | acaattatag | taggaggtgg | aaagatgaga | gaagagttaa | 111240
| aaccttttaa | taggaaacaa | gttaatgtta | aagggtattt | agatgatgtt | aagtactcaa | 111300
| agcgtagaag | acataagggt | aatcaacatg | ggtgtgttaa | aatcacagtt | actgatgtaa | 111360
| agattaatgg | tatacctatt | gaccacgtta | acattgaagt | tggtatctct | ttctatgaaa | 111420
| aactaaagga | gcttcaagga | aagagaatcc | aatttgtagg | cactgtttac | aagtatgtta | 111480
| aacatgctag | agggcgcaaa | ggtagaatta | aaggatttta | taaagaggat | tatagcgtaa | 111540
| ctttagataa | gaagttacaa | aaggaggaaa | aataatgact | gaatggtatg | ctttatgcta | 111600
| ttatgataaa | gtaggtaaaa | agaaaatacc | taggcaagtt | agagcgcaca | gagatatttc | 111660
| agtattagaa | gaattaaaag | aaagattaga | agaaagaaat | cctaatacag | aatactctat | 111720
| aaaaacaaca | aaagaatttg | atgaggagag | ataaggatgt | taacaccaca | acaaaaagat | 111780
| tcattaaaag | aacaacaaaa | gaaattaagt | aaaaagaaga | aataactgtt | gacaaatgag | 111840
| tgtgcatagg | ttatacttaa | gttaacaaat | aaagaggagg | tatgacctat | gttattcata | 111900
| attttattc | tagcagtatt | ctttgtacta | ggatttatta | acggatggaa | ctcagaagac | 111960
| taaaaagga | gtggttatag | tgaagttaga | agataaagta | ttagaaagaa | ttgattctct | 112020
| tggaggtaag | ttaggtgata | ttagccaaca | tgcttgggaa | gctttagtaa | agtaccaaat | 112080
| tatatatggt | attatagacc | ttatagtagg | tattgtagtt | atagcattaa | ctttatttt | 112140
| atggaaggta | tttattaatc | aacataagaa | ggtaaatgat | atggatagag | atgatgatta | 112200
| tagtttacta | tttgaagatt | gtgaagattt | atcaggcata | ggtttgtttt | atgtaatagt | 112260
| tacatcatta | atatcactat | ttgcatttat | atacttaatc | tatggaatac | ctatggatat | 112320
| tataaagata | ttaaaccctg | aagtatttgc | agtaaaagac | ttaatagaac | aagctaaagg | 112380
| aggaaattaa | tatgaaacaa | agagatttcg | aatttgaaga | ggattttgta | ttaacttatg | 112440
| aatgtgagga | ttgcaaacat | ttcgaggatt | ggggtcatga | tgaagagcct | gaagaatgca | 112500
| gtgaatgtgg | tagtagtgac | ttaattaaca | atacaagtca | tgaagacact | gagtgtgata | 112560
| tgtgtaaagg | atacattgat | atgtggcaag | atggttatag | atacatggga | gataataaag | 112620
| cataccttga | aaaagaagat | tcaggtttaa | tttgtgaaga | ttgctatgag | aaattagata | 112680
| tttaataagg | aggaatttat | atgaataaag | cagtagaaca | agcaagtaac | gcagtaggtc | 112740
| aaggattttc | agccatggta | tggcatcaag | tattagtagg | tctagggttt | attttattag | 112800
| ggttgatatt | atccttacta | gtttgggtac | tagtgaaaaa | atttcatgta | ccttttaatc | 112860

FIG. 19III

```
                                    sequence.txt
acccaacagc ttttgttgta tattcaatta tgttagttag tattgttgct agttttattt    112920
ggggcggttt acatgtaatt aaccccgagt attacgctat cttagaactt aaaggtttta    112980
taaagtagga ggaattctat gactaaagaa gagttagagc aaagagtaaa agaacttgaa    113040
gcagagaata aagaacttaa aaaacaaata gaacgttttg aagacgaggg aggaaaaaca    113100
aaagatgaat agtagacaaa agaaaatttt aacattaaca gtaagtaact tttttaattct   113160
agccttagat actgtagcac taattagata taaaaaggt aaaattaaac aagagaatta    113220
taacacaggg caaattacaa gaatgatagc tacaacagct aactcattag gtattcttta   113280
cttagaagag caagagcgta aagaagttaa agatattaaa gtaggtactt ttgaaattgg    113340
agccttaaaa agatttacaa ataataaata aaaaaagttt aagaaaccta ttgacattag    113400
gtttctttta ttatatacta atattataag aaataaggag gttaacttat gaaaggtatt    113460
atcatatttt acaaggaaga gaccaaagag gatttaggat attttcttgg gtttataaac    113520
tttaagctag aaggattatc ttacacaact gaaggtactt tagtagataa tgatgtagta    113580
gttttaaagg ataaccaaat taatgaggat aatttagagc agtttagtat gtcaaacaat    113640
aatttagtta ttggaatact aggtcattca tctctttcag tacgcatcta tgaaaaaggt    113700
attagacaag agtttgatag agtagaagaa tatttagagg agttgagaca ataatgatat    113760
ttatattaat ttttggttta ctatttattt tatctttact aggtattttt atttattcta    113820
tagttttacg aaagaaaaaa caattaatag aagaaagaga atcatttggt atttataata    113880
gaacaaaaga aaaactgggt gatgtaacac gtttagggta tgaggaagat gtatataagt    113940
taatccataa ccaatctaat aaaacaatca tagaggataa aaagagtaaa gttgtagata    114000
caattaaaaa gatgtatgaa ttagaattaa catctgtaga tgtttctaag gtagaaggat    114060
tatctccact tgatacagaa cctatgacaa atatgaaatt actttcatat aagctagata    114120
gagaaggatt atatagttta agtaaattta tttaggagtg atacaatgga atttatagat    114180
aaaaataatg taattaaagc ttatgatata ccaaatgttt atttaaaagg ttatgtatta    114240
caggcatgtg ataaaaatgg agatacaaca gcttatgatg gttatgacca aatacactat    114300
aaagaaggta gagtattaac attccctttt gataaaccat taagaaagat aaatgtacta    114360
tcaggatatt acaaactatt taaaaggag gacataatat gatttatttt gttagtgatt    114420
tacatttcgg tcatgataat attagagaat tcgaagcacc tacaagaagt cactggaact    114480
cagtagaaga aatgaatgaa ggttaattg agttgtggaa taatacaatt acaaataacg    114540
atattgttta taacattgga gacttctttt tcaatatgaa accttctaaa gtagaagata    114600
tacttaatag actaaattat aaagagatga tactgattgc aggtaaccat gaccataaga    114660
aacttataaa actatatgaa cgtaatggta ttacagtaaa gtacgcagac atgattaaaa    114720
aggatggtaa gagatttat ctaagccatt atcctacact aataggtaga aaaaacatgt     114780
```

FIG. 19JJJ sequence.txt

```
ttaatattca tggtcatata cactcacaat taatgggtac tgaatatcac atcaatgtag    114840
gttatgatgt agagggtaaa attgcctata gttttgatga tattataagt agagcaggtg    114900
aatataatgg agaaattcaa aggtaaagat ttatataaaa ctagaattag aaaacaaaca    114960
attaaaaatt tagttataaa aacagagaag ctacataata aacacggaaa gtatagacct    115020
attggtcatg tttattatta tccaaaaaca aaagagttta ctttatctaa acctgagcag    115080
aaaatattta tagagtatat gaaggcatta ggttttagtg ttaaacataa gagacgtaag    115140
aaaataatta tagtatacaa gaatgtgtta gatgaatatc ttagtatgta tcaggaagca    115200
attgaaagta cgtgttgaca attaaggtat actatgctat agtatagaaa aggaggttaa    115260
ctgatgaagc attttatttt gattttaggt attgtaattc tagttattgc attaggtatt    115320
gttttacctg catggatttt acaattagta ttatctgcat tcggtgttaa agtaagtatt    115380
tgggtatgta tcgggatatt tattttaatc agtgcagtag gaagtatgtt tagtagaaat    115440
taaaggagga actataaatg gcaaaatatg aatcaaatat caatggagaa aattatattg    115500
caacaccgtc acaagcttta agagaggcat tggcagaatt aattagagaa gaaaagaatt    115560
ttgcagagta tcaaactaag ggtgaggaac agtatgaatc acagttacaa ctaagacact    115620
ttgattcaat gatttctcag tatgaagagg ctattcgagt actagaggat agatattcac    115680
ctcagatttt tattccaaaa gataataagg aggaaaagta attatgaaag cagaatcaat    115740
agcaagattt tttcaggata aggtattaca aatagaaggg tataaagtaa gattcactca    115800
agctagttca tcatatattt tagatataga tactatggat gaatcagtat tgttttttaga    115860
tactgtagtt ttcactctat caggcaagta cttattagat acgcacatta caattaataa    115920
acctgagaca ctaagttcta atgaattata cacagagatt agtaataaac tacaagagat    115980
tgtaggagac caaactaaaa cagatataga gttatcaaaa tactttaagg aggtaaaata    116040
aatgagttca gaagctatta caaatcattt attaaattta aatcaaataa aaattaaaga    116100
atataatatt catgcttaca ttaaaaaatc tgtttgttcc ggtattgaaa atgcagattt    116160
tgaagtaaga ataaactata tagcagacaa agaccctaac tatattagaa ctattaattc    116220
tattattttt gttgattaca gtaaccgtaa tccaaaagaa attttactac agtttaaaga    116280
aaaaattctt tctattgtaa aagaacaggt agagattgat aatgattttta ttgaggctat    116340
taaagatatt aatacaaatc atgaactaga gaattagaa ccttttatta ataaagaata    116400
ctattctatg tttaagtcat ctattgaaaa agaggtacca gtagctttat catctgaagt    116460
acttaataga tgtacaggta aaacaagcac actagcttat ttagctattg aaaaggattt    116520
acctttaatt gtgtctaaca attctatgat gaaaatgctt aaaaaagatt acccttctgt    116580
taaagtttcg tctgttgaag atttctcaaa ctataatatt aaaggtgaaa ttgtacttat    116640
```

FIG. 19KKK

```
                                   sequence.txt
agatgaagta gatgtagacc agttatatag tgcagataga gtttctgttg atgcactact    116700
agtaggtatc ataaaaaatt aaataaattt gtaaatacct gttgacagca ggtatttttt    116760
atagtatact ttagatgtaa agaaaaagga ggtagtaata tggttggtat tataatttta    116820
attgtcggtt taatattatt tttagctagt ggatataaat tagttttagg taaatattat    116880
gatgacatag atttaaagat gttatttaca atctttggta ttggtgctat actattactt    116940
acaggattta tattataaag gaggaaatta caaatgaact ataaagaagt actagaagtt    117000
attaaaaaga ataagccatg taaggttaga tttactggaa gtattttagc aatcgttaat    117060
aaggaattta atgcagatac tgataaaggt atactacaaa ttgatgtatc aaatattaat    117120
aaaaatgact acattaagtt acaacagtat tgtttagaaa gagatgatta tactgtagca    117180
ggagctattt tattttaagg aggagtaatt atgaattata gagattttat tacggattgt    117240
attagttgtg gttataaagt ccacattagt gttactgaga aaagagttca cattatttca    117300
gaaatgacat cagcatctta tccaaagaaa gaaattaatt tggatgaatt acaagcttat    117360
gtttattata tgaataattt tggaagtcag attacaacgg agggattata aatggaatta    117420
gttattaata ttatagcagt attaattggt atgtatggta tttacttta tgttacaaaa    117480
tttagtactg gtctatcagg tatcttaatt gtactaggta tggctgtagg tctttacttt    117540
tacttagatt acttaaatgt tagagagaat gttattcgat tagtatctgt aatgtttggt    117600
gctttcttat ttagtatcga gatgatttat aataagatta tgtttgaaat taaaaaatct    117660
aagtatgata agactgttag aacgtacaga ggagaccaat aagaattta ctataaagag    117720
tacttaaaat aggttaagtg ccctatatgg taccttaaaa tggcttagaa ttgaaattaa    117780
ggagatgaaa agttattata gctactaaat atattgtatc tattgaacga tggtaaataa    117840
ggaggagtag ttatgaatgc taggaaagca cgtaagaaca ctaaaaatca taaagactct    117900
agtgtagtaa ctaaggagca acacctaact tatatctata ataagataaa ctacttgatt    117960
gcaaatagta gtagtcaggg taagacatat gtggtaatga acctaagaac aggttatcct    118020
gacgagttct ctttatctaa attaaaatat ctaaaagaaa ttaaacagca ctataaagac    118080
ctaggattta ccgtacaaac tcaagtaaga aagtcacggt ggtcagagaa agtataatc    118140
aggtactact ttaacttagg ttatatagat agcgtgttag ttcctattat acacattagt    118200
tggtaattac aaggaggaat agttatggat aatccaaact taaataaaaa gacactgaga    118260
gctgtaataa gagaaatgga taagatata gaagaaagag cagaagcatt aagaagagaa    118320
gagactagat taagtattgc tagggataat agaaaaaggc tttacattga attagagtct    118380
atactagagg aggaataatt atggatttta atttgaaaga ctatgctgta agacctataa    118440
cagacaaaga aggaaatatg gtagtaagaa cagtgtatgt gtgtttaaag agagaataca    118500
gtgattgggt agtagataaa gtatatggta gacaagagag ttctgaaacg tggttaaaat    118560
```

FIG. 19LLL sequence.txt

| | | | | | | |
|---|---|---|---|---|---|---|
| ttatgcaaga | aattagaaac | atagagagag | caaaactaag | agtggagaaa | tggcaagtta | 118620 |
| attagaataa | ttagttaaag | gagggaaaga | tatgagttta | tcagaattat | tagagtatca | 118680 |
| taaaaatagt | ggtaaggaac | gagcagagta | tataagtgat | aatggtaatt | gtagagtagc | 118740 |
| tattatgcat | tatgataaat | gggcagttgt | aggagattta | gagaatgcag | tctttacaat | 118800 |
| tgagaagtaa | tagttatgta | cttatttgct | aaaataatta | ttatatctat | tgatgttata | 118860 |
| cccttaatgt | ctattattgt | tgtacagtta | attacagatt | ataatgatag | acattaagta | 118920 |
| tcgaatattg | ttgactagta | agaagaagaa | aatattacta | ttaagaagtt | aaagttaccc | 118980 |
| gggaatattg | ttgactaaca | ataataagaa | gaaaaaaata | ttattactat | taagtacctg | 119040 |
| ggaattcttt | tacctctccc | actcagccta | ttacttacta | ccgacttccc | taactactta | 119100 |
| ttctatagtt | atagtattca | tttattatac | aatacttaaa | ctatagtatt | ctaaccttaa | 119160 |
| tctatgctga | agcggtatta | atctattgtt | attatataat | aatcttatct | aatagtggta | 119220 |
| taatctaggt | tattacatta | gaatgattct | aatctagtat | tttaatcttt | agaccctagg | 119280 |
| aaaagtggta | ctaaaatata | gaaccctata | ggtacgggat | tcttatttttt | aaaattacta | 119340 |
| aaaagtatta | ggttttccct | agggtaaagt | tttaatgtac | ttaaaatcgt | aagtagctcc | 119400 |
| ttatcattta | ggtctgttta | attgagaata | ttagaagata | tccgcttcaa | ttacaattaa | 119460 |
| gtgttgacaa | tcatgaagcg | gtatgttata | cttagtatat | aaattaatag | gagatgaatt | 119520 |
| aaatgattat | accattaatt | atactcatga | tgaccttcgg | tacatttgca | ttcagttatg | 119580 |
| ttgcacatga | tgcatacagg | gtagatgaaa | aaggtatcat | gtatgctatg | gtagttggta | 119640 |
| ttgtagttat | aaatgtaatt | ggtttagaaa | tgataattgt | agaatgttta | tagaggagat | 119700 |
| gatttaatat | gattgatatt | tatttacaca | gtgaatatga | taaagataag | ttaaaattta | 119760 |
| tccttaaagc | aataagggat | ttttctccta | gagaattaac | ctacgatttt | aggaatccaa | 119820 |
| aagcggatgt | tagtatccag | gaactactag | gagatgacat | agacatattt | gaatctatag | 119880 |
| cattagatta | ccctaatgat | attaatatcc | ttgtaggaga | tagtggatac | tcgatagttt | 119940 |
| atcagaatga | ttttcttaca | attagtggat | tgagtacggc | tatgaaggag | gtaataggat | 120000 |
| gataggattc | acaatattaa | gtacaataat | ggttatctta | gttatagcta | tgtacactca | 120060 |
| ggtgttagta | gatatgattc | agtcaatcag | gtatgataga | tttgataagg | tacttaacat | 120120 |
| agtaacgttt | atagttatga | cagttgtact | agtatcaggt | attttaatta | tgtttgacat | 120180 |
| ttagagctta | tttaagaagc | ggttaagtag | ttaaggataa | attggtctag | aaatatacta | 120240 |
| ccgcttctct | atggctcttt | aaataggctt | agaattgaaa | ggagatggaa | taatgaaagc | 120300 |
| aattgtatat | tgtgctaaaa | gatatagtaa | gcatacactg | aagcatattt | tagaggaatt | 120360 |
| agaagcggag | aatagtgact | taacatttag | tacagaaata | tcagatttag | gggaagtaga | 120420 |

FIG. 19MMM sequence.txt

| | | | | | | |
|---|---|---|---|---|---|---|
| tattgttgta | caacatacta | aattaccttt | ctcagaacta | atggatttgt | gtagtaaagt | 120480 |
| aagtaaaggg | tctgaccgct | tctatgtatt | tgttggtaat | cactcagggt | attatataaa | 120540 |
| cggtgattta | tatatcaacg | agataggtaa | gtttattaca | tctagagaaa | ctaatgttat | 120600 |
| gatgtagagg | aggagatatt | atgatagaaa | ttagattagt | tgaaggctat | gataaaagtc | 120660 |
| agttgaagtt | tatgttaaag | aaaattaaga | gagtagcacc | tagggaatta | acttatgata | 120720 |
| tagaagcggg | gatagattcg | gtagatgtta | atattgaaga | tgtacttcct | cataaatcac | 120780 |
| cccaggagta | tgaaagatat | tcaatgttac | ttgaagaaga | cttatggata | gttatacttg | 120840 |
| agtcaggtta | tatagcttac | tgggatggaa | agaagtatgg | tggtgaagct | ttagatgata | 120900 |
| ttatatataa | tatgtttaaa | gggagaggga | gactataatg | atagaagtat | ttttaagtaa | 120960 |
| agattatgat | aaggatttac | tcaaagctta | tttagagtat | attagaaagt | ccgcttcaag | 121020 |
| agagttaaag | tataatacta | accatactaa | aggaacggat | gttaatattg | aaaatattat | 121080 |
| tagttatact | aatcaagagg | ttcatcattt | tagctcttac | ggtatgtata | gagatgactt | 121140 |
| atgtgtattc | atagataata | caagagtatc | tgagtatctt | aatggtgaac | ctgtaggggt | 121200 |
| agatacaata | tataaatata | taaaggagat | gtaatggatg | tttaaagtat | attatacagt | 121260 |
| ttatcataga | caaagtatga | agactattaa | ggataagtta | gatagaagcg | gtttaatcta | 121320 |
| tttcttatat | gaaacttggt | ataaagatat | aaataatgta | tgtccttcta | actataaccc | 121380 |
| ggaatttggt | agtcttaata | aagatataga | catagataga | ttaattgaag | cggttaatga | 121440 |
| agaagggata | ctacttatta | accatggtaa | ttatgttaca | gtagaagagt | ggtaggatgt | 121500 |
| tgacaaatca | taagtagtgt | ggtatgatta | aggtagaaat | tttacgataa | actcgtagga | 121560 |
| taaaaccgta | ggataaaaaa | ggaggataga | atatgataga | tattgagata | aaaatttggg | 121620 |
| atgaaaccct | taggatgcag | gttgaagaag | aggatgtact | ttccttctta | tctaagttta | 121680 |
| aaaataaaac | aacaggtgat | aaagaagaat | cttatggagt | agggttagat | gaatctaaat | 121740 |
| ggaaagtaca | cccattctat | acacgttatg | aggtacaccc | tgaaggatac | gttaggttga | 121800 |
| aggatactaa | aacacctgta | atatttacta | agtatagaaa | agaacttcac | cataaaccac | 121860 |
| agtttattag | ctctaatata | atggatgatg | aaggtaagca | tacagtagct | ctacataagt | 121920 |
| tagttgctga | tacatttata | cctattccat | ggtatttaca | gggatataac | tatacagatt | 121980 |
| tatcagtagg | cttgaaggat | ggagattatg | aaaataaaga | agcggttaaa | gcatataact | 122040 |
| tagcttggta | tgtaggaagg | atacgaggta | atgctccaat | gattaaactt | atggacttag | 122100 |
| aagatgatag | agtattatac | tttgctagta | ttcctcaaat | agagaacttt | attagagata | 122160 |
| ataaattaga | ccctaaacgt | tttaattaca | aaactgaata | aatgataagt | agagagggct | 122220 |
| taagtagtcc | tcttttattt | aggttagaat | aattagtaag | tagctcctcg | taatactaag | 122280 |
| tagttcctga | ttttttgata | tagttgtaag | tagtcccctg | gtaatccccc | cagtttatcc | 122340 |

FIG. 19NNN sequence.txt

| | | | | | | |
|---|---|---|---|---|---|---|
| caaccgcttc | aagcagaccg | caataagaat | ccccaggaat | tatattccca | gggatttcta | 122400 |
| taatttttt | atttaattaa | gatatgtttc | aatatattct | tcataaattg | cacttgctaa | 122460 |
| atcattgtac | ccgtctttt | gtttttcctc | cattaaccaa | ttgtaatcta | cacttaaact | 122520 |
| gaataaataa | tcttttctt | ttacatcaat | taaatttctt | aattcattct | caaagatatt | 122580 |
| aacttgatac | acatagttta | cttttttaa | taggttgtgc | acctctttat | tcaattcttc | 122640 |
| tttagttccc | tcaaatttaa | attccattgt | tatcaatcct | tttcatttag | ttgttaaggt | 122700 |
| gtttgattac | cttacaaata | ctattatatc | agattgagga | taaattgcaa | taggtttttg | 122760 |
| aaactttttt | aaattctttt | tgtgttgact | tgatcgacct | ataacaacta | tttagtaggc | 122820 |
| ttttttgaat | atgttttttc | tgtttcttcc | attataaaca | aaaataggc | tcataaaact | 122880 |
| ttttaaaaga | atttgtaaat | atgtattgac | ttattaatca | tatgatagta | atataaaggt | 122940 |
| acagcaaggg | aacagcaaca | agatattaga | attatataaa | aaaattattt | aattggagat | 123000 |
| gatttaaatg | gatgtaaaag | aaattgcaaa | tactataatg | gagttgtggc | aaatggacgg | 123060 |
| ctacagatgt | acagaaccac | cattatatga | aagcacatta | aaccatacac | gcacatatac | 123120 |
| ggctttaatc | gtaagcatta | aaggaaacta | tgacactgtt | caaatgttcc | gcaaaacgcc | 123180 |
| tataatgagc | atgagagggc | aagcccaacc | ggctagtatg | ttagtaaatg | taattgatga | 123240 |
| tgtgattata | atcgtatatg | aaaatgttgt | ttacggggta | cagaataaag | aaataaaatt | 123300 |
| tattgaagaa | atttaaaaat | aggggttgca | atacccctta | agatgtagta | atataataga | 123360 |
| tgtaagggat | agcaacacac | cttaaaaaac | ttttaaaaa | gttaaaaaaa | gtgttgacac | 123420 |
| cttacaagat | acatgttatt | attagtatag | aagttaagac | aagccacata | gcaaataacg | 123480 |
| aaattaaata | aaaaaattat | agaataggat | ttgattatta | tgacaaacaa | aaattactta | 123540 |
| tatgaagaag | ctcacacagt | acaagggaac | gaaattacgg | ctttcagaat | tccaaatgac | 123600 |
| gcaaacggca | acccacgtta | tgtagtgcat | ttcatggatt | taaatattaa | actagcagac | 123660 |
| tatgacaaca | tcaataaact | ttacggattt | aataaatatc | gtgctaaatg | gtttggcggt | 123720 |
| ggtgtagtat | tccaaagcta | taatatagaa | gatacattaa | attttgcact | agataaagtt | 123780 |
| aaagaaatag | aagcggttaa | gaattaaaac | cgcttctgaa | ttaaataaaa | aatttatata | 123840 |
| aaaaggatat | gataatatga | aatttaaaat | agaaaaaaat | aacagtgata | taaaaacttt | 123900 |
| atggaattta | gctaaaaatg | gatatatgag | ttatcaaact | gtacacaata | tatttaaaaa | 123960 |
| tgaatcagat | gaatttatta | tatttaacag | taaacaaact | tataataaat | ttatggaatt | 124020 |
| aagatataat | agaagtgcaa | tccaatagta | taaaaaaatt | atacaattcc | ctgggattaa | 124080 |
| attcctaggg | atttttattt | gttttaattt | atataaaaaa | attatttaat | aaataagtta | 124140 |
| gtgtaaaatt | gactattgac | aaggttgtat | tttttatggt | ataatgaagt | gaagacccttt | 124200 |

FIG. 19000

```
                                   sequence.txt
tttagtataa aaaaattatt atataaaaaa tttatattaa atggttttaa agcgggtctt   124260
tctcccaacc ttgtcattta tatagcggaa gggttaggct ggttaccgct gttttacttt   124320
ctatatatag aatactatga ataatggtaa ttgtcaacac ctttcagaaa ctttttttac   124380
tttctttat  tattatataa aaaaattata catattttag ggctccactt ccattatata   124440
ataattcggt attaatgtca atagataaat gtaaaaaagt tttttaaatt aatttcatta   124500
aatccattga cttgtgtttc tttctatagt aatatatagg tataccaaca agggaggcaa   124560
tacaaatgct aaaattcaaa tggaaaaaca aaacaattaa atcaactcaa aaaacggata   124620
acattctatt acttattata ggtggtttag ttgcaacaat cacacctaaa cttgtaaact   124680
ggtttttact actacaagat aatataaata ttttttttaag ataactattg acaacctaga   124740
aacaacatgt taatattaag ataacaaata aatcaataaa ggaaatgata aaaatgaaaa   124800
aaatcacaac aactttaaac ttaatcggca tgaaaaataa tgaaaggttt acagaagagt   124860
taaaaaacta ccgtcaagat gttactttct tgaaagcaaa taaaattgta aaatattcaa   124920
aataaggctt gacaacttaa acactacatg ttattattaa ggtacaaggt aagggaagcg   124980
gtcaaccgct tccaacctaa ataaaaagt ttaaaaaaac tattgacagt cacttgaaac   125040
catgatatta ttaagataac aaaaaacaaa cagaaaagga attgattata atgaaattta   125100
tcaaaactat cgaaaactta ttaactaaag cagaaaacaa agggcaagca attttaaacg   125160
gtcgttatta tgacggatat agaaacggtg agcttgaaga aaaatacgca atcgaaattg   125220
agggaaacaa attagttatg cgtcactggg gaacacaaac aattgagatt gacttaggta   125280
tgaaagaaat tgtttcatac tatggagaaa gcaactcaga ccgtgacagt ttaaacacac   125340
ttgtatattg cttaggaatt gcgccaaact ttagatactt accaagcaaa gacttattta   125400
tttacgaaaa ttaattaaat aaagggcttg acttccaagc cctaccatgt tattattaaa   125460
ttgtaaggta atcaagcaca acgacaaaat aaactgaaaa ggaattgatg aaaatgttca   125520
aattacaaaa taaagtggaa attatcgtac ctaaatatac taatagtggt aaagagattt   125580
caagccctgc aattaaagaa gcggttaaca atgcaactaa aatatgtgga ggttgtacga   125640
taactgaaat caagggacaa tggtggtcag acgatgaaca acgtattatg gaagatgaca   125700
acttaaatct tgagtggtac tatgacaaag gtatgcaaga catgaacgac caacaaggggt   125760
tattacaagc cttatcaaag attgctagac aattgattgt attctatgaa caagaggcaa   125820
tcagtataaa aattaatggt acactatata ttatagatta tgaagattta gatttattat   125880
cttatgactt atatgaatta atgtttaaaa attaaataaa aatttatat  aaaccgcttc   125940
ggattaaatt cttgaagcgg tttttatgt  aaaatttatg cttgacaaat gtattaaaaa   126000
atgagataat agagtgacaa ctttttttag tataaaaata atattatata aaaaagttat   126060
agagttttta aggctccaag tccattatat caattttact actggttgtc aatactttct   126120
```

FIG. 19PPP sequence.txt

| | | | | | | |
|---|---|---|---|---|---|---|
| tttttatat | aataatttaa | ttatcttaaa | gataccgtcc | acctccatta | tctcaaattt | 126180 |
| tgcccccaaa | gtcaagaact | ttctttcaaa | taatttattt | aaaaagttt | ataaaaggg | 126240 |
| ttgacttatt | ttgtactata | gtgtaatata | taaagtgtag | taaggaagcg | gaggaaataa | 126300 |
| cctaaaaaaa | gaatttaaaa | aacttttaaa | aaggtgttga | caaacttcca | aatacatgat | 126360 |
| aatattaaga | tagttagaaa | aacaaaaaac | gaaaaggaat | tgataattat | gaacagatta | 126420 |
| gaaatagtaa | aagatacggc | aatggaatat | atccttatga | tggataacag | tgttatggac | 126480 |
| ggcgttatga | cacaagagga | atacaacgaa | gcggttagct | ttgaaaaggt | gtatgactat | 126540 |
| actctatcag | aagcaaatca | agaatgtaaa | ttcttaggtg | gtaaggtttt | aactttccta | 126600 |
| gtacatgaag | caatcgaaga | atacgcataa | aaaaacttaa | taaaaggggt | tgaatgtcaa | 126660 |
| cccctaccat | gttaatatta | atatatacca | aatgagagga | attgataatt | atgagatacg | 126720 |
| aaatcgtaac | attagttaat | ggagaattat | tcatgtttgc | aacatttaag | aaagcagagg | 126780 |
| cagaaaataa | atatcaagaa | tggtgtgact | tgtacggtca | agaaaatgtg | agcatggaaa | 126840 |
| aaaattaaaa | taagcggttg | acaaactaac | cgcttcatgg | taatattaaa | ctatactaaa | 126900 |
| gaaaaggaaa | tgattacaat | gacaaaaaca | atcaaacaat | tagaaagcca | acttgaaaga | 126960 |
| ctagaaagaa | aatcagatga | gcaactagca | aacggatatt | atgaagcctt | tgaaagaact | 127020 |
| tgcgcacaaa | ttagagaatt | agacctacaa | atcgaattaa | aaaagaattc | agaaactgtt | 127080 |
| taaaaaaatt | aaataagggg | ttgacactta | accccttaga | tgttattatt | aatacataag | 127140 |
| gtaaaacaaa | taaggagga | aaacaaaatg | atgatttgga | tattgatttt | tatggtaatc | 127200 |
| cctttttgtac | ttggattcat | taacggttgg | aactcagaag | aagaaaatta | aaaaaagtgt | 127260 |
| tgacacttta | aaaaatacat | gttaatataa | atatatacta | aagaaaagga | attgataaaa | 127320 |
| atgaaattat | taaacagaga | caatgaaatc | gtaattagca | tagcaacatt | agagagcgta | 127380 |
| aaacaagcct | taatttggga | atacatcgac | cacatagata | ataacatcct | agacagtgaa | 127440 |
| atctatgacc | aagaagcggt | tgtcgttact | tctaagactc | tacaatcaat | aaaatttgca | 127500 |
| gacactatgg | aagacctgca | ggaatacatt | gcagatatca | attggaaatt | agtttaaaaa | 127560 |
| agttttaaat | aactgttgac | accttagcaa | atagatggta | atataagagt | ataagaaaaa | 127620 |
| acaaaaaaac | gaaaaggatt | tgattataat | gacaaacaca | ataaaggat | ttttacaaac | 127680 |
| agaagaagca | agcacagtta | aggacgtagc | aactcacgga | gtacaaagcg | gagcaattgg | 127740 |
| cagattaatc | tatacatcgg | acgtagtaaa | attctttgat | agacattatt | cagatattga | 127800 |
| agcggtagta | ttagacttct | tagaaggctt | tacaggtcaa | agatactatg | acctattaga | 127860 |
| ttatgacttg | atgagagaac | tcgaagagca | tgcaaatgta | gagtttgaag | acgaagacga | 127920 |
| atataataat | attcaatttg | acttagcaga | aaatattgct | tctgatgaga | ttgaaggatt | 127980 |

FIG. 19QQQ sequence.txt

```
cgaagacatg gacgaagccg agcaggcgga tgcagttatc gaagctatgg acgatgtaga    128040
attagagata ctagacacgg ataaggtgca gtttgttaac ttagcagttg agattgtagc    128100
acaacaaatg caagaagcat aagaccctgc aggaagcaca cagagacaca cagagaagct    128160
taaccgcttc tctaatataa aactattagg agatgttgaa catgacaatt aaagagatta    128220
taaaccaatt acaagcagta gaaaataagg aacttgaact attcgtatgt gacaaggaag    128280
gaaataacat ttcaattaaa gatattactt tgtttgatag tgaagcggag cacacagaaa    128340
acaacccatt agggattaac tattaggagg tttataattg aacattagag aggttcataa    128400
tgtcgttaag agtgcaaaga gcaaactcct acaggagcag aataatatta ataatgtaat    128460
gatagatgac tacatcacag aagagcttca cagacgcaca cagagaagcg gaacaataca    128520
gatgaacaat aacaccgctt catatagtaa tggctcatat ggtagcttag aagagattag    128580
agaagcttat gacctatctt cattatctac taatgagatt aaagaactgc ttgaaacatt    128640
tgtttaaatt attttatcaa aacgctttac aactatttaa tttgtatgat ataatgaact    128700
taacaaatta aaagaaaagg aaatgatgaa catgagagac ttacaagaaa gaaaaagaga    128760
attgaaaaca ttactattta acttagctat agagaagaac agagcaactg acgagacact    128820
aagaagtgta ttagaagaag cccatcaaga ggtaggaaac caactaagaa aagtaagaaa    128880
agaaattgaa attttagttg aagaaaaaga aagagaattt tggaacgatt tcgactttaa    128940
tggattagac taagagggaa taaaatccct cttttatttt tatcctatta tataatttt     129000
ttatattata cggggggcagg ggtaaaatgc cactcaatgg gggtgggtct atataccct    129060
atggtctacc caggtactta ttttttgggg aaaattatga aaataaatat tctaaaagtc    129120
aacacccccc tattataagt caacattaca accctaccct ataagtcaac aatttataat    129180
ataaatagat agcccttaaa tataaagtca acatatctaa aataaaaaag ccaccccttt    129240
aggagtgact tagtgtttta atattttatt tcttctccta aaatgagttt gttttgataa    129300
ctacctaatc ttgtatatat cttactatta gggtctgatg aatttatact atttgtgcta    129360
ccataagcta tacaactatc taaccacata tgactacctg atgaagtttg gaaatctttg    129420
ccttggtaac tttcgaaagc ggtacatcct aaattccaag attctgtacc ttcatttaca    129480
tctgcgacat taccgccatc atttctagca taaataccgt ttactcgtat agctttaaga    129540
ccatcatgag ttgtggaacc attatttgat ttagtacctg ctgttccttt ttcgaatcca    129600
ttttctaaag ctgtacaatt aatttcaata actaaaggtt tagagctatc tgcacctata    129660
tgataattaa atccatccat atagttatta ttagctacac tattattgac gataacttct    129720
ttacctccaa caatttctaa accattacca ttgacttggg aagcatagct cagtacacag    129780
ttattaatat atacgctatt gtcttggttt aattcaaacc tagcaggtct agctccaccg    129840
tacagattta aattttcaat ataaaagtca gttggtacac tagatactat taggtgttgg    129900
```

FIG. 19RRR sequence.txt

| | | | | | |
|---|---|---|---|---|---|
| gatgataata | gcggtacaac | ttttttgtta | ggttctatgg | aaccgttatt | aacataaact | 129960 |
| tttgtaccat | cagagtacca | agaaaaaagt | gtcgtatcta | ctttatctaa | ggaggtaaca | 130020 |
| tttgtaaact | ccctatcatt | attaaaatct | actacccttc | taacggcgga | acgtgtaaat | 130080 |
| tcataagtgc | tatctctacc | tgatgtttta | gtccaagttg | gctcatctgc | cataaataag | 130140 |
| tttacatttg | agcccaaacc | aataatatta | atactcttat | tacttattgg | tggaagcaat | 130200 |
| gtgcctccta | ctctaaagta | atccccgtca | ctaacataaa | gtgtatcccc | attatttatt | 130260 |
| atgccttgag | cttttttaaa | tgtttaaag | ggggttgatt | gagaaagacc | gtcattagta | 130320 |
| tcattaccat | tttctccatc | aacatagtaa | gatttacctc | ccctaagttt | aaagttctcc | 130380 |
| atatttaaag | aagtggaaaa | cttacctaaa | ccatctgtaa | aaatattatt | gacaagcggg | 130440 |
| tggtctttaa | ttaagtaatc | tacaggagtg | aaaacaggta | ttttatacga | tgtttctttt | 130500 |
| ttcatagaaa | ttttcatatt | atcaatttct | ttgattaatc | ctttaatgaa | ttcctcatta | 130560 |
| ttaactgttt | gtattttctt | agtagaagaa | ccatcaaaaa | gtagaaactg | ttttatattt | 130620 |
| acaggtgaag | taacttgtct | tgtatctatt | cttaaactaa | ttttgcttga | attttccggg | 130680 |
| atatttatat | tattaattgc | aaatgtcgtg | tcatttattt | tattaagttg | agtaattgtt | 130740 |
| tgtatatatg | aaccatcaga | atcttgtatt | gaatactcaa | atgatgcttt | cgggtcaggt | 130800 |
| acgtcatctg | ttattatttt | agcactaaat | gttttacctg | gtgcaagttt | ttcaacagct | 130860 |
| ttaactgtgt | aaaataacca | accatttgaa | ttaagtgtaa | aagaaccatc | ggggttcatg | 130920 |
| gtatttccg | gtatactgtt | tctaattgta | atattagaga | aatatgtttt | atctactgtt | 130980 |
| gatgggtata | aacgaatgtc | ttctccatta | tcagggtaca | ctattaaact | atcttccatt | 131040 |
| gttttattta | cttccttgtaa | attagagtca | ctaggattaa | caaaaactct | caatgaatct | 131100 |
| aattgttctt | cggtaaatct | atcaaaagta | aagtctttac | ctggttcccc | tgttttacct | 131160 |
| ggctctcctg | gttttcctgg | ctctcctggt | tttcctggct | ctcctggttc | acctttaatg | 131220 |
| gacttaaccc | attcttcttc | tgtacctgta | aaaccattat | ctactgctat | atcataagct | 131280 |
| gttttaggtt | taacagttaa | gatgtcttta | gcataaaaag | taatttctttt | gtaagaagat | 131340 |
| tctaatgtag | taaattcagg | aactacagtt | ttttccgact | catagttatc | cccttcccaa | 131400 |
| gaaacataaa | actccccttg | agggtactta | gtatgaggtt | ttaaatttgg | tataataact | 131460 |
| gaaccttgct | cagtatatac | attataacct | atggctagta | tattgccttc | tttatcataa | 131520 |
| gcttttaaat | gtggcattta | taaatctcct | attctaatgt | gttagtacat | ataatatatc | 131580 |
| aaattgaata | aagaagagt | attagttacc | cttctttatg | tttatatcgc | agtctacgat | 131640 |
| attaagttca | tgaatagtaa | tcatatccat | tccatcgaat | cctcttgggt | ctcctttaat | 131700 |
| gaactcttgt | tctcctctat | aattagtctc | ttccctatac | ccttcttctt | taatacgttt | 131760 |

FIG. 19SSS sequence.txt

| | | | | | | |
|---|---|---|---|---|---|---|
| aattaatttt | tccttatttg | tatatacatt | gtcttctcta | aaatgaaaat | tatcttcata | 131820 |
| aggttcacaa | ttatcatgtt | ctacttgata | tagtttcatt | catttgtcct | cctttactct | 131880 |
| ctataataat | catatatttc | taagtaaggt | gaaaatggtg | aatcacctct | agtattaata | 131940 |
| ataacttcac | cttcatgttt | acttatctct | gtaagctctt | ctagactatt | aatttctaca | 132000 |
| caccatcgtt | ctagtgtaaa | tggattacct | ttttggtcta | caagttctag | tttctttata | 132060 |
| taggcaccct | ctataggctt | tttattaatg | gtgcttgtcc | tatctataaa | aaattccatt | 132120 |
| agttttcctc | cttttcataa | gaccattcac | catattctgc | gttaaaatgg | gctgtatccg | 132180 |
| taccctcgtc | ttcatattct | acactatacc | atgcatcctc | ttctgtttct | gcatctatat | 132240 |
| atcttacttc | ctctgtagta | ataatacgtt | ttactttaaa | tctctccata | ttagttttcc | 132300 |
| tccttatatt | ctttataact | tttaataaca | atcttacaga | tacctctatt | aacagctaaa | 132360 |
| aacaataaaa | atgataacag | agttataact | gctctagtat | ctcctgtgaa | aggtaatact | 132420 |
| ttaaatagta | aaacactttc | taaacactt | gtagctgtga | tagttgttag | gtataagata | 132480 |
| gttagtaaat | aatcttttaa | ttttagctta | acaaaaggtt | ttttattatc | ttgagttctt | 132540 |
| actataccat | atagaattat | aaaccattct | acagttacga | gcatagttat | aaagtaatta | 132600 |
| tttatgtcta | atgcatataa | accataaatg | atacctgcag | gaataccaat | aatgaatgct | 132660 |
| aaaaatacag | agagtataat | tagcattata | agaagagcta | caaggaatcc | taagccttgt | 132720 |
| tttgagtact | ctagtgtatt | cttccctatg | gctttaaaga | atgttttatt | catctgctac | 132780 |
| ctccttgtaa | tatacagtat | ctatatggat | aatattgtct | ttgaaccata | tagatgtatc | 132840 |
| acctttgtta | gattctaaaa | atttaacacc | attaaaaaca | agaccccga | taaaagaatt | 132900 |
| taaattagtt | ttagtatctt | tttgctttat | aatagtagaa | gtccctgata | catcatgaat | 132960 |
| ccttataaaa | ttaatatctt | tttttacttc | ctcttcttta | tgttttttaa | atatcattat | 133020 |
| tcttcctcct | ttatattctc | ttctaatatt | tgttttaacg | tctgacaatc | tttttggtct | 133080 |
| aaagtattcc | aactttctag | attttgtaat | tgatagtgaa | attcatttac | aatttcatcg | 133140 |
| aaggcttctg | cttttttggta | gacttcttgt | aactcttcta | attcttttc | attatcaata | 133200 |
| caccagtagt | tctcgttgtc | agttataata | tcttgaattt | tatttttata | ttcataagcc | 133260 |
| attatttatc | cctcctcttc | tatagaatta | ctttccgtaa | tagttacctc | tagcatgtta | 133320 |
| ttgtaatact | cattcttttg | attgatattg | tagtagtcat | tatattcatt | aaagtctaca | 133380 |
| taagtgtatt | catttgtatc | atcatcataa | ataatatcta | tagctgtaat | atctgagtat | 133440 |
| gctgtaatca | tttcataagc | atttgtatta | tccggataag | caaaaccaac | ttgagatatt | 133500 |
| tctttagggt | tatcaataag | aataccaaaa | taagtacatc | tacgtgttcg | acttatatgt | 133560 |
| gaagtaccat | agtaatctat | accttctgta | attccatcta | catggaacct | ttttacatct | 133620 |
| ttaggttcta | gtcttacaac | atcacaattt | tctaatacta | aatcaatata | ttttatattc | 133680 |

FIG. 19TTT sequence.txt

| | | | | | |
|---|---|---|---|---|---|
| attttaattc | tcctctttat | ttaaacctat | tatatacgca | atggactcta | acatcttcca | 133740 |
| ttactttacc | taatagattc | tgacctttcc | agttgcttc | atctaatatc | ttagggtcat | 133800 |
| ttgctttaat | acctacaccc | catattttat | catagggtga | tgcttctacg | aaatctttac | 133860 |
| gtaaatctgt | atctagtatt | ttttgtttta | agtgtgtagt | cataaattta | tctttaacca | 133920 |
| cttctaccat | aatgtcatat | ctcaccttat | tccattgctc | ttcattaaaa | ttacgaactt | 133980 |
| tacgacctag | acttttagca | tggttcggat | gcttagcatt | taatatttct | cctgctattt | 134040 |
| gccagtcttt | aaaatattga | gctttacgcc | acataaaggc | ttgttctgag | ttattaaatg | 134100 |
| ttcttccttt | gtgtttaaat | gttattgggt | aaaagttaga | atagatatct | tccttacccc | 134160 |
| aaaacataat | gtattcttta | gtctctttca | tattatctct | cctttaattc | cataatgatg | 134220 |
| gtaatacgat | tttaaagtta | tctagaattt | tgttttgtac | ctgttcaatc | tcgtcctcat | 134280 |
| tatcaacatc | aaagctatcc | attgattcgt | ggtagaattg | aattaaactt | aatatatgct | 134340 |
| ttatcatatc | tatctgtgtt | ctttctttc | cttctatatc | agtaaatgta | tggtactcca | 134400 |
| tatccacatg | attactactt | tctacaaaag | catttaaatc | agcatatagt | tgaataaaga | 134460 |
| aggacatatc | atagttccaa | tatttaggtt | catttctacc | taattcttta | ttcattttt | 134520 |
| tgtattttt | attcttttt | aatccaaaaa | cttcttttc | aaagtcattt | aatttaagtc | 134580 |
| ctttaaaata | tctttcttc | atgagtttcc | ctccaattta | ataaaaggta | aatctatatc | 134640 |
| cctgaataca | gcacctacat | cacacattaa | catgtctcca | ttaatttcta | cttctccact | 134700 |
| gtcagttggt | gtatgaccac | atacataggt | aaaaccatct | tttctaggtt | gaaagtctct | 134760 |
| tgaccatatt | aattggtcaa | ttgtttgttc | ttctacaggc | ttccaactaa | ccccgcctga | 134820 |
| atgagagaat | atatacttgt | cttctttata | gtactttcta | caattaacca | taagtatttt | 134880 |
| aaattttcta | tagtcgtctg | attctttaag | tttctttagt | tcacttttaa | taaaatcata | 134940 |
| attacttctt | aggttttctt | ctacactact | atactttaaa | gttaccgtac | tcacaccgta | 135000 |
| agagttaagt | gtttctatac | aatatcttga | gagccattca | atatcataga | tacttaatcg | 135060 |
| gtctacgttt | tccataacat | tataaaactc | atcatcatgg | ttccctaaca | gagttactac | 135120 |
| attatcatca | ttagacatta | aatcaaatat | atagttaaca | acgtcttttg | accttttacc | 135180 |
| tctatctaca | taatcccta | aaaatactat | tgtttctta | ggttttcttt | cattgtttat | 135240 |
| tttatccata | attgttaata | attttggta | ttctccatga | atatcgggaa | caacgtatat | 135300 |
| agccatctaa | tctcctcctt | attgtatata | actatcttac | catacttagt | aaaaaaagtc | 135360 |
| aataaaaaaa | cacctattaa | tttaataggt | gtttatcatt | taatgttatt | ttaaagtatc | 135420 |
| attaccatgt | gctaattttt | tatcatctat | tgcatggtca | ttataaatat | atttaacctc | 135480 |
| tatatactgg | tcttcacttt | tcagtgcatc | tactatagaa | gcattattag | ttattgagct | 135540 |

FIG. 19UUU sequence.txt

```
tgttctaggg taagtaaatt tttgaccgtc agataaaata atagtaacat caacttcaaa    135600
gttaacaggt agtctgtatc cataatcttc caaataatta ataaagttat taagagaaaa    135660
tggtttatac ttgccatcta aggtatagtc aatatattca tttaatgcat cagtaagttc    135720
tgattctgtt aactccattg tatcataatc tttttcgtta tagaatacta caacattatg    135780
ttgttctata ctagaatctc cgtctttata cttagatata aaaaatccaa tatttccttt    135840
atgctctaaa taatctgctt tcataatttt aaatacttct tctgctatag gttttgctaa    135900
tagtgttacc cattcacctt tttctgcgtc ataaacacta ggtagtacgt ttaccatcat    135960
ttaaatctcc tcttcttaat ttattggttt aaaccacaat ttactcttat cacttggttc    136020
tgtttcacta actacgaaag agttagaatc aatgtttaaa gtattaaaaa caatttcttg    136080
tttgtcttca ttacttttg ttgtaaattc gggaacatct gttaatatag actctttacc    136140
attaatagtc catgatattt taaaagaccc ttggctatac actgtattcg gtgtcagttt    136200
ttcaattata attttagcgg atgcacctgt aatttttct gaagatttta ataatttacc    136260
tttggaatca tataagttta atgttctctc cacaaatttt atctccttta ctatattttg    136320
tacaattaat ataacaaaaa aacacctatt agtttaaata ggtgtccgac agagctccg    136380
tacttagatt acggttaata atattttacg acaactatat gagaccctct gtcgttgaaa    136440
ctcttgtcac tgcgttattc cacaagatat tttagaaggt agcttgtgga agaagattgt    136500
ttttaaaggt acaattagcg tttttaagcc tattcgatac ccaggacact atgtccgtac    136560
taactattac gtcaataaag gttctacggt ctcaattacc tactctttat tgttaaaact    136620
aaaattaagc ttgagtgctc tagaagccaa aatcaattaa ttaactatag atacggaatg    136680
gagggacact accatccgga gtctacggtc agatacaaag cctctgccgg gcaacatacg    136740
gtatctctcg tacatcaggt tgactagacc tttagagttt ttcactcctt ctcttataac    136800
cagtaactta ggagaaatag gttttactta gtagatatga aacaataaat ccacatacaa    136860
tattaaatca tagtcaagtg attgcacata tgtctaatac ctataagttt tttgctagcc    136920
tggtatatgg actctgcagg attcgaacct acagtcaaac cgttatgagc ggttggcttt    136980
acctttaagc taagagtcct agaaatatcc tgagagagga ctcgaacctc aacgactagg    137040
tagctacatc tagccaatgc cattactcag gattgctagt aacgctaaat agaattataa    137100
cgttaccgta gacctttct acgcttggta gataggtaaa atataatgat ttcaaagtac    137160
ccatatagtt aggctcttat tctcattata aggttaaaaa ggctaactgt gtttagcatt    137220
atataagagg ctttagttaa ctactatact aatagtatac cataaataat acttaatgtc    137280
aagttaattt atcaattgaa tccataattt ttgatgtact tcttatatcc gcttctttac    137340
tgtgtttaag aagatatttt                                                  137360
```

FIG. 20A sequence.txt

```
<210> 781
<211> 166679
<212> DNA
<213> Unknown

<220>
<223> Description of Unknown: Bacteriophage F387/08

<400> 781
cgttagcacc tttataaccg atggtgaagt aatcctgacg agcatactgg tcgatgtata      60
cacggtagcg accacccaga acaccagcaa atactgcttt agtggtgtcg gtattataac     120
cacgacccag accctgagct gccggagata cgttggtatc aacagctgcc agtacgttaa     180
ctacgttacg ggaagcgata atgaagttac cttcaccgcg accggtctga cgagcgattt     240
cagcggattc tttgtcaatc tggaacagca gagctttaaa gctttcacct gcccaacgag     300
caccgcggat atcaatcggg tcttggaagt cgaatacacc agctttagaa ccaacagtct     360
gggtcatacc agatttacca acctgagcgg agtagttaat ccagtcaaca acttcacggt     420
tgatttccag cataatttcg gtagccagga ttgaactcaa ttcagcatca gcgtccatac     480
cgtgaacagc acggaggtcc tgagccagtt cgatggaata ctgtgctttc agctgacgag     540
atttcgcttc gatagtttgt ttatcgatac ggaagcccat ttcattccac gggttatctt     600
tagaaccgtt aaatgcttct tgcagttcag caacggaagt agccatacct tcggcgattt     660
ctacaacttt accagcttcc agagcagcag taactgcagc gtccagttta gcagcatcgg     720
tagcaccagc gtctacagtg aaatcttcaa caacctgcag atgagcacga ccggtctgtg     780
cgaaatcgtg aacaacgata tcaccaacag tcagagcagc accagcttta actgcttcaa     840
acttctcggt tgcaccctga ccagagaaca ttgcatccgg agcgtacatc ggatggaaag     900
cttctttagc accagcagcc agagggtctt tgccgtaaac agcgcggaga gcgaatacct     960
gaccggttgg gttagacatc ggctgtacac cacagatatc gaaagcaatc aggttaggga    1020
```

FIG. 20B sequence.txt

| | | | | | |
|---|---|---|---|---|---|
| tagcacgacg | aaccataccc | ataactgccg | ggccaatctg | ggttacagca | ccagaggtct | 1080 |
| gaccagctgc | gatgttctgt | gcatcataac | cgtggtcacc | gccaatttct | gcttcagaca | 1140 |
| ggaaagaacc | aaatgcttca | gcgattttt | catcgcggta | ttctggagcc | tgattaatat | 1200 |
| cagcttcctg | gttttcaaaa | atcttagcga | tcagagcttt | tttgctagcg | ccaacaattt | 1260 |
| ccggcagagc | ttcgttctca | agcagcggct | gccattttc | gataagttta | ttctttttca | 1320 |
| tgtgttgtat | aaccttttaa | attaagaaag | acgagccgct | tgggccacat | aagcatccat | 1380 |
| aacggatggg | gttttagtcg | caggagtttc | ttctactgct | tcagttgtga | agtttaaacc | 1440 |
| gtctgcttct | ttgtcgatag | tatttatatc | ggcagattcc | gttacagact | gctctacaga | 1500 |
| accctgcacc | atttcaacaa | tagctttcag | cttagttgaa | aatgcgtcag | aataatccat | 1560 |
| gccctctgtc | agagaaacta | ctttctcttt | tgggtatca | gtcagttcac | gggttgcttc | 1620 |
| ttggatagca | tactcacgtt | gggcataatt | gatatactca | tcgcgcttag | aaacttcttc | 1680 |
| aaataaacga | gcagtttctg | cttttgctc | agcaagttct | tcttccatct | cagctactac | 1740 |
| gtctactgat | tcttcaggaa | ttacaacgtt | gtgctcaaca | aacagctctt | tcataccgac | 1800 |
| aaacatggat | tcaaacaggt | cagctttaat | accgcggtca | accgccagct | ggttttctgc | 1860 |
| catccattct | gcagcgatat | ggtcaaagta | tttagaagca | gcttctttca | gctcttcgcg | 1920 |
| agcttcttct | ttagcttttt | cttttcttc | ttctactttt | tcttctgctt | tctcagcaat | 1980 |
| cttttcaatg | tgagattctg | ccagagctac | ggcgtgtttt | ttgactgttg | cttcgaatac | 2040 |
| agtgctgaag | ttagctttag | cttccggaga | aagctgaact | gattcgaaaa | tactgtcaag | 2100 |
| agcgacggaa | gcatcgatag | ttttagcttc | ggtcattaaa | agttctttaa | gcattttga | 2160 |
| tgtcctgtgt | taagttacat | aattatttat | aacgcttta | acttctctgc | gagagccata | 2220 |
| aaagcatcat | cagcactatt | ggcaacttgt | gccgaggtat | tttccgaaat | ttgtttcggt | 2280 |
| tgtacccatg | catccggagc | actaggaccc | caaactgcgt | ctacaccaac | agtcaggcga | 2340 |
| aagccttctt | gtacgatgtt | atatccttt | cctgagtctt | ttaaagaacc | gagcccgcgg | 2400 |
| cttgatacac | caggaatcca | accagcacgg | atgttagcgg | ctaatttatc | acctggaccg | 2460 |
| tggtctcctt | cgatgattct | tgcacgccca | taaacatcgt | tgccttcca | ccacatatct | 2520 |
| tcgataatga | ttgcggcttg | catcgggtca | acatttgcgc | gaggtggatg | gtttaattct | 2580 |
| cctagagcct | gacgagtagc | aacctgttcc | ttaatataac | gacttaccgc | agtctcaaga | 2640 |
| atgcgttttg | gataaagacg | tttattacgg | tttactactt | ctgcctgcat | aaaaacacct | 2700 |
| tcaatataca | gaccaggttt | taagccagat | tcattttcgc | cttcaacgat | aatagattct | 2760 |
| agcatgggtt | taccatcaat | tacatcgccc | ggttgacccc | aatgctcaat | taaaagttgt | 2820 |
| tcattgaggt | tttccattaa | cttagcccca | gagcctgacg | gcgtttaagt | gctttcttac | 2880 |

FIG. 20C

```
                                sequence.txt
gtttacgtaa tccacgagtt tgagccgatg gattagcacg ttttgatttt actgctttac    2940
gcgcgatttg acggcgttta gctttagaaa gtccagttgt ttggaacgcg ttacgctcac    3000
gtgttttacg atccttagta cgtgtaatag tacctttaga atcaacatgt ttaacgataa    3060
attcatttag ttgtagagat tcattgattg aacctaaagc aattgctaaa tcaggctcag    3120
aaacaacaag attctctaca attttattta tatcatcttt agagagcgct gcggacaact    3180
tatcaaaacg cgcctgggct tcaggaagaa gagcttcgac agtgtcgata actaattcat    3240
gattttcagg cagtataagc attactcgtc ctcttcgtcg tcttcgtctt tatcagactt    3300
atcttcgtct tcgtcgtctt catcttcgtc ctcatcgggc tcttcaccct caatcatgac    3360
agacgctgcg ataaattttt tgcgctcttc aattaaacca gatgtccgtt cagccataat    3420
tgcaccaaaa gcttttttgg ctgctacgag gtctctggat tcaattgcgg aaatataatt    3480
ttccattaga aatcctcttc attttcttgg tcttggaagc gagcctcttt agactctaat    3540
tcaatttgct tggcttcttg ttcaatttct tcatctgaca tctgaaggaa gtctttcatt    3600
gctgtcttat gagaaatata cttgccgata aacggttcag ccattgtgag catattgatt    3660
ctacgctcca taacttcagc atctttcaac tcggtgaaat atgaatcttt atggaacaca    3720
atcttaatat tatttatttc gtcttcccac tcatctttag acaaaacttt tttaagaatt    3780
agattagtgc gaagtggatc aagcataatc tcttcgaatt tatgctgtaa tctacgaata    3840
aatttagcaa aatcaagctc atcgcgagta attgctgtgc cagcatcaaa ctgcacaccg    3900
ccttgattat ttgcatccgg catgcgcgaa agaggaactc gcaatgccat gtataacgct    3960
gttctaaagt aacggacgtc atccatatca ctcatacctg atacaccagg aaagtatct    4020
acttcagtaa ctgctttacc atctctacgc tgcaaccaat agtcttctgt cattgacata    4080
ttatgttgct gattttaat cttaccggtt gatgcatcat atacaacgcg attttcatc     4140
gtgttcataa tatgttgcat atgagctgcc gctttacgag aaggcatatt accagtgtca    4200
atgtaaaaca cacgacggtc aggagcacga gtaatacgat aaattaccaa cgcatcttct    4260
aatagcttta actggttggc gggtttaacg gctcggtgta aataaccgat gatgttttga    4320
cctgaacaat caactagtcc agaatgtgca tatacgatag catcgcgtgg aattttaatt    4380
ttcgttccgg cggaatataa tctgccatct gcataataac tttctttgcc agtatcgtaa    4440
atgaaatact ctttgtaccc cttaacgatt ttagtaccag cgtcatcagc agtaacgatt    4500
tcacggatga attgtaagtt gcgcgggtca agacgtctca gttcctgaat tccgtctttc    4560
attttcttgg tgttgacgat tttatggaag aatattcttg agtcaacata ccaacggcgg    4620
aaatggtcag cgcccttttcg ctcgaaatta aggcatgtta aaactgtatt aaactcttca    4680
agaatgcggt cttaattgc ttgactgaag tcagtagaat ctaaatcaag agaaactact    4740
ggatgaccgt cttcgtatac aactgcgtca gaaactattt cttcaacagc attgtcaact    4800
```

FIG. 20D

```
sequence.txt
tcgtagttat tcattaaact acgataagtg ttgattaaat cagcagttgt tttcattcca    4860
ggttcattgg aaccaaacat catttggttg aatgaattgt actggatttc gttttcgttt    4920
gattcaactt cacgagctcc atcatcaaat tttggagcag tgattgactc taggtcattg    4980
ttgatttgtt gcttatattc agcttcgtcg cgttttccc acggagcgaa taagtccaaa     5040
atatgaaagg ccattggagt ctccgaaatt atctataagt atatttatat cgaagataaa    5100
catgctttat gatatctcat aattgcacta cgtgttgact ccactccgca tactggacaa    5160
gtcattcgtg gctggtttat cttttttcct ttgttagggt gctcttttcc gaacatagga    5220
tttctttcac ccgacattgc tttagaatgg tcaggtcgtt ttcttccgga taatttaata    5280
gagtgatctg gacgttttat tcctaaccgc tgatgacgtt gtttttcttt agactcttca    5340
ctcattttc ttcctttagt tgacatccca aagaaaccgt ttggttgtgc taaagccata     5400
tttatatacg aactggattt aactacgtcg tatttatt gcaactcaag ttcagcttta      5460
gaagcttcct ctcgagtttc atatgtgttt aatatccggg ttttgaataa atgaggatta    5520
tcatgttgct cactcttcca gaggtcttta tatttcttgg atttaactga gccatgataa    5580
ttttcatcaa taattcgtga tacactagta gaaccgatgt agcgacgggg aagtttattc    5640
cccgtgtata ttgtcaaata agtacagaac attaatacct ccacttcgtt gttagaggta    5700
tttattcagc attattccca ccaatcgata gcaaaggtag tttcaaacgt ttctatctca    5760
ttattcgaat cccaatccat ctgtacttca ccaacgttag ttggccacag accagtaatg    5820
gtgtgttcat ttgtgatagt tttgccatca cgactaaact ggcgtaccgt agcaacctt    5880
ttgtaatcgg ctggagtcat accagagata tcattgcctt gagcgtgggc ctgagcctgc    5940
caagcaataa ttgccttacg tacttcgtgt ttatcatcgt tatagatggt aacagtccag    6000
tcgtcataag tacggtcacc agcgacgtta atcttacggt tcatgtaccc gactggaact    6060
ttttctacga tacctgccgg catcggtgct gctttacatt tgaaactgaa gttacgaccc    6120
agataaggaa tttctacctc aaacaggtta ggacgcgcaa agtcaccaga ttcaaacgca    6180
cgagtgatgt ctgttaattc catcgttgtt tcctatagat atttatatag cctctcgatt    6240
gactacatca tcgtagaggc tattaaagtg tgcggtaata taatttatca tctaaagatt    6300
agatgacccc agaatgtcct ggggttcata ttactgtggt ccgattaact catcgaaatc    6360
tgcaccagtt gccgtagcaa cgaagttcag agtgatatag ttaattgaac gtgccggctt    6420
gatgtagaag ctcgctacaa actcgttgcg gtcgataact gctggagtgt tattcgtggt    6480
atcacataca actcggaagt catatacacc acccagagct ttaatacctg cgaggtattg    6540
gctggtttcc atacggaaag aactacgggt aaagttatcg tttaattcaa acagctgcca    6600
cttagaagaa tcaccgatgt tgttcttcag catgttaaac aagcgacgaa cgttaattcg    6660
```

FIG. 20E sequence.txt

```
gtcaaacggt gttggaacag tggttgcagt cttatcaccg aacagaatga aaccttcacc     6720
tgtaccttga ccagtcactg ggttaatacc tgcttggtac atgcggtcac gatgtgcctg     6780
acgcggttca attgccaatt tgatgcaatt taaaatctga ccacgacgat atccagctgg     6840
tgacatccaa ggctgagcaa tatcatcagt acgagcacac aggcctgcaa tatcagcagc     6900
taacggaacc caacggttta cgtcgttata tttatcatac tgatatttat agttaccatc     6960
aattgctgcg tacgtagtat tgatgttcat gttagcagaa tcataagttc catcgccttg     7020
gcgccagtcg attaaattat caacagcacg agtcagagga atatttacaa tcgttgacct     7080
tggaggcgaa atgagtgcta agcagtcttg acgctcatct gcaatagacg aaacgtgttt     7140
ttgtactgta cttgcgattt catcggtttc accagcacaa gcaccagcaa tcagaaggtt     7200
tacacgcaat gcttcacggt caccaaataa atcccagcct tgaattaaat cgccagccgt     7260
aactgattca ttagctgaaa ccccaccacc cagacgaata acgccggaaa atccttcagg     7320
ccatccttgc gcagtagcaa atacatagcg tgaagaaccc ttggagaaat aatcgtccat     7380
aaagatgttg tttccgtaga tatctttatc ttggcggctt gttgataaca ccgctgattc     7440
aactacagca ccatctctac gaacaatgat agcgtactga gtatcggtct gaggaccata     7500
tccaaatacg gcttttgcgg ttgatgcacg ctgtccacca ctcggataaa tcgtcagttg     7560
ttcgccttta tcaaaagcgg cttttgatac aatttcaatt ccagttggt ttccgagctc     7620
gccaggatac gcagctacaa ttccaggcat tttatattgc gcaagcgcag tctggaattc     7680
agtttttgtc atttcttcat gggcagtttc atgttcagtc agtagaactg tagactcaga     7740
aataatttta cctaaagtaa tgacagcgga aacaccagaa ctctgtgaag taatggtagt     7800
tgtccacgaa gaccctaaat caggatattg attaatgctt tttgcatatg caataatctt     7860
cgatgtcgga atgaacaccg acttaatttt tccgtcacta tctacttcag taactgaacc     7920
ggtgtcatct acggtttggt ctgcatattt aaccgtaatt ttatcaccaa cttcatagtt     7980
actaccagca gtagtgatag tccattcaat attatcaacc aatggagatg cgttttagc     8040
agcttcacgg ttaactacac ggacggtgcg tagatcatta ccatattgca gaaagttcat     8100
tgctgacata aagtaatcag cagtttggtt attagggccg ccaaacatat caaccagttc     8160
aacttcatta gtgatttgag taacttgata tgcaggaccc cattggaact tcccgacaat     8220
tgcggcacga cctgtagcgt taagtactac cgtgctctgt acgctcgttt ctttgagctc     8280
aattccagga gagactaaag gcatgatata tcctcaatgt tgtttgcttt ttattattta     8340
tacaaatgaa agaccatgtt cttgaggcgc atattctgcg ctattcacgg cgtcaacgaa     8400
cactacagga gcgtaatcgt cgttcatatc ttctaattcg cgtttaaaaa cttcagatgc     8460
taaacgcatt tcatctttat ccacgaaatc agcaatttt tgctgtgttg ttaaccatgc     8520
gaaaattacg agtgacataa ttaaatcgtc atgatatcca tcttctgccg cccaggatac     8580
```

FIG. 20F sequence.txt

```
tcctttctca gagaaagtac gaaattcttg aacagtagca cgatggtgaa taatgagttt      8640
atcttttcg ataaggtctt ttagtgcaga acatccaacg gcttttgacc ttttcgtctg       8700
tttcattcct aaatcaacta ttgaatcgca aatgacattc tcatattcta aatccatata     8760
aagactcttc gctacagaaa cacctgtaga gttaagttct atatagatcg gagcttcgtt     8820
gtactccatt agatatttaa taactatatc cgggaggatt aagtgagaaa ttgtattaga     8880
atgtaatact ccaacttgtt cccattcaga tgtagtaacg tcaataatat ttagtgcatg     8940
gtaatcctga ccgcgtcctt cagcagagtc aagagttgca atatatttgt ggtctgcttc    9000
cgcttcttta aatttataaa acccgtgcga gtcaggagta acttcaatcc aatccatatt    9060
ggcaagtttc ataccggaaa tgagagtacc ggatgtgcca tgaaattccg cacagtgctc   9120
ttgtttaaac tgttcaagag aagaagcact gatagtttga agtgaccatt gccacccatc  9180
atcaaacata tcttcgtcgt tatatagacg ttctttaacc gagttccaaa ttgcagtata 9240
aggcgtaaag ccggatttac cttcaacagc tgcagtccaa atatcataga agtggtttaa  9300
tccacttggt gtagtcgtga taataatttt agaacgacga cctgatgaaa taacaggttg  9360
gatagcaagc catgcatcta tgaagtttgg aataaacgca cattcgtcaa tgtaaatcat   9420
tgcaaatgag ttaccacgaa cggcatcagg actcgaagcg tatgcccaa tagatgagcc    9480
attatctaat tcgattgagc ctttgttcca ttcaacaata ccaggctgaa gaaagtcagg   9540
aagtaattca attgcttgct tagtacggtc gagaacttcc gcagacattg agcctttatg   9600
cgcaagaata cctactgctt tatccttatt aaaacacacg aagtgcgcaa gaaagattgc  9660
tactacagta gttttaccga gctgacgact gaggttacaa caagtcatac gtttggctgc 9720
catgatttcc agcatgtccc tctggtaatc acgaagctgg actttaatgg taccatagtc  9780
aatgtgagta attgcacagt aggtctctgc gaagtacaca atatcgtctc ggcatttctt    9840
ccattctgca actatttcac gggttagttg cattttaata tttgctcgtt taaggtttgg   9900
caatcccata tagcgggtgc gcttattatt tttgtcctta aacgtttgga aatgagctgg  9960
gtcttcacct tgcaaacgaa ttttaactat cccatgcaac ttaagatagt cttcaaattt  10020
ctcaggatac cacttatcat cccattgcga tttaaagaaa cgaactccgt tttcaatttt   10080
cgtttccatt tcagacgggt gacgaataac cgtcagtttc ccgtcattta aaggatgggc 10140
atcactcaga acgttaaacg gttgagtctg ttccatttac tattttctct cgagcttctt    10200
gtgcttcata ggcatcaccg aattcatcca tcatatcagc ggtagaccct acaaagactg   10260
ttgcattttg aatattcatt ccttgctgag gattagctcc cttccggtg ccaacctgct    10320
cagaagtaat gtctttcatt tctttatgaa gcttaagaat ttctttgttg gttgtagtca   10380
tctgacccat aagagttgca aatacttcca tatgtctagg agaatcagca ttcttagcag  10440
```

FIG. 20G

```
                                    sequence.txt
tttccaaaaa tattttagct gcgtccatta acatctgttg ttggaagtgc atgttcttgc    10500
gaacaaccga ataatcatct tcgaggtcag gtttacggtc atttggatta gatttaactt    10560
caactaattc aagtttttca taaactggaa tttcttgtcc ttctattcca ggaattcctt    10620
cgatgtctaa taatttagcc atatctaatt gtaattcact cattttcac ctctcggtcc     10680
aggagcctcc ggatttaccg gaataggaat atcgtgagaa taagtttgtt tactagaacc    10740
atcccaattt tcgtgttgaa catctcgtgg agtgacttcg ctatctactg attcaaagtt    10800
tccttctgga gttaactcct tgctgttagc gaagaaatct aaataaatgg ttctaatttc    10860
gccatcaatt tcagctacag gcggatacaa ccagccattg acttcaaaca tcagcgacca    10920
ttctaatcta cggcgagtga tattatctcc atcaacagct tcatcctgag aaaatgactg    10980
taatacaatt ctaacatcac gattaaagct tgtgtctttg tcgtaaagct cagttatagt    11040
cgtgttaaaa tgcggctgaa aataaggaac gatttgctcg atgatttgat acatatcatc    11100
ttgattgcgt gtataaattc ccaattcaaa aatcatctta atcggagtag gattatactg    11160
agatgtaatt tttgaagggg ttttatatga tttggttcta ttcaactgtg atgttttata    11220
catcgcattg tattgcatat caaccaagtg caaattcatt cttggcaaaa cagtttctat    11280
ctttgcttta ttctcggtag actgaatagc agtccatttt ccgagttgag aaaggaactt    11340
ttcctttgaa gcataagtga taggtacttt aatatatttt agtccagtgt cttcacgcca    11400
acgagcaatt tgtacatgag aaaataaatc tccaagcaat acaatgtatc ggcgtaagga    11460
cgaattatac caatgtccaa acatgatttc tcctaaggga cccaaaggtc ccatctttat    11520
tttatttatt cgaagaaccc gtcatcaaac gaatctgctt taggagggga ctcaagtcct    11580
cttccgttat taacataata cggatgaaca tattcagagg cttctttatt gatttcatca    11640
ctttctgcgt attgtatatc agaaatatca gcaagagcat ctatattttt gattggttct    11700
aaatcaagct cagaaaattc aggaatatta atgccttcat tacgttgcaa ttctggctga    11760
agctgctcac cagaataaat gtattttgt gcagtaatct tgcgttgaac attttgacct     11820
aactgataaa atggatcgta tggctgaacc cagttaatttt cgaataatga gttatccata    11880
ggaaaataaa ttaggtcacc ggcttttggt tcagaattat tagtttgatg cttgaatagg    11940
ttgggattaa tagtcaaatt gacttcatca ttaaccatca taccaaattt actaaagaat    12000
gtgttatcgc cagaatatcc ttcaaatgaa tctaaataag cagcaaattt ccaagctttg    12060
gtgaatttac ttgatgggtc ttctccaaaa agcaaatcag gattgttata ttcacgagga    12120
aggaaataaa actcaattcc tctcatttga atagcctcag ccgataaagc atctgctaac    12180
gtttggctat ttctgtgatt ataaaaattc acataaggat tgagaatttc agtctcatta    12240
gttttattat atcctcgata atcttcgagt ttagcgaaga gcctagaatc aaatgtagac    12300
atcttttacc ccaacagaat aggacaaccc gggtcaagta aatcaagttc ctctcggagc    12360
```

FIG. 20H sequence.txt

| | | | | | |
|---|---|---|---|---|---|
| ctctcgattt | cttcttgggc | ctctacctta | agtgtttgac | catcaactgt | aactccacct | 12420 |
| gccaattgca | gaccctgatg | tttaaaaaga | atttcacccc | acagcttttt | agttaatgct | 12480 |
| gtagcataat | cttttaccca | acgattatta | tatgcgcctt | ctctatttgt | attaccttca | 12540 |
| ccagcatatt | gaccattatt | acgaaggtca | ggattctgat | atctatctcc | taatccccaa | 12600 |
| tgatcagcag | tttgcggccc | agcaaatccg | tatcctgctg | tattgcctac | catcgcatct | 12660 |
| gtattcataa | atgatttggt | ccagcattca | cagacaatga | tgtcacccct | catgaagttg | 12720 |
| cccattactt | taagcatttc | attatcagag | ttataccaat | aatccgggag | aggagcaagt | 12780 |
| aaatcttgca | tcattgacca | gtaagtcatc | aattgagtaa | aatagccaag | gtcagcacca | 12840 |
| aacgcatttg | gcccatagct | tttattacag | cttgacccca | ttccgccatt | aattcctgcc | 12900 |
| attcccatta | gaaagtcggt | aaaccatggg | tatgtcgcat | taccatccat | tgaagttaat | 12960 |
| gaacctacat | ttgttctaac | aatttgggtg | acagcaaata | cattacggcc | gcgcaaatca | 13020 |
| aatacgccgt | tcaaaaatct | tgcgttgtca | gcttcgtctt | ttccaatata | aaaaacttga | 13080 |
| taacctttat | tcaatccgtt | aaagtggtat | tcaccataca | actctaatgc | tcgttgaata | 13140 |
| caatcataaa | tttggtcttc | agttacttct | acattaatta | ccggcgctcc | tagacgtcga | 13200 |
| agtatagcgt | ctttaagcgt | ttttgggttg | tacgtgttgt | atgacatatg | aactcctctt | 13260 |
| tatattccta | tttatacgaa | aaagggaccc | gaaggtccct | tttgttatac | agctggatga | 13320 |
| atagtaatat | ccaaagattt | aattttaaca | agaacctgtg | attcttctga | agcagctcta | 13380 |
| tacacgattt | tgattgcatc | accagatgaa | aactcaatga | gtttcttggt | tttaatcaac | 13440 |
| tgttcgcccg | ttacagcctt | aacaccgagc | ccgtaggaaa | acacctcgat | gttattaacg | 13500 |
| agaataacaa | ttttcacgcc | tttatctgaa | tcagaagctt | cgataaccgt | atcagtttct | 13560 |
| acgcaaaata | cgccatcgtc | atcaacaaca | atgtcatcga | caatacgaat | gccagcattg | 13620 |
| aatggagcag | cgaccaatga | gttaggattt | accaatgcat | cagaacttaa | atcaacagtg | 13680 |
| aaatcttctt | tactgaattc | acctattgat | gaaggttttt | taaaccattc | gccctgttta | 13740 |
| cggaggtatg | ctccagcttg | ttctacgtca | gtaactgcag | tcacgaattt | atcttgcaat | 13800 |
| tctactacag | tagcgtatac | accatcacgt | tgaactgggt | tttctgacga | aaagtcacca | 13860 |
| ttcatttgag | tctgtaatgt | aaatacagaa | ccctttaacc | cttcattgtt | attgccaagt | 13920 |
| tctacttgaa | tgtcctgaat | agcagactgt | tgagagtttt | gcataccttc | aacattggtc | 13980 |
| attctcgcta | aaattgaccc | aggaggaatc | ggctgctcgc | taggaacaat | accaacctgt | 14040 |
| tggtttatcc | atgctacttg | accctgaagc | cctgatgaag | tatcacgtcc | tacaacatca | 14100 |
| gaaatgtacc | cttggtcagt | tgaaagagaa | ctaattttc | cttcaatagt | atcaggctta | 14160 |
| tcagaagacc | ctaaacgagc | atcaatatta | ttgacacgag | gaactaaccc | ggtttgtgca | 14220 |

FIG. 20I sequence.txt

```
aagttaagtg ttgcgtcaac tatacgataa tcgtttcta atctagtagt acgagctcca   14280
atttttactg gattggtaaa atcaatggct tggttaatag caaagatttc attattagct   14340
gcggaaatag catcagcgtt attcacaagc cttgcataaa ttgaagctga cgtagctccg   14400
gatttaggac caacttcttt acgcaggtcg tttacttcaa tagtcagaga acctacgtct   14460
gaatcattgt atgcatcctc tagcgcctga atacgctcgt catgttttac tatagctgac   14520
gcattattga tgattcggta tttcatacca gaacccggag agtcttgctt cggctgtccg   14580
ttaatatctt gcccaggata cgcaccaatt tcacgtttaa cccaaactat attatcacga   14640
actgttctgt aatagtcatc tttactagaa tcataaacac ctacatcctc ttcgagaaaa   14700
tcaaggtcag ttcgaagttt ttcggtgtct tcttctaatt taagaatttg tccatcatgc   14760
ttttcaatat tcttttat gatataaacc tgctcaatgg cgtcagaaga acctgtaatt   14820
tctaacgatt ttttgatttg gtctacatct acttgaatat tttctacagc agttccaacg   14880
ttgttcaaat cgttatgtac ctgaacaacg tttttctgga tttgaacaga agctctattc   14940
agttctccat catttccata gcgggttgaa gccccattaa gaggctctgt attttttatc   15000
cagttaattc tctgttgaaa atcgtctgga attccgtcta cgaacggaag cgaatctact   15060
agtttggtca tattgttcct tacggtctat ttgtacagaa tgtaagcatg cagtcataaa   15120
atataatacg actgtcttct gttggtctta tttgaacagt ggcatttgga ggaatgttat   15180
tgaagaaaaa gttgctagat gcgtaagctt caaatctcca tgaatgacca tttcgtccgc   15240
ctttagtatt ttcgatgtta agagtaagtt caccgcccca ttgggaaccg ttaactatta   15300
caacaaatct gaaaatacga ttgtcatatc cgtcgttgtt acgctcaaat tttacattaa   15360
catttagagc taatctacta gaagcttccc atggtgcatt acatgtaaac gttgcacctc   15420
gactaatcca agattgacct tcaacccaag taacattacc tactctggtt ccagctggca   15480
tgtaacgccc gtcagattct tgtcttgtat aacaattaat atcattgtta gtaatcgtta   15540
tgtcattgtc aagagttttt ccgtttattc tacgggtttt aaagactgca tctgttgcag   15600
ccgctgccaa tgaagcatca gtagttggag aacctgataa tctggttaat ccatatttat   15660
ccttggtgga ttttagcgct tgaagacttt ttggagtaac agccaaattg ttagaagtag   15720
ctgaagccac atctgagtct ttagcaaatt ttactatacc aaatacgctg tcagacgctt   15780
ttgatgccat gaaggttttt ggagttactg cgtatccatc gtgaacagca cctgctgcta   15840
cctgggcttg ggttgcgaca cgaactaatc ccaagttgct ttctgtcgca gaggtataac   15900
taggaggact gacactgaac tttccaatca tttctacaac acgcttagga gttactgcgg   15960
tagtttcgtc agttcctgct tgcgcttgag ccgcagtagt taacctaaca gttccatcta   16020
cgttttcttg ggctttcaca gttttaaaca catgaccgag agccgccgcg gtaatagttc   16080
tatttcctgc ggttaatgct gcggcttcag tattagtagc ataccgtgtt aagccaagaa   16140
```

FIG. 20J sequence.txt

```
ctgttgtagt tgcttcagga cgggtaactg tggattttaa tgtagcagga gttaccgcag       16200
cattaccaat agttccagca tcaacttcag cctgtgttgc tgtgcgaatt acaccggcta       16260
ctgtaggaga tgctacaggt aatccggtat cagttcttgc ccagctacca atcagctcta       16320
acgctgattg gacgtctttt atagcaacag gccattgtgt atttgttggg tcaaatatcg       16380
tatatttggc caaatcactg tagtgattat agttattctg gccattatc ccatccttct         16440
aaaatagtgg aaagtaaatg tgttcgcgcc gaaggttta gattcgttgc cgatagcatc         16500
ccattgccca taacctgctt tagctggtga agtaatagta aattcaacag ttaaaccata       16560
cttttatat gtttcaaaat tatggttctg ataatctaaa tgaataatat caacatactg         16620
tggtgttgcc ggcgattgag taacctgttg aacaacctt ccaacagctt ctaattcttt         16680
tactttatca taccaacgtg ttgctactgc tgcaaagtca tcaccgtttg caattctaat       16740
tggtaagcca agaatatgaa ttattactgg gtcaccgaca gagccgtctt cttttggctc       16800
taacgcaacg acacctgaaa aagtagcacg cgtaatttgc tgtgcgggct gtggagatat       16860
tccagtgtca ttgcaaataa tagttccaat ttctgctgac tgcaatgaca tcaaatcatt       16920
aatagcagct tcagtatttg gataccaaac ccctaaatcc atttgttcaa aggttaggct       16980
ccctatagga gccgtatttc ctaccgcaat attttgcggg tcaacgcgat attctgaaaa       17040
agcagctaat cttgaattaa ctttagctcc ttcacgagtt ttagtttcaa tcgtcatttt       17100
aacctaccct aatccaacga taaacggtga ttgttggctg aattttagtg atgtcatttg       17160
gaactacacc gttgtttacc gcaacagtgt cttcacggta tttagaataa cctggtccct       17220
gcgcgtctgg gtctaattga catccaccga taactacgct tccatgttca gggtctgaaa       17280
ttagaacttt atctcttgac attagttcag gaatgtgttc ttttcctaac gtaaatgtca       17340
aatctccaac cgttccacct gctgttaatg atggctgacc attttcgttt aagttattgt       17400
tgttacgcga aaaataagga tcagatgaat cattattcca accagcagta acacggcctt       17460
gtgaataaag cttccacacc ccaaatccca tatagtcagc agggtttgcg tggttgtgag       17520
cgttttcata aatcgtgcca atcggataaa ttacgtcaaa aaatgctgca atattattga       17580
ctttaatcat aatatcgtca gcaaccggac gcatattttt ctgattaggt tcatcataat       17640
ttgtgtattc aatgcgattt tttagagtta ctaattgctc agcattcata tacacttggt       17700
cggtttctgc catgatatcg tcaatatcca tagtagtacc gatgttatta ttgaaccaac       17760
ggacggtaag aaggtcttta tcttcaaacg cctcaccaaa aataatagct tcgacgttag       17820
taccagttga gtcaaattcc agtctatagt cttggttaga atttacccat tgaccaccat       17880
tgtttataca gtcttctgcg tatccacctt ccgcaccttc acaataaaat aaaggaagac       17940
ctgcagttcc agcttcgagt aattcctttc cgttcaacga aatttcaagc gaattgggat       18000
```

FIG. 20K sequence.txt

```
tcacacccac acctggaagt acacccatat catctagagt gattcttcga agagcagtaa    18060
ggttatctac tataattgac ccaggaatcg tctgggatgt agtctgggct gaatctcgta    18120
tctggatagc caacttgttg tatgaagacc gataaacacc aattccatct aggaaggttt    18180
caaatgttat tacttcccct tcaacacatg gaactttaa acgaatgtct ttaccgttta    18240
attctaccaa ttgacctgct actgttccag gagaaccgta atcagcattg gctttatcca    18300
taacgctggt ttcaccgtaa tataaaatat taccacgacg atatacatta agcgagtctt    18360
cgttatattc tacgccatca aaaatgttaa gaaagtcagt ctgacccgca gtagcaataa    18420
ttgatttttt cgctacagta cttaagttac cattagttag cttatctaca gttttatttt    18480
caatatattc ccagcggcca ggggcgcaat aaaccaattc caaatcttgg aagttagtat    18540
tgaaaatttt aggagaagct gaaccctta atgtatcgcc ttgagcagga ataactgtga    18600
ttgggcttaa tcgccaggtt gaccaaacat cacgaagttt aataactttg ttatagtcgt    18660
tggctgtacc ctttggaagc tgaacgttaa ctcttgctgc ctgggtatta atagcaaagg    18720
cctgaccaaa cttagcattt aaagtagttc cagtagggct agctttaaaa gttttccatg    18780
cacctgctgc gaatggaact gaaccatcac ctaactctga atataaatca tcaaagttgt    18840
tattaatttt aagaccacct ttacggaggt aatcaccaga cccatcatct actgattggc    18900
ctactatcaa attttgtttc attattgaga taccctacg gtctgtgtag caataacttt    18960
aactgccaaa cgtgcgtttc cataagatgt tgaagctgtg catattaaat ctttctgcgc    19020
gttaatagag tatgaaatag aatacatctt ttcattttca gatgattcac cacttcttaa    19080
cactgcatat tcagtgtcaa atactcttcc gtttggcgct gatgaagtaa tagtcgggtc    19140
aatcataagc atgacttcag atgattgcct tttgatggtt tgaccacctg gatttgcgct    19200
gaagcttaat agcaatttaa cagtagagta atcatcatta tatccaagtc gaatattaat    19260
aggagaactc gttaaattat atgtagcttc taacggcgaa tatgtgctgc caaacatact    19320
tgaaattgaa taatcccaaa cagcagcacc gttagctttt acctcaacac accacaattc    19380
aattctacat cttggtgtgt tgataatcaa ttctcgcgat ccgtctttaa atgcatctgc    19440
tacgccttcg ccgtttgttg ttattttat ggatctagct tttgatgctg agccattact    19500
atttacaacg aatacagctt ctcccgcttt accttttgaa agacgtattt gaactgcgcc    19560
ttctgaacaa tcagcatcta tgcatgaccc cattggaact gtccctgcag agttagcatc    19620
tccaaatttt atcttttggt aatagcttgt tgcatgaatt ttttggttca atgctccgcc    19680
gccagctgca aataatcgtt ggtcggcgaa ggcgttgtaa atggcgtcga agttatcatt    19740
aattttcaca ccgccatcat acagaatgtc gccggtagaa gcattaccaa tctcaccgac    19800
gtcaattatt tttttacccct tatctgtata cataggttaa cctcatatca aagtatagtc    19860
ttatttatat aaaatgggga gccaaaggct ccccataatt aaaactcgaa aattaagttt    19920
```

FIG. 20L sequence.txt

| | | | | | | |
|---|---|---|---|---|---|---|
| aattcttccg | tttggtccat | tgaacgaata | ataggttgcc | gattttccat | gtaaatcatt | 19980 |
| tcacctgact | gtctttcaag | accagaagca | ctataccagc | cttttcagc | cttaacatta | 20040 |
| ggtgaatttg | gcattggctt | aacttcaagc | ggattagtta | taattgacag | ctgtctaaat | 20100 |
| ccagtatttc | ccggaagact | gaactccgga | aaataaaccg | catcaagata | cgctttaaac | 20160 |
| ctgatagtat | tgcatttcat | gcgataaatc | aaattaaagt | cgttttgttg | ccaagttaag | 20220 |
| ttgttttgaa | atccccaacg | ggctggagat | tcttcaatct | cttctggcca | aggaactacg | 20280 |
| atatattcat | ttgtacatct | gttaattgat | acgtcggctg | gaatttcata | tagatattcc | 20340 |
| caaagatatc | catcgcccaa | atcgacggta | ccatttgcat | caccacgacc | tcgaggagct | 20400 |
| gaaccagaaa | tagtggatgg | tgtccattta | cccccaagct | taatacattc | ttctttgctt | 20460 |
| gtaagattgc | caattgaaca | cattccatcc | tttggaacat | caatacatct | ataccatc | 20520 |
| catccaaatc | cagcatcagt | tctgttatat | ggcgcagagt | tagcaacaac | gatatcgcca | 20580 |
| attagaaatg | tgcgtgggtt | aggatatctt | gtatctcccc | agtctcttct | tggaacaaca | 20640 |
| cagtcaagca | ttgatgattc | aattttgacc | gcgcccatca | tatttgtcca | aacatcaact | 20700 |
| accccatctc | cattatcagc | gggatatgga | ggtgcaaatc | cgggttcaga | ttcgttatct | 20760 |
| gaccacggag | tgcttttgcc | aaatgaaaca | tacagtgtgt | tttggtccgt | tcccggacca | 20820 |
| atcgatttat | aaaatgtgta | catcttttca | gttctaaact | tagatgtaat | gatagcacga | 20880 |
| taaatcgtgc | tacgcgttga | acttgctctt | gttgaattac | tcatcaattt | ttacctgtgt | 20940 |
| cggattttca | ggatcgcgag | gattacctgc | atcgtcttta | agacgttggt | taactaaatc | 21000 |
| gcgataatta | gcaaacgtta | ctgctgattg | gtcaaacgta | ggacttaacg | gtttacgtcg | 21060 |
| ttgtccaggg | ttttgtccag | cgataatgct | gttattattt | tcttgattgt | agttagcagg | 21120 |
| taacgggaaa | ggttcaccag | cttgagcacg | tgaagaatac | ctaggctcat | tggttattgg | 21180 |
| gtctcttttct | attgtatcat | ctgaagcgat | aatagcaact | ctatcaggat | aaactgatgg | 21240 |
| cagtcctgca | tcccatttat | agttcttgag | tttatttatg | atagtctcaa | catgcttcat | 21300 |
| atttaagcca | ctattgataa | acattgtcag | caatgttata | ccaatgaaac | cgaaacctac | 21360 |
| cggatgaaca | aaccttaata | catcgtcgcg | gaaacgagaa | gtaggaagct | gagacttaat | 21420 |
| tttcataaca | tagtaagaac | ggctgcggtt | tatataatca | atgttattac | tcagcatatc | 21480 |
| ctttccacga | acaccttgaa | ctataatacc | ctcaaagtcc | gtacgctctg | atttaatttc | 21540 |
| ctggccttca | atgaaccgtc | ctgataagtt | atgaatagta | atacgccata | acagacgacc | 21600 |
| atcccggtat | tctctctcga | tataagtcac | attactacga | ccggaagcag | tataaatcgt | 21660 |
| acgaccaact | aaatcgtcag | aaatatttgt | actttcaaca | ataatgtcat | attcggtagt | 21720 |
| gttctttgac | tcaatatcga | tttcaacatc | ttcattataa | agaagtttaa | acaagaattt | 21780 |

FIG. 20M sequence.txt

```
gtatgagtct tcaattcctt tggtagcata gaaatcattc ttacgggctt caaagaaacg     21840
gacaacagca tcgcgagcgt ctttactcag ataaatattg cgtttataaa cttctgacca     21900
caggtattcc catgcatttt cttcacgagg atatttgttc ttaacaagat taacgagact    21960
gttgtaatgc gttccatttc cgtctgaaag gaattggaga tagtacttac aaaattgctc    22020
aaaattacta tcttgtagca agtaactatc cggcatcatt ttagtaagat acggacgcaa    22080
atctgggtca cgtaagcctg gagtatgttc aggtgtccag tcttcttccc gtgtttggtt    22140
ctgcagaaac gctttaaaca ttacatcagt cggtttccag ttaagcgtta cctggtcacg    22200
aacacgataa tcaaatgcgt aatagcctat cagttttccg tctggttcgt gaaacatgat    22260
gccagaagca tactgcaaaa atccattaaa tgaaactgga gggcaataaa acgttgcgtc    22320
acctttatcc cacacttccg aaagaacacg ctcggtagtt ccctgcgccg ctgcatctac    22380
tcttttttga taaagaatat cattataaat gacaactgca tggtcagctg tacttatcca    22440
gcatctgtta ccttcacgag ccatccagac aaaccaaggc tcagcataaa acctcatcgg    22500
tccaggaaca aatgtttccc atcttgaaaa ttcatctgct ctgaaactca tcatgtgata    22560
atgcttatca gagtgatact gaattggatt aacattttta actgcagtag aaattagttc    22620
tggatatttc gtctcaagtt caatatcctg ggtgtactct gttgtcttaa aattagctga    22680
tgaaaagaat atttcctttc cgtcagttga catagacgtc cataaatgct ctatacgacg    22740
tttttcttca tctgtattac cgaatacacg tttccatgta tttgtgtctt cttgataaac    22800
atagacgcct ttagtagcag aatccacaac attccgcggg tctgttgggt ctaatcctaa    22860
ggttttaact tctccggtaa taagagcgaa gattttgcct ccgacagaat ccattttaaa    22920
gcatacagat ttaggattgc ctgttatatg agatgcttct ttttcgaaca cttttcacc    22980
aaatgtaggg cttaaagggt cagtgtctat tggagcatct tttaatttaa ctctgcgtac    23040
tgtatccttt gcaactacat ataagtggtc atcattgcat gtaaaggctt ctgcatattt    23100
ggtaacatca gcaggtagtg atgcatatgt accaaataac tctacttcaa atcccagttt    23160
taactggtct cccaatttag caaatgtaac ttcgttatcg ctaaatttaa cctcatttga    23220
tgaccagcgt acgtcagatg attttcttcc gtaaaagatt ttatcatagc ctaaaacata    23280
tgatgtggta cttgattgat aaattaccac tctagaaacc ggatttccta cacggtcatt    23340
aaataactga acgtattgcc agttctgtcc tttatcgttt gatactttaa ccatatgttg    23400
gaatctttca aacagataca aaattccgtc tatttctcct agcatggttc tatttttatc    23460
aacacagact gcttcaatag gtccctgaat ttcatgatat ccagattcgc ctactacgaa    23520
attttcaata gctgacaaat gagaatattc aggactaaat tgaaaagact cagtcatcaa    23580
agatgccatc atggcagatg tgttgaagtt aacatacgac atgttattta aagaaaactt    23640
ctgcttaatg aattctttca ctaaactgaa ttcttgcata tgctcaaacg tgtacgcgtt    23700
```

FIG. 20N sequence.txt

| | | | | | |
|---|---|---|---|---|---|
| ttcttcaaaa | gtttggaact | cttctgtttc | aacccattca | gacggttcaa | atcctgctga | 23760 |
| cgtagtttga | acacgcattt | tataataggt | aagcggttca | atacgatttt | gttcgaacca | 23820 |
| atcattatcc | gcggtataac | ccagtgaaga | ccaactcaaa | ttatcagcgg | ggataatttc | 23880 |
| ccccgctctg | tttcgagttt | cggccagttc | tacaaaatag | tagaagtttg | caccaacgtc | 23940 |
| atcccaacga | atattgacct | gattcgcaga | tagcttatga | attcgtaagc | tggtgacgaa | 24000 |
| cggtgcaatt | gtcattgagt | aataggctcc | aatttaatag | ttgtgtattg | aggacgaagg | 24060 |
| tcattctcaa | atacgataag | tgttccatcg | cgggcgaaga | cgatatcctg | ggtaggagta | 24120 |
| gaataaagct | caatactttg | gtcttcaaac | tgaagaggat | cggctccaat | ggctccaaga | 24180 |
| ctccagtaaa | tgttatcacc | ataataatct | acttcaccga | ttttatacca | gcgagttctt | 24240 |
| tcgccgatgg | tagttctatc | aaaatcgttt | tcagtatatg | gctggatatg | agtattctct | 24300 |
| ttaatatcac | ctggtttaaa | tggtccaata | accatatttc | ctttgccatt | tttatctggg | 24360 |
| tcagttccaa | cgatattaac | tgaatacggt | tcagcagttg | gggtaacagt | aaagaccaaa | 24420 |
| tcaccagaac | gtaacgtccg | cggagtaata | gtattatagt | atttaatacc | tgcgctagga | 24480 |
| agagtgaaat | agttgacaat | ttcacgaacc | atctgaatat | ccacagaaga | accgatgatt | 24540 |
| gagtggtcag | tgtcatcaat | gtaagtcaac | aacttagatt | tactgaaatt | tttgttgaac | 24600 |
| atttcaactt | catcaacgta | atatctatta | atcgagtcta | taatttttga | ctgtaaccac | 24660 |
| tgctctgatt | cttgcaactt | attcaatgca | taagaagctt | taatattatg | acgaatgaat | 24720 |
| aagtaatctg | ggctcattac | cgaaggggta | atcggagcaa | gacagaaagg | ttttagataa | 24780 |
| tcctgaatgt | cttcccgttg | aaccgcagtt | aactgcaacc | cagattttgg | tttgattgcg | 24840 |
| ataaatgcat | atccgggttt | gtcctgatca | gtaaagcatt | gtactgcttg | tacgatagaa | 24900 |
| ccaaagcgtg | aactaacgaa | tgattcatag | tcagttttag | acacgcatcg | catttgagat | 24960 |
| tcgcgcttaa | tctgtgcgag | ctcacgaata | cgctcgatgt | cttcaggttc | accaccgcca | 25020 |
| tcagcgccaa | cataatcagg | agaatctgac | cagttttcaa | tgattctatt | tactacgata | 25080 |
| tattgcagag | tatccgcata | actaaattca | gtcgcgccat | tagcagcttc | accgtcagta | 25140 |
| cgaatatatt | caataacgac | ttgcgcaccc | ttagtaggct | tcaatccacc | gatgaagttg | 25200 |
| ctttcaagaa | ctcctcctgc | cacagatgct | tctgccacac | cctcaccaaa | gaagaattct | 25260 |
| gtatttccat | cgacagtttc | acgcatataa | taaattgttg | aaatagacga | agcatgaacc | 25320 |
| attgatcggt | ctgtccagtt | agtccattca | gcgccatcca | cccacagctt | aacttgcttg | 25380 |
| cggtcaattg | attgatcgcg | aataacaata | ggtttcttcg | ggtcatatga | caactgagta | 25440 |
| cgaataatac | gtccctgcgc | caaattgaca | ataggccaat | attttggtc | attatcacga | 25500 |
| atagccacaa | cgttttcagt | aacaacgaag | ttatatgggt | tggctttatc | ggattttgag | 25560 |

FIG. 2OO

```
                                  sequence.txt
tatgctaaaa atttagttcc tcgtggaatt acaactctca acgtgctgct cgggttcatg    25620
tgagttacct caagcataat agatgcagta gccgctgatt tggaacttgg caaatacccg    25680
ttttgctgag ctgcttgaac aacggaactt ctcaagttag ctgttccaat aaagctttcg    25740
tataaagcag tattactaaa ttgctgtatg taaagcgtgt tatatgctaa taagtctaat    25800
agcacgttta aacgcgaacc agcaaaatca aagtcctgaa actcttttg accgctaagc     25860
cagttaataa gctgattttt aatttcgtcg aatgttgctc cagtaaatgc gtctgggata    25920
gcgtttgcag tacgcgttaa ctgataattt aagggttctt taatagccat tagtgtatga    25980
ataccttttga acttgattgc gcgacagtgt cgccacaaga aattggatcg gccatttgaa   26040
cagcttttt gcctgttaca aataccttgg atgtgcgagg ttgaacaact cctccatgcg     26100
tatcatgagg gtcaaccgtc ttggtgtgtg gggtaattga gtcgccatca actaataccg    26160
ctattccacc agtgaatact ttactttgtg tagcatttac ttctgtcgga ggatacgcac    26220
tatgcccggc agttaagcat ttattaaatg atagtccagc catttaattc cccgcatata    26280
cataagcacg aagttggtcg ccccatctac tccagttgcc tttaacggtt tgagagtaaa    26340
tcttttgctt tttatgttct gttatgattg gagcgctaga acctccggat gaacctccag    26400
acgattcttc tgtcactgta tatattatct caactgtata ggtaaatgtc ttctctagtg    26460
ttctgggggc tttccataga tacaaatcag cagttttggg attaggtaaa tcctcccacg    26520
ctgaagcgga ctttagctca tcaccttcac ggtatttaag cacatcgttt ccaaaagtaa    26580
aaactgagtt ataattacct ttataatgag tttcagacac agagatatca gatactggtt    26640
gatagtcgat aatatttatt gattttaatg tttcgttagt agataattga gcagtaaagt    26700
actgctcaac atattcacct tctattactt cacgtaacgt tgtattaata ggaagtatat    26760
cagccatgat taacctacat caattcgtga accatcaaca gtgtattgac cttgggcgat    26820
tgagctcata gaagccattg tttcagtcca gccccacca acattccaat tcacagtacc     26880
tgctacttgc caagttaaat taccaccgac ggtcacgtcg tggttgccat ctactttagt    26940
agtggcatca ccattgactt ggatatcagc atttccttca acgactatct taatgttacc    27000
cttgacaaaa atagtaccat tgccttcaat cgttttagtt tcatttccac gtacgtaaag    27060
cgtgttatcg ccatcaattt gctgtcgacg attatacatg ttataatagg tctcgttccc    27120
tccaacgtta accttcttat caccagagat taaaatattt ccatcaccct gagtcatgtc    27180
atataaatca gctacagttt ttctggtacg acgtccatca ggagcaactt cttcatatga    27240
accggttgga tgaacaatac gatagcgttc atagccaggc gtatcatcaa attcttggat    27300
atggcctgat tctgtttcca tcgtatgtac atatggatat tgaccattat atgaagactc    27360
aggttctttg aaaagaattc ttgaatcctc tggggtccac gggtcttcag gattaccacc    27420
agacttcggt tctacataag ccgcagacag gttttttcct tctggctttg gagcaggaac    27480
```

FIG. 20P sequence.txt

| | | | | | | |
|---|---|---|---|---|---|---|
| tccatatgat | tccatattac | ctgttagaat | aatcatggaa | acacgagaag | cacgaccttt | 27540 |
| tgtctggtta | aaccacacgg | agtttcttgc | ttcagtatag | gctgttttcc | aatcaccaat | 27600 |
| gagcatggca | tcaagcattt | taccaaattt | tgctaatcca | cctacaccca | tttgaaaact | 27660 |
| catattttct | aaagccattt | gccttgattt | gttgacttta | gcatataccg | gtcctacgcg | 27720 |
| tgaattcgtt | ttaatatcag | aaagcatttt | atcacgatct | ttcttaaata | gtgcaactgc | 27780 |
| ttcgtccatt | gtaatgatac | cgggatttcc | tgtaacagta | cgaccaacct | gattagataa | 27840 |
| agttttatta | atgacagaca | tatcacgtac | tttttgtgcc | atgataaggt | gtccaatacc | 27900 |
| tacagtagga | tatccttctg | tatcccaata | gactttcaat | ctaagacctt | catccctatt | 27960 |
| aagcatatct | gttattgtaa | ttgcaggatt | tgggtcttca | ggaatatcgc | ttaggtcagc | 28020 |
| atcgtcagga | ttaatgccaa | tatccaagtt | tctatcttgg | atgatgtttg | gtatagcact | 28080 |
| atacccagtt | tcatcgcctt | gaactagtgg | gttggtatct | gacccaacct | gtctaggata | 28140 |
| ttgacctgtg | gggtcagaaa | aaccttccgt | gtagtttggc | ttagtttttc | tgtgcgcaga | 28200 |
| atatgttcct | attactaatc | ctgctgtttt | gaattcatca | agccataagc | caaataccga | 28260 |
| tgttccttcc | accattccag | ttatagacga | gccaactccg | gaaattccag | ctgagtttgt | 28320 |
| aggctgaatc | actgacatcc | aaggaaggtc | ttcggtagga | agaccggtta | tagctccttg | 28380 |
| tacctttttca | aacggatgaa | gcccgtaaac | acgtactcgc | actcttcctt | gctttaacgg | 28440 |
| gtcttgtctg | tcttcaacaa | caccagtaaa | ccattttaat | gaatcgttca | tttcaatcat | 28500 |
| aaaacttctc | cgatggtagt | ctgggatttg | tatcggcctg | attcgtattc | gctgtcaggt | 28560 |
| gcttttttcca | tttctcgtat | aatatcagaa | agaaatgcct | caatatcact | aggattgata | 28620 |
| atgtttattt | ggcgcagttt | ttcattttct | atgatagagt | cttcataaat | gtcaacacca | 28680 |
| gccaaagcac | cagtatattg | aggatactga | tgattaaagt | ccccctttatc | ataccaaaca | 28740 |
| cctgaatttt | caggatattg | ctcgagattg | taatagcgat | tgccatacgc | atccacgtga | 28800 |
| tagagtattt | ggtctccacc | tacatctgca | tatttttgct | gcgcaaattg | atagcatgca | 28860 |
| tcttgggttt | taatccaatc | tctgaatggg | tcatatacat | tattacacat | taaaagaatc | 28920 |
| cagtacagct | gactatttcc | ataaagaata | tatgctaatt | cttctggtct | aggagctcca | 28980 |
| cttatgtaat | atgtttgtaa | aagatagttt | tctgccacag | tgtcaaaata | tttgcgataa | 29040 |
| ttacgaaata | tgtcagcggt | tgggatagct | tttgccttag | cacctttttac | ggtctttgca | 29100 |
| gaataatcta | tcggactaaa | aaatgagaag | agcatagttt | atcctcttat | aaatattaat | 29160 |
| aacagtattt | ataaggaggc | cactatggca | tattccggca | aattcatgcc | gcagaatctc | 29220 |
| cacaaatata | aaggcgactt | cagaaagatt | acttatcgtt | ctacgtggga | acagtacatg | 29280 |
| atgagatggc | ttgacaatca | tccagatgta | gttcaatgga | acagcgaaga | ggtagtcatt | 29340 |

FIG. 20Q sequence.txt

```
ccatacttta gtaatgcaga tggaaagaaa cgccggtatt tcatggattt ctgggctaag      29400
ttttctaatg gtcaacagtt ctttttttgaa gttaagccga agaaagaaac tagacctccg     29460
gtcaaaccca caaagttgac gacatcagcg aagaaacggt acattgatga aatttacaca     29520
tggtctgtaa acgttgataa gtggaaagca gctcaagcta ctgccagtaa aatgggtata     29580
gaatttaggt taattaccga agattcactt aaaaaattag gatggaaagg ctgatggcta     29640
tatttgaatt tatcactgaa gctgcagaat cgcctaaagc taaatcccgt agtgaaaatc     29700
aatgggtagc attaggagtt gaatactctg ctgctcgtaa aaaaggcatg acatcaaaat     29760
catttgctga aagtaaagga ataaatcctg ctacgttcag taaagctatg gctcgtcatg     29820
catcaagaat taaaacggca attaaagtag cagaaattga gaaaaaacct gctaacaaaa     29880
tgaccaaaca agagcgtgct cttgtgatgg taaattcatt tcgaagctct atcaaagata     29940
aaattcgtaa tgaaggcgca gcagtaaaca ataaatctgc taaatggttt gcagaaacta     30000
taaagaaaaa tatacgtggt cattctgtaa ccaagcctca acctggaaag ctatatgctt     30060
acatgtatga cgctaagcac aaagacactc ttccattctg ggataaattt cctttgatag     30120
tttatcttgg tcttggaaag caaggtacaa ccacattgat gtatgggtta aaccttcact     30180
acattccgcc aaaggctcgt cagcagtttt tagaagaact tctgaaacag tatgctaata     30240
cgccagtgat atctaataag accagattaa agataaactg gagccaggtt aaaggatttg     30300
ctggcgctga caaaatgatt aaagcatata ttcctggtaa tataaagggt gctttaattg     30360
agataaaacc ggctgattgg gcgaatgtag tcatgttacc actgcagcag ttcatgtcga     30420
aaggcaaacg ctactctgct acttctgtat ggaaatcata atgtctactg gactgtttaa     30480
tcaaactaac acaactaact ttatattaga ggtccctgac gggggcctca cccaagcgtt     30540
taaagctaat cttcaaacag ctgtagttcc tggaattcat attcctgcta ctgatactgt     30600
gggttcgccg caaggcatgc accgtgctaa attgcctggg tctaccttg aatttgacgc      30660
tgttcctgtt agatttttag tagacgaaaa ccttgattca tgggtacaaa tgtacaaatg     30720
gatgttaagc tgtcaaaact acattgaccg agacaagtct ggatggaata acggcggtga     30780
aggatttcct ggtgcagttt taatgcatgt tcttgataac gataaacatg atatagtatt     30840
aactgtccgc tacatcggag gttgggtgag tgatttatct gaaattgagt attctttaac     30900
cgaagaatcc gacccagcaa tggtatgtgt agcaactttg cagtacaaat acattgaagt     30960
tgaaaaagat ggtataataa ttactggtag accttctgtc aatgatactc gcgaatccca     31020
gtatcaacag aaagttatgg gaatgcatcc ttcatgaggg taataatttg aagcttttat     31080
ttttgattgg taaaaaacgt agtggcaaag atacaactgc tgactacatt atggataact     31140
ataacgcaac aaagcatcag ttagcaggtc caattaaaga tgctttggct gatgcaatgc     31200
ttactgagtg gtatcgcgat acgtctcgtg agtttccgcg cattactcgg tctatgattg     31260
```

FIG. 20R sequence.txt

| | | | | | | |
|---|---|---|---|---|---|---|
| agggcattga | ttacgatcgc | gaacaagatt | taaatctgtc | tactaaagac | gtgattcgta | 31320 |
| tcatggcgaa | tgcgattgaa | tatgttcatc | atgatttgcc | tttacctggc | gtggtttatg | 31380 |
| ataacaaacg | taaaatactt | gacggcgata | cgatggaagt | catccgtaaa | gttgtaataa | 31440 |
| ataaacctgt | tgagccatgg | tcaattcgtc | gtctcatgca | gacccttggg | actgacattg | 31500 |
| tctgtgataa | gctcgatcgc | atgtattggg | taaaacgatt | cactttggtt | atggctgata | 31560 |
| cttttggtga | ttatgattat | ttcattgtcc | cagatactcg | tcaagaccat | gaacttgatg | 31620 |
| tagccagggc | gatgggtgct | acagttattc | atgtagttcg | tcctgagcaa | gaaggttcta | 31680 |
| aaaaagatac | tcacgtcaca | gagcgtggac | ttccgattcg | cgaaggcgat | atcgtaataa | 31740 |
| ctaacgacgg | ttctctagaa | gaactttatt | caaaaatcaa | cactatatta | ggaattcaaa | 31800 |
| atgactactg | aacaactgca | agcccaagtc | gatactctga | aagttcgtgt | atttgacctg | 31860 |
| tctgaaacta | tccaaggcct | ttctgctctg | cgtgcacaat | atgaagaagt | actgcagaag | 31920 |
| ctgattgctg | tatccggcgt | tgaaattggc | gaagacggcc | aggttaaact | tgatgacctg | 31980 |
| gttgcaaaaa | tcgaagcaca | gttcgcagaa | gaaactactg | aagaatctga | gtgatgaaat | 32040 |
| tcagtgattt | tagcactggc | ttatatgtag | ctgctaaatt | ctctgagaaa | actcttgatg | 32100 |
| ctattgagga | ccttcagcgt | gaattgaagg | tccctaatcc | tgtacctcgt | cataagattc | 32160 |
| atacgacgat | atgctattca | agagttcatg | ttccatacgt | ttgtgcttca | ggaagttttg | 32220 |
| aagttgctac | atcaggtaaa | cttgaagtat | gggacacaca | agacggacgt | acgctagttc | 32280 |
| ttaagctaga | ttcagaatac | ttaaaattcc | gtcaccaata | tgcaagagct | tgggagcaa | 32340 |
| ctcatgattt | cccagattac | tcaccgcaca | ttactctcag | ctacaatgta | ggtccagctc | 32400 |
| acttcgaggg | tgaagttcaa | gtacctgtag | tgcttgatag | agagtaccaa | gagccactaa | 32460 |
| aactgaactg | gtcagaggac | cttaaatgaa | gtcataccaa | gaattttaa | tggaaactga | 32520 |
| ggctcttttg | gagtctactc | tgccagatta | catgattgta | aaaagcttta | atgtaaaaaa | 32580 |
| tggctacgta | attaaatttc | ctatcgctag | tgtcaagcct | ggtgctgaca | tgtcaaatga | 32640 |
| tgctggcatt | agtgttaaag | ttaatgtaca | gtttattaat | tacaactctg | ctaaaaagtc | 32700 |
| gtatgatgct | aaaatgactt | tttccggtgg | cgaaaaggta | gttaaaaaca | ttaagttaga | 32760 |
| ttacgatgaa | tccgcagaaa | gtgtcaagaa | acgctttggt | gataaactgg | taaaatctat | 32820 |
| catggttcat | ccaactttca | aacgcgattt | cacggaactt | tataaataaa | aagttgttta | 32880 |
| cttcctcga | gggctatgat | actatagccc | tatcaaaaca | aatgaggata | aacatgaaa | 32940 |
| cgctgtgaac | tgataagaaa | tgttgcttct | gctatttgcc | ttactgctgt | gggcactagc | 33000 |
| attttcggtg | ccatctttat | gggtgcaaaa | gaaataatgg | ttgtgttagt | agctgcattt | 33060 |
| cttatgggtt | caatttcatt | tattatggat | aaaatttctc | atgaaaaaga | ttaaacaatg | 33120 |

FIG. 20S

```
                              sequence.txt
gtttgttaag acctatgatt taggccgtga agaagtaact aagtatgatt atgttacttt    33180
gggtgtagga ctaggtgcac tactggcagc attgcattca tcattacttg ccattgcagt    33240
gcttcttatt ttggctcact acagctggaa acgtaagtaa tgtatgcact tttaacttgg    33300
tctaattatt atcctgctcc tggctctgac caaatcagag gtgtttactc tacagtagaa    33360
gaatgctatg aagccctcca gggaacgtat caggactatt ttgagatact gaactctcgg    33420
tttgagaccg ttgctaaagg ttcaactgaa gcatacaaag attaattgtg aggaaattgt    33480
gatgaatatc agagctgcat ttaatacttt ctaccaagag aattataagc ttctttccca    33540
tgaatactat gatgcacaag gcgttccaat tcctagtgat ttagttacgc ctaagcatgt    33600
caaaaccgat tctcttgaca atgaaattca acctggtgat ttggtatcat actattgtgg    33660
cgggtcactt tctgcagcaa gcgttggtat tttgctagga tttacgccta aaggttatcg    33720
tgtggttcct ttccatacaa gtccaattcc tgagcaccgg gtattgctct ctcatatgga    33780
ttcaccgcat agggtattcc tggttaaatc aaagagctca ccgattgtgt aatatgcttt    33840
aggttttctt tgttattatt aatctatcaa ctgctctgat taatttcagg gcagtataaa    33900
taaaattacc caatggggag ttagaccgta ggggtagcgg gacagactgt aaatctgttg    33960
ctcaaaaggc tcgagtggtt cgactccatt actccccacc aaatttaagg gatactagct    34020
cagttggtta gagcaccgga cttttaatcc gggtgtacga agttcgaatc ttcggtgtcc    34080
caccaaattc gggtcgttgg ctgagagggt aagcgacgga ctgttaatcc gtgtcagaaa    34140
tgactaggca ggttcgatac ctgcacggcc cgccaaatga agaagtcaga agacgttctg    34200
ataaatcgtc ggcatagaat tccctggcat ggcgtttgta ttaaggagta tgatttcatc    34260
ctgcttaata cttgttcatg ttataatttc ttacggcgtt gaaagttcgc tttcagggat    34320
acatcttaga acagagtgct aaacaagatt catctggtac caaggtgatg agagtcctgt    34380
tcccctttgc ttcggcatag tgccagagta tctctgaaag cgaattatag tgctgtagtc    34440
gagatggtta agacactccc ctgtcacggg agagatcgcg ggttcgacac ccgtcagcac    34500
tgccaaatac gagagcaaca tgaaagatta tgaaaagtac cgcatgcaaa aagtgcatgc    34560
caaataaaga ggtattgaat ttaaattgac atttgatgaa tggttatcat ggtggaaagc    34620
tactggcaaa tatcatttgc ggggtagagc atcagataac tattgcatgt gtcgtaaagg    34680
agatgttgga ccatattctt tagataacat ctattgcgca actaatgcgc aaaacgctaa    34740
agacgctggc gctaacggaa gaataatatc tactggtttt actggacata accattctga    34800
tgaaacaaaa ataaaaatat cagaaaacca tgcacacaag ttaaatgcag acgaaatttc    34860
tttgcgaata gacctgtata attctataga ttttacacag cgtggtgcac tagtaaaatt    34920
tgcaaataaa cttggaatta gtcatactca agctagaaag ttcataaata gtttataaa    34980
gtaacgtggc agttcttgaa gatgagtttg agtcctgtaa gataatgccg aggacgaagc    35040
```

FIG. 20T sequence.txt

| | | | | | |
|---|---|---|---|---|---|
| ggtttgttcc | cacggaataa | gctctatatt | cgtaagatta | tatctttagc | gtgttctaca | 35100
| tcaagctact | tgttagtact | tcaagaaccc | ggataaatgc | ggagtaactt | cagttggtag | 35160
| aatgttgggc | tcatatcccg | acacgcgcag | gttcgagtcc | tgcctccgcc | tccaaacaat | 35220
| tgaatcatag | ccaagttggt | aaggcagtag | gttttgatcc | tacgatccct | ggttcgagtc | 35280
| caggtggttc | agccaaatta | atattcattc | aacgcgatgt | gtaggcagaa | gtcatgaacc | 35340
| tgctttagct | accgtatgaa | gtcctcatga | tggatggagt | gaatattgat | gtggtcgtag | 35400
| ttcagttggt | agaacccgag | gttgtgatcc | tcgatgtcac | ggattcgaat | tccgtcggcc | 35460
| accccaacaa | tgaaggaatg | gtggaaaaat | acacggcccg | caaaacgctg | tggctgtcgc | 35520
| taagcgaatt | gtgtctataa | tggcacttcc | ttcaccaatt | aatggagagt | agcgctagtg | 35580
| gtagcaaacc | ggacttgaaa | tccgggccac | cggaaacggt | gagggttcaa | ctcctttact | 35640
| ctccgccaaa | tttatgaaag | ttaaacgctg | cccatagcag | tggtacatca | acaattagat | 35700
| gattagcttt | ccatgggagt | atagctcatt | tggtagagct | ctcgaccgat | aatcgagcgg | 35760
| tgactggttc | gagtccagtt | actcccacca | aataacaggt | tcttagtata | atggctatta | 35820
| tgctgggctc | caaacccagt | gatgagggtt | cgattccttc | agggcctgcc | aaatttgcat | 35880
| ccatcgtata | gcggatatta | tgtctggctt | ccacccagaa | gatgggagtt | cgattctccc | 35940
| tggatgctcc | aaattactcc | gtatagctca | gcctggtaga | gcgctccatt | tgggatggag | 36000
| aggtcgaatg | ttcgagtcat | tctatggaga | ccaaattaac | ggtatgacac | aatacaagat | 36060
| ggtgtaagct | gagtagcggg | attgcagtct | cgttcagata | tgctatcgag | tatgggtgat | 36120
| atattaaaca | cacggattct | gcaaagtcca | tgtgactcgg | ttcgagaccg | ggcataccgt | 36180
| ccaatcactt | gccattgaga | attatattat | gaaatattac | ggcttcaaaa | catcccattt | 36240
| cgggaaagca | tatcgtacag | aaaacattga | tagacgtcga | gcatattacg | aatcactgca | 36300
| taaagcagga | cgttctcgtg | cacgacaaga | aggccaaaaa | caagcgaagg | aaatagaatg | 36360
| aatattttta | ttggtgttgc | aaataacgta | aatgctatta | cggtgaaatt | acaatggaat | 36420
| cgtccaacta | attttgcttt | aggattatgt | aaatctgaac | gtgatttaat | gcttcatgct | 36480
| gattttgcat | acacttttga | tgaacgcaaa | ggtatgtggg | tatggattaa | atgcagatac | 36540
| gaagcattaa | tcaaatatga | gtacttcagt | gagcgtgata | ttcaagaagt | tattgcttat | 36600
| cattctggct | gtaaagtaag | taaactgcgt | caagttattc | cgtttactaa | tgcttcaaat | 36660
| gtagaagagc | taattactga | ttttaaacga | atttatcagg | cgaaatatga | tgaaagattc | 36720
| taaaggtcga | gacgtacaag | ttggtgatat | cgtttctat | ggagaacgta | catacaataa | 36780
| aggcggtcgt | ggttctatgc | gctgtggtcg | tattactgat | attgcttcag | gattggctaa | 36840
| agtagataac | gactacgttg | caatgcgaag | caaatcattc | gttaaggttt | ctcctatgtt | 36900

FIG. 20U

```
                             sequence.txt
cgcaacaatg tgggaaaacg gaacgattttt cgagatttaa tgctacaaga ataacctgtt      36960
attattacta catcaaaaca aacaaggaaa aagaatgaaa cgtatcgcac tgattgttga      37020
ccaagaagct atgttcgctg ctaccggtaa atttcatccg gtgagtaaat ttgttgctcg      37080
cagcgagaaa atcgttggtc tggtagaaac tgtcgcaggt gatgtaattg tttctattaa      37140
aacgtctgaa atttctccag tagttaaagt agcagttgaa aatgacttct gggaagtagc      37200
tgattttatg tgtgagtaat tctgcctagc aggtggataa gcccgacaag gcgccctctt      37260
cggagggctt ttataaagt cataagattt ctataaaggc cctgtagctc aattggtaga      37320
gcgttcccct cataagggat tggttgcatg ttcgagtctt tgccagggtc accaaattaa      37380
tgaggaaaat attatgatgc gattagttaa agtagttgta gaagaatctg aatacatggg      37440
cgatagccga atgattgaag aattcgttac tgttgaggca gattctgaat ctgaaatcgt      37500
tgataaagtt tatcgtcatt ttgataatat gtctgattcg tatggcacaa tgtatagcat      37560
ttatcgttta gatgtaatag tacatatcaa ctgaggaaat tgaaatgcat attagatttg      37620
gacaagttat tcctaaaggc ttagcaatgg caattaccac ttgggaaaac gatgctgatc      37680
ggtattctac ccaaatggtt tatggcttag aaaaagaaga gattaatcaa gtaattcacg      37740
ttcttgaatg gttctcttct aatggtcggc gtggtgaata ccttggaaat aatgattaca      37800
accatgaagc aattcttgaa aagcttcata ctgaacagaa gtatgtaact cctgaatttt      37860
ccaagaaatt ctttggcgtt gatgttcctg catatgattg cacagacgaa gagtttgatg      37920
cttatttaga taaccactat tcttgttcaa atgaagttat gtatgctatt caggcttggt      37980
tgggtaatcc aattgaatat gattatgatt tcatgcgagt atttgagaaa gtagaaatct      38040
ttgacattaa agaagaaatt cgtattcctg atgctccagt tgcattccat gttggaatta      38100
cgtataaaca aaaagaaagt ccattaaaag ttgattggtt gaaatacgtg aaggaaaagt      38160
aatggatatt ggttcaggca gttcatatcc atcatgtgct ttgagcaact ttgctcctca      38220
taaatttatc tatgatggcg tagaatgtgc ctcaatggag ggattcttgc agtccctcaa      38280
attttcttcg cctgaaatgc aagcacatgt atgtacacta gtcggaaagt ccgctaaatt      38340
taaaggtaag aagaaacgtt ggtggccaac tcaaacactt tattggaaag gcgtgccaat      38400
ccatcgtgct tcagaagcgt atcagaattt actgacagga gcatacgatg cacttagtaa      38460
aaatgaagga ttcagaaaag ctttggctgc tacccggaat gctacgctca ctcacagtat      38520
gggtaaaaat aaaatttctg aaacgatttt gactgaacgc gaattctgta atcaacttta      38580
tcgtttgaga aatgctataa ataatcagta atataattat cttgttcagt gttgaaatcg      38640
gtagacatgg tgacgggcac cttttgagct cgcatattgc atcatatgct ggcgatggtg      38700
gtaaatcgcc gacggaatca gtcgtgcagg ttcgagtcct gcctgaacaa atatttgcgt      38760
cgatgttgga attggtagac aaaggagact taaaatctcc cgggattaaa cccgtacgag      38820
```

FIG. 20V sequence.txt

| | | | | | | |
|---|---|---|---|---|---|---|
| ttcgagtctc | gttcgacgca | ccaaagccct | tatagtgtaa | tggatagcac | acgatcgttc | 38880 |
| taaggtcggt | agtccgggtt | cgagtcctgg | tggggtacc | acgccgattt | agctcagttg | 38940 |
| gtagagcgct | tcacttgtaa | tgaagatgcc | gcgggttcga | ctcctgcaat | cggcaccaaa | 39000 |
| ttcgaaggga | aacttgcgta | taccctcgtt | gagtcgtcag | atagaagaga | atggttcgtc | 39060 |
| cattgccgca | agtcggttgt | tccctgtcgc | aagcataacc | tcctgacgct | atacttcttt | 39120 |
| ggatgagact | gatgcctccg | agtccaaaga | aatgaatttc | gcaggtcatc | tgccagtggg | 39180 |
| tgatgctgtc | gattattaga | gccctgtctt | cggacggggc | tttttagtat | aaatagtaat | 39240 |
| ttaatcggca | ctaaggattt | ttttgcaatg | aaatttaaag | attttttaac | cgaagaagag | 39300 |
| cttttgaag | cagctcctgg | ccgcatgact | aaatcgaaat | ggcgtgacgc | tctggtattg | 39360 |
| gttccacgtg | gtgaacgcca | tgattttagc | aaatttgcgg | cttctgtgga | aaagatttat | 39420 |
| ggtattggga | ttagcgatcc | taaagactat | gctaaggtag | cagctgcctt | tgaaagttta | 39480 |
| ggcggaaagg | ttactacacc | tgcacgtgga | gcttctccgg | cacaagcacc | ggccgcaaaa | 39540 |
| ccggctccgg | ttaaagcgaa | acctaaaaat | attcctggcc | ttaaaattag | tggagaccat | 39600 |
| ggagacatca | ttggttcagg | tgaactgttt | aaagctattg | ataaagctct | tccactagta | 39660 |
| agagataatg | gtcctcttta | taaagcagtt | caattctatt | tcgataatct | gtggaagtat | 39720 |
| cgtgaatccc | aaggtgctaa | accttctgca | cgtgaaactc | agcatatcgg | tgaagtgaaa | 39780 |
| acacttttag | ctaaactgaa | tcatcacctt | gttgaactca | gtcgtcagac | agaattatcg | 39840 |
| tacaatgtat | aataaaatgt | aatcctacag | ccctagaatt | catctagggc | attttgtat | 39900 |
| cctcggctgt | ataaatccat | tctatcttcc | agaaagttcc | tccagatgcc | ctaaaaattt | 39960 |
| ttgcacaaag | ttgtttactt | cctctatcaa | ctcggttact | atagctccat | caaaacaaaa | 40020 |
| cagagtaacg | gagaataaaa | tgtctaaatt | caactttatc | caaattgaac | gtggttataa | 40080 |
| caattacggt | actcctgatc | gttatcgcgc | gatttggatt | aaaggtgaac | atgaacacgc | 40140 |
| agtgttcaat | gtagcagaaa | ctcgtgaact | taaagatttg | attaagcatg | ttcgtaaaga | 40200 |
| ttggcctgct | gttgaagagt | actacgttcg | agtttaccat | gaagaagctc | ctaccgaaac | 40260 |
| tgttcaaatt | aaattcgcaa | aaactgctag | tgctttaacc | aaacgaattg | aagctgtaat | 40320 |
| taactgctaa | taattttggg | gagttataat | gaactcccca | cctactgagg | aaataaaatg | 40380 |
| tctattctga | aaaaacttgt | tgaattcatc | cgttctaaat | tcggtaccttt | tgttgcacag | 40440 |
| aacacttctg | ttgaagacca | gtatacgatg | gcagcaaacc | gtattattga | tgaaatcact | 40500 |
| aaactgcgta | ccacgcatgt | taaatcagta | aatgaagaaa | agcgtctgct | gaaacttgct | 40560 |
| gatgaaaaag | accaagcggg | tgcttctaaa | gagcgtgaaa | ttcgtcgctt | gatggcagaa | 40620 |
| ggtatgaatg | tagaaaccca | tgctaaactg | ggtcttctgt | atcgtcgtac | tgctaaggct | 40680 |

FIG. 20W sequence.txt

```
ttacgtgata aagctgccga atataaagaa atgcgggccc aaattgaaga aaccgtagtt    40740
aagcttgatg accaacgtct tgatttggca gtgaaactcg aatacatccg tgagacccgt    40800
aatgcttctg ctctgggtat tacctctgct gacgacgtga ttgaaatcgc agaactcgct    40860
aaagtagatg tacaagacat catgatgaaa gttgaaacct tcagcggtac tcagcctggt    40920
attgaaacca ccactgctga tgtccaggaa tatctggaaa gtctgaagta attttaccgg    40980
ggccttcggg ccccctaact tggataataa aatgttatat gaatgcgctg gagatattcc    41040
aatggcaaca cctcaaatta aagaattaat tgcagcagga ttcccaacag aaatcactga    41100
tattcttgga aaatttgctt atcctgatac tcggcctgaa aattggaaaa ctcgctataa    41160
cgggtataac accacagttt taccgcgggc tatcgttctt aaagactatt ccaagctgaa    41220
aaacttaatt tctaatattt cgtctatttc cgacggagtt aagcttgtgg atatttttgc    41280
acttcggtac ggaatctact ctttaacga ttctccatca aatttaaaat cagcccgtac    41340
taatgccggt gaatactcta cttctggttc aacaacgtac accatagtta ttgagattat    41400
tcataataaa aatagctatc gtcttggtat taacctagtt aaatatgtga catctcagga    41460
tgattatagc aattatttaa attactgtgt taatgaattg ccatcaaagg ttatgagtat    41520
gtttgactct aacaacatgg taggcaaaca attaatcatt gatgaattta tcaaatactg    41580
ccgtgagagg gtgcagaaat gagtaactta tatctgccaa gtgaacctcc cgtttataat    41640
tatgtctata aatttgatca gattgattat gcccttgttc ctggtattgg tgcaactgtc    41700
ggcgcaatgt gtacctttgc cgcgattgat atcatgcatt taactgatat tacaccggca    41760
gtgttattcg gaattctgct tgcatggtgg ggaactagtt tgctcatcat gggattaatt    41820
gaatgttccc gatgggttaa atggtctcgc aataattata agcgtaaagc tgaatggaaa    41880
gaacagtgca agaatttaac tcttgaatgg aatcgcaaaa agtcgtttga gtttattaaa    41940
gaggtgagaa gaaaatgaat gaatataaac ccgacggatt ttggaatcaa gatgggctcg    42000
cgccaggttt tggaattgtg acatggcttt tatattgtgc tttcgtaatt gttggaggga    42060
cattctttgg attgaacgtc tcagagttta tgattatgct tttattttta ggtgttttcg    42120
cattcagcct catgtggatg ctaattatcg cgttgattaa ttgctgtaca ttttagctt    42180
accgaatgaa atacaagaag tggaaagaaa aagaagattt caacacctgg attaggagct    42240
gcagaaaatg attaaaactt gctaccgtgg aatgattaaa agcgatgagc ctgggtattt    42300
cttcctattt ctgcttattt ggttttcatt atcagccttt gttggatttg aacattctg    42360
ggggttctac ttcttttctc cagtatttgg cgatgcgtta tattacatag gctggatgtc    42420
aggtgttgga acttggtttg caatacttgc ccggtggttg caattcgttt cccagcggca    42480
gaggggtgta ttcgataagc ccaaagtaaa gaaagaaaaa tctaaagatg actctcgtag    42540
tgaaacttta tcctggatta aggagatgaa ataatggctg ttgcagtgca tgtaaaattt    42600
```

FIG. 20X sequence.txt

| | | | | | |
|---|---|---|---|---|---|
| gaaaatggtg | atactcgcct | tctgtgttac | agtgataatg | aatcactgag | cggtatcgag | 42660
| atttcactca | aagaagaact | gcttggtatt | aatggaccta | tctgtgattt | ctcggtagaa | 42720
| ggttcggata | attgtaatga | tgatttggag | tctatggtct | atactgccat | ggaagatatt | 42780
| cttgaagaaa | gttggaacga | atgccaatga | aagagctcag | tgcaggaatt | ttattcttta | 42840
| ccgatgacaa | acggctttta | atgggtcgta | tgacaaatac | atatgtccag | ggcagaggct | 42900
| ctagatggga | tattccaaaa | ggacatgttg | agcctggtga | aacaccaaaa | gaagctgcta | 42960
| ttcgcgaatg | caaggaagag | actggattta | ctgagtttga | ccaagacctc | ttatatgacc | 43020
| ttggacgaca | tgattatgca | agcaataagg | atatccatct | gtttggatat | atgctccctg | 43080
| taagcccaga | aatgttcaga | aattgccgtt | gtacagctta | ccataaagat | gaaaatggaa | 43140
| ttaattttcc | tgaaatcgat | gcatttgctt | taattaaacc | aagccagtgg | aaatatgtga | 43200
| tgggaccaag | tttatacaaa | atcatgacgc | aaatgtatag | cacagctcag | tgaggttatt | 43260
| atggaagaag | ccgttgaatt | aggcattcca | cacatttata | aacatgagct | acgatttatt | 43320
| cacgatggaa | aatggattag | catatttcat | cctagggata | aatgtcgcg | tatactaatg | 43380
| aaatcacggt | atgtcttcag | tgatagtgag | tatataaaat | cagcatatta | tatagcagaa | 43440
| cagctatatc | cgggatttag | tgaattgccc | gaggacgata | aaagagatta | tgtgtggtgg | 43500
| aaagataaat | ggacaccata | cgagaagtgt | agccttgagt | tattcatagc | caagtgcagg | 43560
| gccaaataaa | tactcctata | aattaatagg | aggtccttat | ggatatttt | ggcatgttgc | 43620
| gtattgatga | aggatacgac | agcaaaattt | ataaagatag | cgaagggtat | tggactatcg | 43680
| gtattggtca | cttactgact | aaagacccgt | caaaatcttt | ggctatttct | aatctggaca | 43740
| aactggtagg | tcgttctacc | ggtggccaaa | ttactcaggc | tgaggcagaa | gtaatttttg | 43800
| ccaaagatgt | tgagaaggca | attaaaggta | ttgttgctaa | tgctacatta | agcccggtat | 43860
| ataatatatt | agatgatgtt | cgtagagctg | ctctgattaa | catggtattc | caaatgggtg | 43920
| tgtctggtgt | agccgggttc | ccagcttcaa | tgaagttatt | actcgctaaa | aaatgggatg | 43980
| ctgctgccaa | ggaacttgca | aattcacgtt | ggtatcgtca | gacacctaat | cgtgctcgtc | 44040
| gtgtaattga | aactatgcgg | accggaactt | gggccgctta | tcaaggaaaa | taatgaaaa | 44100
| cctatcaaga | atttttaaat | gaatcccgtt | tagcaacagt | tggcgtaatg | actgaatctg | 44160
| ttggaagtaa | tcttctgaaa | tttaaaaaag | gtcagaagat | gacagccacg | ctagaagatg | 44220
| gcacagaaat | tgaaatggac | gttgttggat | ataactacgt | agtagacggc | aagttatata | 44280
| ataagagcca | tgctaagttt | gattcattcg | atgattttgt | ctcttcggtt | gaagatgaat | 44340
| cttctcgcaa | agcagtagca | tctggcgatg | cacgctcttt | aatggcccat | ggacatatgc | 44400
| gtattaagtc | taagcagaac | aaacctggtg | aagataactt | tgcattagta | ggttatcagt | 44460

FIG. 20Y sequence.txt

```
ctggtaaaac ttctaacggt taccagcgta cggttaccat gtacatgcgt aatggtaaaa    44520
ttgcattcgt aaacgatcgc ggcgctattc gttacgctaa atcaattaag taagcaattt    44580
cctaataaag ccgaacacga cctctcctca tgaacgtcga gtcctctgag tgaagtagct    44640
tttcctacct gtaataaggt cgagcgcaag tgcggtaagg ggtttacata gtgtgtcgat    44700
ggattaaaca tgtgccaagg aatggcccca tttaatttaa aacttttacc tttctggatt    44760
taaaaatgaa aacttataaa gaatttatca ctgaagcgcg agtgagtgca ggtaaattag    44820
aagccgctat aaataaaaag gcccattcat ttcatgattt gtcagataaa gaccgtaaga    44880
aacttgtaag cctttatatt gacaaagagc gtattctcgc tcttcctggc gctaatgaag    44940
gtaaacaggc caagcctttg aatgctgtcg aaaagaaaat tgataacttt gcttctaaat    45000
tcggtatgtc tatggatgac cttcagcaag cggctatcga agcagctaaa gtaattaaag    45060
gtaaataaca gtttactttc tcctagaatt gtgatagtat attcatattt acatttaaac    45120
aacattggaa taacctggac ctcatgattc tatgagggat tcccgcctac ctgtaataag    45180
gtcgagccca agtgtggcaa tgccagttac ataaggtatc ggaatggact cactccatgc    45240
gccaaggaat ggccccatta aaagagagct tatgaaatac ttaacaccaa tttatttgac    45300
cctgatgcat gctttcaaag acgctgcaga cagacgatta ataatccca actacagttt    45360
ttatgaaccg tcttgcctta tgcgagagta cggtacccct cgtctagatg gtggaagaca    45420
aaccggaaag accgcagcct tatgccaatt cgctaccgat tggttgcttg aagatggttc    45480
ggttataatc ttatctactc gatacacaca atcatctgaa ctgatggaag gtattctacg    45540
agaatataat tcatcgcatt taattaataa attaccggct aacgagatag ctaaatcaat    45600
tgttccgatg acaatcaggg aatttctatc caatgattcc tcttataagt ttagaggaag    45660
aaagcttgga agagcattaa ttatcattga agaaccaatg aaagttcccg atatgatgaa    45720
gttctatgat atgtaccagg aagctatcag atggtctatg cctaatgata ccttacccttt    45780
attttcgtg ataggaatgc aatgatgaca cagacagaaa ttgttgatat gattacagtg    45840
atggaaaata caggatttgc cgatatgaag caattaataa caatggttac ggctggcaac    45900
ctgcttgagt acaagcgcta caagtttctg tctggcccgt tcaaaggcgc agaattcatt    45960
tctaatgctc ctaacacgaa gtggatgaat cgctatccta attttagaat tgagtttata    46020
tctggtaagc taaaaggcgt gattagttca agcttaatca catatgacca acgcattcaa    46080
gagaaaacaa tgcaatggct gaaattgtta taaggtgtcc tccacaccta gttgagagct    46140
tctgtgaatg gttcagtaat tctggtgagc aagattttta tgaagctcac cagaatgaaa    46200
cttggaatga acaaccaaa cagtgggaag aagctacaac gtatataggc actcgcggat    46260
atggagttaa cgagcctatt gaaattgtgg aatacgataa agaaactgat gaagaagtta    46320
cttatcatga agataaaata acttatctag aagcagctgc aaagtttcat tcagacgaat    46380
```

FIG. 20Z sequence.txt

```
ggaataaaat gagtgtaatt accgcataca tgcgtggttg gaataaagaa tctaattaag    46440
aggaaatatg aaagcatatc aaattcttga aggtgaactt aaaggcacca tttacatcga    46500
agatggtgat gacgcacgag taatcgtttc aaaagttctt aaagaagata ctattacgga    46560
tgctgaaact ttttatggct acaaggctcg tgaagtagaa attgaatacc agccaacggt    46620
aaaaattgaa ggcggtcagc acctgaacgt taacgtgctg cgtcgcgaaa ccctgctgga    46680
cgcggttgag catccggaaa aatacccgca gctgaccatt cgtgtttccg gctacgctgt    46740
acgcttcaac tccctgacgc cggaacagca gcgcgacgtt atcgcccgta cttttcacaga   46800
ggcactataa tggcaattga agatatcaaa ggatataagc cacataccga tgaaaaaatt    46860
ggtaaagtga atgctattaa agacgcggaa attcgtcttg gattaatttt caaagcgtta    46920
gaagaagaac atgttgaaaa gtacatgaat ttagatgtta gcacaatgag cgacaaagaa    46980
tttgatttag cacatgagcg tattactcaa attcgcaacg cgattcaaca cttgaaggaa    47040
gcttctatgt gggcatgtcg ttcagtgttt caaccagaag aaaaatatta aaaagtagtt    47100
tactttcctt acgggccatg atactatggc cctacaaaca aaggagaatg aactatgtca    47160
actaacccag aagtattcat ccgcagaact aaactacgtc gtaagtttga ggaagcattt    47220
cgctctttga atttatcagt tcgtgcccga gctaaagctg agggcaaaga gcctttcttc    47280
actaagtact ctgatcattt gttggaccgt gctatccaac gtgaaattga tgaagagtat    47340
gtattctctg ttctttccaa aattcctaat catcttaaag aaattaatga attcttagca    47400
atgccttggc ttccaattga cccaaaggac attgatgaaa acattgagta taagccaatg    47460
cggttagaaa ttacggatgg aaatctgtgg ctagggttta ctatggatat tccaagacca    47520
ggaaaaggac ctagtataaa gtgtcgtatg gcattcgtta atgataaacg tttgaaaggt    47580
aaaatcagca caaaagttat acacattaat tgaggtaaac atgaaaaaag cgcttatcgg    47640
tctaatggcc ttatgttcaa cggcctttgg gtctgagcca actttcagta atgttcaact    47700
tgacaacttg cattacgcat ataattttgg tgaacaatat caaaaatccg gaaaagaaaa    47760
atctccgcat aaccgatatg ataataacgg cttaggatat ataatggctg ctatatcatg    47820
gaaagaatct tcggcaggag ccaatttaaa agcaggaaag gggcatcatt cttatggggt    47880
atttcaaaat tacttgccta cggttaaagc cagagctaaa ttagagggca aaaaccttag    47940
tgattctgaa ataagaaaaa tgcttaaatc tagacagaat tccgcggaat gggcatatat    48000
tgagctttca tattggttaa atatacataa cggcaatatg cgaaaagctc ttgctagtta    48060
taatgcagga tggaatgtca aaaggggaaa ctcttatgcg tcagatgtcc tagagaaagc    48120
taatttctta aaaaaacata aaatgctaca tacaaaggtg gaataatggt aaagtacgcc    48180
gcgcttcttg gattggtatt ggcattctct gctaatgctg aaaattcaat gacagattca    48240
```

FIG. 20AA

```
                                 sequence.txt
cttcgtatcg ctaaaacatt ttgcaatacg aactctgaat gtgttgatat attagcgctt    48300
gaattagatt cagcattcag cgatggagta aaagattcac gtagcccggc tcagtggaca    48360
acactaataa atcgtaaggc taagagcatg aaagatttat gtgtcaatgc tcctaacgaa    48420
aatatatgtt taatgtatcg tgaccaatta atggctcgtt atatgtcagg actatcgtca    48480
aaatgaaaaa agcggctatt ttattatgct gcgcattttc agttaatgcc tgggaaaaac    48540
tcccaggcta tcctgaaact gtacttgcag cacagggtac taaaatagaa agcaatggcc    48600
cattcaagaa caacattgaa atagcatttg ttcctagcag cagaaaattg ctaatgtcat    48660
tttataatta tcaagataaa gatgaccagg tgatagttcc acttgtcgaa tataatgctc    48720
gtggatgtgg aatgcagagc gatggcgttt ctgttgatgg agtaatgcat cctaaagaac    48780
aaggagtgct gaaccctatc cttaattgta acaatgctat attttaaga gtatacaata    48840
atcttaatga atatgcaaca tataaaattc cataggtgaa taaatgatta ctggatatat    48900
taagggcaat attgtagaac tattcatgaa gcatgaatgc gatatcgctc atgggtgtaa    48960
ttgctttact acaatgggtg ctggtgtagc aggacaactt gctaaagcat atcctccaat    49020
tctcgatatt gacatcgatg aagaccgtta ttatgacaat aatttagcca agcttggaac    49080
tcatacacga gccattcaca aaaaaggcac tgcatattgc tataatctgt atactcagta    49140
tgctccaggt ccaaacgttg attacggcgc aatttttaat gcattccatg aactaaattc    49200
tggtcgtatt gtttataatc gtcctctata cattccaaaa attggagctg gtattgctgg    49260
cggtgattgg gaactaattg agaaattaat caatttagca acacctgata ttgacattat    49320
ggtggtagaa tatgaagaag ctaaaagcta aatccgtctt gtagaggtaa atagatgatt    49380
actgaagagc aaaaaactaa actgtggcag ttgattgacg attatgcagg tgccgagcaa    49440
gtagtagcta ttagtgccat ttacggaaat ggtctacctg aagaatacga tgaactcatt    49500
cgttctaaga atgctatttc tgattttatg gagacacttt aatggcacag ctttatttca    49560
actacgcgag catgaatgca ggcaaatcag ctaaccttct tacagcagct cataactata    49620
aagaacgcgg catgggaact ctcattctga aacctgctat tgatactcgg gattcggcaa    49680
cggaagttac ttctcgtatt ggtctacgtc atgaagctaa tacagtagac gaatctattg    49740
acatacttga atttttcaag tgggcacaaa cacaacgtga tattcattgt gtatttgtag    49800
atgaagcaca attcttgact gctgaacatg ttcttcagct atgtaaaatc gttgacttgt    49860
atgatgttcc agtaatggca tatgggcttc gcactgattt tcgcggcgag ttattcgaag    49920
gttctaaagc tcttcttttct gtagccgata aacttgttga gctcaagggc gtttgccact    49980
gtggacgtaa ggctacaatg gtagctcgta ttgacgaaaa cggaaatgct attaccgatg    50040
gtgaagtagt agaacttggt ggtgaagaca aatacgtttc tctttgtcgt aaacactggt    50100
gcgaactggt aggtgtttat aatgaagcca agaacgtata acactatcct gatgctagtt    50160
```

FIG. 20BB sequence.txt

```
ttaagtatgt tattcatttg gatgggtgta gcagcatcta ttcaaagcga tagacgagaa    50220
gaacttcaaa atcgtcttga ttctggatgc aaagtattag ctcagggtaa agactttatt    50280
gctaatacaa atgggtgtta tattaaatat gagtagccta tttgctatag cgggtgtata    50340
gtactagtac tcgtgattgg gtttttacta tacgtaatat ttctttcgtt attggtttaa    50400
tatgaaaaaa tatgtgatgt gctatcgttg tcttcatgta tatgattaca acactgctcc    50460
aaagactgct accaagcgtc ttaaaaccaa agaacctgaa tgtccaaaat gtaaatgcaa    50520
ggtcatctat tcatgaatat taaatttttc aaatcaggat tttactatcg ttgaggtaat    50580
ttaacttaac gaggtaataa tgtctagaac aattcgccgt aaaggctggc atgtagtaaa    50640
atcttccaaa tggaacgatc agaataataa cgaatttgct tatattaaaa gctataacga    50700
atacgttaaa actcagaaag ataaagaaaa ccagcagaaa tatgttgaac tgcgtatttc    50760
tgaaaacagt gaaagaccgt tagaggccaa gaaactgatc gctaaatcaa agcgcgatgg    50820
attctggaaa actctacgtt ggacccgtta tgctatgccg gttccgcgtt tatttcataa    50880
agccgaaatt aaacgtgcat tgaagtatga tgaagaatat aactgggacg aagctggtgc    50940
tagaaccatt gagcaaggca tctgcgaatg gctttgggat taagtaacac atacttatat    51000
aaatactatt actaactgat gaggtgtata tgcagcattt aagtgaaaag caacttcgta    51060
atcttactgt agagcagctg gacgaacttc gtcgtgagat tgggcatggt atttcgcacc    51120
ttcaggaaga aattcgtcaa catagttcaa aagcagatta tacccgtaaa cgtacgctgg    51180
aaaaatacct caaagaagtt aaggctgtac ttcagcacaa acgtaatact ggacaaaaat    51240
aataggaggc cgtatggcct ttaatcacat ttgcttagcc ctggtgttgg gctgcgggat    51300
ttcattccca gctgcatcac acgacgacat ttcagattat aattcgtatg ttgagggagc    51360
tctacaagtt tatgctaaat ttaaggagcc tagtaagcaa gagtctgaac agttctatgc    51420
tttcgtacaa agtaaatgga agagcgagtc ttgttctaaa gattgcgatt ctttaggacg    51480
ttcagcaggt gaagaatacg ctaaccgtat gaggatacaa ttcgataatg aagttcaatg    51540
attttgtaaa ggacggtaaa cttactccgc aggatgaatt catcggttta cttatggtgt    51600
ctcaagcgta ttttcattca gcgcattttg ataccaaatc gtatgccaga cataaagcgt    51660
atgaagtttt ctttaacgag attccagatt tgatagatgc ttttggtgag cagtggttag    51720
gattctcagg taagagttat acaccggctt taccatcgca gaaagagctg ccaaaggaca    51780
ccattgaaat gctagacttc attctggcta aggccgatgg tatctacaag tccgttcctg    51840
ccgccctcca aagtgttctg gatgacatta caggcctatg ctacaagact aagtatttgt    51900
tatcattgca gtaatacect ccgcctcctt cgggaggcat tttctttttca aaagttgtt    51960
tacttccctt cattacatga tactatagac atatcaacaa ccaaacgaga aaaacattat    52020
```

FIG. 20CC

```
                                    sequence.txt
gattaagtta actaccgagc ttcaacctgg aaaaatcttt tatcacgtgt gtggtgttaa    52080
tcgcacagaa actaaacccg gcgaaataac gcgttacatt gttgcttcag gcacatatga    52140
tgtagaactt ggtcttagtg gtgtatattc acgtaaatct cctttcttcc aagtgatttg    52200
tgaatatgaa aactatgctg gccaaactga aagctattca actgaacggt ctgcccatga    52260
tatgggtata ttcaagccag gtgaaaagcg ttcggttcat aatcttaatc gtgggttttg    52320
gacgcgtgaa gaagctgaac agttcatcaa agagctccaa gaaaataagt tcagcgatcc    52380
agatgatcaa gcatatgcag acagactgac cccttctgaa gatttccgcc gtcaacaaga    52440
atttatggat tcttatcttg acagttgtga ttatgattac tacgactttg atgatggcga    52500
agaatgagaa acgttttact tatcatctac attgtggtac aataccagca tccgatgttt    52560
acatataatt tggtgcaaat gattctggag agtttgaaat gaatggatgg ggcccatcag    52620
atgacggatt tgcaactcgc gaagctacaa tagcagacgg gattgaatgg gcccgtcttc    52680
agaaacaact ccaagaacag cgggaatccg aagagttctg tgttgattgt gatgaggaaa    52740
tcccagtagc tcgtcgtctg ttggttaaag gctgtcaacg gtgtgtagaa tgtcaaggaa    52800
agtgggatac agtaatgact tctgcttata atcgccgtgg ttcaaaagat tcacaattga    52860
ggtaattatg gaaagtattc ttgatagtac caatttagat aatccgtaca gcgatgtgca    52920
tgtaaaggtt gtgaattcgt attttactaa aaagttgagt cgtgtcgtgc taaaacaagg    52980
taatgatata attcatcttg atactaaaca aattgattca ttaattcaat tcttgataga    53040
ggcaaaagat ggcgagtaaa ttagtatggg acggaaaacc ccgtaaaggc gatgcagtaa    53100
ttgaagatga aagcccgcat gttattgatt tgtatcttac ggtattccac acgtatgaac    53160
ataatactat catcgaaatt gaacgtgacg gagattgtgt agctattgat aaaagcgacg    53220
ctattgaact ggtcaaatat cttaccgcaa tgattccaac tatgaaacag gataacttat    53280
aatgaatatc aataaaaatt cttggcattt caaaatgaac ctatggttta aatctggcaa    53340
tatatggaaa atgccaaaaa ctctatgtgg atacttttgg accacagtac ttcatattct    53400
gttctcttca gcaattgcta tattcattgg ttctgttgca tggatgttcg gttggccgct    53460
tatagcgcag acgggtattc tcgcttggat aggtgttagt ttatccgcct tttggctaaa    53520
tgttgtagca gtaccagttg gtgcagtgtt tatagcaaca tttgtgcttg cgtttgtagc    53580
aatagtgttt ggatttattt tcggttttaga aaaatttaaa gaataccgta aaaataaaca    53640
atttacgaag aaacttgctc gagtaaaagc tggtcttccg gcagaatccg aaccgttagt    53700
attcatccag tatttaaaag ctcgtaaacg gaaagtttgc ccaatgattg attatgtaga    53760
aggtaaaact agtgaagaat gatcaagttt atatcgtgaa cggccgaaag gccgtctttc    53820
gtgctaaaac tgaacgtggt ataatttcta catccctat tgccgaattt acttttgaag    53880
atggcgagca gattaaaatt aaatatgttc cgttatctca gacgtaccga ttcatcggcg    53940
```

FIG. 20DD sequence.txt

```
gcgaaattga tttagacatt tattatgaag gtggcgtatg gaaattgaaa tcgtaacaac    54000
caaaaagaaa ctctctatga gcttgcttaa gcagatgaaa atggcaagct cttctgaaat    54060
caaattcgca atgtttgacc gagttcatcg tgttcttgga tatgttaatg cctttaaatg    54120
gaacaaaatg gatatccaag tagcaatcat taacactggg aacgattggg cattagttcc    54180
tatgtatgat acacatgtta ttaaaaccgc ccggcgcgaa ccacatccag acggtcaaga    54240
atatcatttc catgacgtag tatactacca tactatgcag aaaatcggga atgttcatcg    54300
caattctaag aagagtactg ataaagaaca tgttgaagcc tgtgctaaag cctcaaatga    54360
tttgattaaa ttcgctaaag ggaatcatat ttacttatga aaacaatcgt aaaatcttat    54420
tttggttcac atctgtatgg tacttcaact cccgagtcag atgtggattt taaagaaatc    54480
tttgtacctc atccgcgtga tattctaatg tgtcaggcga tgaaccacac caattgtaat    54540
actaacaaca gcgcaaccaa aaatacgaaa gacgacgtcg accatgagct gttcagctta    54600
aagtatttct tcaagctcgc tgctgacggt gaaactgtcg cgttggatat gctgcatact    54660
ccaccggaat tggtagttgc atctgacctt cctgaagtat ggaaattcat tcaagacaac    54720
cgagctcgtt tctataccac tgacatgaaa gcttatctcg gatatgtccg taagcaagca    54780
ggtaagtatg gtgttaaggg ttctcgttta gctgacctgc ataaagtcct ggatgttatc    54840
agagatgttc ctgaatggaa atatgacgat cgtcctcagc agaagggtat caatgagcgt    54900
tggaaagtac aggatatcgc agagaaactt cctctcggtg aattcctcga atggaccacc    54960
ttcgttgacc acaaatcagg cgagcagaag ttttataacg ttctgggtcg taaattccag    55020
acgactatca ctatcaaaga gatgaagtat tcccttgaga agcttgatgc tgaatacggt    55080
gaacgtgctc gtaaggcaga agctaacgaa ggcgttgact ggaaagcact gagtcatgct    55140
cttcgtgcag gtctgcagct tcaggaaatc tatatgactg gtgaccttca attccctctg    55200
acccatgcta aaatggtcaa gatggtcaaa gcaggtgagt taccgttcaa agaagtacag    55260
gagcttctcg agtctgtagt agatgaagta gaaattctag ctcatactgc tgaaaagaac    55320
ggaatgccta agaaagtaga catgaagttc tgggacgatt cgtcgagaa ggtttatctt    55380
gaaaaccaca attcttacta caatgatac aatgaaggtc ttcttgaatt atggaagacc    55440
tcataaaggt agacggtggt atttggaagc agtttgcaga gagactggtc gtagagaaaa    55500
tgctaaattc tctgctcgac caactcgaaa acaaatccac caatttatgt catgggccgg    55560
agaaactctc cggttctcac tttactgggc tgaaatatga ttttactttg gagcgtagta    55620
gtgccaatcg ttgttgcaat aatttacttt atcgtgggtt ggtctgtctg taaacatcta    55680
atcaaaaacg gaactattga gaaggtagga gagtattggt tctatctcat cttttggttc    55740
cctgctttta ttgttggagc gattatcatg ttcttccgct gggcaggtaa acttccaaag    55800
```

FIG. 20EE sequence.txt

```
cgtatcgcag aaaacgctat caacaagcac gcataactga ggagccttcg ggctcctctt 55860
tttgtttcaa aagaatgcat aaagtagtat acaaactcgc gggctggtga tactatagac 55920
ctgtaccacc caaacagata cattggagaa taaaatgaaa actttagaaa tcgtcgtaaa 55980
caacattgat aaagccttta aagctgctga agcccacggt gtagaatttg aaccaatgat 56040
ggtggggagaa gcgttctcta agcttgctat catccgtggt gaaactgaca acttgattga 56100
ttttgtggat gacttctatc tcggttcaaa ggtccgtcct tactacatca atgaaatttt 56160
agaaaaataa ttaaaagta gtttactttg gagctgtaga atgatactat agctccatca 56220
aaacaaaaca gagtaacgga gaataaaatg tcaactatca ccatcaagaa agggatttac 56280
ttcggcaaag agatttcagg tacttatgag ttactcggtg agtggttccc ggatagctta 56340
agtgctgaag attctcgcca gggtgatggt aaagtctttg ttgaactgaa tggcaaaaag 56400
cgtggtgttt gggtattcaa agatgatatc acaattgacg gagtagctgc taaaattgaa 56460
gttgttgaat ccgttgatga aatgaaagag cgtatcaaga aacgctttaa cgttatggga 56520
ttaatgacta acggtttaat ccacgggaac attcgttctc tgattatctc cggagcagca 56580
ggtatcggta agacttactc tttggataaa gcattacaac atgctcatga tactaacgct 56640
attgattaca aatcagtgaa cggtaaaatc tcaggaattg gtttatactg ccgtctttgg 56700
gaatcacgtg aagcaaattc agttctgctt attgatgatg tagatgtatt ctctgatatg 56760
gacattctta accttctgaa agctgctttg gattcagggg agaaacgtaa agtatgctgg 56820
agcactgcat cttcttcctt ggaagataaa ggaattccta atgagtttga gtttgaaggt 56880
actgtggtct ttatcactaa cgttgatatt gaccgtgaat tagagcgcgg ttctaaactt 56940
gctccgcatc ttcaagcctt ggtatcacgt tcggtttatc ttgaccttgg tgttcacact 57000
aatgaagaga ttatggttcg tgttcaagat gtaataatga ctacttctat gttacagaac 57060
cgtgggttaa gaaattctga agttattgaa gttttggaat ttatgaaaga taacgtaaat 57120
cgtctgcgta acgtatctct ccgtactgct ctttatatcg gtgatttcgt tgcgactgac 57180
cgtaaaaatt ggcggacaat cgctgaagta acaatgctga ataatttaa acgggaggag 57240
aaatcctccc taactgagga aaatataatg gctactttaa tttctaatga tgtaaaacgt 57300
gttttgttta aaggcggaat gtatatcgtt gatactccta aaggtgatac ctcttcctgg 57360
actattaacg agtggattaa ttacattgat gaaaacggag cgtgggtaca atgagtttag 57420
cagctattaa agatattgaa tgttggttaa acgatattaa agtatatccg cctggtcata 57480
tctttgcagg taaacccaag ggtaaagcag agaaagcttg tgaagcaatc tgtgaaaaac 57540
tttataagtt taatttggc gataagaaaa atgtattagc tgaagtccat tcttcttatc 57600
atgaattacg tgtaatggta aacgtatttc gtgctcctcc attcattgag ctcaggaaag 57660
aatacgctaa taaagtattt gatactttcc ttgcaaatgt gcaggatgca gtaaagcatt 57720
```

FIG. 20FF sequence.txt

| | | | | | |
|---|---|---|---|---|---|
| tagacgaaat | gcataaacaa | caccaagatt | taaatgccta | ttataagcct | tggcgtaaat | 57780
| cataccaaga | gcttaaaaat | cgtattgaac | ttattcgtta | tgaggtgcta | aaatgaaaaa | 57840
| ctgggtaatg | acggaaagtg | aagcctatgc | agcgtatgtt | tcaccagacg | atcgtcgtag | 57900
| tgagttgttt | ggttattatg | gttcatattg | cgttgccgaa | gaagcagtta | aggggcagtc | 57960
| ttggtggggc | tcagatggta | cagttaatcg | taagccaacg | gaactaatta | cattcaccga | 58020
| tgaaaatggc | gaatcatgga | cttttcctaa | aagcgctgct | attagtgttc | aggaagaaac | 58080
| acctgaagct | aagcgtaaac | ggttggaaaa | aattaaagaa | tccgctttgg | ctaaattaaa | 58140
| tcctgatgaa | cgcgaggcgc | tcggattatg | agtaaagaat | ttagtactac | tcgtatggta | 58200
| gatgcttttg | gatatccgtg | caacggttat | cgtgaattta | ttcacccgga | agttgaaaat | 58260
| caatttaaag | aagtcgtaag | aaatattttg | ctcaatgcat | ttaaaactca | aggaactaac | 58320
| ccgagagatt | taggcattta | tcttgaagaa | gccatcagag | acgtacaaaa | gagcgtatcg | 58380
| gctaaacttc | attgggctga | agaaaatatt | gcttggtcaa | caagaaacg | ttctgattta | 58440
| aattggcccg | ctgatcgtga | acaaatcgtc | aattatgcta | aagggtaacc | catgtttaat | 58500
| actatagtgt | ctatacatgc | gtattacgaa | gggcagttaa | atgctgcccg | aaccaagtat | 58560
| aagcgaggaa | tggaggaatc | tgtggaatgc | cttaaagata | ttcagacatt | tgcccagaag | 58620
| acccagaacc | tcatcttgat | ggaccgtaaa | caggtctcat | tggctgaaga | gctaaaagcc | 58680
| tctaagatga | ttatagaaga | caataggaaa | caccaactga | aattgcttaa | acggcgacaa | 58740
| caccagtcgc | catggtttaa | cagtgatttc | cgatctttt | aagggccttc | gggcccttt | 58800
| gttgtttaca | tcttagaaaa | gccatgataa | gatagcttcc | gttaactaat | gaggagattg | 58860
| aaatgaaagc | acctacttgg | aacgaacttc | aagaaatgtt | caatactgaa | gaagcttttg | 58920
| gaactatttc | tgaaatggtt | gagaatttag | tagattctcc | ttcagaagat | aatcttctgt | 58980
| gtttagcaca | gttcatcatt | gaaacttaca | tagagaatca | gaaatgacag | tatacgtaga | 59040
| tgtcttgatg | aatcatggtt | ggaaaatgag | aggtcatcaa | gtaaagaact | gccacatgtt | 59100
| tagcgacaat | cttgatgagt | tgcatgctat | ggcagaagcc | atcggaatga | aacgttcttg | 59160
| gttccaggat | aagcgagttc | cacactatga | tttgcgtgat | gttcgtcgca | agcaagcagt | 59220
| tgctctagga | gcagtagaag | tatctcgtag | agacgcagtt | ctgctttgga | gaaaatttt | 59280
| cacaaagtag | tttactttcg | gcgaggctgt | tgataagatg | gtctcgtcaa | ccaaactgga | 59340
| gaataaaatg | aaaactttaa | ccgagattat | ctctgcactt | gttgaagaaa | atcgtgtagc | 59400
| ccgccaagca | caccgagcga | agttgaaaaa | acgcgccgag | gagttgaatg | ctggatgggc | 59460
| gaagacccgc | ttcggtcgtg | aatactttga | taaagtggta | gctcctactt | ggggcaaaga | 59520
| tgatcgtcct | catgctccct | ttgatggtta | tctttgggaa | aatgaattag | gtgaagttga | 59580

FIG. 20GG sequence.txt

```
agcttatcac gcaggcagtt acttgccgta tgttacagaa ttggattcac tggataagcc    59640
tgagtatacc ggtgaccacg gttggtggaa aatccgctta actcaagaag agtacaaaga    59700
acttcgggag tatggttatc ctcttgaagt acgcattcca tataaagagt ggaaattgca    59760
agatggcaca aatgttgtta tggcagaagt tagagctcat aagagcatct tagaggctat    59820
ccaggaacat tcaaaagagg tctttgataa tatattcaat gagctgaata agaataaagg    59880
ggatgcaccg gaaggacgag tgaccgtctc tggtacagta acgtcagtaa aagtttatga    59940
agactattac ggcgtacaat gtaagatgat ggttgtgctt gagaatggag ctacggttta    60000
cggctccctt ccaaaaagta ttccgtttga atacagaggc aaagtacagt ttactgctac    60060
atttgaatta gcgaaagatg ataaaactca tgctttctat aagcgtccaa gcaaagttat    60120
tatgcttgat gaatagttgt tgtataatgg gttcagggag attttgagat actctttgag    60180
cccagtccaa aatagaggaa aagataatga ataagaatga attaaagatg tttgtagaag    60240
ctgaatttaa taagttgaaa gataaaactc tcacgaagcg tgagaaacat gttaaggtgt    60300
tatcagcttt acatgattta aatccaaggg cttatgatgt agcaattgct ggtaacgtag    60360
ctcgtcgtgt gctaaatagc atggcatcac atgaagccaa ttatgctggt tttgttgtag    60420
aaaacattcg tcgttctcgc tggttaggtg caatgtcagc agagaaacag ctcaaaaagt    60480
ttgctatcgg caatgctaaa atttacggtc agcgttatag ctttgcggca ggggcgttta    60540
aaactgaaga aagacatgac cgtagcgctg ctcaaatctt ctgttctgaa tttaatgcaa    60600
acctgcgccg tattcttaat cgttcaattt gcttgcttaa aggcgatgac cgcgtgaaat    60660
accaggcatc ttctactagt tctagaaatc ctaagggtgt ttcatttatt cgtgccgaag    60720
aacttgacaa tgtaactgta cgaattcata ttaatagcca tttatccagc ggaaagtatc    60780
cggctcgggc gcttttagcg caagttcgta ctgcattaga tcatatggat gtagttaaaa    60840
aatcatgctg taaacagcag ggtgaaaact catctgttct tgaagtacat ttggacccat    60900
ttaagatttt tcctaaaaca ttgagcacca ccccagttat tgatgaagat gtagcacata    60960
tgtatctcaa tgttgttaag cctcttccgt taacaccagt aaatcatatt gaaatcgcta    61020
agaatagtat tactgccgaa atggaatcgg ttaagcgatt tattgacaca aaagaagctg    61080
aattggctaa gcatgaattg acgatgcag atttggttaa atcgcttaac gaatacaaag    61140
agcgttatga atctctcgag tatgcccgga gcttactgtg aaaaatcaat taaagaaga    61200
catggtcgtt gatgataacg accttgaaat tgagtttgag tatccacctg tacctgaatt    61260
taaaattgac tgggacgcct gtcttgaaat ggtagaccgt cgagaagctg cagctaaaca    61320
agttgtgcct tgcgaaaaat gtggtagtat tcaagtacag cttgtcgatt ggacaaccga    61380
tattctgaaa atgaaatgcc ggacttgtaa acacagattt gagagaaaat taaaatgatt    61440
actaaaacta ttactggtgc taatactaag ttttttgtcg agtatgctaa taacctcata    61500
```

FIG. 20HH sequence.txt

| | | | | | | |
|---|---|---|---|---|---|---|
| aaagacaaaa | actttgataa | catcattgca | gatatgattc | ttgacgcata | cgaaagtggc | 61560 |
| atcgaccata | tgcagcttaa | agaatatctt | cgagcgacaa | tggatttac | agttcttaac | 61620 |
| atgatgctta | gaactgatac | tgaattcaat | gaaatgattg | ctcgtcgtaa | tgaaggcaag | 61680 |
| ttcaatttga | ctgatgatga | agtattagca | tgcgctgctc | acgaagcttg | gaagaaggtg | 61740 |
| attaaatgaa | aacaactggc | gcgctttgga | aagaatttta | taacgatgaa | gccttctggg | 61800 |
| aaggctatta | tcatgatgac | actttaatac | tctttgatga | tgttgaagta | gaagaatatg | 61860 |
| aagacccttc | gcctgatgcg | gtagtaaaaa | ttgaaagcgg | atatgtttac | aaaaccgatg | 61920 |
| atgattcctt | cacttcccat | gatttgagtc | ttgaaacttt | ctttaaacgt | tggaaaaaga | 61980 |
| aacagaccac | tcgcactatg | gtagtcactg | ttgataaaga | tgacttcgcc | aaagtatttg | 62040 |
| aaactatctc | taatattcct | ggagtgaaaa | aggtaaaatg | attgacatta | aattagatac | 62100 |
| ttatgcagta | cgccagttat | tcccagaagg | tacagcagcc | cgtgctcaac | tgcaacagtc | 62160 |
| agtaatcaat | aacatcgtta | aagaaatggt | gttaaaagat | tcacagaata | agctgaagca | 62220 |
| agcagtacaa | tctgaagtta | atattgctgc | tgtgactatt | ccagatgtcc | gagcagaagt | 62280 |
| taagaagcaa | gttcagcaga | tgttccatac | tcgcggttgg | aatgatatgt | ctgctaaaga | 62340 |
| agaaatgtca | cagatgatgc | gtaacgctgc | ccaatcatgc | gctaaaaatg | ctattgatga | 62400 |
| tatggttcgt | caaactattg | atgacgctgt | taagcaagct | gaaggtcgta | ttaagatgtc | 62460 |
| tattgaaaga | gctaatctcc | gaattcaaga | aatcattgtt | aatgcaatga | ataaaaattt | 62520 |
| cgctgatcaa | attaacgctg | ccattgctgc | taaattggca | gaacacttcc | cggtaactgc | 62580 |
| taatggataa | aattgatttt | agcaaattaa | atataccacg | tatgggaatt | cctgatgata | 62640 |
| ttgccaagca | attagctagc | gttcaaccaa | tgccagataa | ttgcatcaaa | gatattttcg | 62700 |
| atgcgttaga | tggtaaaaca | ttagttataa | ctactaaggc | tgaaaatggc | tcgtaaacga | 62760 |
| tatatgaag | aagccgaacg | agtaatgcta | ctcatgtatt | cggtttatta | taatgagact | 62820 |
| ggtcaaatag | ttgatagttc | taaactcaaa | ggagctatga | ctcgtggccg | aggttttgca | 62880 |
| caagcagcta | ttgataaaga | aattatttct | cgccttggaa | ttaagtatag | ctccaagatg | 62940 |
| tatctccatc | ctggctggaa | ccaagttcaa | gctcaagtat | ttaaggaaat | agaagaagat | 63000 |
| gttcacagtt | tttggctacg | acagcaacat | ccataagtgt | gtattttgcg | ataatgcaaa | 63060 |
| gcgtctgctc | gatgttaaga | aacaagagta | tgcattcatt | aatgtaatgc | cagaaaaagg | 63120 |
| cgtatttgat | gaagtggtta | tcagtgattt | gcttcgtcgt | ttaggtcgtg | aatcacaggt | 63180 |
| tggattaact | atgcctcaga | tttttgctcc | tgacggtaca | catatcggcg | gttttgatga | 63240 |
| actccgtaaa | ttcaaattca | atgcatgatt | atcgtggaac | cctccttcgg | gagggtgata | 63300 |
| ttgtagccct | ttattatggc | tatggcggat | tagaaaccgg | tgagattaaa | caaatcaaaa | 63360 |

FIG. 20II sequence.txt

| | | | | | |
|---|---|---|---|---|---|
| atcatcgagc | aaaggtagag | gtaacttact | ctaatggagt | taaggttatg | tctaaatgga | 63420 |
| aatacggtga | gtgtatggtg | aaattatgat | tagcatgagg | aagagttatg | agttatgata | 63480 |
| ttggtgattt | aaaagctccg | tgcacggtaa | caatttcagc | agaagagttc | atccgcttgc | 63540 |
| aagctattga | agaactgttg | tgggaaattg | aatgtgcgct | tccgtctggt | ttagaaagct | 63600 |
| ggattgatga | tgaagaccta | caaaaactgc | gaggttaaaa | tgactaacgc | tgaattagta | 63660 |
| aaagaaatca | agcatatcgc | tggtgtcact | ggcgaatggg | acgacaacta | tgatttcgaa | 63720 |
| tatccgccta | atgcaccaga | cgatgatgca | gaagaaatct | ttgttttagt | agaagatgat | 63780 |
| gaatggacac | aggaccataa | gtatcaaagc | cgttctcaga | tttggtatta | cccagctcgc | 63840 |
| ggcgtccatt | tcatggtatc | agagtctcgt | tcaggttcat | atcataccga | ttggtattat | 63900 |
| aatcctcctg | aagtagatat | cgtcactcgt | cacgagaaag | tagttactcg | tactgaagtt | 63960 |
| gaatggcgta | ttgaatacga | ttctgttaat | gattccgctc | cggcaccatg | caaagcagca | 64020 |
| aaggcataaa | accttggtac | acggctcgat | gggaaactgt | cgagccagag | gaagatgcta | 64080 |
| ttcctgaaga | agattataat | acttctgaac | ctaccattaa | cgaactactt | gattatgagg | 64140 |
| acaaagtgaa | tggaacttat | tggtaagcag | tttgaagtta | tagaaaatga | tgatgaatta | 64200 |
| actgaacaat | ttccccagtt | tgttcctgga | tttaaatttc | aggttatcaa | tgcagttaat | 64260 |
| gaagatgacc | ttgaaacatg | tggcattaca | gcagtaattg | atttgctcac | aaataaaatc | 64320 |
| atcacaatta | atgacccaac | tccattcggt | gaatcttggt | tctggtgctt | ctatagtgaa | 64380 |
| gataccatgc | accaaattaa | agaaatcggc | caaggtgaag | acgttccaaa | tatttctgaa | 64440 |
| attaaactcg | accattttca | tggaaaaatt | gttccaatta | ccaaagctct | ttatgctttc | 64500 |
| gcaggtcaag | aaaattgtga | ttctgaagaa | tacgatttaa | tgcagaaagc | agctgattat | 64560 |
| atcgtcgcct | tggaaactcg | tcttggagtt | caatatgtct | aaatcatgcg | taaccaaaac | 64620 |
| tattacagta | aaaattttgg | attttgtga | tattcatcgt | attgcaaggg | aaatcttacg | 64680 |
| tagtcatgga | tataaaattg | gtgacattat | taaattcagt | aatggatatt | atgacgatga | 64740 |
| catcggtgga | atggcttggc | caaaaatgag | tattattcac | aaagaaacta | attcatatat | 64800 |
| tgagttcaat | gcggatgatt | atgaaggcat | ctatgctttc | tgtacttctt | tctgcataaa | 64860 |
| agagtctaat | cataacatct | atagtagtta | ctcgttaatt | taactataaa | tactcttatc | 64920 |
| taatcgctga | ggtaagagta | tgttattaac | cggtaagtta | tataagaag | aaaaagaaaa | 64980 |
| actatatcag | gcacagaacg | gattatgtcc | ttgctgcaaa | cgtcctttag | atgaggatat | 65040 |
| tcaaaagaat | cacctcgacc | atgaccatgc | gttagaaggt | gacaatgcag | gaaaggtcag | 65100 |
| aggcttgctc | tgtaacctgt | gtaatgcggc | agaaggccaa | atgaagcata | agttcaaccg | 65160 |
| ctctggttta | aaaggtcaag | atattgacta | cctcgaatgg | ttagagaatt | tgctggttta | 65220 |
| tctccgccag | aatcgtaaag | acagtaatat | tcacccgcaa | tatgttgccg | atatggctaa | 65280 |

FIG. 20JJ sequence.txt

| | | | | | | |
|---|---|---|---|---|---|---|
| acgcttttca | cgtcttggta | aacctgagat | gattgctgaa | atggaattgc | atgggtttac | 65340 |
| atacgaggaa | agtgatggaa | aatcacaact | tgcttcaaaa | tacaagaagc | agcttcgtaa | 65400 |
| gagtttaaaa | tgaatatcga | attagaaatc | cagggactta | ttaataaaac | caacaaggac | 65460 |
| ctcttaaacg | agaatgctaa | caaagattct | cgtgttttc | ctacccaacg | tgacctgatg | 65520 |
| gctggtatcg | tatctaaaca | tatcgccaat | caggtcattc | ctttctctgt | aatggaagca | 65580 |
| cacaaagaag | gtgttatcca | ttttcatgat | atggactaca | gtccagcttt | gcctttcacc | 65640 |
| aactgctgtt | tggtagattt | gaaaggtatg | ttgcagaatg | gctttaaact | tggtaacgct | 65700 |
| caaattgaaa | ctcctaagag | tattggagta | gctactgcta | tcatggcgca | aatcactgca | 65760 |
| caagtagcat | ctcaccaata | tggtggaact | acttttgcta | atgtcgattt | agttctggct | 65820 |
| ccttatgtag | agaagacatt | cgctaaacat | gtacgtgatg | ctcgcaaata | tcaagtagca | 65880 |
| ttagtaaaag | attatgctat | ttcaaaaaca | gaaaaagacg | tatttgatgc | tttccaggcg | 65940 |
| tatgaatatg | aagtgaatac | tttgttcagt | tcaaatggcc | aaactccatt | tgtgactatc | 66000 |
| acatttggta | tgggaacgtc | atgggaagaa | aaattaattc | aacgagctat | tcttgataat | 66060 |
| cgtattcgtg | gattaggacg | tgatggaatt | actccaatct | ttccaaagct | tgtgatgttt | 66120 |
| gtagaagaag | gcattaatct | acgcaaagaa | gacccgaact | atgatattaa | gcagcttgca | 66180 |
| ttagaatgcg | cagctaaacg | catgtatcct | gatatcatca | gtgctagaaa | taatagagca | 66240 |
| attacaggtt | cagaaactcc | tgtatctcca | atgggctgta | gaagtttcct | tggtgcttgg | 66300 |
| agagactctt | ctggcaaacc | cgttcttgac | ggccgtaata | atctaggggt | agtaacattg | 66360 |
| aacctcccta | ggatagctct | ggatgcaaat | tataaaagtt | cagatgatag | taataaactg | 66420 |
| ttcaaactac | tggatgaacg | tcttgatatt | tgtaaagaag | ctcttttaac | tagaattaaa | 66480 |
| tcccttgaag | gtgttactgc | gtcagttgct | cctattcttt | accaggaagg | tgcttttggt | 66540 |
| gtgcgtatga | aacctgatga | tgaaattctt | gagctattca | aaaatggacg | tagttcaatt | 66600 |
| tcattaggat | atattggcat | tcacgaattt | gatatgctta | cttttaaagg | aagcggtaaa | 66660 |
| ctcgtcctga | agtacatcaa | cactaagcta | aacaagtgga | cggaagaaac | cgggtatgcc | 66720 |
| tttagtttgt | attctactcc | ggctgaaagt | ctgtgctatc | gtttctgtaa | gattgaccaa | 66780 |
| gccaagtttg | gtgatgttaa | gggcgtaact | gataaaggct | ggtacactaa | tagtttccat | 66840 |
| gtgtcagtag | aagaaaacct | gtcgcctttt | gaaaagattg | accgtgaagc | accatatcat | 66900 |
| tccattgcta | aaggtggtca | tatttcttat | gttgaactgc | ctgacatgaa | gcgtaacctt | 66960 |
| gaaggtcttg | aagtggtatg | ggactatgct | atcgagaagt | tggattattt | tggtgttaat | 67020 |
| atgccagtag | ataaatgtct | ttcttgcggt | tctactcatg | agatgacacc | tactgaaaac | 67080 |
| ggattcactt | gctcaatttg | cggtgaaact | gatccaaaga | aaatgaatac | aattcgtagg | 67140 |

FIG. 20KK sequence.txt

| | | | | | | |
|---|---|---|---|---|---|---|
| acttgcggct | atcttggtaa | tccttctgag | cgtgggttca | atcttggtaa | gaacaaagaa | 67200 |
| attatgcata | gggtaaaaca | tgttagagaa | accaatgaag | caagttgatt | ggaaccaact | 67260 |
| tagcgaatgg | ggattgattt | ggaaaatcaa | caaagaggtt | ctgcacccgc | ttggaattgc | 67320 |
| tataacccgt | gaccccgaaa | gtggattatc | ggctggggct | attcaaactg | atgagccctg | 67380 |
| gaaatatgat | gcagaagtag | aagcacgtaa | tgaggtaagg | ttcaatgaat | ttcgacagaa | 67440 |
| tctacccttc | tgactttgtg | aatggccctg | gatgcagggt | cgttcttttt | gtcacagggt | 67500 |
| gtttgcataa | atgtgaaggg | tgttataata | aatctacttg | gaatgctcgt | aacggacagc | 67560 |
| tattcactat | gaatactgtt | aaagaaattg | catctcactt | aagcaaatcg | tatatccaag | 67620 |
| gccttacctt | aaccggtggt | gacccacttt | atccacagaa | ccgagaagag | atttcaaatt | 67680 |
| tagtttcttg | ggttaaagca | agatttccgg | agaaagatat | ctggatgtgg | acaggatata | 67740 |
| agtttgaaga | tatcaaagat | ttagatttgc | tacaacacat | cgatgttata | attgatggga | 67800 |
| aatatgagaa | atcactgcca | actactaaaa | actggcgcgg | ttctgacaac | caaagactct | 67860 |
| gggtaagaaa | tggttctacc | tggacacatg | attgaggaaa | tttatatgct | gacttacaaa | 67920 |
| attatgttta | ctctgaacca | catggctact | gaactgtttg | gaccggaatt | tctggctatg | 67980 |
| acagcgttca | tcttaactat | ttaaggaaaa | ttatgaaatt | tattaatgct | attcgtaaat | 68040 |
| ttatttctaa | cgttatcgct | ttggttgcat | taacggcagg | tgctttcgta | gcaattccgt | 68100 |
| ttattgttct | tattatcatc | gcagattgga | ttaatcctac | caagaaagat | gaaaagttat | 68160 |
| ctaatgaaga | atttcagaaa | cgagttaaca | ctctgactgc | taaactccaa | caggtcatga | 68220 |
| aatgatagaa | atctatggca | tccctgaaga | agtttggaga | tgccctggat | gtaaagcagt | 68280 |
| tcgtgacttg | ctcgataagc | tgcaacttcc | gtatgagttc | tataacgtaa | tcaatgaggt | 68340 |
| agacggtcaa | ccggtttatg | accgtccgtt | gattgagtca | cttgctaaac | gcatcgggtg | 68400 |
| ctatccatcg | cttgctattc | ggtatcctgt | catttttatg | gataacgtta | agcagtatga | 68460 |
| cattccaaca | ttcaaaacca | atcttattgc | tgctgggcat | gacccagata | tcatagaaga | 68520 |
| ttaaccggtt | cctttctaag | gtcatcttga | ccaccttctg | tatatttcta | taccttcat | 68580 |
| ttagaggttc | ctgtgggacc | tctctttat | tttaaatcca | tttcacaaag | ttgtttacaa | 68640 |
| gctagctgat | gagtgatact | atagctctat | caacggataa | cagcataccg | tttaactcga | 68700 |
| gaggaaaata | tgaactggtt | aaattggcaa | gaagctctag | aagctatgag | taaaggctgt | 68760 |
| aaagtaaagc | atgtgcattt | tactgatgac | gaatacttct | tgatgaagaa | caaagtcatc | 68820 |
| tgtgacgaaa | atggatatga | tatgactcgc | tggtacaagg | gtgagtcttg | gcaaaacgaa | 68880 |
| cattggtaca | tcgcatgaaa | acttttgctg | taggtgatat | cgtccgtacc | agaatttggg | 68940 |
| atgggcttca | atttgaagta | gttgtctacg | tcggttcaga | tggagttcta | cttcaccgaa | 69000 |
| ttaacaatct | gattaagtgg | caccttgaac | gcttcgtgaa | atatcatgaa | ttcaatagct | 69060 |

FIG. 20LL sequence.txt

| | | | | | | |
|---|---|---|---|---|---|---|
| accactgtac | tgtagctccg | gttgctagta | aagaatacta | cgatatgctc | gaagagttaa | 69120 |
| aatctctcaa | agattgattt | gctacaggag | atttgattta | aaatctcctc | tgtcaagaca | 69180 |
| atcactactg | aggaaaataa | catgtcccaa | gcaattaaaa | acgcactgaa | cgctttcgca | 69240 |
| tactataaag | tttctgcaat | gctggaagaa | ggacgttgtg | taactccgtc | tttgcttgat | 69300 |
| cagtgggaag | ttgagcttca | cggtacgatg | aaagaagaag | gacaaaaaat | tggtaaagca | 69360 |
| cgcatccgtg | aattagtggt | tgcttatctt | ctgtctgaat | ttggtattaa | agcctttggt | 69420 |
| gtagaaccca | tcgtagttgg | tgttggtgaa | atttctgaat | ccgctattcg | caaaatgaaa | 69480 |
| aaccaacgca | agaaaggttt | tcgtgatgtg | aaagcggtta | aggcggcaaa | atgaaactaa | 69540 |
| atcaaaacgg | atgtccttct | cgcgtacgat | tttgcattct | agaattacga | tctaacattg | 69600 |
| tcgttattga | cgaatacacc | acgattgtag | gtgtacaaca | atatcttgat | agacgttttg | 69660 |
| atacacgaac | ccatatgaaa | tatggatttc | caggcaaatg | taaattttat | ccaatgagtg | 69720 |
| ctgatcatca | atctgtagta | aatgatgaat | acaagtgggc | agaaggtctt | actttaaaag | 69780 |
| aacttgagga | atatcttgat | gcgtaaagtt | attctataca | cagaaatttt | taccagccgt | 69840 |
| tgggtgtttg | acagtgtcag | aatttcaaac | gcttcaaaag | aagatgttcg | taacgctcag | 69900 |
| cgattagcat | acgatgaagc | tggaaaatca | ccagcatttg | taaaaattga | gtatatcatt | 69960 |
| actgattctg | ctttaattca | taatgtatca | gaatcagtat | taaagaagtt | ctgcgttgat | 70020 |
| cgcatcaata | aaggaacttc | aatggaatat | tttctattag | cgagagaact | gaaatggtag | 70080 |
| aagaacaaat | tgcagaaatc | ggtttactcg | gatggttcgt | gtctaaaact | aaagacggca | 70140 |
| gaaacttgat | tgaaactcca | gaaggagaat | tcattattga | agaagatttt | gacgcgtttt | 70200 |
| ggatttatga | acgctctgga | gagaatgaat | acacatccgt | ggatgctttc | tctaaatttg | 70260 |
| aagatgctat | tgactcggtg | aaagcatggc | taaagtaaac | caaattatga | ttgtagtaga | 70320 |
| aggcattggc | ggatttacta | tagattctta | tatgggtgtt | tggtttgaca | atgaagaggg | 70380 |
| catgtattgg | gaaacgcatg | cctctatgtt | aaatgaaact | cattatgaaa | gtttatactc | 70440 |
| ttcattcatg | gaaatgatgc | atgaagtaga | tgaatctgat | tggtttgaac | ttagtttggt | 70500 |
| tgagttcaaa | cgtatcatgg | aacagctgtt | ccaatgctat | cgtattatga | agggtgaact | 70560 |
| atgaaaattc | aattgactct | tacacatgaa | aatattaaag | gtgtgttctg | tcttgaaaat | 70620 |
| agccaaataa | cttttgcaca | agatggaacg | tactggtatg | ctgaatcaga | tgatatcgct | 70680 |
| ggttatggaa | tggaacgtgt | atttgaagat | tttgaagccg | tcattgatgt | tccattagat | 70740 |
| ttcacgtata | acgatttta | tcgtatcatg | atgaaattaa | ttgcatgcgc | tgaattgatt | 70800 |
| aagtaatgct | ttaatcctct | cgcttcccaa | atttgttata | atagatatta | ttaattgaag | 70860 |
| cgaagaggca | atatgagtaa | ttatgtaaat | aacaaggagt | tgtataaatc | aatctgttca | 70920 |

FIG. 20MM

```
                              sequence.txt
tggaaagaga agtgtcggga gtctgaagct gctggcggtc ctcgagtagt aaaacagaac   70980
gatacgatcg gccttgctat tatgctgatc gcagaaggtc tgagtaagcg tttcaacttt   71040
tcaggataca cccaatcctg gaagcaagaa atgatttcag acgggattga agccgcaatt   71100
aaaggcttaa tcaacttcga tgaaactaag tatgataacc cgcatgcgta tataacccaa   71160
gcttgtttca atgcattcgt tcagcgtatc aaaaaagaac gcaaagaaat ggcaaagaaa   71220
tacagctatt ttgtccacaa cgtgtatgat tcacgggacg atgatatggt tgcgttagca   71280
gatgaaacct ttattcagga catctacgat aaaatgacgc agtatgaatc caccgcttat   71340
aaggcgccag ggtctgctaa aaagagcgaa cctacaagtg atggacctaa tctggaattt   71400
ttatatgagg ctgaagatta acctcgacgg gtttttagaa gatgtgcaag acctagacgc   71460
tatcccttat ttgctaaaga tgtatttaag ggaggtgctt gatcttgata ttcacattga   71520
cccgaaaaat ccacatgacg ctgatttcag atcagattct gctataattg aacatagtta   71580
taattggact gatactgaat tcacatttga aataaattac catccaaagg aataacatga   71640
acaatattac ccaggaagag cgcgacgaac tgcagcagaa actaatggaa gcggcagaag   71700
aacaagctat tgctcgagcc aacaaaattg ttcgtaaaaa ccgtcgtgaa attgagcgat   71760
taaaagctca tgctggagac gcggtattag acaacaattt ccctgcttac aagtatgcta   71820
ttgaaaaact gcgtactatt ttaaaacaac ctttaccga tgagattatt ctcacctgtt   71880
ggaataccte tcgtaaatct gtttgggaca ttctaaatgc tggtacaagt aaaatttaaa   71940
cgtgttcgta aagacgcagg atttactttg aacactgcta ctggaacaat ggcagtaaaa   72000
gtagcagata atcaatatcg cgtgttaggc tctaccgaag gatgtaagct aatagataag   72060
aactctcttg tctgggttga caccttccaa gttaaacggt ggtatgaatg gtaaatgaag   72120
agaattggga tgtatgacga atttgatggg ttctaatcct gggcatgatt ggcctgaagg   72180
aaattacgcg tgtcggtgta gtaattgttc agaacgttat acaggaccaa agcgtagtta   72240
cttctgctat aaatgcgata ccgccaggag agaagcaccc gctcccgatt atgaagcaat   72300
tcgtaatgct aagatagata tgctcaagcg ctttgaagaa gctaagcgta tatgcgaagc   72360
agcgggttat gttgtgtata agaaatttta aagggcttcg gccctttgc tttattacgg   72420
gaatggtaaa atatccaaaa ttaacaacaa aggtcaatat atgaagatta atattttaat   72480
ggctcgcgga cttgagggat gcggcgtaac caagttcagt ctcgagcatc gtgagtggtt   72540
agtaaaacat ggccatgaag taaatatcat ttacgctaaa gataaagcgt ttactcgtaa   72600
tagagcacat agctataaag atgtaactat tcctgtgtct ctggcagatg actacgataa   72660
gactttatct ctgcttaatg catgtgacat tcttatcatt aactcagtac ctgctgtcaa   72720
cgctccagaa gcagcgattg ataactataa gaagctcata gagaacatta aacctgaagt   72780
tcgggtagtc gtatatcaac atgaccatag agcattgtca cttcgtagaa atgctggtct   72840
```

FIG. 20NN sequence.txt

```
tgaagaaacc gttaagcgtg ctgatgtact gtttagtcat agctcaaacg gcgattttaa      72900
taccgtgcta atggaagaat attttccaag cggcgggttg agtttctttg atgattctga      72960
ctcagctcct ccggtttata actttcaacc tgctatgaac atcaaagcaa ttcgtgataa      73020
gtattggaaa gacttctctg ccattgattt tgatatccat cgttggattg gtcgtactac      73080
tacgtggaaa ggctatttct tgatgtttga ctttcatgaa agtcatctgc gtcccgcagg      73140
caaaacgact atcttggaag ggttagaacg cagtcctgcg tttattaaca tcaaagaacg      73200
ctatgaaatt gactattgcc gtcattatca tcaggttaaa actgggccag gtctgaatcc      73260
tcaagttctt gaccgatatg ttaactctga aatgcttgag cgtatgtctc aatctggatt      73320
tggctatcag ctgtcacgtc ttccggataa attccttgag cgttcgttgg aatatactca      73380
tttggaatta ggtgcatgtg gtactattcc tgtgttccat aaagccaccg gtgatgcttt      73440
gaaattccga gttgatggaa agccattgac ttctcatgat tctggcattc tgtggttgaa      73500
tgatgaaaat aaaaatgaag tctttgaacg aatgaaacat ctgtcatctg accagaagct      73560
ctatgataaa gagcgaaata aagcatttga attcctggta gaacaccaag attctgagca      73620
ttgctttaaa gaacaatttg agttaatgac aaaataagta atgggccttc gggcccttt       73680
tgctattcat ggaataatat aaaattaaac tctactagag aggttatatg aaaattattc      73740
actcaggcga ttggcattta ggtgtccgcg cagatgaccc gtgggtacag gatgtacaac      73800
gacacggaat taagcagcat attgattatg ccaaaaagca tggaattaaa actatcattc      73860
aatacggtga tattttgat gttcgtaaag ctatcactca taagacaatg gaatttgctc       73920
gtgaaattgc agagtctctt gagaagaag gaattaactt aattacgatc gtcggaaatc       73980
atgacatgca ctacaagaat acgttgacgc ctaatgcatc aaccgaagtt cttggtaagt      74040
ataagcatat tactgttatt gaaaagcccg tgactatgga ttttgatggg actttgattg      74100
acttgtgtcc atggatgtgt gaagagaaca catcagaaat catgaagcat atcaaagaat      74160
cgtctgctga atactgcatt ggtcattggg agcttaatgg cttttatttt tataaaggaa      74220
tgaaatctca tgggctggaa ccagatttcc tcaaaaagta caaacaagta tggtctgggc      74280
acttccacac catatcaagc gcagcaaacg ttaagtacat cggaacgcct tggacgctta      74340
cagcgggtga cgagaacgac ccacgcggct tctgggttca agacactgaa ttatcaacct      74400
ttgatttcgt ccctaatgaa atcacttggc acagaaaact gatttatcct gtcacagggc      74460
aagttgattt tgaagagttc agaaatcttg cagtgcgaat tattatcact gcggtcgatg      74520
aagaccttcc taagtttgaa tcagaacttg aaaaggtagt acatgaatta agaactgttt      74580
ctaaagttga caactcggtt gagtctgaag atggcgaaga agtagaagtt aaaagcttat      74640
tggatttaat ggaagaatat atccaagcac ttgaagacct gtccgcagat gatatcaaag      74700
```

FIG. 2000

```
                                    sequence.txt
ccttaaaggt  tatgtctaaa  cagttataca  ttgaggcaca  aaatcagtga  agacttttaa      74760
actaaatcgt  gtcaagtata  agaatataat  gtcagttggc  caagcggcca  ttgacattca      74820
acttgataaa  tgtcaaaaga  ccttaatcac  aggtaagaat  ggtggtggca  aaagtactat      74880
gcttgaagct  attacttttg  ccttatttgg  taaaccattc  cgtgatatta  agaaaggtca      74940
attaattaac  tcattcaata  agaaggactc  tgtagtagaa  ctgtggatgg  agtatgacgg      75000
tcatagtttc  tacattaaac  gtggacaaaa  accgaatgtc  tttgagattt  tacgagatgg      75060
caataagctt  gatgaagccg  caagttcaaa  ggattttcaa  tcctactttg  aaagcctcat      75120
cggcatgtca  tacacatcgt  ttaagcagat  tgtcgtatta  ggaacggcag  gatatactcc      75180
gttcatgggg  ttatcaactg  ctaatagacg  aaagctcgtt  gaagatttgc  ttgaagtgtc      75240
tcttttagct  gatatggaca  aactgaacaa  gacacagata  agagaaatca  atcagcaaat      75300
ccaggttaat  gatgttcagc  gtgaagcatt  gactaatgaa  attaaaactc  accatgagta      75360
tgcagaaaag  cagaagaaac  tttctggtga  taacgttgct  cgcctgcagg  cgatgtatga      75420
tgaacaggtc  aatgaagccc  gtgggtataa  agcagaatta  gaaactcttc  agagagaact      75480
gcttgagtta  gtaattggag  acgacccagc  agagtcaatc  caagaagttc  aaggtaaaac      75540
atttaaaatt  cggtctaaaa  ttgaatcata  ttcaaaggtt  cttgggctgt  atgataaagg      75600
tggtcattgc  ccaacgtgct  tgcaggattt  gcattctaat  gacactctaa  tcactaagat      75660
taatcatcat  gttgaagaat  gtaataccat  tcttggtgag  ttaaagacgc  gccagagtga      75720
actggatgaa  ctagctcgcg  agtataacac  ggtccgggct  cgcgctagag  atatcaaaac      75780
ccaaatgggt  agtttaaagc  aaatgactat  cactgctgtg  gaaaaggcac  gtcgtattaa      75840
agcagctatt  gataaagcat  ctcaggagtt  tattgataac  tcagacaaga  ttaaactgct      75900
acaagaagaa  ttagataaaa  ttatcctcgt  caaaactaat  ttggttatgg  aaaaatatcg      75960
tcgtggtatt  ttaactgaaa  tgctgaaaga  ctccggtatt  aaaggagcta  tcatcaagaa      76020
gtacatcccg  atgttcaata  agcaaattaa  cagctaccta  aaaattatgg  aagctgatta      76080
ttcgttcaca  ctgaacgaag  agttctctga  aacgattaaa  tcacgtggac  gagaagagtt      76140
tagttatgcc  tcgtttagtc  agggtgaaaa  agccagaatt  gatatagcat  tactattcac      76200
gtggcgtgat  attgctgaaa  aagtttctgg  tgttaaaata  aactgtctgt  tccttgatga      76260
agtttatgat  tcggctaccg  acgcagaagg  tgttaaggca  ataactgcta  ttcttaataa      76320
gatggtagat  gccaatgtgt  ttattatttc  tcaccgtgac  cacgacccgc  aggcatatgg      76380
ccaacacctt  caaatgaaga  aggtcggacg  attcacggtg  atggaatgaa  tgagtttact      76440
acgggccaac  atctgttggc  ctttcctgaa  ttaaagcgtt  atgtgttagt  taatttattt      76500
tctgatgaac  gtcatcttgt  aactgaagaa  atgttacgag  atgcttttac  gggaaatgaa      76560
tataatagag  tcatgtccaa  caggaatccc  ggttggatgg  ttgaagatta  ctacgattaa      76620
```

FIG. 20PP sequence.txt

```
ggtaaatata atgattaatt ttgttgatgt gaaagatatc caggttaaaa acgtacgtgc    76680
agattccaac ccgaataacc aaaatcgtat tcgtaaatct tgggttctgg ctctaactga    76740
agaaactaaa caggctatca aagataagat taaagattct gaagctcgct ttgctttcta    76800
taaatctatc gatgatgaag tcgcagaaaa atggattgaa ctgatgcgta agcattacaa    76860
tgaatcaatc aaggctggtg ctaaaattgt tactgatcgt cacggtggcg aacgtctaga    76920
aaatgattac tgtgtagatg ctgatgagca actcgttgcg gcaggtcaga ttgttgcaga    76980
agaattaact gctacattcg cagcttgata taattatcct gaacttaatt aaaaggtatt    77040
gaaatgaaat tctctaaaga aactctgaac attctgaaaa atttctccac catcaactct    77100
ggtatcatgc tgaaacctgg caattttatc atgactcgtg ctgttaatgg tacgacttat    77160
gctgaagcaa caatttctga taccatcgat actgatgtag caatttatga cctgaacagt    77220
ttcctgagca ttctgtcttt ggttggtgat gatgcagata ttatcatgca ggaagatggt    77280
aatctggcaa ttaaagatgc tcgctcaact atcttctggc cagcagctga cccgagcaca    77340
atcgtgttcc cgactaaacc aatcccattc ccggtggcaa acgtaattat cgattttaaa    77400
ggtgaagacc tgcaacagct gatgcgagta tctcgtggca tgcagattga cacaattgct    77460
atcaccaatg ttgatggtaa aattgttctg cgtggttata caaagtaga agatgctgca    77520
ctgacccgtc cgaagtattc tctgacactc ggtgattatg aaggtgaggg taacttcaac    77580
tttatcatca acatgagcaa tatgaagatg actatcggcg attataaact gatgctgtgg    77640
gcaaaaatga atggctccaa gaaacagact gccgcaaaat ttgaaggtgc atcagcctct    77700
tatgtagtag caatggaagc agacagtacc tttgattttg agtaataact tcggggcttc    77760
ggccccatct ttaatctgaa tgaggaaata taatgaaat tgacagtaaa cgaagcagac    77820
ttcatgtggg aacagaaata tcgtccaggt actatttctg agtgtgtact tcctgctgaa    77880
gataaagaaa ttttttcagc tttagtagct aaaggaaaaa ttcctcattt aattctccat    77940
agcacttctc ctggtactgg taagactaca gtagctaaag cattatgtaa tgacattaat    78000
gctgaaatga tgttcgtgaa tggttctgac tgtaagattg atttcgttcg tggaccgtta    78060
actgcatttg caagttctgc ttctattgca ggcaagcaga aaattatcgt tattgatgaa    78120
tttgaccgtg caggtcttgc agaatctcaa cgacatctgc gttcattcat ggaagcgtat    78180
agcacaaact gtactattat cattactgca aacaatcttg atggtatcat taaacctctt    78240
cagtctcgtt gccgtgtaat taattttggt aaaccatctc catctgatgt taagccaatg    78300
caaatcgaga tgctcaagcg ttgtctcgca atttgtgaaa acgaaggcgt ggtagttgaa    78360
gataagaaag ttgtagctgc tttggtcaaa aagaattttc cagaattccg taagaccatt    78420
aacatgcttg accattattc ttctaagggt gtgattgatg caggtatctt gtctatcgtt    78480
```

FIG. 20QQ sequence.txt

```
ctgaatgacc gtggttcaat tgaagatgtc atcgaagcta ttaaaactaa gaacatcaaa    78540
gaactccgtg ctcttgcccc gaaatatgca gcagactata cttggttcgt agataaactt    78600
tcttcggaac tgtatacaat ggttactggc ccaagcatta tccgaatgta tgaaatcatt    78660
ggtgaaaata accagtatca tggcatagca gcttcgattg aattacactt ggtttatatg    78720
cttattcaac ttgttgtaga gatgcagtgg aaatgatgag tttatttgaa gatgatgatc    78780
agtataacga gcaccaaata gcgtggttag gtaaagactg gacgaaagtc caggaattat    78840
ctgattcata taaagaaaaa gcagaaaatc aattcttcac aattattggg tctattaacg    78900
aaaagcaaga gcatttgaat atctcgacga tggattattc aaaattcatg gttgaaaacg    78960
ctctttctca acaccctgac tgtatgcctt cggtttatgt tatgaacctt gttggtcaag    79020
ggttatctga ccaagcacac tataactata tgatggcctc tgttcctaga ggtcgtcggt    79080
atggtaaatg ggctaagtta acagaaaaca tccaggatgc attgattctt caagttataa    79140
tgacatatta caaggtcaat gcgattgacg ctaggatgta tagagagacc ctggaagcta    79200
aaaacaagct taaacctgct ctcaagaaaa tgaaaggtct tgtgactgat gaattggtca    79260
agacaatcac gaaaaacgtg aaagaacaga aaaatcttaa gaaaacagca ttggaatggt    79320
aaagatgatt gaaattacac tgaaacagcc tgaagacttc ctgaaagtta agaaactct    79380
gacccgtatg ggaattgcta ataacaaaga taaggtacta tatcaaagct gccacattct    79440
tcagaaacaa ggtcgttact atattgttca ttttaaagaa atgttgaagc ttgatggccg    79500
ccctgttact attgatttgg aagatgaaat tcgtcgagac tcaatcgcac aactacttgc    79560
tgactggggt ctactgagta ttaatcgtgg tcaaactctt gctcagatgc agaataactt    79620
ccgggtcatt acgttcaagc agaaacatga atggaccttt aaatctaaat atacgattgg    79680
tgcataatga cagaccaaga atttttacgac aaacttaaaa atatcaggat tactgctcct    79740
gaatggttca gtcttcctat tgatgaacaa attcagtatc aggtaaaaga aactttagaa    79800
aaatatcctg gccgaaaagt tatgatgtgc ttcacatatg ataagaatcg agttcctcga    79860
attcagaagc aagtaattga agtttaagaa aaggccttcg ggcctttttac tttataaaac    79920
tcggagtata attatcccac ctaaagacta ataactcggt ctataaacaa aggaaaccca    79980
tgaaagaatt ttatattagc gttgaatctc taggcaatga cattgtagaa cgttatatcg    80040
attctactgg tgaggaacgc atgcgtcgtg ttccgtattc tcctgtgatg tttagtcatt    80100
gcatggaaga aacaaagtac aaagatatct acggcaagta ttgcaagaaa aatacattcc    80160
caactatgaa agatgcccgc gattggatgc gtcgtatgga agatatggga atggaagcaa    80220
tgggtatgga tgatttcaaa ctcgcgtata tcagtgatac ttacggttca gaaatcgtct    80280
ataataaaaa attcatccga attgcaaact gtgacattga ggttactgca tctcaattcc    80340
cagacccaat gaaagcagaa tatgaaattg acgctatcac tcattatgat tcggttgatg    80400
```

FIG. 20RR sequence.txt

| | | | | | |
|---|---|---|---|---|---|
| acaagttcta | cgtatttgat | ttactgcatt | ctctttatgg | ttctgtttcc | gagtgggaca | 80460 |
| agaaacttgc | tgctcgttta | gattctgaag | gcggtgatga | agttccacaa | catattcttg | 80520 |
| accgcgtagt | atatatgccg | ttcaattcag | aaaagaaat | gatgcttgag | tacatcaatc | 80580 |
| tttgggaaca | gaaatgccca | gcaatcttta | ctggatggaa | cattgaagga | tttgatattc | 80640 |
| cgtacatcat | gaatcgtgtg | aaacagattc | ttggtgagcg | tgcgatgaaa | cggttctctc | 80700 |
| ctctgaataa | agtttcatct | aagattatca | caaacatgta | tggtgataaa | gaaatttatt | 80760 |
| ctatcatggg | tgtgactatt | cttgattaca | tggatttgta | taagaaattt | agtttcacga | 80820 |
| accaaccgac | gtataagttg | gatttcattg | cttattatga | aaccaagaaa | ggtaaattag | 80880 |
| catatgacgg | tccgatcaat | aaaattgcgtg | aaactaacca | ccaacggtat | atttcgtata | 80940 |
| acatcatcga | cgttgaatca | gtacaagcga | ttgatgctgt | tcgtggattt | attgacctgg | 81000 |
| ctatctcgat | gtcttattat | gcgaagatgc | catatcaagg | tgtaatgagt | ccaattaaaa | 81060 |
| catgggacgc | aatcatcttt | aacagtctga | aagaacaaga | caaggttatt | ccgcaaagtc | 81120 |
| gttctcatgt | taaacagtca | tatcctggtg | cgtatgttaa | ggaaccagtt | cctgctgcat | 81180 |
| atcgctatat | catgtcgttt | gacttgacat | ctctgtatcc | gtcaatcatc | cgacaagtta | 81240 |
| atatttcacc | agaaaccatc | gttggacagt | ttaaacttca | tccgttgggt | gagtacatta | 81300 |
| acaagactgc | tcctcgtccg | tctgatgaat | attcatgttc | accaaatggt | tggatgtatc | 81360 |
| gtaaagatgt | agatggtgtc | attccagttg | aaatcgcgaa | ggtatttat | cagcgtaaag | 81420 |
| agtggaaaaa | taaaatgatg | ggtgccaaac | gaaatcaaga | actgattaaa | aaggttctga | 81480 |
| atgataagaa | gtttggaact | atcgataaat | tcgcagaagt | taatgtctat | gaagatttct | 81540 |
| ctgatgatat | gaaagcagaa | ctgctgacat | ataccgaaga | gtgtcttgac | aaactgatgt | 81600 |
| ttgaatgtaa | acacgctgaa | atcttgggta | cactaacca | gttaaaccgt | aagattctga | 81660 |
| tcaactcact | ttatggtgca | ttgggtaaca | tttacttccg | ttattatgat | ttgcgcaacg | 81720 |
| catcagcaat | cacattgttt | ggtcaaatgg | caattcaatg | gattgaacgt | aaagttaatg | 81780 |
| aatacctcaa | caaggtatgt | ggcaccgaag | gacattcgtt | tgtagtagct | ggtgatactg | 81840 |
| actcaattta | cgtttgtgtt | gataaggtta | tcgagaaggt | aggtcttgag | cgtttcaaag | 81900 |
| aaactaacga | tttggtcgaa | ttcctgaacc | aattcggcaa | gaagaaaatg | gaaccatgga | 81960 |
| ttgaccaatc | atatcgtgag | atgtgtgaat | acatgaacaa | caaagaacat | ttaatgttca | 82020 |
| tggaccgtga | agctatttct | tgtcctccgt | tggggtcaaa | cggcattggc | ggattctgga | 82080 |
| aagcgaagaa | acgatatgct | ctgaacgtgt | atgatatgga | aggtactcga | tatgcagaac | 82140 |
| ctcatctgaa | aatcatgggt | atggaaactc | agcaaagttc | tacgccaact | gctgttcaga | 82200 |
| atgcattgga | agaatctatt | cggcgtatgc | tgcaggaagg | tgaagaatct | ttacagcaat | 82260 |

FIG. 20SS sequence.txt

```
attataagca gtttgagtct gaatatcgtg aacttgatta taaagtaatc gccgaagtta    82320
agactgcaaa caacatcggt aagtatgatg acggtgcagg atatccagat aaaggtacac    82380
catatcacgt taaaggtgct ttggcatata accgagcaac cgcaggattt gaaggtataa    82440
caccaatcat ggaaggtgag aaagtgatgg tcatcccgct gcgtgaaggt aacccgtacg    82500
gtgagaaatg catggcatgg ccatcgggca ctgagctgcc acaagaaatc cgacaggaag    82560
ttctagtgtg gcttgaccac agtgttctgt tccaaaaatc gttcgttaaa cctctgacgg    82620
gtatgtctga agcggcaggg ttagactatg aagagaaatc gtctcttctt gacatgttcg    82680
attttttaaaa aagttgttta ctttaccaca aggatgtggt actatagctc tcgaaataac    82740
atactgagga gattacaatg aaatcgttac ttgctgttat tgttgctctc acgctgactg    82800
gttgtcaaat gccacaaggt gatatcgtcc cggcttcttc tgttgggcag gtgcgagcaa    82860
ttggcggtac tgtaggatac tatcgtgcta gcaaccaggt ctctgctgaa tcgctcgcgg    82920
ttgagcgtcg gttggcgaaa gaaaaagcta atcctaatcg tcagctgtct gcgatggaac    82980
ttgacatgat tgagcagaat aagcatgaac tggaagaaat taagcgtctg cgtaaaactc    83040
aaaaagaacg tacgtgcact gctcaagcgg cagcagtgaa tgaccagatt cgtttaactg    83100
attttgctaa cggcggattg agttataatg agcataaaca acgtatggag cagttaaaat    83160
ctctccaaaa tcacatctac aacaaatgca tgtctaactg aggagattaa catggaagca    83220
gtatttggtt taatcattct tttcttcatc tatttttgc cgacctttgt agcttgcagt    83280
cgtaagcata aatcacgggg tggaatcttt atcacaaatc tagtattcgg ttggtccatt    83340
atcggttggt taattgcgct gatttggtct gcttctaacg cacagcagaa tacaattatt    83400
atccagcaag ttaaataaga ggtctcatga ttgtaactcc aatgacagta caagatatcc    83460
gtcaagaatt cgctgatgct ttgctcaaca aagaatttgt gattgataag acgggtgtga    83520
agactattga aatcgtaggt gcatcattta ttgcagatga aaacctaatt tttggcgcag    83580
ttaatgatgg atacattgct cgtgaacttg agtggtataa atctcaaagt ttattcgtta    83640
aagatattcc gggtgaaacc ccagctattt ggaaagcaat tgcatccaaa cacggcgaga    83700
ttaattctaa ctatggctgg gcagtttggt caacacaaaa ctattcacag tttgctaact    83760
gtgcgaaaga acttatcaat aatcctgatt ctcgccgcgg aattatgatt tatacacgac    83820
ctcaaatgca gtatgatttt gagcgcgatg gcatgagtga tttcatgtgt actaacaatg    83880
ttcagtatct gattcgtgat aatcgtgtgc atgctgtggt aaacatgcgt tcgaatgatg    83940
tcgtctttgg atatcgtaat gactatgcat ggcagctcta tgttttggaa cagttaacca    84000
aacttctgaa tgcatcaggt aaaaattatt cagttggtga cattatttgg aacgtcgggt    84060
ctttgcacgt atattctcga catttctatc tcgtagataa ttatgctcac acgggtgaaa    84120
ctcacatcgc aaagaaagac tataaaggtg aatggaaatg attcagtttg taattccaag    84180
```

FIG. 20TT

```
sequence.txt
ttataagcgc gccggggcag ttactgccct gactatgttt cctgaaggtt atgttccaca    84240
tcttgtagta cgtgaatcag aaaaagaagc atacgaaact tggcacggtc atgctgctaa    84300
aatcgttact gtccccgatg atgtcgatgg aattgcggga actcgccgtc tgattactga    84360
aatgtatgca gggcaacgaa tttggatgct tgatgatgat acgaccattc atctgactga    84420
aattcgtgaa cgcgacgatc gccgggttcc acttggtgtc ggcgaggcaa tgagtcaaga    84480
ggtatttgat gatatggtca aatacgtcga gactgccatg gattgtggtt attatcacgg    84540
tcatgctcgc ttaccgattt tcaaaatcac atcaagctgg ggtcattatc gtgagaatag    84600
ctttggggttc accaatactt tctatgattt gactaaactt accgcagaag acattggcta    84660
cggaattatt gaccttaacg aagatgctta tgcttttcta aaattaatta acatgggtca    84720
tcctcatctg gctctgttta agtacctcgt taaatctggt aaggtgcagt cacctggtgg    84780
ttgttctaca cagcgtgata ctgctcgcca gaatagagcc cttgaacagc tgcatgctgc    84840
tttcccaaat caagcccgtt ggaaatctaa agacggtgaa agacgtggtt tattcggtga    84900
tgacgaacca ctaaaatcaa ttcgtatgtg tattaacact cgagtgaaat cccaggcctt    84960
ccatgaattt ggtaaggtag aaccatatct gtgagggcga agccctcca aggacctctt    85020
atgaacatct atgataaatc tgatgtagct ggtaacatat tcaaggctga agaattcaga    85080
tgcttcgtat gtaaatctga tgagtttgtt catgaaggaa ctactggctc agatggaatg    85140
cattgctggt ggcacggcat gtgtgttgga tgtaaaatac actacgaaat agatatggaa    85200
acagtggttt ataacaccaa gaagaaatgg aacttctgtt aatagcttca agaacaaagt    85260
aatataatta ctctatcctt taacctgtga gaaaaatata atggagactt atggaatata    85320
atgaatgtct gacttaaaat ctcgcctgat taaagcatcc acttctaaaa tgacagcaga    85380
actgactaaa tcaaaattct ttaacgagaa agatgtagtt agaaccaaaa ttccgatgct    85440
taatatcgca atcagtggag cgttggatgg tggtatgcag tccgggttga ctatcttcgc    85500
aggtccatct aaacacttca aatctaacat gtctctgaca atggttagtg cttatcttaa    85560
taagtatcct gatgcggtct gcttgttcta tgattcagaa tttggtatca ctccagctta    85620
tctgaaatct atgggtgttg accctgaccg tgtaattcat acaccggttc agtcggttga    85680
acaattaaaa atcgatatgg ttaaccagct tgaagctatt gagcgtggtg aaaaagtcat    85740
cgtgtttatc gactctattg gtaacatggc gtctaaaaag gaaaccgaag atgctttgaa    85800
cgagaaatct gttgcagata tgactcgtgc gaaaagtctg aagtcgctct tccgtatcgt    85860
aactccttac ttctctatta agaacattcc ttgtgtagcg gttaaccaca caatcgagac    85920
tatcgagatg ttcagtaaga cggtaatgac aggtggtaca ggtcctatgt attctgcgga    85980
tactgtattc atcatcggta aacgtcaaat taaagatggt tctgagcttg agggatatca    86040
```

FIG. 20UU sequence.txt

```
gtttgtcctg aacgctgaga aatcgcgtac tgtcaaagag aaaagtaagt tcttcatcga    86100
tgttaaattc gatggtggta tcgatccata tagtggtctg cttgatatgg ctctagatat    86160
cgggtttgtg gttaaaccga aaaatggatg gtatgcacga gaattcctgg atgttgaaac    86220
cggtgagatg attcgtgaag aaaaatcctg gcgggcaaaa gatacgagca gtacggaatt    86280
ttggggtcct ctgtttaagc atgagccatt ccgtgacgct atcaaagccc ggtatcagtt    86340
gggtgctatt gattcaaacg ctgcggttga tgaagcggta gcagaaatga ttaactcaaa    86400
agtttcaact aaggttgatg gtgttaaact tcctgagagt ggttcagtat cagctgctga    86460
agttgaagat gaattagaga acttcatgaa tgaagactga gtttgattta gaatctgaac    86520
tcgagaaatt tgaacaagaa tctccctcgg aagagggaga cttcgagcgt caagaacgag    86580
tgttcaagaa aagccatgaa ataatccaag aagctatgaa gactgttatc caagaaattg    86640
tgataaaatt aaatggtcaa tcacacttgg tttatgttca taaattaaat atttctcctt    86700
cggggggaagt aactattgag ttcagtacac catctgaagc tcataaggat gaactttatc    86760
ctcatgtgga agcttgtgtt aaacaacaaa tccagagtgc attaaagacc aagaaaaaat    86820
cattatggaa aatctttaa gaggttaaag tggtagaaac aatcttagct aatctgattt    86880
acaaccaggc tttctttacg aaggtttggc catatatgga caaagagtac ttcgagcaag    86940
gacctgctca gacggtgttt aacataatta agaaacacgt taatgaatac acagcaattc    87000
cttcaaagac tgcgttatgt gtagcactgg ataattcgtc tataactgaa acggaacatg    87060
aaggtgcaaa gaaacttatt gataagttat ctgatgctcc tgaagatttg aattggttag    87120
ttaaggaaac agagaagtac gttcaagaaa aggctatgta caacgcaacg tctcgaatta    87180
ttgaaattca gactaatgcc cagcttgagc caaataaacg cgataagcgt cttcctgata    87240
ttggggctat tcctgatatc atgcgtgaag cgttatcagt atcgtttgat agctatattg    87300
gccatgattg gatggaagat tatgaagctc gttggttatc ataccagaat aaagctcgta    87360
aagttccgtt taaacttagc attctgaaca aaattactaa aggtggtgcc gagactggta    87420
cactgaacgt attgatggct ggcgtcaacg ttggtaaatc attaggatta tgttcattgg    87480
ctgcagacta tcttcagatg gggcataacg tcctttatat ttccatggaa atggccgaag    87540
aagtttgcgc taaacgtatt gatgctaact tgcttgatgt atcacttgat gatattgacg    87600
atggatgtgt atcatacgct gaatataaag gcaagatgga aaaatggcgt agttctagta    87660
ctcttggtcg tttaatcatt aaacagtatc cgactggtgg cgctaacgct aatacattcc    87720
gagctcttct gaatgagttg aaactcaaga agaactttaa accgactgtt atcatcattg    87780
actatcttgg tatttgtgct tcttccgta ttcgtcaata tactgaaaac agttacacgt    87840
tagttaaagc tattgcagaa gaacttcgtg cattggctgt agaatctgaa actgttcttt    87900
ggaccgcagc tcaggtaggt cgttcagcgt gggatgcttc tgatatggac atgagtgata    87960
```

FIG. 20VV sequence.txt

| | | | | | | |
|---|---|---|---|---|---|---|
| ttgcagaatc | tgcgggtcta | cctgctacgg | cagactttat | gctggctgtg | attgaaaccc | 88020 |
| ctgaacttgc | tcagatgaag | cagcaattaa | ttaagcagat | taaatcacgt | tacggtgata | 88080 |
| agaacatcaa | caataagttc | tctatgggtg | tacataaggc | taatcagcgt | tgggtagaaa | 88140 |
| ttgagcagca | aaacgaccca | actaagccta | atccaagcaa | taccgtccga | gaaggtgccg | 88200 |
| gtgcacagaa | ccgtgtagcc | gaatctaatc | gtcaagaacg | agtatcacgt | tctaagcttg | 88260 |
| atgctctagc | agaagagttg | aaattctagg | gtaaatttta | tgattttgt | gtttagcgta | 88320 |
| attcgcgacc | aatcaggtcg | ctcctttgtg | gtgacggcgt | ctgatagcgt | ccatcgtgga | 88380 |
| gtcatagctt | acaacaaagc | agatttatct | tcatatgact | atggtgaagt | taaggcatat | 88440 |
| aatgacgaag | gtatctgggt | taactctgcg | atataccttc | caaccaagaa | tttgacatcc | 88500 |
| gacgaagtcc | tcgaaaaatt | attcaaaaga | tagtttactt | ttaagtttgg | ccatgttatt | 88560 |
| atggccttac | tgaaacaaac | tgaggaaaac | aaaatgaaaa | agattgtact | tgctttaatc | 88620 |
| ttcgcagtat | caagttgctc | tgctgttccc | gctctggcga | actatgacaa | agacctctgc | 88680 |
| gaatggtcaa | tgactgcaga | tgaaaaagat | gttgctgagc | agattcgtgc | tgatgtaggt | 88740 |
| catatcattg | ataacactga | cccaagcaag | atgaaagaag | ttcaggcaga | aatctccaat | 88800 |
| gatggcgcag | caattaaact | gaactatgct | ctgtactgcg | atgctaattt | tgataacttc | 88860 |
| acaattgcaa | gctggattct | cggatgatta | catacgtatt | agtaatggct | ataatgactg | 88920 |
| gtgccggcgg | tgtttctact | gaaaagttat | cattcacagg | aatgaacgag | tcttcgctgg | 88980 |
| ctcagaaatg | tgaagatgcg | ggaaaacaat | ttactggcat | caaagccgat | tccgggttcg | 89040 |
| gttcaccatc | agtctacact | acgtacaagt | gtattcgtat | tgatggtgga | aataataaat | 89100 |
| agtttggagg | ctctatgaaa | acatttaaag | agtttgttaa | acttaatgag | gaaatggttg | 89160 |
| ctggcgatgc | cggcggtaat | cctcagaaca | ttgcatcagg | cactacttcg | ggcgcagtag | 89220 |
| taaataaagg | cccagaaact | ctcccaaaga | aaaagcgaga | taaatcaaaa | cctgaaacgt | 89280 |
| gatacaatgg | ccttattagt | ttaaggccag | aggaatataa | tatgtcatgg | gttgataacg | 89340 |
| aattcgctat | ccgcgcaata | tctcacctac | ctaagtttag | acacgttact | acatcttcaa | 89400 |
| catttaagtt | aaactgccgt | tgcccaattt | gtggtgactc | acagaaagat | atcaataaag | 89460 |
| cccgattctg | gattttgat | gcgggtcaag | gattacgctg | ccattgcttc | aactgtgagt | 89520 |
| ataacaagtg | gctatcacaa | tatcttaaag | ataatgaacc | cgatctctat | cgagagtatc | 89580 |
| ttcttgagaa | aagaaaggag | caggtctttg | ataagccaaa | gaccgtagaa | ccgtctgaga | 89640 |
| aaattaatgc | aaaactcccc | gtaatagaaa | aacttaattt | ctgtgagcga | ttagatagac | 89700 |
| ttcctaagga | acatccgata | gttaaatacg | tgactgccag | atgtattcca | agcacttctt | 89760 |
| ggaaaaggtt | atggtttact | aaccaatggc | cttctcttgt | taactccgtt | aatccaggaa | 89820 |

FIG. 20WW sequence.txt

```
cctataagaa tgagacgaac gaaccacgtt tggttattcc tatcttcaac aagaaaggag   89880
agattgagtc gtttcaagga cgagcactac gaaaaaatgc tccacaaaaa tacatcacaa   89940
tcaaagccca tgaacacgcg accaaaattt atggtctcga cactattgat gagtcaaaac   90000
tcgtattcgt catggaagga ccaatagatt cgttgttcat tgataacgct attgcaatca   90060
ctggcgggtc tttagattta gctcaagttc catgccatga taaccgagcg tggattatgg   90120
accatgaacc tcgtcatccc gatacaatta agcgtatgaa acgtttagta gatgctggtg   90180
aaaaggtagt tttctgggat aagtcgcctt ggaaaagcaa agatataaat gatatgatta   90240
tgaaagaggg ggcaactgct tctgaaataa cggattatat taatcaaaat atatcgcaag   90300
gtttaatggc taaattacgt cttgacaaat atgcgaagat atagggccca aagcccctta   90360
aattaaagca atcctccagt cataataaac gacacaactt tttctaacgg cattggagga   90420
agaactagcc cgtgtgtgct agctaatgga actaccacat aattccatgc agctaaagca   90480
gcagtggcga ttccgacgta aagatatctt ccaaatcctc ctttgtcttt acattctcgt   90540
ttcacttcag acatgaatcc tcctgctatt tatgttaagt gatataatat ttatctaatt   90600
taattgaaag gaaaaataat atgccacatt tcaacgaatg tagtcaactg atcgctggtg   90660
cagataaagc tgaagctcga tacgcaggta tcgtacgcaa agttggtggt gaccctctgc   90720
aagtaatgct tgatatgcaa aaatctcttc aggttcgtct tgcaaatgac aagcctggta   90780
ctaacatgca tcctgatgaa ttggcccaag ccggtgatat cgtgcagtgg ctgcgtaacc   90840
aaaaagatta cattgatgac gaattccgcg aattgctgac gtctcttggc ggtatgagta   90900
atggtgaaaa ggcagctagt gctgtgtgga aaccatggaa atctgaccac gtcaaaatgc   90960
aggaaactta tatcaaagac ctgtctgata agaccagct tgaaatcaaa tttgaaatga   91020
ttgatatcct gcactttgtt ctgaatatgt ttatggcgct tggtctggat tctgaagaaa   91080
tctttaagct gtattatctg aaaaacgccg agaactttgc tcgccaagac agtggttact   91140
gatggccaaa agaatatcta agcgtcgttt aaaaattatc agaaaacaaa aagaaagggc   91200
cttagtattg gcccttcgag aagaaatcac tcgagaaatt gataaagaaa tattaaaggc   91260
gcttacagca gctatataaa tactcctgta aactaaatag gagattaaaa tggcttacgt   91320
aaacatcaaa acttttgacc atacaactgc tgatggtgaa gttaaaggta cagaagtatc   91380
tgtagctttt aaggtgtatt ctgattcaca tcgcattgct aacgcacagt atcagatttt   91440
cccatctgaa aaagctgctt attcaacagt agttgatgat gctgcaactt gggcaaccac   91500
caacgctaaa atgtttgaag ctgttccatc tgatgcagaa gtataaaaat taaggactcc   91560
tccgggagtc cttttatgct atactgggaa tagtatatta ttcctactaa ctgaggagaa   91620
gaaaatgata tgttatacta agccctggta tcaatcgtca ttaaagaagt ctcatttga   91680
ttgttggtac agaggtgtaa gagctgcagc gttattactc aaagctgcgc cggctttaat   91740
```

FIG. 20XX sequence.txt

| | | | | | | |
|---|---|---|---|---|---|---|
| taaagcaaat | gataagtggt | ttgaagacaa | caacatgact | gaaggagctc | tttgtggcaa | 91800 |
| acgcaaaaat | ctataacgca | aaaatctata | aagtaagctt | acaacgcgca | gttcaatcaa | 91860 |
| gaagtgatgc | aaatggagtt | ttgcgtctag | accaagatag | aatttttact | gttgctctat | 91920 |
| acagtacgtt | cgacaaagat | ttcaaagacc | tagttaataa | attcgaagcg | tttggttggt | 91980 |
| gtccttctga | agattatggc | attattaaga | ctgcccatgt | ctttgacgta | gatacagttc | 92040 |
| caggaagtcc | tgttgctata | ctacgtgctc | tccacttgaa | aggatacact | aatgtatgtc | 92100 |
| atgaaactag | cttatatgaa | tacgaaaatg | acataatttc | aagaggcaaa | aagattatca | 92160 |
| ttgatagcac | agattctcta | atagaattta | ctaagttagt | ttggttgtat | atgggcgcag | 92220 |
| attttatcaa | actgactcca | agcccgctgt | tgcaaaaagc | ggctgatgga | tataacagca | 92280 |
| gtagttgtct | gtatcgcaat | aatgagtggt | tcatgtgatg | gatttgtttg | aaatgatgga | 92340 |
| agagcctcag | gaagaggttc | aagttcatcc | agtgatttct | aaggacatca | aagacgaata | 92400 |
| ccgtataatt | atacagaagt | atggtattaa | agccccagaa | gctcttctag | atgaactagc | 92460 |
| ttcaatctgg | tctgacccgc | cgccctggtc | tccgtgggca | aaataatttc | acaaagtagt | 92520 |
| ttactcttcc | aaaagccatg | ataagatacc | tctcgtaacc | aaaaaatgga | gaatatcatg | 92580 |
| gctatttcat | taaacccatc | tatttcagta | aaattatcaa | aggttattcc | tatcgaaaaa | 92640 |
| cccattcgtt | ccattgatgt | tcttaacttc | gcgcgagaaa | gcaaaggatt | acctttatat | 92700 |
| gatttaagcg | tgtgggaagc | attagccaat | cgttttgact | gcaaagaaca | gtcaattcta | 92760 |
| tggcaatgca | tgaacaataa | gattggcgaa | gaatttcata | agaaacttga | ctctatcgtt | 92820 |
| agacgtcatc | aaattgataa | tagtgacatt | ctctatagag | gtctatcatg | ccgcgagtct | 92880 |
| aaagcctttt | atgacgccct | tattaaagga | gagaaatttg | gctttggaaa | ggttgcgtca | 92940 |
| ttcacaacag | atgaaacgat | cgccagagag | tttgcaggca | aatggcatta | ctcgaccttt | 93000 |
| gtagtcattg | aagtcaataa | ttgccatcaa | tcatttgatt | atcataccaa | catgaaatcg | 93060 |
| cttttaatta | ctgcaccaga | ttctgaattc | atgcgtccaa | atgatgtgat | tgataacatt | 93120 |
| gctcagcgca | gaagcgctga | catcgagatg | attgataaag | aacaagaaag | gatgctaccg | 93180 |
| atgggaacta | agttcaaagt | ggtgggtcat | aacaaagttg | aaaaatctgg | tttacttatg | 93240 |
| gactacttta | gtgttactat | agcttagtca | actagtgatt | atctagaact | agggacctag | 93300 |
| acccattata | ccgtccgtaa | gacgaaagca | tttttgagga | aaacatgatg | aaatttactg | 93360 |
| ctgaaaccgc | taagatttat | actcgcctga | ttacaacttt | aggttctgcc | cagcgtcgga | 93420 |
| acaaggagtt | caatcttacc | cctgagtatc | tgtttaacat | catgcaacag | actcattgcg | 93480 |
| catactcggg | tgaaaagttt | ggaaccgtca | aaggaaacca | tcctgacagc | atgacgcttg | 93540 |
| aacgctggaa | taatgacttg | ggatatgtaa | tggggaatgt | tattcctgtc | aagcaaaagt | 93600 |

FIG. 20YY sequence.txt

```
ataatacttt gcgtggaaat aatacgattg aaggccttga gcgaaaagcg aatgaaatcg    93660
cagcacgcat agttcgttct tcagattctg ttaagccaac aagtgataaa gaagcttctc    93720
gtttggaaaa gattcgtgag tatgaaaaaa ctataacatc aattaaaact aacttacaca    93780
atcgtgaaaa tcatctttct caatttgtgc aaaaagaaaa gaatggaact gcaacctcgg    93840
ctgatttaga acttattaat gcattgagaa ctcgtatcag cggtggtaag tctgaattag    93900
ctaaagttga gcgtaagtta tctgctattt tagcgtcagt tccgaatcgt ccgtcagatg    93960
ctgaaatccg tgtacaatca atacggttaa ttgttagctc acttcgtcgg ttagaagaat    94020
gctcaatgtt agataagtta aaattgaaaa aaggtcttcc attgactgct tccttcttcc    94080
aacttttgag aggtaaaatg taatgcaaca ctatggatat gtagtagcgt ataaggataa    94140
agacggattt gaccatccag tcacaactga tatgtatgat ggagaacgat gtgtagtctt    94200
cactaatgaa gaatcagcca ataaagcacg gattcgtaca atgtcggttt aacagacaa    94260
attggcaaag gggaatttta ctgggaaaag caaaaccaaa gggatgcttt ggtggaaaac    94320
aactgagcta gtgtatgaac cacttagcga tgttgagcgt gaaaaactca aagcaaaaat    94380
taaaaatcta catgtagtga gggtaaaagt ggcatgatta cgtttgacca attaaaagaa    94440
agtcaaaaag cgatttttaa taaagtcatt gaaatggtca acaaggagc taaaggtcaa    94500
catattacga ttaatggacc cgccggtaca ggtaaaacaa ctttaaccaa atttatcatt    94560
gacgctttga tttctcaggg tatctctgga attgcattgg cagcacctac gcatggggcc    94620
aaaaaggttt tatctaagct cagcggaatg caagccagta ctattcatag tcttctgaaa    94680
attaacccga cgacatatga agaaaacgtt ctgtttgagc aaaagaaagt tccggatatg    94740
gcatctattc gagttcttat ctgtgatgaa gcttcaatgt atgaccgtaa gctgtttaag    94800
attttgatgg caactattcc tgcctggtgt attgtcattg ccattggtga taaggctcaa    94860
atacgtccgg tagaacctgg aagtaatgaa cctgcactga gtccattctt cactcataaa    94920
gatttcttac aacttcattt gaccgaggtg atgcggagta atgctccaat cattgaagtt    94980
gctactgaaa tcagaaacgg tgggtggatt cgtgactgtg tagttgatgg tcatggcgtc    95040
cgtggttta ctaaaggaac cgcccttaaa gattttatgc taaattattt taatttagtt    95100
aaaacaccag aagatttatt tgaaaacaga atgcttgcat tcactaataa atctgtggat    95160
aaattgaacg aaataatcag acgcagaatc tatgaaactg aacgaccatt cgtagtaggt    95220
gagattgttg ttatgcaaga acctcttacc aaggaactta aatttgaagg gaagaaattc    95280
agcgaaattc ttttcaataa tggtcagttt gttcgcatat tagatgcaat tgaaaccacg    95340
tcatttttag gtgccagagg tgttccaggt gaatatctgg ttcgtcattg ggtattagat    95400
attgaaacct atggcgacga tgaagagtac gctagagaga aaatctgtgt catctcatcc    95460
gaagaagaaa tgaataagtt tcaattcttc ttggcaaaaa cagcggatac atataagaac    95520
```

FIG. 20ZZ sequence.txt

| | | | | | | |
|---|---|---|---|---|---|---|
| tggaataaag | gcggtaaagc | accttggtct | gaattctggg | atgctaagcg | caagtttcat | 95580 |
| aaagtgaaag | cattaccagc | ttcgactttc | cataaggccc | agggcatctc | aattgacaga | 95640 |
| agcttcattt | atactccatg | cattcacatg | gcagatgctt | ctctcgcgca | acagttatta | 95700 |
| tatgttggta | ctactcgtgg | tcgctatgat | gtattctatg | tgtgaggtaa | tatgtttgaa | 95760 |
| ttgaaattag | aagaccttca | aacaatgatt | gttggcttac | aagaatctaa | gtttgaagca | 95820 |
| ccagataatg | ttaagcgtgc | tattaacatt | aaaattgata | tagttctgaa | tgagcttcgt | 95880 |
| gatatagcag | ataatgctaa | tgctattact | tggttcacag | gatatgaccc | aaaggtgtat | 95940 |
| ctgagcgaat | atattggttg | ccagttacgc | gaaattaaat | ttatgctaga | ggctcaaaat | 96000 |
| ggctaaagac | tttattattg | attttgaaac | attcggaaat | gtgtcaagct | cttctgtgat | 96060 |
| tgaccttgct | ctaatcacat | tgattctga | ccccgaagtt | ttggaaagct | tcgatgaatt | 96120 |
| ggttaaacgt | ggtcatcgta | ttaagtttga | ccttaaatcc | cagaaaggtc | atcggttgtt | 96180 |
| tggtaagtct | actcttgagt | ggtggaagaa | acaatcagct | gaggcccgtg | ctaacctggc | 96240 |
| ctcaacgcca | gacgatttat | cagtaattgc | tggaattaaa | gaagctcagc | aatatctgat | 96300 |
| tgataatgga | attcacccat | gggattcctt | tggctggtgt | cgtggacaga | gctttgactt | 96360 |
| tccaattttt | gttgattgtc | ttcgcgatgt | tcaacgagcc | caaggaattt | ccgaagaaga | 96420 |
| aattgataca | tttaaagaag | aaccatgtaa | gttctggaat | cagcgtgata | ttcgtaccgc | 96480 |
| gattgaatca | ctgcttctta | cccgcgggct | gacaactacc | cctcttccaa | agggtactct | 96540 |
| caacgggttt | attgcgcatg | atagtatcca | tgactgtgct | aaagatattc | taatgcttaa | 96600 |
| atatgctcaa | cgctatgctc | taggcctaag | cgaagcacca | agtccagaag | ataccgatcc | 96660 |
| actgagttta | cctaagggc | gtggctaatg | gaagagtttg | agttcgatga | aaactttgaa | 96720 |
| gagtggttca | accgggaaat | cctcccgaaa | atctctccaa | cgatggttct | ggtggccaag | 96780 |
| gctttgatgg | ctaaaggctg | ggacgcaggg | tatatgttcg | gcgtcgatgt | tgggtgtgaa | 96840 |
| atttctcacc | gatagctatt | tactttatga | aagagccgtt | atataatggc | tctacattaa | 96900 |
| caaactgaga | gaaacatgat | gaaaaatttg | gttgtaggcg | aaaacgttaa | agtaattggt | 96960 |
| ggtaagcata | tcggtaaaga | aggcgtaatt | gttggaatct | ttaaccgttc | taacaaaatg | 97020 |
| tcttcatatt | tgcttcaatt | ggaaaatgaa | gacaaagccg | tgtattcgct | gcaaaaattc | 97080 |
| gtagttgctc | tagaatcgcg | cgatttgctt | gattctatgt | ttaacgaaag | ctatctgcgc | 97140 |
| aagtgggtac | atgtgaattc | acttgacaat | gttattaccc | aatcggtgag | ttctactaat | 97200 |
| tcagccacta | atctgtcgct | gcataaaaat | gttcttgtca | ctgatgagtg | ggaagaagac | 97260 |
| ggtaaaaccc | tagtaaacgt | agtgtttcaa | ggcaactatg | cagttctgcc | taaagccgat | 97320 |
| gtagagccga | cagaatcgca | acgtcaaggt | ttagtataaa | aagttgttta | ctttgccaca | 97380 |

FIG. 20AAA sequence.txt

```
aggatgtggt actattatct tatcaactac tgaggagaat aacatgaaaa ctgaaaacac    97440
cgtaaaaatt actgccgaag cttttgaaga cattctgttc aacccggact taatcgtcgt    97500
tcagaaagag aaaaccttcg gtaaagaaga gcattggacc tggttgtatg tattcgcgaa    97560
ccatggtgat atcgtcccag ttcgtacctt tgctcgtgta attacagttg atggcccaga    97620
atacatggag attgtgtaat gaattttaaa gaaggcgtac agtacaaatt cgtcaatgat    97680
gaagcggaag aagaattttc ttcacgttat gaggttaatg aagactttgt gtatgaactc    97740
tatgaaaatg gcgggagttt tactgttact aaagttgacc gccaaaataa tagagtatca    97800
ggaattatgt gggctaatgg cacagaatgt gatgaagtcg gcggtgaaga ccttgtaatt    97860
tttgatagcg aattcaaata ctttactgaa gttggaactt ccgcgaatgt aattccaacc    97920
gatttggtta tgaatcttc tattcataac cgtggtcaag caatcgctgc tattgcagca    97980
ctgcagagtg catatcaatg ttaaatttag ctcctatttt tgaagcatca aaactgtctt    98040
atcctattcc taaccgtagc attgggaatg tcatgctgca actttcttca gaaactggag    98100
aaatgtgtga ttggattaat cgtccatggc ggcagaaaga agagtttgaa ggtgagtgcg    98160
cagatgttat taactgtgta gtagatgcac tttggctgca tttcagaaat cgtcataaaa    98220
atgataccca tgtatcagat gatgaaatct ccatgatggt tactcgtgca ctaaatgagc    98280
aaatcatggt caaaacacaa aaatggaagg atgctgttaa tgccaatgta tgattacaag    98340
tgtgaagtct gtggaaaaaa gatagaaatt atgcgtaaaa tttcccatcg tgactatact    98400
gttaactgct ttaaccctaa gtgtgaaggt caaatgaagc gggtggtttc tgctccggca    98460
gttcactacg atggattaaa gagtggtgat tattgatggg aactaaagca cgcattacca    98520
tgaaacccgg agaaatccgg gttattaaag taggtaatat aacttatagg gttaaattga    98580
aatgaaaaag attttaatta cagcgcttgc cttcatgatg attggatgca ctgacgctga    98640
taacgcaact cgagtattag aaaatgcagg attcactgaa gttgatatca ctggatacaa    98700
atttttctca tgttcagaag atgattttca gcataccggg ttcaaagcgg tcggtcctac    98760
cggaaagacg gttaaaggta cagtgtgttc tgggattttc ttgaagaata gtactattcg    98820
ttttgaataa aaaggacctt cgggtccttt agttgtttac acgaatagtc ttctgcggta    98880
ttatagactt ataaactact ggagaataaa acatgaaata catcatctta actttaatcg    98940
cattagttat ctcaattgga gttctggttt ccttagcaga ttctacggaa tcttctaatg    99000
aagttcagaa aagctcaatt ggtattggtg tgaatggaca agtggtgtt aagatttcag    99060
ataatctttg tgttaatcct tctactggtg ctgctgaagt atgctttaa aatgtattga    99120
tataatgcct ccactaactg aggaaatgta atgattaaga acgaaattaa aattctgagt    99180
gaccgagaac atatcattaa gcgcagcgga atgtacatcg gtagttctgc gtgtgaggca    99240
catgaccgtt ttcttttgg taaattccaa tcagtaaagt atgttcctgg tattattaag    99300
```

FIG. 20BBB sequence.txt

| | | | | | |
|---|---|---|---|---|---|
| cttattgatg | aaatcattga | taactctgtt | gatgaagcaa | ttcgtacaaa | ttttaaacat | 99360 |
| gccaataaaa | tttccgttga | tatcaaggga | aataagatta | tcgtaactga | taatggtcgt | 99420 |
| ggtcttccac | aggctccggt | agtaactcct | gaaggagaaa | ctattccagg | cccagtcgcc | 99480 |
| gcatggactc | gtcctcgtgc | gggtggtaac | tttggcgatg | atgctgagcg | taaaactggt | 99540 |
| ggtatgaacg | gtgtcggttc | tgcattaact | aacatctttt | cagtatcttt | cactggtgca | 99600 |
| acatgtgatg | gtaaaaatga | aatcattgtc | cgttgttcta | atggctcaga | aaatatctcc | 99660 |
| tgggaagaac | atccagcaaa | agacaaagaa | ttcatcaaag | ataagactgg | tactgtagta | 99720 |
| tcattcattc | cagatttcag | tcactttgaa | agcacaggat | tgactgatgt | tgaccaatca | 99780 |
| atcattcacg | atcgtctgat | gacattagca | gtagtttatc | ctgatattga | attcaaattc | 99840 |
| atgggtaaac | gtgttcaagg | taagtttaaa | gcttacgccc | agatgtatga | tgaaaatgcg | 99900 |
| gtagtgcagg | attctgatac | ttgtgctatt | gctattggtc | gctcagatga | tgggttccgc | 99960 |
| cagctttcat | atgttaataa | cattcacacc | aaaaatggtg | gtactcacgt | tgacctagtt | 100020 |
| cttgatgaac | tgagcaatga | acttattcca | gcattaaaac | gcaagtacaa | actagaagtt | 100080 |
| aataaagcac | gaattaaaga | gtgtctgact | gtcattatgt | ttattcgtga | catgtctaac | 100140 |
| atgcgatttg | attctcagac | taaagagcgt | ttgacttctc | cttggggcga | aattcgtagt | 100200 |
| catattgata | ttgattacaa | gaaacttgct | aacgctatta | tgaaatctga | agatattcat | 100260 |
| atgccgatta | ttgaggcgat | gttagctcgt | aaacttgctg | cagagaaagc | tgcagaaact | 100320 |
| aaagccgcca | agaaagcgca | gaaagctaaa | gtagctaagc | acatcaaagc | caacaaatat | 100380 |
| ggtaaagatg | ctgacaccac | tttattcttg | accgaaggtg | attctgcgat | tggttatcta | 100440 |
| ctcacaactc | gcgaccgtga | acttcatggt | ggatatcctc | tacgtggtaa | gttcatgaat | 100500 |
| acatggggaa | tgtctgctgc | agatgctatg | aagaacaagg | aagtatttga | catttgtgca | 100560 |
| atcaccggtt | tgacgattgg | tgagcctgct | gaaaatacta | actaccgaaa | tattgctatc | 100620 |
| atgaccgatg | cggatgttga | tggtgttggt | tcaatttttcc | caagtctttt | agcgtttttc | 100680 |
| agtaattggc | ctgaactgtt | tgaacaaggt | agaatccgct | tgtgaaaaac | tccggttatt | 100740 |
| attctcacca | aaggtaaaga | acaacgttgg | ttctattctc | ttggcgaata | tgaagaccat | 100800 |
| aaagatgatt | tcaaaggttg | gaaacttcgt | tatattaaag | gtcttggttc | tcttgaagaa | 100860 |
| gatgaatatg | aacgtgttat | tcaagacccg | gtttatgatg | tagtatctct | tcctgaaaac | 100920 |
| tggaaagaac | tgtttgaatt | aattatgggt | aatgatgctg | ctccacgtaa | gacctggatg | 100980 |
| agtgaataaa | tagtacgggt | aatattgccc | tgctatagaa | ggaattacta | tgcaacgtta | 101040 |
| ttggattact | ttggtctcag | gcgattacgg | atacatgttt | gccgaaaaga | aacctctccc | 101100 |
| tggtacttgg | gttactatct | gggtggaaaa | ctcggatggt | tctaaacatg | aggtgtatgg | 101160 |

FIG. 20CCC sequence.txt

| | | | | | |
|---|---|---|---|---|---|
| ccgcgttagc | agagtgcatt | aatcccgagg | ggcttcggcc | cctcttttct | gaggaaatta | 101220 |
| ttatgaagtc | aactatcatt | tcaatactcc | gcactgaggc | actaaaatac | tcagtcgacc | 101280 |
| cctccaatga | ataccaagaa | cttttaatca | aacggttatt | aaattctata | gctgaccgtt | 101340 |
| tggaaagtaa | ccagagtgtc | cctattaatc | acagcctttt | tgctatgaaa | gtgatacgct | 101400 |
| ttttacgtcc | tgatattaaa | attgctgaca | tggtcaaagt | gattaaatcg | tcaggagcag | 101460 |
| taaaatgcta | aagaaaagtt | atgttccaaa | taaagaatta | tttgatgatg | ctatatatcg | 101520 |
| agagtatcgt | atcatccaac | gtttctttga | tatccaagca | gcagaggaat | tcaaagaccg | 101580 |
| ctttaaacaa | atcagtgata | aaattttac | aactaacacc | gctactgctg | aagagctcct | 101640 |
| tgaagtagca | gaaatcatta | aacgacacaa | ttgataggaa | taaaatgaaa | attaaatgtg | 101700 |
| atgatgaagt | aattattggt | tcttctgacg | ctgaggattc | aacgtttacc | attaaagctt | 101760 |
| caggtaaagc | ttttgacatc | ttgtcaaaca | aactctataa | gtataaagtt | cgtgcggttg | 101820 |
| ttcgtgaact | ttctactaac | tgtgatgatg | ctcataaact | gaacggtaat | gaaaatcgtc | 101880 |
| cattttacat | caaagcacca | actcgtcttg | acccgcgctt | tgtaattcgt | gattatggtc | 101940 |
| caggtcttaa | tcataatgac | atgatgacga | tgtacaaaac | gttctttgaa | tctacaaaga | 102000 |
| ataatagtaa | tgatttcatc | ggtgctcttg | gtcttggttc | taaatcgcct | ttaagctata | 102060 |
| caagtacatt | taacgtagta | tcatatcata | atggtaaagc | caccggttat | actgtcatga | 102120 |
| aaaaccgcgg | tgaacctact | attcgtccga | tgtttgtcga | tgatatgaaa | gaagacgaag | 102180 |
| aaactggtct | tgaaattaca | gttccggtta | aagtagaaga | tattgatacc | tggcactatg | 102240 |
| aaatcgcata | tattttgcgt | acatttggtg | ctgtacctcc | aaaggtagat | tctcttcgcc | 102300 |
| gtgaaattga | atatttccca | gtagataaaa | ctgattggtt | tagcgttaat | agctcttacg | 102360 |
| aaagttatgg | cctgtatgca | gtttatggaa | aaatcgtata | tcctatcagc | ggtgtagatg | 102420 |
| ttaaggcaga | ttggctgctt | aatcgctatg | gtaaggttta | tgttcatttc | ccactgggtg | 102480 |
| aattggatat | cactccatct | cgtgaagagc | tttctcttga | cgaagaaaca | attgctaata | 102540 |
| tccagaagcg | tgtgaatgct | cttgaagaag | aggtaattac | cgcagatatt | aaagcgtttg | 102600 |
| aagcgtatga | atctgaccgt | gaattcctgc | gtgagttcaa | taagctgagt | tctaaggaac | 102660 |
| gctctattct | tcagagccgc | ggtattacca | ttgggaaccg | cgatattaaa | caagtagttg | 102720 |
| cgaagtataa | tcttgataaa | attcgttcat | actatgtaga | taacgaagta | tcagtttatg | 102780 |
| tttcatgcga | tgaacctgct | cgtcgtaaag | tgtcaagcag | ttcttggcat | cgtcataacc | 102840 |
| aagtaaacat | ttctgatatt | tgcggggttg | atagaactaa | agcgtttgtt | cttattgacg | 102900 |
| ataaagcggg | taagcgtatt | gctacggttc | gtgctctgtg | taaatctggg | ttagttccaa | 102960 |
| tctgggcaca | cattactgta | atcaaagaca | atgaagatga | attacatgtc | attgatgagc | 103020 |
| tgaagaaaat | catggatact | gatgaagttg | tagtattccg | tgtgtctgaa | cttgaagccc | 103080 |

FIG. 20DDD sequence.txt

```
agagaaaagc tcttcctgat tacgacactg gtccaaaaga gaaacgtcct aaatcaccaa    103140
atgtttctct gcattggatt gataaagacg ggtactggga agaagaccgt cagactttat    103200
tatcatctga aattactgag cttgaaggtt atgctatcgg tcgcaatcgt gatgaaatcc    103260
acactttccc agataatgtt tggtggtgga atatgagcat cacagatatg cgttctttgg    103320
cagaagcatg tggaattaag aaattctatg caattcgtcc gagtgctatg aaagccgcgg    103380
ccaaagctga tggattgctt tcatttgacc ggtttattat tgaccaatac atcaagtgta    103440
ttgataaggt agactacgac cagtacatgc catcaaatgc tactggaaac cgtatctgtg    103500
gaaatattgc gcattacgat aaattgaatt tcttgtcgag taagtttact gcgtctggaa    103560
tgaaaaatcc gttcctgaca aaactaaaca aaatcgctaa agtttgtcgt acaagtaaaa    103620
tcaaagatga aaatgatgaa aacaatgatt tagctttatg taataaaatt tataataaac    103680
tgtctagtga tgctgagaca atcttctata aaagattga acagtttaaa gatgattatc    103740
ctgtcatcgc aagtgtcttg gatacttggc ggactgacag caaactcgtc gatgatatcg    103800
taaaaatcat ggagctcctt gatggagctt ctactcaaaa ttctgaaaat aaaggtgaat    103860
aaatggctgt tacctgtctg tctgaaatcc aaaaagatgc aatcgttaaa aacttcaaaa    103920
acggtctgta cactaagaaa gagctcgccg agaattatgg tgtttcccgt gacactattc    103980
ggcgtgtttt taaagagcgt gaagctcgag ctgccgcggc agctgttcct gctaaagtag    104040
aagctccagt tgagcgtgaa tttaaatggg cagcaagttc caaattcatt tcaattactg    104100
aaggccgtac tacttataac gctgatagcc aacatcccgg gtttaaatct gcactgcaga    104160
aacttgtaga tggtgatatc gctggtgcta ttgaccacat taacctggaa caaggcatca    104220
agaaattcgt tcagggtaac gtccgaattg aagatggtac tttgttctat aaagatatcg    104280
agctgaaatc tggtctgact gagcgtatcg ttcgagctat ggaagatggc gaagacttta    104340
aacgttatct gcctttcctg gaaaacctga tgctgaaccc gtctcgtcgt gcagtttatc    104400
gtctgtttga tttcctgaac gcaaacgata tcgacatcac tgatgatggc cacttcattg    104460
gttggaaagt agttcgttcc aattacttcg attgtgcttc aaacacattt gataactctc    104520
cgggtaaaac tgttacgatg ccgcgtaacc aggtagatga agatgatcag cgtacttgtt    104580
ccacaggtct gcatgtctgc tctaaatctt acatcggtca cttcggtagt ggttccgatc    104640
gtatcgtttc agttaaagtt catccgcgtg atgtagtatc tatcccggtt gattacaacg    104700
atgctaaaat gcgtacatgt ggttatgtag tacttgaaga tgtaaccgat cgttggggtt    104760
cagaacttcg ctaattataa ggagccttcg ggctcctctt ttattatggg tgaaacatga    104820
ttaatccatt taacgtatct cattctaaag ttgttaatct tcgtggtact catcatgctg    104880
ctacggtatt ttgccatcat gtagttaaac atgaaggtga tgttcactat gcttggttgc    104940
```

FIG. 20EEE sequence.txt

```
actgtgatga actcgtagaa cttggtgatg attttgttgt ggaaccagac acatgtaacc    105000
acgacgatcg tgtttatttt ggtgaattac atatcagagg aatttatggc attgatgaac    105060
aaagccctgc agagattgaa ccaactccgg acatttaccc tagatttgaa taagctaagg    105120
ggtgaagcaa aagtaaaaat cattgatact gccagatata gcttagatat cgatccatct    105180
caagatagaa ttgacgttct taaacgatgc agaattgcta taccggcaga gtatgtggta    105240
gcggattttc ttgatggata cgtgaacgat caagttgttg accataataa caacgaccca    105300
tatgaatggg cctgggacgt attagctcat ccacactacc aaggtgttag ggttgaagtt    105360
aaaacacact ttgttcatga ccgagcaaat cataagccat ggattaatgt tacaactggt    105420
aaagacggtc cattcccaga tggaagtgga ataaatctag gcccatgtt taaacataaa    105480
gtcgcagact gtataattat attcgttgca gaagaagtgt cccagaatgt catacggtac    105540
acaccaatgt ttgccggcgg tatcgaacag ctcatggaag tagtaaaacc ttcacgtgtt    105600
ggagctggcg ggtatatcat gcacaaattt taaaaagttg tttacttccg ggattggcca    105660
tgatactatg gccctacaaa ctgaacggga gtaaaacatg agttacttag agctaaaatc    105720
acttcgagcc aaacgcggaa atgcttctat taaagctgag cttttgaaag agtatagaat    105780
tctcgaatct atgaattggc attatgctat cattgcttgt gataatggcg attcaactta    105840
cggtggattg tatcccaatg gagccgctgc tgcccgtgat gagcataaag ataaagttaa    105900
agccttagaa gaaaaaattc gtaacttgtg catttaacgg tttactttcc tgttcttcgg    105960
tgatactata atcttgttag ctaaactgga gaacaaaaat gaaaagtta cttacgattt    106020
tgaagaacac ctttgtagta ttctgcctta tcgttacttt cattggtgtt ttcgcatggg    106080
atttagttaa cgtttggatt aatgctttca tctgaggaaa atataatgat tcgtagtagt    106140
tttgatcgtc gctttaactt aatgagaact gttgttctgt cctttatcgt tgcggtagcg    106200
cttggaattg ttgctatatt cgggttcgga atttattttg ctattcaagc ggtagatatt    106260
attcagaccg atggccttaa atctttagta gaaaccgtat gggaaggtca aaaatgaaac    106320
gacacatcgt gtatcgtctg ttggcttcgg gtcttcttgc attttgggtt ggtatcgtga    106380
cagtggtagt agtattttgg taataagagg ggcttcggcc ccttatcgga gaataaactt    106440
taatcaactg aggaaattaa catgcgtaat attatgactt tgctgatct cgataacgct    106500
ggtgcagaac tgatcggttc tattcgtaac ggtgattggg cagcaggtgc tccatctcgt    106560
gaaattactg agcgtgaagg attttatttc ctgatgttca atgatggcaa agcaggttat    106620
atcggtgcat ctgctcgttt ctttgtagct aaacaacgtt caaaggcagg atttgagagt    106680
gttctttctc atatccgttc tggacgttct cagttgggtc gtaccttcg ttcaaactgt    106740
gtaacatacg gtgtgttctg gattcctgcc aataaaatga aaccgctcac caccggttat    106800
ggcaaaggtc aacttgcact ggcgtttact cgtcagcatt caagcgccgc gcagacctac    106860
```

FIG. 20FFF sequence.txt

```
tctgaactga atcgtattct gaatgataac ttcatcttta ctttgcagaa atactaatga  106920
gaaccttctt cgtgatgggc tatgtgtttc tgatggccct aatgatttgc tcaggaacat  106980
tcatgtggta tggccttgtg cctaccacta aagtaatcgg aagcattgcg ttcactgcag  107040
catttattat gtttgagcgc atttgtaaaa ttgtaggagt ttacaaatga ttaaaggaat  107100
tgctggcgga atttgggctg ctctatgcgt atcgacattg actaccggtg aaacttctgt  107160
tatttcgcag gcgttagcgc aaggaacttt atcaattatt cttattatag cagccttttc  107220
caatgattaa gaaaattttg attggagcgg ctttagtagc cgctttgctt ttaattttgt  107280
actatggaat gatttacggg atgatttata ttgtgctttt catttccgat gttatagtac  107340
aaatcggctc actaatttgg taggtacaat ggatattttt gacactctat taaaacaagc  107400
aggttctatc gatgatttgg ctaaggcatc aaatcttcgt catcgcgatt tgaaatctat  107460
cattgataat gaagcaaaag agtatgcgat ttacactgta gaaaaccgtg ctattccgaa  107520
cttgattgat gggtttaaac ctgtacagcg ttttgttatt gctcgggctc ttgatttagc  107580
tcgtggtaat aaagaaaaat tccataagct tgcgtctgtc gccggtggtg tagctgattt  107640
aggatatcat catggcgaaa cctctgctca agatgctggt gcattgatgg caaacacatg  107700
gaataacaac tatcctctgt tagatggaca aggtaacttc ggttcgcgtc tggttcaatc  107760
tgctgcggca agtcgttata ttttctgccg gatttctgac aacttccgta aaatctacaa  107820
agacacagaa atcgctccgg tgcataaaga caaagaacat gttccacctg cgtattatct  107880
tccggtaatt ccgactgttc ttctgaatgg cgttcgcggt attgcaacag gttattcaac  107940
ttctattctt ccgcatagtt ttgaatctgt tttggaatgc actaaagcag cacttcgtgg  108000
cgaaatgatg gaacctgaag tacagtttcc taaatttaac ggaaaaatcg ttcaaacaga  108060
agacggttct gttgagctgc acggcgtgta taagaaaact cacggaact caatctatat  108120
cagtgaaatt ccatacaagt ttgaacgagc ttcttacgtt gaaaaagtac ttgacccgtt  108180
ggaagatgca ggatatatca catatgatga tgactgttct aagactggct ttggctttaa  108240
ggttaaattc cgtaaagact atgctttaag cgaagaccct gagcagcgtc atgctaaaat  108300
catgaaggat tttaaactca ttgagaaaat gagtcaatac attgtggtca tcgatgagaa  108360
tggtaagctg aacgacaagt tcaaaacttc cggtgagctg attcgtcatt ttgtagaagt  108420
ccgtaagaca ttcactgcca aacgaatcga gcataaaatc gctgaaacta agcaggcgtt  108480
taatcttgct caggcaaaag ctcaatttat caagaggtt atcgcaggta acatcgttat  108540
ccaaggtaaa actcgcaagc aactgactaa agaaattgaa caaatgaac tattcaaaga  108600
ccattctgaa aaactcgttt caatgaacat ctatcacatc actgatgatg aagcgaagaa  108660
acttgctcag gaagcaaaac gcctagcaca agaggttaag tactgggaaa agacaactcc  108720
```

FIG. 20GGG sequence.txt

```
tgaagccgag tatctgaaag acctggaaga actatgatag aatttattt aattataggt    108780
tctgtaattg ccgtattagg tttagtttta ttgctcctca gttaatctag ggaacctgga   108840
ggtcatctcc aggtccttcc atataaatct atatccctcc aaaatccttc cttagaatgc   108900
cccaaattat tttcacaaag ttgtttacat gcttactcgg ttgtggtatt atagcaatat   108960
caaaacaaca cggagtaaaa caaaatgatt acatcattaa aatctgatat caaaaacatt   109020
ctttatattt ccactcaagc cgatggcact cgactgagcc actatgtcaa aggtaacatt   109080
gtggtgctcg atgagttcga agttaatcgc gagtatccta tgcgtcaggt aattcaagca   109140
agtaactatg aagacggtga agagtatcaa gtcgttcttt gtgtatatga tgatttctgg   109200
gtgcttaaac ttgagaatgg cgataagttc ttgatcttta acgtataaca tttttactgc   109260
tctttgaaga aaattttca gagagcagaa taaaatggtt tacaactgct ttaaaccatg   109320
gtattatagt ctcataccaa acaaactgaa taaaacatca tggagaatca caatgtctaa   109380
agtaacttac atcatcaaag cttccgaaga tgctctgaac gaaaaaactg ctgctatcct   109440
ggttcaggta gctaaaaagg atttcatcac ttcttctgaa ctgcgtgaaa tccttgaaga   109500
aaccatgaac gcaagttctg ttaactcaaa catcggcgtt ctgattaaga aaggtctcat   109560
cgagaaatct ggtgacggtt taatcatcac tggtgaagca caggacatca tctctaaagc   109620
ggcagttatc tatgcagaag agaacaagcc tgaacttctt aagaaacgca atactcgtaa   109680
agctcgtcct ctgactgaag atatgaatga gcacaaagac ctgatgatga aacttctcgg   109740
tgagatggaa gatatcttgc ctttgaaaga actgactgtt taccgcagta actatatcgc   109800
agttctggaa aaacgtacct tcggtattcg tagtcttgaa gttaacaaca aaggtacttt   109860
ccgcatcttc ggttacaaga tttctgaaga gcatcagaaa cacttcactg acctcggaat   109920
gtcttgccgt gtagctgcaa caggcaatac ttacttagat atcgcccgta ctgctgaaaa   109980
cattgaaacc atcatccgct ctattaagga actgtaatgg aactttggga aattatatat   110040
gaagatgatg tgaatatcag aggcagcatc ttcattaagg ccctggacaa atatcacgcg   110100
attgaattgt ttgaacagtt acagcaacaa acttatatca atgaatcgcg ttatttaatt   110160
aaactcgcaa tgttttggt ggaataatga acaagtttaa agtattgaat gagcttcagc   110220
gttgtgttga aaaggttaac ttgaatgcta atatcccaac tgattgttgg gatgtatggt   110280
tccgtggaca ctttatcgga tacattgata agaaattcac aaaatgctat gctatctaca   110340
atgcagatgg taaacatatc atggatgtag ataattacca aaaggcccctt gctaaatttg   110400
ttccattagc ggaagctgtt aactcaatgg aatggttaga gaaaatacag ggtgaacctg   110460
ttattcgcca gattggtatt cgtgaaaaga aagtttgtg gcagaaaatt aaaggattct   110520
ttaaatgagc aagttttccg aacaaatgaa taaatttgtt gatgcttctc gtcacggtgc   110580
tctaattaat gaaccagaag aagttagtat tcctgaaatt tgctttaaag tagctgattg   110640
```

FIG. 20HHH sequence.txt

| | | | | | |
|---|---|---|---|---|---|
| gtgggatgga | cgattacttc | aacgccgtat | cgtttgtgca | gcaaatcgtt | ttgaattgaa | 110700 |
| atctggtgga | acaattgtgg | ttccaggcac | tcgccattat | tctgttgata | tggcgaacgt | 110760 |
| tctagatatg | ttccgtgaca | aactggtttc | tgaccatgtc | catggagaca | atcaaggatt | 110820 |
| tgtcgaccag | tggggtgagt | acttcacacg | tgaagaagca | ttaatcatcg | ctacacatgc | 110880 |
| aggtcaagtt | aatacagttc | gtcctaaatc | aggacccgcc | aatgaattat | tctcagagga | 110940 |
| tttatactaa | tgattagtac | attaaagaat | aacattacgc | ttttaaaaat | tcaacgtaaa | 111000 |
| tcgcttcagc | gctcattaga | aatgatggac | gataattggg | gtacatatac | caatgaagcc | 111060 |
| gggtttaaaa | tggcagatag | caaattcatg | aaaactctca | tggataagga | atacatctgc | 111120 |
| ccgtttagcc | atccatttaa | tggcggtgct | aagccatttc | ttgctgaaat | gtacaaaata | 111180 |
| atgacagaag | aaatgattaa | agatattgac | tattacatca | aggaacttga | atgcaaggaa | 111240 |
| gataaagtgt | gagagcaata | agcgccaagg | cagattactt | caatagctta | aatcgttcag | 111300 |
| aaaaggctca | aattaaacgg | tttatcttgg | aattgggata | tgtgcatgcc | ggagatttaa | 111360 |
| aagcacatat | ccaagaatgt | ggtattgcta | agcgttttga | tattacacgc | aactgcttaa | 111420 |
| atgaggtaat | tgcacatgta | caacccagta | gcgaagaatg | actttaacaa | aggaggcgcg | 111480 |
| cataaagata | aaaagcgtgc | tgctaaagaa | tcaaaacgta | agcaaaaaca | taaaggtaaa | 111540 |
| gacaatgcgc | attctgaata | attctaaatg | tactacttta | accattattt | gtgatgacct | 111600 |
| agaagctctc | cataaaaaat | taggggacca | ttctggatta | gtagcagata | tccattctga | 111660 |
| actaatggaa | gacctccaga | atgctggata | tggggactgg | atggtacatg | attggaataa | 111720 |
| tggtaccttt | actgtagcta | ttattgctaa | cgttgaacct | gaagaagttc | ttgaacaatt | 111780 |
| tcagaaatgc | gttgatgctt | atgatattgg | agattatcta | tgaatactga | aactttacgc | 111840 |
| agagaagatg | aagccaaggc | atatcataaa | cgtgttgaat | tactttcagc | aattaaagta | 111900 |
| gaatacactt | tacaagttag | gcttaaagtt | cttaactctt | gggctaatga | cttagaagta | 111960 |
| aaacatttag | aacaagcagt | aatgtttacg | tttactcagg | aagcttctaa | accgtttagt | 112020 |
| ctatcagcag | atttccacac | gtatggaatt | attactatta | aagcaaagga | tagaggtgac | 112080 |
| attataagtg | gagttgagta | tattgaaagc | attttaggta | atcgcggaga | ggttgtttta | 112140 |
| gcatgagtca | taacttagaa | tctgtcattg | aatcacaaag | atatctcgaa | gcgttaatga | 112200 |
| ataaaatcgc | gcttggaagt | ctaatcgact | tgtcctttca | ggaggcaatg | gacgtatgtc | 112260 |
| actggatgaa | tcgtagggtt | cgtccaattg | gaaaggaatg | gtatttaacg | gctaaagtaa | 112320 |
| aagatggtcg | ctacgggctc | tggatgtcct | ctggtgctga | gtatatcact | accaaggaag | 112380 |
| atttgaattc | tcgttgggaa | ttggcataaa | ctggtttaca | acgtggtatc | aagatgatac | 112440 |
| tataatcaca | taatccatta | tgttgtagga | aaaataatga | ctaagtttga | aattgtccaa | 112500 |

FIG. 20III sequence.txt

```
gaaattgtta ccgttgcttc tattctgact aagttcaatg ctgaacatat catggagaag    112560
cgagatgaat ttattgcgtt cttgaacgaa attggaatca agaacgagca ggggcgtcag    112620
ttaaatcaga gcaacttccg taaaatggtt tctgagttaa ctgacgaaga gaagagaatt    112680
ctcgttgaag aatacaacga gggatttgag tctatctatc gaacaatggc tatgcatagt    112740
aataagtaat cacttagctc ttcctagagc tctaaccgcc tgaccacata tcgatgttag    112800
tctttcgtta gataatgcag gtttggaatt gtaccagtac atttcaacag ttccagcata    112860
aacattgtct aaattgaaat acggacagct aaacatgtac gatatttcag gtggttttct    112920
ttttgtcggt aagaaaacaa attccttatc cgtccaaaaa tatctacccg ataaatgcgt    112980
gctatattca gcagacgttt tgtcgattgg atatcctccc aggtttttag aatctaccgt    113040
gctaggtaaa gtcccctcat aagcaattaa gtctacgaag tagttcaagt ttttaggtct    113100
gaacgtaaag accgcagaaa aatctgcacc acttgagata tgtactatct ggagttgttc    113160
gagtgctgta ttatcaaatc gggtatccct atccttttga accagtttat catacttgtc    113220
atatgtacta tcgacgtaag cagtaataag actatctgac ttataaccag caaacgccaa    113280
caatgctaaa agtatgacaa caaaaacacg ggaaaagaga actcttcccg tggctccatc    113340
tttgaataat agctcgagca acccaagaaa catatcaaaa aatggtattg attgtttgct    113400
tgccatattg ctctccttac agagctattt attgctatct tctagttata agaccttgcc    113460
agtattggtc agttctgtca ctaaaccagt ttttaagctt attagcttcg tcatttgaag    113520
ctatttgata gtttcttaca tctccatcca ttttacctgg agtaaaatca aaggtagtgc    113580
catctgacat cattacccga agatttattg cgtcgccatt tcttattccc aaggttgtac    113640
cttgagggtc accgttccaa tagttaaccc caccttgtcc agatacagac acaaataaag    113700
taacctcttt accttcgaag ttaccttgta ctgtattttt ggttgtcggt ttagggctcc    113760
agttccagcc accaacttgc catgaacctc tatagtaaat attgttccag ttacgatatt    113820
gcactgttaa actaaagtta aaaacacttc gtcctatcat attagacatc cagaaaggtg    113880
ttcctagtct taatttggct ccggcttggg ccatccacgg ctcgccggtt tcagccttcg    113940
cggaacttcc aacccatggt cctgttactg ccatgatatc tccttaaaga tggggccgaa    114000
gccccatgca ttatttagat ttaagttctt caatttccgc tttaaggcct ttaacctcag    114060
cagaaagctc tttaacagat tcaacaagaa gtgcaattac tgagttgtaa ttcagacgca    114120
ataatccgcc gtccgcttca atatcttgag taactgcttc cggaagaact tcttgaactt    114180
cttgagcaat caacccagca gaacgagtag taccgccaga agtattatga agctcataag    114240
tattaccgct taaggtctct acttttccca aagcgttttc aataacttta atatcagatt    114300
tagctctacg gtcagaacga atctcaacgt tatcaaatga accattgcga gtacagatga    114360
agtcaccgcc agctctgaaa tagaaactgt catctcgacc gaatccatta acattaatga    114420
```

FIG. 20JJJ sequence.txt

```
tagcttggtg gaagttacca acatattctt ggaaatacag agaggcataa gcaccattac    114480
taaatctgct tactaaccca gcggtattgt tatatgtgcc attgggttgt cctgcaggat    114540
aattagtagt gctgctaatt ccgttatagt tagaaatggc tcctgggaat tgacatgaac    114600
cacttgccca gaaattccat actggtccag aagcaccgcc ggctcttata ctaacattac    114660
caggctcatc agcccaaaga agaccttttt ctgtaccatc tgctttacgg aagaacacat    114720
ggctattacc ggtgttctga acgttaacag aagtggatac actgaactct tgattaaacc    114780
tagcctttcc atcaacagtt aaaacnccat taacggcagc atctccggta gtccatagag    114840
aagtagtttt cagttgatta cctgtaacta ttaatgtacc agttacagta ccacctgcta    114900
atggaagata agtatcgcca gcattactaa tagcagaagc aaccttatca tcaacatatt    114960
tcttgttggt taggtgcgag ttatcagtag gagcttgacc tgcaataaca aacttaccag    115020
aagcgacgtt gatgtttcca tcagcattaa tcacaccgct gaagcgggaa ttgcctttaa    115080
ctatcaagtc tgagttcaag ttagtattac ttgttactgt aagctgcctg ttaatttggg    115140
catttccgta aacagtttgg tttccgctag catcaacttt gaatatatcg ctaaacgtgt    115200
cagcaggatt aatttggttg ttggtatttg cagataccat aacggtaaat gagttagatt    115260
taccgatggc cattttcct ggcataccgt ttttcttgac taaaccaata tcagagtttt    115320
tgccaagaac gatcattctg ttatcttcag aaacgttcaa gttgcctgtg attttcgagt    115380
tctgggcctc gaactcacca ccgacagtca ttttaccttt ttggtcaata actgtagctt    115440
ggttggaatc atcgccgtta ggtcttaaat gaagagcttg acctgttttt gcgtagataa    115500
caaaagcacc agagtcgttt gaacgaatac ccgggccata ggaccactca agcagaggct    115560
cagaaccgtt agctttaact ctaatctcag acccagaaga atcaccgaat ggtctaaaag    115620
caatatattt cgctgatgct gcggctgtag cagaagctga catgatcaat gcaccagtac    115680
taccaccttg ggcttcacga actactgcgc cattttaaa tgtgatagtt ggatcacttg    115740
ttccgacgcc attaacaact aaccagccga acttcacact ctgtccttca ccaacaccga    115800
ggttattacg agcagcagcc acagaagttg ctccggtacc gcccaagttg attggttgaa    115860
cccctgcaac aacctctttc catgcagacc atgtgccgtt tggcagtat ctaacatatg     115920
tgccttcaac attaccgttc tttgtagtaa aggtctgctt acacgtccaa tcactgtcag    115980
aaattttacg caaagacaga acttcaagaa caaagttacc atcagatgta ggtttattag    116040
atatattaga accaccacca gatgatacac atttatacag ctgacgagta cctaaatcac    116100
tgcctttaat aaccatgttg ttaaggtcat tagtcttatc agtaatatta attgcatctt    116160
cagtaccgcg atatgtctga ttaaaaacca atcccttc tacatcaagg ccatcaggct      116220
taactcggat gtacttgctg ggagctggag tagcaactgc atcttgataa ccaaactgca    116280
```

FIG. 20KKK sequence.txt

```
cgtatccttc aggagtaatt ttaagcattg ctacggcagc gccagagcca actttacgtg    116340
caagggtcaa tctgctatac ttatctgagt tctctgaacc taaatcaacc attgatccat    116400
tagggttttc gacttttaag ttagcgttaa tagtcaagtt accggtcatg gtatcaccag    116460
tcttgcttac ttgcttacta tcaccagtgg tgatatcatt tttaatagaa gtcaaatagt    116520
tgttaaggtt accgccaaac attgaaccag aggtaatatt cccgtctttg gttagcattg    116580
ctgctccacc aactttaact gctacaggaa catcaaggcg gccatcagaa cggaagctaa    116640
aatcaccggc agaaacatca ccagtagttt ttgcacgaat attaatctga cccaagtccg    116700
cggtattcgg agttgcccaa attacaccac gctcattacc tcctgttcta aaccatacat    116760
gagcgtttcc gcttcctgcg ttaacatata ctgatgcagt accagtgccg gaagcatgta    116820
aattaggaac agttaaatca ccagtcatgg tatcgccggc tttcttaact tgagtatcgt    116880
ttgtcagatt accaagtccg acatcagcct tagatggttt gtttgctgtg ccgtagagaa    116940
cattagaatt tactcttcca cttgctaaac cgctatcgtt tatagcaaat actctgacgt    117000
tgccagttgc ataatctata ttaagcgcag acattgtatc gccagttcta gaaaagaatc    117060
ctgcgccatg ggagtaataa ggagccccgg tataaccact cgctacgttg gctctaaatg    117120
ttgtaccacc aagagcctta aggcgagtca ttaaatcaac atcagaagta atatctacta    117180
gtgattttcc gttaccgcca ataccaaagg caccaacttc catcacattt ccgctggatt    117240
caccaacatc acgaacagcc gcagttctaa gacctaggtt atttctagca tctcctacgt    117300
tagtagcacc tgtaccacca cggttaaccg gaagagtacc ggtagtatcg ctgaaatctg    117360
gttttgagat actatcaaaa acctgtttca ttgaaacaag aatgcttcca gatggtgtag    117420
tagcaccagt atcttggcca gtttcataga taattacttt accgctatct tggccgttgt    117480
attcagcagt gtttagcact gtaacataaa gtccatttcc gtatcgagga actttagcgt    117540
aaaaatcaaa tgaagcctct gaatctgtag cagcatcatt tttaacaacg taatactctg    117600
gaacgtttcc tttattagga gaaccaatcc tgcgccattc aacccagtta tctaaattgc    117660
tagtgctcca ggatgttaaa ttgcgaccag ataacgtgat aaaatcaaca taatgccttc    117720
cgtgtccaga atcaatgcca ccagtaatca ttaaatctaa ctgcgaagat gcatctcctg    117780
ggtgtttaat tgtagctact ttaacccagc gcggagttcc agcggttgca gcagaaatta    117840
cgtattgcca tgcctgacgg ttgttttcta cattcgtcag aagagtaccg gatttaccag    117900
gacctcttcc gttcatggcg taataaacct gtgaatttct gaatgtcaga ttactgtcat    117960
tggttaattg aagaacacct acgcctcgtt ggttttaat gtaagcgtcg ttagagccta    118020
cacccatttc aaggacaagt gtgcttccat tgttaatttt aacagtttta ttagtggata    118080
atcttaaatc accaggaaga gtggtattac ccgagccgtc aagcaagacc agttttcggg    118140
cttcaacgtt gccgcttccg cgttgtacga attgaatagt ttcagcgcca tcgtcaatag    118200
```

FIG. 20LLL sequence.txt

```
taccgatttc aagaataccg ctattgcttg taccacctgc accgatgtac cagccatcgt  118260
tagtagcgca tttgccgacg atatgacgca ctattgctcc gcttaaatca gtggcttcaa  118320
aattgatagc tttattcgga gaaatagtaa cgttgtcttt taatgtagta attccatcaa  118380
cattaagatt acctgcagta tctaagaaag gaacaccttt acctgcaagc tgaacaacgt  118440
tatcggcttc atctttagtg taaatggcaa gagtacgccc gtgtgtattc aacacgattt  118500
cgccacgggc tacgatatct gcacctggtg ctttattctc tgtgctagtt cttttaaatt  118560
gtatttgttt taagttttga tcggccatgg ctacctctta gtatgtgcca aaatctattg  118620
ttaccccgcg tgaaataacc tgatctaatc taggagcata ttcaccggat gttgctttat  118680
ttactataac tacgccagcg ttagctctaa gtacaccggt catggtgtcg ccagctttct  118740
tgactgctgc gttagctacg ttgctaacag tatttattag ctcatcgaca tagtctttgc  118800
gtgttaagtg tgaatttgct gttggagctg cagccgcaac agaaacttga ttgttagaag  118860
tgattccacc tttagtagta atattaccag atcgtaaatc gaatgcgata gttattccgt  118920
ttgaaccaga attagattca aatcccaagc cccaccaagt ttttattttg gcattgacac  118980
catttaaagt ggctccatca actccgccat ttacgagttc catgcccccg gagccagtag  119040
tttgaactct taaacctgtt tcaaacgtta ctgttctaga gtaacttccg ccattagctt  119100
ttgacacaaa gtcgttatct gcggcttgtg gtttatctat ctcagtataa acctttttac  119160
ctctataagt tagggagttt cctgccggca caagaggaaa agtacccgcg tgccaaatag  119220
gatttccgcc aactgttgaa cctgcttta aatcggccat agtttatcct cttatatatt  119280
ttctatttat acgaaaaaag gaagcccgaa ggcttcctta gtctgatgtt tctctgaacg  119340
attgaactgg aataacaccg ctcggatcga cttttgaatt tggaagttcc ataatcatag  119400
tagttcctcc ttcaacgcct ttattcattc ttataccatt cacaccaaac tcctgaataa  119460
cactattcaa ttgttcgcca tgagaagttt gaacaaatac gaggtttttg attttagagt  119520
caccaactac agacgttttt ggatatcgcg ataccacgat agtaaatcca tcagcgtctg  119580
taggaacagc ggtaaatctt tcaaatctta accatctatc agctccattt tttggaactt  119640
ctaatgatac gtttgaagat aataaagatg tacccttgaa ccaccgcaag ctagctctag  119700
tagtagaacc agcatcaaga aggcttttag atgcatacat atcacatact aaaaataccg  119760
aatccccagg agatagtcca taatcagcta ttttgcttat agattcattt tgtactggat  119820
atcgtttata ttcatatcca gtagaatccg agtattcatt ggtatcttca atagaacgat  119880
aaggacaccc agtatatcct acatctccta cattgtcata taccgtatct actttagccc  119940
ttgaatcttc tttaaccttt ccgtcattcc cataaaatga ctcaattaat atacgtcctt  120000
ttgctgctcc gagcactcct acataagcag agtttggaaa tgatttggaa aaatcagaac  120060
```

FIG. 20MMM sequence.txt

```
ctggccaaga tgcagaccac ttatttttaa accatctgtc tattaacggg ctggattgaa    120120
atcgttcatg cgtcattata atatacaatc ctgaagttaa tccatttgca tattctacaa    120180
acgctttgtt attagcgttg ttgtcatcag tggtaacgtc aaacgtttta aagttaataa    120240
atctgtcacc attaacttga acaacattaa tcccccctccg taaggaggag gtcatatcaa   120300
aggcaccgtt aatattcaat tctggcttat tcggaacagc attagaatgt gtagcataag    120360
cttttagcca atacttcaca gagtttgcct cagagaggat tcgtgtttcc acgaaatcct    120420
caccaaaggc tgccattaaa attggatcag ccattaatca cctacccatt caaatttgag    120480
agtttggttt ggacggtctg gccagatttt aactggacca agcttaatcc attccaaaac    120540
ttcaagggtt ttaacctgag ttgatactga gcttggagct ccgatatcag ctgcagttgg    120600
aggagtagca gacgtgaaca ctcgcatcca atcatcaaac ttattaaggt ttggattata    120660
aatcctcatc cacacagtat gcgcgaaacg cttatcagca gtttcggttg ttggaggata    120720
aggtgtccaa agctgataag tgttgtttgt agttacacca acctgagtta aaacaccgcc    120780
agcagcagtt ttttcttcat atccggtcac tactaaagtg cttgggttag cagggtcaat    120840
cggtgttctg attggaacca tataaccacg aagacctttc aatttagtag cgtctttaat    120900
ttcagcagtc caagaacctt gtcgcaatac agtatcatta gtcggcacat accacgattc    120960
agaacctgta atgacgatag ccgaactatt tatgttaaga ttgccggtca tggtatcacc    121020
agctttcttg acataacgac catcagctaa tcttgcgtag ttttggtag ttaaaatcgg    121080
atacgagtta gtattatctc gagcaaaaat ttgcgtatca gcgtcacgag tatcaataaa    121140
cgcagagtga gacctagcac caataatagc attttgggtt tcaatagtta atagaaccgt    121200
atcttttacc ataacagttc cgccaactat tgtatttcca gaagacctca gagttttagt    121260
tgatacttca ttaggaacat ccagcgtgcc gtttccacca aatgtgtagg tctggcttgc    121320
agcagtagtt cctgttccgt ttttgacacg aactttttaaa tttccagctg aagctgtttg    121380
ggtttctgca taaattatac cgcgttcagt tccatctcta ttttgaaaac gaacatgcgc    121440
atttccagtg tcagcagttg gagaaatttt tacttcgcca ccattagcgt ataaaatatt    121500
ctggacagaa atgttgttat taaacacagt atcctggcta aatgtccaag ctccagaaat    121560
tgtctgcgct atatcgcgac gagcatattt gtctggggtt tgaccaccta gcattccggt    121620
gtcatacgct ttaccaagac gaggcaagta atgtttcaac gtgaggttca attcatacgg    121680
agacactgcg acgcccttag aggcataccc gttatccgga agagttgagc cattggtatc    121740
attacctttc cacgttccat cgcctgtaga tagcctgacg gtccctctaa cgctgtctgt    121800
agcttgccat gactctgtta cctgaatagt ttgtttcaag taagcaggag gaacaattct    121860
atcacttaat gtgcctgcat caacttgcgc ctgtgtagca tactgagcaa gaccgatagc    121920
tccttcggtt gctgttttcg cgtgcaacgt ggcagcagta actattttct tggcgtcggt    121980
```

FIG. 20NNN sequence.txt

| | | | | | |
|---|---|---|---|---|---|
| gccggttctg | acctcagcag | cagttgcaag | agtagttgta | cctctttgag | aagtacttgc | 122040
| ttcctgtatg | ttgatggtat | aatggtccca | gaggttccca | gtaatagtta | agccagaact | 122100
| agtattaact | tggatacgac | tagtattagc | aaatttatcg | aacagtaatt | tagggtttac | 122160
| cattactgta | cttgaagtac | cagcttcaaa | ttcaccctgg | gcaccaggtg | tcgcgaagcg | 122220
| agcaatacca | gtacgatcgt | tagttgctgt | acggtcattt | aatgttttag | gtgtaactgc | 122280
| tttattagtc | acgccaccag | cattaacttc | tgtctgtgta | gctatttgga | ttaaaccaat | 122340
| tgctccatca | gtagcaactt | ttttatgcaa | agattctggt | gtaacaaccg | taggaatatt | 122400
| tgaagaagca | ggagttccgt | ttctaacttc | gctatcactt | gctaaccaaa | ctattcctga | 122460
| ctgatttaca | gtagctttat | actcacgaag | agttttgga | gtaactgcat | ttttgtaatc | 122520
| agaatgatcg | aatataccgg | tgccagcaga | agaacgatca | gcagttgtgt | taggagcacc | 122580
| accagttttt | actaactgaa | taacacctaa | ccgtgaatcc | gacgtagtac | gataaagcaa | 122640
| cttcttagga | gtaacaattg | taaaatcgtc | tgttcctgca | tccattttag | cattagacgc | 122700
| aatttcagct | aaacctctac | gagtttcagt | agcagatctt | tcgttaagct | ttttaggagt | 122760
| aacgattacg | ttatccaagt | aagaagcagt | tgttgcctga | ttaacttcgc | cggaagttgc | 122820
| aattcttgct | ataccagtct | gagtttcagt | agaacgacgt | ccatttaaag | tttctggagt | 122880
| aattgctaat | tcttttctg | gatttgactc | cgcgttggct | tgagcttgcg | tagcaagagc | 122940
| aataacacct | aatcgtgctc | tggtagtatt | gtctttagca | tcaacacgtt | ctacagtagg | 123000
| gtcagattca | gttacaatcc | aatagctttt | tccggatgct | ttatcttcaa | tatatgcaag | 123060
| ctcaagaaca | ggaacatatg | acgtagttcc | attaaaggta | atcgagcttg | attgaaccca | 123120
| tgctgcatca | ggtggatact | ctgagcgttt | tggaaactgc | agtaaattca | aattactagc | 123180
| gatggtatca | ccatcagaag | ctttaattac | tactgtctgt | cctttacgca | tataattcat | 123240
| tgcgattttg | acagtatccc | caacagctac | gtcagtaggt | aaagtaatgt | taattgtttt | 123300
| aactgtacta | ttatctgcgc | caaatacaga | aatatgctca | ttaggcatta | agtaacgtc | 123360
| agaagtaatt | attcttacac | gtgtacgtaa | atcattttca | aagatgcgcc | atattttgtc | 123420
| aatagcgtca | tacaccaaaa | atccactacc | tgaagtacgt | acttgaattt | ccgtttgtcc | 123480
| aggagtccca | attgagatag | ttgggtcaaa | cgtacgcaca | gtcatatggt | taatcggcga | 123540
| tgtaccatca | aggtcagtaa | aattaatgat | atcgtttgaa | ttagcgaaca | acggcagagt | 123600
| aataaaaatc | tctgagttgg | aagtataacg | acgaactacg | ttatcacctg | actgtacctg | 123660
| ggttggaaca | atcccgttcg | gaactaccat | tttagcagta | tcgccaaaat | cggttaaact | 123720
| agcacgccat | gcaccattac | taaacgtaag | cataatttgt | gaatacggac | gagtaagtct | 123780
| tacctcacgc | agacgcgatt | caccaaatac | gatagacgca | ccagtatctt | gtgctttaat | 123840

FIG. 20OOO sequence.txt

```
taagattccg ttatagccag gacgacctcc aatatcacga actacaatgg tatcgccttc    123900
gtctggtgct aacggaagaa gtagtgtagc attaccggca gcgttcgagt caacgttgat    123960
gaactgacca gattgaattt caaactctcc tttacggacg gtataaatcc agttcgggtc    124020
aacacgtaaa gaagtccaat tggcctgatt aaattctccg gctggttttg gaatatcttt    124080
gtttgcaatc caaatgcgtc gtccataagt cacagcaaaa tcggtgagat acccacgcgt    124140
cgggtcatat ttttggatag tattttcttg aataacgtac tcgacagaga cgccgtcggt    124200
tttaacgttg cggtcagcga gtgccacatt tataacttta tttccgccgg catccaaacc    124260
gttagttgca cggaaatgtt gtttcagtaa atcgctcata gagtctccta tggggttatg    124320
cttcattata gaagtattta taatggctgt actaactaat tgaacgaggt tcaaatgtct    124380
gatttaaatt gcttattcgc cgaagaagac caagtaaaag aaggtgtcat tctgattgac    124440
ttgtcgcaaa tcgcaatggc gacaattctt catacgtata aagaaggaga taaactaacc    124500
actcctatgg ttcgtcatct tattctttct actttaaaat ttaatgcttt taagtggaag    124560
aaagatgggt acactaaaat tgtcatttgt gttgataacg cagttaatgg atattggcgc    124620
cgagatgtag cgtactacta taaaagaac cgtgctaaag cccgcgaaga atcaaattgg    124680
gattgggaag gttactttga aggtcttcgt actgtaattg atgaatttaa gcagtatatg    124740
ccttattacg tcattgatat tgataaagca gaagctgatg atagtattgc tgtactgacc    124800
aaaaagttca gtctcgaagg ccatccagtc atgattgttt cttcggatgg tgactttact    124860
caattgcata agtatcctaa tgttaagcaa tggtcaccaa tgcagaagaa attagtgaaa    124920
tctaaaaccg gctctcctgc tttagattgc atggttaaaa ttattaaggg tgataagaaa    124980
gataacgtag cttctattaa agttcgttca gattttggt acacccatgt tgatggcgag    125040
cgtactcctt caacgaaaat gacgtttgtt gaagagtgtc ttgatgctgg cgaaaacatc    125100
aaagatttgc ttaccgaaga acagtataag cgtttcttag aaaaccgagt gttaatcgat    125160
tttgattata tccgtgaaga cattgttgct aacatttttag attgttataa taattatcaa    125220
ctaccgggtc gtggtaaaat ttatagctac tttgttaaat ccggtctgtc taaattaatg    125280
aaagaaataa acaacttta aggtgaatat aatggctaag aaagaaaaag agcaagtagt    125340
atttgatgaa gcagtacacg gacaggctct gcgagatatg attaaggaag cctcaggtaa    125400
taagctaaaa gcagaaagct atcttgagct taacaaagac attaaagacc gcgccaagaa    125460
agaacttggc gtagaaggca aattatttaa tcagctgctt gccctgttcc ataaaggtac    125520
acgcgatcgt tttgaaactg aaaaagatga agtggtagaa gcttatgact ctattttcgc    125580
ttaaagatga gggggacaca tcccctccg aatccattaa ccagctgcta gataagcaag    125640
ctaatggatt tgctatcgaa tctatggtaa cagaacttgg aatggggtat ctcgaggcaa    125700
cgacacaatg gctagaagaa aattctattc ctgagggaaa cttcagtaga tatattccac    125760
```

FIG. 20PPP sequence.txt

```
ctgcaatcat agaaaaaatt atgtcagaag cattagaaga aaatatgctt cgaccatcat    125820
ttagtcaaac acataaaacg aatagtctgg atttttatt atgattcgtc tacgcatgcc     125880
ccaaaacaat aatagatacg ttaacggtaa gagcgtttat cttttatatt taatgctcaa   125940
acaacacttt gccggtcgtt atgatgttgt taagtataat tgggtcatgc gtgtctctga   126000
taaagcttat caaaagcgca gagacaaata cttctttgag aaacttgccg agaagtatac   126060
gctaaaggaa ttgactctga tattcatgag caatcttgta gctaatcaag atgcttggat   126120
tggtgatatc agtgacgctg atgcgttgat attctatcgt gaatacatcg gtaagttgaa   126180
gcaaatcaaa actacattct ctgaagatgt aaagaatatt tactactttg ctaagaaagt   126240
taatgtagat aagcttcatg atattttga atataatgag aaagtcggaa catcttatgt   126300
gttcaaactt cttcagtcaa acgttatatc tttcgagaca ttcatcatgc ttgactcgtt   126360
tttagatata ataaatacac atgatactgc aacggataac ttagtttgga gtaattactc   126420
cactaaatta aaagcttata aaaactttt aaacgttgac ggtgctgaag ctaagaaact    126480
ctttattagc ataatcaaat cttgtaaaga aattagtata taattaatct atcgtccagt   126540
tgcaaggacc catgttgcaa caacaactgt taaattaaaa aggtaatcat atgttcaagc   126600
gtaaaaatcc tgctcaactt caacaacaac tggctggtct gaaaggtggt tcttctttct   126660
ctaatgaaga taaaaacgaa tggaaactga agaccgataa tgctggtaat ggtcaagcag   126720
taattcgctt cctgcctggt aaagatgaaa actctctacc gtttgtaaaa ctgatcaatc   126780
acggtttcaa acatgctggt aaatggtaca tcgaaaattg tacttctacc cacggtgatt   126840
ttgattcttg cccggtttgt gctcatctga gcaaaaacga ttcttataac agcaacccag   126900
ctgaatataa actgctgaaa cgtaaaactt ctttctggtc taacatcctg gttattaaag   126960
acccggctaa cccagaaaac gaaggtaaag tatttaaatt ccgtttcggt cagaaaatta   127020
tggacaaaat caacgcgatg gttgaagtcg atgttgatat gggtgaaact ccggttgatg   127080
taacttgtgt gtatgaaggt gcaaacttcg tcatgaaagt taagaaagtc ggtggtttcc   127140
agaactatga tgaatgtaaa ttccttggtc agtccgagat tgcaaacatc aatgatgaag   127200
aaactcagaa attcctgacc gaaaatatgg ctgacctcag cgaaattgtg gctccatctc   127260
agtttaaatc gtttgaagtt aacgaagcta aatttaaaca gattatgggt acagcagctc   127320
ttggtggtgc cgcggcaaaa gcagcagctc aagccgataa aattggtgat gacctggatt   127380
cctttgacaa agacctgtct gattttgaat ccaaaccgac ctcttctcgt tccgcagacg   127440
atatcatggg cgatgctggt gacagtgttg gcgatgacga tctgaatgat attttgaacg   127500
acctctaata taagggacc ttcgggtccc tttttcttta tccctccaaa aatattttca     127560
caaaattgtt tacaagccag ttgatgagtg atactatatc tacatcgaaa caaaacgagt   127620
```

FIG. 20QQQ sequence.txt

```
agaggaaaac atcatgggta aattaaacat tgatatcgtg gcagaacctt acatcaataa    127680
atcaggattt tgtactgatt taatttttga agatggttca cgttttatg acactgacca     127740
tggtattgat tttgatttag ttatcaaaga aggccctggt ggtggttggc caaatattga    127800
cctccgcggt tctaaagaag cagttcgtgc ttggttagaa gcaaacgagt gggaagatat    127860
tgatttgatg atggaagact ggaaagagta attacctttg gggacttcgg tccccacttt    127920
gaggaaatga taatggcaca ggttactgta gaaatatatg attatgaaca cttcattgaa    127980
accattgaaa aatacggttt gattgaagtt agtaacaagt ctgccccatg gggaggaaac    128040
gaaatcactg tagaaggtga tactcctacc ctatggttat ggcttgaaca agaatatttt    128100
cctggcatgg atgatgaatg ccgtgaagat acattaacga cttttagcgg gtaaattatg    128160
aaactgaaca cagaatatcg cattatccca agtcttgctg ccgagtggga cctttcatct    128220
agcggaaatc gccggatgcg cttgatgatt gaagaacatg gtggttcgtt ctttcctact    128280
aaaatgctcg acgaagataa tagtttcatc acagaagtaa aatttaaaga tggaacaact    128340
gctgacgctg aaggatttgg agatgcatac tttgaaatat ctgattatga attcaaatac    128400
ttcgaaccag tatatgaaat tggtagtgca atccaacctg gtcctactcg cttggacttg    128460
atcgttaccc cagaaaatgc agaagaaatg attgacttga tcaaaaaagt tttcaaaaag    128520
tagtttacac ggagctatgc ttgtgatagt atagctccat aatctactgg agaataaaaa    128580
tgaaacttca acgtcaaagc attaaacttg gttctgaata tcgtggtaaa tggaatttct    128640
gcatttgcga taaaaaccca gaagaattag agcgtgttga agaagtactg tgccaaatgg    128700
aagctccatt cactatgggt ggtgaaactg tctattggaa tgattactgt gataactgcc    128760
catgctatga agatgggtat ggctcaggct tctggattcc agttgaagat gttgaagaat    128820
tcaaaaaagc atttaaactt gctaaggcca agaaatgatt gaggctgaat tagtagtttt    128880
gttaatttct gttactgtcg cttttattag cggcgttata ttaggattat ttttatatgt    128940
ctaaatttag tgtaacggga tatcctcgcg ttaatattcg ctgccagttt gatgaaattc    129000
ctggagtaac tcatattgag ctcgtatttg accctcattc gcgatgcaat caggtttcag    129060
gtaaaattga ttcagcgtat ggcgaatttt taattaatga ccaagttgtg gtttcagcta    129120
tttctggtga acaagcaggt tcgttgtata ttctgaaaag ggaagtattt gaggaaattt    129180
cagaagccat aaaagaaggg tttaaaactc ttcagagcat gattaaagct agtgagtaca    129240
agtcatgtgg attttaactg actgggattg taagtactgt ggcggtagct tatggcaatt    129300
aggtggccgg tgttttaagt gtggaatgag gcaaggttaa tggaaaattt cgcagtagat    129360
gattacgatg atttgatttg gtgggacggc cgtgaatggg taactatctg cgcaatgtcc    129420
aatatcgata gcgctatcaa acgtctccaa gagcttcaac agaagtggga agacggtaat    129480
gttgaacggg ttgaatttta ttgaggttta aatgattcaa atagtttatg cctttgctcc    129540
```

FIG. 20RRR sequence.txt

| | | | | | | |
|---|---|---|---|---|---|---|
| tacaaaaact | gtagacggca | aaaatgaaaa | tgctttcggt | ttaggcgatg | gtcttccatg | 129600 |
| gaaacatatt | tcccaggaca | tgaaaaactt | tgctaatcgt | actcgagata | ctatcttgat | 129660 |
| ttgcggagca | aagacttta | tgagttttcc | tgaacctctt | cctgggcgta | agacaatcgt | 129720 |
| tgtccaagac | atgagtcgtg | cgttggcaac | tgctaaaaat | ggcttctttg | cagatgctta | 129780 |
| tgtaagtgaa | ttagaattta | tcggtttctt | gggtggtgac | attatggccg | ctcatacttc | 129840 |
| ttacaacagt | actatcactt | ttaatagaga | ccttaattat | tctatcatag | gtggtgccgg | 129900 |
| aatcatccag | aaggcatatc | catacgcgga | tagggttatc | caaacaatca | ttagaaaaag | 129960 |
| tcatagagtg | aattctgatg | tcactctacc | tgctgaattt | gtaacagctc | ctacttggcc | 130020 |
| agaatcagga | ttcattacta | aagaaaatca | ctggtatcat | attgatgaag | tgactaacat | 130080 |
| ttcagaggtg | gtctatgagc | gcaaactatg | atatcactca | gctatcagaa | gacaaagtcc | 130140 |
| aaaagaggtg | gaaaagattt | ccatttaagc | atggtattca | tcttctagtt | ttcagttata | 130200 |
| atggtcttag | cacttataac | ggttcaacta | cagtatataa | ccgaaatgga | aatataccta | 130260 |
| ttgaaattga | acgtgattat | aagaagatgt | tcatcggaat | gtcacacggt | aatgtgacgg | 130320 |
| ttaatgatga | tgtagtgtct | attattgggc | gatttgaaaa | gcgtggtgat | cagcttttct | 130380 |
| ttacacctct | tcaggaaaaa | tttaatgcgt | gaataccaag | aattaattaa | agacattttt | 130440 |
| gaaaacggct | atgagacgga | tgaccgtact | ggtaccggta | ctattgcaaa | gtttggtact | 130500 |
| caacaccggt | ttgatttaca | agaaggattt | ccggcagtaa | ctaccaagcg | tcttgcgtgg | 130560 |
| aaagcgtgca | ttgcggagct | gatttggttc | atgtgtgggt | ctactaatgt | gcatgaatta | 130620 |
| cgtcttattc | agcatgactc | attactagaa | ggtaaaactg | tctgggacga | caactatgaa | 130680 |
| aaccaggcaa | aagacatggg | gtattccggt | ggtgagctag | gtcctgtgta | tggtaagcaa | 130740 |
| tggcgtgatt | tcatgggtgt | tgaccaactg | aaattgatca | ttgatcgtat | caagcaactt | 130800 |
| ccatatgacc | gtcgtcagat | tgtgactgct | tggaacccgg | ttgatttgga | taagatggca | 130860 |
| ttgccaccat | gtcatttgct | gtatcaattt | aacgttcgtc | agggcatct | tgacctccaa | 130920 |
| tggtatcagc | gttctgtaga | tgtattcctt | ggcctcccct | tcaatattgc | gtcatatgca | 130980 |
| gcattggttc | atatcattgc | taaaatgaca | aatcttaaac | ctgggcattt | ggtattcact | 131040 |
| ggtggtaaca | ctcatattta | cctgaaccat | attgagcaat | gtaaagaaat | cttgcgtcga | 131100 |
| gagccaaaag | agttgtgtga | acttgaaatt | gcattcccag | atacgtatga | aacttggcag | 131160 |
| actagttctc | agattcgttg | gttagaacaa | tttgcacgtc | ctcatcattt | tgaactagtt | 131220 |
| gggtataaat | cccatccaac | aattaagggg | aaaatggcta | tatgaatatt | cgatttgttc | 131280 |
| gtaaaggaca | tcagtctaaa | accgtattag | gagaaatgca | ggacgcattc | tctagtgatt | 131340 |
| tgcctgaggt | taatgacacg | atagtttttg | acggaaccga | acaacgtgtt | ttatctgtca | 131400 |

FIG. 20SSS sequence.txt

| | | | | | | |
|---|---|---|---|---|---|---|
| ttaaatcata | tgaatggtct | attggcaaaa | cacaattaat | ctgctggttt | gaagttgata | 131460 |
| taacatgaag | atatgtcggg | tggttaataa | ataccattcc | gacttcgatg | taaatatcca | 131520 |
| acgtggaaca | atgtggggaa | attacgtcgg | taaagattgc | gataatcgtc | ctgatgctat | 131580 |
| tgcggcattt | aaggacgatt | ttattgctaa | gattcggaac | ggagaaataa | agcgagagca | 131640 |
| cttagaaact | ttaagaggaa | tgagattagg | atgcacctgc | aaaccgcttc | cttgccatgg | 131700 |
| tgatataata | gctcttgtag | tgaataaact | ttttaaagat | acatttgaat | tagaggactt | 131760 |
| atgcaagtaa | ttaagagctc | aggtgttagt | caagaatttg | acatgcagaa | aatcattaaa | 131820 |
| gtcctcgaat | gggcgtgcga | aggaactaaa | gtagacccat | acgagttgta | tgaaattatt | 131880 |
| aaatctcatc | tgcgtgatgg | catgagcact | gcagatatcc | agaagactat | cgttaaggta | 131940 |
| gcggcgaata | gcatttctat | tgatgagcca | gattatcaat | atgtagcatc | caatgcagca | 132000 |
| atgtttgaaa | tccgtaaacg | tgtttatgga | cagtttgaac | cgcctgcatt | tattgaccac | 132060 |
| atttcacgtt | gtgttaacgc | aaataagtac | gataaagaaa | ttctaagtaa | gtggtctgca | 132120 |
| gaagaaatta | ctttgcttga | ttcttatatt | aagcatgagc | gtgatttcac | tatgacttat | 132180 |
| gctggaacaa | tgcagcttat | cgagaagtat | ctcgtaaaag | accgtcatac | tggtgaattg | 132240 |
| tatgaaactc | cacagtttgc | ctttatgctg | atcggtatgt | gcttgcacca | agatgatggc | 132300 |
| gaaaatcgtt | tagcaaacgt | tattcgtttc | tatgatgcag | tttctactaa | aaagatttca | 132360 |
| ttgccaacac | caattatgtc | tggtgttcgt | actccgacac | gccagttcag | ttcatgcgtg | 132420 |
| gttattgaag | gtggtgacag | tcttaattca | attaacgaag | ctgctgcgtc | aattacgaaa | 132480 |
| tacatcagta | agcgtgcagg | tattggtatt | aatgcaggca | tgattcgcgc | agagggttca | 132540 |
| aaaattggat | ttggtgaagt | caaacatact | ggagttattc | ctttctggaa | acacttccag | 132600 |
| acagcagtta | aatcctgctc | ccaaggtgga | gtccgtggtg | gcgcggcgac | actgtactat | 132660 |
| ccaatctggc | acttggaagt | tgaaaacctc | ctcgtactta | agaacaacaa | aggtgtagat | 132720 |
| gaaaccgta | ttcgtcattt | agattatggt | gttcagatta | ataacctaat | gattgaacgc | 132780 |
| ttgattaaga | atgattacat | cactctgttt | agtcccgatg | tatgtcttgg | cgcgctgtac | 132840 |
| acagaatact | tccgtgatgc | acaagcgttc | cgtactttat | acgaagagct | ggaaaagaac | 132900 |
| ccagatataa | gaaagaaacg | tattaaagcc | cgtgaactgt | ttgagttgtt | ccttactgag | 132960 |
| cgtgctggta | ctgctcgaat | ttacccgtac | atggtagata | acgttggtga | atatggtcct | 133020 |
| tttattcgtg | atgtggctac | ggttaagcaa | tcaaacctct | gcctcgaaat | tgcgttacca | 133080 |
| acttcggatg | ttggccaaga | agatggcgaa | atcgcgctgt | gtacactcgc | agcattcgtg | 133140 |
| ctcgacaact | tcaactggca | agaccaagaa | gaagttaacg | aaatcgcaga | agtaatggta | 133200 |
| agagctttgg | ataacctttt | ggattaccaa | gattatccag | tagacaaagc | gttaaaagca | 133260 |
| aaagaccgca | gagcattagg | tgttggcatt | actaactatg | cagcttggtt | agcaagtaac | 133320 |

FIG. 20TTT sequence.txt

```
tttgcttcat acgcagatgc taatgatatt actcacgaaa tgatggaacg tattcaatat    133380
gcactcatca aagcctcagt taaacttgct agcgaaaaag gtccgtgcgc gctttacaaa    133440
gaaacacgat atggacgtgg cgaactgcct attgactggt acaataaacg aattgaccaa    133500
ctcgcagctc caaactatgt ctgtgactgg gaactcctgc gagaagacct caagcgatac    133560
ggtatccgaa attcaacgtt atctgcgctt atgccatgcg aatcgtctag tcaggtatca    133620
aactctacca acggtattga accaccacgt ggaccagtgt cagttaaaga atcaaaagaa    133680
ggaagcttca accaagtcgt tccaaatgtt gaacacaatg cttccct tta tgattatgcc    133740
tggcagctcg cgaaacaggg taataagcct tatctgaacc aggttctgat tatgcagaaa    133800
tttgtagacc aaagcatctc tgctaatact tattcgacc cggcgaattt ccctaaaggt     133860
aaagttgaaa tgtcggtaat gatggacgac ttgctttatt tctggtactt tggcggtaag    133920
actctttact atcataacac ccgtgatggt tccggtaacg atatatgat tcaagactct     133980
gctgactgcg cggcctgtaa attataatga attatcaaaa cgtatataat agtttaatct    134040
cccgggctag agcccgggaa tctttattag gatataaaga gactcatcat ataattccta    134100
gatgcatagg aggttctgat gataaagaaa acttagttga attaacaggt agagaacatt    134160
ttatagcgca ctggctttta tgtaaaatat atgaagcgcc gggattaaag aaagcctttg    134220
gtttaatgtg tttgaccggt aaaaatcgct catataaagt ttcctctcaa ttgtatgaat    134280
taggcaaacg gcgtttatct gaagctgcta caggacgtaa agcttctata gaaaccagag    134340
aaaagataag caaatctctt aaaggaaggg aatttaccga agagcattta gccaacatga    134400
gaaagcctaa aactgaagaa accaaaaaga atatagctgc tgctaaagtg ggcgtgctta    134460
atcctatgta tggtaaaatt tctccaacaa gagatgttcc ccatactaaa gaaacccgtg    134520
atgtgatttc tttgagaact aagcaaggta cagagtatcc accttgtcca cattgcggca    134580
agaaagttaa taaaggtaat gctcttcgtt ggcattatga taaatgtaaa tttaaggacc    134640
ctaaatgagt acagttttta ataaagaacc cgtagacatt atgaacgaac cgatgttctt    134700
aggctctggt ctaggaatcg ctcgttatga tgtccaacgg cacaaagtat ttgaagaact    134760
tattgagaag tctttatcat ttttctggcg tcctgaagaa gttaacgtta tgatggaccg    134820
tggtcagttt gaaaaactcc cagaacacca gcgtaatatc ttcactgata acttgaagta    134880
ccaatctctt cttgattcaa ttcaaggacg agctccagca gcagttttat ctgcacttat    134940
ttctgaccca agcctagata cttggaacca gacttggacg ttcagtgaaa ctattcacag    135000
ccgttcgtac acgcatatca tgcgtaacct ttatgtagac ccagctaaaa tctttgatga    135060
aatcgttctt gacgaagcaa tcatgaaacg cgctgagtca attggtgttt actatgatga    135120
tgttatagcg aagactcgcg catgggaaaa tgccaaaaat cgctgcttta atcaagataa    135180
```

FIG. 20UUU

```
                                    sequence.txt
tatcgaaatt aaagaagcta aacgtgattt aatgaaatct ctttatcttt gcttacatgt    135240
tattaacgca ttagaagcta ttcgtttcta tgttagtttt gcatgtacct tcaacttcca    135300
taaaaatatg gaaatcatgg aaggtaatgc taaaatcatg aagttcattg ctcgcgatga    135360
acaacttcat ctgaagggca cacagtacat tctgcgtcaa cttcaaactg gaactgatgg    135420
cgaagaatgg gttgagattg ctaaagagtg tgaacaagaa gcaattgaaa tcttcatgga    135480
agttaaccgc caagaaaaag attgggctat tcatcttttc cgcaatggtg gtcttccggg    135540
tctgaatgtt aaaattcttc atgacttcat tgactatctg actgtatctc gtatgcgtag    135600
ttgtggtctt ccttgtccga ttactgatgc accaactcgt catcctattc cttggattcg    135660
cgaatatctt aactctgatg cagtccaatc tgctcctcag gaagttgaga taagttctta    135720
tctggtagct cagattgaca atgatgtcac tgatgatgtt ctaattggat ttaaaaggta    135780
cttataagga aaggggcttc ggcccctctt tattatgaat gatattgcta acgagttttc    135840
ttttataaaa tatgttcaac ttgagttaga accagatttc agtattaaac ctgttttggt    135900
agcaaacaag ttgaatgtag tttatgccat cgcagttgat gatgaactag tttacattgg    135960
taagactaaa aatcttcgta aacgtataaa ttattataga actgctatta atcggaaaga    136020
ccaaacctct gattcggcta aatctgccaa gattttttgaa gcactaatgg ctggcaaaaa    136080
agtagagttc tatgctcgtc agtgttttaa tcttttgatt aataatgaac ttggcgagat    136140
gtcaatatcc actatggact tggaagaacc gatgtttatt aaaaagttca atcctccatg    136200
gaacacacaa cataaggtaa agaaatgtta gagctatata aaaatttaat gaatctatgt    136260
gaaagctcag aagttgcaaa attcttttat aaagatttta ccggtcctat ggatggtaag    136320
ttcagagtgt tttcatacca ctatgcaagc tacagtgagt ggttaaaacc tgatgctctt    136380
gagtgccgcg gtatcatgtt tgagatggat ggcgataccc caattcgaat tgcttcgcgt    136440
ccgatggaaa aattcttcaa tttgaatgaa aacccactaa cgatgggaat tgatattagt    136500
gatgtagaat acattatgga taaggctgat ggttctctag tatcatctta tgtcgatgat    136560
gggtatctat accttaagtc aaaaacatct ctctacagtg accaggcaag acaagcttca    136620
gctttgctta acagtgaaga atattcttcg cttcatcagg ttattcttga gctagcgcta    136680
gatggttata cggtaaacat ggaatttgtt tcacctaata atcgcgttgt tttagcatat    136740
caggagccac agctgtttgt gttaaacgtc cgtaataaca caactggcga gtatattaaa    136800
tatgatgatt tgtacgctaa tgctaagatt cgtccttatt taattaatgc ttacggaatt    136860
tctgatccca caacttgggt tgaaggtgtt cgtgaacttg aaggcgtaga agggtacatt    136920
gcagttctaa acactgggca gagatttaag gttaaaaccg aatggtattc tgctcttcat    136980
cacactaaag actcaataac gtcaaatgaa agactgtttg cgtctgtcgt atctgcaaat    137040
tccgacgatt tgcgttctct ttttgctgga gatgaataca caattaagaa aatttctgcg    137100
```

FIG. 20VVV sequence.txt

```
tttgagcaag cttatctaga ttacctcgga aagtcacttg agctgtgtca gtcattctat    137160
gatgaataca gaggtcgtgc tcgtaaagat tatgctattg ctgctcagaa agcaacggtt    137220
aatcagcgcc atcttttgg tgttatcatg aacatgtacg aaggaactgt agatgtagat    137280
aaactgctta agacctcga aagggtgttc ttgaagtact gggcaggata tgttccaaaa    137340
gagtacgaaa aggaaattga aatttccgaa gaataattgt ttacatcctc atcagggtgt    137400
gataccatag acttacacca actgatgagg ataatgaaat ggatatgcaa gcaattactt    137460
tagatatggt tgttaacaaa tacggtactc attctgacgg gattttgtg tggaatggta    137520
ccaagaaagt gggattcgtc actgatctac gtacccatat ggctcgcaag gaagctgctc    137580
gtaagaagca aaaagagtac actaatcgtg tgaacgagca gcgtgccgaa gcccttcctg    137640
aagccgtaga tgaaatgatt gatttcctag ataatcatct cgcgaagtat ggtgcagagg    137700
tgttcaagaa catcacccag ccaaacgttc atgctaacgg gtgcaaatgc tatgtaatcg    137760
ttgacccgat ttatggtaag catcgtcttg gtattatgca tcgtgagctg aattattctg    137820
agatggcaga atatgtagaa gcgtgcttca agtgttctcc ttcggaaagt tctgatcgtc    137880
acatcctcat ttcgggatta tcccgtgatg atatcgtaga ggttatcctt aaactatgct    137940
caaaataaac acaacttggt tgttgattgg agtgttagca ttatccgcag gaggattgaa    138000
atatctttcg tggcgggtag aaaatcttaa agctgacctc aaagtcgtcc aagatgaatc    138060
tgatcgacaa gcaaaagaaa tagaaaatat tggtgtttct ataaaaaatc tgcagacaac    138120
atataaaggc tatcaggaaa accgagcagc tcgtgatact tctaacgcta agatgaataa    138180
agattctaag cgtggaaacg tagttgcagc caaacctgga ttagttgaaa aacagattaa    138240
tgcaagcttc aataagtttg cagaagatat ccaggaggct accagatgaa acgaagtcta    138300
ttagccatgt gtattatcag cttattagct ggatgctctt ctagtgcccc agatgttccg    138360
gttttacatc ctgagtggcc agatccaatt caaaaatggg aaggacattg ggaagtaaaa    138420
gtaattgacg gtaaagcctg ggttggtatg ccgtttgaag agtcgcaaga atatcgtatc    138480
tggatgaatg acattttacg atatactaaa gatgctaatg gaatgatatg ttattatcgt    138540
tctgaactta agaacctcg ttgcgttaag taaactaaac aagaggaaaa tattatggaa    138600
ccgtcacatt tttattctta ctttgtaaaa gacgcatcgc atcttttatc gattaaaaat    138660
acacagctca gaaatatgct agctgttggg tcgtgccagt taactcctct tgctaagaaa    138720
gctactgtta taccggaaaa tatttctaat ggatatgttt atacagtccg tgttagtgtg    138780
cctggcgctt taaagaaag attgtttgag cttaatgacc aaacacgaat ttcgtttgat    138840
gtgtggttta aactattcat ggtagaattc atgtatcctg atttcttgaa gtttgttcag    138900
cgtaaagagg cattgaagga agcaatttct gaattggaag atgcctcaat tgaatttggt    138960
```

FIG. 20WWWW sequence.txt

```
aaggcactcc aatttgtaga aagtggcggt gtagagcaag atgctgttaa cgggttttg    139020
aagaaatatg gaaagcgccg ctcattggcg catcgtaatc tttctaaaat ggtgatgtag   139080
tgaatcaaga acagtatgaa acacttaaag gattaattgc tgaaaatgaa ttggcgtgca   139140
tcgtgtttgg acgcgcagct gaaaattatg acaaaaatga tatactgtca atgaataagc   139200
cattgcgagc aattaaagaa aaatatcgtg ctaattgggg tgaaaagtct aaggctcttc   139260
atgattttat tgacactctt aaggacgtat aatgaaaaaa ttggttttga cacaggggc    139320
tccaggctct ggtaaaacaa cctgggctaa cgaatacgta gcagctaatc caggttggta   139380
tgttttgtct cgtgatgatt tgcgtgaagg catctttggc cttgataagc gtaatgatta   139440
caaatattct aagcttcgtg agaagtccgt atctgtatgc cagttttcta tggcgaagac   139500
tctactcgag atggaaacca ctaaaggtgt catcattgct gatactaacc ttaatccaac   139560
gactatcaag aagtggcaag agttggcata tgaaattgat ggtgtcaagt gggaaattaa   139620
acgctttgac gttccttgga ctgaactagt taagcgtaac ctctatcgtg gcgcgaatgc   139680
agttcctatt gaagtgctcc gtagcttcta ctctaagatg catccgtatg atttgtacat   139740
tccagatgaa tcattgccaa aagcagttat cttttgacctt gatggcacgt tagcagataa   139800
caatcatcgt tctccttatg acttggccaa atgtggtaaa gaccatccaa aggaaatggt   139860
aattgaattt cttaaaatgc ttcgtaacaa aggatataaa attcttactg tttctggtag   139920
agagtctgga actaaagaag accctacagt ttatcaacgt attacgaaga aatggctgtt   139980
ggaccatgtt ggcgaaacag gcgaacactt ccaacgtaag caaggcgatt cacgcaaaga   140040
cgatgtggta aaagaagaaa tcttctggga ccgaattgct gatcgttata atgtaaaact   140100
tgcagtagat gacagggcgc aggtagttga aatgtggcgt cgtatcggtg ttgaatgctg   140160
gcaagtagcc cacggtgatt tttagaggaa agtataatgt ttccaaagta ttctgaagta   140220
gtaaaagtat catttacgca agttgttgct aatcatttaa cagatgagtt tactccggct   140280
gaagtagcca aaatgcatgc agagtttttta tctgccatga atgcacttat tccaaatggc   140340
gaagttgtta aattttcaat tgaccgtcta ggcggttcgt ctgaaattaa aatttcttgt   140400
ggcgaaggtg aacacgactg gtttatcgtt ggaattattg ctaattttga aacccaacag   140460
gttgagactt atgttgtctg acgctaaatt ttcacatgat gaatttatt cgaaggttaa    140520
aatcttcgca caggaagtag caaaccgggt tcctggaagt aaagtgactc tccgacgaga   140580
gtcatccttt aactatgttg atgcttatat cattacagtt aataatggaa agagcaatca   140640
acatactcaa ttggctttaa ctggaacagg ccaagttgaa atgactaaca ttttaggaca   140700
tatctaatga cttacgtga agcggtagaa gctctttaa ttgaacatgc tcgtggcatt     140760
aaagcagaaa tcagcccaaa tggtattcgg ctgatcagtg ctgttattgg ttctgaccaa   140820
ggtgtttggt caattccacg cgaagaatat gatgctattt tgtacagtaa cgttaatgtc   140880
```

FIG. 20XXX sequence.txt

| | | | | | | |
|---|---|---|---|---|---|---|
| aaggaaggac | aacctatgta | tggttatgtc | ttctctgact | cgcttgaacg | aggaaaccat | 140940 |
| ccgtttccag | atggcacagg | cattcgtact | tctcgagtag | agagttttgc | ttctcctacc | 141000 |
| gacgagttaa | aattggttaa | aacaaataac | acaacttatc | tggtgattta | aatgaaagcg | 141060 |
| tcgacggtac | tacaaattgc | gtatctcgta | tctcaagagt | caaaatgctg | ctcgtggaaa | 141120 |
| gtcggcgcag | taattgaaaa | gaacggacga | attatttcta | ctggctataa | cggttcacct | 141180 |
| tctggtggtg | tgaactgttg | tgaccatgca | gcagaacaag | gttggattgg | tgaaattcct | 141240 |
| tacaaatcta | cgggattgcg | tcaagacgga | ttccaagtca | aaaaagtcgg | attgctcaaa | 141300 |
| gaacatcgag | cagcccactc | tgcatggtct | aaagtcaatg | aaatccatgc | tgagcttaat | 141360 |
| gctattcttt | ttgctgcccg | gaacggcagt | agtattgatg | gagcaacaat | gtatgtcaca | 141420 |
| ctgtctccat | gtccagattg | tgcaaaagcc | atcgctcagt | ctggtattaa | aaaattagta | 141480 |
| tactgtgaaa | catacgacaa | gaacgaacct | ggctgggacg | atattcttcg | ttctgctgga | 141540 |
| atcgaggtgt | tcaatgttcc | aaaacgtaat | ttggataagt | tgaattggta | taacattaaa | 141600 |
| gaattctgtg | gaattgaata | atgaaactta | gaattgttga | aattaataaa | cttaacctaa | 141660 |
| gtggtgatgt | tgttatatca | tactcagtag | aacgccggta | ttggtttaaa | tggaaaccat | 141720 |
| tagcaacatt | taaatttgaa | gatcaagcag | ttcgattatt | aaaagaatta | tccaagcgca | 141780 |
| aatctgtaat | tatcaaaact | attaaagaga | catcaaaatg | aaactgacta | ctgaacaaaa | 141840 |
| catccatatt | cgtgaaactc | tgaaggctgt | gctgagcatg | ggcgaatccc | agattgtgtt | 141900 |
| tgaaaaagct | gatggcacta | ttcgtactct | gcgctgtact | cgtgataaag | acattattcc | 141960 |
| atctgatttg | gtagaaagca | ctactaaatc | tgctcgagca | gaaagcacta | cttcacttcc | 142020 |
| agtatatgat | accgagaaag | aaggttggcg | ctcatttgcc | tttgataaac | tgatctcggt | 142080 |
| aaatggtatg | aaagttgagc | atctgctgca | gatgatcggt | aagtaatttg | ctttaaactg | 142140 |
| accatgttaa | tataactaca | tggtcaaaca | ataaaggtaa | cacatggaac | ttccaattaa | 142200 |
| agctctaggc | gagtatgtaa | ttctcgtatc | tgaacctgca | cagcaaggtg | atgaaattgt | 142260 |
| ttctccttct | ggtattattc | ttggtaaaga | agaacaagga | caactgccgg | atatgtgtga | 142320 |
| aatctattct | atcggtgatg | atgtaccgaa | aggatttgtc | gaggtcggtg | atttgactcc | 142380 |
| gttgcctgtt | ggtaatatca | gaaacgtacc | tcatccgtta | gtagcagcag | gtgtgaagaa | 142440 |
| acccaaagaa | attcggcaga | agtttgtgac | ttgtcattat | aagtcccttg | catgcgtata | 142500 |
| taaataataa | tatgaattgg | gcgtcggaca | attagttacc | cgagcaattc | tacgtggtgg | 142560 |
| atgcccgagc | taaacctcgg | ttaccgtcca | ccaaatttta | acctcatttg | aggaacgatt | 142620 |
| caatgaacaa | acaacttact | aaagctctgg | aactccaacg | taatgcatgg | aattccggtc | 142680 |
| acgaaaacta | cggtgcttca | atcgatatct | atgcagaagc | actggaagtt | ctgaaagggt | 142740 |

FIG. 20YYY

```
                              sequence.txt
ttaaacacct gaacccagca caagctgaat ttcgtgatac tttagaagcg atggacgaac    142800
tgaagtatgc taagcatctt ggttctgctg ctcgcaaagc tgttcgccac tttgtggtaa    142860
cgctgaagta atttgtacgc ccaccatgtg tacgcatggg taacgtatga tgtggacgtt    142920
gttggttatc cccacgtaaa acatccgaaa ccaacggtga tttgctacca aagtgcagct    142980
agaaataaac ggcaagtgca tgctaccccg aggcgatggc caatcgggag tacgcctcaa    143040
ggcctataca tccatcggtg tatatcttat ccccgataaa tcggacccgg aacctttaag    143100
ctaacggtgt gcaacagata agagtttaaa cgtacccctt gagggctttc gggagctaca    143160
accgaaagaa ctgtcgaaag aagttgaacc tcggaagaac gtgctcccat gtatttctcc    143220
aaaatggaag atgataaaat ggctaaacaa gctaaagcaa aaactgcagt aaaagaagtt    143280
gttggtacct ctaaacgcgc tggctacaag cgtgggtcga acaagcgtat caatcagacg    143340
gttgagaaaa tcatgcgtcg agctcgtgcg gttcttcgcg atgatgcttc tcgttttggt    143400
aagccgaaag cataagttca gggactcctt cgggagtccc tttttattt tccacagaat    143460
gaaaaaagtt gtttacttct aggctcaaca aggttactat agacctgtac cacccaaacg    143520
gacaacggag aataaaatga acttcactaa cttcaaccgc aaatacgtac agaacaatgc    143580
ctgggacgtc tctactactt tgctgtggga acacaacaac ggcacagtgg ctcaaatcga    143640
tatgtactgg gaagataact acgtattttt cagctttgaa aatggtccta ctctggatat    143700
tcagttcaac ggttctgaaa tcaaagttgg attccatgat gaagttcgta acgtgatttt    143760
atcttcacat ccgtcttgga acacaaatcg tcagctgctt gttaaaattt atctgcgcca    143820
catcctcggt cgtaaaacaa ccgaagaaca acgtgaagca atctgggata tcgtttcaaa    143880
cgaaataaag ttttaactaa ctcggggctt cggcccccact attgaggaaa tgataatgga    143940
aaaaggtaaa ttctataagc ttaaaaagac tccaagcttg tctccaggcg ctcttatcaa    144000
gggtgttttt gagcaaatcg gtaataatcc aattaaaatt accagaacct ttaaatatgc    144060
ggaaaacact ggattagttg aatttgaaat cattaagccc gatggggaat acaaacgcgt    144120
tagtatagat gaagttcgct tttctcgcat gtggtgtatt attactaatc aagagtttca    144180
gcattatttt gaagaaacca cccacaaaga acctgaaccg aagaccgatg acggaagcaa    144240
tgattggggt gtttggacct caaataaagg aaatgatacc tacaaaggtg gattaacaaa    144300
ggaagaagct gttaatcttg caaaagtaca acgcctgaat gcaactaaag acacaaaagt    144360
tgtaatcatg caaccttttg ctgtccctgt ggttcacgtt aatattcgcc cgtttttaaga   144420
ggaaattgaa atgattgtat cagctttcta tgattcacga aagaaaaaag ttgaaaccat    144480
tatcagcgat acccgcgatg gtacacctgc taataaaaat ggtgtgaaag catacattga    144540
taagtattgc cctcctgaat ttcgtatgat tgacggtgta gattctctga gcattaacat    144600
tataaatgct aaaattgaat ttattaatga aactgtgcca attgggtatt ctgacggtga    144660
```

FIG. 20ZZZ sequence.txt

| | | | | | |
|---|---|---|---|---|---|
| tggctcaaat | gctaaaatgc | cgaaagaaaa | attcataact | aaattttgag | gaaatcaaca | 144720 |
| tgattgtatc | cgtgcctaaa | tctaaagatg | gtatttttc | ttgcggcttg | aaaaaccacc | 144780 |
| caatggttga | tatcatgtca | gctaacgtta | aacaacacac | cgttgagtat | gaaattgatg | 144840 |
| ctccggattt | ctttgaattg | cctgaatggg | cagtgaggct | tgatgcatga | aatatcatat | 144900 |
| cttcaataca | gtaagattag | caaatggaat | tcctggagtt | gtatgtgata | cggctccagc | 144960 |
| cattaaagcc | tactcggttg | aaccttggta | tgaagttaat | tgggttgatg | gcaatcgttc | 145020 |
| aatccatgca | gaatccgagc | tttatccaat | tactcaatta | agggctgcta | acgacgatgt | 145080 |
| ctattaatcc | tcacttcggt | catatggttg | cccgacgtat | caccagggaa | atgctaaaga | 145140 |
| ctgctgagta | ttataatata | gaattaattg | atatagaacc | ctcggacgct | ccagggttaa | 145200 |
| tctggttcaa | tttcaccggt | gccgcaaata | gcgtcgccaa | atttaaacaa | gcattgagga | 145260 |
| atttccccga | atgtcaaaac | cagtaatcgc | aaccgatgtt | gatggaatca | tcgttaagtg | 145320 |
| gcaaagtggt | ctgccttact | ttgcccaaaa | atataacctt | ccggtagagc | atatccttga | 145380 |
| tatgatgact | actgaaaaat | tcattaaacc | cgctgagctg | tttgattgtg | aagaagacct | 145440 |
| ggctgttaag | cttcttctga | aatataacaa | cagtgatttt | attcgttatc | tggcgccgta | 145500 |
| tgcggatgct | ttagctacag | ttaataagct | caaagaaaaa | tacgattttg | tcgctatcac | 145560 |
| ggctcttggt | aattcagtag | atgctaacct | taatcgtcgt | ttcaatctga | atgctttgtt | 145620 |
| ccctgatgca | tttacagaaa | tcatggtctg | cgattatgat | gaatctaaag | atgctttact | 145680 |
| ggaaaaggct | aaagtaaaat | acggcgatcg | catcgtctgc | tatgtagatg | atttgcctaa | 145740 |
| acatattgct | gcggccagca | aagtatttga | agacactgaa | acccgtgtgt | tctatatgcc | 145800 |
| tcgtggtgag | cgagagggtt | cagtgactgc | tcctggaatt | atggttgaag | attggcatca | 145860 |
| aattgtaact | tgcctggaat | ctttggaatc | tgttaagaaa | ccgcagaagt | ctctttctag | 145920 |
| attgtgggaa | gaagctatca | aagaccaaat | tcgtaaagag | caacatcctt | ttaattggcc | 145980 |
| tccacggcaa | gttccaggag | attggtggaa | acaacctatc | attccgttta | gtcctagtcc | 146040 |
| gcatgttcct | cctggaaacg | actggtggaa | taacggtcgt | attacatgtg | ataaccacca | 146100 |
| aattaattgc | taacacactg | ggtatggtat | aatagccata | ccctaggagg | aaatatgttt | 146160 |
| gtagttcata | ctaaggtagg | taaacgttgg | ttatcatgtg | attatggcca | tgttaatcag | 146220 |
| ttttatcgtt | ggaatccaat | ttggcgtgaa | gcaaaggcgt | gcccgatttg | gaatgaatgc | 146280 |
| atcaataacg | ggtttgttta | tatcgatgga | ttaacttatc | atcgtagcgt | aagcgaactt | 146340 |
| tcaaaagaat | taggtgaata | atgattttg | atatcatcaa | agcgattgaa | gatgctaagg | 146400 |
| gttctaaagc | caaaacccaa | attctcattg | acaataaaga | taacgttgat | ttaaaacgag | 146460 |
| cttatctgct | ggcgtattcc | gggcgattta | agttctttat | taagaaagtt | ccagaatata | 146520 |

FIG. 20AAAA

```
                                sequence.txt
ctcccgttaa atatccaaat gttccttcaa agacgttttc tgatggtcta gattacctcc    146580
aagacattct ggcagcacga gtacttactg gtaatatggc aatccagggg ctagtagatt    146640
tgctctctaa gatgaacgag ggtgatgcta gtgtactggt ccgtgtactt cttaaggata    146700
tgcgttgcgg cgcttcaggt tctattgcta acaaggtatg gaagaagtta attcctgaga    146760
tgccacagat gttagcatca gcttattctg agaaagcgct atcgtatatt aagttccctg    146820
catttgctca gcttaaagcc gatggagccc ggtgcttcgc tgaaatccgc ggagatgatt    146880
tagatgatgt aactcttctt actcgttccg gtaatgaata cctgggtcta gataaactta    146940
agcgtcaact tatcgagatg accaaagaag cccgagaacg ccatcctaat ggtgtgatga    147000
ttgatggcga gttggtatat catgtcgaag tgaaagaaga agaaaacgac ctgtttgata    147060
tgtttaaaga gcctgagctt cctgaactaa gtaaagctaa ggaattccaa cagacggctc    147120
gtacagaatc aaacggcttg gctaataagg ccattaaagg aacaatctct gccgaagaag    147180
cagaaggcat gagattccaa gtttgggatt atgttccgct tgatgtagta tattccgaag    147240
gtaaagttcc tggatttgct tatgatgtac gcttccgtgc actggaaatg atgagcaaag    147300
gctatgacaa gattattcta attgaaaatc atgtcgtaca caacatccat gaagctcgtg    147360
ctatctataa gacatatgta gaccaaggtc tcgaaggtat tatccttaag aatatcggtg    147420
cttattggga agataagcgt tctaagaacc tcgttaaatt taaagaggtt atcactgtag    147480
atttgaaatg tgtcggttcg tacgagcata gaaaacaacc tggtaaaatg ggcggcttga    147540
tgttcgtatc agaatgtggt cgtattcgtg ttaacgctgg gtcaggtctt aaagataagc    147600
ccgaagaact gcacgagctt gaccgtactc atctatggaa aattagagat tctcttccag    147660
gaactatctg ggaacttgaa tgtaatggtt gggtaactgc tgaaggtcgt gatgatggta    147720
cggtaggatt gttcttgcct atcattaaac agcgcagata tgataaagaa gtggctaata    147780
cattcgaagc cgcatttggc gtgaacttta cagaggcaac aggaataaaa tgaaagtatt    147840
atacgaagta attgctaaaa ctgatgatgg gcgaggaggt atttccgtcc ataccgaagt    147900
tcttgatttt gataatatcg atgtattcaa aaacttcaaa gaaaacattg aagagtatga    147960
gtctgtaaat ggattacagg tttggcgtac tgccacaata attaattaaa ggccttcggg    148020
cctttttcg tataaataga ataaacaaac gaggatatgt catggaactt ttaaatgaag    148080
ttttcgatga agagaatagc aaaatctatc ctgtcgagaa cgttaaacca aaactaaagg    148140
tgcctcaggt atttctgatt aaggtgccgg gtaataacaa tctaatgatt cgcttagtac    148200
atgggtcagg tcaaggtgat gcagttaaga atatcaaaat gggtgataaa ttcattcagg    148260
tatatgtttt ctctgtgtca gaaaaggta atattggagc cctcaagggt gggttaggac    148320
aagacccgat tggtgctatc aatacaatct ttgaaactgt caacaaagta gttaaacaaa    148380
ttaaagccga tgcagtaatg ttccgcttta atccaaagaa aatgcaagga caagataaag    148440
```

FIG. 20BBBB sequence.txt

| | | | | | |
|---|---|---|---|---|---|
| ctattcaacg | cattcttgct | cggttgatta | ctactcgcac | cggtggtcgg | ttcaatctaa | 148500 |
| tgaaagatat | ggcttactat | aaaggtaagt | atgcttattc | cattatggtt | cacaaaggta | 148560 |
| agaagcttga | agagattgaa | ggaattcctg | aaatttcaga | tgagttatac | acaaaggttg | 148620 |
| aatccaaagt | aggtgaaatt | tatgtgtcta | aagaaaccgg | cgaaagcgtt | accaaagccg | 148680 |
| aagcattggc | taattctatt | ggcgaaaaag | aagacaagaa | atctgaactc | gctgtaatga | 148740 |
| gtaaaatgaa | agtgtctcga | aaagatttaa | tccgagcaca | gtacggcaaa | tttgtttcat | 148800 |
| atgttgatga | agattggcca | gaaaataaac | gcgaacgttg | gtacgaatta | actactaaca | 148860 |
| ctccagtact | aaacgcagaa | ggcgatacgg | tagacctcca | aaaagatatc | aaagccggat | 148920 |
| tagaaaaatc | aattcctttt | tatgttgatg | atatcaagca | ctatcgtgtt | cgtggcggat | 148980 |
| atggaagtaa | ttttggcgat | gcagttgaga | gattatttgt | aggccaaatg | tcgagaatgc | 149040 |
| atgacgactg | gaaggttttc | attccttcgg | gttcagacaa | aatgaaaatc | gctgaacaac | 149100 |
| gaatttcaga | cgttgctgac | gttattgctc | aagctaaaaa | tcctgcatct | atggaaacaa | 149160 |
| tgcgtaaaat | cgttgaagta | gctactcgtg | gatttgatat | gcctccagct | gacgatttcg | 149220 |
| gagctttgcg | tcaataccaa | aatcttgtca | attatatgat | atccgcttat | gtgtcaattg | 149280 |
| ttggcgattc | tatatccaaa | gcaattgaat | ataaccgtga | aatgcaatct | cgtttaagcg | 149340 |
| aagaagaaag | agatgcaata | catcattact | gtggttctgg | ttattcattt | gttaataact | 149400 |
| atcttattgg | tatggaaagc | ttaggcgatc | cgattattga | caagaaaatt | cgtccgctcg | 149460 |
| attctgcctt | tgaaaaaggt | ttgcgtcttg | aaccaggcac | tcttttgtat | cgtggtcagc | 149520 |
| gaggaaaata | tgaagacttt | aaagataaca | ttgagtctaa | aatgttttat | ttccagaact | 149580 |
| atgtttctac | ttcgttaagt | ccaattatct | ttggtgctta | ttcaaatgct | ggtgattcat | 149640 |
| taatgccaga | cgcacctagt | tctgatttag | aaaacaaaga | aacaactgct | aatgcggtat | 149700 |
| cttctgttat | tggaacagac | aacttggaaa | gagttgatag | aggcgaggaa | gttgcctatg | 149760 |
| gcgatgagtt | taagtttgga | ttcgttattc | atggggctga | taaagttaag | gtagttatcc | 149820 |
| caggtgtctt | gtcaagctttt | agcgatgagg | ctgaagttat | tcttcctcgc | gggttggcaa | 149880 |
| tgaaagtcaa | caaagtatgg | ggaactcctt | ttagaaatgg | agttggtgta | gcgaataaca | 149940 |
| agacattcat | ggtagaaatg | acggtagttc | cgccagagca | aatcgatgaa | tccgttcatc | 150000 |
| tctatgatgg | tgacatcttg | atggaacaag | gaaaagtgga | acctcttgaa | gaaagcaagt | 150060 |
| tcaaaggctt | tttaaatgag | atttacttttt | cgccagaccg | ttctacagat | aaggttagct | 150120 |
| acacacgtac | catggagcta | ctggctggtg | ctatcaacct | ggatggtatc | ccagaaaaac | 150180 |
| ttgcataaag | ttgtttactt | atcacaagga | cgtgatacta | tagacttaca | caaaccaatg | 150240 |
| aggaaattga | tatgaaacac | gtattccgct | ttaacggtat | tgaatggtct | gctgatgtta | 150300 |

FIG. 20CCCC sequence.txt

| | | | | | | |
|---|---|---|---|---|---|---|
| aagatgcaga | gaagttcaat | gaagaagttc | ttatcatgct | tgaagggttt | aacgaaggta | 150360 |
| ctccgacggt | tcttattcaa | gatatcttcc | gtaagccaac | tgaaccatcg | tttgttgaag | 150420 |
| cggttctaaa | cggtaaagca | gaaggtatta | ttccggtcaa | agtagtttgg | actactaaag | 150480 |
| aaatgaaact | tcttcgtact | gagccagggt | ttattggctg | cattgcataa | aacaaagggg | 150540 |
| ccataaggcc | cctaaattat | tctgcttgtt | gaagtagtga | tattagaaat | tccaccacct | 150600 |
| gccccgccta | aacgagacaa | tcttgaagca | gacgtactca | agccctgatt | tggattaatc | 150660 |
| gtctcaattt | tctgaatagt | tttatcttct | aaccaatcca | ttgcggcttg | ttttccgact | 150720 |
| gaacctgttt | gcatgctgcg | ataagcaaac | gtgacatcaa | acacagctat | tgtgttttct | 150780 |
| ccatcgtaag | taaattcggg | agctccacat | gctacaggca | tagcccctga | gaacaggcat | 150840 |
| acagtatgtg | gtaatccatt | tctagcatga | aggttaactt | ggatatcaca | ttctacgtct | 150900 |
| tgtggcaatc | ctcgcagacc | agtcaccggg | tcttcaactg | catttaccca | atcttgcatt | 150960 |
| gctctatagt | tgcttgcttc | tgggtccatc | ctaaatgaaa | gaaccaacgg | ctccatatct | 151020 |
| cttccagtga | tttttatgtt | aggagcgtta | tggaacttat | ccatttcata | tgacagtcta | 151080 |
| ttctctggta | ttttagcaga | atacaccatc | aagcctgctg | tcggaaatgc | catgttaaag | 151140 |
| aaatcaagca | gataagtacc | tactgtgaat | tcacctaaca | acgactgtac | aacacgctgt | 151200 |
| gtcattgcgc | caatcataaa | tgtattcaca | cctgatttgc | gaacaacctg | tcgagttcct | 151260 |
| tgtgtcacta | tggttgttat | accctgattg | aattcacctg | gtgtcaatcc | aagccaattt | 151320 |
| ccatctaaac | ccatattatt | atacagctct | ccgccaaagt | cgtttagaag | agcctgggtt | 151380 |
| ttactagagg | gtacagtagc | gaatacaaca | gagaacatat | tagttctctg | gaaatcgatg | 151440 |
| tcagcagctt | gactcttaaa | ttcttcgaga | gtaaacatta | ttcaatacct | ccgatataaa | 151500 |
| cgttccctct | attaagagta | agtatttcac | gcatagtaat | ttcaagcgta | aacgtgcttg | 151560 |
| gaaggttagg | agcgattgct | aacccattaa | aatgaccgtt | cggtgtttta | tcaaagcgga | 151620 |
| tgctctgaat | ttggcacgga | ccaaatatat | cctctctacc | atccattgat | gtagaatatc | 151680 |
| caaaattacg | aacagtccaa | atcgttgggt | tagaaactac | aataacattg | cttaaaaacg | 151740 |
| atgttatttg | ctcaaacaca | gtgttttcta | ctttagctcc | atccggtgct | gccgatttaa | 151800 |
| gtgttccttt | ataccattca | tcaatagcag | ctttaacttc | ttttgcatat | gatgaattcc | 151860 |
| ccgtcacacc | gtaagaatag | tagttaaaaa | tttcatagat | gcgaataatt | tgtataaggt | 151920 |
| catctgcaga | cctaggagtt | aaatcccaag | taaacacttt | cgttctatta | tcaggtccgg | 151980 |
| catacatact | acgggcagtg | ttataaattt | gctcaccgtt | atcggccatt | aatccctgcg | 152040 |
| ttaaagattc | tatcgaccca | aacaccgcag | tagaagccac | gttgcttaat | acaccagtag | 152100 |
| cagtaccgct | gccgcgagta | acaagagaat | cgccaacatc | attaaattta | tggctaaccg | 152160 |
| aatcaacgtc | tgacttagac | cgtggtaata | gaatattagc | taccggcgca | gtacttgtag | 152220 |

FIG. 20DDDD sequence.txt

| | | | | | |
|---|---|---|---|---|---|
| tagaacttga | tgaattagcc | agtgctgaca | ttggtgaatc | gaatacagac | gataacatta | 152280 |
| catctcgtct | aaatgaacgc | aaatcaggag | tagttcttcc | tttaaaatca | tatgctgtga | 152340 |
| ataataatcc | gttacgatac | aagtcatgta | ctctcatatc | ttgtgcggaa | tcgtttccgg | 152400 |
| ctgagcgttc | ggccggaaac | tgcgccacct | tagtggtagg | cgcattcgtc | agtttagatt | 152460 |
| taccttggga | aattcgagtt | cctgattttt | tgatgttttc | aaggccatcg | gccagttctt | 152520 |
| caaaaatcat | tgttttcct | taagaggttt | tcatagcgcc | ttgcattcca | ggagcagctg | 152580 |
| ttgaagtctg | tggaggcgtt | ctataaacgt | atgtgctatt | cttatttaca | gcggtattaa | 152640 |
| cctgaatagg | ttgcgactgt | gtattagatt | cacgtgtacg | agctgcttca | cgactatctg | 152700 |
| cggcggcttt | aatagaagca | gactgcttaa | cctcaggctg | ttctgttgca | ggtatagctt | 152760 |
| cggcagttgg | agcaggttct | gatattttag | aatcaagaag | cttttgcaat | tggtctaatt | 152820 |
| caacctttaa | atcttttgca | acttctggag | ataatttctc | caattcttta | tatctggtgg | 152880 |
| ttgtgctttg | tactgcatcc | ttagcagagt | ctaatcgagt | ggaatcagat | gcatcagttt | 152940 |
| tttcaacata | tgcttttgta | cgcttgagtt | ctgcctcagc | attattacga | gctgtgatga | 153000 |
| ttttgaggcg | ttcgtcttct | ggcaagtctg | catacgctga | ctgcttttc | tctccgctca | 153060 |
| gcaatttatt | atattcatcg | tcatcaatct | gaccggtgaa | tttttggaat | ttagcagaaa | 153120 |
| gctttctttt | ccattcaggt | tgttcgtcat | attctctttc | ttgacggtca | acatattttg | 153180 |
| ctctcatttt | agcatcttct | tcatctagtt | ctgccccagt | aacagtttga | aatctgtcta | 153240 |
| aagcagcgcc | ttcaatgtta | tctgccgaat | cgttaaatcc | taatgcgcgt | aacattccag | 153300 |
| cgagaagctt | actcattccg | agcataatag | tttctccgag | cttgtcaatt | acatcaacca | 153360 |
| agccagaacc | aatggcttta | gctaatccgc | cccaatcccc | tttgacgaat | gattttacta | 153420 |
| tttcattcga | catctcgctt | attgctgtta | atagcggacc | ccattctttg | gcttgcttgt | 153480 |
| taaattcaac | aaagttcttt | tcgaacagtt | tagtccaata | attaaaatga | actttaatta | 153540 |
| aatctataag | cattatcacg | cccaaaacca | tggcggcagt | tttcgccatt | tgagccaaag | 153600 |
| cgctaacagt | atagctaaat | agcatgctgc | taattttatc | tgttaatgaa | atagttttc | 153660 |
| caaaaccaga | tttaacactt | ttaattaatt | ctccaaattt | taggccaaga | aactttttat | 153720 |
| tcttatcctc | agtttctttg | ttaggttctt | ttctttcctc | ttgctcttct | gtgttaggaa | 153780 |
| agaaatccgc | gtcaggacgt | ctatcatcct | gtggaggaat | aagcctttcg | agtaattcct | 153840 |
| ctagcggctg | ctgaaccgga | gcatcaggta | cttgttccgt | tattgtttct | aacgatgttc | 153900 |
| cagtaccagt | cttttggaca | tcttgctgaa | catcatgctt | tttagataac | aagtcggcaa | 153960 |
| gtttcgtgag | cttatcatta | attaacgatg | ctgtatcatt | tagtttagag | acagcatctg | 154020 |
| ttgtgcgttc | tgaagcttca | gcagttaatt | caacaccagc | tgaaacatct | tctactgatt | 154080 |

FIG. 20EEEE sequence.txt

```
tgataatttc atttgattta gtttctatta catccgaaat caaatcagta gacgcttgtt    154140
ggtcgtctaa gcgacgacca atatcttcta gcgtattaat ctgagcatca gcttgagact    154200
cagcctttt  ctgtggagcc gagtcagcaa taactcttct acgcattgaa ttcatttctg    154260
atttcttagt cattcaaata tttccattac gttaagcatg cctttgattg gtccttcagg    154320
tccatcaatg gctatagtgt ttactaagtc atcagcccac tttgttacaa aagctggaag    154380
cttcataaag tttatatcca ttggttttcc atctactgat tcaagaaatt cgcttaaaat    154440
tgaatctact gaacctagtt tggaataacg aggaggagct ctgaatttga attctttacc    154500
atctaaccgc tgagttaatc gttggcaaat gtaaacttta ttcaaatcgt aggtaaaatc    154560
atctttaaca accgtttctt ttattcggtt gttaaatgct aataaatgta gtacaacgat    154620
atcggattcg gctgccgtta atcctgggca aattgaatct aaaagaagat tcatgttttc    154680
gtctggtccc ttaacatctt tcatcagatt atggtgcttt aatccaagtt ttggaattga    154740
tatcgtcttt tcgtttatta ctattttctt aataggaaga atcacgttta agttcatttt    154800
tcaccttaat caaatctaca ggttcaaggg cagagccatt tgtgaacata tataagttag    154860
ttatagatgt gttatttgat atttcatgga taacttcatc tacataaaag tcagttctga    154920
actggtcctt taaatcaaca aaattgattt tcattccagg agttagttca aaattaccgt    154980
aacatttagt ttgagcatac ccgtcatatt gagccatcgt agaaatgcgt agtgcttctt    155040
catagccatt tctaaaaatc atgtcagaat atccgcctga cctattaatg aatacgctgt    155100
tttggccttc tccattaata attcgggtaa catctttgtc cacaaacgag tgtgcataaa    155160
atgttgcgtt tttcatggga tttctattat atctgtttga tttaacaagc cattcaaaat    155220
cccatgccaa tggatatttt aatcctgctg caaactgacc tattgtttga ggagctccaa    155280
acatgaatac atttgggttc tgggatatca ttgattcata atccatcatg ttaatcccag    155340
tgatatcttc ccatgcaaaa ataaattggt cgttatcagt agaaatgcct acgtttctaa    155400
cgtatcgcaa gtaatctttg agagtactag tccatggaac tcgtgggacg taggcgttaa    155460
ttccgttgat aggaggagca atcaatggtt ggtcaacata catcgcgcct atcatttctt    155520
ttatagtttc atatgcagaa ctaaaaaacg ctctactgaa cttgagattc attatgtcat    155580
gcagcgttcc aagctgaagg gtgataatgc tatcacctt  atcatcaaca ccgactgtaa    155640
agtgtttaat tccgtaaatt cgagtttgcg ttcttgatgt gttactgttt gcaacagata    155700
tttgaactag ttcatcaccg ttcatacgcg tgtgcatatt tttcgaatca taaaactgaa    155760
gtagaccctc attagtcccg cgtaatgaat ctctcattgt taatgtaata aatgtagctg    155820
ctaattcaac gaatctatta gctagccacg catcatatcc agaatataat tttatgctta    155880
tattaggata tcctaatctt tgtgctgtca tgatttaagg tccttttcaa taagcgataa    155940
ggttatgcca cgttctatag gcagcatttt cattatagaa ttcaaatcgt atttaccctg    156000
```

FIG. 20FFFF

```
sequence.txt
agaaaccaat ctatggttaa tctgataaaa tgtgaaaatc tcgtcaggat gtagcaatag    156060
cttaaaaata tcgacaatgt tatcatattt taatattgtc gtggtatcac agcatgatgt    156120
ttttaattca aaattaaagg gcttcatctg tgataaaatc ttttccaagg tttcaacatc    156180
tatagcatcg ataacggtca atttattgct atcgctcaat tcattccatg cgtattcccc    156240
agatgaatcc ttcacagata taatgttatc taaaatcatt ttacctgtat cgtcaattat    156300
ttctatgggt tttttgaact tgagcgttaa tccagcaacc tctactttg gatttaccaa     156360
tggaggttgg ttaagattaa aaagatactg cttatatttt ccgcattttg ggcacttcat    156420
tctgacaggt attttggttt taccaatact tgaaagaaat accttaagaa atatataagg    156480
acgatactcg gcaggatggt catgaaaata atcatccatt aattctgcta taagttgttt    156540
ttgttcttct tcagacttgg tgttcatgtc gtttctaacc aataaaaggt ctctataatc    156600
ttctactgta aatggcttaa aacgttggac accatctggt aattcgcatc taactatatt    156660
ggccataagg taatcctctt tatactattt ataataatt gaataagagg agtggatatg     156720
aacatcacat acaaatttga aacaagaata aatggcaaga atatccagtg ccgagctttt    156780
acactagaag aatacgctaa tttaattgca gcgaagaaaa acggcacaat cgatgaatgc    156840
attaaagcat tgctcagaga atgcactaat gccactgaat taaacaaaca ggaatcggaa    156900
ttacttatag ttatactctg ggcccatagt attggcgagg ttaatcacga ggtgacctgg    156960
aattgcacct gcgggcgtaa aattcctgtg ccattaaatt atacacacgc gcaaatcgat    157020
cctccagaag acctctggta tgacttaaag ggatttaaaa taaagttcaa gtatccgagt    157080
cttttgacg attcagacat tccaatgatg atatcaaaat gcatagatta tatcgtggtt     157140
ggaaatgagc agatttactt taatgattta aacgatgcag aaatcgatga tttatattct    157200
gctattacaa ccgaagatgt agttaacatc aaaaatatgc tattgaagcc gcaggttcaa    157260
ttagcagttc ccattacttg tgaatgcgga atttctcaca ttcatgtaat taaggggctt    157320
aaagaattct ttaagattat gtcatgagca atatcgataa attatattct gaccttgacc    157380
cagagatgcg acttgcttgg gatactgatg tgtcaaaaac ggtaggagca cgatcggtta    157440
aaaatagcct tcttggaata ataaccacca gaaagggggtc tcggccattt gacccagcgt   157500
ttggctgtga tatcacaaac gaattatttg aaaacatgac tccattaact ggtgatacga    157560
taaagcgtaa tatagtctct gccgtgcgta attatgagcc taggattaat cgtctatcgg    157620
ttgatgtgct tccgttatat gacgataatg ctataattgt tacggtgcag ttttctatag    157680
tagacgaccc tgatacgcta gagcgtatac gcatacagat gcgtagtaat gctaactcta    157740
gcagtagagt ataatgggac tagtccttcc aaagaaacag tagagtggag atagaatgag    157800
attagaagaa ttacaggatg aattggataa tgatttgatt atcgaccaga ctaaactaca    157860
```

FIG. 20GGGG sequence.txt

```
gtatgaagcg gctaataacc ctgttctgta tggtaaatgg gtgcgtaagc actcgacttg    157920
tcgaaaagaa atgttaagat tagatgccct caaaaagcaa aatcttaaag cacgattgga    157980
ttattacact ggccgtggag aggttggtgg tgaagtatgc atggatgtat atgaaaaatc    158040
agaaatgaaa actgttttaa gcgctgataa agaaatcttg ggtgtagata ctaaattgca    158100
atattgggga attcttttgg agttctgtag cgatgcaatg gatgctatca agtcacgagg    158160
ttttagcatt aagcacatta ttgaccttcg tcagtttgaa gctggcgcgt aataaataaa    158220
cttgtaaact aaggagacaa tcatgtcgaa tacggtatgt gtcgtctgta aaggaccaat    158280
cgatgaagca ttggttgtcc aaacagacaa aggcccggtt catcccggag cttgctataa    158340
ttatgcgatt gaattgcctg tcactgaaga cacagaagag caattacaag aaacgcagct    158400
tttaatttag tctagtgttg atgtagccaa ttggctttgc cccttccttt cggttggggc    158460
tttttatat cagaagtctt cgtcttcgtc atcttcagaa tcagcttcaa gagcctgtct    158520
acgccccgcc aaagcatccc gcacaatgat gtcatcagaa tcagcaagag tagtttcttt    158580
agagcgctta tcgtaatact tctcgagttc tttcagacca tctaaggttt ggcaagcatt    158640
aattttactc atgaagttat cgatagtagc ctcacgaatt gtggcttcgt aaatatcttc    158700
aaatttaatc atagatttac cgttttcatt acgtagttaa attttcatc agcatatcgt    158760
tgaatacgct ctaatgcatg ttttaagcaa tagtttaaat gtgtgtattt cttttagca    158820
ttggctgact tcggctttac gcccaggtca tcaatgatat cccacactgt agccaaagat    158880
ttatctttat gcttacgaag aacacgacca atagtttgga gtacgataat cttcgattta    158940
actggatggg ctaaaattac atgatgcagg tttttaacag aaatacctgt agaaaataca    159000
ccgtagcttg cgacgataat aattcccttt ccgttttctg ccatagcctt taaagcatta    159060
cgtgtttcgg tattaacttc gcctgacaca taatatacat gctcatgacc cgcagcttta    159120
atcatctcga acagctcttt accatgagct acatgtttaa acatcacaaa ggcatttcg    159180
tcacgcgctg caagtttagt agcaagatta gcaatccaac gatttctttt cttaacattg    159240
gtgatgaatt taatttcttc ttgatacgtt ttgcctttta aagcgtttgc ggctgcatct    159300
gggtatctta agaagattgt attaatttta agctcagtta cttgtccatc ttccattaac    159360
ttagaagttg atactggacg gaagatttca ccaaacatac caacatattg catgatatta    159420
gctttgccgt ctttaagaga accagacagt ccgtacttaa acatgcaatt tgtaagacct    159480
gcaatgattg ttgaaattga cttttcctgtt gcaagatgac attcatcatt catcatcatg    159540
ccgaattgag aaaaccattc tttaggctgc ttaacagcgg tctgccaggt agatacataa    159600
actaatgcat tcgaatcacg agcagtacca cctcgaatac ccagcatagc attgcgagga    159660
aataaacgat aatcacaaaa atcatcaatc atctggtcaa ctaacgctgt ggtaggaacg    159720
atgataagaa ccttgccttc gtaattttct acataatatc gagcaagtaa tgcctggata    159780
```

FIG. 20HHHH sequence.txt

| | | | | | | |
|---|---|---|---|---|---|---|
| agagacttac | cagcagatgt | tggaagatta | agaattctac | gccgattaac | tagaccttca | 159840 |
| tatacagcat | ctttctgata | ccagtgaggt | tcaatcttag | ttaatcctga | ataaatttct | 159900 |
| ttagttgata | accaattatc | aaaatcctcc | cgcgaaagag | tttcttgctc | gaatatagct | 159960 |
| ggatcgaaat | aaaccttata | tccgaattgg | tcagcgaatt | ttctgatttg | gccaacaaga | 160020 |
| ccaaacggta | agagacgatt | ataatctagc | agacgaattc | gtccatccca | atgtccatag | 160080 |
| cgatatttcg | ggttgaatct | gtatccatcg | gcttcgaagc | taaaatagtc | tctgagttca | 160140 |
| tagaaaatcg | agtcatcaca | ctcaatatga | acatgactaa | aatcttttaaa | tttgacttgg | 160200 |
| atgtcgtgca | ctgtactatc | ctcagttata | aatacaatca | tatttataca | ttacatgagg | 160260 |
| cacacccaat | gctagataaa | gactatatta | aagaaattca | ggcactcgat | aaaaaagaag | 160320 |
| ctaaagataa | gctcgacgag | tatgcccaaa | ctttcggtat | taaactgaaa | aagacccgtt | 160380 |
| catttgacaa | tatggttgct | gacttagaaa | aagaactggc | taaattggcc | aatgagccta | 160440 |
| tgccagaaga | taatgatggg | ctgtcaattg | ctgatttaat | tcaagcagat | gatgaaattg | 160500 |
| agggtaaagc | agtatttaaa | gatgaagcgt | ctgatgaggc | aaaactactg | tttgacgctc | 160560 |
| cagttaatgt | tggtattaaa | attcatgata | ttgacccagg | ttttataaa | gaaacccta | 160620 |
| aggtaaatga | cccagggttt | gaagtaaaaa | caccttctat | caatgataaa | ggattttatg | 160680 |
| ctgaagctcc | tattggagac | agcgttattc | atatagatga | tgaaggacaa | gttaccaata | 160740 |
| ttccggttag | tatcacggac | cctgaagaat | tctccaaagc | aatggacaaa | gtagttaaaa | 160800 |
| ttattaaaac | agacgaaatc | attgagcttc | ctgaaaactt | tagtccaaat | atgcaattgc | 160860 |
| taggtaagaa | cccaggatat | attactcttc | catggtggat | ttaccaatgg | attaaagata | 160920 |
| acccagattg | gaaatctcgg | ccaacgtcgt | ttgaacaccc | atcagcacac | cagacactgt | 160980 |
| ttagtttaat | ctattacatc | aaaagaaacg | ggtctgttat | gattcgtgaa | acacgtaatt | 161040 |
| cttcatttgt | aactttaaaa | taaggaacac | ctatggctta | tagcgtatct | attgctcctt | 161100 |
| tggctgcttc | ggcagtcatt | ggagcaacaa | ccaattttac | tgcaacaact | tctggagccg | 161160 |
| cagctgaagg | cacagaaacg | tttgtatgga | cagtaaatgg | cgtaaaacaa | tcttctgtca | 161220 |
| ctgcagctat | gaattatgtc | actgcaggac | ctgccggtag | taagactgtt | aaagtagttg | 161280 |
| ctactgttac | cccagcagag | ggtgaggtag | aaaccgctga | agcagaaact | actttgacag | 161340 |
| ttaagaacaa | aactatgcct | gcgattactt | taactttgag | cccgacttct | gtttctaaag | 161400 |
| aaattggaca | atcacaagta | gtcacggctg | atgttactgg | cgcaccgtca | ggagcaagca | 161460 |
| ttgcttatgt | ttggaaacgt | ggctcttctg | ttatttccgg | tcaaactggt | aaaacaatta | 161520 |
| ccttaactga | atcaacggaa | accagctaca | cactgaattg | tgaagtgacg | gtttctgctc | 161580 |
| cagactataa | taatggaact | gcaactaaag | gtattgctgt | tgctttact | aaaaagacca | 161640 |

FIG. 20IIII sequence.txt

```
tgagtggtgt ttcagttact ttgagcccaa cttctgtttc taaagaaatt ggccagtctc    161700
aggtagttac ggctaacgtt gttggtgctc cagaaggggc aagtattgct tatgtctgga    161760
agcgtggtac tgtcgttatt gaaggtcaga ctgctaaaac gattaccata actgagtcag    161820
cagaggctaa ttatactctg aattgtgaag caacagtttc tgcaccagat tacaatccag    161880
tgactgtaag caaaggtgct agcgtaacca tcactaaaaa gacaatgagt ggtgtttcag    161940
ttactttgac tcctgaatct attacagtcg agcagggggtc tgatgcatct tttaaagccg    162000
acgttatcgg ttctccagaa ggtgcatccg gaacttattc atggaccaaa gacggttccc    162060
ctgttgaagg ttcaactagt actttagtga ttgacacgtc tgatataggg tctcaagtga    162120
ttggggtttc tgttgaggtt tccgcagaag attataactc agtcacagta actacaactg    162180
gtaatgtaac tattaccaaa agggtagctc ctactcctaa cggagagctt ccgtatattc    162240
atcctctgcc gttccgtgaa acagcttata tctggtgcgg ttggtgggta atggatgaaa    162300
tccagcgaat gactgttgag ggcaaagatt ggaaactcga cgaccctgac agcgattatt    162360
acctacaccg atatactctg gctaaaatgc tagacgatta tccagaagtc gatgtacaag    162420
aatctagaaa tggatacatt gttcatcgta ctgcgctgga agcaggtatt atctatcctt    162480
aatattcggg agccttcggg ctcccttttt gctattcata gactggttta atatgtcttc    162540
atcacataga tgaggttatt atgaaagcaa tacaagctca cttgatgcat gaaagtggta    162600
aagatttcca agaaattgcg agagcattag atatcactcc agcggaagct gctaaattgt    162660
gggtctcagt tgagaaagca cacgaacggt ttaagcaaaa agaaaaagtc gtatatcgga    162720
aacgcttaac aaacgttggt ataaaatctc gtcataagaa acttgttaaa cacatgagga    162780
ctttatgatg tctaaagtag acccaattgt agtagaacga tttgaagaaa tgctttctaa    162840
gaaatttacg ccagctgcta atggggtaaa tgtctggttg tttgcatcta aatttgttag    162900
taaaatgatg gctgttcaga gttcttacta ctataaaagt ggtgcacgta aaataacgga    162960
tttgattaat gaacggtatg gaaaaattga ttggatgctg atggataaag atattccatt    163020
agtacttgag gttggaagca aaagtcaatt tgaaatcatg ctaactaaaa gcggatatat    163080
catgtatcgc ttcgtgccga gcggttatta attgctttaa aaatcgatgt ggtataatgg    163140
gctcagggga aatcctctga taccattatc cttatcccaa gatagatgga ctcctggttt    163200
tatattattt attgagagaa aaattatgaa ccttgcagat agaatggcta atacagctat    163260
taatgttgct acagaagaat tgagtgcagc aaaagaagaa gtattaccc agattgagaa    163320
aaccgcttta gcgggtaagc gtgagctaat tatgtatcct agcagtttag ttaagaaaca    163380
tatcacaaac gttcttaatt atttgcatga tgaaggattt gttacaaatt ataccagtgc    163440
ccagcgtaat ggtgatactg actttatgaa aatcacattc taaggaaatt ataatgtttg    163500
caaaatattc tagtctcgag aaccattaca acaataagtt catcgagaag attcgtggtg    163560
```

FIG. 20JJJJ sequence.txt

| | | | | | |
|---|---|---|---|---|---|
| ctggttttga | tatgcatact | gttgagtggg | tggctcgtga | gaaaattcat | ggcactaact | 163620 |
| tcagtgtgat | tattacccct | accgaaattg | ttccggctaa | gcgtactggt | cctattttag | 163680 |
| aaggtgaaag | cttctttggt | catgagatta | tcatgaagaa | gtacaaggat | tctttcgtta | 163740 |
| agatgcagaa | catgctgaac | accatggatt | tagtatctgt | tcaaatcttc | ggtgaatttg | 163800 |
| ctggcggtgg | tattcagaaa | ggcgtagatt | atggtgataa | agatttctac | gtgtttgata | 163860 |
| tcctgtcgga | ttccggtaac | gaaaaagttt | attgggacga | ttatgtagta | gaatcgtttg | 163920 |
| ctactggtct | tggtcttaaa | ttagctccac | tgcttggtcg | tggttcattc | gctgagctat | 163980 |
| ctcagtatgt | aaatgacttt | aaatctattg | tcaattacta | taatgaactt | gttgacacga | 164040 |
| ctgaccttga | acatgcaaat | aaacatgtgt | tcggtccaca | ggcttcttct | gaaaccggtg | 164100 |
| tagctgaagg | ctatgttctt | aaaccggtta | atcctaaatt | ctttaataac | ggtacccgtg | 164160 |
| tagctattaa | gtgtaagaat | tctaagttca | gcgagaaagc | taaatctgat | aagcctatta | 164220 |
| aagctaaggt | tgaactcact | gatactgata | agcgtgttct | ggaaatcttt | tccgagtatg | 164280 |
| taacctggaa | ccgtgtaagt | aacgttctgt | ctcatattgg | tactgtaact | gccaaagatt | 164340 |
| ttggtcgagt | tatgggactg | actatgaaag | atatcattaa | cgaagcagct | cgtgaaggtc | 164400 |
| atgacatgct | attcgctgat | aatccttctg | ctgttaagaa | agaactgact | actttaattc | 164460 |
| aaaacactat | tcgtagcaaa | tggcatgagg | ttttagaata | atgaggctgg | cgctgattgg | 164520 |
| ttcaagagaa | gcgccacgca | gagttctgag | tctaatgact | ataatcggtc | aacgcctctc | 164580 |
| ggaagagggg | cattttcat | attcaggtgg | agctccgggt | tcagatgaag | cgtggttggc | 164640 |
| gaaatacgat | aggtcaaatt | cttgtaggat | tattccttat | tctggctttt | gtggccatgt | 164700 |
| tcctgataca | ggtgttgttg | tatggtctga | attatcaaac | gaagccaaaa | tcaaaagcat | 164760 |
| cattaaggcg | agagaagtta | cgtcgtactg | ggatgaatgc | tcgaagatag | tacagacact | 164820 |
| atttgcacgg | aattctatgc | aggtattggg | cctagaatgc | actgagcctg | tagataaggt | 164880 |
| attatattgg | gcgcctgaaa | aaagatgtgg | gagtgtatct | ggagggacga | gagtagctgt | 164940 |
| tgatatagcc | cgtagacatg | gaatagaatg | cgtcaacctc | tatgataaga | atgtgtttaa | 165000 |
| atccctcgag | gaggaatact | ccccgaggtt | tgacatattt | agtttataac | aaaaagggga | 165060 |
| gccgaagctc | cccataaatt | agtccgcaat | aagcttaggt | aacttaacac | cgagcagtac | 165120 |
| agacatctta | cttcttcctg | ccatcttatc | catatccgca | gcattaatca | cacgagcttc | 165180 |
| gtcctcgtcc | aatcctacag | tatatggtt | aactgacaat | gcatatcgta | ccagtaaagc | 165240 |
| aacagaaggc | tgcaagctag | ctgggtcaac | aataacttta | aatgcaccaa | catgctcagg | 165300 |
| gtcgtctaaa | tccaagcctt | cggtatatgg | cgcataaaat | aaagaaccta | cagtttcctt | 165360 |
| cccaccaaat | tctgccttaa | caccaacaat | aacgtaatca | accggactgt | tagtatcaca | 165420 |

FIG. 20KKKK

```
                              sequence.txt
ataaagaggt aaaccgttat tcagcatacc gtatgcgttt tccggaatac ttccatcatt    165480
cttctgtgtt aaccaaccgg aagctgcaag caccgcagca caacgagtag atgctactgc    165540
ataagtacca gaataagaag tattacgttg aactgctgaa ttcatttcac aaatgaaacg    165600
atacagagta cgaccttgtt ccggagcaga atcttgttta gttaaatcta atacacccct    165660
atcggataca ccagctactt taaaccgaga agaaaccgta atcaatgatt gcaagatgtc    165720
tttattaatg tcttctgcca tttcagtagc aagtaaatca tcaataagtt ctggagcatc    165780
gaacccatta gcttctaaat cttgagctaa ttctaccgtt aaatctgttt taagcttacg    165840
tgatttaacc tgggtctgcc atttatcaat tttaaaactg gcttcggtga ttgggtctga    165900
atcgggtcct tcaaattttt cagtgactgc agcatctgac aacatacgaa tattattagc    165960
tgctactgct tcagacacaa ttccaaattc atcggtttct gctgtatcgg taaacgggct    166020
atctttaagt actttaaaga ccacattctg atatttgaac atatcgtctt tattgaatga    166080
gtctttattt gccatagtga gttcttcaat tgactcacgt tctggcgccc cgatttgacc    166140
tgcataagtt gcacccgtat taaacgtcag gtcaccatta gggttaagat atttgatacc    166200
atatagcgct gctacaggct gtttagtacg ctgtgtagca acaagatcgg tatagattaa    166260
tttagtagtt gcgcgcgtta atgcaacgag attagggcga ccaattaagt tgctactcgt    166320
tgtagttgac tcgcgcagaa gttcgttgat tttagccatt gcgctttcct ctgtggattt    166380
ataagtttat ttatatccat taaaacaact aaagggagcc cgaaggctcc cttattggta    166440
ttagatacct ttacccata cacgacggaa gtaagcattc ttaccaacag agttgacgat    166500
agaaggcata ccagaggtaa tacgaccttt cggctgttga gcagcagaat cggcaacgg    166560
gttaataccg ataccgtaac gggttttgaa ccccatgacc ggttggaagt tcttcggatc    166620
ggaaccacgc agcggggtca gtgcaacata cggagcatag tagataccag catccattt    166679
```

FIG. 21A sequence.txt

<210> 1074
<211> 144994
<212> DNA
<213> Unknown

<220>
<223> Description of Unknown: Bacteriophage F125/10

<400> 1074

| | | | | | |
|---|---|---|---|---|---|
| ctttgttcaa | attcctatat | ttagtttaat | accaatacta | aggtataaat | tagaagaaca | 60 |
| aggtatagga | ttaatagaaa | cagaagaatc | ctacacaagt | aaaacgtctt | ttattgataa | 120 |
| tgaaaaacca | atcaaacata | atgtttataa | aggtaaaaga | gtaaaaagag | gtctctttaa | 180 |
| aacagaagag | ggtagaatat | taaatgctga | tgtaaatggt | gcatttcaaa | taatgaaaaa | 240 |
| agtattccct | gatgtagaaa | taccaaggga | taatgggttt | gtgtataacc | cattcttaat | 300 |
| aaattgttaa | aaaaacaaca | aaataagaaa | aaatttctca | aaaagtagca | ttatgtgaag | 360 |
| agaagtgtta | cattattatc | gagaattcaa | taataaagca | tagggaaggc | tttttctatg | 420 |
| tcttatagaa | tgctttaaaa | tagattacta | aaataaagat | tggagattaa | gcttatggct | 480 |
| aaaaagaatg | ttaatgatgt | attacaacaa | gaatctgtta | cagtagcaga | taagtattta | 540 |
| caagttaaag | ttaaccgtga | cggttatact | cgtacacatg | aaggacaata | tgcgtacaaa | 600 |
| gtagtttcag | agggagaaga | actattctta | taccctgtac | aaacagatgg | taaaggtaca | 660 |
| ttaaatgtaa | tgaagaaatc | acctattgct | tacactgatg | gggacaatat | ccatttcgta | 720 |
| gtaaacacag | tagtagaccc | ttataatcac | tcatttatcc | gtactgaaga | tatcaaagga | 780 |
| ttagataaag | gtaaacaact | tattcaagct | ttcttagctt | tcgttgaaga | ccgtttcaaa | 840 |
| tttggtgttt | ataacgtatt | tgttgcaaac | agcaaagagg | atgtattatc | tattgtagac | 900 |
| cctacagata | atgatgcaga | tgaagttaaa | gatagtttag | agcacgcaca | tgaagatgta | 960 |
| attgcggatt | tccctgctag | ccctgctcgt | aaggacgtta | aaggcgtaga | ttcaggagaa | 1020 |
| ggtcaaggag | acacttcaga | accatcagca | cctaagaacg | ttcaagttac | tcctaaggaa | 1080 |

FIG. 21B

```
                                sequence.txt
gacggagcag acgtatcagc agaataatat atagataagg atggtaaatt tggctaagtt    1140
aaatttatac aaaggtaatg agttactaaa cagcgtagag aaaacagaag gaaaatcaac    1200
aatcacgatt gagaatttag atgctaatac ggattatcct aaaggtactt ttaaagtatc    1260
attctcaaat gattcaggag agtcagagaa ggtcgatgtc cctcagttta agacaaaagc    1320
aattaaagtt atttcagtta cccttgacgt tgatagttta gaccttacag ttggagatac    1380
tcaccaacta tcaacaacta tcacgcctag tgaagcatct aacaaaaatg tgtcatttga    1440
atcagacaaa tcaggtgttg ctagcgtaac atcagaaggc ttaattgaag cagttagtgc    1500
aggaacagct aatgttactg taactactga agatggtagt cacactgata ttgttgctgt    1560
aacagttaag gaacctattc ctgaagcacc tgcagacgta acagttgaac ctggtgaaaa    1620
tagcgcagat attactgcat aggaggacaa taaagaatgg aaaagacatt aaaagtttat    1680
agtaatggtg aagttgtagg ctctcaagta gctaataacg atggagctac tacagtatct    1740
attacgggct tagaagccgg aaaaacttat gctaagggag cttttaaagt agcatttgct    1800
aatgattcag gtgaatcaga aaaagtagat gttcctgaat ttacaactaa aactcctact    1860
gaagaacctt caggagaagc atagtaatta agaccaacta aaaagttggt cttttttat    1920
tgacaattta taatatctat gatacactat ataagaatta agaaaggag ggaaagtaat    1980
ggatattcca acaatattat ttagaaatcc atatgattat acgaaagtaa aaaaactaat    2040
ggaaaacaaa gagcagtaca ttgtagtaaa gtttgattct gtttctgttc ataatttaaa    2100
tgttcaaggt atgatgaatg tcatccaaga ttacctacac atctatggtt ataggggttaa    2160
agagtacggg caagaaaatg cttctaaaga tgatgaaaga gacgttaaag gttacttata    2220
tgaaagagta ggtgagtagg atatgggaat tatagtaaac tccaaccata ttcaatcaga    2280
cactttatat gagtatgata gcttttttga tattgagaaa gtagatacat ttgaagaagg    2340
attgctttca atacaagatg aaccaactgt tttagcagga ttcatctatg atgacatcac    2400
atttaataag gttattaatt ctaattcaga tattgatgat tatattaaga ataatgatat    2460
ttattatgtc tctgatatag ggttactccc tgatactttt atcactgttg attctgataa    2520
aaaatattat tcattattac aacaggtagt tgagttaagt aaagacctt ttcctaaatg    2580
ggtagaggat gatgcaaaag gcttaactaa gtattataac tttcaagact ttgaagatgt    2640
atttgattta aatagttttt acaaaaaaga agttgacatg gtaagagaaa agtgctataa    2700
taatggtaat gtatatttat tatatgaggt tctgcctgat tataaattac ctctagctta    2760
tagtttactt tcaaacaaag agcatggtat tgttattatc ggttcacaga cacgttctaa    2820
taatgatata ctgactttt atgttaaagg tatggatgct aaagcaatag ctagtatgtt    2880
caatgtagaa catgattatg attctaatat tttccataca tttgtaaaca gtcacattaa    2940
tattttagga aatcaaataa ctaagtttat aagagagaaa ggaagcagtt atgagtaact    3000
```

FIG. 21C sequence.txt

| | | | | | | |
|---|---|---|---|---|---|---|
| ataaaacaat | agaagaagta | caagcagtta | ttattggggt | attatttaaa | gatgaaggta | 3060 |
| aaattgtaac | atctaagttt | aataaaatta | ctaaagagtt | tggtttagat | agaatcggta | 3120 |
| aagatgacct | taaagaaatt | gtagaggata | ttagacaaga | cgcttatcta | aatgaactta | 3180 |
| aaaacaaagc | aattaaaggt | aaagtaacgt | taggtgattt | aaaagatgtt | gcagataacc | 3240 |
| aagtattcga | aggtaataac | taccatgaag | aagtatctac | ttacgtagta | gctaaagaaa | 3300 |
| aagaattgtc | tcacttaaga | gaacagcgta | agcacaatag | gcatactgca | taccctcaaa | 3360 |
| ttatgtttga | tgaacttaaa | gaacatatgg | ttaaagaatt | acaaggggaa | acattagtag | 3420 |
| aacatcatgg | aagtaaagct | aatattaatg | atacagagct | aattgtgtta | ttatcagatt | 3480 |
| tccatattgg | aagtattgta | tctgatatga | ctaatggtaa | atatgatttt | gaagttctta | 3540 |
| aagcaagatt | aaatcatttt | attaatacaa | cagttaaaga | aattgaagat | agagaaattt | 3600 |
| ctaatgtaac | tgtttacttt | gttggggact | tagtagaaca | tattaatatg | agagatgtta | 3660 |
| accaagcatt | tgaaacagag | tttactttag | cagaacaaat | ttctaaaggt | actcgattac | 3720 |
| ttattgatat | tctgaatgta | ctatctaatg | tagtttcagg | agaattaaga | tttggtatta | 3780 |
| ttggtggtaa | ccacgaccgt | atgcaaggta | acaagaatca | gaagatttat | aatgataata | 3840 |
| ttgcttatgt | agtgttagat | tctttattat | tattccaaga | acaaggatta | ctaaatggtg | 3900 |
| tagatattat | tgataaccgt | gaagatattt | atactattag | agatacctttt | ggcggtaaat | 3960 |
| ctattatcat | taatcacgga | gatgggttaa | aaggtaaagg | taatcatatc | aataaattta | 4020 |
| tcctagatag | tcatatcgac | ttattaatta | caggtcatgt | acatcatttc | tcagtaaaac | 4080 |
| aagaagattt | taatagaatg | catatcgtag | cttcatctcc | aatgggatat | aataactatg | 4140 |
| ctaaagagtt | acatttatca | aaaactaaac | cttcacagca | gttattattt | gtaaataagg | 4200 |
| aaaataaaga | tattgatatt | aaaacagtat | ttttagatta | aggatggtta | ataaatggat | 4260 |
| acaattttta | ttataggtgt | agcgtttata | acttttgcaa | catttaacat | agtctttaga | 4320 |
| ctatttgatt | tatggactac | cgagaaaaaa | atggtaagtc | aaggacaacc | cccgctaagt | 4380 |
| aattttgagt | actatcatgt | gatagtacct | tacttagtag | gtgttattgt | tattacacta | 4440 |
| agtattattt | ttagagattc | cttgtattcc | gcacaatcag | ggttcggtat | tattattaca | 4500 |
| agctttattt | acatgctagt | ttatgttata | attggtcttg | tagggtcatt | tatacttaca | 4560 |
| atattccaag | ctagaaaagc | tagacagtat | caaacacagg | aggataataa | tgaagttcaa | 4620 |
| tgatatttat | gagcaattaa | ttaaaaatga | tacagtacaa | aacattcatg | agtctcaaga | 4680 |
| tgacaaagga | aatatttata | caatccaatt | tgataaaggt | aatgataagt | atttatttaa | 4740 |
| tgttattaat | gatggattct | tgaaagaaat | gacaaacggt | atggtagacc | atcctgaagg | 4800 |
| tcagccatac | tcagtaagtt | taatcaataa | agaaacacct | agtatgtcag | tgaaacaata | 4860 |

FIG. 21D sequence.txt

| | | | | | |
|---|---|---|---|---|---|
| tttaacagat | gtagaagata | ttgtacctac | tattagaaaa | atggaaaagg | atttcttata | 4920 |
| gagtcaagtc | tttacttgac | tcttttact | atatatggta | tattaatata | gaggtgactt | 4980 |
| aaaaatggat | tttaatttta | gtgcttttga | taatagctca | ttagcaatga | gaattagtga | 5040 |
| gggtgtatac | tatttcaatg | atactcctta | ttactttatt | gagcatgtag | aagaagaaat | 5100 |
| gtctgagtat | gttattgtgt | atgacataca | tgacagagag | gaaaagaaa | atcctcagaa | 5160 |
| gaaatataga | atagaacctt | accaacgtac | aatacctggg | ggaacacctc | ttagtaactt | 5220 |
| aattaagagt | atgatgcctc | aacgtaagta | tcctaagaag | gttacagaag | accctatatt | 5280 |
| tgtagctaat | gttattcctt | taggaacaga | tacagtaaca | ggtaaaaccg | gtaaaggatt | 5340 |
| ttttgaaaga | gataaggata | gaactatcta | ttctcaaaag | gaaccaacta | aagtcgttca | 5400 |
| tggtcaatat | acaggtgttt | ttataggtct | aacaagtgtt | aagtggaata | gaacatatac | 5460 |
| ccctctagaa | agtgttgttg | agtactacaa | aagggttaaa | ggggataggt | taaatgtcta | 5520 |
| atgatgtagt | taagttttat | gaaaaagata | ttaaagacct | tatcagaact | aaaaaacaca | 5580 |
| tgttcaaaga | cgatgaaata | actagtgata | taaacgatat | acgaatcttt | aatgagaaag | 5640 |
| tcatttgtca | aggtaagtgc | agaacagatt | gtttagtact | agaccgtaat | ggtacagtaa | 5700 |
| tgggtataga | gataaaaaca | gaacgagact | ctacacagag | actaaataac | caattaaagt | 5760 |
| attatagtct | agtatgtaag | tatgtatatg | taatgtgtca | tgataaacat | gtacctaaag | 5820 |
| tagaacaaat | acttaaaagg | tataaacata | atcatgtagg | tataatgagc | tacattagtt | 5880 |
| ttaaaggcaa | acctgttgta | ggtaaataca | aagatgctac | accatcacca | catagaagcc | 5940 |
| cttatcatac | aatgaatata | ttatggaaga | caaacttaat | gacaatactt | agattgatta | 6000 |
| gagaccctca | tacgtataga | acagggtata | gctataatgc | tagtggtaga | tatagtggcg | 6060 |
| gagaaggtaa | tttctcccaa | acaactcaaa | gtaaaagaat | gaaaaaacct | gctattatta | 6120 |
| atcaaataat | tcattatgta | ggggtagata | atacttataa | actctttaca | agaggtgtta | 6180 |
| tctatggtta | taataatagg | tgggaagtta | tagaagaaga | tttctttaat | actatgaaga | 6240 |
| atggggtaag | agtaatcaat | gagcaaagac | aaaccaaata | gacgtaaaga | gatacaacat | 6300 |
| cagcctgtta | actttgcccc | tatgaatact | ctaacagggg | ctaataatag | tttctttgct | 6360 |
| aaaaagcctt | cagagcctaa | ggatgcaaca | tctgttattg | aatatcgtat | actatttatt | 6420 |
| aaagatttg | ataacgtaac | aagtacagat | gtgaaattac | agaaaaagta | tgcactaaat | 6480 |
| cttattagtg | aagcacttga | tgttaaagaa | acttacttgt | ctcttaagca | aaaaggaaaa | 6540 |
| aaaacagaat | ctattttgca | tacagataga | gtttattatg | ttcatagagg | taaaaaactt | 6600 |
| attggaaagt | gtagtatcag | agaacaaaga | acatttaaag | gtaaacattt | gatatttata | 6660 |
| ttcaaaacaa | gacatagagt | taaagcagaa | aggaaagata | aataatgtta | aaaggatttt | 6720 |
| cagaacatgt | agacaaacct | acaactacta | agaccttata | caagaccttta | acaagtggta | 6780 |

FIG. 21E sequence.txt

| | | | | | |
|---|---|---|---|---|---|
| aagtagaatt | actaggtgta | tcctacgata | gtgattactt | cccttcaggt | gttacagtac | 6840 |
| aatcttacat | tgaggatata | ggtaatgaag | atgagggtct | acagtttgtt | aataagataa | 6900 |
| atgtagtaga | atcaatgaaa | caggctgtag | taggtatgaa | taatcagtta | ggttcttcag | 6960 |
| gtcttggcta | tgtgagaact | gaacaactta | aaaaagagtt | agaagagact | ggactaatga | 7020 |
| cagatttact | tgctagaggt | actaacttaa | cctctactaa | gaaagtagat | attgtaagta | 7080 |
| cttttattga | gcctgaggta | acataccagg | atattactat | agctaaagat | attaaactac | 7140 |
| gtttgtataa | attagaagaa | gaatcaccat | taaatggtta | cactcatatt | gtatacttac | 7200 |
| ttactacaga | aaagctatat | gatggtcaaa | cactattcgg | tatgctctct | aaaaaagata | 7260 |
| agttatctaa | aggagatact | gataaattat | tagcattctt | cagaaacaat | agcttaataa | 7320 |
| gtaaaagtgt | attttgtgtt | aagttattaa | gtaaagacta | ctactttaat | ttatataaca | 7380 |
| cacatgagac | agggatattc | tttttagaag | acacagatgt | tattactatt | gcttgtggtc | 7440 |
| agtcatatgt | taaagttaat | actaaagata | ttaaatctag | ttatgttaaa | attgaagaca | 7500 |
| agactcataa | attaactgag | ctagtaatta | acttaaaagg | tgacgacaca | ttaactattt | 7560 |
| tattctaaga | gaatgttata | aatatgtgat | aattaagtat | aaatatacgt | tatatgagaa | 7620 |
| gttttcataa | tgtttttaat | acagaaacta | gttaagtttt | ttctacttgc | tctagtttct | 7680 |
| gtgaaattat | atttatgaaa | agttaaaata | tcttttaggt | aaaggctttg | taaatagtta | 7740 |
| aaaaatatat | taaaatttta | tacaaagtag | ttaataaaat | tatattacat | ttatatatta | 7800 |
| tgaaataata | acagaaattg | tgatatatta | tatagtgtaa | ccttgaaaca | gttgatgttg | 7860 |
| tagggtttgt | ttatgttcgt | taaactggtt | tcagaacacc | agttaccata | aataaatgac | 7920 |
| agttaaggag | agctatataa | tggctagaaa | aaagaattta | cgaaataaaa | acagtgatat | 7980 |
| aaaagttgtt | cctgataaag | aaaaagaaag | catattatct | aagctatatc | ataataaatt | 8040 |
| actacgctca | aaggtagata | atgcattaga | tgaagatatg | agttatgatg | atattataga | 8100 |
| attatgtaaa | gaatatgatt | tagaattgtc | taagtcagct | attacaagat | ataaaagtaa | 8160 |
| aagaaaagaa | gctattgaaa | acggttggga | tttagaagaa | ttaattgata | aacgtaaaaa | 8220 |
| aacaagtgta | aaagatatta | aggaaaaaga | aactcctata | ttagaagagg | agcaactttc | 8280 |
| tccatttgaa | caatcaaaac | atcacacaca | aacaatttac | gatgatattc | aagtactaga | 8340 |
| tatgattatt | tctaaaggtg | caaaaggact | agaatttgta | gaaactttag | accctgcgtt | 8400 |
| gatgatacgt | gcaatggaaa | caaaagataa | gattaccgga | aaccaattaa | aaggtatgtc | 8460 |
| atttattgga | cttagagagt | tacaattaaa | acaaacagct | caagatacag | ctatgagtga | 8520 |
| agtattatta | gaatttatac | ctgaagagaa | acatgaagag | gtattacaac | gattagaaga | 8580 |
| actacaaaat | gaattctaca | aaaacctaga | tttagatgag | gaaagtagaa | aattaaaaga | 8640 |

FIG. 21F

```
                                  sequence.txt
agctcttgat agagtaggct acacaattta gatagtgagg ttagagtaat ggcagatgag    8700
attagtttaa atccaataca agatgctaag ccaattgatg atatagtaga gattatgaca    8760
tatttaaaag acggaagagt actgagagtt aagcaagaca accaagggga tatccttgtt    8820
agaatgagcc cagggaaaca caaatttact gaagtatcta gagacttaga taaagaatca    8880
ttctactata aaagacattg ggttctctat aatgtatctg ttaactctct tataacattt    8940
gatgtttatc tagatgaaga atattcagaa acaactaagg ttaagtatcc taaagatact    9000
attgtagaat atacaagaga agaccaagaa aaagatgttg ctatgattaa agaaatactt    9060
acagataata atggtaatta tttctatgca cttacaggag aaacaatgct ctttgatgaa    9120
aataaattaa ataaagttaa agattagggt tgacagcttc tatagtttat gatatagtat    9180
atgtatacta aaaataaagg agctaacaat tatgtttatt tcattaaatc aagaagagaa    9240
agaattatta actaaagagg aaagtaaata cacaccacta gaaacatcaa gagagtttaa    9300
cacacctaaa gaagaattca ttgtaacaag ttataacgaa ggtaaacctt tagattacat    9360
tgcaaaagaa gctaaggtaa gtatgggatt aatttacaca gttctaaact actataaagt    9420
aggtaagcgt aataagaaat cacctgtaga agaaagaatt gcacatatct taaaagataa    9480
aaacttagtc aaagagatta ttaaggatta ccaatatatg aatttacagg acatttatag    9540
taaatataat cttcataaga atggtttata ttacatctta gatttatacc atgtagaaag    9600
aaaatctgaa cttaaggaca aagcattaga agaggataat attgtcgttg agtaagtaaa    9660
gaggttataa tatgagaaat aaaaaatcat ttcaagagca gttaaatgac atgcgtaata    9720
aagagaaatg ggtatctgaa gaggagttca ctgaagaagt ggctccttct gaagaacctg    9780
aagtagaaga agaaaaacta tatactttaa atgagttaaa agagaactta ctagatgctc    9840
aaggattaaa agatgttgta gctgattttc ctgcatctaa agatttatat gaacctaata    9900
aactatatat ctgtacaata cctaaaggat atcagtctac tgaagtacaa ccaggacaat    9960
atattggtat tagtactgga ttattatcag agtcagaaga cttcagtcat ttaagaggtc   10020
aaatgcctag aaatctttat gaaacttctc atgttttaaa acctttagtc cgtattaata   10080
atacaagtat cgaatatcaa cagcatgagt tacttgaaga tattaaagaa gacaagaatg   10140
tatatgatgt tgaattagaa gacttgagat tagcaacagg agaagaaatt tcttatttag   10200
agattgttga tagtaagttt tttgaaagtc gtattaatga agttcttgat ttttaccatg   10260
aactaacgga ttccgatgat ttgcttgagt attataacaa attacgagag ttagtcggaa   10320
atgatagaat gatttattgt ccgctttttaa ataaatgtgt taaaattata gattaatagt   10380
agtctcctct tatattataa ctgtaagagg agacattttt gtatagaggt gttaattatg   10440
tcaagaaaag caagtatatt ttatatacta gtggttattg ttttggcttt ctctatctca   10500
tcttattata tatcttcttt catgtatcac gacaaagcaa aaaatgaagt ctctactgag   10560
```

FIG. 21G sequence.txt

| | | | | | |
|---|---|---|---|---|---|
| ttatcgaaca | caggaaagat | taaagaagaa | aagaacgtag | aatttgttgg | tgactacaca | 10620 |
| ttgaaaaaag | tggaagataa | taaagcttat | tttatggaaa | cattacctac | ttacctacca | 10680 |
| ggtagaacag | gagataacag | catagatatg | aggtactaca | aaacaagtag | atttaaggaa | 10740 |
| ggggtaaatt | tcaagcttat | tagggtatat | actgaagatg | gagaagataa | tccaattcat | 10800 |
| aagtataggt | ttgaagcagt | accaaccaaa | aagtaataag | gaggtgactt | aaatgacaac | 10860 |
| attaattgtc | gtcatcttta | ttgctatcat | ttattactta | tggaacagtg | attgagtcaa | 10920 |
| gttaattctt | gactctcttt | ttgttttatg | gtatattaat | atatagaaag | gagagattaa | 10980 |
| ttatggaaat | ggcagattta | gaaagatttg | atgcatttgt | aagactaatt | tcagatgatg | 11040 |
| agctttcgga | ggaaagaata | ctggagttaa | gcgtagactt | actaaacccg | atactagaag | 11100 |
| gaggtacagc | ttacagagct | aaaaaacgta | ttaaaagtaa | atttggtaag | ttagaagcaa | 11160 |
| aaaactttaa | acgaaactat | aaattcttac | ttaagtcgat | agctcaaata | gaccaaagga | 11220 |
| gataggacaa | tgacagaaag | ggaaaaatta | attaaagaga | ttgaagaggc | taacagagac | 11280 |
| atacagttac | agttaaaaga | agtagataat | tataaggata | gtatacgctc | taaaggaaca | 11340 |
| agaaattata | tctctacaaa | ggtattagat | tctattacgg | ttggtttcat | agttagtttt | 11400 |
| ttaatactca | ttataatgcg | tgtacttgaa | tactttgtaa | caggtaatgc | tgtttattca | 11460 |
| cctttagcgc | ctgcagttat | cattatgttt | gttttagcac | tcggtacatg | gaaagtaagt | 11520 |
| aagatgaaca | aaatagtatc | ttatagagga | actattaaga | tgtactggga | gctaagtaat | 11580 |
| gctgagcaaa | aacaagctaa | ggtatttaag | tatcctaatg | atgaagtaga | tattgtatca | 11640 |
| aaacataact | taaggcaaat | aactttagt | gagattaata | tacttcatct | taaatatatg | 11700 |
| agatataata | aagcagtaga | acagcatact | aaattatcta | aagaactttt | taaaaaagat | 11760 |
| aaagaaacgg | ttgacaagaa | taaataagtg | tagtatagta | ttactaaagg | aggagagata | 11820 |
| ttatggttat | acctagtatt | aaagcacaaa | acaaattcaa | gaatgaatta | gagtattata | 11880 |
| aacaaggtca | cattagtgaa | agtaaaatgt | tagaattagc | ttttgattac | atccaagaat | 11940 |
| tagaacaaaa | taacgaatac | gttactaatt | tgctagaaga | ggagagatat | ggtgagtaaa | 12000 |
| tttatcggag | tgtacttatt | taatttacta | gtggtagctc | tagtttacac | agtaggattt | 12060 |
| ttattctttt | atggtgtagc | tagcttagtt | attattttaa | ctcatgctac | tattgacccg | 12120 |
| ttcgtattag | ctactttctt | aggaatagga | ttcttagtta | ttagaactgc | acacagaatt | 12180 |
| atggcacgag | taatcaatga | cgcagtagcc | caagccatta | aggataaaga | aaatgaataa | 12240 |
| aggggaattt | attatggata | aaacattacc | aaagtttagt | gtatatgaag | ttattgtaaa | 12300 |
| gactgtaatt | atgacaccaa | cagaaggaag | ttctgaccta | gaatcatttt | actttcaac | 12360 |
| tagagagtta | gcagaaagat | ttgttgaaga | gaacacagtg | gaaacaaaaa | acggtaaacg | 12420 |

FIG. 21H

```
                                         sequence.txt
tgtatctttt gctgttaaag aacgtaaagt aaatcaacca ggctaacatt aatttgttag     12480
ctttttttta ttgacaaatc attttatata gtgtatagta atattataca gaaaaggagg     12540
aattattatg aaagtttcag aagaagtaaa acagagttac ctagagaata aagctaatac     12600
taaaatggat aagataagtt ggtctgagtt aaaagctagt cctttaggta ttaccttagg     12660
tgatattata ttttatagtg tagttattat agataacatt atagctatta ttttaacttt     12720
aaccttgata ggtactatta ctgactcaat tgagagtact ttagcccaaa taatcgtagg     12780
ggtgttcata atcattacta tatatggaat cctatcagcg ttaatacccta ttctaattca    12840
taaagctgta tcaccgggat ggagttatac tgaatggaat gaatcctatt acatcagatt     12900
acctggggaa gagaactaca aatactatag taaatggtat ttagatttat taggagttaa     12960
agaattttac tataaaagag atagtggaga agaagtaaaa gaaaaaaata tatcatgggc    13020
ttttcaagct gaagtgaaaa gacctgaaga tgttaaccac tggaaaaacc agttgcttac     13080
taatagacct ttaacaattt tagaatataa aaaattaaag aaattagata aggaaagtga     13140
aattaggaaa caagaagatt tagaagaata caaacaatac aatagtaatt aaagaggtgg     13200
aaagcaatga taagctcatt tgatagtata ctacttgtca tatacattat tatagctttt     13260
gcagtagcta tggcaattat ctacttagta tttaaaggta tgactatttt actagataaa     13320
ctaatgatgt tattattaag taaaactaca ttagatgtag aagcttgttc tatgataatg     13380
gcagtcatca gtacaattgt gtttggaatt attgtacttt taatatggct agcagtaaac     13440
aatattttac tataaggagt tttattatgg atttttaatga ttttataaac agtgaatcgg    13500
atagagtagg taatcctaaa caaaagaaga aggtagagaa taagctacct tcttctattc     13560
ctattgaaga tagagaaaag aaattaaaag agataagaaa gaaatcatta tatattgatt     13620
taaggagaaa aagaaatgac taaagaaaca aatgtacttt acaaagataa gtatagagat     13680
tatactatag ttgtaagact agcaggtaat attattgtta ctgaggtaga taagaaacat     13740
aaaacagcat ttacacctat tatatttgac aatggtgtag aaggcgtaga gcttgtaatg     13800
cgtataggtt ctgtagagct tagcatgaca gatttacgtg agttcacaaa ggaagtatct     13860
acagctcaga aagctttaga atattttaat aaaaaacttt acattaaagg cttgacagat     13920
gaagcatttt aatatatact aaaagtataa ataaaataaa gaaagagga atgattatta     13980
tgttattagg aattttatgg tttatatggg gatttgtatc gtactttgta ttgatgtttg     14040
gaattgagtt ttgtaaagat agatggatgc caggtgttat cggagcagga gccttactac     14100
tattcttatt ttggattatg aaatctatcc ataatgctat gacagtagta tacttgtatt     14160
aggaggttgt atagatggat atactaatta ttcattataa agaaacaaat aaacgagttt     14220
taaaagaaac aatacaaaca atacaaaatc atttaaatga tgaacatggt ttggttaaga    14280
tgacagcaac aaaacttagc agagagaata tagagaaaag atttaataac tataatatag    14340
```

FIG. 21I sequence.txt

```
tcattgcaga agatgaccct gataattcgt atcattacag tgaagctgta gaagaagcag    14400
attttattat agacatacca atttcatatt tagatataca tgcaggagta gaatgggatg    14460
ttgataatcc tgtagatatg ctagatagga atccggattt tatagaagct gtaaataaat    14520
taaatgaaga cttaatgtta taaggaggaa atagaatgct aaatgaaaaa ctaaaaaacc    14580
tggaagatac aaaagtatac atgattaata gtattgcaag tttactaagc gcaagtacag    14640
gaaaatcaag taaagtattt tttgatgaag gaactattaa aattgtaagt ggtgaaacaa    14700
aagcagtaga agttattgat aacttagttc acccacactc aggacgttta cctattaaaa    14760
caacagaacg tattgcgcta ggtagattaa cagattcttt acagtttgtt atttcagaaa    14820
tagaagtagt taaagaccaa attatagatg aagaaaatga agcttacatt gattttgtga    14880
tggaagactg ggactgggat taatacctat ggacttatta actattgctt ctgttgcttt    14940
tatagctgta gtcattattg atttgattaa tgatgatatg agctatatgc ttactggtac    15000
tgcaatctta ataaatattt gggcaggatt ttatggatgg ttttcttac tacaagcagg     15060
tatgttactt ttcttactat tagctaggaa agttaaagat gataaggagt caatactata    15120
ctctagtgct tcattaatat gtgcactagg aatgataata aatcttcttt catttctta    15180
aaaataagta ttgacacctt tgtactttg tattatactt agtatataac aagtacagga     15240
gatgattaat atgagtaaag aaacaatcag aagacaattt caaacgcaa ttgagattat      15300
ggcaacaact aaggaatggt ggaatttcc taaaagtttt aatacaagta aagagtttaa     15360
aattaaaact tttaaaaatg acacacttgt atttgaagtt agggaaggta gtagaaattt    15420
aggaagcttt gtaattttta caaacattga ttttgattac gataaactag aaggaacttc    15480
aacacaatat atgattaatt actttgctaa gaaattaact aaagatatgt ttaactatca    15540
taagttacaa ttatagtagg aggtggaaag atgagagaag agttaaaacc ttttaatagg    15600
aaacaagtta atgttaaggg ttacttagat gatgttaagt attcaaagcg tagaagacat    15660
aaaggtaatc aacatgggtg tgttaaaatc acagttactg atgtaaagat taatggtata    15720
cctattgacc acgttaacat tgaagttggt atctctttct acgaaaaact aaaggagctt    15780
caaggaaaga gaattcaatt tgtaggtact gtttataagt atgttaaaca tgctagaggg    15840
cgcaaaggta gaattaaagg attttataaa gaggattata gcgtaacttt agataagaag    15900
ttacaaaagg aggaaaaata atgattaaaa gaagaaaaca tttagaccac tcattacagc    15960
ctgagaaagg atggagaaca gtacctttta atgggtatta tgaagcgcat cctacgggtt    16020
taattagaaa taaagtaacg aaaaagttaa ttaaaggtac acagacaaga aagaaccatc    16080
ctaagtggac tgctcatgag attgtatact taattaaccc taagaaaaca agttattcta    16140
ggggagtagt tattgcacat acattccctg aaatgattag ccaatcaaga ggagacctta    16200
```

FIG. 21J sequence.txt

```
agaacggtca tgtgtgtttt aaagatggtg accgaagtaa ttgtcatgta gacaacatgt    16260
ttattggtaa aggtaatgtt aacaaaaata tctataaatt aaatgattct tatttaacta    16320
gaaaagatat tgaagaggat gttaataatt tagttaatga aagattattc tctcaattag    16380
aattattgat taagaaaaat gaaccggaaa gaattacacc tagtaatcac tttattaaaa    16440
gagataataa tgtgttcagt atcacagatt tatctaaaaa ctcactagta gagtttgagt    16500
tagaaatcaa gaatattaag taaggtggtt atataaatga atgagtggta tgctttatgt    16560
tattacgaca aagtaggtaa aaagaaaata cctaggcaaa ttaaagctca cagggatgta    16620
tctgtattag aggatttaaa agatagatta gaagaacaaa atcctaaaga agaatacaag    16680
attaaaacaa caaaagaatt tgataaggag agataattaa tgttaacacc tcaacaaaag    16740
gattcattaa aagagcaaca aaaaaaatta agtaaaaaga agaaataagt cttgacaatt    16800
gagtatacat aggttatact taagttaaca aataaagagg aggtatgacc tatgttattc    16860
gtaattttta tattggcagt actgtttgta cttggattta tgaatggatg gaactcagaa    16920
gactagataa ggagtggttg taatgaagtt agaagataaa gtgttagaga gaattgattc    16980
tcttggaaat aaagcaggta acttaagtaa tcaagcaatg gagtcattag taaagtatca    17040
aattacgtac ggtattatag atattgttgt aagtatttta gttattgcac taacaatatt    17100
tttaggtaag gtttacctta aagaatataa gaaggttaaa atggatttaa aagaaagctt    17160
attgtatgat gactacgata ttctctcttt acgcaatagt tgcaggtata ccaactgata    17220
ttatgagatt aattaatccg gaagtttatg cagtaaaaga tttaattgag caagttaaag    17280
gaggaaattg atatgaagca gagagatttt gaatttgaag aggattttgt attaacttac    17340
gagtgtgagg attgtaagca ttttgaagac tggggtcatg atgaagagcc tgaagaatgt    17400
agtgaatgtg gaagtagtga cttaatcaat aatacaagtc atgaagatac tgagtgtgat    17460
atgtgtcgag gatatattga tatgtggcaa gatggatata gatatatggg agataataaa    17520
gagtatattg aaaaagagga atcaggttta atttgtgaag attgttatga gaaattagat    17580
atttaataag gaggaaatta atatgaataa agcagtagaa caagcaagta atgcattagg    17640
tcaaggattt tcagctatgg tatggcatca agtattagca gggttagggt ttattttatt    17700
aggattggta ttatctttac tggtttgggt attagtaaaa aaattccatg taccttttaa    17760
tcacccgaca gcttttgtag tgtactcaat tatgttagtt agtattgttg ctagttttat    17820
ttggggcggt ttacatgtaa ttaaccctga gtattatgct attttagaac ttaaaggttt    17880
tataaagtag gaggaattct atgactaaag aagagttaga gcaaaagta aaagaacttg    17940
aagcagagaa taaagagctt aaaaaacaaa tagaacgttt tgaagacgaa ggaggaaaaa    18000
caaaagatga acagtagaca aaagaaaatt ttaacattaa cagtaagtaa cttttttaatt    18060
ctagccttag atactgtagc actaattaga tataaaaaag gtaaaattaa acaagagaat    18120
```

FIG. 21K sequence.txt

```
tataacacag ggcaaattac aagaatgata gctacaacag ctaactcatt aggtattctt    18180
tacttagaag agcaagagcg taaagaagtt aaagatatta aagtaggtac ttttgaaatt    18240
ggagccttaa aaagatttac aaataataaa taaaaaaagt ttaagaaacc tattgacatt    18300
aggtttcttt tattatatac taatattata agaaataagg aggttaactt atgaaaggta    18360
ttatcatatt ttacaaggaa gagaccaaag aggatttagg atattttctt gggtttataa    18420
actttaagct agaaggatta tcttacacaa ctgaaggtac tttagtagat aatgatgtag    18480
tagtttttaaa ggataaccaa attaatgagg ataatttaga gcagtttagt atgtcaaaca    18540
ataatttagt tattggaata ctaggtcatt catctctttc agtacgcatc tatgaaaaag    18600
gtattagaca agagtttgat agagtagaag aatatttaga ggagttgaga caataatgat    18660
atttatatta atttttggtt tactatttat tttatcttta ctaggtattt ttatttattt    18720
tatagtttta cgaaagaaaa aacaattaat agaagaaaga gaatcatttg gtatttataa    18780
tagaacaaaa gaaaaactgg gtgatgtaac acgtttaggg tatgaggaag atgtatataa    18840
gttaatccat aaccaatcta ataaaacaat catagaggat aaaaagagta aagttgtaga    18900
tacaattaaa aagatgtatg agctagaatt aacgtcagta gatgtttcta aggtagaagg    18960
attatctcca cttgatacag aacctatgac aaatatgaaa ttactttcat ataagctaga    19020
tagagaagga ttatatagtt taagtaaatt tatttaggag tgatacaatg gaatttatag    19080
ataaaaataa tgtaattaaa gcttatgata taccaaatgt ttatttaaaa ggttatgtat    19140
tacaggcatg tgataaaaat ggagatacaa cagcttatga tggttatgac caaatacact    19200
ataaagaagg tagagtatta acattccctt ttgataaacc attaagaaag ataaatgtac    19260
tatcaggata ttacaaacta tttaaaaagg aggacataat atgatttatt ttgttagtga    19320
tttacatttc ggtcatgata atattagaga attcgaagca cctacaagaa gtcactggaa    19380
ctcagtagaa gaaatgaatg aaggtttaat tgagttgtgg aataatacaa ttacaaataa    19440
cgatattgtt tataacattg gagacttctt tttcaatatg aaaccttcta agtagaaga    19500
tatacttaat agactaaatt ataaagagat gatactgatt gcaggtaacc atgaccataa    19560
gaaacttata aaactatatg aacgtaatgg tattacagta aagtacgcag acatgattaa    19620
aaaggatggt aagagatttt atctaagcca ttatcctaca ctaataggta gaaaaaacat    19680
gtttaatatt catggtcata tacactcaca attaatgggt actgaatatc acatcaatgt    19740
aggttatgat gtagagggta aaattgccta tagttttgat gatattataa gtagagcagg    19800
tgaatatat ggagaaattc aaaggtaaag atttatataa aactagaatt agaaaacaaa    19860
caattaaaaa tttagttata aaacagaga agctacataa taaacacgga aagtatagac    19920
ctattggtca tgtttattac tatccgaaaa caaaagagtt tactttatct aagcctgaac    19980
```

FIG. 21L

```
sequence.txt
aaaagatatt tatagagtat atgaaagaat taggtttttaa tgtaaaacac aggagacgta    20040
agaaaacact tattatttat aagaatgcat tcactgaata cattagtatg tatcatgaag    20100
caatagagca gattgaagga gggacataat ggaatattta tttttattta taggtattgg    20160
catgataatt tggggtttca tagcacctta tcttgcattt gtagtttact ataaacatgt    20220
aagagaaaat cataatggat tcagtgatga ggaatctcta gaagaggcta cagtacttgg    20280
tatgggattc atgtttatag catttattcc tataggtata ctagttgtaa ttgaagaaat    20340
taagatttta ttctttttaag tgttgacaac tacaatatag tgtgttacag tataaaaaag   20400
gaggttaact aatgaagcat tttattttaa ttttagggat tgtaatccta gttattgcat    20460
tagggattgt aatcctagtt attgcattag gtattgtttt accggcatgg attttacagc    20520
tagtattatc tgcattcgga gttaaagtaa gtatttgggt atgtatcgga atatttattt    20580
taatcagtgc aataggaagt atgtttagta gaaattaaag gaggaattac aaatggcaaa    20640
atatgaatca aatattaatg gagagaatta tattgcaaca ccgtcacaag ctttaagaga    20700
agcactagca aaattaataa ctgaggaaaa gagctttgca gagtaccaaa ctaaaggtgg    20760
ggaacagtat gaatcacagt tacaactaag acactttgat gcaatgatat ctcagtatga    20820
ggaagctatt agagtactag aagataaata tagacctcag attttttattc cgaaagataa    20880
taaggaggaa aattaattat gaaagcagaa tcaatagcaa gatttttttaa tgacaaagta    20940
ttacaaatag aaggttataa agtaagatttt ccgcaggcta gttcatctta tattttagat    21000
atagatactg tagatgaatc agtattgttt ttagacgctc aagtatctac actttcaggt    21060
aagcatttat tagatacagc tattacaatt gagagacctg aaacattaag tgctaaagag    21120
ttatatacag aaattagtaa taaactgcaa gctattgtag gagaccaaac taaaacaact    21180
atagaactat caagatattt taaggaggaa aaataagtgt ctaataaaac tattacaaat    21240
catttattaa atttaaaagg aataaacatt gaaacgtata gtattattgc tcgtatcaag    21300
aaacaaacta gttggggtga taaaggagat tcttttgaaa taagcataag ttataaagct    21360
gataaagacc ctagaacagt gagatatatt acaactgaaa ttactattga ttatagtagt    21420
aataatccaa aagaaatttt attacaatta aaagataaga tttttttctat tgttgaggaa    21480
caggtagaga ctgacaatga ttttattgaa tctattaaag aaattaattc aactaaagca    21540
ttagaaaaac taaagcctta tatcaataat gaatattatt caatgtttaa atcttctatt    21600
gaaaaggaaa tacctgtagc tttatcttct gaagtactca atagatgtac aggtaaaaca    21660
agcacattag cttatttagc actagaaaag gatttaccct tagtagtgtc aaatgaacct    21720
atgagaaaaa tgcttaaaaa taaattccct caccttagag tatcttctgc tgaagattat    21780
tcaaattatg atattaaagg tgaaattgta ttaatagatg aagtagatat tgaccagtta    21840
tatagtgctg ataaagtatc tgttgatgca ctattagtag gtatcattaa aaattaaata    21900
```

FIG. 21M

```
sequence.txt
aatttataaa tacctgttga caacaggtat tttttatagt atactttaga tataaagaaa    21960
aaggaggtaa tataatgata cctataatag ttatacttat tggactcata ttatttttat    22020
ctagtggtta taagttggta ttaggtaagt actatgatga tgtagattta aaaatactat    22080
ttaccatatt tggtgttggg attgcattac tacttggagg atttatatta taaaggagga    22140
aacaataaat gaattatgaa gaggtactaa gaactattaa ggaaaataaa ccctgtaaag    22200
ttagattcac aggaaatatt ttagcaattg ttaatgagga atttaatgca gatactgata    22260
aaggagtttt acagcttgat gtatcgaata tcaacaaaga gggctatata agattacagc    22320
aatattgttt agaaagagat gactatacgg tagtaggagc tattttattt taaggagagg    22380
taaatatgaa ttatagagat tttattacag attgtattag cggtggttac aacgtacaca    22440
tcagtgttac agaaaaaaga gtgcacatca tttctgagat gacatcagca tcttatccta    22500
aaaaggaaat taacttagat gaactacaag cttatgtgta ctatatgaat aactttggaa    22560
gtcaaattac aacggagggg ttataaatgg aattggttat taatattgta gcagtattgg    22620
tcggtatgta tgctatttat ttctatgtta caaaatttag tactggctta tcaggtalttt    22680
taattgtttt agggatggct attggtcttt acttctactt agactattta aatgtcagag    22740
aaaatgttat tcgattagtt tcagtaatgt ttggagcttt cctatttagt attgaaatga    22800
tttataataa aattatgttc gaaattaaaa aaagcaatgt tcagaagact gttagagtgt    22860
atgataaaga gcagtaatga ttttttaccat aaagagtatc taaattactt taagtgctct    22920
ctatggtacc ttaaaatagc ttagaattga aattaaggag atgaatattt atgtatcctg    22980
aaatagatgt agaaaaatta gcgtacaagc taaaaagtac gagagaatat ttagaaagca    23040
ttaaaataaa agaagtagaa atttatgaaa tctatcatct taaaacaggt aagttagttt    23100
ttaaaggtga atatattgaa gtaaaagaat tactgaggaa aatgtataaa gagaattta    23160
cacttgtaga tgtagataca atgttaagta ttggtaaagg atttattgat gtaattaaga    23220
atatatcagc agaaaatgta ttccaaataa catataaaaa ggagctctca acaaaatgat    23280
taaaatattt tcagaagtag ataaagaata caaacccatt attactgaaa agtttcctaa    23340
tggtgagatt aattttaaat acgatgattt aaagtattta gtagaagaga acttaagatt    23400
tgatgttttc tttaaatggg aaaatgacgc agatttaatg catttgtata tgtttactaa    23460
gtatttagag caactaggta ttaaagataa agctgaattt ttagagattg catatctacc    23520
ttatagcaga atggatagag tagaagaagg gcataataat atgttcagtc ttaaatacat    23580
tacagaattt attaataacc ttaattataa atcggtatgg gtagtagaac ctcatagtcc    23640
tgtaacagaa gaattactta ctaattctgt tgctattgat gttacactta aattattaaa    23700
tcagtatatt gaaatgtccg aagagcctgt aacaatagta ctacctgata aaggggcata    23760
```

FIG. 21N

```
                                    sequence.txt
cgatagatat ctatttgatg tagaacgtat cttaatggaa tctaatattg aatcatattc    23820
aattgtatat ggtgagaaga aacgagattt tgaaacaggt aagattaaag gtattaaaat    23880
aattaaagat aaaaatactt tatatgataa ttgtattata ctagatgact taacaagtta    23940
cggcgggaca tttgtaggtt gtaaaaaagc ccttgacaaa cttaaggtaa gtagtgtatc    24000
attaatattg actcatgcag aacgagcttt tgcagaagga gcattactta gctcaggatt    24060
taaagatatt attgtaacag actctatgtt ccctaaaaat aattgggaaa aagctattgc    24120
taaacataga gctagaatca acggaactga attacaaata aaagatatcg aaagatattt    24180
ataaaaggag aaaaacaaat tatgctaaac ccaactttaa tgtgtgactt ctataaacta    24240
agtcacagag aacaatatcc tgaaggtaca gaaattgtat atagtacatt agtacctaga    24300
agtaataaat attatgaaca cagtgataat attgtagtat tcggtattca atcacttgtt    24360
aaaaaatatt ttattgatat gtttaataaa gagttcttta acagacctaa agaggaagtt    24420
attaatgaat acaaacgtac agttaaattt acactaggac aagaaaatcc tgatgctaaa    24480
cacttagaac aattacatga cttaggttat ttacctattg atgtaagagc tttaaaagaa    24540
ggtactgttg ttcatcctaa cacacctgtt atgacaattg aaaatactca ctcagatttc    24600
ttttggttaa ctaattactt agaaacgatt attagtactc aaacatggca agcaatgact    24660
agtgctacac tagcatatga tatgcgtaaa atgctagata aatatgcaat ggaaacagta    24720
ggtaatattg aagcagtgga tttccagggt catgacttca gtatgcgtgg tatgagttct    24780
ttagaaacag ctcaattaag ttcagcaggt catgcaatta gttttaaagg cagtgataca    24840
gtacctgtag tggatttctt agaatcatat tacaatgcag acgtagagaa ggaaatggtt    24900
gttgcttcta tccctgctac tgagcactca gtaatgtgcg caaatggtaa ttatgaaacc    24960
atggatgagt atgaaacata taaacgtatg ttaacagaaa tatatccaac aggaattttc    25020
tctattgtat ctgatacttg ggactttgg ggtaatatga ctaaaacttt acctagatta    25080
aaggatatta ttatggaacg tgatggtaaa gtagtaatca gacctgatag tggagaccct    25140
gttaaaatta tttgcggaga ccctgatgca gatactgaat atgaacgtaa aggtgcagta    25200
gaagtacttt gggatacctt tggaggtact gaaactgaaa aagggtacaa agtattagat    25260
gaacatgtag gattaattta cggagactct attaactatg aacgtgctca acaaatttgt    25320
gaaggattaa agaaaaagg ttttgcaagt attaatgttg tattaggtgt aggtagtttc    25380
tcttaccaat ttaatactcg tgatactcac gggtttgcaa tcaaagcaac gtatgctaag    25440
attaaaaatg aagaaaaact tatctataaa aatcctaaaa cagatagtgg taaacgttca    25500
cataaaggtc gagtagctgt atataaagac ggttcatggg aagataactt aaccttacat    25560
caatggctaa acaaacaaaa tgttaatcaa ttagaaagag tatttgaaga tggtaagctt    25620
tatagagacc agtcgttaag tgaaattaga gaataatta aaaataatta ataaatattt    25680
```

FIG. 210 sequence.txt

| | | | | | | |
|---|---|---|---|---|---|---|
| aaactcccta | ttgacaaagg | gagtttttta | ttatatagta | gggttatagt | aaataaagga | 25740 |
| gtgaaagaaa | tgatttataa | aatatcaaaa | cataattact | atagtaggtt | tgaatattca | 25800 |
| tcttatttac | ctgatgaagg | atttgcatac | atagattatg | tagatgtcat | tcttataggt | 25860 |
| gtagataatc | cgaggaagag | aaaagttatt | actttaaaag | cagatgagtt | taatcctagt | 25920 |
| gattttaagg | ttggtcataa | atataatatt | ataaaaatac | tatggtttga | gaaatgggaa | 25980 |
| tggttacagc | catagggagg | agaggtatac | aatgattata | gataaattaa | atggagttaa | 26040 |
| attagagatt | ggcggtcatg | ttgtatcatt | tagtgtaagc | aaatttaaaa | cgattaatgg | 26100 |
| tgagagacaa | ttacttgatt | accaccatat | caaaagacgt | aaacagaaat | attttagaac | 26160 |
| tactgaagaa | ttctataatg | agtacaaaga | aataaaaccc | gataagaatg | aaatagatga | 26220 |
| aatgtttgaa | tctttaggtt | atgtagatac | taaactagaa | gatgtagtaa | gaaaccaaga | 26280 |
| gaaagtgaca | gagatattag | gagttagtga | acaatactta | aaccaattgt | cttataaggc | 26340 |
| tatagaggaa | tatgtagaca | aaatagttac | cttagaaatt | aaagaattaa | aaggagaaaa | 26400 |
| atagtatgag | taatagttgg | gaaaaagaag | gagttaacta | ctgggaaaat | gaagattgcc | 26460 |
| ctagagaata | cttagagaaa | gcatttatag | aattagttga | atacgtagaa | ggtgttacag | 26520 |
| taccatctag | agatgttcag | cagttgagag | aggataagct | tagagaagat | attggatttt | 26580 |
| atgagtatgt | agcagataaa | taaatacaca | tctacctatt | gacttaggta | gatacttatt | 26640 |
| atataatagt | atacaaggag | atgaagtatg | atgaatggaa | aacaaattta | tgtattttta | 26700 |
| agtgaccagt | atagtaaaga | tatactcagt | ttacaattag | gacttattaa | ggaatggtct | 26760 |
| agaagagaac | taacttattc | agatgatgtc | gggtcagatg | cagatgttgt | tatttgtact | 26820 |
| gatatagtaa | gagatgattt | cgtaaaaaaa | ctaagtaaaa | ataatagcaa | tgcattattt | 26880 |
| gtgtttatta | gttcttttta | ttggataggt | tataaaggcg | gagaatttt | tgttgcagtt | 26940 |
| caagactatg | tgaaaggtat | gtaagatatg | aaaaaattat | taatattatt | tacattagct | 27000 |
| agtactttac | tattagcagg | atgtacaccg | gataatcatg | aaggaaaagt | tttaggaaca | 27060 |
| ggagaatata | gagagccaac | tacttatatc | aagtcaggaa | gtgttactgt | accagttatt | 27120 |
| ggtgaaatga | aatactatgt | agatttagaa | acagataaag | gtgaagaccg | tgtttatctt | 27180 |
| aatagagaag | tttatcataa | atttgataaa | ggtgatgatt | tctctaatgt | aggtaaaaaa | 27240 |
| gtatataaaa | atgatgaatt | aatatataaa | ggggactaat | tagtatgaaa | caatttatac | 27300 |
| atgataaaaa | agatagttat | aatagtacaa | atcgtaattt | tgatattcaa | tattataaag | 27360 |
| gtataccttt | acaacaaatt | gatagggggat | atggtcaagc | aagagctagg | agatttacaa | 27420 |
| taaataatac | gaaccaaaat | atatggatac | ctatgacata | tttaaaacct | aatggtactc | 27480 |
| ttaaaaataa | cattgatata | gattggatac | ttgttaaaga | aaaatgtagt | ttaaagaaag | 27540 |

FIG. 21P

```
                                sequence.txt
caggattagt aataaaaata aaaattacag gagatgtatt ataatgtata tattagaaag    27600
aacaattaga ggttttgccg gtcaaacaga agatatttta ccttattact ttaaaagtaa   27660
gaaagaaatt gttaattttt taaaactaat ggagttcctt aaagaagaaa caaattattg   27720
ggttaaaaag aacggtaatt atactattat aatcagggct aaaaggatat tatacattga   27780
agaacatata cagaagttaa aggagtggga gaatgactta tgatgtttat gtattatata   27840
aaagaggaga acctattgca caaggtagta tggaacattg cttagatgtc tattattggg   27900
aaagggtaca cggttatagt aataaaggtt atgaactatt acctatggga tatgaacagg   27960
aggaataact aatgataaat atagaacatg attatacaat aagaactgta gataatagaa   28020
agtatactta ctatagtaaa catgaatctc cagttacttt atataaaaat attataggta   28080
aagattgtat tgaagtaact aaatacggga aagataaaaa agttattata gctactaaat   28140
atattgtatc tattgaacga tggtaaataa ggaggtataa ctaatgaatg ctaggaaagc   28200
acgtaagaac actaaaaact ataaggactc taatgtagta actaaagagc aacacctaac   28260
ttatatttat aataagttaa actacttgat tgcaaataat agtagtcagg gtaaaacata   28320
tgtggtaatg aacctaagaa cagattatcc tgatgagttt tctttatcta aattaaaata   28380
tctaaaagaa attaaacagc actataaaga cctagtattt aatgtgaaaa cgcaagtaag   28440
gaaggcacag tggtcagaga aaagtataat caggtactac tttaacctag gctatataga   28500
cagcgtgtta gtacctatta tacacattag ttggtaatta caaggagagg tagttatgtt   28560
tttaaaaaa aagaagttaa gcaatgtaga gaaacaaata agacaaaacc gtaataaaga   28620
agacaaagaa agaaaagaac atcaagataa gttagataca gatatgtata aaacatatga   28680
attagataaa attgtagaag aacatttaag aaagttaaac actatatccc ttgaagaatt   28740
ataattaact tcagtgtgtt tagggacaag acttgtttat tattactcaa taggtaagga   28800
ttggaataaa caagtatata gtttaaacga attagaatat atgaagaaga aatttaagaa   28860
attaggattt gaaactcaga taacaaacga agatataggg tttcaacctt atatttattt   28920
aagattatta tgggatgcat aagtaattat tattaaagga gggatagttg gtgctgtacc   28980
tctaatgact attattattg cacagttaat tacagattat catgatagac attaagtatt   29040
gaatactgtt gactaataag gaggatatat taagaagtta aagttacctg gtaatattgt   29100
tgactagcaa gaagaagaaa atattattac tattaagtac ctgggaaaac ttttacctct   29160
ctcactcagc ctattactta ctaccgactt ccctaactac ttattctata gttataatat   29220
tcatttatta tacaatggta aactatagta ttccacctgt aaactatgct gaagcggtag   29280
taatctattg ttattatata ataatcttat ataatggtac gttaatctag tatattacat   29340
tagaatgatt ctaatctagg attttaatct ttagacccta ggaaaagtgg tactaaaata   29400
taaaacccta taggtatggg attcttattt ttaaaattac taaaagtat taggttttcc    29460
```

FIG. 21Q

```
sequence.txt
ctagggcaaa gttttaatgt acctaaaata gtaagtagct ccttatcatt tagggttcta    29520
taattgagaa tattgaaagc taatccgctt caattgtaat taattgttga caactatgaa    29580
gtgggtatgt tatacttagt atataaaata ataggaggaa ttaataatga atctgacatt    29640
tgaagataag ttagaagact tactaaaaaa ggtacgtagt ggtgagatag aacctatcga    29700
gtactctcaa gttaatgatg agcaccctaa tggtaaaact acttgtggcg ttacttttaa    29760
gtttgatatc gacacaccaa ctaaatagga atatgaagcg gttaattccg cttctcttac    29820
ttagagtata taagtaactg tatattgtaa gtaggagtaa tcaaatttag gagatgagat    29880
agatgataat attatttacg caggattatg ataaaccct aatgaaagtg atattagggg     29940
atattaatac tatgagacct aattggaagt acagtgttaa ccatcctgag aaagaagagg    30000
atgttcatat acaagcttat gaaggggaag atatatttga tgatatagag gagttatcag    30060
atagtacaca ggatatagtt ataggtgtta ctgaagatga ttgtatatca gagtctcctt    30120
atgactttaa tggtgggctt agattagtca ctaaacatat taaggaacat atagagaaat    30180
tcttataggg agtgataata tgattgatat atacttagga gaaggttata ataaagaata    30240
cttgtctaag gcactcagat taatcaatga ccatgctcct agggagttaa gttatgattt    30300
taataatgta gaagcggatg ttaatattca cacgatgtta tatgttaaac ctgaagatag    30360
gtatgtctat aaggatatat cttatgactt cccgggtgat ttaattattt gtatagttga    30420
agatgatgct attgtgtatc accaaggtaa acaggtttca ggtattagta ttttaagaat    30480
aatagaagag ctcatttaag aagcagttaa gtaaaaaagg ataaattgta ctagaaaatg    30540
tataccgctt ctgtatggaa ggctgagagg gcttagaatt gaaaggggag atataatgat    30600
agagatatac cttagtgaaa attatgataa ggatttatta aaagcggaat taaaatggat    30660
taaggagacc gcttcaagag aactaactta tgatgttaat aggaatccta acttagatgt    30720
acatgttagc ccatttagat atactaaaga tgaagtaaaa gaaataagtt tacatcctca    30780
atttgaagac gatgtatgtg tatttatagc ggagacgtgg atacatgaat accatagagg    30840
taaatcaata ggcgtagata gtatggaaga atatgtaaag gagatgtaag tatgtttaaa    30900
gtatattaca cagtctacca taaaggtagt atgaaaacaa ttaaagataa gctagataga    30960
agtagtttaa tatacttctt gtatgatact tggtataaag atattagtaa tgtattccct    31020
aatcactata ataaagagtt tggaagtaat agtgatgata tagacataga taaacttatt    31080
gaagcggtta atgaggaggg tatattactt atcaatagag gtaattatgt tacaataaga    31140
gaatggtagg ataggataaa cttaggatag aaaataattt aggatgagtt acgataggat    31200
aggatacgat aggataggat acgataggat aggatacgat aggataggat aggggttaa    31260
gttaggatgg ttactttaac atacactatt attcataaag aatctgatag ggtaatagct    31320
```

FIG. 21R

```
                                   sequence.txt
agtggtttag atgagttaga ggttataaac ttagttcaaa ggatggtaaa tactaatcta    31380
gttactgata tatcattaga tgattatata cgcagaccaa gtggagatat agatgtactc    31440
aatttactag tagatattag aagacaaggc gtatttgatt tcaatcacac ttggcacgta    31500
ggataggagg gataggatga tagttatata tacagatgtt tctaaggatt atttaaaaga    31560
cgagttctta ccttggctta atgaaaggga tagatactta gaagactata aagatgaatt    31620
acctgaggat atagattcct cttatattgt atcagttgta tactgtaagg atatggaagg    31680
tctattagaa agaaaagaca ttgttattgg taatagctat aatgaacctg tagctttatt    31740
aggtgttcct gagtttttg gtaattatag taattatttc tactatagag gagaaagtat    31800
tagtaaacat gacctaggag aaattgttag gttaaaagct tggcaacgta tgggcggaga    31860
ttgactaagt agctctccct aatttcacta agtagctccc taggaattgc ctaagtagct    31920
cggtatgatt ttaccctaag tagctccctc tgttttctac tagtttattt taaccgcttc    31980
aggtgtctat atatagacgg ttggaataat agcagaccgc aaaaataaat acactaggat    32040
attattccca gtgtattata taattttttt atttaaatct ttttatattt ctatttattg    32100
ttattctact tacattatac atatttgata attcttcttg tgtaaaacct ttttcagtat    32160
ataatttata aatattttt ctttcattat ctgttaatga tttaccacgt ttaaaattgt    32220
ttattgtttc atctttatga tgtaaattat tatgttctgt agggctaata cattgtaaat    32280
tatttatatg gttattttgt ttattgccat ctatatggtg tatatgataa tcttgattaa    32340
aatcattgcc aaaatattca tatactaaac gatgtataga atgatgttta taattaattt    32400
taactatttt atagccttgc ttatgattat gaggttttac taacttttca atcatataat    32460
aattaccgtg tcttttatt ctaccatagt tagatactga ataattaaat atattattaa    32520
tattattttc tatgcgtttc catttctcat taggtaaatt attaatacta ttataatctt    32580
ttaaattgta ttgtaataaa gtatcaattt taacttttct tgccttgttt atatcatctg    32640
tcatacgata aaagttattt ttatctttt ttaattcctt atttgttttc tttgaatata    32700
ctttgttttc ttttatatag tattttgaaa acatttcaat gttatttata ttatgtttca    32760
tcttctcaac tccttaacta tattctacta tataataggt aatttgtcaa gttaaaaaag    32820
tttttaaaaa cctattgact tattactttt tagggtgtaa tatagatact gtaataaata    32880
acacgaaggg aattgatgaa aatggaaatc aaagaaattg ccgatacaat tatgtattta    32940
tttaatatgg atggttacag atgtgcagaa cctccattat atgaaagcac actaaaccac    33000
acacgcacac acacggcgtt aattgtttct attaagggaa actatgacac agtgcagatg    33060
ttccgcaaaa cgcctataat gagcatgaga gggcaaagcc aaccggctag tatgttagta    33120
aatgtaattg atgatgtaat tataatagta tatgaaaatg tagtgtacgg agttcaaaac    33180
aaagaaataa aattcattga agaaatttaa aatagggggt tgcaatcctc aagcatctat    33240
```

FIG. 21S sequence.txt

| | | | | | | |
|---|---|---|---|---|---|---|
| agtaatataa | taggtgtagg | ggatagcaac | acacctcaaa | aaaactttt | aaaaagtta | 33300 |
| aagaaaagtg | ttgacacctt | ataagataca | tgttattatt | aagataacaa | ataagacaag | 33360 |
| ccacttagca | aataacgaaa | ttaaataaaa | aaattataga | ataggatttg | attattatga | 33420 |
| caaacaaaaa | ttacttatac | gaagaaactc | acacagtaca | agggcaagac | attacggctt | 33480 |
| tcagaattcc | aaacgacaca | aacggcaacc | cacgttatgt | agtgcatttc | atggatttaa | 33540 |
| atattaaact | agcagactat | gacaacatca | ataaactata | cggatttaat | aaatatcgtg | 33600 |
| ctaaatggtt | tggcggtggt | gtagtattcc | aaagctataa | tatagaagat | acattaaatt | 33660 |
| ttgcactaga | taaagttaaa | gaaatagaag | cggttaagaa | ttaaaaccgc | ttctgaatta | 33720 |
| aataaaaaaa | ttatataaaa | aggatatgat | aatatgatat | tagaaataga | aactaaacca | 33780 |
| gttaaaacat | tgaaagcaat | taaagacgat | acaaaaaata | ttaaaaatag | tatagcagaa | 33840 |
| catttaggat | taaatagaga | acaatttaaa | ttatcaaatg | gttaataac | tttaaaaggt | 33900 |
| tattcagaag | aatttaaatg | ttggtataat | ttaactagca | caattggtaa | ttttcctaaa | 33960 |
| tatttaaaat | cagaattata | taatgaatat | aaattatatt | gtaatgtaga | attaaaaact | 34020 |
| aaataaatta | aataaaaaaa | ttatacaatt | ccctaggatt | agatttctag | ggatttttat | 34080 |
| ttattttaat | ttatataaaa | aatttattta | ttaaataaat | tagtgtaaaa | ttgactattg | 34140 |
| acaaggttgt | atttttatg | gtataatgaa | gtgaagacct | ttttagtat | aaaaaaatta | 34200 |
| ttatataaaa | aatttatatt | aaatgatttt | agaaccgctc | tttctcgtta | cctcgtcatt | 34260 |
| tatatagcgc | aagggatagg | caacttagcg | ctttgtttta | ctttctatat | atagtatact | 34320 |
| atgaataatg | gtaattgtca | acacctttca | gaaactttt | ttactttctt | ttattattat | 34380 |
| ataaaaaat | tatacatatt | ttatggctcc | acttccatta | tataataatt | cagtcttaat | 34440 |
| gtcaatagat | aaatgtaaaa | aagttttta | aattaatttc | attaaatcta | ttgacttgtg | 34500 |
| tttctttcta | tagtaatata | taggtatacc | aacaagggag | gcaatacaaa | tgctaaaatt | 34560 |
| caaatggaaa | aacaaaacaa | ttaaatcaac | tcaaaaaacg | gataacattc | tattacttat | 34620 |
| tataggtggt | ttagttgcaa | caatcacacc | taaacttgta | aactggtttt | tactactaca | 34680 |
| agataatata | aatattttt | taagataact | attgacaacc | tagaaacaac | atgttaatat | 34740 |
| taagatacaa | ggtaagggaa | gcggttgacc | gcttccaacc | taaataaaaa | aagtttaaaa | 34800 |
| aaactattga | cagtcacttg | aaaccatgat | attattaaga | taacaaaaaa | caaacagaaa | 34860 |
| aggaattgat | gaaaatgttc | aaattacaaa | ataaagtgga | aattatcgta | cctaaggaag | 34920 |
| ataacaacgg | cgttgagatt | gcagacaaac | gtattaaaga | atatgtaaac | agtatcacaa | 34980 |
| tggaagcggg | cggttgcact | attacagaaa | ttaaggggca | atggtattca | gaagatgaaa | 35040 |
| agcgtatcat | ggaagataac | aacttaaatc | ttgaatggta | ctacattcca | gaccgtgcaa | 35100 |

FIG. 21T

```
                                    sequence.txt
aattcatgac agttgaatta aaaggcattg taagacgttt aattgaagtt tacggacaag    35160
aggcaatcag tattaaagtt aatggcacat tgtacattgt agaccaatca gacattgaag    35220
aattacacac aacattatta aatatcatga aataaaaaat ttatataaac cgcttcggat    35280
taaattcttg aagcggtttt tttatgtaaa atttatgctt gacaaatgta ttaaaaaatg    35340
agataataga gtgacgactt tttttagtat aaaaataata ttatataaaa aagttataga    35400
gtttttaagg ctccaagtcc attatatcaa ttttgctact ggttgtcaat actttctttt    35460
tttatataat aatttaatta tcttaaagat accgtccact tccattatct caaattttcc    35520
cccaaagtca agaactttct ttcaaataat ttatttaaaa aagtttacaa aaagggttga    35580
cttattttgt actatagtgt aatatataaa gtgtagtaag gaagcggagg aaataaccta    35640
aaaaagaat ttaaaaaaac ttttaaaaag gtgttgacaa acttccaaat acatgataat    35700
attaagatag ttaaaaaaac aaaaaaacga aaaggaattg ataattatga acagattaga    35760
aatagtaaaa gatacggcaa tggaatatat ccttatgatg gataacagtg ttatggacgg    35820
agttatgaca caagaggaat acaacgaagc ggttagcttt gaaaaggtgt atgactacac    35880
tctatcagaa gcaaataaag aatgtaaatt cttaggcggt aaagttttaa ctttcctagt    35940
acatgaagca atcgaagaat acgcataaaa aaacttaata aaaggggttg acattcaacc    36000
cctaccatgt taatattaat atataccaaa tgagaggaat tgataattat gagatacgaa    36060
attgtaacgc tagttaatca agaattgttt atgtatgcaa cattcaacaa gcaggaagca    36120
gaagcaaaat atagtgaatg gtgtgaactg tacggtcaag aaaatgtaag catggaaaaa    36180
aattaaaata agctgttgac aaactaaccg cttcatgata atattaaact atactaaaga    36240
aaaggaaatg atacaaatga aattattaaa ccaagaaaac caaatcgtaa ttagcatagc    36300
aacattagag agtgtcaaac aagccctaat ttgggaatac atcgaccaca tagattataa    36360
catctggaac aatgaacttg atgacacaga agcggttgta aaaatttctg gtattcttca    36420
atcaatcaaa tttgcagaca ctatggaaga cctgcaggaa tatattgggg atattggttg    36480
gaaattaatt taaagaatt tcaaataact gttgacacct tagcagatag atggtaacat    36540
tagggtagtt aaaaaatact aaatgaaaag gatttgattt attatgaaaa aaaatgttaa    36600
agcaagcact attgaatggt tagaattgac tcaagggcat ggggagtttg atggtttcga    36660
tgaagaagat atggacttca gaaaactaga tgatgaagat attaaatggt attttgaaaa    36720
ttggtacttt acagaggaaa aacaagaaca gattatagac gaaataggtc aagaggaatt    36780
tgaagaagcc tattcagatg atattaaaga atacaacaat taatacagga agcacacaga    36840
gacacacaga gaagcttaac cgcttctcta atattaaact attaggagat gtttataatg    36900
acaaaattta aattgattga taaaaatagc ttttacgtaa atgacaatta caataacgaa    36960
acttatttaa cttctcaaat tgttctatca ggtgaagcgg gtagattgtt agatgatatg    37020
```

FIG. 21U sequence.txt

| | | | | | | |
|---|---|---|---|---|---|---|
| atagaagatt | gtgaagacga | acacgacaaa | gacaattaca | agaaactaga | cactaacaat | 37080 |
| attgatgata | ttgattatat | attggaatgt | gctaacgttt | atatttaccc | ttacaataaa | 37140 |
| acggaattta | aatattaaaa | taggagatgt | tgaatatgaa | cacaagacgg | gcaaataaag | 37200 |
| cgttaaacga | agcggttaga | ttattagata | agcaaataga | agacacacag | aagaccatgc | 37260 |
| aggagctaaa | caaacaacta | gaacaacaaa | taaaagctaa | acaggaacta | atgacactag | 37320 |
| ttgacgttat | gactggtgat | gatgagtaat | gaacattaaa | gaagctcaca | aggtcgttag | 37380 |
| gagtgcaaag | agcaaactcc | tgcaggagca | ggagcacata | acaaaccata | tcatagagga | 37440 |
| ctacatcata | gaggagcttc | acagacgcac | acagggaagc | ggaacaatac | agatgaacaa | 37500 |
| taacaccgct | tcatatagca | atggctcata | tggtagctta | gaagagctta | gagaagctta | 37560 |
| tgacctatcg | tcattatcta | ctggtgagat | taaagaattg | cttgaaacat | ttgtttaaat | 37620 |
| ttatttaaaa | aagtttagtc | aaaactattg | caatatcttc | agaatactgt | ataatagtac | 37680 |
| ttgtaagata | aataaaacaa | agaaaaggaa | tgattaatta | tgaaagaaca | aatcaaacaa | 37740 |
| tttgagaaag | aattagaaat | ggcggtaaat | aacttattcg | tattacatga | ttgtggcgta | 37800 |
| tcacaagcaa | agattgaaga | acaaaaccaa | aaagttgtgt | accttaaagc | tatcgttgag | 37860 |
| aacatgaaag | cctacgaaga | aatcagagtt | gagccaaaga | gtgaagagca | attttcaaa | 37920 |
| gaacttgaag | aagaacttga | agaagaagaa | aaaatttta | aaggaattta | agaggagggc | 37980 |
| aaacgccctt | ctttattttt | atcctattat | ataattttt | tatattatac | gggggcaggg | 38040 |
| gtaaaatgcc | actcaatggg | ggtgggtcta | tataccccta | cggtctaccc | aggtacttat | 38100 |
| tttttggagg | aaattatgaa | aataaatatt | taaaagtcaa | caccctatat | gataagtcaa | 38160 |
| cattataacc | ctaccctgta | agtcaacaat | ttatagtata | aataagaagc | ccttaaatat | 38220 |
| aaagtcaaca | tatctaaaat | aaaaaaagag | aaagaatatt | attcttcctc | tgaggtatta | 38280 |
| ttaataactt | ctaattcatg | aatagtaatc | atatcttctc | taaataatgg | tacatcttct | 38340 |
| atattatctt | tataatagta | agtatacccg | tcttgaaggt | atccgcttat | tttttcttca | 38400 |
| tagccttctg | ctttaatacg | tttaattaag | ttctccttat | ttgtgtaaac | tttatcttct | 38460 |
| ctgtaagaat | agttatcttc | atagggttca | caattatcgt | gttctacttg | atatagtttc | 38520 |
| atattagtta | tcctcccttt | cataagacca | ttcaccgtat | tctgcactaa | agtgggctgt | 38580 |
| gtctgtaccc | tcatcttcat | attctacact | ataccatgca | tcttcttctg | tttctgcatc | 38640 |
| tatatatctt | acttcttctg | tagtaataat | acgttttacc | ttaaatctct | ccatttgttt | 38700 |
| ttcctccttt | atattttcct | ctagtatttg | ttttaatgtt | tggcagtctt | tttggtctag | 38760 |
| agtatcccaa | ctctctagat | tttgtaattg | ataaagtaac | tcatttacaa | tttcatcgaa | 38820 |
| ggcttctgct | tttctatata | cttcttctag | ttctgtttct | gctaattttc | tatcccctt | 38880 |

FIG. 21V sequence.txt

```
aatttgttct gctttagtta ctaagatatg ggctttattc atttcctcta taataaagtt    38940
tttatagttt tccattatta tttatccctt ctattttcta tccgttgttt tatctcttcc    39000
ctattgcggt ggtgctcctt actcatttct ttacgttcct tatttgttaa ccttattcta    39060
taaacaaggt aattaatgta tagggtgccg gctgaccata gtagcaagaa tgttattaga    39120
taagtccatg agatactaat ttctatcatt gtgattcctc cttatctatt gtaaaggatt    39180
tacctgttct agagaatagt ttaaacattt cttcttcaaa atgcccatca ctcatatctt    39240
tatctttcag catttcacag agtttgtccc atgcttctgc tttattataa attgtttcta    39300
cttctctatc tgtttcatca ctaatttt catatataat ttgtaataca aatccttct     39360
catcgtaaca tttttcatta atatcatatc tcattataat tcctccttat attctttata    39420
gctcttgatg gctatttac aaatacctct atttacagca acaaatacta taaatgataa     39480
tagtgttata actgctctta catctcctgt aaaaggtaat aattggaaga gcaaatagct    39540
ttctaaaaca ctaatagctg taatggtagt tagatataat atagatagta agtaatcctt    39600
taattttagt ttaacaaatg gttttttgtg ctcatctgtt cttacaatac cataaagtat    39660
tataaaccac ataacaggta ctaactgtat aataaaatca ttatctatat tcaatgcatg    39720
tagagcgtaa ataataactg caggaatacc tataatgaat gctaggaata cagaaaatat    39780
aattaacatt atagggaggg ctacaagaaa acctagcccc tgttttgaat actctaatgt    39840
gttttacct aggaacttaa aaaatgtttt attcatcttc ttcctccctg gaattacttt     39900
ctgtaattgt aatttctaac atattattgt aataatcatt cttttgattg atattatagt    39960
tatcattgta ttcattaaag tctacataaa tatattcatt tgcgtcattt tcataaataa    40020
tatctatagc tgtaatatct gaatatgctg taatcatttc ataagcgttc gtattatcag    40080
gataagcaaa accaacttga ggtatttcca taggcttatc aataagaata ccaaaataag    40140
tacagtgacg tgttcggctt atatttgaag tctctttata tgtaccgtag taatctatac    40200
cttctgtaat acctgatata tggaacctgc ttacgtcttt agattctaat cttacaacat    40260
cgcaattttc taatactaaa tcaatatatt tgatattcat tttaactctc cttttatatt    40320
aataattctt tccattcttt atcaaccttt ttaagttctt ttttattata gtctccatct    40380
ttagttacta cagtgttcca ttgaaacttc tgtaataagc taaaattatt tataatccat    40440
atattacttt tactataata catattatct tcaaatctta tatcttttc tataaaatat    40500
ttatatattt tatatcttct ttcatctgca cctgatattt taataatttc attagtattt    40560
aattgagtgg ataactggaa gataacatct tttactttca ataggtcttt aacattacct    40620
ctacctacat ggtcattata ataatcgtac ttaacttttt tcttttgttt tctatcatta    40680
actacaatga atatattata tacgatataa gctttaaaat gggtataggt agtaggtgct    40740
tctgaatcat cacattcttt tcttaggtct gtacattgta tttttaacat aatattattt    40800
```

FIG. 21W sequence.txt

```
gatatgttga ctacggtaga accatcatgt tttttattga gatttatctt atccatttta    40860
taattaccta cttattgtag atacaatgta ctcgaacatc ttccattact ttgcctaata    40920
gattctgacc tttccagtta ctttgctcta atattttagg gtcatttgct ttaagaccta    40980
ctccccatat tttatcataa ggtgaagctt ctacgaaatc tttacgtaca tctgtgtcta    41040
atattctttg ctttaggtgt gtagtcataa atttatcttt aactacttct accataatat    41100
catatcttac tttattccat tgctcttcat taaaattacg aactttacga cctaaacttt    41160
tagcatggtt tggattctta gcatttagta tttcacctgc tatttgaaag tcattaaagt    41220
atcttgcttt acgccacata aaggcttgct ctgagttatt aaatgttctt ccttgatgtt    41280
taaactttat agggtagaag ttagaataaa tatcctcttt accccaaaac ataatatatt    41340
cacttgtttc tctcataata tttctccttt aattccatag tgatggtaat acaattttaa    41400
aattatctaa tattttactt tgtacctgtt caagctcatc atatttatcc atcaaaat    41460
catccatttc tttatgataa tattttatta agcttaaaat atgttttatc atatctattt    41520
gtgttctttc tttgccgtct acatctacaa aagtatggta ttccatatcc acatggttac    41580
tactctctac aaatgcgttt aagtcagcgt ataactggat aaagaaggac atgtcataat    41640
tccaatactt aggctcattt ctacctagtt ttttcttcat tttcttatat tttttattct    41700
tttttagtcc aaaaacttct tttttcaaagt catttaattt aagaccttta aaatatttt    41760
tcttcatttc ttaacctcca atttaataaa tggaaaatca atgtttctaa atactgcgcc    41820
gacatcacac attaatatgt ctccattaat ttctacttct ccactgtcag ttggtgtatg    41880
accacataca taggtaaaac catctttttct aggttgaaaa tctcttgacc atattaattg    41940
gtcaattgtt tgttcttcta caggcttcca actaaccca cctgaatgag agaatatata    42000
cttgtcttct ttatagtact ttctacaatt aaccataagt attttaaatt ttctatagtc    42060
gtctgattct ttaagtttct ttagttcact tttaataaaa tcataattat ttcttagatt    42120
ttcctctaca ctactatatt ttaaagttac cgtactcaca ccgtaagagt taagtgtttc    42180
tatacaatat cttgagagcc attcaatatc atagatactt aatcggtcta cgttttccat    42240
aatattataa aactcatcat catggttccc taacagagtt actacattat catcattaga    42300
cattaaatca aatatatagt taacaacatc ttttgacctt ttacctctat ctacataatc    42360
tcctaaaaat actattgttt cttcaggttt tctttcatta tttattttat ccataattgt    42420
taataatttt tggtattctc cgtgaatatc gggaacaacg tatatagcca tctaatctcc    42480
tccttattgt atataactat cttaccatac ttagtaaaaa aagtcaataa aaaaacctac    42540
cttagtaggt aggtaattaa aattatttat atgttaattt aatttcaaca tttttatact    42600
ttttacgacc atctgttcct gttgactcta gtgtaagaac agatacaaaa tctttaacct    42660
```

FIG. 21X sequence.txt

| | | | | | |
|---|---|---|---|---|---|
| ccggtgttct | gttattagtt | gtaccttccg | ttgcagtagg | tactgttaac | cagtaagggg | 42720 |
| agttagatgc | taagcttgta | ttattaacta | gtgttttgcc | attatattct | aacttagtaa | 42780 |
| cagacttacc | tgttaaatct | aacttagttt | tatctatatt | aatcatgaaa | ctttggtctt | 42840 |
| ctttccagta | tatagctgtt | ggtgtgaatg | ttgctgtata | cgtaccatca | ccattactta | 42900 |
| caggtgttat | agttcctgat | gtatctcctg | ttggtggtgt | actggctgta | gtatctttgt | 42960 |
| aacctacttg | agtatattcc | cctacaatat | tagttttttgt | tttatctaca | tagataactt | 43020 |
| taatgtaatc | tctcataaac | tctagtcctt | gagcattatc | atctatagtt | atgaaagcat | 43080 |
| ttaagaagtt | ttgaacttcg | gaaattctat | tatatttgtt | accatcttca | taagcaggta | 43140 |
| aagtatacca | gtaaggtgaa | ttagatgtgt | agccttcggg | gtttatcaag | ctcttaccat | 43200 |
| tataagaaac | atttaatatc | ttattagcag | ttaagtctat | atcatctgta | ctcatgttca | 43260 |
| taacaaagct | tgtatctttc | ttccatctca | ttccagttgg | tctgattaat | ttagaataaa | 43320 |
| caccattacc | taaatcctta | acagaagtgt | caatagatgg | tgggcttgct | atagcaccta | 43380 |
| cagtaccttt | actttctaag | aatgattgta | tagtgtatga | tataaattca | tgacctttag | 43440 |
| cattaggatg | taagccatcc | tccatgcctt | ctttccaagc | aaagaatgtt | ttatttacat | 43500 |
| tgttatccca | tactctaata | ttactctccc | tatataagtc | taatacagga | aatgaaaatt | 43560 |
| gttttgctat | ttctttata | acatctacca | attgtcctaa | agtatatcct | tgtccgtttt | 43620 |
| caacttcttt | aaaaggatta | ctttcaatcc | taggtgttgg | tgttagaaca | acaataggta | 43680 |
| ctgtaggaaa | aaccttagat | agttgataat | aagtataata | gattgaacct | gctactgtag | 43740 |
| tgtaagagtg | ttctttagct | gttcctaggg | gttttgtttt | accccaact | aaaccatagt | 43800 |
| catttgtacc | taacataacg | caaattaaat | caggtttatc | tgtaatagtg | taggctacgt | 43860 |
| ttttacggtc | ttggtagcct | gttccacttg | tacctttatt | aacatttatt | aatcctgttc | 43920 |
| tgtcagcaat | aaattggtgg | tagtttttg | ttgttcttgc | atttacttcc | gtaatactat | 43980 |
| ctcctatgaa | tataactttc | ttatctttca | aaggtgagat | agttgttgta | cttggttgtt | 44040 |
| gtgttggttt | attatcagct | ataagcttat | ttatttctgc | cataaattct | tcttttatat | 44100 |
| ggtcgttaaa | ttgggtatct | ataacatcct | gtaaacctat | aatatttct | gcttttatat | 44160 |
| tcataggttc | tacttcatta | taagtaacaa | taataagttt | gtcctgggat | gatgttaagg | 44220 |
| taacaaattt | tggtatatct | actttattg | attcttcacc | attaatatcc | caacaaattt | 44280 |
| taaagtgccc | tgcttcgtat | gttgtatcag | gatttaaatt | ctctataact | atttgaccta | 44340 |
| ttgaatcttc | tatgttttca | cttgatttta | aaagattatt | ttcatagtca | taaagcttca | 44400 |
| atttcttagt | catatttact | tctcctttta | ttgaattttg | tacaactata | atatatcaaa | 44460 |
| aaaaatttaa | aaaaacacct | atttaactta | aataggtgtc | cgacagagct | cccgtactta | 44520 |
| gattacggtt | aataatattt | tacgacaatt | atatgagacc | ctctgtcgtt | gaaacgctcg | 44580 |

FIG. 21Y sequence.txt

```
tcactgcgtt ataccctcaca agatatttg acagttagct tgtgagaaga agattgtttt    44640
ttattgtact tagtttatac actctcaaaa gtacatgtgt actatatatt tatacaccaa    44700
gcgtttggtg ttagatacgg aatggaggga cactaccatc cggagtctac ggtcagatac    44760
aaagcctctg ccgggcaaca tacggtatct ctcgtacatc aggttgacta aacctttaga    44820
gcttttcact ccttctctta taaccagtaa cttaagagaa ataggtttta cttagtagat    44880
atgaaacaat aaatccacat acaatattaa atcatagtca agtgattgca catatgtcta    44940
ataccTataa gttttctgct agcctggtat atggactctg caggactcga acctacagtc    45000
aaaccgttat gagcggttgg ctttacccttt aagctaagag tcctagaaat atcctgagag    45060
aggactcgaa cctcaacgac taggtagcta catctagcca atgccattac tcaggattgc    45120
tagtaacgct aaatagaatt ataacgttac cgtagacctt ttctacgctt ggtagatagg    45180
taaaatataa tgatttcaaa gtacccatat agttaggctc ttactctcat tatcaggtta    45240
aaaaggctaa ctgtatttag cattatataa gaggctttag ttaactacta tactaataat    45300
ataccataaa ttatacttaa tgtcaagtta atttatcaat tgaatctata atttttgatg    45360
tgctacgtat atccgcttct ctactatgtt taaggagata ttttaatttc attaaaaaag    45420
aatttttttc tttttctata atatcttctt tatcattgta ttctgaaaac ataatgaatt    45480
ctatacctat actatttcta ttatgtgaaa acatatttat agaaaaaggt gaatcaaaat    45540
ttttatcatc tttattaata ctaaagtctt cagtaacatg taattcattt atttcagata    45600
tttcaaagta cccattaact cttttaagtt caagataact attatatcta aaataacgct    45660
gttcttctat taacttctct tttgttagat aaggatactc atttataaat ataggattac    45720
ttgttccata gttatctcta atatattctg cgtcctctaa agaatcagta taacctaaaa    45780
cttcataact tgttgtatac actgtatctt cttcccacaa gtcatagtcc atttcctcta    45840
tttcttcttc taatatataa attttttcca tatattactc ccaaatacca ataagatttt    45900
taagcttagc tataacctct tcttctgttt gataagaaaa tacccctgta atatgttcat    45960
agttacctac aatttcataa tcttgtgtac catgtttatc tactaagtat gagttattca    46020
taacatttaa actatcttct gagtaactaa aatttatgtt atagtctact aaaaaattaa    46080
taatattttt catttacata acctctccta tcggatattg tcctagcatt cttgttccat    46140
tttcattata aaaagtatat tctactacaa taatattcat catatctaca tatatagctt    46200
ctatatatgg tgtaatattt tcctcttctt gtatgtgctt acctatgata tcatataata    46260
attctgagtg tattctttta tctctcatta tagacctccg taaggaatgc tacagttttg    46320
tctttcaaag attttttctac taattccata gcatctttat agtgtttgat attagattca    46380
ttatacttaa gtttatcttt tacttcttga attagaggct ctactttatt aaccaaatct    46440
```

FIG. 21Z

```
                                    sequence.txt
tttttcttt   caatacttac  attgcttctc  ttattgtcta  atacttcttt  tggcatatat    46500
ttaacttttg  caaagtcttt  atagctaaca  tttaagttat  ctaaatcatc  taataaatca    46560
ttatagtatt  ctaaatgatt  atagaatgta  taaaacttaa  caaggtcttt  accagttaat    46620
tctccttttt  ttagtatgtt  attaatatta  ccgataaccg  aatatgctat  aggcttaaaa    46680
ttagctctaa  cataagttaa  aaatataaaa  tcatcataaa  ataaatctaa  aacagtttta    46740
ttaaatctag  tatttttagc  ttgctctaat  tgagcacata  aattaagaac  attatcaaac    46800
ccacttttta  gcactaaaga  gataaatctt  tctactgcat  agtatcttga  tacttctgta    46860
tgcttacttg  cttttcatt   attcctaaat  atagtatctg  ataaaggttg  aacaactaaa    46920
ctcatgtaat  ctttatctga  atgctcatct  gatgttcctt  gataagtact  tccaaattct    46980
attgttgata  ataagaaact  tttttctagg  ttcattataa  catcctcctt  ttatttgtta    47040
tttaaataat  aacatatatt  gataataatg  tcaatactta  tatatcttct  tctgtatcaa    47100
cttcatcttg  tttatactta  aagtgttcat  agactttaaa  tagtataatc  cctagtgtta    47160
ttaatcctaa  aatatatttc  atagtaatcc  tccttaataa  ccatgtttag  ttacccatcc    47220
tgctaaagca  tccatagcca  tatcatattc  ttcttcattt  ttaattctta  taattttctc    47280
tatttcttcc  tttgctttct  tagaactaat  aaaatcaata  tcagtatcct  ctaggttagt    47340
taattctaaa  ttttctctaa  taaaattctt  ttgacttggt  gttatagaat  taactcttac    47400
attttcgtga  tttagaaatt  ggtaaaagtc  catattactc  atcctttta   acgtattctg    47460
ccatatcttt  taaaatactt  agtacatact  ctaaatctct  atattggtca  tctaatgacc    47520
ctataatagc  atatggtgtc  atatcccagg  catgtgcaca  gtcaaaccct  aatactctct    47580
taccctcata  gtcataatca  tcgtaagtga  tacctctatg  agcacgtctt  tctaaggagt    47640
catattcttt  ttcattgata  tctgaaggta  aagttatata  tccatttaga  tgaccagttt    47700
cagggtgtct  cttaacagtt  agtttaactc  ctttataata  aatatcaaga  cttaaatctt    47760
ctcctagaat  attgttttct  ttttctactt  tttccataat  gtattgaggt  gcttttttaa    47820
acataatcag  tcatctcctt  tttatttata  tctttactat  acactatttt  ttctattttg    47880
tcaacaaaaa  aaggctacta  attaaagtag  cctaaatact  aattatttag  cattgtattt    47940
ccattgccaa  taaccatttt  tctgtgagaa  ctcaaagtga  aaaccatcat  agtcaaattc    48000
aatattatag  tctccatctt  gaagtggttt  tgaatttagt  acaggactat  tactctttgc    48060
caattctgct  agaaactcat  gatttacttt  ttccataggg  tttactcctc  ctaattattc    48120
ttacagtact  aatatatcat  aggtcttttt  ctaagtcatt  tttaaaagtt  tcctcgtagg    48180
aactagcgta  agtaacctca  taacccacta  cgttagtata  tcctacatat  aatgacttat    48240
aattagattt  tatcttaata  tcttctgatt  gttctagctt  atttaagact  tcatttaaat    48300
catctgagga  atagtgttca  ttatctattg  ttattgtttt  tccttgggta  tagatatcaa    48360
```

FIG. 21AA sequence.txt

```
tttcttgtat catcatttca tccttttgat tattcattat ttgattataa gtttctaaat    48420
catcaatgtt atctgtatct gaacctttta ctaaccattc tcctctcttc ttaaggaggt    48480
catcaaactt ctcatgctct ttaattatct tttctacctc acttggtatt aacacagccc    48540
tagcatagtt tatatgccac atagacatat tatcaataag ataattaacc attcttataa    48600
tctcttttc atttgccata taccaacctc cttatatcta ttattaatat aagagaaaag     48660
cagacttatt aaaagtctgc ttctttacct aattctaatc ttctatttt catatgagga     48720
atcgtttttt tatttcctgt taataatgat aattctctag cttttctttt agataatgtt   48780
agtagtccat tataattatc tactttacta ttatattgtc tgactaagta ctctagttca    48840
tcttctatac ctgctagttc tcctgattta actccaagta actttctata catgtcataa    48900
tcttcagaaa gactttctac tttgttttta gatacagaat cataaactgc ttgtaaatta    48960
ccttcttcaa taagtttaaa attatattca ccaatgatta attcttttc agaagagtca     49020
agggtaacta aaccacttgt attacctgta aagtcacctt tataatctac aacaattcct    49080
tcagttattt tatctcctaa ttcaatagtc ccatcttcat tttctttaaa tttatgagca    49140
tcataaactt ctactttgtc acctaatctc aaatcttgag ttaagttatg tttaccgata    49200
attctatcca ttacttaacc tctcctttat taatagggtc tgtgttaag aacatttcta     49260
agttctcttt tgtaataggt aaccaaaaat atttactttc cggaattgta actgtataga    49320
agtcttcatc attattaact ttgatgttaa catctgtaaa ctcatcttgc attaaccaat    49380
gagttacagt taagttatat gacccatcac taacatacc taaatcaata tcatgtctaa     49440
aagccaaatc ttctaaatgt tctaataaat cattcttttc attatgtttt tcttcttctg    49500
tattattttt aattgggtta attaactctg tacaaacgat atcgtacaat tcaccatctg    49560
taacctcata gttcttttca attaatacat cttgtatttt attgattgaa tttgtaacta    49620
ctttcccata ttcttcttct gtaaatttac atttatctaa atcaacatct gtaattaatt    49680
ctgcaatcca tttatttaaa attgatactg ccattgttct agaaataata ctatcgtata    49740
ccatatttat ttaatctcct tatttaggtg aatgtggtct tctaatgaaa aatcaaaagg    49800
cgctacacca tttctttat tatttgtttc ttttttaagt ataacataag ttagtgaaaa     49860
agtcaagata gttactacag ctattgataa aagtttaatc gggttttca tagttactct     49920
aactccttaa gtttattttt tactttctct ttatcgtact tataatcttt actagagttt    49980
tcattttttt ctttctcttc ttcattaagt tctctatact gagcttcttc tacctcttgt    50040
tctttattat cgttattttc ttctgctttt tgaatttcta cattttact attaccacca    50100
tttaccttt ttctaaaaag aaaccaaagt attaataaaa tgatgagtaa aataataatg     50160
cttaatacaa cagcccaaat attattagcc attacaacct acctccgaat agtttttta    50220
```

FIG. 21BB sequence.txt

```
cagctcttaa attttcagat gaatcgttat ttatatcaat ccctacgcta gaatcaaaaa    50280
ttacagcatt atcaagtata tgctctgtta atttattacc ataactactt ttacttacca    50340
cactaccata accatgatta gttaggtcaa ccatatcagg ttcaacttct agtactctaa    50400
aagatattct acgtaagaat gaaggattta ctaagtaaaa ggaagattta aaaacattta    50460
atctttgata agaatgtttt atattaacaa caaaccctgt taacttatct tcatacccctg   50520
aatttgataa tttacctaag taaaggttta tactatatcc ttttgtttct aatgtttgaa    50580
tagcacttaa cattatagca cctctataag caagattttc agggtcttcc ctccaactaa    50640
tactagaatt ataaaataca tcaataactt tcttctctgc tttaactctt tgctgagaca    50700
tcatagaatt aggtaatcct tttatagcat taggtacgtg aggttgatat ccttccggag    50760
ctacgacagg ttttcttttt actgacttat ccattctaaa taatgcatct gtcatttttt    50820
taagtttaac taccatatca tatgactctc tatcacccctt aaccattaag ttataggctt    50880
cttgaaaact atgagtccct gtaaaatcat agctacctgt atcggatgaa ttatctctac    50940
ctgaaactct attctttttt aaagcagaaa agaaatcagg tagaccatca tatttaatta    51000
catttaattc tgagttatct attaatcgtc tacccattga tttgcctcct attctaatcc    51060
taatttatcc ataattgtat caaaatccat tgaatctttt gatgtactat cagattttct    51120
aggttcctgc ttaggctctt gttgcatacc taaaagcttt cttgttgctt ctgtgtatct    51180
gttaccttca ggtaaagagc taataaattg attaatctca tctttcggta cagatttaaa    51240
gataatactt tctacaacaa actcatcttc cattactcca tctaatttac taccattaat    51300
aattgcacgc attgagaata cataaggtaa tccttttttca tcattctcat gtcttaattg    51360
ttgtacaaag tttactaggt cttcattgct tgatagttga tgttccacct tagtatcata    51420
gtcaaattca acttgagcaa agcggtctaa tgtagctccg tctaattgtt gtctacctac    51480
ataaatatgg tctgctcctg ttcccatagt attacctgct gacacaactc tgaaatcttc    51540
atgagctgtt acacgtccaa tagggaagtc aaagtattta tttgcaatag ctgaattaag    51600
aattaatagt acttcaggaa tagatgcatc catttcatct aagaagaata acccacctttt    51660
tgtaaatgct ttatagaatt gagtttcatg aaacttacca tttgcatcaa taaatcctgt    51720
taatttaaat tcttgcgtaa ttgcattact aaaatagaaa tctaaatcta gggcttctgc    51780
tacttgttcc aatacatggt tcttacctga acctgctcca ccttttaaaa atactggaat    51840
attttggtta actagcttta gtatatcttg gtatctataa tgaaagattc ctgagatatc    51900
tttaattgtt tttccttctt gttgtaattc aatttaact ggtaaattac taagttgttc    51960
ttctacatat tcttcaattt gtttttaac gtcagtaata ataatttctc tactctcagt    52020
tcctgctttc tcaacaattg catctacaat tgcttgttcg tacggattag agtttttctc    52080
tcctagtttt tttgctaaat ctgctgttgt ttccatttgt tgctctacca atctctctaa    52140
```

FIG. 21CC

```
sequence.txt
tctttcaata gtatcttgct ttgccatatt tatcattctc ctttgatttg ttatacattt        52200
attatattac aagtatttga atttgtcaac aactttctaa aactttttt agttgctaat         52260
aaaaaaatac cttacaccta taacttaaca tagggtaagg taattgtcaa cacttttgtt        52320
aaaaatacat taatttaaaa aaatcatcaa tatctttagt ttcatgtgta tccatatcat        52380
acataaacat acaattatat gtatgattat tcattatttc taacatgtta tgcatagaag        52440
ttgcattatt gaattcctct aaatcaatag ttaccgtaag ttcttgacct tcataaagta        52500
tgtttgctat ataatatttc ttaacacctt ccattgttcc atgagaagtt tcattatgat        52560
taagtacttc tacacctagt gaaggtaaat attctgaaaa gtaatattta cagaaatata        52620
taaaattgtc tgttctttta gacacgagta ctatctccgt actttatatt tctttctaat        52680
cgtacataat atgttttaat tttttgtact tctttatcta ctgcatcctt tcttcctaac        52740
cttgtagtat attttacaat attaaatatc atagaatcaa caaagccatc ataagaaaaa        52800
tgttcttcta gaaaagaaat aacatccttg ctacctttat agtgctcagg taaatgtgca        52860
tctacttgta tattataata attttctaaa agacctatac tctcaccaag actagacaaa        52920
gcgtaaccta aatcatttga atcattagac cattccttag atactgatag tgcatcttct        52980
ataattgtta cttttaattt atctaaataa tcttctactt gagcttgtgt tttcataaat        53040
tcttttgcgt tcatgtaata ccctcctaaa ttatataaaa aaacaccctg cttggctaca        53100
agcaaggtga aaaaggaaag atattatgga agtgtactat ctaagtacac ctcataatat        53160
aacagttttc cttgctagtt attacttatt ttttaaggtc ttcttctttt acaaacactc        53220
cattaataag cttaccttt ctgtctttta tctcatcata agccatatca atacactctt         53280
caatatctat atctaactgt aagcatagta ctgttaatac tacaaaaata tccccaacac        53340
tatctcttgt tacatggtca ttactttag caatacctga agctaattct cctgcttctt         53400
ctaataattt tagcatttga ccctcgggtt tacctgtttg taagtttcta tcttttgccc        53460
attgtttaat aagttctact ttttccatta ttctatatct cctttaattt ctgtatcttt        53520
gataattagg ctatcagagt cacttgttac atttaaatta tcttcaacta attcatgtaa        53580
attattagta atatcttctt catacctata acctacacga acataagctt taactctgat        53640
atctatatta acataatctt cttggaattt ttccatttct aacttccttt attgtatcat        53700
attattatac tattgtcaat taatctgagt agtttccttt agcaagttga tactttttgt        53760
gtaattcttc atataattct ctcataccttt cgtagtttct catatcatct tccagaaaac      53820
taagataatc taataatact tttacatcct caggttctaa agttataact ggttttacca        53880
ttaggcaacc tccttaaatt cttctttatt tattttctta atatcttttt ctaatgcttc        53940
ttttaattca ttaggtaatt tataggcatc aattgattgt tgttgcccta gtacatatcc        54000
```

FIG. 21DD

```
                                        sequence.txt
attatctgta atacgtattt caactgtaaa ccatgaatta tctaaatctt cttctagtct    54060
tgctaacaat attaagcaac tgttctttat aattcgatta gcatacccgc caacacaatg    54120
agatagcatt ttaccttcat ttttcagttt acttacggta tctgcaggaa ggaattttac    54180
ttttctacca tcttttaatt tataagtttt atcaattatt ttttctaatt tattttcata    54240
tttagattta agctctgcat catctaattg ttgttgaata gattgtttct cgtctgtaac    54300
tatatcatgt tctaatttta gagagaatgg tgttaagtta acactttcta atgttctata    54360
accttctcgt attaatattg ataaatcatg aagataatct aaatagtagc tatccagtgc    54420
atatcctgtt atacgttgtc tatcttgagc atctacatct aaataatgag tcattttttt    54480
gtaattagca aaagatatag ataatatttc atttacaata ggttttactt taaaagcatc    54540
tgtaacattt cttacatcct gaaccattaa aaatgtatca tcaaatagtt gatgtagatt    54600
aacttcattg tgtaaatgat tatagtaatt atacaatgta tctgaaaatc ttaaataatt    54660
actctgttca aaattattta atgttagtaa tttttttatac gtttgctttg taagattaaa    54720
tgcttcatgt attttccact taggattttt aggtatatga aatagtaatg aatttctttc    54780
aaataattca aattcctcta agttatttat tttgtcaata tttttaacaa tatctgttaa    54840
gattgttaag taattagaag ttgaattttc tcctttgagt ggtttatatt tgtttcctcc    54900
ataatttaca cgcccatata catcaacctc atcaaggcac caactagaaa gtccaaaacc    54960
atcatttctt aatgtttctt caattatttt aataataaca ttcttactta aattaggtgt    55020
tgaataattt tttaaaataa catttaataa aacagccaaa tttaattcat ttttatattc    55080
acttttacta atatcgtctt tgtatagatt taaagttatt tctttattaa caagactgtc    55140
tgttaagaaa accttaactt ctcctgtttt aacatcaaat gaacttttat tttctaaaac    55200
ccatctattt cccatattat atttatctct aatgtgtcta actttaagac caaaagatga    55260
actattctca gtacttggat gcatgtacca agtactactg tacaatgaat ctgatatttc    55320
cttataatac ttactagagc ttttttctgt atcttcatta agtctggaag taatagatga    55380
ctttattaaa ccgtacttac cttggtataa gatatccata atatcattat tcaaactatc    55440
tactacttcc ttatactcat ctaattgtct agattcatac caccttaaac gggtttcatt    55500
ttctaattct ttaattttt cttctacata acctttagat tttatttgtg ttatacgttt    55560
actaccatat aaaggaaatt cttttctttc ttctctactg gatgcaatat attctttgta    55620
acttcttcct ttattttctt caattacacc ttcaactaat ttttcaattg tttcataagg    55680
attacctgta aagtttgtta cttctttatt accacatagt gctaagaata aatgtatttc    55740
tgtagcagta tcaaaactaa atatattatg aatatctcta aatagttcct tagagcctaa    55800
gttaattata ttattttct tcttcttaag gaatacatct tcttctccta tatagataca    55860
tcctttatta actttaggta aattaataat ttcttgttct gttaatcctt tttgtttata    55920
```

FIG. 21EE sequence.txt

```
tgttattgcc atttaaaatc actccttatt tgttatgtac taatcatacc atagtaaata  55980
atatttgtca acaaaaaaag aagaactttt taaagttctt ctaagtgagt ttcgtagata  56040
accttttgaa ttttatttaa tggtttcaaa tctaaattac gaataagttt ttcgtacttt  56100
ctagaatttt taaaattgat agtatttggc atagcaagag cctcatcaat gtctttagta  56160
tagcttataa catctgaata aatatctact tcttttacat atagaccttg agttaaactt  56220
ttaaatacta cctcattatg tgctacaact tcttctttct tttctatgct cattttgta   56280
aacctcctgg tctattctac acaaacaagt acgtactcta aactagttaa tgttactgat  56340
ttaatattat ttaattcttg taatttctta atatctacac catagttttt acttatagtc  56400
cataatgtct ctcctgctct tactttatgg taatacttat tcccttcttt aataaggtca  56460
ttcaatatta cctacctcct tgagtaatag ttagcttgta gataacatat aagtataaga  56520
acaaagttta caaattcagt agctataatg tgaacataag tatgtgataa aaccatactt  56580
aatattaatg aagctaatcc taatccaata ataaggaata gaaatctgtt tgttccttct  56640
gcacttttag ttttatagaa tgttgttatc tgagttacat acgcaaggat aatagtaata  56700
gttgcaatag tttgtgttaa ggctgtaaag tcacttaata aaaatagtaa cactgagaac  56760
acaataataa aaggtataga gaaataatcc tttttctat acgaagctac taataagcaa   56820
acaataccaa gagttaaatt aacaccaact gatactactt gaaacattgt agcgtcagtt  56880
ataagtaaat tgtaaaagct aataccact gtagctacaa ttaaatacca aaaataacta   56940
ctaactcctt taacactatc tgatttaact aaagctatta gacctggtat ataacctact  57000
gtaactaata tagcatataa tatacttaag taatgtgata agttatccat cttgtcctcc  57060
taatttctct agtcttttta aaacttcttc ccaagaaata aacccttctc cattagttag  57120
gcttagcaca catccgtaaa taaattggtt cgtactaaat tcagccctat cagggtcatc  57180
ataacctttt ccatgtcctt gacgaatatc agagcaatag attaaaacag gtttatttac  57240
aatattataa gcttctaaaa tatcatattg tgttaagggc tctaagtctc taaagtctat  57300
atcttcatat ttatcaataa ttttttgagc ttggtgtttc attcctaata aaataccaag  57360
ttctgcaatc gttcctagcc cctcattaag aatgtcaaat acaaaaatat ctgattcttg  57420
catagcttta aaatcattgt ttaagatacg ttcagctaat ccagtttgtt ctgcattagc  57480
tttatcgttg attgatttgt cctgatgagg gctataagga gttactccta caataccctc  57540
tacttgttcg tgttgtttag ttctatattc taccatagct tggttaagta gatgacctcc  57600
catgtaacaa accttatctt tagtataatt aaccatctat agtatctcct ttttcttcta  57660
gaatacctct taaaatgtgt ggcatctttt tcttaatttg tttttctata attttcatca  57720
tattttcttt ttcttcttcc atgatatcat caacaaaatt ttgacctact tgtttcataa  57780
```

FIG. 21FF sequence.txt

```
ttaaaccaaa attttccaat tctaaatcat ctttagacaa tctgttttct tctatagctc    57840
taaaaatcat tttttccatt cttgattttg tgatagcata atctgctaca gaatcattac    57900
ttctaacttc tgatttcatt ttcttacgac taaactcttt aaattcctta gatactaatt    57960
taaaataatc atcatgttct gatttaccat ctaaatattt aataacaata ccttctcctg    58020
tattaggttt aacagtcata tctgattttc ctactaaatc ttgaatttct tgagggttta    58080
atttattaag ataaaaagat ggttctataa tcattaaagt ttttacagtt ttcaaaccta    58140
atgtttctga taaagaaatg acttctgaat aaggtaaata ggtttcacta tccttatcgt    58200
atacatcgaa tacataaaaa ttattataac actcttcttt ataatttacc ttatgtttaa    58260
ctaaccattc tccaaatata ataataccttt ctaatataga taaatctaat ttatctgtca    58320
tgttttcatg tacccaatta taaaaaccgt ttaatgtttc gttttcattt aattttttc     58380
tacgagagaa acatactaac tcaccattct ctgtagtaaa acttgcgttg cttccatcta    58440
attttttcttg aactacaaaa cctctatctt taaatttgtc taaagataat cctttatttt   58500
ttactttagt ataagatttc attaattagt tatcctcctt tgaattatgt actattgaaa    58560
ataaaataag acttacactt gccaaaaatg ctaatactac taaaccaggt aaatttagaa    58620
ctgttgataa gaataatgct actgcactta taacataaac tagaccgcct aataataaag    58680
ttaataatac aattgttata agttttacca accagttatt attaataaat actttagcta    58740
aataattcat aaaaaagcct ccttagttat tataatataa gtataccata tctaaggagg    58800
tttgtcaaca tattatttta ccatttgaaa ttatctgcgt attgggctaa cttagaacgg    58860
aaattaactg taaaattatg gaatactgca ccatcatatt ttttaaaata ctccatgtaa    58920
tccccaaaac ctgatttact ttcatttttt aaatctattt gtttaaagtt accttctact    58980
attacagtag aattttttgt atgaacccttt gtaagaactt ttttaagttc actacgttta    59040
aagttctgtg cttcatttat aattatagta gaatctctta gatttccacc tcttaggaat    59100
agatgtgata tttgagatac ccaacaatct cctagtttat cttctttaac attatcttcc    59160
atcattaaca tttcagttat ttgttgttca ggattcatat taagttcaat aagggcatcg    59220
tgtaatccca tgaaataagc catttctttt tctgtctgat tacctggtct gcttcctaaa    59280
tcctctgata ctggtgaaat tataaatact agctttctat ctttattaag atagtctgcg    59340
taagcacagg ctactgagca cattgtttta cctgtaccgg cttgactctc attccaaagt    59400
atttcaacat tatcattaaa gaaatcctca cagaaatcta actgctcggt tgtagcttt     59460
tcaaggaatt cattaaagac tagatgttct cccatgttgt atcttacatt aggataatct    59520
tttaacttaa agtctaactc ttttagttgt attgccatat tttaaagttc ccctatctat    59580
aaatagtttt actctctttt aatatagtac taatttccga tatattctcc tgttgaagag    59640
caataattac tacattcaca ttcagggtag ttatcacaaa cttcttcgtc ttctacatca    59700
```

FIG. 21GG sequence.txt

| | | | | | | |
|---|---|---|---|---|---|---|
| tcataaccaa | tatcataatt | attataatta | aaatctacaa | tacaattttc | actattacct | 59760 |
| ttagataatc | ctgtataaat | aatatcatcc | acagaatccc | aatcgttatc | tgccaaataa | 59820 |
| tttacgctat | ctaatactga | ttcattatca | ggtaaataaa | tactaccgtc | tgaaaattta | 59880 |
| attagaatat | caccttgagg | taaagtatca | ttaattaaat | caatctttgt | ttcttcttca | 59940 |
| atagtgaata | cagttccttc | taatctttcc | ggtgtagtat | gcgttaaatg | ttttacagta | 60000 |
| tctcctgatt | cttcatagaa | tcctactgca | ttcatatctt | tattatattt | tgcaataaat | 60060 |
| ttaccattgt | cacttaccaa | atattgacta | gttgaattat | agtcgtttgc | gtcatctact | 60120 |
| gtcatgcaag | ggttataatc | tttaacataa | taactaattt | tcctaacatc | tgttgtttgt | 60180 |
| actttcttac | cttcaccttt | aattactgaa | ttaatttttt | tcataatatt | ttctcctttt | 60240 |
| tatatatcaa | ttgattttt | tgcaagatta | tcggcatagt | cattccattt | atcatttgaa | 60300 |
| tggctcttta | cttttacaaa | atttatatct | attactttt | ggtattctct | tatcatattg | 60360 |
| atatatgttt | tacttagaat | atttcttgca | gaccaagtac | cttcatacca | atgtattaaa | 60420 |
| ccaatataat | ctatataaac | tattgcctga | ttgtatccta | gttttatagc | ctcttcaata | 60480 |
| ccataacaac | aagccaatat | ttcacctgca | acattattat | actttattaa | tcctggtttg | 60540 |
| tcaacacttt | tactaatttc | cgctattata | tttccttctt | tacttaccaa | gacagcacct | 60600 |
| gagcctactt | tacctttatt | atatgaggag | ctaccatctg | tgtatatatt | tacactatcc | 60660 |
| tgcatattta | taatcctcca | taaattgagg | gaattcacaa | tctgagtata | cttctctaca | 60720 |
| aaaagatact | gagatataat | taaaatcaaa | acatttgaaa | cagtgttctt | gaacttcttt | 60780 |
| tttatctta | gcaatcacat | taaatttaaa | accatcagct | attactgtaa | atactccttt | 60840 |
| tttcataaaa | caaatacctc | caccaatttt | attttaaatt | aataactaat | tcaataaatg | 60900 |
| atttaatagt | tttattttta | ccttcatcaa | tatctgaaaa | gaagttaatt | aaactatcat | 60960 |
| cctcatcaaa | taaatcttca | acatcatcaa | atttatttaa | tatgtctgta | acactataac | 61020 |
| cttcttctga | tatatactca | tgcaagtctt | ctccatcttc | tgacagtgtt | gcttctattt | 61080 |
| taccattttt | actttcaatt | aaatataaag | tatttaacac | tttaacagaa | tctacaacta | 61140 |
| cactgtagtt | actaatagta | ggatattctg | tataaagtat | ttctacatta | gtattcatat | 61200 |
| aactatcaat | tacagagtta | actgtatctc | tttttagctc | agatacatta | tgttttcgta | 61260 |
| tagtagggaa | ttcttcatca | tattctacta | attcttttct | atctgtgttc | aataacttgt | 61320 |
| ctaaagaaga | caacaatact | attttatact | ggttatcagg | gagactatct | gtaatttcca | 61380 |
| ttattgttaa | aaacgtatct | tcacctagaa | ctttgtttat | atcttgtaac | tcaaatgaat | 61440 |
| ctaccatttc | aatagtatca | tctatatcat | ctgtagtcat | taaaaaatta | actaaattat | 61500 |
| tattctccat | catcttcctc | caattctttg | aataactctt | ttcctggagt | atttaacgct | 61560 |

FIG. 21HH

```
              sequence.txt
ttctctaacc gcattaaatt agcgcttctt ggtttctttt ttccatactc ccaataagat    61620
ataagagagt aatgaacacc tatctcagaa gctaggctcc ttaatgtatg tcctttttct    61680
actctaattt tttgaaggtt tagaggttta ctttccttt tttcatccat aattatttct     61740
cctctacttt taaaaattta aaatcctcag atgcttttgc atttttagt atatactcgt     61800
gtgacttatc tcttgcctct gccttgcttt tagcatataa ctctatatga aatacatgag    61860
gttttttaa agacggtgat tcatatctcc aataaacttt aaaagtagt gtttctttt       61920
ttaaaacatt aattcgaaac catcttttaa atttattcat tcattatcct cctttattta    61980
tttgttaaac taattatagc atagttaact tatgaagtca actataatat acaaaaaaga    62040
ctaagaaatt aatcttagtc taaatcgtta ctaatagttt ccgttggcat tatggaagtt    62100
taaagctcct gatgttgaac cgtaacggtc aatcatatat tgttttgcac ctttagtttg    62160
ttctgctata gaaccaccac tccatgattt acctaatcct tggaataacc cttgggctcc    62220
tgatgttgga ttaacagcat tcgggttcaa tgtagattca cgcatagcaa tttcaatcat    62280
tgcttcatct ccgcctgctt gtctaatctg ttctgctaca gaaccacctg tacttttagt    62340
agctgtagtc ttagtttcta ctttaggagc ttctactgac ttaggagctt cttgagtagt    62400
tgtttcttgt ttaggttgtt ctactgcttt attttgtgta tcaaattgtg cttgttgttg    62460
gtctactttt tgttcaggtg tttgctcttc tcctgctaat ctagatactg tattatctac    62520
ttgagttgaa cctgaatgat attcataacc aaagttacca ttataattat agaaatgata    62580
agtaaattca ccatcactaa atgagaaatc ataattacct tcttgaattg gttttgtatt    62640
aacttctact gaatttgatt tagcttgttc tgctaactta ttatagtcaa tttcgtctgc    62700
actagcttcg tttgtagcca tacctccaaa agtaatagct gtacctaatg ctaatgttgc    62760
aaaaattgtt ttcttcataa atttaaaact ccttaaataa tttttttagaa ttgtttattt   62820
gtaaaccgac ataagtaatc ataacatata tctttaaata acgcaagtat aatatagcac    62880
taattagtgt aatattatta aggttttatt acaaacatta cagttatcag ataattaaat    62940
acaaaaaaga gaggtattaa cctatctaat ttattatttt cctgttacat ctacaatagt    63000
tccgtctccg ccaatttgaa taggttgttt tccatcccat ttttcaatta gctgttgttg    63060
taaaacttca tctgttaatg attcacttct gatatcatta gctttcttct caccttttgc    63120
ttctacttct tttttcttag cattttcttc agctatctgt ttatcgactt ttgtacgttc    63180
taattcttga tttgctttta ctctttcgtc aattgctttt tgagtattct tatctgcttt    63240
aggactagat aatgcaatat cttcaattac aaatccttgt ttttctaaat tatcatttaa    63300
gctatctaaa gtatcttttt taatttgtcc tgttttaaca ccaaatgcat caattactga    63360
gtacttagat actgattgac gtacattatc ttgtacacga gaacgtaagt aacctttttc    63420
taattcttca atgtcagcac taccaaaacg attaaataag tctacagctt tagttgcatc    63480
```

FIG. 21II

```
sequence.txt
tactttatat gaaacatcaa tatccatttg taaattctta ccgtctgaag ttgccacgtt    63540
taaatcttta tatttatgtg tttgtgtttt agttggatat ttgtttacct tatcaaaagg    63600
tgctgttaag tgccaacctg gtgatttagt atcttcctta acaccattta ctgagtacac    63660
aactccaaca tgaccttgtg gaatctttgt aatacacatt aataaaataa taaatcctat    63720
aattgctaaa aaccctatta ctcctgaaat aactactgac ttcctcattt acatttctcc    63780
tttttctatc tcttttatta aactatttaa agcttttttcc tctttgtcta tttcctgttt    63840
gtctgctttg gtaacaagag attgcctacg gtcatttaag aattgttttt tatattttac    63900
atattgttct aaaccgtatt cttctaatgt accttgccta actaattccc tgtattgttt    63960
tcttatgtta cttttcttct ctcttcattga aagaaaatca aatacgtaac tcataccaaa    64020
acctacaagg actagaaaaa caataaaaat agcaaagtat gttaaaaata atgccatgta    64080
attcctcctt tatttgatta catatataac tatacactat gtattacgtt ttgtcaacac    64140
tttttttgcaa aaaaaataga cggatttaaa atccgtctaa atttatactt tatttaaata    64200
ttgttatact tttagtttct tcatactctt tcaacattct atctctaaga tttattgctt    64260
cttttatact atctacttga tatgattggt accttatatt atttcttgtt atagaaactc    64320
tatatttacc attagttctt tcttgtatgt ttttttaatcc ttctagtta gagggtctat    64380
taactatatt ttcacttcta gtagtccatc tacaattttc cggagaatag ttaccatcat    64440
tatctttttct atctaattgg tatttatcag aaggtctttt acccatatca tataaaaaag    64500
attcgaaaga gtttttccat ctatcacaaa cttcaatacc tcttcctcca taatatggat    64560
aactgtcttg atttttgtta tagcatcttt ctttcatttt tctccatact gtatactcag    64620
gatgtttttt agaaccatta cgtgatttca tacaaccaca acttttataa tagtataatt    64680
gacttttaga taaaactcta tccataccgc aatcacataa gcataaatat aatttaccctt    64740
taatcttatc tgaacctaca tattcttcaa caaataattt ttctatttttt ttacctataa    64800
tattttccat aaaatctctc ctttgaaaat attataacat atatataagg ggtattgcaa    64860
ccccctttatt tattaacctt tgaatacacc ccaggcaact ccaggtacat gtgaaggtgg    64920
aacaccttga caagttctaa cagggcaata tactctgtta ccattgtaag cattataacc    64980
tatccaaata tgacctgctt ggatacaaac ttcgtcatat acaattgtag ccctgccgg    65040
taagttaccg cctactggag catttaagaa tggagaacct attctagtta ctataggttg    65100
gttaccatta acaaatgttg catttttccgg tttataccaa gttccgtact ggttctttt    65160
ccaagagcct gtaactggtc tagttgccgg tgtacttgcg ctacttgttt ttccatcttt    65220
aactactgta gaacttgaag tcccttttatc catgtagttt ttaatttgtt taatgaaata    65280
atcttttaat ttattcatta ttgcttgtga tggtcttcct tgtgttactg gattaaatcc    65340
```

FIG. 21JJ

```
                              sequence.txt
tgtatgaaga accatagaac ggtgagggca ggcagttggt acaaattcca tatgcaatct    65400
tacagtttta cggttaggag taagacccca ttctttaaat ttctccgctg taaattggaa    65460
tactgcttgt tcatttttaa ggaattgagc atcactagca ctcattgatt gacagacttc    65520
aatacctgca aatctaaagt tacctgagtt tgctcctgtt ccatctcctg tgtgccaagc    65580
aatttgattc ttagcatcta ttgcttccca tacataacct tcagagccgt agtaatgagc    65640
aataccatta gcgtatctag cataacctgc attagctaat gaattctcgt attgttgtcc    65700
tgaagaacga cctgcatcgt tgtgtattac cattccttca ggttttttac cacgtttatc    65760
cattgtatag ttaatgtgat tcttagaaac ttttagtgtt gctttctttt taggtgcagg    65820
agttttactt gcgcttttct tagctgtttc tttttttaaca gtagttcctg cttttacagg    65880
tatttcaatg aagtgagtta atccgtaata attatctaca cgttttgtag gttttttatt    65940
agcataacca ttccagtttt gctctaaaat agtaaacgta gaagtattac ctccatcata    66000
tacaatacct atgtgacccc actgttcata actaccggat gtaaataccg caatccaacc    66060
ttttttaggt acagtagaag gtttattttc atgtattta aatccagtac cataactctg     66120
tttaatttgg tctttagcat taccccaagt tctaacttta ttatctgtta accataaaac    66180
atagtctgta ataaggtctt gacactgagc gtgatagtaa ccatctgcgt caatggctcc    66240
tgcttccatt acaccaaatg atgggtcata acttgtagct tttttaactc tgtaagggct    66300
atctactgtt cctttgcat aagcgtctaa acgtttattt atttctgctt gagtcttagc     66360
cattacttaa cttcctcctc tgcaaatact ttaccatgtt cctcggtatc ttcttcatct    66420
tgagaaggtg ctgaaccacc atcaatttca tcttcaatag caggtacttc atcactatca    66480
tctgtgtcag gttctgcatt gttttcgtag ctgtctatct caaaagtact agcgttattt    66540
gcatttgctt gccattgaac gaattcatta gggtctttac tatcacgagg tttaagatag    66600
tctgtttgaa caatatcact atctttaaga ccttagtat tattatcaac aataatacct     66660
aaacctgcta atagtgttag tatagaacct acaatattta caccttgctc aatttgagct    66720
gagtagtcta aaccgaaagc acctgtaatt tggttagcaa ataatgctac tgctgatata    66780
attgctaccc aaaatgtttt gctcttagtt cttgtgctaa ggtttattcc tccaacaact    66840
ttaggttgtt tagtttcatt agccattaaa aaaccgacct ttctattata tttatttcta    66900
acaataatat aacagtaggt cggtcatgtt tatctatatt aatttaacac ttactcatta    66960
atttggttta gttttttgat aacttcagac atttgtttgt tatctaaatc ttctaatta     67020
gtttcaggaa gtagctctaa cttatcccaa acttcttctt tattagatac tttattatta    67080
ataattgcct taccaactaa actttccgta taatataatt gttttgctga tgccatttgt    67140
atctctcctt ttaaatatgt aaagtatata gctagtatcg tatcctagga acaaacactt    67200
gcgctatata ctcaatgaaa tcctaccctc attcgaggac acagcaaacc ggttcgtcaa    67260
```

FIG. 21KK

```
sequence.txt
ccgcacatat gaattctcag atttcattta tgtaaaacac accctctttg atttgcacaa    67320
agactaaggg ttttggagac ccttgtacta ctaattatac taagggtgtt tattatggtt    67380
tctattggat ttgaaccaat gacacctaga gcttcaatct agtgctctac catctgagct    67440
aagaaacctt aaaacgaccc atacgagact cgaactcgta ctctctgccg tgacagggca    67500
gtgtgttaac cagttacacc aatgagccaa aattataatg ctataccctc accttacctt    67560
aatgtatagc aggtttttat ataagctcga agcaacgatt attaccactc ataacaacta    67620
tatattaagt gaaaggaggt gaaatgaaca aaacgtggta attggtactt atataggaaa    67680
tatgtataat ctacaaggag taagttattg gttcataaag gagtgtgaac aataaataca    67740
tgaaagagtg aaagtttact ccctgtagat tctttttttaa ttatcaatca aaggaggaaa    67800
ctgataattg ttaataataa actataaaga ggaaaatatt tatagtcaca ttctgatata    67860
atgcaactaa atatccaagc ataacccgtc tcacgaggaa cctacctata agacctgtta    67920
ttaagtgaat cactacgatt gactctatta aggagctacc ttaagtccat ctcacgcaat    67980
ttaaaaggga cttacaaacc gtaaaacggt aataagttta ttaaataatg tgatattaac    68040
atattagtta ataactttca catggtcgaa gaaaagtaaa tttatttgat taccaaatta    68100
tttttatcaa atatagctct tttgaacctg tagatttatg ctactcatac tgataacctc    68160
tattatctaa cacatttctg tgctccaact acagttagtc gttacagcgt atctttctag    68220
gattccgcta agaccctaga aagaaattaa accctagccg ttatcatact ctacagacct    68280
tataagtaag taccaagtat accaatcgta tttaacaata ctaatgacga cccatcctac    68340
cgatatatct ccgataggtt ttgattcgtt tgattatctt gtaccttatg actaccaaat    68400
cattattcag tcactatgct cagatattta gttgtattat ttatatatta attataacat    68460
aatttttatt acttgtcaag ttaatttttaa aaaaaattat agaagtaggg acgtttacct    68520
acttccatt aatttacaca aggatgataa cattgttatt gttttatact ggaaaacaat    68580
gtaataaaaa cagtgatgtg taaggtattt gttttattgt taattacatt atagcatata    68640
ctgataccttt tgtcaagtta atttaatact ttttttaaaa tattagttat cttttgttaa    68700
ttcttcctga atagcatccc atcttctttc tgcttcacta cgattatctt ctatatgctt    68760
tgtagtttta caacatttaa tacaatatat atctttgata tgaccttctt ctctttttatt    68820
tgctcttttt cttggtactt tgaatacatt tccacattct ttacatatta aacttgagta    68880
aaacattttt tgtcttttca taattaatca attccttttc tcttttattt gataatttaa    68940
ctatatacta tactgataaa taagtcaaca gttttctaaa aaataattta aattattttg    69000
aagaatcctt taatatcagt acttacaaga gaaaaagtac gtatttagaa aataaggagt    69060
actcctatta tatataatta tattctgata tacagtaatt aataatatta aatatataat    69120
```

FIG. 21LL sequence.txt

| | | | | | | |
|---|---|---|---|---|---|---|
| tataattaat | agggttggga | aaattgatat | aaacataact | gatactgttt | ataaatactc | 69180 |
| agtataaaag | taaaatccct | tagtatcagt | acttacaggc | aaaaaagtac | gtatttagaa | 69240 |
| aataaggagc | tctcctatta | tagttatata | tatatattta | ttactattat | taattactat | 69300 |
| ttaaatatat | aattataatt | aacaatgtta | gaaagtcaac | aatagcataa | ataaaaaagt | 69360 |
| gactacttaa | agtcactcaa | taattagaat | actattttaa | aagattctat | tctgtttgga | 69420 |
| ttaatatata | cttgaggtga | agtatagca | ctttcagtat | atactttat | agaggtttca | 69480 |
| tccattcctc | ttaacatata | atctatatct | tgcctattgt | aactcttttc | atcagtagat | 69540 |
| actaaaaagt | atttagctcc | acttgacatt | gttatttcaa | tatgttttga | catctacaat | 69600 |
| ctctcctatg | caaatttgtt | aaagacaaag | gataatatag | ctcctagaac | aagtaaaaga | 69660 |
| accttctcag | ttgtatcctt | tttcttagta | tccttagttt | ttgtactttc | agcaagttct | 69720 |
| gaaatctttt | catcaagtct | ttctaattgg | acgtaaattg | ctgattgttt | ttcactattg | 69780 |
| acagctacat | ctttatctat | actaactatc | attttctta | gttcagctac | ctcaacttct | 69840 |
| aaatctttga | aagttcctct | atctatataa | ttaccttctt | gtatcttaga | cttaatagtt | 69900 |
| tctacttgag | aaacaaggtt | gtttatctcc | ttatccaact | agaatcacct | ctaaggtcta | 69960 |
| accgtttcag | attcagaatg | gatatcataa | ttttctaaga | aatcattgat | aatctccata | 70020 |
| taattatccg | taacgacttt | tccgtaagat | gttttgtat | caatttcgaa | tctaagttta | 70080 |
| ccgaagtctt | ggaggtctaa | ctctttat | acaatattcg | ggtcatcaga | aggaaggtaa | 70140 |
| taatagtcga | agtatataat | tgagccattt | attagtagac | ggtctattct | atacatatga | 70200 |
| aagaatcttc | tgtctcgttt | gaaatgagct | agtgaatctt | taaactctaa | cttaagtata | 70260 |
| tccttatatt | tagtcaaagt | ggtaacctcc | ttactattaa | tttttaaatt | tacttatttt | 70320 |
| gtgttataat | agttatgata | aaggcagtta | ttataattat | attaagaata | aagataataa | 70380 |
| ttatttttc | tgagaaaata | agccaaatac | tacaaacaga | taaaacatag | atagctgata | 70440 |
| gatatactat | attaatagtt | accttacttt | tatcttttct | atagatagaa | taacctaaag | 70500 |
| aagttgtaac | accactaagt | ataaataat | agaaacaaaa | aagaggtata | gacagaaaaa | 70560 |
| aagatacgat | aatcattgtt | aaacacctat | ttcttttga | cctattattt | ctagaacttt | 70620 |
| tagattatac | cactaatata | acattaaaag | ccagtcataa | aagtcaattg | ttagattaat | 70680 |
| aatataataa | aaaagacaa | taggaggtta | aagtggttga | ataataacat | agctatattc | 70740 |
| atattcaaaa | cattggttat | cattatattc | ttactgctat | ttttgtctgt | tgttaattcc | 70800 |
| ttatcccta | tttactcaat | aagaccgagt | gtagttatgg | catactttac | ctttggaggt | 70860 |
| attgtttctg | atgtcgcact | tactatgaca | gataagttct | tacttaagaa | agaagaccct | 70920 |
| ctacctgagt | atgttcttaa | aaaagtagag | ataaatgata | aagaaataag | cataattaag | 70980 |
| aaaatcatag | aaagtaatta | tgatataaca | tcagaagaga | taaagttag | agctaaagca | 71040 |

FIG. 21MM sequence.txt

| | | | | | | |
|---|---|---|---|---|---|---|
| caacagagat | tagaggaaga | tagcaaagag | gaagataacg | atgaaaacga | agaaagaaat | 71100 |
| taaagaacaa | aggaaagaac | ttaaagacgg | tgctacaact | gtttctttag | taaaaaaagg | 71160 |
| ggataagaga | atagctagcc | ctagtagaat | ttgtagttta | tgtggtcagc | agttatcagg | 71220 |
| tatgagttac | actaaggaa | aagcattatc | aaaagttaat | cattttcatt | tacagtactc | 71280 |
| taagtacatt | tattttgata | tttgtgcaga | tattaacaat | tgttataaaa | atttaagaaa | 71340 |
| acgaggtgaa | atggattgag | tgcagaaaat | attagagata | taattaataa | gaaaaagtta | 71400 |
| gaagaagagg | atacaagaaa | atatatagct | gatggattta | tgaatggtat | cggtaaatta | 71460 |
| atgtatgaat | tcaataaaaa | agtagataat | aaagaaatag | aagttaaaga | ccctaacgat | 71520 |
| ttatataaac | tatttgtgat | attctctcaa | atgcagaata | tggttaatga | aacttctgaa | 71580 |
| ggtggagcaa | tacctcaact | atctagacct | caacaagaat | tatttgaaga | gattacaact | 71640 |
| gaagatagta | atggggagtc | tactgtagac | ttacaaaaaa | tatcagaaat | gtcagcagaa | 71700 |
| gatattacag | aaatgatttc | tgaaaaagag | aaagtaatga | atgaggaaaa | ttcaaaaaca | 71760 |
| ttctaagggg | aaagatataa | catggatgga | aaagaactaa | ttaaaatagc | acaagaaaca | 71820 |
| tttcaaacag | aaaaaataac | aagagagcag | atagaccata | taatcaatat | gttaaaccct | 71880 |
| tctacctata | tgcttaagta | tcacacgcta | agaggtcacc | ctataacttt | cagtattcct | 71940 |
| aatagggata | gaagtaaagc | acaagcacac | cgaccttggc | aagtccgtaa | acatactatg | 72000 |
| cggactataa | accttttcta | aaattggaaa | ctcctaacaa | gtgaagttga | ggacaatcaa | 72060 |
| ttgctaaatc | gtaactaaga | taaatatttt | aattacgtaa | atgcctaacg | actaaatttc | 72120 |
| caagtaagca | ataaaatggt | attgtgtaga | attggaagag | agggaaaccg | taacgaaaag | 72180 |
| gactttacg | cctaactgta | aaagtatgat | atagtctaat | cccctaataa | atatcgggaa | 72240 |
| accgagggta | gtaaatgata | gtaaatgaca | ctcatccaaa | caaagcagtt | attaaaagca | 72300 |
| gacaattggg | gcttagtgag | atgggtgtaa | tggaaatggt | tcattttgca | gatatgcata | 72360 |
| gctatgccaa | tgcaaaatgt | ttatatacct | ttaattagag | aggcttcacg | tagcaatgcg | 72420 |
| tgttgaaaaa | ccttgttaaa | cggggaaacc | cctaacgtaa | agacgagggc | aatcccgtgc | 72480 |
| taaatgttga | ctaacctaat | attatgat | atattagtta | tagtcagcta | aatgccgaac | 72540 |
| gactaaattt | ctaggtaggt | atctaaatgg | aggtactgag | aactagataa | aaaaactact | 72600 |
| taaaataatt | agacttaaaa | aaatactgtt | ggaaggagga | tatttaatgg | gaaaaaaatt | 72660 |
| aactaatact | gagttttaa | atagagtatt | tcagttagtt | agtgatgaat | actcattttt | 72720 |
| agaagagtat | aaagggagac | ataccaaatt | aagatgtaaa | cataatttat | gtagttacga | 72780 |
| gtgggatgta | gaacctggag | cttttttagg | taataagaac | aaagcaggaa | gtagatgtcc | 72840 |
| tagttgttat | ggtaatgtta | ctaaaacaac | agataaattt | aaaaaagaaa | tatacaattt | 72900 |

FIG. 21NN sequence.txt

| | | | | | | |
|---|---|---|---|---|---|---|
| aactaaagat | gaatataggt | tactttctga | gtatattaat | gctaaaacaa | aagtaaaaat | 72960 |
| taaacattct | aaatgtggta | atactttttc | tatgacacct | aatactttta | taaatggaag | 73020 |
| tagatgtcct | gaatgtaacc | ctcaaaaacc | gtataataca | gattctgcta | aagataggat | 73080 |
| aaataaagaa | acgaatggta | cttttgaact | agttagtgaa | tacaaaggtt | gttatgagct | 73140 |
| tatgaagtta | aagcatcatg | aatgtggaaa | tattgtagaa | ataaatatgc | agagtattga | 73200 |
| tagcaataga | ctaaattgtc | cttattgtta | taataggtct | agaggtgaat | tactagtatc | 73260 |
| ctcatttctt | cttcaaaaa | acataccatt | cgaagtccaa | aaaagatttg | atgggtttaa | 73320 |
| gaaatatcct | tatgattttt | atatagctga | ttataatacg | gttatagaat | atcatggaga | 73380 |
| acaacattat | aaacctatta | agttttatgg | tggagaagat | agattggtaa | ggcagaaaaa | 73440 |
| tatagattta | aagaagaaaa | attttgttga | gggtaaaggt | ataaattact | tagaaatacc | 73500 |
| ttacacatta | aacaatcaaa | ataaagtaaa | tgagttttta | attaattatt | ttaagtagaa | 73560 |
| gtaaagcaag | gaacccttaa | ccaaacttaa | gggttatgat | atagtctaaa | ccgtatataa | 73620 |
| atactaggaa | actagcggta | taattgtcct | acaaatgaac | aaatgaagaa | atttgttcag | 73680 |
| tctcgtttaa | atcctgtatt | agaaaaagaa | tattttaggg | atattgttga | ttgggataaa | 73740 |
| gactctttag | gttttaaaaa | gataagaaat | tctagtttat | tctttagaac | aagttctaaa | 73800 |
| gcaagtactg | tagagggtgt | ggatattgac | tatttatctt | tagatgagta | tgacagggta | 73860 |
| aacttattag | cagaatcgtc | tgcactagaa | tcaatgtctt | catcaccttt | taagattgtg | 73920 |
| agaagatgga | gcacaccttc | tgtaccgggg | atgggtatac | acaaattata | ccaacaatca | 73980 |
| gaccaatggt | attacggtca | tagatgtcaa | cattgtgatt | acttaaatga | aatgagttat | 74040 |
| aatgattaca | accctgataa | tcttgaagaa | agtggaaata | tgttatgtgt | taatcctgaa | 74100 |
| ggggtagatg | agcaagctaa | aacagtacaa | aatggtagtt | accaatttgt | ttgccaaaaa | 74160 |
| tgtggtaaac | cactagatag | atggtataat | ggtgagtggc | attgtaagta | ccctgagcgt | 74220 |
| acaaaaggta | ataaggggt | acgaggatac | ctaataacac | aaatgaacgc | tgtatggatt | 74280 |
| tctgctgatg | aattaaaaga | gaaagaaatg | aatacagaat | ctaaacaagc | attctacaac | 74340 |
| tatattttag | gttatccttt | tgaagatgtt | aaacttagag | ttaatgaaga | agatgtttat | 74400 |
| ggtaacaaat | cacctattgc | agaaacacaa | ttaatgaaac | gagatagata | ttctcatata | 74460 |
| gctattggta | tagattgggg | aaatactcac | tggataactg | ttcatggtat | gttacctaat | 74520 |
| ggcaaggtag | acttaatacg | attattctct | gttaaaaaaa | tgacaagacc | tgatttagtt | 74580 |
| gaagcagatt | tagaaaaaat | aatttgggaa | atatctaagt | acgaccctga | tattataatt | 74640 |
| gcagataatg | gagactcagg | taataacgtt | ttaaaactca | ttaatcattt | tggaaaagat | 74700 |
| aaagtatttg | gatgtactta | taaatcttct | cctaaatcta | caggacaatt | aagacctgaa | 74760 |
| tttaatgaga | acaataatag | ggttacagtg | gataaattaa | tgcagaataa | aagatatgta | 74820 |

FIG. 2100 sequence.txt

| | | | | | | |
|---|---|---|---|---|---|---|
| caagcactta | agacaaagga | tataagtgtt | tatagtacag | tagatgatga | tttaaaaact | 74880 |
| ttcttaaaac | attggcaaaa | tgttgttatt | atggatgaag | aagatgaaaa | aactggagaa | 74940 |
| atgtaccaag | ttatcaaacg | taaaggtgac | gaccactatg | cacaagcaag | tgtttacgcc | 75000 |
| tatataggat | taacaagaat | aaaagaactt | cttaaagaag | gaaacggtac | aagctttggt | 75060 |
| tctacatttg | tttctactga | ttacaatcaa | gaaggaaata | aacaattcta | ctttgatgaa | 75120 |
| tagaggtgaa | atagacttga | cagataaatt | attttatggt | acaattagta | atgaagaaat | 75180 |
| taataaaagt | gtattgaatt | tgttattggg | tgaggaatta | tccttagatt | atgtttctaa | 75240 |
| aaatagtgat | actttagatg | ttaaatatga | acatgtctat | aaatctctag | gattcgataa | 75300 |
| tttctttgat | tgttttttat | atgctaatag | agagcctgaa | atagtccaca | aaggtggaga | 75360 |
| taaaaatctt | ggtggactaa | ataaggttaa | acgtactgtt | attcgtaatg | gtaaagaaat | 75420 |
| ggaaatgaca | gtttacgaag | acggtaataa | agagaacgat | agtaaagaaa | aacaagaagg | 75480 |
| aaaagaagaa | gttagtagaa | gtgcagtagg | agcaagagct | atttctaatg | gtgaagaagg | 75540 |
| aaaggtaaac | cctaaaaaag | tagcaaattc | attatctagt | ttaagtaaaa | agggtgtaga | 75600 |
| tgtatcccat | attaatacaa | acttatcatt | gtataaagag | tttgttgatg | ataacggtga | 75660 |
| tacattagga | attacatctt | ttaaacgaac | tgaaaatgat | ataatattag | aatcttatgc | 75720 |
| aagttcacct | gattcagatg | gtgtaggagc | aagagctatt | atggaattat | tacgtttaag | 75780 |
| tattaaggaa | aataaaaatg | cagttgtgta | tgacatagaa | ttacctgaag | cagtagagta | 75840 |
| tttaaaaact | ttaggattta | aacctaataa | agatgggtac | atcttaagaa | aaaaagatgt | 75900 |
| aaaacaattc | ttaggtgatt | atagtgattt | tatttagcac | tatagtcatc | tattctattg | 75960 |
| tatttattct | atatattgta | ttaaaaacaa | tttatataaa | gtctaatatg | agtagaatag | 76020 |
| ataacacaac | tgaattatta | aaaatattac | aggaagatat | tgaaggtaag | ataaaaaagg | 76080 |
| aaggaagaaa | taaatgactt | tagaagaaaa | taaattaaca | ttagaagaat | caataactcc | 76140 |
| acttagtaaa | gaggagaaag | aagatagtat | taaagaattt | agtagtttat | tatgtgaaat | 76200 |
| ggtaaatagg | ctatacaagt | cttataatgt | atttagacaa | gaccctatgg | atgaaactca | 76260 |
| acgtctagat | ggctctttaa | tggtctttca | aagtagatta | aatgaccctt | taacaggaga | 76320 |
| tttacatgat | aagatgtata | aacttgcttt | ttcaaaacgt | attgatattt | tcgaagctaa | 76380 |
| taagcaattt | agaaaagatg | tagaagcagg | taaagcaatt | gagttaggtg | atgtagctat | 76440 |
| tatagataca | gcattaagta | acatcctttc | aggcaatgag | ttccaaggaa | gtatttcatt | 76500 |
| tatgcttaga | aaagactttg | aagaaaaaga | acgaattaga | aaagaagaag | aagagaaact | 76560 |
| taataactta | taaaagggaa | gaattatgag | actatataaa | atgaggtatc | ataattgaaa | 76620 |
| aagaaaccac | aaggcaatga | ggtaatcata | accataataa | cggttatgat | agcagtattt | 76680 |

FIG. 21PP sequence.txt

```
gtagtcatta tgaccatatt ttttaataaa tatcaagatg ctaaagaaga taaagataga    76740
tatcaaagat tagtagagat ttataaaaaa gcagatgata atgatggtga gactaaaaag    76800
aaatatgtta aaagattaaa taaggctgaa gaagaactta aaaaagtaaa aaaagaaaca    76860
aattataaag attataataa gaagtcaagt aaagaaagac aaaaagaaga taaagaaact    76920
agagagaaaa tatatgatgt aactggtgat gatgacttaa tattagtaaa aaataatatt    76980
gattttagtg ataaagtaga caagcccgaa atacttatta gtgaagatgg aattggtacg    77040
ataactgttc ctgtagatag tgggtatgaa aaacaaacag taggttctat tattactagt    77100
gtattaggtt ctcctttcct atcacctggt tcaaatagta tagatggttt aagtgttatt    77160
aacgataatg tttatccaaa tacagtagat agcatagtag aagatacaaa accttctatt    77220
aacttaccaa tggataatcc tattataaca aatccggttg aaccaactat accttcagat    77280
actatacctc ctattgataa tccttcagtt ccggtatttc ctgagaatcc agtagataat    77340
aatcaaggaa atacagataa tccaaaccca ccgcctccag gatatacaga tgaagatggt    77400
ggaaggggct ccggtggtgg aggaaattct gaaccaccat caacggaaga accttcggat    77460
aatggtaaca ctggaggagg agattgggaa gaaaaacctg acccaggaga agaaccttca    77520
gataatggta atacaggagg caatggtgga gaagttacgc ctgaacctga ccctacccct    77580
tctgaacctg aacaaccgaa tgaaaattct gatgaaggta atgaagaaaa accatctgaa    77640
ccgtctgaca atcctgatga aaatggagga tgggaaactg aaccaactga acctgagtca    77700
ccttcagagc cggacgataa agtggacgaa gaggataaaa atgaagatac tacagatgat    77760
aaacagccca ctgaacaacc ggacgataac aacatagata atgaagataa aactgaagag    77820
gagtaattac tcctcttttt tgtttgctat attaaataag agttaaatat aaaaaaaatt    77880
gaacattacg gtggtgaaaa ctttgttagg aatgaatatt ataacgtcac tatcagtagt    77940
atttacctgt ttaagtcttt taactttaat gattttgtt catagtaagt tctctagtaa     78000
aaacgttttt gttttgtatg taatttatgc tataatagga ataggtacat acatagtttt    78060
aactatgttt caaacaacat ctgtacttat taagaatgat gtaatagatt ccatagaaaa    78120
tactgaacat tatattggat tcaatgaccc tataattata tttactataa gttttatagg    78180
tgcaatactt ggaggaattt ggtacaagat gatgaaaatt attaaaaaga gtaactttaa    78240
agataaaaaa taaaaaagac ggtgaatagg ttgatattct ctaaagataa aaaatgggat    78300
gaagcaaaag atttcatcaa aggtcaaggt atgcaagata attggataga gattgtagat    78360
tattatagac atataggtgg aaaacacgta gctgttttta ttgctttaaa caaagtaaaa    78420
tacatgattc tagaagcaac aaaagacaat aaagtaatat tagtagataa agataataat    78480
atactattag aagattatga tattgttatg gaaagtaaga agatgttttta ttacattgaa    78540
gaaccgttcg aggttaaaat aaatatccct caacatatta gagatgtaac ttataataat    78600
```

FIG. 21QQ sequence.txt

| | | | | | |
|---|---|---|---|---|---|
| actgttgtat | taactacagt | aagagggagt | agaggtgact | agtaattggc | agatttattt | 78660
| aagcaattca | gattaggtaa | agactatggt | aataatagta | ccattgctca | agttcctatt | 78720
| gatgaaggat | tacaagctaa | cattaaaaaa | atagaacaag | acaataaaga | gtatcaagat | 78780
| ttaactaagt | ctttatacgg | acagcaacag | gcttatgcag | agccatttat | agaaatgatg | 78840
| gatactaatc | ctgaatttag | agataagaga | agttacatga | agaacgaaca | taacttacat | 78900
| gatgttttga | aaaagtttgg | taataaccct | atccttaatg | ctatcatact | tacacgttca | 78960
| aatcaagtag | ctatgtattg | tcaacctgca | agatattcag | agaaaggttt | aggttttgag | 79020
| gtaagattaa | gagacctaga | tgcggaacct | ggtagaaaag | aaaaagaaga | aatgaaacgt | 79080
| atagaagatt | ttattgttaa | tactggtaaa | gataaagatg | tagatagaga | ttcatttcaa | 79140
| actttctgta | agaaaattgt | tagagatact | tatatctatg | accaagttaa | ctttgaaaaa | 79200
| gtatttaata | agaataataa | gactagacta | gaaaaattca | tagcagtaga | cccttctact | 79260
| attttttatg | caacagataa | aaaaggtaaa | attattaagg | gtggtaagag | atttgttcaa | 79320
| gtagtagata | aagagtagt | agctagtttt | acttctagag | aattagctat | gggtataaga | 79380
| aaccctagaa | ctgaattatc | ttcctcagga | tatggattat | cagaagtaga | gatagctatg | 79440
| aaagagttta | ttgcctataa | taacactgaa | tctttcaatg | atagattttt | ctcacatggt | 79500
| ggtactacta | gaggtatttt | acagatacgt | tcagaccaac | aacaatcaca | acatgcatta | 79560
| gagaacttta | agcgtgaatg | gaaatctagt | ttatcaggta | ttaatggttc | atggcaaatt | 79620
| ccagtagtaa | tggcagatga | tattaaattt | gtcaatatga | caccgactgc | taatgatatg | 79680
| caatttgaga | aatggttaaa | ttaccttatc | aatattatat | ctgctttata | tggtattgac | 79740
| cctgcagaaa | ttggtttccc | taatagagga | ggagctacag | gttctaaagg | tggctctact | 79800
| ttaaatgagg | ctgacccagg | taaaaaacaa | caacaatctc | aaaataaagg | tttacaacct | 79860
| ttacttagat | ttattgaaga | tttagttaat | agacatatta | tatcagaata | tggagataag | 79920
| tatacattcc | aattcgtagg | tggagatact | aagagtgcta | ctgataaact | taatattctt | 79980
| aaactagaga | ctcaaatatt | taaaacagtt | aatgaggcta | gagaagagca | aggtaagaaa | 80040
| cctattgaag | gtggagacat | tattctagat | gcttcattct | tacaaggaac | agcccaatta | 80100
| caacaagata | aacaatataa | tgatggtaaa | caaaaagaac | gtttacaaat | gatgatgagt | 80160
| ttactagaag | gagacaatga | tgattctgaa | gaaggacaat | cagcagattc | tagtaatgat | 80220
| gataaaagta | accctgaagt | aggaactgac | tctcaaataa | aaggggattc | aaacgtttat | 80280
| agaacagaaa | cttctaacaa | gggtcaaggt | aaaaaagggg | aaaagtcttc | tgattttaaa | 80340
| cactaataag | gaggtaaaat | taatgtcag | ttatatataa | agataataat | tggattgatt | 80400
| taactaatgt | tccttattta | caaaaaggtg | atagtggata | tcgtaaagat | ataccaagga | 80460

FIG. 21RR sequence.txt

```
aaaattggaa aaagtgttta aatacagaag taagtttttc ttataaaggt aaaaagggtc    80520
tattttatgt aacttatcgt aaggaagata aaggaaaagt taaagttgaa tatgataagt    80580
atgttaagat aatagaccct catgatttaa agacactaaa tataaataaa atagttaatc    80640
ctcctaataa agctaagtat cgtgagcagg aagtaattaa tggtgatact gtaagaaata    80700
ttagaaaagt taagaataca ggaattgttt atactatgtt atgttcagag tatgaagaag    80760
aatatgatat aagagaaagt gatttattaa gagggagagg tagcccttat aaatcaggta    80820
gaaaagtatg ttataacaat tcattatatt ctgttgaaaa tttgagagaa tatatctgtg    80880
atttagaata tgctaaaact gtaactaagt tttcacataa agatataaaa tgcaagtgcc    80940
ctatatgtag tgaagagaaa gttatgaagg ttaataaatt agttaataac ggtttttctt    81000
gtcatagatg tagctcaact ataacatatc ctgaacgatt aatgatagga ttactagaat    81060
taaataattt aaactatgaa tatcaaaaag tatttaaaga cctacctaat agaaaatttg    81120
attttattt acctaaatta aatatggtta ttgaaactca tggattacaa cattataggg    81180
aattaaatgg ttacatgaat catgaaaaaa caaaggaatc ggatttagag aagtataact    81240
attgcaagaa taataatata gattatattg aaatagattg tagttacagt gatttatcct    81300
ttatattaag taatgttgag aatagtaagt taaatagcat acttaaaaat aagaattacg    81360
ataatcttag caattatatt ataagaagta aaaatgatga tgttaagtat aatatatatt    81420
tggattactg caaaggatta agcaagaaag aattgaaaga taaatataat aaaacgagtt    81480
attatataaa caggtctatt gagatattta acattaatt aataagccta gaataaatct    81540
aggctttgtt tattttttt gtaatttaat tttgataaat gtaataacta tggtatacta    81600
tatgtaattg atattaatac ataaaaaata ttaatatttc acttacaagt tattattgtt    81660
atattattaa cgtaaaagta aataaaataa caagtggagg tgtagacacc tttggaagaa    81720
ataaaattta atgcttttgt acctatggat ttgaagaaat ctgtatcaac agcttctgat    81780
actaatgagt attctatcgt ttcaggatgg gctagtactc caagtatgga tttacagaat    81840
gatatagtta atcctaaagg aatagatata gagtatttta agtcacaagg gtacattaat    81900
tatgagcatc aaagtgataa ggttgtaggg atacctacag agaattgcta tgtggatata    81960
gaaaaggtt tatttattga agcaaagcta tggaagaatg acgaaaatgt tgttaagatg    82020
cttgatttag ctgagaaatt agaaaaatca ggtagtggaa gacgtttagg ttttttctatt    82080
gaaggtgcag ttaaaaaacg taatataaat gacaatagag ttattgatga agttatgata    82140
accggagttg cattagttaa aaaccctgct aatcctgaag caacatggga aagctttatg    82200
aaatcatttt taactggtca tggtacatca cctgacactc aagttgatgc aggagcttta    82260
agaaaagaag aaatagcatc tagcattaca aatttagctt acgtcactaa gattaaagat    82320
ttaaaagagt ttaatgatgt atggaatggc gttgttgaag atttgagtaa atctaatagt    82380
```

FIG. 21SS sequence.txt

| | | | | | | |
|---|---|---|---|---|---|---|
| atgggatatg | aggaatcagt | ccttacgtta | caactagcta | aaggtttatc | tcgtaaagat | 82440 |
| gcagaactag | cagtaatgga | tataaacaaa | caaaaactag | aataggtaag | gagaatacat | 82500 |
| tctatgagta | aagaaatgca | aaatatttta | gaagagtatg | ataagttaaa | tgctcaagag | 82560 |
| gcagtttcga | aatctgtaga | agatgatgaa | aagaatacag | tagaatctac | cgaagagcaa | 82620 |
| gtagcagaaa | caactgaaga | acctgctaaa | gaacctgaaa | aagtatctga | ggaagatgct | 82680 |
| aaagaagcac | aagagcaagg | tgaaaaagtt | gaatctgaag | aggtagcaga | ggacaatgaa | 82740 |
| gatgaggaag | ttgaaaaatc | agctaaagaa | tcaaaagacc | ctgtagacca | aaaagatact | 82800 |
| aagacagaaa | ataaagacaa | cgagaaacgt | aaaaataaaa | aagataaaaa | agaagattct | 82860 |
| gattctgacg | atgaagataa | agatactgac | gatgataaag | ataagaaaga | agataagaag | 82920 |
| gaaaaaactt | ctaaatcaat | ttctgatgaa | gatatcacaa | cagtatttaa | atctatctta | 82980 |
| acatcttttg | aaaacttaaa | taagagaaa | gaaaactttg | ctactaaaga | agatttaagt | 83040 |
| gaagttagta | aatctattaa | tgagttatca | gcaaaaattt | ctgaaatcca | agctgaagat | 83100 |
| gtttctaaat | cagtagacac | tgatgaagaa | gctgtagaaa | aatcagtaac | atctacaaat | 83160 |
| ggagagcaag | aaaaagtaga | aggttatgtt | tctaaatcag | tagacactga | agaacaagct | 83220 |
| gaaactggtg | aagcaaaatc | agaagaagct | gaagaagtac | aagaagataa | cacatttaaa | 83280 |
| ggattaagtc | aagaagaacg | aactaagttc | atggattctt | acaaagcaca | agctaaagac | 83340 |
| cctagagctt | ctaaacatga | cttacaatca | gcttaccaat | cttacttgaa | cattaacact | 83400 |
| gaccctacta | acgcatcaga | gaaagatatt | aaaactgtaa | aagactttgc | acaaatttaa | 83460 |
| ttaatgcaca | aagttgtgtt | atattatacg | gtgtaactaa | agaatataaa | tagggtacat | 83520 |
| tttactgtac | cctacataaa | ataaaaagaa | cacaaatgaa | aggtgataaa | tttatatgac | 83580 |
| tatcgaaaag | aacctgtcag | acgttcaaca | aaagtacgct | gaccaattcc | aagaagacgt | 83640 |
| agtaaagtca | ttccaaactg | gttatggaat | cactcctgat | acacaaattg | acgcaggagc | 83700 |
| tttacgtaga | gaaattttag | atgaccaaat | cacaatgtta | acatggacta | atgaagtttt | 83760 |
| aatcttctat | cgtgatatct | cacgccgtcc | tgctcaatct | acagtagtaa | aatacgacca | 83820 |
| atatttacgt | catggtaacg | taggtcactc | tcgtttcgtt | aaagaaatcg | gagtagcacc | 83880 |
| agtatctgac | ccaaatatcc | gtcaaaaaac | tgtatcaatg | aaatacgttt | ctgatactaa | 83940 |
| aaacatgtca | attgcatcag | gtttagtaaa | taacattgct | gacccatcac | aaatccttac | 84000 |
| agaagatgct | atcgcagttg | ttgcaaaaac | aattgagtgg | gcttcattct | acggtgacgc | 84060 |
| ttcattaact | tctgaagttg | aaggtgaagg | tttagagttt | gatggtttag | ctaaattgat | 84120 |
| tgacaaaaat | aacgtaatta | acgctaaagg | taaccaatta | actgagaaac | acttaaatga | 84180 |
| ggcggcggta | cgtatcggta | aaggtttcgg | tacagctaca | gatgcttaca | tgcctatcgg | 84240 |

FIG. 21TT sequence.txt

```
tgtacacgca gacttcgtta actcaatctt aggtcgtcaa atgcaattaa tgcaagacaa      84300
cagcggtaac gttaacactg gttacagcgt aaatggtttc tactcatctc gtggattcat      84360
taaattacat ggttctacag taatggaaaa tgaattaatc ttagatgaat cattacaacc      84420
attaccaaat gctccacaac ctgctaaagt tacagctact gttgaaacta agcaaaaagg      84480
tgcttttgaa aatgaagaag accgtgcagg attatcatat aaagtagtag ttaactcaga      84540
tgacgctcaa tcagctcctt ctgaagaagt aacagctaca gtatctaacg tagacgatgg      84600
tgttaaactt tcaattagtg ttaacgctat gtaccaacaa caaccacaat tcgtttctat      84660
ctaccgtcaa ggtaaagaaa caggtatgta cttcctaata aaacgtgtac cagttaaaga      84720
tgcacaagaa gatggaacaa tcgtattcgt agataagaac gaaacattgc ctgaaacagc      84780
agacgtattt gttggtgaaa tgtcaccaca agtagttcac ttattcgaat tacttccaat      84840
gatgaaatta ccattagctc aaattaatgc ttctattaca tttgcagtat tatggtatgg      84900
tgcattagca ttacgtgctc ctaaaaaatg ggctcgtatt aaaaacgttc gttatatcgc      84960
agtttaatag aataagaaaa actgaataca agagaatagg gataaactta gggtttatcc      85020
ctttttttatt aaaataaact tgaagggatt taataaatat gttatactat aagaaactat      85080
tagataaaaa aatggctact gtttatggta cagtggagat tgacaaagat ggagtagtta      85140
aaggattaac taaagagcaa gaaaaagaat ttgcaaatgt tccaggtttt gaatttgaag      85200
aagaaaagaa aactactaga aaacaatcag cttctactag taaagaagaa gagcctaagg      85260
aagaggaaaa gaaagcctct actagaaaaa ctacaagtac tactagaaaa tctacagcac      85320
gtaaaacaac agccaaaaaa gatgaaaata agtaaagggt gaattaaatg gttaactcaa      85380
tgtttggagg ggacttagac ccttatgaaa aatcattaaa ctatgaatat ccttatcatc      85440
ctagtggtaa tcctaaacat atagacgtaa gtgagataga taattttaaca ttagctgatt      85500
atggatggtc accggatgca gttaaagcat atatgttcgg tatcatagtt caaaatcctg      85560
atacaggaca acctatgggt gatgagtttt ataaccatat attagaaaga gcggtaggta      85620
aagctgaaag agcattagat atatctatac tacctgacac tcaacatgag atgagagatt      85680
atcatgagac agagtttaat agttatatgt ttgtacatgc ttatagaaaa cctatattac      85740
aggtagagaa cttacagcta cagtttaatg gtagaccgat atataaatac cctgctaact      85800
ggtggaaagt agagcatcta gcaggacatg ttcaattatt ccctacagca cttatgcaaa      85860
caggacaatc aatgtcatat gatgcggtat tcaatggata ccctcaatta gcaggtgtat      85920
acccaccatc aggagcaaca tttgcacctc aaatgatacg attagaatat gtatcaggta      85980
tgcttccacg taaaaaagca ggaagaaata aaccttggga aatgcctcct gagttagaac      86040
aattagttat aaaatatgca ttgaaagaaa tataccaagt atggggtaac ttaatcattg      86100
gtgccggtat tgctaataaa acattagaag tagacggtat tacagagaca ataggtacca      86160
```

FIG. 21UU

```
sequence.txt
ctcaatcagc tatgtatggt ggagctagtg ctcagatact tcaaataaat gaagatataa    86220
aagaactatt agatggttta agagcttact ttggatataa tatgatagga ttataaggag    86280
ggttagaaaa tggaaaaacc gtatatgata ggagccaact ctaaccctaa tgttattaat    86340
aagtcaacaa catatactac tacaacacaa gcagatgaac aagataaacc taagtatact    86400
actagactag agtttgatac gattgacatg attaggttta ttaatgaccg aggtataaaa    86460
gtattatggg aagaagcata tttctgccct tgtcttaatc ctgatacagg acatcctaga    86520
gtcgattgtc ctagatgtca tggtaaaggg attgcatatc tacctcctaa agagactata    86580
atggcaatac agtctcaaga gaaaggaact aaccagttag ataggtat attagacaca     86640
ggtactgcaa taggtaccac tcaattagaa aagaggattt cctatagaga caggtttact    86700
gttcctgagg tattgatgcc tcaacaaatg atttattttg tgaataaaga tagaattaaa    86760
aaaggtatac ctctatacta cgatgtaaaa gaagtaactt atatagccac tcaagatggt    86820
acagtctatg aagaagatta tgaaattaag aataatagat tgtatttaaa tgaaaaatat    86880
gagaatcata cagtaacttt aaagatactt atgactttaa gatatgtagt atcagatata    86940
ctaaaagaaa gtcgttacca atatactaag tttaatcaac ctaaatcaaa atttgaaaac    87000
ttacctcaaa aattacttct taaaagggaa gatgttattg tactacaaga cccttataaa    87060
gttaatgatg gtatagaaga agacctagaa attcaagtag atgacctaa ggcttcggca    87120
tctaatccta gtaatttagg tggattcttc ggaggtgcat ttaaataatg ccagttcacg    87180
gaaagagacc taatttattt aaaaataaaa actataagca ggtaggtaag agaacaattg    87240
atggtatgcg ttcagaagtt cttgataaat tacaagcaac agcacagcaa gtagagaata    87300
ctagtattaa acgtatgcct acttacctac aaataacaga gaaaaagctt gaaaaagaag    87360
gagtagtaga ccttaaaaaa gcttttgctc actcatctaa aaagaaaact agtaaagatg    87420
gcggatggta tttaactgta ccaatccgca tcaaaactag tagaatgaat aacagtactt    87480
accaagatat gagaacttta aaagtagata aggtacagg ttcagtctct aagataactg     87540
attacctaga aggacgtaga aagaatgtaa gccacccttc aatgaagcct gagcctatga    87600
ctcataatat gactaaagtt aaaagaggaa agcaatcttc ttactttata tttagaactg    87660
tttctagtaa gtcacctgct agttcttgga tacttaacag agataaagtt aatgaagata    87720
acttctctaa aacaactcta aaaactgtta agcaattaat gaactggaag atgaaaaatt    87780
taaattaaga ggagggatag tattaaatgg caataacatc agttgattca tatttattat    87840
cagaaataaa gcctagactt aacactgtgc tagagaattg ttatattata gatgaagttt    87900
taaaagactt tgattatcaa actagagaga gctttaaaga agctttctgt ggtaagaatg    87960
cacaacatga agtaacggta ggatttaact tcccaaaatt taaaaataac tatgaagctc    88020
```

FIG. 21VV sequence.txt

```
attacttgat acaattaggt caaggacaag agacaaaaaa ctctttaggg agtattcagt    88080
catcttactt tgaggcaaca ggagatacct tagtcgaatc ttctacagca ataagagaag    88140
atgataagtt agtttttact gtttctaaac caataggaga gttaataaag gtagaagata    88200
tagagtttgc taaatacgat aatcttcaag ttgaaggtaa taaggtatca tttaagtatc    88260
aaacaaatga agattatgag aactacaatg ctaacattat atttaccgaa aagaaaaatg    88320
attctaaagg tttagtaaaa ggattcacag ttgaagaaca agtaacagtt gtaggtctttt   88380
catttaatgt agacgttgca agatgtttgg atgctgtact gaaaatgatt ttaatatcta    88440
tgagagatag tatagaagag caacaaacat tccaattaca gaatttgtct tttggtgata    88500
ttgcaccaat aatagaagat ggtgactcaa tgattttttgg tagaccaaca attattaagt   88560
acacaagttc tctagatttg gattatacta ttacacaaga tattaataaa ctaactttta    88620
aagaaagaaa ggattggaag taggatggct agaaaaaaga cacctgaaaa taacactcct    88680
aaatttaatg gttatgttca tatagataca ttccttgata ctgcaaaaac cctttttaat    88740
atgaaggatt cacaagtagc aggatttaaa gcttatatgg aaggtagtca ttatttgttt    88800
agtgagcaag aattcttacc atcattagag aagtatctag gtaggaaatt agatatataa    88860
taacattcag ataaggagaa ttaaatatgg cagtagaacc attcccaaga agacctatta    88920
cccgtcctca tgcatctatt gaagtagata cttcaggtat cggtggctca gcaggttcaa    88980
gtgaaaaagt attttgctta atcggtcagg ctgaaggcgg agaaccaaat acagtttatg    89040
aattacgtaa ctatgcacaa gctaaacgtt tattccgttc aggagaatta cttgatgcaa    89100
tagaattagc atggggttct aaccctaact atacagcagg taagatttta gctatgcgta    89160
tagaagatgc taaacctgct tcagcggaaa tcggtggatt aaaagtaaca tctaaaatct    89220
atggtaatgt tgctaacaac attcaagtag gattagaaaa gaatacatta agtgattcat    89280
tacgtttaag agtaatcttc caagatgacc gtttcaatga ggtttatgat aatatcggta    89340
atatcttcac aatcaagtac aaaggagaag aagctaacgc aactttctct gtagaacatg    89400
atgaagaaac tcaaaaagca agtcgtttag tattaaaagt tggagaccaa gaagttaagt    89460
catatgattt aactggtgga gcttatgact acactaatgc tattattaca gacattaatc    89520
aattacctga tttcgaagct aaattatcac ctttcggaga taagaactta gaatctagta    89580
aattagataa aattgaaaat gcaaatatca aagataaagc tgtatatgta aaagcagttt    89640
ttggtgactt agaaaaacaa acagcttaca acggtatcgt atctttcgag caacttaatg    89700
cagaaggaga agtaccaagt aatgtagagg ttgaagcagg agaagaatca gctacagtaa    89760
ctgctacttc acctattaaa actattgagc cgtttgagtt aactaagtta acgggcggta    89820
ctaatggaga accacctgct acatgggcag acaagttaga taaatttgca catgaaggcg    89880
gatactacat tgtcccatta tcatctaaac aatcagttca tgcagaggta gcttcttttg    89940
```

FIG. 21WW sequence.txt

```
ttaaagaacg ttctgatgca ggggaaccaa tgagagctat tgttggtgga ggattcaatg    90000
aatctaaaga acaattgttc ggtagacaag catcattatc taatccacga gtatcattag    90060
tagctaactc aggtacttttt gttatggatg atggacgtaa aaaccacgta cctgcttaca    90120
tggtagccgt agctctaggt ggtcttgcaa gtggtttaga aatcggtgaa tcaatcacat    90180
tcaaaccact acgtgtaagt tcattagacc aaatctatga gtcaatagat ttagatgaat    90240
taaatgaaaa tggtattatt agtatcgagt ttgttcgtaa ccgtactaat acattcttca    90300
gaatcgttga tgacgtaact acattcaatg ataaatcaga cccagttaag gctgaaatgg    90360
ctgttgggga agctaatgac ttcttagtaa gtgagcttaa agttcaactt gaagaccaat    90420
ttattggtac tcgtactatc aatacaagtg cttcaatcat taaagacttt atccaatctt    90480
acttgggtcg taagaaacgt gataatgaaa ttcaagactt ccctgctgaa gacgtacaag    90540
ttattgttga aggtaacgaa gcaagaattt caatgacagt ttacccaatc agaagcttca    90600
agaaaatctc tgttagcttg gtttacaagc aacagacatt acaagcctag tctaggtgac    90660
ggagtacctg gattaggtac tcctattaat ataatttgaa tactttagga gagtgaatac    90720
agatggcatc agaagctaaa caaaccgtcc atactggtaa taccgtccta cttatgatta    90780
aaggtaaacc ggtaggaaga gcacaatcag catcaggtca acgtgaatac ggtacaactg    90840
gtgtatacga aatcggttct atcatgcctc aagaacacgt atacttacgt tatgaaggta    90900
caattacagt agaacgttta cgtatgaaaa aagaaaactt tgcagattta ggatatgctt    90960
cacttggtga agaaattctt aagaaagata tcattgatat tttagtggta gataacttaa    91020
cgaaacaagt tattatctca tatcatggtt gctctgcaaa taactacaat gaaacttggc    91080
agacaaatga aattgtaaca gaagaaatcg agttcagtta cctttaacta atagaggcta    91140
tgtttggtga caagcataga aaacacttta aattgcgtga agtcttaaa gactagataa    91200
ctacaacgta actcgaaagg gtaagcgtga atgttgagaa atcagaaaaa atatctagta    91260
tagtataagg ttaaatccta agtacagtaa aatagatgat acgcaggcaa gcctacaaat    91320
gtgggaagct tcaacgacta taataggtga gtcttagtta cacattaaga ttatggtata    91380
gtctactccc tttaaaatat atcgaaagat agggtacaaa ggacagcatc agataaagct    91440
agaacttaaa tttcttatta agaccaacaa taaaagttgg tcttatattt tatacttgct    91500
ttgtctgagg cagtgtgcta taattaaaat acaaggaggt aataatatgg gaaaaaatca    91560
atatacattt aatattaaag aaaataaaaa taatggtat gaatggtgta aactacaaaa    91620
cgtaaaacct ttagtagaat atgaaaatgc acaacaaata ttttattttg aatttcttga    91680
aggtaaattt aaaggactaa taggaaaaac atattgggct agtataaata gaggttctaa    91740
tatgcgtatg agttgtttaa catcagaaag taaagataaa tatttaaaaa atttaggaaa    91800
```

FIG. 21XX sequence.txt

| | | | | | |
|---|---|---|---|---|---|
| aagaaaaggt | atagaggtag | tagaagacta | taagggtggc | agaaaattaa | aacataaatt | 91860
| tatagtttta | gaaggtaagt | accaaggatg | tgaaggatat | ataactttaa | atgatttaga | 91920
| gaatttaggt | agagtagata | atagaagttt | atctgaaaaa | ggaaggaaac | aatactttga | 91980
| taaacaggca | agacttagag | attgtattat | tctagagtac | cctaaagact | atagaataaa | 92040
| aactaaagat | aagatagtag | taaaagataa | agaagggcat | gttcataata | ttattgttca | 92100
| ggactttttt | gagaaatcat | ctttattgga | gttatcttgt | gctagtgaag | gagagaaaat | 92160
| agttaaagaa | atacttacta | aaaattctat | aaaatttgaa | aaagaaaaat | catttagaaa | 92220
| caaagaaggt | aaagtacaaa | gatttgattt | ttatattaat | gaaaataata | aagaatatgc | 92280
| aatagagtac | aatggtgcac | agcactacat | agattctaca | ggatatctta | agatactttt | 92340
| ggaaacaacc | cagaaaagag | ataaactaaa | aaaagaatac | agtaaagata | aaggtataaa | 92400
| tttattaatt | attccttaca | caataacaga | taagaaagaa | atggaaaaaa | ttatttttaaa | 92460
| ttttttaaac | aaataaccct | tgacactccc | tcaagggata | tgttattata | ataacaggtt | 92520
| aggagtaata | agtatgaata | ataggcaagc | taaaataaaa | ggatataacc | aatttcatta | 92580
| ttatgatttt | ccaacaacta | aaggtaagtt | taaagatata | atgaaaagaa | aatctagaac | 92640
| agaacttaaa | aaagatttac | aaaaagaaag | gaagtattat | cttgacaaat | aagagaaaaa | 92700
| cgataggtaa | gatgagtaac | acaagagcaa | catggaatat | taatccggta | actaaagtta | 92760
| aaaagataa | aacaaatat | tctagaaaaa | ataaacataa | aggtcttgac | aattataatt | 92820
| aactaaggta | tattattagt | ataacaaaaa | aggagatggg | tatatgagta | catttggtc | 92880
| agaaagaaga | acaactaata | aagataggca | agttaaaaaa | cattatactc | aaatgagtat | 92940
| gtatgaaaga | aagaaatgtg | tagagttatt | acaagagaca | attactgaaa | atagaattat | 93000
| taattttaca | cgacatagtg | caaagaaagt | taaaggtaaa | ccaacaacaa | atatacctaa | 93060
| attaataggt | tttatttta | aaaataagtt | tgcctacgaa | aatatcatag | aatacaataa | 93120
| cacagattat | aatggtaata | ttgagaggag | aattgttgtt | aaacatccta | aagttataac | 93180
| tgtagaagga | aaacctagct | atcagttttt | gacaattagt | cttgaagatg | ctagagttat | 93240
| tacagtatgg | tacaacagtg | tagatgatac | acatagaaca | ctagatttaa | attattatag | 93300
| taaagacttg | acaattcaat | aaggaggtat | tataatgggt | atcacaatag | taaatagtta | 93360
| ttttattctg | tctaacatct | tcctcatcat | attaaccata | ttaaatggta | agggtactgt | 93420
| tacaagggaa | tcactaacta | tgagtaaaat | attagtagta | ataacatcaa | ttcaattttt | 93480
| agcatgttta | attattaatg | gtatttattg | gtcactaaaa | ttttagaata | aagtattga | 93540
| caaattaaaa | ctaataaatt | ataataaagg | tataacaaat | taaaggagaa | gatataaaat | 93600
| gtcacaagat | aaattaagag | caatttacac | agaaatgaaa | gtagaattac | acaaatttcc | 93660
| taaagaggta | gatataacaa | gtaaatcaac | tgcaattgca | atcaatcaga | ttttagataa | 93720

FIG. 21YY sequence.txt

| | | | | | | |
|---|---|---|---|---|---|---|
| attcaaaaca | ttaacagaac | aagcaggaaa | gattactaga | aaatatttag | aaggtcaaga | 93780 |
| aatattaact | attgattatg | agtattatga | ttcattacaa | gaatactata | tttacctact | 93840 |
| tagaaatagt | gaaaagattg | aacaaagttt | acaagaaatt | actaagcgca | caggtgaata | 93900 |
| tgtaaagtaa | ttttgattta | aaaacaaaat | atgatatact | atgtttaaag | tagtaagcct | 93960 |
| acactagtcc | gtgttatatt | aatattgaat | cggataagcg | taggctttat | taatatttaa | 94020 |
| aaaaggaagg | tatatcatat | tatggcagaa | gaaattaaaa | aggaacaaga | tgtacaagaa | 94080 |
| acaactaaag | aagaaaaaaa | agatgttagt | aaaatgacac | cggaagaaat | agataaatta | 94140 |
| aaatatcaag | acaaacaaga | aaaagaacaa | gttattaaca | aagttattaa | aggtgttaat | 94200 |
| gatacttggg | aaaaagaata | taactttgaa | gaattagact | taagatttaa | agttaaaatt | 94260 |
| aaattaccta | atgcacgaga | acaaggtaat | atatttgcgt | tacgttctgc | ttacttaggt | 94320 |
| ggtatggata | tgtaccaaac | agaccaagta | attagagcat | atcaaatgtt | agctacatta | 94380 |
| caggaagtag | gtattgaagt | tcctaaggaa | ttccaagacc | ctgacgatat | ttataactta | 94440 |
| tatcctttaa | ctgttatgta | tgaagattgg | ttaggattct | taaactcctt | tcgttactaa | 94500 |
| tagtatagaa | acattagata | aagatataga | acgattgggc | ggtatggaat | caattgttaa | 94560 |
| acaaccttta | tctagaaatc | tatgggctat | tatgaaagag | tttaatgttt | tacctactga | 94620 |
| gcaaagattt | aaggacttag | atgattatca | gatagagttt | attattggga | atatgaacag | 94680 |
| agatgtttat | gaacataaca | aacaacttaa | acaagctcaa | aaaggtggaa | aattcgatag | 94740 |
| tcaattcgaa | gatgatgata | gtagttggtg | gaatgaatct | catgaagact | ttgacccagt | 94800 |
| acctgatttc | ttagatgctg | atgatttagc | acaacaggtg | gaagctaaat | tatccgatag | 94860 |
| agataaggaa | gaaagagcta | agagaaacga | tgcggagtta | aatgatgaaa | cagaaggact | 94920 |
| tactacacaa | catctagcta | tgatggaata | catcagacag | aaacaacaag | aattagatga | 94980 |
| tgaagtagga | aatggtaaga | ctagtgaaga | ggatgctact | atatcacaag | atagcgttaa | 95040 |
| taaagcacta | gaagacctag | atgatgactg | gtatatgtaa | agggtggtag | gtgatactac | 95100 |
| catccttatt | ttttttaaaat | ggatggtgaa | taatgatggc | aatgaatgac | gattatagat | 95160 |
| tggtcttgtc | cggtgatagt | tcggatttag | agaatagtct | gaaggcaata | gaactttata | 95220 |
| tggattcttt | agagtctaag | aatattgatg | ctcctttaga | taatttctta | aaaaaattaa | 95280 |
| aagtaattgc | taaagaagtt | aaaaatgtac | agaacgcaat | ggataaacaa | gatggtaaat | 95340 |
| ctgttatatc | ttctaaagac | atggatgaat | ctattaaatc | cactcaatct | gctacaaaga | 95400 |
| atataaatga | attaagaaaa | gctttagatg | accttcaaaa | agagaatata | tctaaaggta | 95460 |
| ttgcacctga | ccctgaagtt | gaaaaagcat | atgctaagat | gggtaaagtt | gtagatgaaa | 95520 |
| ctcaagaaaa | acttgagaaa | atgtcttcac | aaaaaatagg | ttctgatgct | agtattcaaa | 95580 |

FIG. 21ZZ sequence.txt

| | | | | | | |
|---|---|---|---|---|---|---|
| atagaattaa | ggaaatgaaa | accttaaatc | aagtaactga | agaatacaat | aaaataagta | 95640 |
| aagattctag | cgcaactaaa | gattatacaa | aacgattaag | agctaatcgt | aatatgacta | 95700 |
| gaggttacat | ggagcgttca | gaaggaacag | gacgtttgac | atatgaccaa | ggtgcacgag | 95760 |
| ttagaagtga | actaggtaaa | ataagttctt | atgagagcca | agaaaacaa | aaccaacgta | 95820 |
| atttaggaca | agcaagagag | caatatagca | actatagaaa | ccaacaacaa | gacttgacta | 95880 |
| aacgtagagc | tagcggtcaa | attaataagg | cacaatatga | acaagaatta | gcttctatta | 95940 |
| aacaggaaat | gaaagctaga | gaagaactta | tatctaacta | cgagaaacta | ggagcagaac | 96000 |
| ttgataaaac | agtccagtat | tataagggtt | cagttcaaaa | ggatttccaa | tctagagatg | 96060 |
| tagaccaaca | acgaggaaca | tttggtagaa | tggttcaaga | acgtttgcca | tctattggtt | 96120 |
| ctcatgctat | gatgggtact | acagctatgg | ctacaggttt | atacatgaag | ggtgcctcat | 96180 |
| taagtgaaac | taatagaccg | atggttacat | cattaggtca | aaattccgat | aatatggata | 96240 |
| tagattctgt | aagaaatgca | tatggagact | tgtcaattga | caacaaatta | ggttataata | 96300 |
| gtactgacat | gttaaaaatg | gctacttcat | atgaagcatc | agtagggcat | aaaagtgacg | 96360 |
| aggacacaat | ggcaggaact | aaacaacttg | ctattggagg | acgttctta | ggtattagag | 96420 |
| accaagaagc | ttatcaagag | tctatgggtc | aaatcatgca | tactggtgga | gtaaattctg | 96480 |
| ataacatgaa | ggaaatgcaa | gatgcattcc | taggtggtat | taaacaatca | ggcatggttg | 96540 |
| gtcgtcaaga | tgaacaactt | aaagcactag | gttctatagc | ggaacaatca | ggagaaggaa | 96600 |
| gaactctaac | taaagaccaa | atgagtaatc | ttactgccat | gcaatctact | tttgcagagt | 96660 |
| caggaagtaa | aggattacaa | ggtgaacaag | gtgccaatgc | tattaacagt | atagaccaag | 96720 |
| gacttaaaaa | tggtatgaat | agttcttatg | ctcgtatagc | aatgggatgg | ggaacacaat | 96780 |
| accaaggtct | tgaaggtgga | tatgatttac | aaaaacgtat | ggatgaaggt | atatctaatc | 96840 |
| ctgaaaactt | gacagatatg | gctgatatgg | ctactcaaat | gggtggcagt | gaaaaagaac | 96900 |
| aaaaatacct | atttaataga | agtatgaaag | aaataggcgc | taacctaact | atggagcaat | 96960 |
| ctgatgaaat | atttaaagat | gctcaatccg | gaaaactatc | taaagaagag | ttagctaaga | 97020 |
| aagctaagaa | aatggaaaaa | gaaggtaaaa | aagaaggaga | agataacgcc | actgattata | 97080 |
| aagaatctaa | atcaggaaaa | aatgaccaaa | ataaatctaa | gactgatgat | aaagcagaag | 97140 |
| atacttatga | tatggctcaa | ccattaagag | atgctcatag | tgctttagca | ggtcttcctg | 97200 |
| cccctatata | tttagctata | ggagctatag | gagcatttac | agcttcacta | attgcatctg | 97260 |
| caagtcaatt | tggagcaggt | cacttaattg | gtaaaggagc | caaaggactt | agaaataaat | 97320 |
| ttggtagaaa | taagggtggt | agctccggcg | gtaatcctat | ggcaggtgga | atgcctagtg | 97380 |
| gtggtggttc | acctaagggc | ggaggctcac | ctaaaggtgg | aggcactcgt | tctactggag | 97440 |
| gaaaaatact | tgatagcgct | aaaggtcttg | gaggattcct | agtaggtggc | gcaggatgga | 97500 |

FIG. 21AAA sequence.txt

| | | | | | |
|---|---|---|---|---|---|
| aaggtatgtt | tggtggggag | tctaaaggta | aaggctttaa | acaaacatct | aaagaagcct | 97560 |
| ggtcaggtac | tagaaaagta | tttaatagag | ataatggtag | aaaagccatg | gataaatcta | 97620 |
| aagacatagc | taaaggtact | ggtagtggtc | ttaaagatat | ctataatgat | agtatatttg | 97680 |
| gtaaagaaag | aagacaaaac | ctaggagaaa | aagctaaagg | ttttggtggc | aaagctaaag | 97740 |
| gtctttatgg | taaatttgct | gataagtttg | gtgacggagg | taaaaatggt | atcctttcac | 97800 |
| aatcaccaaa | agcaggtgga | agtggcatag | ggaaacttgg | aaaacttgca | ggtggacttg | 97860 |
| gaaaggagc | cggagtttta | ggtgttgcta | cgtctgcctt | atcattaata | cctgctttag | 97920 |
| cttccggaga | tagtaaagct | atcggcggtg | gaataggctc | tatgggtgga | ggaatggcag | 97980 |
| gtgcatcagc | aggagcttct | ataggagctt | tatttggtgg | tgtaggtgca | atacctggag | 98040 |
| ctttaatagg | tggagctata | ggttccttcg | gaggaggagc | tgttggtgaa | aaagtcggag | 98100 |
| acatggctaa | aaaagctaac | actaaagaag | gatggaacct | aggatggact | aatggagata | 98160 |
| aagatggtaa | gaataaattc | caagattctt | tattaggaaa | acctatatct | aaagcatgga | 98220 |
| gcggtataac | aggtctcttt | gataatgacg | ctgaagcatc | cgaagaagat | agtaaagata | 98280 |
| agaaaaaagg | tgttaaaggc | gttaaaggag | atactaagaa | gaaagaaaaa | atgacagcag | 98340 |
| aacaacttag | agaaaagaat | aaccaatctg | aaactaagaa | tcttaaaatc | tatagtgatt | 98400 |
| tacttgacag | agctcagaaa | attattgaga | gtgctaaagg | tattaatata | gatggaggaa | 98460 |
| cttctgatag | tggttctgat | agtggaggct | ctgcatctga | tgtaggtgga | gaaggtgcag | 98520 |
| agaagatgta | caagttcctt | aaaggaaaag | gactatctga | taatcaggta | ggagctgtta | 98580 |
| tggggaactt | acaacaagaa | tctaatcttg | accctaatgc | taagaatgct | tctagtggag | 98640 |
| catttggtat | tgctcagtgg | ttaggagcta | gaaaaacagg | attagaaaac | tttgctaaat | 98700 |
| ctaaaggtaa | aaaatctagt | gacatggatg | ttcaattaga | ttacctatgg | aaagaaatgc | 98760 |
| agtctgatta | tgaaagcaat | aatcttaaaa | atgcaggttg | gagcaaaggt | ggaagcttag | 98820 |
| aacagaatac | aaaagcattt | gctactggat | ttgaacgtat | gggagcaaac | gaggctatga | 98880 |
| tgggtactcg | tgttaacaat | gctaaggaat | tcaagaagaa | atatggaggc | tccggtggcg | 98940 |
| gaggtggtgg | aggagcttta | tcctctactt | atcaagaagc | tatgagtaat | cctgtattaa | 99000 |
| ctactggttc | taattataga | ggctctaatg | atgcttctaa | tgcttctaca | actaacagaa | 99060 |
| taacagtcaa | tgttaatgtt | caaggtggaa | ataatcctga | agaaactgga | gacattatcg | 99120 |
| gaggaagaat | tagagaagtt | ctagatagta | atatggatat | cttttgcaaat | gaacataaga | 99180 |
| gaagttatta | gtaattttgt | attgacacaa | gagtagtatc | atagtatact | actcttatac | 99240 |
| atataaaaaa | taaaggaag | tatgtgtata | tgcgtagaat | aagaagacct | aaggtaagaa | 99300 |
| tagaaatcgt | tacagatgat | aatacattta | cattgagatt | tgaagataca | cgtgactata | 99360 |

FIG. 21BBB

```
                                    sequence.txt
atggtgatga gtttggagct aaacttttag gattccaaac taaaaactct atggaagatg      99420
atagttcagt tttccaaata aatatggcag gagatactta ttgggataag ctagttatgg      99480
ctaatgatat cataagaata tttattcac ctaatgatga ccccaacgat aaagaaggaa       99540
gacaagaacg acttatccag gtaggtatgg tttctcaagt atcaaaagta ggtagttacg      99600
gtaatgacca aactcaattt agaataacag gtcaatcttt tgtaaaacct tttatgaaat      99660
ttggattagg cgttattcag gaagttcaag ctgtattgcc tgaagtaggt tggcttattg      99720
atggtgatgg agataatgaa gtaaaattta ctggtagctc agctcatgaa gtaatgactg      99780
gcattatacg tagatttata ccttatatga aatataacta tactgaaaaa acatataata      99840
caattgataa ctatcttgat tatgatgatt taagtagttg ggatgagttt gaaaaactta     99900
cagaagtttc agcctttact aattttgacg ggtcattaaa acagttaatg gatatggtaa     99960
cagctagacc ttttaatgag ttattcttca aaaattcaga aaaacacct ggaaaggctc     100020
aacttgtatt aagaaagacc ccttttaatc ctactgagtg gagagcttta gatatgatta    100080
aagtacctac tgaggatttt atagaagagg atgtaggtaa aagtgatgta gagacatatt    100140
ctatatttac agcaacacct gcaggtatgt tgaaagagct taacggtgat gtattttcca    100200
aaccacaatt ccatcctgaa ttaactgata gatacggtta taccaaattt gaagtagaaa    100260
atatttatct tagtacaaaa tcaggttcag ccactgagga ttcagattct tcaggtgatg    100320
ataatggtac agaacgagga acttactcta aaattatgaa agatttaagt aactatggaa    100380
gagataatat atctaaaggt atagataagt atacaagtaa attatcttca aaatataaaa    100440
acttaaaaaa agcccaagct aaaaaaatta tagagaagtt tgtcaaagaa ggaaaagtaa    100500
cagaaaaaga atatgaaaaa ataacaggta ataaggtaga tgatgaatta acatcagata    100560
acagaccgaa gttgacaaaa gataaattaa agagtatact aaaagagaag tttaaaacac    100620
aagatgattt taataattct aagaaaaaga aaaaagctaa gacagatgca cttaaagaat    100680
tgacaactaa atatcgtttt ggtaataaaa cacatgctac aactttgtta gatgaatata    100740
ttaaatacaa aggagaaccg cctaatgatg aggcttttga taaatatctt aaagctattg    100800
aaggtgttag taacgtagct acagacacag gttcagatgc aagtgatagc cctctagtta    100860
tgttttctag aatgttattt aattggtatc atggtaaccc taacttctat gcaggagata    100920
ttattgtttt aggagaccct aagtatgacc taggtaaaag attatttatt gaggataagc    100980
aacgaggaga cacatgggag ttctatattg aatctgtaga acataaattc gattataaac    101040
aagggtatta taacactgta ggagtaacta gaggtttaaa agacgctatt ctagaagatg    101100
gtaaaggtag tcctcataga tttgcaggat tatggaatca atcatcagac ttcatgggag    101160
gtcttatggg tgaagatact tctaaagaac ttaaagaaaa aggtgtagca gagaaacaaa    101220
gtagtggagg taaagatggt ggttctgata gtggcggagc tcaagatggt ggctctttag    101280
```

FIG. 21CCC sequence.txt

| | | | | | | |
|---|---|---|---|---|---|---|
| attcacttaa | aaaatataac | ggcaaacttc | ctaaacatga | cccaagtttt | gttcaacctg | 101340 |
| gtaaccgaca | ttataagtat | cagtgtacat | ggtatgctta | taatagaaga | ggtcaattag | 101400 |
| gcattcctgt | gcctttatgg | ggggacgccg | ccgactggat | aggcggtgct | aaaggagcag | 101460 |
| gttatggtgt | aggtagaaca | cctaaacaag | gtgcttgtgt | tatatggcaa | agaggagttc | 101520 |
| aaggaggtag | cccacaatat | ggtcacgtag | cttttgtaga | gaaagtatta | gatggaggta | 101580 |
| aaaaaatatt | tatctctgaa | cataactatg | ctaccccta | tggatatggt | actagaacaa | 101640 |
| tagatatgag | ttcagccata | ggtaagaatg | ctcaattcat | ttacgataag | aaataaagga | 101700 |
| ggatagtcta | tggcaacaga | taaagaagct | aaagatgtta | ttgataaatt | tatagacaat | 101760 |
| gtatttaatt | ttgatgtact | tacaaaagaa | agaataaaag | aaaaagatga | agaaattaaa | 101820 |
| aaaataacta | cagatgatat | gtatgaaaag | gttgtgtata | tacgacccta | cgttggagta | 101880 |
| atacaaagtc | ttaaccctca | acatgtgcag | tatgaatcat | tttctaataa | tggttatgat | 101940 |
| atagaggcag | aattaagttt | caggaaagta | agttatttag | ttgataaagg | gtctatacct | 102000 |
| acagattctt | tatctacttt | aacagttcac | ttagtagaac | gaaatcaaga | actattaata | 102060 |
| gattactttg | atgagataca | agatgtgttg | tatggagaat | atatggaaga | agaatatgta | 102120 |
| tttgatgaag | atgtaccatt | aagtacgata | ctagcattag | acttaaatga | taatcttaaa | 102180 |
| tccttatcaa | atataaagta | tatgttcaaa | ggtgctccta | aagagaatcc | atttggaaca | 102240 |
| gataaagatg | tttatataga | tacttataac | ttattatact | ggttatattt | aggtgaagat | 102300 |
| gaagagttag | catacctat | gaatattaat | tacttcttta | cagagggaag | attctttact | 102360 |
| atattcggta | aaggacataa | gtataaggta | gatgttagta | aatttatagt | tggagatata | 102420 |
| ttattctttg | gtagaagtga | tactaatata | ggtatttatg | taggagatgg | ggagtttata | 102480 |
| tctatgatgg | gtaaattccc | taaagatgaa | acacctatag | gaaaatataa | acttgatgat | 102540 |
| tactggaatg | aatttaacgg | aagagttatg | agattcgatg | aagaggtgta | tatttaatgg | 102600 |
| tagtaagatt | ccaatcttcc | atggggagaa | gtttaaaaag | agtagattca | gatgatttaa | 102660 |
| atgtaaaagg | attagtttta | gctacagtta | gtaaaattaa | ttataaatat | caatcagtag | 102720 |
| aagttaaagt | taacaactta | actctaggaa | gccgtatagg | tgacgatggt | agcttagctg | 102780 |
| taccttatcc | taaatctttc | ataggaagaa | cacctgaagg | aagcgtattc | ggtacaaaac | 102840 |
| ctcttattac | tgaaggttct | gtagtattaa | taggatttct | aaatgatgat | ataaatagtc | 102900 |
| ctattatttt | aagtgtttat | ggtgataatg | aacaaaataa | aatgattaat | accaatcctt | 102960 |
| tagatggggg | taagtttgat | acagaaagtg | tctataaata | tagtagttca | ctatatgaaa | 103020 |
| ttttaccatc | tttaaattat | aaatatgatg | atggagaagg | aacaagtatt | aggacttata | 103080 |
| atggtaaatc | atttttctct | atgacatcag | gtgaagaaga | gaaacctcag | gcaacagatt | 103140 |

FIG. 21DDD sequence.txt

```
tttatactgg aactgagtat caagatttat ttacttctta ttatggtaat aagacattaa    103200
ttgagcctag aatacaaaag gctcctaata tgttatttaa acatcaaggc gtttttatg     103260
atgatggcac gccggataat catataacta ctttatttat atctgaaaga ggggatataa    103320
gagcctcagt tttaaataca gaaacacaga aagaaccac acaggaaatg tcaagtgatg     103380
ggtcttatag ggttataaaa caagatgacg atttaatgtt ggatgaagct caagtttgga    103440
ttgagtatgg tattagtgaa gataataaat tctatattaa aaatgacaag cataaatttg    103500
aatttactga tgagggaatt tatatagatg ataagcctat gttagaaaac ttagatgaga    103560
gtatagcaga ggctatgaag aatttgaatg aaatacaaaa agaactcgat gatataaatt    103620
accttctcga gggtgtaggt aaggataact tagaagaatt aatagagtct acaaaagagt    103680
ctatagaagc ttctaaaaaa gcaacttcag atgtcaatag acttacaact cagatagcag    103740
aagttagtgg tagaactgaa ggtattataa cacagttcca aaaatttaga gatgagactt    103800
ttaaagattt ttatgaagat gcttctactg ttattaatga agtaaatcag aatttcccta    103860
ctatgaaaac agatgttaag accttaaaga ctaaagttga taacctagag aaaactgaaa    103920
taccaaatat taaaactaga ttaacagaac tagagaacaa taataacaat gctgataaaa    103980
taatatcaga tagaggagaa catataggtg ctatgataca gttagaggaa aatgtcactg    104040
tacctatgag aaaatatatg ccaataccat ggagcaaagt tacttataat aatgcagagt    104100
tttgggattc taataatcct actcgattag tagtacctaa aggaataaca aaagtaagag    104160
ttgcaggtaa tgttttgtgg gactctaacg ccacaggaca acgtatgttg agaatattga    104220
aaaatggtac ttatagtata ggattacctt atacaagaga tgtagctata tctacagcac    104280
ctcagaatgg tactagtgga gttattcctg ttaaagaagg agattacttt gagtttgaag    104340
ctttccaaga ctcagaaggt gacagacaat tcagcagca cccttataca tggtttagta    104400
ttgaagctat agaattagaa actgaaacta tggagaaaga ctttatgctt ataggacata    104460
gaggagcaac cggatacaca gatgagcaca cgataaaagg atatcaaatg gctttagata    104520
aaggtgcaga ttatatagaa ttagatttac aattaacaaa agataataag ttattgtgta    104580
tgcatgattc tactatagac agaacaacaa caggaacagg taaggtagga gatatgacct    104640
tatcttatat acaaactaac tttacatccc tcaatggtga gccgatacca tctcttgatg    104700
atgtactaaa tcattttgga acaaaagtta aatattatat agaaactaaa cgtccgtttg    104760
atgctaatat ggataaagaa ttattaactc aattaaaagc aaaaggatta ataggaatag    104820
gttcagagag attccaagta attattcaat catttgctag agaatcgtta attaatattc    104880
ataatcaatt ctctaatata cctttagctt acttaacaag tacattctct gaaagtgaaa    104940
tggatgattg tttaagttat ggttcttatg ctattgcgcc taaatataca actataacta    105000
aagaattagt agatttagct catagtaaag ggcttaaagt ccacgcatgg acggtaaata    105060
```

FIG. 21EEE sequence.txt

| | | | | | | |
|---|---|---|---|---|---|---|
| caaaagaaga | aatgcaaagc | ttaatacaaa | tgggtgtaga | tggattcttt | acaaactacc | 105120 |
| tagatgaata | taaaaagatt | taatattaaa | gacctattaa | tttaggtctt | ttttttagttg | 105180 |
| taatttaaac | tagttcgtga | tatattagta | gtatgagatt | tatatacata | ctgaaaagga | 105240 |
| gaggataaaa | tgccacaatc | agatggaata | agtaatcttc | atagaatagc | tttacgtttc | 105300 |
| cctaaagaag | gcggtggtta | tgatatgtat | agatttaaag | ttaaccctga | gaactacaca | 105360 |
| atagattcac | cacaacgtac | gacagcaatt | aaaacaaaat | cagatatcgt | aatagaagat | 105420 |
| tatggtaaag | atatagaagt | tattaacttc | acaggtacaa | ctggttttag | acctgttaga | 105480 |
| gaagcagatg | ggttaaaaac | aggtaagcag | aaaatggaag | agttacaaag | tagagttagt | 105540 |
| gaatatgcta | tgcaaggtgg | cagtggtaat | gtaagtggtt | cttacttaca | atttttttaac | 105600 |
| tttacagatg | atagttatta | taaagttcat | ttagctcctc | aggggttaaa | gataactagg | 105660 |
| tctaaagatg | aaccattact | ttttagatat | gaaataacat | tagtagttat | tggttcatta | 105720 |
| acagaagcag | atagaagtgc | tgtaactact | gaagagtttg | gtaatgttaa | acctaatgct | 105780 |
| tctcaaagag | tagatgaagg | tataaaagaa | ttagataaaa | atgctcgtaa | aacgagagat | 105840 |
| agaaacaatc | aagaaatatc | tagaagagaa | aatacaatac | ctaaatccac | aggagataat | 105900 |
| acgaacgagg | gtaatagact | taagcaaagc | ttccctagta | gttctatata | taatcctaga | 105960 |
| caatctacta | atggattaaa | aggtaatatt | gacaatatgg | ctctgataat | aggttacggt | 106020 |
| gatggaggtg | tatctagcta | atgaataatt | ttataccaca | acctcaaggt | ctacttagat | 106080 |
| tttaaatgc | cctagataca | gatttaactt | cttctcatat | gaatttactg | gatgaagagg | 106140 |
| tatcatttgt | atctaaattt | tatacaccac | agttacaatt | aagtgaatta | gcaaaaaaag | 106200 |
| tattgacaaa | tataaagaca | gatgatatac | ctgtattaga | aagggaattt | aatgataata | 106260 |
| caattatcca | taaagctaac | gatacattac | taaaagtaca | ggctccaaga | atgtatatga | 106320 |
| ttctacagtc | tattgtactt | gaagcatatg | ctattgttaa | ttgctttgta | gaaaatccaa | 106380 |
| gttctttaaa | atacttaact | gaagaagatg | ttagtataac | acgagaaaac | ttaaattatg | 106440 |
| tagctgacta | cttaggtaac | tatgatgact | acaatagtgt | tgtattagac | ttaagagatt | 106500 |
| tagacttatg | ttttagtgct | atagaattac | aattacctct | aattaaaaag | gaggctaacg | 106560 |
| tataatgaga | tttaagaagc | acgtagttca | acatgaagaa | acgatgcaag | caatagcaca | 106620 |
| gagatactat | ggtgatgtta | gttattggat | agacctagta | gagcataata | atttaaagta | 106680 |
| tccctatta | gtagaaactg | atgaagaaaa | aatgaaagac | ccggaacgat | tagcttctac | 106740 |
| cggtgataca | ctgattatac | ctatagaatc | tgatttaaca | gatgtatcag | caaaagaaat | 106800 |
| taattctaga | gataaagatg | tactagttga | attagctttta | ggaagagatt | taaatattac | 106860 |
| tgcagatgaa | aagtattta | atgaacatgg | tactagtgat | aatatactag | cattcagcac | 106920 |

FIG. 21FFF

```
                              sequence.txt
aaatggtaat ggagatttag atactgtaaa aggcatagat aatatgaaac agcaattaca    106980
ggcacgttta ttaactccta gaggttcctt aatgttacat cctaattacg gttcagattt    107040
gcataattta tttggtctta atatacctga acaagctacg cttatagaaa tggaagtatt    107100
gagaacatta acatcagata atagagtaaa atctgctaat ttaattgatt ggaaaataca    107160
aggtaatgtt tattcaggtc aattttcagt ggaaataaaa tctgttgaag aatcaataaa    107220
ttttgtctta ggacaagatg aggaaggaat ttttgcttta tttgaatagg aaaggattaa    107280
attatgaaaa ctagaaaatt aactaacata ctatcaaaat taatagataa gacaatggca    107340
ggtacaagca agataacaga ctttactcct ggttcagctt cccgttcatt attagaagct    107400
gtatcattag agatagagca attctatatt ctaacaaaag aaaatattga ttggggtata    107460
caagaaggta tcattgaagc ttttgatttt caaaaaagac aatctaaaag agcttatggt    107520
gatgttacta ttcaattcta ccaacccttta gatatgagaa tgtatatacc tgcaggaaca    107580
acttttactt caacacgaca agaatacaat cagcaatttg aaacattagt tgattattat    107640
gcagagcctg attctactga gattgttgtt gaagtttatt gtaaagaaac aggggttgca    107700
ggtaatgttc ctgaaggaac gattaatact atagcatcag gttctagttt gattagaagt    107760
gttaataatg agtattcttt taatacagga actaaagaag aaagtcagga agactttaaa    107820
cgtagattcc actcttttgt agaatctaga ggtagagcaa ctaataaatc agtaagatat    107880
ggtgcactgc agatacctga tgtagaaggt gtttatgttt atgaagaaac agggcatatt    107940
acagtatttg ctcatgatag aaacggtaat ttatcagata ccttaaaaga agatataatt    108000
gatgctttac aagactatag accaagtggt ataatgttag atgttacagg tgtagaaaaa    108060
gaagaagtta atgtttctgc tacagtaact atatctaata aatctagaat tggtgataca    108120
ttacaaaaac atatcgaaag tgttattaga agctatttaa ataatttaaa aacttctgat    108180
gacctaataa ttacagacct tattcaagct ataatgaata ttgatgacgt attaatatat    108240
gatgtgtcat tgataacttt agatgagaac attatagtac caccacaagg gattattaga    108300
gcgggagaaa taaagtaga attaaagtaa agagaggtga aacttaagtc gtggctaatt    108360
ttttaaagaa tcttcatcca ttattaagaa gagatagaaa taaaaaagat aatcaagacc    108420
ctaactttgc tctgatagat gcactcaatg aagagatgaa tcaagtggag aaagatgcta    108480
tagaaagtaa attacaatcc tctctaaaga catctacaag tgaatattta gataagtttg    108540
gggattggtt tggagtttat cgtaagaccg atgagaacga tgatgtttat agagcaagaa    108600
ttataaaata tttactcttg aaaagaggaa ctaataatgc tataatagat gctataaaag    108660
attatttagg tagagatgat attgatgtaa gtgtatatga gccctttaca aatattttt     108720
atacgaacaa atcacattta aatggtgaag accatttaat gggatactat tatagatttg    108780
ctgttattaa tgtatctata ggtgattatt ttcctgtaga gattatagat gtaattaatg    108840
```

FIG. 21GGG sequence.txt

```
aattcaaacc tgcaggtgta actctatatg tcacttatga tggagcttct actattagag    108900
gtggagcaat tattaagtgg ttagatgggt tacctaaaat agaaacatac caagagtttg    108960
atagatttac aggttatgat gatacattct atggtcatat taatatgaat caaagtaaag    109020
atactgataa cagttcatca gatatttta aaacaaatca tagcttaatt aatagtttag    109080
atgttttaac aggttcatct agtgtaggta gacagtatat taactatgga tatgtaacat    109140
catatgttta taatccaggt atgacatcct ctgtaaacca aataagtgct agtacagaag    109200
gtagaggtca agaagtacct actgattact atatgtatac tagtactaag aataacaata    109260
cagtagaact tagtatgcaa actacttccg gtgtgtctta tttatataat aactttaatt    109320
ttagagatta tatgagtaaa tatagacctc aagtagattt acaatctgat gaggctagaa    109380
gaattgtatc tgattatata aaagaattaa gtattgatta ctatcttagt gctgtgatac    109440
ctcctgatga aagtatagaa attaaactac aagtttatga ttttctatt aatagatggc    109500
ttacagtatc aattaataac ttatctttct atgaaaaaaa tattgggagt aatatagggt    109560
atataaaaga ctatctaaac agtgaattaa atatgtttac taggttagag ataaatgcag    109620
gtaaaagaga ttcagtagat attaaagtta attacttaga tttaatgttt tattactatg    109680
aacgaggtat ttatacaata aaaccttata aagcattaat agaaaattat ttagatatat    109740
ctagagagac ttatgtagaa gcatttaaaa tagcatcatt atctaatgga gatattataa    109800
ctaaaacagg ttttcagcct ataggggtatt taaaactagt tggtaattat gaaaatacaa    109860
gacctagcac aataaatata gtagctaaag atacagataa taaccctata gaatctaatg    109920
aattagatgt atataataca gtagagaata gaaatctatt acaatcttat aaaggtgcaa    109980
atacgatagc tagagaaata acttctacaa aagagtttac tgtatcagga tgggctaaag    110040
agatatactc aactaattat cttttctaaag tattaaaacc aggtaaagtg tatacgttat    110100
cttttgatat agaaataaca ggtaatgacc taactcttaa atcttattct gataatcatg    110160
gtatatattt atacagtaat actaagggaa ttgttgttaa tggtgttaaa tctatggaac    110220
gtactatagg taacaaagta tccgtaactc aaactttac agcccctact attactgacc    110280
atagattatt aatatatact ggaagatata catctgatgg taaagcatca actcctccag    110340
tgttctttaa tacagttaaa attacggaat taaaattgtc tgagggtacc tctaatctag    110400
agtactcacc tgctccggaa gataaaccta acgtaataga aaaaggaatt aaatttaata    110460
atatcctaac taatatacag actttaagta ttaattcgga tactatctta aaaaatgtaa    110520
ctttatatta ttcttactat ggtgataatt gggtagaact aaagactcta ggaaatatta    110580
gtactggaga aacaacagaa accaataact taatagattt atatggatta cagacagtag    110640
attattctaa tataaatcca atgtctaaag tatcattacg ttccatttgg aatgttaaac    110700
```

FIG. 21HHH sequence.txt

| | | | | | | |
|---|---|---|---|---|---|---|
| taggtgaatt | gaacaatcaa | gaaggttctt | tatctaatat | gcctaatgat | tactttaatg | 110760 |
| ctgtatggca | ggatatagat | aaattatcag | atattgagat | aggttctatg | agaatggtta | 110820 |
| aagacactga | gggtggagta | ttcgatggag | ctacaggtga | aattattaag | gctactctat | 110880 |
| ttaatgtcgg | ttcttatact | gatttagaca | tgttagctta | tactttgact | aactatactg | 110940 |
| aaccgttaac | tttaggctct | agtcgattaa | taagtgagtt | aaaagaagaa | cttctaacat | 111000 |
| cagaatcatt | taatgttgat | aatagaatta | agtaattga | ctcaatatat | gaggagttac | 111060 |
| caaatacaag | cattattaaa | aatggatttg | ttgaaagaga | ggttacaggc | tctaaatatt | 111120 |
| tagattatgg | tttatatgag | cctatagaag | atggtactag | atataaactt | attgtcgaag | 111180 |
| gagaatttaa | agataatata | gaatttatat | atttatacaa | ttctaaccct | aactttaatg | 111240 |
| aaacatttat | atatccatca | gagataatta | atggagttgc | tgaaaaagaa | tttattgcaa | 111300 |
| aaccatccac | cgaagacaaa | ccaaggttaa | atacagatgt | tagaatatat | atacgacctt | 111360 |
| atgattcaac | tatctctaaa | gtaagaagag | tagaattaag | gaaagtttaa | taaataagtt | 111420 |
| gacagaaagt | taataatatg | gtatacttat | aaagtaatat | ttagtgggta | taccatgtta | 111480 |
| tattaataaa | gaaaacaaca | gatgaaagga | attaaaaaat | atggcaattg | caacgtataa | 111540 |
| ttctcatgtt | gagttagcaa | aatatctagt | tagtaaagct | gattcagttt | acttaacaat | 111600 |
| tggaaagagc | acaccgtggt | ctaatgaaac | aaacccaccg | caacctgatg | aaaatgcaac | 111660 |
| agtattacag | gaggttattg | gatacaaaaa | agctactaaa | gttactttag | ttagaccttc | 111720 |
| taaatcacct | gaagatgata | ataagaattt | aatttcttat | ggtaataaat | catgggtaga | 111780 |
| agtaacacct | gaaaatgcta | aagctgaagg | agctaaatgg | gtttacttag | aaagtagtat | 111840 |
| tgttggtgac | gaactgcctc | ttggaacata | tagacaggta | ggatttgtta | tggacttagt | 111900 |
| agcaaaaagt | ggtattagta | aatttaactt | agtacctagt | gaagtagaat | caactggaac | 111960 |
| attattattc | tttgataata | aacaattcca | aaatagaagt | gagcagacaa | ctgctaaaga | 112020 |
| aagatttatt | gtagaagttt | aaagaaaggg | agataattct | aaatggcaat | taatttttaaa | 112080 |
| ggttcacctt | atttagatag | atttgacccg | tctaaagata | gaacaaaagt | attatttaat | 112140 |
| cctgatagac | ctctacaaca | ggcagaatta | aatgaaatgc | agtctataga | ccaatattat | 112200 |
| ttaaaaaatc | taggagacgc | tattttttaaa | gacggagata | aacagtcagg | acttggattc | 112260 |
| acattgtctg | aagataatgt | attgacagta | aatcctggtt | atgtatatat | caacggtaaa | 112320 |
| ataagatatt | acgataatga | cgattcagtt | aaaataactg | gcgtaggtaa | agaaactatc | 112380 |
| ggtattaagt | taacagaacg | tattgttaca | cctgatgaag | atgctagtct | attagaccaa | 112440 |
| actagtggag | taccaagtta | cttctctaaa | ggtgcagata | gattagaaga | aaagatgtca | 112500 |
| ttaacagtta | atgaccctac | atcagcaact | atttatactt | tcatggatgg | agatttatat | 112560 |
| attcaatcaa | ctaatgctga | aatggataaa | atcaataaag | tattagctga | acgtacttat | 112620 |

FIG. 21III sequence.txt

| | | | | | |
|---|---|---|---|---|---|
| gatgagtcag | gttcatataa | agtaaatggt | tttgagttat | tctcagaagg | taatgctgaa | 112680 |
| gatgatgacc | acgtttctgt | agttgtagat | gcaggtaaag | cttatgtaaa | aggttttaaa | 112740 |
| gtagataaac | ctgtatcaac | aagaattagt | gtacctaaat | cttatgactt | aggaacagca | 112800 |
| gaaaatgaaa | gtactatctt | taataagtct | aataattcta | ttagtttagc | taatagccct | 112860 |
| gtaaaagaaa | ttagacgtgt | tacaggtcaa | gtacttattg | aaaaagaacg | agttacaaga | 112920 |
| ggagcccaag | gtgatgggca | agattttctt | tcaaataata | cagcatttga | aattgtaaaa | 112980 |
| gtttggactg | aaacaagccc | tggtgttact | acaaaagagt | ataaacaagg | agaagacttc | 113040 |
| agattaacag | acggtcaaac | gattgattgg | tcacctcaag | gtcaagaacc | ttcaggaggt | 113100 |
| acttcatact | acgtttctta | taaatataac | aaacgtatgg | aagccggtaa | agattatgaa | 113160 |
| gtaacaactc | aaggtgaagg | tttgagtaag | aaatggtaca | ttaacttcac | accttcaaat | 113220 |
| ggtgctaaac | ctattgacca | aacagtagta | ttagtagact | atacttacta | cttggctcgt | 113280 |
| aaagattcag | tgtttattaa | taaatatggt | gatattgcaa | tattacctgg | tgaacctaat | 113340 |
| attatgagat | tagttacacc | accattaaac | acagaccctg | agaatttaca | attaggtaca | 113400 |
| gttacagtat | tacctgattc | agatgaagca | gtatgtattt | catttgcaat | cactagattg | 113460 |
| tctatggaag | acttacagaa | agttaaaaca | agagtagata | acttagagta | taaccaagca | 113520 |
| gtaaatgctc | tagatgatgg | tgctatggaa | ggacagaacc | cactaacatt | acgttcagta | 113580 |
| tttagtgaag | ggttcattag | tcttgacaaa | gcagatatta | cacatcctga | cttcggaatt | 113640 |
| gtatttagtt | ttgaagatgc | agaagctact | ttggcttata | cagaagcagt | taaccaacct | 113700 |
| aagattattc | caggagatac | aacagctcat | atttggggta | gattaatttc | agcaccattt | 113760 |
| actgaggaac | gtacaatcta | tcaaggtcaa | gcatcagaaa | cattaaatgt | taacccttat | 113820 |
| aatattccta | acaaacaagg | tgtgttaaag | ttaacaccta | gtgaggataa | ctggattgat | 113880 |
| actgaaaatg | ttacaatcac | tgaacaaaaa | actaaaaaag | taactatgaa | acgattttgg | 113940 |
| agacataatg | agagttacta | tggtgagact | gagcattact | tgtattctaa | cttacagtta | 114000 |
| gatgcaggac | aaaagtggaa | aggtgaaact | tacgcttatg | atagagagca | tggacgtact | 114060 |
| ggtactttat | tagaatcagg | aggacaacgt | actctagaag | aaatgattga | attcattaga | 114120 |
| atcagagatg | tatccttcga | agttaaagga | ctaaacccta | atgataataa | cttatattta | 114180 |
| ttatttgatg | gggtaagatg | cgctataaca | cctgcaactg | gttatagaaa | aggctctgaa | 114240 |
| gatggtacga | taatgacaga | tgctaaagga | acagctaaag | gtaaatttac | tattcctgca | 114300 |
| ggtattcgtt | gtggtaaccg | agaagttaca | cttaagaatg | ctaactctac | aagtgctaca | 114360 |
| acttacacag | cccaaggacg | taaaaaaacc | gttcaagata | ttattatcag | aactcgtgta | 114420 |
| acagtaaact | tagtagaccc | attagcacaa | tcattccaat | atgatgagaa | cagaactata | 114480 |

FIG. 21JJJ

```
                              sequence.txt
tcatcattag gattatactt tgcttctaaa ggtgataaac aatctaatgt tgttatccaa    114540
attagaggta tgggtgacca aggttatcct aataaaacaa tctatgcaga aacagttatg    114600
aatgctgatg atattaaagt atctaataat gctagtgctg aaactagagt atactttgat    114660
gaccctatga tggctgaagg cggtaaggaa tacgctattg ttattattac tgagaacagt    114720
gattatacaa tgtgggtagg tactagaact aagcctaaga ttgataaacc taatgaggtt    114780
atctcaggta acccatacct tcaaggtgta ttattcagtt catcaaatgc atcaacatgg    114840
actcctcatc aaaactctga ccttaaattt ggtatttata cttctaaatt taatgagaca    114900
gcaacaattg aattcgaacc aattaaagat gtatcggcag atagaatagt tcttatgtct    114960
acgtacttaa ctcctgagag aacaggatgt acatgggaaa tgaaattaat tctagatgat    115020
atggcatctt ctacaacatt cgaccaatta aaatgggagc ctatcggtaa ctaccaagat    115080
ttagatgttt taggtctagc aagacaagtt aagttaagag caactttcga atctaataga    115140
tatatctcac cattaatgag ctctagtgat ttaacattca ctacattctt aacagagtta    115200
acaggttcat atgttggtag agctattgat atgacagagg ctccttacaa tacagtaaga    115260
tttagttatg aagctttctt acctaaaggt actaaagttg ttcctaagta ttctgcggat    115320
gatggaaaaa cttggaaaac atttactaaa tcccctacaa ctactagagc caataatgag    115380
tttacacgct atgtcattga cgagaaagta aaatcatcag gaacaaatac taaactacaa    115440
gttagattag atttatcaac tgaaaatagc tttttacgtc ctcgtgttcg tagacttatg    115500
gttactacta gggatgaata aactagaggg gttgattgac ccctctttat ttaataagga    115560
gagatttata tgcctagaga agttagagac ccttattctc aagctaaatt atttatacct    115620
acagttgaag aaaaatcaat taaggaatta gaaaaaacat acaaagaaaa aattgatgaa    115680
gctactaagt taatcaatga attaaagaaa gagagaggag aaaaatagat ggcatttaac    115740
tacacgcctc ttactgaaac acagaagtta aagatatgt atcctaaagt taatgatata    115800
ggtaactttt taaaaacaga agttaacctt agtgatgtaa acaaatatc acaacccgac    115860
tttaataata ttttagcatc tataccttgat agtggtaact actatgtaac taattcaaaa    115920
ggtgctccta gtggagaagc tacggcagga tttgtaagat tggataaacg aaatgtaaat    115980
tattataaaa tttactattc accatatagt agtaataaaa tgtatatcaa gacttatgct    116040
aatggtactg tatatgattg gattagtttt aaattagatg aaggtaactt atacaatgaa    116100
ggtaatactt taaatgtaaa ggaacttact gaatctacaa ctcaatatgc aacactagtt    116160
aatcctccaa aagagaactt aaatacaggt tgggttaatt acaaagaaag taaaaatggt    116220
gtttcttctt tagtagaatt taacccggtt aactccactt caacttttaa gatgataaga    116280
aagttaccag tacaagaaca aaagcctaac ttattgaaag atagtttatt tgtttatcct    116340
gaaactagct attctaatat taaaacagat aactgggata cgcctccatt ttggggatat    116400
```

FIG. 21KKK sequence.txt

```
tcttctaata gtggtcgttc aggagttaga tttagaggag agaatacagt acagatagat    116460
gatgggtcta atacgtaccc tttagtagtt tctaataggt ttaaaatggg taaagaactt    116520
tctgtaggtg atactgtaac ggtatcagta tatgctaaaa ttaatgaccc tgctttactt    116580
aaagataact tagtttactt tgaattagca ggatacgata ctgtagatga tactagtaaa    116640
aatccttata caggaggacg tagagaaata acagcaagtg agataacaac tgagtggaaa    116700
aaatactctt tcacatttac gatacctgaa aatacaatcg gagcatcagg cgttaaagtt    116760
aattacgtat ctttactact aagaatgaat tgttcatcta gtaaaggtaa tggtgctgta    116820
gtatactatg ccttacctaa attagaaaaa tcacctaaag ttacaccatt tattacacat    116880
gaaaatgatg ttcgtaaata tgatgagatt tggtctaatt ggcaagaagt tattagtaaa    116940
gatgaattaa aaggtcactc tcctgtagat attgaatata atgattattt taaatatcag    117000
tggtggaaat ctgaagttaa tgaaaagagt ttaaaagatt tagctatgac agtacctcaa    117060
ggatatcata cattttattg tcaaggctct attgccggga cgcctaaggg acgttctatt    117120
agaggaacca ttcaggtaga ttatgacaaa ggtgacccct acagagctaa taagtttgtt    117180
aaattattgt ttactgacac agaaggtata ccttatacat tatactacgg agggtataat    117240
caaggttgga aactcttaaa gcaatcagaa acttctactt tactatggga aggtacttta    117300
gattttgggt ctacggaagc tgttaactta aatgactcat tagataatta tgatttaatt    117360
gaggtaactt attggactcg ttcagcagga cattttctca caaaaagatt agatataaaa    117420
aatacatcaa atttactgta tattagagac tttaatattt caaatgatag tacaggttct    117480
agtgtagact tttttgaagg gtattgcact ttccctacta gagcatcagt acaacctggt    117540
atggtaaaat ctataacttt agacgggtct acaaatacaa caaaagtagc atcatggaat    117600
gaaaaggaac gtataaaggt atacaatatt atgggaatta atagaggata aagaaaggtg    117660
gaataaaaaa ctatggctgt taaatatgat ataggtaata atgagatagt attcacactta    117720
agagaaggta aatatataac agggtttaca acagtaggag ggtatgacaa ggagttaggg    117780
caagtaaaag ttaatagaga aatcttacct gcttacttct ttgataattt tgcctatgaa    117840
agatatttgt attatagtaa acctgaagag gttatagaaa ataaaaacta tgtaccacca    117900
caaatcaatg atgatgagga atcccaacaa attactgtac ctaaagaaca atatgatagt    117960
ttaaaagaag agctagagct tatgagaaaa caacaagaag ctatgatgga aatgcttcaa    118020
aagctcttag gtcaaaaggg gtaattataa atggcattaa attttactac aataacggaa    118080
aacaatgtta ttagagacct gactactcag gtcaataaca ttggagaaga attaacaaaa    118140
gaaagaaata tatttgacat taccgatgat ttagtttata attttaataa atcacagaaa    118200
attaaactaa ctgatgataa aggattaact aaatcttatg gaaacataac agcccttaga    118260
```

FIG. 21LLL sequence.txt

| | | | | | | |
|---|---|---|---|---|---|---|
| gatataaaag | aacctggtta | ttactatata | ggtgctagaa | cattagcaac | attattagat | 118320 |
| agacctgata | tggaatctct | tgatgttgtt | ttacatgtag | tacctcttga | tacttctagt | 118380 |
| aaggtagttc | aacatttata | tacactatct | actaacaata | accaaattaa | aatgttatat | 118440 |
| agatttgtct | cagggaactc | tagttcagaa | tggcaattta | ttcaaggatt | acctagtaat | 118500 |
| aaaaatgctg | ttatatcggg | cactaatatt | ctagatatag | cttcaccagg | tgtttacttt | 118560 |
| gttatgggaa | tgacaggagg | aatgcctagt | ggagtaagct | ccggattttt | agacttaagt | 118620 |
| gtagatgcta | atgataatag | attagctaga | ctaactgatg | ctgaaactgg | taaagaatat | 118680 |
| actagcatta | agaaacctac | aggaacatac | acatcttgga | aaaaagaatt | tgagccaaaa | 118740 |
| gatatggaga | aatatttact | aagtagtatc | agagacgatg | gtagtgcatc | attcccactc | 118800 |
| ctagtttata | ctagtgataa | taaaacgttt | caacaagcta | ttatagacca | tatagataga | 118860 |
| acaggtcaaa | caacctttac | tttctacgtt | caaggtggtg | tatcaggttc | ccctatgtct | 118920 |
| aatagttgtc | gaggtctatt | catgtcagat | acacctaaca | cttctagttt | acatggtgtc | 118980 |
| tataatgcta | taggtacaga | tggtagaaat | gtaacaggtt | cagtggtagg | aggtaattgg | 119040 |
| acttcaccaa | agacatcacc | ttcccataaa | gaattatgga | cgggagcaca | atcattccta | 119100 |
| tctgtaggta | ctactaagaa | tctagcagat | gatattagta | attactctta | tgtagaggtt | 119160 |
| tatactaaac | ataagacagt | agagaagact | aaaggtaatg | atgactcggg | tacaatttgc | 119220 |
| cacaagttct | acttagatgg | tagcggtact | tacgtttgct | caggaacttt | tgtttcagga | 119280 |
| gatagaacag | atacaaaacc | acctgttaca | gagttctata | gagtaggtgt | atctttcaaa | 119340 |
| ggttcaacat | ggacgcttgt | agatagtgca | gtacaaaata | gtaaaactca | atacgttaca | 119400 |
| agaattatag | gtattaatat | gccatagact | aggataagtt | tcctagtctt | tttttcttga | 119460 |
| cttgaaaagg | attctatggt | atactataac | tcgtgtaagg | atataaggag | attaaaatga | 119520 |
| gattaagaat | taagaactta | tatacctatg | tagaatttga | ggaggatgat | aaatacttaa | 119580 |
| aagatatatt | tttaaagaga | gtccatacta | ctataggagc | aaggcaagaa | ggttttcaat | 119640 |
| atagccctgc | gtacaaaaga | ggtagttggg | atggttatgt | agacttttat | gtttatgagg | 119700 |
| aagataaatt | ccctactgga | ctttttattta | aaattgagtt | attattaggt | gagttacaat | 119760 |
| caaggtataa | cttccagttt | gaaacaattg | atgagcgtga | tgaaagtttc | ttatctgaag | 119820 |
| aagatattga | tgatgagata | acattgcttg | ataataatgt | cggtcaaatt | accttaagag | 119880 |
| attaccaata | tgaagcagtg | tacaatagct | taacatttta | caatggtatt | gctcacttag | 119940 |
| ctactaatgg | tggtaaaact | gaggttgcta | gtggtattat | agaccaacta | ttacctcaat | 120000 |
| tagaaaaagg | tgaaagagta | gcgttcttca | caggctctac | ggagatattt | catcagtctg | 120060 |
| cggatagact | acaagaacgt | ttaaatattc | ctattggtaa | agtaggtgca | ggtaaatttg | 120120 |
| atgttaaaca | ggttacagtt | gtaatgatac | ctactttaaa | tgcaaacctt | aaagacccaa | 120180 |

FIG. 21MMM sequence.txt

```
cacaaggggt aaaggttaca cctaaacaaa atattagtaa aaagattgct caagagatat    120240
tacctaaatt tgaaggtgga acaaatcaaa agaaattact aaaagtatta cttgataaca    120300
caacacctaa aacaaaagta gaacaaaacg tattaagtgc cttagagata atttaccaaa    120360
atagtaagac agatgcagaa gttttattaa acttaagaaa tcataatgca cattttcaaa    120420
aaattgttag agaaaagaac gaaaagaaat atgataaata tcaagatatg agagattttt    120480
tagactcagt tacagttatg atagttgatg aggcacacca ttctaaatct gattcttggt    120540
acaataatct aatgacatgt gaaaaagctt tatatcgaat tgcattaaca gggtctatag    120600
ataaaaaaga tgaattactt tggatgagat tacaggctct atttggtaat gttattgcac    120660
gaactactaa taagttttta attgatgaag gtcattctgc tagaccaaca ataaatatta    120720
tacctatagc taatcctaat gacatagata gaattgatga ttatagggaa gcttacgata    120780
gaggtataac aaataatgat tttagaaata aacttattgc aaaactaaca gaaaagtggt    120840
ataatcaaga taaaggtaca ttgattattg taaacttcat tgaacatgga gacacgatat    120900
cagaaatgtt aaatgattta gatgtagagc actacttctt acatggagaa atagactctg    120960
aaactaggag agaaaaatta aatgatatga gaagtggtaa gcttaaagta atgatagcta    121020
catcacttat tgatgagggt gtagatatat ccggtattaa tgcactaata ttaggtgcag    121080
gaggtaagtc attaagacaa acattacaac gtattggtcg tgctttacgt aagaaaaaag    121140
acgataatac aacacaaata tttgatttta atgatatgac aaatagattt ttatatactc    121200
atgctaatga gcgtaggaaa atttatgaag aggaagattt tgaaataaaa gacttaggaa    121260
aataggaggg taagagatgg caacaaaaac acaagaaag ctataccaat atctagagga    121320
aaatgctaca gaaaataaat ttcatatttc tactaagaaa gagctagcag attctctagg    121380
tgtttccatc tctgctttat ccaataacct taaaaagtta gaagaagaaa ataaagtcgt    121440
tactgtttct aaaagaggaa aaaacggcgg agtaataata actttagtta gagagtatga    121500
tacagaagaa ttgaaagaat ttaataattc tacagataat attattactt ccgatttaca    121560
gtatgctaag gcattaagag aaaagcactt cccttcttat agatatgaga gaaaagaaca    121620
acgtagacgt actaaaatag aaatggcaca atacaatgcc attaaggatg agaagagaag    121680
aattatagca gatatgaact tctattcaga aggtcttcct tatccttcta aagatatttt    121740
taatatgtct tatgacccgg aagggtttta taagcatac atcttatgta agttatacga    121800
ccaatatgct atttctcata tggatgctaa acatacaagt catcttaaag caatgagtaa    121860
ggcaacaact aaagatgaat atgactatca tcaacatatg tctgaatact atagaaataa    121920
aatgattcaa aatttaccta gaaatagcgt tagtgataat ttctttggta gtaaaatgtt    121980
taataccttt tataattttt atttaaaaat aaaagataaa aatattaatg tatttaaata    122040
```

FIG. 21NNN sequence.txt

```
tatgcaaaac gtatttaaaa atgtaacatt ttattatgag aatggtatgc aacctaatcc      122100
aataccttct cctaacttct ttagttcaga taagtatttt aaaaactata ataattatat      122160
taaaggaata aaaaaaggtg ttaacagtac gaatagacac ctaggtgata cagacagcat      122220
cattaattca tcagactacg tgaaaaaccc tgctgtatta catctacacc aactatatac      122280
tacaggatta aattctactt tacatgatat tgatactatg tttgaacaag ccttagacct      122340
tgaaaatgcc tcctatggac tatttggaga tatgaaacat attattttac tacagtataa      122400
ttctatgatt gaagaagaaa ttaagaattt acctagagaa gaaaaggata ttattaataa      122460
atatgtaaaa caatgcataa ttaatgatta ttcaccaaca agtatttcac catctgcaag      122520
gttatcaatg tttactatgc agaaagagca tatagtttac aataagcagt taaataaggg      122580
aatcaagaga gaggatttat taccattaag tctaggaggt atagtgaata aagattcatt      122640
gagtggtatg gatatacaaa acttagaaca gaatggtaat gaatacctgt atatgagaca      122700
acatacttca acttattata tattaagaat gtttggtgac tatttaggat atgaggtaaa      122760
cttaagagaa gtaaaatata ttgtagagaa atataattta attgataaaa taccattgac      122820
aaaagagggt atgttggatt ataataaact tatacattta gtagaggaag aggttaataa      122880
ctatgagtaa gaagataaag gagcttatcc ttcataaatc aatgaaggat atacattttg      122940
caagagaagt attagataac ttacctaaga atctattttc agcagagtct gaggacatgg      123000
gttacttatt tacagctata aagagaacag cacatatttc cgataagatg tcaaatgaag      123060
cattagcaat taaagtagaa cagcttatgg gtaataataa ggaagatgaa gagaaagtaa      123120
ccaagacatt aacttactta gaagatttat ataaagtaga cgttaatgaa aaagatgaat      123180
ctgttaatta tgaaatagag aagtatatta aaacagaaat gtcaaaagaa gttttagtta      123240
aatttattgc agaaaataaa caagaagact ctgataatct acatgaactt gtagacaaac      123300
taaagcaaat agaagtaagt gacatctcag gaggtaatgg agagtttatt gacttctttg      123360
aagatacaga aaagaaacaa gaactattga gtaatttagc tacaaataaa ttctctactg      123420
gatttacttc tattgacaac catattgaag gtggtatagc aagaggagaa gttggattaa      123480
ttatagctcc tactggtaga ggtaaatcat taatggcttc aaacttagct aagaattatg      123540
ttaaaagtgg attaagtgtt ttatatattg ccttagagga aaaaatggat agaatggttt      123600
tgcgtgctga gcaacaaatg gcaggagcag aaaagagtca aattgtaaat caggatatgt      123660
ctttaaataa taaagtttat gatgcaatac aaaatcatta tcagaagaat agaaagttat      123720
taggtgactt ttatatttct aaacatatgc caggtgaagt tacaccaaac caattagagc      123780
aaattattgt taatacaaca attaagaagg ataaaaatat tgatgttgtt attattgact      123840
atcctcactt aatgagaaat ccttatgcta aatatcattc agaatcagat gcaggaggaa      123900
aattgtttga agatattcgt agattatcac agcaatatgg atttgtttgt tggacgttag      123960
```

FIG. 21000 sequence.txt

```
ctcaaactaa ccgtggtgct tatggttcag atgttattac aagtgagcat gtagaaggtt    124020
ctcgtaagat tgtcaatgct gttgaggtgt ctttagcagt aaaccaaaaa gatgaagaat    124080
tcaagagtgg tttcttaaga ttatatttag ataaaattcg taatagctcc aacacaggag    124140
aacgatttgt taatcttaaa gtagaaccaa ctaagatgat tgtaagagat gaaacacctg    124200
aagaaaaaca agagcatata caattgctat cagataatgg aaaagaagac acaagtaaat    124260
ttcaaaataa agataataaa atagaagcta taaataacac attcggagga ttaccgggag    124320
tttaatttt taaaatatac cacttgacat tttatatgtt aggtggtata attattttat     124380
aaagaataaa ggagagatta ataatgaaat ttgtattctt tacagatagt cattttcacc    124440
tatttactaa ctacgctaaa cctgataatg aatttgtgaa tgatagattt aaagaacaga    124500
tagaagcatt acagaaagtt tttgatattg ctaaaaaaga agaagcaaca gttatatttg    124560
gtggagattt atttcataaa cgtaactcgg tagatactag agtatacaac aaagtattta    124620
gtacatttgc caaaaatgat gaggttcctg tattattact tagaggtaat catgatgcta    124680
caactaattc attatatact gattcaagta tagatacatt tgagtatcta cctaatgtaa    124740
gtgtaataaa atcattaaat acaattttaa aagataatgt taatattgtg tttactgctt    124800
atggggatga gacgaaggaa ataaagacat acattaatag taattacgat aaagatatgg    124860
tcaatatact agtaggtcac ttaggtgtag aaggttcatt aactggaaaa ggctctcata    124920
gattagaagg ggcatttgga taccaggatt tattacctga taaatatgat ttcattttac    124980
taggtcatta tcaccgtaga cagtatttcc aaaatccgaa tcatttttat ggtggctcat    125040
taatgcaaca atcatttct gatgaacaag aagctaatgg tgttcattta atagatacag    125100
aaaaaatgac tacagaattc atcccaattc atacacgtag atttattact attcaaggag    125160
aagatattcc tgagaacttt gaacagttaa tcgaggaagg taatttttatt agggttatcg    125220
gtacagcaaa tcatgctaag gttttagaaa tggatgacag tatgaaagat aagaatgttg    125280
aagttcaaat taaaaagaa tatactgtag agaaacgtat tgatagtgat gtatctgatg    125340
acccttaaac aattgctagt acctatgcta acaatactc acctgaatca gaacaagaaa     125400
tacttgagtg tttgaaggag gttttataat gaaaaatat agagaatacc taaataagac    125460
agatgcagaa aatttagcag aggattggga gaaagtaacc gaagatttat ggaaagtgtt    125520
taaagatatg aaacctaaaa ttaatacatt agatattagt aatgtagaaa gtaaaaactt    125580
agataaaagt aaacctatac tacaattcca agattcagat ggagtaatag agaatatttg    125640
taatgttgag ggtttagaag atggtttaag taaaatgaaa aaggtttttg atgatagtaa    125700
ctttgaaaag cattattata gtagagtcgt agaccatgat gagtattact ggattgatta    125760
tggttctcat cattgtttct ttagagttac gaaagggat aagtaatggt tgtatttaaa     125820
```

FIG. 21PPP sequence.txt

| | | | | | | |
|---|---|---|---|---|---|---|
| caagtagaag | ttaataattt | tttagcaatt | aaagaagcta | cgctagagtt | agacaataga | 125880 |
| ggattaattc | taattgaagg | tgagaataaa | tccaatgagt | catttcattc | aaacggttca | 125940 |
| ggaaaatcaa | ctttaatatc | tgccattact | tacgctttat | atggtaaaac | tgaaaaagga | 126000 |
| ctaaaagcag | acgatgtagt | aaataatatt | gagaagaaaa | atacatctgt | taaacttaag | 126060 |
| tttgatattg | gggaagatag | ctatttaatt | gaacgttatc | gtaaggacaa | agagaataag | 126120 |
| aataaagtaa | aattatttgt | taatgaaaaa | gagattacag | gttcaacaaa | tgacgttact | 126180 |
| gataaacaaa | tacaagactt | atttggtatt | gagtttaata | cttacgttaa | tgctatcatg | 126240 |
| tatggtcaag | gagatatccc | tatgttctcc | caagcaacag | ataaaggtaa | gaaagaaatt | 126300 |
| cttgaatcta | ttactaagac | agatgtatat | aaacaagcgc | aagatgtagc | aaaagagaaa | 126360 |
| gttaaagaag | tagaagaaca | acaaaataac | ataagacagg | aaatctataa | actaggttat | 126420 |
| cagttatcta | caaaagatga | gtacttccaa | agagaaatag | aacagtacaa | ccagtataaa | 126480 |
| gaacaattgg | ttcagataga | aaacagtaat | aaggaaaaag | atagattaag | agaacaagag | 126540 |
| gagaagcaaa | tagaagctca | aatagagcaa | ttagcttcac | agataccaac | aatacctgaa | 126600 |
| gatgaattta | agcactcaga | ggagtataat | aaagcttctc | aaagcctaga | tttactttct | 126660 |
| aataaattaa | cggagctaaa | tcaagtatac | tcagaatata | ataccaaaga | acaagtacta | 126720 |
| aaatctgaaa | tagctacatt | aagcaatagt | ctaaataagt | tagatacaaa | tgaccattgt | 126780 |
| cctgtttgtg | gctcccctat | agataattct | cataaattaa | aagaacagga | aatatattaat | 126840 |
| aatcagattg | agaataagaa | acaagagatt | actagtgtat | tagaaatgaa | agatacgtat | 126900 |
| aaagaagcta | ttgataaagt | aaaagataaa | tcacaagaaa | ttaaagataa | aatgtcacag | 126960 |
| gaagaccaac | aagaacggga | gcacaataat | aagattaaca | gtataattca | agaggcttct | 127020 |
| aggattaaat | cagacattag | ctcattagag | aataataaaa | cttatttaaa | agtgaaatac | 127080 |
| caacatcaat | ctgttcaagg | attagagaga | gaagaaccaa | gtaaagaaaa | acatgaggaa | 127140 |
| gataaaaaag | aattacaaga | atctattgac | aaacatgaag | agaatatagt | acaattagaa | 127200 |
| actaagaaag | gtaaatatca | acaagctgta | gatgctttta | gtaataaagg | tatacgttca | 127260 |
| gtagtgttag | actttattac | accattctta | aatgagaaag | caatgagta | ccttcaaact | 127320 |
| ttatcaggtt | cagatattga | aatagagttc | caaactcaag | tgaagaatgc | taaaggagaa | 127380 |
| ctaaaagata | agtttgatgt | tattgttaag | aatagcaagg | gtggaggctc | atacaaatct | 127440 |
| aattcagcag | gagaacaaaa | acgtattgat | ttagcaatta | gttttgcaat | tcaggattta | 127500 |
| attatgagta | aagatgagat | atctacgaac | attgcacttt | acgatgagtg | ttttgatggg | 127560 |
| ttagatacta | tcggttgtga | aaacgtgatt | aaattattaa | aagatagact | taatacagta | 127620 |
| ggaacgatat | ttgtaattac | tcataatacc | gaacttaaac | cactatttga | acaaacaatt | 127680 |
| aaaatagtaa | aagaaatgg | agtatcaaaa | ctggaggaaa | aataatgaaa | ttaaagattt | 127740 |

FIG. 21QQQ sequence.txt

```
tagataaaga taatgcaaca cttaatgtgt ttcatcgtaa taaggagcac aaaacgatag   127800
ataatgtacc aactgctaac ttagttgatt ggtaccctct aagtaatgct tatgaataca   127860
agttaagtag aaatggagaa tatttagaat taaaaagatt acgttctact ttaccttcat   127920
cttatggttt agatgataat aaccaagata ttattagaga taataaccat agatgtaaaa   127980
taggttattg gtacaaccct gcagtacgca aagataattt aaagattata gagaaagcta   128040
aacaatatgg attacctgtt ataacagaag aatatgatgc taatactgta gagcaaggat   128100
ttagagatat tggagttata ttccaaagtc ttaaaactat tgttgttact agatatctag   128160
aaggtaaaac agaggaagaa ttaagaatat ttaacatgaa atcagaggaa tcacaattga   128220
atgaagcact taaagagagt gattttctg tagacttaac ttatagtgat ttaggacaaa   128280
tttataatat gttgttatta atgaaaaaaa ttagtaaata gtaaggaagg atattatgag   128340
gtttgaagac tttttaaccc aagaattagg agaaccaaaa gaaaatacta taggtgagct   128400
aagatactgt tgtccgtttt gtggagaaaa aagttataag ttctatgtta agcaagccct   128460
agactctagt aatggtcagt atcattgtaa aaaatgtgat gaatcaggta atcctattac   128520
atttatgaag acttattata acattacagg taagcaagct tttgatttat tagagtctaa   128580
gaatatagat atagagagag ccccttact tacaaccaat aataaggatt taacagaatc   128640
agagaaactt atattaatgc ttagaggtgt gcatcaagat aagggaacta ctagtattaa   128700
acctcctcga ttacctgaag gatataaatt attaaaagat aacttaaata ataaagagat   128760
tatacctttt ttaaaatact taaaggtag aggtataact ttagaacaaa tcattaataa   128820
caatataggt tatgttatta atgggagctt ttataaagtt gacggggaat ccaaagtatc   128880
attaaggaat agtattatat tttttactta tgataatgat ggaaactacc agtactggaa   128940
tacaagaagt atagagaaga acccttatat taaatctatt aatgctcctg ctaaacaaga   129000
tgaagtaggt agaaaagatg tcatatttaa tttgaatata gcaagaaaga aaaagttctt   129060
agttataact gagggtgtat ttgatgcttt aacctttcat gagtatggag tagcaacatt   129120
aggtaaacaa gtaactgaga atcaaataaa aaaataatt gattatgtta gtatagatac   129180
atcaatatat attatgttag acactgatgc attagataat aatatagact tagcttataa   129240
gttaaaaaca cattttaaca aagtttactt tgtaccacat ggtgatgaag atgcaaatga   129300
tatgggaaca aggaaagctt ttgagttatt aaaacagaac cgggtgttag taacacctga   129360
aagtatacag agttacaaaa tacaacaaaa acttaaactt taggcttgac cttagagaag   129420
ttttatgtta tactagtaat taagtaatta ataaggaga aaaaataat gtcaaataat   129480
aaaaaagata ttttagaatt tgtagatgaa tacattacag ctttaagagt tggtaatgag   129540
caacgacaac atcaattaga agaaatgggt aaagaagaaa cagcaacatt aacagatgta   129600
```

FIG. 21RRR sequence.txt

| | | | | | | |
|---|---|---|---|---|---|---|
| gctaaagcta | ttactaacct | tatgttaggt | gttaatgagc | agatgacaga | cttagaatat | 129660 |
| aataacgagt | taaacttaaa | tattttaatt | gatgctttat | ataaagcaga | gcttattaat | 129720 |
| gaagatgtat | tagactacat | tcaagaatca | attgataaat | cacaagaaga | acctaaaaat | 129780 |
| gaagaagaaa | aaggagaaca | agaataatgg | aaaaaaatat | tagcacacac | acaaaaggta | 129840 |
| ttagtcaagc | agacatggag | aaatggattg | aagctgtagt | acaaggaact | gttgatggta | 129900 |
| aacaagttga | tgagaaaaca | gctaaacaat | tagatagaat | tggttcacga | agtgtttctt | 129960 |
| tagaagaagc | aactcgtatt | gctaaagtcc | ttaatgctgt | aacagctcaa | gaggttacag | 130020 |
| gagactttaa | tgatgcattt | aatgcaattg | acttaatgat | gattatcatg | gaagatgagt | 130080 |
| taggagtaac | tcaagaaaaa | gtaggtaaag | ctaaagataa | actaaatgaa | aaacgagaag | 130140 |
| cttacctaaa | agagaaacaa | gaagaattac | gtcaaaaaca | acaagaagag | gcacaaaaag | 130200 |
| aaactgaatc | tgacagcaat | gaaaaagtaa | ttcagttgaa | gaaaaatgac | gaacagtaag | 130260 |
| aaaaaagggg | atacattcga | acgtaaaata | gctaaagaat | taactgcttg | gtggggatac | 130320 |
| caattcaata | ggtctcctca | atcaggtggt | gcttcatggg | gtaaagataa | taatgctgtc | 130380 |
| ggagatatag | tagtaccca | ggaagctaat | tttcctttag | tagtagaatg | taaacataga | 130440 |
| gaagaatgga | ctatagataa | cgttcttttta | aacaacagag | agccacacac | atggtgggag | 130500 |
| caagtcatta | atgatagtag | taaggtgaat | aagacacctt | gcttaatatt | tactagaaat | 130560 |
| agagctcaga | gttatgttgc | tttaccttat | aatgaaaaag | tatatgaaga | tttaagaaat | 130620 |
| aatgaatacc | ctgtcatgag | aacagatttt | attattgata | atattagaaa | agataaattt | 130680 |
| ttttatgatg | tccttataac | taccatgaat | gggttgacct | catttacacc | ttcttatatt | 130740 |
| atatcttgct | acgacaaaaa | agatataaaa | ccatacaaga | aggtcgagtc | taatttatct | 130800 |
| gaggtaagta | agcatgaaga | tgaattgatt | aatgaccttc | ttagtgatat | ataaggaagg | 130860 |
| taagataagt | atgacaagca | aagaaagacc | attaatcgta | tatttttcag | gtacaggaca | 130920 |
| aacagaaaga | ttagtaaaca | aaattaatat | taataattca | tttgaaacat | ttagggttaa | 130980 |
| gagtggaaaa | gaaaaagtaa | ataaacctttt | tatactaata | acacctactt | ataagaaagg | 131040 |
| tgcaatacct | aaacaaatag | aaagattcct | agaaattaat | gggagcccta | aagaagttat | 131100 |
| tggcacagga | aataaacaat | ggggctctaa | tttctgtgga | gcaagtaaaa | agatttcaga | 131160 |
| gatgtttaag | attcctttaa | ttgctaaagt | agagcaatca | ggacactta | acgagataca | 131220 |
| accaatatta | gaacacttta | gtaataaata | taaagtagcg | taaaggatga | gagatatatg | 131280 |
| gcaacatatg | gaaaatggat | tgagttaaat | aatgaaataa | ctcaattaga | tgacaatgga | 131340 |
| aaaaataaac | tctataaaga | ccaagaagct | ttagatgagt | atttaaaata | tattgaagac | 131400 |
| aatacaagaa | agtttaatag | tgaagtagaa | agaattagag | tattgacaaa | agaaggaaca | 131460 |
| tatgataaaa | tatttgacaa | ggttcctgac | actattattg | atgagatgac | taagttagct | 131520 |

FIG. 21SSS sequence.txt

```
tacagtttta attttaaatt ccctagtttc atggcaggac aaaagtttta tgaatcttac    131580
gcatcaaaac agtatgatga aaacaaaaaa cctattttg ttgaagacta tgaacaacat    131640
aatgttcgag tagctttata tttatttcaa aatgactatg taaaggctag agaattacta    131700
gtacaactta tggagcaaac attccaacca tctacaccta cgtataataa ctcaggtcaa    131760
gctaatagag gtgaactaag ctcatgttat ctatttgtag tagatgattc aattgagtct    131820
ttaaactttg ttgaggatag cgtagctaat gctagttcta atggtggcgg agttgcaatt    131880
gatttaacta gaattagacc taaaggagct ccagtacgta atagacctaa ttcaagtaaa    131940
ggtgttattg cttttgctaa agctattgaa cataaagtta gtatttatga ccagggcggt    132000
gtaagacaag gtagtggtgc tgtttaccta aatatattcc acaatgatat cttggattta    132060
ttaagctcta agaaaatcaa tgccagtgaa tctgttagac tagataaatt atctattggt    132120
gttacaatcc ctaacaaatt tatggagtta gttaaagaag gtagaccttt ctatactttt    132180
gatacttacg acattaataa agtgtatggt aagtatttag atgagctaaa cattgatgaa    132240
tggtatgata agttactaga taatgatagt atcggtaaag taaaacatga tgctagagaa    132300
gttatgacag atattgctaa aacgcaatta gaatcaggat acccttatgt attctatatt    132360
gataatgcta atgataatca tccattgaaa aacctaggta agttaaaat gagtaactta    132420
tgtacagaaa tttcacaatt acaagaggta tcagaaattt atccgtactc ttacagtaat    132480
aagaatgtta ttaatagaga tgttgtttgt acattaggtt ctcttaactt ggttaatgtg    132540
gttgaaaaag gtttattgaa tgaatctgta gatattggta caagagcatt aacaaaagtt    132600
actgatatta tggatttacc ttacttacct agtgttcaaa aagcaaatga tgatattaga    132660
gctatcggtt taggttcaat gaatttacat ggacttttag ctaagaatat gattagttat    132720
ggttctagag aagcattaga cctagtaaac agtttatata gtgctattaa cttccagtct    132780
attaagacat ctatgttaat ggctaaagaa acaggaaaac catttaaagg atttgagaag    132840
tccgattacg ctacaggtga atactttgta agatatatta gagaatccaa tcaacctaag    132900
acagataaag ctaagaaagt cctagataag gtttatattc aacacaaga tgattgggat    132960
gaattagcta aagcagtaaa agtacatggc ttgtataatg gttatagaaa agcagaagca    133020
cctactcaat ctatatctta tgtacagaat gctacaagtt ctattatgcc agttcctagt    133080
gctatagaga atagacaata tggagatatg gagacatatt acccaatgcc ttacctaagt    133140
cctataactc agttcttcta tgaaggagaa acagcttata agattgacaa taaacgtatt    133200
attaatacaa gcgcagttgt tcagaaacat acagaccaag cagtatctac aatcctttat    133260
gtagagtcag aaatacctac taataaacta gtatcattat actattatgc ttgggaacaa    133320
ggattaaaat cattatacta tacacgttca cgtaaacttt ctgttattga atgtgaaaca    133380
```

FIG. 21TTT sequence.txt

```
tgttcggttt agaaaggaaa tagatatgga tattacacaa aaagtaaaac aacataataa    133440
aaatgctgta ttaaaagcaa caaactggaa tattgaagat gacgggatgt ctgatattta    133500
ttgggagcaa ggaatttccc aattttggac tcctgaagag tttgatgtat caagagattt    133560
aagttcttgg aatagtttaa ctgaaagtga aaagaacact tataagaaag tccttgcagg    133620
gctcacaggg ctcgatacca agcaaggagg agaaggtatg aacttagtat cctaccacga    133680
accaagacct aaataccaag ctgtatttgc gtttatgggt ggtatggaag agatacatgc    133740
taaatcctat agtcatatct ttacaacatt actaagtaat aagaaacaa gctatctatt     133800
agatacttgg gtcgaagaaa acgactttt aaaagtaaaa gctcagttta tcggatatta     133860
ctatgaccaa ctattaaaac ctaaccctac tgtatttgat agatacatgg ctaaagtagc    133920
tagtgccttt ttagaaagtg cactattcta ctcaggattt tattatcctt tacttcttgc    133980
agggagagga cagatgacac aatcaggagc tattatttat aaaattactc aagatgaagc    134040
ttaccatggt tcagcagtag gattaacagc tcaatatgat tataatcttc taacagaaga    134100
agagaaaaaa caagcagata aagaaactta tgaattatta gatattcttt acactaatga    134160
agtagcgtat acacatagtc tatatgaccc attagaatta agtgaagacg taattaacta    134220
cgttcagtat aattttaata gagctcttca aaaccttgga agagaggact attttaatcc    134280
tgaaccttat aaccctattg tagaaaatca aactaatgta gacagattac gaaatgttga    134340
tttctttagt ggtaaagcag actatgaaaa atctacaaat attaaagata ttaaagatga    134400
agattttca ttcttagata gtaaagaata cagtactgcc aaggaattcc tataaaaagg      134460
agaaaagata ttatggatag aaaagaagca atggatttac taagtaaagc agaaatatta    134520
tttaaaaaac atgatgagtt ttcatgtgta agtgatatca atgaccctat gaagttattc    134580
agtaactcta aggatgctaa agctgatgat acgtctaagt cttttcagtt agagtttatg    134640
catgatatga ccatgtatac tttatcttat ggctcaggac agttaaaact tattgattta    134700
gcagaaggtt atgaagcaca aaaagctaca gtagttaact catttcccga aattattaaa    134760
acattagaaa aggatgattc agaagatgga aaaatgaat agtttagtag atttaaatac      134820
agcaattaga caaaagaaag atgttattgt catgattaca caagataatt gtggtaagtg    134880
tgagattta aaaagtgtaa tccctatgtt tcaagagtca ggtgacatta aaaaacctat     134940
cttaacatta aatctagatg ctgaagatgt agatagagaa aagctgtta agttattcga     135000
tatcatgagt acaccagtat taattggata taaagatggt cagttagtta aaaagtatga    135060
agaccaagtt acacctatgc aattacaaga attagagtca ctttaatttg gaatttccta    135120
ctatctgtgc tatactataa tagtacaagg tagtaggatt ttttaatgga aggaagatga    135180
catatcgcaa agaataaaac attaacgata tataatagtg atagatattt aatatacac     135240
acaaaagata aagataaaat taatgaggct attaaagtca cacatggtaa tgaagaagaa    135300
```

FIG. 21UUU sequence.txt

| | | | | | | |
|---|---|---|---|---|---|---|
| attgaaaaga | atatggatga | attaatatct | aagtctagac | gatatatcat | gagagatgaa | 135360 |
| aatcattaca | tgttatttaa | tgaaaagtac | aataatgata | gacttataga | aaaagtatgt | 135420 |
| aaacacggtg | gcaaagttac | atactatact | gattcagtat | taccctatta | tgttttaaaa | 135480 |
| gacttatcta | gtcaccctga | ctcagaagtc | gtttatcgta | tgcgcaatgg | ttttactgca | 135540 |
| aaagaagtag | ataatatagc | tttgtcattt | atgggtacaa | aagttattat | tgatatttct | 135600 |
| gtagtatttc | cttatgtaaa | cccttatgat | attattagaa | gtttacatga | tattaaaaca | 135660 |
| aatgtagatg | aagttcattt | atcatttcca | cgaatattag | aagtagatga | aaaacaagaa | 135720 |
| aaattttatt | tctttgatgg | tgaagcttat | gatttaaaac | ctgagtataa | agtagatttt | 135780 |
| gcggataaaa | ttagagtatc | tttatcagta | tggaaaatgt | atatctatat | cttaacaagt | 135840 |
| agtcgtgatt | ttgaggatgt | agacaatgta | attacgaaac | taaaacaaca | acgaaagatt | 135900 |
| aagatataag | gtgattatat | gagtacagca | aatagaagag | atatagcaag | aaagatatca | 135960 |
| gagaatacag | gttactatat | ccaggatgta | gaggaaatac | taagtgcaga | gacagatgct | 136020 |
| atttctgact | tactagaaga | aggatatact | aaagtaaaga | atcataaatt | tatgcaaata | 136080 |
| gaagttattg | aaagaaaagg | taaaaaagcg | tgggatggtc | tgaataaaga | atacttccat | 136140 |
| ttacctaata | gaaaagctat | aaaattcaaa | ccactaaaag | aactagaaga | ggttattgat | 136200 |
| agacttaatg | aagaagagaa | ataattctct | tcttttttta | ttgacaaggt | ttaaaatata | 136260 |
| tggtatagta | ttattaagtt | aaaaaaggag | aggaattaaa | tgaaagtatt | aatcttattt | 136320 |
| gaccacatta | gagaagagca | tttttctgta | agtaaagatg | ggagtgtgaa | atctaatgta | 136380 |
| ctaaatacac | ctaatggaaa | aacacttaag | aaattacttg | agaagtgttc | taatttaaag | 136440 |
| agagataaaa | caaacagaga | ttatgatatt | gattttctct | acaatgcagt | acctacacct | 136500 |
| atcagaaatg | actatggtaa | aattattaaa | tatcaagatg | ttaaacaagc | agaagtaaag | 136560 |
| ccatactatg | agagaatgaa | taatattatt | attgataatt | cttatgatat | gataattcct | 136620 |
| gtaggtaaac | taggcgttaa | atacttatta | aatgttacag | ctattggtaa | agtaagaggt | 136680 |
| gtaccaagta | aagtaactat | tgaaaatgga | acatcttctc | atgacgtgtg | ggtattacct | 136740 |
| acttacagta | ttgaatatac | taatgtaaat | aaaaatagtg | aacgtcatgt | agtatcagat | 136800 |
| ttacaaacag | ttggtaagtt | tgtagagcaa | ggagaagagg | catttaaacc | taaggaagta | 136860 |
| tcttacgagt | tggtagataa | cattgaaaga | gtaagagaaa | tattcaataa | ggaagtaaag | 136920 |
| aatgataatt | atgatggcgt | agatattacc | gcatgggact | tagagactaa | ctcattaaaa | 136980 |
| cctgataaag | aaggaagtaa | acctttagta | ctatctctat | catggagaaa | tggtcaaggt | 137040 |
| gtaactatac | ctttatacaa | atcagacttt | aactgggaaa | acggtcaaga | tgatattgat | 137100 |
| gaagtcttag | aattacttaa | gaactggtta | gctagtaaag | aagatattaa | agtagcacat | 137160 |

FIG. 21VVV

```
                                      sequence.txt
aatggtaagt  acgatattaa  attcttgatg  agtactgaga  actttaaaga  ttttgagagt    137220
attcaagata  ctaaagtagg  ttggtaccta  gctgttaccc  aagaagttaa  agaatcttta    137280
agattatctg  atttagctta  tgaggttaca  gatgtcggag  gttatgataa  accattagaa    137340
gattttaaat  tatggtttgt  tactaagtta  ttaagattct  tctcagataa  aattaaagag    137400
atacagaaag  aaaataaaaa  gattgctaag  aaggagtatg  atgttaaagc  tcccgaatat    137460
aaagaatggc  tagagaataa  actaaatgaa  acagtagtag  aactagatga  tactgagaag    137520
aaatttagag  ttagtgaatt  agagaaaaag  tatattcaac  taggtctttc  acctgaaatt    137580
gtaaatatga  atttagttat  gaataacgat  gagttcataa  gtattgcaga  acaatcacct    137640
gagtacatgg  ggttatctga  ctatgctaag  tcttacacat  taaatactgc  aattaattta    137700
attaatgagt  atagagatgt  aaaagatgta  gttaatgata  ttgatggagg  taactttaat    137760
tatgattggt  tccctattga  attaatgcat  ccatacgcat  caggagatac  tgatgtatgt    137820
agaagaattc  attgtgatgt  agttaagaaa  cttaaagaac  aagatagacc  taaatcaatg    137880
catttattag  aagttaatta  cccaagactt  actaagtctt  tagctagaat  tgaatcaaat    137940
ggtttatatt  gtgacttaga  ttatatgaaa  gaaaatgatg  agtcatacga  gtctgagatg    138000
gctaaaaatc  atgctacaat  gagagagcac  tgggctgtta  aagaatttga  agaataccaa    138060
tacaatcttt  accaaatggc  gttagaagaa  catgagaaaa  agccaaaaga  tagagataaa    138120
gatatccatc  agtatagaga  taaatttaaa  gatggtaaat  ggatgttttc  cccaagttcc    138180
ggagaccata  aaggtagagt  aatttatgat  attttaggaa  ttcaattacc  ttatgataaa    138240
gaatatgtta  aggaaaaacc  atttaatgct  aatgttaaag  aagcagacct  tacttggcag    138300
gactataaaa  cagacaagaa  agctattggt  tatgcgttag  ataatttaga  attaaaagat    138360
gatgttagag  aacttcttga  gttacttaaa  tatcatgcta  gtatgcagac  aaaacgtaat    138420
tcatttacta  agaaattacc  taatatgatt  aataaacaaa  acgaacatt   acatggttct    138480
ttttctgaga  caggtacaga  gacatcaaga  ctaagtagta  gtaaccctaa  cttgcaaaac    138540
ttaccggcac  acacatcaga  tgtaaacaag  tttgattaca  aacatccaat  taaacgttca    138600
tttgtttcta  gatttgaaaa  tggagtacta  ctgggagccg  actatagcgc  cctagagatg    138660
cgtattattg  gattatttac  taaagaccct  gatatgctac  aatcattctt  aaatggggaa    138720
gatattcata  aggctactgc  aagtattgtt  tataataaac  cagtagaaga  ggtaactaag    138780
gaagaacgac  aagcaactaa  agcagttaac  ttcgggttag  ccttcggtga  atcacccttc    138840
tcatttgcag  gtaaaaataa  tatggaagta  agtgaagcag  aagaaatatt  gaaaagtac    138900
ttccaaacaa  aaccaagtgt  aaaaacttct  attgacaatg  tacatgagtt  tgtgcaacaa    138960
tatggttatg  ttgatacaat  gcacggacat  agaagattta  tccgttcagc  ccaatcaaca    139020
gataaaaaga  taaaaaatga  aggtctaaga  cagtcattta  acactattat  ccaaggttca    139080
```

FIG. 21WWW sequence.txt

| | | | | | | |
|---|---|---|---|---|---|---|
| ggcagtttct | taacaaacat | gtctttaact | tacttagatg | attttatcca | atctcgtaac | 139140 |
| ttaaaatcaa | aagttattgc | cacagtacat | gatagtatct | taattgattg | tcctcctgaa | 139200 |
| gaagctaaaa | ttatggctaa | agtgacaatt | catattatgg | aaaacttacc | atttgatttc | 139260 |
| ttaaaagcag | aaattgatgg | aaaagaagta | caatatccta | ttgaagctga | tatggaaatt | 139320 |
| gggttaaact | ataatgatat | ggttgaatat | gatgaggaag | aaatagatac | atttaattct | 139380 |
| taccaaggtt | atattaagta | tatgatgaat | ttacagacct | tagaagatta | taaagagtca | 139440 |
| ggtaaactaa | cagatgaaca | atttgaaaag | gctactaatg | ttgttaaaag | tgaaaaacat | 139500 |
| atttaccaag | aaatttaata | aaagtattga | caatacattt | aacttatgtt | atactatata | 139560 |
| ggtaataaat | ataaggagga | aaacagagtg | aatacaggag | agattagatt | taatcgttct | 139620 |
| atggatgaat | ggattataac | aagtatgtac | caggatgagc | taggtgagat | gaatattgtt | 139680 |
| gttacattct | ataatagaga | agaaaataaa | catggttcta | cagttttacc | aacagagtca | 139740 |
| tctactggag | aagtagcaga | ggaattggca | agtcttgaag | aagaatatcc | tctagcttta | 139800 |
| cctttaagta | gtatctcagt | taatatttaa | aaggaggaac | tgataaatgg | aaatacacat | 139860 |
| tgattcccta | gattttacaa | actttactat | taaagataga | aatgggaact | cacaagagtt | 139920 |
| tgatattaca | gatgagttaa | gaattacaga | gtatacaata | caagaggact | ttatgcaaca | 139980 |
| atcagctaaa | tatgcttttt | gggcttctat | attagagaag | gtaagagcat | attctgaaat | 140040 |
| ggaacaaaga | aatctagaaa | caattggtag | taagctaaac | cttacaatta | gacaagagta | 140100 |
| cgaacaacaa | ggtaaaaagc | ctactaaaga | tatgattgaa | tctagtgttt | atattcatga | 140160 |
| ttcttaccaa | caacaactta | aagttgttga | ggcttggaat | tataaagtta | aacaacttca | 140220 |
| atatgttgta | aaagcttttg | agacaagaag | agatatgatg | attcaattag | gtgcagaatt | 140280 |
| acgacaaaca | aataaaaatg | gtggaattac | taatccattt | tcacattaaa | aaataaagta | 140340 |
| aagaatataa | ttgacaaata | taaaaaacta | tgttataata | aataagtaaa | ttaattaaaa | 140400 |
| ggagaaaaga | taattatgga | tttcaatcaa | tttattaaca | atgaggcaag | caaattagaa | 140460 |
| agcaataaca | gttcttttaa | caataatgta | gagagctaca | aacctaaaaa | ccctgtacta | 140520 |
| cgtttaggta | atattaaaga | tgcaacggaa | ataaggttg | ttaaagaaaa | tgcttttgta | 140580 |
| cgagtattac | ctcctgcaca | aggaacaaat | gttttcttta | aagaatttag | aacaacaggt | 140640 |
| attaactatt | ctaagaaaga | tggttctcaa | ggattcacag | gattaacatt | acctgcagaa | 140700 |
| gaaggttcat | ctgtccttga | cccgtacatt | caggactgga | taacaaatgg | tgttcaattt | 140760 |
| agtagattcc | ctaataaacc | aggagtacgc | tattcattc | atgtgattga | atactttaat | 140820 |
| aacaatggtc | aaattcaacc | aaaaacggat | gctcaaggaa | atgtaatgat | tcaacctatg | 140880 |
| gaattatcta | acacaggata | taaagaatta | ttagctaact | taaagatac | tatgttaaaa | 140940 |

FIG. 21XXX sequence.txt

```
ccatcaccta atgcacctca tagctttatc tcagcaaatg aagcattctt agttaatatt   141000
gttaaagcta agaaaggtga aatgtcatgg aaagtaagtg tttatcctaa tgctccttta   141060
ggtgcgttac cgcaaggttg ggaacaacaa ttatctgacc tagaccaatt agcaaaacca   141120
acagaagaac aaaatcctaa ttttgttaac ttcttaatca ataatgttaa taacacagag   141180
ttaagtcatg ataactttaa atttaaccgt gaaacaaatg tcttaggtga agaaccttca   141240
gagcctaaac aagcacctac gcaacaagat gtagatagtc aaatgccaag taatatggga   141300
ggacaaccta atcagcctca gcaaggtcaa gtaggtcagt atgcacaaca aggtcaaagt   141360
aatggtcaag gacagcagtt acaaggtaca caacaaccta tcaataacac gcaatttggt   141420
caaggaactc cttcaggaca acaaccaagt aacacaggtt ctgttgattg ggataactta   141480
gcgcaacaac aatcacaacc tgattcaaac ccattcaatg attttgatgt tagcagtgtt   141540
gatgattcac aggtaccttt tgagacacaa cctcaaaata cacaacaagc acctgaacca   141600
caccaaacta cacaagagcc tccaaaacaa aaacaaacac aaagtattga cgatgtatta   141660
ggtggtctag acttagataa cctataagat atagagtgcc ttagagcact cttttattta   141720
agatatataa ttactaggag gatattaaat ggcaagagca aaaaaaggta agaagtaga    141780
tttaacagat ttaaatacaa ttgatttagg taaagaatta ggattaacat tattatcgga   141840
tagcaataga gcagacatta aaatattgt acctactatg gttcctcagt atgatagaat    141900
tctaggagga ggcatcccat taggtagatt gacagaggtt tacggattaa caggttcagg   141960
taaatcaagt tttgcagtcc atctctctag aatttcaaca cagttaggtg ttataactat   142020
ttggattgat attgaaggta ctgcggacaa taatcgtatg gaacagcttg gcgtagatgt   142080
ttcaaaacta ttctctattc aggcaggtga aggtagactt aaaaatacag tagagttatc   142140
tgtagagact gtaggtaagg aattagatta ctggatagat actttcaacg agaaagcccc   142200
tggagtacct attttattta tttgggattc attaggagca acaagaactc aagcggagat   142260
tgaagaagga gtagaccata ggaaattagg gacaaaagcc acagctactc aaaaagttat   142320
caacgcagta tctcctaaat taaatgatac aaatacagga ttaattgtta ttaatcaagc   142380
tagagataac ttgaatatgt ctaacccta tgatgaccct attaagtcca caggagggcg    142440
tgcgttcgag catggagcca gtctaagact taaaattact aaaggtaaag agtccgacct   142500
taaacaatct gattcaatga caggtaaacc tacctataaa ggtcatgtga tgagagtaga   142560
gactaaaaaa tctaaactat ctagaccagg acaaaaagca gaagcagact tactatcagg   142620
atatgaggta ggttctggtt cggatattac ccaactaaat ggaattgacc cttaccatac   142680
tatctataag gaagcagttg aaagaggtct aattacgaaa gggacttgga gaaattatat   142740
cacacttaat ggggaggaaa ttaaacttta tgataaagat tgggttcctc gtttaataga   142800
tgaccatgag ttatacttgg aattatttag tagagtctat ggagaacatt tccctaatgg   142860
```

FIG. 21YYY sequence.txt

| | | | | | | |
|---|---|---|---|---|---|---|
| ttattcacca | ttacttaata | ctaaagtaat | tgtaactcag | ttagaagaat | atcaagcatt | 142920 |
| agagaattac | tatgaagagt | gggctaaaga | taataaacaa | gaagaacaag | aggaagaatc | 142980 |
| aaaaggagaa | tctcaagaaa | aggattctga | ataatagatg | tataatttaa | tagataaaaa | 143040 |
| catgagacag | gtaaaagaat | ctttggggaa | tgcaaattcc | tcagatgttc | ttcctttacc | 143100 |
| ttataaagac | atagcaaaga | aatttgaaga | agtaaaagaa | aaaggtgaat | caattatcat | 143160 |
| tgaagagggt | ggattccctt | acacagattc | tacagtgatg | tatatagaac | atgtaacaga | 143220 |
| tagatgggca | ggaggatact | ccctaattag | gcatgaaggt | gaagaggtta | aagtacctaa | 143280 |
| aactatccat | ttctctgata | tatatgttaa | ggataaatca | cataaagtaa | gaataatctt | 143340 |
| cgaggggggct | aatccttatg | aagaaggcta | aaaatggtaa | tagatatgta | atagatatag | 143400 |
| atggtattcc | tgttgatttt | gaaagagact | tggatagttt | acttaacagg | tataaaaacc | 143460 |
| ttaggtggtc | attatatcat | aagtacgcag | ggatttatc | taatgatttt | gaaagacaag | 143520 |
| aactaagaga | atatattgat | gagcaattta | ttaaattagt | taaagaatat | aatattagaa | 143580 |
| gtaaagtgga | ttttcctgga | tatattaaag | ctaaactaac | tttaagagtt | caaaatagtt | 143640 |
| atgttaagaa | gaatgaaaaa | tataaacgta | ctgaaattat | tggtaaaaaa | gattatacag | 143700 |
| tagagtcctt | aacagaagat | ttaaatgaag | acttcgagga | taatcaaatt | atgagttacg | 143760 |
| tatttgatga | tatagaattt | acagaagttc | aaagtgagtt | acttaaagaa | ttacttatta | 143820 |
| atcctgaaag | agaagatgat | gcctttatcg | tttctcaagt | agcggaaaag | tttgatatga | 143880 |
| aaagaaaaga | agtagcaagt | gagttgacag | aactcagaga | ctatgttaga | tttaaaataa | 143940 |
| atgcatacca | tgagtactat | gctaagaaag | aattaaataa | ccatagagtt | aatactgaaa | 144000 |
| atcatatttg | ggaaaactag | ttacagtgcc | ttccttgtgt | tatataagta | ctactaataa | 144060 |
| tattattagt | agtacttttg | atatattatt | tatgtagaag | agaagtgaaa | atagtgagaa | 144120 |
| tagaaaagca | taaaataaag | aataataaag | taattaatga | aatgtctata | acagcaaata | 144180 |
| acctctataa | tcatgctaat | tttatttttaa | gacaaaattt | ctttaataat | aagactaata | 144240 |
| aaggatacag | aaagttttta | aattataata | ctattcatag | aatattaaaa | aatatgaatg | 144300 |
| aagagaatta | tattaaactc | ccaagacaaa | catctcaaca | agtattaagg | gatttaatta | 144360 |
| ataactggtc | tagttttaga | aaatcagaaa | aagattattt | taaaaaccct | aataaataca | 144420 |
| gaaatagacc | aaaaccacct | aaatataaag | ctaaaggcgg | taaaggaaca | attaagttta | 144480 |
| ctaatcaaca | atgtagaatt | cataaaaaag | atggtttaat | acatttacct | acacctttac | 144540 |
| aagatataac | tataaaacct | tataaagcta | agaatataag | agaacttgtt | tgtattccta | 144600 |
| aaagtgatta | ttttgaagtt | ttagtatgtt | ataaagaaga | aaatagtaat | aaaacactaa | 144660 |
| atgataacga | aaacatagca | agtattgatt | taggtttaga | taacttgata | accatggttt | 144720 |

FIG. 21ZZZ

```
                              sequence.txt
ctattgtaga taaaccaata attataaatg gtaaaggtct aaaatctaaa aataaatatt    144780
ttaataaaaa aataaggtat tatcaaagtc tattacaaaa caatagttac tcttcgaaaa    144840
gaatattaaa atattgggaa aaaagacaca atattatact agattacttt cataaagcaa    144900
caaacgaagt tgttaaatac tgcgtaaaaa atgatattag taaagtagtt atagggtata    144960
ataaacagca aaagtataaa tctaaattaa aaaa                                144994
```

ANTIBACTERIAL PHAGE, PHAGE PEPTIDES AND METHODS OF USE THEREOF

1. RELATED APPLICATION

This application is a divisional application of U.S. patent application Ser. No. 14/943,082, filed Nov. 17, 2015. This application is also a divisional of U.S. patent application Ser. No. 13/823,519, filed on Oct. 28, 2013, now U.S. Pat. No. 9,222,077, which is a national stage application of PCT/PT2011/000031, filed on Sep. 19, 2011, which claims benefit of priority to U.S. Provisional Application No. 61/384,015, filed on Sep. 17, 2010, the contents of each of which are hereby incorporated by reference in their entirety.

2. SEQUENCE LISTING

The instant application contains a Sequence Listing which has been submitted in ASCII format via EFS-Web and is hereby incorporated by reference in its entirety. Said ASCII copy, created on Sep. 14, 2011, is named 16395US1.txt and is 3,295,858 bytes in size.

3. FIELD OF THE INVENTION

The present invention is directed to the field of phage therapy for the treatment and control of bacterial infections. In particular, the present invention is directed to the novel bacteriophage F387/08, F391/08, F394/08, F488/08, F510/08, F44/10, F125/10, isolated polypeptides thereof, compositions comprising one or more of the novel bacteriophage and/or isolated polypeptides; and methods for the treatment and prevention of bacterial infections caused by, e.g., *Staphylococcus aureus, Klebsiella pneumoniae, Acinetobacter baumannii, Escherichia coli*, and/or *Pseudomonas aeruginosa*, either alone or in combination with other therapies, e.g., antibiotics or other phage therapies.

4. BACKGROUND

Bacteriophage (phage) are viruses that specifically infect and lyse bacteria. Phage therapy, a method of using whole phage viruses for the treatment of bacterial infectious diseases, was introduced in the 1920s by Felix d'Herelle. Initially, phage therapy was vigorously investigated and numerous studies were undertaken to assess the potential of phage therapy for the treatment of bacterial infection in humans and animals. Early success prompted the development of multiple commercial phage preparations. For example, in 1940 Eli Lilly Company produced 7 phage products for human use, including phage preparations for treating different sicknesses caused by *Staphylococcus* sp., *E. coli* and other pathogenic bacteria. These preparations were used, for example, to treat infections that cause abscesses, purulent wounds, vaginitis, acute chronic upper-respiratory tract infections, and mastoid infections.

With the development of antibiotics in the 1940s, however, interest in phage-based therapeutics declined in the Western world. One of the most important factors that contributed to this decline was the lack of standardized testing protocols and methods of production. The failure to develop industry wide standards for the testing of phage therapies interfered with the documentation of study results, leading to a perceived lack of efficacy as well as problems of credibility regarding the value of phage therapy. Further, problems related to the production of phage samples/specimens complicated initial study and research. Diverse stabilizers and preservatives were initially used in attempts to increase the viability of the phage therapeutics. However, because the biology of both the phage and the various stabilizers were poorly understood, many of the ingredients added in an attempt to prolong the viability of phage preparations proved to be either toxic to humans or to negatively impact long term storage. Another problem in phage production related to the purity grade of the commercial preparations of the phage. At the time, phage therapy preparations generally consisted of raw lysates of host bacteria that had been treated with the phage of interest. Thus, many preparations contained what are now recognized to be undesired bacterial components, e.g., endotoxins. Accordingly, adverse events were often associated with the preparations, particularly in patients receiving them intravenously. Nevertheless, in Eastern Europe and the former Soviet Union, where access to antibiotics was limited, the development and use of phage therapy continued jointly with, or in place of, antibiotics.

With the rise of antibiotic resistant strains of many bacteria, however, interest in phage-based therapeutics has returned in the Western world. Even though novel classes of antibiotics may be developed, the prospect that bacteria will eventually develop resistance to the new drugs has intensified the search for non-chemotherapeutic means for controlling, preventing, and treating bacterial infections. There are three main phage-based strategies for using phage therapy in a clinical environment: 1) administering virulent phage; 2) using endolysins or purified lysins encoded by bacteriophage 3) using structural proteins of phage as metabolic inhibitors of key bacterial enzymes, such as enzymes that synthesize peptidoglycan.

There is therefore a need to develop novel bacteriophage and phage products as potential therapeutic and/or prophylactic agents for use in vivo against pathogenic bacteria. In particular, there is a need for bacteriophage capable of lysing nosocomial bacteria, including *Staphylococcus aureus, Klebsiella pneumoniae, Acinetobacter baumannii, Escherichia coli*, and/or *Pseudomonas aeruginosa*. Because most phage and phage peptides studied to date exhibit activity directed specifically against the species (or subspecies) of bacteria from which they are isolated, the novel phage-based therapies may find particular use in the hospital setting, selectively targeting nosocomial pathogens without affecting the normal surrounding flora.

5. SUMMARY OF THE INVENTION

The present invention is directed to isolated bacteriophage and to isolated antibacterial polypeptides of bacteriophage origin for the treatment, prevention, or management of conditions associated with infection by Gram-positive or Gram-negative bacteria. In particular, the isolated bacteriophage or polypeptides of the invention may be used in pharmaceutical compositions for the treatment, prophylaxis, or management of infection by nosocomial pathogens, e.g., Gram-negative bacteria including but not limited to *Klebsiella pneumoniae, Acinetobacter baumannii, Escherichia coli*, and *Pseudomonas aeruginosa*; and Gram-positive bacteria including but not limited to *Staphylococcus aureus*. In certain embodiments, the pharmaceutical compositions of the invention are of use in the treatment of conditions associated with infection by antibiotic resistant strains of bacteria, e.g., methicillin resistant strains of *Staphylococcus aureus* (MRSA). In particular embodiments, the isolated bacteriophage or polypeptides of the invention are used for the topical treatment of infection by nosocomial pathogens in a subject in need thereof. In other embodiments, the isolated bacteriophage or polypeptides of the invention are used for the diagnosis of the infective agent in a sample (e.g., tissue, blood, urine, sputum sample) derived from a patient. In other embodiments, the isolated bacteriophage or polypeptides of the invention are used as a prophylactic disinfectant or anti-infective for the preparation of solid surfaces, including skin or other epidermal surfaces.

In certain embodiments, the invention provides an isolated bacteriophage, F391/08, having a genome comprising the nucleic acid sequence of SEQ ID NO:1 (FIGS. 15A-15III) and exhibiting antibacterial activity against one or more strains of *Klebsiella pneumoniae*. In other embodiments, the invention provides an isolated bacteriophage, F394/08, having a genome comprising the nucleic acid sequence of SEQ ID NO:2 (FIGS. 16A-16Q) and exhibiting antibacterial activity against one or more strains of *Acinetobacter baumannii*. In yet other embodiments, the invention provides an isolated bacteriophage, F488/08, having a genome comprising the nucleic acid sequence of SEQ ID NO:3 (FIGS. 17A-17KKKK) and exhibiting antibacterial activity against one or more strains of *Escherichia coli*. In still yet other embodiments, the invention provides an isolated bacteriophage, F510/08, having a genome comprising the nucleic acid sequence of SEQ ID NO:4 (FIGS. 18A-18X) and exhibiting antibacterial activity against one or more strains of *Pseudomonas aeruginosa*. In still yet further embodiments, the invention provides an isolated bacteriophage, F44/10, having a genome comprising the nucleic acid sequence of SEQ ID NO:560 (FIGS. 19A-19UUU) and exhibiting antibacterial activity against one or more strains of *Staphylococcus aureus*. In still yet further embodiments, the invention provides an isolated bacteriophage, F387/08, having a genome comprising the nucleic acid sequence of SEQ ID NO:781 (FIGS. 20A-20KKKK) and exhibiting antibacterial activity against one or more strains of *Klebsiella pneumoniae*. In still yet further embodiments, the invention provides an isolated bacteriophage, F125/10, having a genome comprising the nucleic acid sequence of SEQ ID NO:1074 (FIGS. 21A-21ZZZ) and exhibiting antibacterial activity against one or more strains of *Staphylococcus aureus*.

The invention also encompasses isolated bacteria infected with one or more bacteriophage of the invention. In specific embodiments, the invention provides an isolated *K. pneumoniae* infected with a bacteriophage having a genome comprising or consisting of the nucleic acid sequence of SEQ ID NO:1. In other embodiments, the invention provides an isolated *A. baumannii* infected with a bacteriophage having a genome comprising or consisting of the nucleic acid sequence of SEQ ID NO:2. In still other embodiments, the invention provides an isolated *E. coli* infected with a bacteriophage having a genome comprising or consisting of the nucleic acid sequence of SEQ ID NO:3. In yet other embodiments, the invention provides an isolated *P. aeruginosa* infected with one or more bacteriophage having a genome comprising or consisting of the nucleic acid sequence of SEQ ID NO:4. In still yet other embodiments, the invention provides an isolated *S. aureus* infected with one or more bacteriophage having a genome comprising or consisting of the nucleic acid sequence of SEQ ID NO:560. In still yet further embodiments, the invention provides an isolated *K. pneumoniae* infected with one or more bacteriophage having a genome comprising or consisting of the nucleic acid sequence of SEQ ID NO: 781. In still yet further embodiments, the invention provides an isolated *S. aureus* infected with one or more bacteriophage having a genome comprising or consisting of the nucleic acid sequence of SEQ ID NO: 1074.

The present invention encompasses polypeptides isolated from bacteriophage F387/08, F391/08, F394/08, F488/08, F510/08, F44/10, and/or F125/10, which polypeptides exhibit antibacterial activity against one or more species or strains of Gram-positive or Gram-negative bacterium, e.g., *K. pneumoniae, A. baumannii, E. coli, P. aeruginosa,* and/or *S. aureus*. In specific embodiments, the polypeptides of the invention isolated or derived from F387/08 and F3910/08 exhibit antibacterial or antimicrobial activity, e.g., lytic killing activity, against at least *K. pneumoniae*; those isolated or derived from F394/08, against at least *A. baumannii*; those isolated or derived from F488/08, against at least *E. coli*; those isolated or derived from F510/08 against at least *P. aeruginosa*; and those isolated or derived from F44/10 and F125/10 against at least *S. aureus*.

In certain embodiments, a polypeptide of the invention comprises or consists of an isolated lysin, or fragment thereof (e.g., a CHAP domain) that exhibits antibacterial activity against one or more species or strains of bacteria, e.g., Gram-positive bacteria, such as *S. aureus*; and/or Gram-negative bacteria, such as *K. pneumoniae A. baumannii, E. coli,* and/or *P. aeruginosa*. In specific embodiments, the polypeptide of the invention is an isolated lysin protein, e.g., an endolysin or tail lysin, comprising or consisting of the amino acid sequence SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, or SEQ ID NO: 1261. Predicted functions of said lysin proteins include, for example an Ig-like virion protein (SEQ ID NO: 20), cell wall hydrolase (SEQ ID NO: 80), N-acetylmuramoyl-L-alanine amidase (SEQ ID NO: 192), soluble lysozyme (SEQ ID NO: 282), T4-like lysozyme (SEQ ID NO: 547), endolysin (SEQ ID NO: 556), lambda Rz1-like protein (SEQ ID NO: 557), endolysin (SEQ ID NO: 598), endolysin (SEQ ID NO: 1216), and tail lysin (SEQ ID NO: 1261).

In other embodiments, a polypeptide of the invention comprises a fragment, variant or derivative of SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, or SEQ ID NO: 1261, wherein said fragment, variant or derivative has antibacterial activity or antimicrobial activity, e.g., lytic killing activity, against one or more strains of *K. pneumoniae A. baumannii, E. coli, P. aeruginosa,* and/or *S. aureus*. In specific examples in accordance with this embodiment, the variant, fragment or derivative of the amino acid sequence of SEQ ID NO: 20 and/or SEQ ID NO: 80 exhibits antibacterial or antimicrobial activity (e.g., lytic killing activity) against one or more strains of *K. pneumoniae*, for example, against the bacteriophage having a genome comprising or consisting of the nucleic acid sequence SEQ ID NO: 1. In other examples in accordance with this embodiment, the variant, fragment or derivative of the amino acid sequence of SEQ ID NO: 192 exhibits antibacterial or antimicrobial activity (e.g., lytic killing activity) against one or more strains of *A. baumannii*, for example, against the bacteriophage having a genome comprising or consisting of the nucleic acid sequence SEQ ID NO: 2. In other examples in accordance with this embodiment, the variant, fragment or derivative of the amino acid sequence of SEQ ID NO: 282 exhibits antibacterial or antimicrobial activity (e.g., lytic killing activity) against one or more strains of *E. coli*, for example, against the bacteriophage having a genome comprising or consisting of the nucleic acid sequence SEQ ID NO: 3. In other examples in accordance with this embodiment, the variant, fragment or derivative of the amino acid sequence of SEQ ID NO: 547, SEQ ID NO: 556, and/or SEQ ID NO: 557 exhibits antibacterial or antimicrobial activity (e.g., lytic killing activity) against one or more strains of *P. aeruginosa*, for example, against the bacteriophage having a genome comprising or consisting of the nucleic acid sequence SEQ ID NO: 4. In other examples in accordance with this embodiment, the variant, fragment or derivative of the amino acid sequence of SEQ ID NO: 598, SEQ ID NO: 1216, and/or SEQ ID NO: 1261 exhibits antibacterial or antimicrobial activity (e.g., lytic killing activity) against one or more strains of *S. aureus*, for example, against the bacteriophage having a genome comprising or consisting of the nucleic acid sequence SEQ ID NO: 560 or SEQ ID NO: 1074.

In specific embodiments, the isolated polypeptide of the invention comprises or consists of the CHAP domain of SEQ ID NO: 20, SEQ ID NO: 80, SEQ ID NO: 192, SEQ ID NO: 282, SEQ ID NO: 547, SEQ ID NO: 556, SEQ ID NO: 557, or SEQ ID NO: 598. In yet still other embodiments, a polypeptide of the invention comprises a fragment, variant or derivative of the CHAP domain of SEQ ID NO: 20, SEQ ID NO: 80, SEQ ID NO: 192, SEQ ID NO: 282, SEQ ID NO: 547, SEQ ID NO: 556, SEQ ID NO: 557, or SEQ ID NO: 598, wherein said fragment, variant or derivative has antibacterial activity or antimicrobial activity, e.g., lytic killing activity, against at least one or more strains of *K. pneumoniae A. baumannii, E. coli, P. aeruginosa*, and/or *S. aureus*.

In other embodiments, a polypeptide of the invention comprises or consists of an isolated tail protein (e.g., tail component, tail fiber protein, tail length tape measure protein, adsorption associated tail protein, major tail protein, major tail sheath protein, baseplate wedge subunit), or fragment thereof, having a biological function associated with the bacteriophage from which it is derived, e.g., antimicrobial or antibacterial activity (e.g., lytic killing activity), which function is directed against at least one or more species or strains of *K. pneumoniae, A. baumannii, E. coli, P. aeruginosa*, and/or *S. aureus*.

In specific embodiments, the polypeptide of the invention is an isolated tail protein comprising or consisting of the amino acid sequence SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266. In other embodiments, a polypeptide of the invention comprises a fragment, variant or derivative of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266, wherein said fragment, variant or derivative exhibits a biological function associated with the bacteriophage from which it is derived, e.g., antimicrobial or antibacterial activity (e.g., lytic killing activity), which function is directed against one or more strains of *K. pneumoniae, A. baumannii, E. coli, P. aeruginosa*, and/or *S. aureus*.

Predicted functions of said tail proteins include, for example, a receptor-binding tail protein (SEQ ID NO: 15), major tail protein (SEQ ID NO: 26 and SEQ ID NO: 1077), minor tail protein (SEQ ID NO: 27), pore-forming tail tip protein (SEQ ID NO: 30), tail protein (SEQ ID NOs: 32-33), minor tail protein (SEQ ID NO: 34), phage tail protein (SEQ ID NO: 35), tail sheath protein (SEQ ID NO: 180), tail tape measure protein (SEQ ID NO: 183), tail protein (SEQ ID NO: 185), tail-fiber protein (SEQ ID NO: 190), tail tube protein (SEQ ID NO: 231), tail sheath monomer (SEQ ID NO: 232), tail sheath stabilizer and completion protein (SEQ ID NO:235), short tail fibers (SEQ ID NO: 239), base plate wedge completion tail pin (SEQ ID NOs: 240-241), base plate wedge completion tail fiber socket (SEQ ID NO: 242), base plate wedge subunit (SEQ ID NO: 243), base plate wedge initiator (SEQ ID NO: 244), base plate wedge (SEQ ID NO: 245), base plate hub subunit and tail lysozyme, cell-puncturing device (SEQ ID NO: 248), base plate wedge completion (SEQ ID NO: 249), tail completion and sheath stabilizer protein (SEQ ID NO: 252), chaperone long and short tail fiber assembly (SEQ ID NO: 254), tail fiber protein (SEQ ID NO: 433), tail fiber protein (SEQ ID NO: 434), hinge connector long tail fiber (SEQ ID NO: 435), tail fiber hinge (SEQ ID NO: 436), proximal tail fiber subunit (SEQ ID NO: 437), base plate-tail tube initiator (SEQ ID NO: 489), base plate (SEQ ID NO: 490), baseplate hub subunit, tail length determinator (SEQ ID NO: 491), base plate distal hub subunit (SEQ ID NO: 492), base plate hub subunit (SEQ ID NO: 493), base plate hub assembly catalyst (SEQ ID NO: 494), baseplate hub subunit (SEQ ID NO: 495), baseplate wedge subunit (SEQ ID NO: 496), tail tubular protein (SEQ ID NOs: 544-545), tail fiber protein (SEQ ID NO: 549 and SEQ ID NO: 551), major tail sheath protein (SEQ ID NO: 629 and SEQ ID NO: 1250), major tail protein (SEQ ID NO: 686), tail tube protein (SEQ ID NO: 789), fibritin (SEQ ID NO: 796), short tail fibers (SEQ ID NO: 797), base plate wedge completion tail pin (SEQ ID NO: 798), base plate wedge subunit and tail pin (SEQ ID NO: 799), baseplate wedge tail fiber connector (SEQ ID NO: 800), baseplate hub subunit and lysozyme (SEQ ID NO: 806), lysozyme (SEQ ID NO: 854), holin (SEQ ID NO: 999 and SEQ ID NO: 1217), distal long tail fiber assembly catalyst (SEQ ID NO: 1000), L-shaped tail fiber protein (SEQ ID NO: 1001), hinge connector of long tail fiber distal connector (SEQ ID NO: 1002), hinge connector of long tail fiber proximal connector (SEQ ID NO: 1003), long tail fiber proximal subunit (SEQ ID NO: 1004), baseplate tail tube initiator (SEQ ID NO: 1053), baseplate tail tube cap (SEQ ID NO: 1054), baseplate hub subunit, tail length determinator (SEQ ID NO: 1055), baseplate distal hub subunit (SEQ ID NO: 1056), baseplate hub subunit (SEQ ID NOs: 1057 and 1059), baseplate hub assembly catalyst (SEQ ID NO: 1058), baseplate wedge subunit (SEQ ID NO: 1060), and baseplate protein (SEQ ID NO: 1266).

In certain embodiments, the invention encompasses a variant, fragment or derivative of the amino acid sequence of SEQ ID NO: 15, SEQ ID NO: 26, SEQ ID NO: 27, SEQ ID NO: 30, or SEQ ID NOs: 32-35, which exhibits a biological function associated with the bacteriophage having a genome comprising or consisting of the nucleic acid sequence SEQ ID NO: 1, e.g., antimicrobial or antibacterial activity (e.g., lytic killing activity), which function is directed against one or more strains of *K. pneumoniae*. In other embodiments, the invention encompasses a variant, fragment or derivative of the amino acid sequence of SEQ ID NO: 180, SEQ ID NO: 183, SEQ ID NO: 185, or SEQ ID NO: 190, which exhibits a biological function associated with the bacteriophage having a genome comprising or consisting of the nucleic acid sequence SEQ ID NO: 2, e.g., antimicrobial or antibacterial activity (e.g., lytic killing activity), which function is directed against one or more strains of *A. baumannii*.

In certain embodiments, the invention encompasses a variant, fragment or derivative of the amino acid sequence of SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-495, or SEQ ID NO: 496, which exhibits a biological function associated with the bacteriophage having a genome comprising or consisting of the nucleic acid sequence SEQ ID NO: 3, e.g., antimicrobial or antibacterial activity (e.g., lytic killing activity), which function is directed against one or more strains of *E. coli*. In certain embodiments, the invention encompasses a variant, fragment or derivative of the amino acid sequence of SEQ ID NO: 544, SEQ ID NO: 545, SEQ ID NO: 549, or SEQ ID NO: 551, which exhibits a biological function associated with the bacteriophage having a genome comprising or consisting of the nucleic acid sequence SEQ ID NO: 4, e.g., antimicrobial or antibacterial activity (e.g., lytic killing activity), which function is directed against one or more strains of *P. aeruginosa*. In still other embodiments, the invention encompasses a variant, fragment or derivative of the amino acid sequence of SEQ ID NO: 629 or SEQ ID NO: 686, which exhibits a biological function associated with the bacteriophage having a genome comprising or consisting of the nucleic acid sequence SEQ ID NO: 560, e.g., antimicrobial or antibacterial activity (e.g., lytic killing activity), which function is directed against one or more strains of *S. aureus*. In still other embodiments, the invention encompasses a variant, fragment or derivative of the amino acid sequence of SEQ ID NO: 789, SEQ ID NOs: 796-800, SEQ ID NO: 806, SEQ ID NO: 854, SEQ ID NOs: 999-1004, or SEQ ID NOs: 1053-1060, which exhibits a biological function associated with the bacteriophage having a genome comprising or consisting of the nucleic acid sequence SEQ ID NO: 781, e.g., antimicrobial or antibacterial activity (e.g., lytic killing activity), which function is directed against one or more strains of *K. pneumoniae*. In still other embodiments, the invention encompasses a variant, fragment or derivative of the amino acid sequence of SEQ ID NO: 1077, SEQ ID NO: 1217, SEQ ID NO: 1250, or SEQ ID NO: 1266, which exhibits a biological function associated with the bacteriophage having a genome comprising or consisting of the nucleic acid sequence SEQ ID NO: 1074, e.g., antimicrobial or antibacterial activity (e.g., lytic killing activity), which function is directed against one or more strains of *S. aureus*.

In certain embodiments, the invention provides for isolated polypeptides that exhibit antimicrobial or antibacterial activity (e.g., lytic killing activity) against one or more strains of bacteria, e.g., Gram-positive bacteria (e.g., *S. aureus*), Gram-negative bacteria (e.g., *K. pneumoniae, A. baumannii, E. coli,* and *P. aeruginosa*) or bacteria not classified as either Gram-positive or Gram-negative, wherein the isolated polypeptides have an amino acid sequence with at least 60%, 65%, 70%, 75%, 80%, 85%, 86%, 87%, 88%, 89%, 90%, 91%, 92%, 93%, 94%, 95%, 96%, 97%, 98%, 99%, or greater sequence identity to a second amino acid sequence of the same length (i.e., consisting of the same number of residues), which second amino acid sequence is of SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, SEQ ID NO: 1266, and/or a fragment thereof.

The invention further provides isolated polypeptides comprising or consisting of the amino acid sequence of any of SEQ ID NOs: 5-176, SEQ ID NOs: 177-223, SEQ ID NOs: 224-506, SEQ ID NOs: 507-559, SEQ ID NOs: 561-780, SEQ ID NOs: 782-1073, and SEQ ID NOs: 1075-1300. In other embodiments, isolated polypeptides of the invention recombinantly fused or chemically conjugated (e.g., covalent or non-covalent conjugation) to therapeutic agents (e.g., heterologous polypeptides or small molecules) are provided.

The invention also encompasses polynucleotides that encode the polypeptides of the invention. In a specific embodiment, the invention provides an isolated nucleic acid comprising a nucleic acid sequence encoding the polypeptide of any of SEQ ID NOs: 5-176, SEQ ID NOs: 177-223, SEQ ID NOs: 224-506, SEQ ID NOs: 507-559, SEQ ID NOs: 561-780, SEQ ID NOs: 782-1073, and SEQ ID NOs: 1075-1300. In other embodiments, the invention provides an isolated nucleic acid comprising a nucleic acid sequence encoding the polypeptide of any of SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266, or active fragment, variant or derivative thereof, which polypeptide or active fragment, variant or derivative exhibits a biological function associated with the bacteriophage from which it is isolated and/or derived, e.g., antimicrobial or antibacterial activity (e.g., lytic killing activity). The invention also relates to a vector comprising one or more of said nucleic acids. In one specific embodiment, said vector is an expression vector. The invention further provides host cells containing a vector comprising one or more polynucleotides one or more encoding the polypeptides of the invention.

The present invention encompasses methods for the production of polypeptides of the invention or active fragments thereof, in particular for use in pharmaceutical compositions, i.e., antimicrobial compositions. For example, the polypeptides of the invention may be isolated directly from cell cultures (e.g., bacterial cell cultures) infected with bacteriophage F387/08, F391/08, F394/08, F488/08, F510/08, F44/10, and/or F125/10. Alternatively, the polypeptides of the present invention may be derived by recombinant means using expression vectors comprising nucleic acid sequence encoding polypeptides of the invention, e.g., SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266, or active fragments, derivatives or variants thereof. The polypeptides of the invention or fragments thereof can be produced by any method known in the art for the production of a polypeptide, in particular, by chemical synthesis or by recombinant expression techniques.

In specific embodiments, the invention relates to a method for recombinantly producing a phage protein, e.g., a lysin protein, tail protein, or active fragment, variant or derivative thereof, said method comprising: (i) culturing under conditions suitable for the expression of said protein in a medium, a host cell containing a vector comprising a nucleic acid sequence encoding the amino acid sequence SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, or SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266, or fragment thereof; and (ii) recovery of said protein from said medium. In certain embodiments, the nucleic acid sequence encoding the polypeptide of the invention is operably linked to a heterologous promoter.

The invention also encompasses methods for the diagnosis of the causative agent in a clinical presentation of bacterial infection. The isolated bacteriophage or polypeptides of the invention may be used to aid in the determination of species of bacteria in a patient sample by establishing susceptibility of the bacteria in the sample to the bacteriophage and/or polypeptides of the invention. Such methods further encompass methods of evaluation of antibacterial activity of the isolated bacteriophage and/or polypeptides of the invention. Antibacterial activity of the bacteriophage or the polypeptides of the invention, or susceptibility of an unknown sample to such activity, may be assessed by any method known in the art and/or described herein. In certain embodiments, antibacterial activity and/or susceptibility is assessed by culturing known bacteria and/or patient tissue, blood, fluid or swab samples according to standard techniques (e.g., in liquid culture or on agar plates), contacting the culture with bacteriophage and/or polypeptides of the invention and monitoring cell growth after said contacting. For example, in a liquid culture, the bacteria (e.g., *K. pneumoniae, A. baumannii, E. coli, P. aeruginosa*, and/or *S. aureus*) may be grown to a optical density ("OD") representative of a mid-point in exponential growth of the culture; the culture is exposed to one or more concentrations of one or more bacteriophage and/or polypeptides of the invention and the OD is monitored relative to a control culture. Decreased OD relative to a control culture is representative of a bacteriophage and/or polypeptide exhibiting antibacterial activity (e.g., exhibiting lytic killing activity) against the tested sample or bacterial species and/or strain in the culture. Similarly, bacterial colonies can be allowed to form on an agar plate, the plate exposed to a bacteriophage or polypeptide of the invention, and subsequent growth of the colonies evaluated relative to control plates. Decreased size of colonies, or decreased total numbers of colonies, indicates a bacteriophage and/or polypeptide with antibacterial activity against the tested sample and/or cultured species or strain.

The present invention is also directed to pharmaceutical compositions comprising or consisting of a bacteriophage having a genome comprising or consisting of the nucleic acid sequence SEQ ID NO: 1, SEQ ID NO: 2, SEQ ID NO: 3, SEQ ID NO: 4, SEQ ID NO: 560, SEQ ID NO: 781, or SEQ ID NO: 1074. In certain embodiments, the pharmaceutical composition of the invention comprises a bacteriophage having the genome comprising or consisting of the nucleic acid sequence SEQ ID NO: 1, SEQ ID NO: 2, SEQ ID NO: 3, SEQ ID NO: 4, SEQ ID NO: 560, SEQ ID NO: 781, or SEQ ID NO: 1074, in addition to one or more other bacteriophage. The one or more other bacteriophage may be one or more bacteriophage of the invention (e.g., having a genome comprising or consisting of a nucleic acid sequence of SEQ ID NO: 1, SEQ ID NO: 2, SEQ ID NO: 3, SEQ ID NO: 4, SEQ ID NO: 560, SEQ ID NO: 781, or SEQ ID NO: 1074), one or more strains thereof, or may be one or more bacteriophage known in the art other than a bacteriophage having a genome according to SEQ ID NO: 1, SEQ ID NO: 2, SEQ ID NO: 3, SEQ ID NO: 4, SEQ ID NO: 560, SEQ ID NO: 781, or SEQ ID NO: 1074. Further, the one or more bacteriophage in the pharmaceutical composition of the invention may target the same or different species or strains of bacteria. In certain embodiments, the pharmaceutical compositions comprising one or more bacteriophage of the invention further comprise one or more polypeptides of the invention and/or other phage products as described herein or known in the art.

In certain embodiments, the invention provides pharmaceutical compositions comprising polypeptides, or active fragments thereof, in particular those having anti-microbial and/or antibacterial activity, isolated from bacteriophage having a genome comprising or consisting of the nucleic acid sequence SEQ ID NO: 1, SEQ ID NO: 2, SEQ ID NO: 3, SEQ ID NO: 4, SEQ ID NO: 560, SEQ ID NO: 781, and/or SEQ ID NO: 1074. In specific embodiments, the pharmaceutical compositions of the invention comprise one or more polypeptides having an amino acid sequence of SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266. In other embodiments, the pharmaceutical compositions of the invention comprise a polypeptide that is a variant, derivative or fragment of SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266, wherein the variant, derivative or fragment retains a biological function of the polypeptide from which it is derived, e.g., antimicrobial or antibacterial activity (e.g., lytic killing activity), preferably against one or more strains of *K. pneumoniae, A. baumannii, E. coli, P. aeruginosa*, and/or *S. aureus*.

The pharmaceutical compositions of the invention may additionally comprise a pharmaceutically acceptable carrier, excipient, or stabilizer. In certain embodiments, the pharmaceutical compositions of the invention are antibiotic compositions (in that they exhibit antibacterial activity) or therapeutic compositions for the treatment, prevention, and/or amelioration of symptoms of a disease or disorder associated with infection by bacteria in a subject in need thereof. In specific embodiments, the pharmaceutical compositions of the invention are antibacterial compositions or therapeutic compositions for the treatment, prevention, and/or amelioration of symptoms of a disease or disorder associated with infection by *K. pneumoniae, A. baumannii, E. coli, P. aeruginosa*, and/or *S. aureus*. In certain embodiments, the subject receiving a pharmaceutical composition of the invention is a mammal (e.g., bovine, ovine, caprine, equid, primate (e.g., human), rodent, lagomorph or avian (e.g., chicken, duck, goose)).

The present invention provides for methods for the treatment or prevention of bacterial infection comprising administering to a subject in need thereof a pharmaceutical composition comprising one or more bacteriophage or phage products (e.g., an isolated bacteriophage polypeptide or active fragment, variant or derivative thereof), optionally in addition to one or more other bacteriophage or other phage products, as described herein. In the context of the present invention, "treatment" refers to both therapeutic treatment and prophylactic or preventative measures, wherein the object is to eliminate, lessen, decrease the severity of, slow the progression of or delay or prevent the symptoms or underlying cause (e.g., bacterial infection) associated with the pathological condition or disorder. The pharmaceutical compositions of the present invention may be used in the treatment or management of infections associated with any bacterial infection, including, but not limited to *K. pneumo-*

*niae, A. baumannii, E. coli, P. aeruginosa*, and/or *S. aureus*, as well as, in certain embodiments, *S. epidermidis, S. auricularis, S. capitis, S. haemolyticus, S. hominis, S. saprophyticus, S. simulans, S. xylosis, M. luteus, B. subtilis, B. pumilus, E. faecalis, E. hirae, E. faecium, E. avium*, and combinations thereof. In certain embodiments, the pharmaceutical compositions may be used to treat conditions or disorders associated with bacterial infections including, but not limited to, post-operative endophtalmitis, endocarditis, infections of the central nervous system, pneumonia, osteomylelitis, wound infections (e.g., diabetic foot ulcers), mastitis, septicemia, food poisoning, meningitis, skin infections, abscesses, toxic shock syndrome, bacteremia, and/or other conditions associated with nosocomial bacterial infections.

In certain embodiments, the invention provides for the use of a bacteriophage or an isolated phage product (e.g., an isolated phage polypeptide or active fragment, variant or derivative thereof) as a single agent therapy. In other embodiments, the invention provides for the use of a bacteriophage, or phage product (e.g., an isolated phage polypeptide or active fragment, variant or derivative thereof), in combination with a standard or experimental treatment for bacterial infection. Such combination therapy may enhance the efficacy of the standard or experimental treatment. Examples of therapeutic agents that are particularly useful in combination with a bacteriophage and/or polypeptide of the invention are anti-inflammatory agents, standard chemotherapeutic antibiotic agents (e.g., penicillin, synthetic penicillins, bacitracin, methicillin, nafcillin, oxacilin, cloxacillin, vancomycin, teicoplanin, clindamycin, co-trimoxazole, cephalosporin, polymyxin, cefaclor. Cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate and chelating agents), local anesthetic agents, and/or corticosteroids. In yet another embodiment, the compositions of the present invention may be combined with one or more bacteriophage or phage products known in the art. The combination therapies encompassed by the invention may be formulated into a single pharmaceutical composition or may be administered in separate compositions, but as part of an overall treatment regimen.

The pharmaceutical compositions of the invention may be administered by any method known in the art suitable for administration of an antibacterial compound, e.g., via oral or parenteral (e.g., inhalation, intramuscular, intravenous, or epidermal) delivery. In preferred embodiments, the pharmaceutical compositions of the invention are administered topically, e.g., in a topical formulation. The compositions of the invention may be used topically to treat and/or prevent common nosocomial infections, such as infections at surgical incision sites or associated with catheters or drains. In other embodiments, the compositions of the invention are use to treat bacterial infections of the skin or upper dermal layers (e.g., infections of diabetic ulcers of the foot or carbuncles).

The pharmaceutical compositions of the present invention may also be used for traditionally non-therapeutic uses such as antibacterial agents in cosmetics, or in sprays or solutions for use on solid surfaces to prevent the colonization of bacteria (i.e., as disinfectants).

The present invention is also directed to methods for screening peptides for antibacterial activity. In one embodiment the method comprises screening contiguous amino acid sequences of at least 6, 10, 15, 20 or 25 residues in length that are encoded by the open reading frames of the nucleic acid sequence SEQ ID NO: 1, SEQ ID NO: 2, SEQ ID NO: 3, SEQ ID NO: 4, SEQ ID NO: 560, SEQ ID NO: 781, or SEQ ID NO: 1074, for antibacterial activity, said antibacterial activity measured by the peptides ability to inhibit bacterial growth, e.g., in agar or liquid culture.

5.1 DEFINITIONS

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguousamino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a protein. In a specific embodiment, the fragment is a functional fragment in that it retains at least one function of the protein from which it is isolated (e.g., antimicrobial or antibacterial activity (e.g., lytic cell killing)).

As used herein the terms "active bacteriophage products" and "bacteriophage products" refer to polypeptides, or fragments, variants or derivatives thereof, isolated from a bacteriophage of the invention, which polypeptide, or fragment, variant or derivative thereof, exhibits a biological function or activity associated with the bacteriophage from which it was isolated or derived (e.g., antimicrobial or antibacterial activity (e.g., lytic cell killing)).

As used herein, the term "isolated" in the context of a peptide, polypeptide, or fusion protein or refers to a peptide, polypeptide or fusion protein that is substantially free of cellular material or contaminating proteins from the cell or tissue source from which it is derived, or substantially free of chemical precursors or other chemicals when chemically synthesized. The language "substantially free of cellular material" includes preparations of a peptide, polypeptide or fusion protein in which the peptide, polypeptide or fusion protein is separated from cellular components of the cells from which it is isolated or recombinantly produced. Thus, a peptide, polypeptide or fusion protein that is substantially free of cellular material includes preparations of a peptide, polypeptide or fusion protein having less than about 30%, 20%, 10%, or 5% (by dry weight) of heterologous protein (also referred to herein as a "contaminating protein"). When the peptide, polypeptide or fusion protein is recombinantly produced, it is also preferably substantially free of culture medium, i.e., culture medium represents less than about 20%, 10%, or 5% of the volume of the protein preparation. When the peptide, polypeptide or fusion protein is produced by chemical synthesis, it is preferably substantially free of chemical precursors or other chemicals, i.e., it is separated from chemical precursors or other chemicals which are involved in the synthesis of the peptide, polypeptide, or fusion protein. Accordingly, such preparations of a peptide, polypeptide, fusion protein, or antibody have less than about 30%, 20%, 10%, 5% (by dry weight) of chemical precursors or compounds other than the peptide, polypeptide, or fusion protein of interest.

As used herein, the term "isolated" in the context of nucleic acid molecules refers to a first nucleic acid molecule which is separated from other nucleic acid molecules which are present in the natural source of the first nucleic acid molecule. Moreover, an "isolated" nucleic acid molecule, such as a cDNA molecule, is substantially free of other cellular material, or culture medium when produced by recombinant techniques, or substantially free of chemical precursors or other chemicals when chemically synthesized and may be free of other cDNA or other genomic DNA molecules, e.g., where it has been isolated from other clones in a nucleic acid library.

The term "purified" means that the peptide, polypeptide, fusion protein, or nucleic acid molecule has been measurably increased in concentration by any purification process, including but not limited to, column chromatography, HPLC, precipitation, electrophoresis, etc., thereby partially, substantially, nearly completely, or completely removing impurities, such as precursors or other chemicals involved in preparing the peptide, polypeptide, fusion protein, or nucleic acid molecule. One of skill in the art will appreciate the amount of purification necessary for a given use. For example, isolated protein meant for use in therapeutic compositions intended for administration to humans ordinarily must be of high purity in accordance with regulatory standards and good manufacturing processes.

As used herein, the term "derivative" in the context of polypeptides refers to a polypeptide that comprises an amino acid sequence which has been altered by the introduction of amino acid residue substitutions, deletions or additions. The term "derivative" as used herein also refers to a polypeptide that has been modified, i.e., by the covalent attachment of any type of molecule to the polypeptide. For example, but not by way of limitation, a polypeptide may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide may be produced by chemical modifications using techniques known to those of skill in the art, including, but not limited to specific chemical cleavage, acetylation, formylation, metabolic synthesis of tunicamycin, etc. Further, a derivative polypeptide may contain one or more non-classical amino acids. A polypeptide derivative possesses a similar or identical function as the polypeptide from which it was derived. The term "derived" as used in reference to a polypeptide "derived" from an organism may also refer to isolation of a polypeptide directly from said organism (e.g. bacterial cells or phage).

As used herein, the term "host cell" refers to the particular subject cell transfected with a nucleic acid molecule and the progeny or potential progeny of such a cell that contain the nucleic acid molecule or chromosomally integrated version thereof. Progeny of such a cell may not be identical to the parent cell transfected with the nucleic acid molecule due to mutations or environmental influences that may occur in succeeding generations or integration of the nucleic acid molecule into the host cell genome. For the expression of bacteriophage proteins and polypeptides, the host cell is preferably not of the same species or strain from which the bacteriophage was isolated or cultured.

As used herein, the term "in combination" refers to the use of more than one prophylactic and/or therapeutic agent. The use of the term "in combination" does not restrict the order in which prophylactic and/or therapeutic agents are administered to a subject with a disease or disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject in need thereof, e.g., a subject with a disease or disorder.

As used herein, the terms "nucleic acids" and "nucleotide sequences" include single-stranded and double-stranded DNA and/or RNA molecules, or combinations thereof. As used herein, the term "encoded by the nucleic acid" refers to an amino acid sequence that results from the translation of the forward, reverse, complementary or reverse-complementary sequence of the referenced nucleic acid sequence using the standard genetic code (i.e., standard codon triplets) as well known in the art.

As used herein, the terms "prophylactic agent" and "prophylactic agents" refer to bacteriophage and/or polypeptides of the invention, which can be used in the prevention, treatment, management or amelioration of one or more symptoms of a disease or disorder, in particular, a disease or disorder associated with a bacterial infection.

As used herein, the terms "therapeutic agent" and "therapeutic agents" refer to bacteriophage and/or polypeptides of the invention that can be used in the prevention, treatment, management or amelioration of one or more symptoms of a disease or disorder, in particular, a disease or disorder associated with a bacterial infection.

As used herein, the term "therapeutically effective amount" refers to that amount of a therapeutic agent sufficient to result in amelioration of one or more symptoms of a disease or disorder, in particular, a disease or disorder associated with a bacterial infection.

As used herein, the terms "treat", "treatment" and "treating" refer to the amelioration of one or more symptoms of a disease or disorder, in particular, a disease or disorder associated with a bacterial infection, which results from the administration of one or more bacteriophage and/or polypeptides of the invention. As noted above, "treatment" and related terms refer to both therapeutic treatment and prophylactic or preventative measures, wherein the object is to eliminate, lessen, decrease the severity of, slow the progression of, or delay or prevent the symptoms or underlying cause (e.g., bacterial infection) associated with the pathological condition or disorder.

As used herein, the terms "antibacterial activity" and "antimicrobial activity" with reference to a bacteriophage, isolated bacteriophage protein (or variant, derivative or fragment thereof), or bacteriophage product, are used interchangeably to refer to the ability to kill and/or inhibit the growth or reproduction of a microorganism, in particular, the bacteria of the species or strain that the bacteriophage infects. In certain embodiments, antibacterial or antimicrobial activity is assessed by culturing bacteria, e.g., Gram-positive bacteria (e.g., *S. aureus*), Gram-negative bacteria (e.g., *K. pneumoniae, A. baumannii, E. coli,* and/or *P. aeruginosa*) or bacteria not classified as either Gram-positive or Gram-negative, according to standard techniques (e.g., in liquid culture or on agar plates), contacting the culture with a bacteriophage or polypeptide of the invention and monitoring cell growth after said contacting. For example, in a liquid culture, the bacteria may be grown to an optical density ("OD") representative of a mid-point in exponential growth of the culture; the culture is exposed to one or more concentrations of one or more bacteriophage or polypeptides of the invention, and the OD is monitored relative to a control culture. Decreased OD relative to a control culture is representative of a bacteriophage or polypeptide exhibiting antibacterial activity (e.g., exhibits lytic killing activity). Similarly, bacterial colonies can be allowed to form on an agar plate, the plate exposed to a bacteriophage or polypeptide of the invention, and subsequent growth of the colonies evaluated related to control plates. Decreased size of colonies, or decreased total numbers of colonies, indicate a bacteriophage or polypeptide with antibacterial activity.

As used herein, a "CHAP domain" refers to a conserved amidase domain found in several phage-encoded peptidoglycan hydrolases and stands for "cysteine, histidine-dependent amidohydrolases/peptidases." See, e.g., Rigden D, et. al., Trends Biochem Sci. 2003 May 28(5): 230-4. It is found in a superfamily of amidases, including GSP amidase and peptidoglycan hydrolases. The family includes at least two different types of peptidoglycan cleavage activities: L-muramoyl-L-alanine amidase and D-alanyl-glycyl endopeptidase activity. CHAP domains generally contain conserved cysteine and histidine residues and hydrolyze γ-glutamyl-containing substrates. These cysteine residues are believed to be essential for the activity of several of these amidases, and their thiol groups appear to function as the nucleophiles in the catalytic mechanisms of all enzymes containing this domain. CHAP domains are often found in association with other domains that cleave peptidoglycan, e.g., acting in a cooperative manner to cleave specialized substrates. See also, Bateman A, et al., Trends Biochem Sci. 2003 May 28 (5): 234-7.

6. BRIEF DESCRIPTION OF THE FIGURES

FIGS. 1A-1B: Schematic of the organization of the F391/08 genome, comprising the nucleic acid sequence of SEQ ID NO:1. The open reading frames ("ORFs") predicted in the approximately 113 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 2.

FIGS. 2A-2II: Features of the bacteriophage F391/08 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1-172 listed in FIG. 2 encode the amino acid sequences of SEQ ID NO:5-176, respectively.

Figure 3:
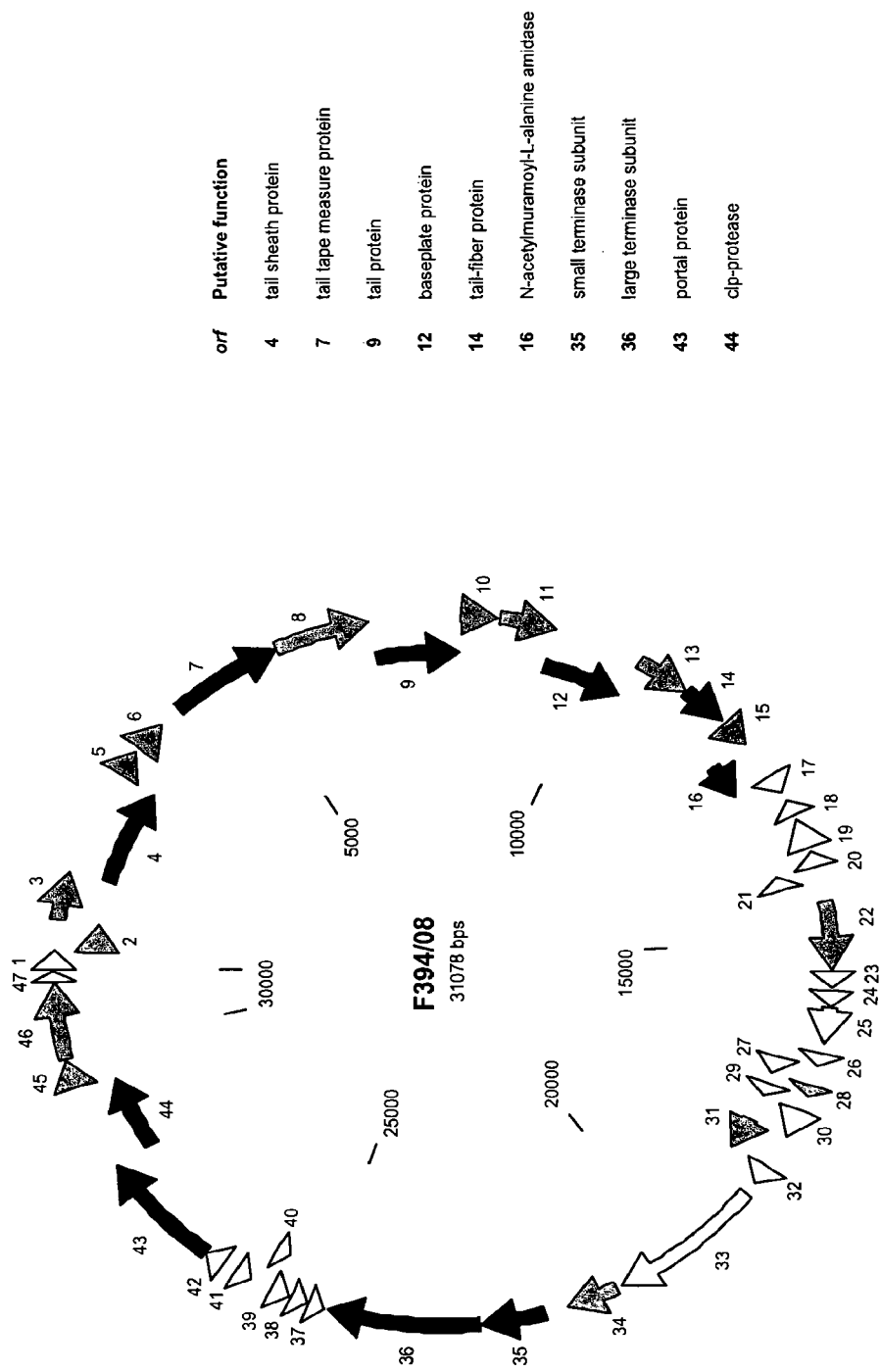

FIG. 3: Schematic of the organization of the F394/08 genome, comprising the nucleic acid sequence of SEQ ID NO:2. The open reading frames ("ORFs") predicted in the approximately 31 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 4.

FIGS. 4A-4K: Features of the bacteriophage F394/08 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1-47 listed in FIG. 4 encode the amino acid sequences of SEQ ID NO:177-223, respectively.

Figure 5A:
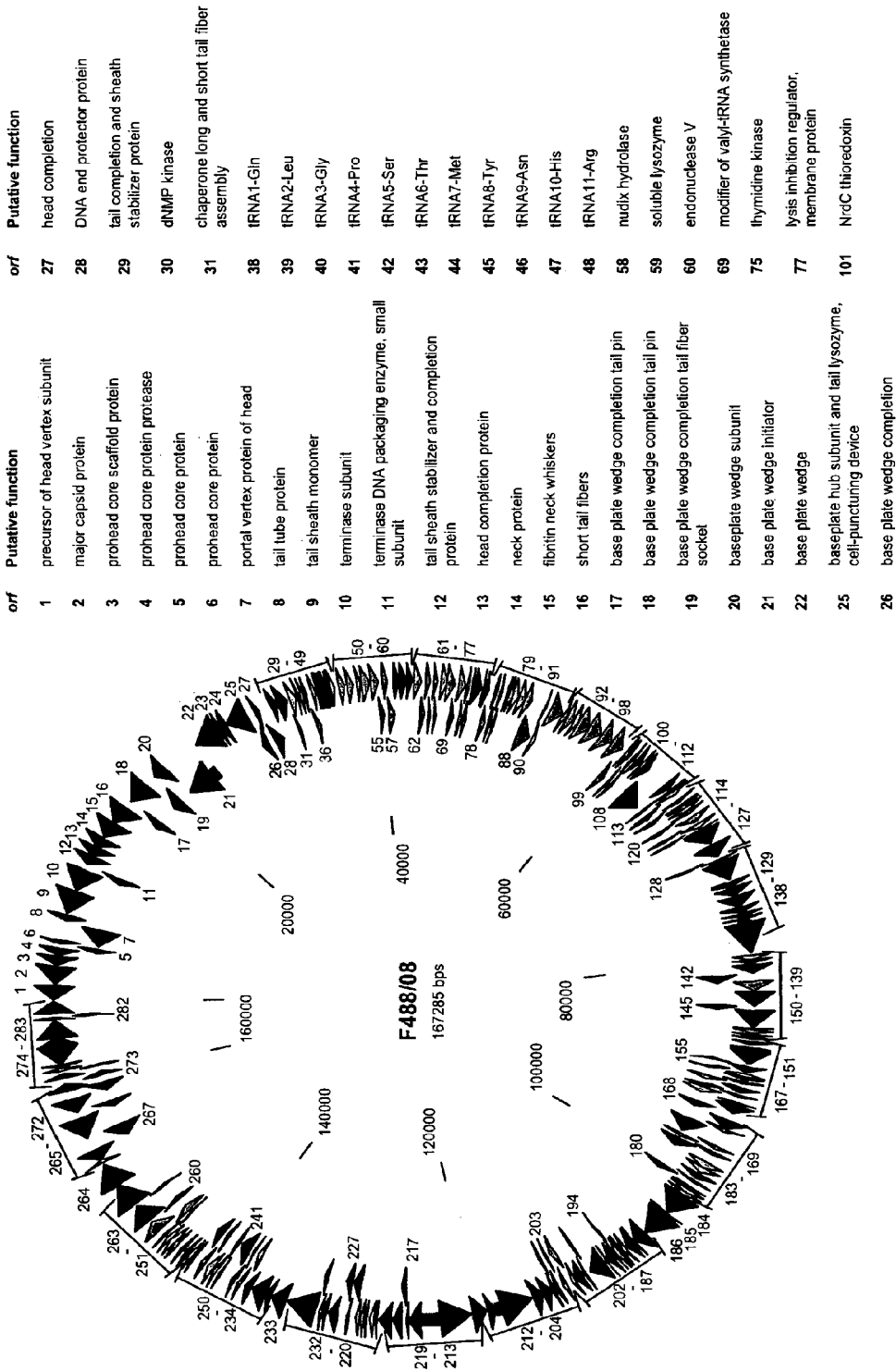

FIGS. 5A-5B: Schematic of the organization of the F488/08 genome, comprising the nucleic acid sequence of SEQ ID NO:3. The open reading frames ("ORFs") predicted in the approximately 167 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 6.

FIGS. 6A-6DDD: Features of the bacteriophage F488/08 genome, including gene products and assignment of putative functions. The figure includes a listing of the ORFs of the genome and provides for each ORF (i) its position within the genome, (ii) the encoded amino acid sequence, (iii) a listing of homologous proteins, and conserved domains within its encoded polypeptide, and (iv) an assignment of putative function. ORFs 1-283 listed in FIG. 6 encode the amino acid sequences of SEQ ID NO:224-506, respectively.

Figure 7:
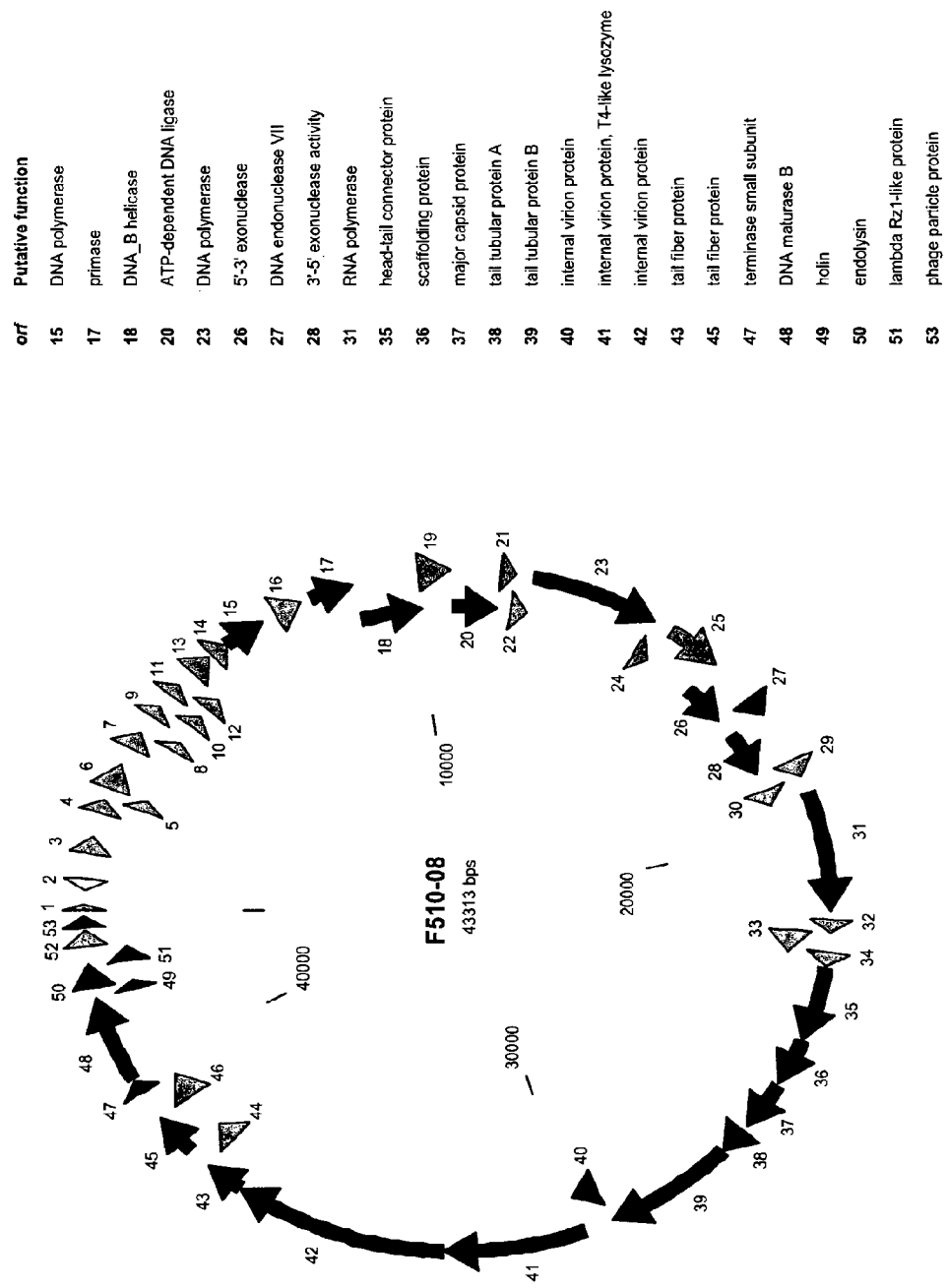

FIG. 7: Schematic of the organization of the F510/08 genome, comprising the nucleic acid sequence of SEQ ID NO:4. The open reading frames ("ORFs") predicted in the approximately 43 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 8.

FIGS. 8A-8S: Features of the bacteriophage F510/08 genome, including gene products and assignment of putative functions. The figure includes a listing of the ORFs of the genome and provides for each ORF (i) its position within the genome, (ii) the encoded amino acid sequence, (iii) a listing of homologous proteins, and conserved domains within its encoded polypeptide, and (iv) an assignment of putative function. ORFs 1-53 listed in FIG. 8 encode the amino acid sequences of SEQ ID NO:507-559, respectively.

Figure 9:
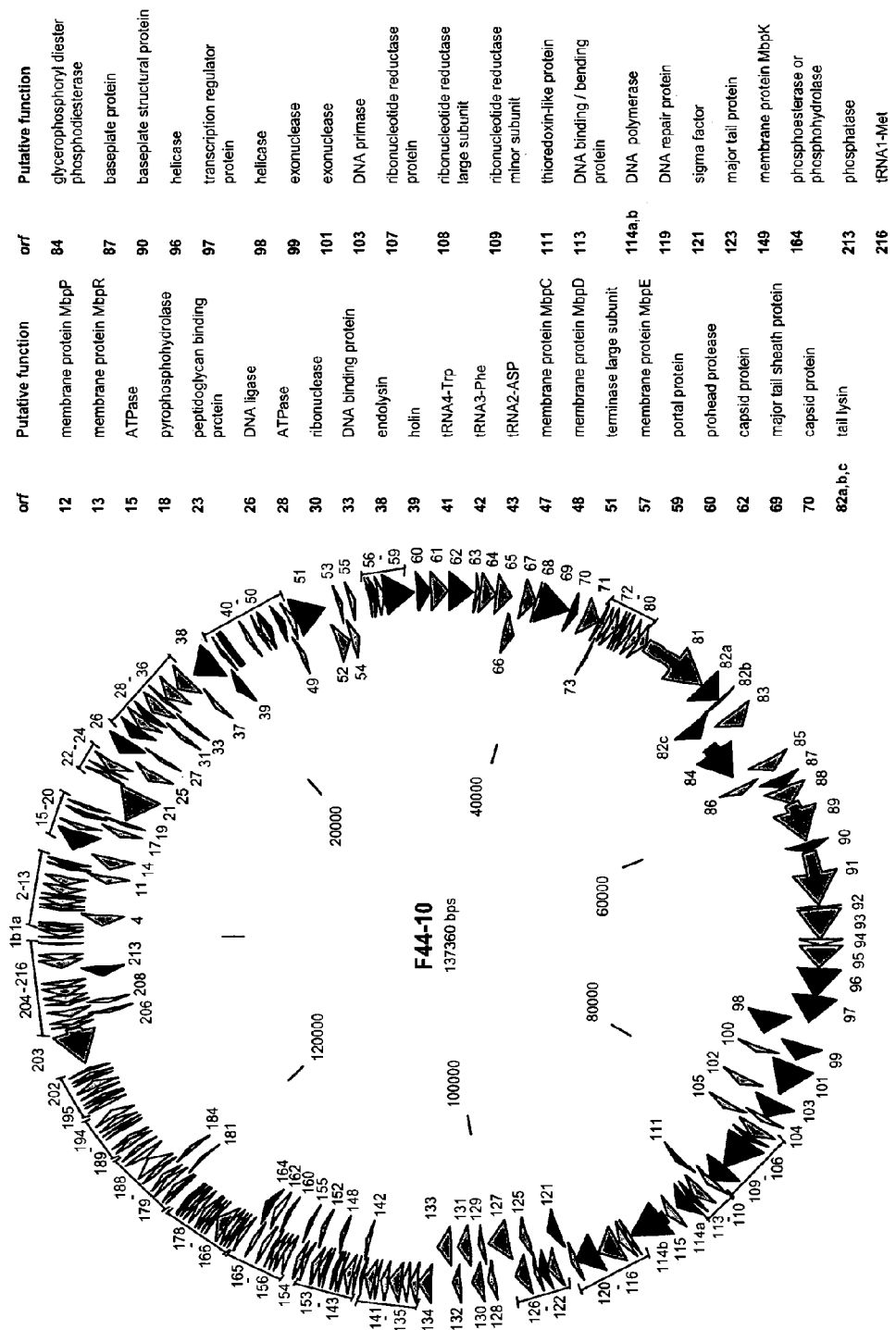

FIG. 9: Schematic of the organization of the F44/10 genome, comprising the nucleic acid sequence of SEQ ID NO:560. The open reading frames ("ORFs") predicted in the approximately 137 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 10.

FIGS. 10A-10QQ: Features of the bacteriophage F44/10 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1-216, including ORFs 1a, 1b, 82a, 82b, 82c, 114a, and 114b, listed in FIG. 10 encode the amino acid sequences of SEQ ID NO:561-780, respectively.

Figure 11A:
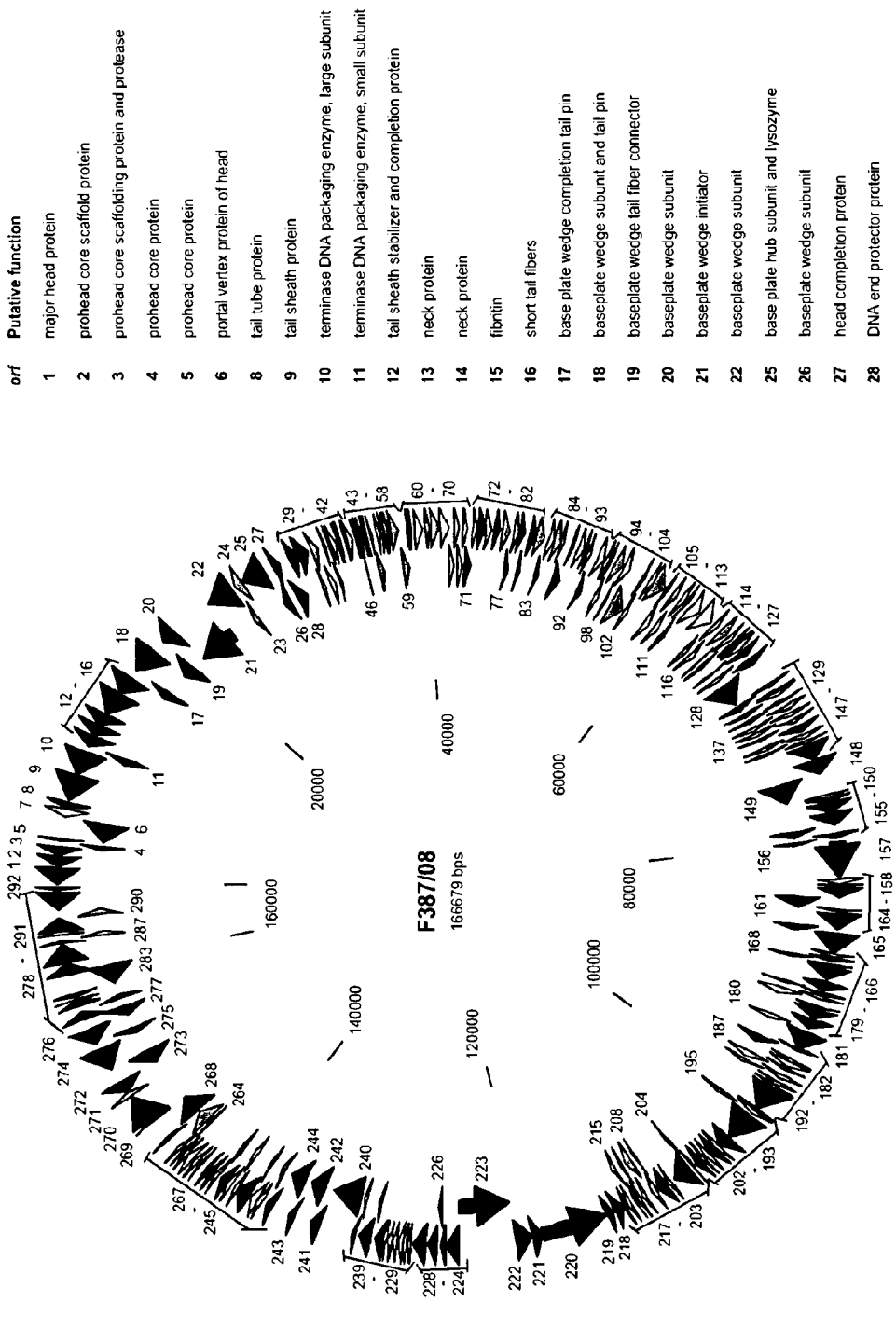

FIGS. 11A-11C: Schematic of the organization of the F387/08 genome, comprising the nucleic acid sequence of SEQ ID NO:781. The open reading frames ("ORFs") predicted in the approximately 167 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 12.

FIGS. 12A-12UUU: Features of the bacteriophage F387/08 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1-292 listed in FIG. 12 encode the amino acid sequences of SEQ ID NOs: 782-1073, respectively.

Figure 13A:
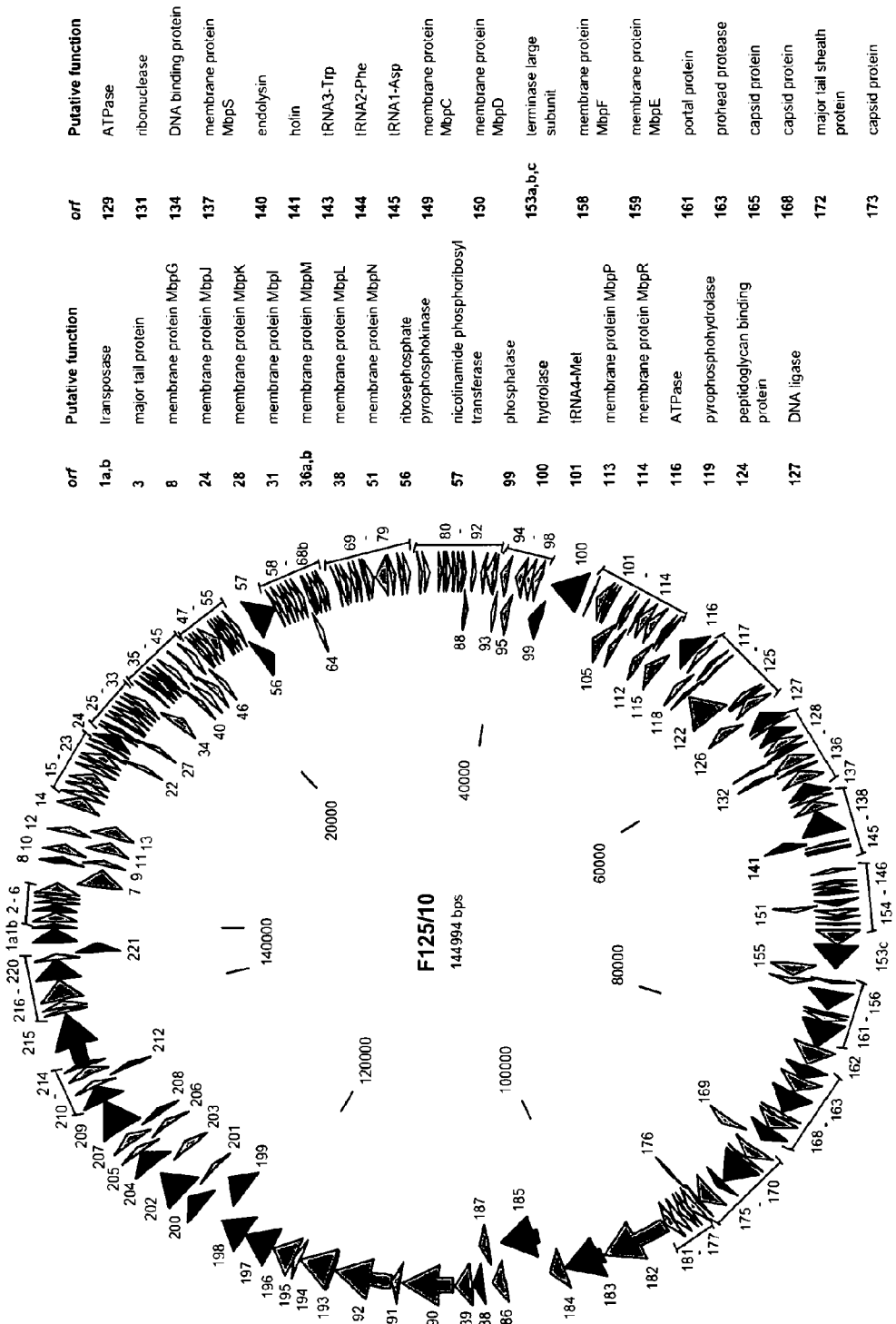

FIGS. 13A-13B: Schematic of the organization of the F125/10 genome, comprising the nucleic acid sequence of SEQ ID NO:1074. The open reading frames ("ORFs") predicted in the approximately 145 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIGS. 14A-14ZZZ

FIGS. 14A-14ZZZ: Features of the bacteriophage F125/10 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1b-221, 1a listed in this Figure encode the amino acid sequences of SEQ ID NO:1075-1300, respectively, including 36a and 36b, 68a and 68b, and 153a and 153b.

FIGS. 15A-15III: The nucleotide sequence of the genome of bacteriophage F391/08 (SEQ ID NO:1).

FIGS. 16A-16Q: The nucleotide sequence of the genome of bacteriophage F394/08 (SEQ ID NO:2).

FIGS. 17A-17KKKK: The nucleotide sequence of the genome of bacteriophage F488/08 (SEQ ID NO:3).

FIGS. 18A-18X: The nucleotide sequence of the genome of bacteriophage F510/08 (SEQ ID NO:4).

FIGS. 19A-19UUU: The nucleotide sequence of the genome of bacteriophage F44/10 (SEQ ID NO:560).

FIGS. 20A-20KKKK: The nucleotide sequence of the genome of bacteriophage F387/08 (SEQ ID NO:781).

FIGS. 21A-21ZZZ: The nucleotide sequence of the genome of bacteriophage F125/10 (SEQ ID NO:1074).

6.1 DETAILED DESCRIPTION

The present invention is directed to isolated bacteriophage, and their isolated polypeptide products, having antibacterial activity against one or more species or strains of the nosocomial pathogens *Klebsiella pneumoniae, Acinetobacter baumannii, Escherichia coli, Pseudomonas aeruginosa*, and *S. aureus*. In one embodiment, isolated bacteriophage or polypeptides are provided that exhibit antimicrobial and/or antibacterial activity against methicillin-resistant strains of *S. aureus* (MRSA). In addition, the bacteriophage and polypeptides of the invention may exhibit antibacterial or antimicrobial activity against one or more species or strains of pathogenic bacteria including, but not limited to, *S. epidermidis, S. auricularis, S. capitis, S. haemolyticus, S. hominis, S. saprophyticus, S. simulans, S. xylosis, Micrococcus luteus, Bacilus subtilis, B. pumilus, E. hirae* and *E. avium*.

In some embodiments, the invention provides a bacteriophage having a genome comprising or consisting of the nucleic acid sequence of SEQ ID NO: 1. A specific example in accordance with this embodiment is the isolated bacteriophage F391/08, which targets a number of strains of *Klebsiella* species, including *K. pneumoniae* and *K. oxytoca*. A schematic organization of the F391/08 genome, comprising the nucleic acid sequence of SEQ ID NO: 1, is provided in FIG. 1. Open reading frames (ORFs) in the F391/08 genome are provided in FIG. 2. Also provided are the positions of the ORFs within the genome, the amino acid sequences encoded by the ORFs, homologous or similar proteins and conserved domains within the encoded polypeptide, and the assignment of putative functions. ORFs 1-172 listed in FIG. 2 encode the amino acid sequences of SEQ ID NOs: 5-176, respectively.

In some embodiments, the invention provides a bacteriophage having a genome comprising or consisting of the nucleic acid sequence of SEQ ID NO: 781. A specific example in accordance with this embodiment is the isolated bacteriophage F387/08, which targets a number of strains of *Klebsiella* species, including *K. pneumoniae* and *K. oxytoca*. A schematic organization of the F387/08 genome, comprising the nucleic acid sequence of SEQ ID NO: 781, is provided in FIGS. 11A-11C. Open reading frames (ORFs) in the F387/08 genome are provided in FIG. 12. Also provided are the positions of the ORFs within the genome, the amino acid sequences encoded by the ORFs, homologous or similar proteins and conserved domains within the encoded polypeptide, and the assignment of putative functions. ORFs 1-292 listed in FIG. 12 encode the amino acid sequences of SEQ ID NOs: 782-1073, respectively.

*Klebsiella pneumoniae* is a Gram-negative, non-motile, rod-shaped bacterium, found in the normal flora of the mouth, skin, and intestines. As an encapsulated, facultative anaerobe, the bacterium also naturally occurs in the soil and about 30% of strains can fix nitrogen in anaerobic conditions. Clinically, it is the most important member of the *Klebsiella* genus of Enterobacteriaceae, and also is closely related to *K. oxytoca*. *Klebsiella* infections tend to occur in people with a weakened immune system from improper diet, e.g. in alcoholics and diabetics. *Klebsiella* is also an opportunistic pathogen for patients with chronic pulmonary disease, enteric pathogenicity, nasal mucosa atrophy, and rhinoscleroma. New antibiotic resistant strains of *K. pneumoniae* are appearing, and it is increasingly found as a nosocomial infection, for example, due to contact with contaminated instruments.

In some embodiments, the invention provides a bacteriophage having a genome comprising or consisting of the nucleic acid sequence of SEQ ID NO: 2. A specific example in accordance with this embodiment is the isolated bacteriophage F394/08, which targets a number of strains of *Acinetobacter* species, including *A. baumanni, A. calcoaceticus*, and *A. lwoffi*. A schematic organization of the F394/08 genome, comprising the nucleic acid sequence of SEQ ID NO: 2, is provided in FIG. 3. Open reading frames (ORFs) in the F394/08 genome are provided in FIG. 4. Also provided are the positions of the ORFs within the genome, the amino acid sequences encoded by the ORFs, homologous or similar proteins and conserved domains within the encoded polypeptide, and the assignment of putative functions. ORFs 1-47 listed in FIG. 4 encode the amino acid sequences of SEQ ID NOs: 177-223, respectively.

*Acinetobacter baumannii* is a species of bacteria that causes a number of severe clinical infections, particularly in individuals with compromised immune systems. *A. baumannii* is a pleomorphic aerobic gram-negative bacillus that is commonly isolated from the hospital environment and from hospitalized patients. The bacterium often enters the body open wounds, catheters, or breathing tubes. *A. baumannii* usually colonizes aquatic environments and is often cultured from hospitalized patients' sputum or respiratory secretions, wounds, and urine. In a hospital setting, *A. baumannii* commonly colonizes irrigating solutions and intravenous solutions. It is also known to be resistant to multiple antibiotics and the number of nosocomial infections caused by *A. baumanni* has increased in recent years.

In some embodiments, the invention provides a bacteriophage having a genome comprising or consisting of the nucleic acid sequence of SEQ ID NO: 3. A specific example in accordance with this embodiment is the isolated bacteriophage F488/08, which targets a number of strains of *Escherichia* species, including *E. coli*. A schematic organization of the F488/08 genome, comprising the nucleic acid sequence of SEQ ID NO: 3, is provided in FIG. 5. Open reading frames (ORFs) in the F488/08 genome are provided in FIG. 6. Also provided are the positions of the ORFs within the genome, the amino acid sequences encoded by the ORFs, homologous or similar proteins and conserved domains within the encoded polypeptide, and the assignment of putative functions. ORFs 1-283 listed in FIG. 6 encode the amino acid sequences of SEQ ID NOs: 224-506, respectively.

*Escherichia coli* is a Gram negative rod-shaped bacterium that is commonly found in the lower intestine of mammals, comprising the primary facultative anaerobic of the human gastrointestinal tract. Most *E. coli* strains are harmless and may form part of the normal flora of the gut, where they may benefit their hosts, e.g., by producing vitamin K2 and/or by preventing the establishment of pathogenic bacteria within the intestines. Certain virulent strains of *E. coli*, however, may cause food poisoning, typically manifesting as a bout of diarrhea. More virulent strains, such as O157:H7, can cause serious illness and even death in the elderly, the very young, or the immunocompromised. Strains such as O157:H7, as well as O121 and O104:H21, produce potentially lethal toxins. Virulent strains of *E. coli* also can cause gastroenteritis, urinary tract infections, and neonatal meningitis, as well as, in rarer cases, haemolytic-uremic syndrome (HUS), peritonitis, mastitis, septicemia, and Gram-negative pneumonia. Further, if *E. coli* bacteria escape the intestinal tract through a perforation (for example from a ruptured appendix, and ulcer, or a surgical error) and enter the abdomen, they usually cause peritonitis that can be fatal without prompt treatment. Intestinal mucosa-associated *E. coli* also are observed in increased numbers in the inflammatory bowel diseases, Crohn's disease and ulcerative colitis.

Antibiotics that may be used to treat *E. coli* infection include amoxicillin as well as other semi-synthetic penicillins, many cephalosporins, carbapenems, aztreonam, trimethoprim-sulfamethoxazole, ciprofloxacin, nitrofurantoin, and the aminoglycosides. Nonetheless, as Gram-negative organisms, *E. coli* are resistant to many antibiotics that are effective against Gram-positive organisms and antibiotic resistance is a growing problem. Resistance to beta-lactam antibiotics, for example, has become a particular problem in recent decades, as strains of bacteria that produce extended-spectrum beta-lactamases become more common. These beta-lactamase enzymes can render many, if not all, penicillins and/or cephalosporins therapeutically ineffective. Extended-spectrum beta-lactamase producing *E. coli* strains that are resistant to an array of antibiotics result in infections that are particularly difficult to treat.

In some embodiments, the invention provides a bacteriophage having a genome comprising or consisting of the nucleic acid sequence of SEQ ID NO: 4. A specific example in accordance with this embodiment is the isolated bacteriophage F510/08, which targets a number of strains of *Pseudomonas* species, including *P. aeruginosa*. A schematic organization of the F510/08 genome, comprising the nucleic acid sequence of SEQ ID NO: 4, is provided in FIG. 7. Open reading frames (ORFs) in the F510/08 genome are provided in FIG. 8. Also provided are the positions of the ORFs within the genome, the amino acid sequences encoded by the ORFs, homologous or similar proteins and conserved domains within the encoded polypeptide, and the assignment of putative functions. ORFs 1-53 listed in FIG. 8 encode the amino acid sequences of SEQ ID NOs: 507-559, respectively.

*Pseudomonas aeruginosa* is a common Gram-negative rod-shaped bacterium found in soil, water, skin flora and most man-made environments. It thrives not only in normal atmospheres, but also with little oxygen as a facultative anaerobe, and can infect damaged tissues or immunocompromised individuals. When such colonisations occur in critical body organs such as the lungs, the urinary tract, and kidneys, the results can be fatal. Because it thrives on surfaces, this bacterium is also found on and in medical equipment including catheters, causing cross infections in hospitals and clinics. *P. aeruginosa* is one of the most relevant opportunistic, nosocomial pathogens, and it has been estimated that one in ten hosptical-acquired infections are from *Pseudomonas*. *P. aeruginosa* is also the most common cause of burn injury infections and the most frequent colonizer of medical devices, such as catheters.

In some embodiments, the invention provides a bacteriophage having a genome comprising or consisting of the nucleic acid sequence of SEQ ID NO: 560. A specific example in accordance with this embodiment is the isolated bacteriophage F44/10, which targets a number of strains of *Staphylococcus* species, including *S. aureus*. A schematic organization of the F44/10 genome, comprising the nucleic acid sequence of SEQ ID NO: 560, is provided in FIG. 9. Open reading frames (ORFs) in the F44/10 genome are provided in FIG. 10. Also provided are the positions of the ORFs within the genome, the amino acid sequences encoded by the ORFs, homologous or similar proteins and conserved domains within the encoded polypeptide, and the assignment of putative functions. ORFs 1-216, including 1a, 1b, 82a, 82b, 82c, 114a, and 114b, listed in FIG. 10, encode the amino acid sequences of SEQ ID NOs: 561-780, as indicated in the Figure.

In some embodiments, the invention provides a bacteriophage having a genome comprising or consisting of the nucleic acid sequence of SEQ ID NO: 1074. A specific example in accordance with this embodiment is the isolated bacteriophage F125/10, which targets a number of strains of *Staphylococcus* species, including *S. aureus*. A schematic organization of the F125/10 genome, comprising the nucleic acid sequence of SEQ ID NO: 1074, is provided in FIG. 13. Open reading frames (ORFs) in the F125/10 genome are provided in FIG. 14. Also provided are the positions of the ORFs within the genome, the amino acid sequences encoded by the ORFs, homologous or similar proteins and conserved domains within the encoded polypeptide, and the assignment of putative functions. ORFs 1-221, including 1a, 1b, 36a, 36b, 68a, 68b, 153a, and 153b, listed in FIG. 14, encode the amino acid sequences of SEQ ID NOs: 1075-1300, as indicated in the Figure.

*Staphylococcus aureus* is a Gram-positive spherical facultative anaerobe, which grows as grape-like clusters with a characteristic golden color, and the most common cause of staph infections. It is frequently part of the flora of human skin and responsible for a range of infections, including pimples, carbuncles, scalded skin syndrome, pneumonia, gastroenteritis, meningitis, osteomyelitis, endocarditis, toxic shock syndrome, bacteremia, and sepsis. It remains one of the five most common causes of nosocomial infections, often causing post-surgical wound infections. It has been estimated that about 50,000 patients in American hospitals contract a staph infection. Of particular concern are the methicillin-resistant *Staphylococcus aureus* strains (MRSA). MRSA remained an uncommon occurrence in hospital setting until the 1990's, when there was an explosion in MRSA prevalence in hospitals, where it now is considered endemic, especially in the UK. Johnson A. P., et al., *J. Antimicrobial Chemotherapy*, 48(1): 143-144 (2001). *S. aureus* has proven to be a very hardy bacterium, and was shown in one study that it could survive on polyester for almost three months, polyester being the main material used in hospital privacy curtains. Neely, A. N., et al., *J. Clin. Microbiol.*, 38(2): 724-726 (2000).

The following organisms were deposited on Sep. 16, 20011, with NCIMB Limited, located at the Ferguson Building, Craibstone Estate, Bucksburn, Aberdeen, AB21 9YA, Scotland UK, under the provisions of the Budapest Treaty for the International Recognition of the Deposit of Microorganisms for the Purpose of Patent Procedure ("Budapest Treaty") and the NCIMB has assigned the corresponding NCIMB accession numbers as follows: host strain Pseudomonas aeruginosa 433/07 B2, NCIMB 41861; host strain Staphylococcus aureus 743/06 B1, NCIMB 41862; host strain Acinetobacter baumannii 1305/05 B3, NCIMB 41863; Pseudomonas aeruginosa phage F770/05, NCIMB 41864; Acinetobacter baumannii phage F1245/05, NCIMB 41865; Staphylococcus aureus phage F125/10, NCIMB 41866; Staphylococcus aureus phage F44/10, NCIMB 41867; and Pseudomonas aeruginosa phage F510/08, NCIMB 41868, all of which are incorporated by reference herein.

In certain embodiments, the bacteriophage of the invention comprises or consists of a genome having a sequence identity of at least 85%, 90%, 95%, 96%, 97%, 98% or at least 99% with the nucleic acid sequence of SEQ ID NO: 1, SEQ ID NO: 2, SEQ ID NO: 3, SEQ ID NO: 4, SEQ ID NO: 560, SEQ ID NO: 781, or SEQ ID NO: 1074, which bacteriophage exhibits at least one biological activity, e.g., antimicrobial or antibacterial activity (e.g., lytic killing activity), of one or more of bacteriophage F391/08, F394/08, F488/08, F510/08, F387/08, FF44/10, and F125/10. Alternatively or in addition, the bacteriophage of the invention may have a genome comprising a functional fragment of the nucleic acid sequence of SEQ ID NO: 1, SEQ ID NO: 2, SEQ ID NO: 3, SEQ ID NO:4, SEQ ID NO: 560, SEQ ID NO: 781, or SEQ ID NO: 1074, including the sequences of any of the open reading frames described in FIGS. 2, 4, 6, 8, 10, 12, and/or 14.

The invention also provides for isolated bacteria infected with one or more of the bacteriophage of the invention. In certain embodiments, the invention provides isolated K. pneumoniae infected with a bacteriophage having a genome comprising or consisting of the nucleic acid sequence of SEQ ID NO: 1 and/or SEQ ID NO: 781. In certain embodiments, the invention provides isolated A. baumannii infected with a bacteriophage having a genome comprising or consisting of the nucleic acid sequence of SEQ ID NO: 2. In certain embodiments, the invention provides isolated E. coli infected with a bacteriophage having a genome comprising or consisting of the nucleic acid sequence of SEQ ID NO: 3. In certain embodiments, the invention provides isolated P. aeruginosa infected with a bacteriophage having a genome comprising or consisting of the nucleic acid sequence of SEQ ID NO: 4. In certain embodiments, the invention provides isolated S. aureus infected with a bacteriophage having a genome comprising or consisting of the nucleic acid sequence of SEQ ID NO: 560 and/or SEQ ID NO: 1074.

The invention provides for methods of production and isolation of a bacteriophage having a genome comprising or consisting of the nucleic acid sequence of SEQ ID NO: 1, SEQ ID NO: 2, SEQ ID NO: 3, SEQ ID NO: 4, SEQ ID NO: 560, SEQ ID NO: 781, or SEQ ID NO: 1074. In certain embodiments, the invention provides for a method of producing and/or isolating a bacteriophage having a genome that comprises or consists of the nucleic acid sequence of SEQ ID NO: 1 and/or SEQ ID NO: 781 comprising (i) obtaining a culture of K. pneumoniae, (ii) infecting it with the bacteriophage having a genome comprising or consisting of the nucleic acid sequence of SEQ ID NO: 1 and/or SEQ ID NO: 781; (iii) culturing until significant lysis of the culture is observed; and (iv) isolating from the culture the bacteriophage. In other embodiments, the invention provides for a method of producing and/or isolating a bacteriophage having a genome that comprises or consists of the nucleic acid sequence of SEQ ID NO: 2 comprising (i) obtaining a culture of A. baumannii, (ii) infecting it with the bacteriophage having a genome comprising or consisting of the nucleic acid sequence of SEQ ID NO: 2; (iii) culturing until significant lysis of the culture is observed; and (iv) isolating from the culture the bacteriophage. In still other embodiments, the invention provides for a method of producing and/or isolating a bacteriophage having a genome that comprises or consists of the nucleic acid sequence of SEQ ID NO: 3 comprising (i) obtaining a culture of E. coli, (ii) infecting it with the bacteriophage having a genome comprising or consisting of the nucleic acid sequence of ID NO: 3; (iii) culturing until significant lysis of the culture is observed; and (iv) isolating from the culture the bacteriophage. In yet still other embodiments, the invention provides for a method of producing and/or isolating a bacteriophage having a genome that comprises or consists of the nucleic acid sequence of SEQ ID NO: 4 comprising (i) obtaining a culture of P. aeruginosa, (ii) infecting it with the bacteriophage having a genome comprising or consisting of the nucleic acid sequence of SEQ ID NO: 4; (iii) culturing until significant lysis of the culture is observed; and (iv) isolating from the culture the bacteriophage.

In yet still further embodiments, the invention provides for a method of producing and/or isolating a bacteriophage having a genome that comprises or consists of the nucleic acid sequence of SEQ ID NO: 560 and/or SEQ ID NO: 1074 comprising (i) obtaining a culture of S. aureus, (ii) infecting it with the bacteriophage having a genome comprising or consisting of the nucleic acid sequence of SEQ ID NO: 560 and/or SEQ ID NO: 1074; (iii) culturing until significant lysis of the culture is observed; and (iv) isolating from the culture the bacteriophage.

Bacteriophage may be isolated from a bacterial sample using any method described herein or known in the art (see, e.g., Carlson, "Working with bacteriophage: common techniques and methodological approaches," In, Kutter and Sulakvelidze (Eds) Bacteriophage: Biology and Applications, 5$^{th}$ ed. CRC Press (2005); incorporated herein by reference in its entirety).

The invention also provides for polypeptides isolated from bacteriophage of the invention. The isolated polypeptides may be full length bacteriophage proteins or may be fragments, variants or derivatives of the bacteriophage proteins provided that the fragment, variant or derivative exhibit at least one biological activity associated with the bacteriophage or polypeptide from which it is derived. In certain embodiments, the polypeptides of the invention are isolated from bacteriophage F387/08 or F391/08 (which typically infect K. pneumoniae), F394/08 (which typically infects A. baumannii), bacteriophage F488/08 (which typically infects E. coli), bacteriophage F510/08 (which typically infects P. aeruginosa) or bacteriophage F44/10 or F125/40 (which typically infects S. aureus).

In specific embodiments, the polypeptide of the invention is a lysin isolated from a bacteriophage having a genome comprising or consisting of SEQ ID NO: 1, SEQ ID NO: 2, SEQ ID NO: 3, SEQ ID NO: 4, SEQ ID NO: 560, SEQ ID NO: 781, or SEQ ID NO: 1074 (e.g., bacteriophage F391/08, F394/08, F488/08, F510/08, F44/10, F387/08, or F125/10, respectively). In specific embodiments, the polypeptide of the invention is a lysin, e.g., an endolysin or tail lysin, having the amino acid sequence comprising or consisting of SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, or SEQ ID NO: 1261. Predicted functions of said lysins include, for example an Ig-like virion protein (SEQ ID NO: 20), cell wall hydrdolase (SEQ ID NO: 80), endolysin; N-acetylmuramoyl-L-alanine amidase (SEQ ID NO: 192), soluble lysozyme (SEQ ID NO: 282), T4-like lysozyme (SEQ ID NO: 547), endolysin (SEQ ID NO: 556), lambda Rz1-like protein (SEQ ID NO: 557), endolysin (SEQ ID NO: 598), endolysin (SEQ ID NO:1216), and tail lysin (SEQ ID NO: 1261).

In other embodiments, the isolated polypeptide of the invention is a fragment, variant or derivative of an endolysin or lysin isolated from a bacteriophage of the invention, which fragment, variant or derivative exhibits at least one biological activity, preferably antibacterial activity (e.g., lytic killing activity), of the endolysin, lysin or bacteriophage from which it is isolated or derived. Accordingly, in certain embodiments, the invention provides isolated polypeptides that are fragments, variants or derivatives of endolysins or lysins isolated from bacteriophage of the invention, which fragments, variants or derivatives exhibit antibacterial or antimicrobial activity (e.g., lytic killing activity) against one or more of K. pneumoniae, A. baumannii, E. coli, P. aeruginosa, or S. aureus. In other embodiments, the isolated polypeptides are fragments, variants or derivatives of endolysins or lysins isolated from bacteriophage of the invention that exhibit antibacterial or antimicrobial activity (e.g., lytic killing activity) against one or more species of bacteria other than K. pneumoniae, A. baumannii, E. coli, P. aeruginosa, or S. aureus. In certain embodiments, the polypeptide of the invention comprises or consists of the amino acid sequence SEQ ID NO: 20 and/or SEQ ID NO: 80, or a fragment, variant or derivative thereof, which polypeptide exhibits antibacterial or antimicrobial activity against one or more strains of K. pneumoniae, e.g., against the bacteriophage having a genome comprising or consisting of the nucleic acid sequence SEQ ID NO: 1. In other embodiments, the polypeptide of the invention comprises or consists of the amino acid sequence SEQ ID NO: 192, or a fragment, variant or derivative thereof, which polypeptide exhibits antibacterial or antimicrobial activity against one or more strains of A. baumannii, e.g., against the bacteriophage having a genome comprising or consisting of the nucleic acid sequence SEQ ID NO: 2. In yet still other embodiments, the polypeptide of the invention comprises or consists of the amino acid sequence SEQ ID NO: 282, or a fragment, variant or derivative thereof, which polypeptide exhibits antibacterial or antimicrobial activity against one or more strains of E. coli, e.g., against the bacteriophage having a genome comprising or consisting of the nucleic acid sequence SEQ ID NO: 3. In yet still other embodiments, the polypeptide of the invention comprises or consists of the amino acid sequence SEQ ID NO: 547, SEQ ID NO: 556, SEQ ID NO: 557, or a fragment, variant or derivative thereof, which polypeptide exhibits antibacterial or antimicrobial activity against one or more strains of P. aeruginosa, e.g., against the bacteriophage having a genome comprising or consisting of the nucleic acid sequence SEQ ID NO: 4. In yet still further embodiments, the polypeptide of the invention comprises or consists of the amino acid sequence SEQ ID NO: 598, or a fragment, variant or derivative thereof, which polypeptide exhibits antibacterial or antimicrobial activity against one or more strains of S. aureus, e.g., against the bacteriophage having a genome comprising or consisting of the nucleic acid sequence SEQ ID NO: 560. In yet still further embodiments, the polypeptide of the invention comprises or consists of the amino acid sequence SEQ ID NO: 1216 and/or SEQ ID NO: 1261, or a fragment, variant or derivative thereof, which polypeptide exhibits antibacterial or antimicrobial activity against one or more strains of S. aureus, e.g., against the bacteriophage having a genome comprising or consisting of the nucleic acid sequence SEQ ID NO: 1074.

In certain embodiments, the polypeptide of the invention comprises or consists of a CHAP domain isolated from an endolysin or lysin of bacteriophage F387/08, F391/08, F394/08, F488/08, F510/08, F44/10, or F125/10. Isolated CHAP domains have been demonstrated to retain the antibacterial activity, e.g., lytic killing activity, of the endolysin or lysin from which they are derived; CHAP domains may be identified and isolated by methods routine in the art (see, e.g., Rigden et al., 2003, Trends Biochem. Sci. 28:230-234; Bateman et al., 2003, Trends Biochem. Sci. 28:234-237, each of which is incorporated by reference herein in its entirety). In specific embodiments, the polypeptide of the invention comprises or consists of a CHAP domain isolated from a polypeptide having an amino acid sequence of SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, or SEQ ID NO: 1261. In other embodiments the invention provides for a fragment, variant or derivative of a CHAP domain of isolated from an endolysin or lysin of bacteriophage bacteriophage F387/08, F391/08, F394/08, F488/08, F510/08, F44/10, F125/10, which fragment, variant, or derivative exhibits at least one biological activity, e.g., lytic cell killing, of the CHAP domain from which it was derived.

In certain embodiments, a polypeptide of the invention comprises or consists of a tail protein (e.g., tail component, tail fiber protein, adsorption associated tail protein, tail length tape measure protein, baseplate wedge subunit), or fragment, variant, or derivative thereof, isolated from a bacteriophage having a genome comprising or consisting of SEQ ID NO: 1, SEQ ID NO: 2, SEQ ID NO: 3, SEQ ID NO:4, SEQ ID NO: 560, SEQ ID NO: 781, or SEQ ID NO: 1074 (e.g., bacteriophage F391/08, F394/08, F488/08, F510/08, F44/10, F387/08, or F125/10 respectively), wherein the tail protein, or fragment, variant, or derivative thereof has a biological function associated with the bacteriophage from which it is derived, e.g., antimicrobial or antibacterial activity (e.g., lytic killing activity). In specific embodiments, the antimicrobial or antibacterial activity of the tail protein is directed against at least one or more species or strains of K. pneumoniae, A. baumannii, E. coli, P. aeruginosa, and S. aureus. In specific embodiments, the polypeptide of the invention is a tail protein having the amino acid sequence comprising or consisting of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629; SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266. In other embodiments, the isolated polypeptide of the invention is a fragment, variant or derivative of the amino acid sequence of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629; SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266, which fragment, variant, or derivative exhibits at least one biological activity or function of the bacteriophage from which it is isolated or derived, e.g., antimicrobial or antibacterial activity (e.g., lytic killing activity). In preferred embodiments, the at least one biological activity or function of the fragment, variant or derivative is directed against one or more strains of *K. pneumoniae*, *A. baumannii*, *E. coli*, *P. aeruginosa*, and *S. aureus*.

Predicted functions of said tail proteins include, for example a receptor-binding tail protein (SEQ ID NO: 15), major tail protein (SEQ ID NO: 26), minor tail protein (SEQ ID NO: 27), pore-forming tail tip protein (SEQ ID NO: 30), tail protein (SEQ ID NOs: 32-33), minor tail protein (SEQ ID NO: 34), phage tail protein (SEQ ID NO: 35), tail sheath protein (SEQ ID NO: 180), tail tape measure protein (SEQ ID NO: 183), tail protein (SEQ ID NO: 185), tail-fiber protein (SEQ ID NO: 190), tail tube protein (SEQ ID NO: 231), tail sheath monomer (SEQ ID NO: 232), tail sheath stabilizer and completion protein (SEQ ID NO:235), short tail fibers (SEQ ID NO: 239), base plate wedge completion tail pin (SEQ ID NOs: 240-241), base plate wedge completion tail fiber socket (SEQ ID NO: 242), base plate wedge subunit (SEQ ID NO: 243), base plate wedge initiator (SEQ ID NO: 244), base plate wedge (SEQ ID NO: 245), base plate hub subunit and tail lysozyme, cell-puncturing device (SEQ ID NO: 248), base plate wedge completion (SEQ ID NO: 249), tail completion and sheath stabilizer protein (SEQ ID NO: 252), chaperone long and short tail fiber assembly (SEQ ID NO: 254), tail fiber protein (SEQ ID NO: 433), tail fiber protein (SEQ ID NO: 434), hinge connector long tail fiber (SEQ ID NO: 435), tail fiber hinge (SEQ ID NO: 436), proximal tail fiber subunit (SEQ ID NO: 437), base plate-tail tube initiator (SEQ ID NO: 489), base plate (SEQ ID NO: 490), baseplate hub subunit, tail length determinator (SEQ ID NO: 491), base plate distal hub subunit (SEQ ID NO: 492), base plate hub subunit (SEQ ID NO: 493), base plate hub assembly catalyst (SEQ ID NO: 494), baseplate hub subunit (SEQ ID NO: 495), baseplate wedge subunit (SEQ ID NO: 496), tail tubular protein (SEQ ID NOs: 544-545), tail fiber protein (SEQ ID NO: 549 and SEQ ID NO: 551), major tail sheath protein (SEQ ID NO: 629); major tail protein (SEQ ID NO: 686); tail tube protein (SEQ ID NO: 789); fibritin (SEQ ID NO: 796); short tail fibers (SEQ ID NO: 797); base plate wedge completion tail pin (SEQ ID NO: 798); base plate wedge subunit and tail pin (SEQ ID NO: 799); baseplate wedge tail fiber connector (SEQ ID NO: 800); baseplate hub subunit and lysozyme (SEQ ID NO: 806); lysozyme (SEQ ID NO: 854); holin (SEQ ID NO: 999); distal long tail fiber assembly catalyst (SEQ ID NO: 1000); L-shaped tail fiber protein (SEQ ID NO: 1001); hinge connector of long tail fiber distal connector (SEQ ID NO: 1002); hinge connector of long tail fiber proximal connector (SEQ ID NO: 1003); long tail fiber proximal subunit (SEQ ID NO: 1004); baseplate tail tube initiator (SEQ ID NO: 1053); baseplate tail tube cap (SEQ ID NO: 1054); baseplate hub subunit, tail length determinator (SEQ ID NO: 1055); baseplate distal hub subunit (SEQ ID NO: 1056); baseplate hub subunit (SEQ ID NOs: 1057 and 1059); baseplate hub assembly catalyst (SEQ ID NO: 1058); baseplate wedge subunit (SEQ ID NO: 1060); major tail protein (SEQ ID NO: 1077); holin (SEQ ID NO: 1217); major tail sheath protein (SEQ ID NO: 1250); and baseplate protein (SEQ ID NO: 1266).

In certain embodiments, the invention encompasses a variant, fragment or derivative of the amino acid sequence of SEQ ID NO: 15, SEQ ID NO: 26, SEQ ID NO: 27, SEQ ID NO: 30, or SEQ ID NOs: 32-35, which exhibits a biological function associated with the bacteriophage having a genome comprising or consisting of the nucleic acid sequence SEQ ID NO: 1, e.g., antimicrobial or antibacterial activity (e.g., lytic killing activity), which function is directed against one or more strains of *K. pneumoniae*. In certain embodiments, the invention encompasses a variant, fragment or derivative of the amino acid sequence of SEQ ID NO: 789, SEQ ID NOs: 796-800, SEQ ID NO: 806, SEQ ID NO: 854, SEQ ID NOs: 999-1004, or SEQ ID NOs: 1053-1060, which exhibits a biological function associated with the bacteriophage having a genome comprising or consisting of the nucleic acid sequence SEQ ID NO: 781, e.g., antimicrobial or antibacterial activity (e.g., lytic killing activity), which function is directed against one or more strains of *K. pneumoniae*. In other embodiments, the invention encompasses a variant, fragment or derivative of the amino acid sequence of SEQ ID NO: 180, SEQ ID NO: 183, SEQ ID NO: 185, or SEQ ID NO: 190, which exhibits a biological function associated with the bacteriophage having a genome comprising or consisting of the nucleic acid sequence SEQ ID NO: 2, e.g., antimicrobial or antibacterial activity (e.g., lytic killing activity), which function is directed against one or more strains of *A. baumannii*.

In certain embodiments, the invention encompasses a variant, fragment or derivative of the amino acid sequence of SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-495, or SEQ ID NO: 496, which exhibits a biological function associated with the bacteriophage having a genome comprising or consisting of the nucleic acid sequence SEQ ID NO: 3, e.g., antimicrobial or antibacterial activity (e.g., lytic killing activity), which function is directed against one or more strains of *E. coli*. In certain embodiments, the invention encompasses a variant, fragment or derivative of the amino acid sequence of SEQ ID NO: 544, SEQ ID NO: 545, SEQ ID NO: 549, or SEQ ID NO: 551, which exhibits a biological function associated with the bacteriophage having a genome comprising or consisting of the nucleic acid sequence SEQ ID NO: 4, e.g., antimicrobial or antibacterial activity (e.g., lytic killing activity), which function is directed against one or more strains of *P. aeruginosa*. In certain embodiments, the invention encompasses a variant, fragment or derivative of the amino acid sequence of SEQ ID NO: 629 or SEQ ID NO: 686, which exhibits a biological function associated with the bacteriophage having a genome comprising or consisting of the nucleic acid sequence SEQ ID NO: 560, e.g., antimicrobial or antibacterial activity (e.g., lytic killing activity), which function is directed against one or more strains of *S. aureus*. In certain embodiments, the invention encompasses a variant, fragment or derivative of the amino acid sequence of SEQ ID NO: 1077, SEQ ID NO: 1216, SEQ ID NO: 1217, SEQ ID NO: 1250, SEQ ID NO: 1261, or SEQ ID NO: 1266, which exhibits a biological function associated with the bacteriophage having a genome comprising or consisting of the nucleic acid sequence SEQ ID NO: 1074, e.g., antimicrobial or antibacterial activity (e.g., lytic killing activity), which function is directed against one or more strains of *S. aureus*.

In certain embodiments, the isolated polypeptide of the invention is a variant of a bacteriophage polypeptide, which variant comprises or consists of a amino acid sequence having at least 60%, 65%, 70%, 75%, 80%, 85%, 86%, 87%, 88%, 89%, 90%, 91%, 92%, 93%, 94%, 95%, 96%, 97%, 98%, 99%, or greater sequence identity to a second amino acid sequence of the same length (i.e., consisting of the same number of residues), which second amino acid sequence is SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, SEQ ID NO: 1266 and/or a fragment thereof, and wherein the variant exhibits at least one biological function or activity of the bacteriophage from which it was derived (e.g., antimicrobial or antibacterial activity (e.g., lytic killing activity)) against one or more strains of bacteria, e.g., Gram-positive bacteria (e.g., *S. aureus*), Gram-negative bacteria (e.g., *K. pneumoniae, A. baumannii, E. coli, P. aeruginosa*) or bacteria not classified as either Gram-positive or Gram-negative.

In certain embodiments, the invention provides an isolated polypeptide having an amino acid sequence of any of SEQ ID NOs: 5-176, SEQ ID NOs: 177-223, SEQ ID NOs: 224-506, SEQ ID NOs: 507-559, SEQ ID NOs: 561-780, SEQ ID NOs: 782-1073, and SEQ ID NOs: 1075-1300 and active biologic fragments thereof. In preferred embodiments, the variant polypeptide of the invention exhibits at least one biologic activity associated with the polypeptide or bacteriophage from which it was isolated or derived, e.g., lytic activity directed against at least one or more strains of *K. pneumoniae, A. baumannii, E. coli, P. aeruginosa*, and/or *S. aureus*.

In other embodiments, the invention provides an isolated nucleic acid sequence encoding the amino acid sequence of one of SEQ ID NOs: 5-176, SEQ ID NOs: 177-223, SEQ ID NOs: 224-506, SEQ ID NOs: 507-559, SEQ ID NOs: 561-780, SEQ ID NOs: 782-1073, and SEQ ID NOs: 1075-1300 and active fragments thereof. In other embodiments the invention provides the nucleic acid sequence encoding any of the open reading frames identified in FIGS. 2, 4, 6, 8, 10, 12, and/or 14.

In certain embodiments, the polypeptides of the present invention are recombinantly fused or chemically conjugated (including both covalently and non-covalently conjugations) to therapeutic agents, e.g., heterologous polypeptides or small molecules, to generate fusion proteins or chimeric polypeptides. The fusion does not necessarily need to be direct, but may occur through linker sequences or through chemical conjugation. Non-limiting examples of therapeutic agents to which the polypeptides of the invention may be conjugated are peptide or non-peptide cytotoxins (including antimicrobials and/or antibiotics), tracer/marker molecules (e.g., radionuclides and fluorphores) and other antibiotic or antibacterial compounds known in the art.

6.2 ANTIBIOTIC COMPOSITIONS

The isolated bacteriophage or polypeptides of the present invention may be administered alone or incorporated into a pharmaceutical composition for the use in treatment or prophylaxis of bacterial infections, e.g., infections caused by bacteria including, but not limited to, *K. pneumoniae, A. baumannii, E. coli, P. aeruginosa* and *S. aureus*. The polypeptides may be combined with a pharmaceutically acceptable carrier, excipient, or stabilizer. Examples of pharmaceutically acceptable carriers, excipients and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The pharmaceutical compositions of the present invention (e.g., antibacterial compositions) can also include a lubricant, a wetting agent, a sweetener, a flavoring agent, an emulsifier, a suspending agent, and a preservative, e.g., in addition to the above ingredients.

The bacteriophage and/or polypeptides of the present invention may also be combined with one or more therapeutic and/or prophylactic agents useful for the treatment of bacterial infection as described herein and/or known in the art (e.g. one or more lysins). The pharmaceutical compositions of the invention may therefore comprise two or more isolated bacteriophage of the invention (with antibacterial activity against the same or different bacterial species or strains), the combination of a bacteriophage and a polypeptide of the invention or the combination of a bacteriophage and/or polypeptide of the invention and a bacteriophage and/or polypeptide known in the art. In specific embodiments, the therapeutic components of a combination target two or more species or strains of bacteria or exhibit differing enzymatic activity. For example, lysins in general exhibit one of amidase, endopeptidase, muramidase or glucosamidase activity. Accordingly, the combination of lysins exhibiting different activities may provide synergistic enhancement to the therapeutic activity of the pharmaceutical composition of the invention.

In some embodiments, a number of different bacteriophage are combined to provide a "phage cocktail." In some embodiments, the phage cocktail comprises at least 2 phage, at least 3 phage, at least 4 phage, at least 5 phage, at least 6 phage, at least 7 phage, at least 8 phage, at least 9 phage, at least 10 phage, or more. In some embodiments, the phage cocktail comprises 2-20 phage, 2-15 phage, 2-10 phage, 3-8 phage, or 4-6 phage.

In some embodiments, at least one phage of the cocktail is a phage with antibacterial activity against at least one Gram-negative bacteria, including but not limited to *Klebsiella pneumoniae, Acinetobacter baumannii, Escherichia coli*, and *Pseudomonas aeruginosa*; and/or against at least one Gram-positive bacteria including but not limited to *Staphylococcus aureus*. In certain embodiments, at least one phage of the cocktail is F391/08, having a genome comprising the nucleic acid sequence of SEQ ID NO:1 and exhibiting antibacterial activity against one or more strains of *Klebsiella pneumoniae*. In certain embodiments, at least one phage of the cocktail is F394/08, having a genome comprising the nucleic acid sequence of SEQ ID NO:2 and exhibiting antibacterial activity against one or more strains of *Acinetobacter baumannii*. In certain embodiments, at least one phage of the cocktail is F488/08, having a genome comprising the nucleic acid sequence of SEQ ID NO:3 and exhibiting antibacterial activity against one or more strains of *Escherichia coli*. In certain embodiments, at least one phage of the cocktail is F510/08, having a genome comprising the nucleic acid sequence of SEQ ID NO:4 and exhibiting antibacterial activity against one or more strains of *Pseudomonas aeruginosa*. In certain embodiments, at least one phage of the cocktail is F44/10, having a genome comprising the nucleic acid sequence of SEQ ID NO:560 and exhibiting antibacterial activity against one or more strains of *Staphylococcus aureus*. In certain embodiments, at least one phage of the cocktail is F387/08, having a genome comprising the nucleic acid sequence of SEQ ID NO:781 and exhibiting antibacterial activity against one or more strains of *Klebsiella pneumoniae*. In certain embodiments, at least one phage of the cocktail is F125/10, having a genome comprising the nucleic acid sequence of SEQ ID NO:1074 and exhibiting antibacterial activity against one or more strains of *Staphylococcus aureus*.

In certain embodiments, at least one phage of the cocktail is F170/08, having a genome as disclosed in WO 2010/090542, and exhibiting antibacterial activity against one or more strains of *Enterococcus faecalis* or *faecium*. In certain embodiments, at least one phage of the cocktail is F168/08, having a genome as disclosed in WO 2010/090542, and exhibiting antibacterial activity against one or more strains of *Enterococcus faecalis* or *faecium*. In certain embodiments, at least one phage of the cocktail is F770/05, having a genome as disclosed in WO 2010/090542, and exhibiting antibacterial activity against one or more strains of *Pseudomonas aeruginosa*. In certain embodiments, at least one phage of the cocktail is F1245/05, having a genome as disclosed in WO 2010/090542, and exhibiting antibacterial activity against one or more strains of *Acinetobacter baumannii*.

In some preferred embodiments, the cocktail comprises a phage having biological activity against *Acinetobacter*. For example, the cocktail may comprise F394/08 and/or F1245/05, exhibiting antibacterial activity against one or more strains of *Acinetobacter baumannii*. In certain embodiments, the phage cocktail comprises at least one phage exhibiting antibacterial activity against one or more strains of *Acinetobacter baumannii* and at least one phage exhibiting antibacterial activity against a different bacteria. For example, in some embodiments, the phage cocktail comprises F394/08 and/or F1245/05 in combination with at least one other phage selected from F391/08, F488/08, F510/08, F44/10, F387/08, F170/08, F168/08, F770/05, and F125/10. In certain embodiments, the phage cocktail comprises at least one phage exhibiting antibacterial activity against one or more strains *Klebsiella pneumoniae* and at least one phage exhibiting antibacterial activity against a different bacteria. For example, in some embodiments, the phage cocktail comprises F391/08 and/or F387/08 in combination with at least one other phage selected from F394/08, F488/08, F510/08, F44/10, F1245/05, F170/08, F168/08, F770/05, and F125/10. In certain embodiments, the phage cocktail comprises at least one phage exhibiting antibacterial activity against one or more strains of *Escherichia coli* and at least one phage exhibiting antibacterial activity against a different bacteria. For example, in some embodiments, the phage cocktail comprises F488/08 in combination with at least one other phage selected from F391/08, F510/08, F44/10, F394/08, F387/08, F170/08, F168/08, F1245/05, F770/05, and F125/10.

In certain embodiments, the phage cocktail comprises at least one phage exhibiting antibacterial activity against one or more strains of *Pseudomonas aeruginosa* and at least one phage exhibiting antibacterial activity against a different bacteria. For example, in some embodiments, the phage cocktail comprises F510/08 and/or F770/05 in combination with at least one other phage selected from F391/08, F394/08, F488/08, F44/10, F387/08, F170/08, F168/08, F1245/05, and F125/10. In certain embodiments, the phage cocktail comprises at least one phage exhibiting antibacterial activity against one or more strains of *Staphylococcus aureus* and at least one phage exhibiting antibacterial activity against a different bacteria. For example, in some embodiments, the phage cocktail comprises F44/10 and/or F125/10 in combination with at least one other phage selected from F391/08, F394/08, F488/08, F510/08, F387/08, F170/08, F168/08, F770/05, and F1245/05. In certain embodiments, the phage cocktail comprises at least one phage exhibiting antibacterial activity against one or more strains of *Enterococcus faecalis* or *faecium* and at least one phage exhibiting antibacterial activity against a different bacteria. For example, in some embodiments, the phage cocktail comprises F170/08 and/or F168/08 in combination with at least one other phage selected from F391/08, F394/08, F488/08, F510/08, F44/10, F387/08, F770/05, F1245/05, and F125/10.

In certain embodiments, the phage cocktail comprises at least four (4) phage selected from the group consisting of F391/08, F394/08, F488/08, F510/08, F44/10, F387/08, F170/08, F168/08, F770/05, F1245/05, and F125/10. In certain embodiments, the phage cocktail comprises F391/08, F394/08, F488/08, and F510/08. In certain embodiments, the phage cocktail comprises F44/10, F387/08, F170/08, and F168/08. In certain embodiments, the phage cocktail comprises of F391/08, F394/08, F770/05, and F1245/05. In certain embodiments, the phage cocktail comprises F391/08, F394/08, F510/08, and/or F44/10. In certain embodiments, the phage cocktail comprises F391/08, F394/08, F44/10, and/or F387/08. In certain embodiments, the phage cocktail comprises F391/08, F394/08, F387/08, and/or F170/08. In certain embodiments, the phage cocktail comprises F391/08, F394/08, F170/08, and F168/08. In certain embodiments, the phage cocktail comprises F391/08, F394/08, F168/08, and/or F770/05. In certain embodiments, the phage cocktail comprises F391/08, F394/08, F770/05, and F1245/05.

In certain embodiments, the phage cocktail comprises F125/10, F391/08, F394/08, and F488/08. In certain embodiments, the phage cocktail comprises F125/10, F394/08, F488/08, and F510/08. In certain embodiments, the phage cocktail comprises F125/10, F488/08, F510/08, and F44/10. In certain embodiments, the phage cocktail comprises F125/10, F44/10, F387/08, and F170/08. In certain embodiments, the phage cocktail comprises F125/10, F170/08, F168/08, and F770/05. In certain embodiments, the phage cocktail comprises F125/10, F770/05, F1245/05, and F391/08. In certain embodiments, the phage cocktail comprises F125/10, F510/08, F44/10, F387/08. In certain embodiments, the phage cocktail comprises F125/10, F387/08, F170/08, F168/08. In certain embodiments, the phage cocktail comprises F125/10, F168/08, F770/05, and F1245/05. In certain embodiments, the phage cocktail comprises F125/10, F1245/05, F391/08, and F394/08.

In certain embodiments, the phage cocktail comprises F394/08, F488/088, F510/08, and/or F44/10. In certain embodiments, the phage cocktail comprises F394/08, F488/088, F44/10, and/or F387/08. In certain embodiments, the phage cocktail comprises F394/08, F488/088, F387/08, and/or F170/08. In certain embodiments, the phage cocktail comprises F394/08, F488/088, F170/08, and/or F168/08. In certain embodiments, the phage cocktail comprises F394/08, F488/088, F168/08 and/or F770/05. In certain embodiments, the phage cocktail comprises F394/08, F488/088, FF770/05, and/or F1245/05. In certain embodiments, the phage cocktail comprises F394/08, F488/088, F1245/05 and/or F391/08. In certain embodiments, the phage cocktail comprises F488/08, F510/08, F44/10, and/or F387/08. In certain embodiments, the phage cocktail comprises F488/08, F510/08, F387/08, and/or F170/08. In certain embodiments, the phage cocktail comprises F488/08, F510/08, F170/08, and/or F168/08. In certain embodiments, the phage cocktail comprises F488/08, F510/08, F168/08, and/or F770/05. In certain embodiments, the phage cocktail comprises F488/08, F510/08, F770/05, and/or F1245/05. In certain embodiments, the phage cocktail comprises F488/08, F510/08, F1245/05, and/or F391/08. In certain embodiments, the phage cocktail comprises F488/08, F510/08, F391/08, and/or F394/08.

In certain embodiments, the phage cocktail comprises F387/08, F170/08, F168/08, and/or F770/05. In certain embodiments, the phage cocktail comprises F387/08, F170/08, F770/05, and/or F1245/05. In certain embodiments, the phage cocktail comprises F387/08, F170/08, F1245/05, and/or F391/08. In certain embodiments, the phage cocktail comprises F387/08, F170/08, F391/08, and/or F394/08. In certain embodiments, the phage cocktail comprises F387/08, F170/08, F394/08, and/or F488/08. In certain embodiments, the phage cocktail comprises F387/08, F170/08, F488/08, and/or F510/08. In certain embodiments, the phage cocktail comprises F387/08, F170/08, F510/08, and/or F44/10. In certain embodiments, the phage cocktail comprises F387/08, F170/08, F44/10, and/or F387/08. In certain embodiments, the phage cocktail comprises F387/08, F170/08, F387/08, and/or F170/08. In certain embodiments, the phage cocktail comprises F387/08, F170/08, F170/08, and/or F168/08. In certain embodiments, the phage cocktail comprises F387/08, F170/08, F168/08, and/or F770/05. In certain embodiments, the phage cocktail comprises F387/08, F170/08, F770/05 and/or F1245/05. In certain embodiments, the phage cocktail comprises F387/08, F170/08, F1245/05, and/or F391/08. In certain embodiments, the phage cocktail comprises F387/08, F170/08, F391/08, and/or F394/08. In certain embodiments, the phage cocktail comprises F387/08, F170/08, F394/08 and/or F488/08. In certain embodiments, the phage cocktail comprises F387/08, F170/08, F488/08, and/or F510/08. In certain embodiments, the phage cocktail comprises F387/08, F170/08, F510/08, and/or F44/10.

In some embodiments, the phage cocktail comprises of F510/08, F44/10, F387/08, and/or F170/08. In some embodiments, the phage cocktail comprises F510/08, F44/10, F170/08, and/or F168/08. In some embodiments, the phage cocktail comprises F510/08, F44/10, F168/08, and/or F770/05. In some embodiments, the phage cocktail comprises F510/08, F44/10, F770/05, and/or F1245/05. In some embodiments, the phage cocktail comprises F510/08, F44/10, F1245/05, and/or F391/08. In some embodiments, the phage cocktail comprises F510/08, F44/10, F391/08, and/or F394/08. In some embodiments, the phage cocktail comprises F510/08, F44/10, F394/08, and/or F488/08.

In some embodiments, the phage comprises F44/10, F387/08, F170/08, and/or F168/08. In some embodiments, the phage comprises F44/10, F387/08, F168/08 and/or F770/05. In some embodiments, the phage comprises F44/10, F387/08, F770/05, and/or F1245/05. In some embodiments, the phage comprises F44/10, F387/08, F1245/05, and/or F391/08. In some embodiments, the phage comprises F44/10, F387/08, F391/08, and/or F394/08. In some embodiments, the phage comprises F44/10, F387/08, F394/08 and/or F488/08. In some embodiments, the phage comprises F44/10, F387/08, F488/08 and/or F510/08.

In some embodiments, the phage cocktail composition may or may not involve phage selected for increased in vivo half-life, e.g., as disclosed in U.S. Pat. No. 5,688,501, the contents of which are incorporated herein by reference.

In some embodiments, the cocktail comprises one or more polypeptides isolated from one or more phage, and/or a fragment, variant, or derivative thereof, in particular a polypeptide, fragment, variant, or derivative thereof which has antibacterial or antimicrobial activity. In some embodiments, the polypeptide, or fragment, variant, or derivative thereof comprises or consists of a lysin (or fragment thereof, e.g., a CHAP domain) and/or a tail protein. In more specific embodiments, the polypeptide corresponds to an isolated polypeptide, fragment, variant, or derivative thereof, as described herein and/or in WO 2010/090542, the contents of which are incorporated by reference herein. In some embodiments, the cocktail is administered in the absence of an isolated polypeptide, such as in the absence of a lyase.

Other examples of other therapeutic agents that may be used in combination with the polypeptide of the invention include, but are not limited to, standard antibiotic agents, anti-inflammatory agents, antiviral agents, local anesthetic agents, and corticosteroids. In some embodiments, the cocktail is administered in the absence of an antibiotic.

Standard antibiotics that may be used with pharmaceutical compositions comprising a bacteriophage and/or polypeptide of the invention include, but are not limited to, amikacin, gentamicin, kanamycin, neomycin, netilmicin, paromomycin, rhodostreptomycin, streptomycin, tobramycin, apramycin, rifamycin, naphthomycin, mupirocin, geldanamycin, ansamitocin, carbacephems, imipenem, meropenem, ertapenem, faropenem, doripenem, panipenem/betamipron, biapenem, PZ-601, cephalosporins, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, cefcapene, cefdaloxime, cefdinir, cefditoren, cefetamet, cefixime, cefmenoxime, cefteram, ceftibuten, ceftiofur, ceftiolene, ceftizoxime, ceftriaxone, cefoperazone, ceftazidime latamoxef, cefclidine, cefepime, cefluprenam, cefoselis, cefozopran, cefpirome, cefquinome, flomoxef, ceftobiprole, azithromycin, clarithromycin, dirithromycin, erythromycin, roxithromycin, aztreonam, penicillin and penicillin derivatives, actinomycin, bacitracin, colistin, polymyxin B, cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, garenoxacin, gemifloxacin, stifloxacin, trovalfloxacin, prulifloxacin, acetazolamide, benzolamide, bumetanide, celecoxib, chlorthalidone, clopamide, dichlorphenamide, dorzolamide, ethoxyzolamide, furosemide, hydrochlorothiazide, indapamide, mafendide, mefruside, metolazone, probenecid, sulfacetamide, sulfadimethoxine, sulfadoxine, sulfanilamides, sulfamethoxazole, sulfasalazine, sultiame, sumatriptan, xipamide, tetracycline, chlortetracycline, oxytetracycline, doxycycline, lymecycline, meclocycline, methacycline, minocycline, rolitetracycline, methicillin, nafcillin, oxacilin, cloxacillin, vancomycin, teicoplanin, clindamycin, co-trimoxazole, and any combination thereof in amounts that are effective to additively or synergistically enhance the therapeutic effect of the bacteriophage and/or polypeptide of the invention for a given infection.

Local anesthetics that may be used in pharmaceutical compositions of the present invention include tetracaine, tetracaine hydrochloride, lidocain, lidocaine hydrochloride, dimethisoquin hydrochloride, dibucaine, dibucaine hydrochloride, butambenpicrate, and pramoxine hydrochloride. An exemplary concentration of local anesthetic is about 0.025% to about 5% by weight of the total composition.

Corticosteroids that may be useful in combination with the polypeptides, bacteriophage, and/or pharmaceutical compositions of the invention include betamethasone, dipropionate, fluocinolone, actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide. An exemplary concentration of corticosteroid is about 0.01% to about 1% by weight of the total composition.

In certain embodiments, a formulation comprising a bacteriophage and/or polypeptide of the invention further comprises SM buffer (0.05 M Tris-HCl (pH 7.4-7.5); 0.1 M NaCl; 10 mM $MgSO_4$). In other embodiments, the formulation further comprises SM buffer and 10 mM $MgCl_2$. In still other embodiments, the formulation further comprises SM buffer and about 20% or about 30% ethanol.

Pharmaceutical compositions comprising a bacteriophage and/or polypeptide of the present invention can be formulated in a unit dose or multi-dose formulation. Suitable formulations can be selected from the group consisting of ointments, solutions, suspensions or emulsions, extracts, powders, granules, sprays, lozenges, tablets, or capsules; and additionally may include a dispersing agent or a stabilizing agent.

The pharmaceutical compositions of the invention can be administered by inhalation, in the form of a suppository or pessary, topically (e.g., in the form of a lotion, solution, cream, ointment or dusting powder), epi- or transdermally (e.g., by use of a skin patch), orally (e.g., as a tablet, which may contain excipients such as starch or lactose), as a capsule, ovule, elixirs, solutions, or suspensions (each optionally containing flavoring, coloring agents and/or excipients), or they can be injected parenterally (e.g., intravenously, intramuscularly or subcutaneously). For parenteral administration, the compositions may be used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner. In a preferred embodiment, a bacteriophage and/or polypeptide of the present invention is administered topically, either as a single agent, or in combination with other antibiotic treatments, as described herein or known in the art.

A bacteriophage and/or polypeptide of the present invention may also be dermally or transdermally administered. For topical application to the skin, the bacteriophage and/or polypeptides of the present invention may be combined with one or a combination of carriers, which can include but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose carmel, and combinations thereof. A topical mode of delivery may include a smear, a spray, a bandage, a time-release patch, a liquid-absorbed wipe, and combinations thereof. The bacteriophage and/or polypeptide of the invention may be applied to a patch, wipe, bandage, etc., either directly or in a carrier(s).

The patches, wipes, bandages, etc., may be damp or dry, wherein the phage and/or polypeptide (e.g., a lysin) is in a lyophilized form on the patch. The carriers of topical compositions may comprise semi-solid and gel-like vehicles that include a polymer thickener, water, preservatives, active surfactants, or emulsifiers, antioxidants, sun screens, and a solvent or mixed solvent system. U.S. Pat. No. 5,863,560 discloses a number of different carrier combinations that can aid in the exposure of skin to a medicament, and its contents are incorporated herein. The carrier may or may not involve a controlled-release formulation, e.g., as disclosed in US 2008/0260697, the contents of which are incorporated herein by reference. The carrier may or may not involve phage adsorbed on a matrix, e.g., as described in any one of US 2008/0038322, US 2008/0138311, US 2009/0130196, EP 1 812 025, EP 1 817 043, and EP 1 833 497, the contents of which are incorporated herein by reference. In some embodiments, the carrier may or may not involve a viscous formulation, e.g., a gel, e.g., as disclosed in US 2009/0191254, the contents of which are incorporated herein by reference.

For intranasal or administration by inhalation, the bacteriophage and/or polypeptide of the invention is conveniently delivered in the form of a dry powder inhaler or an aerosol spray presentation from a pressurized container, pump, spray, or nebuliser with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide, or other suitable gas. In the case of a pressurized aerosol, the dosage unit may be determined by providing a valve to deliver a metered amount. The pressurized container, pump, spray, or nebuliser may contain a solution or suspension of the active compound, e.g., using a mixture of ethanol and the propellant as the solvent, which may additionally contain a lubricant, e.g., sorbitan trioleate. Capsules and cartridges (made, for example, from gelatin) for use in an inhaler or insufflator may be formulated to contain a powder mix of the bacteriophage and/or polypeptide of the invention and a suitable powder base such as lactose or starch.

For administration in the form of a suppository or pessary, the therapeutic compositions may be applied topically in the form of a gel, hydrogel, lotion, solution, cream, ointment, or dusting powder. Compositions of the invention may also be administered by the ocular route. For ophthalmic use, the compositions of the invention can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

Dosages and desired drug concentrations of the pharmaceutical compositions of the present invention may vary depending on the particular use. The determination of the appropriate dosage or route of administration is within the skill of an ordinary physician. Animal experiments can provide reliable guidance for the determination of effective doses in human therapy. Interspecies scaling of effective doses can be performed by one of ordinary skill in the art following the principles described by Mordenti, J. and Chappell, W. "The use of interspecies scaling in toxicokinetics" in Toxicokinetics and New Drug Development, Yacobi et al., Eds., Pergamon Press, New York 1989, pp 42-96.

6.3 THERAPEUTIC USE

The bacteriophage and polypeptides of the present invention have activity against a plurality of strains of K. pneumoniae, A. baumannii, E. coli, P. aeruginosa, and/or S. aureus, e.g., as described in Tables 1-7, in the Examples below. Therefore, the compositions of the present invention may find use in methods of preventing and/or treating infections associated with K. pneumoniae, A. baumannii, E. coli, P. aeruginosa, and/or S. aureus in both humans and animals. In other embodiments, the compositions of the present invention may be used to treat infection associated with related species or strains of these bacteria, including, but not limited to S. epidermidis, S. auricularis, S. capitis, S. haemolyticus, S. hominis, S. saprophyticus, S. simulans, S. xylosis, Micrococcus luteus, Bacilus subtilis, B. pumilus, E. hirae.

In specific embodiments, the subject receiving a pharmaceutical composition of the invention is a mammal (e.g., bovine, ovine, caprine, equid, primate (e.g., human), rodent, lagomorph or avian (e.g., chicken, duck, goose)). In the context of the present invention, "treatment" refers to therapeutic treatment, wherein the object is to eliminate, lessen, decrease the severity of, ameliorate, slow the progression of or prevent the symptoms or underlying cause (e.g., bacterial infection) associated with the pathological condition or disorder. "Treatment" refers to both therapeutic treatment and prophylactic or preventative measures, wherein the object is to eliminate, lessen, decrease the severity of, slow the progression of or delay or prevent the symptoms or underlying cause (e.g., bacterial infection) associated with the pathological condition or disorder. It is also contemplated that a bacteriophage and/or polypeptide of the invention acts as a prophylactic or preventative measure, preventing the onset of infection caused by one or more bacteria.

K. pneumoniae, A. baumannii, E. coli, P. aeruginosa, and S. aureus are responsible for many severe opportunistic infections, particularly in individuals with compromised immune systems. The pharmaceutical compositions of the present invention are contemplated for treating any infection associated with K. pneumoniae, A. baumannii, E. coli, P. aeruginosa, and/or S. aureus, or associated with other species or strains of bacteria, including, but not limited to, infections of the skin (including but not limited to skin ulcers, carbuncles, bed sores, and diabetic foot ulcers), infections in and around wounds, post-operative infections, infections associated with catheters and surgical drains, and infections of the blood.

Diabetic foot ulcer is one of the major complications of diabetes mellitus, occurring in about 15% of all diabetic patients and resulting in about 85% of all lower leg amputations. (Brem, et al., J. Clinical Invest., 2007, 117(5):1219-1222). Diabetes mellitus impedes the normal steps of the wound healing process. Non-healing chronic diabetic ulcers are often treated with extracellular matrix replacement therapy, advanced moist wound therapy, bio-engineered tissue or skin substitutes, growth factors, debridement, arterial revascularization, and/or negative pressure wound therapy. (Blume et. al, Diabetes Care, 2008, 31: 631-636). The ulcers may become infected with opportunistic bacteria, which further exacerbate the condition. Accordingly, foot ulcers in diabetes also often require antibiotics, e.g., against Staphylococcus, as well as other anaerobic bacteria, such as Klebsiella pneumonia, Escherichia coli, and/or Pseudomonas aeruginosa.

One or more compositions of the present invention find use in the treatment of diabetic foot ulcer. For example, an isolated phage or polypeptide of the invention can be used for the treatment of infections associated with diabetic foot ulcer, in a subject in need thereof. In particular embodiments, the composition used for treating diabetic foot ulcer is a topical composition, formulated for topical administration, e.g., a composition for direct application to an ulcer, wound, lesion, and/or sore associated with diabetic foot ulcer.

In certain embodiments, the composition for use with respect to diabetic foot ulcer comprises isolated F44/10, having a genome comprising the nucleic acid sequence of SEQ ID NO:560 and exhibiting antibacterial activity against one or more strains of Staphylococcus aureus. In some embodiments, a composition is used comprising a polypeptide isolated from bacteriophage F44/10, or a fragment, variant, or derivative thereof, which polypeptide, fragment, variant, or derivative exhibits antibacterial activity against one or more species or strains of S. aureus. In certain such embodiments, the polypeptide, or fragment, variant, or derivative thereof, is a lysin, a CHAP domain, or a tail protein, exhibiting antibacterial activity against one or more species or strains of S. aureus. In certain embodiments, the composition for use with respect to diabetic foot ulcer comprises isolated F125/10, having a genome comprising the nucleic acid sequence of SEQ ID NO:1074 and exhibiting antibacterial activity against one or more strains of Staphylococcus aureus. In some embodiments, a composition is used comprising a polypeptide isolated from bacteriophage F125/10, or a fragment, variant, or derivative thereof, which polypeptide, fragment, variant, or derivative exhibits antibacterial activity against one or more species or strains of S. aureus. In certain such embodiments, the polypeptide, or fragment, variant, or derivative thereof, is a lysin, a CHAP domain, or a tail protein, exhibiting antibacterial activity against one or more species or strains of S. aureus.

In certain embodiments, a composition comprising a phage cocktail is used, e.g., where the phage cocktail comprises at least one phage exhibiting antibacterial activity against one or more strains of Staphylococcus aureus and at least one phage exhibiting antibacterial activity against a different bacteria. In particular embodiments, the phage cocktail comprises F44/10 and/or F125/10 in combination with at least one other phage selected from F391/08, F394/08, F488/08, F510/08, F387/08, F170/08, F168/08, F770/05, and F1245/05. In particularly preferred embodiments, the phage cocktail comprises F44/10 and/or F125/10 in combination with one, two, three or more other phages selected from F391/08, F387/08, F488/08, F510/08 and/or F770/05.

In certain embodiments, the composition for use with respect to diabetic foot ulcer comprises isolated F391/08 and/or F387/08, having a genome comprising the nucleic acid sequence of SEQ ID NO:1 or SEQ ID NO: 781, respectively, and exhibiting antibacterial activity against one or more strains of Klebsiella pneumoniae. In some embodiments, a composition is used comprising a polypeptide isolated from bacteriophage F391/08 and/or F387/08, or a fragment, variant, or derivative thereof, which polypeptide, fragment, variant, or derivative exhibits antibacterial activity against one or more species or strains of K. pneumoniae. In certain such embodiments, the polypeptide, or fragment, variant, or derivative thereof, is a lysin, a CHAP domain, or a tail protein, exhibiting antibacterial activity against one or more species or strains of K. pneumoniae. In certain embodiments, a composition comprising a phage cocktail is used, e.g., where the phage cocktail comprises at least one phage exhibiting antibacterial activity against one or more strains of Klebsiella pneumoniae and at least one phage exhibiting antibacterial activity against a different bacteria. In particular embodiments, the phage cocktail comprises F391/08 and/or F387/08 in combination with at least one other phage selected from F394/08, F488/08, F510/08, F44/10, F170/08, F168/08, F770/05, F1245/05, and F125/10. In particularly preferred embodiments, the phage cocktail comprises F391/08 and/or F387/08 in combination with one, two, three or more other phages selected from F44/10, F488/08, F510/08 and/or F770/05.

In certain embodiments, the composition for use with respect to diabetic foot ulcer comprises isolated F488/08, having a genome comprising the nucleic acid sequence of SEQ ID NO:3 and exhibiting antibacterial activity against one or more strains of *Escherichia coli*. In some embodiments, a composition is used comprising a polypeptide isolated from bacteriophage F488/08, or a fragment, variant, or derivative thereof, which polypeptide, fragment, variant, or derivative exhibits antibacterial activity against one or more species or strains of *E. coli*. In certain such embodiments, the polypeptide, or fragment, variant, or derivative thereof, is a lysin, a CHAP domain, or a tail protein, exhibiting antibacterial activity against one or more species or strains of *Escherichia coli*. In certain embodiments, a composition comprising a phage cocktail is used, e.g., where the phage cocktail comprises at least one phage exhibiting antibacterial activity against one or more strains of *Escherichia coli* and at least one phage exhibiting antibacterial activity against a different bacteria. In particular embodiments, the phage cocktail comprises F488/08 in combination with at least one other phage selected from F394/08, F510/08, F44/10, F170/08, F168/08, F770/05, F1245/05, F391/08 F387/08, and F125/10. In particularly preferred embodiments, the phage cocktail comprises F488/08 in combination with one, two, three or more other phages selected from F391/08, F387/08, F44/10, F125/10, F510/08 and/or F770/05.

In certain embodiments, the composition for use with respect to diabetic foot ulcer comprises isolated F510/08 and/or F770/05, having a genome comprising the nucleic acid sequence of SEQ ID NO:4 or as disclosed in WO 2010/090542, respectively, and exhibiting antibacterial activity against one or more strains of *Pseudomonas aeruginosa*. In some embodiments, a composition is used comprising a polypeptide isolated from bacteriophage F510/08 and/or F770/05, or a fragment, variant, or derivative thereof, which polypeptide, fragment, variant, or derivative exhibits antibacterial activity against one or more species or strains of *P. aeruginosa*. In certain such embodiments, the polypeptide, or fragment, variant, or derivative thereof, is a lysin, a CHAP domain, or a tail protein, exhibiting antibacterial activity against one or more species or strains of *Pseudomonas aeruginosa*. In certain embodiments, a composition comprising a phage cocktail is used, e.g., where the phage cocktail comprises at least one phage exhibiting antibacterial activity against one or more strains of *Pseudomonas aeruginosa* and at least one phage exhibiting antibacterial activity against a different bacteria. In particular embodiments, the phage cocktail comprises F510/08 and/or F770/05 in combination with at least one other phage selected from F394/08, F488/08, F44/10, F170/08, F168/08, F1245/05, F391/08, F387/08, and F125/10. In particularly preferred embodiments, the phage cocktail comprises F510/08 and/or F770/05 in combination with one, two, three or more other phages selected from F44/10, F488/08, F391/08, and/or F387/08.

*K. pneumoniae, A. baumannii, E. coli, P. aeruginosa*, and *S. aureus* are also associated with infections that involve organ systems that have a high fluid content, and it is contemplated that the bacteriophage and/or polypeptides of the invention have therapeutic use in the prevention and treatment of these infections. For example, the pharmaceutical compositions of the invention may be used for the prevention or treatment of infections of the respiratory tract, of the cerebrospinal fluid, of peritoneal fluid, and of the urinary tract. The compositions of the invention may also be used to prevent and/or treat nosocomial pneumonia, infections associated with continuous ambulatory peritoneal dialysis (CAPD), catheter-associated bacterimia, and nosocomial meningitis.

In a preferred embodiment, a bacteriophage and/or polypeptide of the invention is used prophylactically in hospital setting, particularly to prevent infections associated with wounds, ulcers, and openings in the skin, e.g., due to catheterization and any other medical procedures or devices.

In certain embodiments, a bacteriophage and/or polypeptide of the invention is used as a single agent for treating or preventing infections associated with *K. pneumoniae, A. baumannii, E. coli, P. aeruginosa*, and/or *S. aureus*, and/or other bacterial species. In other embodiments of the invention, a bacteriophage and/or polypeptide of the invention is used in combination with other agents, including other bacteriophage (for example, that target a different species or strain of bacteria), or with antibiotics that target the same or different kinds of bacteria, including bacteria selected from any gram-positive bacteria, any gram-negative bacteria, and any other groups of bacteria that is not classified as gram-positive or gram-negative. The compositions of the invention may also be used in combination with any other means of treating bacterial infection known to one of skill in the art.

Also contemplated by the invention are methods of preventing and methods of treating an infection caused by bacteria including, but not limited to, *K. pneumoniae, A. baumannii, E. coli, P. aeruginosa*, and/or *S. aureus* comprising administering to a mammal in need thereof a composition comprising a lysin comprising or consisting of the amino acid sequence of SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, SEQ ID NO: 1261, or a fragment, variant, or derivative thereof, wherein the fragment, variant, or derivative exhibits antibacterial or antimicrobial activity against the species of bacteria from which the parent bacteriophage was isolated. In a specific example in accordance with this embodiment, the invention provides methods of preventing or treating an infection caused by a bacteria including, but not limited to, *K. pneumoniae, A. baumannii, E. coli, P. aeruginosa*, and/or *S. aureus*, comprising administering to a mammal in need thereof a composition comprising an isolated CHAP domain of a lysin, or a fragment, variant, or derivative thereof that exhibits at least one biologic activity of the CHAP domain from which it was isolated (e.g., lytic cell killing).

In certain embodiments, the invention provides methods of preventing and/or treating an infection caused by bacteria including, but not limited to, *K. pneumoniae, A. baumannii, E. coli, P. aeruginosa*, and/or *S. aureus*, comprising administering to a mammal in need thereof a composition comprising a tail protein comprising or consisting of the amino acid sequence of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, or SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, SEQ ID NO: 1266, or a fragment, variant, or derivative thereof, wherein the fragment, variant, or derivative exhibits a biologic activity associated with the bacteriophage from with it was derived.

In still other embodiments, the invention provides methods of preventing and/or treating an infection caused by bacteria including, but not limited to, K. pneumoniae, A. baumannii, E. coli, P. aeruginosa, and/or S. aureus, comprising administering to a mammal in need thereof a composition comprising bacteriophage having a genome comprising or consisting of the nucleic acid sequence of SEQ ID NO: 1, SEQ ID NO: 2, SEQ ID NO: 3, SEQ ID NO: 4, SEQ ID NO: 560, SEQ ID NO: 781, and/or SEQ ID NO: 1074. Combinations of the lysins (or fragments, variants, or derivatives thereof as described above) and tail proteins (or fragments, variants, or derivatives thereof as described above), optionally with one or more bacteriophage of the invention or with other treatments, such as antibiotics, are also contemplated, as well as methods of treating and/or methods of preventing a bacterial infection using one or more of the combinations herein described.

As used herein, the term "in combination" refers to the use of more than one prophylactic and/or therapeutic agent. The use of the term "in combination" does not restrict the order in which prophylactic and/or therapeutic agents are administered to a subject with a disease or disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject with a disease or disorder.

6.4 DISINFECTANT AND ANTI-INFECTIVE USE

Bacterial pathogens most often infect at a mucous membrane site (e.g., upper and lower respiratory, intestinal, urogenital, ocular, and the like). The mucous membranes themselves are often the reservoir, sometimes the only reservoir, for many pathogenic bacteria found in the environment (e.g., pneumococci, staphylococci, and streptococci). There are very few anti-infectives that are designed to control the carrier state of pathogenic bacteria. However, studies have shown that by reducing or eliminating this reservoir in environments such as hospitals and nursing homes, the incidence of infections by these bacteria will be markedly reduced. The prevention of nosocomical infections involves routine and repeated cleaning of affected surfaces.

The bacteriophage and/or polypeptides of the present invention may be used in anti-infective compositions for controlling the growth of bacteria (e.g., Gram-positive bacteria (e.g., S. aureus), Gram-negative bacteria (e.g., K. pneumoniae, A. baumannii, E. coli, and P. aeruginosa), or bacteria not classified as either Gram-positive or Gram-negative), in order to prevent or reduce the incidence of nocosomial infections. In addition to use in compositions for application to mucous membranes, a bacteriophage and/or polypeptide of the present incorporation may also be incorporated into formulations such as gels, creams, ointments, or sprays for controlling or preventing colonization of bacteria on body surfaces (e.g., skin and mucus membranes) (e.g., for sterilization of surgical fields or of the hands and exposed skin of healthcare workers and/or patients) and other solid surfaces (e.g., appliances, countertops, and, in particular, hospital equipment).

6.5 USE IN NANOTECHNOLOGY

The bacteriophage and/or polypeptides of the present invention also may be used in nanotechnology, e.g., in the development of nanoscale devices. The combination of nanotechnology and molecular biology has led to a new generation of nanoscale-based devices, such as nanoscale conductors. Biological systems function based on the structure of macromolecules, mainly proteins and nucleic acids, which are structurally organized at the nanoscale. Accordingly, biological macromolecules may find use in nanoscale applications. In particular, proteins with highly organized structures can be used in the development of nanoscale devices.

In some embodiments, a polypeptide of the invention comprising or consisting of a tail protein (e.g., tail component, tail fiber protein, adsorption associated tail protein, tail length tape measure protein, baseplate wedge subunit), or fragment, variant, or derivative thereof, isolated from a bacteriophage having a genome comprising or consisting of SEQ ID NO: 1, SEQ ID NO: 2, SEQ ID NO: 3, SEQ ID NO:4, SEQ ID NO: 560, SEQ ID NO: 781, or SEQ ID NO: 1074 (e.g., bacteriophage F391/08, F394/08, F488/08, F510/08, F44/10, F387/08, or F125/10, respectively), may be used in nanotechnological applications. For example, tail proteins from tail fibers of the phage may have highly organized structures and may find use in nanoscale conductors. Such conductors may be used, e.g., to deposit gold and/or other ions.

In specific embodiments, the polypeptide of the invention used in nanotechonology is an isolated tail protein comprising or consisting of the amino acid sequence SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266. In other embodiments, the polypeptide of the invention comprises a fragment, variant or derivative of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266, wherein said fragment, variant or derivative possesses a highly-organized

6.6 DIAGNOSTIC METHODS

The present invention also encompasses diagnostic methods for determining the causative agent in a bacterial infection. In certain embodiments, the diagnosis of the causative agent in a presentation of bacterial infection is performed by (i) culturing tissue, blood, or fluid samples of a patient according to standard techniques; (ii) contacting the culture with one or more bacteriophage and/or polypeptides of the invention; and (iii) monitoring cell growth and/or evidence of lysis after said contacting. Because the activity of bacteriophage and/or their isolated products (e.g., polypeptides, or biologically active fragments, variants, or derivatives thereof) tends to be species or strain specific, susceptibility, or lack of susceptibility, to one or more bacteriophage and/or polypeptides of the invention may be indicative of the species or strain of infective bacteria. For example, decreased growth of test cultures after contacting with a bacteriophage having a genome comprising or consisting of the nucleic acid sequence SEQ ID NO: 1 or 781, or with an isolated polypeptide thereof or derived therefrom, may be indicative of the test sample comprising *K. pneumoniae*. Similarly, a bacteriophage having a genome comprising or consisting of the nucleic acid sequence SEQ ID NO: 2, or an isolated polypeptide product thereof or derived therefrom, may be used to identify infection by *A. baumannii*; a bacteriophage having a genome comprising or consisting of the nucleic acid sequence SEQ ID NO: 3, or an isolated polypeptide product thereof or derived therefrom, may be used to identify infection by *E. coli*; while that having a genome comprising or consisting of the nucleic acid sequence SEQ ID NO: 4, or an isolated polypeptide product thereof or derived therefrom, may be used to identify infection by *P. aeruginosa*; and that having a genome comprising or consisting of the nucleic acid sequence SEQ ID NO: 560 or 1074, or an isolated polypeptide product thereof or derived therefrom, may be used to identify infection by *S. aureus*.

Additionally, in some embodiments, bacteriophage and/or polypeptides of the present invention may be used in biosensors in the scope of diagnostics. As used herein, "biosensor" refers an analytical device for the detection of an analyte that combines a biological component with a physicochemical detector component. In particular, proteins involved in the recognition of bacterial receptors can be used in the development of diagnostic biosensors.

In some embodiments, a polypeptide of the invention comprising or consisting of a tail protein (e.g., tail component, tail fiber protein, adsorption associated tail protein, tail length tape measure protein, baseplate wedge subunit), or fragment, variant, or derivative thereof, isolated from a bacteriophage having a genome comprising or consisting of SEQ ID NO: 1, SEQ ID NO: 2, SEQ ID NO: 3, SEQ ID NO:4, SEQ ID NO: 560, SEQ ID NO: 781, SEQ ID NO: 1074 (e.g., bacteriophage F391/08, F394/08, F488/08, F510/08, F44/10, F387/08, or F125/10 respectively), may be used in biosensor applications. For example, a phage tail protein may specifically recognize one or more bacterial species and/or strains, and thus may find use in biosensor diagnostics. The detection of a certain bacterial species and/or strain, by one or more bacteriophage and/or polypeptides of the invention, can indicate the species or strain of infective bacteria.

In specific embodiments, the polypeptide of the invention used in biosensor applications is an isolated tail protein comprising or consisting of the amino acid sequence SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266. In other embodiments, the polypeptide of the invention comprises a fragment, variant or derivative of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266, wherein said fragment, variant or derivative is capable of specifically recognizing a bacteria, e.g., a specific species and/or one or more specific strains of the bacteria. Such polypeptides find use, e.g., in biosensors for detecting specific bacteria and/or diagnosing certain infections, as described above.

Generally, the phage tail protein for use in a biosensor will detect its host bacteria, or one or more specific species and/or specific strains of the host bacteria. Accordingly, in certain embodiments, the invention encompasses a tail protein corresponding to the amino acid sequence of SEQ ID NO: 15, SEQ ID NO: 26, SEQ ID NO: 27, SEQ ID NO: 30, or SEQ ID NOs: 32-35, or a variant, fragment or derivative thereof, which recognizes and can detect one or more strains of *K. pneumoniae*. Such detection may be indicative of a *K. pneumoniae* infection. In certain embodiments, the invention encompasses a tail protein corresponding to the amino acid sequence of SEQ ID NO: 180, SEQ ID NO: 183, SEQ ID NO: 185, or SEQ ID NO: 190, or a variant, fragment or derivative thereof, which recognizes and can detect one or more strains of *A. baumannii*. Such detection may be indicative of an *A. baumannii* infection. In certain embodiments, the invention encompasses a tail protein corresponding to the amino acid sequence of SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-495, or SEQ ID NO: 496, or a variant, fragment or derivative thereof, which recognizes and can detect one or more strains of *E. coli*. Such detection may be indicative of an *E. coli* infection In certain embodiments, the invention encompasses a tail protein corresponding to the amino acid sequence of SEQ ID NO: 544, SEQ ID NO: 545, SEQ ID NO: 549, or SEQ ID NO: 551, or a variant, fragment or derivative thereof, which recognizes and can detect one or more strains of *P. aeruginosa*. Such detection may be indicative of a *P. aeruginosa* infection. In certain embodiments, the invention encompasses a tail protein corresponding to the amino acid sequence of SEQ ID NO: 629, SEQ ID NO: 686, SEQ ID NO: 1077, SEQ ID NO: 1217, SEQ ID NO: 1250, or SEQ ID NO: 1266, or a variant, fragment or derivative thereof, which recognizes and can detect one or more strains of *S. aureus*. Such detection may be indicative of an *S. aureus* infection. In certain embodiments, the invention encompasses a tail protein corresponding to the amino acid sequence of SEQ ID NO: 789, SEQ ID NOs: 796-800, SEQ ID NO: 806, SEQ ID NO: 854, SEQ ID NOs: 999-1004, or SEQ ID NOs: 1053-1060, or a variant, fragment or derivative thereof, which recognizes and can detect one or more strains of *K. pneumoniae*. Such detection may be indicative of a *K. pneumoniae* infection.

In some embodiments, the invention encompasses the use of more than one tail protein, e.g., a combination of two of more of the tail proteins provided above, in a biosensor for detecting more than one bacterial species and/or strains. The biosensor also may comprise additional proteins and/or other agents for detecting the same or different bacteria.

6.7 AMINO ACID VARIANTS

Amino acid sequence variants of the polypeptides of the invention can be created. In some embodiments, they may be substitutional, insertional and/or deletion variants. Deletion variants lack one or more residues of the native protein which typically are not essential for function (e.g., antimicrobial or antibacterial activity). Insertional mutants typically involve the addition of material at a non-terminal point in the polypeptide. Substitutional variants typically involve the exchange of one amino acid for another at one or more sites within the polypeptide, and may be designed to modulate one or more properties of the polypeptide, such as stability against proteolytic cleavage, preferably without the loss (or substantial loss) of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Once general areas of the gene are identified as encoding a particular antibacterial activity, e.g., as a lysin as described herein, point mutagenesis may be employed to identify with greater particularity which amino acid residues are important in the antibacterial activity. Thus, one of skill in the art will be able to generate, for example, single base changes in the DNA strand to result in an altered codon and/or a missense mutation that preserves desired function.

Preferably, mutation of the amino acids of a protein creates an equivalent, or even an improved, second-generation molecule. For example, certain amino acids may be substituted for other amino acids in a protein structure without detectable or substantial loss of function (e.g., antibacterial or antimicrobial activity). In making such changes, the hydropathic index of amino acids may be considered. The importance of the hydropathic amino acid index in conferring interactive biological function on a protein is generally understood in the art. It is accepted that the relative hydropathic character of the amino acid contributes to the secondary structure of the resultant protein, which in turn defines the interaction of the protein with other molecules, for example, interaction with a peptidoglycan within the outer coat of a gram-positive bacteria. Each amino acid has been assigned a hydropathic index on the basis of their hydrophobicity and charge characteristics; for example: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan 0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is also understood in the art that the substitution of like amino acids can be made effectively on the basis of hydrophilicity. Like hydrophobicity, values of hydrophilicity have been assigned to each amino acid: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). Equivalent molecules may be obtained by substitution of one amino acid for another where their hydropathic and/or their hydrophilicity indices are within ±2, preferably ±1, or most preferably ±5 of each other.

In certain embodiments, the invention encompasses isolated peptides that comprise 1, 2, 3, 4, 5, 6, 7, 8, 9, or 10 or more amino acid modifications (e.g., insertion, substitution, deletion, etc.) relative to an amino acid sequence disclosed herein. In preferred embodiments, the mutation(s) are made such that biological activity of the particular polypeptide is retained or substantially retained. For example, the present invention encompasses polypeptides isolated from bacteriophage F387/08, F391/08, F394/08, F488/08, F510/068, F44/10, and/or F125/10, which are mutated to comprise 1, 2, 3, 4, 5, 6, 7, 8, 9, or 10 or more amino acid modifications relative to an amino acid sequence listed herein, and which exhibit antibacterial activity against one or more species or strains of Gram-positive or Gram-negative bacterium, e.g., against *K. pneumoniae*, *A. baumannii*, *E. coli*, *P. aeruginosa*, and/or *S. aureus*. In specific embodiments, the polypeptides of the invention derived from F387/08 or F391/08 exhibit antibacterial or antimicrobial activity, e.g., lytic killing activity, against at least *K. pneumoniae*; those derived from F394/08 against at least *A. baumannii*; those derived from F488/08 against at least *E. coli*; those derived from F510/08 against at least. *P. aeruginosa*, and those derived from F44/10 or F125/10 against at least. *S. aureus*.

6.8 POLYNUCLEOTIDES ENCODING POLYPEPTIDES OF THE INVENTION

The invention provides polynucleotides comprising a nucleotide sequence encoding a polypeptide of the invention. The invention also encompasses polynucleotides that hybridize under high stringency, intermediate, or lower stringency hybridization conditions, e.g., as defined supra, to polynucleotides that encode a polypeptide of the invention and that encode modified polypeptides that have antibiotic and/or other biological activity.

The polynucleotides may be obtained, and the nucleotide sequence of the polynucleotides determined, by any method known in the art. For example, a polynucleotide encoding a polypeptide of the invention may be generated from nucleic acid from a suitable source (e.g., bacteriophage F387/08, F391/08, F394/08, F488/08, F510/08, F44/10, and/or F125/10). Nucleotide sequences may be isolated from phage genomes by routine methods known in the art (see, e.g., Carlson, "Working with bacteriophage: common techniques and methodological approaches," In, Kutter and Sulakvelidze (Eds) Bacteriophage: Biology and Applications, 5th ed. CRC Press (2005); incorporated herein by reference in its entirety). If a source containing a nucleic acid encoding a particular polypeptide is not available, but the amino acid sequence of the polypeptide of the invention is known, a nucleic acid encoding the polypeptide may be chemically synthesized and cloned into replicable cloning vectors using any method well known in the art.

Once the nucleotide sequence of the polypeptide of the invention is determined, the nucleotide sequence of the polypeptide may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate polypeptides having a different amino acid sequence, for example to create amino acid substitutions, deletions, and/or insertions.

In some embodiments, a nucleotide sequence encoding one or more ORFs of FIGS. 2, 4, 6, 8, 10, 12, and 14 are provided. In some embodiments, a nucleotide sequence encoding a variant, fragment or derivative of one or more ORFs of FIGS. 2, 4, 6, 8, 10, 12, and 14 are provided, where the variant, fragment or derivative exhibits antibacterial or antimicrobial activity (e.g., lytic killing activity) against one or more strains of *K. pneumoniae*, for example, against the bacteriophage having a genome comprising or consisting of the nucleic acid sequence SEQ ID NO: 1 or SEQ ID NO: 781; and/or one against or more strains of *A. baumannii*, for example, against the bacteriophage having a genome comprising or consisting of the nucleic acid sequence SEQ ID NO: 2; and/or against one or more strains of *E. coli*, for example, against the bacteriophage having a genome comprising or consisting of the nucleic acid sequence SEQ ID NO: 3; against one or more strains of *P. aeruginosa*, for example, against the bacteriophage having a genome comprising or consisting of the nucleic acid sequence SEQ ID NO: 4; and/or against one or more strains of *S. aureus*, for example, against the bacteriophage having a genome comprising or consisting of the nucleic acid sequence SEQ ID NO: 560 or SEQ ID NO: 1074.

6.9 RECOMBINANT EXPRESSION OF MOLECULES OF THE INVENTION

Once a nucleic acid sequence encoding a molecule of the invention (e.g., a polypeptide) has been obtained, the vector for the production of the molecules may be produced by recombinant DNA technology using techniques well known in the art. Methods which are well known to those skilled in the art can be used to construct expression vectors containing the coding sequences for the molecules of the invention and appropriate transcriptional and translational control signals. These methods include, for example, in vitro recombinant DNA techniques, synthetic techniques, and in vivo genetic recombination. (See, for example, the techniques described in Sambrook et al., 1990, Molecular Cloning, A Laboratory Manual, 2d Ed., Cold Spring Harbor Laboratory, Cold Spring Harbor, N.Y. and Ausubel et al. eds., 1998, Current Protocols in Molecular Biology, John Wiley & Sons, NY).

The present invention provides expression vectors encoding the polypeptides of the invention. An expression vector comprising the nucleotide sequence of a molecule identified by the methods of the invention can be transferred to a host cell by conventional techniques (e.g., electroporation, liposomal transfection, and calcium phosphate precipitation) and the transfected cells are then cultured by conventional techniques to produce the molecules of the invention. In preferred embodiments, the host cell is other than the species of the parent bacteria from which the bacteriophage comprising the sequence was derived. In specific embodiments, the expression of the molecules of the invention is regulated by a constitutive, an inducible or a tissue, specific promoter. In specific embodiments the expression vector is pQE-30 (Qiagen) or pET-29(a) (Novagen).

The host cells used to express the molecules identified by the methods of the invention may be either bacterial cells (preferably non susceptible to the bacteriophage protein or variant, derivative, or fragment thereof of the invention). A variety of host-expression vector systems may be utilized to express the molecules identified by the methods of the invention. Such host-expression systems represent vehicles by which the coding sequences of the molecules of the invention may be produced and subsequently purified, but also represent cells which may, when transformed or transfected with the appropriate nucleotide coding sequences, express the molecules of the invention in situ. These include, but are not limited to, microorganisms such as bacteria that are not susceptible to the bacteriophage protein or variant, derivative, or fragment thereof of the invention (e.g., *B. subtilis*) transformed with recombinant bacteriophage DNA, plasmid DNA, or cosmid DNA expression vectors containing coding sequences for the molecules identified by the methods of the invention; yeast (e.g., *Saccharomyces Pichia*) transformed with recombinant yeast expression vectors containing sequences encoding the molecules identified by the methods of the invention; insect cell systems infected with recombinant virus expression vectors (e.g., baculovirus) containing the sequences encoding the molecules identified by the methods of the invention; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules identified by the methods of the invention; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter) containing sequences encoding the molecules identified by the methods of the invention.

In bacterial systems not susceptible to the bacteriophage protein or variant, derivative, or fragment thereof of the invention, a number of expression vectors may be advantageously selected depending upon the use intended for the molecule being expressed. For example, when a large quantity of such a protein is to be produced, for the generation of pharmaceutical compositions of a polypeptide, vectors which direct the expression of high levels of fusion protein products that are readily purified may be desirable. Such vectors include, but are not limited, to the *E. coli* expression vector pUR278 (Ruther et al., 1983, *EMBO J.* 2:1791), in which the protein sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus preferably grows in *Spodoptera frugiperda* cells. The polypeptide coding sequence may be cloned individually into non-essential regions (e.g., the polyhedrin gene) of the virus and placed under control of an AcNPV promoter (e.g., the polyhedrin promoter).

Once a molecule of the invention (i.e., polypeptides) has been recombinantly expressed, it may be purified by any method known in the art for purification of polypeptides, for example, by chromatography (e.g., ion exchange, affinity, and sizing column chromatography), centrifugation, differential solubility, or by any other standard technique for the purification of polypeptides or antibodies.

Certain modifications and improvements will occur to those skilled in the art upon a reading of the foregoing description. It should be understood that all such modifications and improvements have been deleted herein for the sake of conciseness and readability but are properly within the scope of the following claims.

7. EXAMPLES

It is understood that the following examples and embodiments described herein are for illustrative purposes only and that various modifications or changes in light thereof will be suggestive to persons skilled in the art and are to be included within the spirit and purview of this application and the scope of the appended claims. All publications, patents, and patent applications cited herein are hereby incorporated by reference in their entirety for all purposes.

Unless otherwise indicated, the bacteriophage of the invention were isolated, processed and analyzed according to the following methods.

7.1.1 Purification of Phage

Stock preparations of bacteriophage isolated from clinical samples were prepared according to protocols described in Carlson, "Working with bacteriophage: common techniques and methodological approaches," In, Kutter and Sulakvelidze (Eds) Bacteriophage: Biology and Applications, 5$^{th}$ ed. CRC Press (2005) ("Carlson," incorporated herein by reference in its entirety).

The bacteriophage stock preparations were concentrated by precipitation with PEG according to the protocol described in Carlson and Yamamoto et al., 2004, *PNAS* 101:6415-6420. Briefly, the stock preparation was incubated in 1 M NaCl for one hour at 4° C. with agitation. Next, PEG 8000 (AppliChem, Cheshire, Mass.) was gradually added to a final concentration of 10% (w/v). The composition was then incubated overnight at 4° C. After the incubation period, the composition was centrifuged at 10000×g for 30 minutes at 4° C. The sediment was then re-suspended in SM buffer (0.05 M Tris-HCL at pH 7.4, 0.1 M NaCl, 10 mM MgSO$_4$) with gelatin at 1% w/v and centrifuged again at 1000 rpm at 4° C. for 10 minutes. The supernatant containing the suspended phage was saved for further purification. The supernatant was purified using a CsCl gradient according to the methods in Carlson.

CsCl was removed from the purified and concentrated phage stock by dialysis. A dialysis membrane, Cellu.Sep H1 High Grade Regenerated Cellulose Tubular Membrane (Cellu.Sep, River Street, USA), was prepared according to the manufacturers' instructions. The dialysis involved a first incubation of 30 minutes in 100 mM Tris-HCl and 3 M NaCl (pH 7.4) at 4° C. This was followed by a second incubation of 30 minutes in 100 mM Tris-HCl and 0.3 M NaCl (pH 7.4) at 4° C. After dialysis, the suspended phage was removed from the interior of the dialysis bag and stored at 4° C.

7.1.2 Extraction of Phage DNA

To 5 ml of the purified and concentrated bacteriophage samples was added 20 mM EDTA at pH 8.0, SDS at 0.5% (p/v) and Proteinase K at a final concentration of 40 µg/ml. The mixture was incubated at 56° C. for one hour. Successive extractions in phenol:chloroform:alcohol at a proportions of 25:24:1 were performed until the interface between the aqueous and organic phases was clear. The aqueous phase was then treated with an equal volume of chloroform and centrifuged at 13,0000×g for 10 minutes at 4° C. The aqueous phase was once again removed, and the DNA was precipitated by adding two volumes of absolute ethanol and incubating for thirty minutes at 20° C. The samples were then centrifuged at 11,000×g for 30 minutes at 4° C. The pellet was washed with 70% ethanol at room temperature and resuspended in 50 µl of ultra-pure water (Gibco, California). DNA concentration was determined by measuring the absorbance at 260 nm in a ND-1000 Spectrophotometer. Integrity of the isolated phage DNA was analyzed by electrophoresis on a 1% agarose gel.

7.1.3 Analysis of Phage Genomes

Sequencing of the bacteriophage genome allowed identification of potential open reading frames (ORFs) within the genome. The putative ORFs of the bacteriophage were used to search the NCBI nucleotide collection database for homologous DNA sequences using the BLASTN program (see, e.g., Zhang et al., 2000, *J. Comput. Biol.* 7:203-214).

7.2 Example 1

Bacteriophage F391/08

Comparison of the putative ORFs of the bacteriophage F391/08 genome with the sequences in the NCBI nucleotide database revealed that only small portions of the genome (≤11% genome coverage) exhibited homology with known sequences. A schematic organization of the F391/08 genome is provided in FIG. 1. F391/08 ORFs, their encoded amino acid sequences, and known homologous proteins are provided in FIG. 2. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 2. Identification of putative transfer RNA genes (tRNA) was carried out using the tRNAscan-SE program (Lowe, T. M. et al., 1997. Nucleic Acids Res., 25: 955-964).

Table 1 below provides the results of spot tests that assessed the host range and activity of the bacteriophage F391/08 against 100 *Klebsiella* sp. strains (86 *K. pneumoniae* strains; 12 *K. oxytoca* strains; and 2 *Klebsiella* sp. strains) isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 1

| Phage | Titer (pfu/ml) | Phage sensitivity (%) of *Klebsiella* sp. strains (n = 100) | | | | | | Total of infected strains (%) |
|---|---|---|---|---|---|---|---|---|
| | | ++++ | +++ | ++ | + | pfu | − | |
| F391/08 | 2.72 × 10$^{10}$ | 3 | 26 | 8 | 11 | 0 | 52 | 48 |
| | 2.72 × 10$^{8}$ | 1 | 5 | 6 | 1 | 0 | 87 | 13 |
| | 2.72 × 10$^{6}$ | 0 | 1 | 3 | 1 | 1 | 94 | 6 |
| | 2.72 × 10$^{4}$ | 0 | 0 | 0 | 0 | 3 | 97 | 3 |

7.3 Example 2

Bacteriophage F394/08

Comparison of the putative ORFs of the bacteriophage F394/08 genome with the sequences in the NCBI nucleotide database revealed no significant homologies with known sequences, other than that observed for small portions of the genome (≤1% genome coverage). A schematic organization of the F394/08 genome is provided in FIG. 3. F394/08 ORFs, their encoded amino acid sequences, and known homologous proteins are provided in FIG. 4. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 4. Identification of putative transfer RNA genes (tRNA) was carried out using the tRNAscan-SE program (Lowe, T. M. et al., 1997. Nucleic Acids Res., 25: 955-964).

Table 2 below provides the results of spot tests that assessed the host range and activity of the bacteriophage F394/08 against 100 *Acinetobacter* sp. strains (93 *A. baumannii* strains; 6 *A. calcoaceticus* strains; and 1 *A. lwoffi* strain) isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 2

| Phage | Titer (pfu/ml) | Phage sensitivity (%) of *Acinetobacter* sp. strains (n = 100) | | | | | | Total of infected strains (%) |
|---|---|---|---|---|---|---|---|---|
| | | ++++ | +++ | ++ | + | pfu | − | |
| F394/08 | 2.2 × 10$^{9}$ | 67 | 3 | 1 | 0 | 0 | 29 | 71 |
| | 2.2 × 10$^{8}$ | 66 | 1 | 2 | 1 | 0 | 30 | 70 |
| | 2.2 × 10$^{6}$ | 9 | 38 | 8 | 0 | 0 | 45 | 55 |
| | 2.2 × 10$^{4}$ | 0 | 7 | 1 | 0 | 32 | 60 | 40 |

7.4 Example 3

Bacteriophage F488/08

Comparison of the putative ORFs of the bacteriophage F488/08 genome with the sequences in the NCBI nucleotide database revealed that approximately 94% of phage F488/08 DNA is highly similar to that of Enterobaceria phage RB 14, with individual ORF identities ranging from 70 to 100%. A schematic organization of the F488/08 genome is provided in FIG. 5. F4884/08 ORFs, their encoded amino acid sequences, and known homologous proteins are provided in FIG. 6. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 4. Identification of putative transfer RNA genes (tRNA) was carried out using the tRNAscan-SE program (Lowe, T. M. et al., 1997. Nucleic Acids Res., 25: 955-964).

Table 3 below provides the results of spot tests that assessed the host range and activity of the bacteriophage F488/08 against 100 *Escherichia coli* (ECO) strains isolated from clinical samples. Each spot contained 5 µl of bacteriophage suspension with the indicated titers, prepared from a lysate purified by ion exchange chromatography. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 3

| Phage | Titer (pfu/ml) | Phage sensitivity (%) of ECO strains (n = 100) | | | | | | Total of infected strains (%) |
|---|---|---|---|---|---|---|---|---|
| | | ++++ | +++ | ++ | + | pfu | − | |
| F488/08 | 1 × 10$^{10}$ | 0 | 60 | 1 | 2 | 0 | 37 | 63 |
| | 1 × 10$^{8}$ | 0 | 42 | 15 | 0 | 0 | 43 | 57 |
| | 1 × 10$^{6}$ | 0 | 8 | 10 | 7 | 0 | 75 | 25 |
| | 1 × 10$^{4}$ | 0 | 0 | 0 | 0 | 10 | 90 | 10 |

7.5 Example 4

Bacteriophage F510/08

Comparison of the putative ORFs of the bacteriophage F510/08 genome with the sequences in the NCBI nucleotide database revealed that approximately 95% of phage F510/08 DNA is highly similar to that of Pseudomonas phage LUZ19, with individual ORF identities ranging from 89 to 97%. A schematic organization of the F510/08 genome is provided in FIG. 7. F510/08 ORFs, their encoded amino acid sequences, and known homologous proteins are provided in FIG. 8. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 8. Identification of putative transfer RNA genes (tRNA) was carried out using the tRNAscan-SE program (Lowe, T. M. et al., 1997. Nucleic Acids Res., 25: 955-964).

Table 4 below provides the results of spot tests that assessed the host range and activity of the bacteriophage F510/08 against 100 Pseudomonas aeruginosa (PSA) strains isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 4

| Phage | Titer (pfu/ml) | Phage sensitivity (%) of PSA strains (n = 100) | | | | | | Total of infected strains (%) |
|---|---|---|---|---|---|---|---|---|
| | | ++++ | +++ | ++ | + | pfu | − | |
| F510/08 | $5.7 \times 10^{10}$ | 35 | 18 | 4 | 10 | 3 | 30 | 70 |
| | $5.7 \times 10^{8}$ | 18 | 25 | 6 | 9 | 4 | 38 | 62 |
| | $5.7 \times 10^{6}$ | 13 | 14 | 4 | 2 | 4 | 63 | 37 |
| | $5.7 \times 10^{4}$ | 10 | 12 | 0 | 1 | 10 | 67 | 33 |

7.6 Example 5

Bacteriophage F44/10

Comparison of the putative ORFs of the bacteriophage F44/10 genome with the sequences in the NCBI nucleotide database revealed that approximately 81% of phage F44/10 DNA is highly similar to that of Staphylococcus phage K, with individual ORF identities ranging from 80 to 99%. A schematic organization of the F44/10 genome is provided in FIG. 9. F44/10 ORFs, their encoded amino acid sequences, and known homologous proteins are provided in FIG. 10. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 10. As previously reported for Staphylococcus phage K, the putative polymerase gene (orf114a, orf114b) may contain an intron-like sequence. (O'Flaherty et al., 2004). Identification of putative transfer RNA genes (tRNA) was carried out using the tRNAscan-SE progam (Lowe, T. M. et al., 1997. Nucleic Acids Res., 25: 955-964).

Table 5 below provides the results of spot tests that assessed the host range and activity of the bacteriophage F44/10 against 100 Staphylococcus aureus (STA) strains isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 5

| Phage | Titer (pfu/ml) | Phage sensitivity (%) of STA strains (n = 100) | | | | | | Total of infected strains (%) |
|---|---|---|---|---|---|---|---|---|
| | | ++++ | +++ | ++ | + | pfu | − | |
| F44110 | $2.25 \times 10^{11}$ | 53 | 35 | 10 | 1 | 1 | 0 | 100 |
| | $2.25 \times 10^{10}$ | 35 | 52 | 10 | 2 | 1 | 0 | 100 |
| | $2.25 \times 10^{8}$ | 19 | 51 | 5 | 5 | 1 | 19 | 81 |
| | $2.25 \times 10^{6}$ | 5 | 22 | 0 | 0 | 34 | 39 | 61 |
| | $2.25 \times 10^{4}$ | 0 | 0 | 0 | 0 | 42 | 58 | 42 |

7.7 Example 6

Bacteriophage F387/08

Comparison of the putative ORFs of the bacteriophage F387/08 genome with the sequences in the NCBI nucleotide database revealed no significant homologies with known sequences other than small portions of the genome (≤12% genome coverage). A schematic organization of the F387/08 genome is provided in FIGS. 11A-11C. Functionally assigned orfs are indicated on the right and in FIGS. 11B-C. DNA homology searches were carried out with BLASTN program (Zhang, Z. et al., 2000. J. Comput. Biol., 7: 203-214), using the NCBI nucleotide collection database.

F387/08 ORFs, their encoded amino acid sequences, and known homologous proteins are provided in FIG. 12. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240).

Table 6 below provides the results of spot tests that assessed the host range and activity of the bacteriophage F387/08 against 100 Klebsiella sp. strains (86 K. pneumoniae strains; 12 *K. oxytoca* strains; and 2 *Klebsiella* sp. strains) isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 6

| Phage | Titer (pfu/ml) | Phage sensitivity (%) of KLE strains (n = 100) | | | | | | Total of infected strains (%) |
|---|---|---|---|---|---|---|---|---|
| | | ++++ | +++ | ++ | + | pfu | − | |
| F387/08 | 1.0 × 10$^{10}$ | 1 | 38 | 20 | 9 | 0 | 32 | 68 |
| | 1.0 × 10$^{8}$ | 0 | 10 | 14 | 9 | 0 | 67 | 33 |
| | 1.0 × 10$^{6}$ | 0 | 2 | 2 | 0 | 1 | 95 | 5 |
| | 1.0 × 10$^{4}$ | 0 | 0 | 0 | 1 | 2 | 97 | 3 |

7.8 Example 7

Bacteriophage F125/10

Comparison of the putative ORFs of the bacteriophage F125/10 genome with the sequences in the NCBI nucleotide database revealed that approximately 87% of phage F125/10 DNA is highly similar to that of *Staphylococcus* phage A5W, with individual ORF identities ranging from 77 to 99%. A schematic organization of the F125/10 genome is provided in FIG. 13. F125/10 ORFs, their encoded amino acid sequences, and known homologous proteins are provided in FIG. 14. Prediction of orfs was performed by integrating the results obtained with GeneMark.hmm and MetaGeneAnnotator programs (Besemer, J. and Borodovsky, M. 1999. *Nucleic Acids Res.*, 27: 3911-3920; Noguchi, H. et al., 2008. *DNA Res.*, 15: 387-396). Protein homology searches were carried out with BLASTP program (Alschul, S. F. et al., 1997. *Nucleic Acids Res.*, 25: 3389-33402) using the NCBI non-redundant protein sequences database. Protein conserved domains were predicted using NCBI specialized BLAST (Marchler-Bauer, A. et al., 2007. *Nucleic Acids Res.* 35: 237-240). orfs whose products presented homology with the same protein(s) are indicated with the same number with the addition of a lowercase letter, in FIG. 14. As previously reported for *Staphylococcus* phage K (O'Flaherty et al., 2004, *J. of Bacteriology* 186(9):2862-2871), and phage Twort (Landthaler et al., 2002, *Nucleic Acids Research* 30(9):1935-1943), introns interrupting genes involved in DNA metabolism were found; and the putative terminase large subunit gene (orf153a, orf153b) may contain an intron-like sequence (orf154*).

Table 7 below provides the results of spot tests that assessed the host range and activity of the bacteriophage F125/10 against 98 *Staphylococcus aureus* (STA) strains isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Phage dilutions originating from isolated phage plaques are indicated as (pfu) and resistance to phage infection is indicated as (−). The percentage of strains displaying a particular sensitivity phenotype is indicated also.

TABLE 7

| Phage | Titer (pfu/ml) | Phage sensitivity (%) of STA strains (n = 198) | | | | | | Total of infected strains (%) |
|---|---|---|---|---|---|---|---|---|
| | | ++++ | +++ | ++ | + | pfu | − | |
| F125/10 | 8.30 × 10$^{9}$ | 49 | 27 | 12 | 10 | 0 | 0 | 100 |
| | 8.30 × 10$^{8}$ | 21 | 38 | 21 | 16 | 0 | 2 | 98 |
| | 8.30 × 10$^{6}$ | 4 | 29 | 27 | 15 | 0 | 23 | 77 |
| | 8.30 × 10$^{4}$ | 0 | 9 | 20 | 10 | 22 | 37 | 62 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09737579B2). An electronic copy of the "Sequence Listing" will also be available from the USPTO upon request and payment of the fee set forth in 37 CFR 1.19(b)(3).

What is claimed is:

1. A method of treating or reducing the incidence of an infection caused by at least one of *Staphylococcus aureus, Acinetobacter baumanni, Klebsiella pneumonia,* and *Escherichia coli* in a subject in need thereof, said method comprising administering to said subject an effective amount of a pharmaceutical composition, said pharmaceutical composition comprising:

a pharmaceutically acceptable carrier; and a purified bacteriophage having a genome which comprises at least 99% sequence identity to the nucleotide sequence selected from the group consisting of SEQ ID NO:1074, SEQ ID NO:1, SEQ ID NO:2, SEQ ID NO:3, and SEQ ID NO: 781, and having antibacterial activity against at least one of *Staphylococcus aureus, Acinetobacter baumanni, Klebsiella pneumonia,* and *Escherichia coli.*

2. The method of claim 1, wherein said bacteriophage has the genome comprising at least 99% sequence identity to the nucleotide sequence of SEQ ID NO:1074 and has antibacterial activity against *Staphylococcus aureus*; and wherein said pharmaceutical composition further comprises (i) three additional purified phage selected from the group consisting of F391/08, F394/08, F488/08, F510/08, F44/10, F387/08, F170/08, F168/08, F770/05, and F1245/05;

(ii) three additional purified phage selected from the group consisting of F44/10, F391/08, F387/08, F488/08, F510/08, and F770/05; or (iii) two additional phage corresponding to F510/08 and F44/10.

3. The method of claim 1, wherein the infection is a nosocomial infection.

4. The method of claim 1, wherein the pharmaceutical composition is administered topically.

5. The method of claim 1, wherein the infection is an infection of the skin.

6. The method of claim 5, wherein the infection is an infection associated with at least one condition selected from the group consisting of diabetic foot ulcer, scalded skin syndrome, pimples, and carbuncles.

7. The method of claim 6, wherein the pharmaceutical composition is administered topically.

8. The method of claim 1, wherein the infection is pneumonia or other infection of the respiratory tract.

9. The method of claim 8, wherein the pharmaceutical composition is administered by inhalation.

10. The method of claim 9, wherein administration by inhalation uses a pump, a spray, or a nebulizer; or wherein the pharmaceutical composition for administration by inhalation comprises a dry powder inhaler or an aerosol spray.

11. The method of claim 1, wherein the infection is an infection associated with at least one condition selected from the group consisting of gastroenteritis, osteomyelitis, endocarditis, and peritonitis.

12. The method of claim 11, wherein the pharmaceutical composition is administered orally or parenterally.

13. The method of claim 1, wherein the infection is an infection associated with at least one condition selected from the group consisting of meningitis or other infection of the cerebrospinal fluid, toxic shock syndrome, bacteremia, and sepsis.

14. The method of claim 13, wherein the pharmaceutical composition is administered intravenously.

15. The method of claim 1, wherein the infection is an infection of the urinary tract.

16. The method of claim 15, wherein the pharmaceutical composition is administered by a catheter.

17. The method of claim 1, wherein the subject is a human.

18. The method of claim 1, further comprising administering to said subject an antibiotic for treating said bacterial infection.

19. The method of claim 1, wherein said pharmaceutical composition further comprises one of more additional bacteriophage known to have antibacterial or antimicrobial activity against at least one of *Staphylococcus aureus, Acinetobacter baumanni, Klebsiella pneumonia*, and *Escherichia coli*.

20. The method of claim 1, wherein said pharmaceutical composition further comprises one of more additional bacteriophage known to have antibacterial or antimicrobial activity against a bacterium other than *Staphylococcus aureus Acinetobacter baumanni, Klebsiella pneumonia*, and *Escherichia coli*.

21. The method of claim 1, wherein said infection is a *Staphylococcus aureus* infection by a methicillin-resistant strain of *Staphylococcus aureus* (MRSA).

22. The method of claim 21, further comprising administering to said subject at least one antibiotic known to have antibacterial or antimicrobial activity against MRSA.

23. The method of claim 22, wherein said antibiotic is selected from the group consisting of vancomycin, teicoplanin, clindamycin, and trimethoprim-sulfamethoxazole.

* * * * *